US010646575B2

(12) United States Patent
Phillips et al.

(10) Patent No.: US 10,646,575 B2
(45) Date of Patent: May 12, 2020

(54) HETEROCYCLIC DEGRONIMERS FOR TARGET PROTEIN DEGRADATION

(71) Applicant: C4 Therapeutics, Inc., Watertown, MA (US)

(72) Inventors: Andrew J. Phillips, Arlington, VA (US); Chris G. Nasveschuk, Syoneham, MA (US); James A. Henderson, Weston, MA (US); Yanke Liang, Brookline, MA (US); Mark E. Fitzgerald, Watertown, MA (US); Minsheng He, Watertown, MA (US); Ryan E. Michael, Newton, MA (US)

(73) Assignee: C4 Therapeutics, Inc., Watertown, MA (US)

(*) Notice: Subject to any disclaimer, the term of this patent is extended or adjusted under 35 U.S.C. 154(b) by 0 days.

(21) Appl. No.: 16/186,339

(22) Filed: Nov. 9, 2018

(65) Prior Publication Data
US 2019/0076541 A1 Mar. 14, 2019

Related U.S. Application Data

(63) Continuation of application No. PCT/US2017/032051, filed on May 10, 2017.

(60) Provisional application No. 62/334,395, filed on May 10, 2016.

(51) Int. Cl.
| *A61K 47/54* | (2017.01) |
| *A61K 31/438* | (2006.01) |
| *A61K 31/439* | (2006.01) |
| *A61K 31/547* | (2006.01) |
| *A61K 31/55* | (2006.01) |
| *A61K 31/4035* | (2006.01) |
| *C07D 403/04* | (2006.01) |
| *A61K 31/454* | (2006.01) |

(52) U.S. Cl.
CPC ........ *A61K 47/545* (2017.08); *A61K 31/4035* (2013.01); *A61K 31/438* (2013.01); *A61K 31/439* (2013.01); *A61K 31/454* (2013.01); *A61K 31/547* (2013.01); *A61K 31/55* (2013.01); *A61K 47/554* (2017.08); *C07D 403/04* (2013.01)

(58) Field of Classification Search
CPC .............. A61K 47/554; A61K 31/4035; A61K 47/545; A61K 31/55; A61K 31/439; A61K 31/438; A61P 35/00; A61P 37/00
See application file for complete search history.

(56) References Cited

U.S. PATENT DOCUMENTS

| 5,635,517 | A | 6/1997 | Muller et al. |
| 6,306,663 | B1 | 10/2001 | Kenten et al. |
| 7,041,298 | B2 | 5/2006 | Deshaies et al. |
| 7,208,157 | B2 | 4/2007 | Deshaies et al. |
| 9,125,915 | B2 | 9/2015 | Miyoshi et al. |
| 9,249,161 | B2 | 2/2016 | Albrecht et al. |
| 10,414,755 | B2 * | 9/2019 | Beckwith ............. C07D 513/04 |
| 2006/0069067 | A1 | 3/2006 | Bhatnagar et al. |
| 2013/0190340 | A1 | 7/2013 | Hedstrom et al. |
| 2014/0302523 | A1 | 10/2014 | Crews et al. |
| 2014/0356322 | A1 | 12/2014 | Crews et al. |
| 2015/0119435 | A1 | 4/2015 | Crews et al. |
| 2015/0274738 | A1 | 10/2015 | Gray et al. |
| 2015/0291562 | A1 | 10/2015 | Crew et al. |
| 2016/0016966 | A1 | 1/2016 | Amans et al. |
| 2016/0022642 | A1 | 1/2016 | Crews et al. |
| 2016/0045607 | A1 | 2/2016 | Crew et al. |
| 2016/0046661 | A1 | 2/2016 | Gray et al. |
| 2016/0058872 | A1 | 3/2016 | Crew et al. |
| 2016/0176916 | A1 | 6/2016 | Bradner et al. |
| 2016/0214972 | A1 | 7/2016 | Jin et al. |
| 2016/0272639 | A1 | 9/2016 | Crew et al. |
| 2017/0008904 | A1 | 1/2017 | Crew et al. |
| 2017/0037004 | A1 | 2/2017 | Crew et al. |
| 2017/0065719 | A1 | 3/2017 | Qian et al. |
| 2018/0015087 | A1 | 1/2018 | Liu et al. |
| 2018/0085465 | A1 | 3/2018 | Bradner et al. |

FOREIGN PATENT DOCUMENTS

| BR | PI1100318 A2 | 5/2013 |
| CN | 103421061 A | 12/2013 |
| WO | WO 1998/011111 A1 | 3/1998 |
| WO | WO 2002/059106 A1 | 8/2002 |
| WO | WO 2006/102557 A2 | 9/2006 |
| WO | WO 2008/027542 A2 | 3/2008 |
| WO | WO 2008/033567 A1 | 3/2008 |
| WO | WO 2008/039489 A2 | 4/2008 |
| WO | WO 2008/115516 A2 | 9/2008 |

(Continued)

OTHER PUBLICATIONS

Bartlett, et al. "The evolution of thalidomide and its IMiD derivatives as anticancer agents." Nat Rev Cancer 2004, 4(4):312-322.
Berndsen et al. "New insights into ubiquitin E3 ligase mechanism" Nat. Struct. Mol. Biol. 2014, 21:301-307.
Buckley et al. "HaloPROTACS: Use of Small Molecule PROTACS to Induce Degradation of HaloTag Fusion Proteins" ACS Chemical Biology 2015, 10:1831-1837.
Buckley et al. "Small-Molecule Control of Intracellular Protein Levels through Modulation of the Ubiquitin Proteasome System" Angewandte Reviews, 2014, 53:2312-2330.
Buckley et al. "Targeting the Von Hippel-Lindau E3 Ubiquitin Ligase Using Small Molecules to Disrupt the Vhl/Hif-1alpha Interaction" J. Am. Chem. Soc. 2012, 134:4465-4468.

(Continued)

*Primary Examiner* — Alexander R Pagano
*Assistant Examiner* — Ebenezer O Sackey
(74) *Attorney, Agent, or Firm* — Knowles Intellectual Property Strategies, LLC

(57) ABSTRACT

This invention provides heterocyclic compounds that bind to E3 Ubiquitin Ligase (typically through cereblon) ("Degrons"), which can be used as is or linked to a Targeting Ligand for a selected Target Protein for therapeutic purposes and methods of use and compositions thereof as well as methods for their preparation.

28 Claims, 389 Drawing Sheets

(56) References Cited

FOREIGN PATENT DOCUMENTS

| | | |
|---|---|---|
| WO | WO 2008/122038 A1 | 10/2008 |
| WO | WO 2009/042177 A1 | 4/2009 |
| WO | WO 2009/139880 A1 | 11/2009 |
| WO | WO 2009/145899 A1 | 12/2009 |
| WO | WO 2010/053732 A1 | 5/2010 |
| WO | WO 2010/107485 A1 | 9/2010 |
| WO | WO 2011/097218 A1 | 8/2011 |
| WO | WO 2011/143669 A2 | 11/2011 |
| WO | WO 2012/079022 A1 | 6/2012 |
| WO | WO 2012/178208 A2 | 12/2012 |
| WO | WO 2013/059215 A1 | 4/2013 |
| WO | WO 2013/106646 A2 | 7/2013 |
| WO | 2013170147 * | 11/2013 |
| WO | WO 2013/170147 A1 | 11/2013 |
| WO | WO 2014/145887 A1 | 9/2014 |
| WO | WO 2015/173764 A1 | 11/2015 |
| WO | WO 2016/065139 A1 | 4/2016 |
| WO | WO 2016/105518 A1 | 6/2016 |
| WO | WO 2016/146985 A1 | 9/2016 |
| WO | WO 2016/169989 A1 | 10/2016 |
| WO | WO 2016/191178 A1 | 12/2016 |
| WO | WO 2016/197032 A1 | 12/2016 |
| WO | WO 2016/197114 A1 | 12/2016 |
| WO | WO 2017/007612 A1 | 1/2017 |
| WO | WO 2017/024317 A2 | 2/2017 |
| WO | WO 2017/024318 A1 | 2/2017 |
| WO | WO 2017/024319 A1 | 2/2017 |
| WO | WO 2017/176708 A1 | 10/2017 |
| WO | WO 2017/176957 A1 | 10/2017 |
| WO | WO 2017/176958 A1 | 10/2017 |
| WO | WO 2017/180417 A1 | 10/2017 |
| WO | WO 2017/197240 A1 | 11/2017 |
| WO | WO 2017/201069 A1 | 11/2017 |
| WO | WO 2017/201449 A1 | 11/2017 |
| WO | WO 2018/023029 A1 | 2/2018 |
| WO | WO 2018/051107 A1 | 3/2018 |
| WO | WO 2018/052945 A1 | 3/2018 |
| WO | WO 2018/052949 A1 | 3/2018 |
| WO | WO 2018/053354 A1 | 3/2018 |
| WO | WO 2018/071606 A1 | 4/2018 |
| WO | WO 2018/085247 A1 | 5/2018 |
| WO | WO 2018/102067 A2 | 6/2018 |
| WO | WO 2018/102725 A1 | 6/2018 |
| WO | WO 2018/118598 A1 | 6/2018 |
| WO | WO 2018/118947 A1 | 6/2018 |
| WO | WO 2018/119357 A1 | 6/2018 |
| WO | WO 2018/119441 A1 | 6/2018 |
| WO | WO 2018/119448 A1 | 6/2018 |
| WO | WO 2018/140809 A1 | 8/2018 |
| WO | WO 2018/144649 A1 | 8/2018 |
| WO | WO 2018/169777 A1 | 9/2018 |
| WO | WO 2018/183411 A1 | 10/2018 |
| WO | WO 2018/189554 A1 | 10/2018 |
| WO | WO 2018/191199 A1 | 10/2018 |

OTHER PUBLICATIONS

Bondeson et al. "Catalytic in vivo protein knockdown by small-molecule PROTACs" Nature Chemical Biology 2015, 11:611-617.
Burkhard et al. "Synthesis and Stability of Oxetane Analogs of Thalidomide and Lenalidomide" Organic Letters 2013, 15(7):4312-4315.
Chamberlain et al. "Structure of the human cereblon-DDB1-lenalidomide complex reveals basis for responsiveness to thalidomide analogs" Nature Structural and Molecule Biology, 2014, 21(9):803-809.
Chang, X. and Stewart, K. A. "What is the functional role of the thalidomide binding protein cereblon?" Int J Biochem Mol Bio. 2011, 2(3):287-294.
Corson et al. "Design and applications of bifunctional small molecules: Why two heads are better than one" ACS Chemical Biology 2008, 3(11): 677-692.
Crew, C. M. "Targeting the undruggable proteome: the small molecules of my dreams" Chemistry and Biology 2010, 17(6):551-555.
Deshaies et al. "Ring domain E3 ubiquitin ligases." Ann. Rev. Biochem. 2009, 78:399-434.
Faden et al. "Generic tools for conditionally altering protein abundance and phenotypes on demain" Biol. Chem. 2014, 395(7-8):737-762.
Fischer et al. "Structure of the DDB1-CRBN E3 ubiquitin ligase in complex with thalidomide" Nature 2014, 512:49-53.
Fischer et al. "The Molecular Basis of CRL4DDB2/CSA Ubiquitin Ligase Architecture, Targeting, and Activation," Cell 2011, 147:1024-1039.
Gosink et al. "Redirecting the Specificity of Ubiquitination by Modifying Ubiquitin-Conjugating Enzymes" Proc. Natl. Acad. Sci. USA 1995, 92:9117-9121.
Gustafson et al. "Small-Molecule-Mediated Degradation of the Androgen Receptor through Hydrophobic Tagging" Angewandte Chemie 2015, 54:9659-9662.
Hines et al. "Posttranslational protein knockdown couple to receptor tyrosine kinase activation with phosphoPROTACs" PNAS 2013, 110(22):8942-8947.
International Search Report and Written Opinion for PCT/US17/32051 dated Sep. 28, 2017.
Ito et al. "Identification of a Primary Target of Thalidomide Teratogenicity" Science 2010, 327(5971):1345-1350.
Itoh et al. "Protein knockdown using methyl bestatin-ligand hybrid molecules: design and synthesis of inducers of ubiquitination-mediated degradation of cellular retinoic acid-binding proteins" Journal of the American Chemical Society 2010, 132(16):5820-5826.
Jacques et al. "Differentiation of antiinflammatory and antitumorigenic properties of stabilized enantiomers of thalidomide analogs" PNAS 2015, 112:E1471-E1479.
Kronke et al. "Lenalidomide induces ubiquitination and degradation of CDK1[alpha] in del(5q) MDS" Nature 2015, 523(7559):183-188.
Kronke et al. "Lenalidomide Causes Selective Degradation of IKZF1 and IKZF3 in Multiple Myeloma Cells" Science 2014, 343(6168):301-305.
Lai et al. "Modular PROTAC Design for the Degradation of Oncogenic BCR-ABL" Angewandte Chemie International Edition 2016, 55:807-810.
Lee et al. "Targeted Degradation of the Aryl Hydrocarbon Receptor by the PROTAC Approach: A Useful Chemical Genetic Tool" ChemBioChem 2007, 8:2058-2062.
Li et al. "Genome-wide and functional annotation of human E3 ubiquitin ligases identifies MULAN, a mitochondrial E3 that regulates the organelle's dynamics and signaling" PLOS One 2008, 3:1487.
Liu et al. "Design and biological characterization of hybrid compounds of curcumin and thalidomide for multiple myeloma" Organic and Biomolecular Chemistry 2013, 11:4757.
Lu et al. "The myeloma drug lenalidomide promotes the cereblon-dependent destruction of Ikaros proteins" Science 2014, 343:305-309.
Lu et al. "Hijacking the E3 Ubiquitin Ligase Cereblon to Efficiently Target BRD4" Chemistry and Biology 2015, 22(6):755-763.
Nawaz et al. "Proteasome-Dependent Degradation of the Human Estrogen Receptor" Proc. Natl. Acad. Sci. USA 1999, 96:1858-1862.
Neklesa et al. "Small-molecule hydrophobic tagging-induced degradation of HaloTag fusion proteins." Nat Chem Biol 2011, 7(8):538-543.
Raina et al. "Chemical Inducers of Targeted Protein Degradation" Journal of Biological Chemistry 2010, 285:11057-11060.
Rodriguez-Gonzalez et al. "Targeting steroid hormone receptors for ubiquitination and degradation in breast and prostate cancer" Oncogene 2008, 27:7201-7211.
Ruchelman et al. "Isosteric analogs of lenalidomide and pomalidomide: Synthesis and biological activity" Bioorganic and Medicinal Chemistry Letters 2012, 23:360-365.

(56) References Cited

OTHER PUBLICATIONS

Sakamoto et al. "Protacs: chimeric molecules that target proteins to the Skpl-Cullin-F box complex for ubiquitination and degradation" PNAS 2001, 98(15):8554-8559.

Sakamoto et al. "Development of Protacs to Target Cancer-Promoting Proteins for Ubiquitination and Degradation" Molecular and Cellular Proteomics 2003, 2(12):1350-1357.

Schneekloth et al. "Targeted Intracellular Protein Degradation Induced by a Small Molecule: En Route to Chemical Proteomics" Bioorganic and Medicinal Chemisty Letters 2008, 18:5904-5908.

Schneekloth et al. "Chemical approaches to controlling intracellular protein degradation" Chembiochem 2005, 6(1):40-46.

Schneekloth et al. "Chemical Genetic Control of Protein Levels: Selective in Vivo Targeted Degradation" Journal of the American Chemical Society 2004, 126(12):3748-3754.

Smith et al. "Targeted Intracellular Protein Degradation Induced by a Small Molecule: En Route to Chemical Proteomics" Bioorg. Med. Chem. Lett. 2008, 18(22):5904-5908.

Spratt et al. "RBR E3 ubiquitin ligases: new structures, new insights, new questions." Biochem. 2014, 458:421-437.

Toure et al. "Small-Molecule PROTACs: New Approaches to Protein Degradation" Angewandte Chemie International Edition 2016, 55:1966-1973.

Vassilev et al. "In Vivo Activation of the P53 Pathway by Small-Molecule Antagonists of MDM2" Science 2004, 303:844-848.

Wang et al. "Roles of F-box proteins in cancer." Nat. Rev. Cancer 2014, 14:233-347.

Winter et al. "Phthalimide conjugation as a strategy for in vivo target protein degradation" Science 2015, 348(6241):1376-1381.

Zengerle et al. "Selective Small Molecule Induced Degradation of the BET Bromodomain Protein BRD4" ACS Chem. Biol. 2015, 10:1770-1777.

Zhou et al. "Harnessng the Ubiquitination Machinery to Target the Degradation of Specific Cellular Proteins" Molecular Cell 2000, 6:751-756.

* cited by examiner

FIG. 1AAA
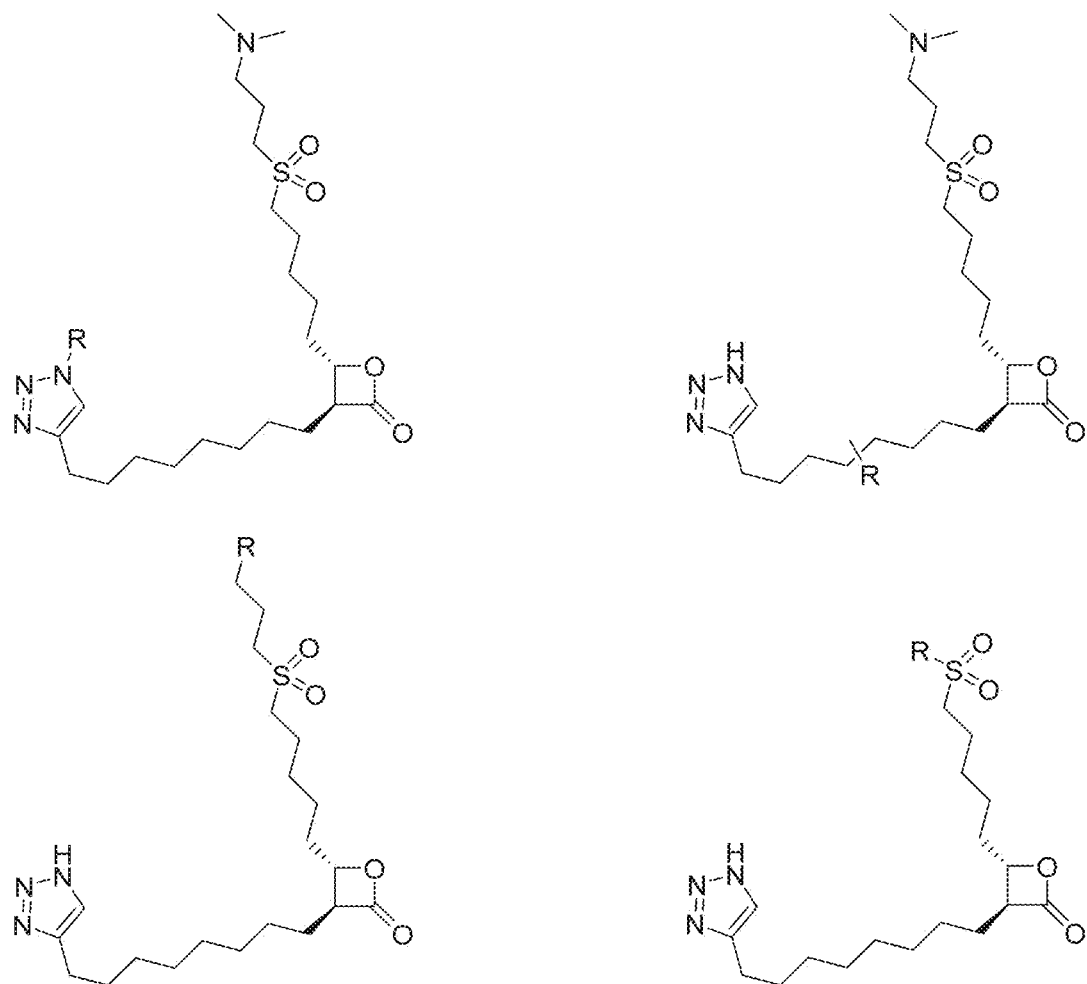
FIG. 1BBB
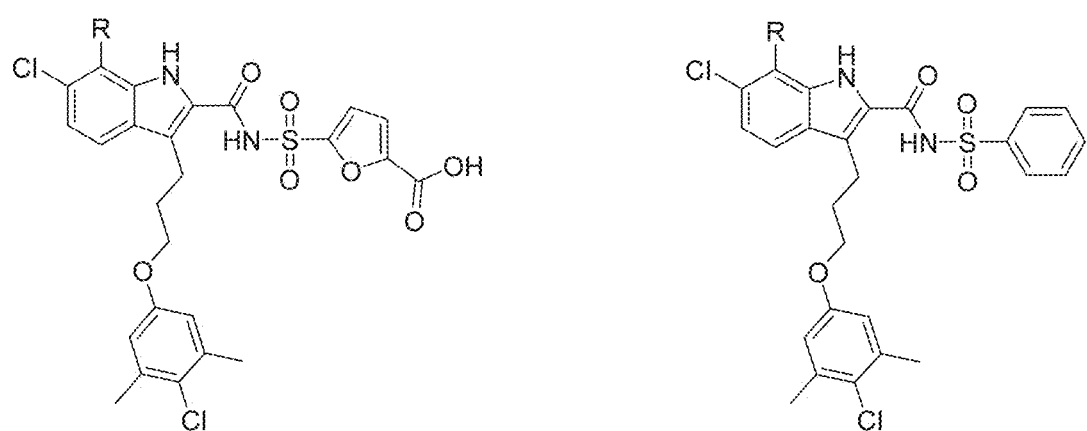

FIG. 1CCC
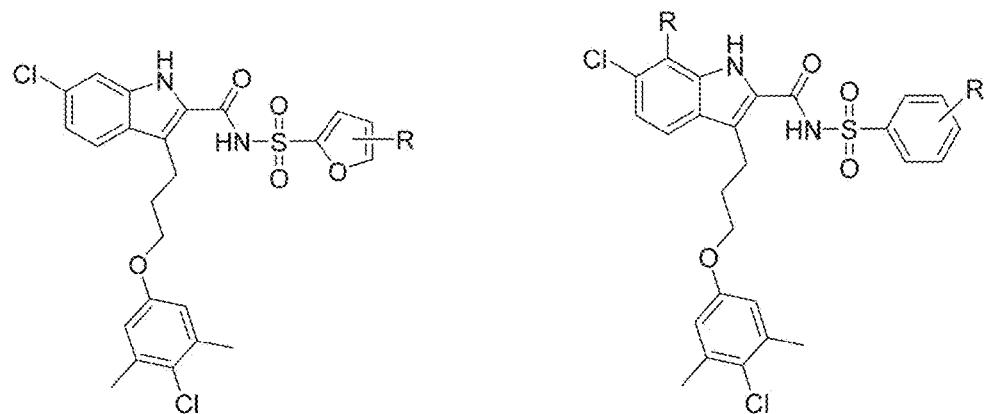
FIG. 1DDD
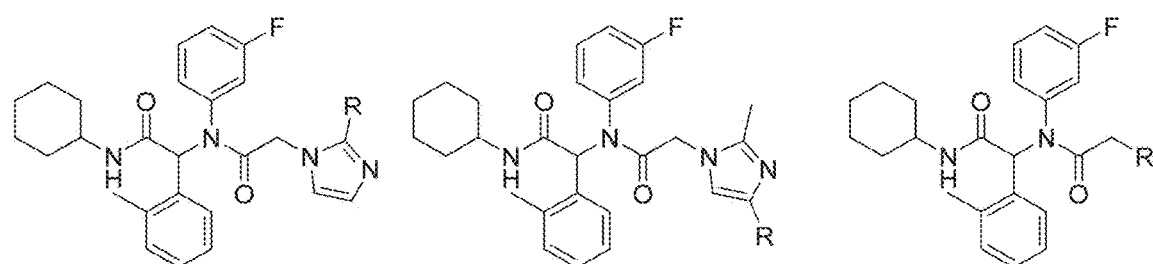
FIG. 1EEE
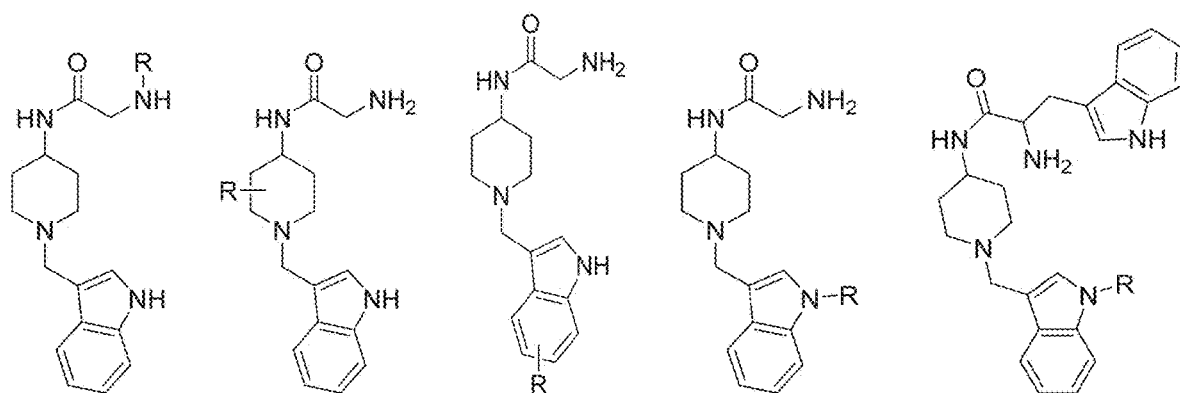

FIG. 1FFF
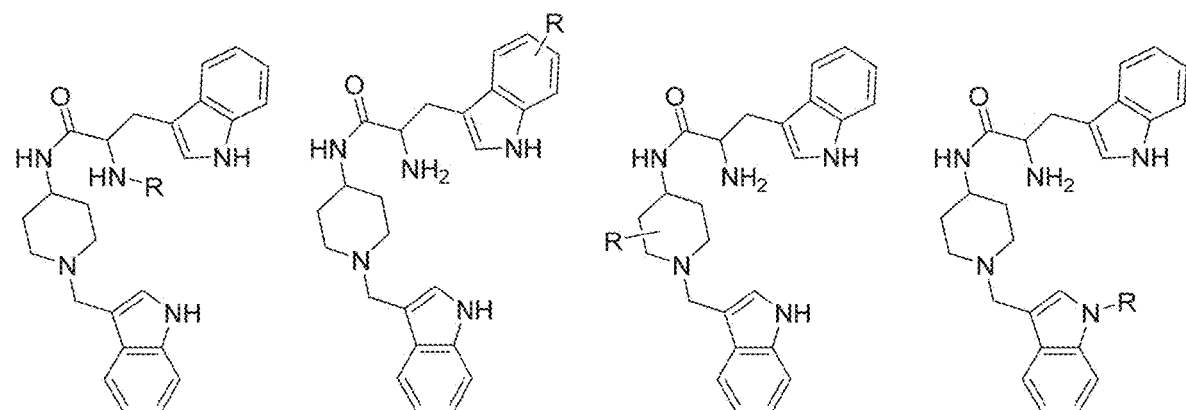
FIG. 1GGG
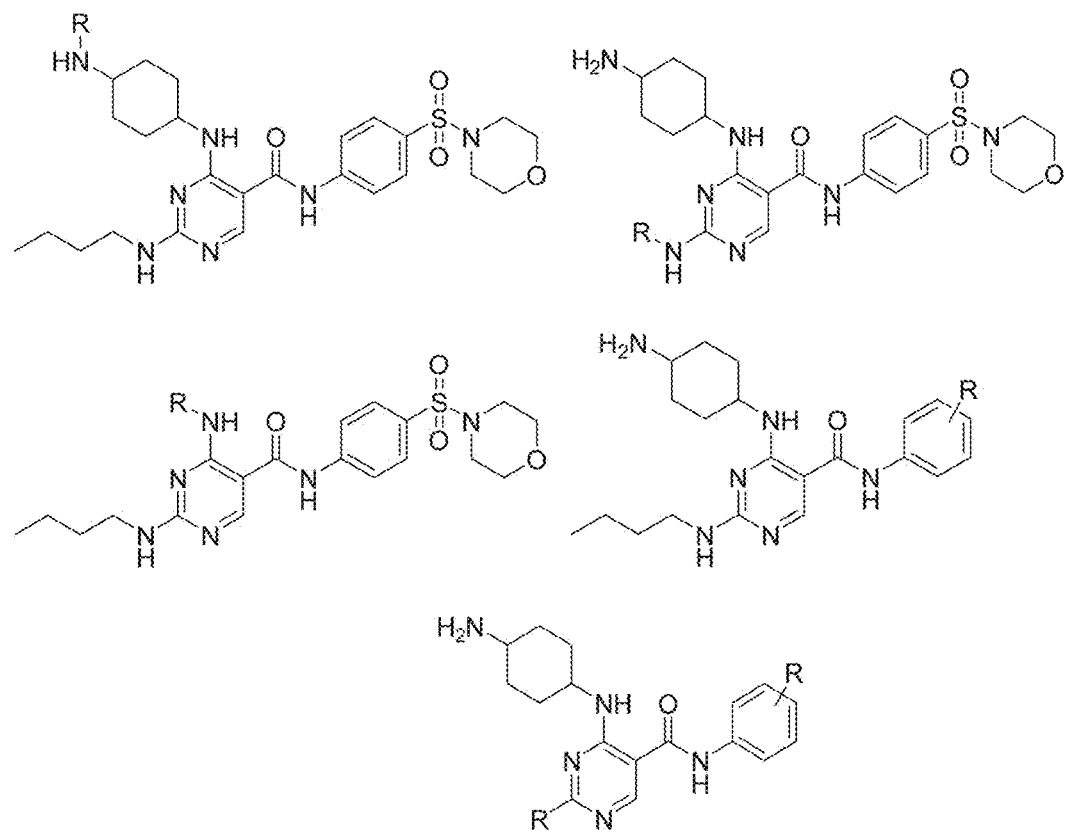

FIG. 1HHH
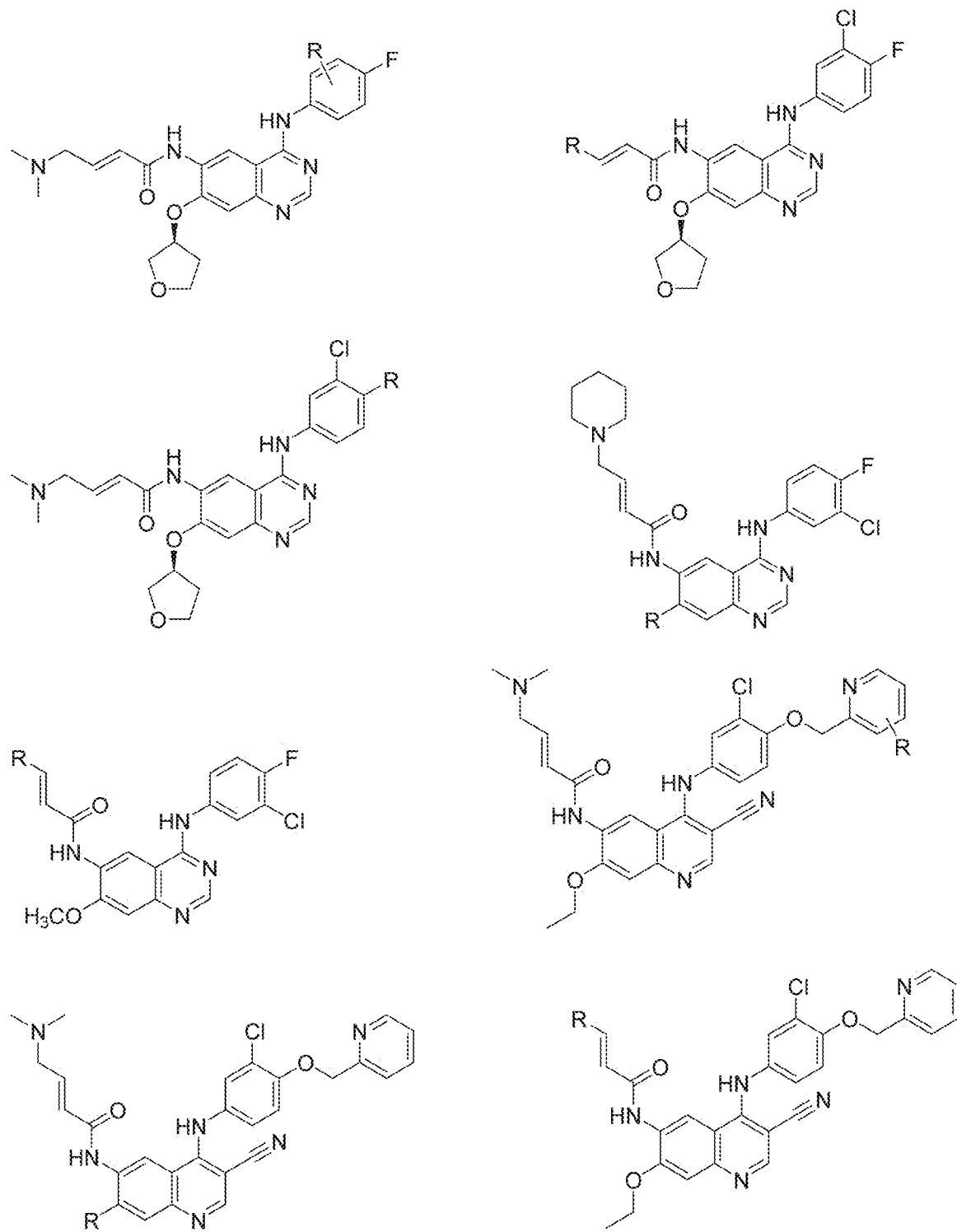

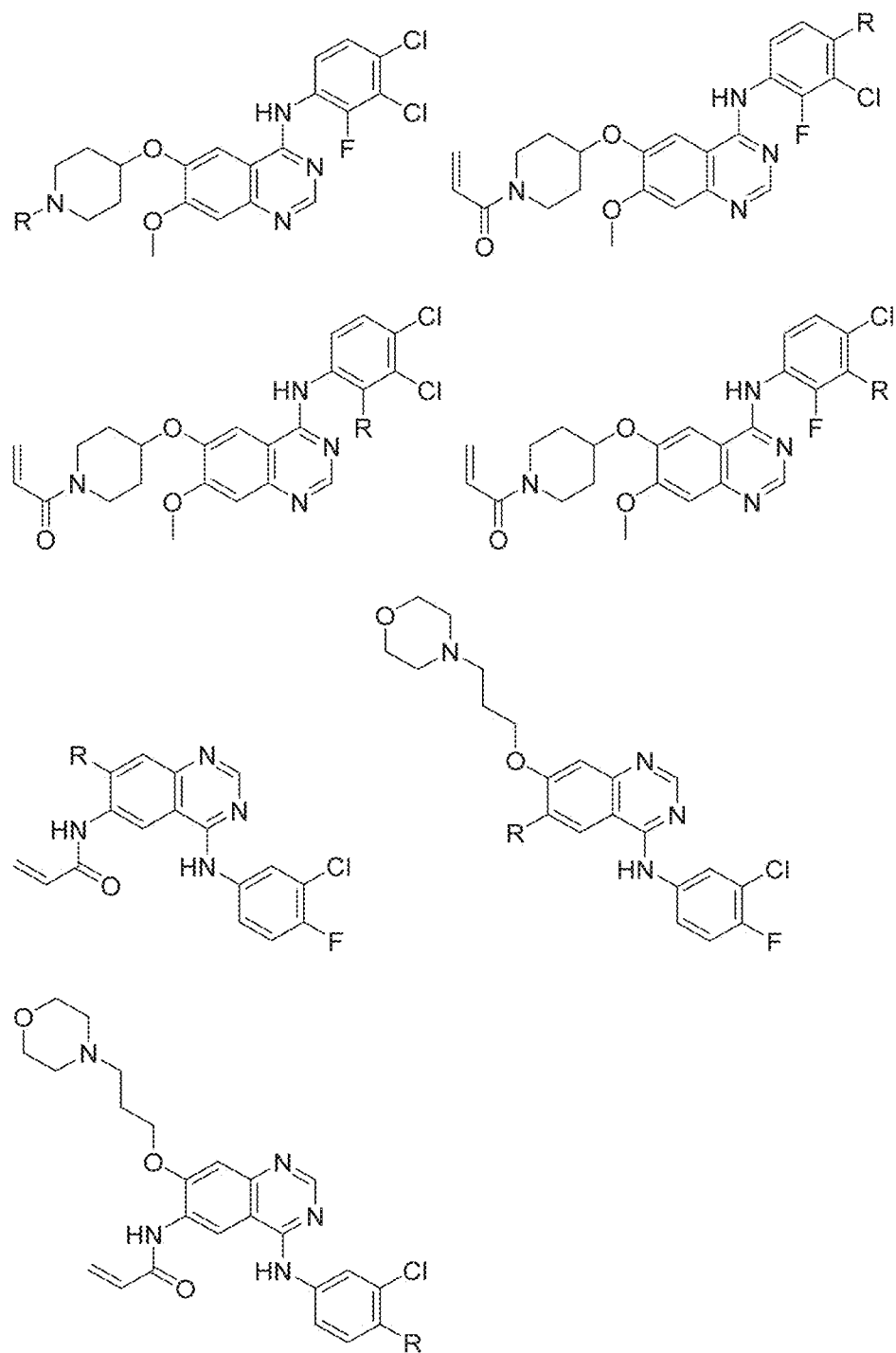
FIG. 1III

FIG. 1JJJ
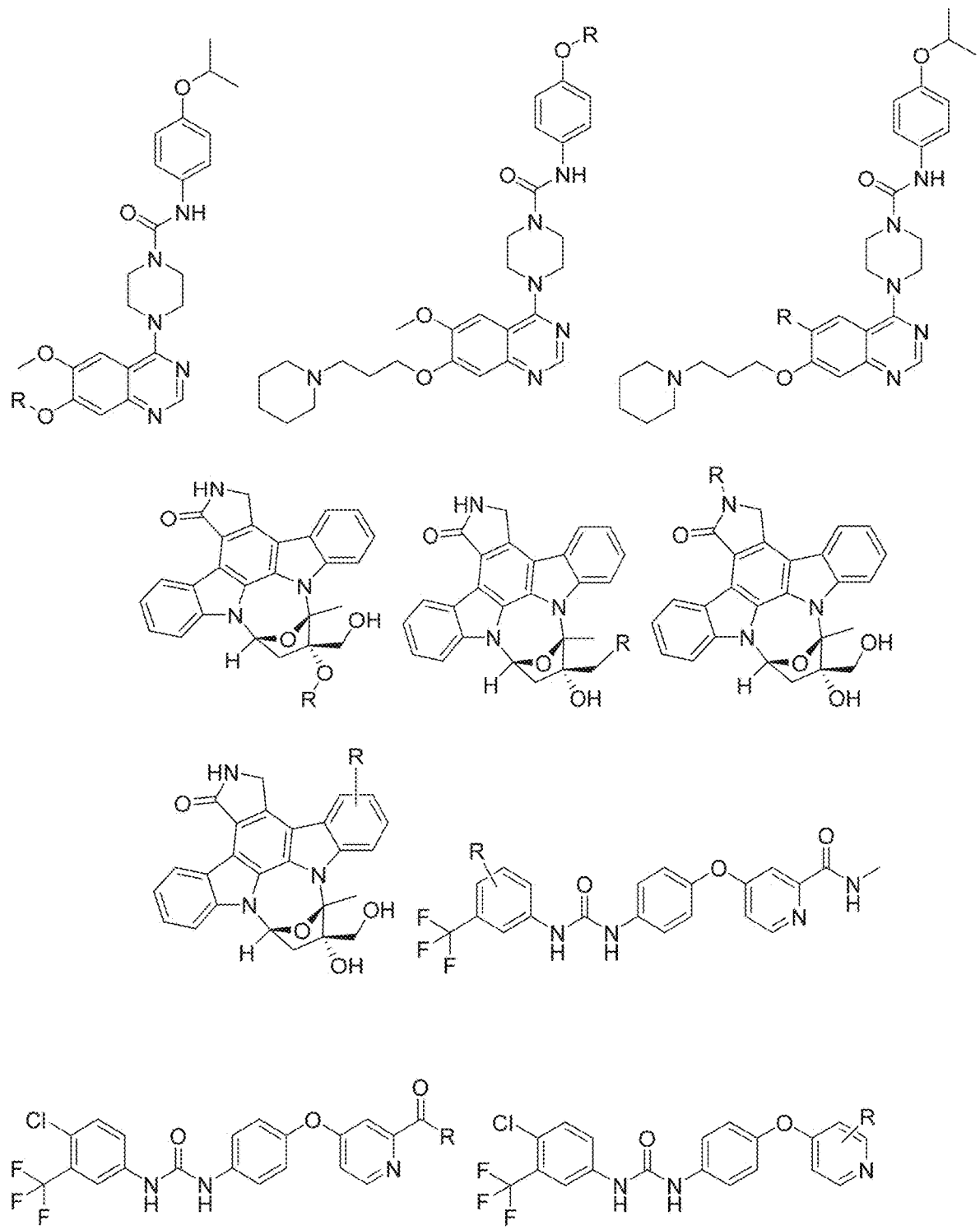

FIG. 1KKK
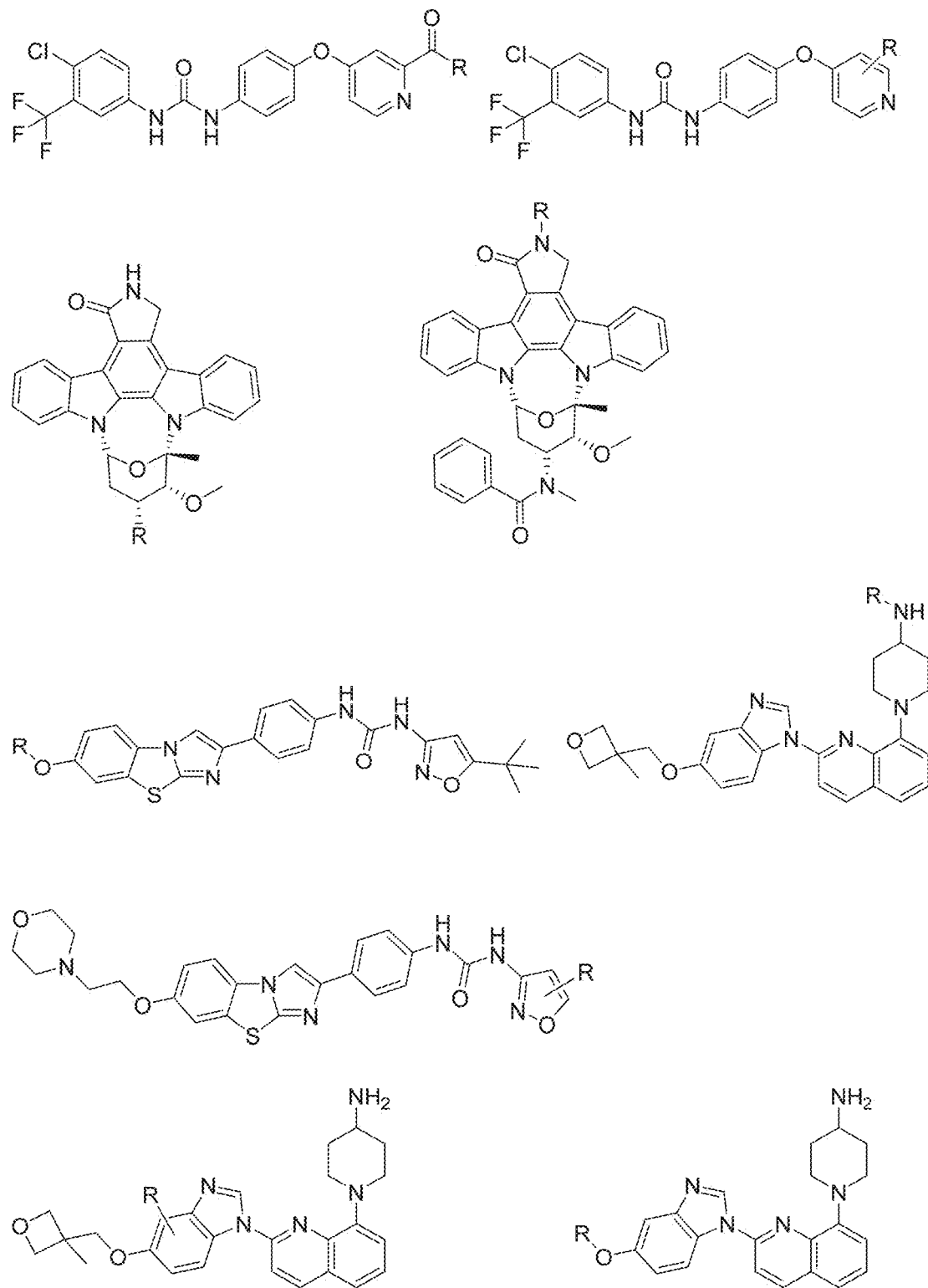

FIG. 1LLL
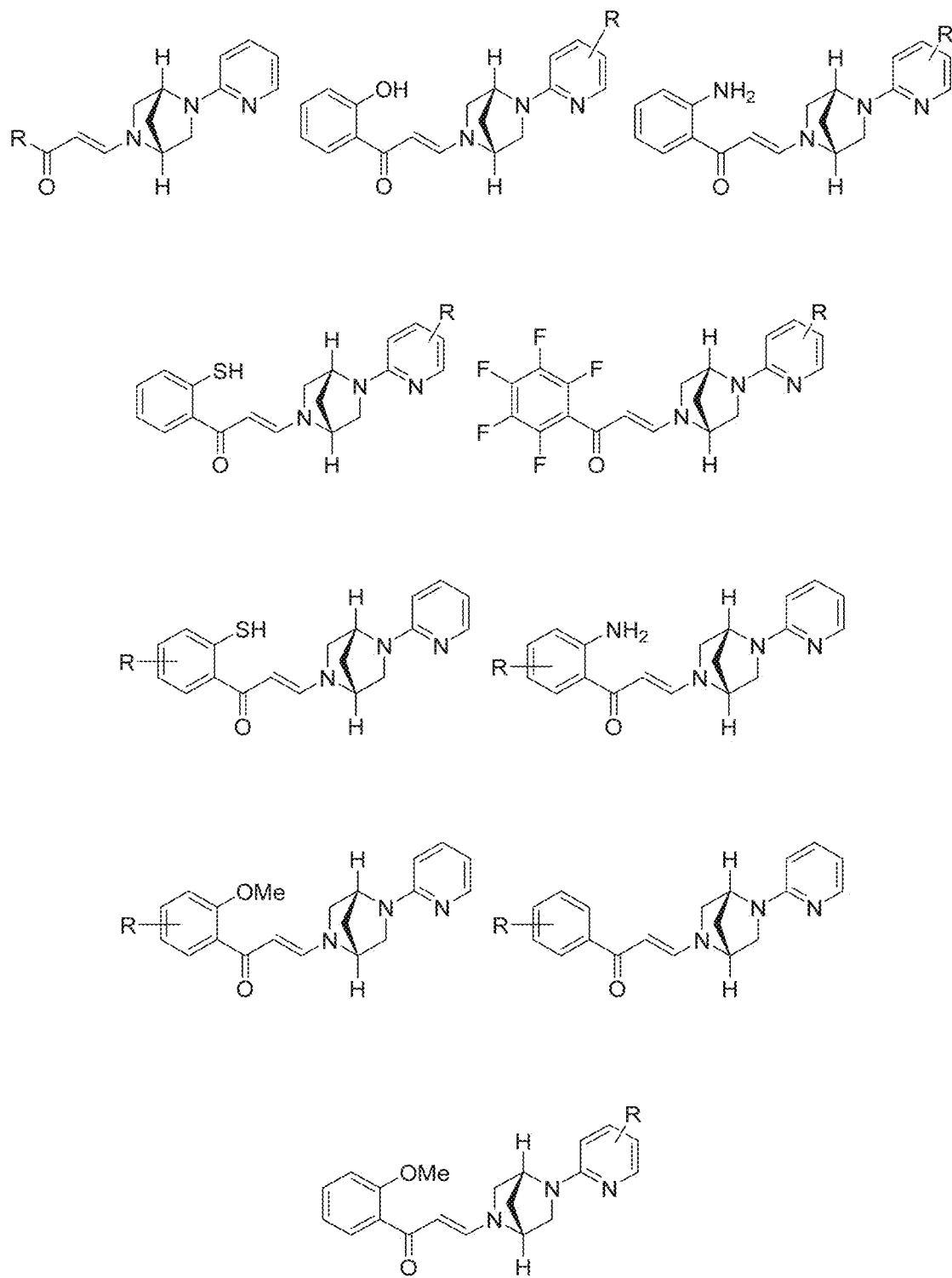

derivatized pazopanib derivatized AT-9283 derivatized TAE684 derivatized nilotanib derivatized NVP-BSK805 derivatized Crizotinib derivatized JNJ FMS derivatized Foretinib derivatized inhibitor of SHP-2 Domain of Tyrosine Phospatase

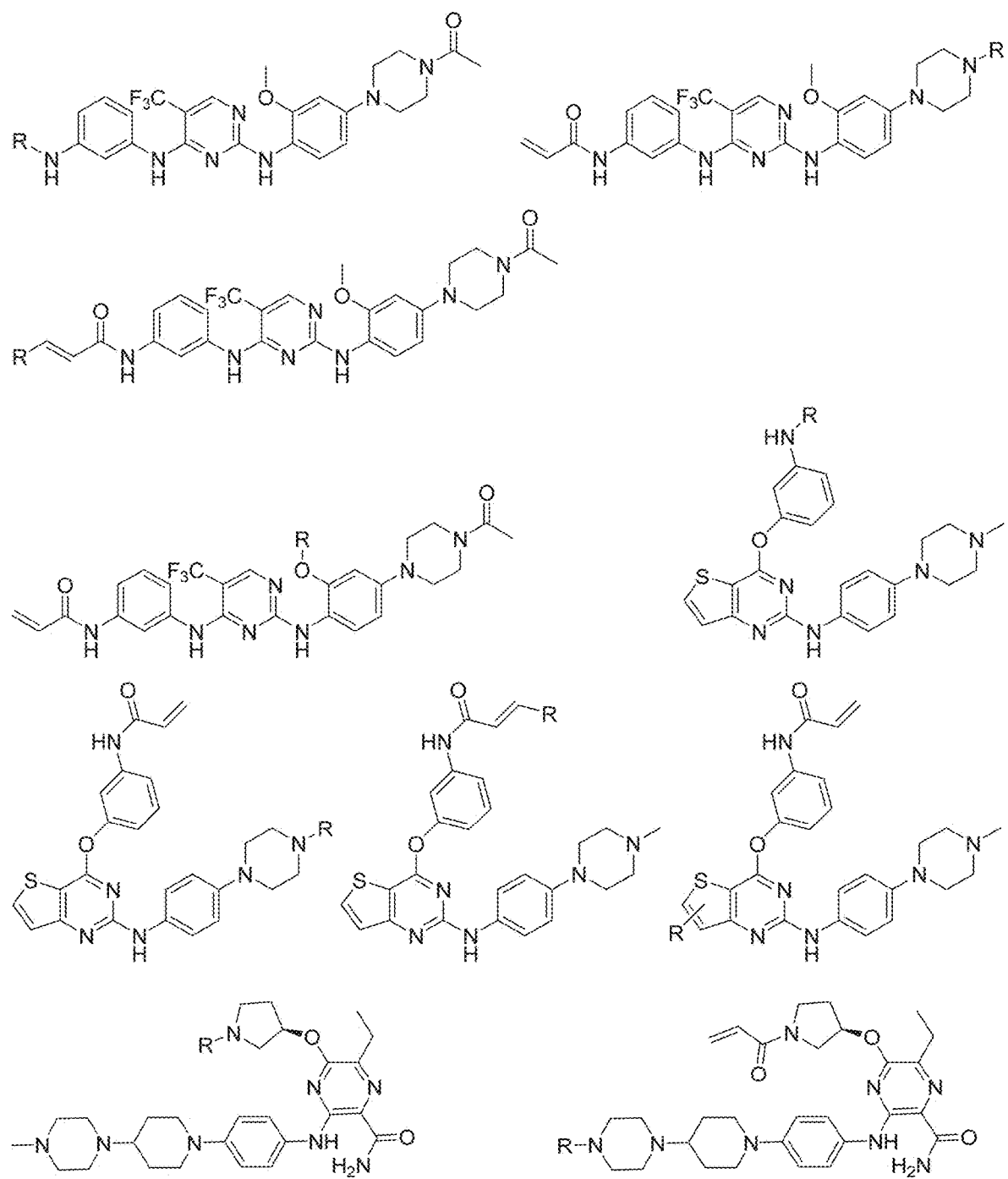
FIG. 2AAA

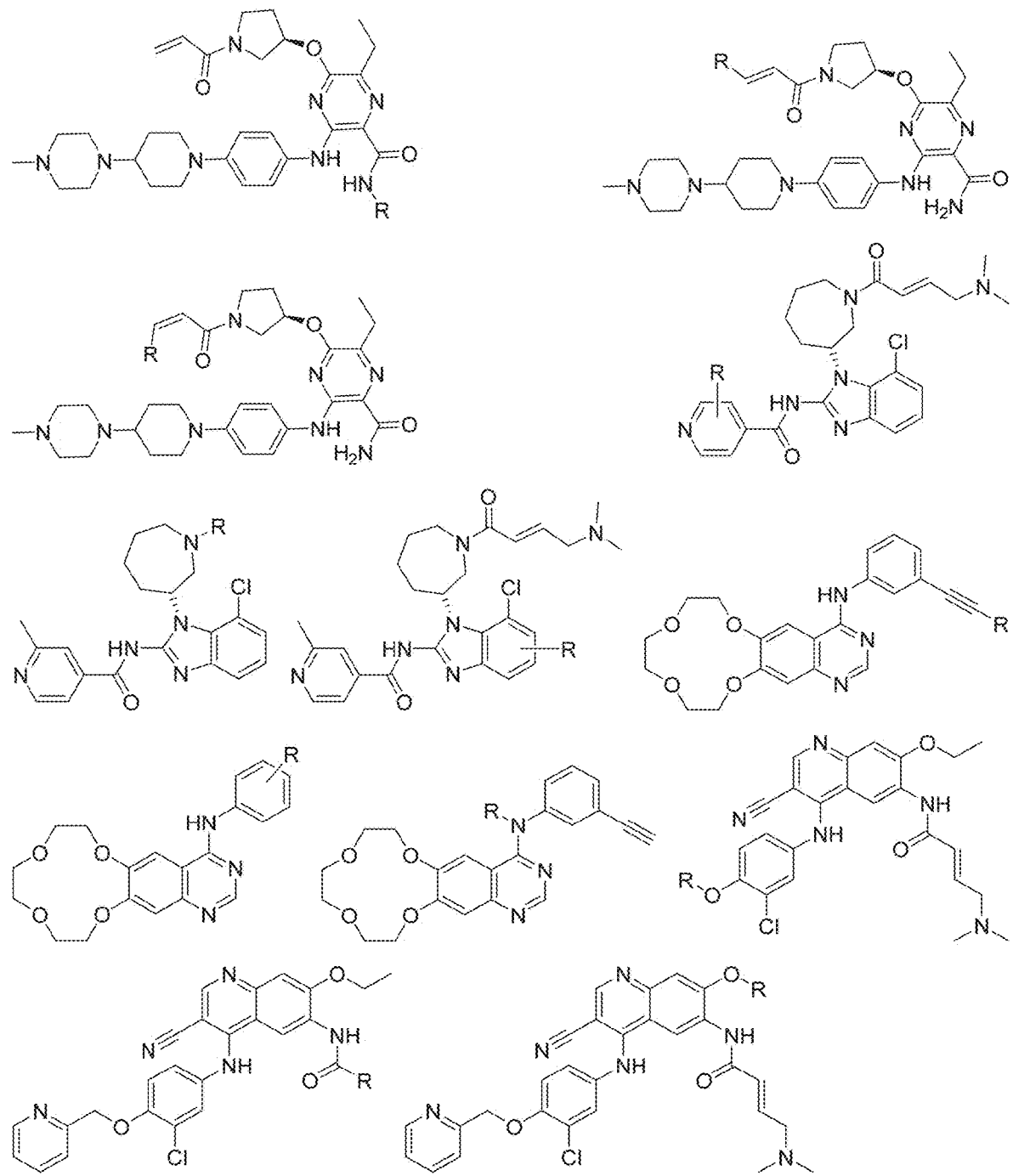
FIG. 2BBB

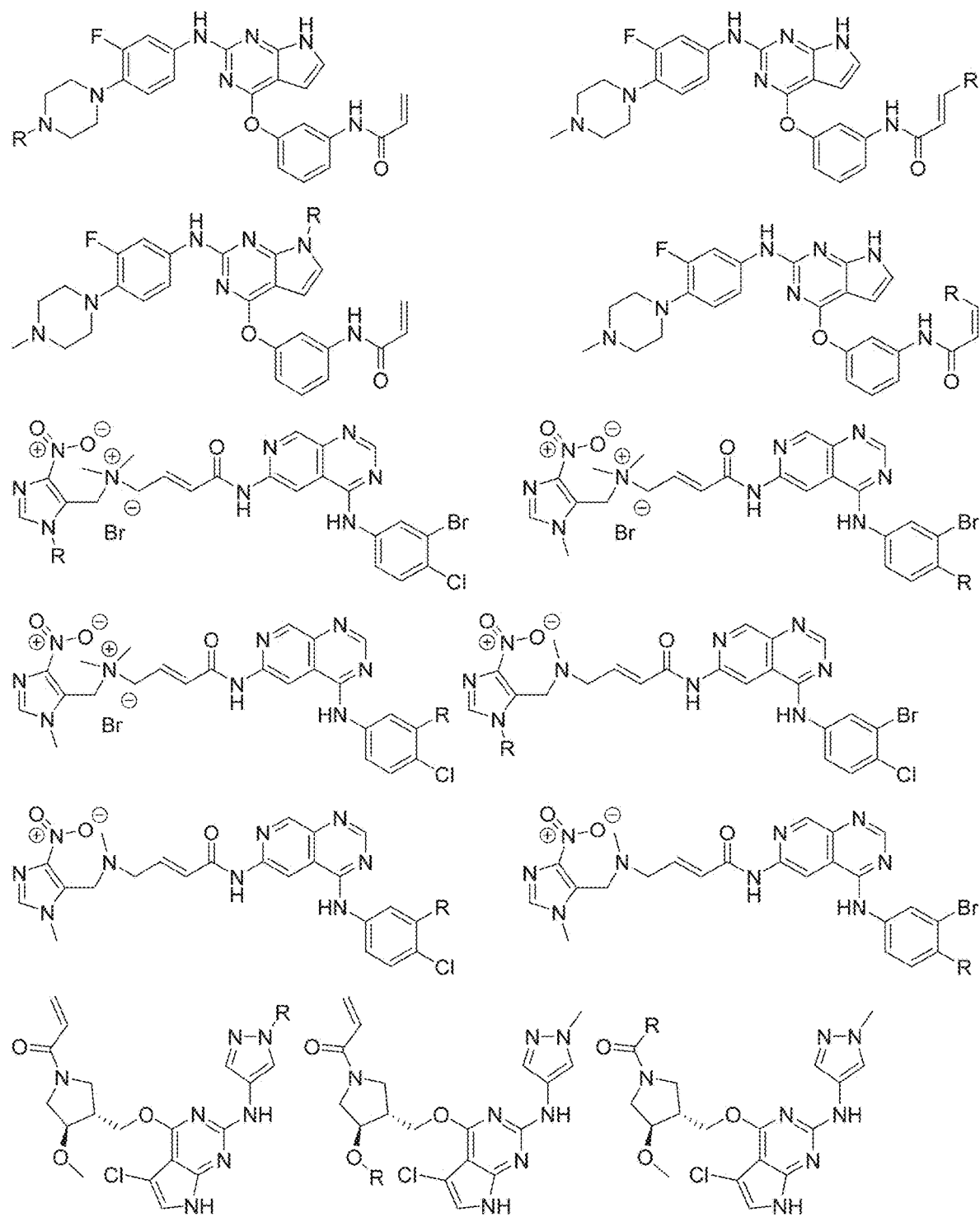
FIG. 2CCC

FIG. 2DDD
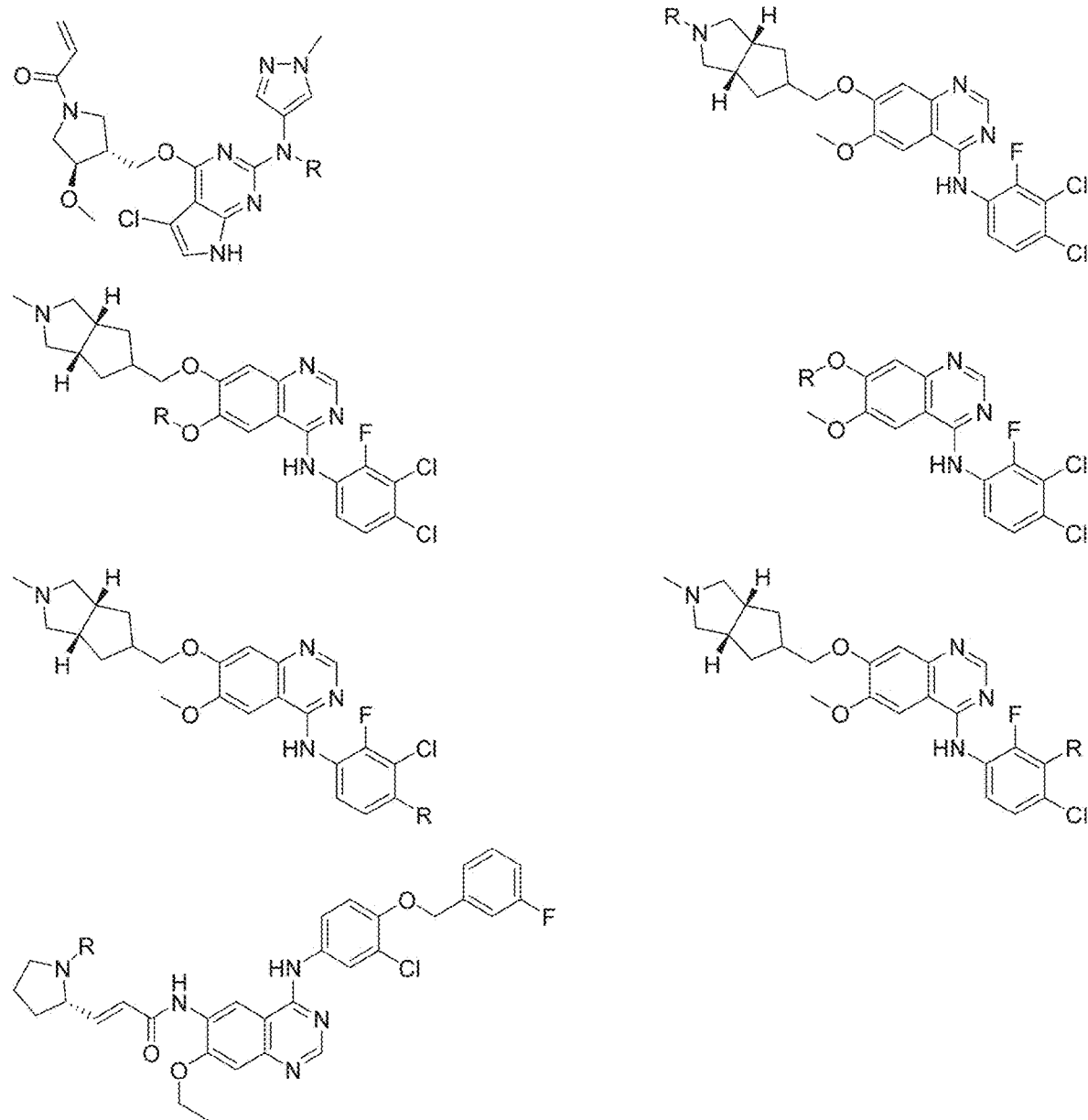

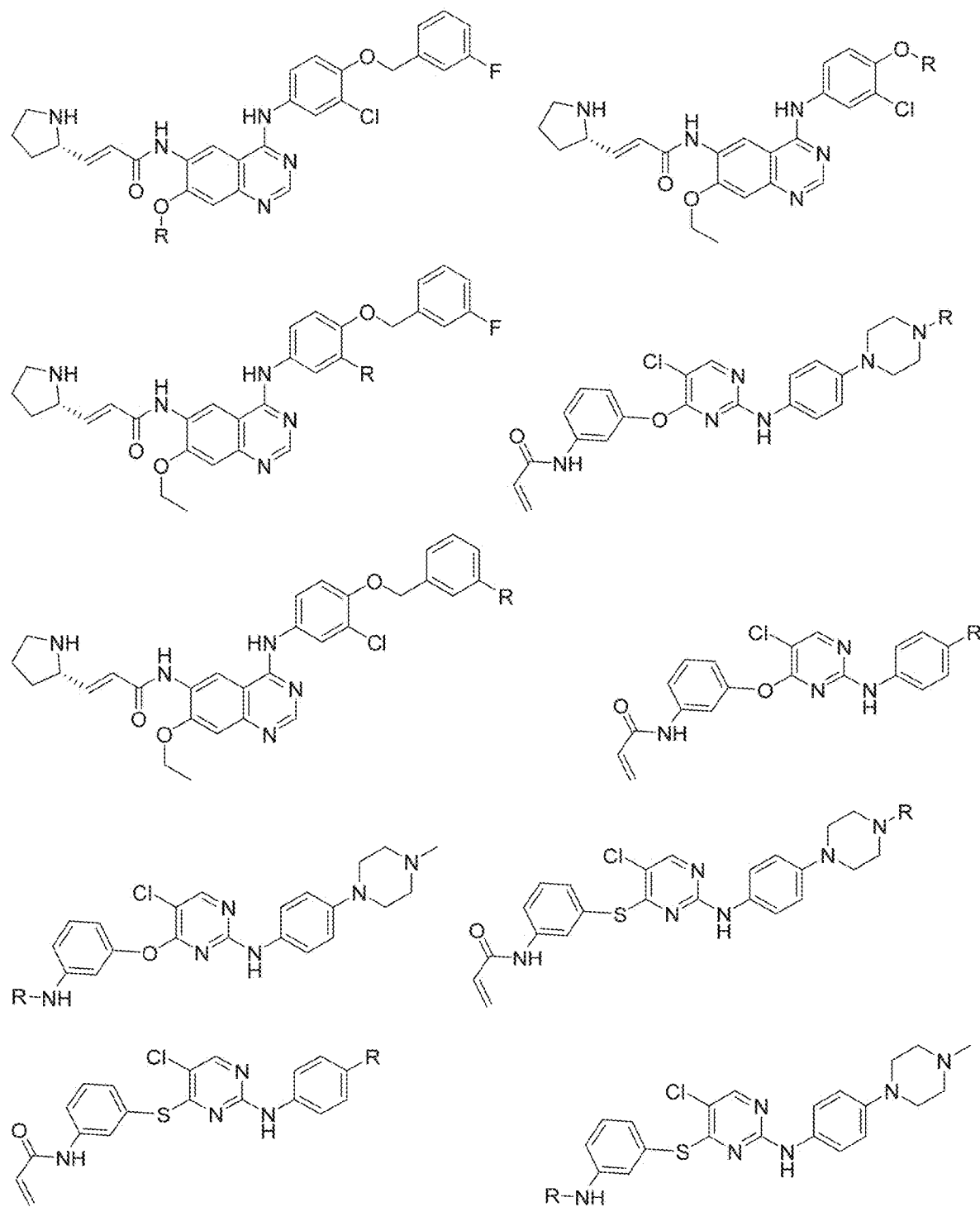
FIG. 2EEE

FIG. 2FFF
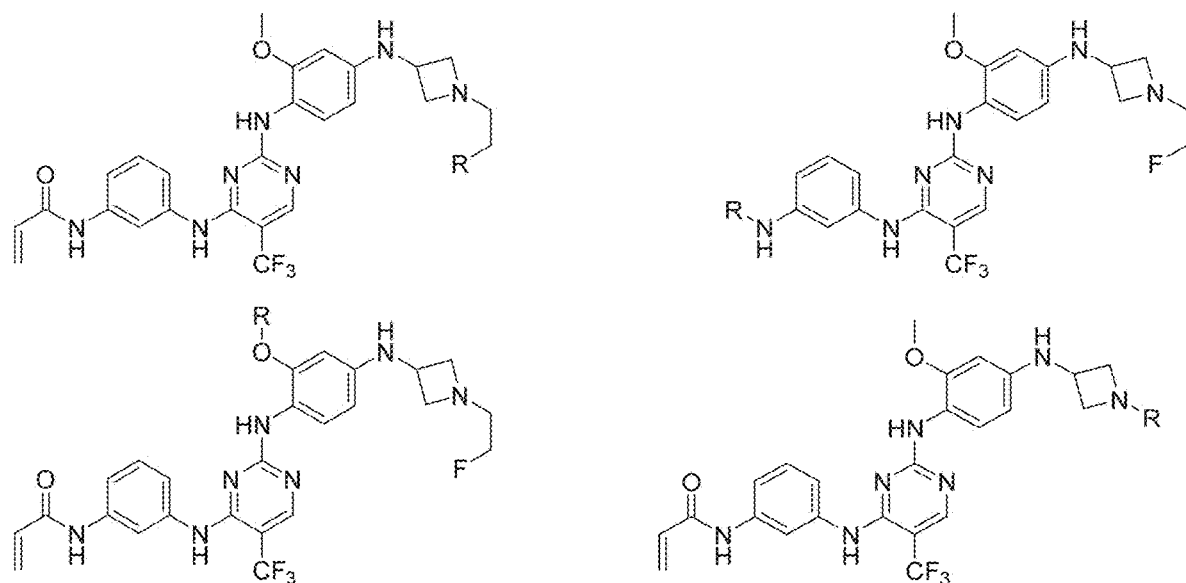
FIG. 2GGG
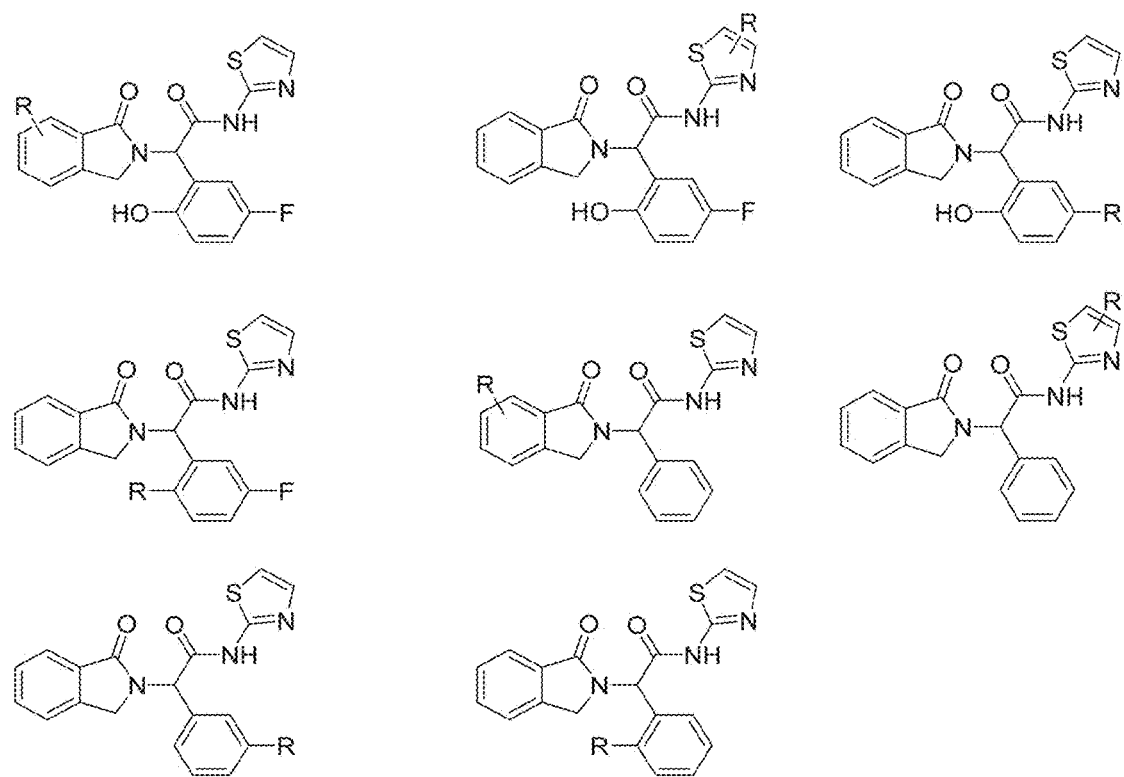

FIG. 2HHH
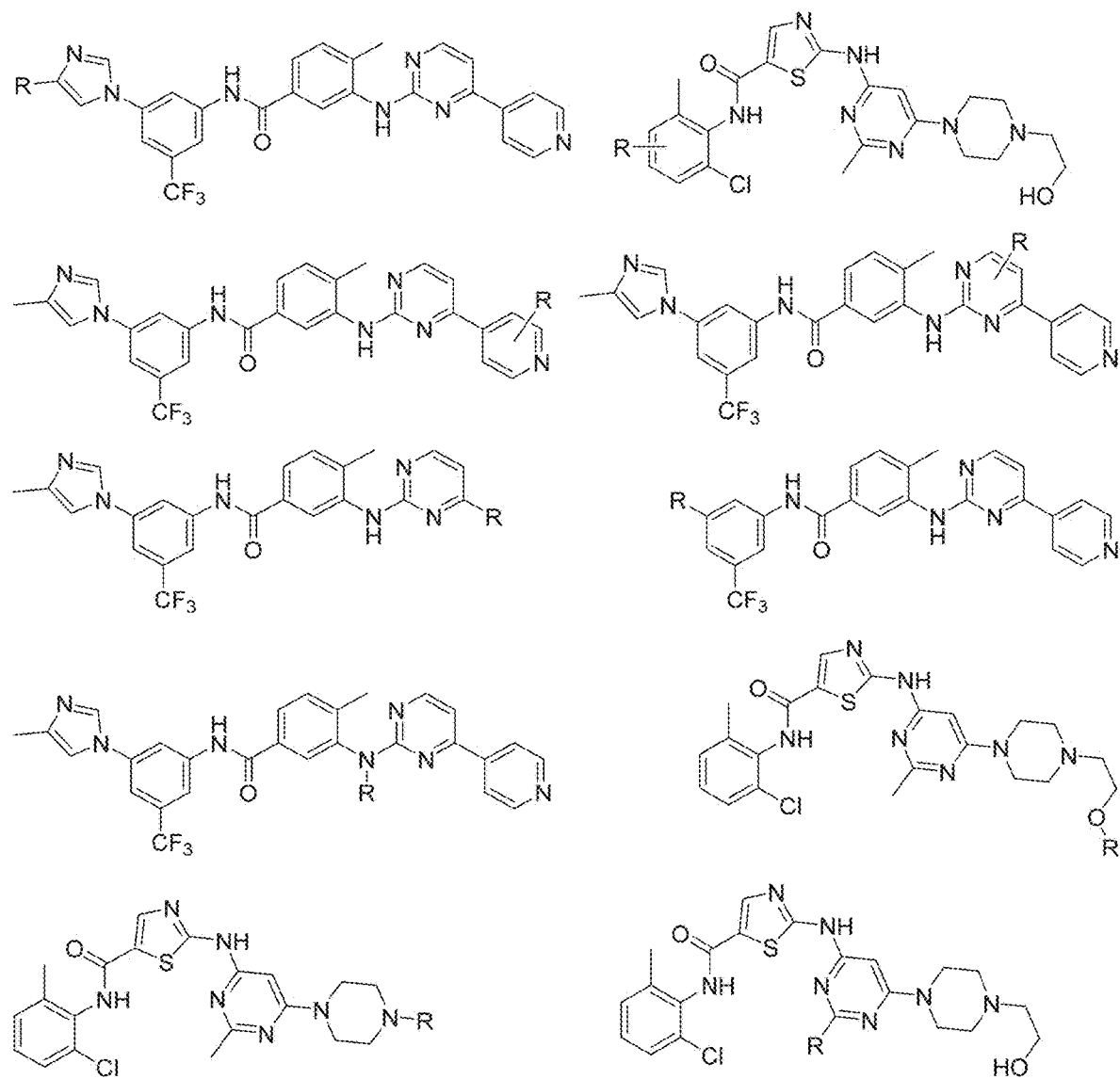

FIG. 2III
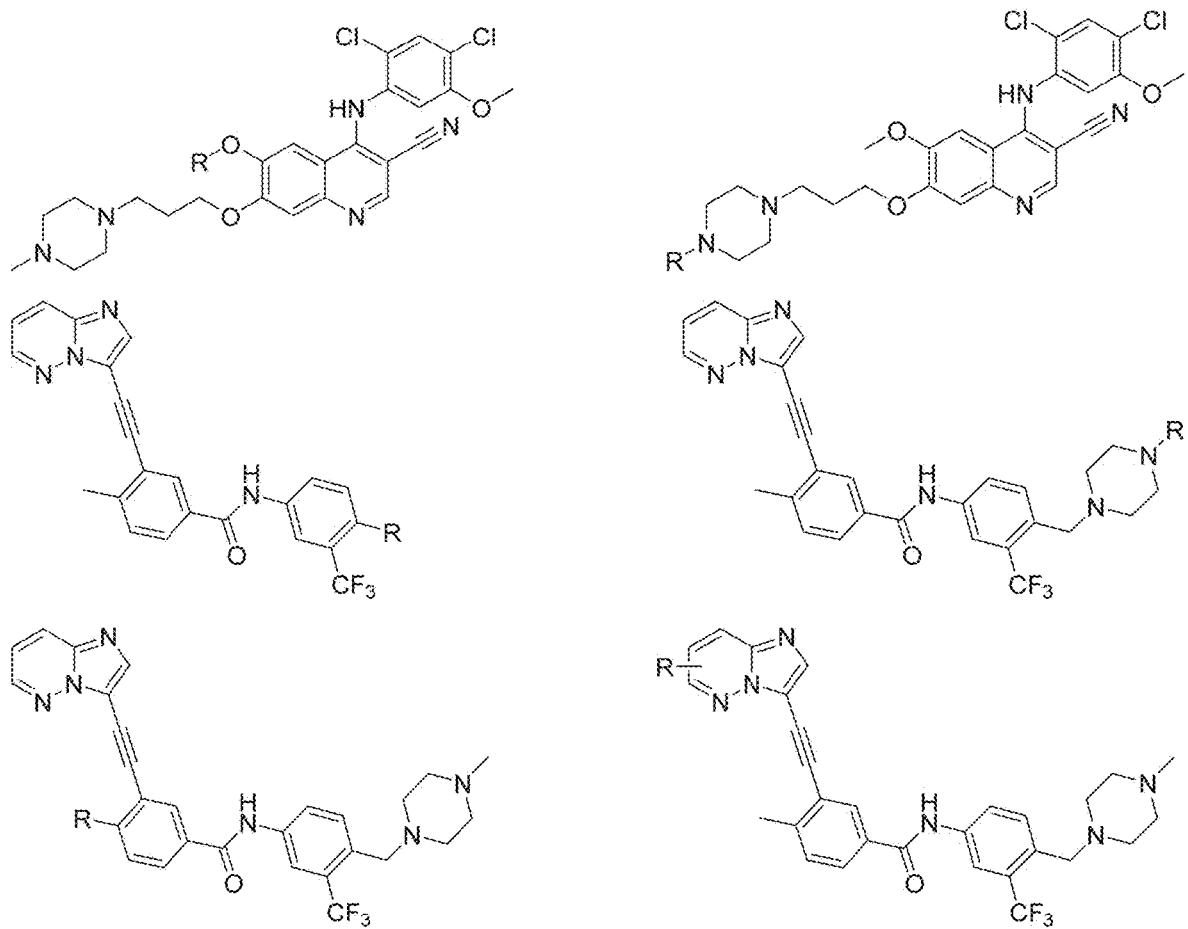
FIG. 2JJJ
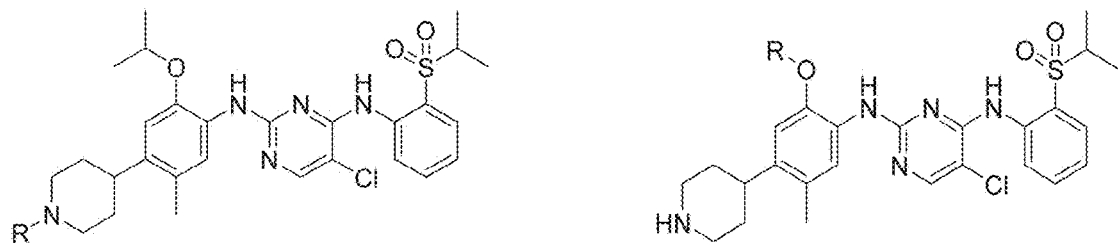

FIG. 2KKK
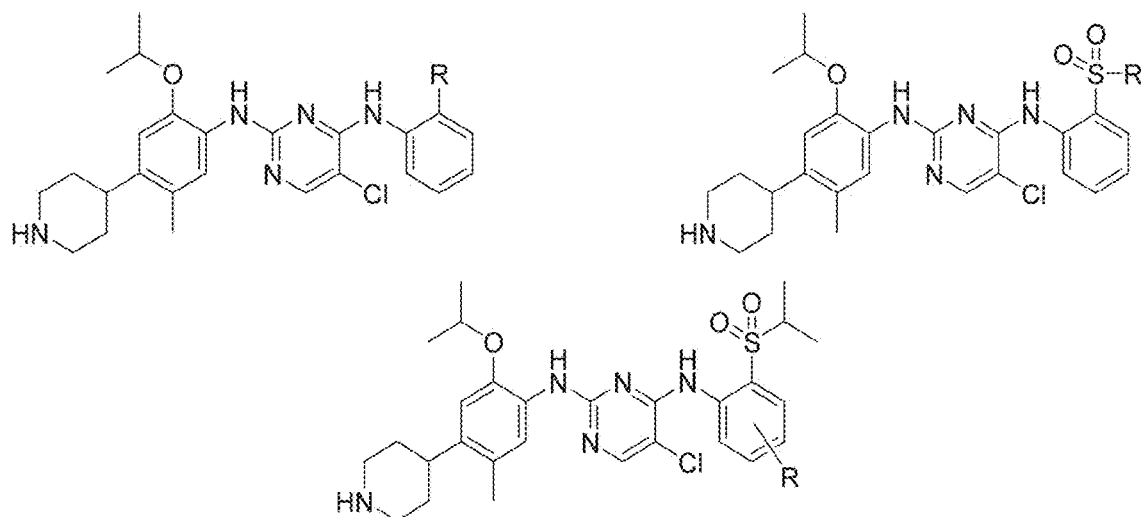
FIG. 2LLL
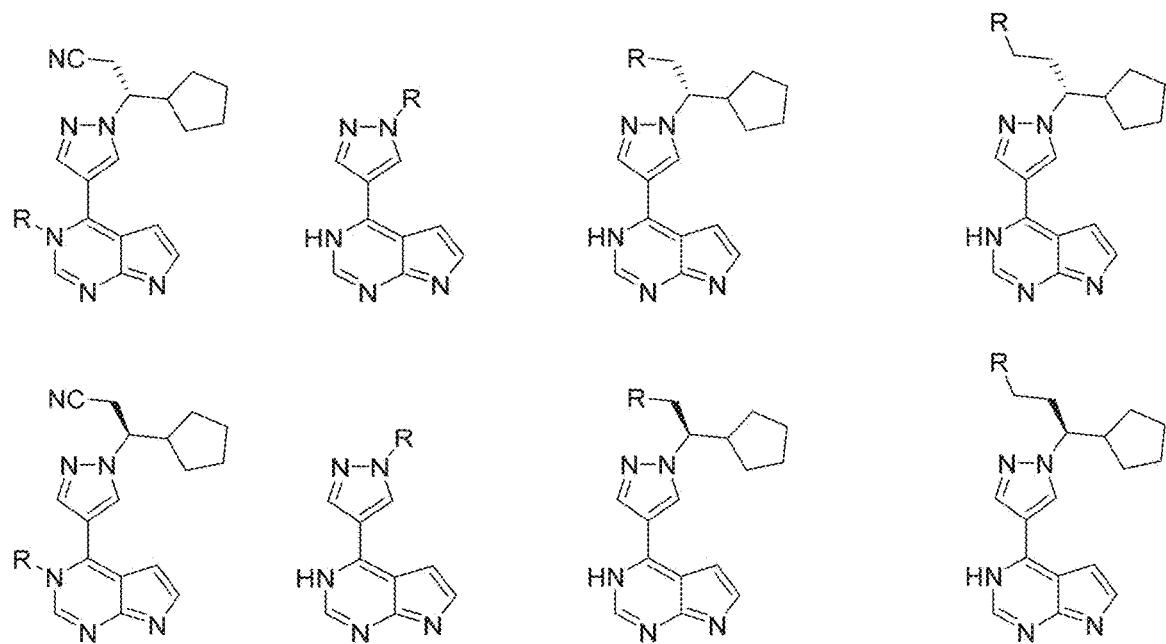

FIG. 2MMM
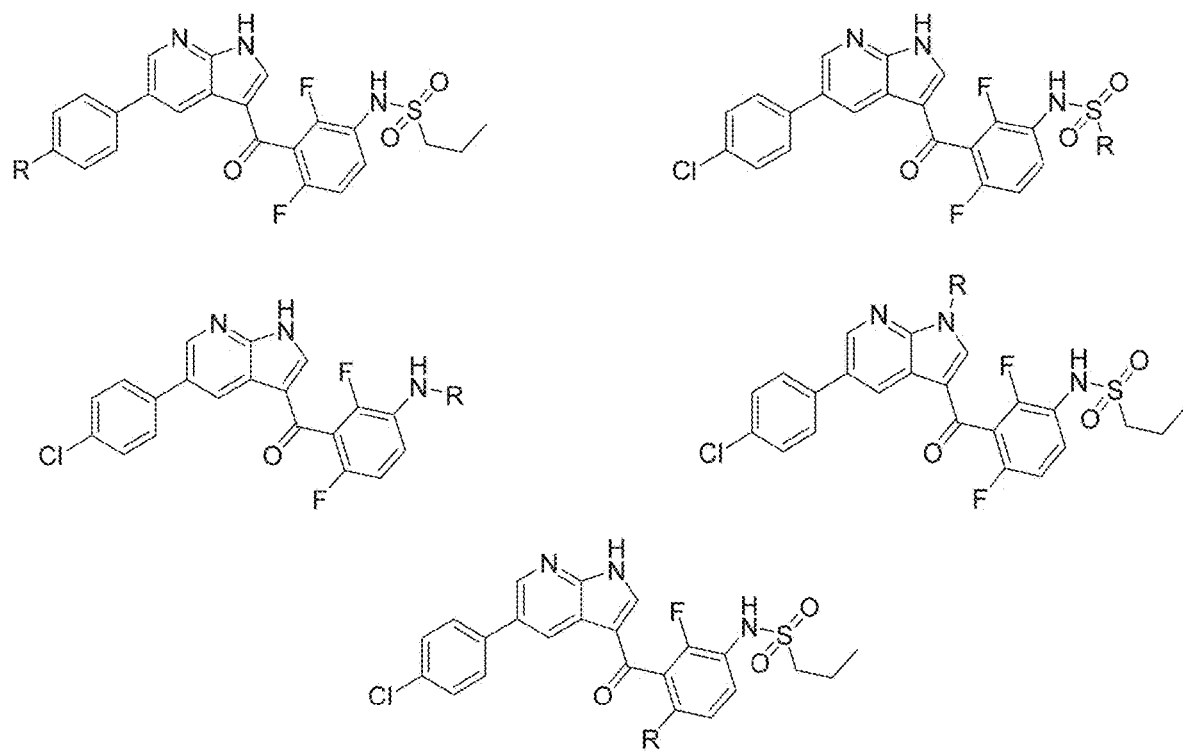
FIG. 2NNN
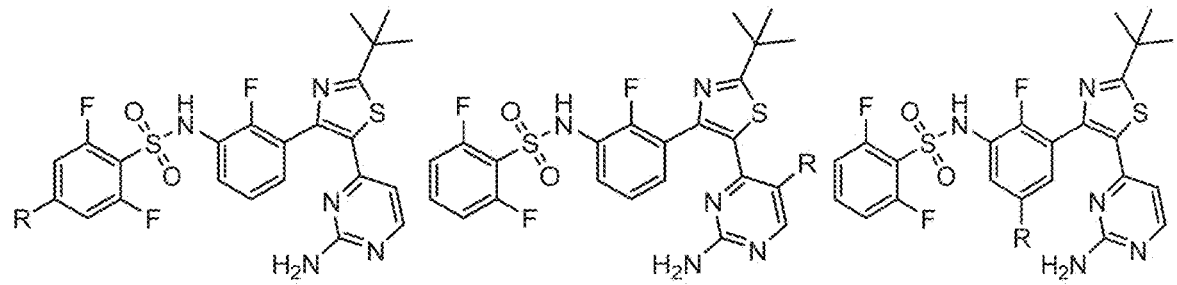

FIG. 2OOO
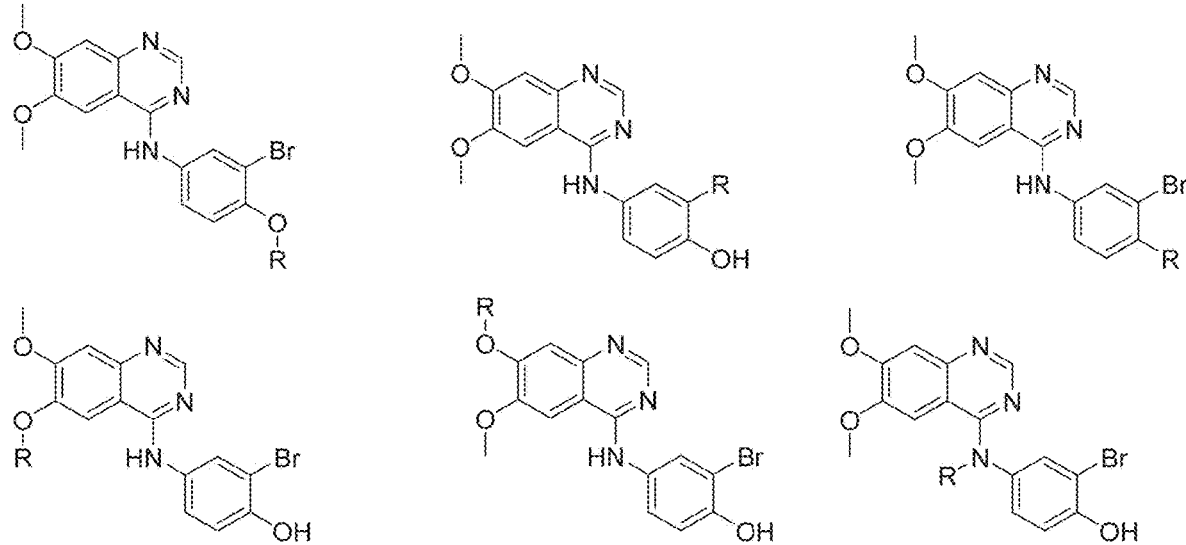
FIG. 2PPP
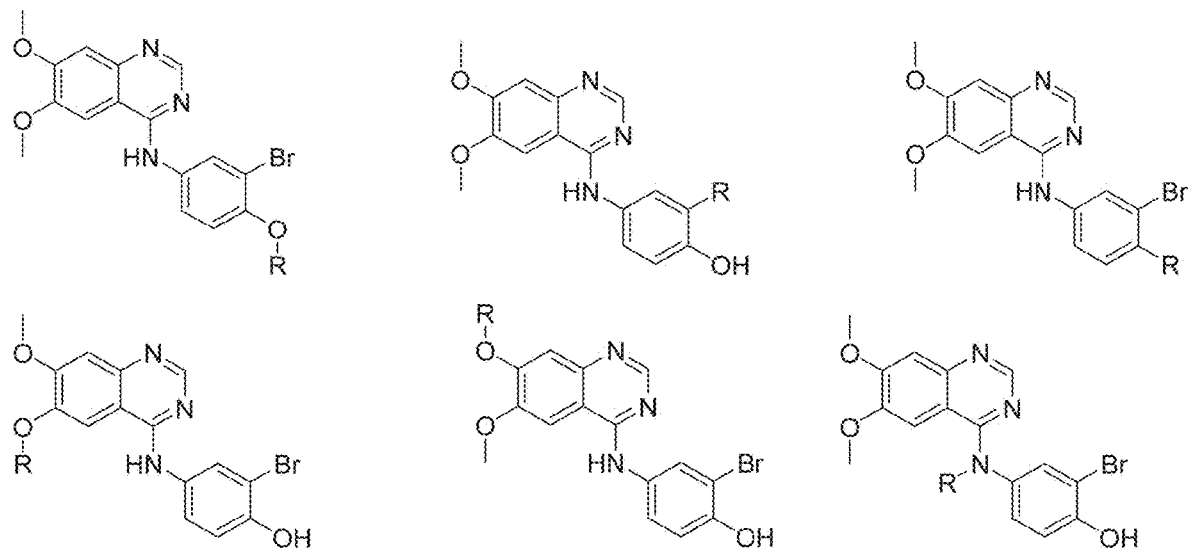

FIG. 2QQQ
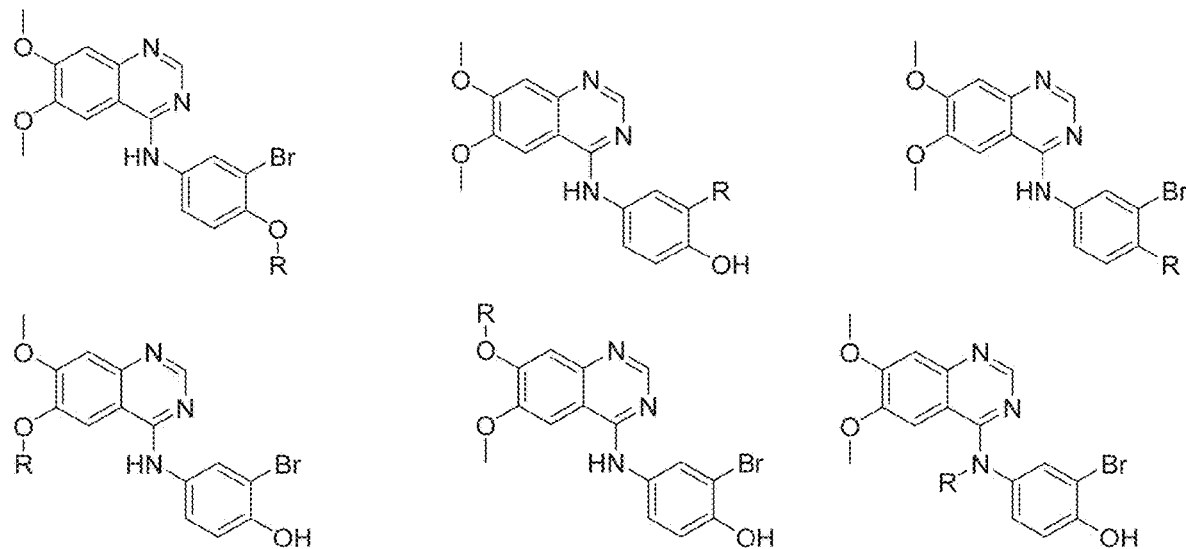
FIG. 2RRR
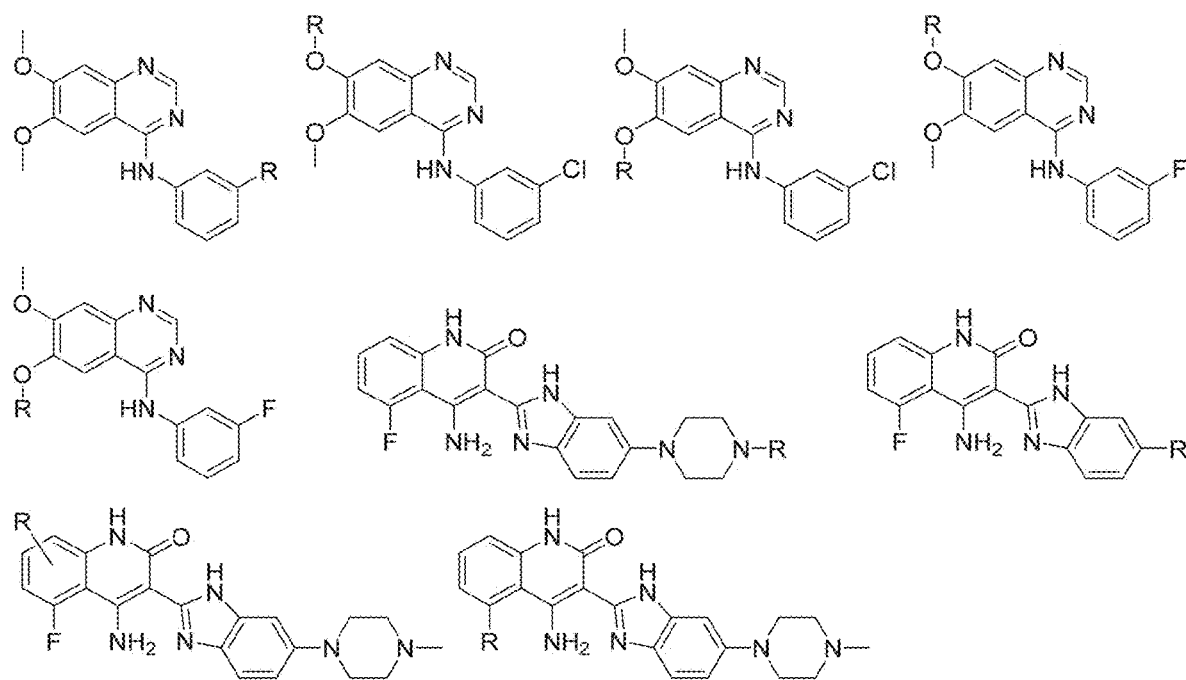

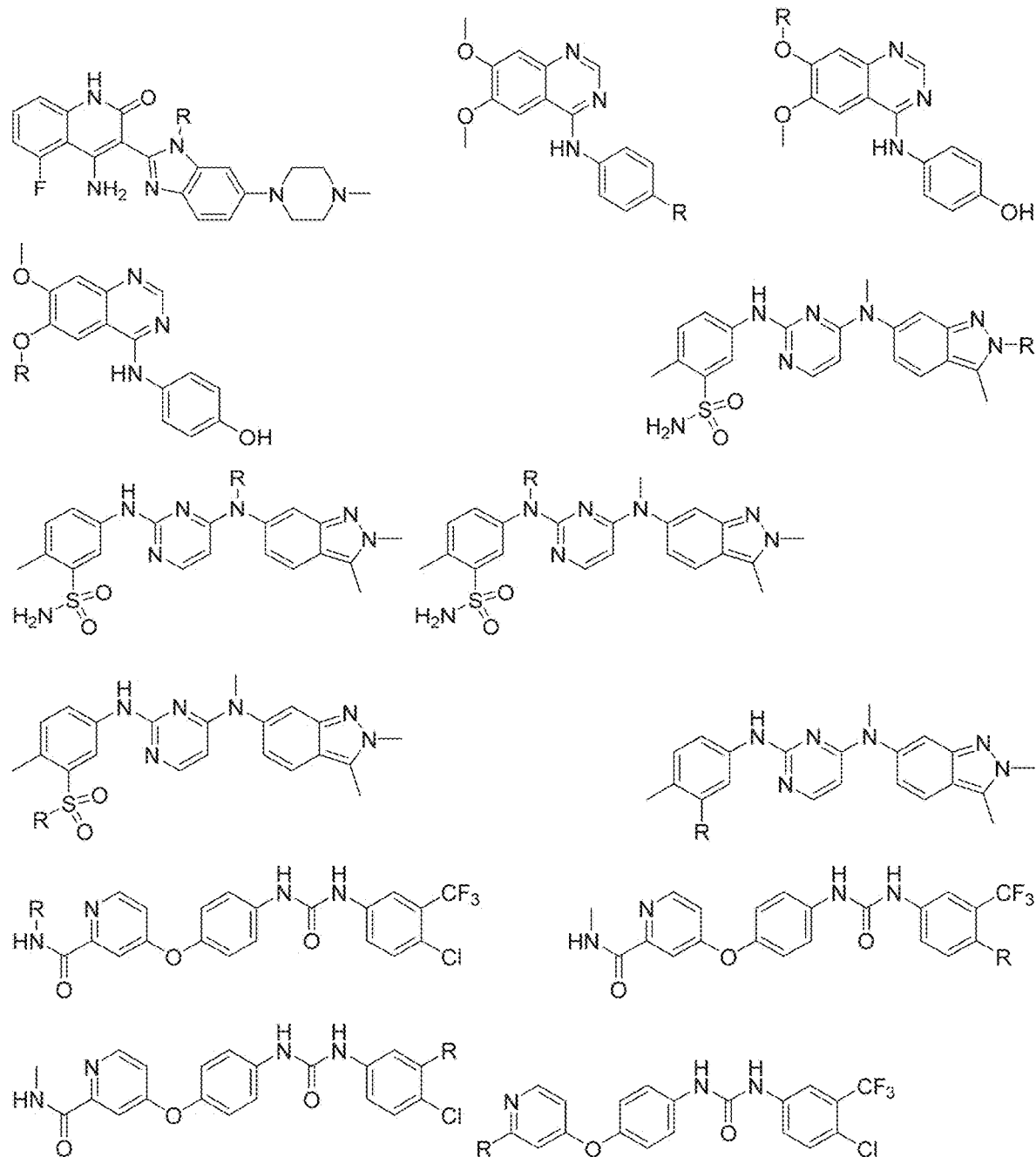
FIG. 2SSS

FIG. 2TTT
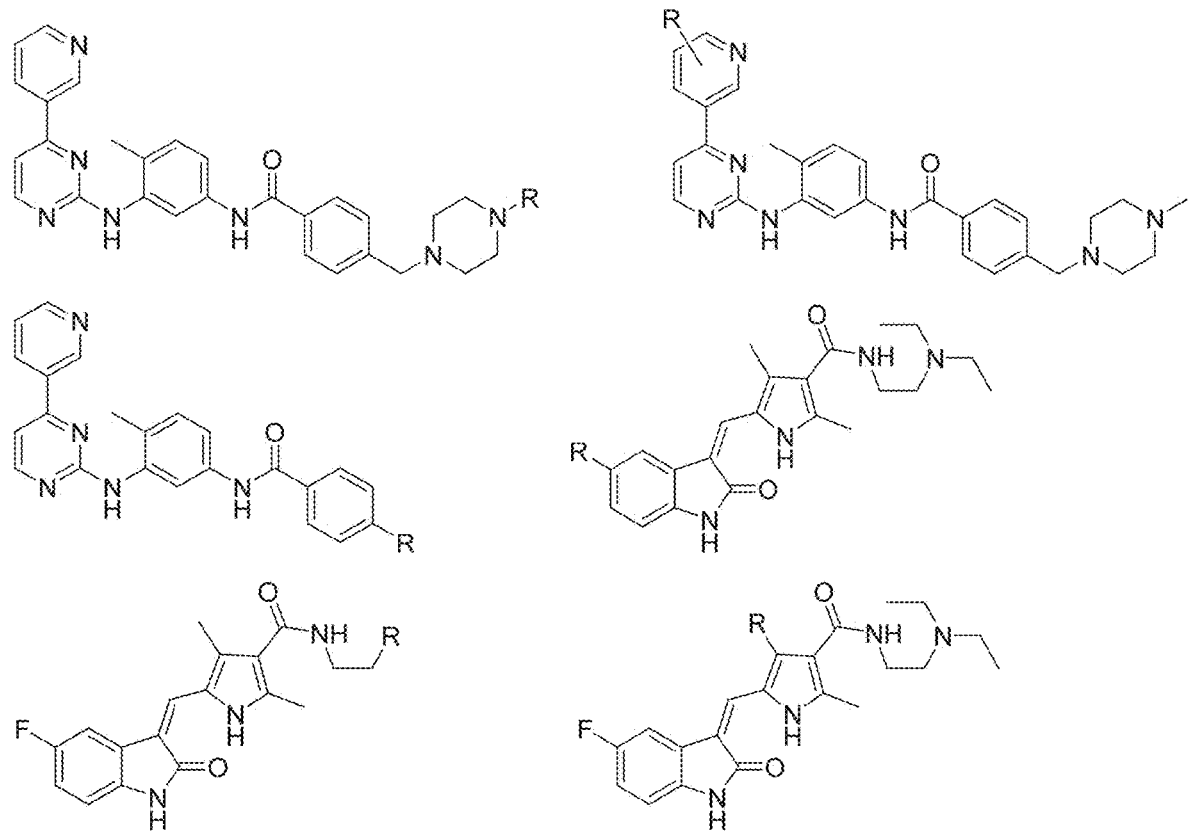
FIG. 2UUU
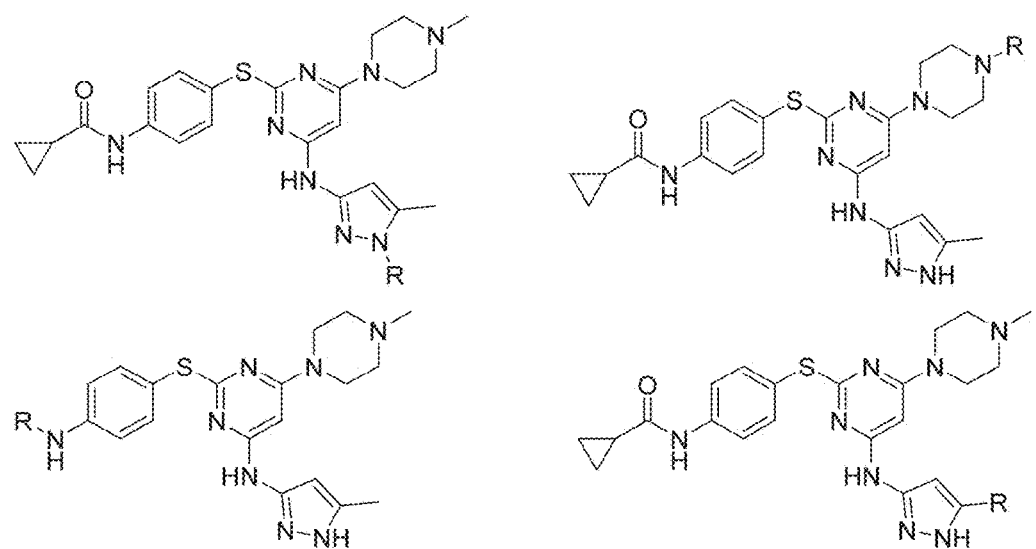

FIG. 2VVV
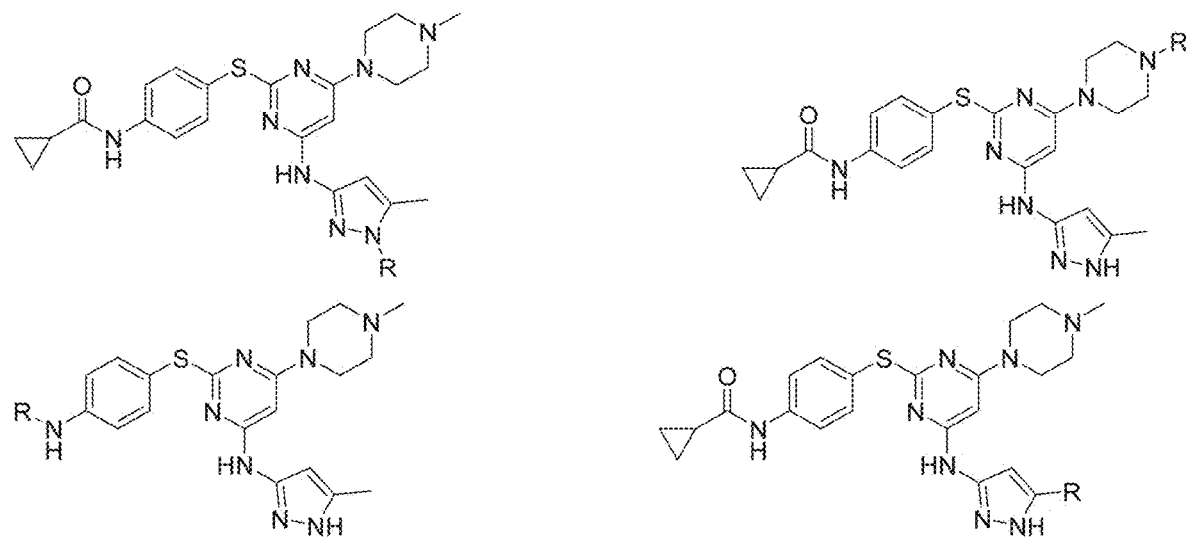
FIG. 2WWW
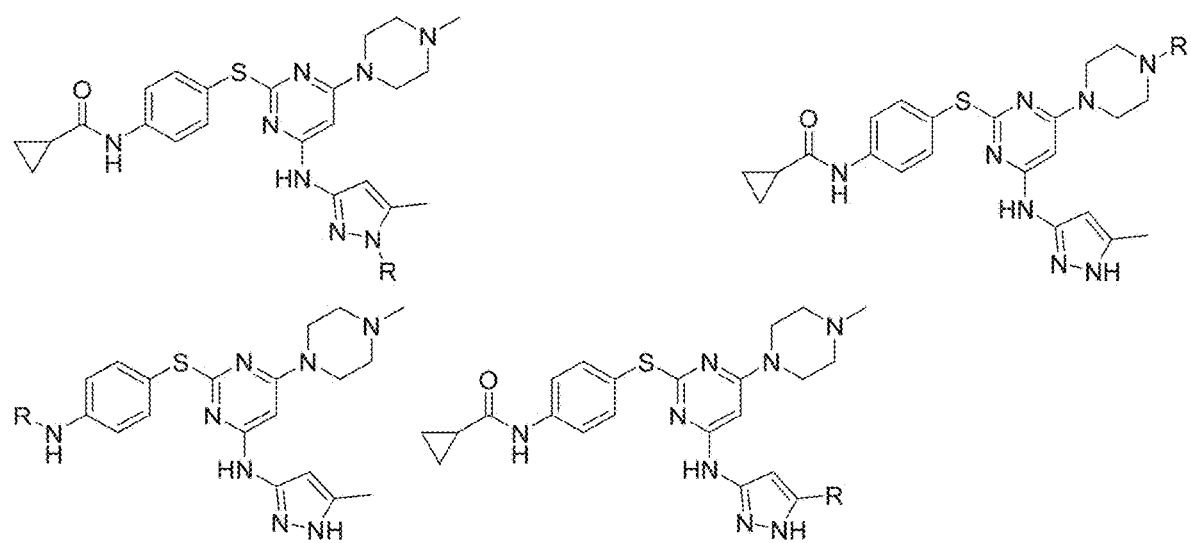

FIG. 2XXX
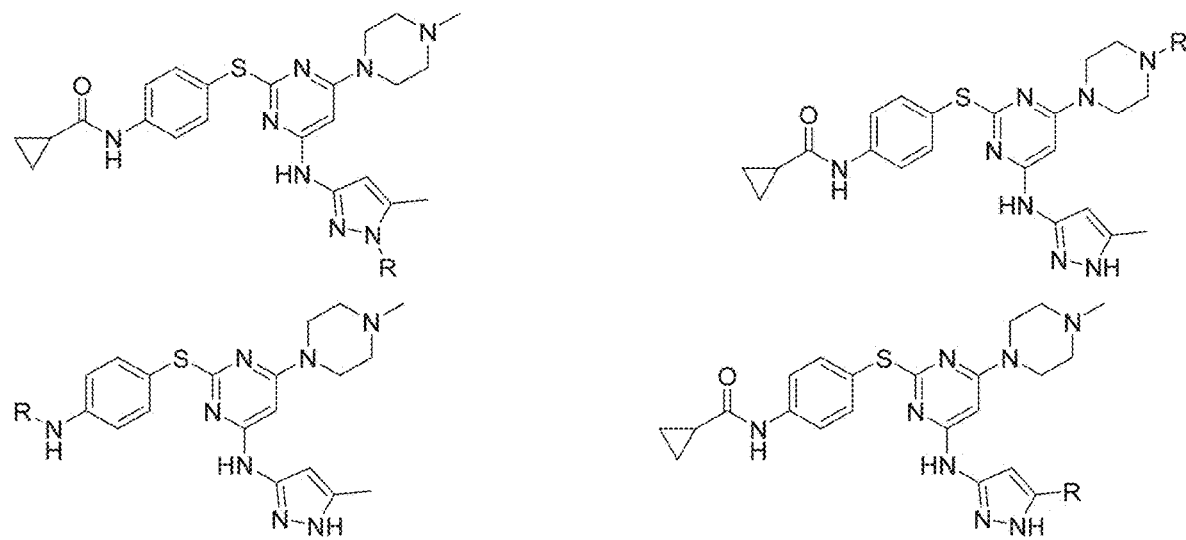
FIG. 2YYY
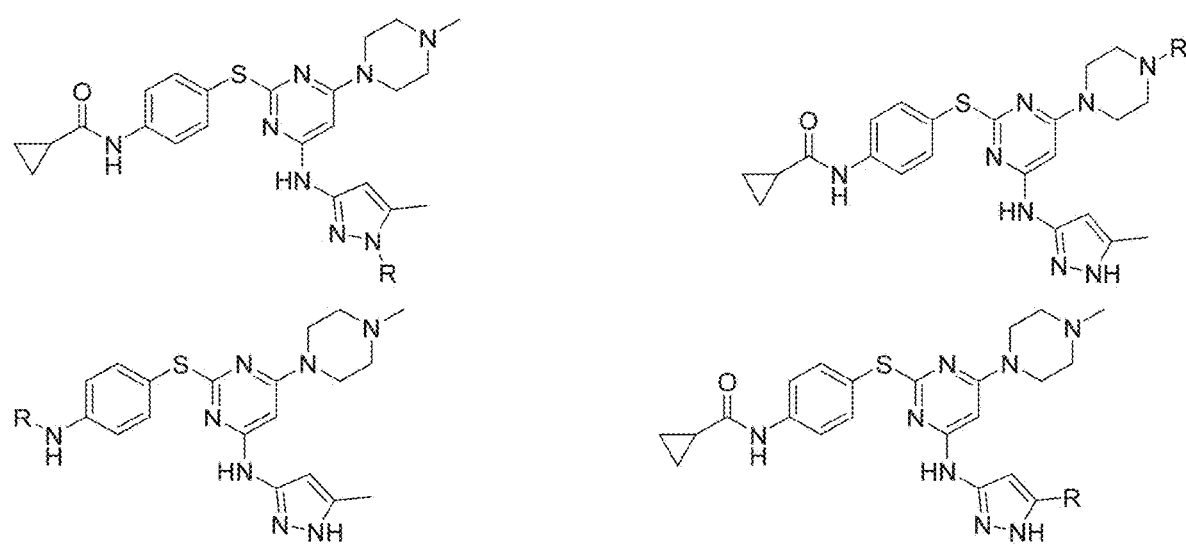

FIG. 2ZZZ
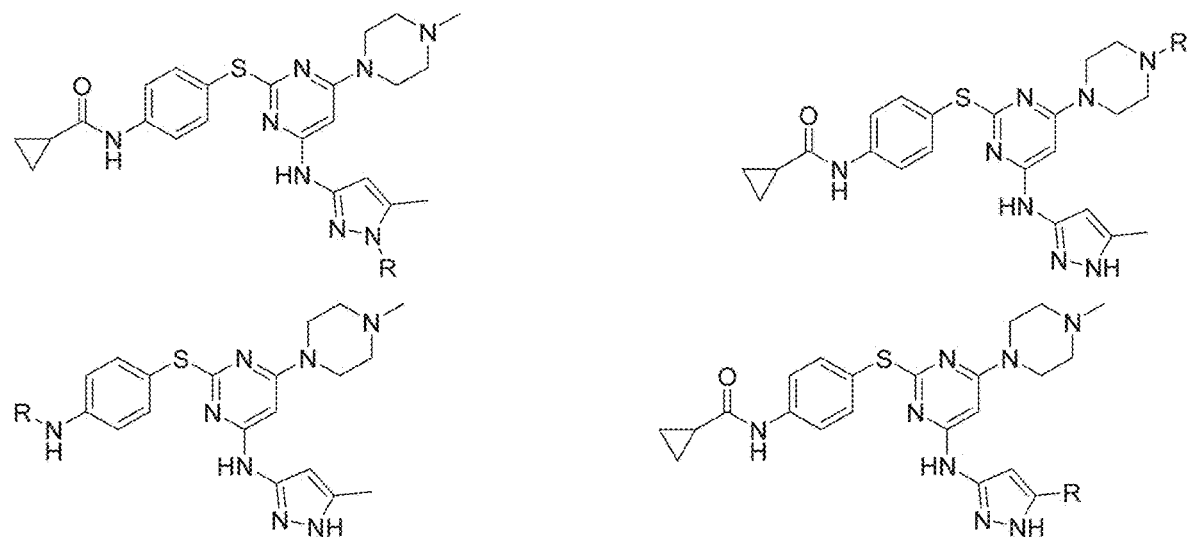
FIG. 2AAAA
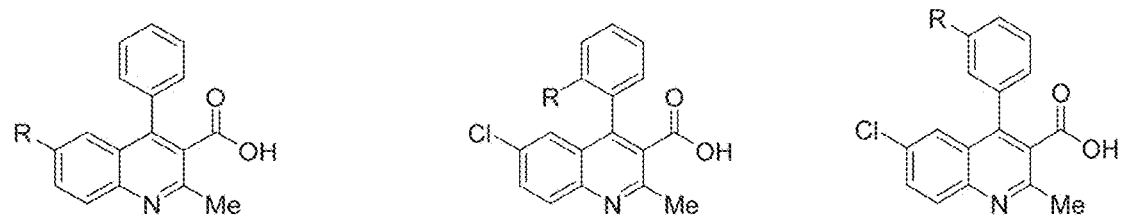
FIG. 2BBBB
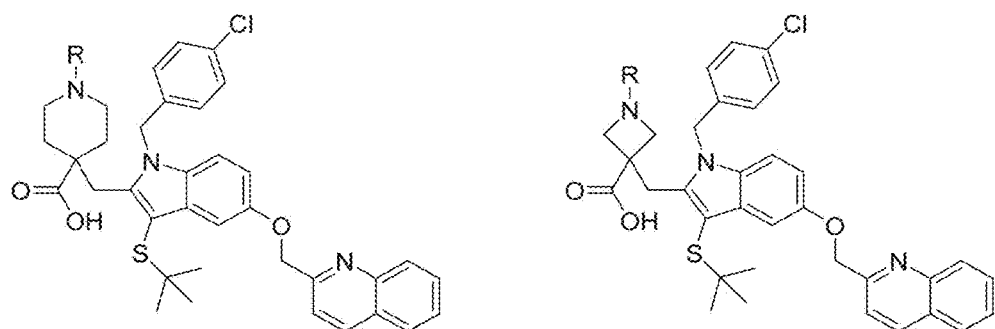

FIG. 2CCCC
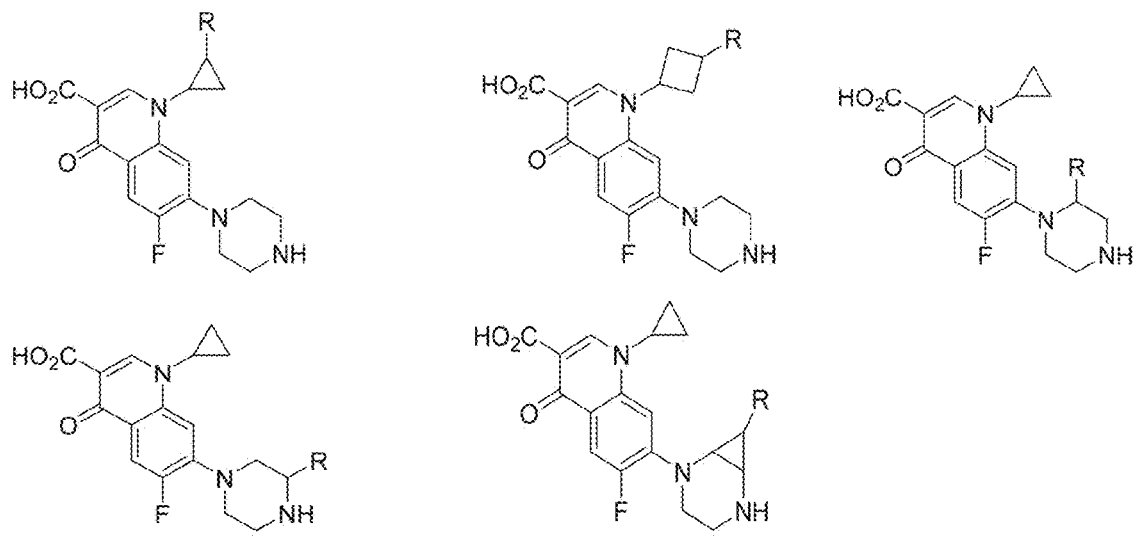
FIG. 2DDDD
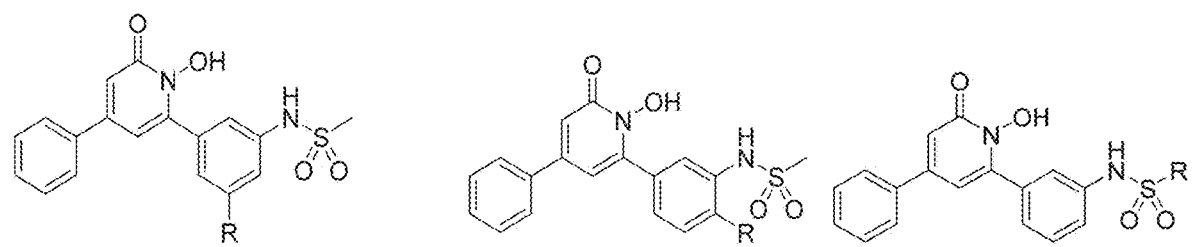
FIG. 2EEEE
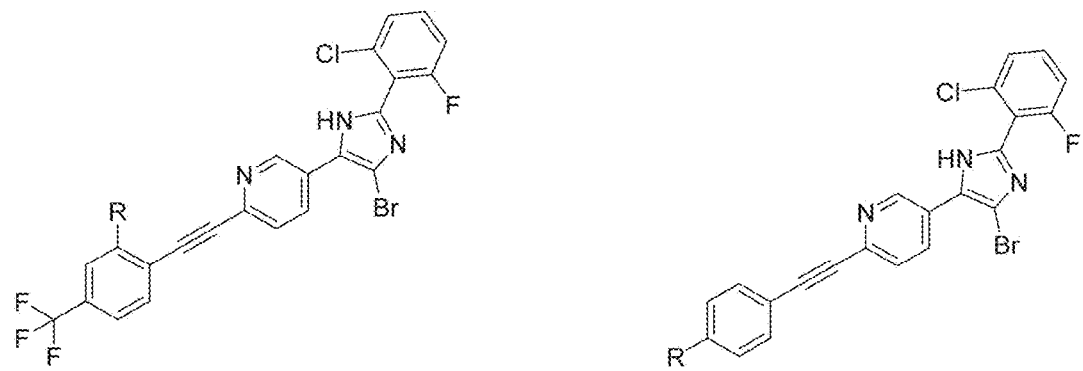

FIG. 2FFFF
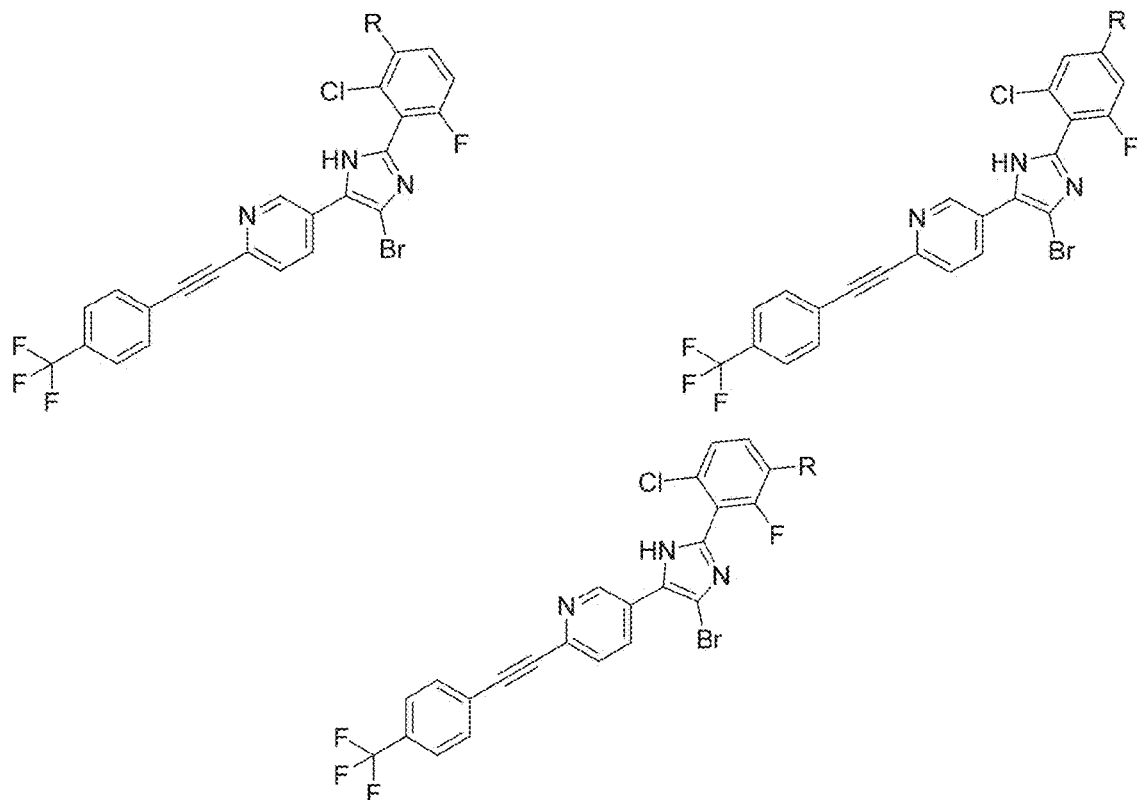
FIG. 2GGGG
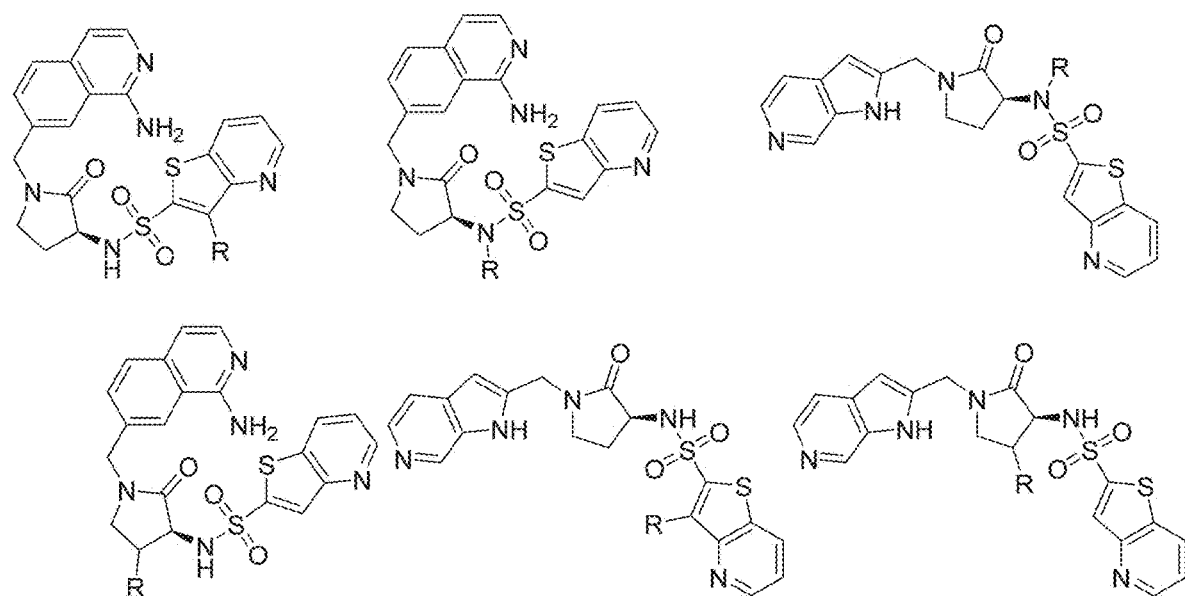

FIG. 2HHHH
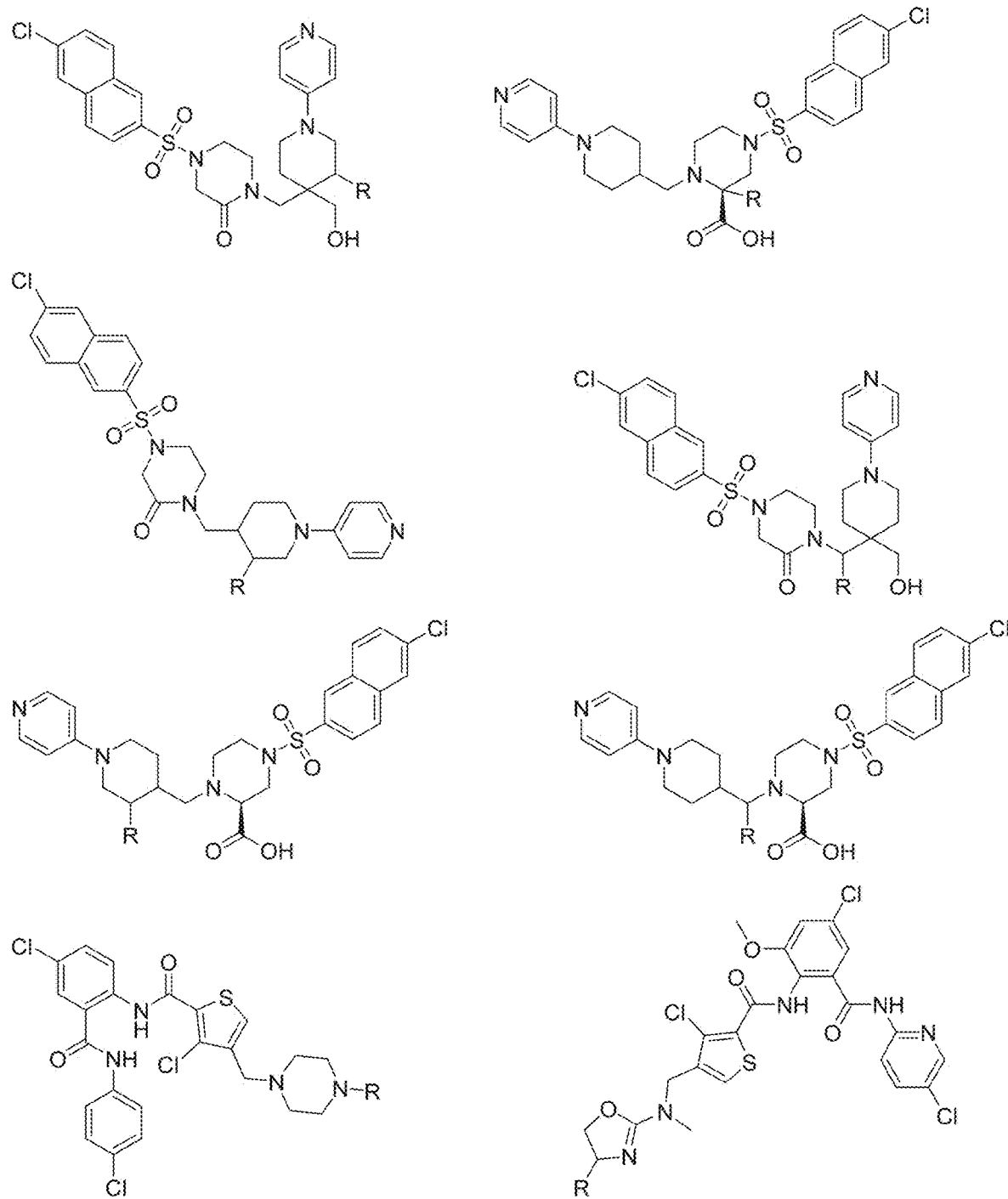

FIG. 2IIII
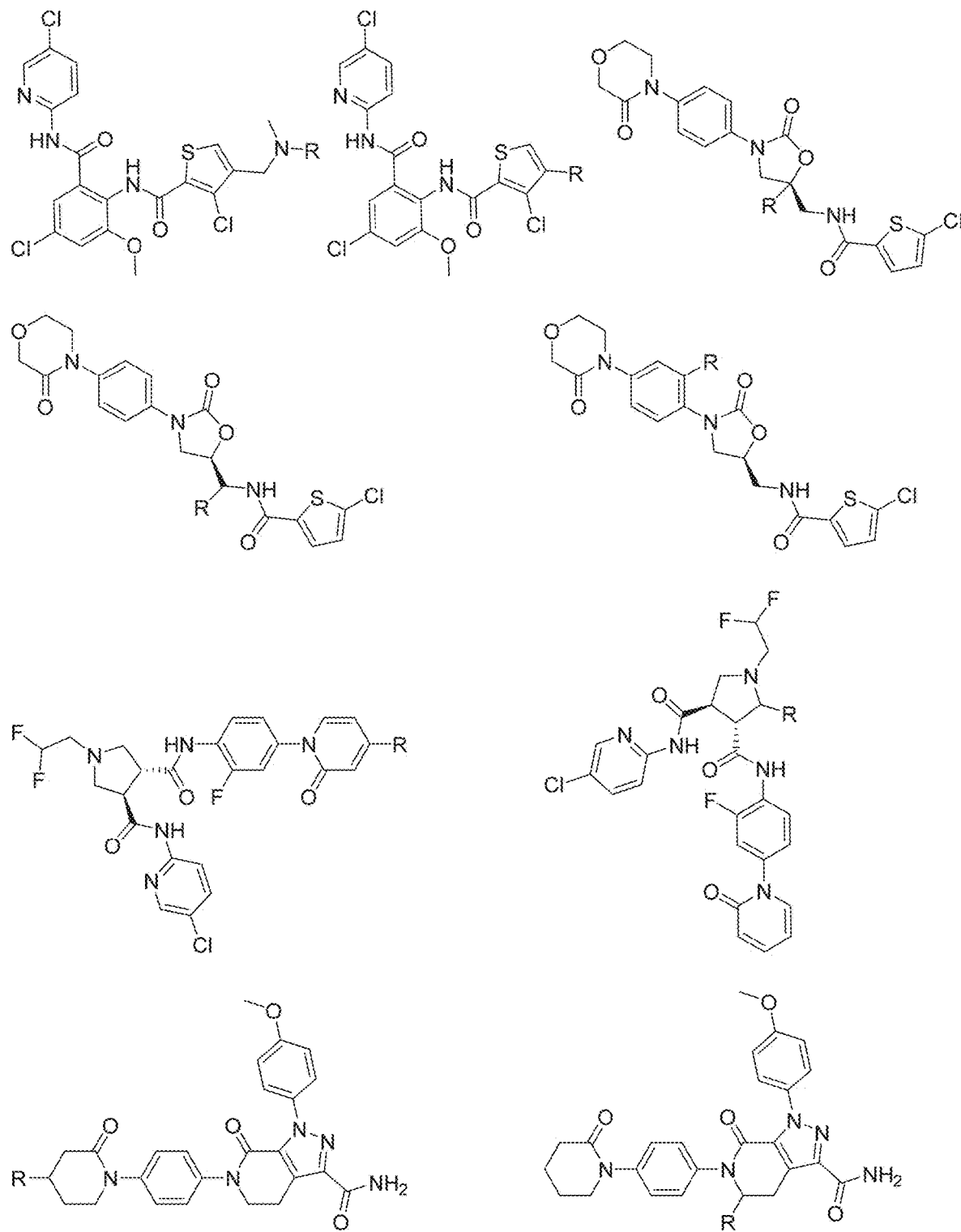

FIG. 2JJJJ
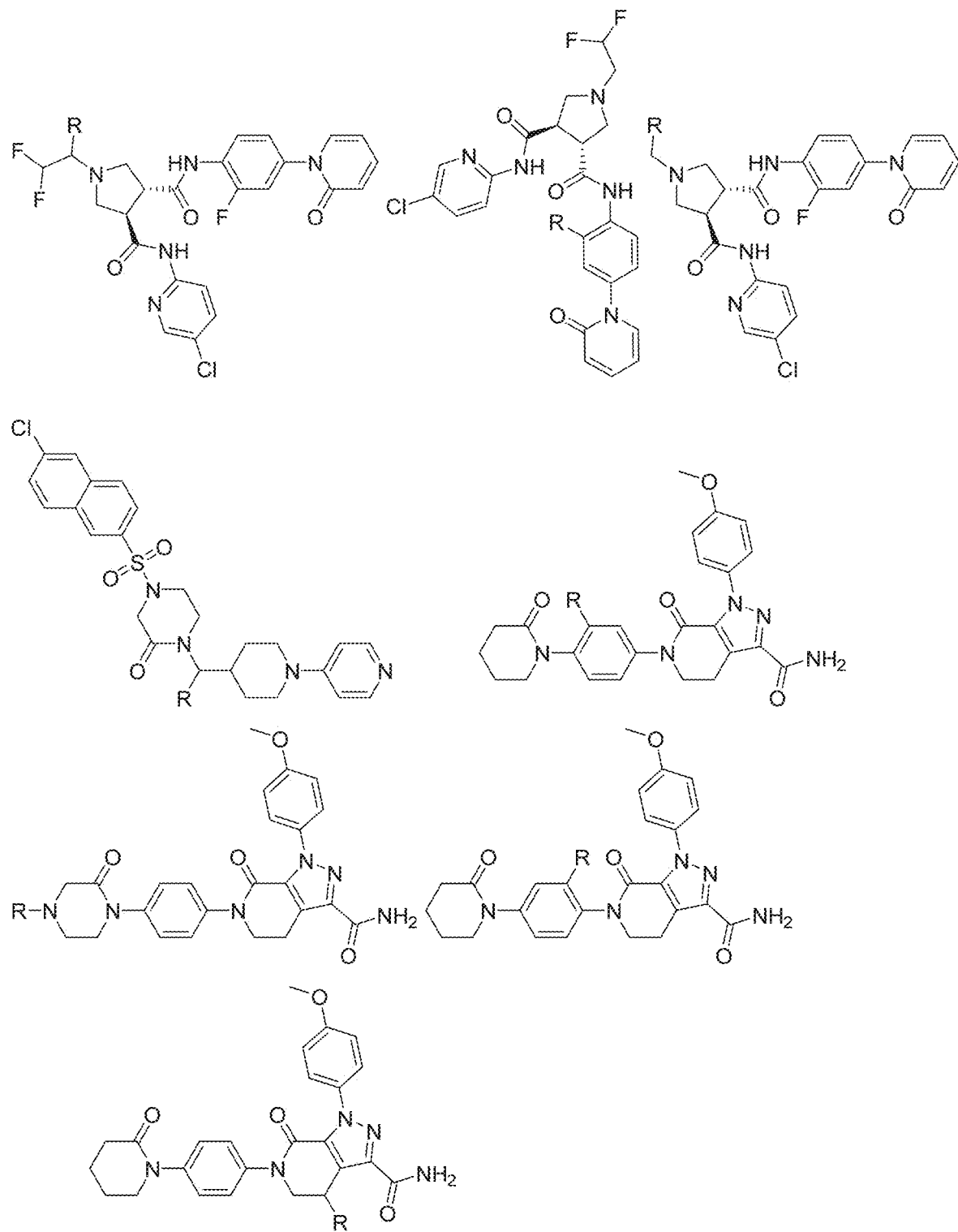

FIG. 2KKKK
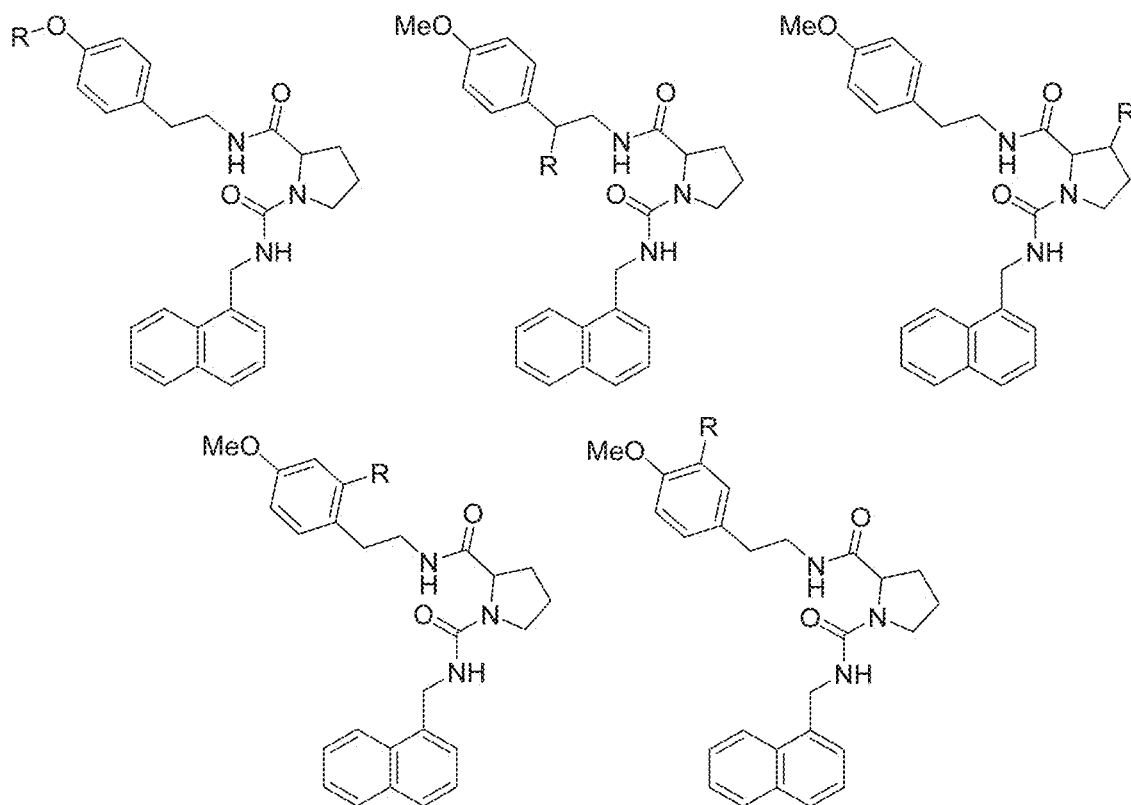
FIG. 2LLLL
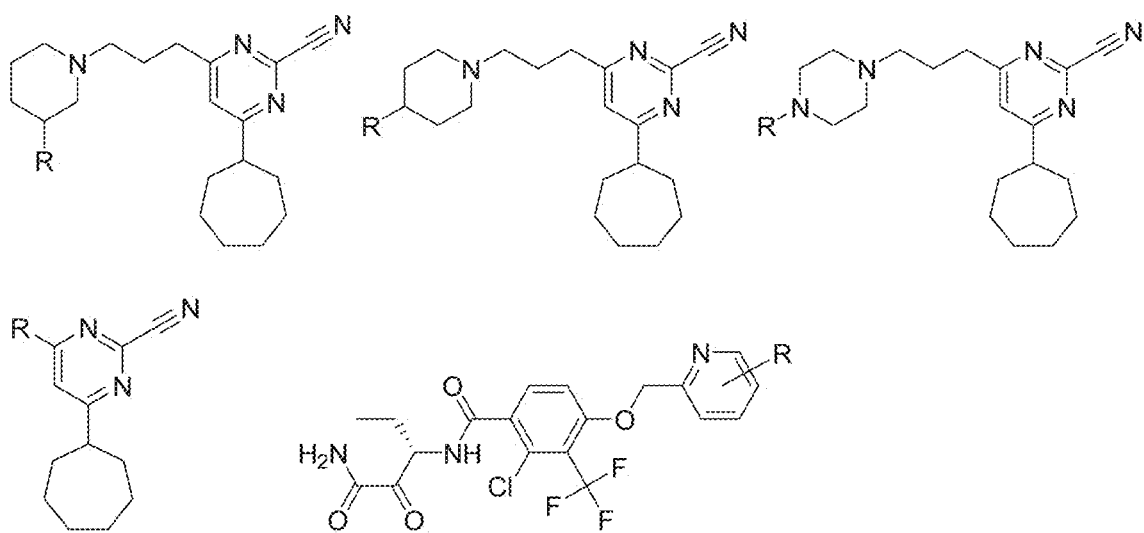

FIG. 2MMMM
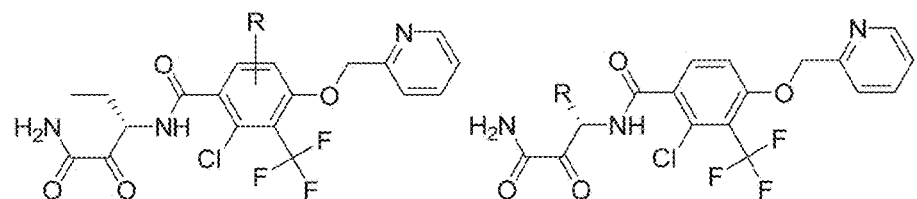
FIG. 2NNNN
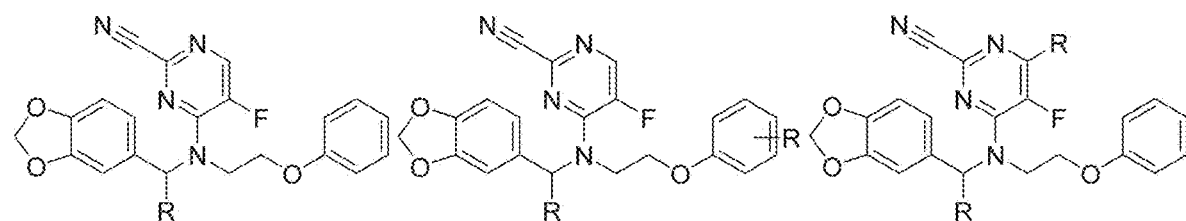
FIG. 2OOOO
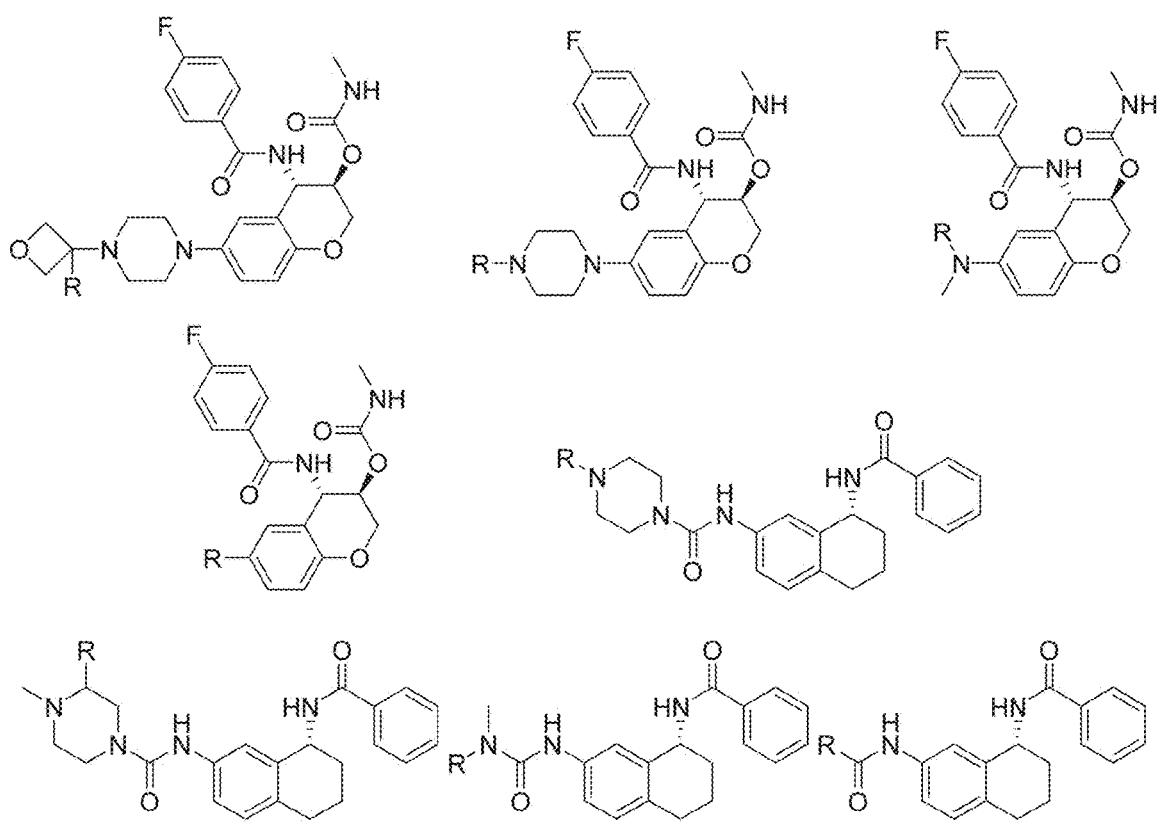

FIG. 2PPPP
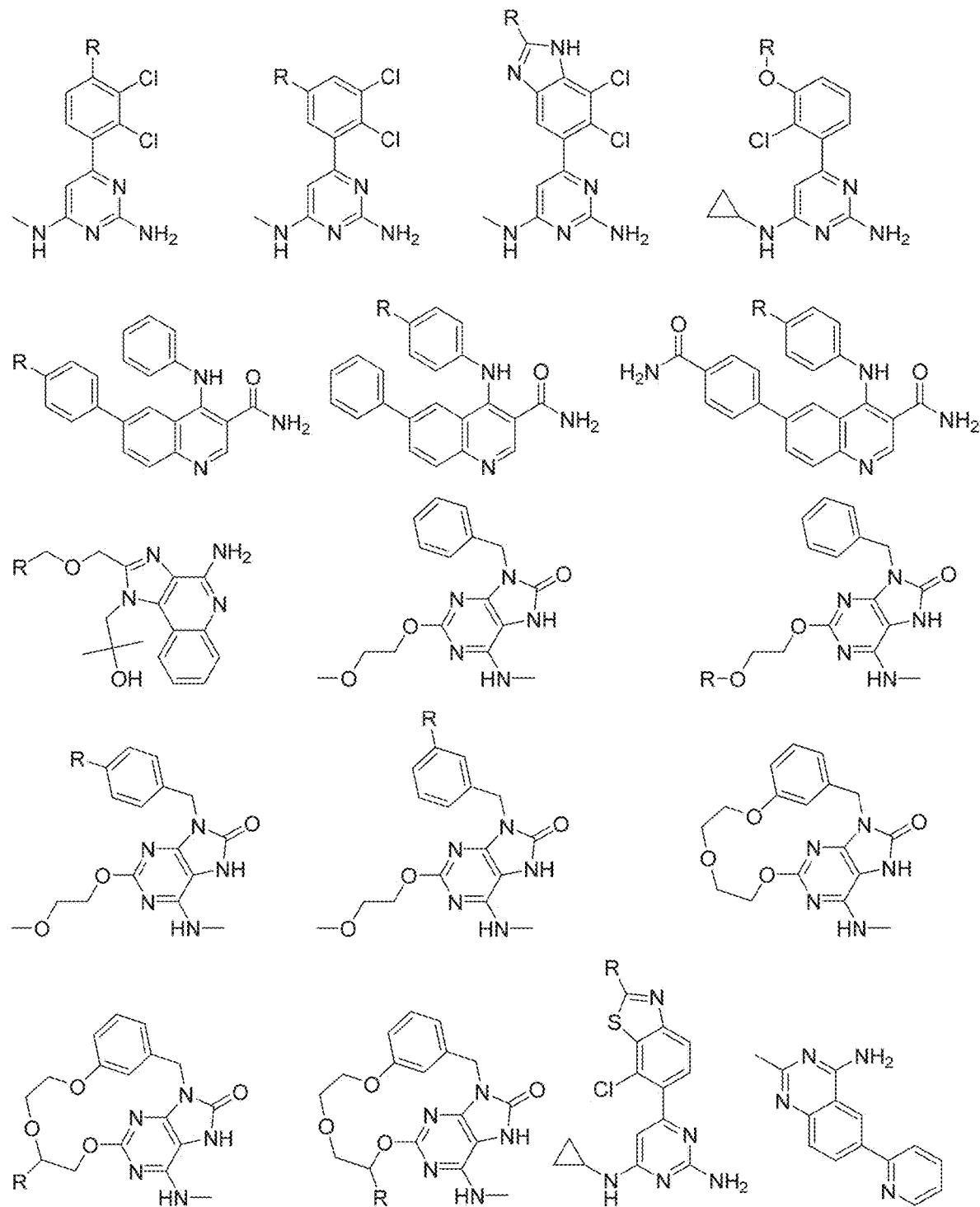

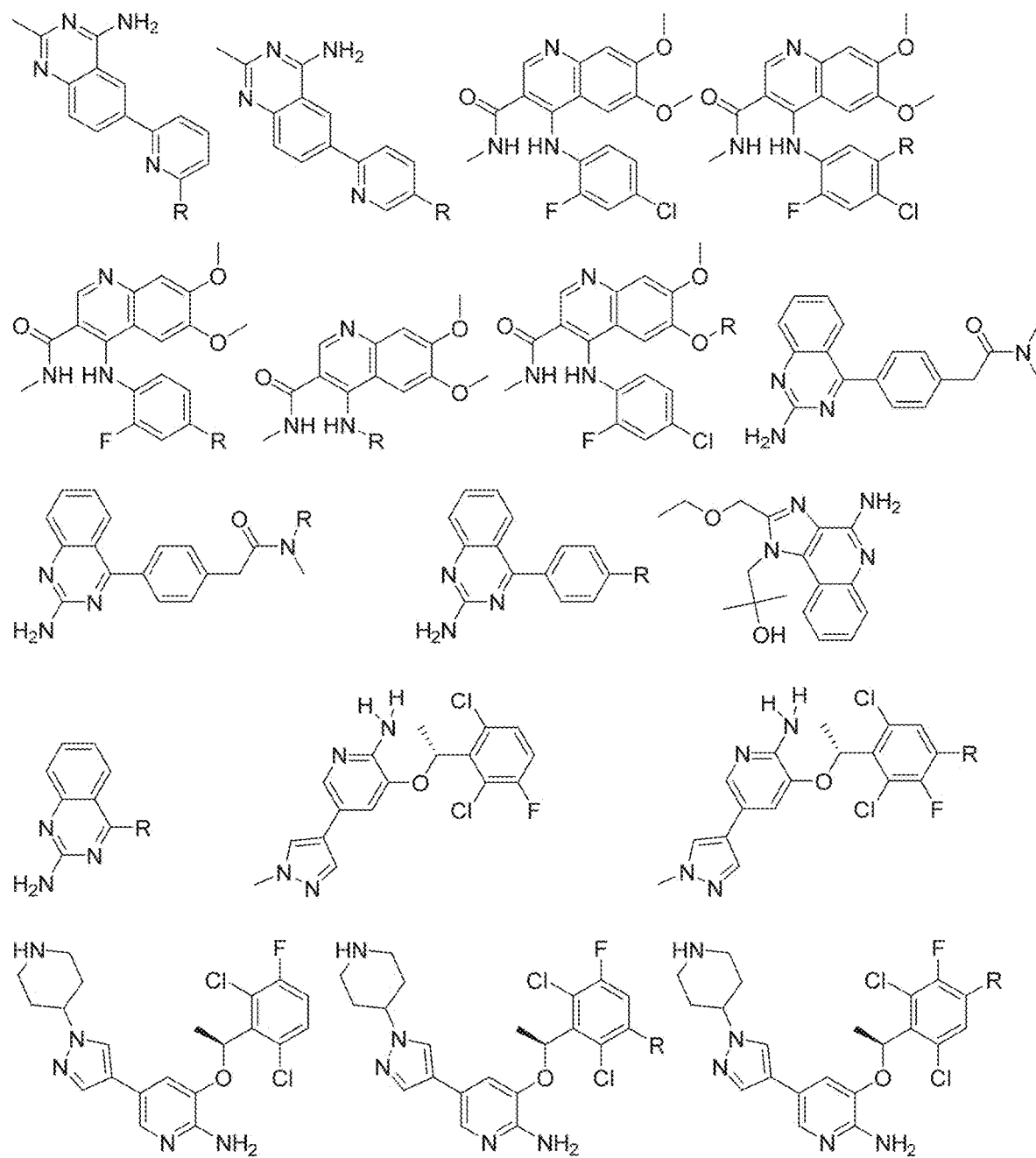
FIG. 2QQQQ

FIG. 2RRRR
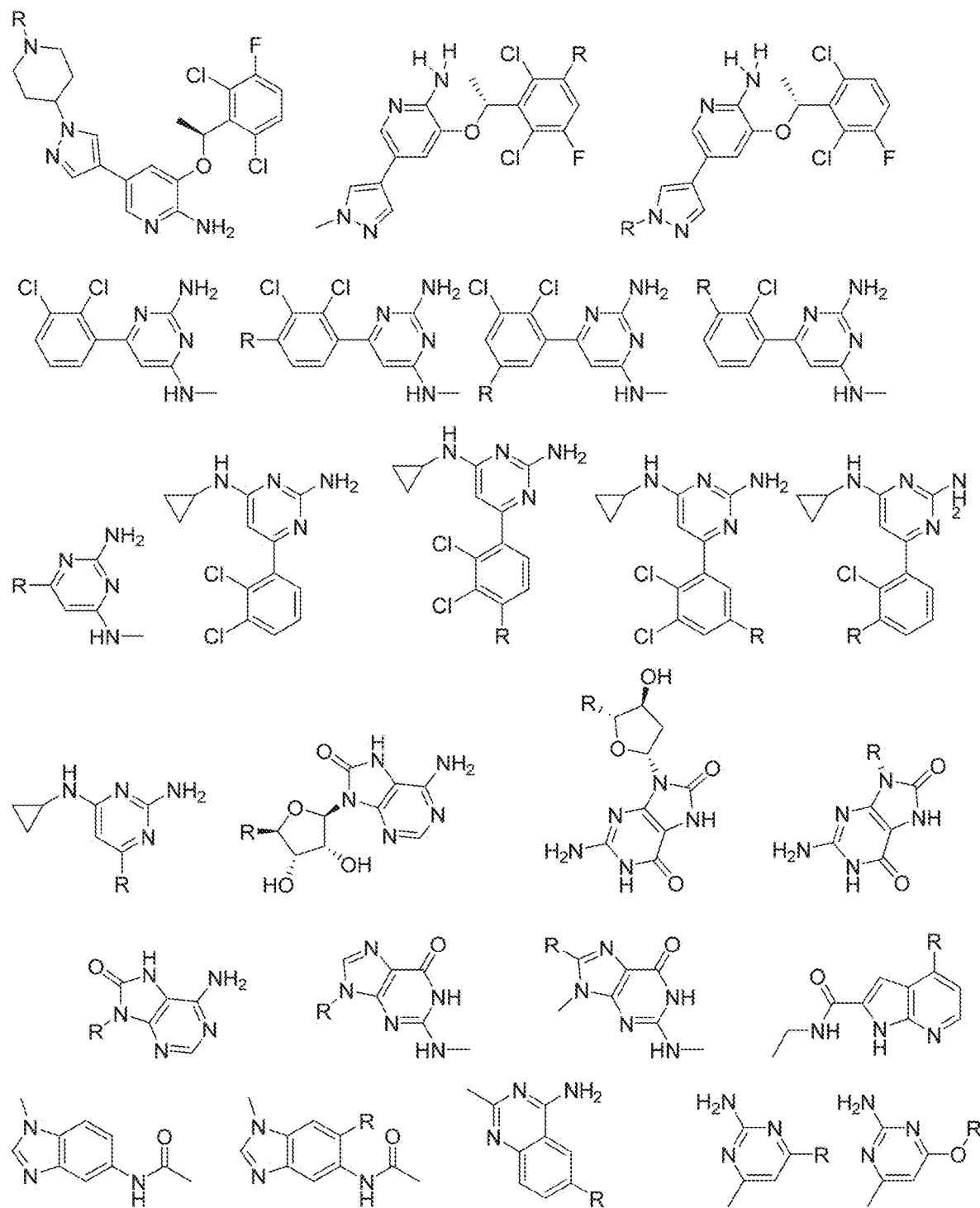

FIG. 2SSSS
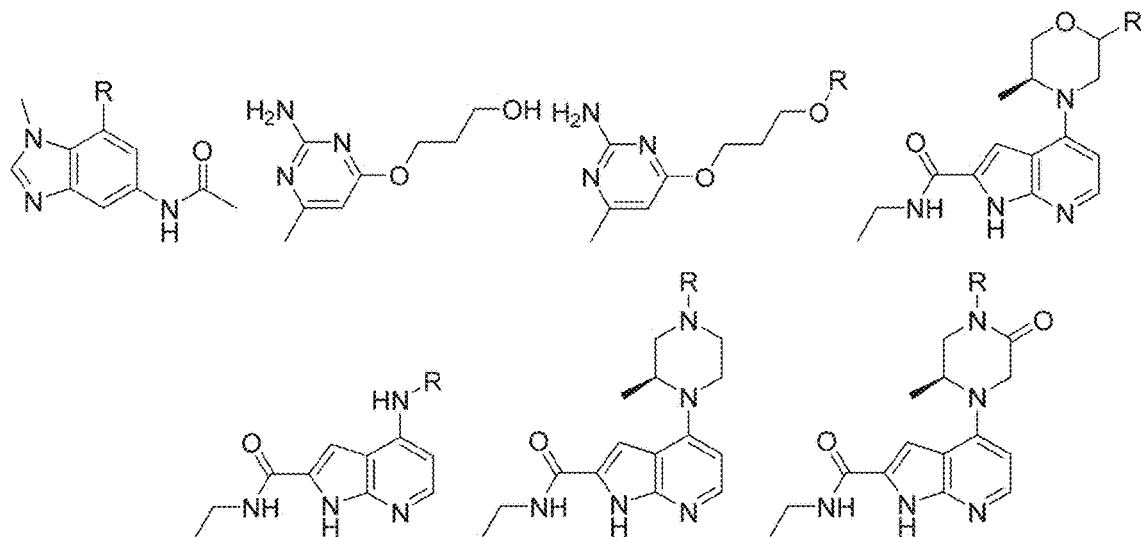
FIG. 2TTTT
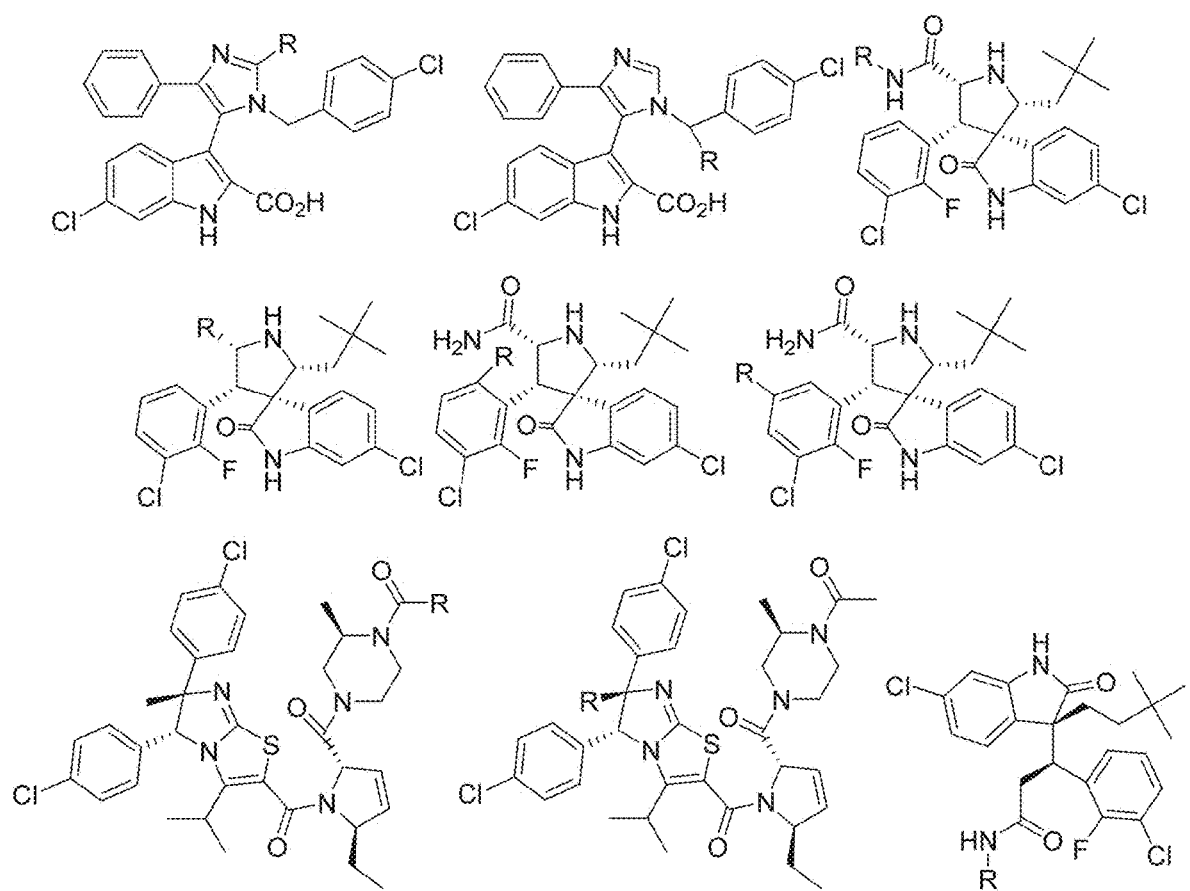

FIG. 2UUUU
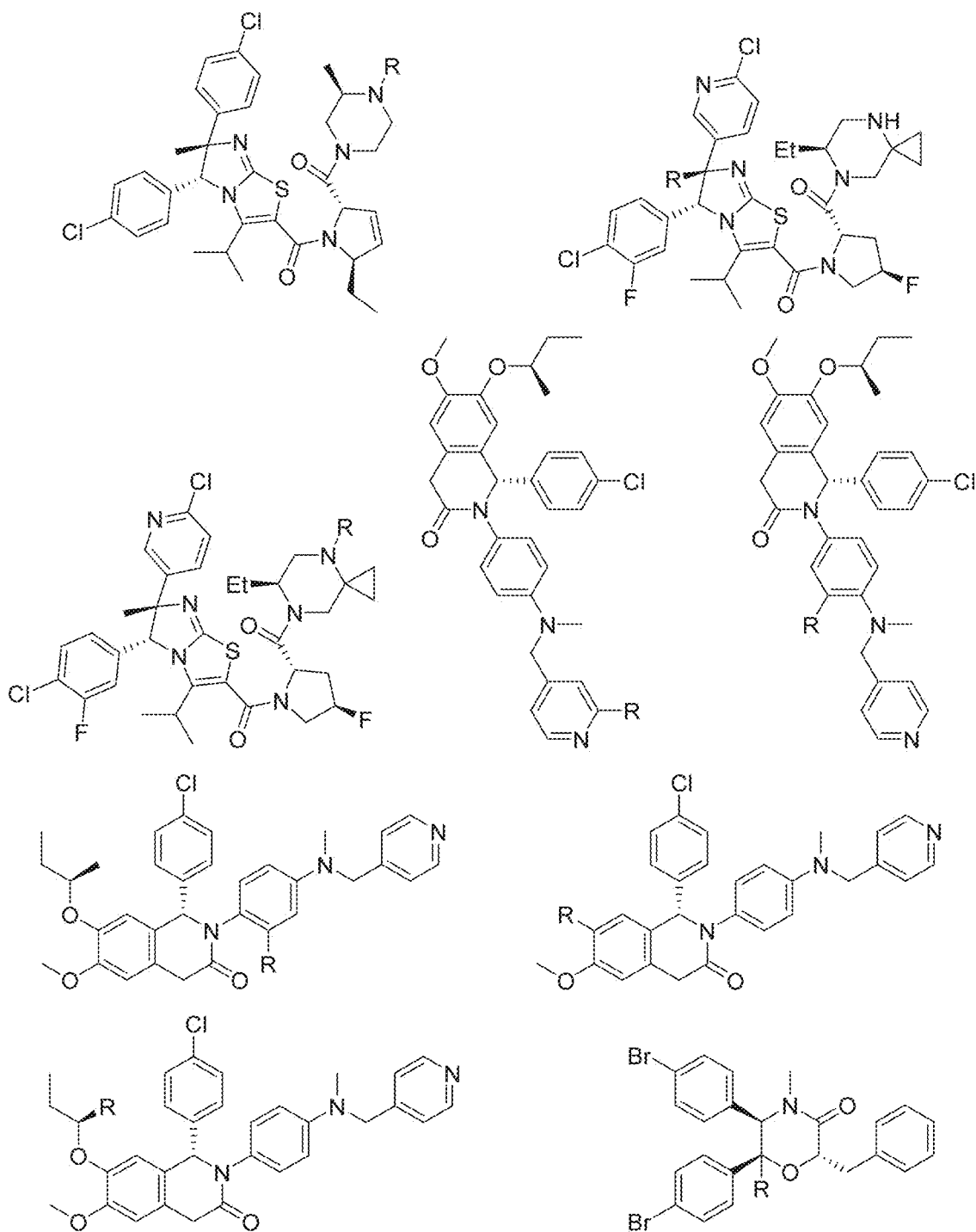

FIG. 2VVVV
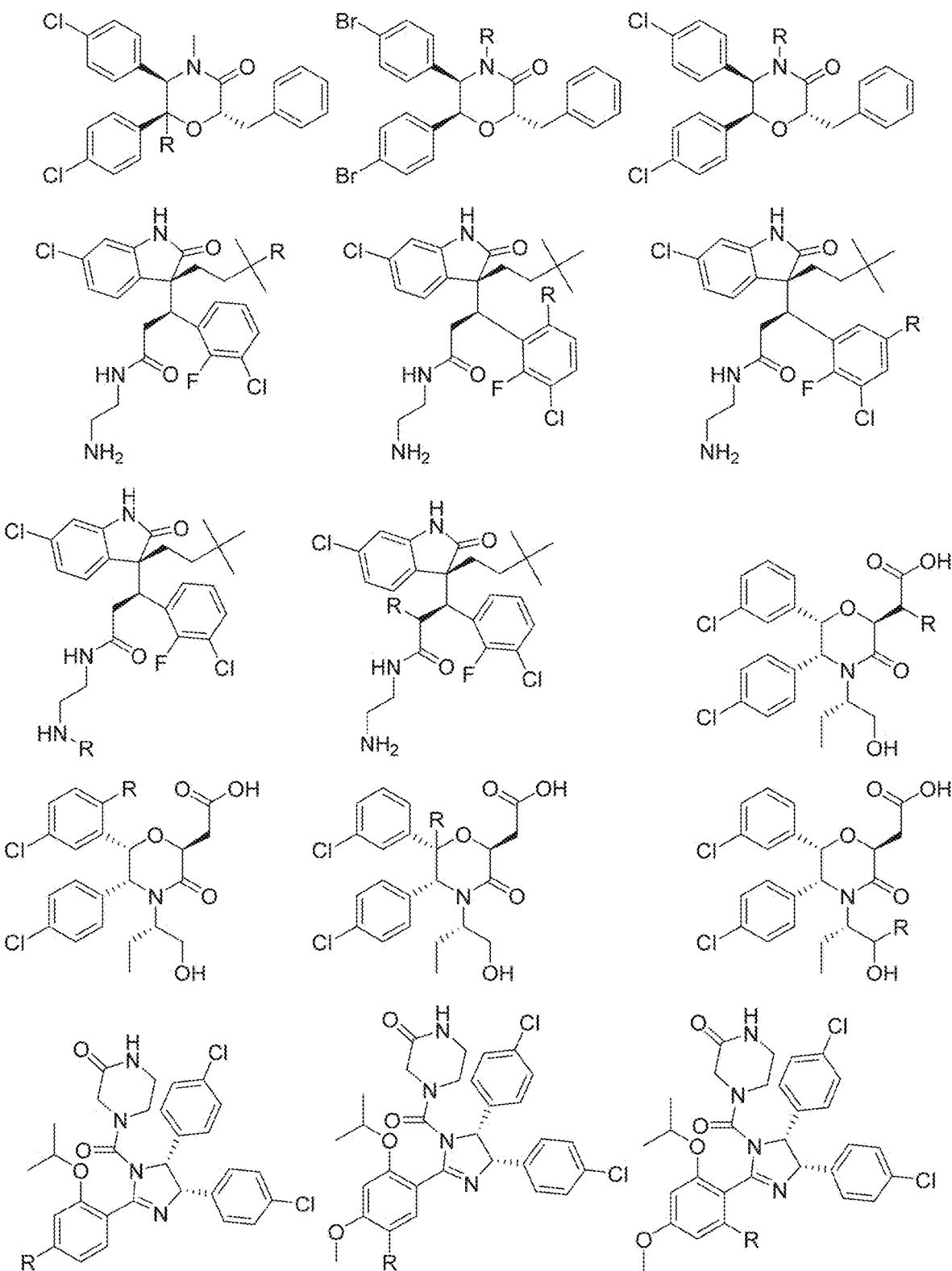

FIG. 2WWWW
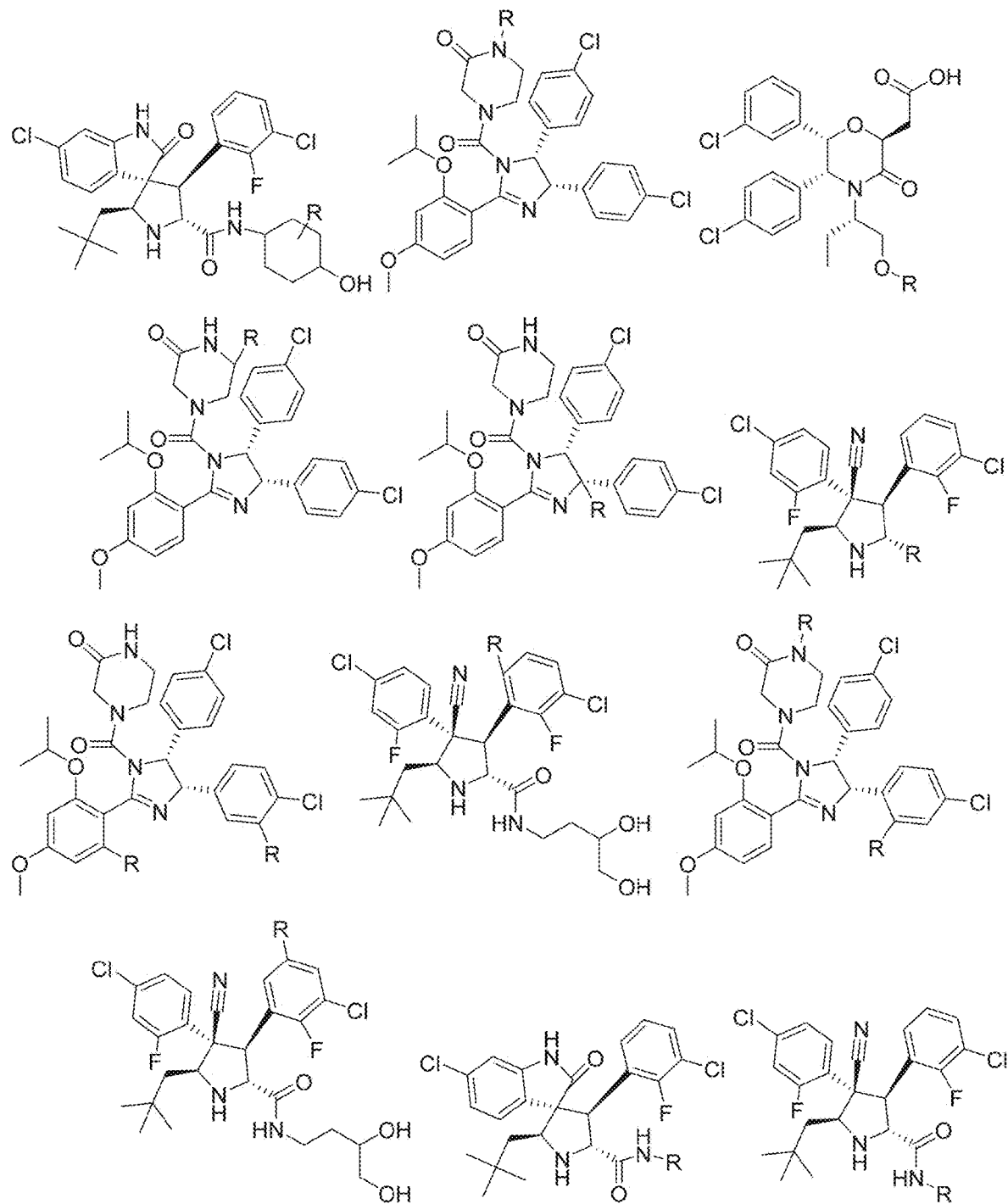

FIG. 2XXXX
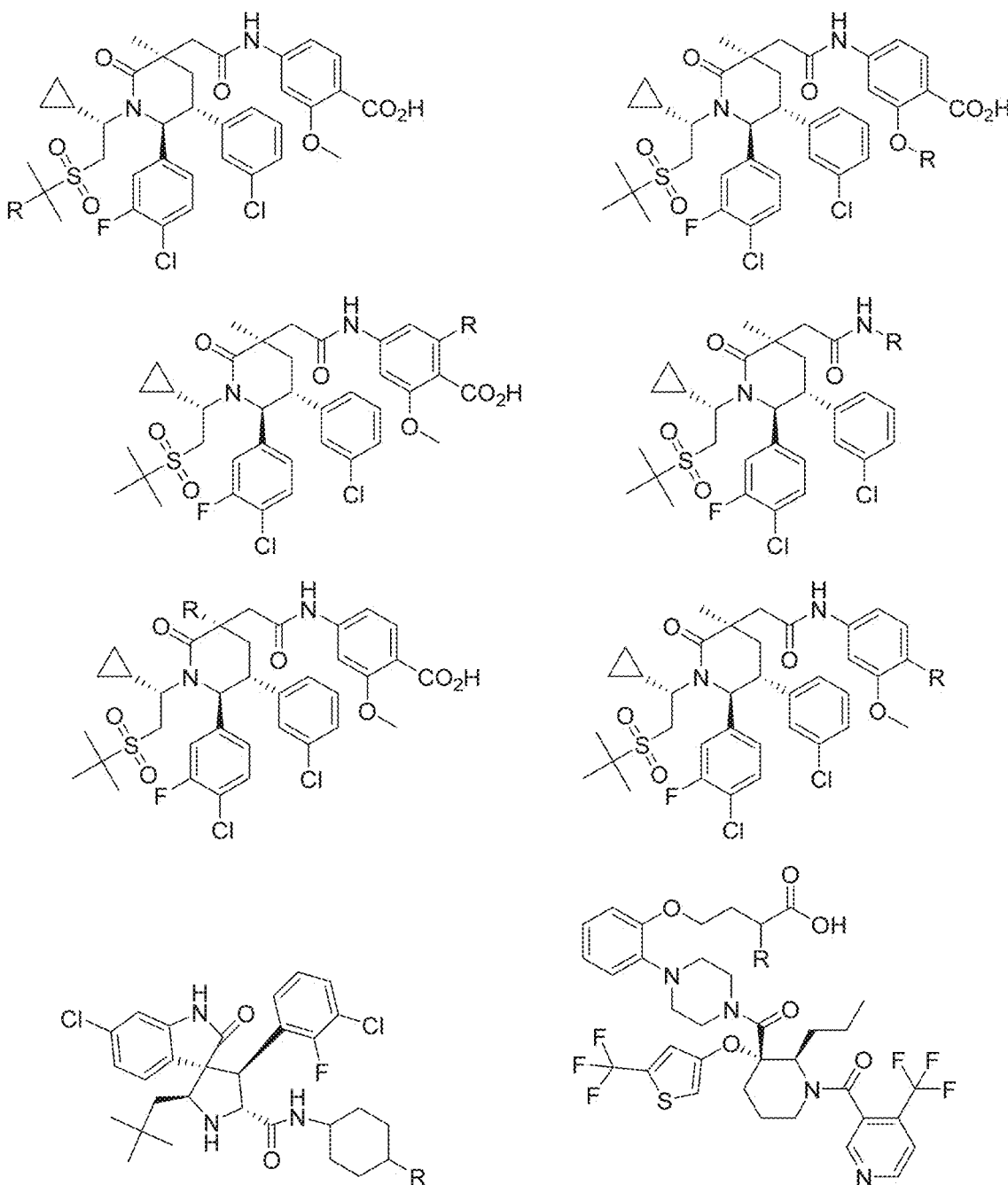

FIG. 2YYYY
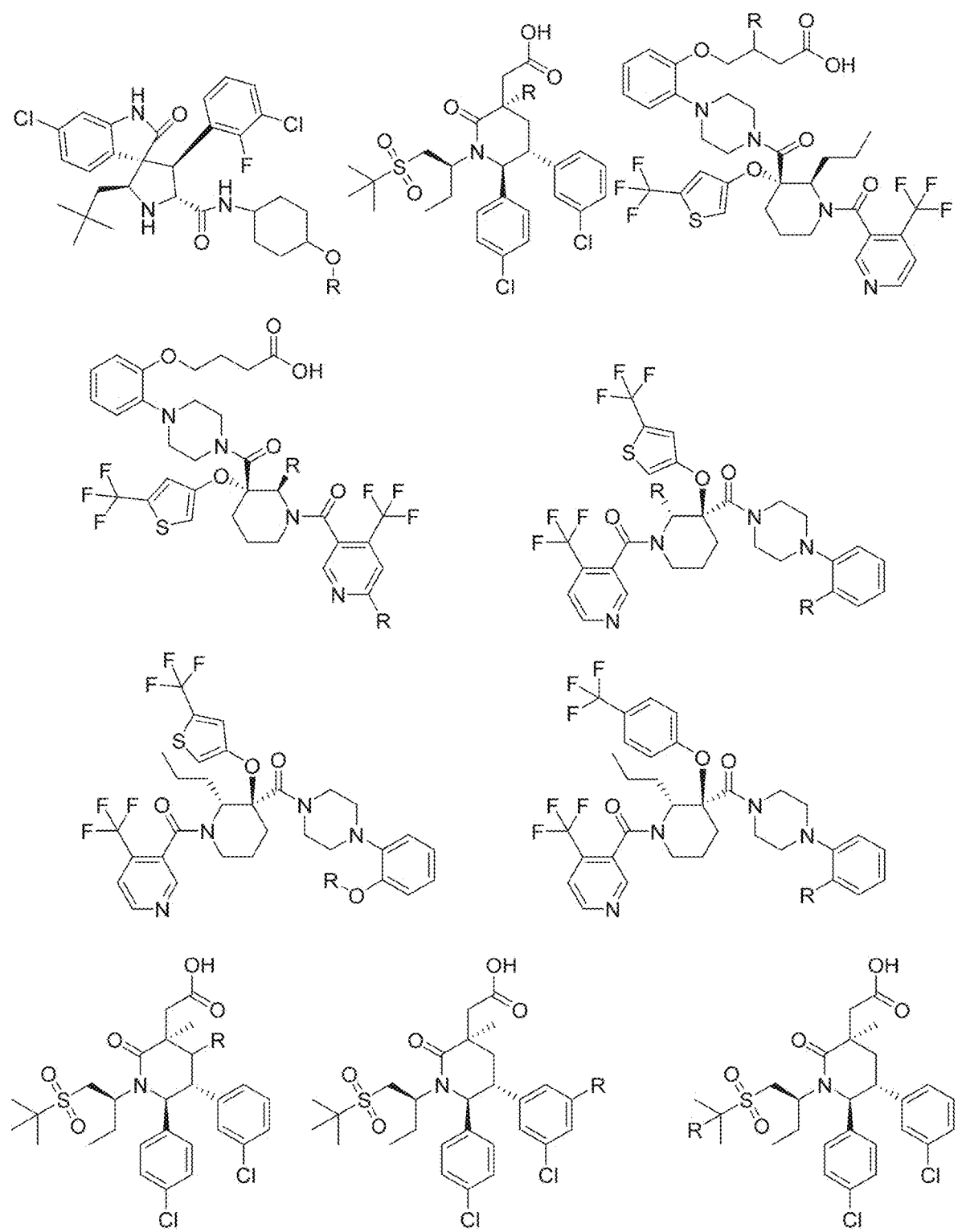

FIG. 2ZZZZ
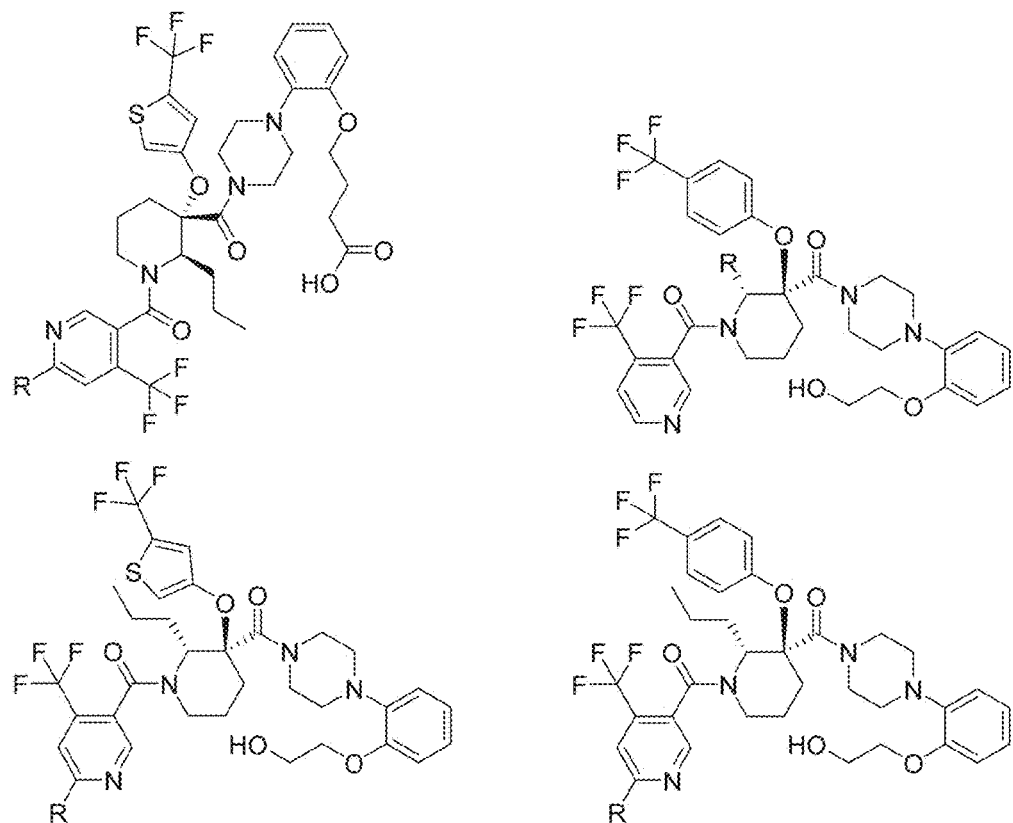
FIG. 2AAAAA
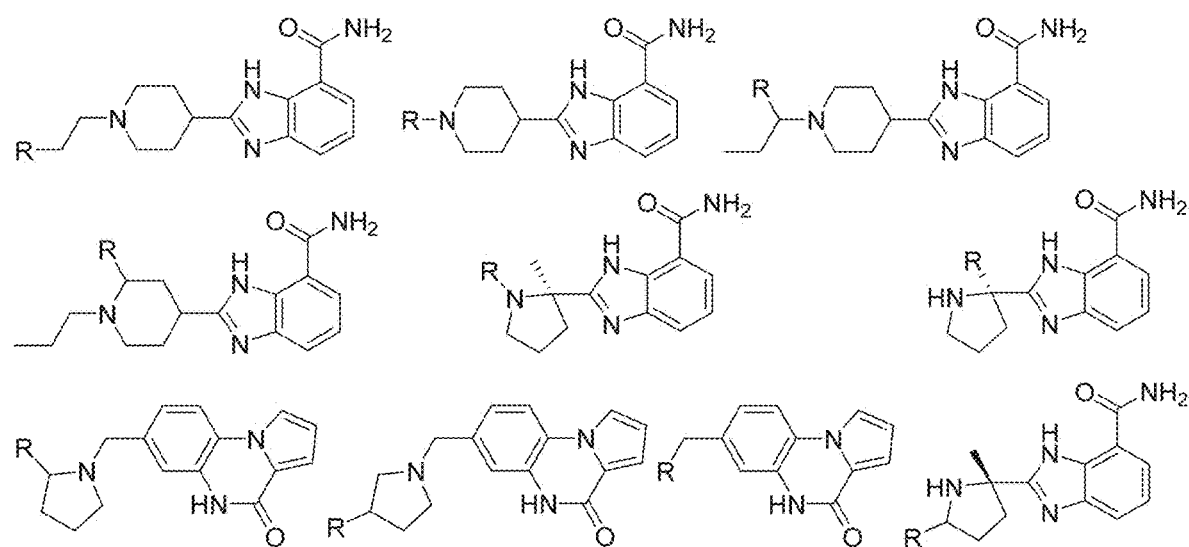

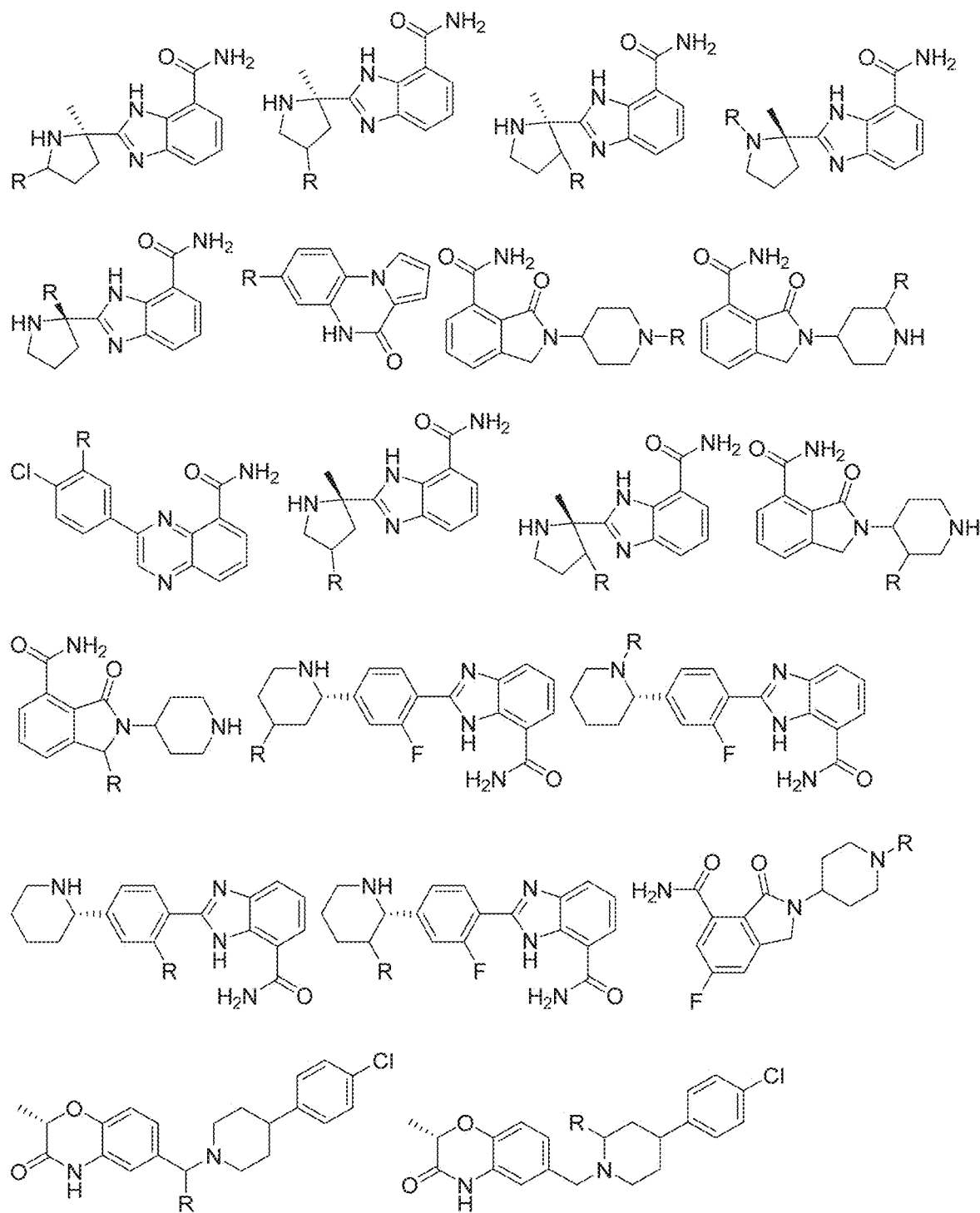
FIG. 2BBBBB

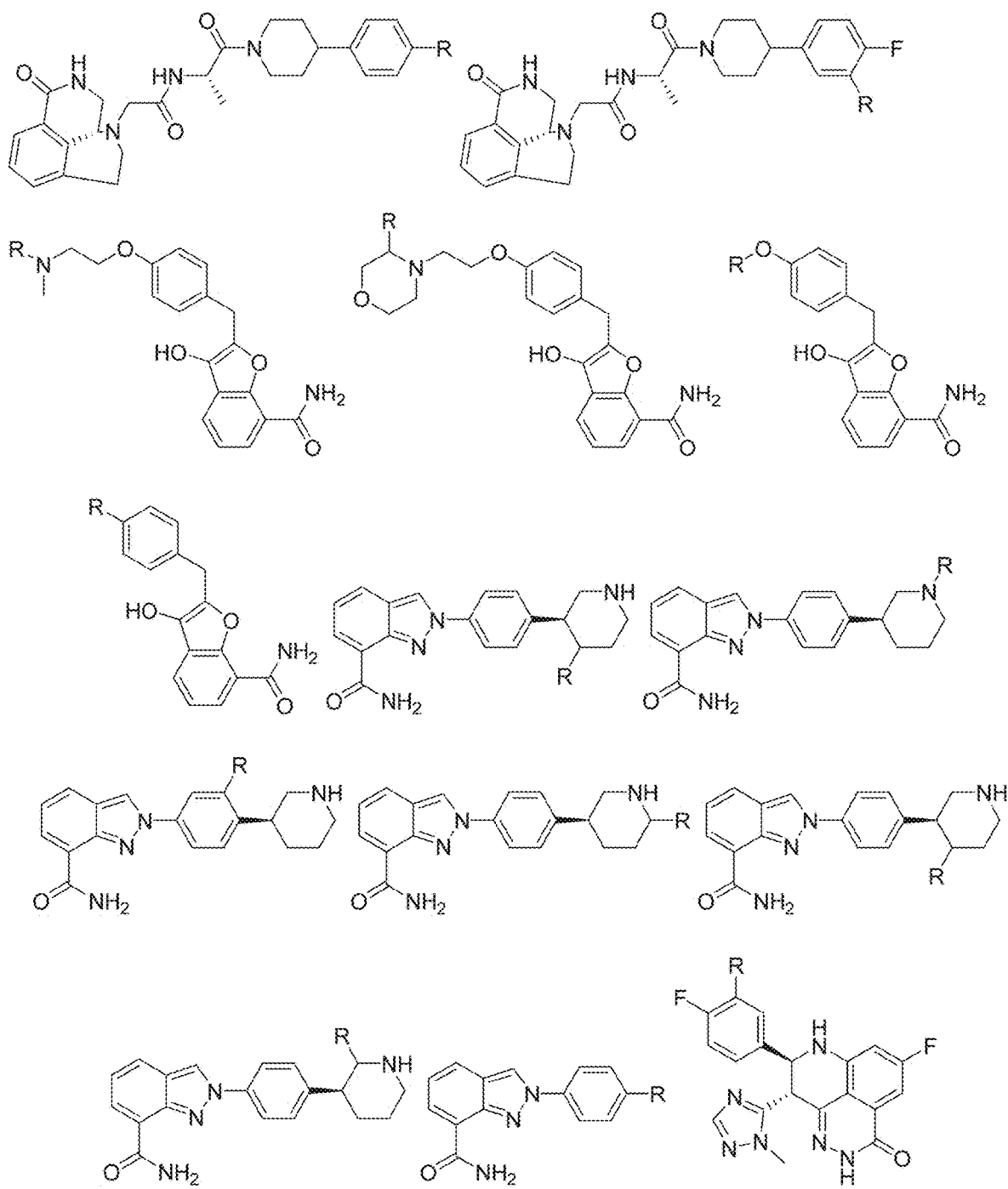
FIG. 2CCCCC

FIG. 2DDDDD
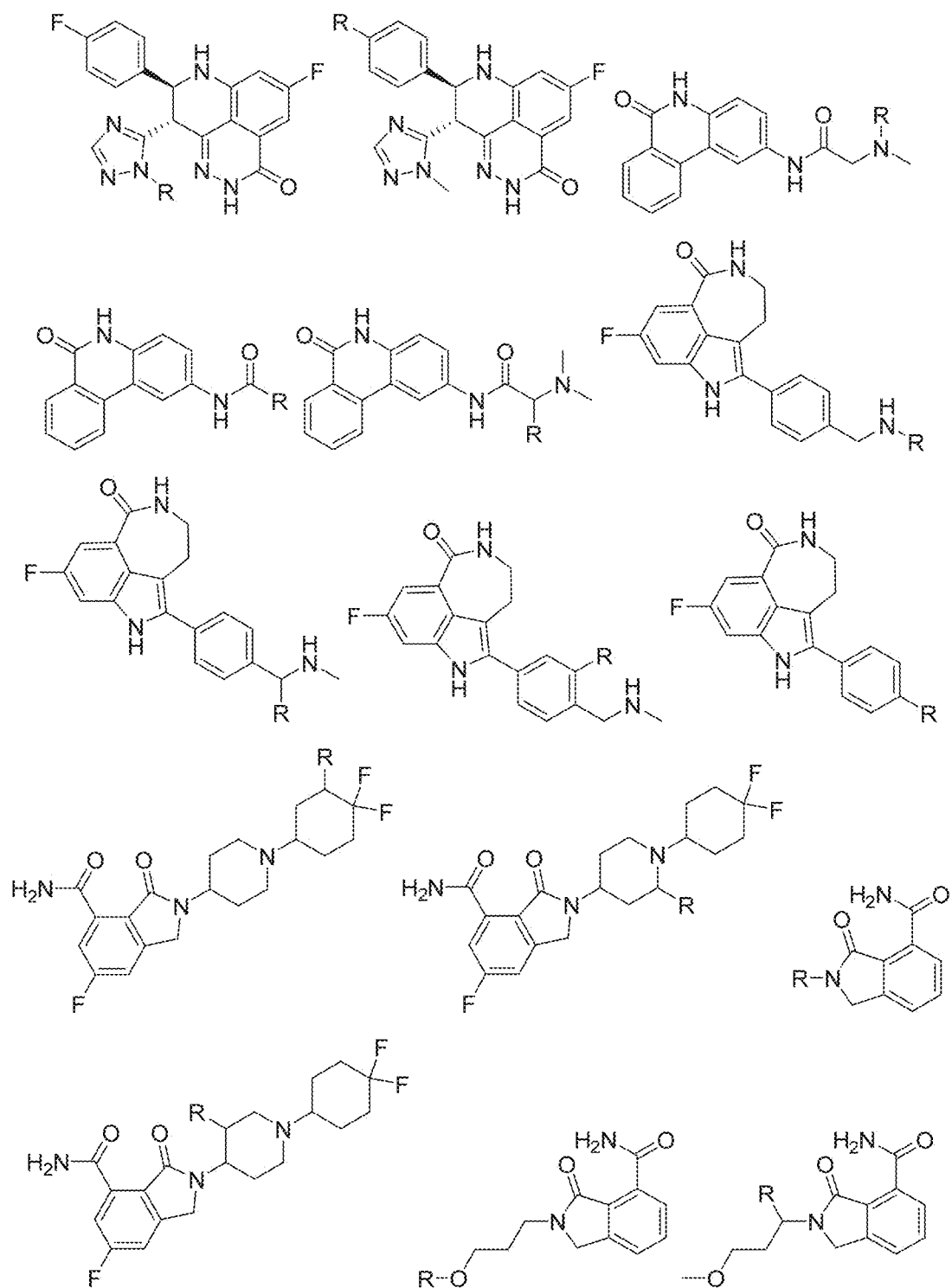

FIG. 2EEEEE
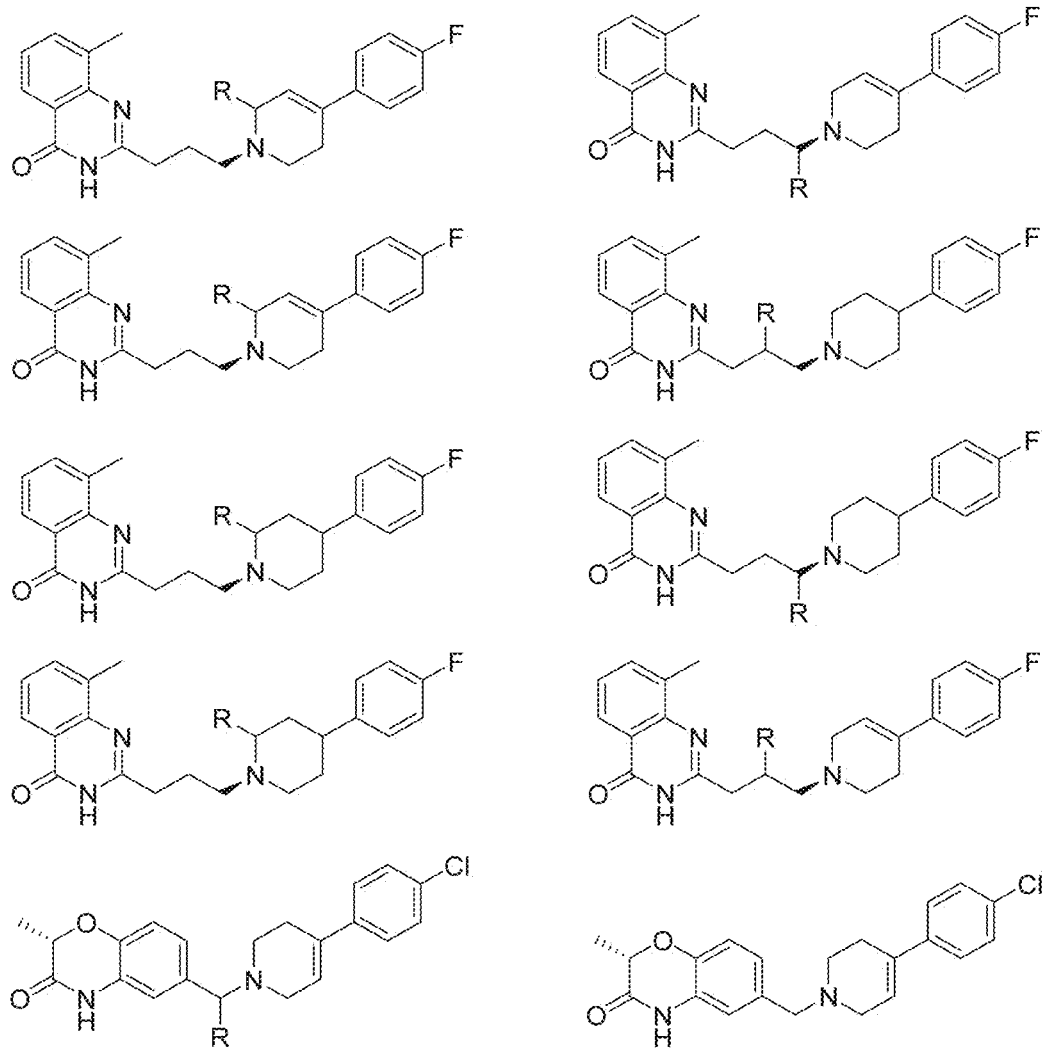
FIG. 2FFFFF
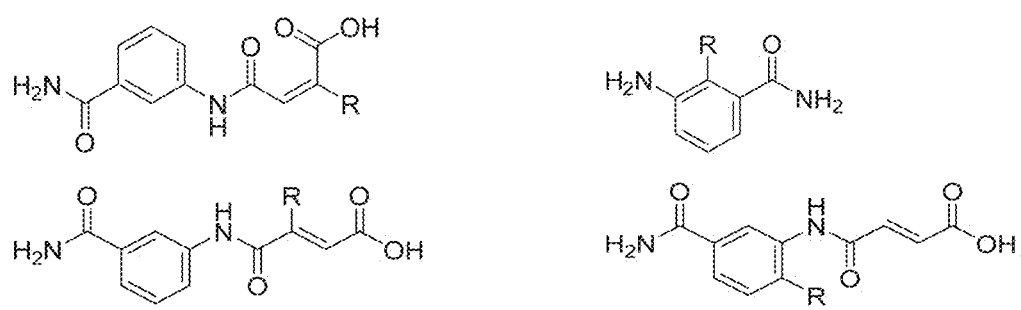

FIG. 2GGGGG
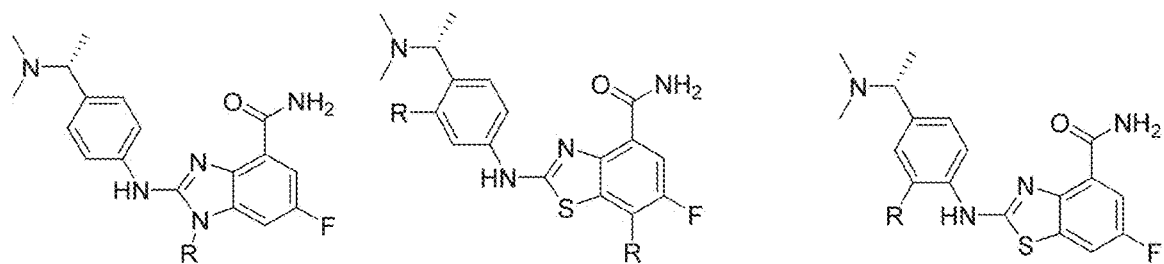
FIG. 2HHHHH
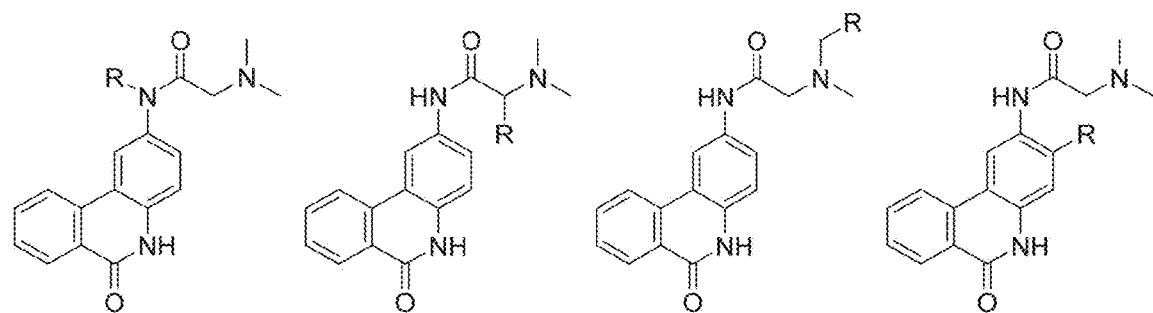
FIG. 2IIIII
FIG. 2JJJJJ
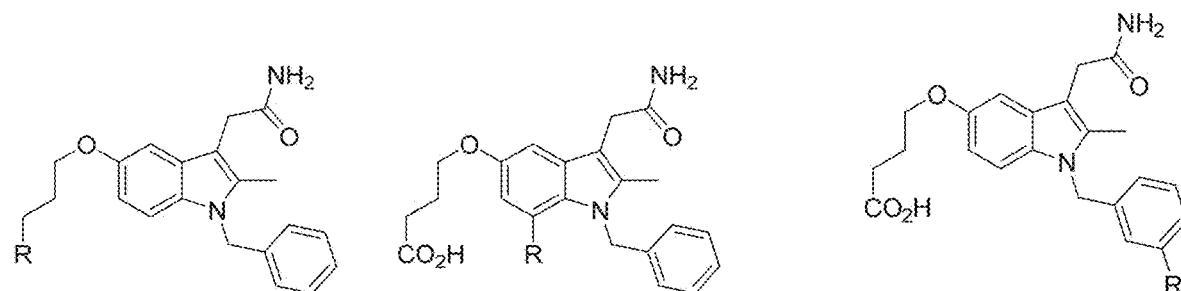

FIG. 2KKKKK
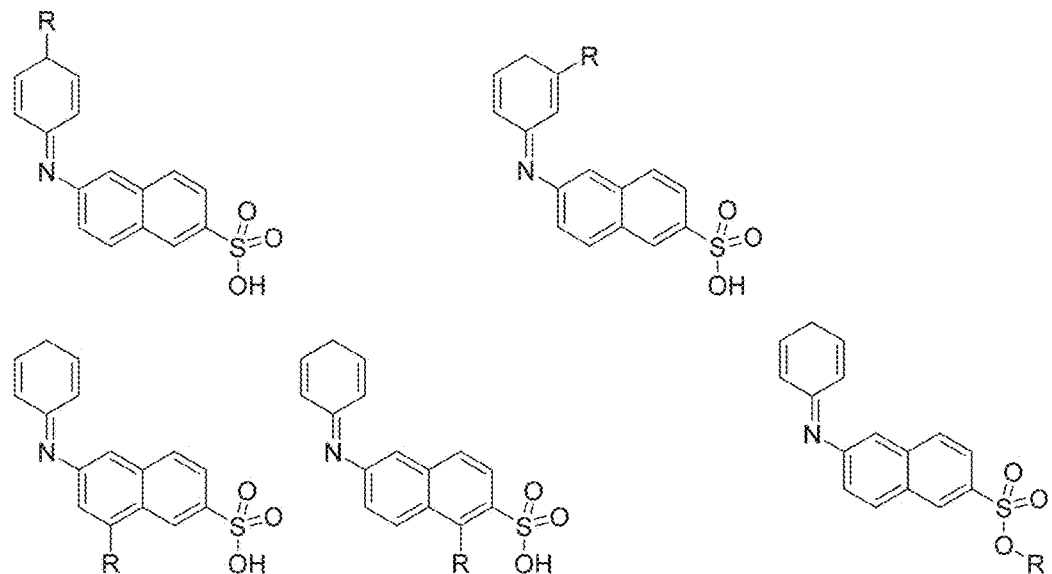
FIG. 2LLLLL
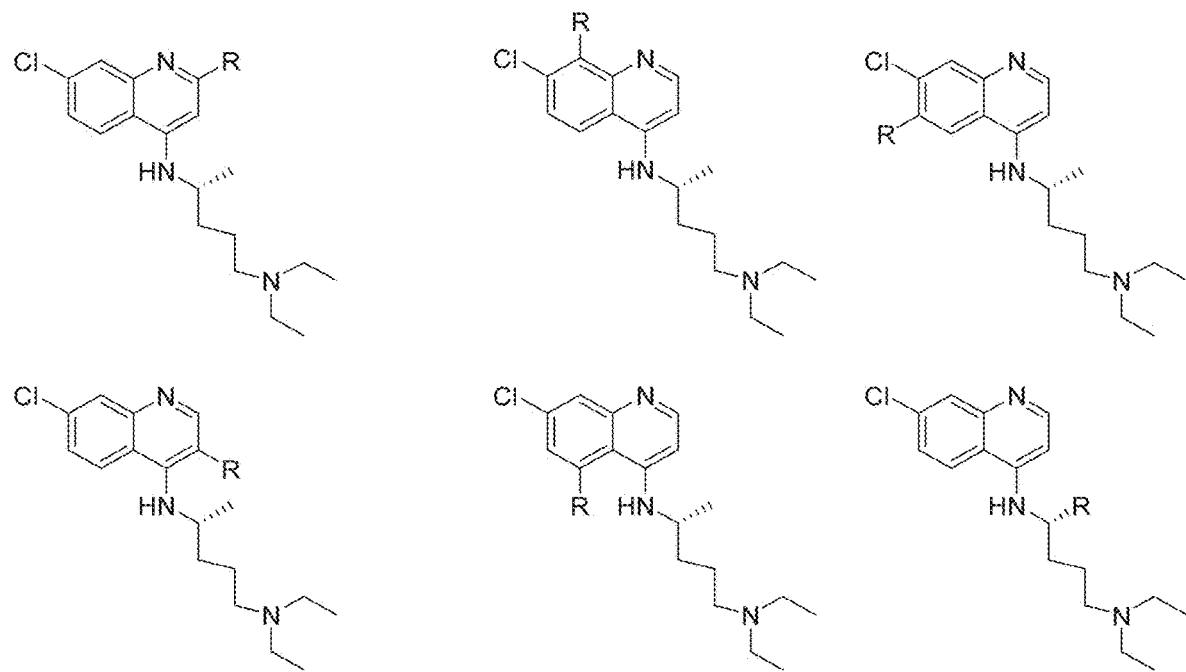

FIG. 2MMMMM
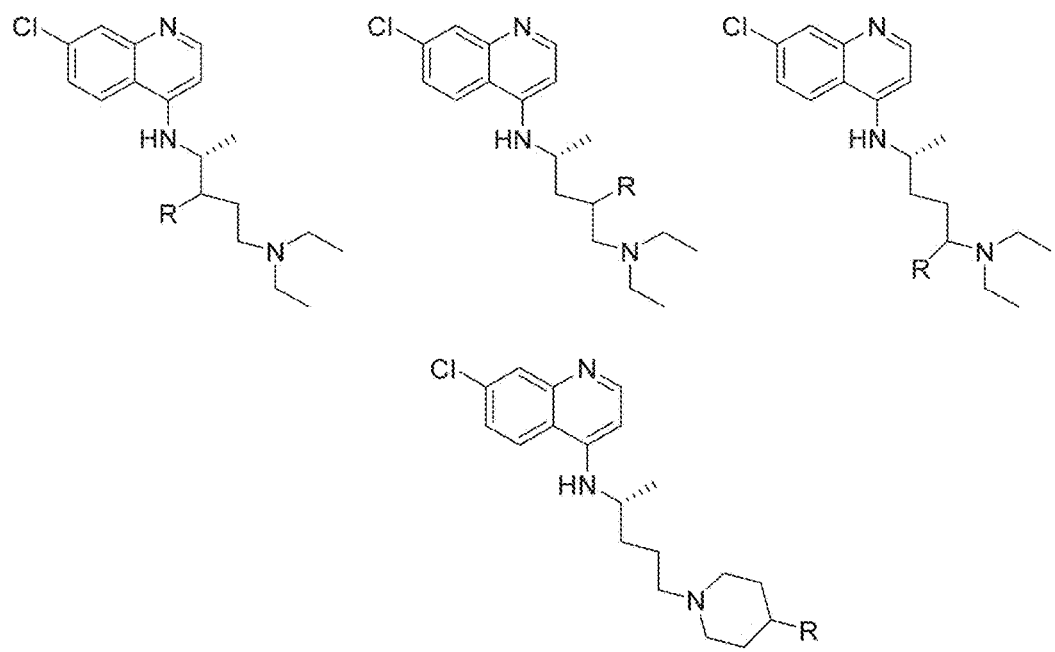
FIG. 2NNNNN
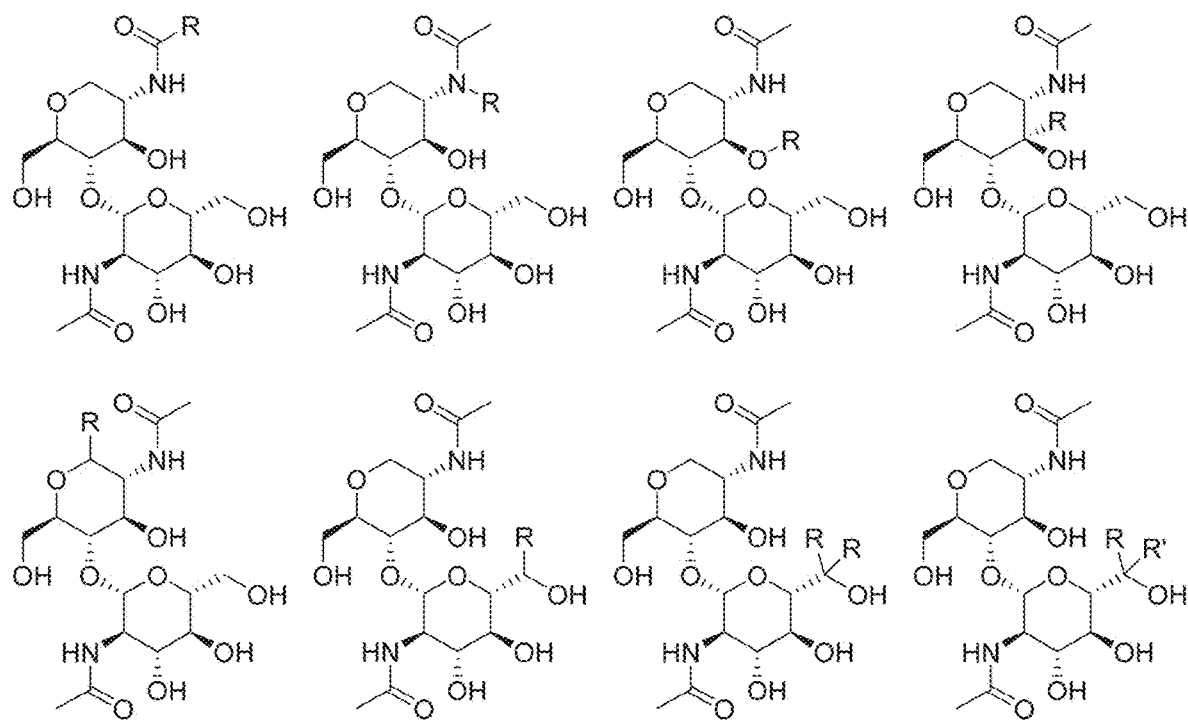

FIG. 2OOOOO
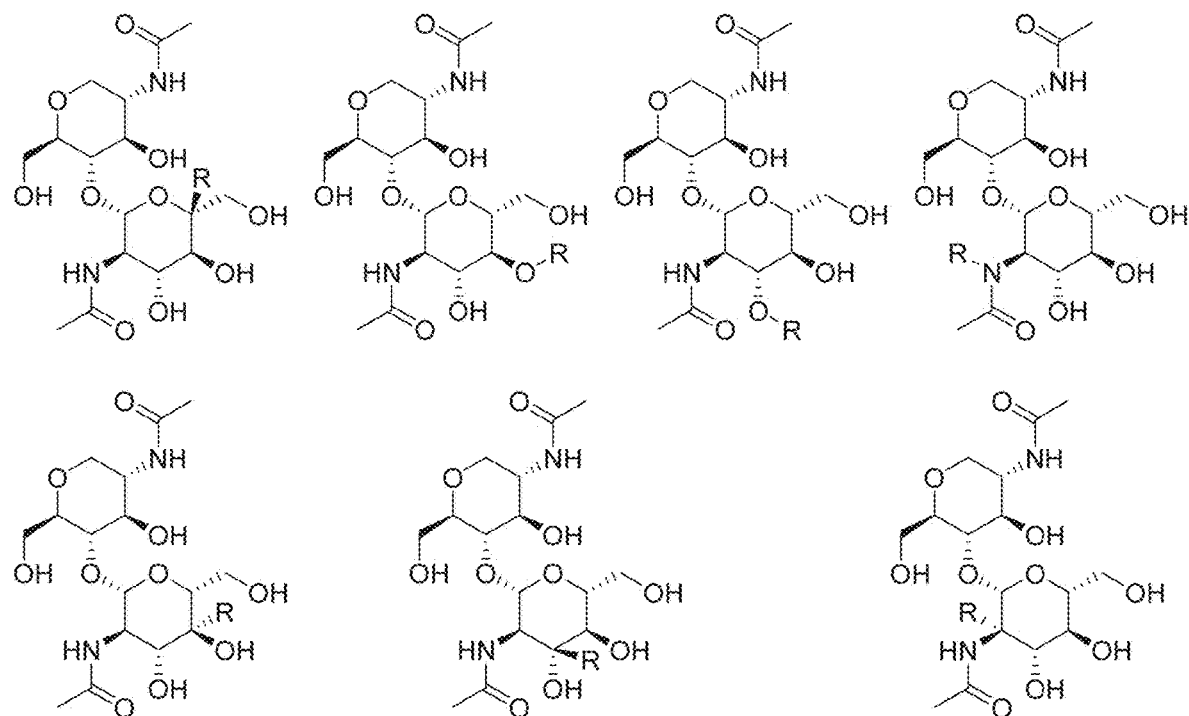
FIG. 2PPPPP
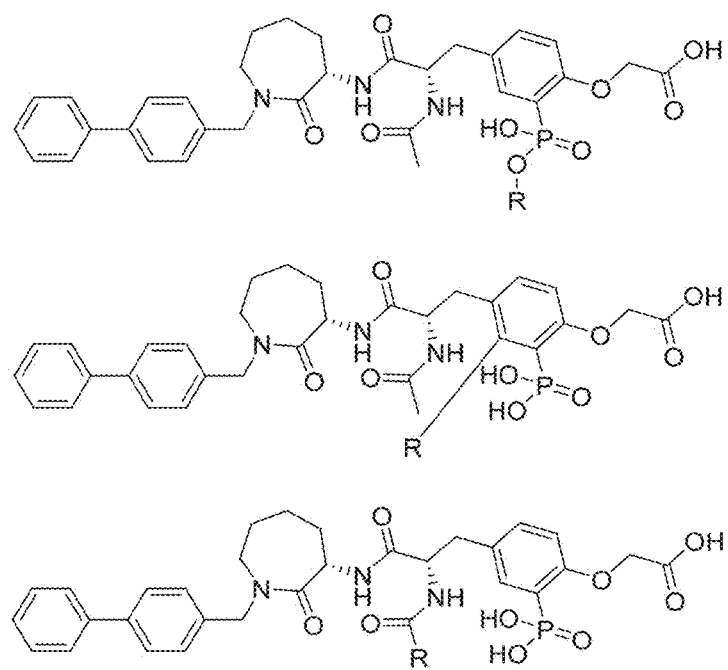

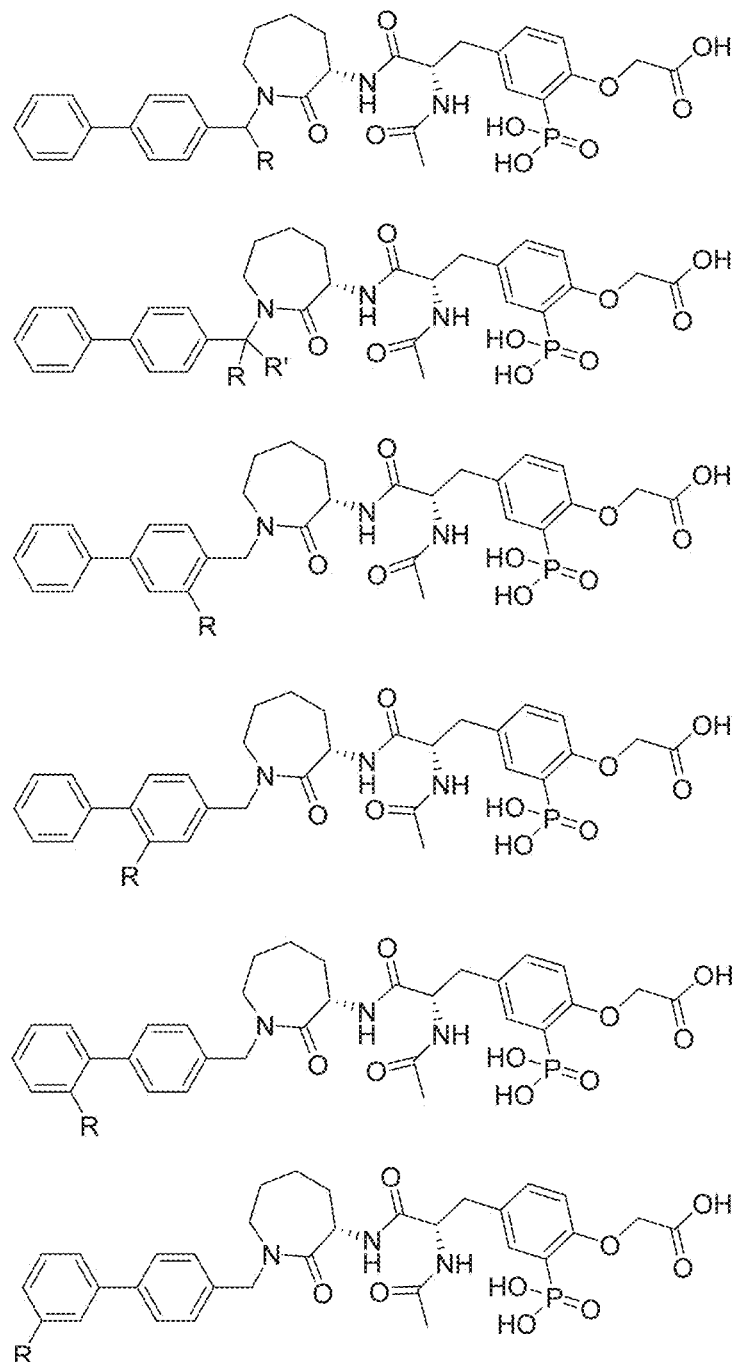
FIG. 2QQQQQ

FIG. 2RRRRR
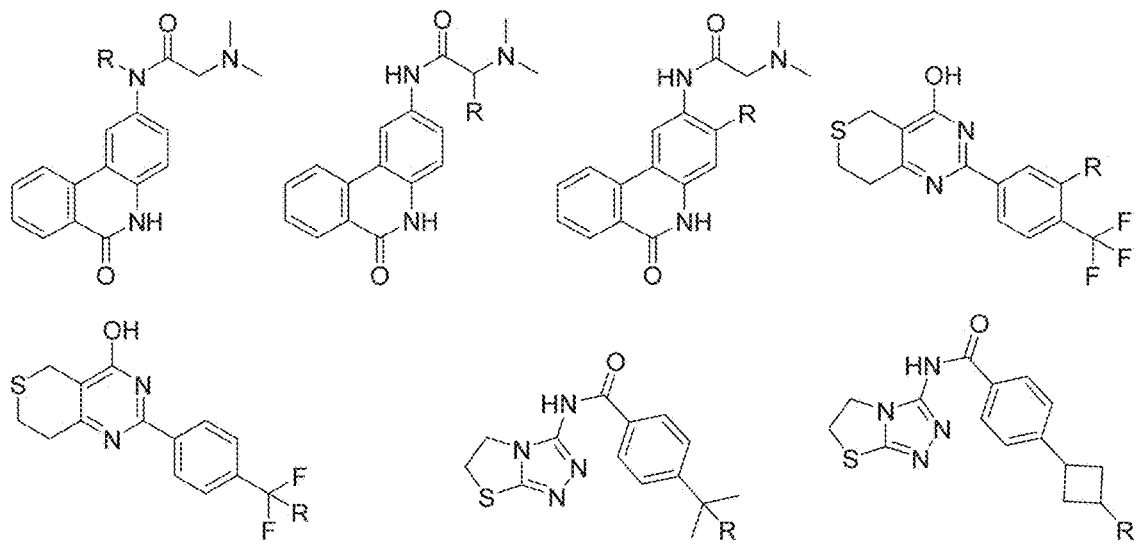
FIG. 2SSSSS
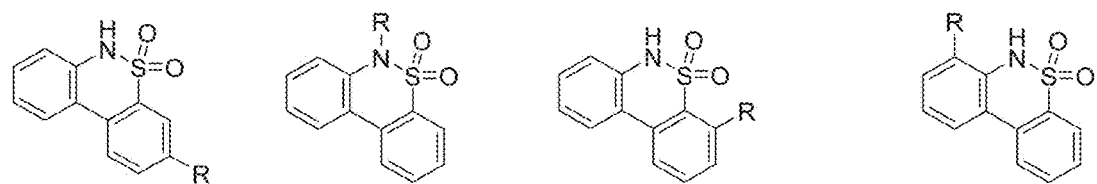
FIG. 2TTTTT
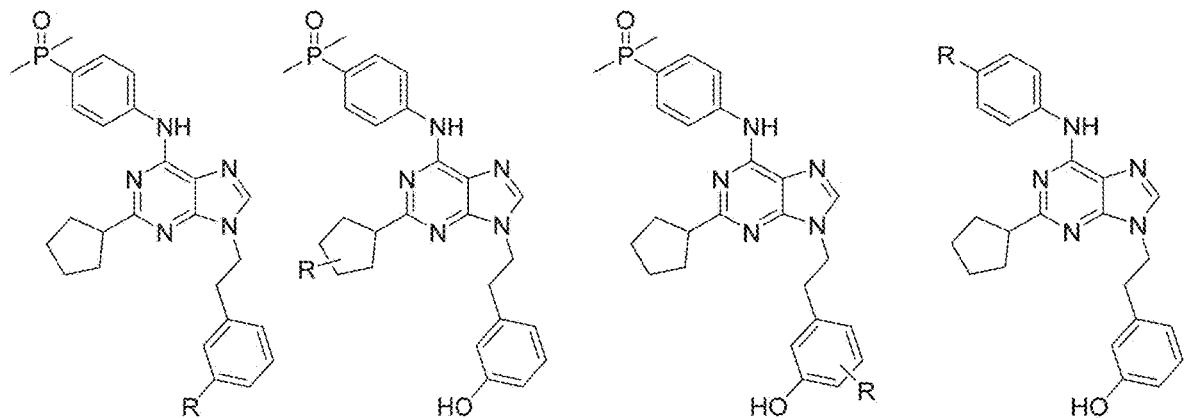

FIG. 2UUUUU
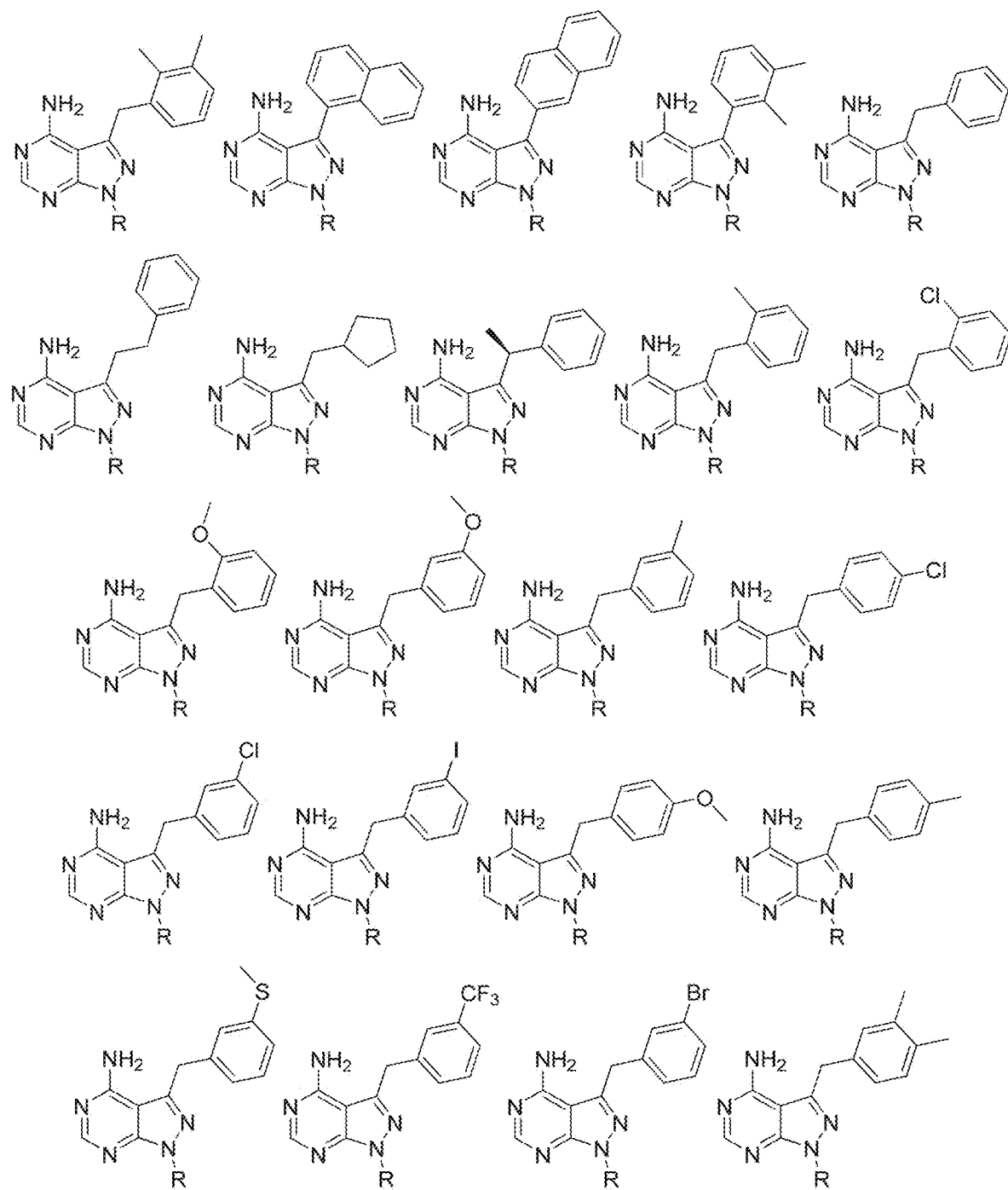

FIG. 2VVVVV
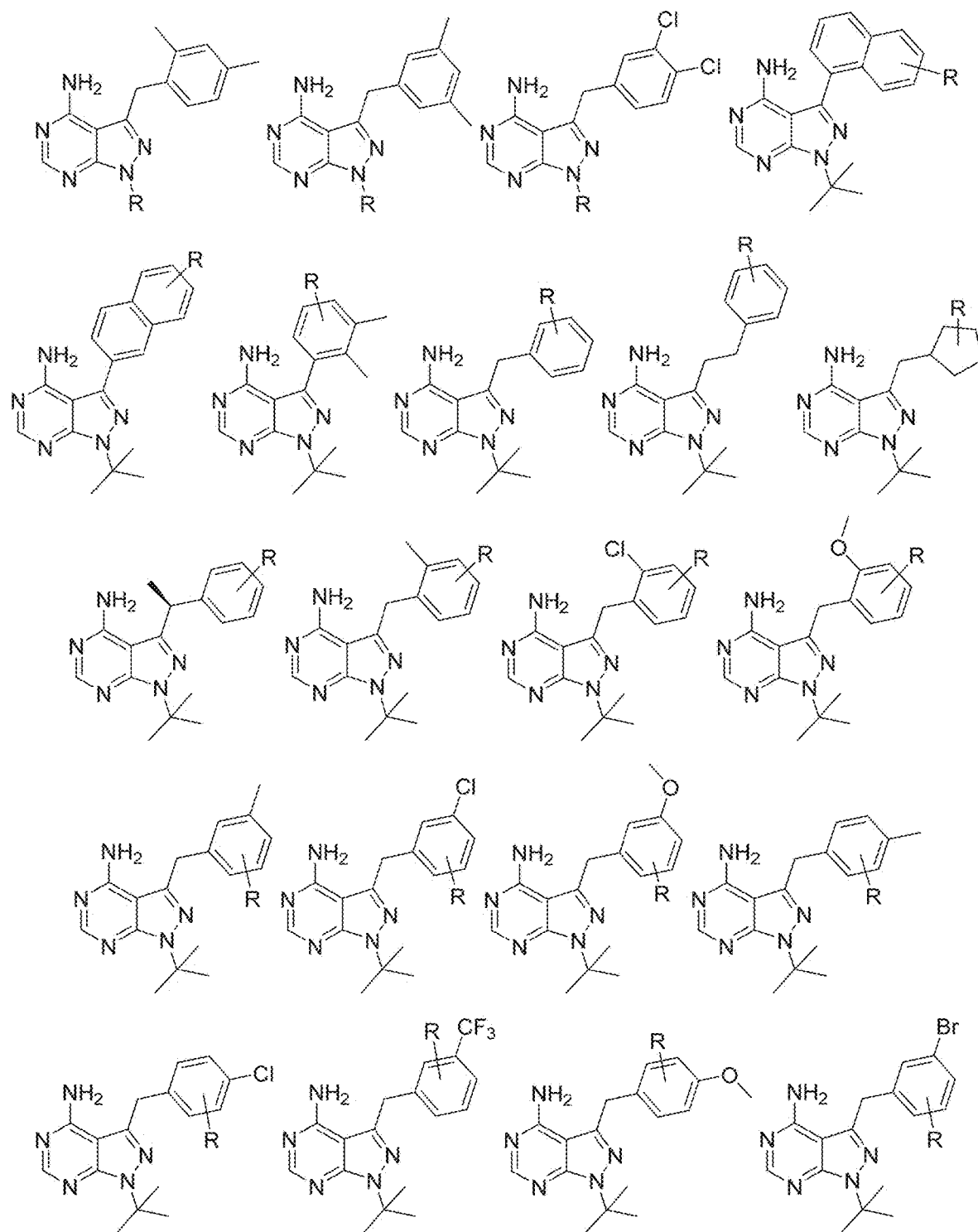

FIG. 2WWWWW
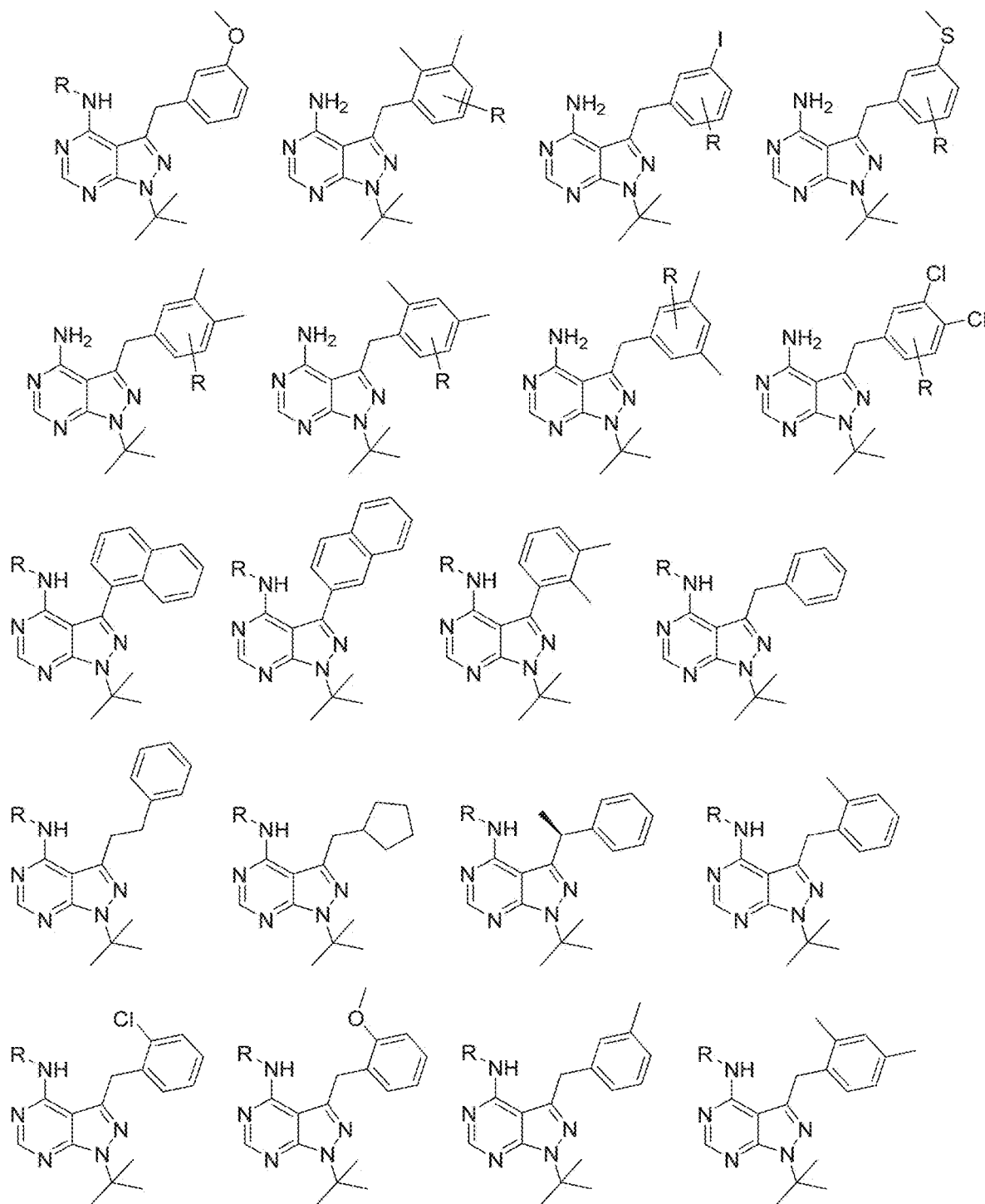

FIG. 2XXXXX
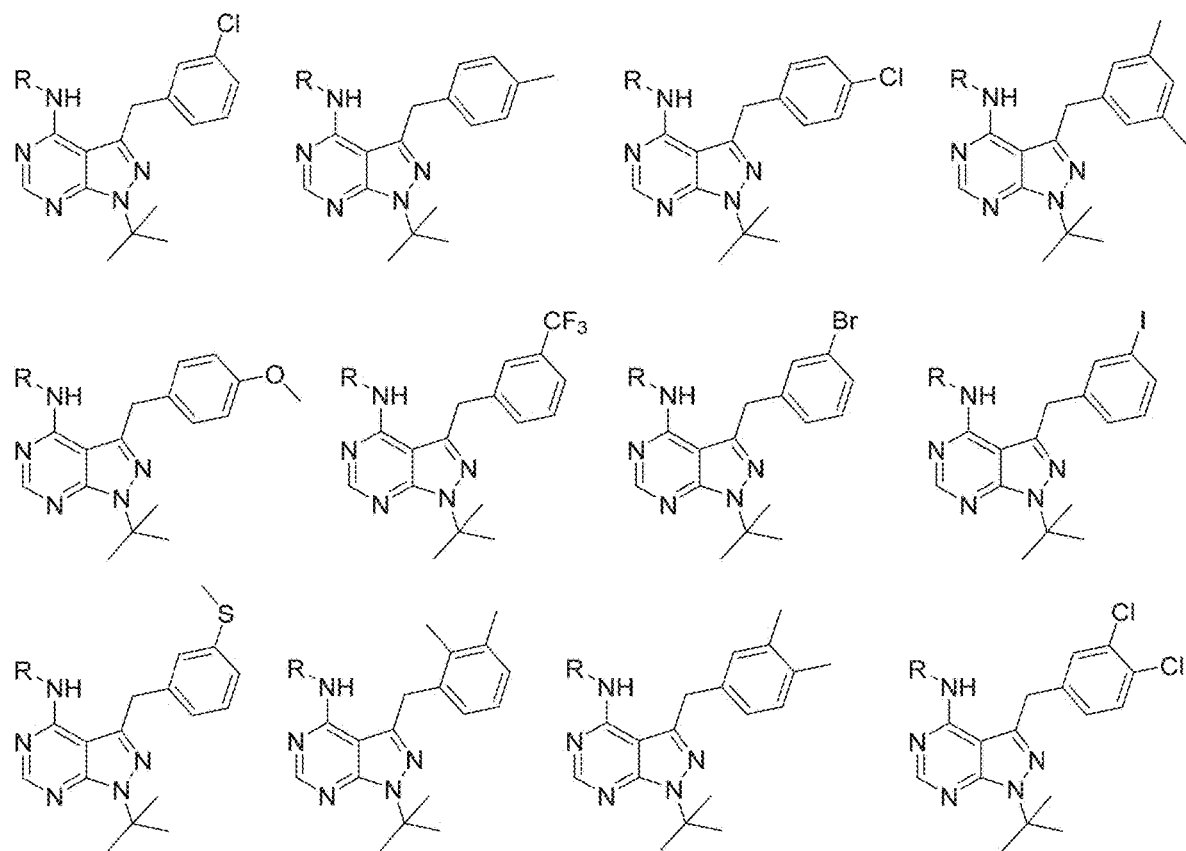
FIG. 2YYYYY
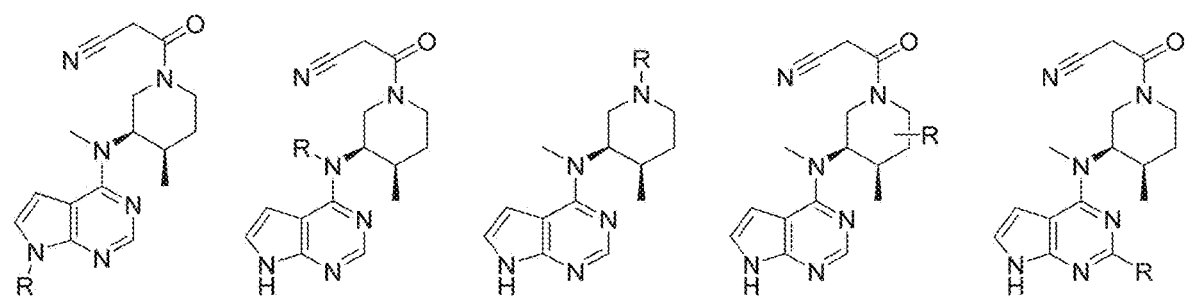

FIG. 2ZZZZZ
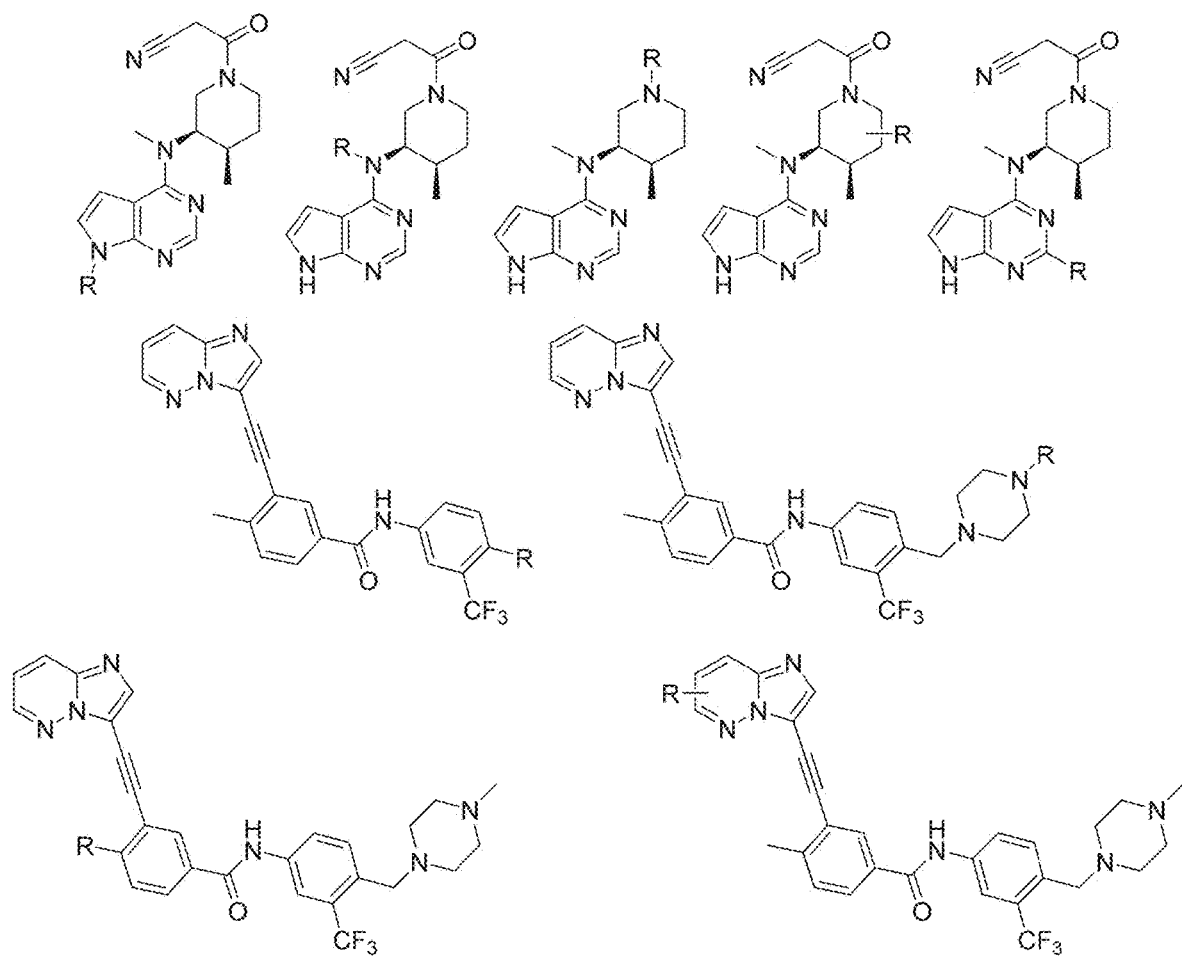
FIG. 3A
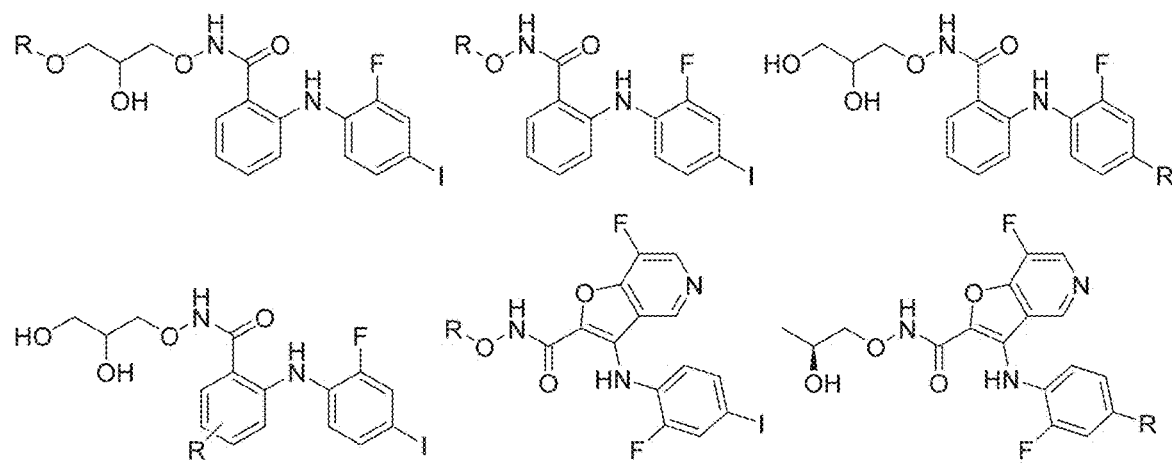

FIG. 3AAA
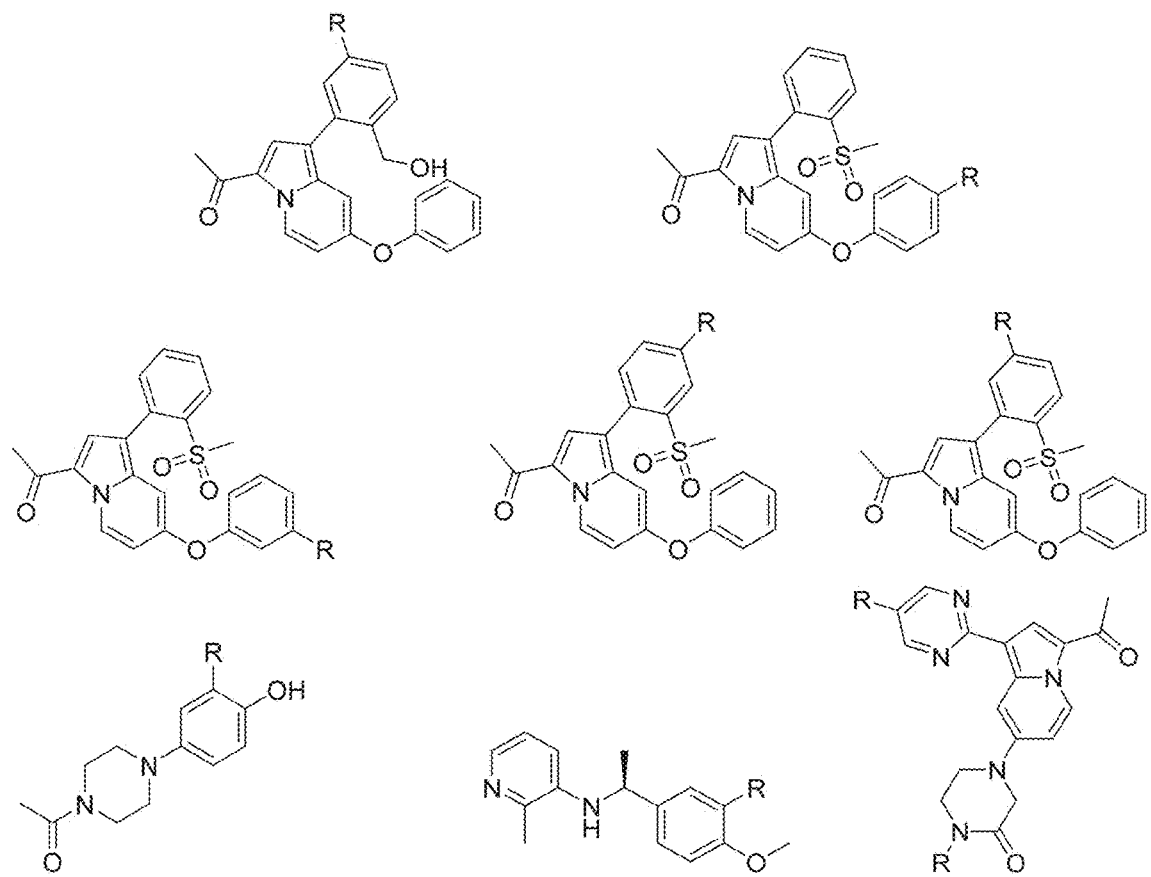
FIG. 3BBB
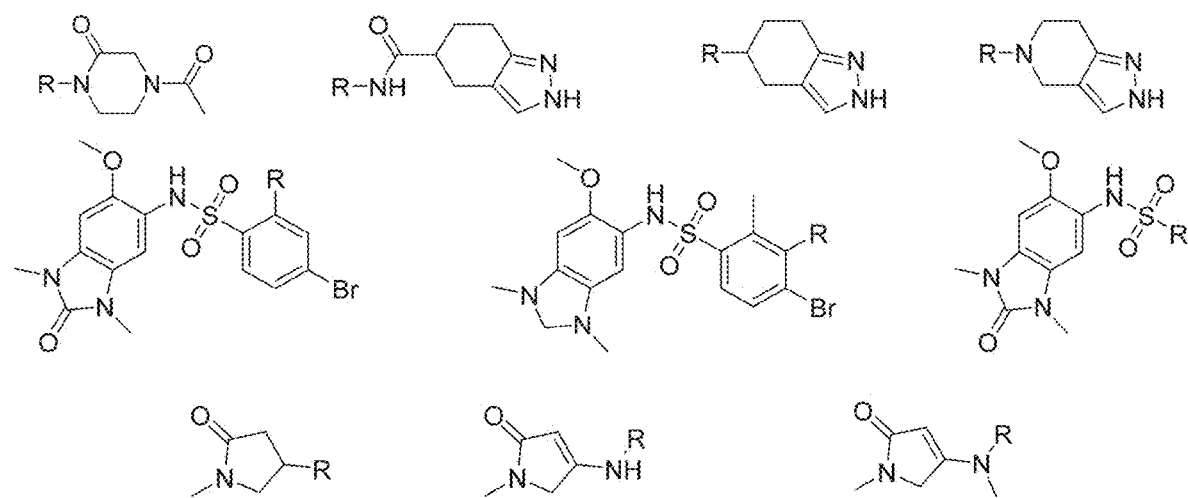

FIG. 3CCC
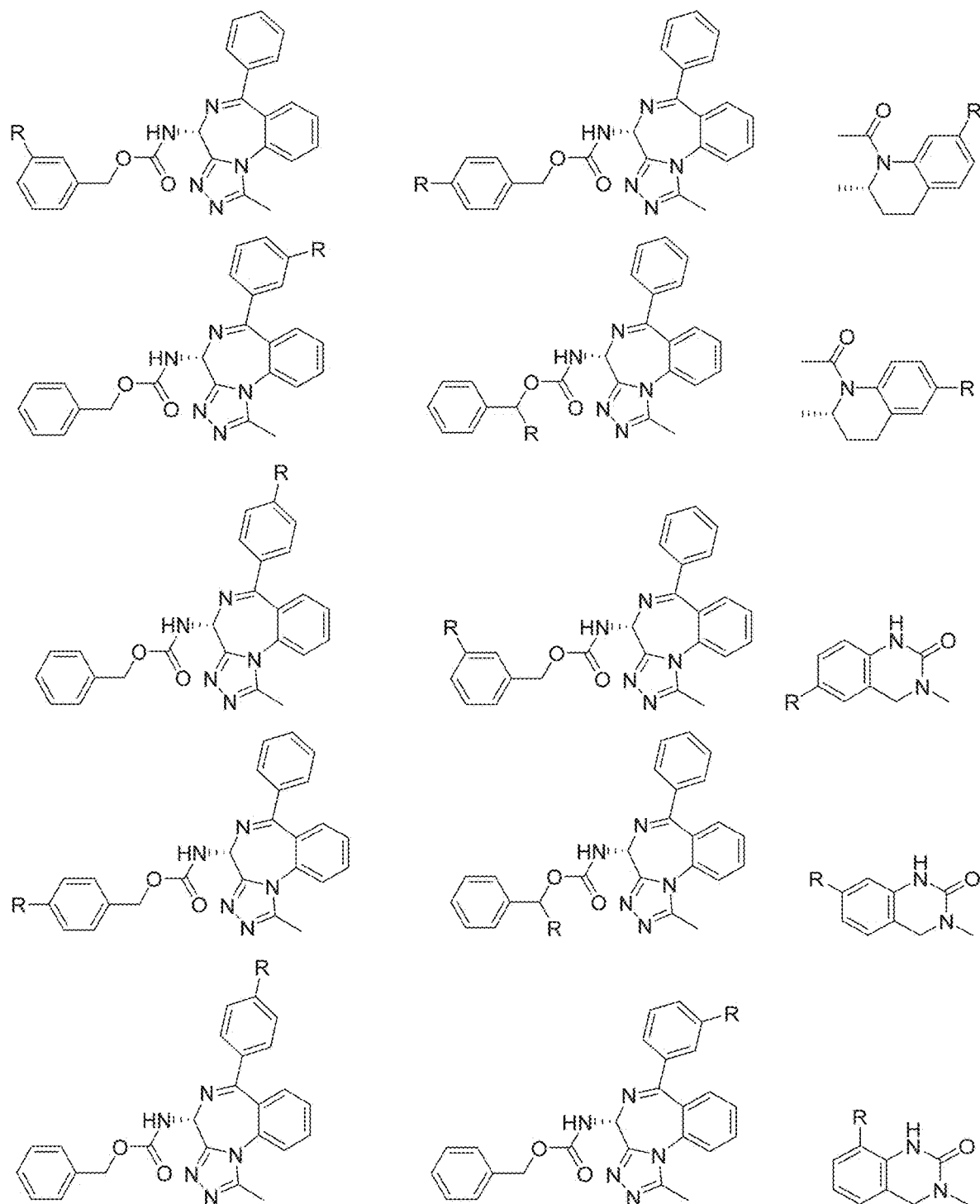

FIG. 3DDD
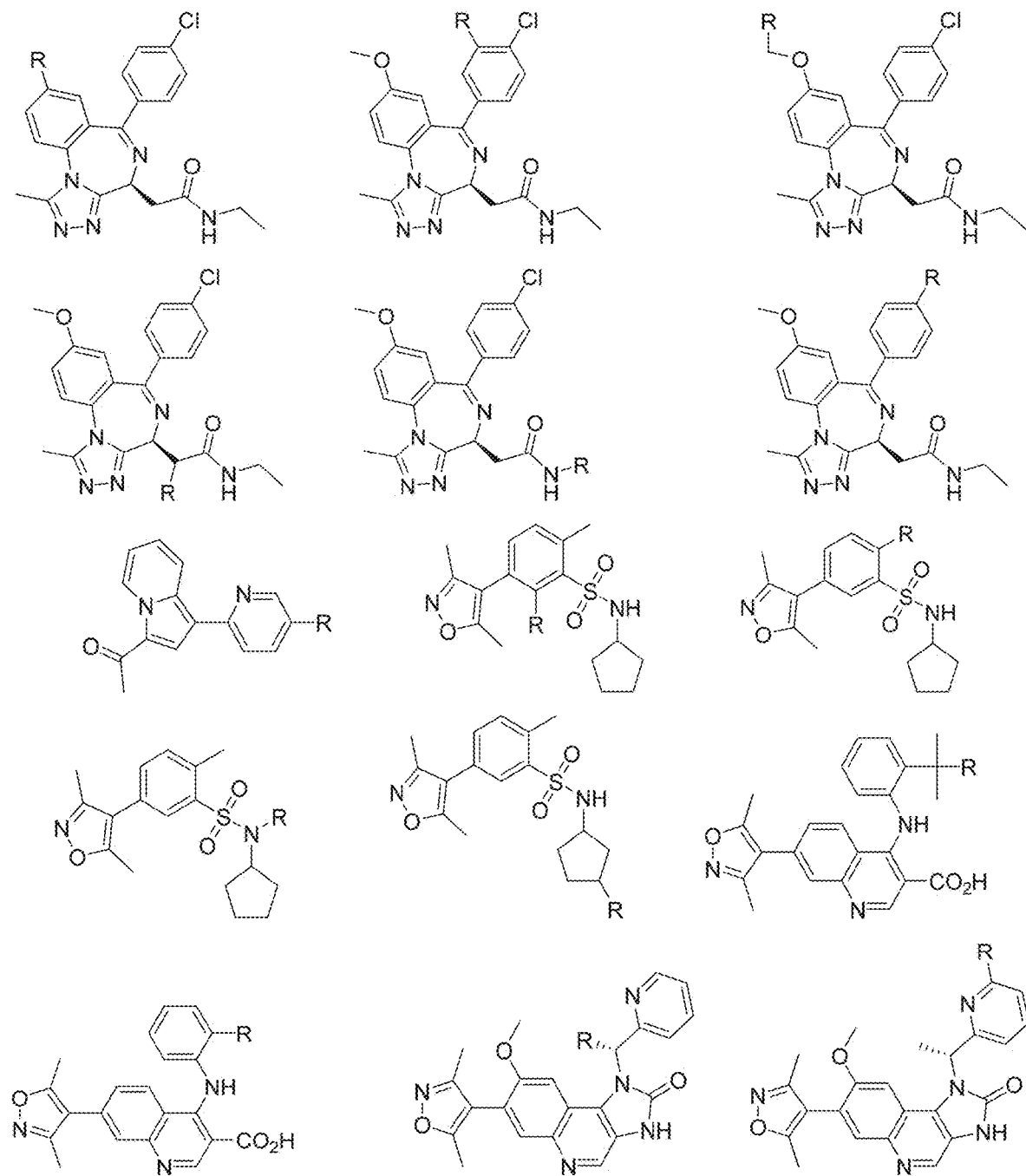

FIG. 3EEE
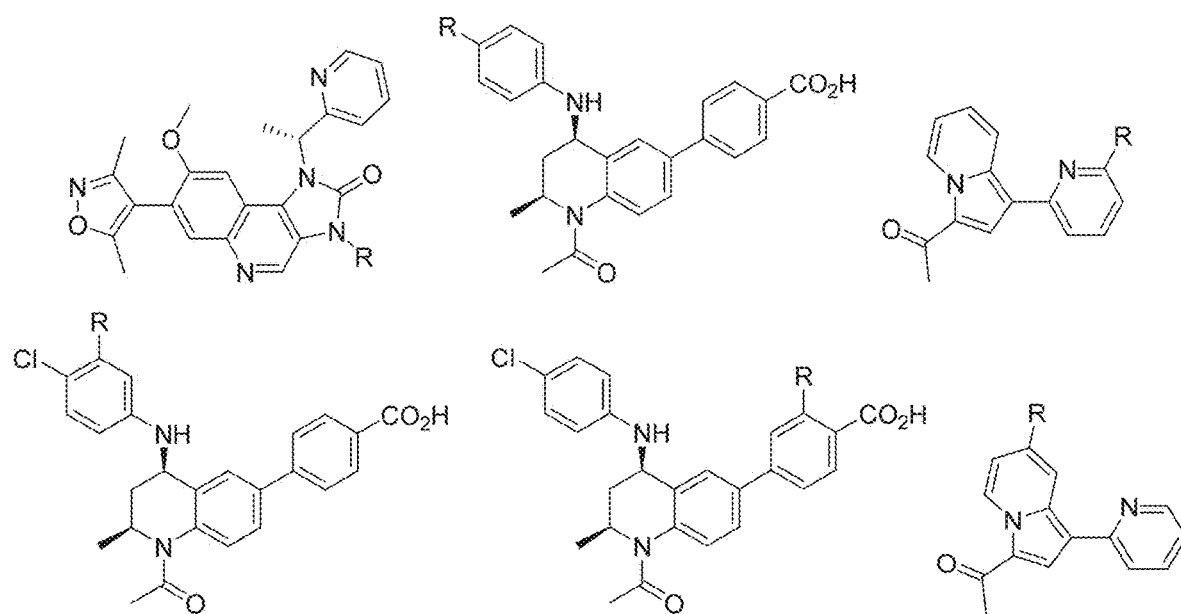
FIG. 3FFF
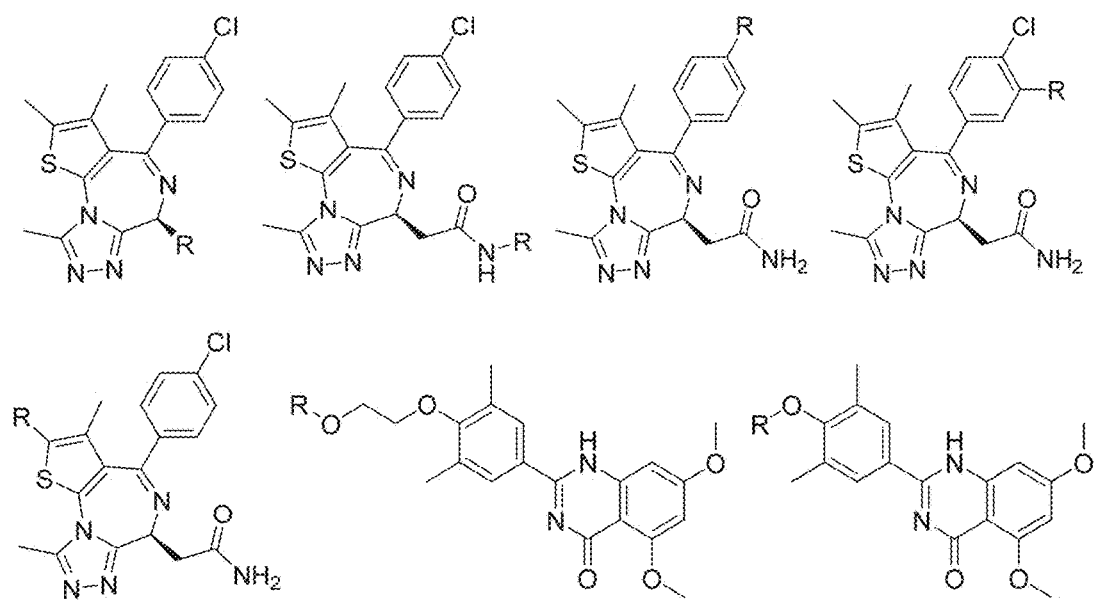

FIG. 3GGG
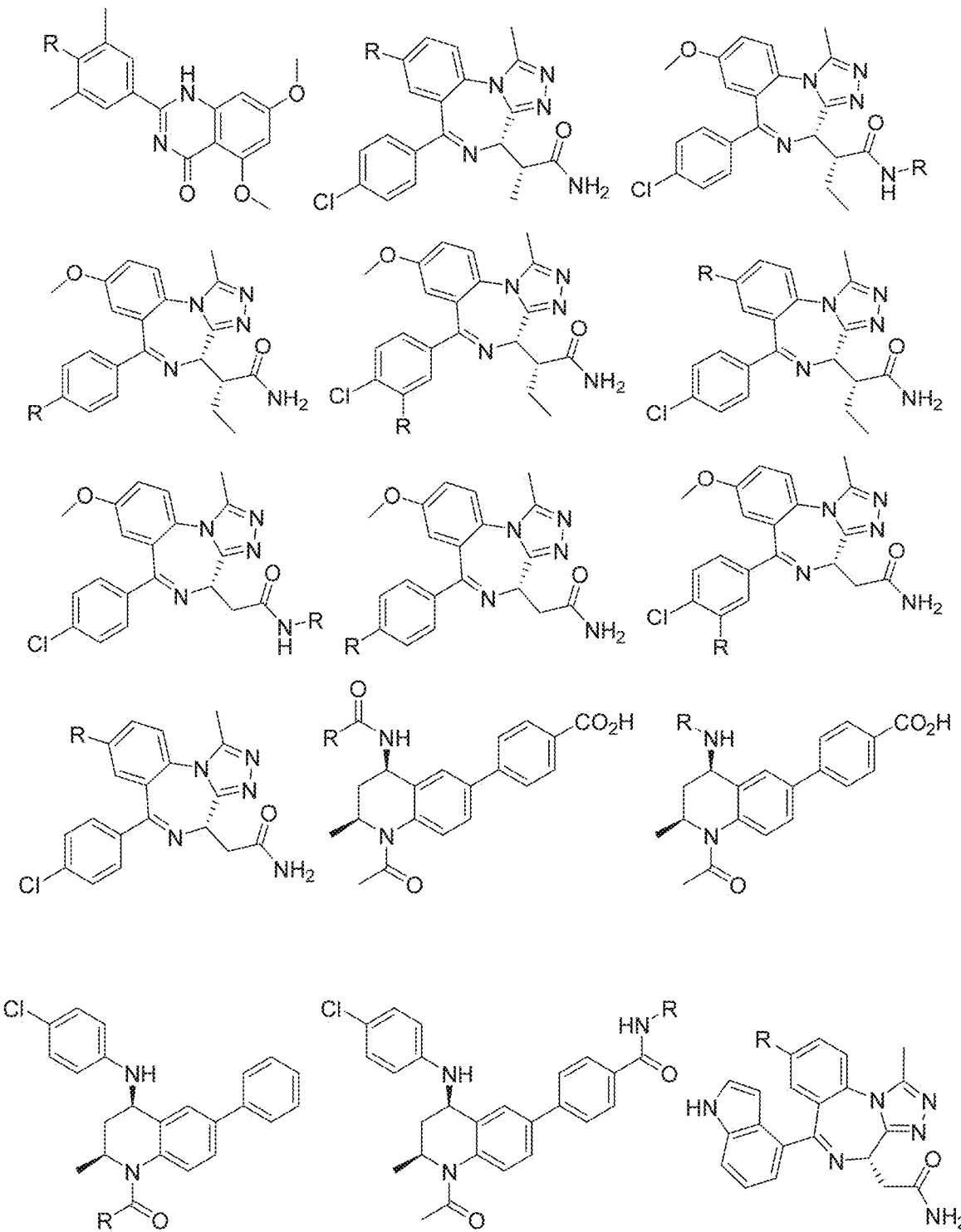

FIG. 3HHH
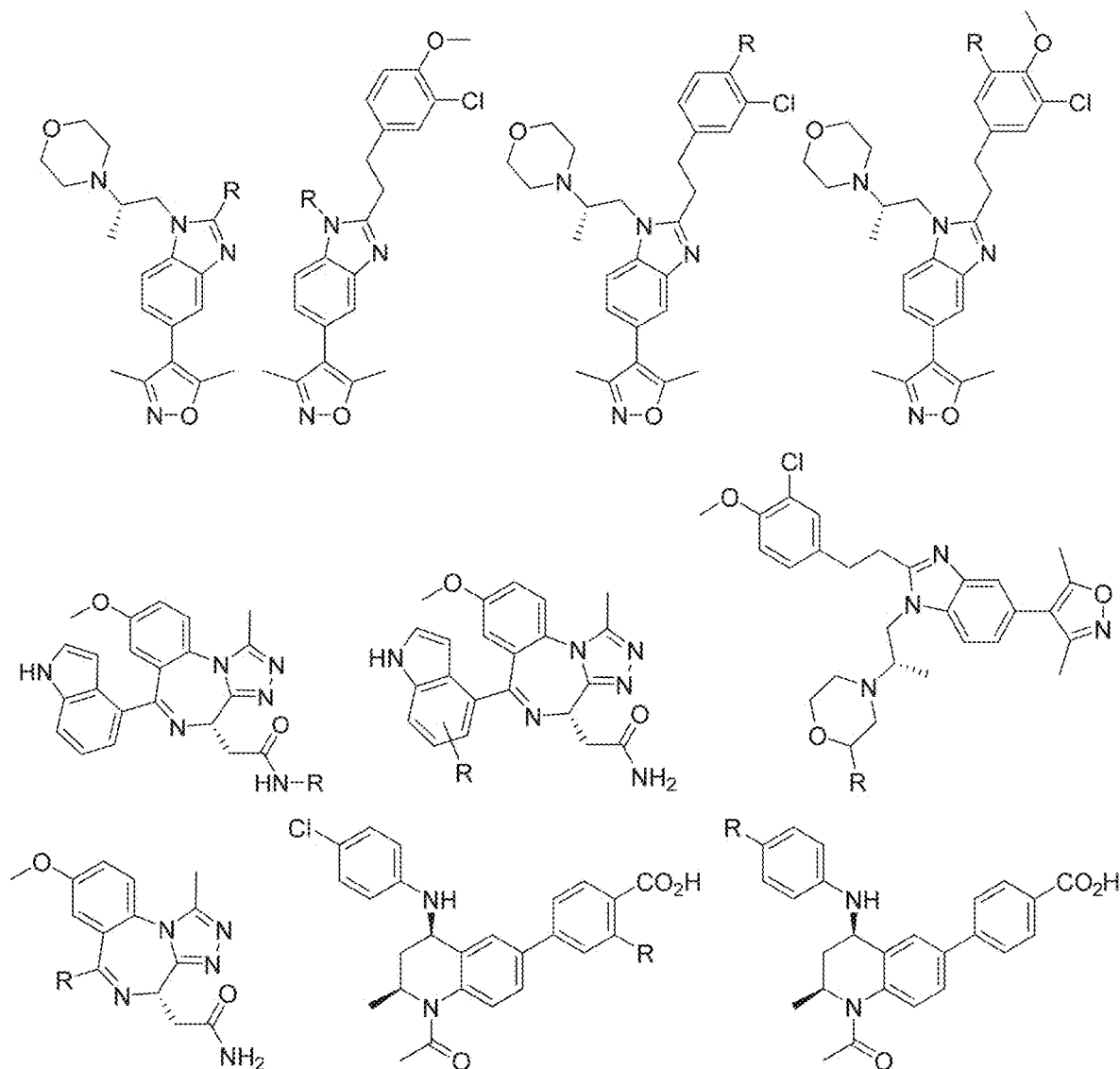
FIG. 3III
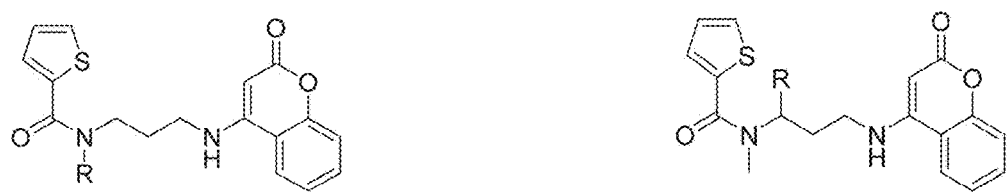

FIG. 3JJJ
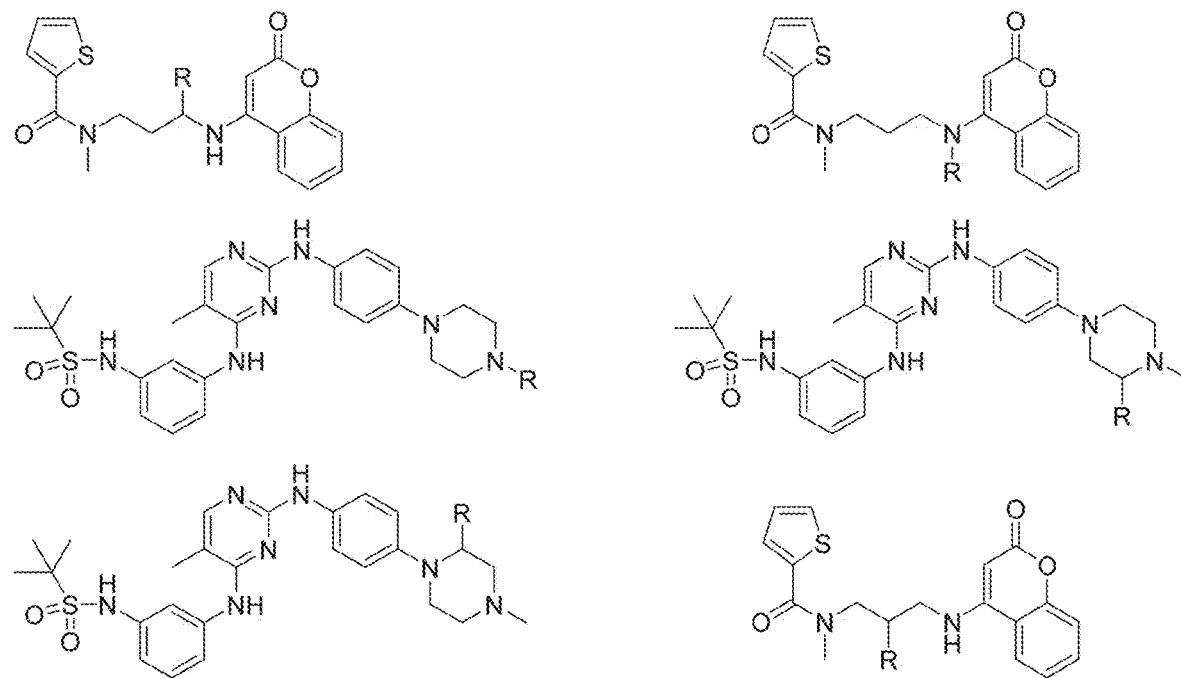
FIG. 3KKK
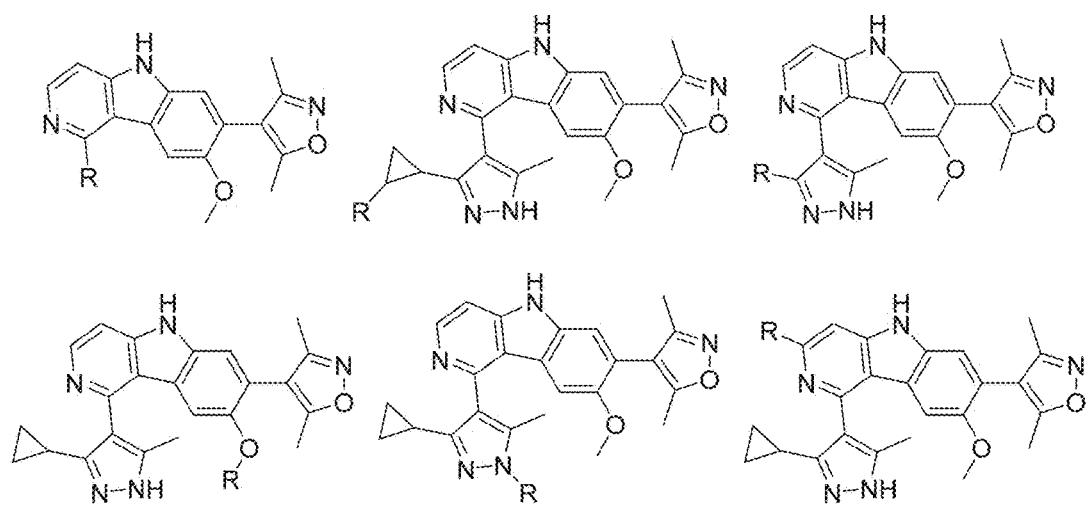

FIG. 3LLL
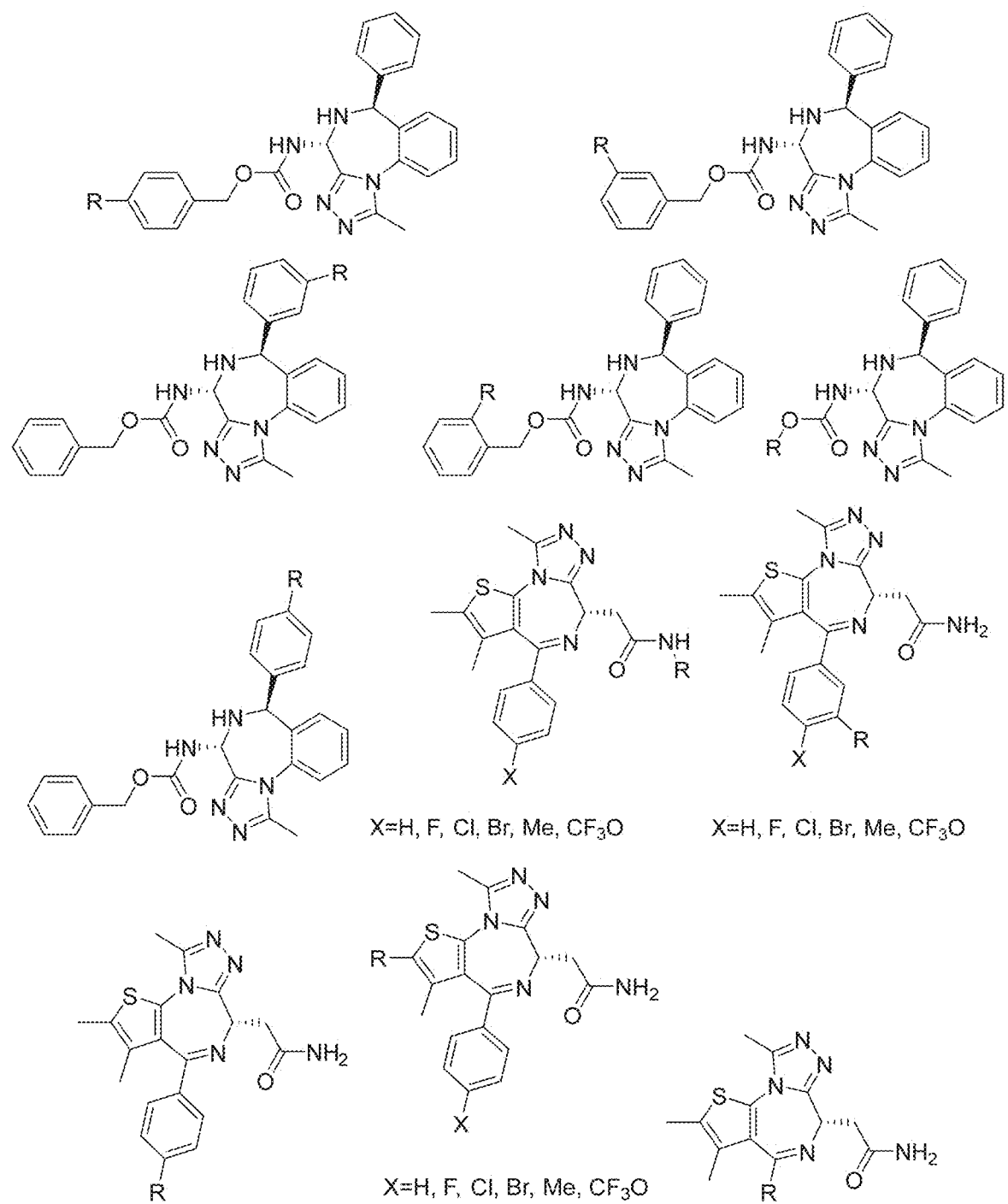

FIG. 3MMM
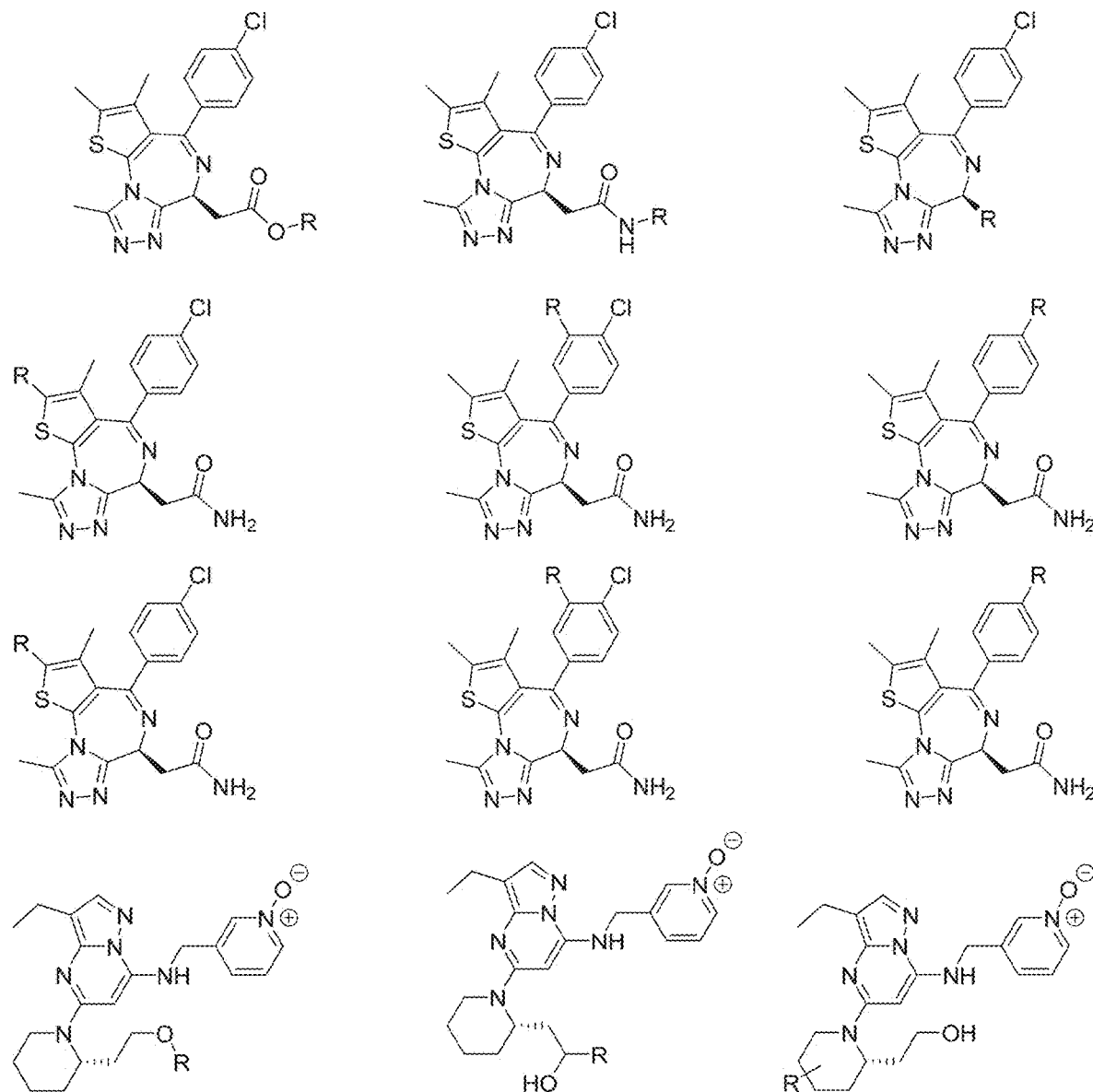
FIG. 3NNN
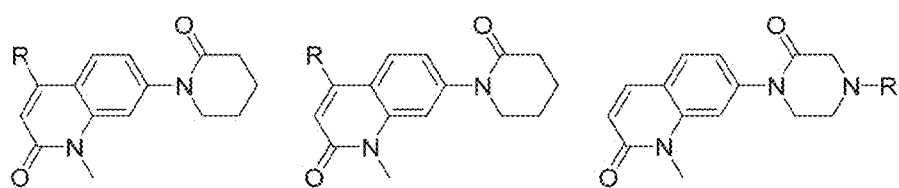

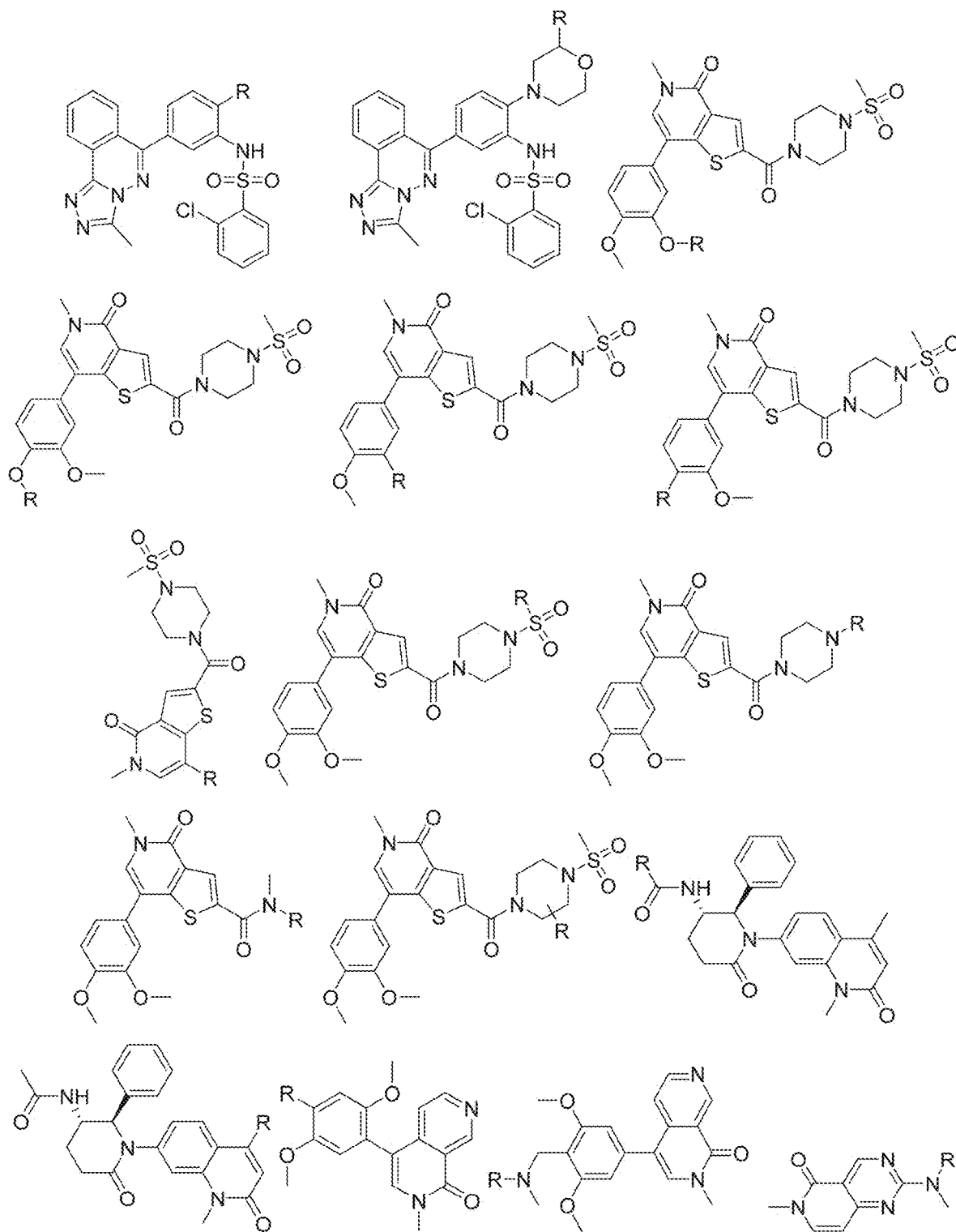
FIG. 3000

FIG. 3PPP
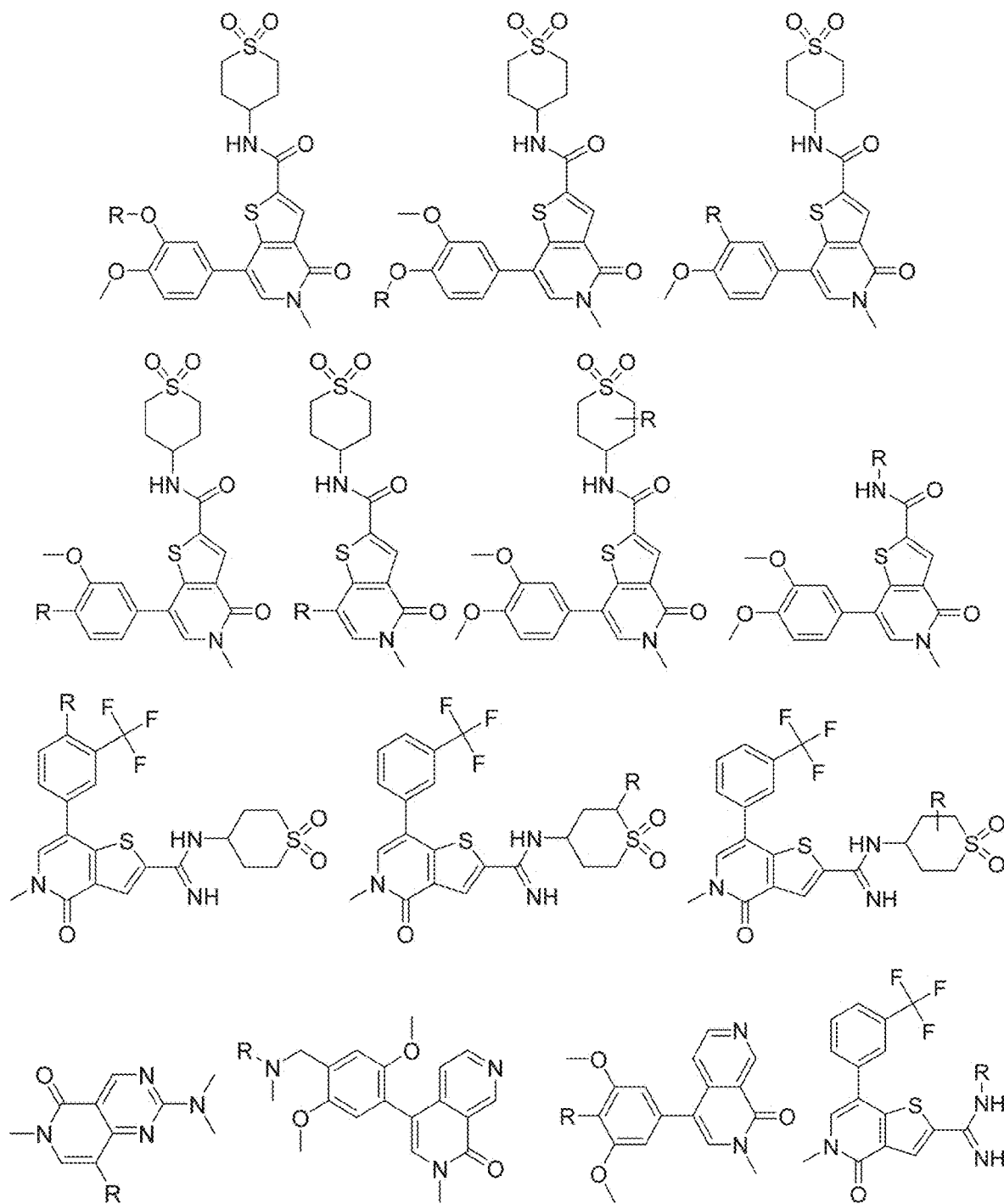

FIG. 3QQQ
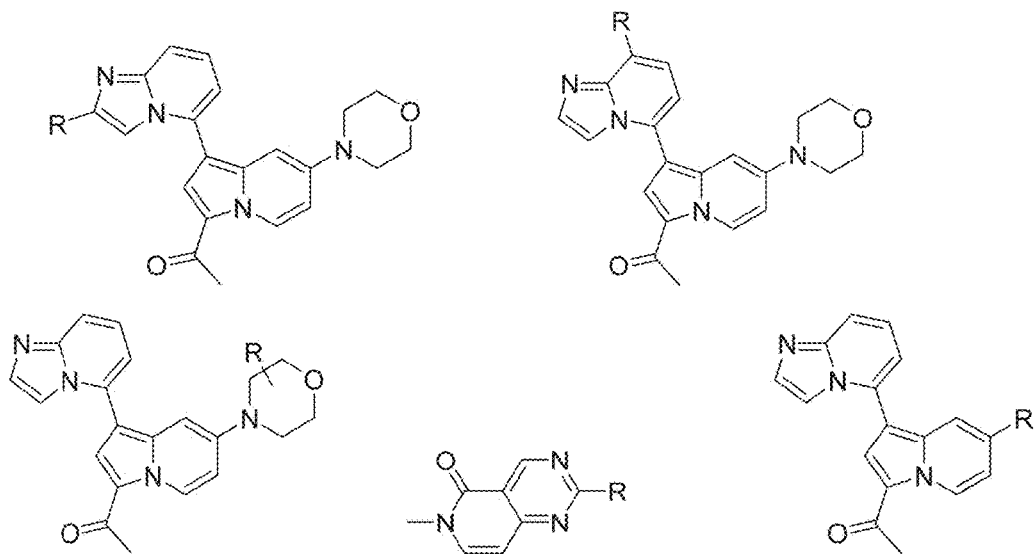
FIG. 3RRR
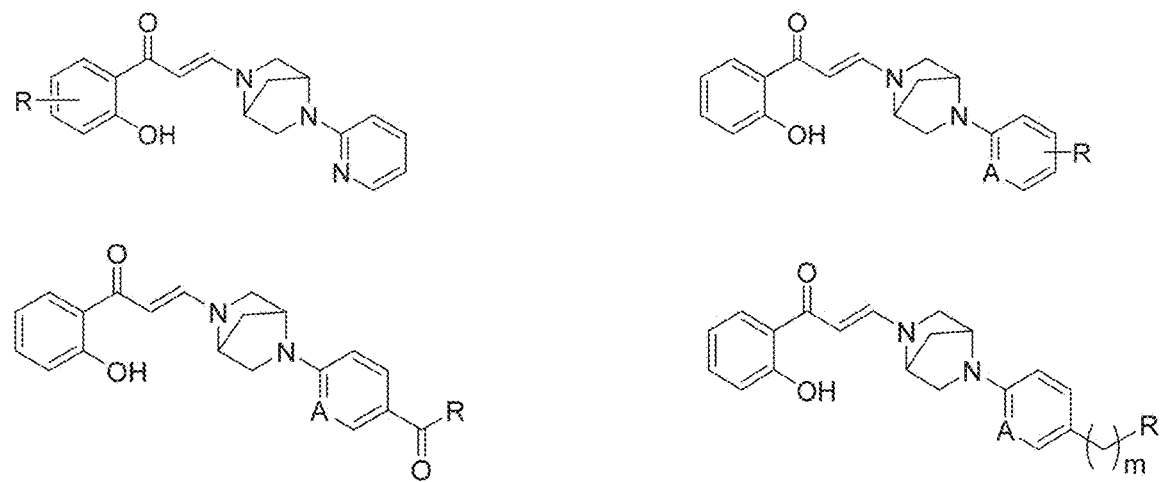
FIG. 3SSS

FIG. 3TTT
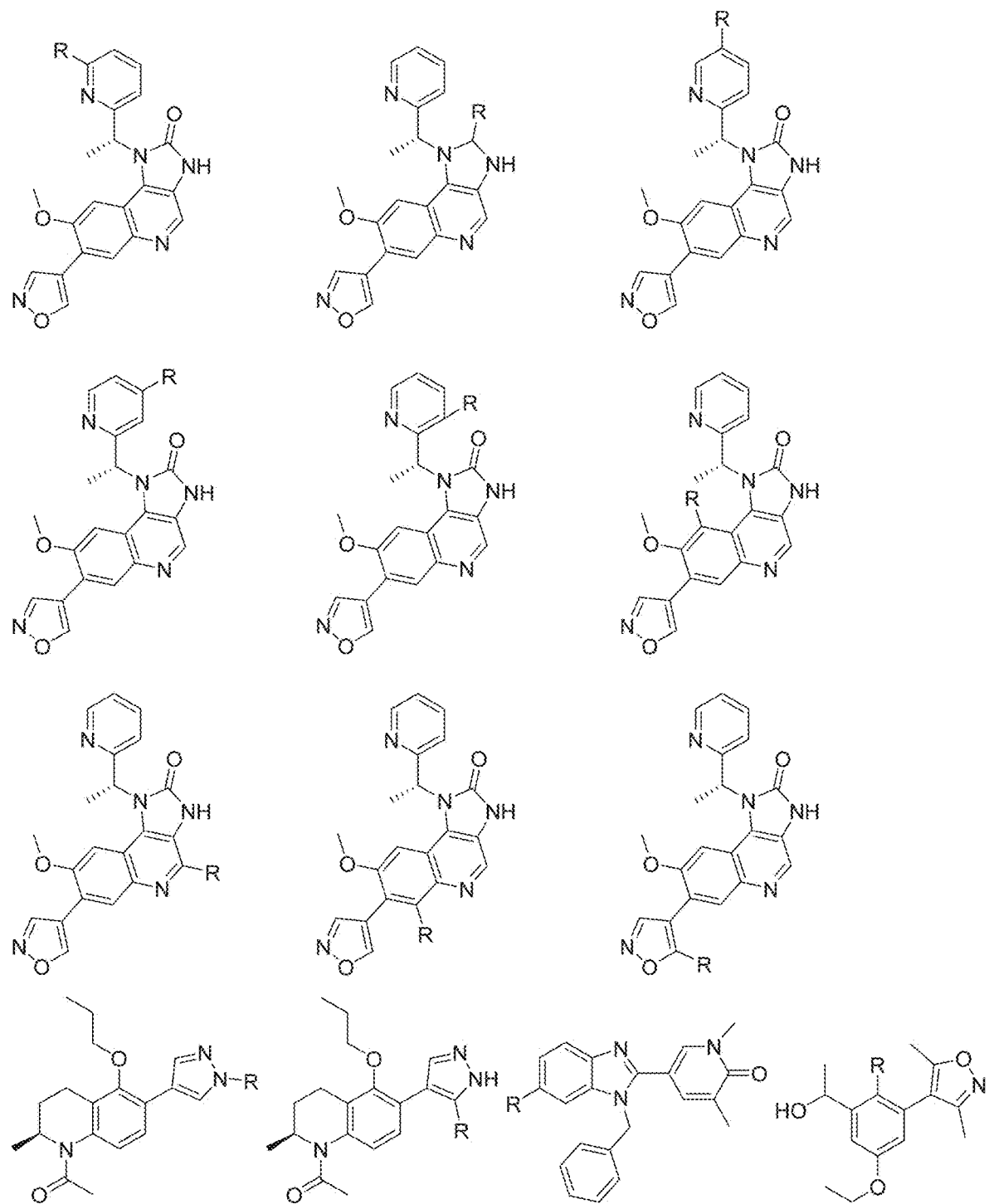

FIG. 3UUU
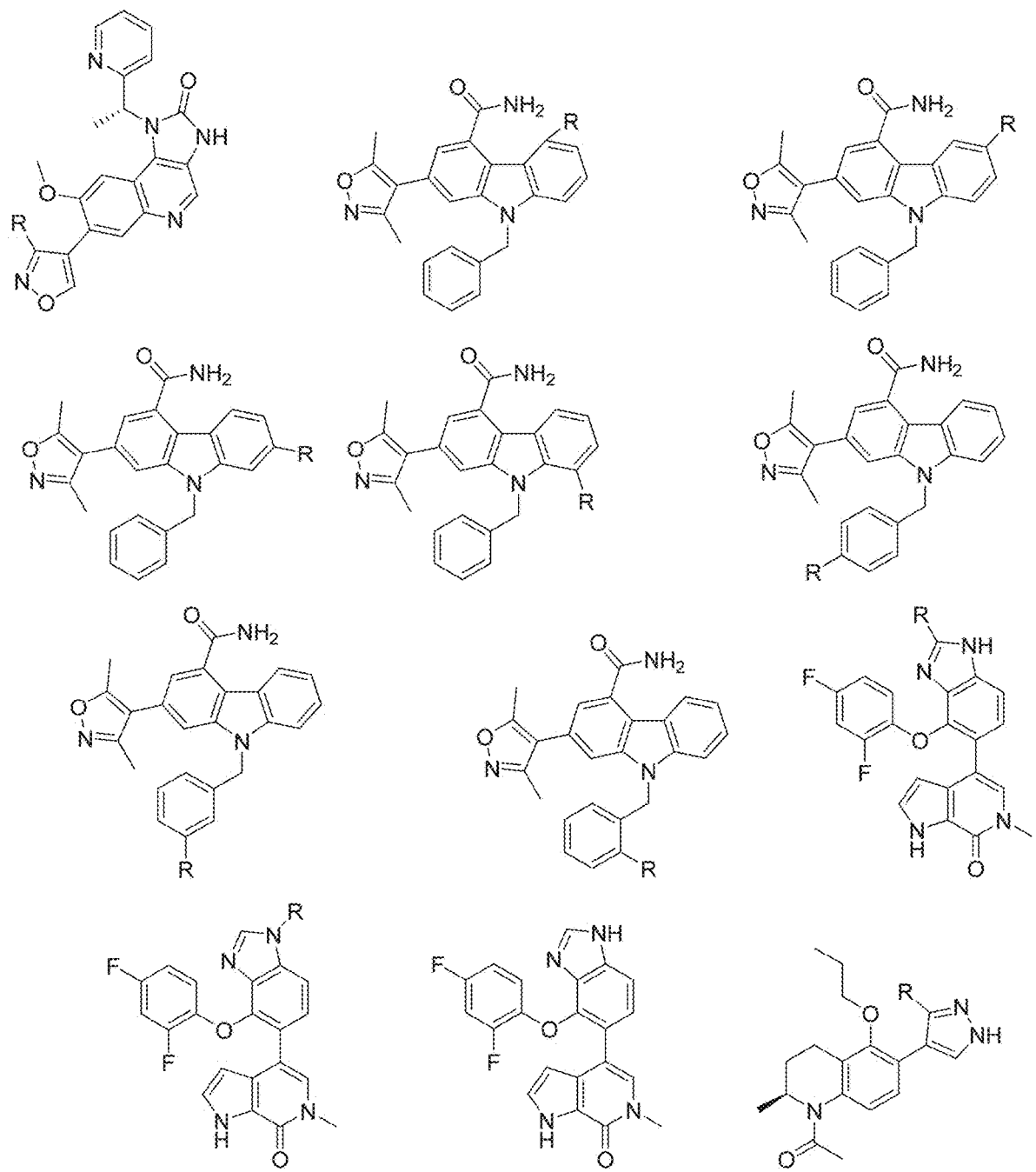

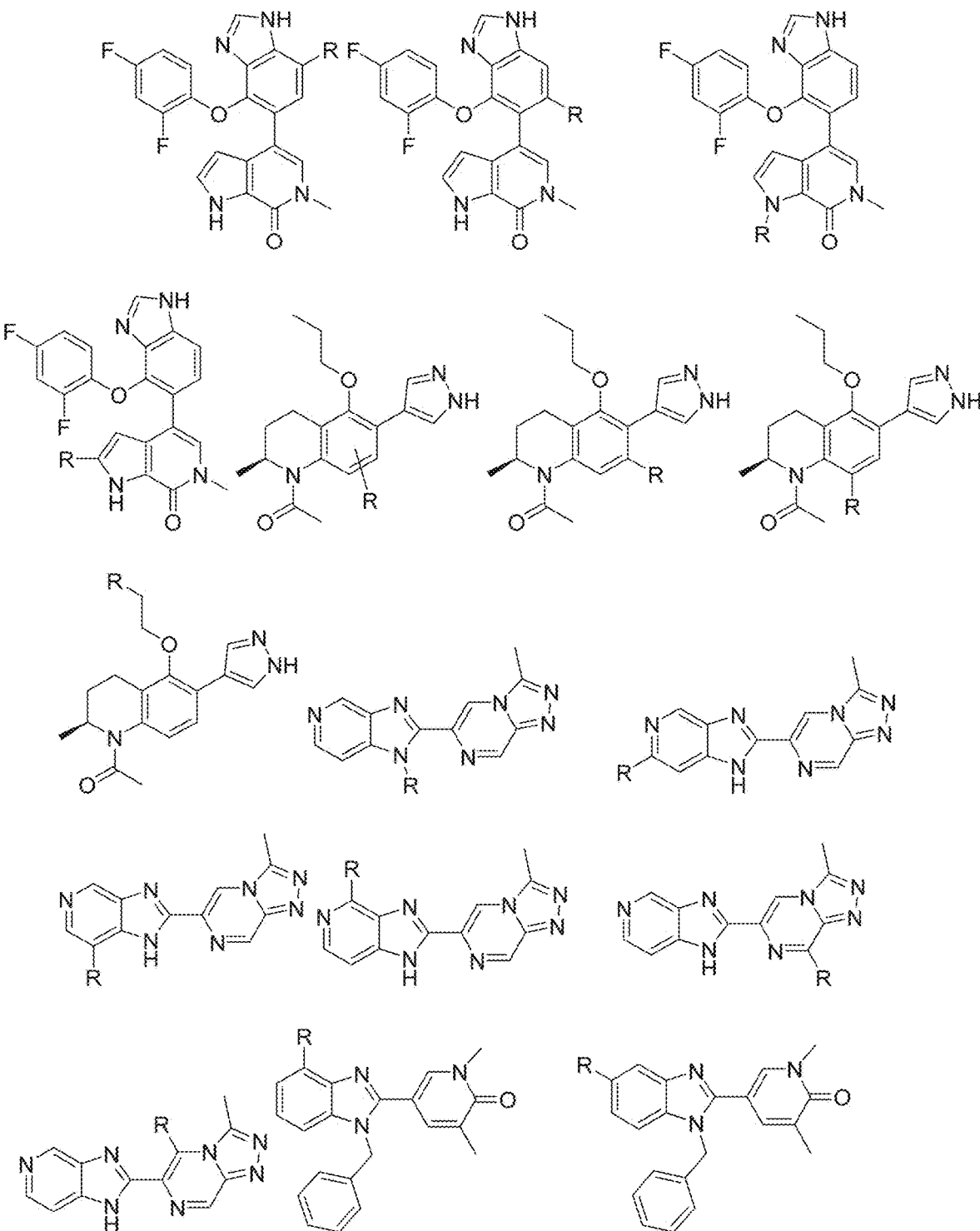
FIG. 3VVV

FIG. 3WWW
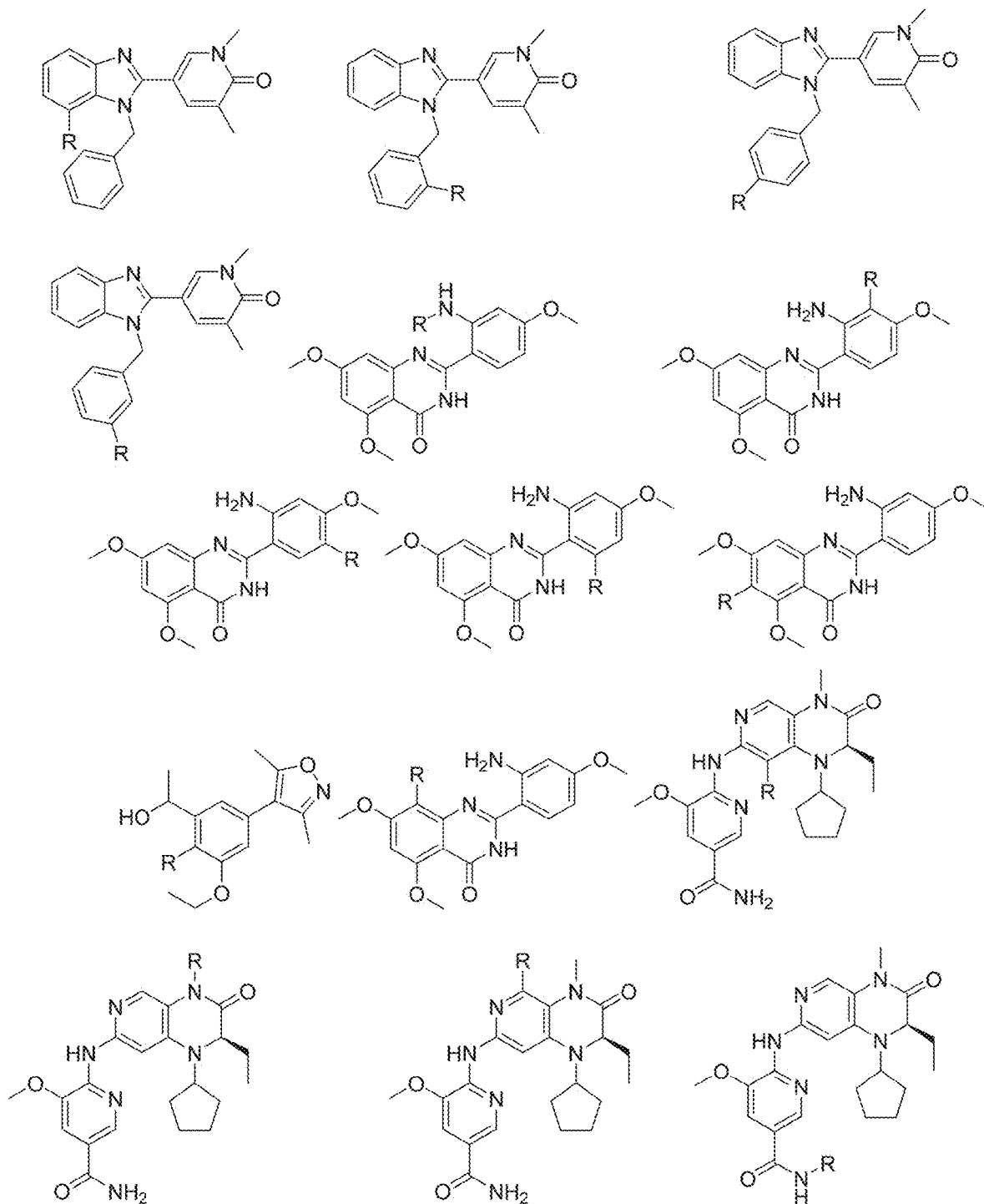

FIG. 3XXX
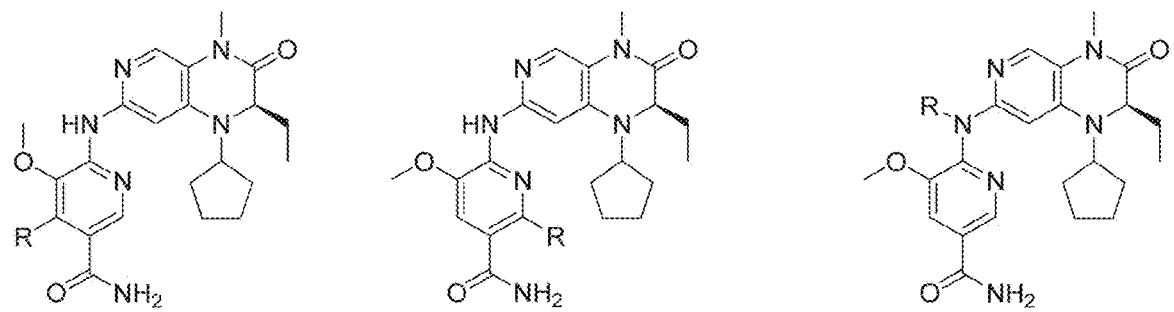
FIG. 3YYY
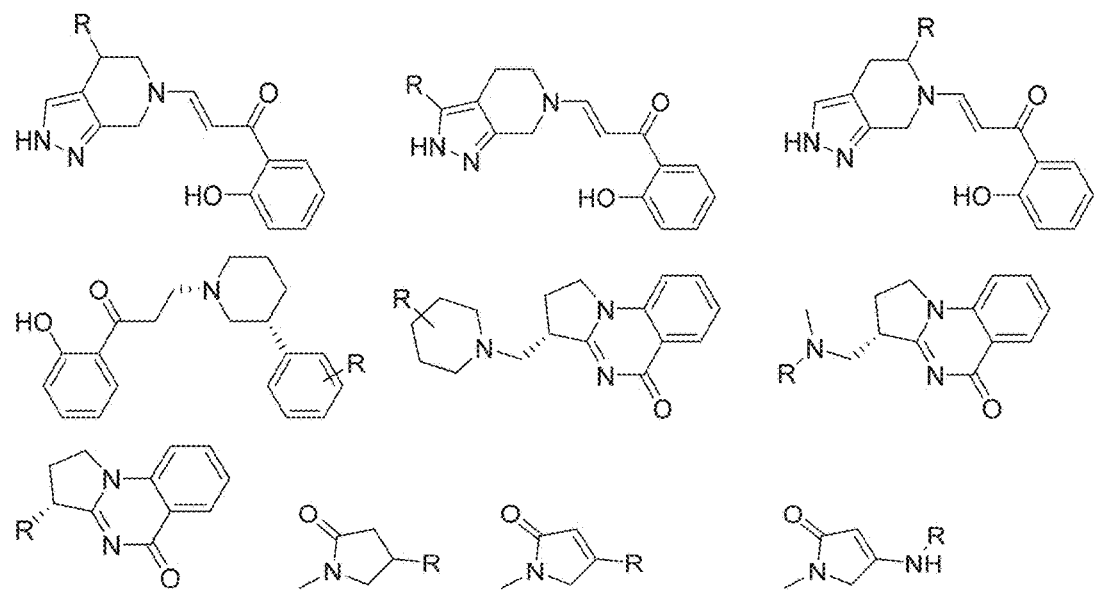
FIG. 3ZZZ
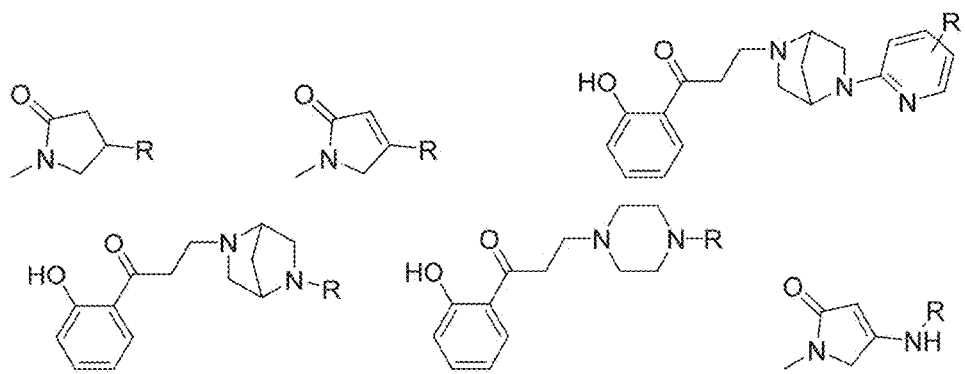

FIG. 3AAAA
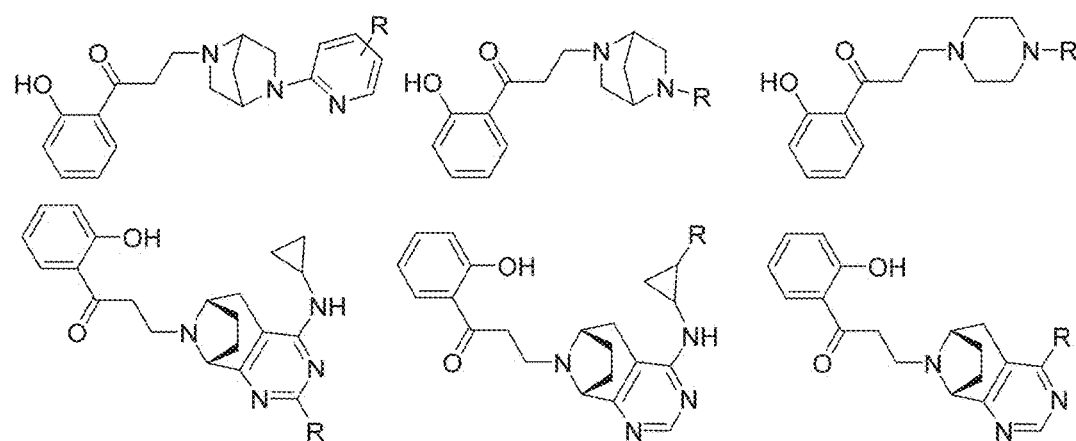
FIG. 3BBBB
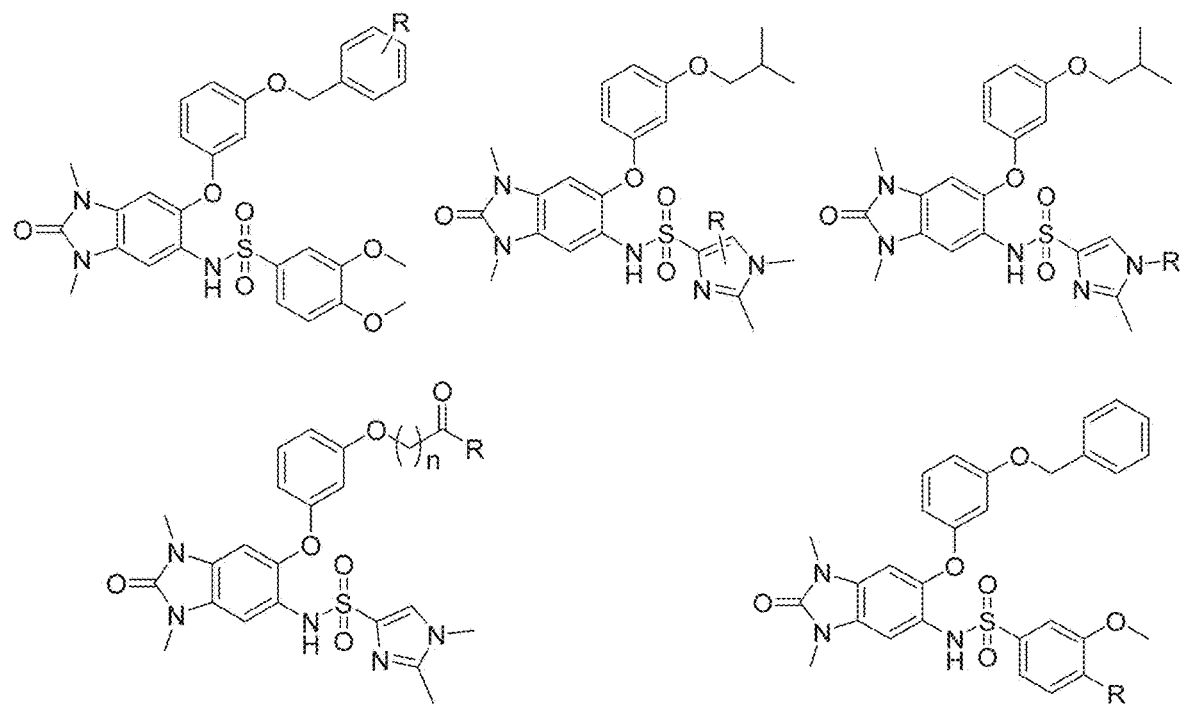

FIG. 3CCCC
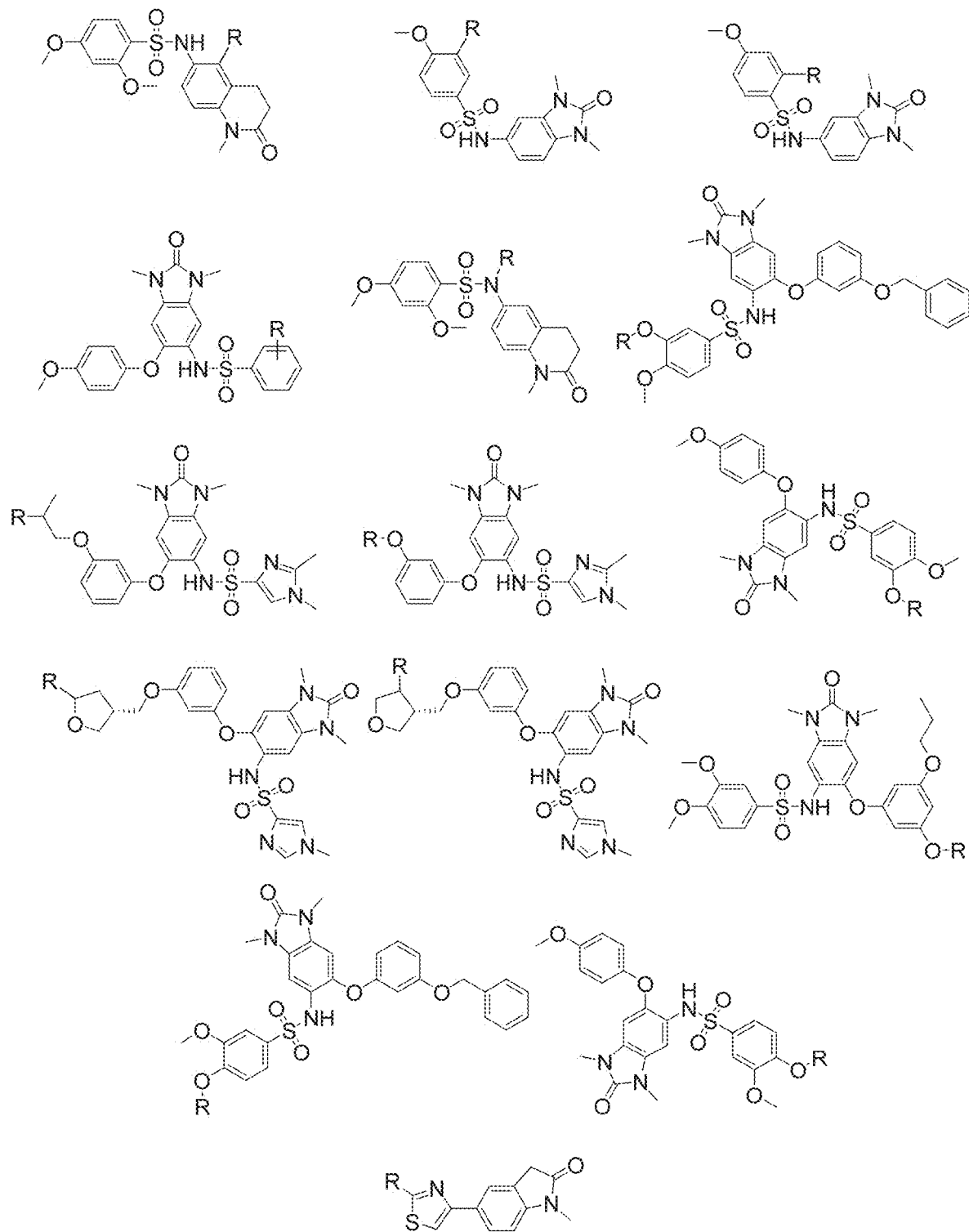

FIG. 3DDDD
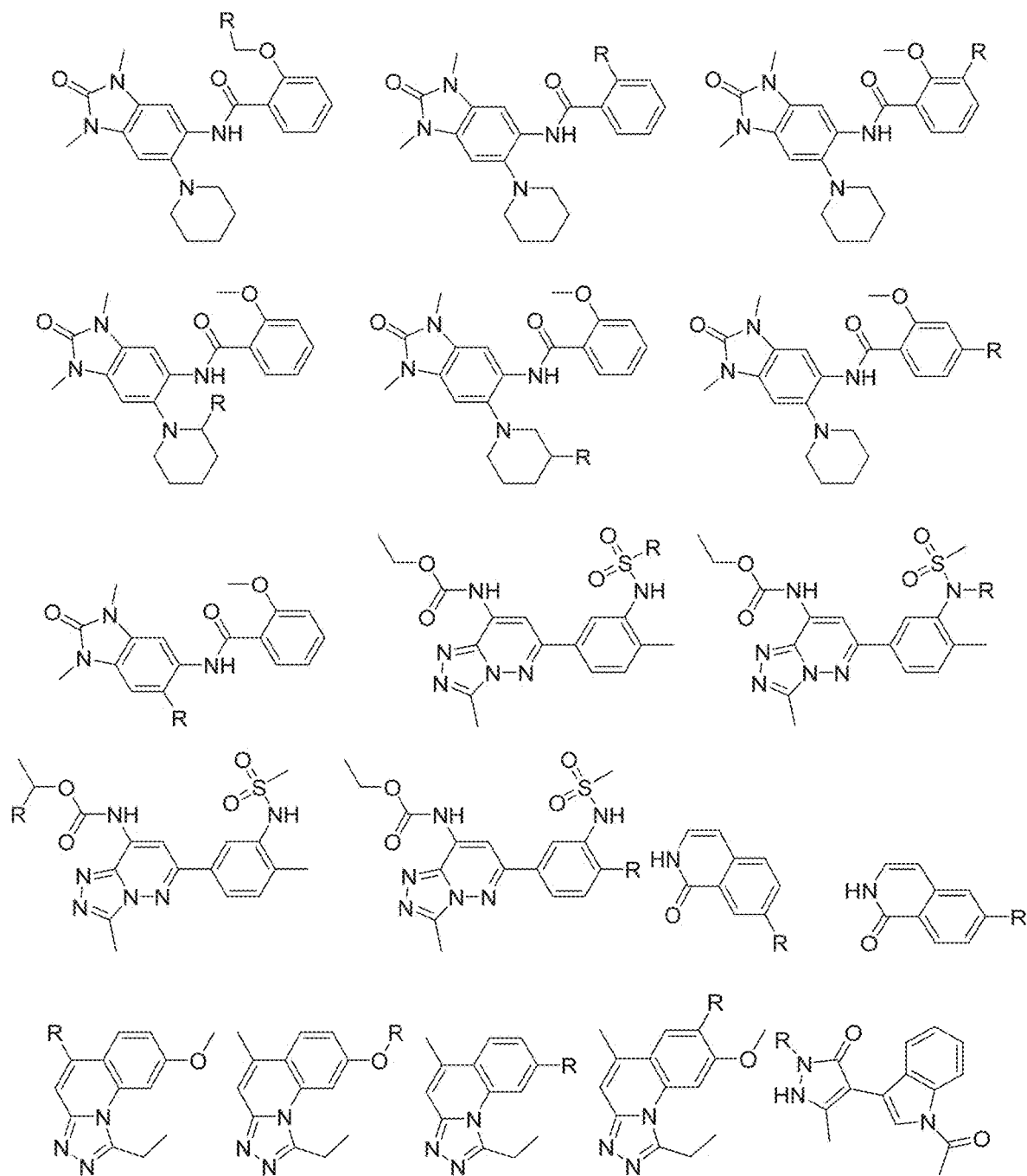

FIG. 3EEEE
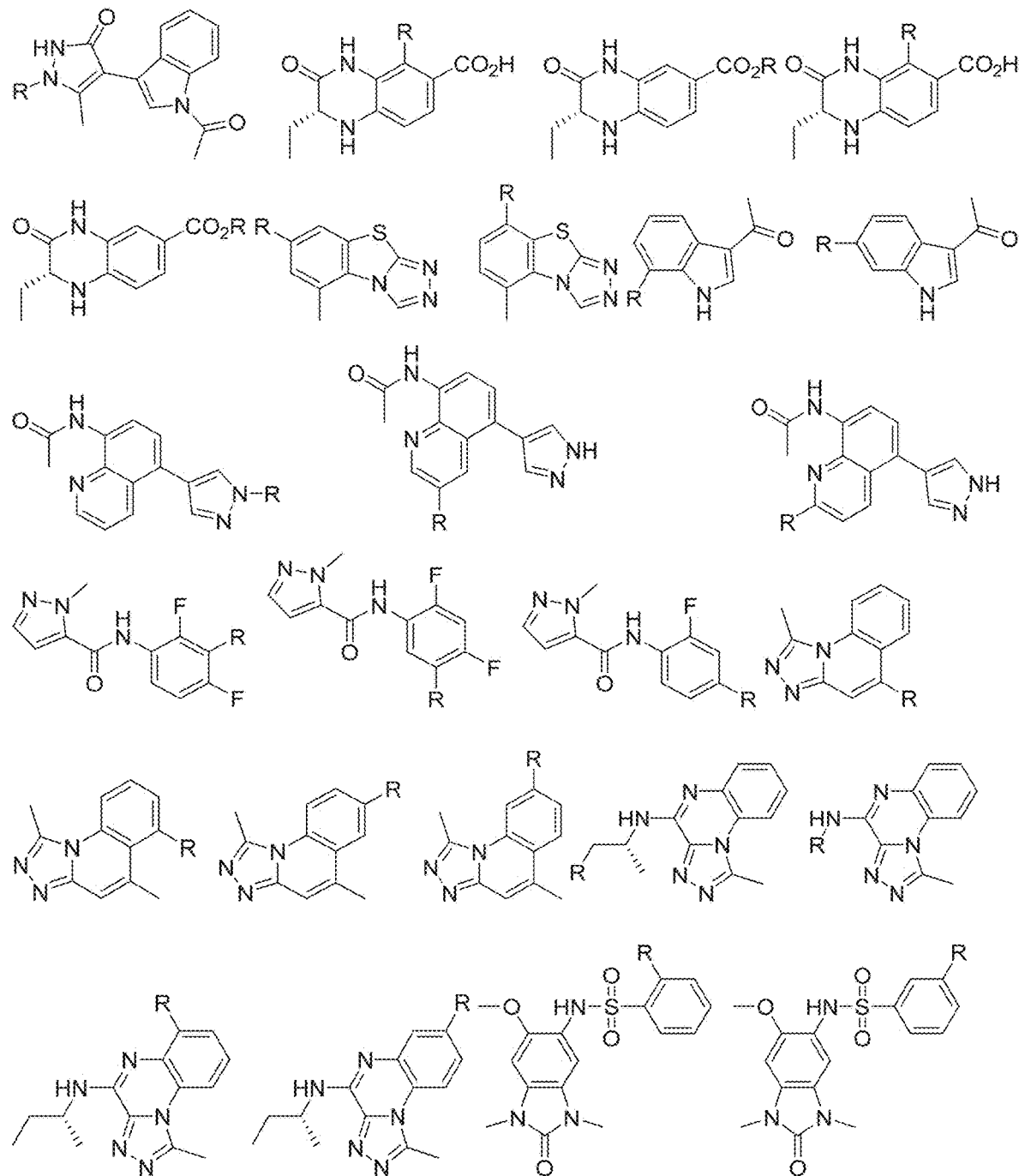

FIG. 3FFFF
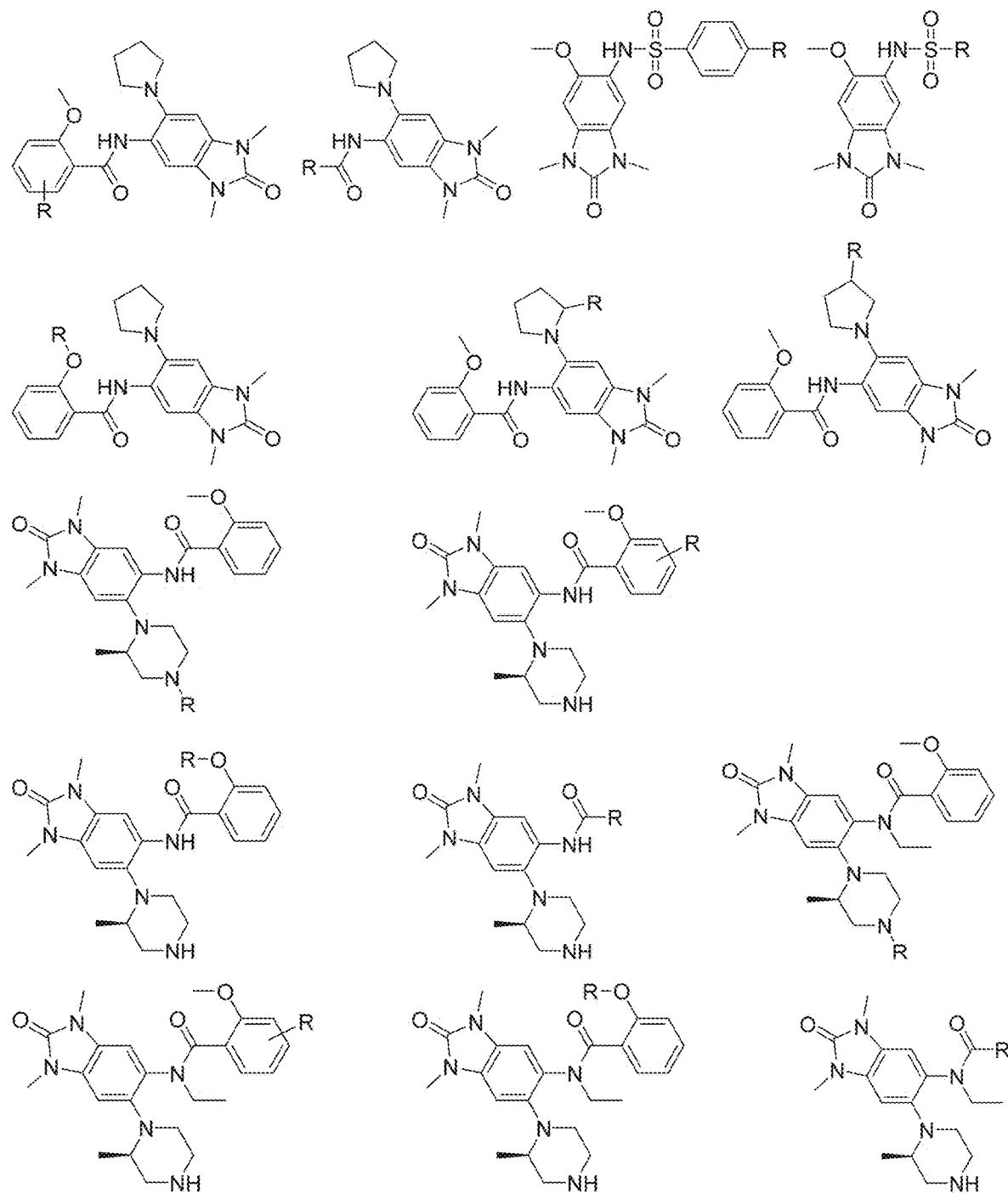

FIG. 3GGGG
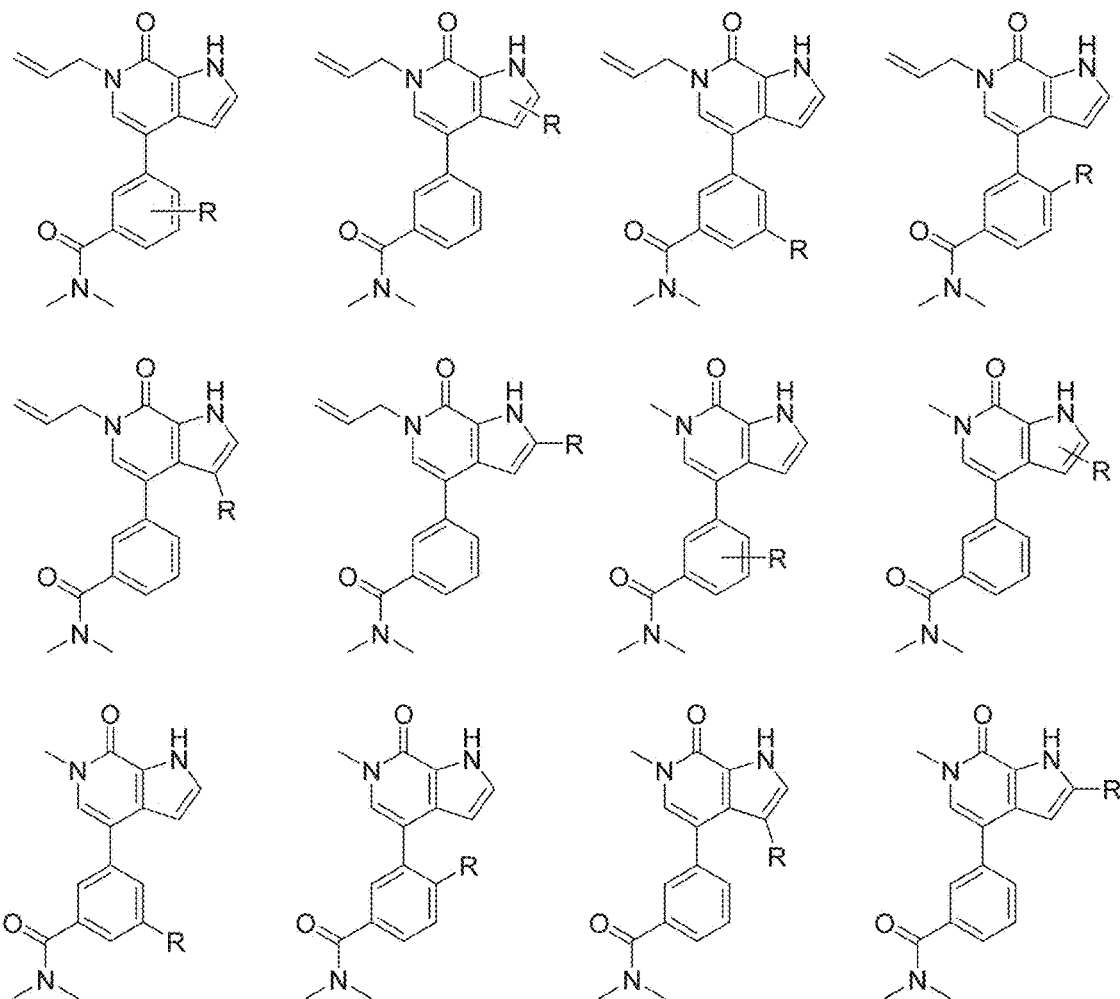
FIG. 3HHHH
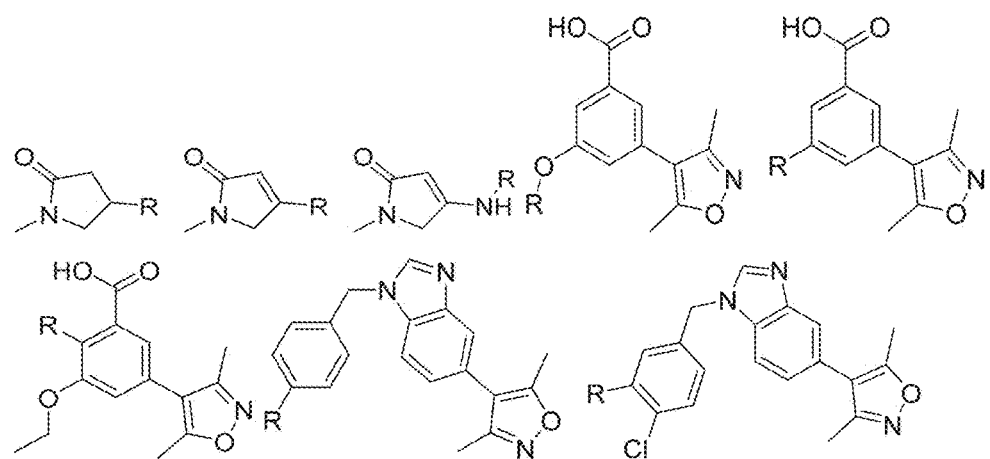

FIG. 3IIII
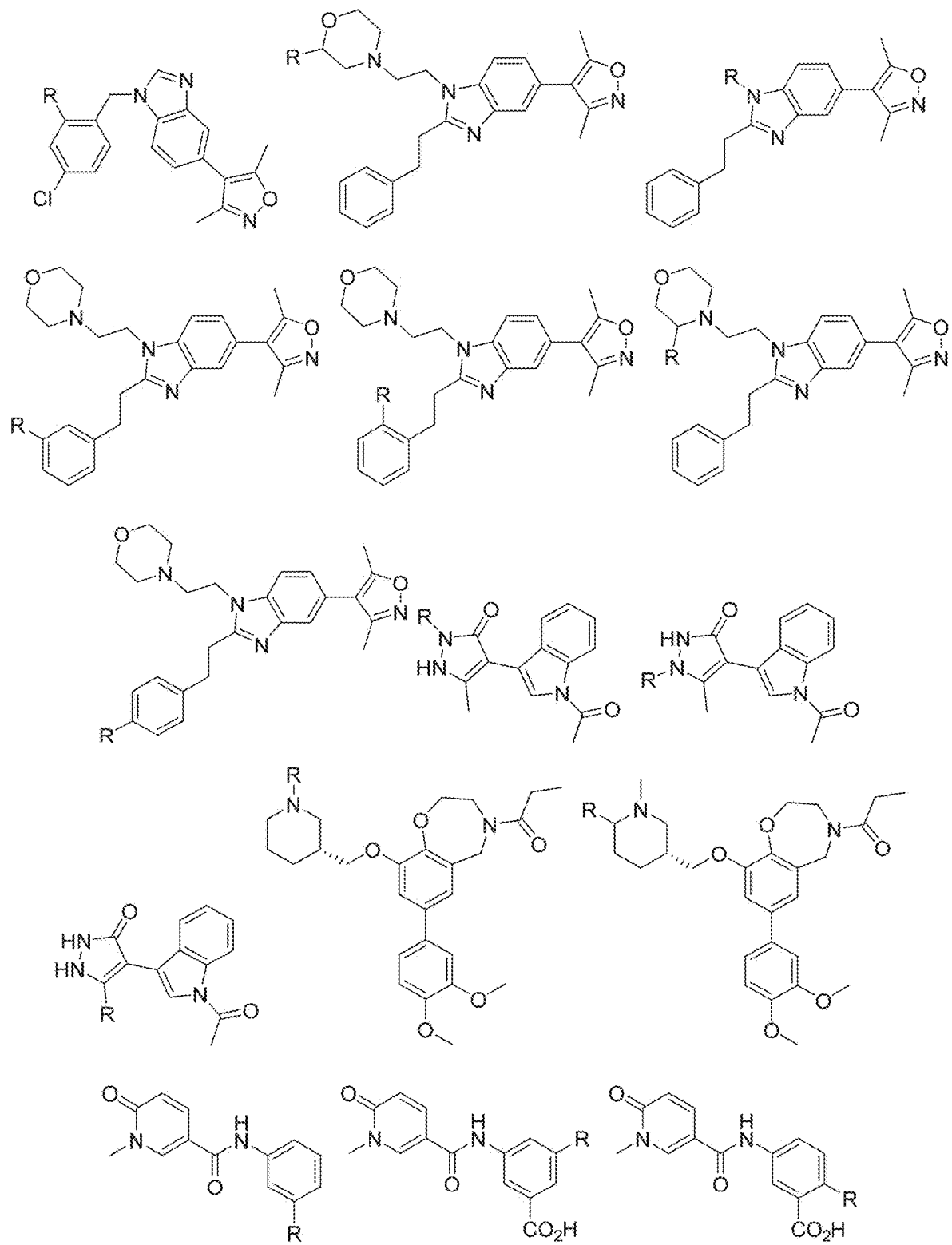

FIG. 3JJJJ
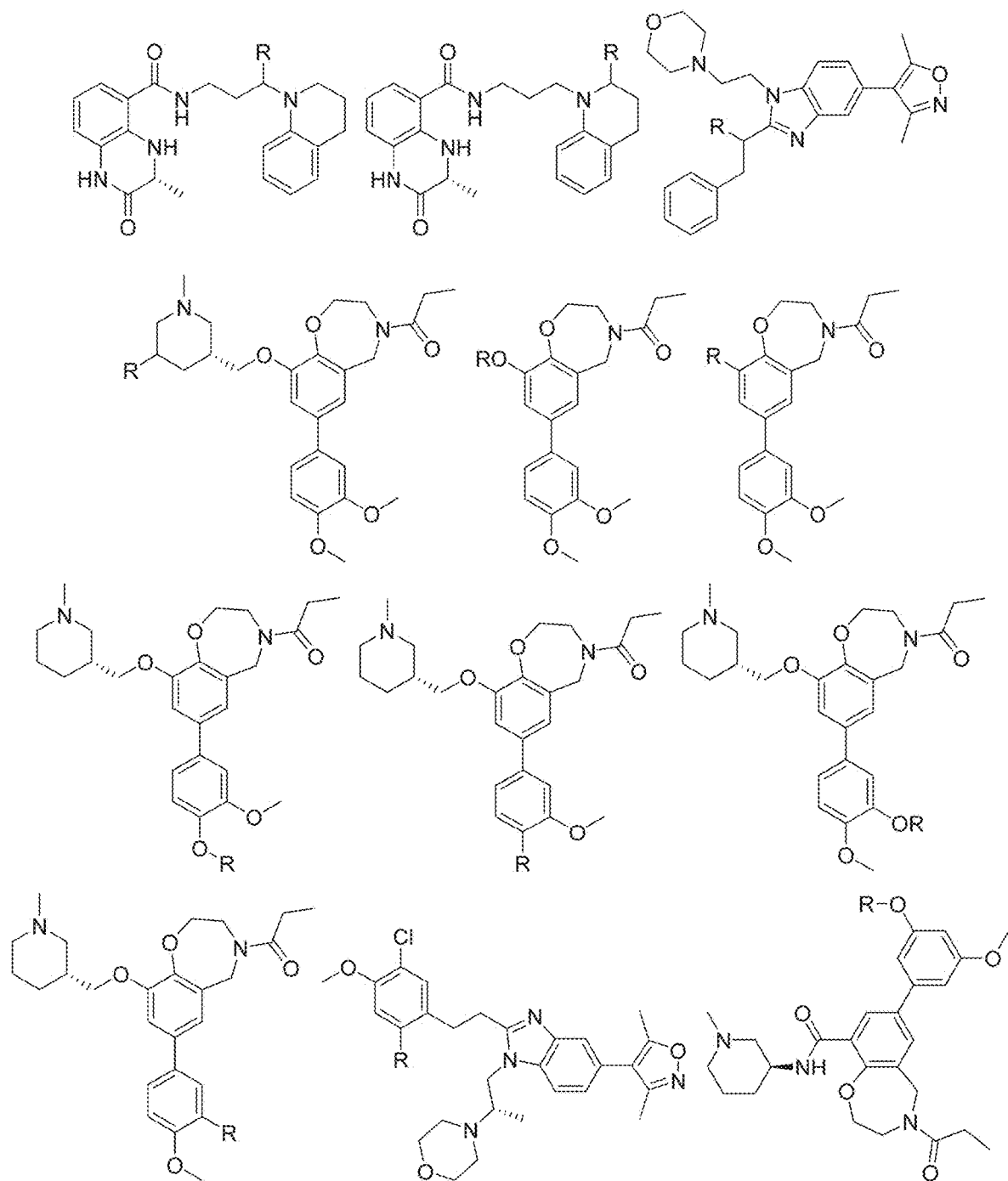

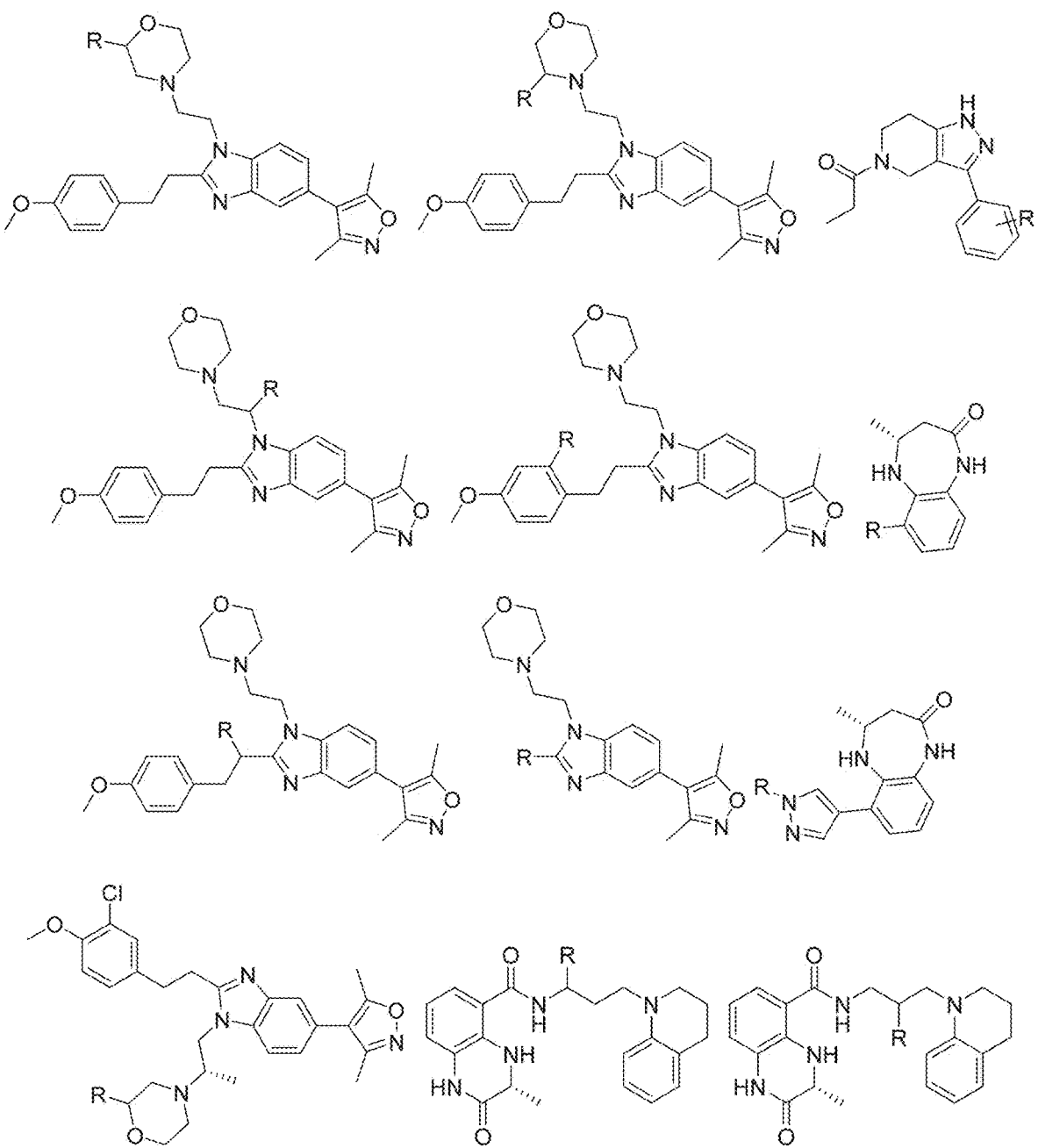
FIG. 3KKKK

FIG. 3LLLL
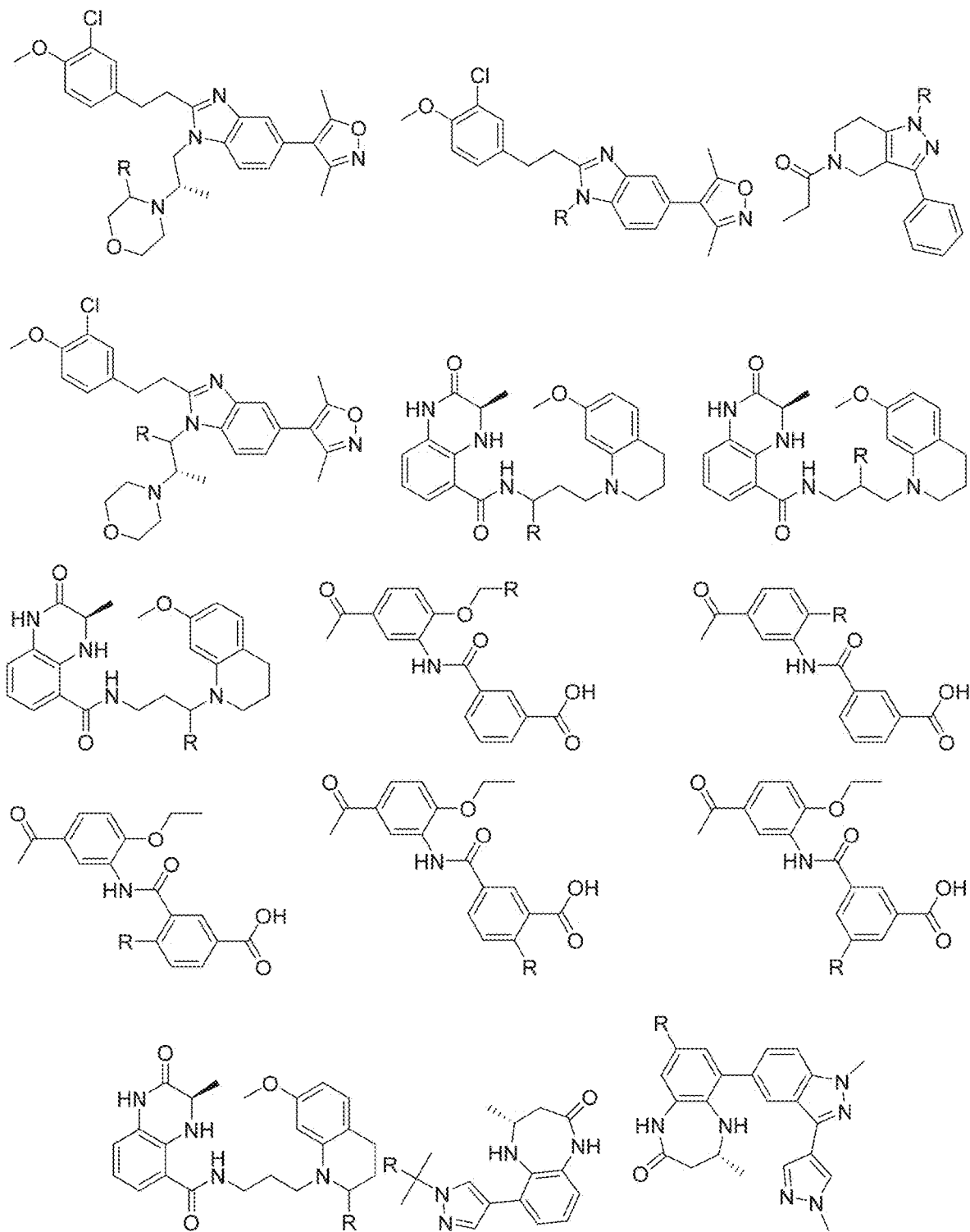

FIG. 3MMMM
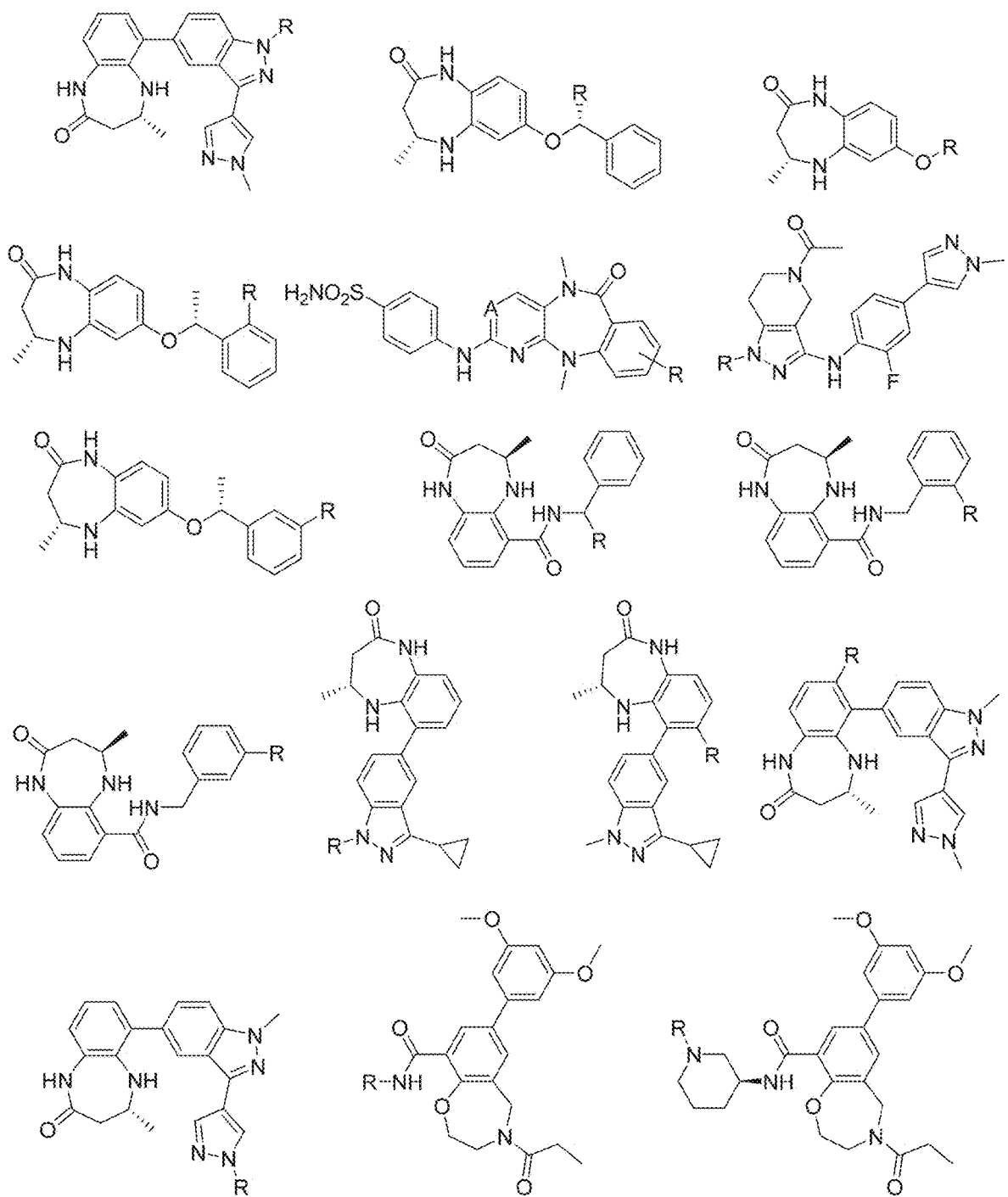

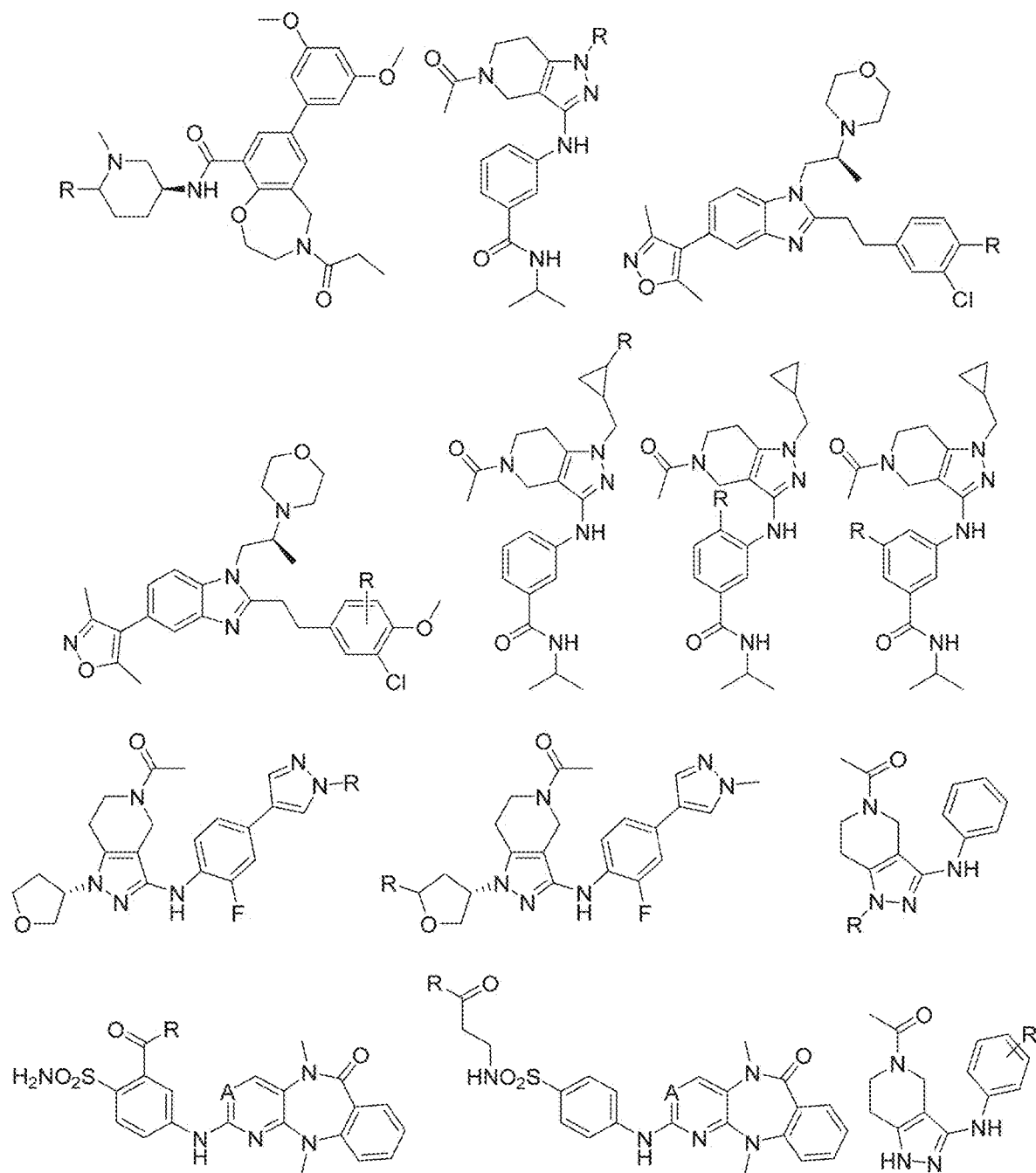
FIG. 3NNNN

FIG. 3OOOO
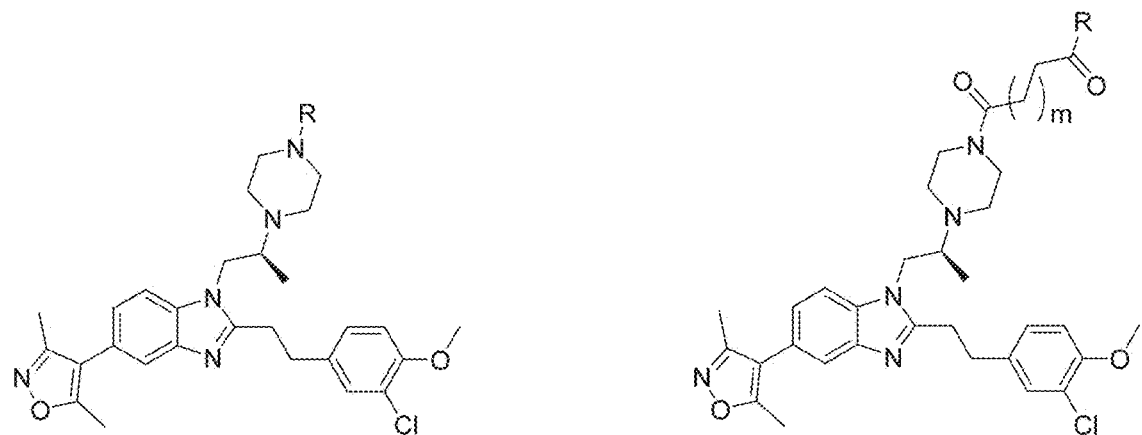
FIG. 3PPPP
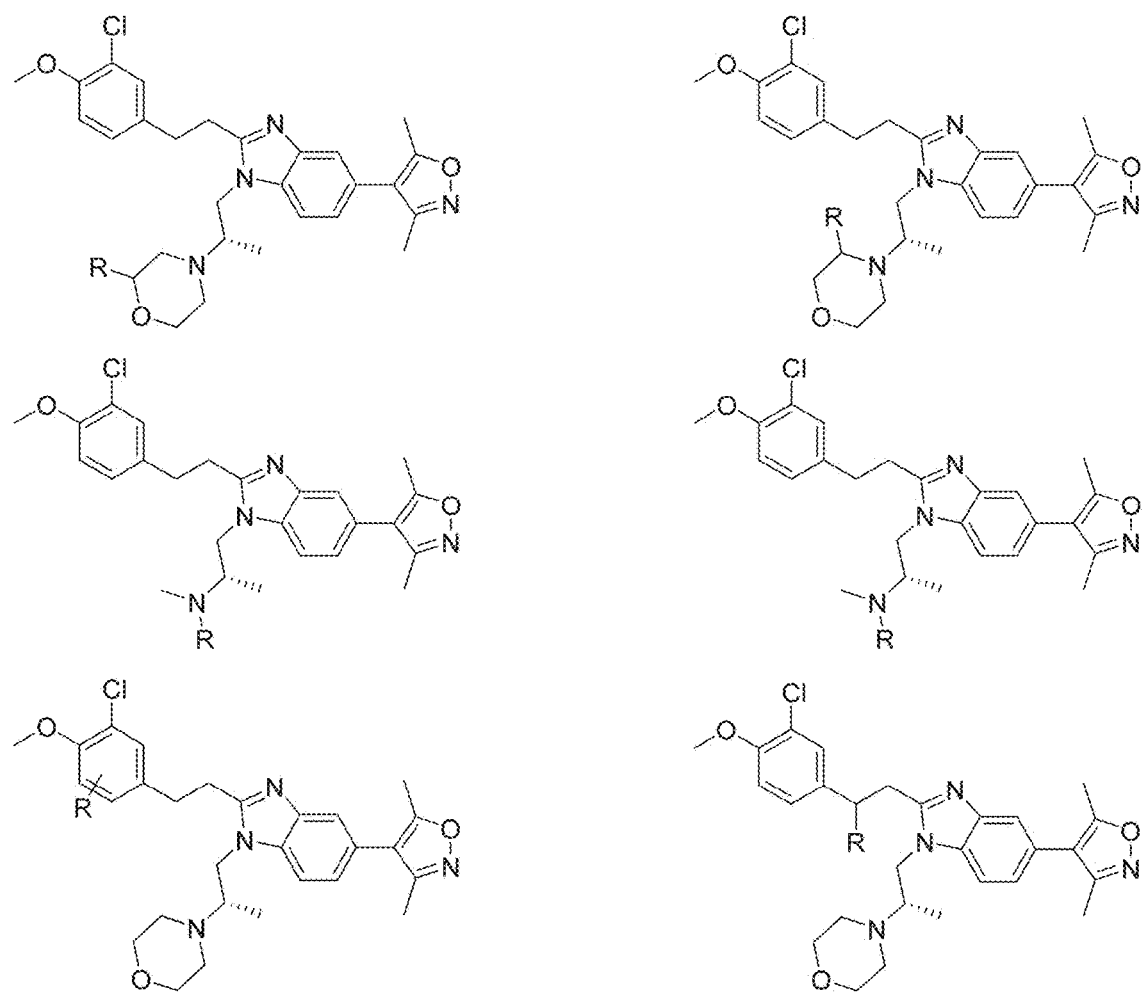

FIG. 3QQQQ
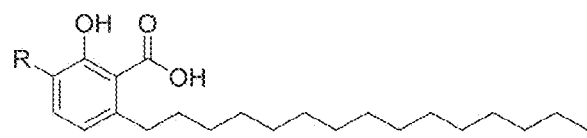
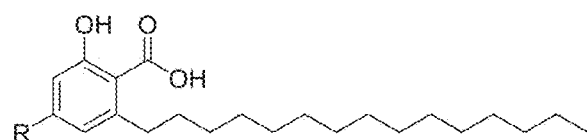
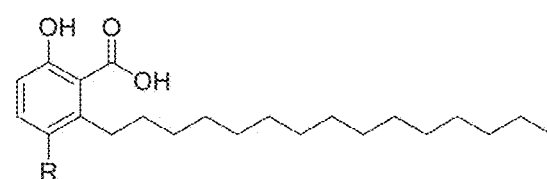
FIG. 3RRRR
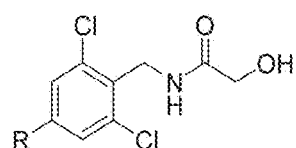 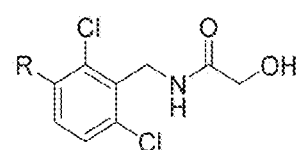 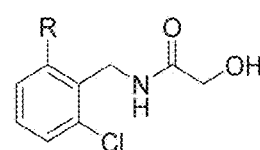
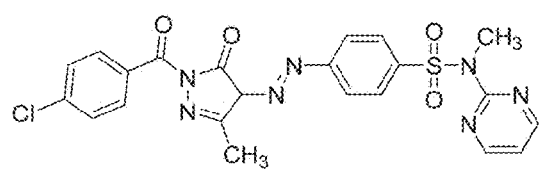 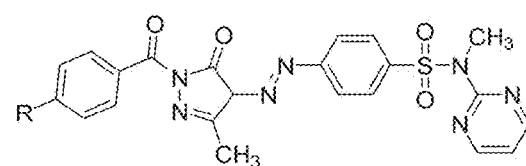
FIG. 3SSSS
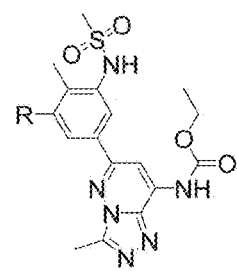 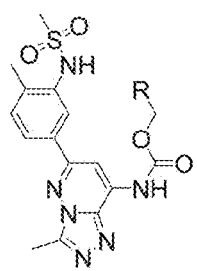 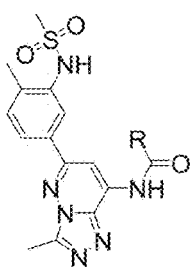 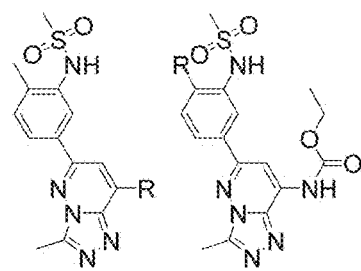

FIG. 3TTTT
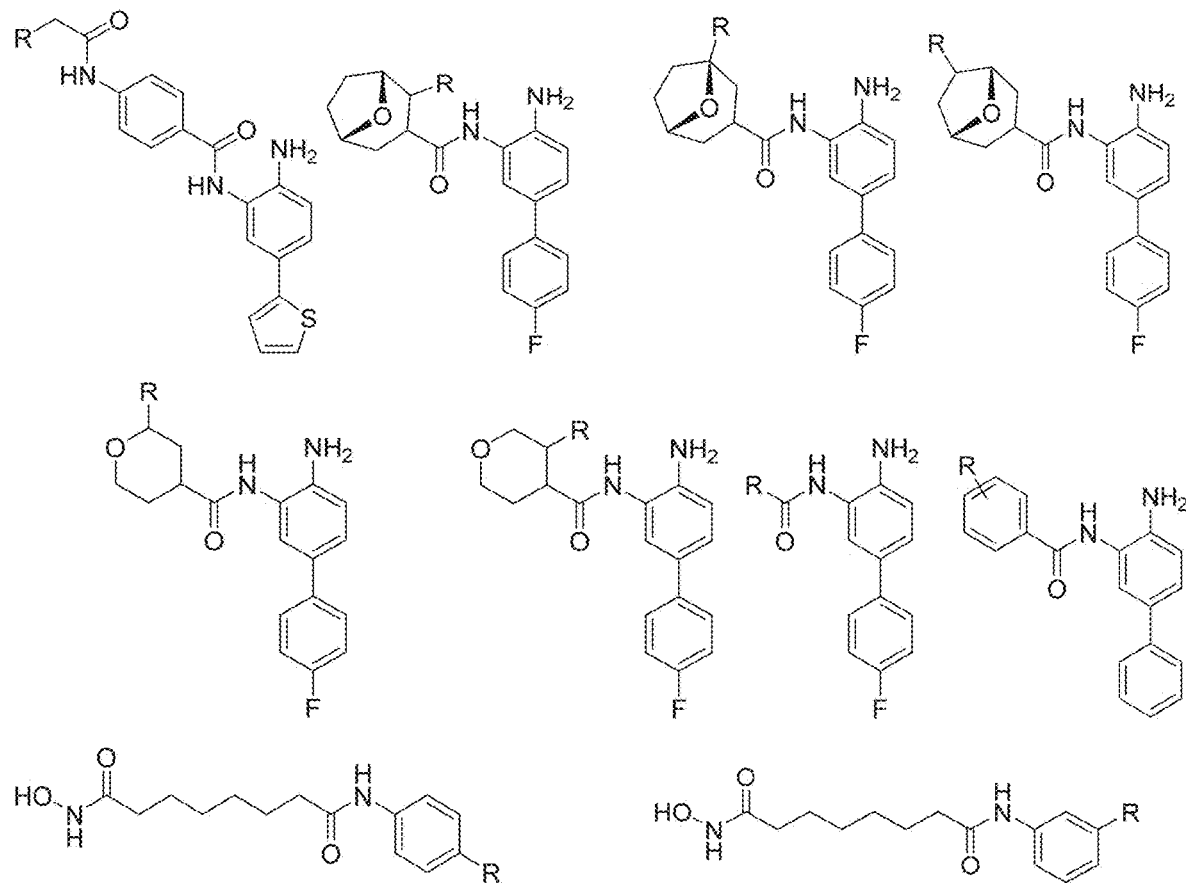
FIG. 3UUUU
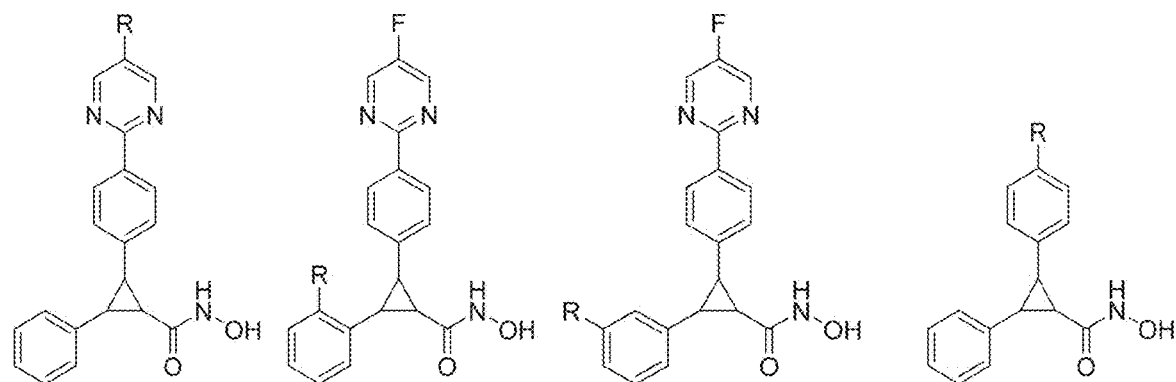

FIG. 3VVVV
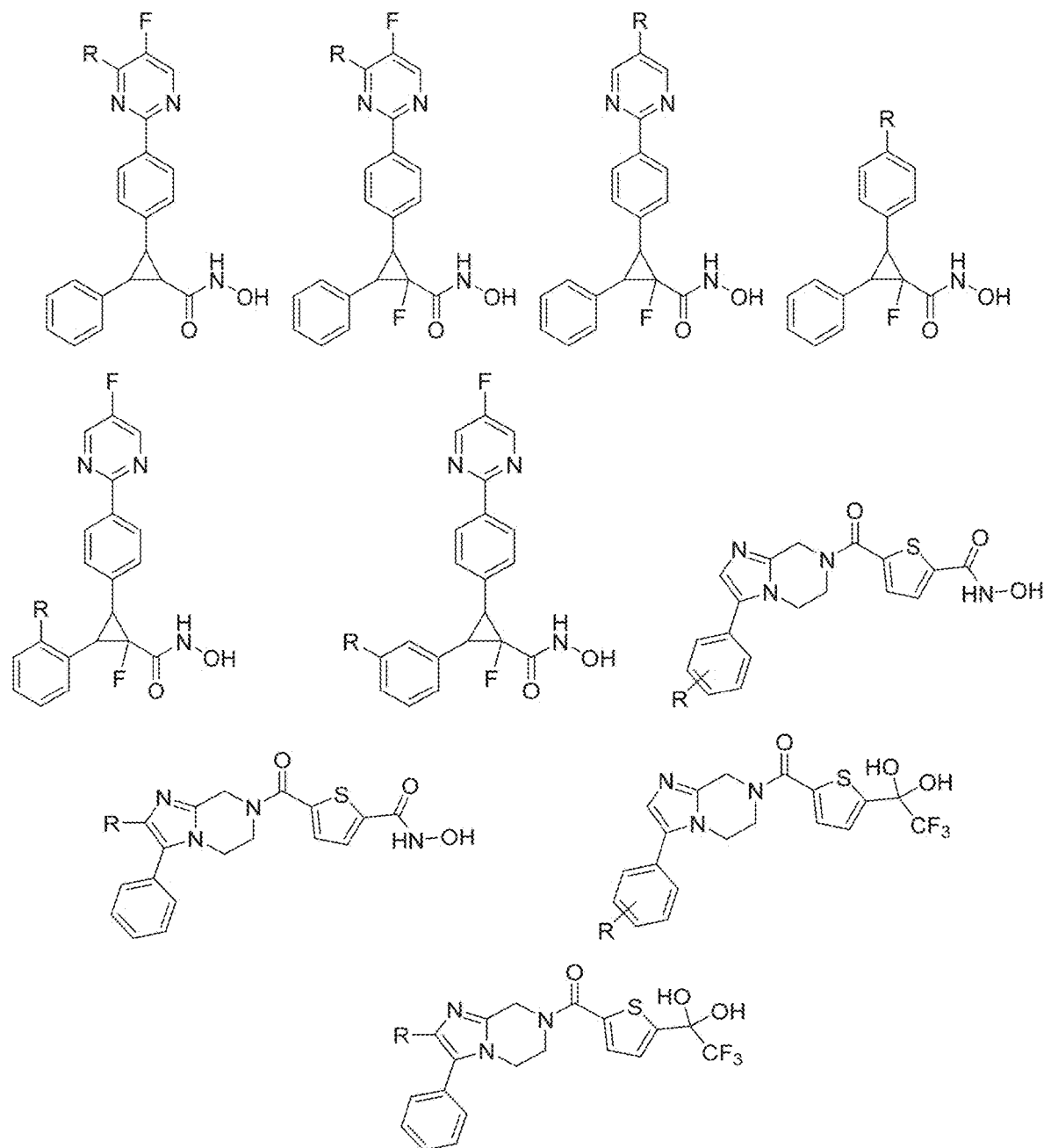

FIG. 3WWWW
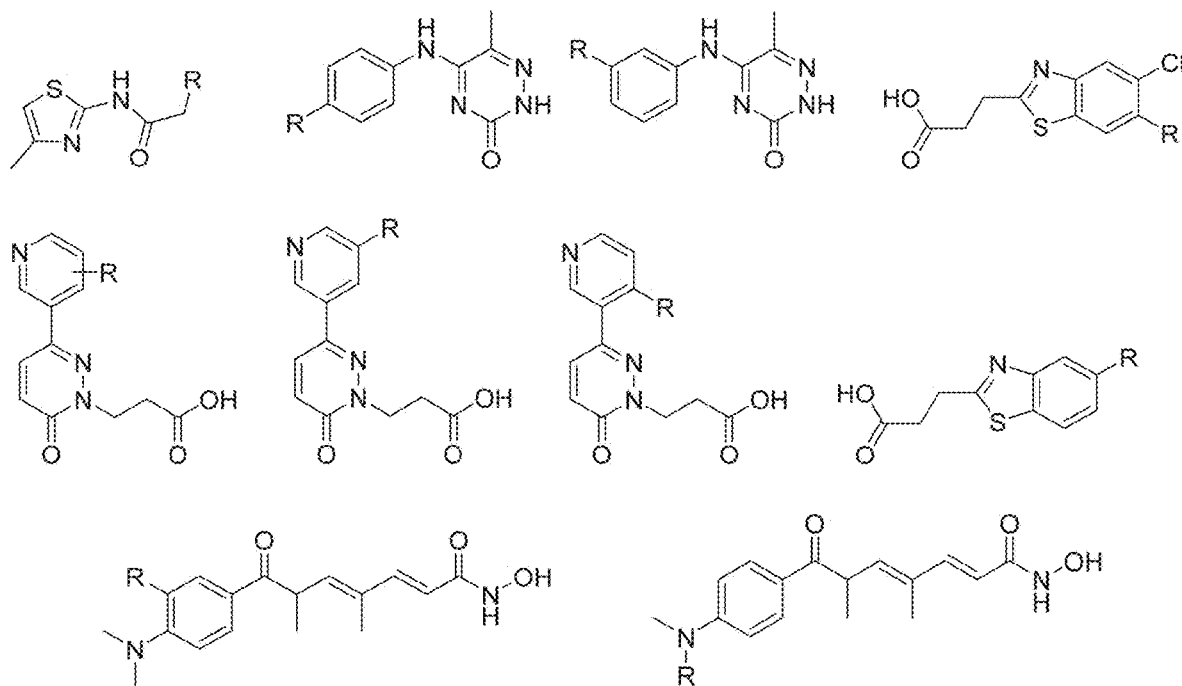
FIG. 3XXXX
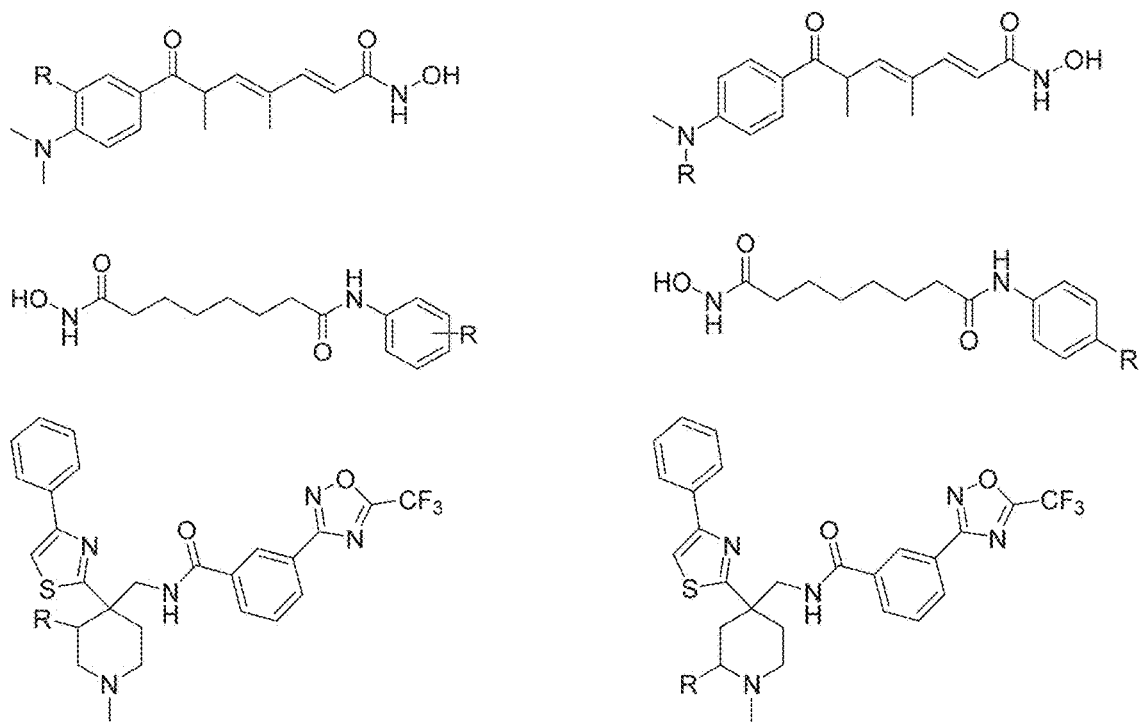

FIG. 3YYYY
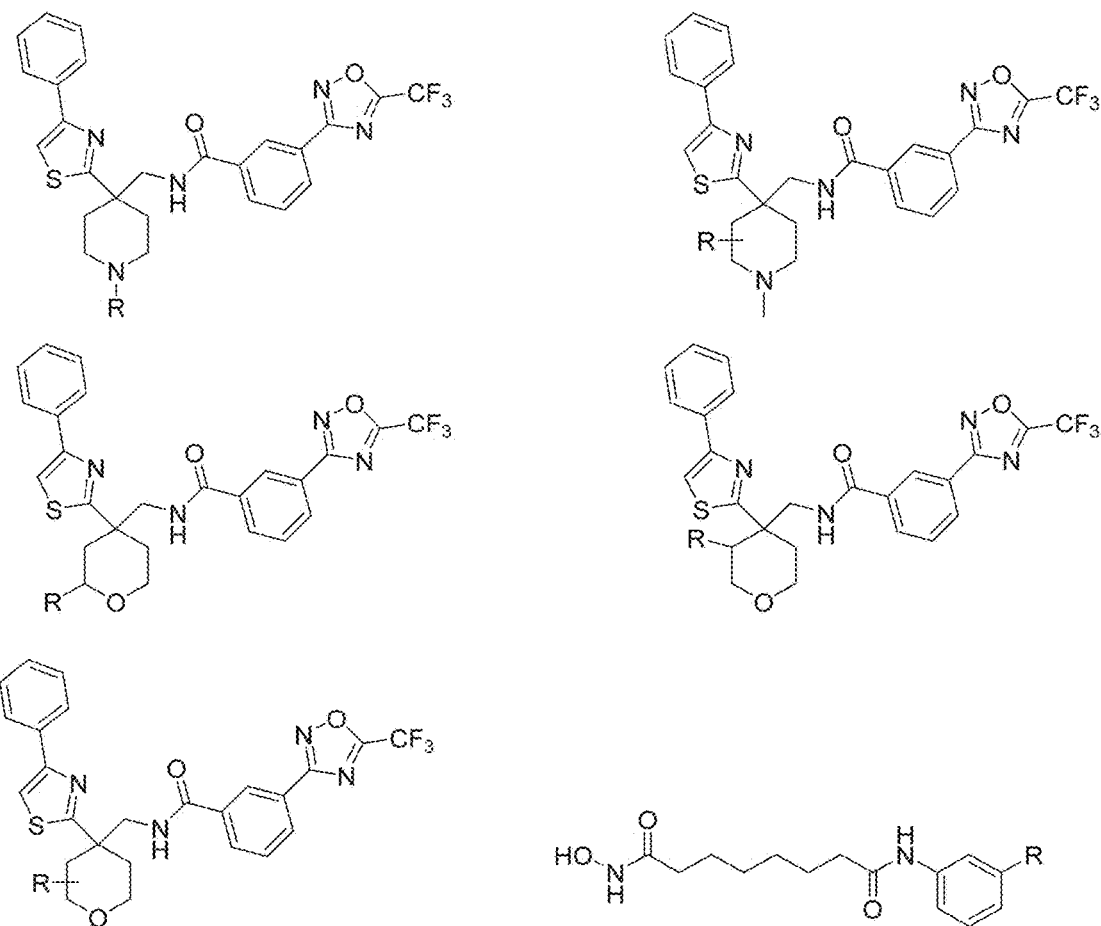
FIG. 3ZZZZ
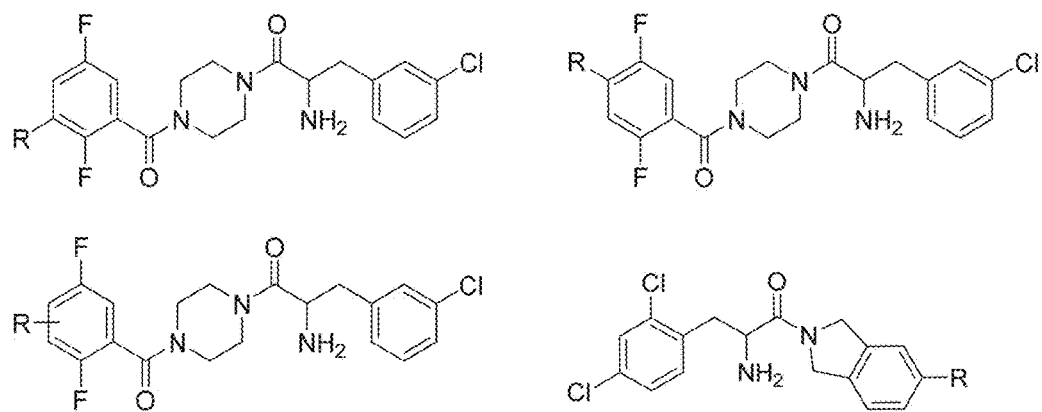

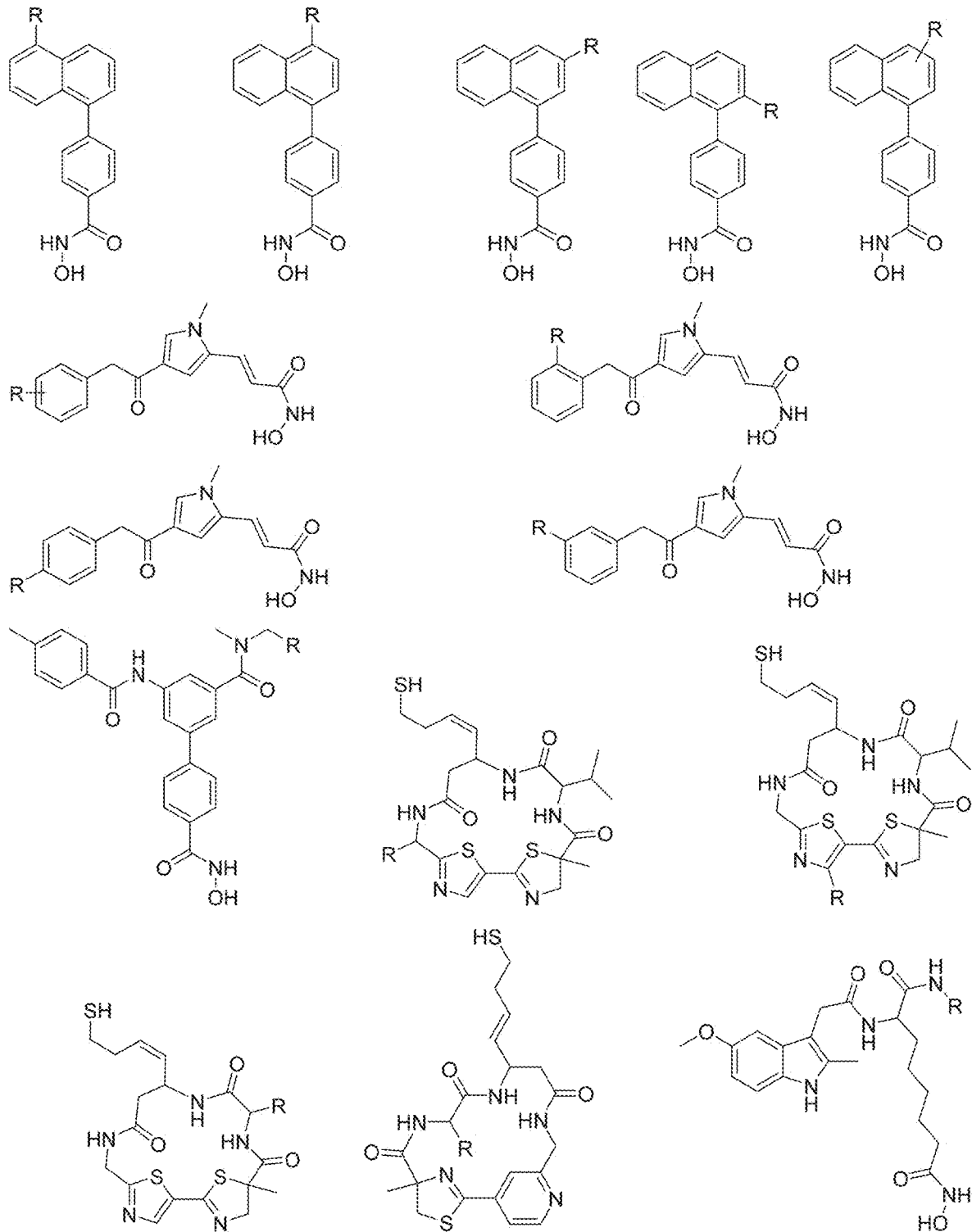
FIG. 3AAAAA

FIG. 3BBBBB
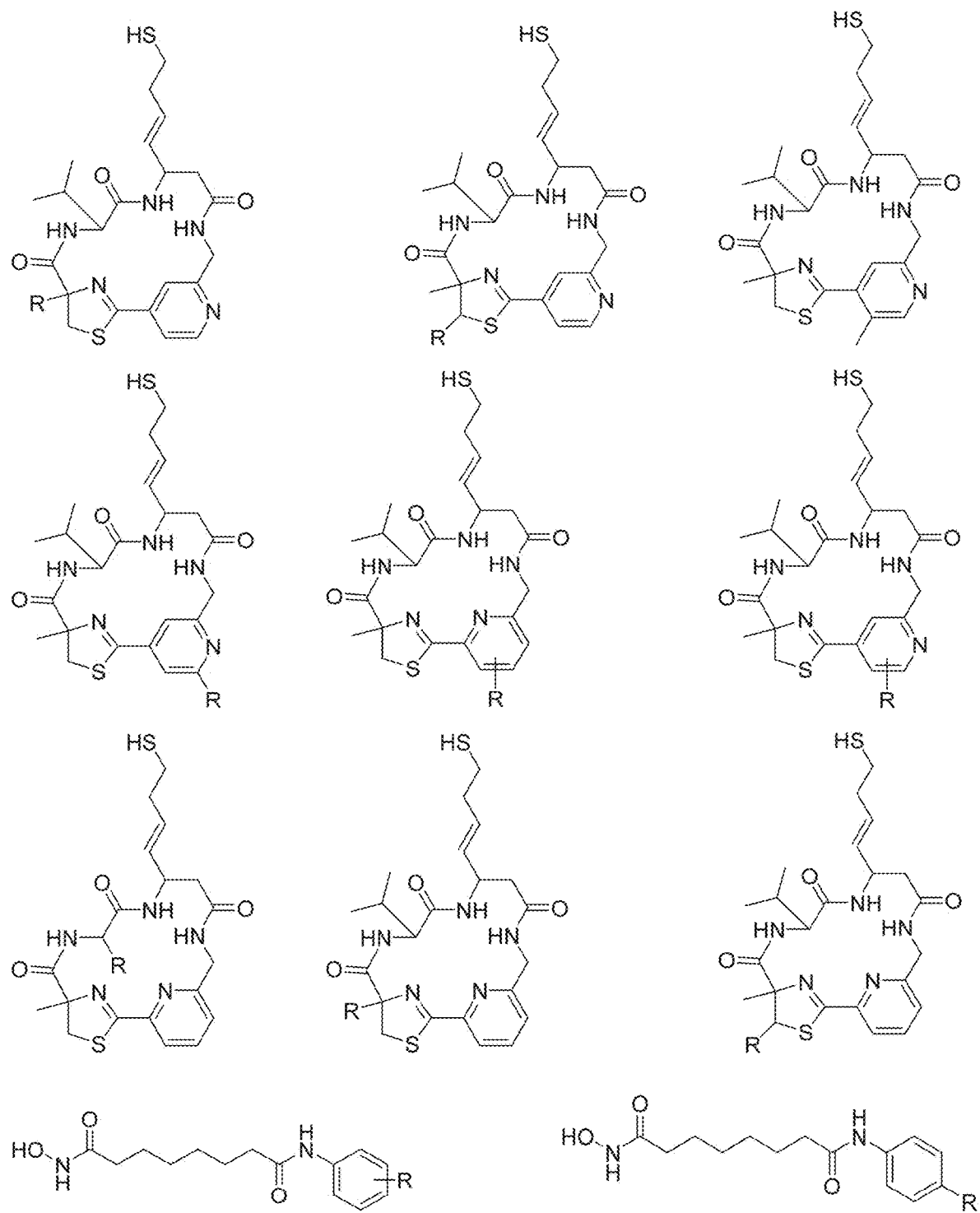

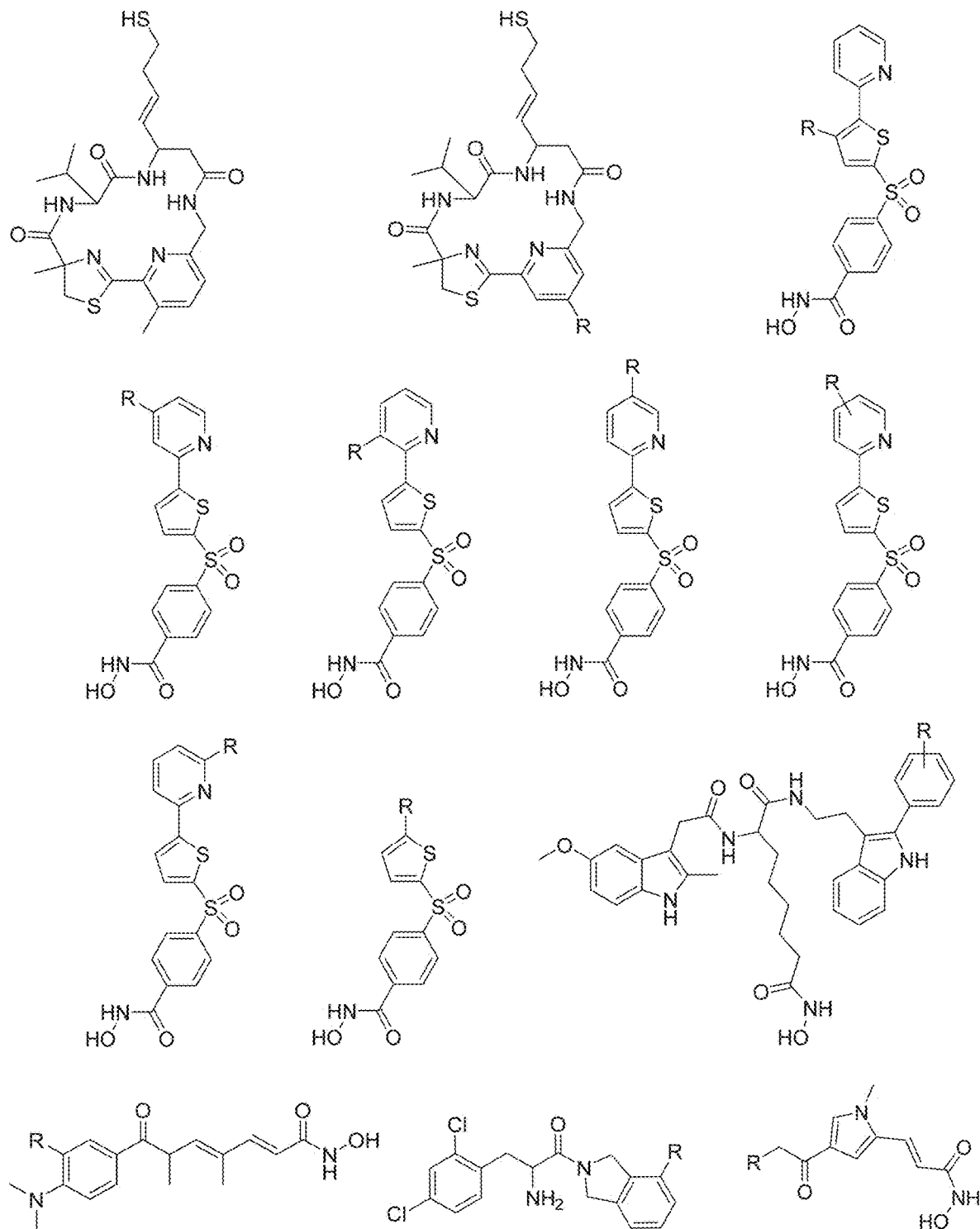
FIG. 3CCCCC

FIG. 3DDDDD
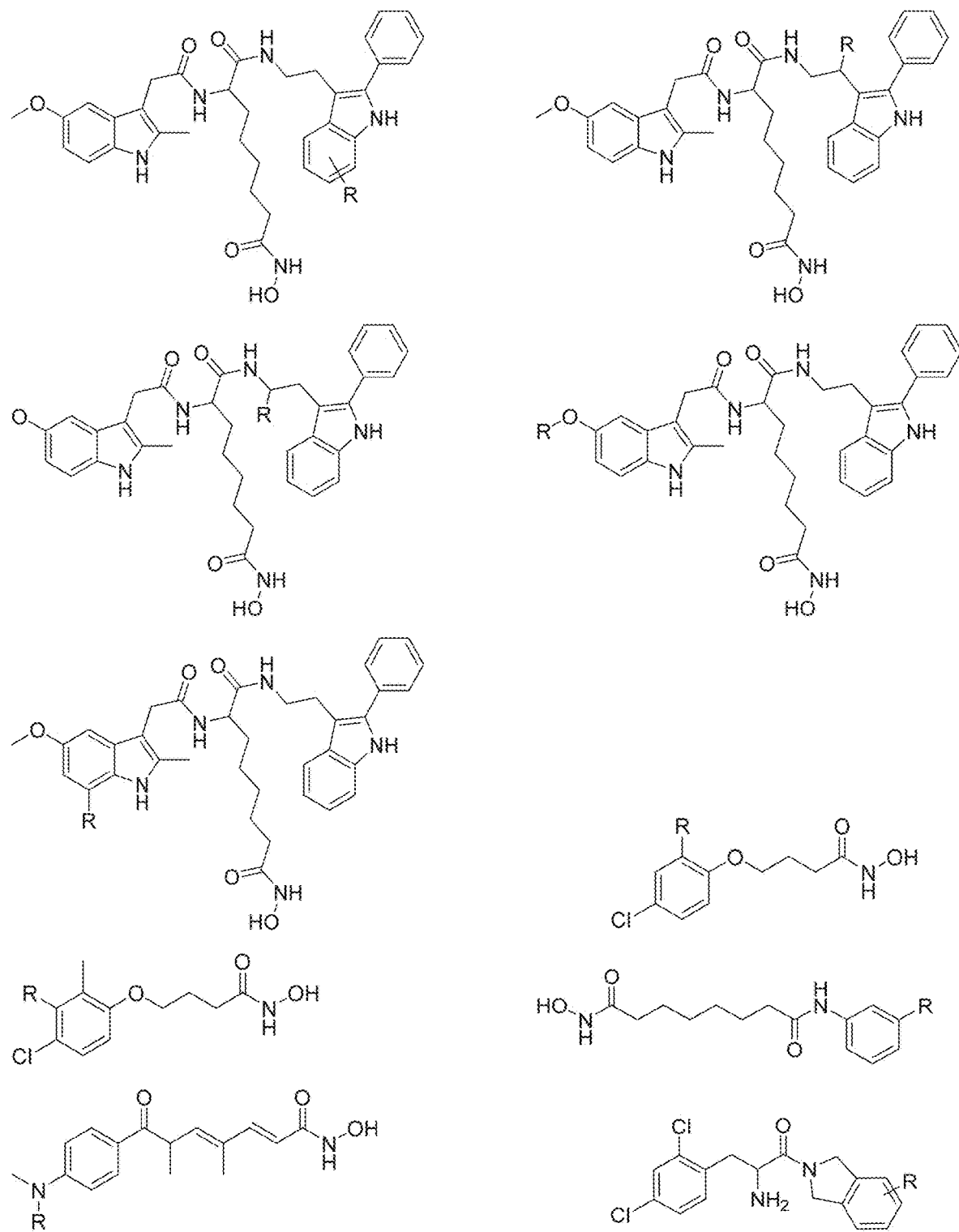

FIG. 3EEEEE
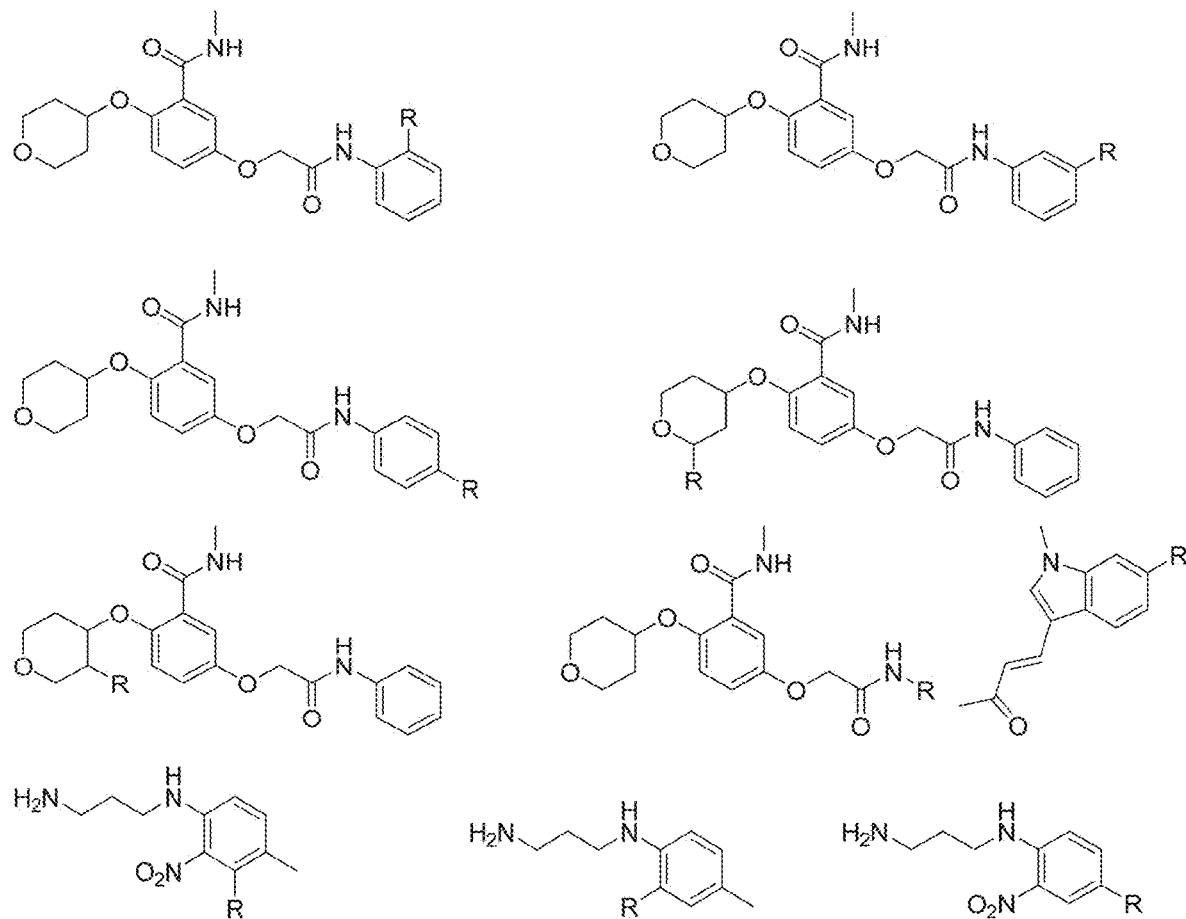
FIG. 3FFFFF
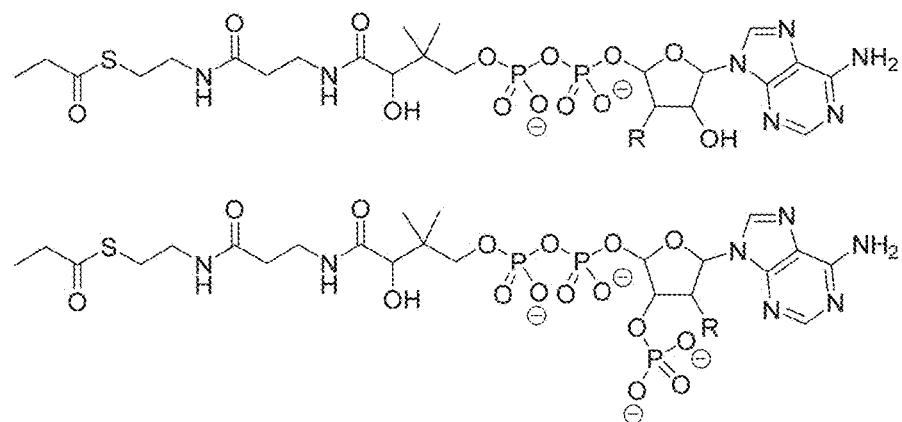

FIG. 3GGGGG
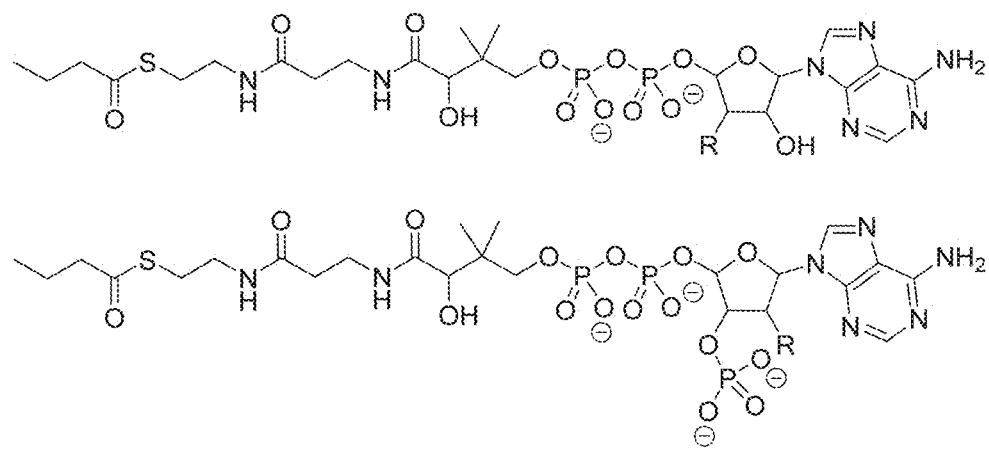
FIG. 3HHHHH
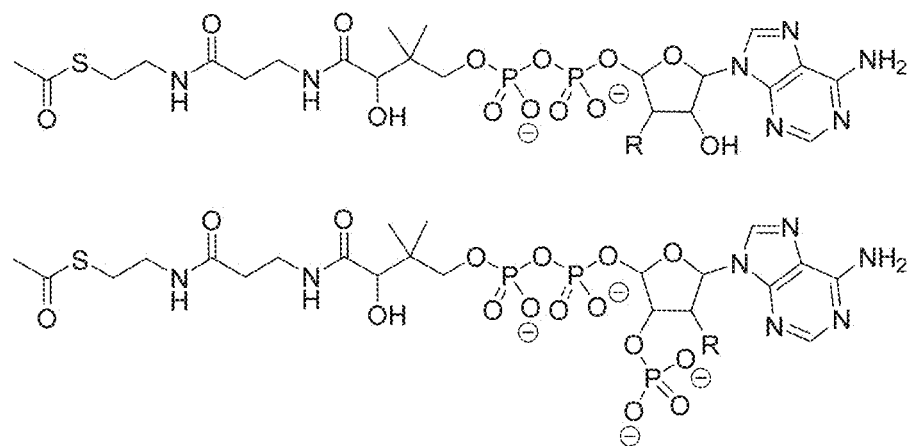
FIG. 3IIIII
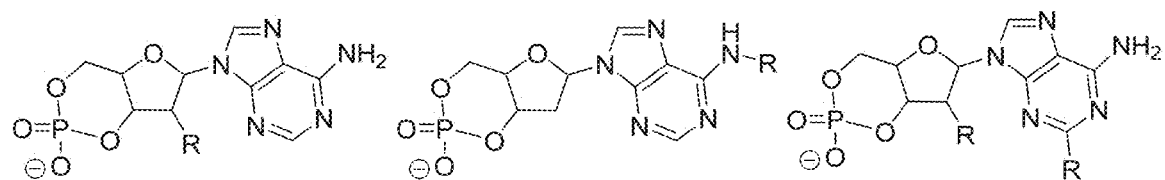

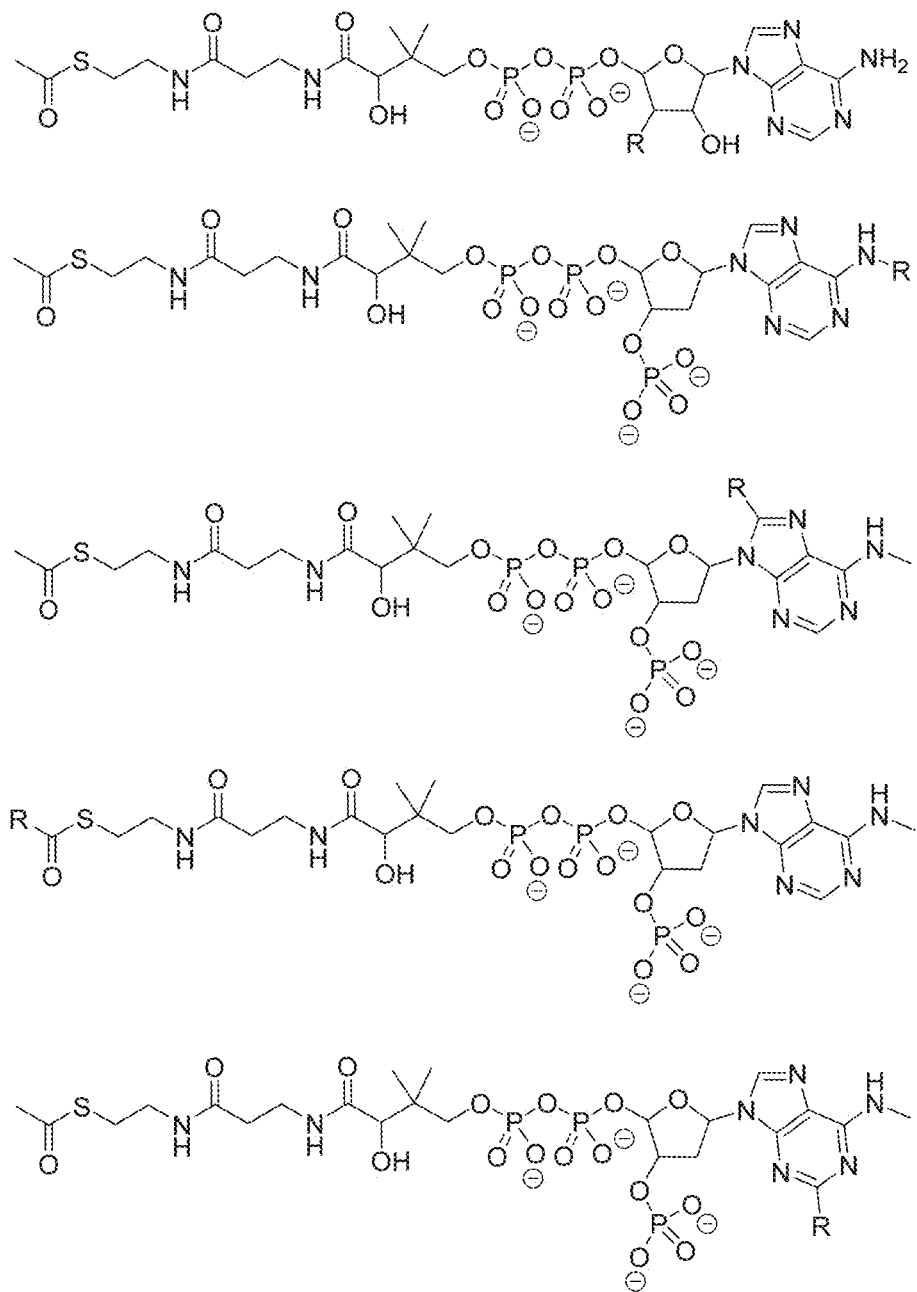
FIG. 3JJJJJ

FIG. 3KKKKK
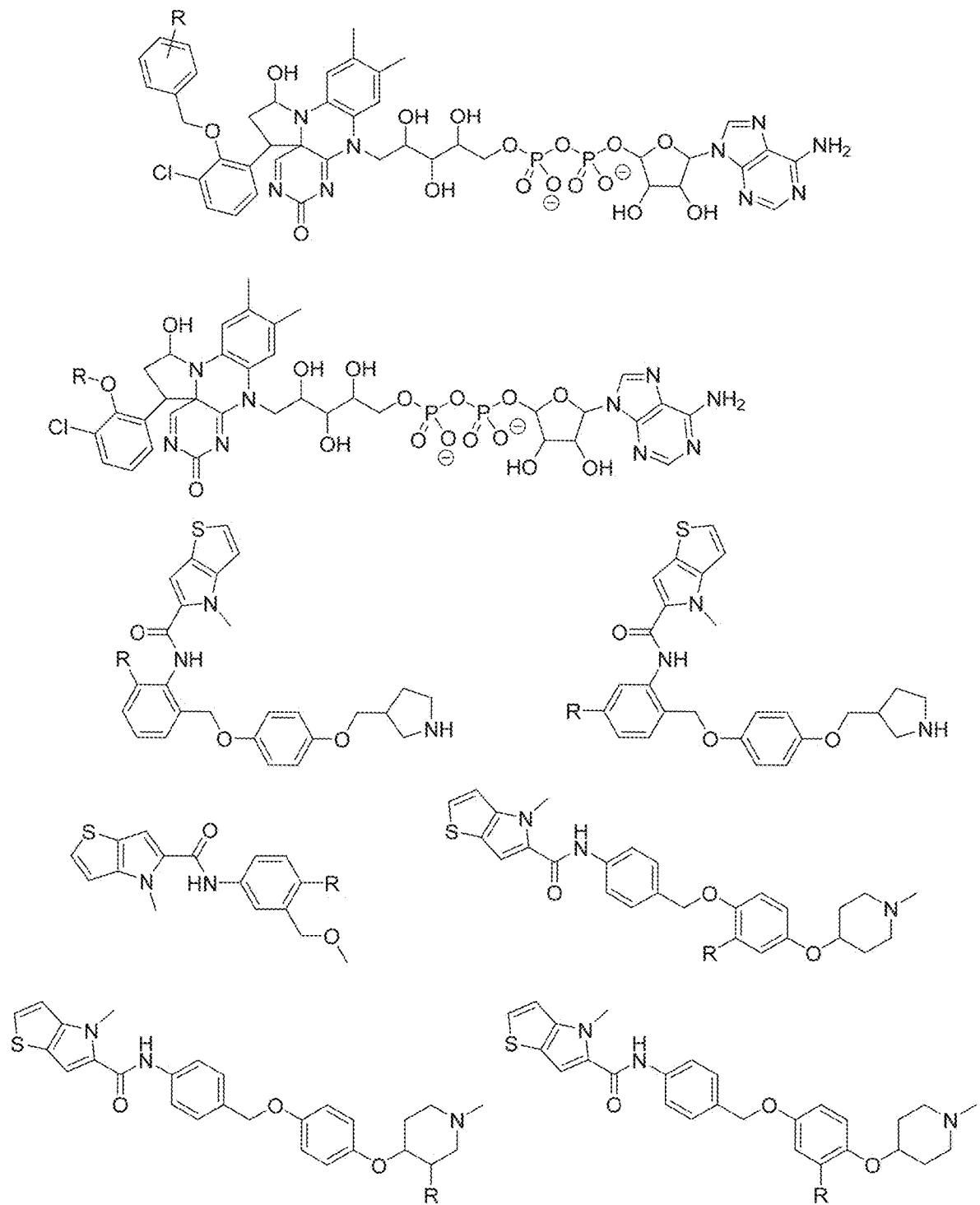

FIG. 3LLLLL
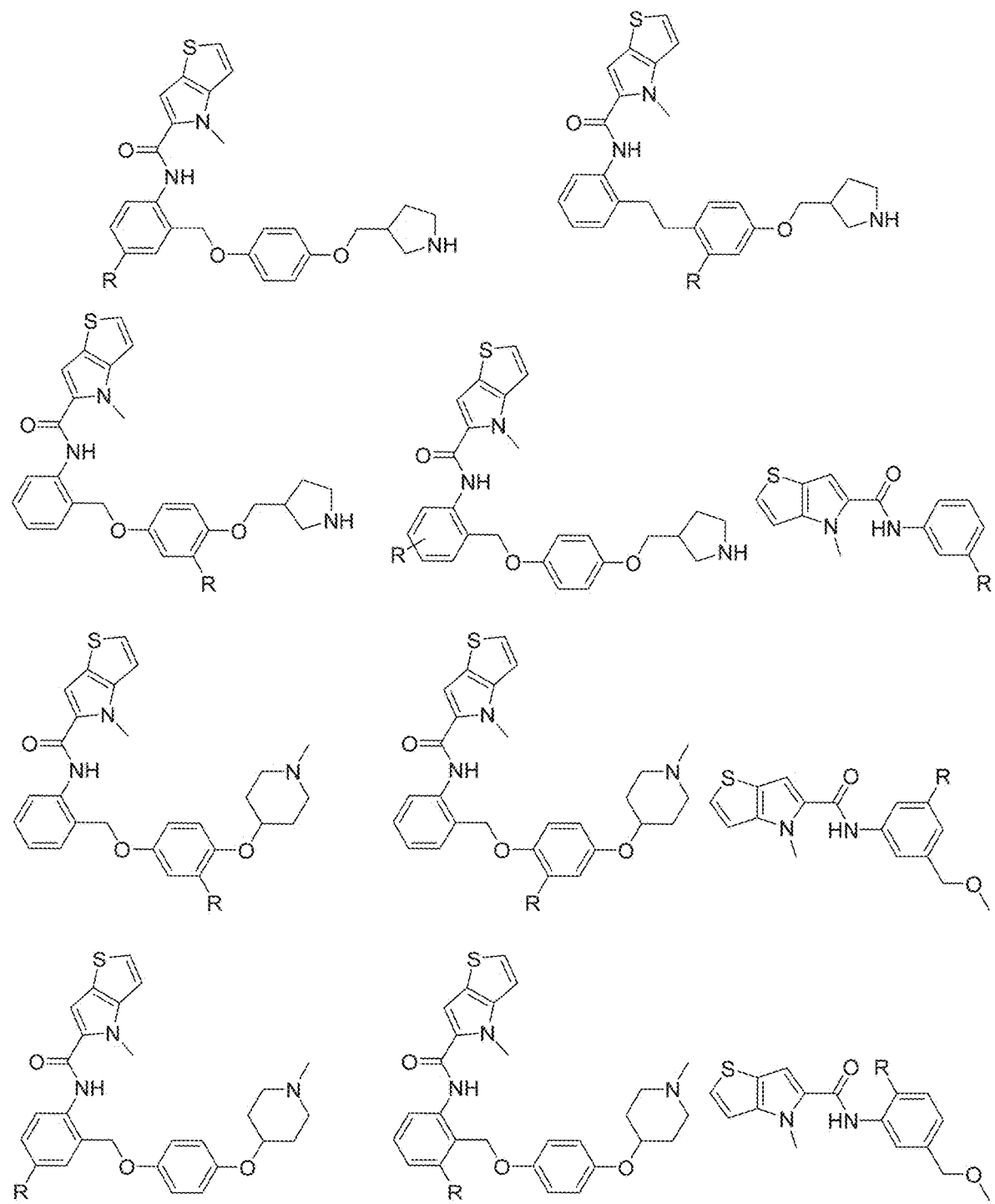

FIG. 3MMMMM
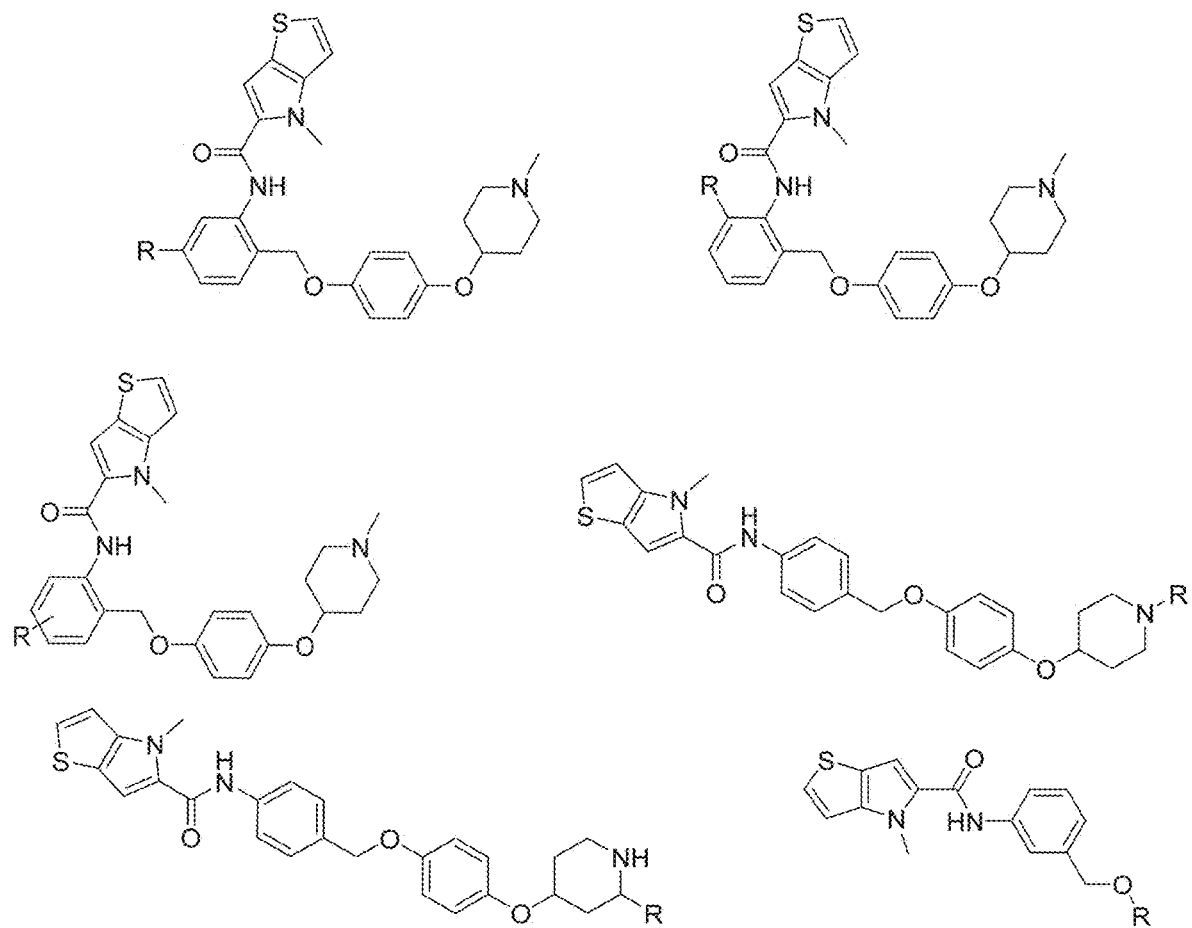
FIG. 3NNNNN
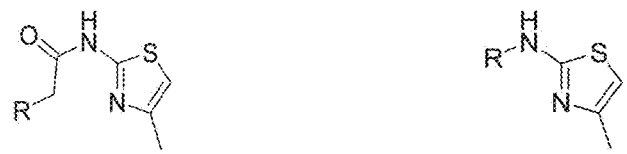

FIG. 300000
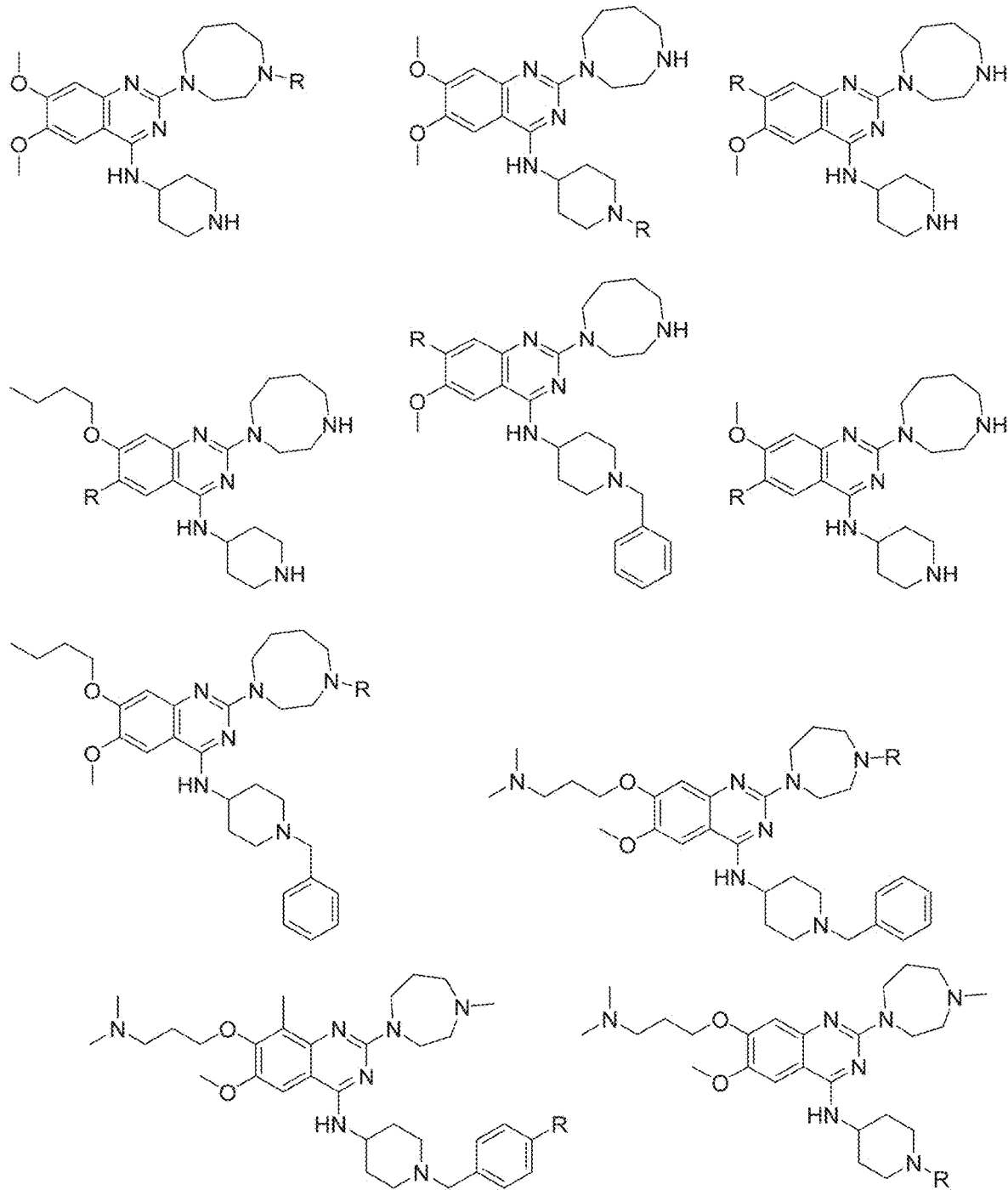

FIG. 3PPPPP
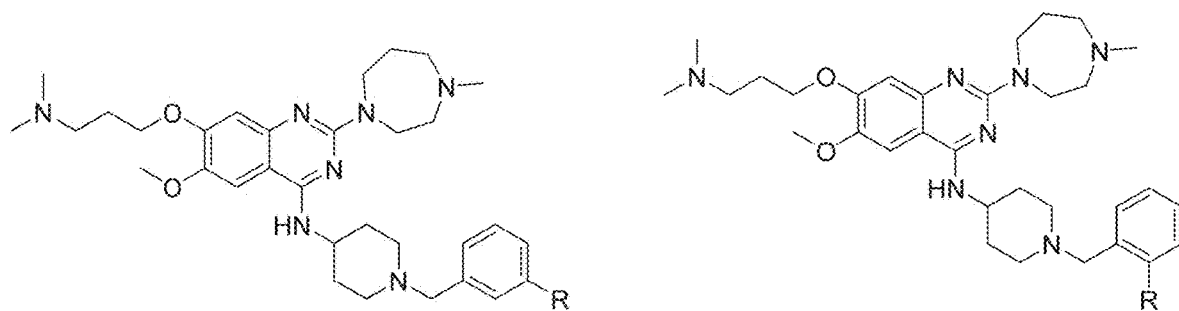
FIG. 3QQQQQ
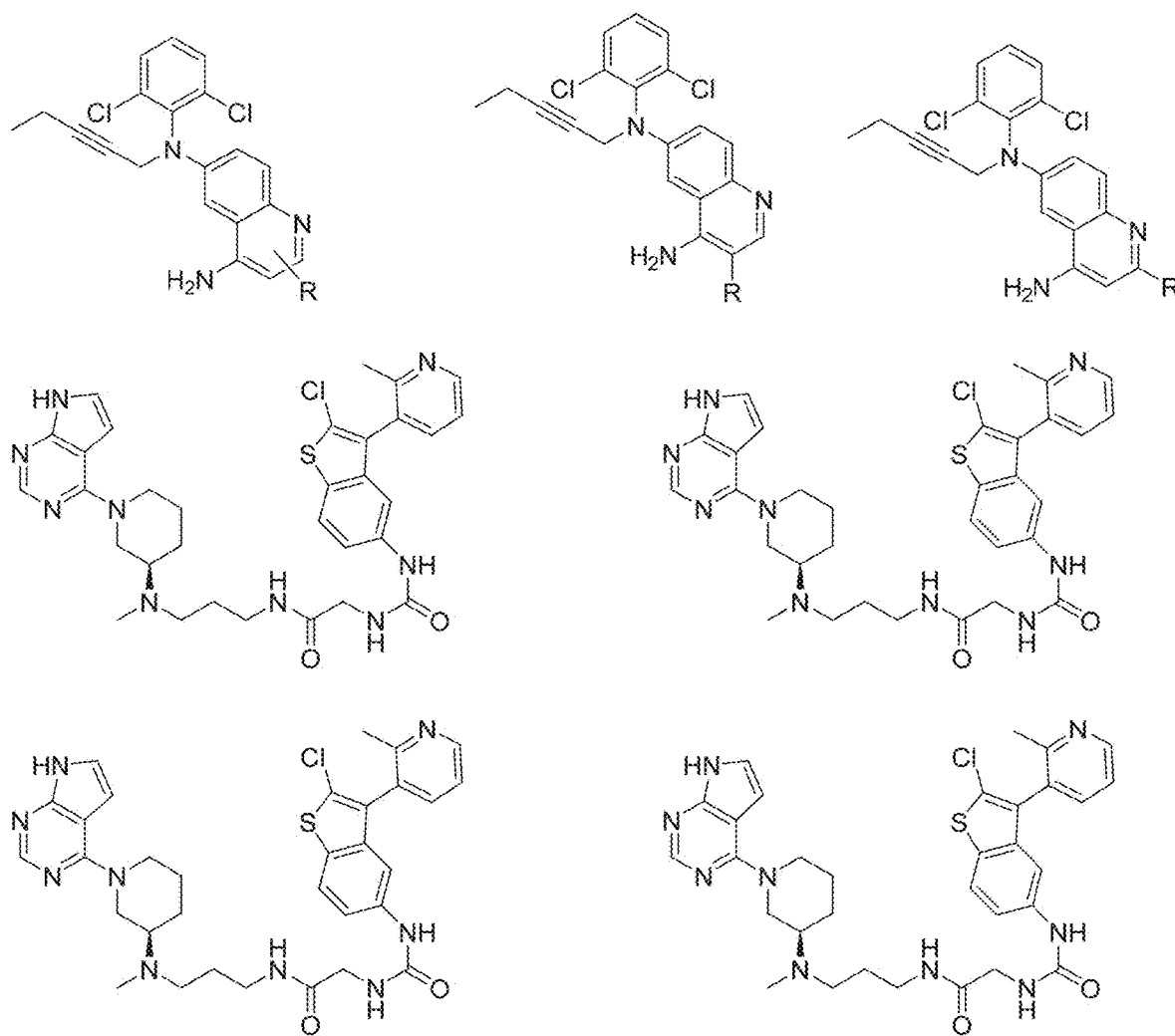

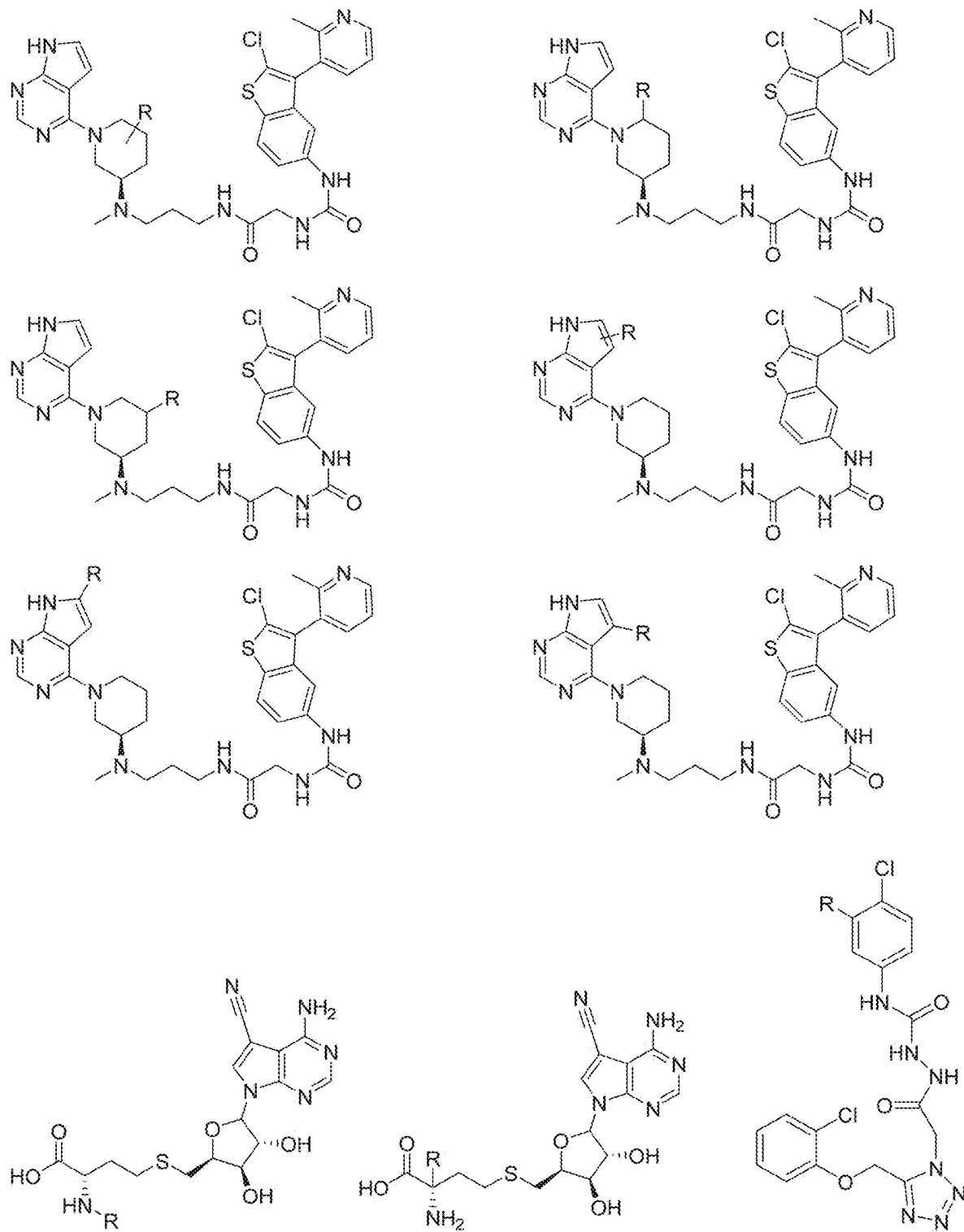
FIG. 3RRRRR

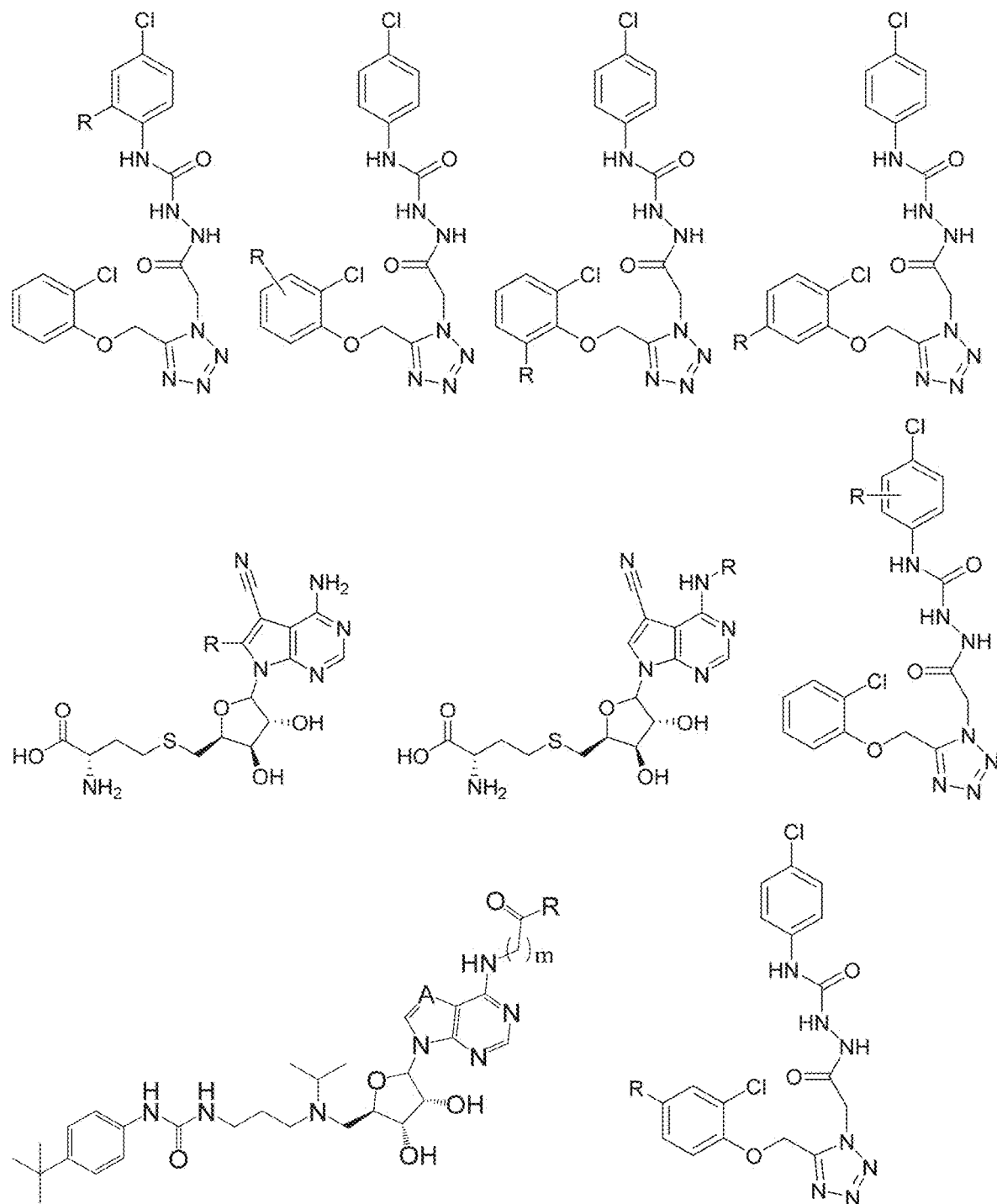
FIG. 3SSSSS

FIG. 3TTTTT
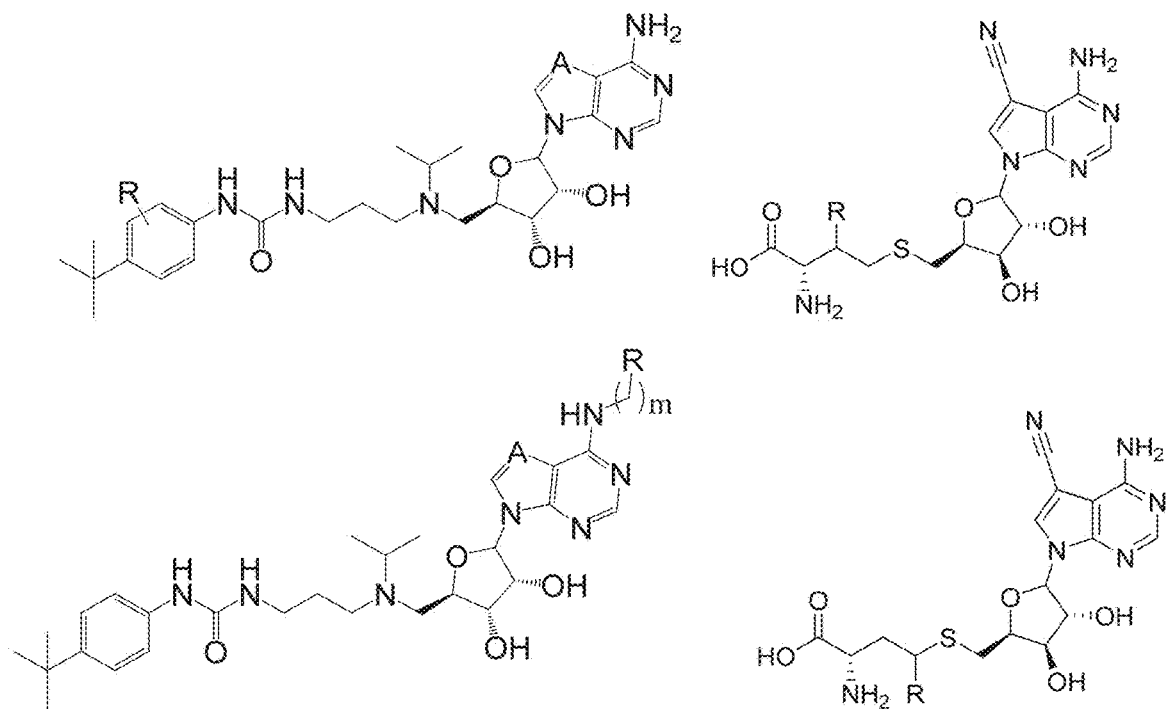
FIG. 3UUUUU
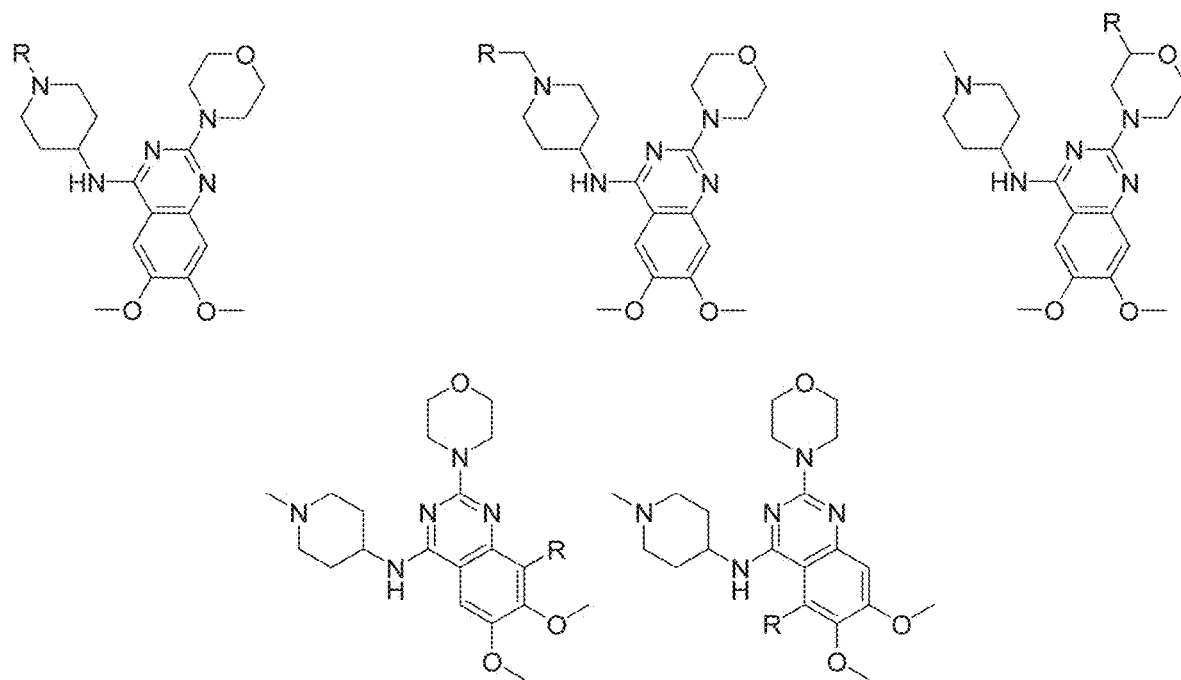

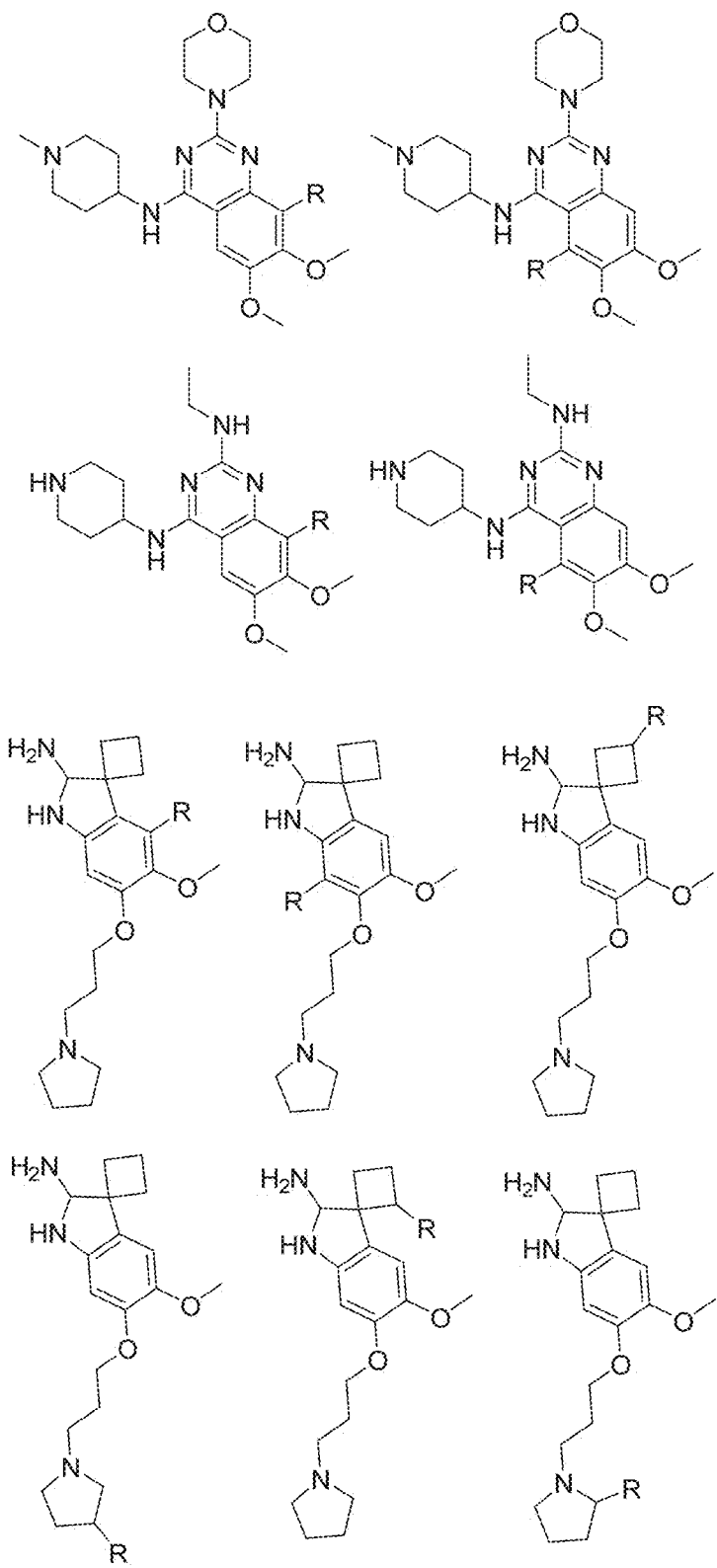
FIG. 3VVVVV

FIG. 3WWWWW
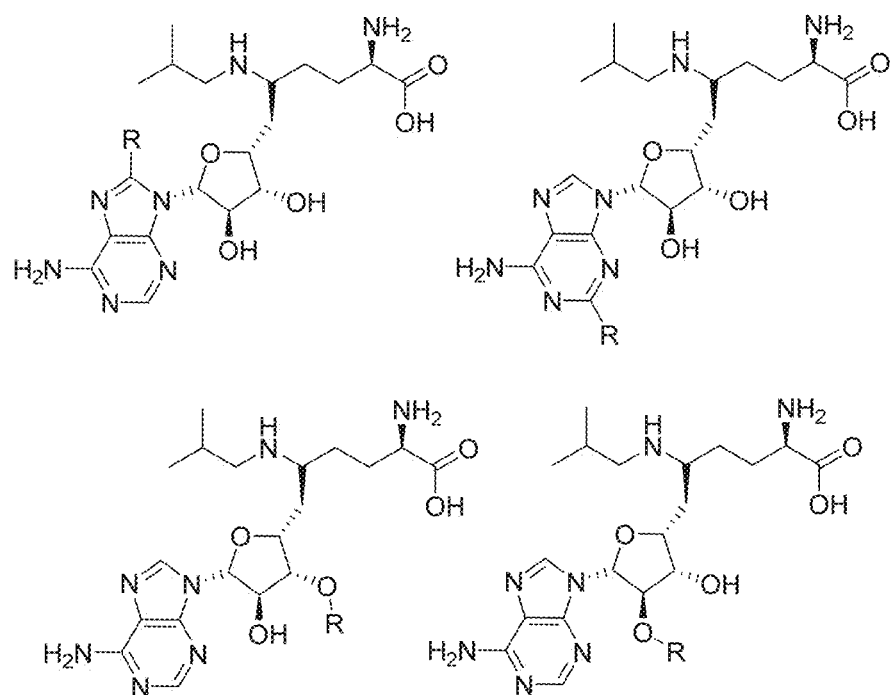
FIG. 3XXXXX
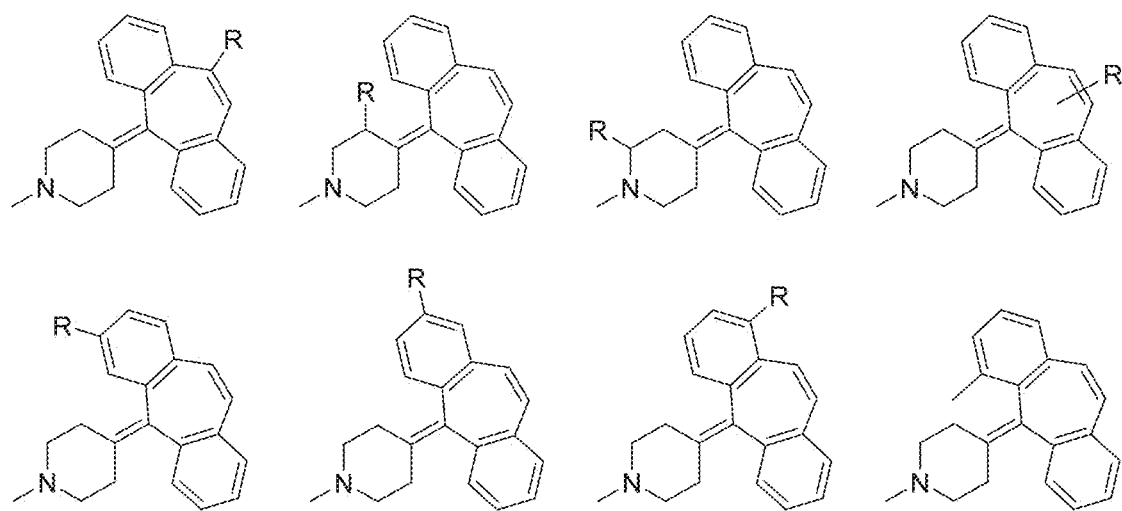

FIG. 3YYYYY
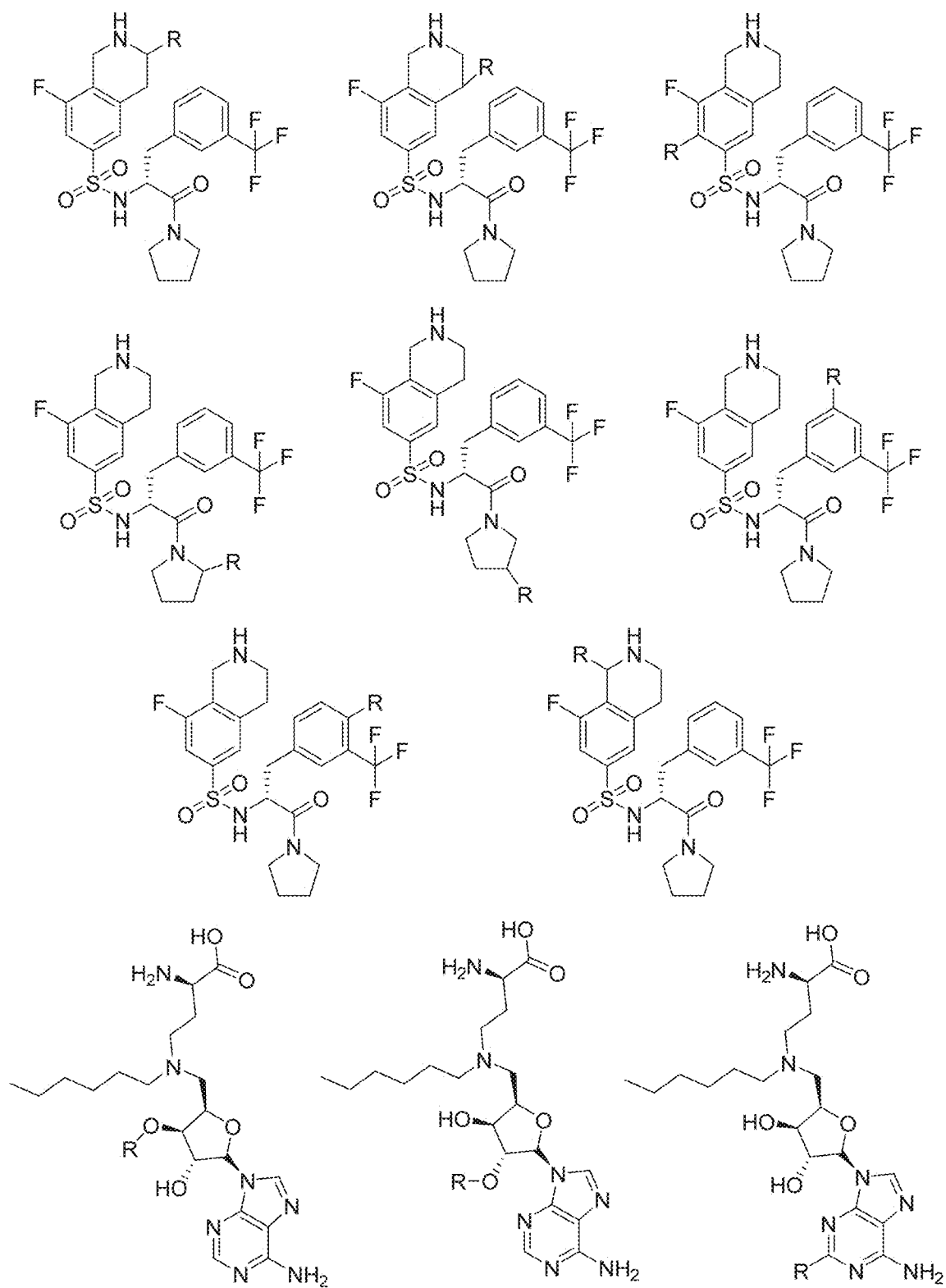

FIG. 3ZZZZZ
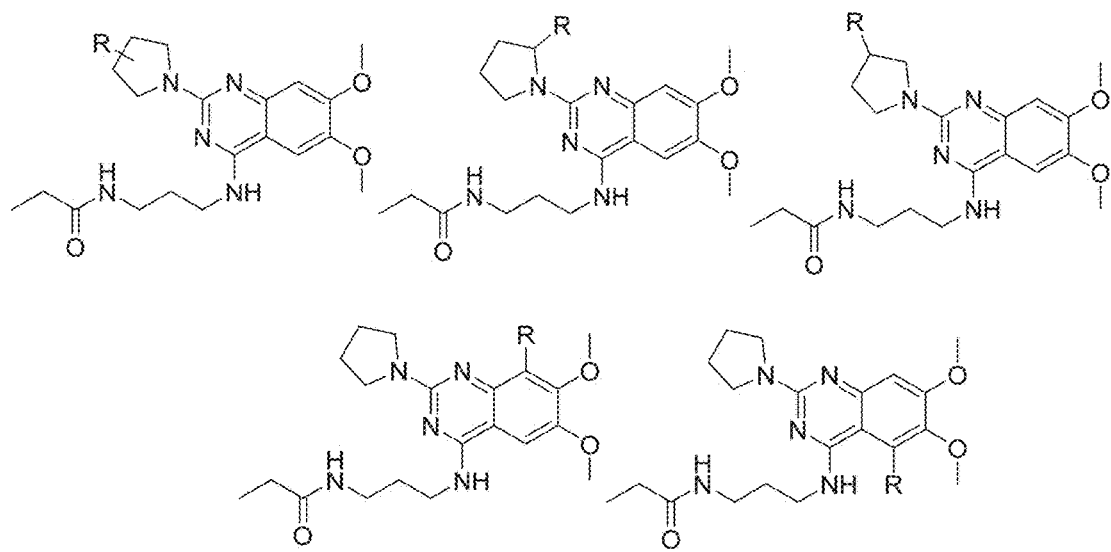
FIG. 4A
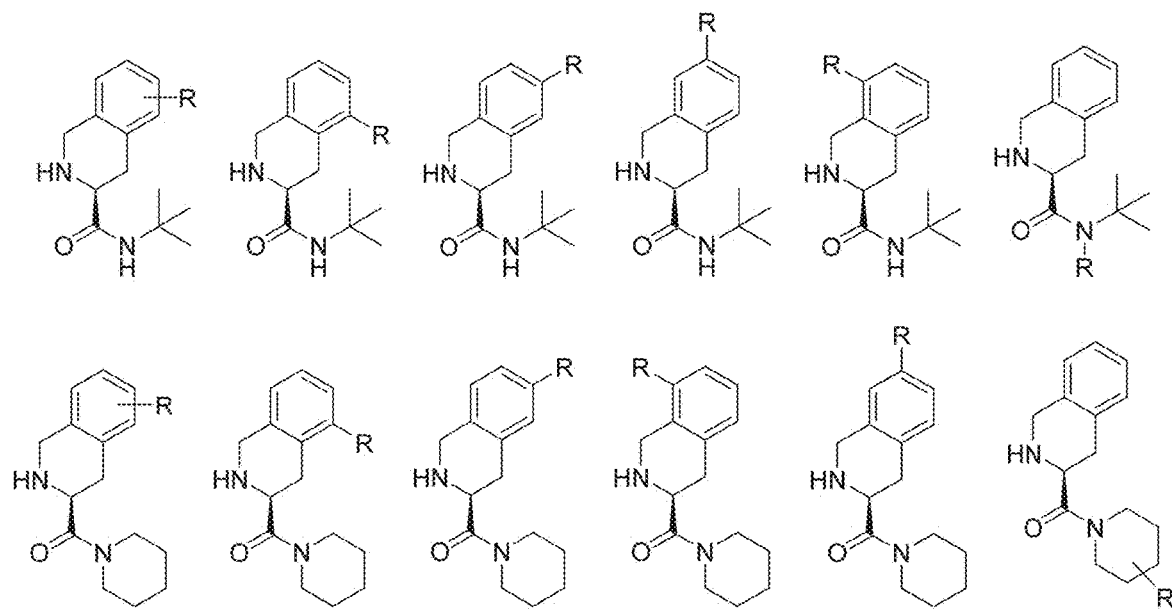

X=H, F, Cl, Br, Me, CF₃O

X=H, F, Cl, Br, Me, CF₃O

X=H, F, Cl, Br, Me, CF₃O

FIG. 8AAA
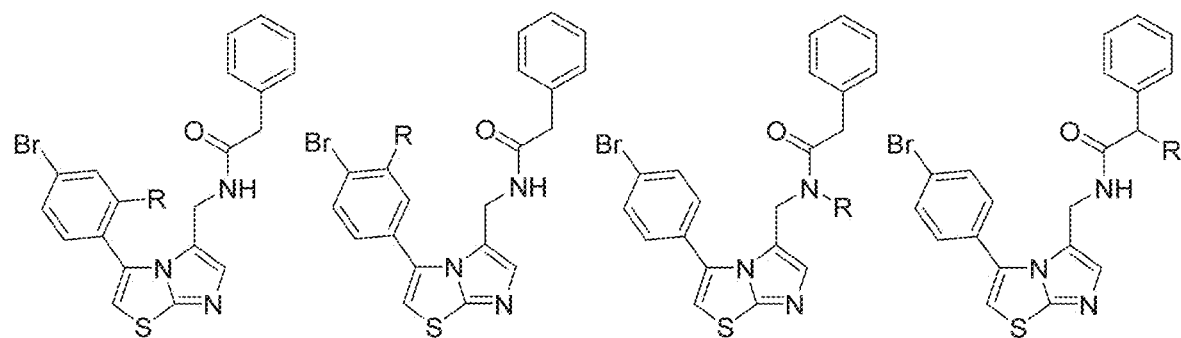
FIG. 8BBB
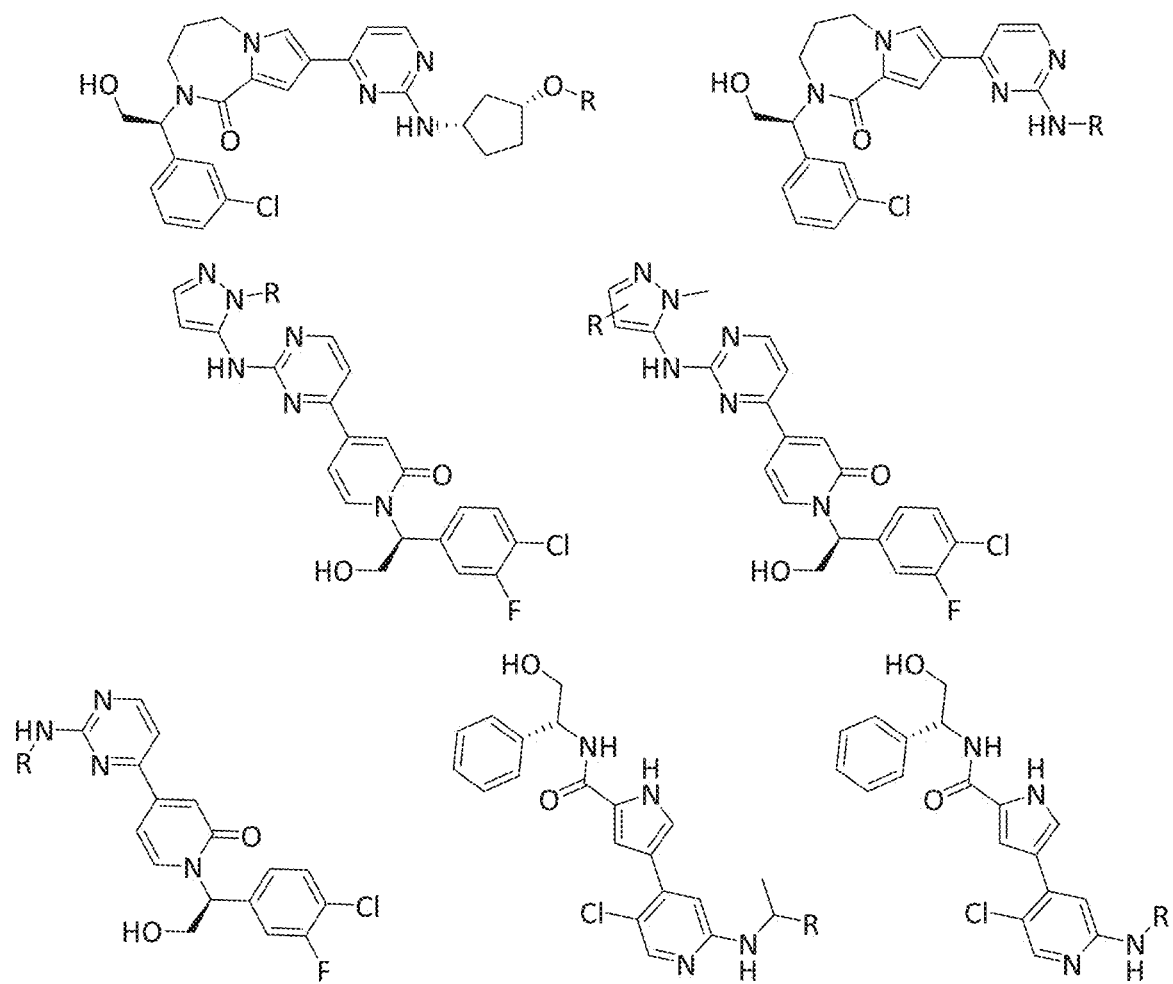

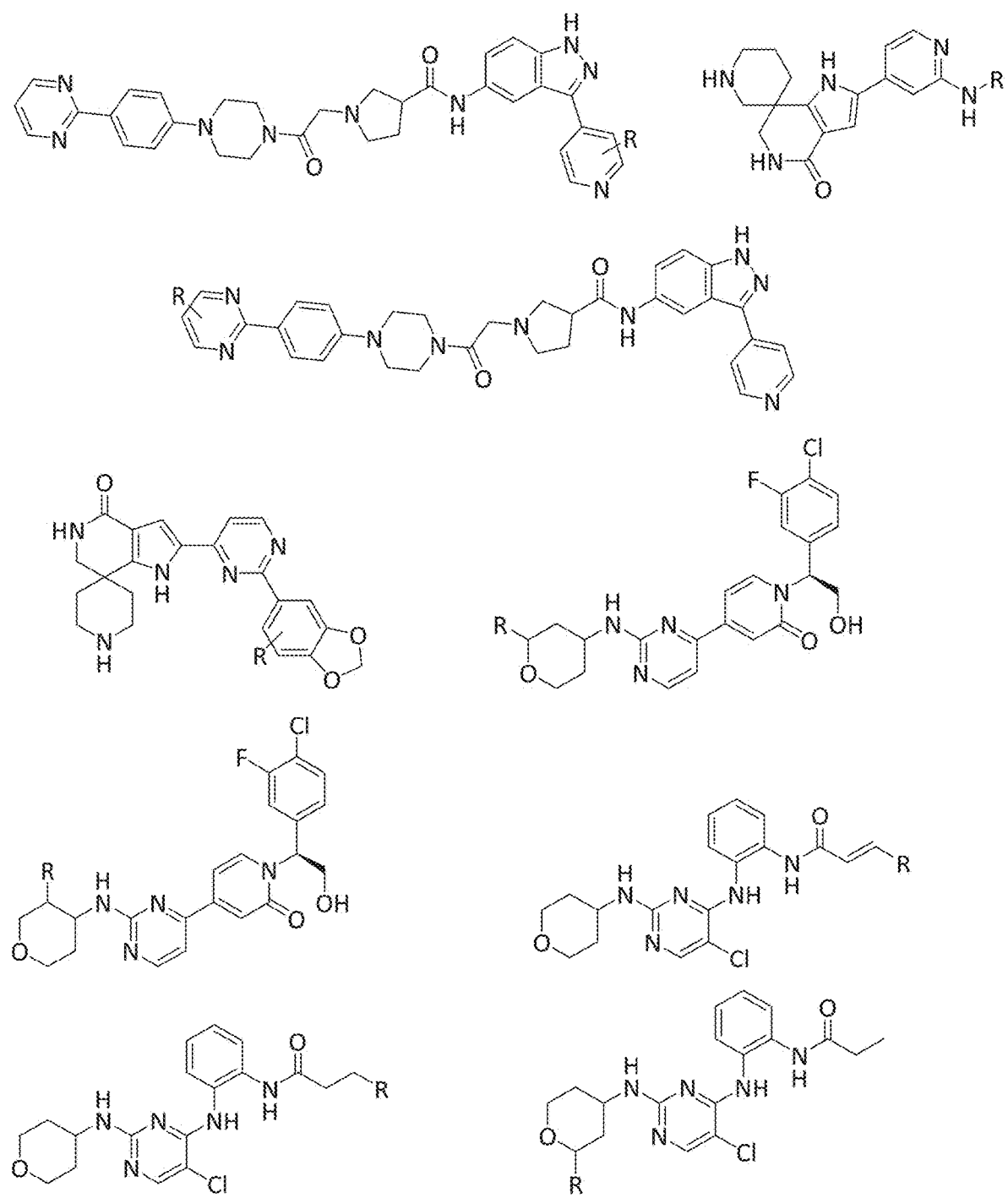
FIG. 8CCC

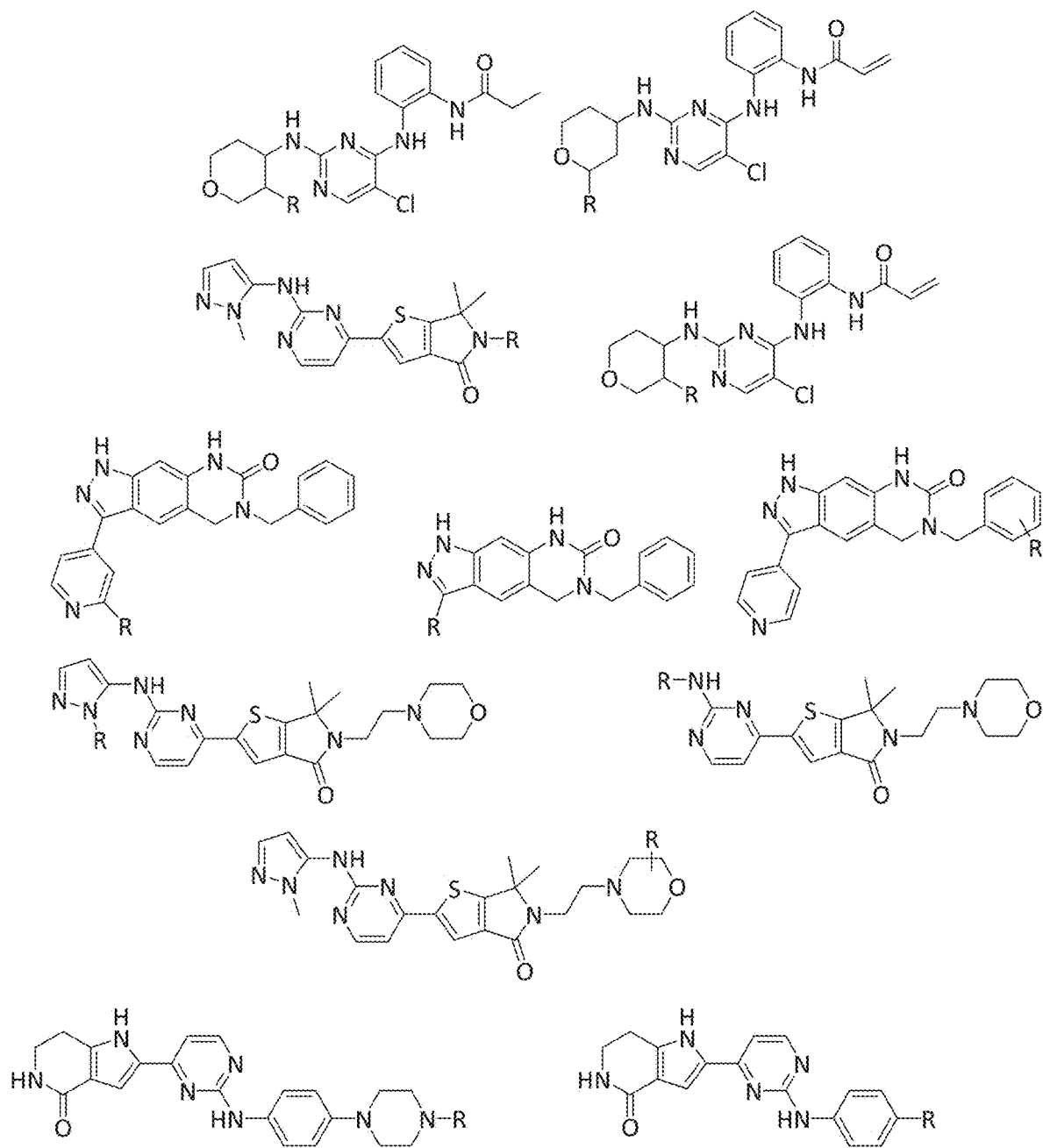
FIG. 8DDD

FIG. 8EEE
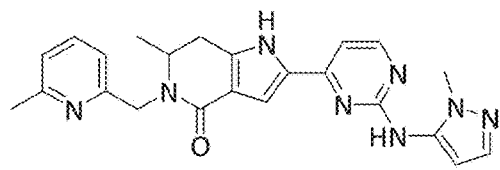
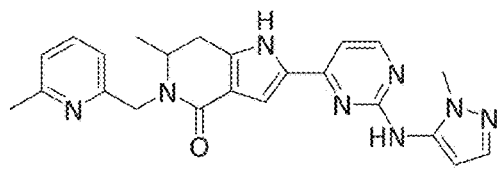
FIG. 8FFF
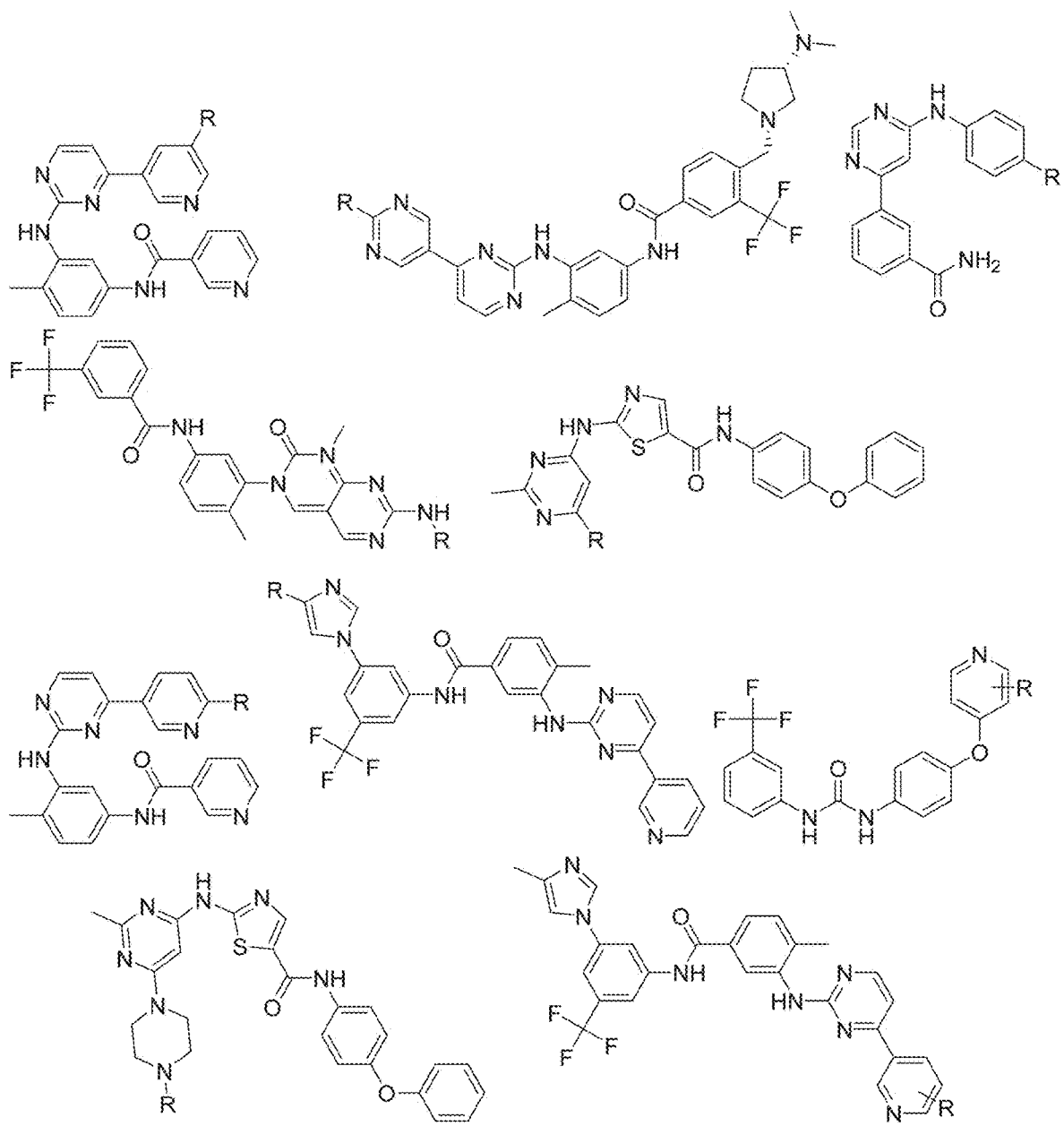

FIG. 8GGG
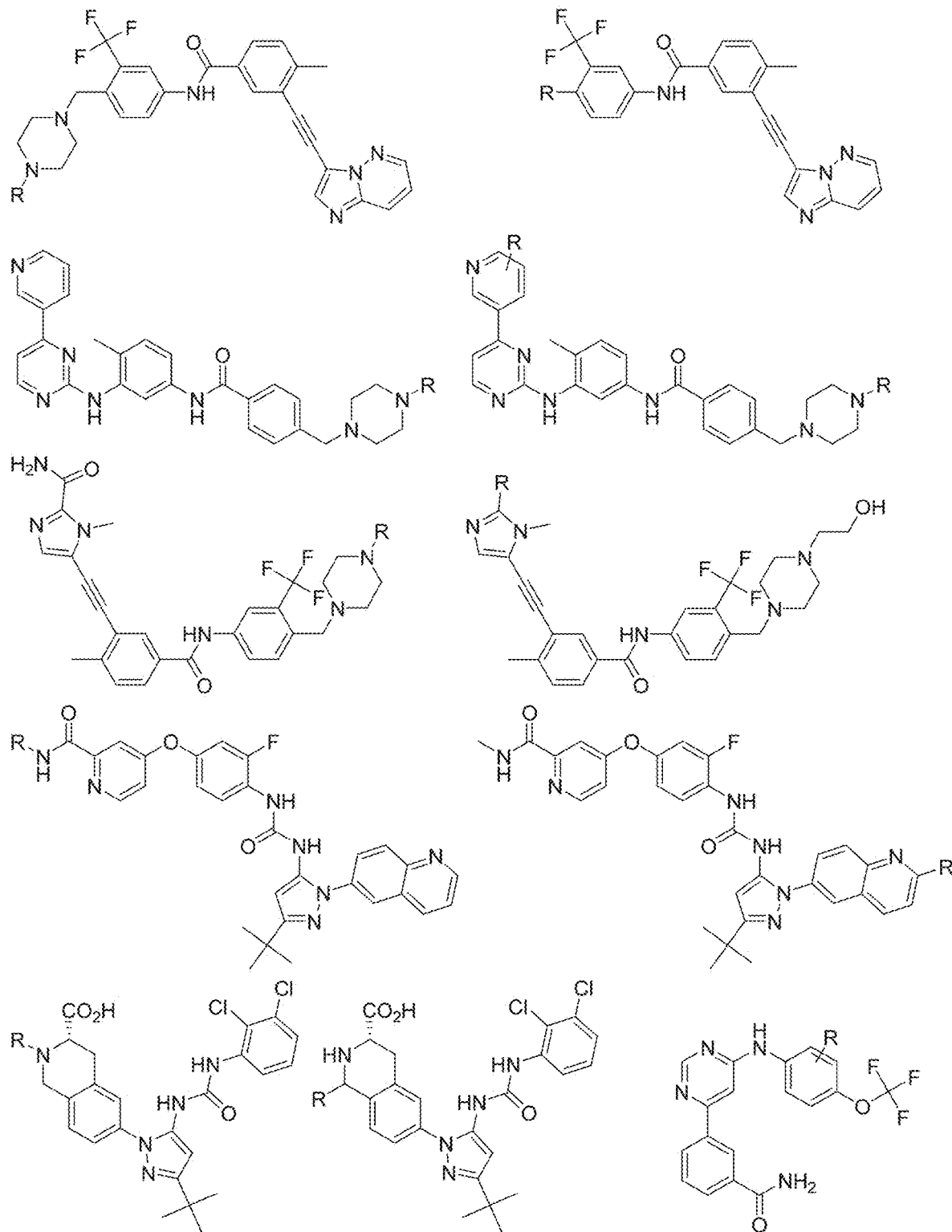

FIG. 8HHH
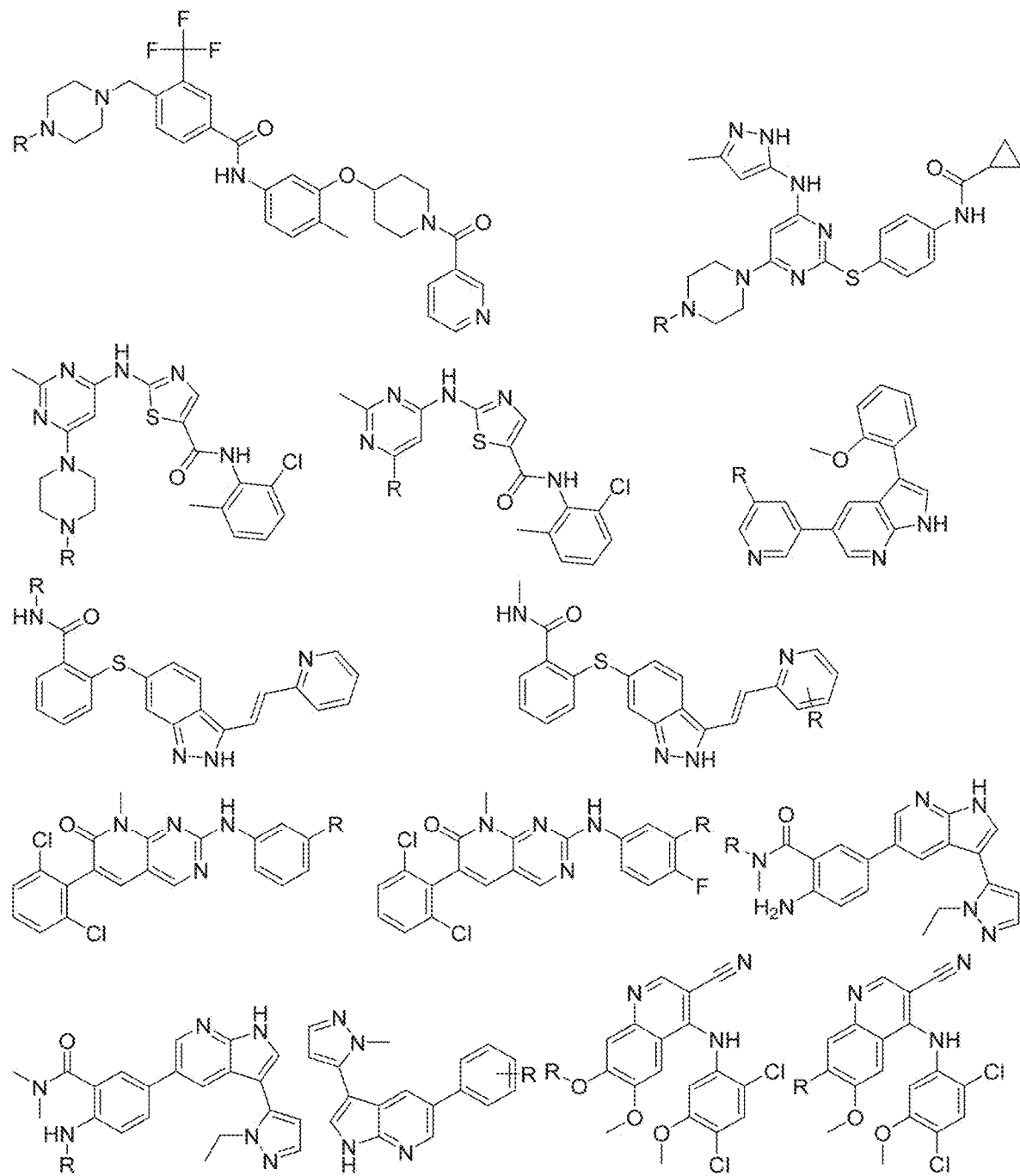

FIG. 8III
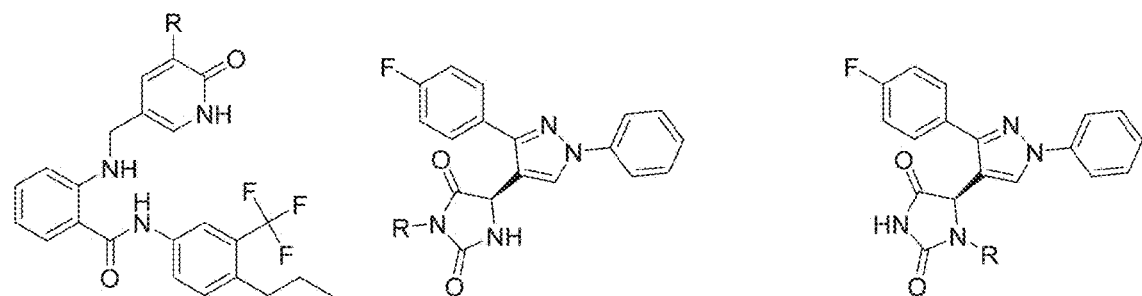
FIG. 8JJJ
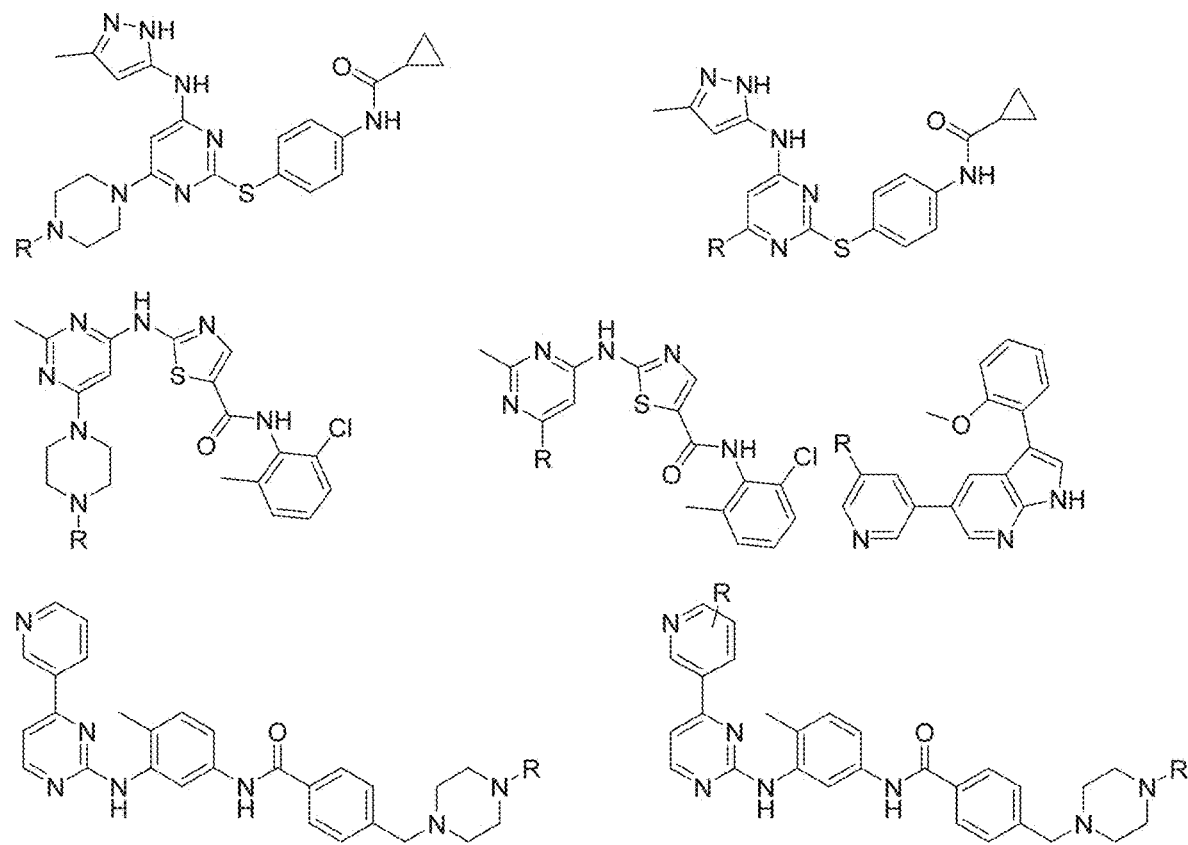

FIG. 8KKK
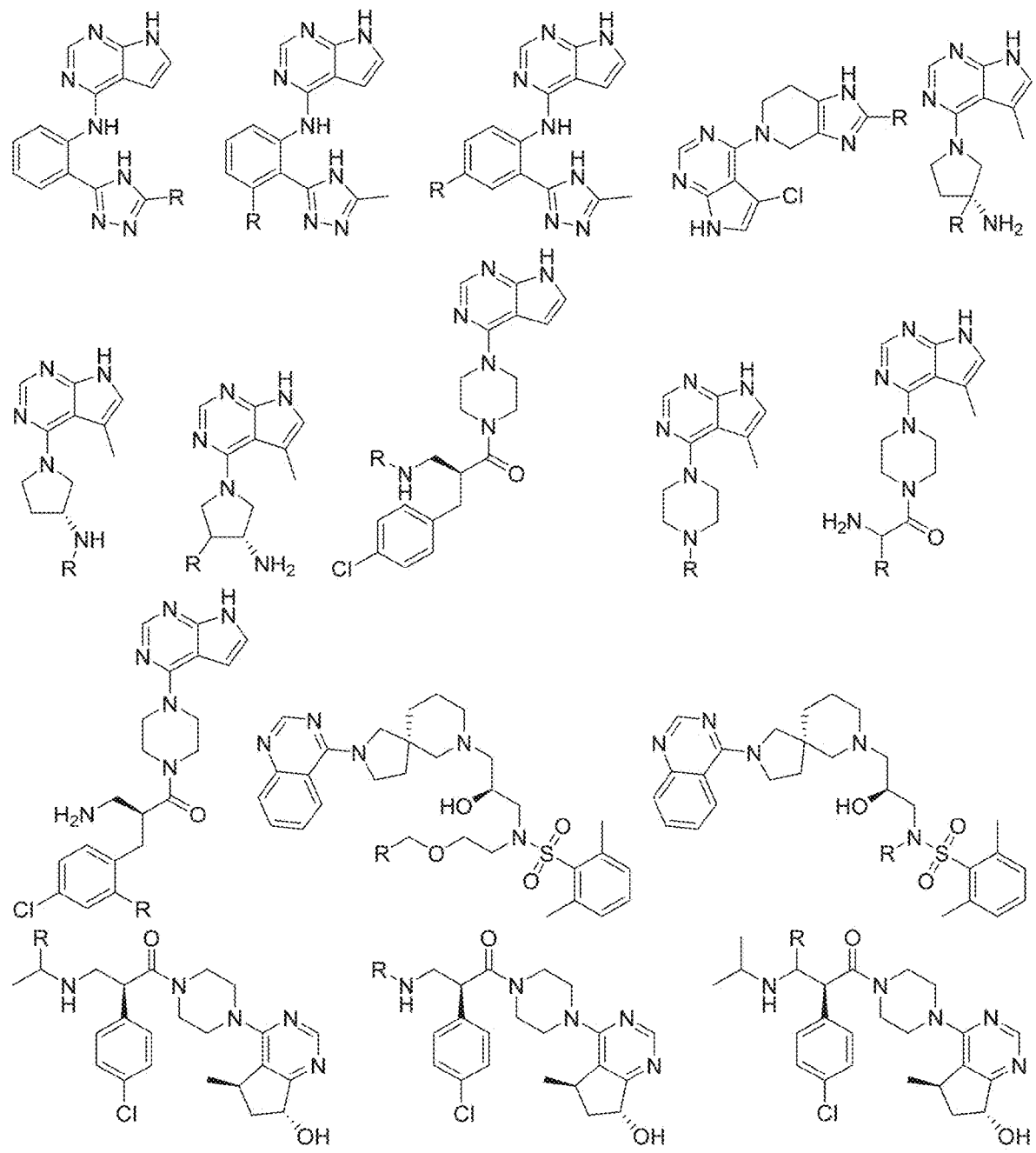

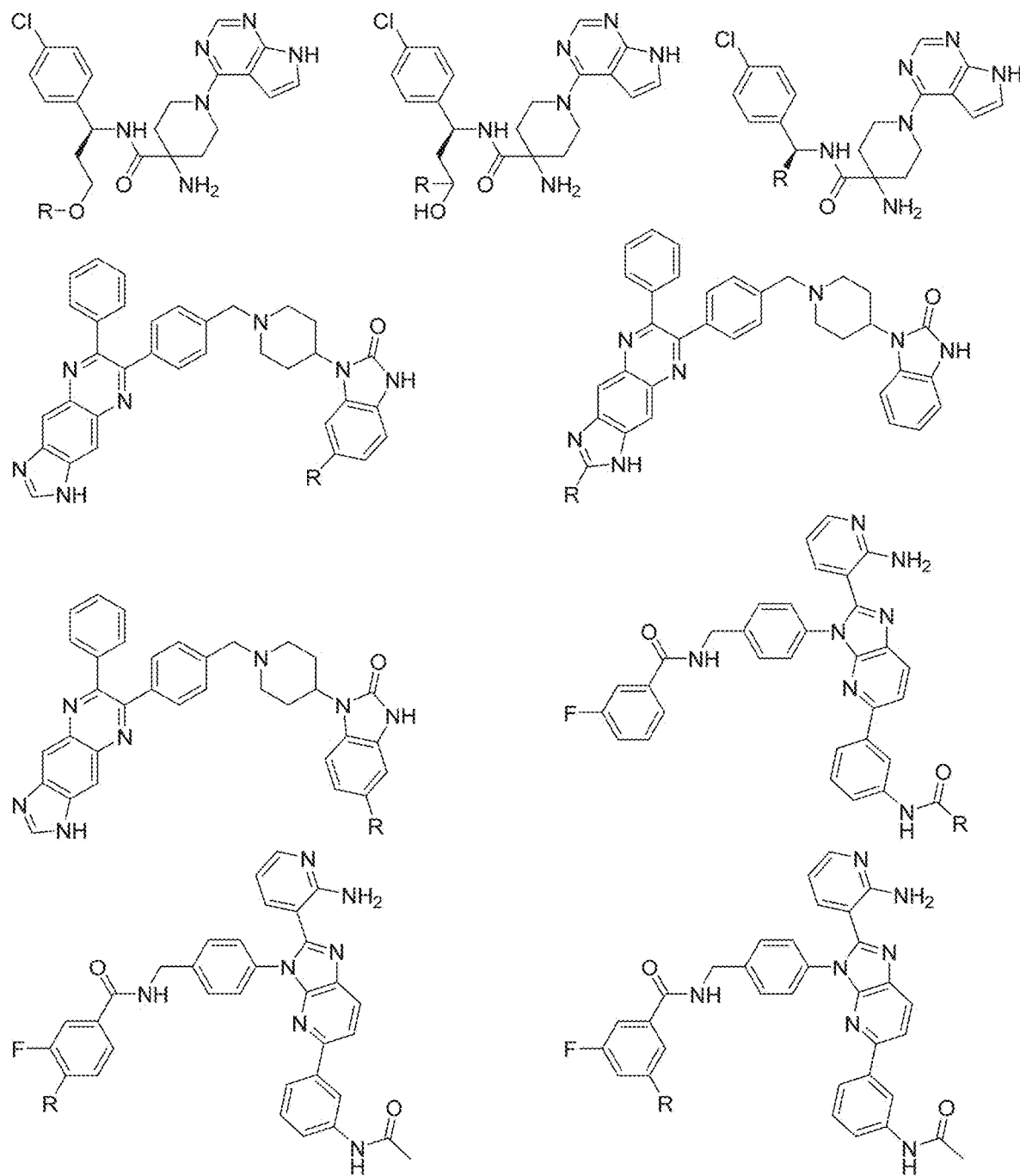
FIG. 8LLL

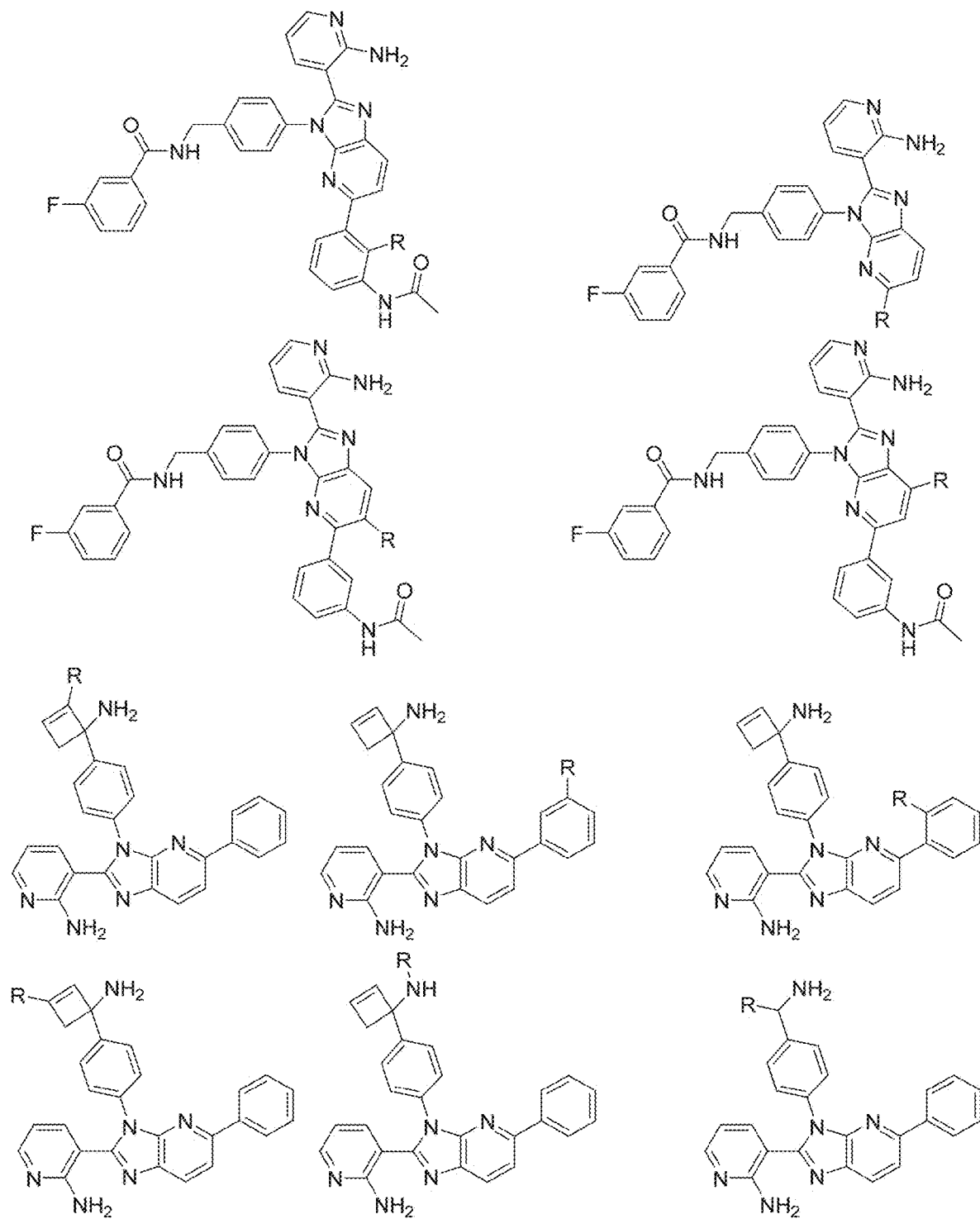
FIG. 8MMM

FIG. 8NNN
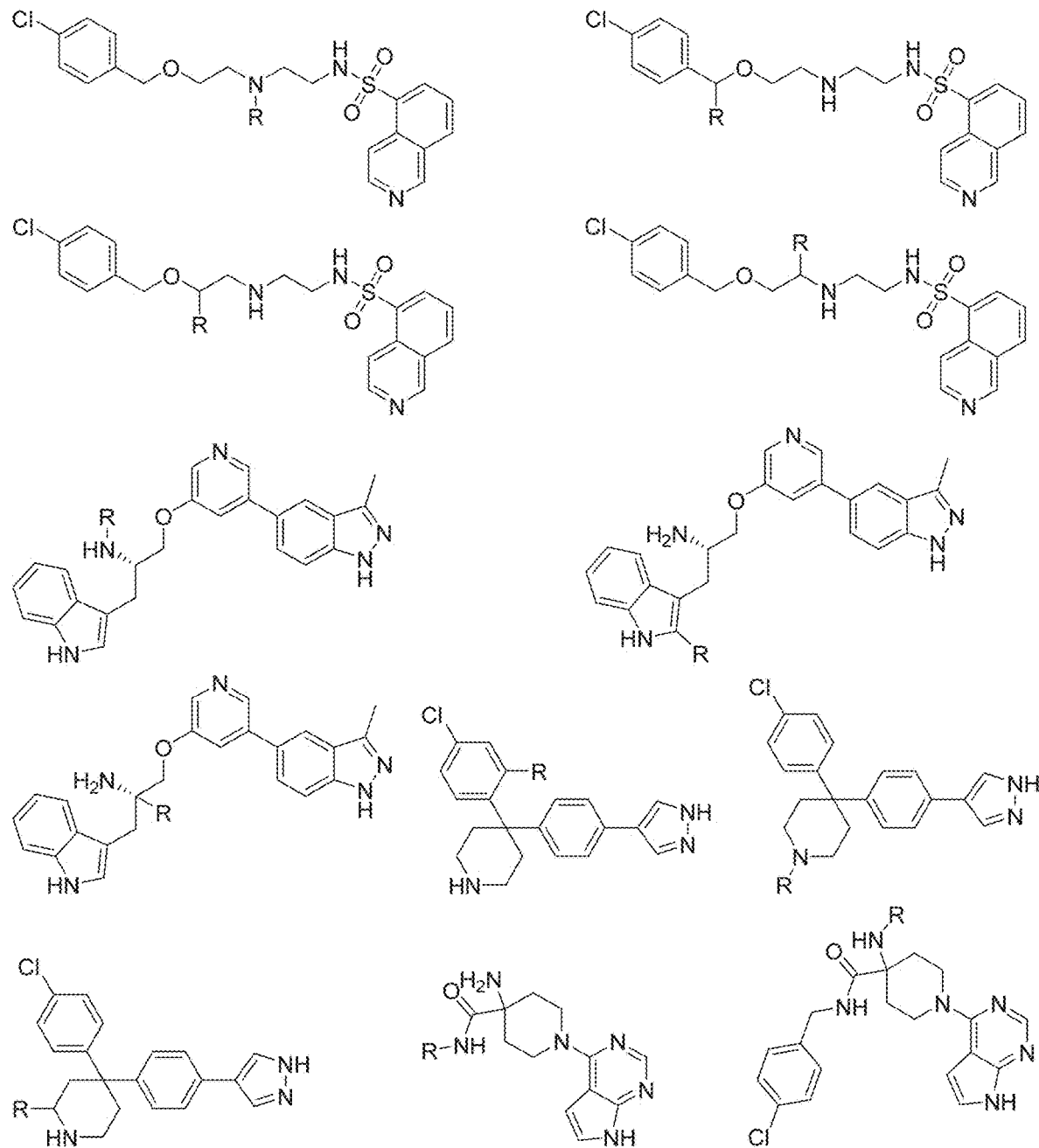

FIG. 8OOO
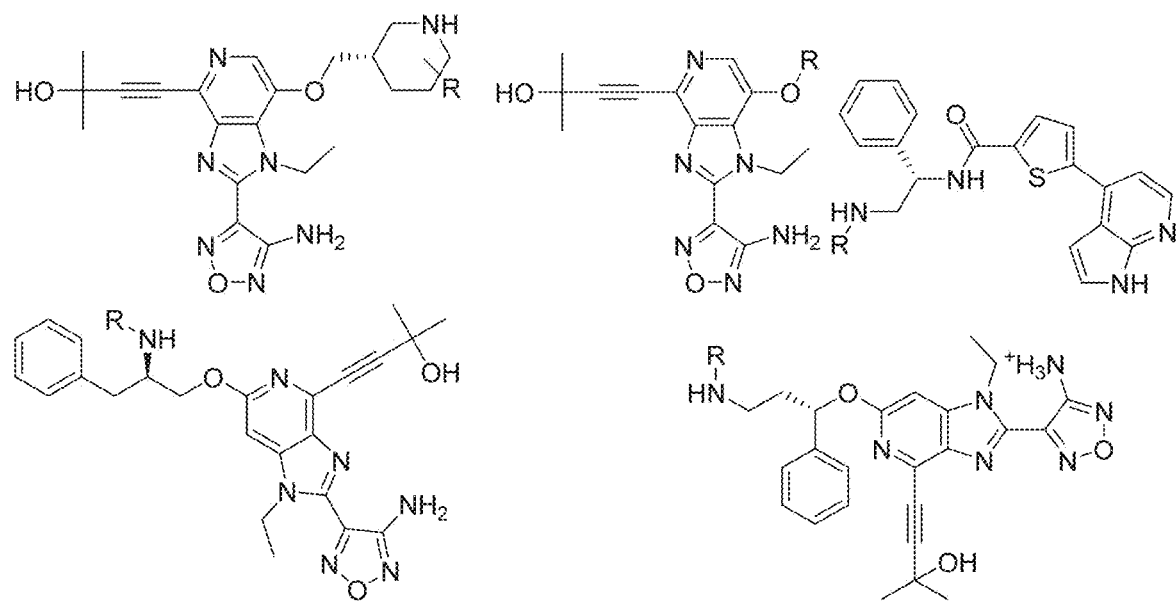
FIG. 8PPP
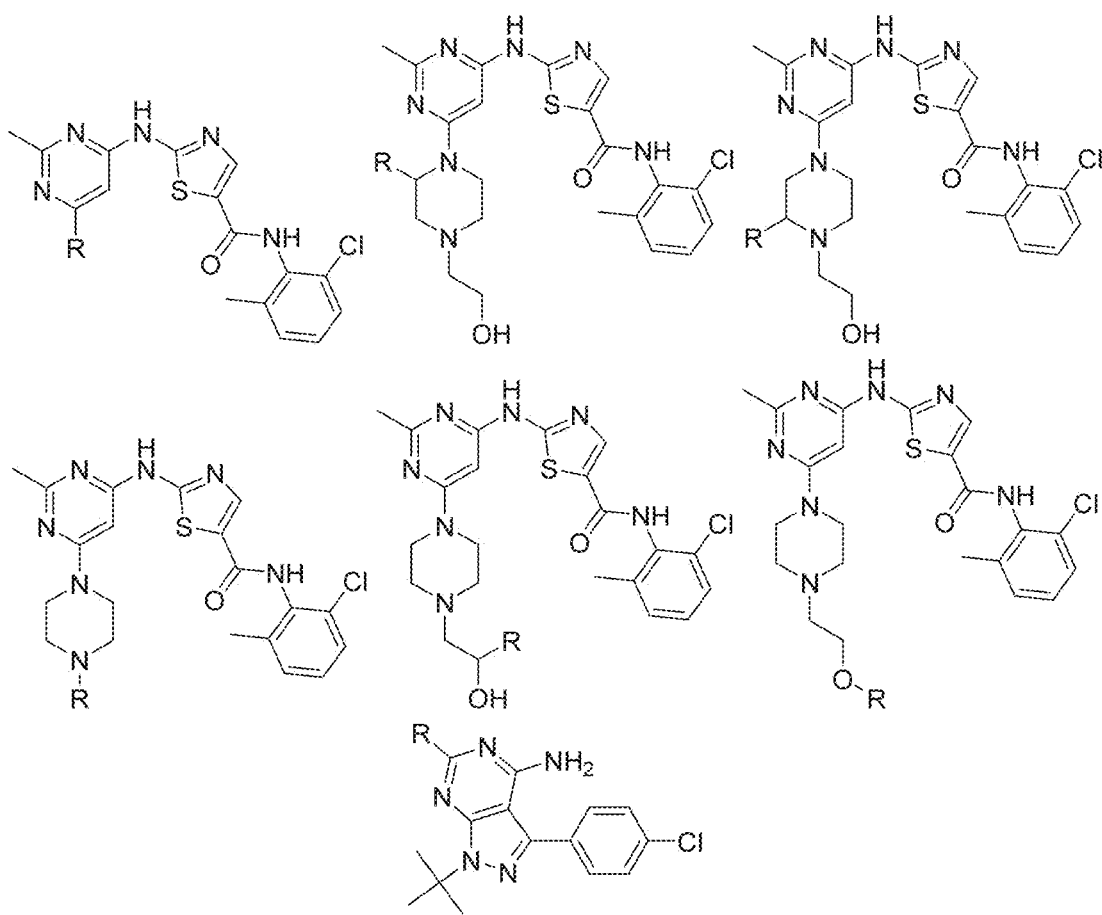

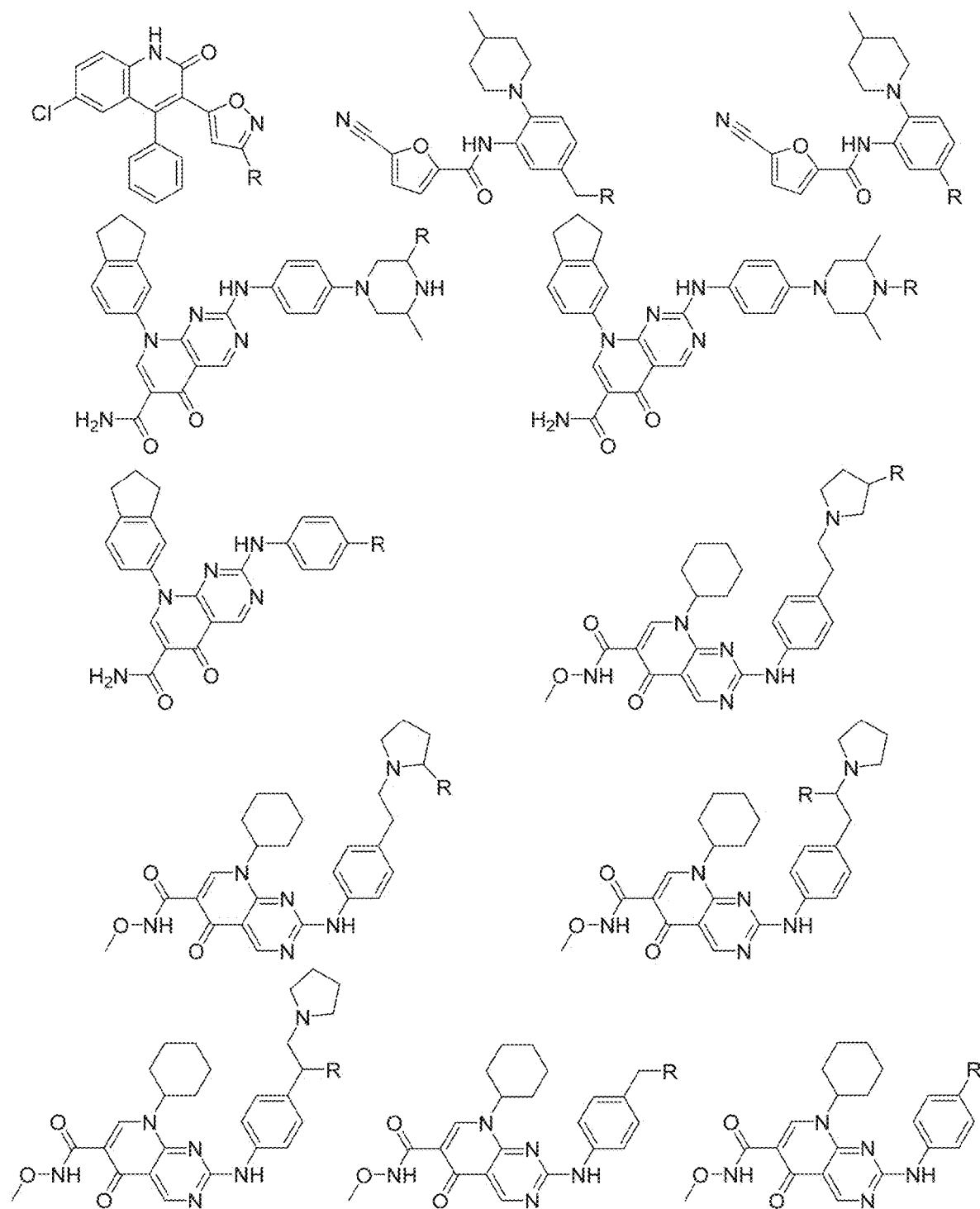
FIG. 8QQQ

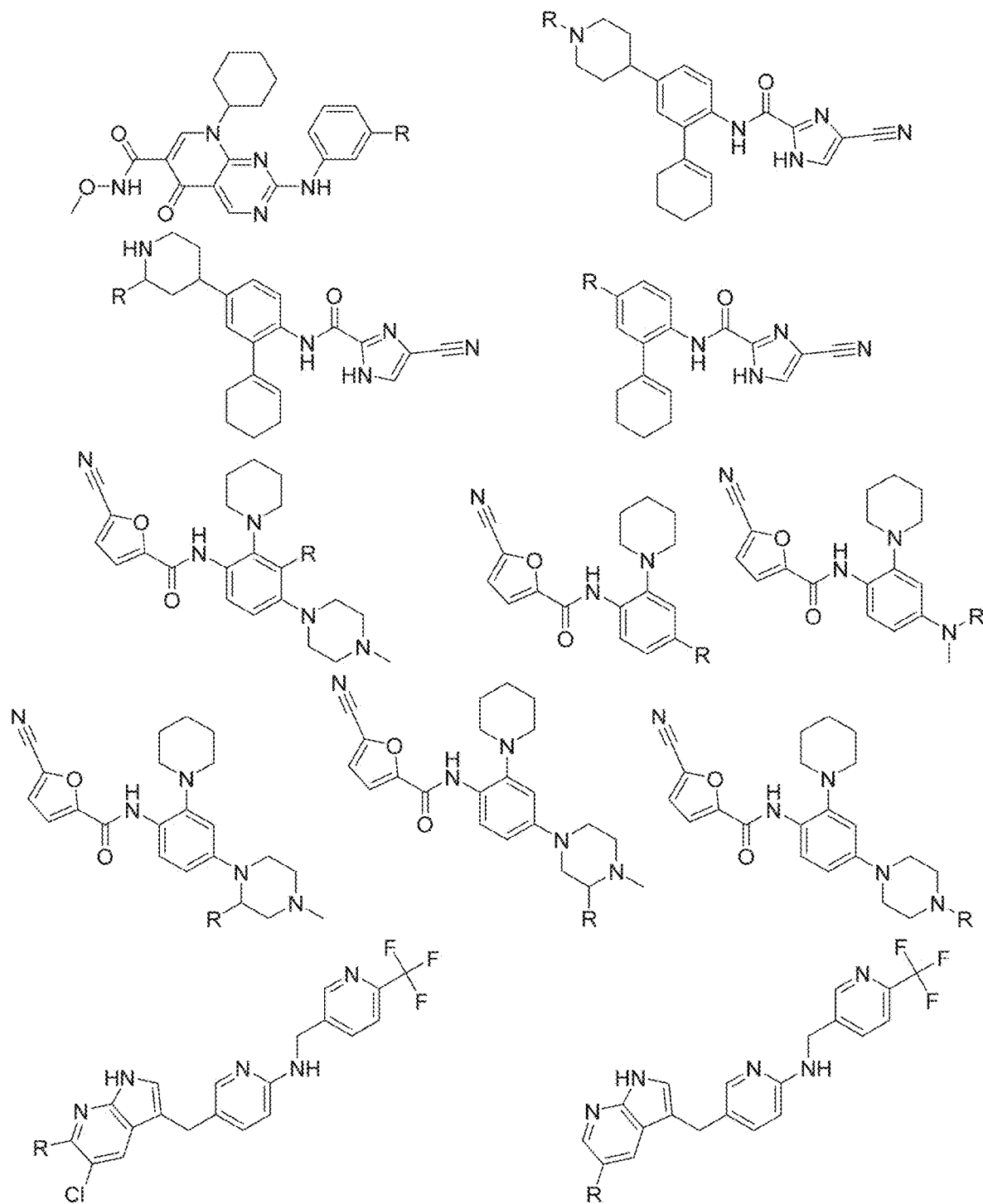
FIG. 8RRR

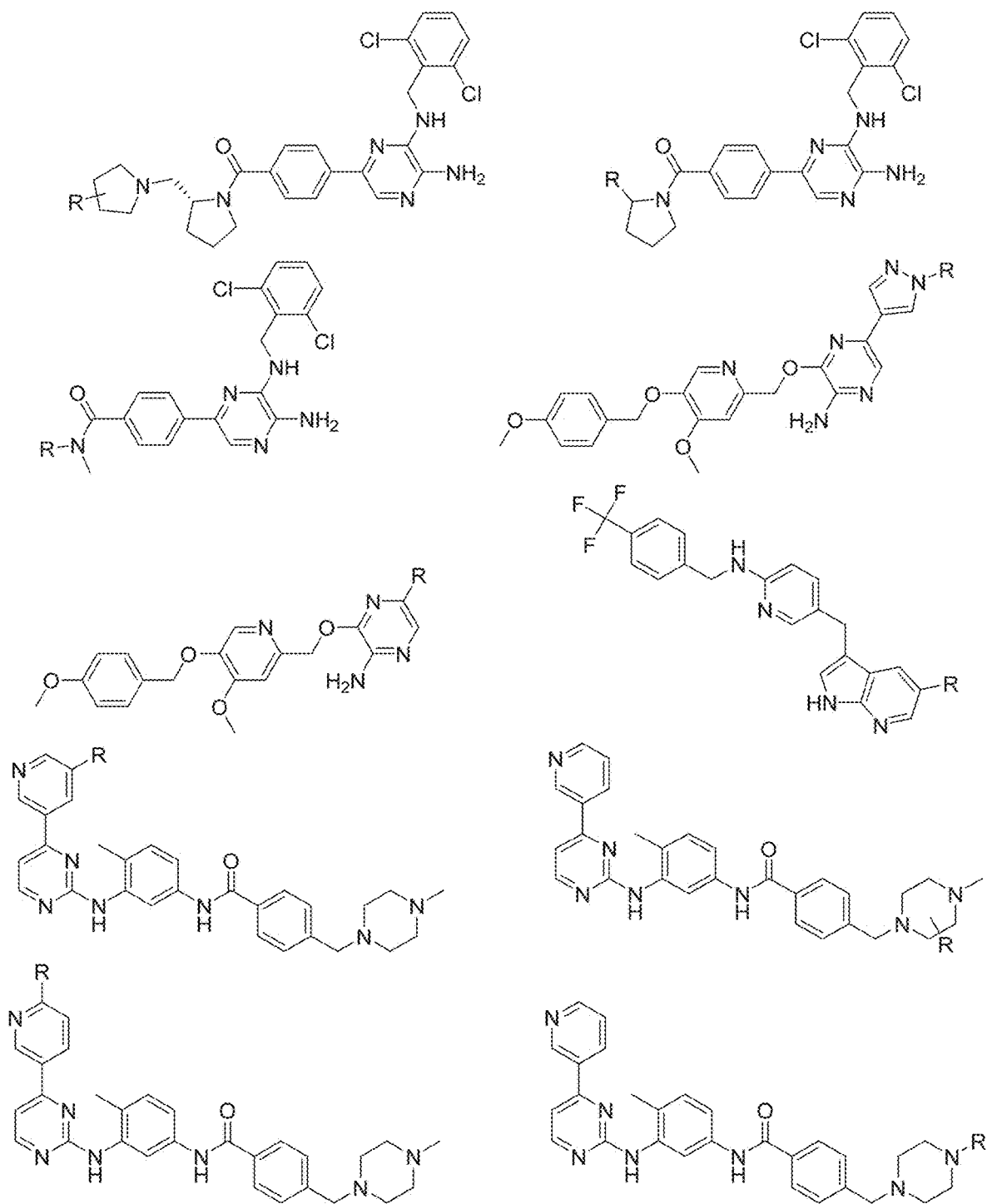
FIG. 8SSS

FIG. 8TTT
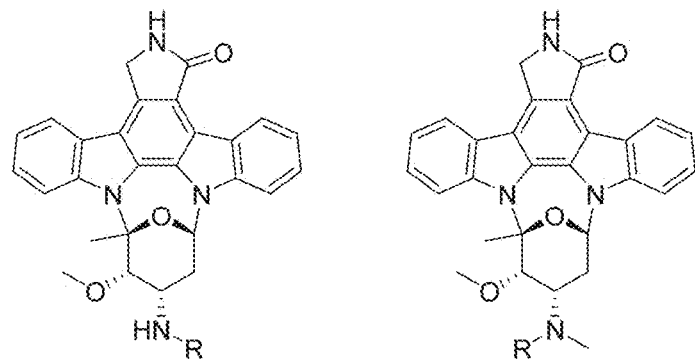
FIG. 8UUU
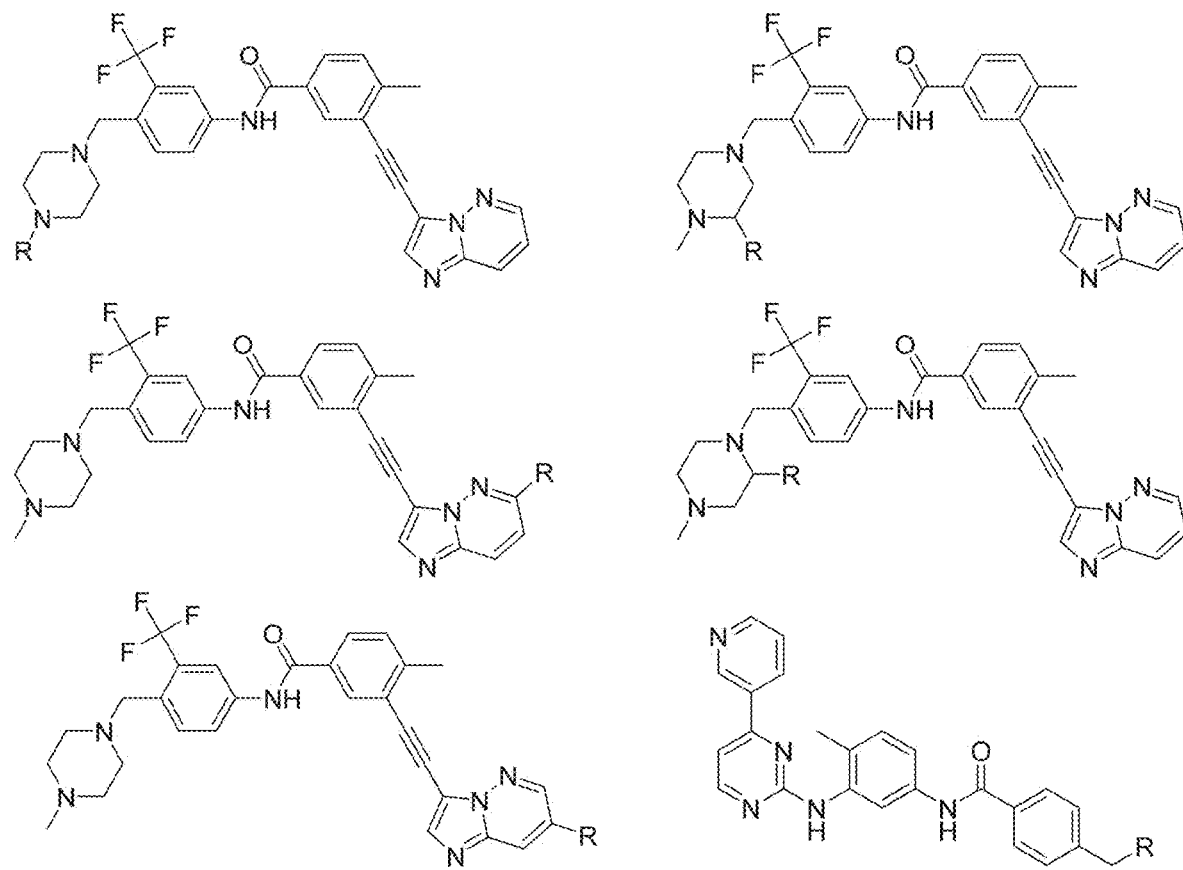

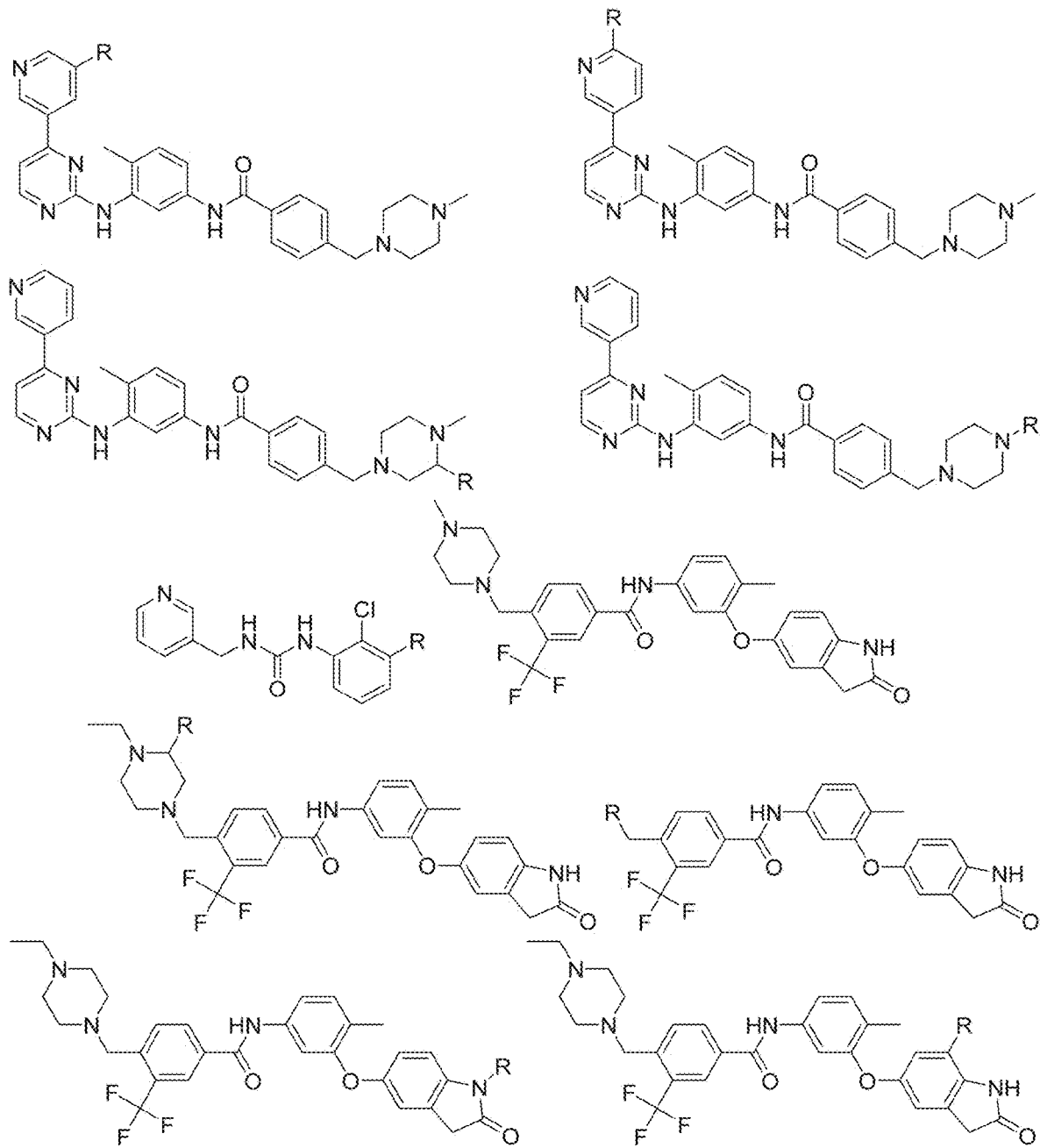
FIG. 8VVV

FIG. 8WWW
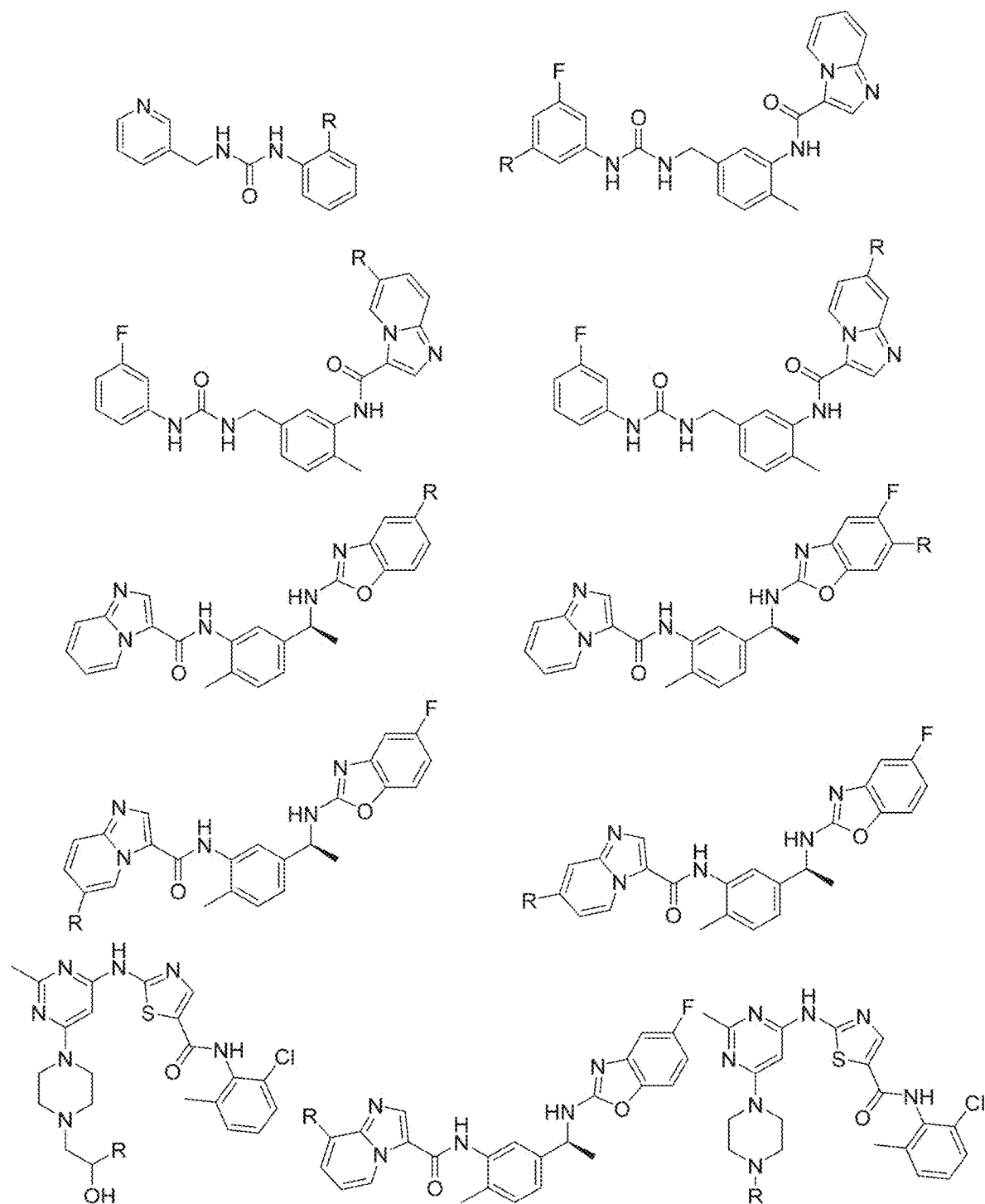

FIG. 8XXX
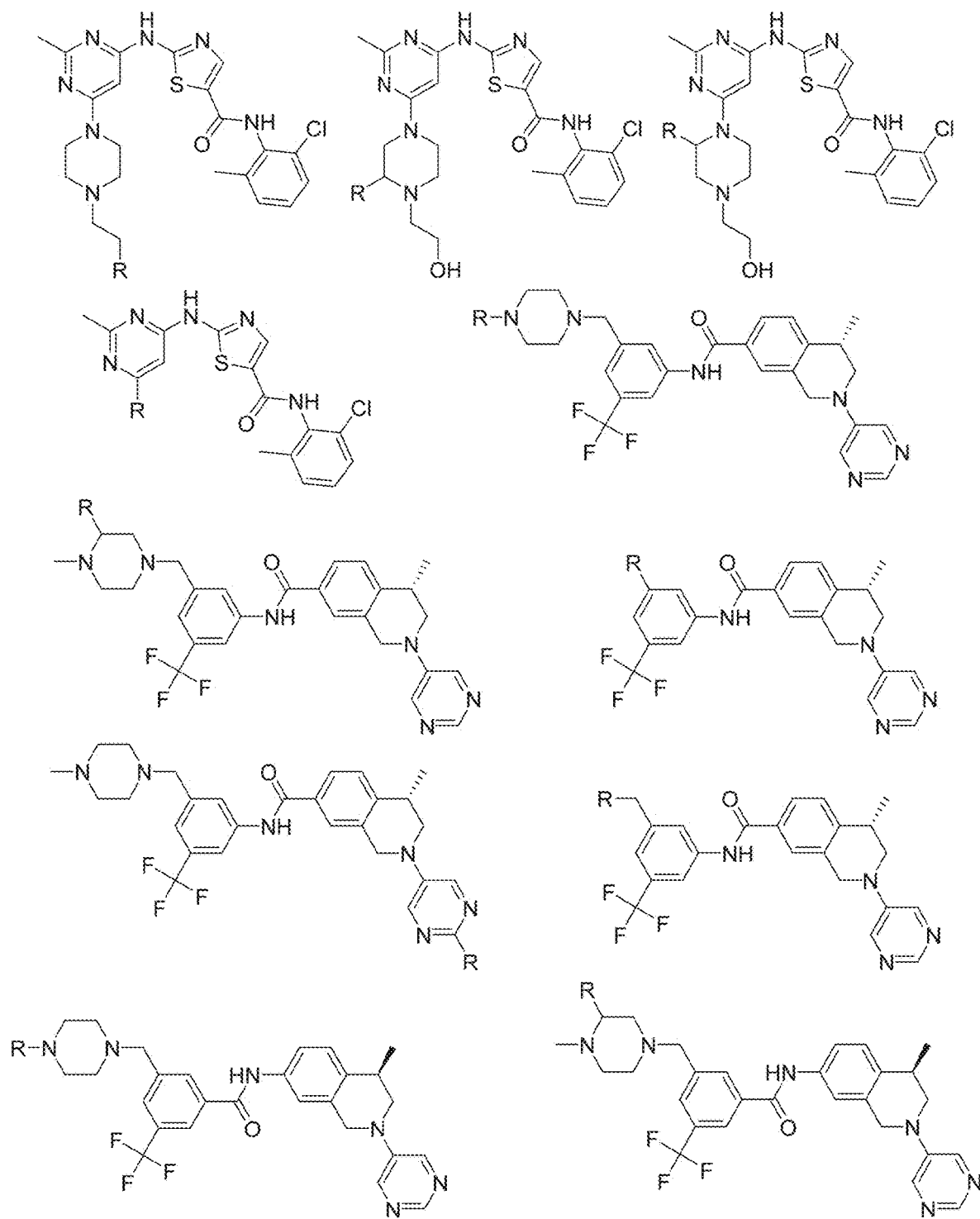

FIG. 8YYY
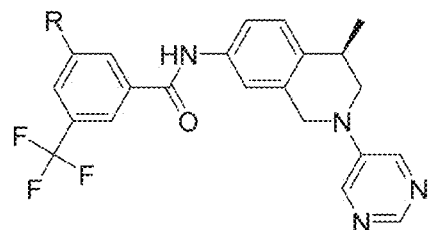
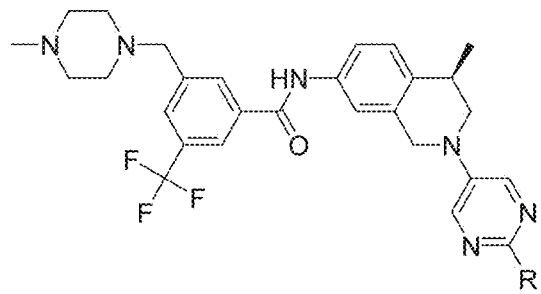
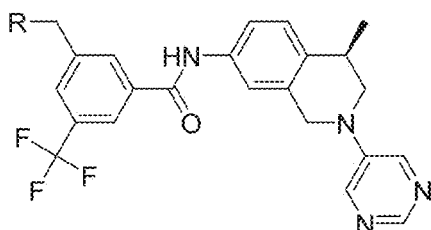
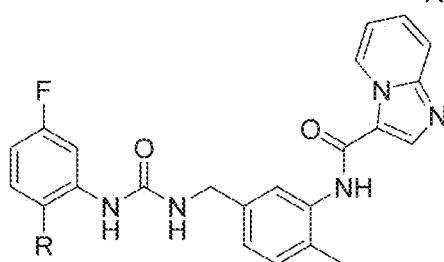
FIG. 8ZZZ
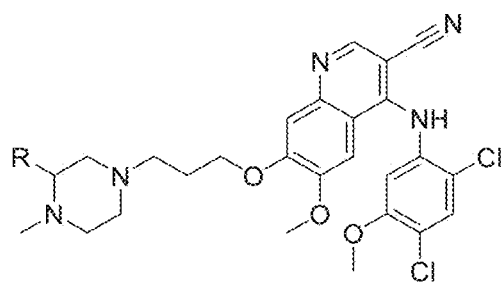
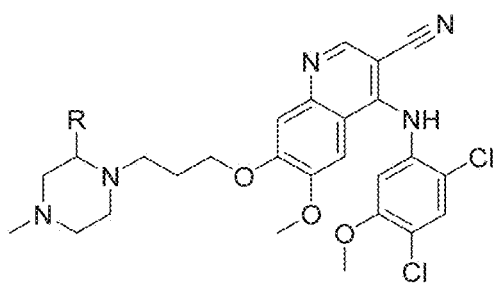
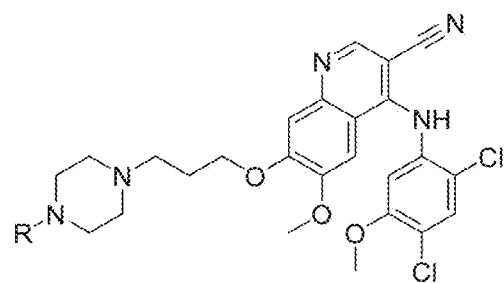
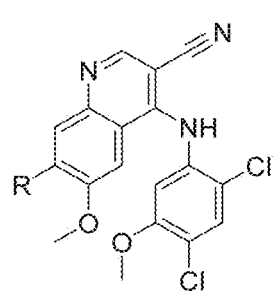
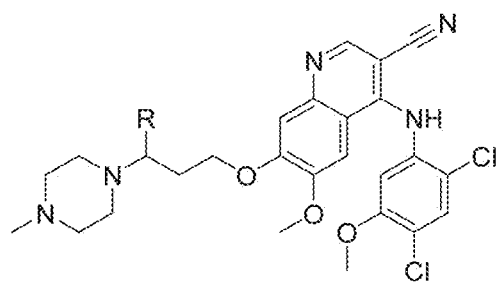
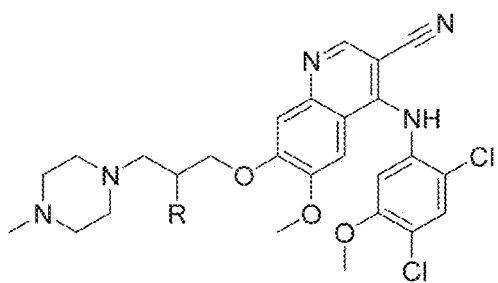

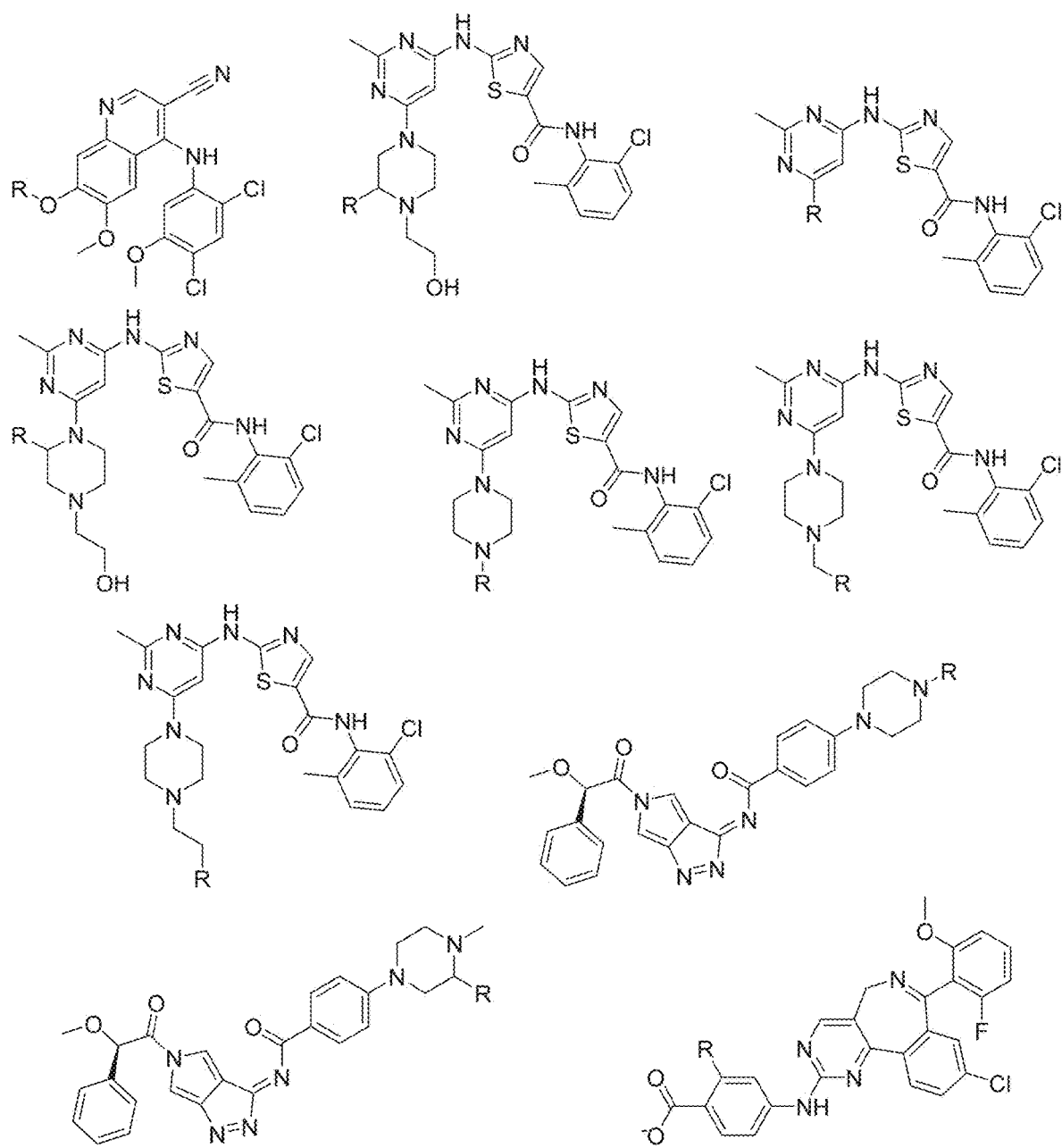
FIG. 8AAAA

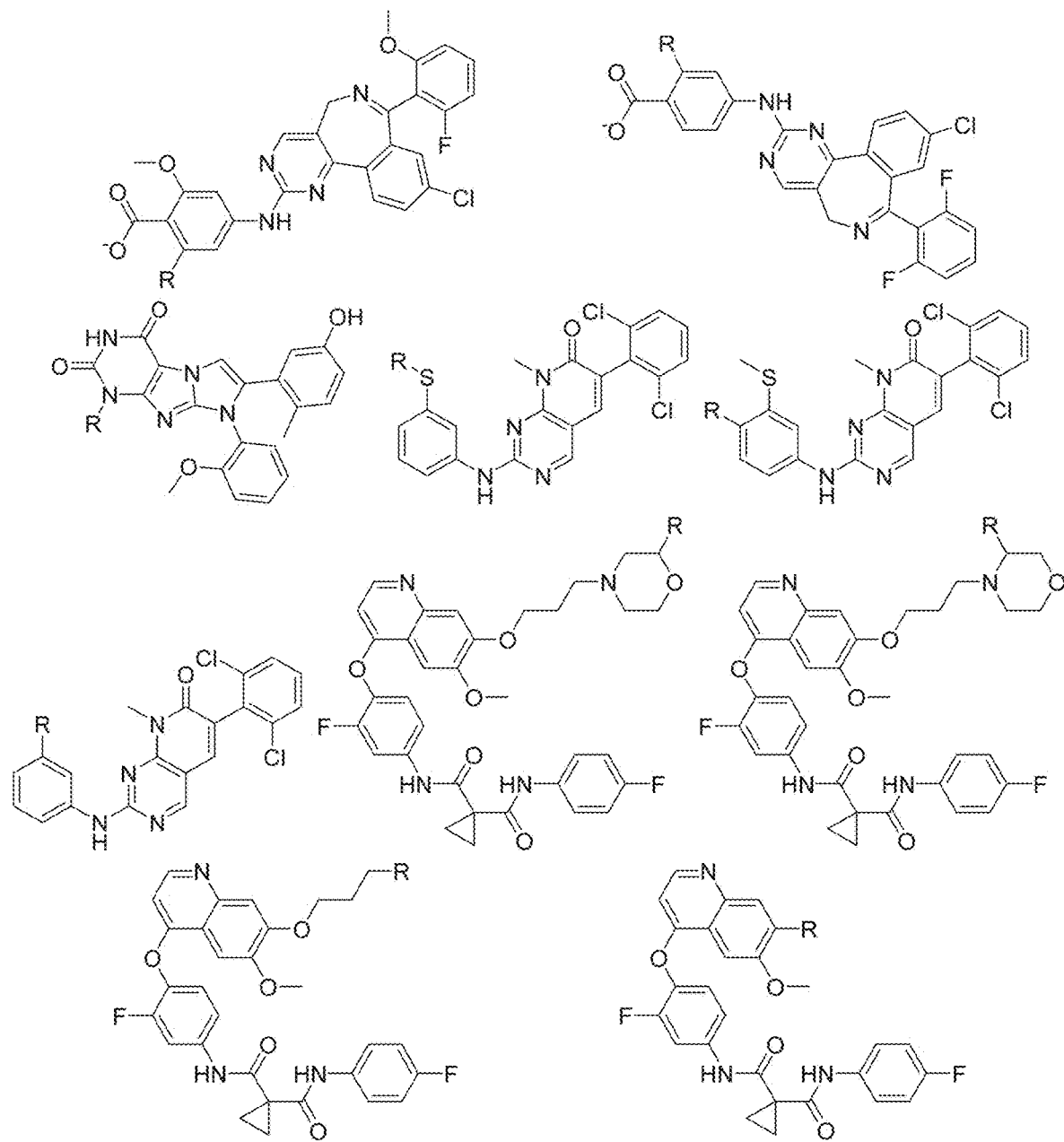
FIG. 8BBBB

FIG. 8CCCC
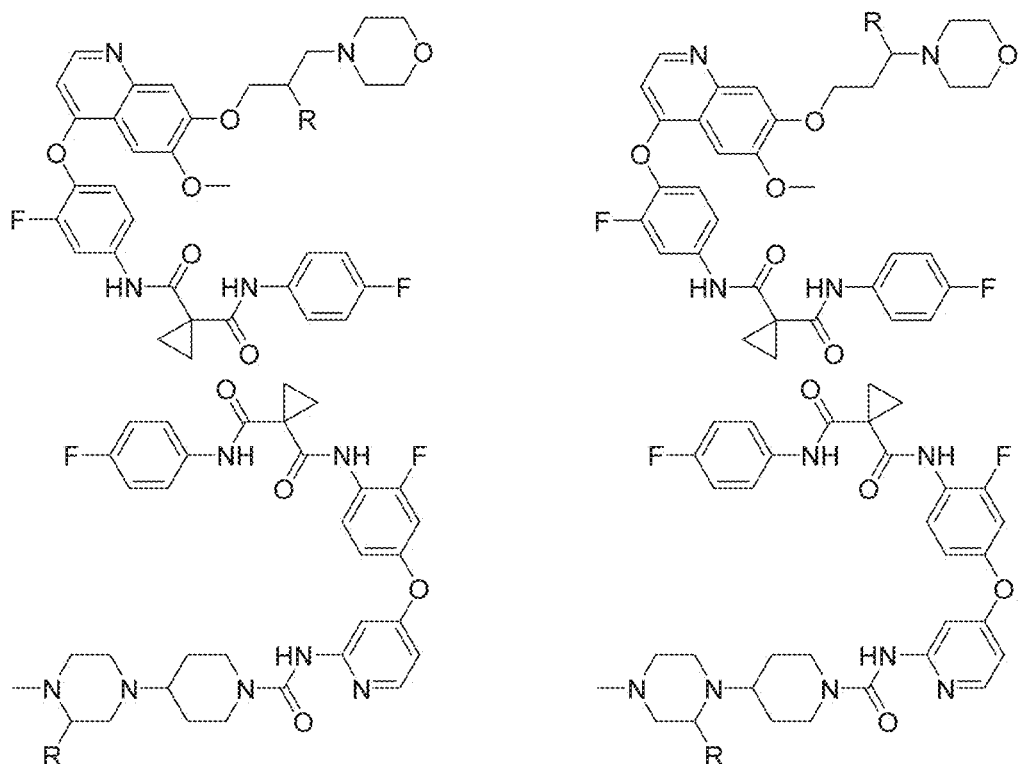
FIG. 8DDDD
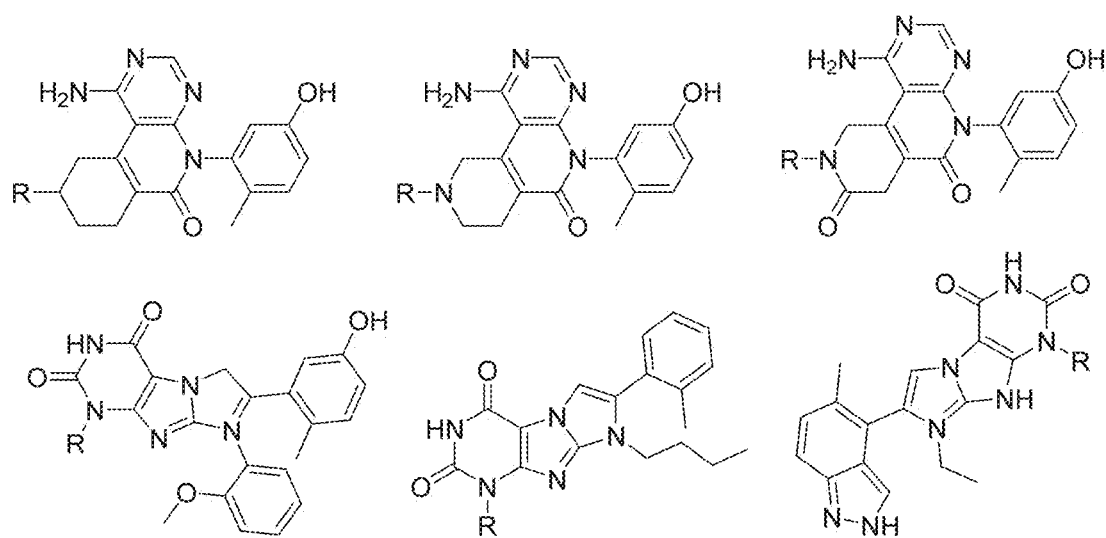

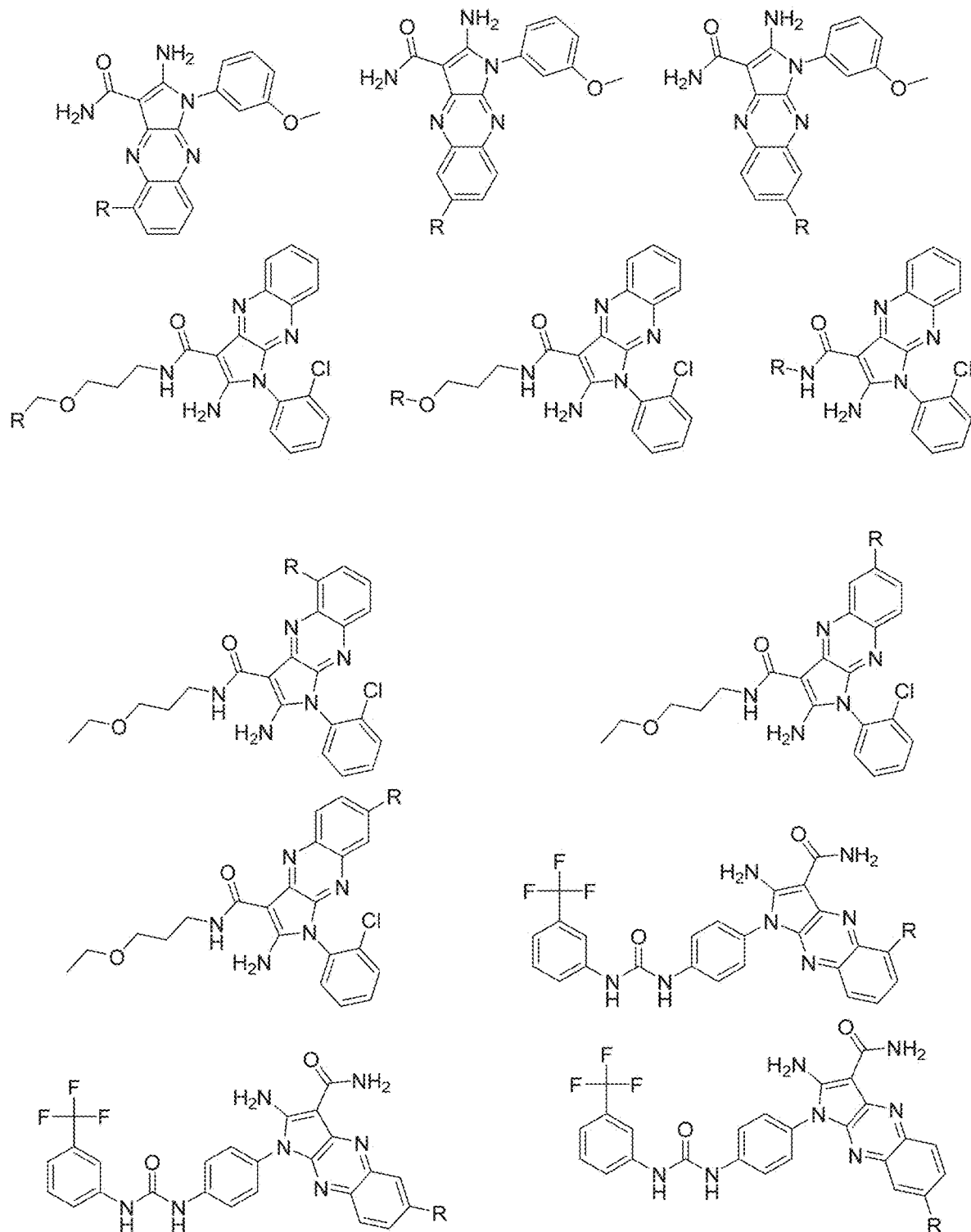
FIG. 8EEEE

FIG. 8FFFF
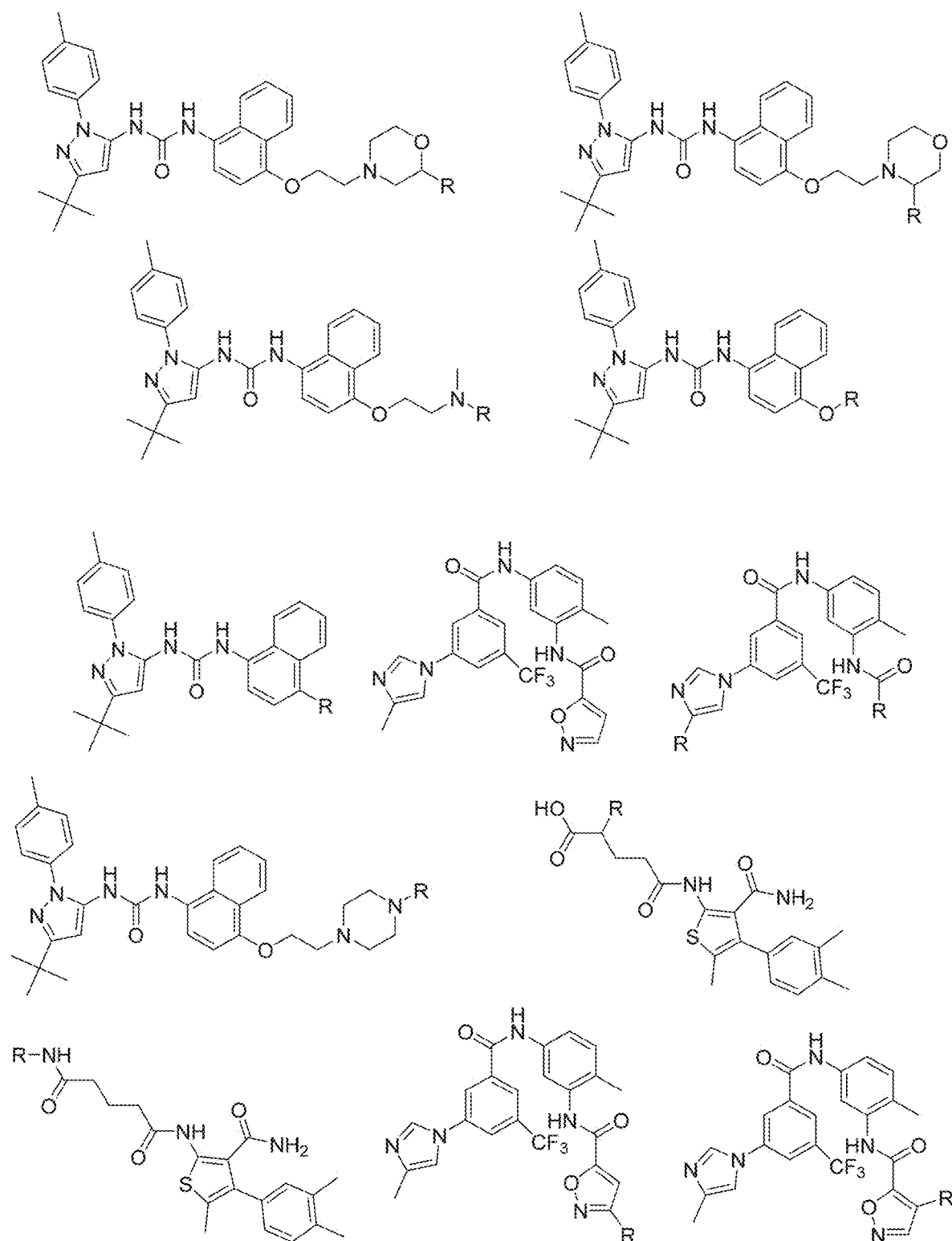

FIG. 8GGGG
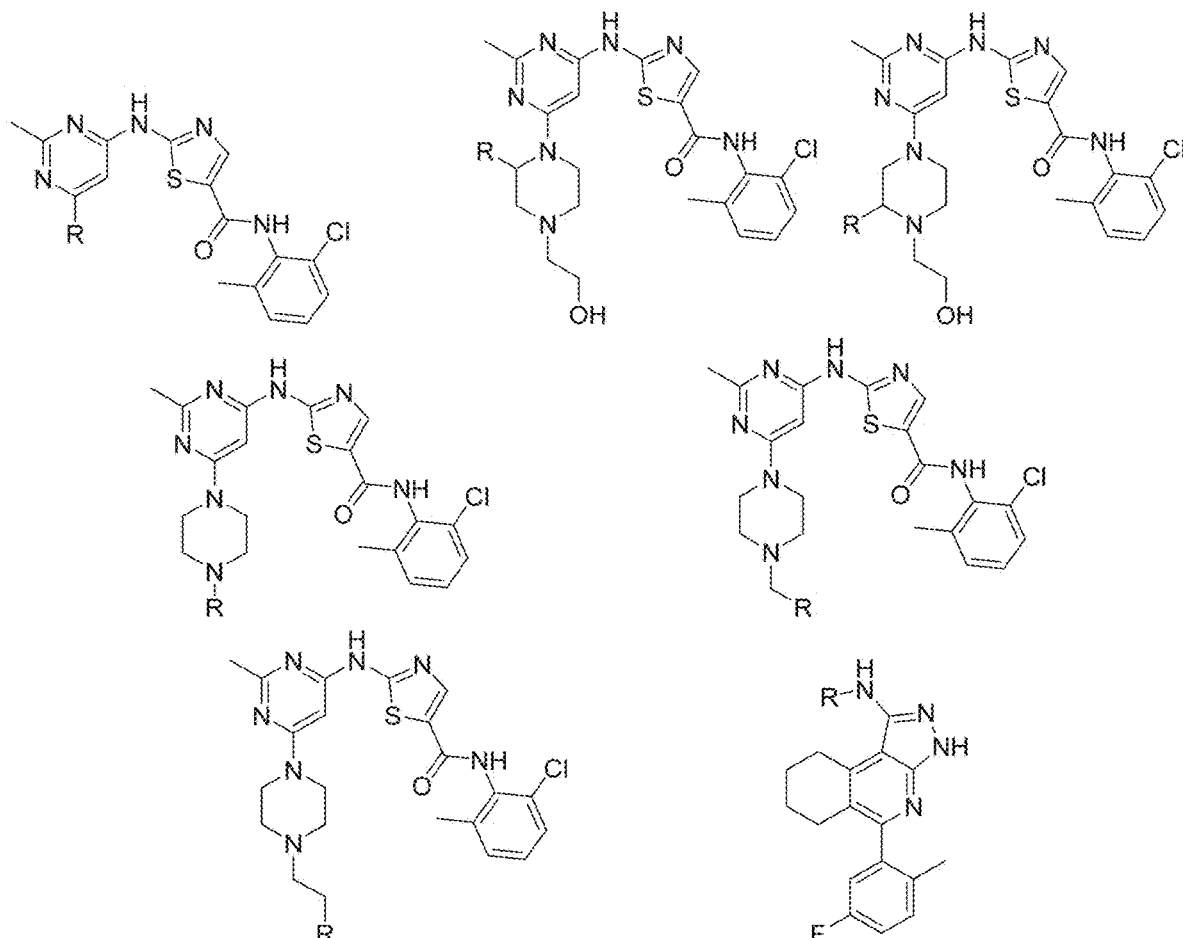
FIG. 8HHHH
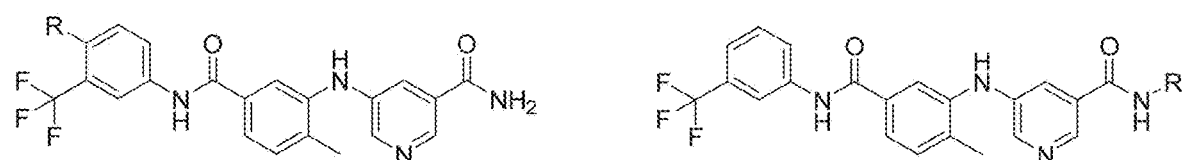
FIG. 8IIII
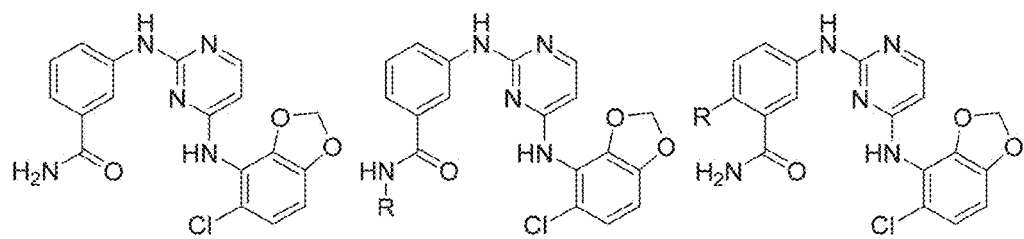

FIG. 8JJJJ
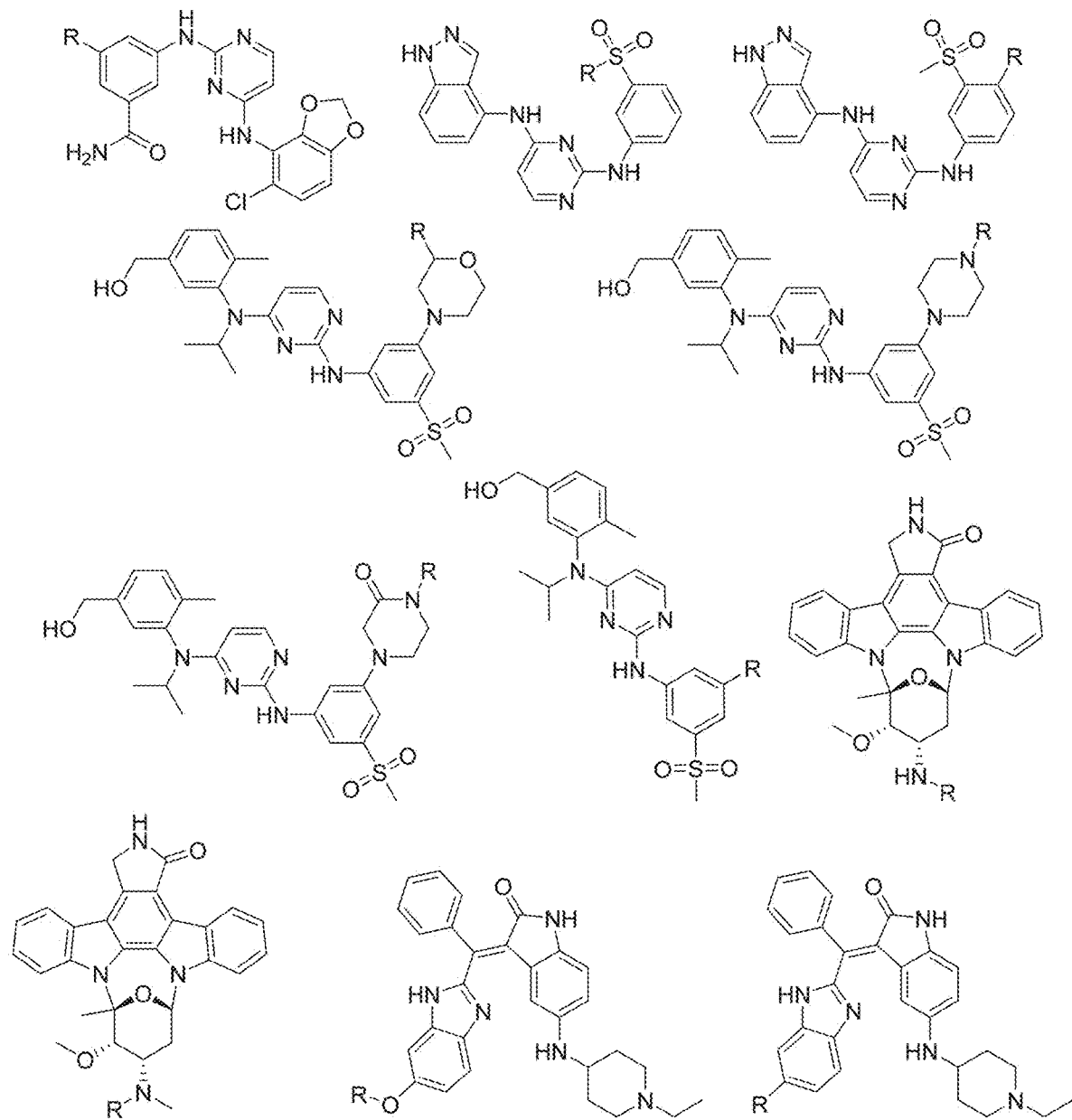

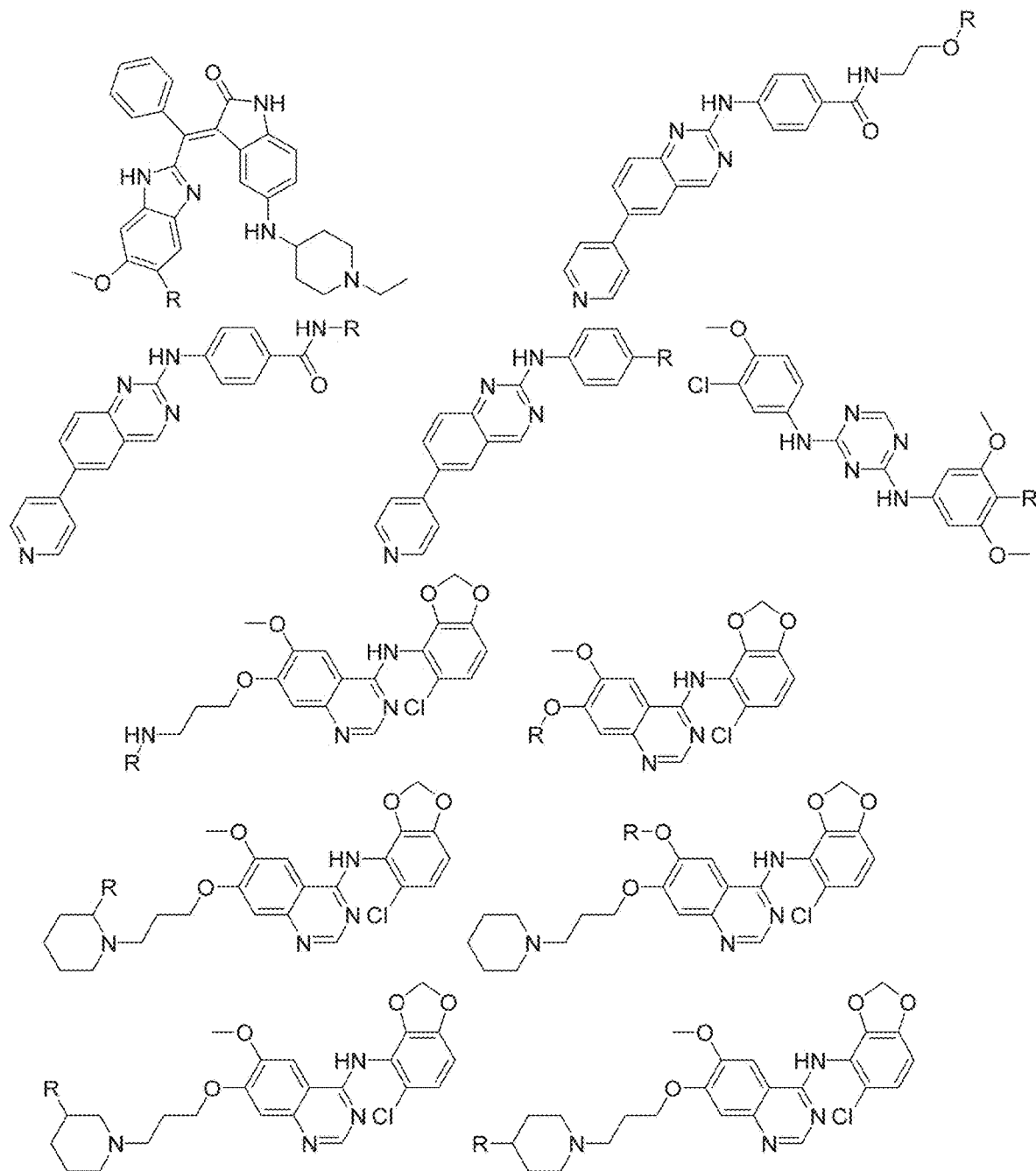
FIG. 8KKKK

FIG. 8LLLL
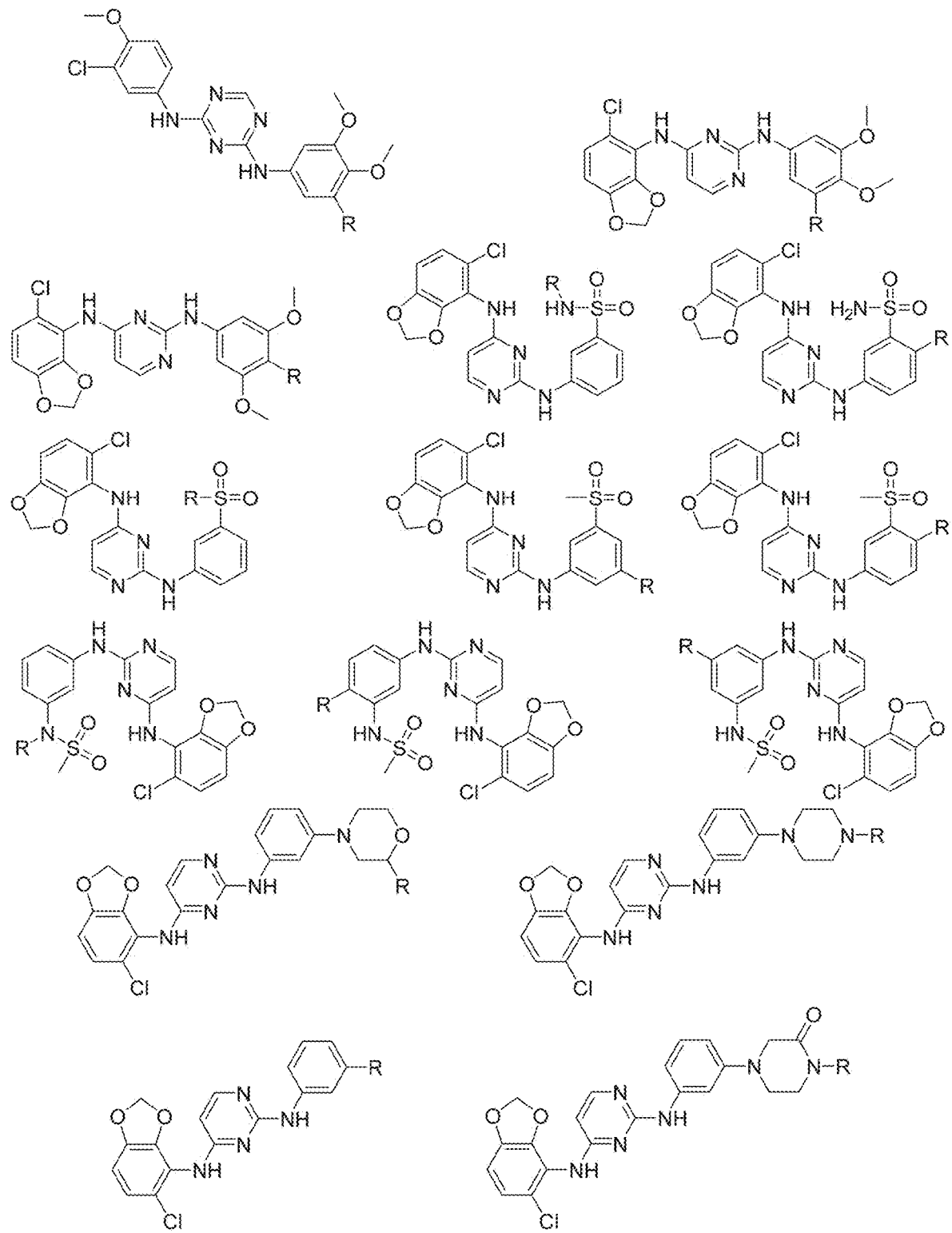

FIG. 8MMMM
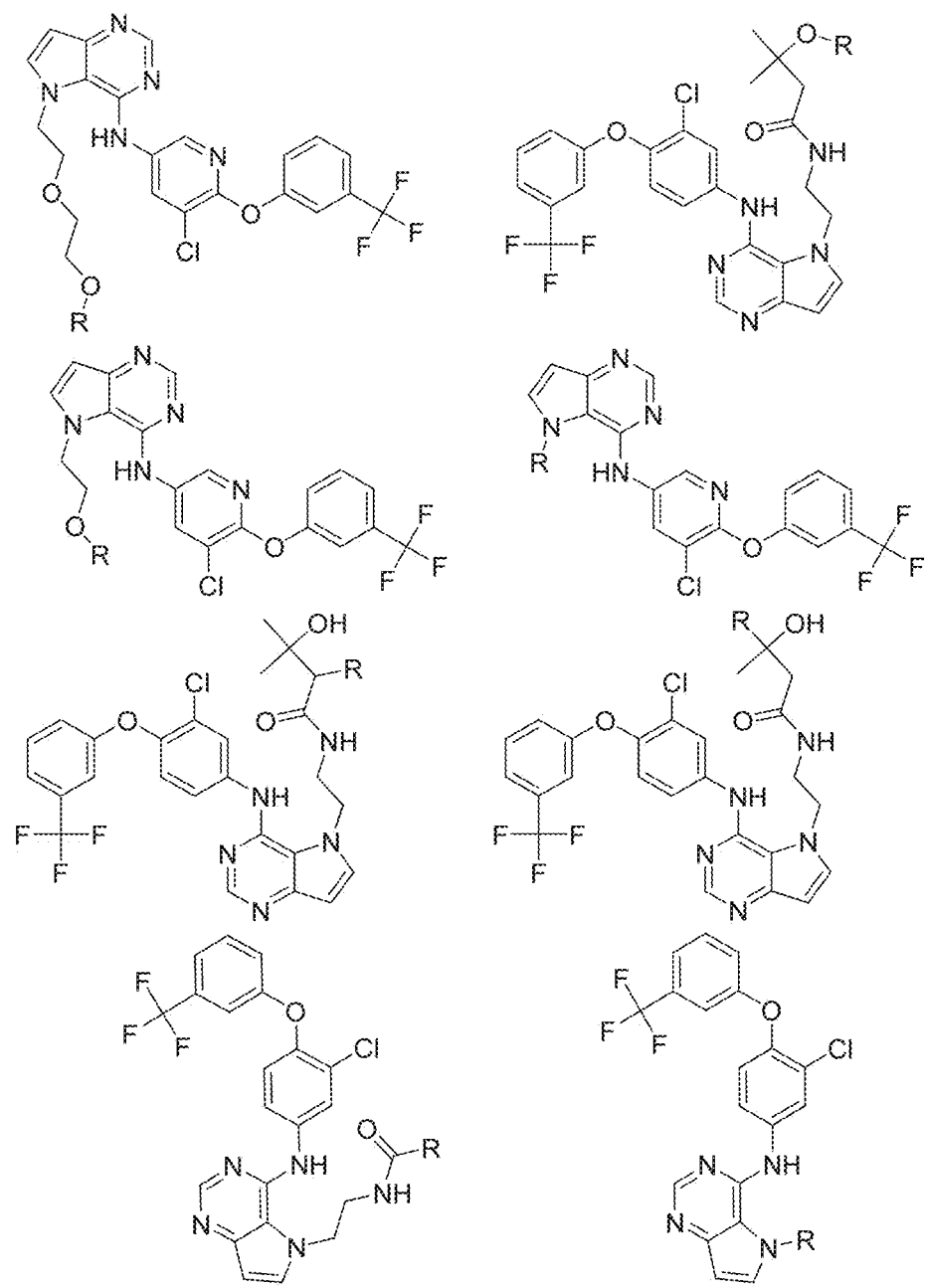

FIG. 8NNNN
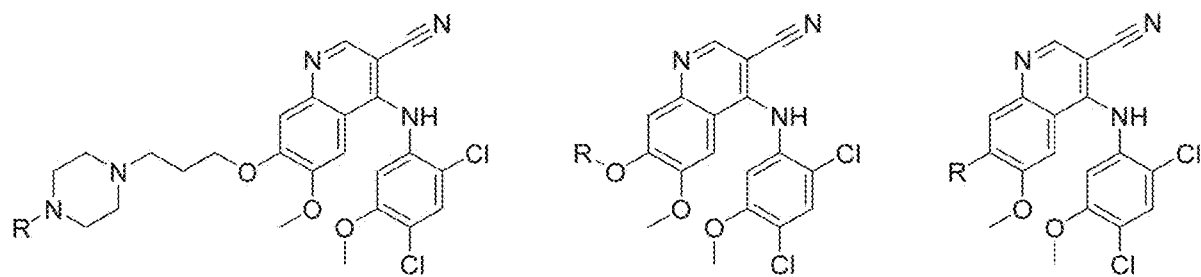
FIG. 8OOOO
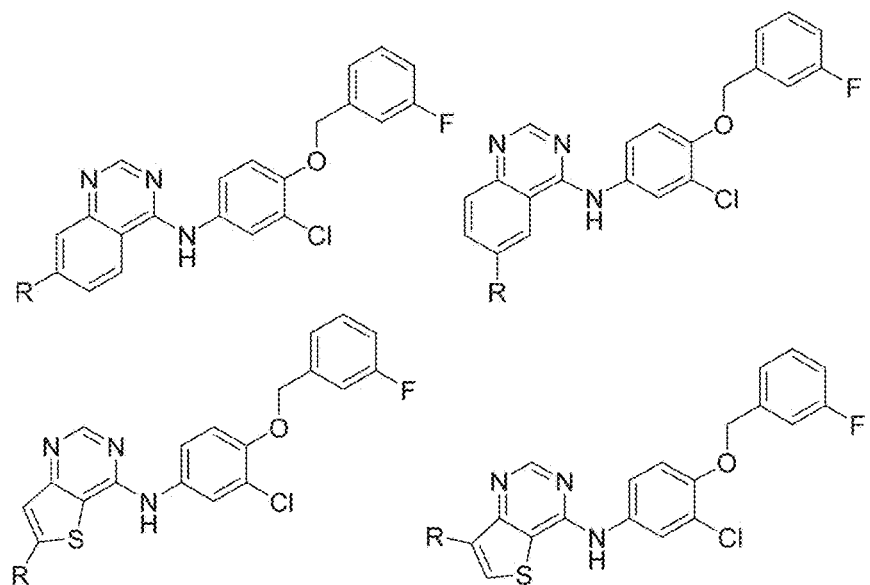
FIG. 8PPPP
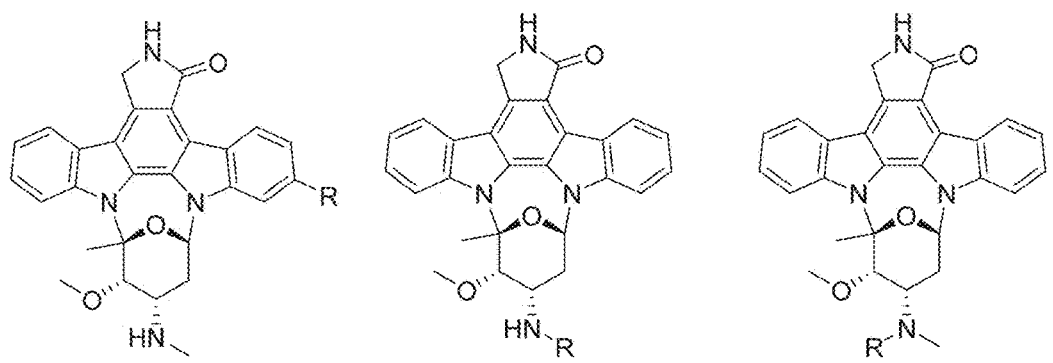

FIG. 8QQQQ
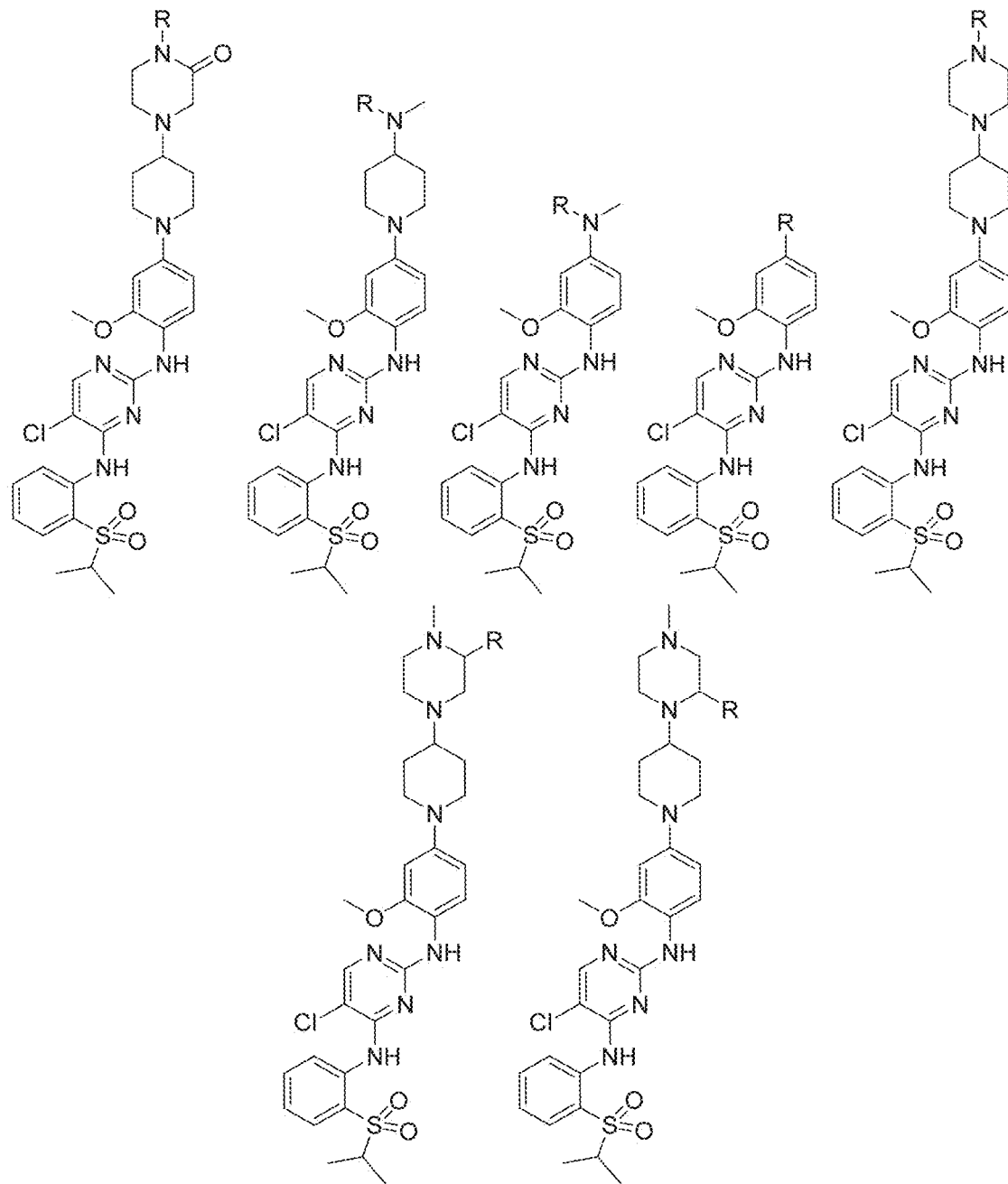

FIG. 8RRRR
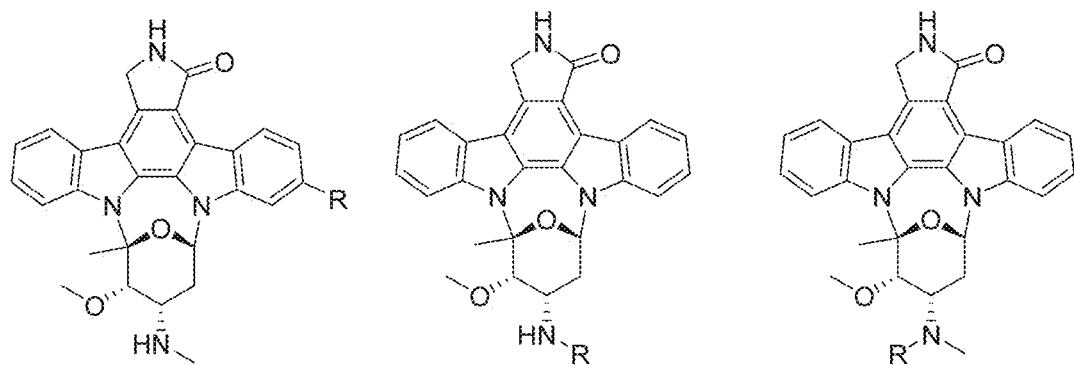
FIG. 8SSSS
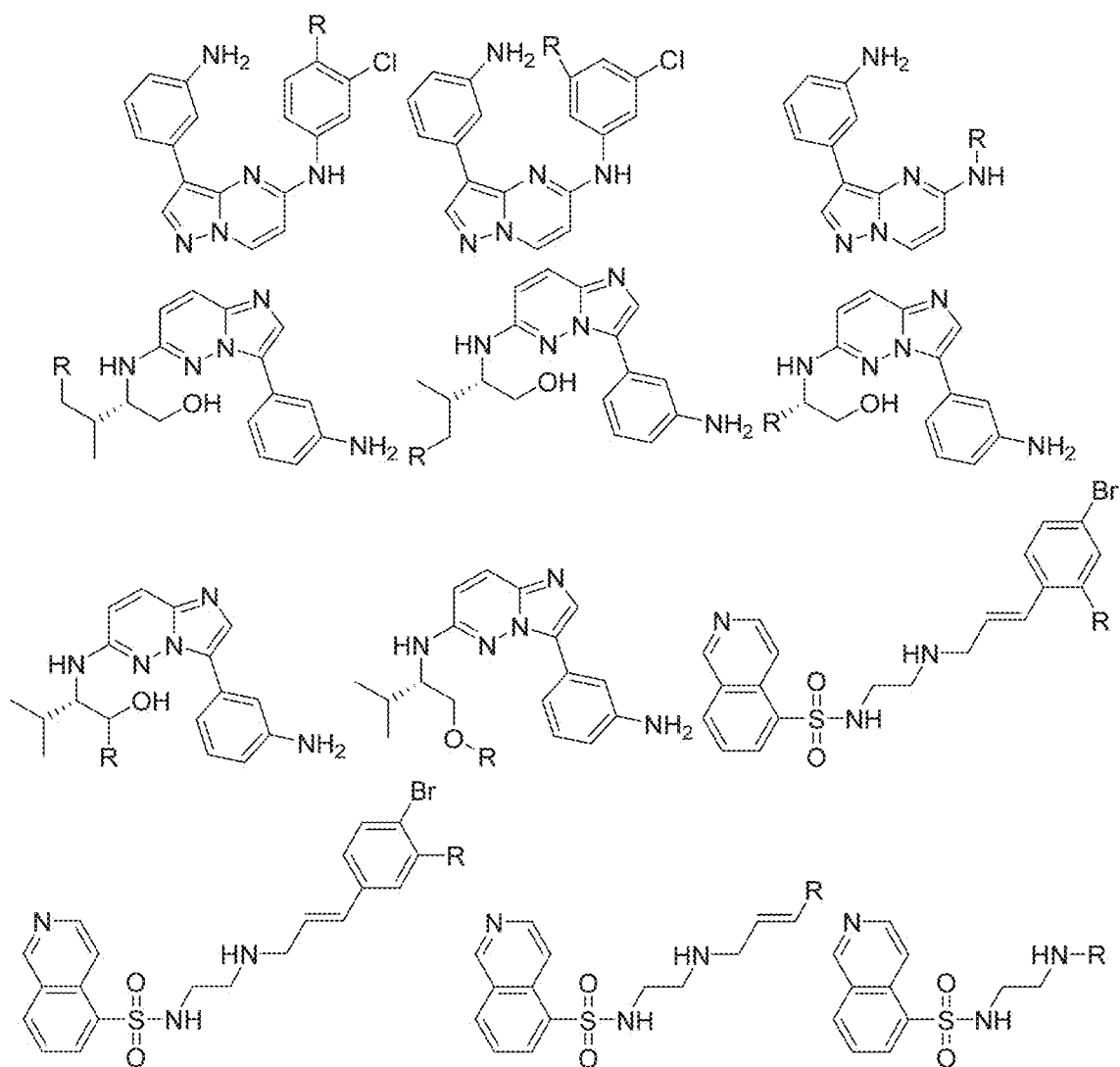

FIG. 8TTTT
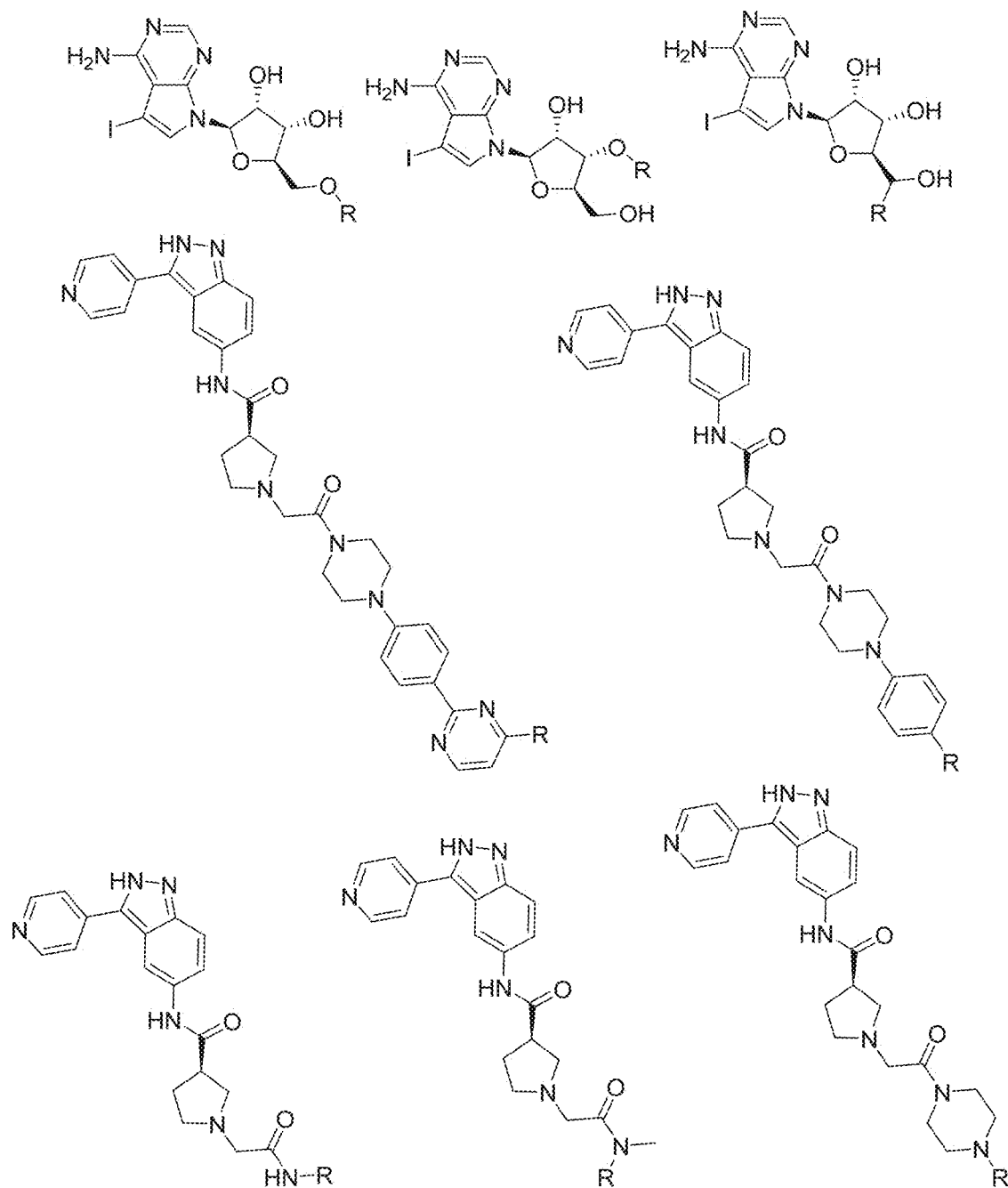

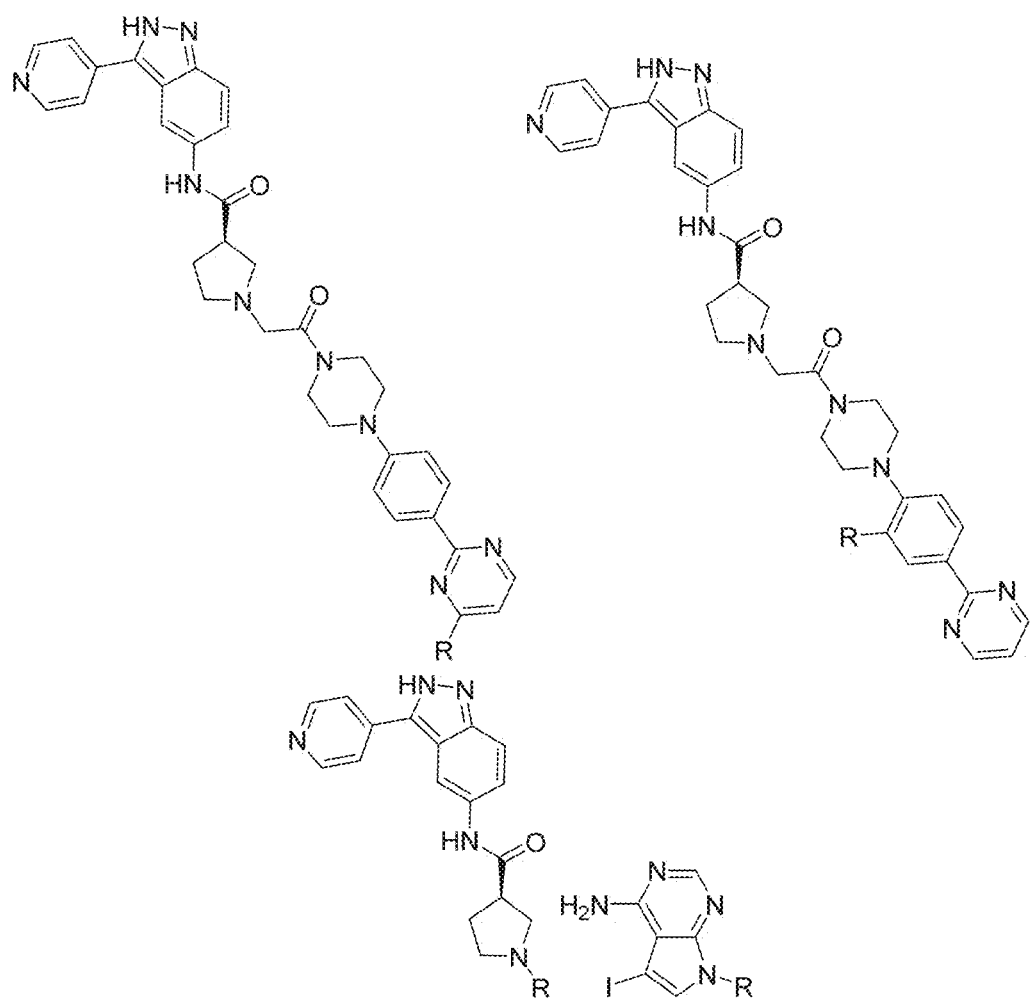
FIG. 8UUUU

FIG. 8VVVV
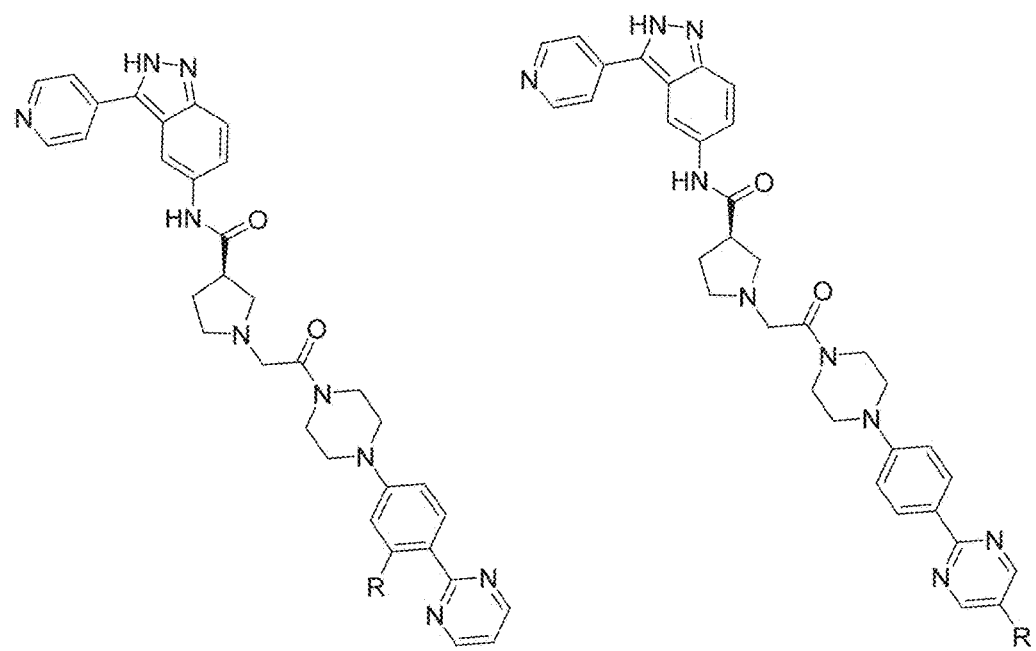
FIG. 8WWWW
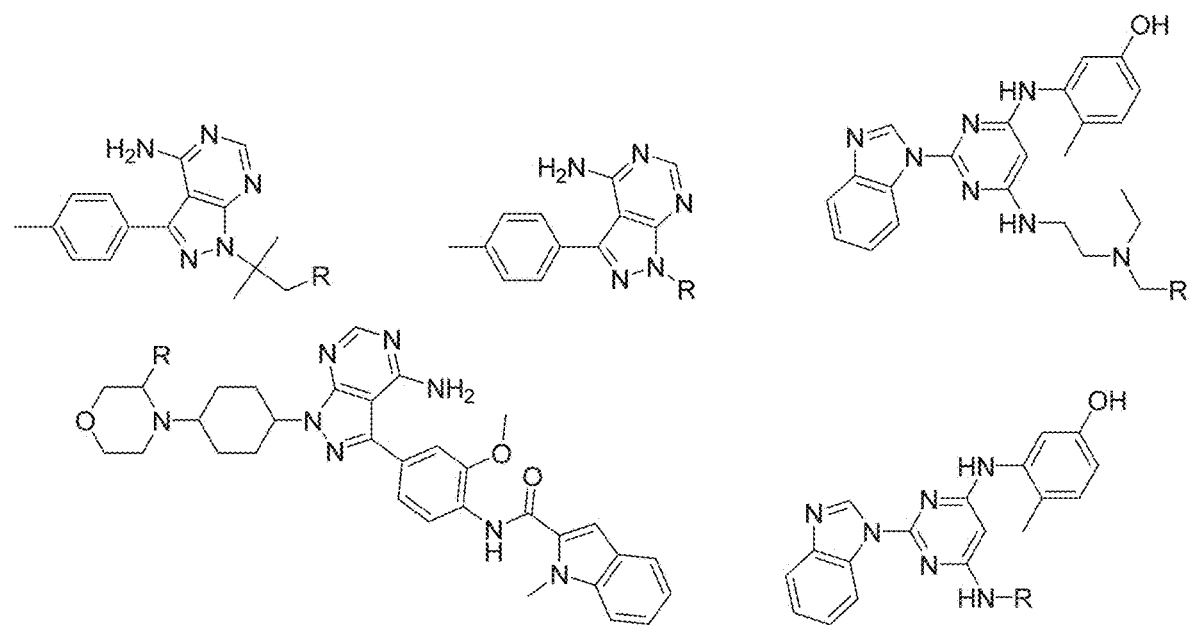

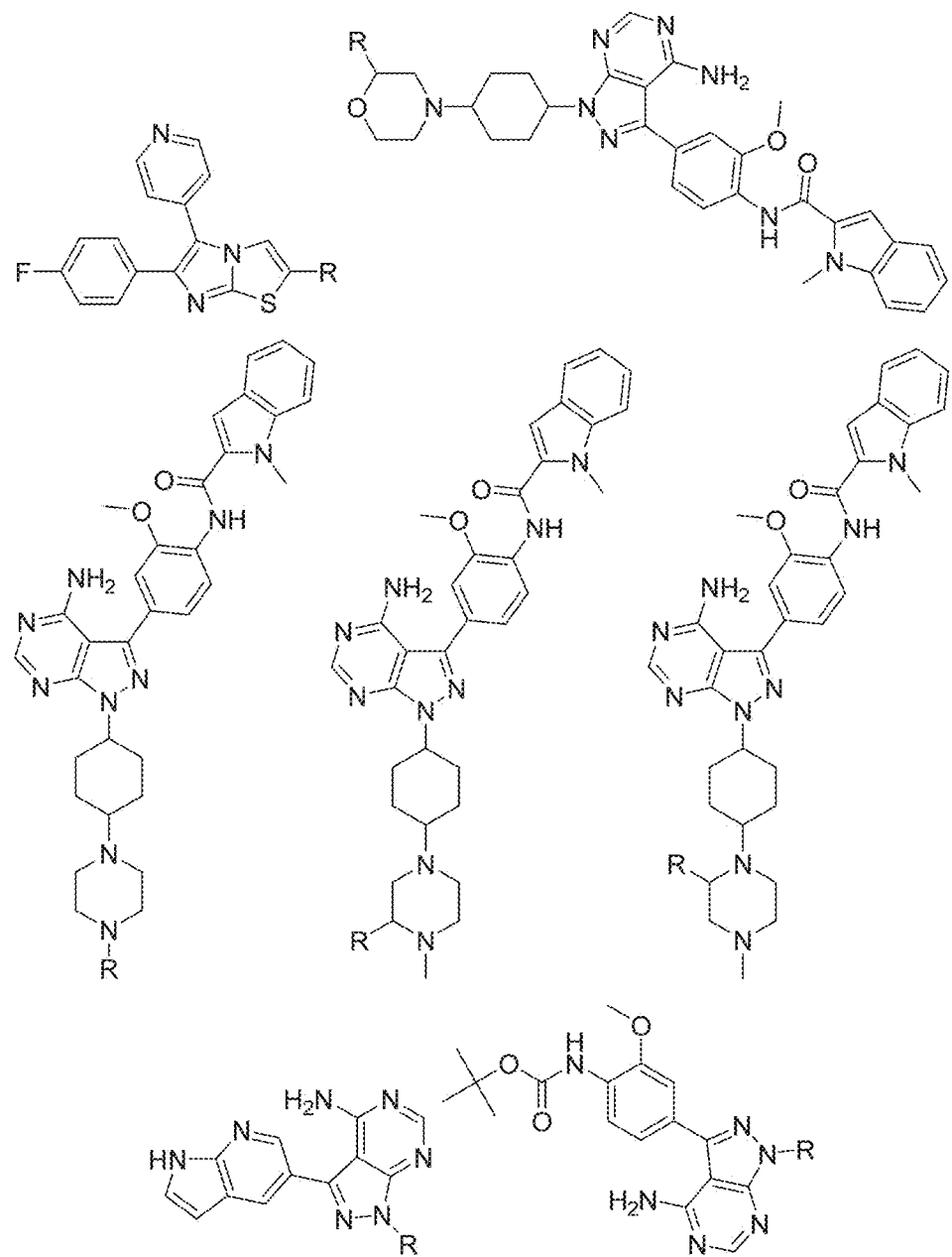
FIG. 8XXXX

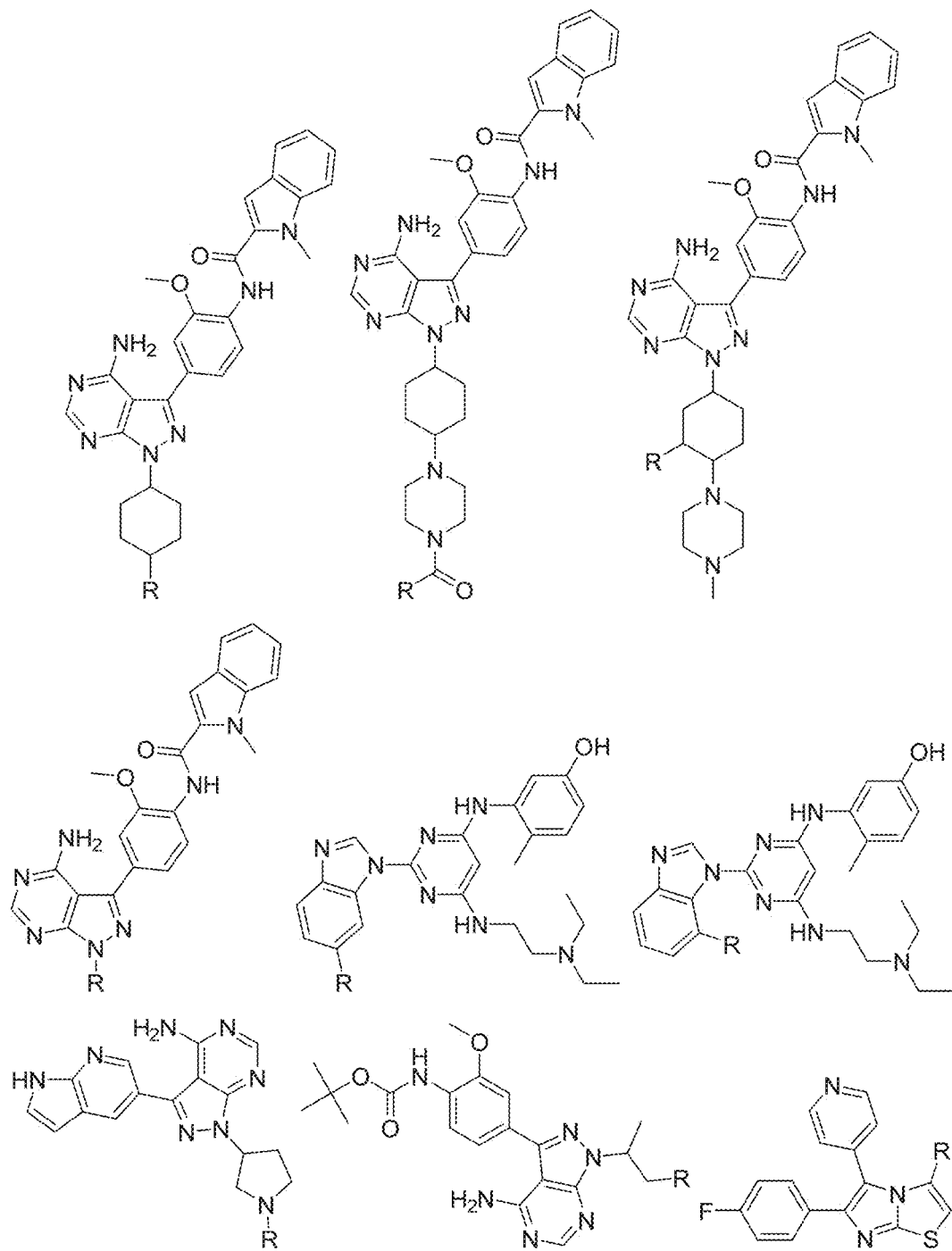
FIG. 8YYYY

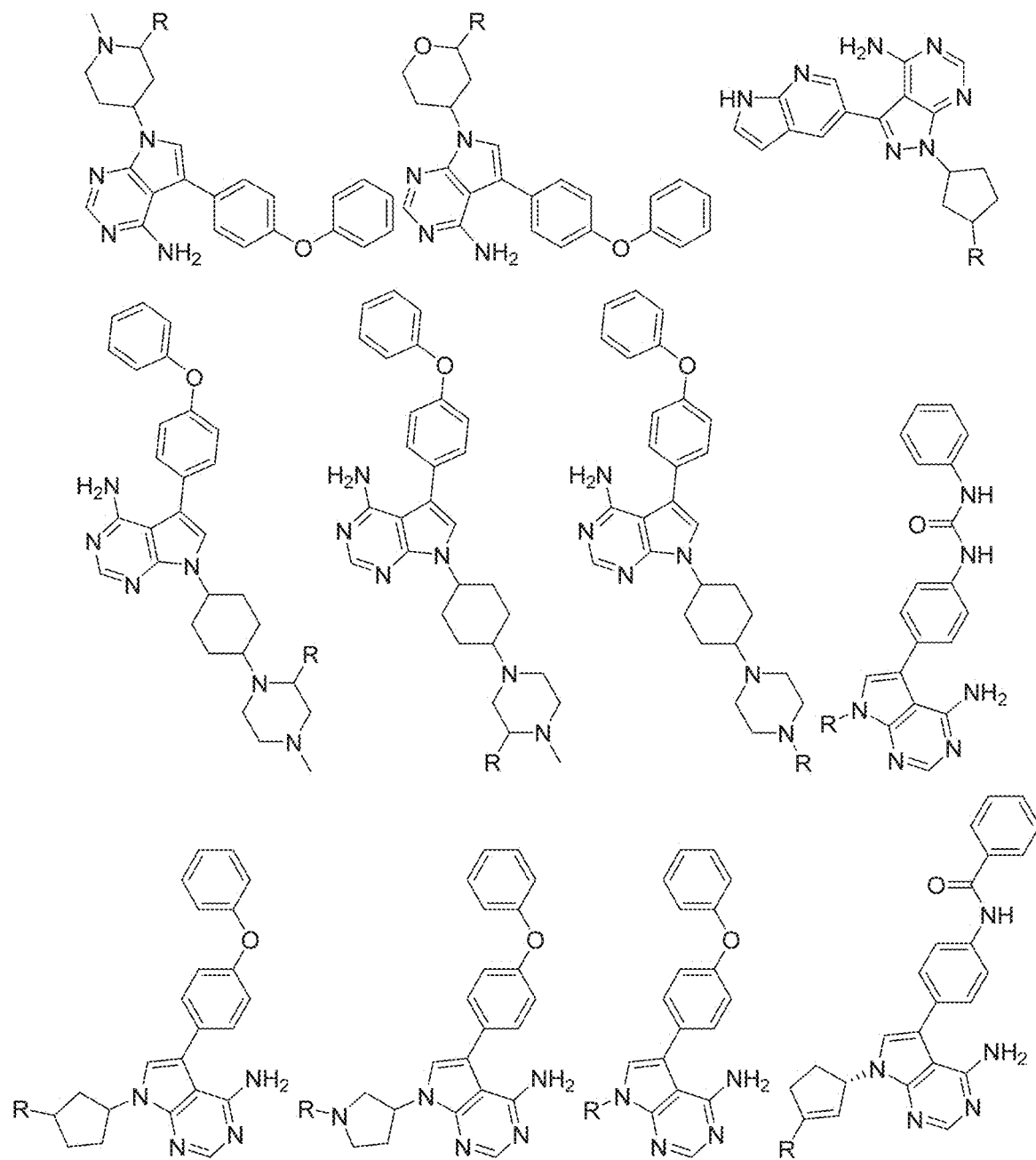
FIG. 8ZZZZ

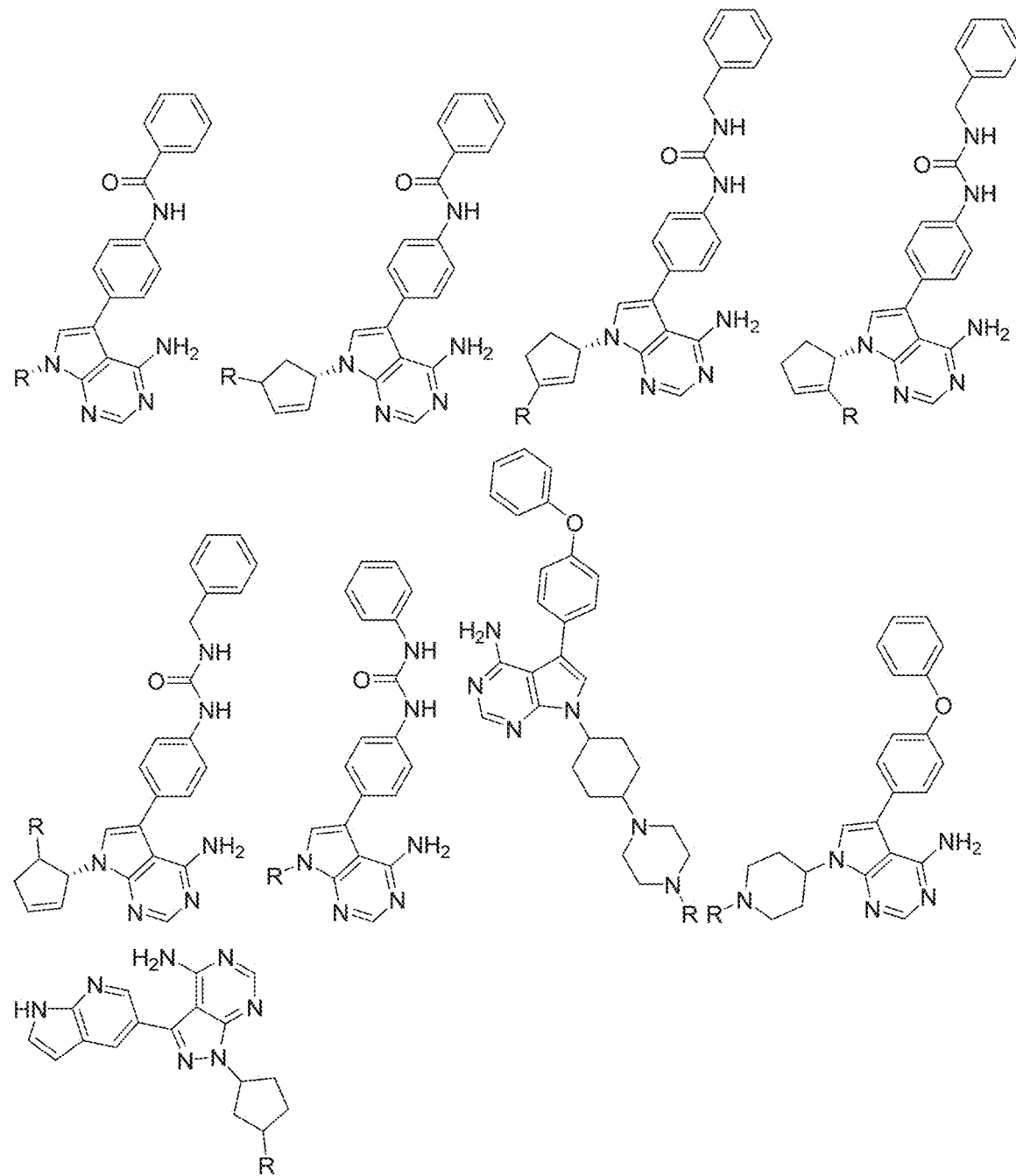
FIG. 8AAAAA

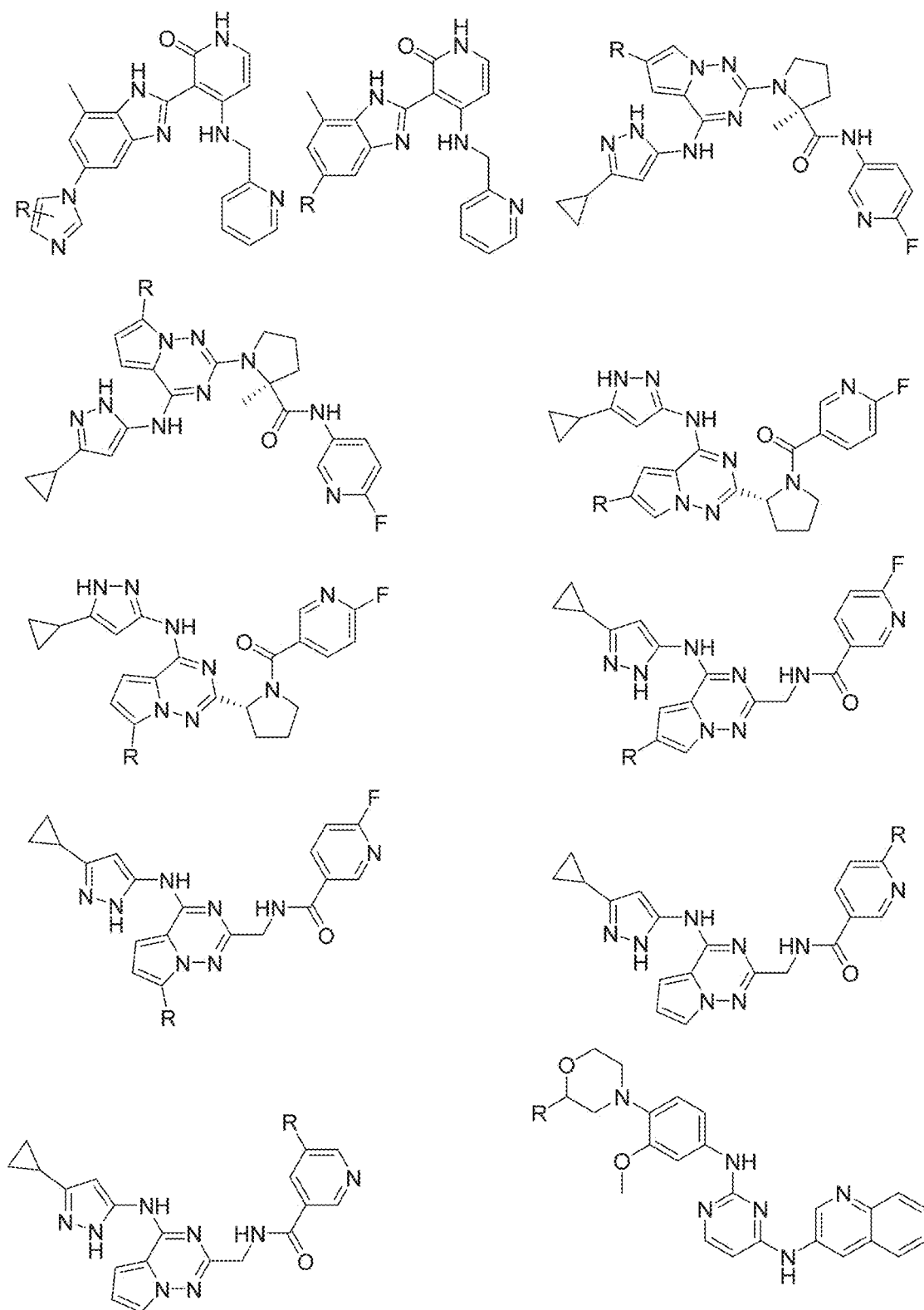
FIG. 8BBBBB

FIG. 8CCCCC
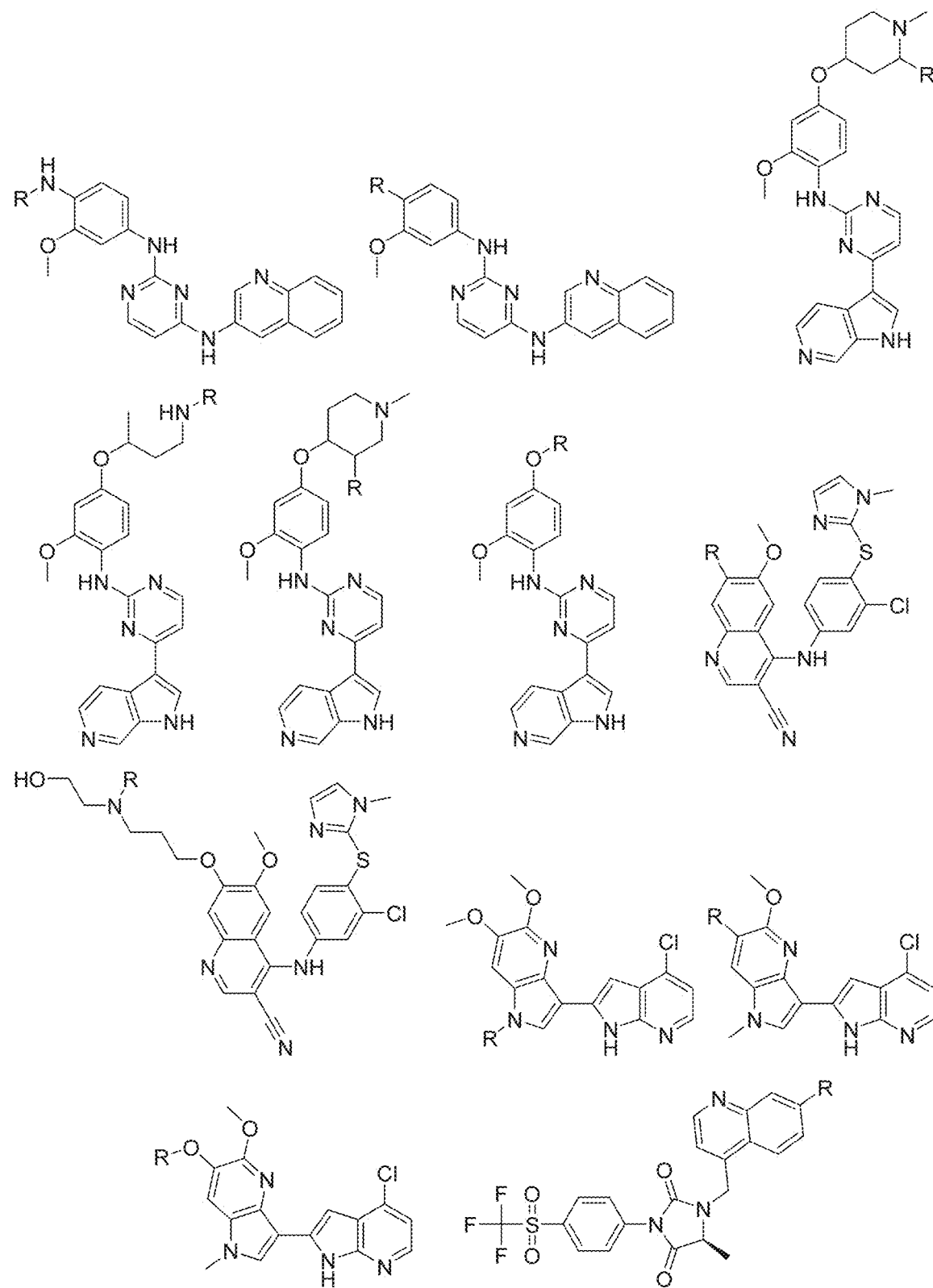

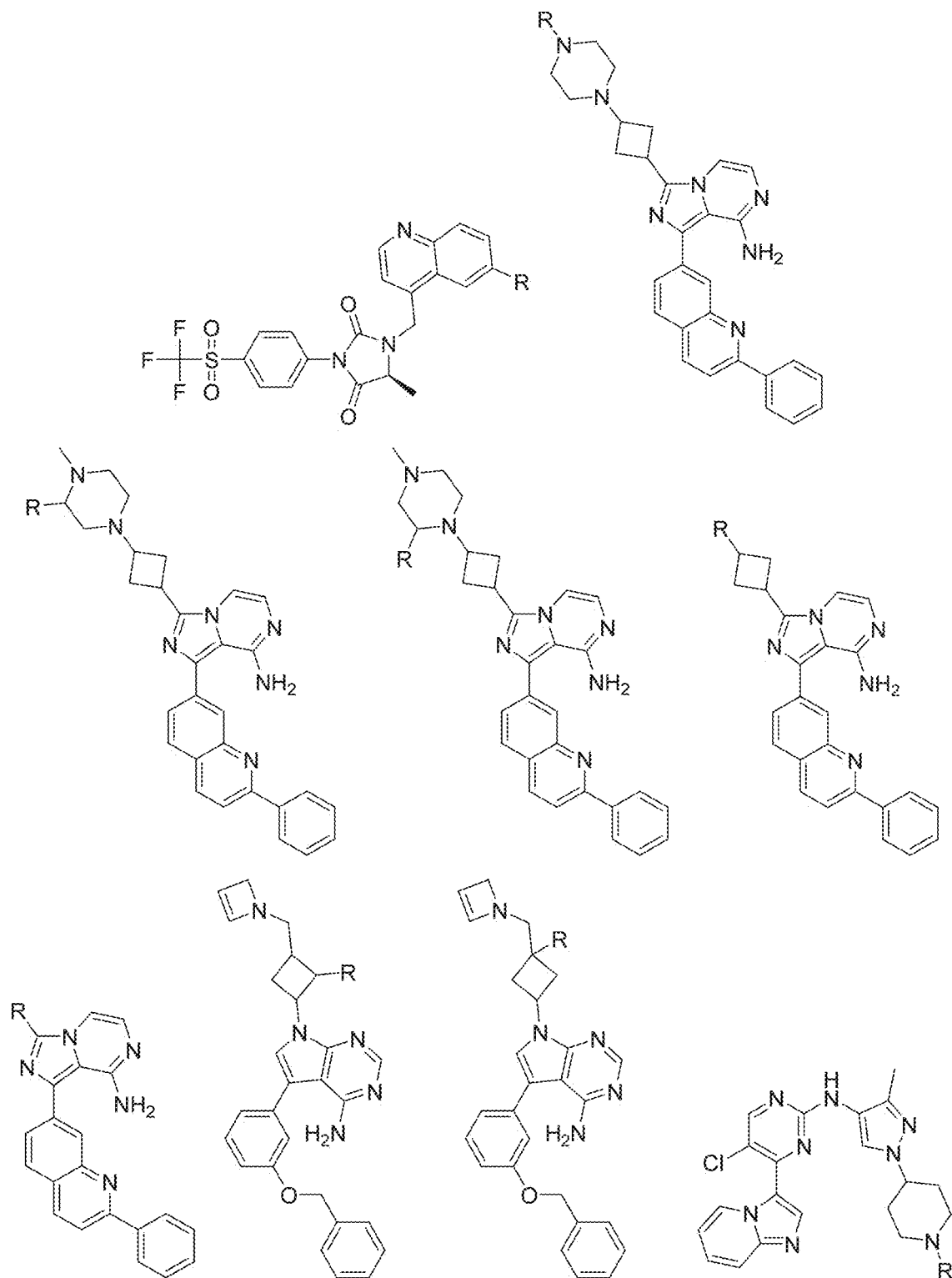
FIG. 8DDDDD

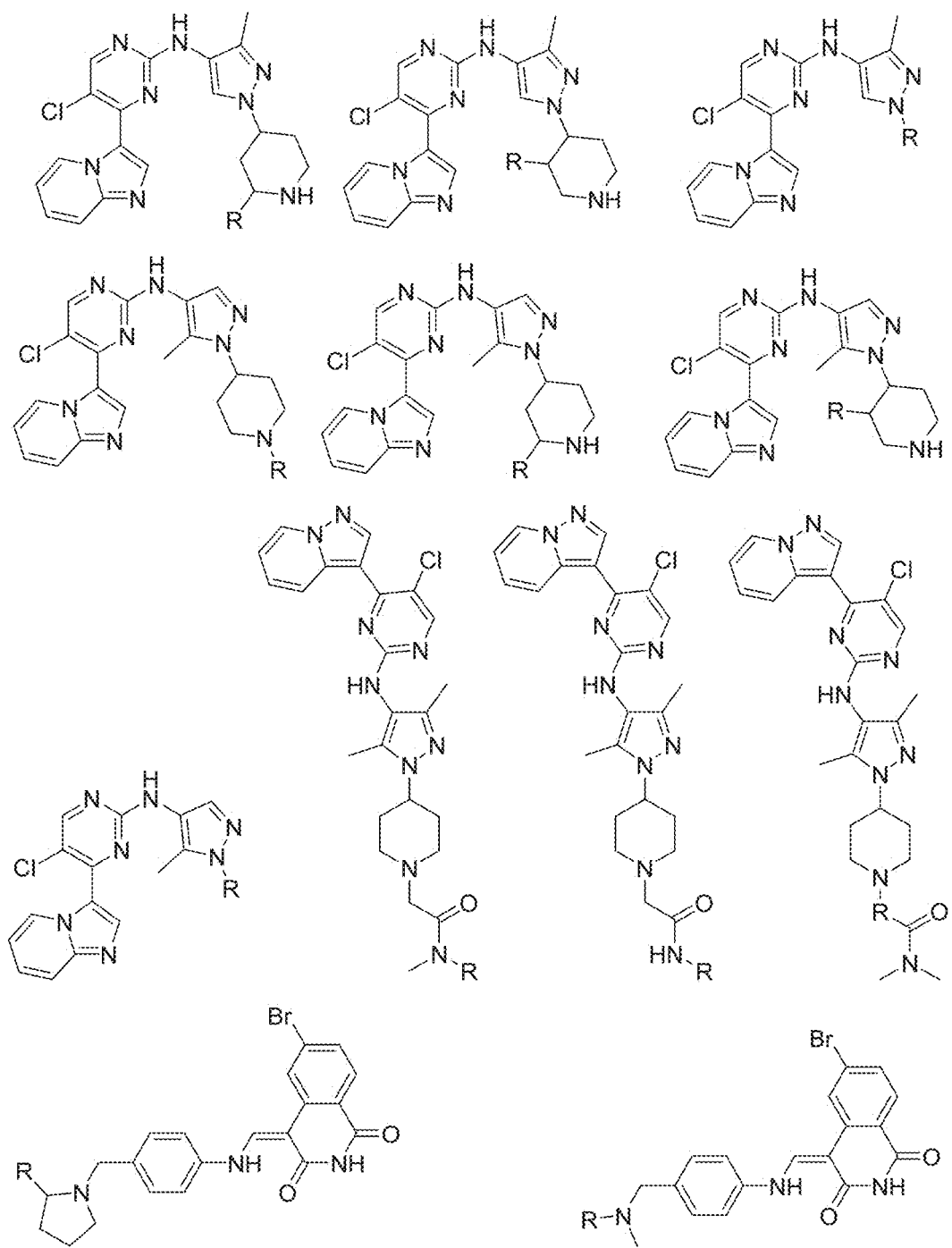
FIG. 8EEEEE

FIG. 8FFFFF
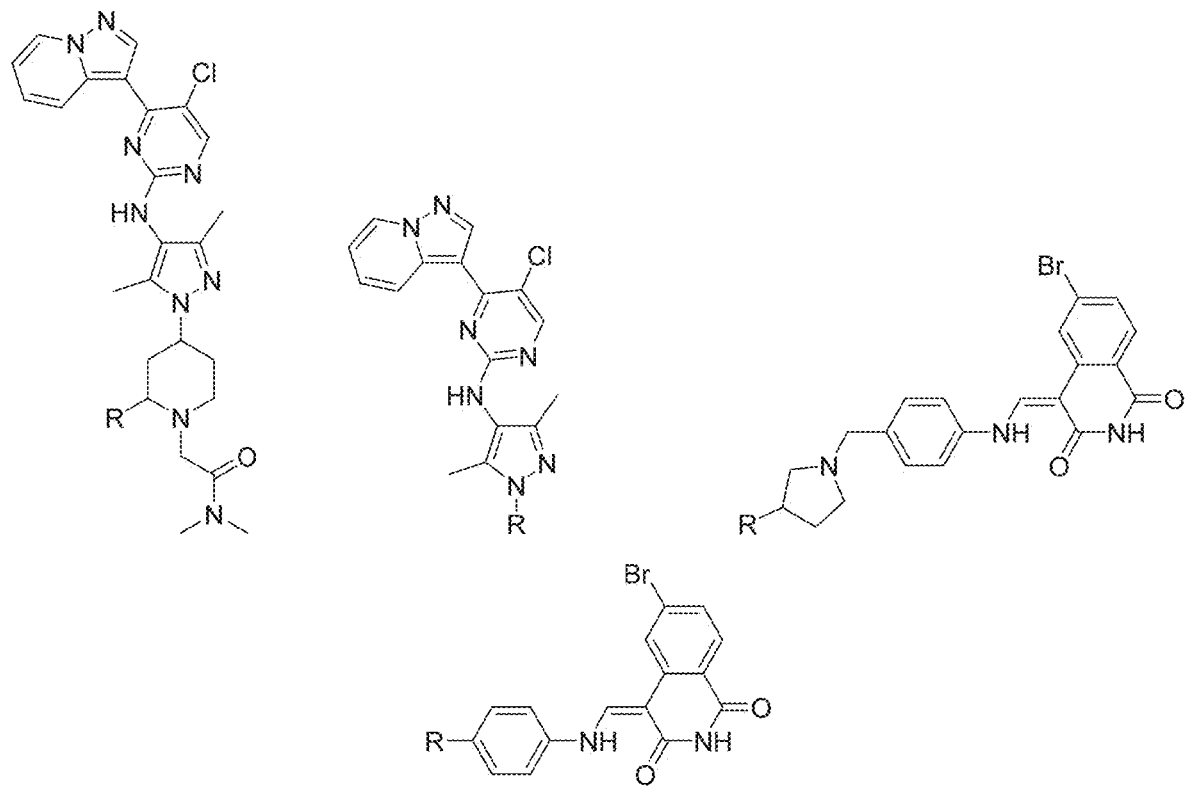
FIG. 8GGGGG
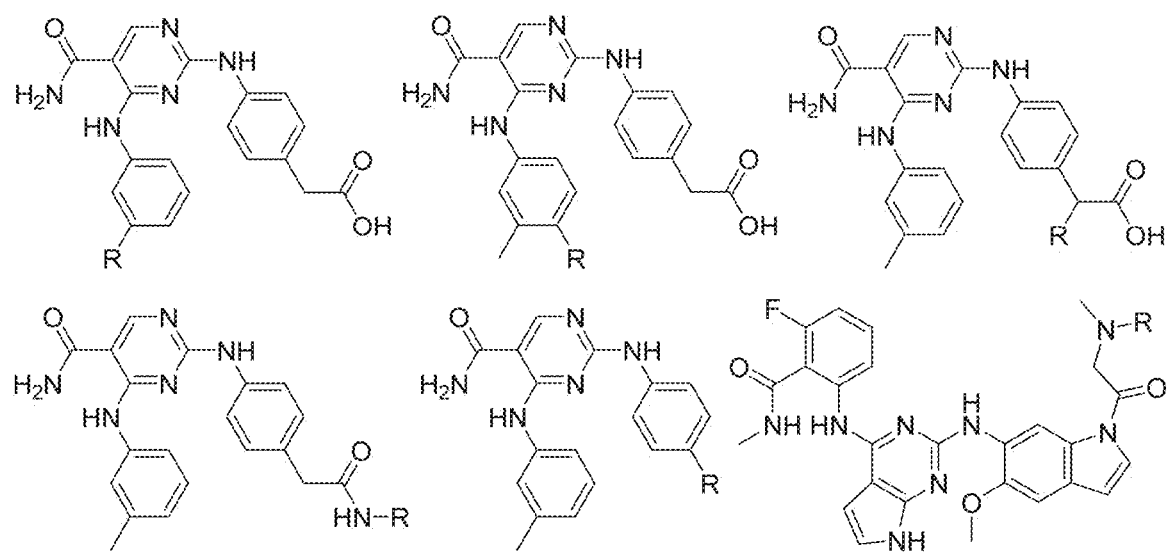

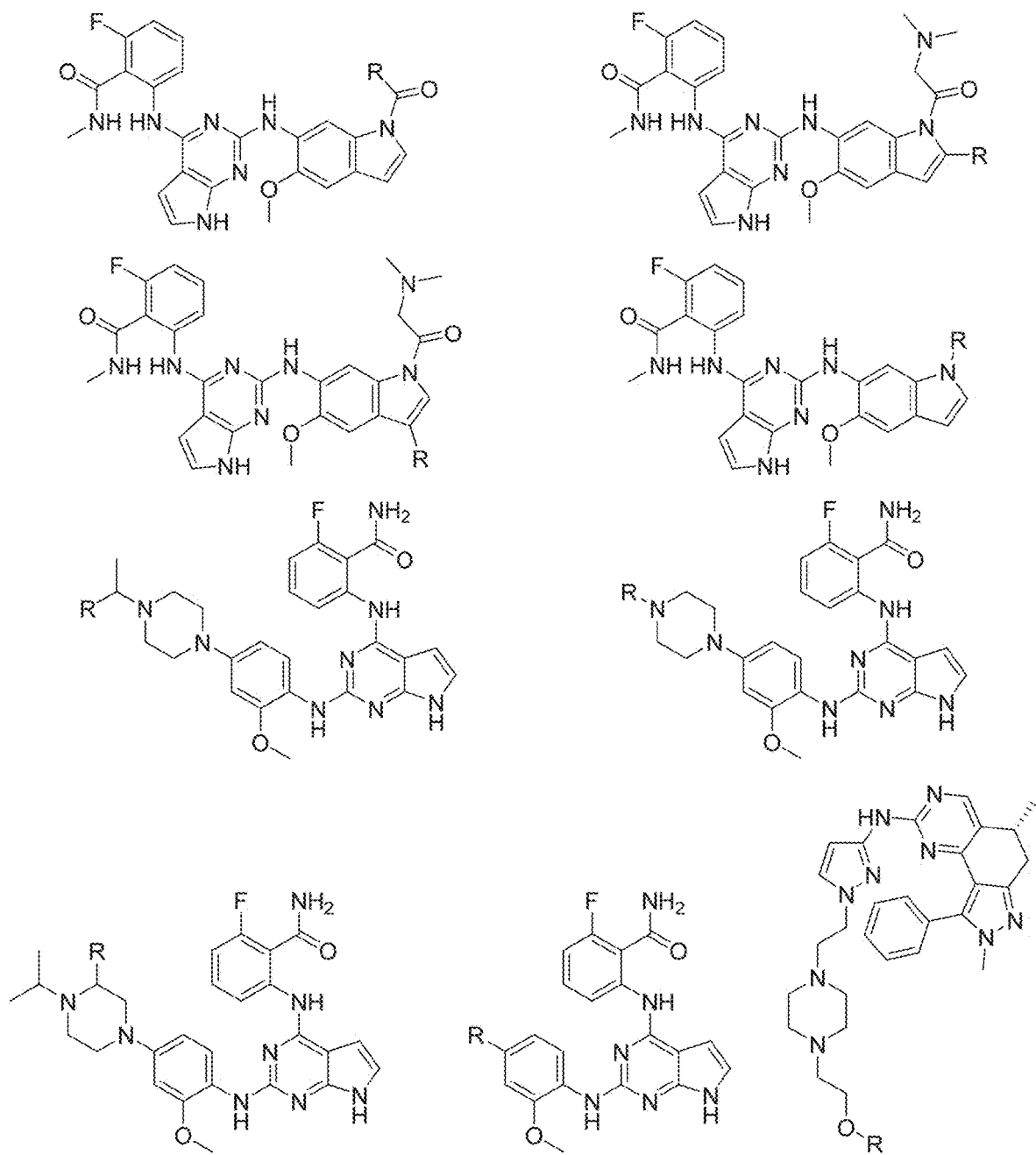
FIG. 8HHHHH

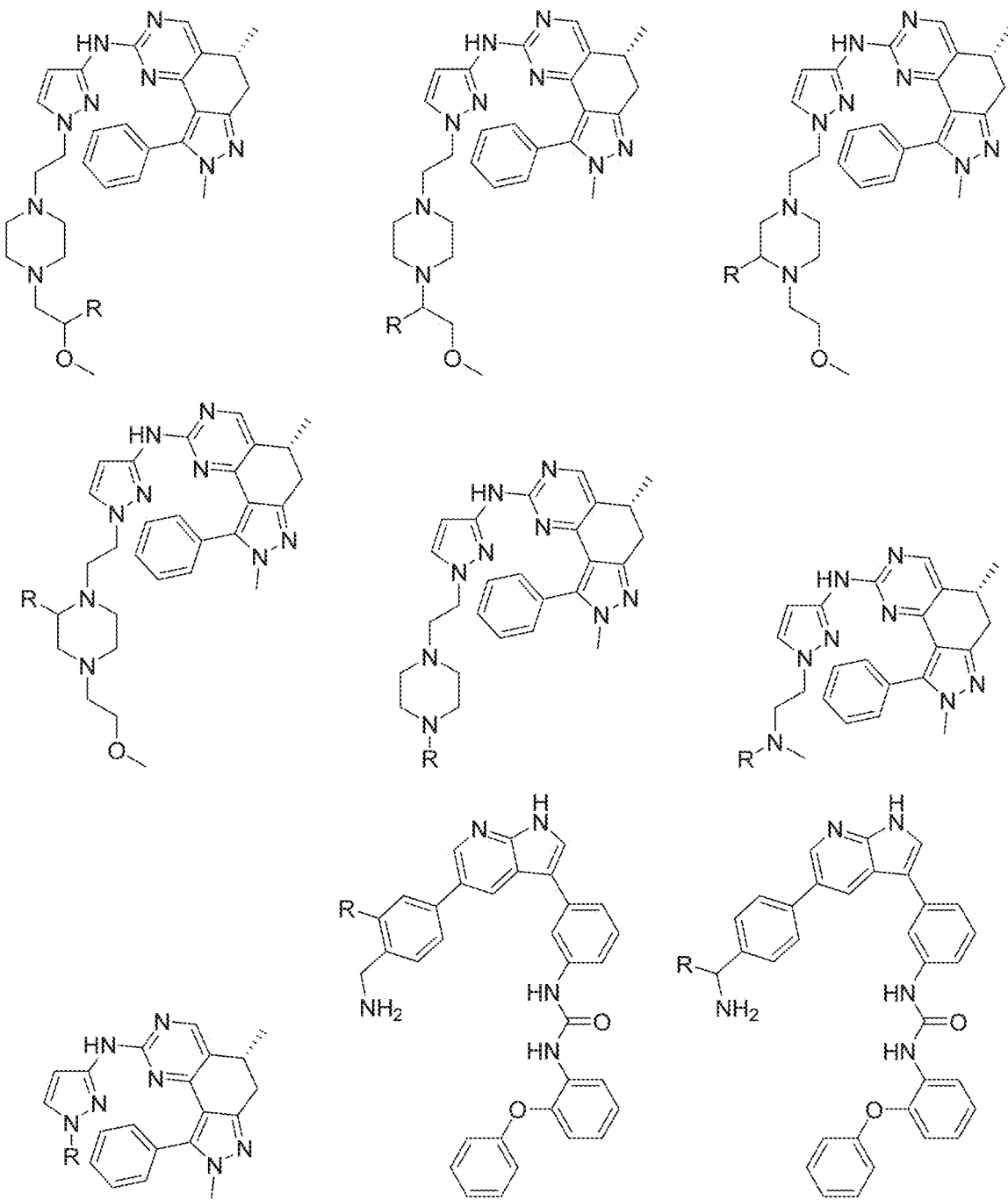
FIG. 8IIIII

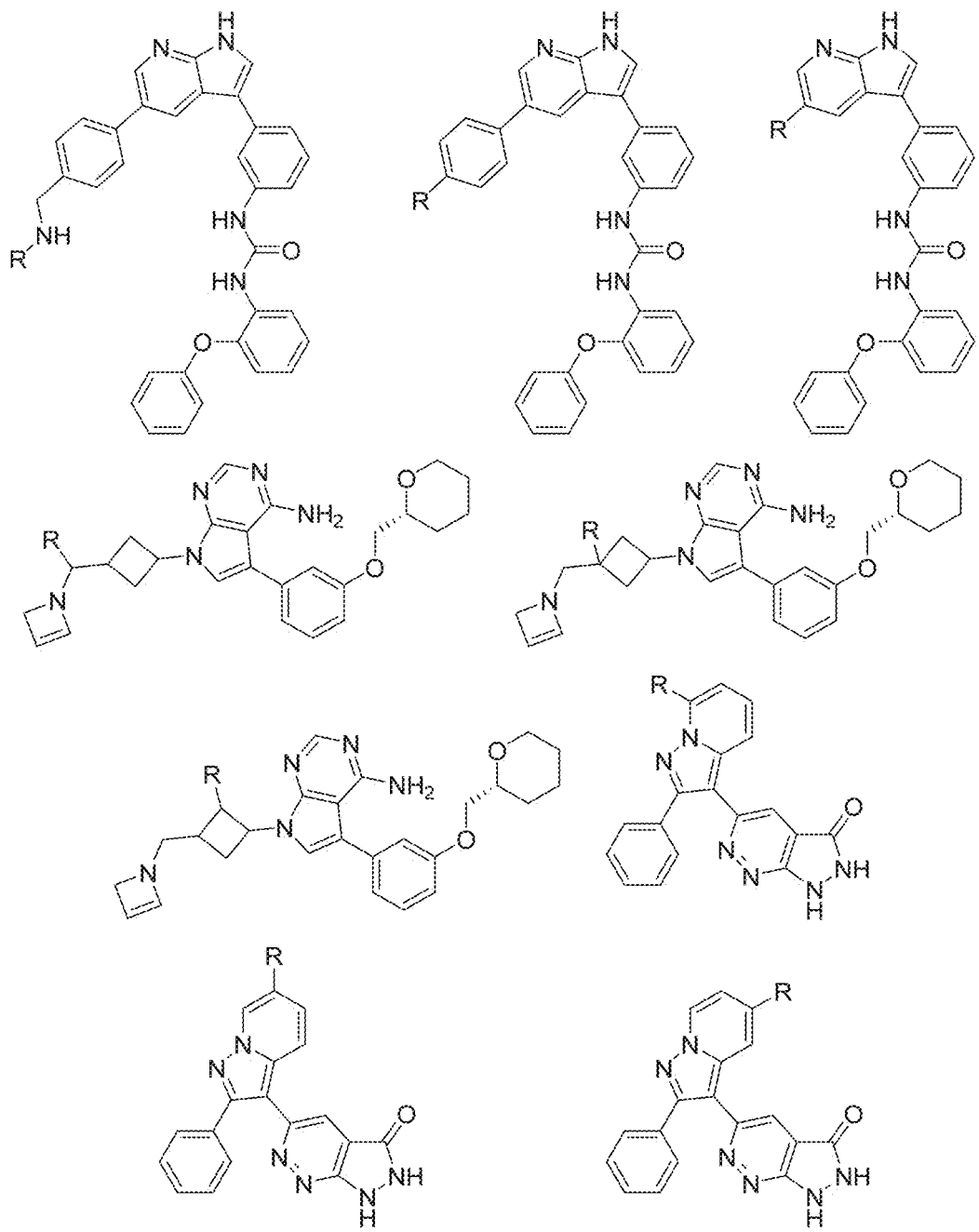
FIG. 8JJJJJ

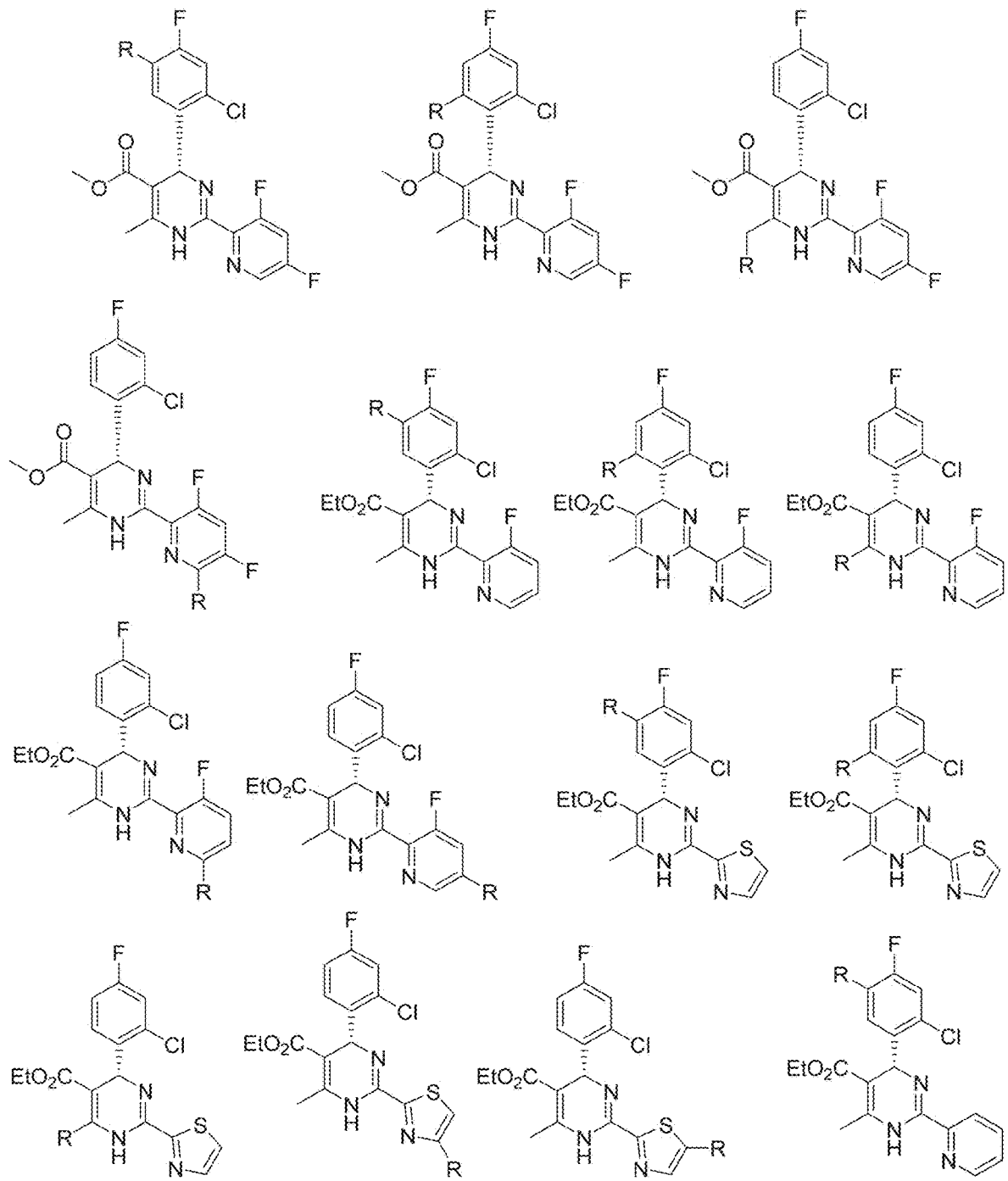
FIG. 8KKKKK

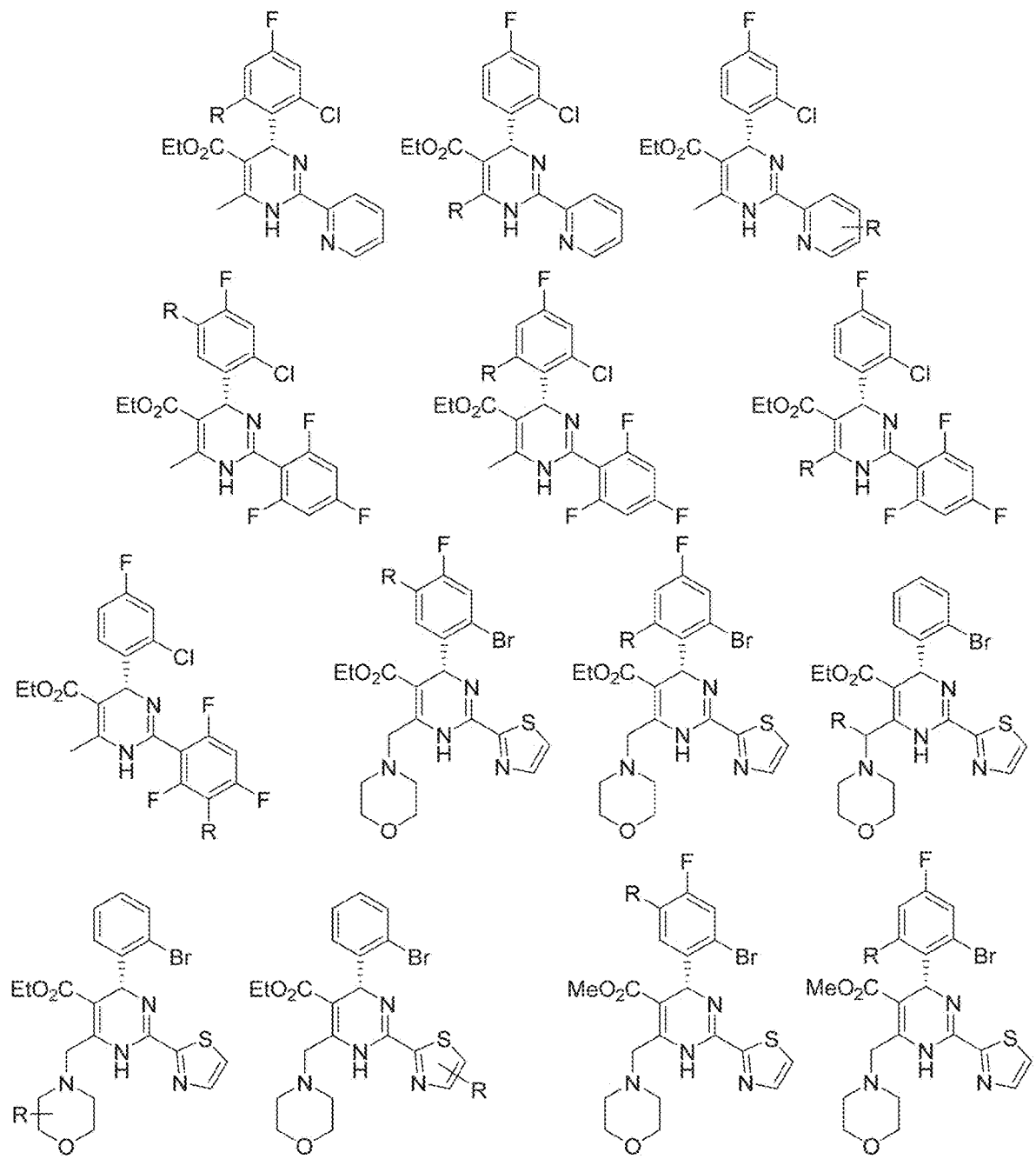
FIG. 8LLLLL

FIG. 8MMMMM
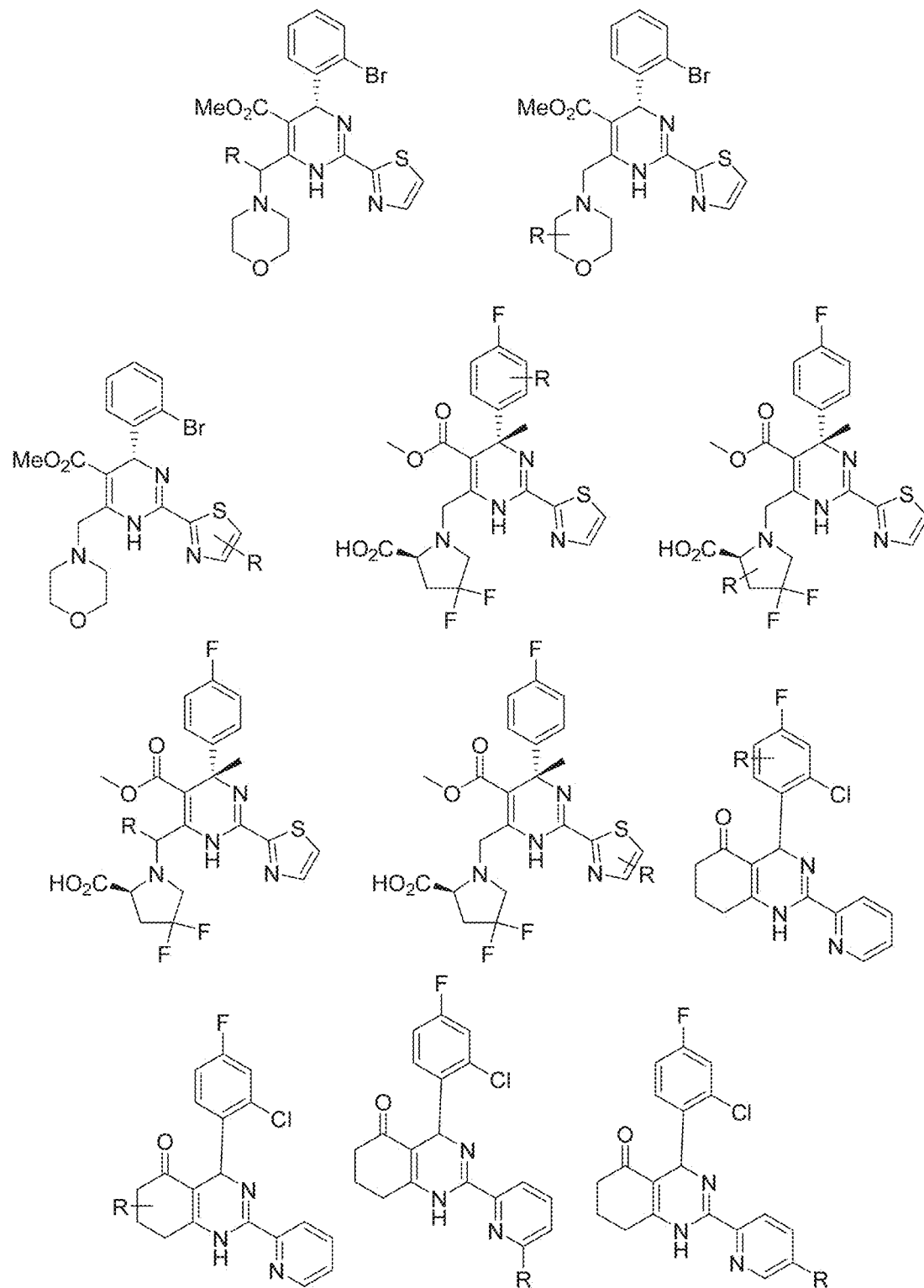

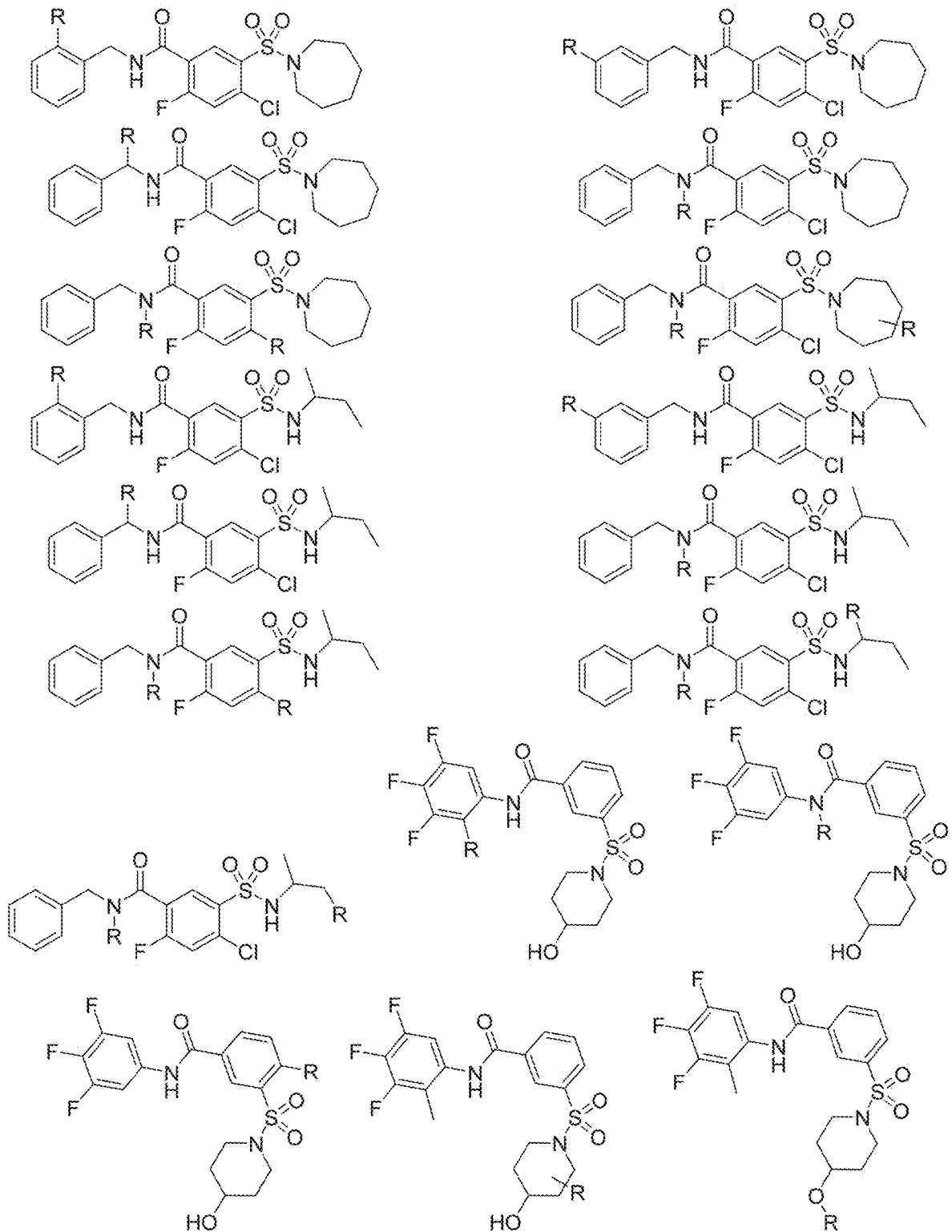
FIG. 8NNNNN

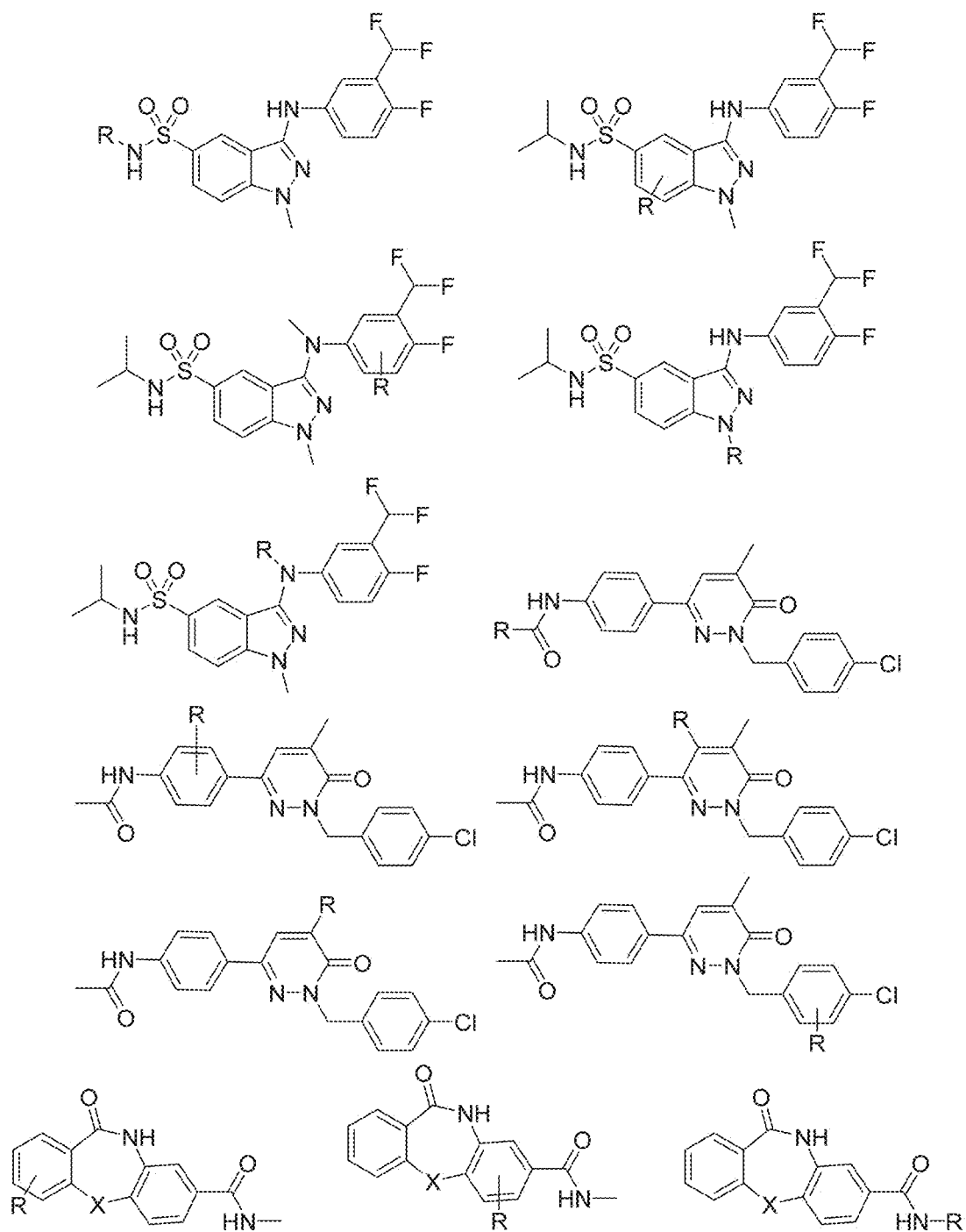
FIG. 800000

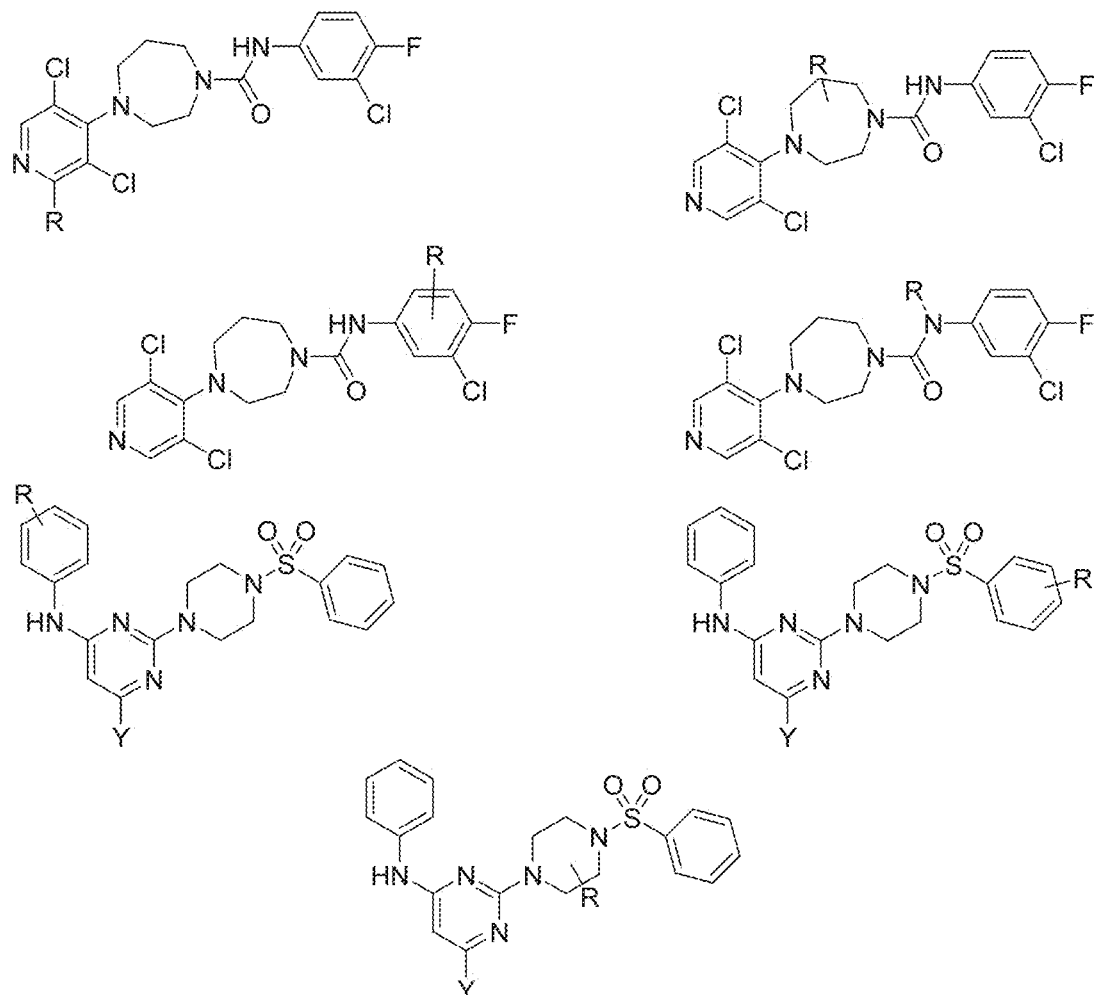
FIG. 8PPPPP

HETEROCYCLIC DEGRONIMERS FOR TARGET PROTEIN DEGRADATION

CROSS-REFERENCE TO RELATED APPLICATIONS

This application is a continuation of International Application No. PCT/US2017/032051, filed in the International Patent Cooperation Treaty, U.S. Receiving Office on May 10, 2017, which claims the benefit of priority to U.S. Application No. 62/334,395, filed May 10, 2016. The entirety of these applications are hereby incorporated by reference herein for all purposes

FIELD OF THE INVENTION

This invention provides heterocyclic compounds that bind to E3 Ubiquitin Ligase (typically through cereblon) ("Degrons"), which can be used as is or linked to a Targeting Ligand for a selected Target Protein for therapeutic purposes and methods of use and compositions thereof as well as methods for their preparation.

BACKGROUND

Protein degradation is a highly regulated and essential process that maintains cellular homeostasis. The selective identification and removal of damaged, misfolded, or excess proteins is achieved via the ubiquitin-proteasome pathway (UPP). The UPP in fact is central to the regulation of almost all cellular processes, including antigen processing, apoptosis, biogenesis of organelles, cell cycling, DNA transcription and repair, differentiation and development, immune response and inflammation, neural and muscular degeneration, morphogenesis of neural networks, modulation of cell surface receptors, ion channels and the secretory pathway, the response to stress and extracellular modulators, ribosome biogenesis and viral infection.

Covalent attachment of multiple ubiquitin molecules by an E3 ubiquitin ligase to a terminal lysine residue marks the protein for proteasome degradation, where the protein is digested into small peptides and eventually into its constituent amino acids that serve as building blocks for new proteins. Defective proteasomal degradation has been linked to a variety of clinical disorders including Alzheimer's disease, Parkinson's disease, Huntington's disease, muscular dystrophies, cardiovascular disease, and cancer among others.

There are over 600 E3 ubiquitin ligases which facilitate the ubiquitination of different proteins in vivo, which can be divided into four families: HECT-domain E3s, U-box E3s, monomeric RING E3s and multi-subunit E3s. See generally Li et al. (*PLOS One*, 2008, 3, 1487) titled "Genome-wide and functional annotation of human E3 ubiquitin ligases identifies MULAN, a mitochondrial E3 that regulates the organelle's dynamics and signaling."; Berndsen et al. (*Nat. Struct. Mol. Biol.*, 2014, 21, 301-307) titled "New insights into ubiquitin E3 ligase mechanism"; Deshaies et al. (*Ann. Rev. Biochem.*, 2009, 78, 399-434) titled "RING domain E3 ubiquitin ligases."; Spratt et al. (*Biochem.* 2014, 458, 421-437) titled "RBR E3 ubiquitin ligases: new structures, new insights, new questions."; and Wang et al. (*Nat. Rev. Cancer.*, 2014, 14, 233-347) titled "Roles of F-box proteins in cancer.".

In 1995, Gosink et al. (*Proc. Natl. Acad. Sci. USA* 1995, 92, 9117-9121) in a publication titled "Redirecting the Specificity of Ubiquitination by Modifying Ubiquitin-Conjugating Enzymes", provided proof of concept in vitro that engineered peptides can selectively direct ubiquitination of intracellular proteins. The publication by Nawaz et al. (*Proc. Natl. Acad. Sci. U.S.A.* 1999, 96, 1858-1862) titled "Proteasome-Dependent Degradation of the Human Estrogen Receptor" describes ER degradation which takes advantage of the ubiquitin-proteasome pathway.

Proteinex, Inc. filed a patent application in February 1999 that issued as U.S. Pat. No. 6,306,663 claiming a method of generating a compound for activating the ubiquitination of a Target Protein which comprises covalently linking a Target Protein binding element able to bind specifically to the Target Protein via a ubiquitination recognition element. Proteinex described that the invention can be used to control protein levels in eukaryotes. While the '663 patent may have been based on the first patent application to describe the high level concept of how to manipulate the UPP system to degrade selected proteins in vivo, the patent did not provide sufficient detail to allow persons of skill to easily construct the range of proposed compounds. For example, for the ubiquitination recognition elements, the skilled person was told among other things to use standard methods for drug discovery and screen for appropriate small molecules that would bind to the ligase. Proteinex also emphasized the use of peptides as ubiquitination recognition elements, which can pose significant difficulties for oral drug administration.

Since then, harnessing the ubiquitin-proteasome pathway for therapeutic intervention has received significant interest from the scientific community. The publication by Zhou et al. from Harvard Medical School (*Mol. Cell* 2000, 6, 751-756) titled "Harnessing the Ubiquitination Machinery to Target the Degradation of Specific Cellular Proteins" described an engineered receptor capable of directing ubiquitination in mammalian and yeast cells.

Following from these early publications and others in the mid to late 1990s, it was also recognized by Craig Crews and coworkers (Yale University) that a molecule that is capable of binding a Target Protein and a ubiquitin ligase may cause the Target Protein to be degraded. Their first description of such compounds was provided in U.S. Pat. No. 7,041,298 filed in September 2000 by Deshaies et al. and granted in May 2006 titled "Proteolysis Targeting Chimeric Pharmaceutical", which described a "PROTAC" consisting of a small molecule binder of MAP-AP-2 linked to a peptide capable of binding the F-box protein β-TRCP. Information in the '298 patent is also presented in the corresponding publication by Sakamoto et al. (*Proc. Natl. Acad. Sci. USA* 2001, 98, 8554-8559) titled "Protacs: Chimeric Molecules That Target Proteins to the Skp1-Cullin-F Box Complex for Ubiquitination and Degradation". The publication by Sakamoto et al. (*Mol. Cell. Proteomics* 2003, 2, 1350-1358) titled "Development of Protacs to Target Cancer-Promoting Proteins for Ubiquitination and Degradation" describes an analogous PROTAC (PROTAC2) that instead of degrading MAP-AP-2 degrades estrogen and androgen receptors.

The first E3 ligase successfully targeted with a small molecule was MDM2, which ubiquitinates the tumor suppressor p53. The targeting ligand was an HDM2/MDM2 inhibitor identified in Vassilev et al. (*Science* 2004, 303, 844-848) titled "In Vivo Activation of the P53 Pathway by Small-Molecule Antagonists of MDM2".

Other examples of direct small molecule-induced recruitment of Target Proteins to the proteasome for degradation on addition to cultured cells were described in 2004 (Schneekloth et al. (*J. Am. Chem. Soc.* 2004, 126, 3748-3754) titled "Chemical Genetic Control of Protein Levels: Selective in Vivo Targeted Degradation"). Schneekloth et al. describe a degradation agent (PROTAC3) that targets the FK506 binding protein (FKBP12) and shows that both PROTAC2 and PROTAC3 hit their respective targets with green fluorescent protein (GFP) imaging. The publication by Schneekloth et al. (*Chem Bio Chem* 2005, 6, 40-46) titled "Chemical Approaches to Controlling Intracellular Protein Degradation" described the state of the field at the time.

The publication by Schneekloth et al. (*Bioorg. Med. Chem. Lett.* 2008, 18, 5904-5908) titled "Targeted Intracellular Protein Degradation Induced by a Small Molecule: En Route to Chemical Proteomics" describes a degradation agent that consists of two small molecules linked by PEG that in vivo degrades the androgen receptor by concurrently binding the androgen receptor and ubiquitin E3 ligase.

WO 2013/170147 filed by Crews et al. titled "Compounds Useful for Promoting Protein Degradation and Methods of Using Same" describes compounds comprising a protein degradation moiety covalently bound to a linker, wherein the C log P of the compound is equal to or higher than 1.5. In particular, the specification discloses protein degrading compounds that incorporate certain small molecules that can bind to an E3 ubiquitin ligase.

In unrelated parallel research, scientists were investigating thalidomide toxicity. Ito et al. (*Science* 2010, 327, 1345-1350) titled "Identification of a Primary Target of Thalidomide Teratogenicity", described that cereblon is a thalidomide binding protein. Cereblon forms part of an E3 ubiquitin ligase protein complex which interacts with damaged DNA binding protein 1, forming an E3 ubiquitin ligase complex with Cullin 4 and the E2-binding protein ROC1 (also known as RBX1) where it functions as a substrate receptor to select proteins for ubiquitination. The study revealed that thalidomide-cereblon binding in vivo may be responsible for thalidomide teratogenicity. After the discovery that thalidomide causes teratogenicity in the mid-1960's, the compound and related structures were notwithstanding found to be useful as anti-inflammatory, anti-angiogenic and anti-cancer agents (see Bartlett et al. (*Nat. Rev. Cancer* 2004, 4, 314-322) titled "The Evolution of Thalidomide and Its Imid Derivatives as Anticancer Agents").

The disclosure that thalidomide binds to the cereblon E3 ubiquitin ligase let to research to investigate incorporating thalidomide and certain derivatives into compounds for the targeted destruction of proteins. Two seminal papers were published in *Science* in 2014: G. Lu et al., The Myeloma Drug Lenalidomide Promotes the Cereblon-Dependent Destruction of Ikaros Proteins, *Science*, 343, 305-309 (2014); and J. Kronke et al., Lenalidomide Causes Selective Degradation of IKZF1 and IKZF3 in Multiple Myeloma Cells, *Science*, 343, 301-305 (2014).

U.S. 2014/0356322 assigned to Yale University, GlaxoSmithKline, and Cambridge Enterprise Limited University of Cambridge titled "Compounds and Methods for the Enhanced Degradation of Target Proteins & Other Polypeptides by an E3 Ubiquitin Ligase" describes protein degrading compounds that bind to the VHL E3 Ubiquitin Ligase. See also Buckley et al. (*J. Am. Chem. Soc.* 2012, 134, 4465-4468) titled "Targeting the Von Hippel-Lindau E3 Ubiquitin Ligase Using Small Molecules to Disrupt the Vh1/Hif-1alpha Interaction".

WO 2015/160845 assigned to Arvinas Inc. titled "Imide Based Modulators of Proteolysis and Associated Methods of Use" describes protein degradation compounds that incorporate thalidomide and certain derivatives which bind to a cereblon E3 ligase.

Additional publications in this area include the following: Lu et al. (*Chem. Biol.* 2015, 22, 755-763) titled "Hijacking the E3 Ubiquitin Ligase Cereblon to Efficiently Target Brd4"; Bondeson et al. (*Nat. Chem. Biol.* 2015, 11, 611-617) titled "Catalytic in Vivo Protein Knockdown by Small-Molecule Protacs"; Gustafson et al. (*Angewandte Chemie, International Edition in English* 2015, 54, 9659-9662) titled "Small-Molecule-Mediated Degradation of the Androgen Receptor through Hydrophobic Tagging"; Lai et al. (*Angewandte Chemie, International Edition in English* 2016, 55, 807-810) titled "Modular Protac Design for the Degradation of Oncogenic Bcr-Abl"; Toure et al. (*Angew. Chem. Int. Ed.* 2016, 55, 1966-1973) titled "Small-Molecule Protacs: New Approaches to Protein Degradation"; and Winter et al. (*Science* 2015, 348, 1376-1381) titled "Drug Development. Phthalimide Conjugation as a Strategy for in Vivo Target Protein Degradation" describes thalidomide based Target Protein degradation technology.

U.S. 2016/0058872 assigned to Arvinas Inc. titled "Imide Based Modulators of Proteolysis and Associated Methods of Use" and U.S. 2016/0045607 assigned to Arvinas Inc. titled "Estrogen-related Receptor Alpha Based PROTAC Compounds and Associated Methods of Use" describe certain estrogen receptor degrading compounds.

While progress has been made in the area of modulation of the UPP for in vivo protein degradation, it would be useful to have additional compounds and approaches to more fully harness the UPP for therapeutic treatments.

It is an object of the present invention to provide new compounds, methods, compositions, and methods of manufacture that are useful to degrade selected proteins in vivo.

SUMMARY

Heterocyclic compounds that bind to E3 Ubiquitin Ligase (typically through cereblon) ("Degrons") are provided, which can be used as is or linked to a Targeting Ligand for a selected Target Protein for therapeutic purposes and methods of use and compositions thereof as well as methods for their preparation and manufacture. A Degron as described herein when covalently linked (Linker) to a ligand (Targeting Ligand) for a Target Protein is referred to as a "Degronimer" because they accomplish degradation of the Target Protein by the proteasome. The Degronimer includes a "Targeting Ligand" that binds (typically non-covalently) to a selected Target Protein, a "Degron" which binds (typically non-covalently) to an E3 Ligase and optionally a linker that covalently links the Targeting Ligand to the Degron.

A Degronimer provided herein or its pharmaceutically acceptable salt or composition can be used to treat a disorder which is mediated by the Target Protein bound to the Targeting Ligand.

In one embodiment, the selected Target Protein is derived from a gene that has undergone an amplification, translocation, deletion, or inversion event which causes or is caused by a medical disorder. In certain aspects, the selected Target Protein has been post-translationally modified by one, or combinations, of phosphorylation, acetylation, acylation including propionylation and crotylation, N-linked glycosylation, amidation, hydroxylation, methylation, poly-methylation, O-linked glycosylation, pyrogultamoylation, myristoylation, farnesylation, geranylgeranylation, ubiquitination, sumoylation, or sulfation which causes or is caused by a medical disorder. In an alternative embodiment, the Target Protein is covalently modified by a Targeting Ligand that has been functionalized to produce a degrader, and the covalent ligand can be irreversible or reversible.

In one aspects a compound of Formula I or Formula II is provided:

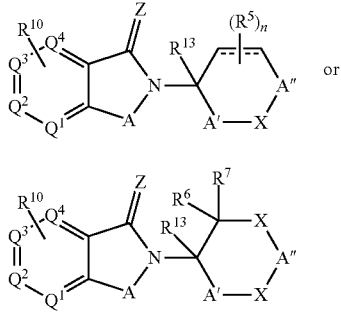

or a pharmaceutically acceptable salt, N-oxide, isotopic derivative or prodrug, optionally in a pharmaceutically acceptable carrier, to form a pharmaceutically acceptable composition; wherein:

A is $CR^8R^9$, C=O, C=S, $C=CH_2$, $SO_2$, S(O), P(O)Oalkyl, P(O)NHalkyl, $P(O)N(alkyl)_2$, P(O)alkyl, P(O)OH, $P(O)NH_2$;

A' is $CR^1R^2$, C=O, C=S, $C=CH_2$, $SO_2$, S(O), P(O)Oalkyl, P(O)NHalkyl, $P(O)N(alkyl)_2$, P(O)alkyl, P(O)OH, $P(O)NH_2$;

A" is $CR^3R^4$, C=O, C=S, $C=CH_2$, $SO_2$, S(O), P(O)Oalkyl, P(O)NHalkyl, $P(O)N(alkyl)_2$, P(O)alkyl, P(O)OH, $P(O)NH_2$;

X is independently NH, $NR^{11}$, $CH_2$, $CHR^{12}$, $C(R^{12})_2$, O, or S;

Z is O, S, $CH_2$, $CH(C_1-C_4alkyl)$, and $C(C_1-C_4alkyl)_2$;

n is 0, 1, 2, or 3;

---- is a single or double bond;

$R^1$, $R^2$, $R^3$, $R^4$, $R^6$, $R^7$, $R^8$, $R^9$, and $R^{13}$ are independently selected from hydrogen, alkyl, hydroxyl, alkoxy, amine, —NH(aliphatic, including alkyl), —Nalkyl$_2$;

or $R^1$ and $R^2$ form a 3-, 4-, 5-, or 6-membered spirocarbocycle, or a 4-, 5-, or 6-membered spiroheterocycle comprising 1 or 2 heteroatoms selected from N and O;

or $R^3$ and $R^4$ form a 3-, 4-, 5-, or 6-membered spirocarbocycle, or a 4-, 5-, or 6-membered spiroheterocycle comprising 1 or 2 heteroatoms selected from N and O;

or $R^6$ and $R^7$ form a 3-, 4-, 5-, or 6-membered spirocarbocycle, or a 4-, 5-, or 6-membered spiroheterocycle comprising 1 or 2 heteroatoms selected from N and O;

or $R^8$ and $R^9$ form a 3-, 4-, 5-, or 6-membered spirocarbocycle, or a 4-, 5-, or 6-membered spiroheterocycle comprising 1 or 2 heteroatoms selected from N and O;

or $R^1$ and $R^3$ form a 1, 2, 3 or 4 carbon bridged ring;
or $R^1$ and $R^7$ form a 1, 2, 3 or 4 carbon bridged ring;
or $R^3$ and $R^7$ form a 1, 2, 3 or 4 carbon bridged ring;
or $R^{13}$ and $R^1$ form a 3, 4, 5, or 6 carbon fused ring;
or $R^{13}$ and $R^6$ form a 3, 4, 5, or 6 carbon fused ring;
or $R^{13}$ and $R^4$ form a 1, 2, 3 or 4 carbon bridged ring;
or $R^{13}$ and $R^5$ form a 3, 4, 5, or 6 carbon fused ring wherein $R^5$ is on the carbon alpha to $R^{13}$ or a 1, 2, 3, or 4 carbon bridged ring wherein $R^5$ is not on the carbon alpha to $R^{13}$;

in a typical embodiment $W^1$ is C=O;
in another typical embodiment $W^2$ is C=O;
in another typical embodiment both $W^1$ and $W^2$ are C=O and X is NH;

$R^5$ is selected at each instance from: alkyl, alkene, alkyne, halogen, hydroxyl, alkoxy, azide, amino, —NH(aliphatic, including alkyl), —N(aliphatic, including alkyl)$_2$, —NHSO$_2$(aliphatic, including alkyl), —N(alkyl)SO$_2$(aliphatic, including alkyl), —NHSO$_2$(aryl including heteroaryl), —N(aliphatic, including alkyl)SO$_2$aryl, —NHSO$_2$alkenyl, —N(alkyl)SO$_2$alkenyl, —NHSO$_2$alkynyl, —N(alkyl)SO$_2$alkynyl, aliphatic, heteroaliphatic, aryl, heteroaryl, heterocyclic, and haloalkyl;

or two $R^5$ substituents together with the carbon atom(s) to which they are bound can form a 3, 4, 5 or 6 membered ring;

$R^{10}$ is Linker-Targeting Ligand;

$Q^1$, $Q^2$, $Q^3$, and $Q^4$ are independently selected from CH, $CR^{12}$, N and wherein in certain embodiments the number of nitrogen atoms is 0, 1, 2, or 3 per ring (as allowed by context) and is selected to produce a stable ring and a pharmaceutically acceptable Degronimer. When the Q is in a six-membered ring (unfused or fused), and at least one Q is nitrogen, the ring can be, in non-limiting embodiments as allowed by context, a pyridine, diazine, triazine, pyrimidine, pyridazine, pyrazine, triazine or tetrazine.

$R^{11}$ is independently selected from alkyl, alkenyl, alkynyl, C(O)H, —C(O)OH, —C(O)alkyl, —C(O)Oalkyl, aliphatic, heteroaliphatic, aryl, heteroaryl or heterocyclic;

$R^{12}$ is independently selected from alkyl, alkenyl, alkynyl, halogen, hydroxyl, alkoxy, azide, amino, —C(O)H, —C(O)OH, —C(O)(aliphatic, including alkyl), —C(O)O(aliphatic, including alkyl), —NH(aliphatic, including alkyl), —N(aliphatic, including alkyl)$_2$, —NHSO$_2$(aliphatic, including alkyl), —N(aliphatic, including alkyl)SO$_2$(aliphatic including alkyl, —NHSO$_2$(aryl, including heteroaryl), —N(aliphatic, including alkyl)SO$_2$aryl, —NHSO$_2$alkenyl, —N(alkyl)SO$_2$alkenyl, —NHSO$_2$alkynyl, —N(alkyl)SO$_2$alkynyl, cyano, nitro, nitroso, —SH, —Salkyl, and haloalkyl, aliphatic, heteroaliphatic, aryl, heteroaryl and heterocyclic;

Linker is a chemical group that attaches the Degron to a Targeting Ligand;

Targeting Ligand is a moiety that is capable of binding to or binds to a Target Protein, and wherein the Target Protein is a mediator of disease in a host, as further defined herein;

wherein in certain embodiments the compound satisfies at least one of a, b, c, d, e, f, g, h, i, j, k, l, or m:

a. n is 1 or 2;
b. at least one of $R^1$, $R^2$, $R^3$, or $R^4$ is alkyl;
c. $R^1$ and $R^2$ form a 4, 5, or 6 membered spiroheterocycle or 3, 4, 5, or 6 membered spirocarbocycle;
d. $R^3$ and $R^4$ form a 4, 5, or 6 membered spiroheterocycle or 3, 4, 5, or 6 membered spirocarbocycle;
e. $R^6$ and $R^7$ form a 4, 5, or 6 membered spiroheterocycle or 3, 4, 5, or 6 membered spirocarbocycle;
f. $R^8$ and $R^9$ form a 4, 5, or 6 membered spiroheterocycle or 3, 4, 5, or 6 membered spirocarbocycle;
g. $R^1$ and $R^3$ form a 1 or 2 carbon bridged ring;
h. $R^1$ and $R^{13}$ form a 3, 4, 5, or 6 carbon fused ring;
i. $R^4$ and $R^{13}$ form a 1 or 2 carbon bridged ring;
j. A is $SO_2$, S(O), P(O)Oalkyl, P(O)NHalkyl, $P(O)N(alkyl)_2$, P(O)alkyl, P(O)OH, or $P(O)NH_2$;
k. A' is $SO_2$, S(O), P(O)Oalkyl, P(O)NHalkyl, $P(O)N(alkyl)_2$, P(O)alkyl, P(O)OH, or $P(O)NH_2$
l. A" is $SO_2$, S(O), P(O)Oalkyl, P(O)NHalkyl, $P(O)N(alkyl)_2$, P(O)alkyl, P(O)OH, or $P(O)NH_2$; or
m. X is O, or S.

In one embodiment, the compound of Formula I is selected from:

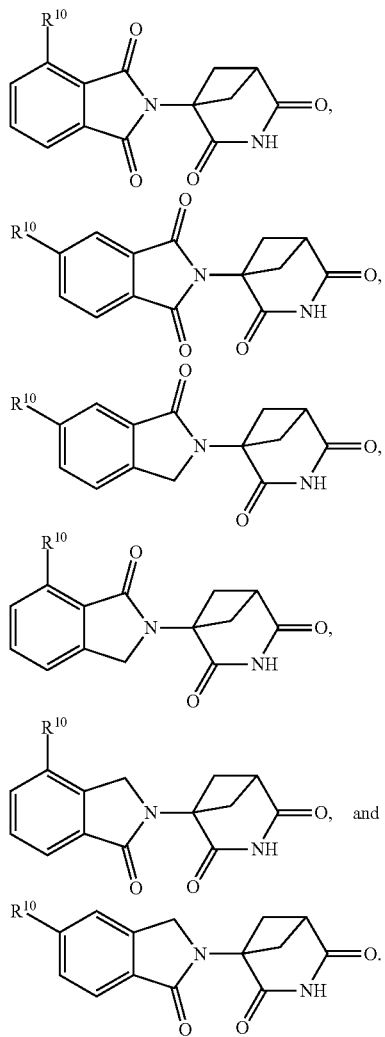

In another aspect of the present invention a compound of Formula III is provided:

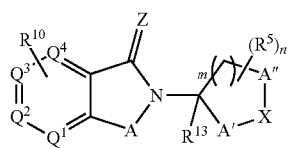

(III)

or a pharmaceutically acceptable salt, N-oxide, isotopic derivative or prodrug, optionally in a pharmaceutically acceptable carrier to form a pharmaceutically acceptable composition thereof;
wherein m is 1 or 3, and the other variables are as described above.

Linker is a chemical group that attaches the Degron to a Targeting Ligand.

Targeting Ligand is a moiety that is capable of binding to or binds to a Target Protein, and wherein the Target Protein is a mediator of disease in a host, as defined in detail below.

Formula I, Formula II, and Formula III are bifunctional compounds with heterocyclic E3 Ubiquitin Ligase targeting moieties (Degrons) linked via a Linker to a Targeting Ligand (described in more detail below), which function to recruit Target Protein to E3 Ubiquitin Ligase for degradation. In certain embodiments, the disorder is selected from a benign growth, neoplasm, tumor, cancer, immune disorder, autoimmune disorder, inflammatory disorder, graft-versus-host rejection, infection, including a viral infection, bacterial infection, an amyloid-based proteinopathy, a proteinopathy, or a fibrotic disorder. In a typical embodiment, the patient is a human. One non-limiting example of a disorder treatable by such compounds is abnormal cellular proliferation, such as a tumor or cancer, wherein the Target Protein is an oncogenic protein or a signaling mediator of an abnormal cellular proliferative pathway and its degradation decreases abnormal cell growth.

In one embodiment, the present invention provides heterocyclic moieties which are covalently linked to a Target Protein ligand through a Linker which can be of varying length and functionality. In one embodiment, the heterocyclic Degron moiety is linked directly to the Targeting Ligand (i.e., the Linker is a bond). In certain embodiments, the Linker can be any chemically stable group that attaches the heterocyclic Degron to the Targeting Ligand. In a typical embodiment, the Linker has a chain of 2 to 14, 15, 16, 17, 18 or 20 or more carbon atoms of which one or more carbons can be replaced by a heteroatom such as O, N, S, P, as long as the resulting molecule has a stable shelf life for at least 2 months, 3 months, 6 months or 1 year as part of a pharmaceutically acceptable dosage form, and itself is pharmaceutically acceptable. In certain embodiments the chain has 2, 3, 4, 5, 6, 7, 8, 9, 10, 11, 12, 13, or 14 contiguous atoms in the chain. For example, the chain may include 1 or more ethylene glycol units, and in some embodiments, may have at least 2, 3, 4, 5, 6, 7, 8, 9, or 10 or more contiguous, partially contiguous or non-contiguous ethylene glycol units in the Linker. In certain embodiments the chain has at least 1, 2, 3, 4, 5, 6, 7, or 8 branches which can be independently alkyl, heteroalkyl, aryl, heteroaryl, alkenyl, or alkynyl substituents, which in one embodiment, each branch has 10, 8, 6, 4, 3, 2 carbons or one carbon.

In one embodiment, the Target Protein is a protein that is not druggable in the classic sense in that it does not have a binding pocket or an active site that can be inhibited or otherwise bound, and cannot be easily allosterically controlled. In another embodiment, the Target Protein is a protein that is druggable in the classic sense. Examples of Target Proteins are provided below.

In an alternative embodiment, a heterocyclic Degron of Formula III, IV, or VI as described herein can be used alone (i.e., not as part of a Degronimer) as an in vivo binder of cereblon, which can be administered to a host, for example, a human, in need thereof, in an effective amount, optionally as a pharmaceutically acceptable salt, and optionally in a pharmaceutically acceptable composition, for any therapeutic indication which can be treated by modulating the function and or activity of the cereblon-containing E3 Ubiquitin Ligase Protein Complex, including but not limited to uses known for the cereblon binders thalidomide, pomalidomide or lenalidomide. In certain alternative embodiments, the compound of Formula III, IV or VI can activate, decrease or change the natural activity of cereblon.

Thus, in another aspect of the present invention a compound of Formula IV or Formula V is provided:

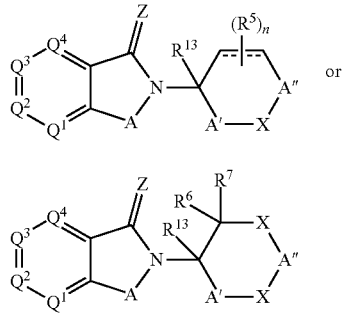

(IV)

(V)

or a pharmaceutically acceptable salt, N-oxide, isotopic derivative, prodrug, and/or a pharmaceutically acceptable composition thereof;
wherein:
wherein the variables are as described above and in certain embodiments at least one of: a, b, c, d, e, f, g, h, i, or j is required:
  a. $R^1$ and $R^2$ form a 4, 5, or 6 membered spiroheterocycle or 3, 4, 5, or 6 membered spirocarbocycle;
  b. $R^3$ and $R^4$ form a 4, 5, or 6 membered spiroheterocycle or 3, 4, 5, or 6 membered spirocarbocycle;
  c. $R^6$ and $R^7$ form a 4, 5, or 6 membered spiroheterocycle or 3, 4, 5, or 6 membered spirocarbocycle;
  d. $R^8$ and $R^9$ form a 4, 5, or 6 membered spiroheterocycle or 3, 4, 5, or 6 membered spirocarbocycle;
  e. $R^1$ and $R^3$ form a 1 or 2 carbon bridged ring;
  f. $R^1$ and $R^{13}$ form a 3, 4, 5, or 6 membered fused ring;
  g. $R^4$ and $R^{13}$ form a 1 or 2 carbon bridged ring;
  h. A is P(O)Oalkyl, P(O)NHalkyl, P(O)N(alkyl)$_2$, P(O)alkyl, P(O)OH, or P(O)NH$_2$;
  i. A' is SO$_2$, S(O), P(O)Oalkyl, P(O)NHalkyl, P(O)N(alkyl)$_2$, P(O)alkyl, P(O)OH, or P(O)NH$_2$; or
  j. A'' is SO$_2$, S(O), P(O)Oalkyl, P(O)NHalkyl, P(O)N(alkyl)$_2$, P(O)alkyl, P(O)OH, or P(O)NH$_2$.

In one embodiment, the compound of Formula III is selected from:

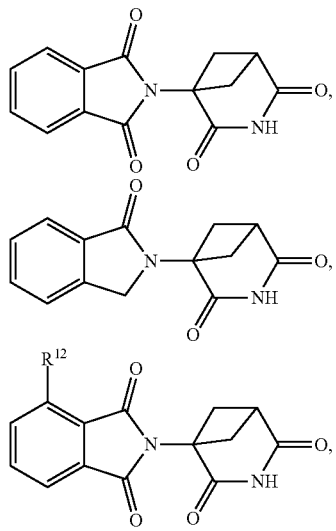

In another aspect of the present invention a compound of Formula VI is provided:

(VI)

or a pharmaceutically acceptable salt, N-oxide, isotopic derivative or a prodrug, optionally in a pharmaceutically acceptable carrier to form a pharmaceutically acceptable composition;
wherein the variables are as described above and in certain embodiments at least one of: a, b, c, d, e, f, g, h, i, j, k, l, or m is required:
  a. m is 3 and n is not 0;
  b. $R^1$ and $R^2$ form a spirocycle;
  c. $R^3$ and $R^4$ form a spirocycle;
  d. $R^6$ and $R^7$ form a spirocycle;
  e. $R^8$ and $R^9$ form a spirocycle;
  f. $R^1$ and $R^3$ form a 1 or 2 carbon bridged ring;
  g. $R^1$ and $R^{13}$ form a 3, 4, 5, or 6 carbon fused ring;
  h. $R^4$ and $R^{13}$ form a 1 or 2 carbon bridged ring;
  i. $R^{13}$ and $R^5$ form a 3, 4, 5, or 6 carbon fused ring;
  j. $R^{13}$ and $R^5$ form a 1 or 2 carbon bridged ring;
  k. A is SO$_2$, S(O), P(O)Oalkyl, P(O)NHalkyl, P(O)N(alkyl)$_2$, P(O)alkyl, P(O)OH, or P(O)NH$_2$;
  l. A' is SO$_2$, S(O), P(O)Oalkyl, P(O)NHalkyl, P(O)N(alkyl)$_2$, P(O)alkyl, P(O)OH, or P(O)NH$_2$; or m. A" is $SO_2$, S(O), P(O)Oalkyl, P(O)NHalkyl, P(O)N(alkyl)$_2$, P(O)alkyl, P(O)OH, or P(O)NH$_2$;

The compounds of Formula IV, Formula V and Formula VI do not include a Linker or a Targeting Ligand. These Formula IV, Formula V and Formula VI compounds for example, are useful as therapeutic agents for any disorder that can be treated by binding to the cereblon subunit of the E3 Ligase, when administered in an effective amount to a host, including a human, for the treatment of a medical disorder. Disorders include, but are not limited to, abnormal cellular proliferation, including a tumor or cancer, or a myelo- or lymphoproliferative disorder such as B- or T-cell lymphomas, multiple myeloma, Waldenstrom's macroglobulinemia, Wiskott-Aldrich syndrome, or a post-transplant lymphoproliferative disorder; an immune disorder, including autoimmune disorders such as Addison disease, Celiac disease, dermatomyositis, Graves disease, thyroiditis, multiple sclerosis, pernicious anemia, reactive arthritis, lupus, or type I diabetes; a disease of cardiac malfunction, including hypercholesterolemia; an infectious disease, including viral and/or bacterial infections; an inflammatory condition, including asthma, chronic peptic ulcers, tuberculosis, rheumatoid arthritis, periodontitis, ulcerative colitis, Crohn's disease, or hepatitis.

In certain embodiments, the compound of Formula I, Formula II, Formula III, Formula IV, Formula V, or Formula VI has at least one desired isotopic substitution of an atom, at an amount above the natural abundance of the isotope, i.e., enriched. In one embodiment, the compound of Formula I, Formula II, Formula III, Formula IV, Formula V, or Formula VI includes a deuterium or multiple deuterium atoms.

Unless otherwise defined, all technical and scientific terms used herein have the same meaning as commonly understood by one of ordinary skill in the art to which this application belongs. In the specification, the singular forms also include the plural unless the context clearly dictates otherwise. Although methods and materials similar or equivalent to those described herein can be used in the practice or testing of the present invention, suitable methods and materials are described below. All publications, patent applications, patents, and other references mentioned herein are incorporated by reference. The references cited herein are not admitted to be prior art to the claimed application. In the case of conflict, the present specification, including definitions, will control. In addition, the materials, methods, and examples are illustrative only and are not intended to be limiting.

Other features and advantages of the present invention will be apparent from the following detailed description and claims.

The present invention thus includes at least the following features:

(a) a heterocyclic compound of Formula I, Formula II, Formula III, Formula IV, Formula V, or Formula VI as described herein, and pharmaceutically acceptable salts, isotopic derivative (including a deuterated derivative) and prodrugs thereof;

(b) a heterocyclic compound of Formula I, Formula II or Formula III, for the treatment of a disorder that is mediated by a selected Target Protein, wherein the compound includes a Targeting Ligand for the Target Protein, and wherein the heterocyclic compound is optionally linked to the Targeting Ligand through a Linker;

(c) use of a compound of Formula I, Formula II, or Formula III in an effective amount in the treatment of a patient, including a human, with a disorder mediated by a Target Protein, including abnormal cellular proliferation such as a tumor or cancer, an autoimmune disorder or inflammatory disorder, a cardiac disorder, an infectious disease, or other disorder that responds to such treatment;

(d) use of a compound of Formula IV, Formula V, or Formula VI in an effective amount, in the treatment of a patient, including a human, with abnormal cellular proliferation such as a tumor or cancer, an autoimmune disorder or inflammatory disorder, a cardiac disorder, an infectious disease, or other disorder that responds to such treatment;

(e) use of a compound of Formula I, Formula II, Formula III, Formula IV, Formula V, or Formula VI, and pharmaceutically acceptable salts and prodrugs thereof in the manufacture of a medicament for the treatment of a medical disorder;

(f) a method for manufacturing a medicament intended for the therapeutic use of treating a disorder characterized in that a compound of Formula I, Formula II, Formula III, Formula IV, Formula V, or Formula VI as described herein is used in the manufacture;

(g) a compound of Formula I, Formula II, Formula III, Formula IV, Formula V, or Formula VI as described herein, and pharmaceutically acceptable salts and prodrugs thereof that are useful in the treatment of an abnormal cellular proliferation such as cancer, including any of the cancers described herein;

(h) use of a compound of Formula I, Formula II, Formula III, Formula IV, Formula V, or Formula VI and pharmaceutically acceptable salts and prodrugs thereof in the manufacture of a medicament for the treatment of an abnormal cellular proliferation such as cancer, including any of the cancers described herein;

(i) a method for manufacturing a medicament intended for the therapeutic treatment of an abnormal cellular proliferation such as cancer, including any of the cancers described herein, characterized in that a compound of Formula I, Formula II, Formula III, Formula IV, Formula V, or Formula VI as described herein is used in the manufacture;

(j) a compound of Formula I, Formula II, Formula III, Formula IV, Formula V, or Formula VI as described herein, and pharmaceutically acceptable salts, isotopic derivatives and prodrugs thereof that are useful in the treatment of a tumor, including any of the tumors described herein;

(k) use of a compound of Formula I, Formula II, Formula III, Formula IV, Formula V, or Formula VI, and pharmaceutically acceptable salts and prodrugs thereof in the manufacture of a medicament for the treatment of a tumor, including any of the tumors described herein;

(l) a method for manufacturing a medicament intended for the therapeutic treatment of a tumor, including any of the tumors described herein, characterized in that a compound of Formula I, Formula II, Formula III, Formula IV. Formula V, or Formula VI as described herein is used in the manufacture;

(m) a compound of Formula I, Formula II, Formula III, Formula IV, Formula V, or Formula VI as described herein, and pharmaceutically acceptable salts and prodrugs thereof that are useful in the treatment of an immune, autoimmune or inflammatory disorder;

(n) use of a compound of Formula I, Formula II, Formula III, Formula IV, Formula V, or Formula VI and pharmaceutically acceptable salts and prodrugs thereof in the manufacture of a medicament for the treatment of an immune, autoimmune or inflammatory disorder;

(o) a method for manufacturing a medicament intended for the therapeutic use of treating an immune, autoimmune or inflammatory disorder, characterized in that a compound of Formula I, Formula II, Formula III, Formula IV. Formula V, or Formula VI as described herein is used in the manufacture;

(p) a compound of Formula I, Formula II, Formula III, Formula IV, Formula V, or Formula VI as described herein, and pharmaceutically acceptable salts and prodrugs thereof that are useful in the treatment of an infection, including a viral infection, including but not limited to HIV, HBV, HCV and RSV;

(q) use of a compound of Formula I, Formula II, or Formula III, and pharmaceutically acceptable salts and prodrugs thereof in the manufacture of a medicament for the treatment of an infection, including a viral infection, including but not limited to HIV, HBV, HCV and RSV;

(r) a method for manufacturing a medicament intended for the therapeutic treatment of an infection, including a viral infection including but not limited to HIV, HBV, HCV and RSV, characterized in that a compound of Formula I, Formula II, or Formula III as described herein is used in the manufacture;

(s) a pharmaceutical formulation comprising an effective host-treating amount of the compound of Formula I, Formula II, Formula III, Formula IV, Formula V, or Formula VI or a pharmaceutically acceptable salt or prodrug thereof together with a pharmaceutically acceptable carrier or diluent;

(t) a compound of Formula I, Formula II, Formula III, Formula IV, Formula V, or Formula VI as described herein as a mixture of enantiomers or diastereomers (as relevant), including as a racemate;

(u) a compound of Formula I, Formula II, Formula III, Formula IV, Formula V, or Formula VI as described herein in enantiomerically or diastereomerically (as relevant) enriched form, including as an isolated enantiomer or diastereomer (i.e., greater than 85, 90, 95, 97 or 99% pure); and, (v) a process for the preparation of therapeutic products that contain an effective amount of a compound of Formula I, Formula II, Formula III, Formula IV, Formula V, or Formula VI, as described herein.

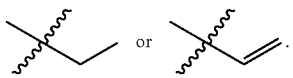

Figure 1A:
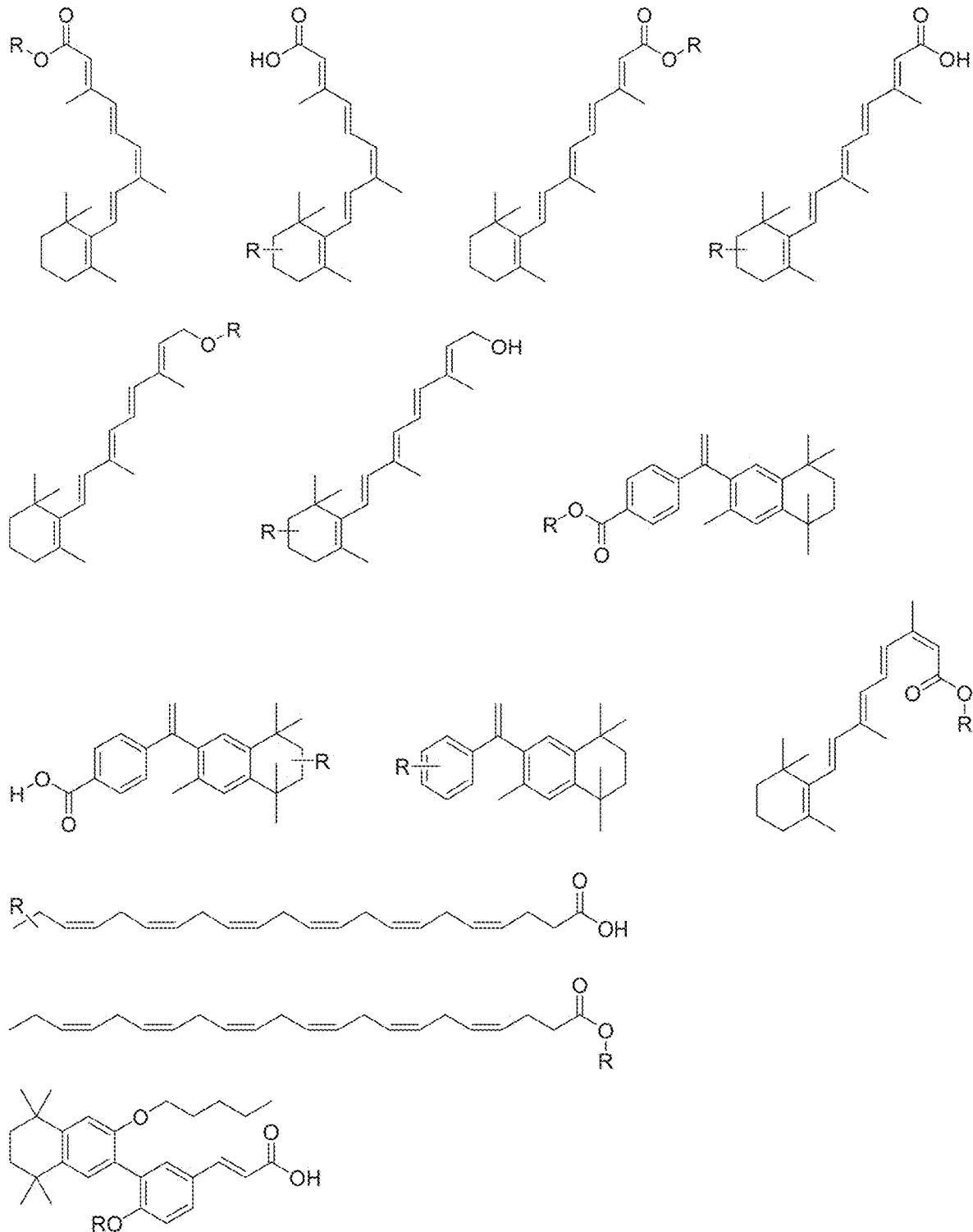
FIG. 1A-1C present examples of Retenoid X Receptor (RXR) Targeting Ligands wherein R is the point at which the Linker is attached.
Figure 1B:
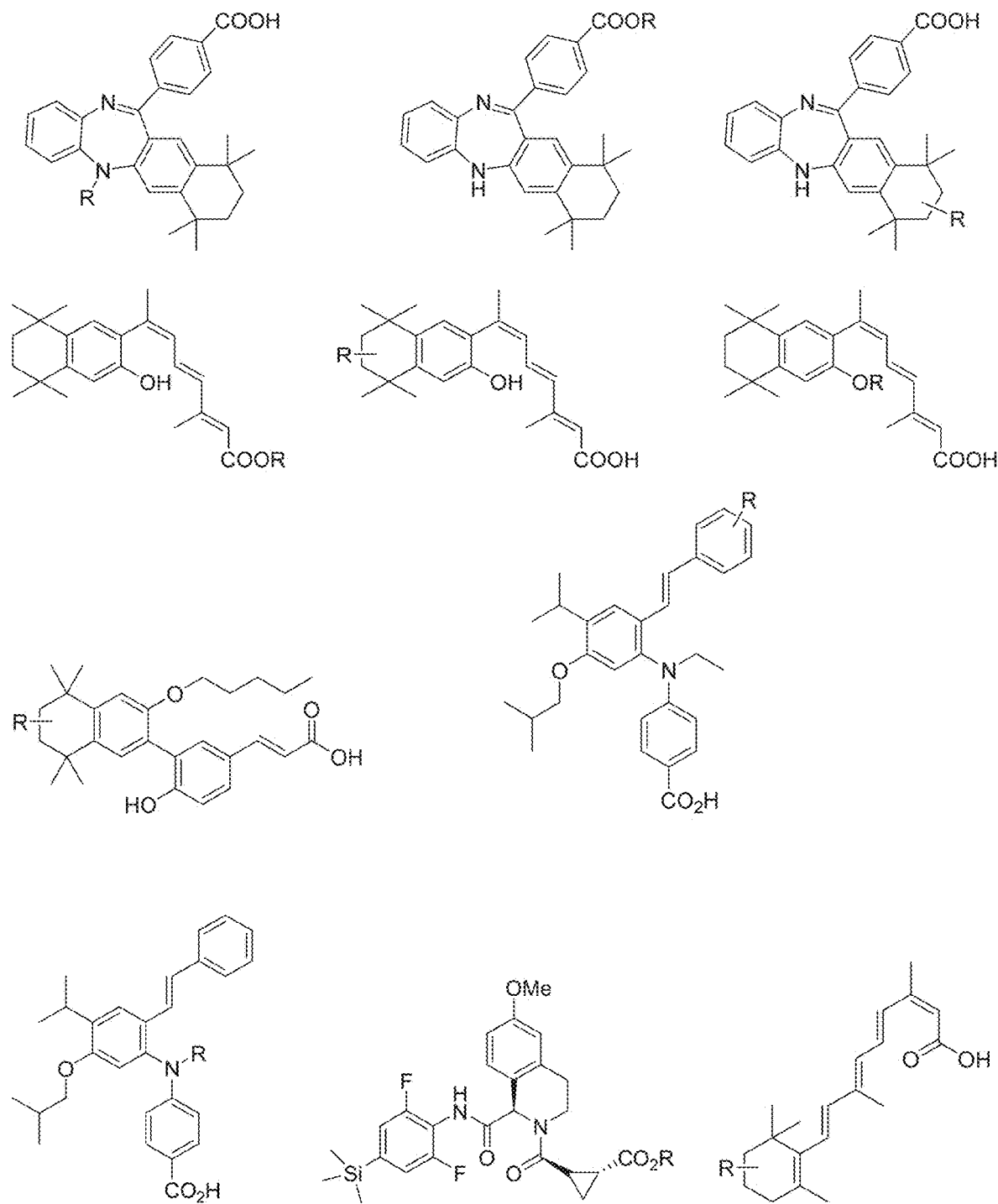
Figure 1C:
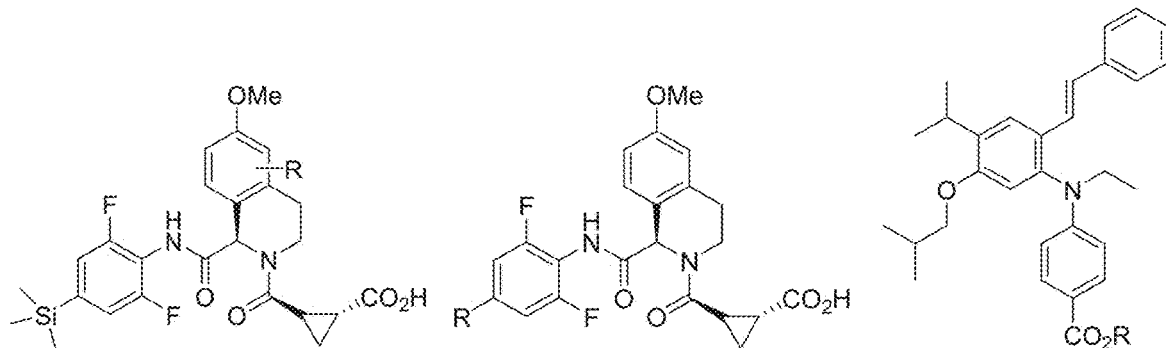
Figure 1D:
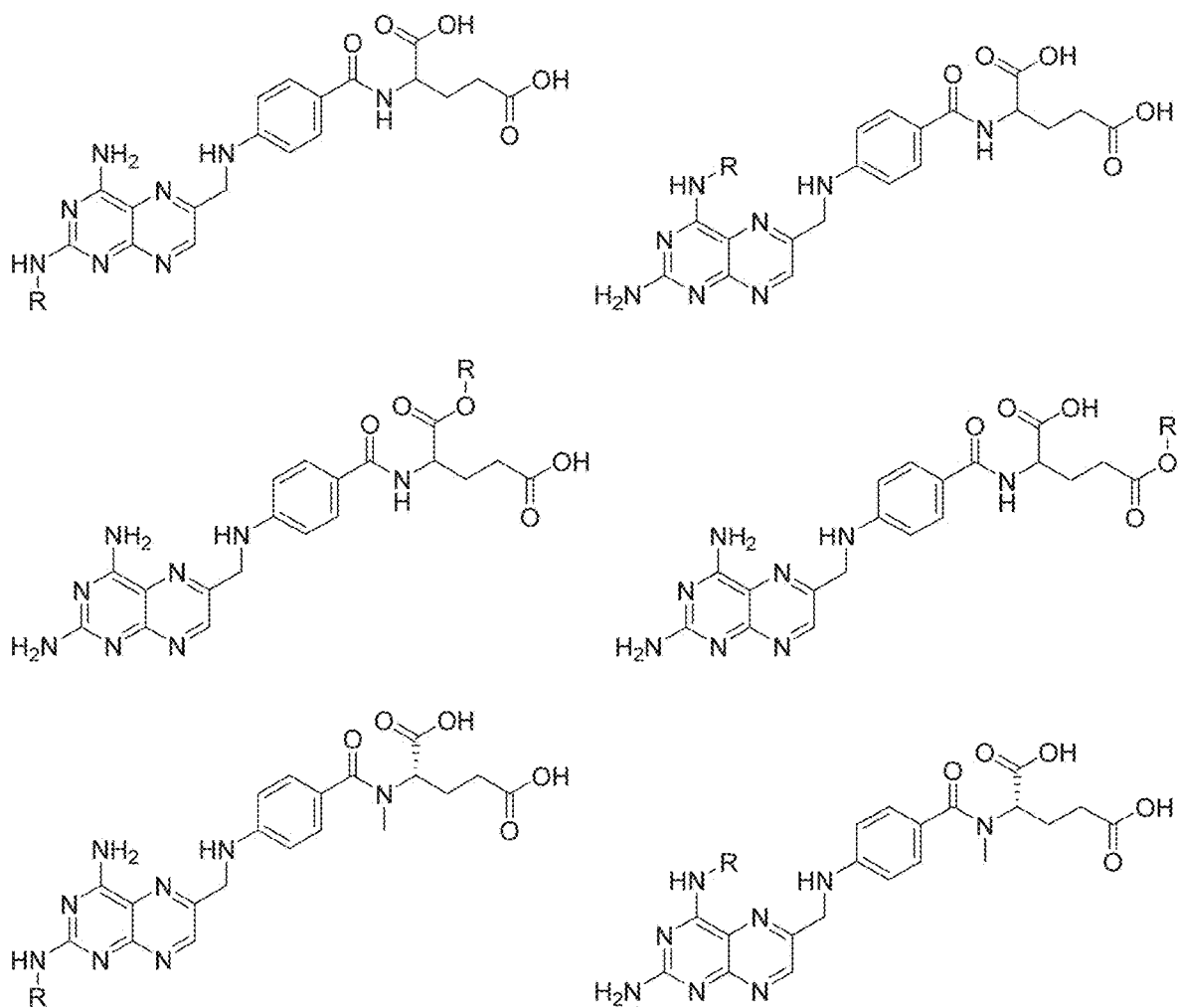
FIG. 1D-1F present examples of general Dihydrofolate reductase (DHFR) Targeting Ligands wherein R is the point at which the Linker is attached.
Figure 1E:
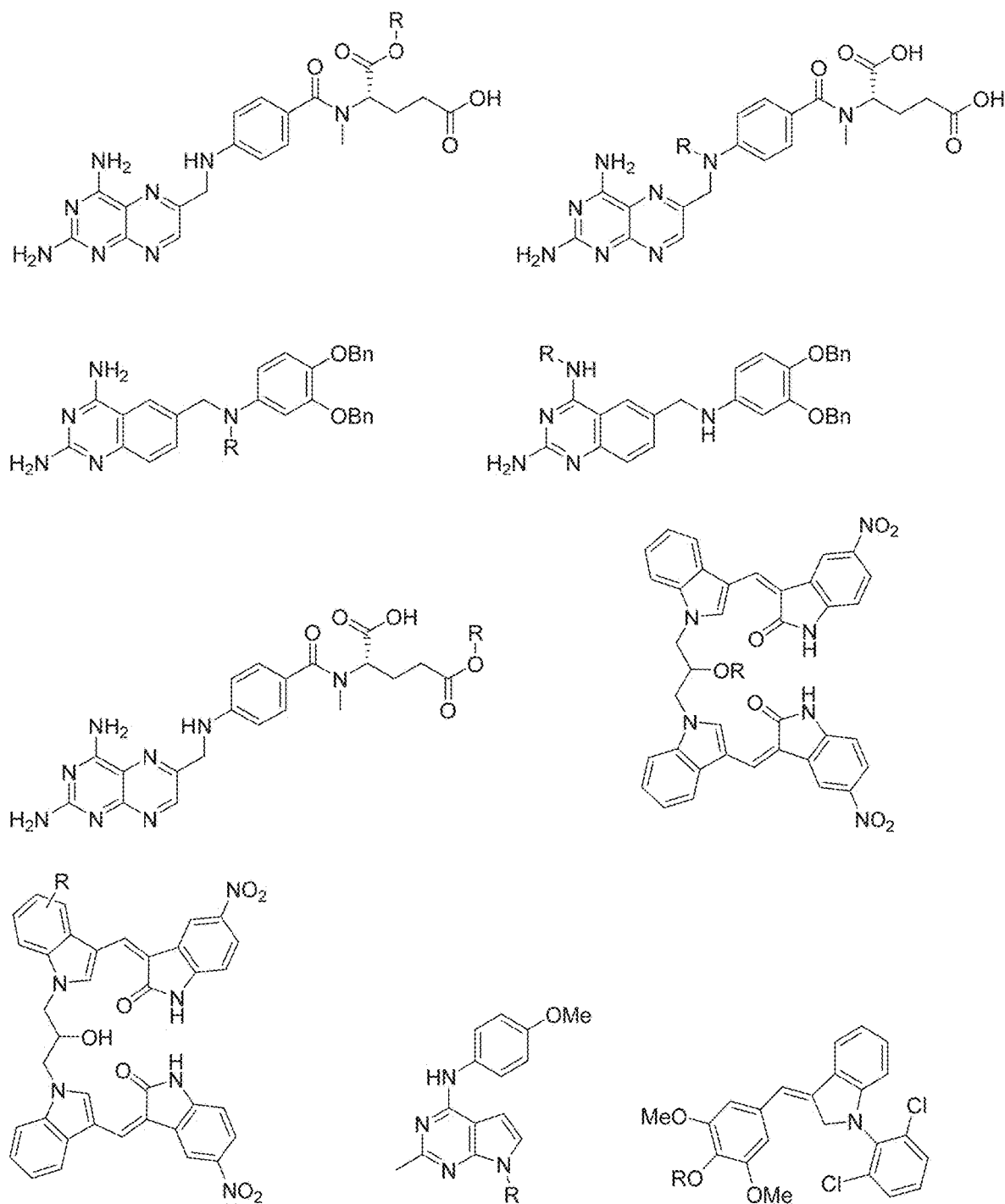
Figure 1F:
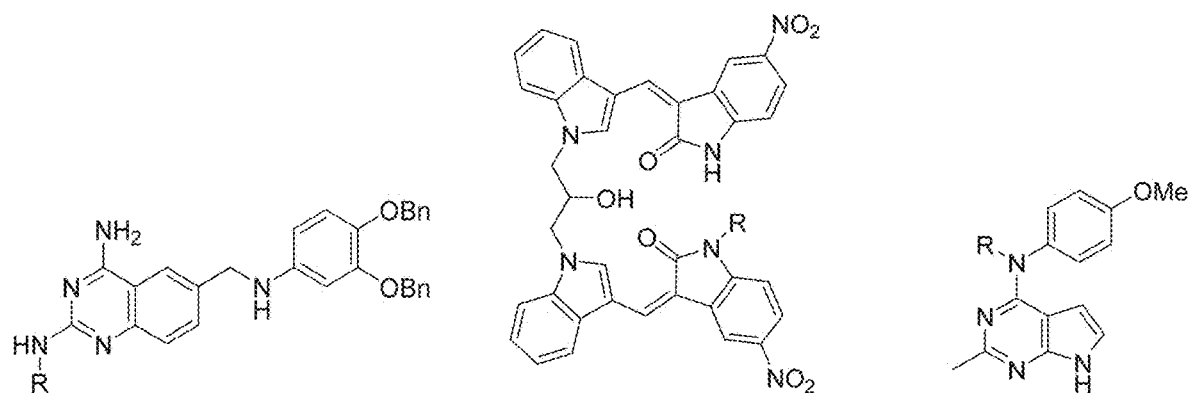
Figure 1G:
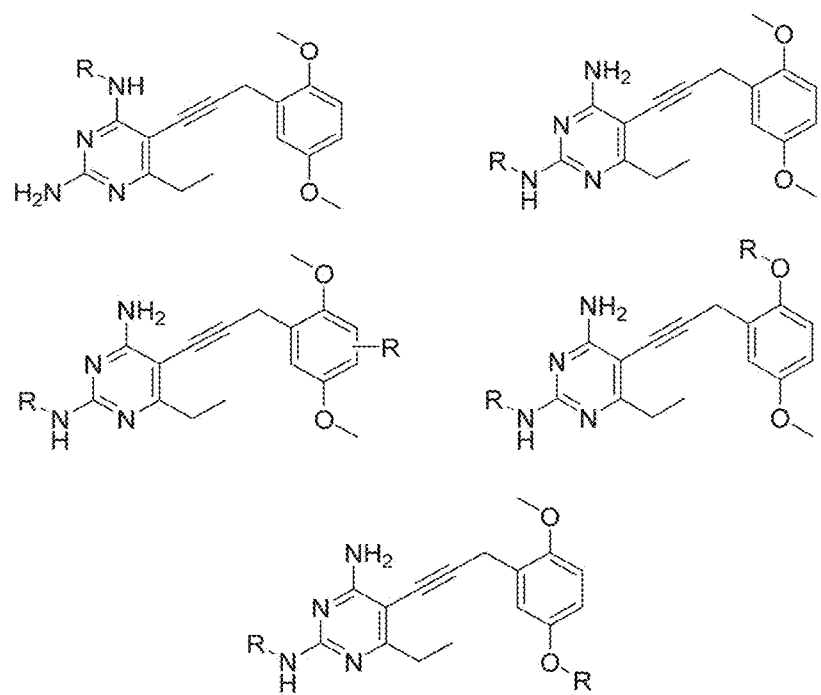
FIG. 1G presents examples of *Bacillus anthracis* Dihydrofolate reductase (BaDHFR) Targeting Ligands w FIG. 1HHH-1III present examples of EGFR Targeting Ligands wherein R is the point at which the Linker is attached.
Figure 1H:
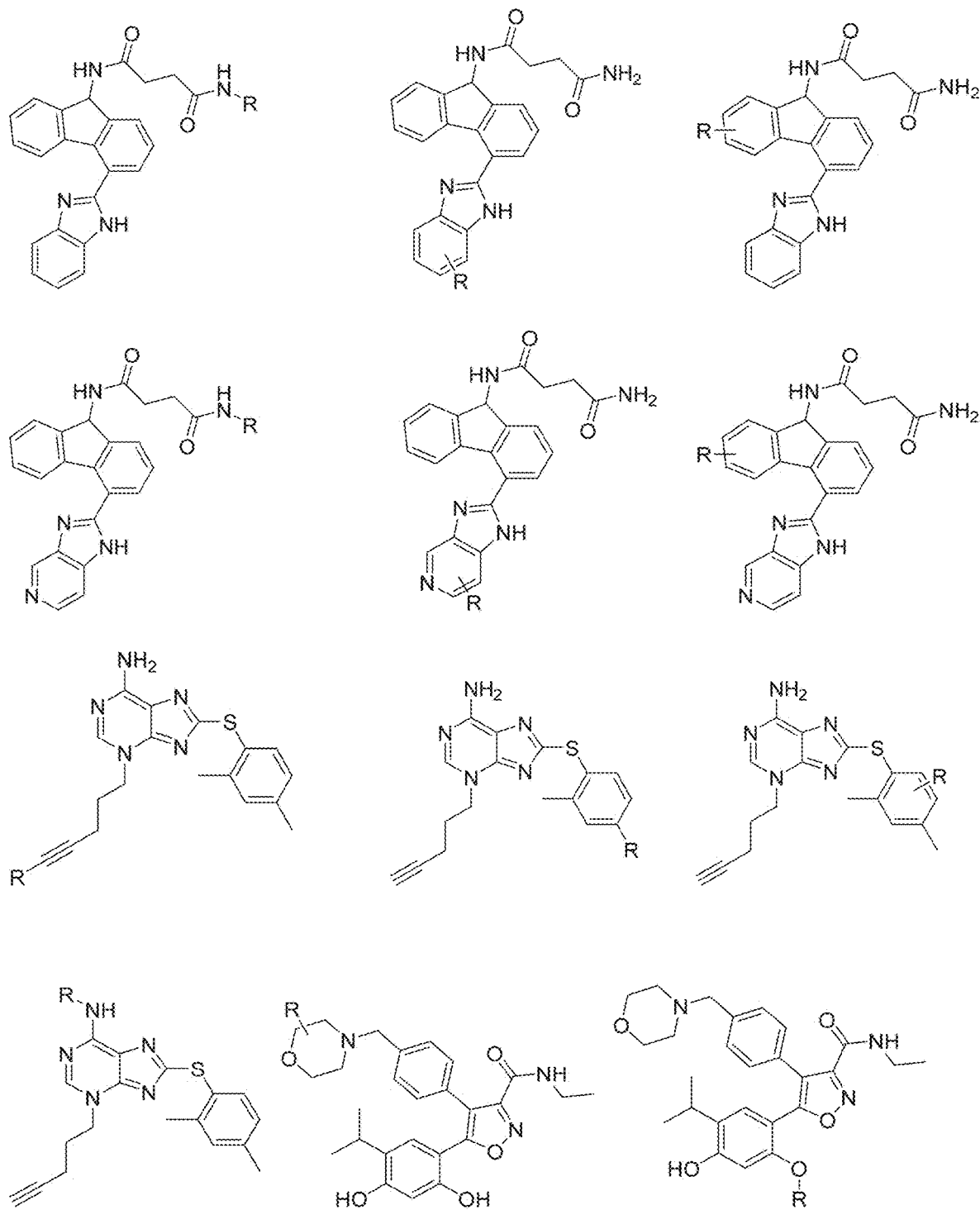
FIG. 1JJJ-1KKK present examples of FLT3 Targeting Ligands wherein R is the point at which the Linker is attached.
FIG. 1LLL presents examples of SMRCA2 Targeting Ligands wherein R is the point at which the Linker is attached.
Figure 1I:
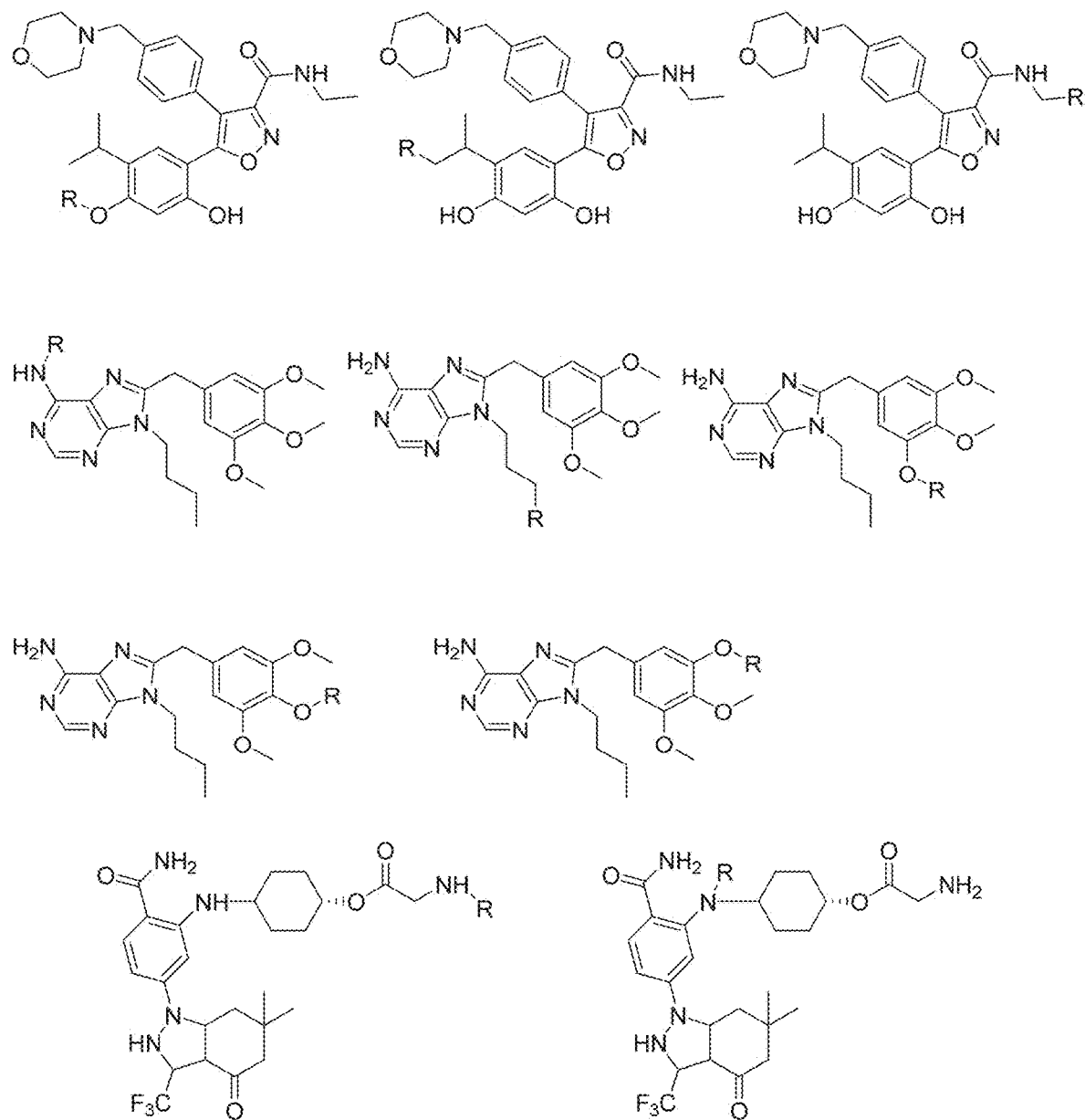
Figure 1J:
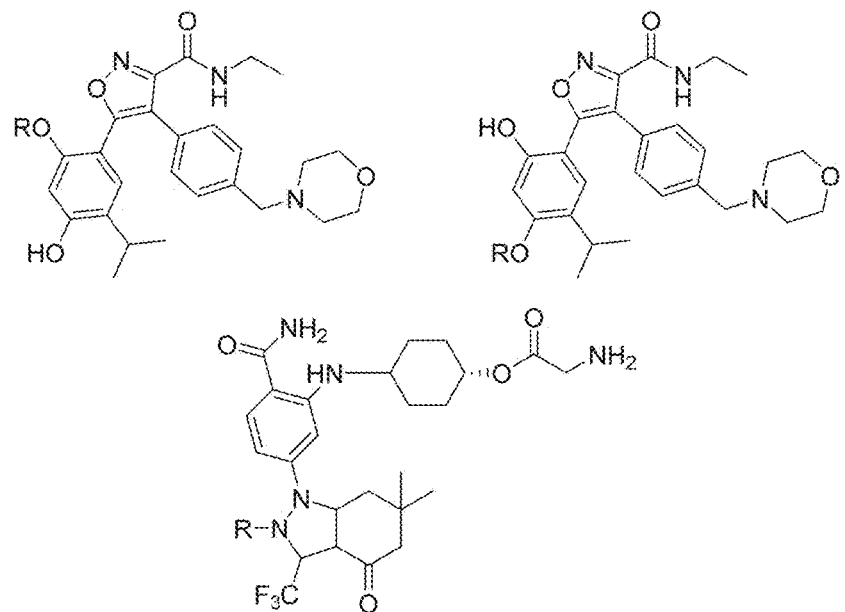
Figure 1K:
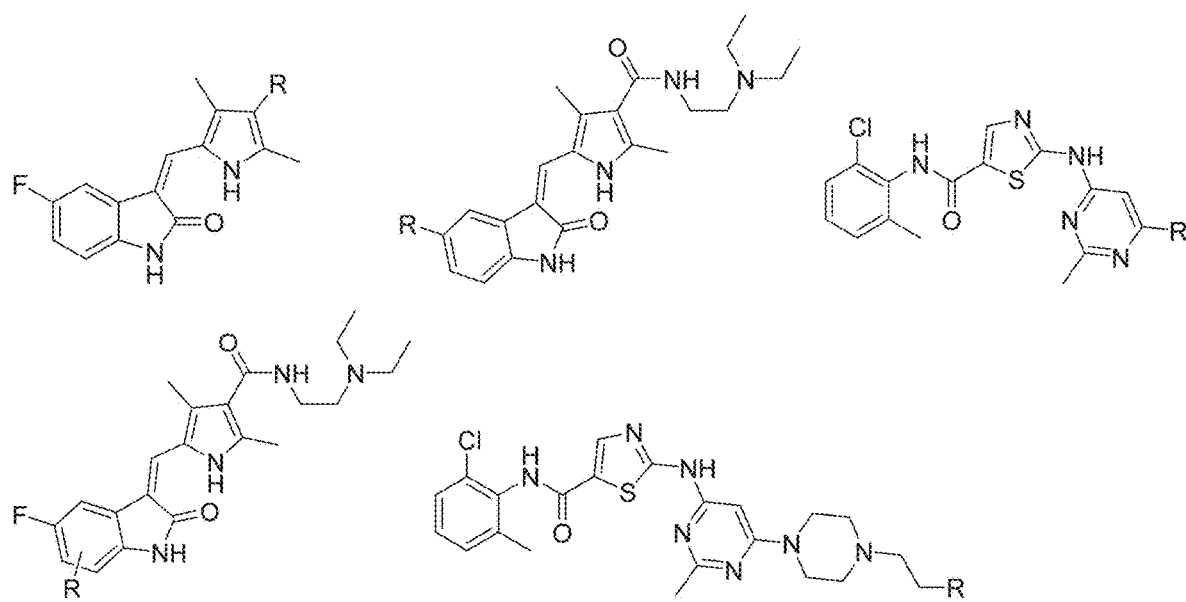
Figure 1L:
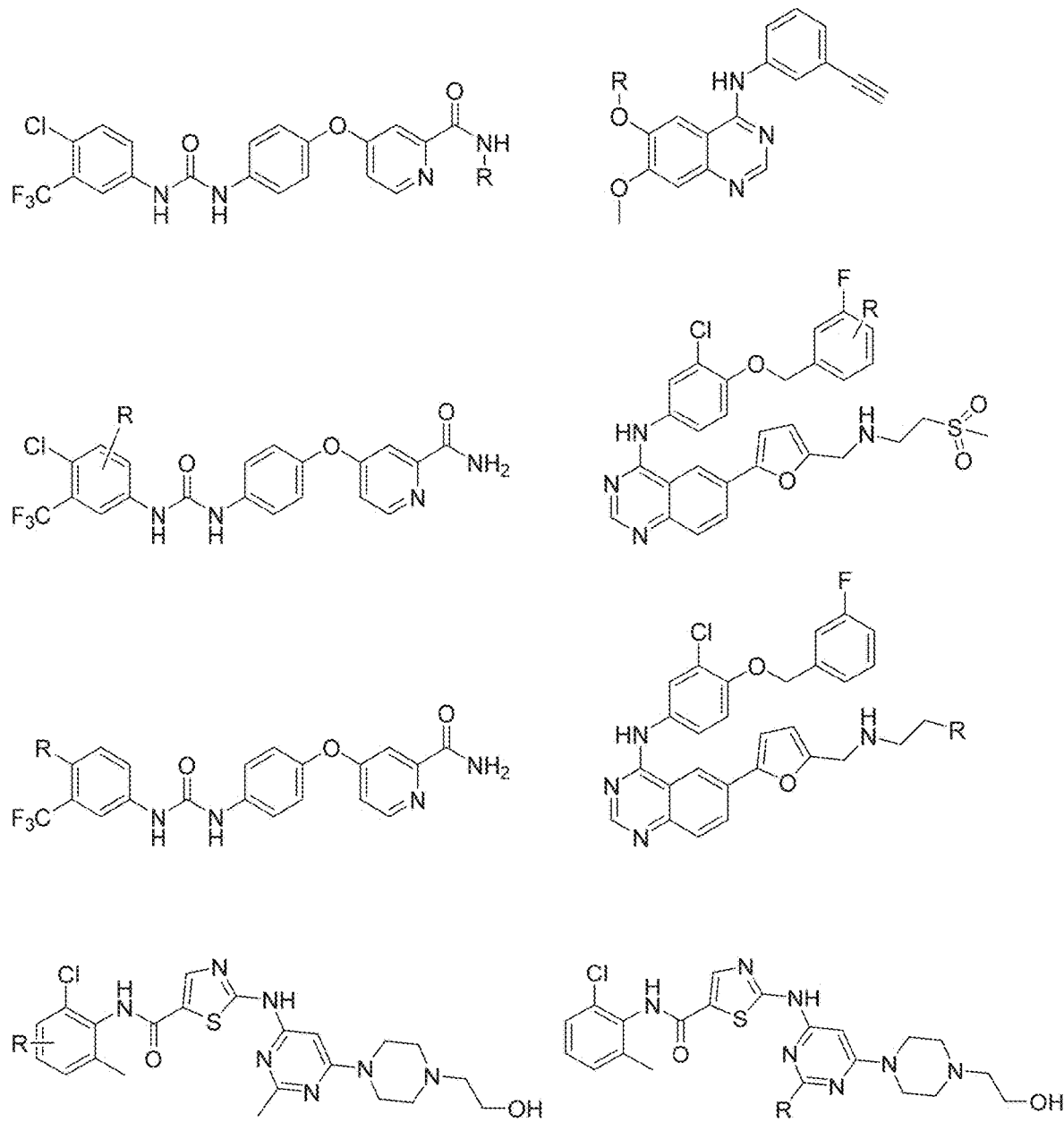
Figure 1M:
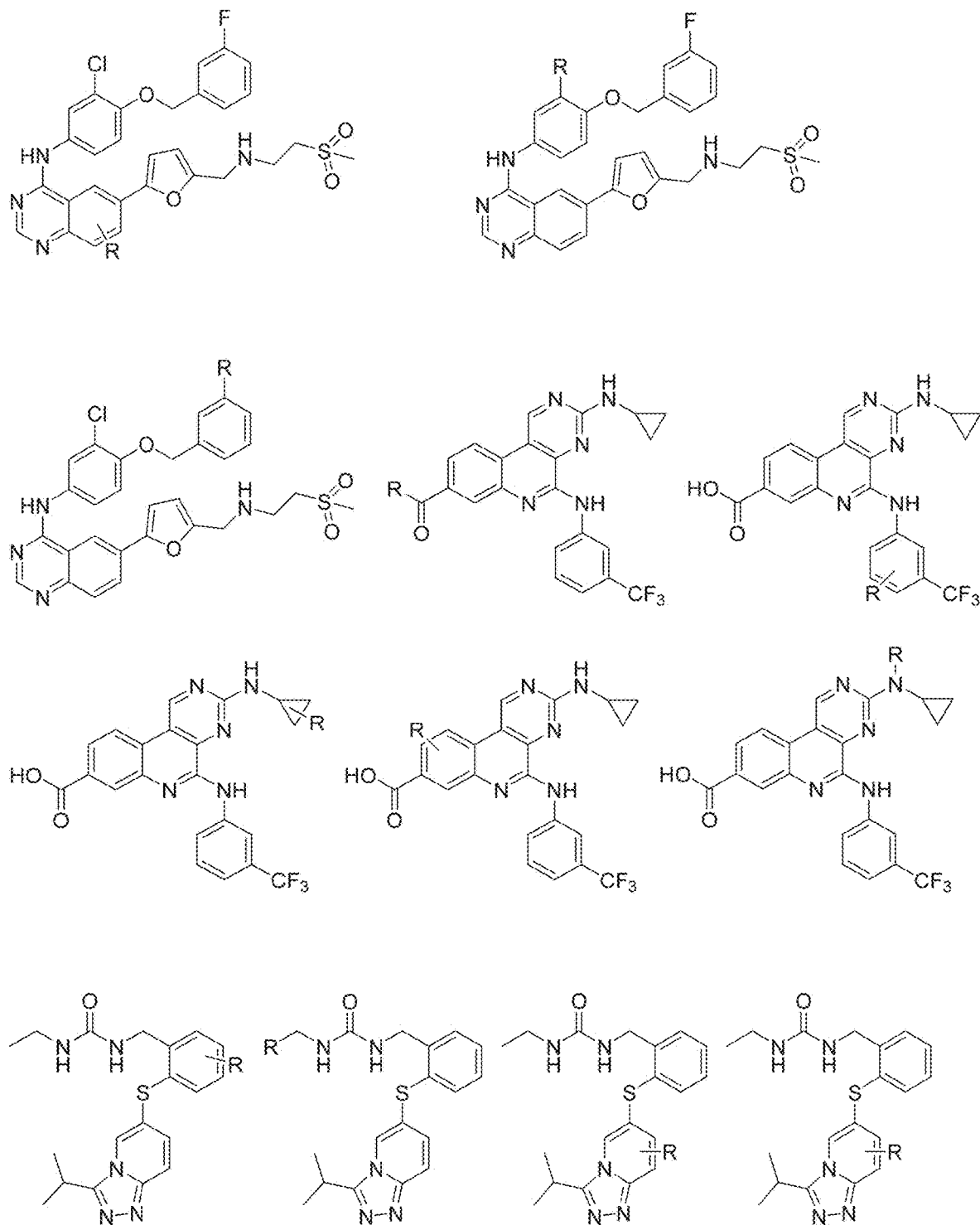
Figure 1N:
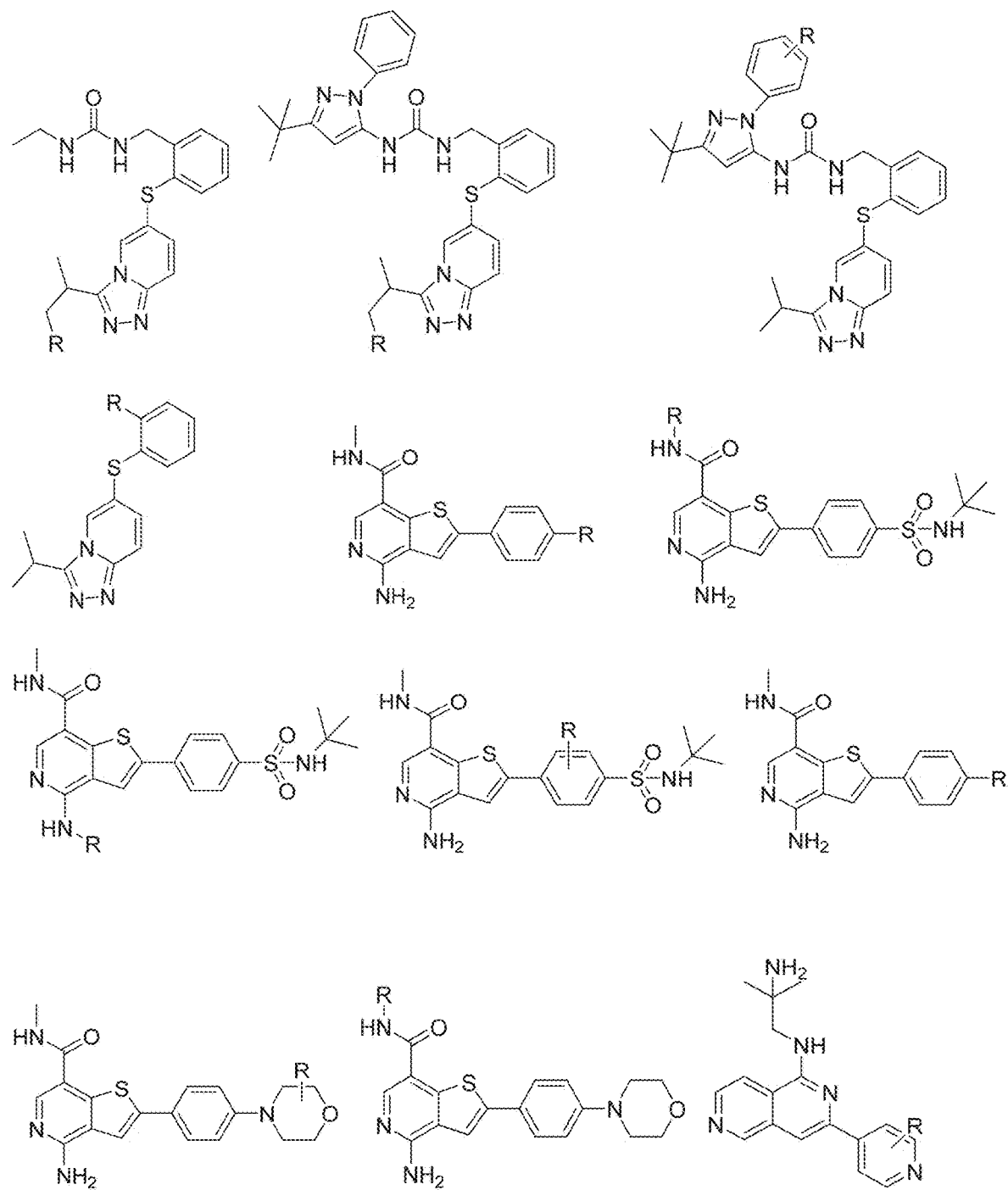
Figure 10:
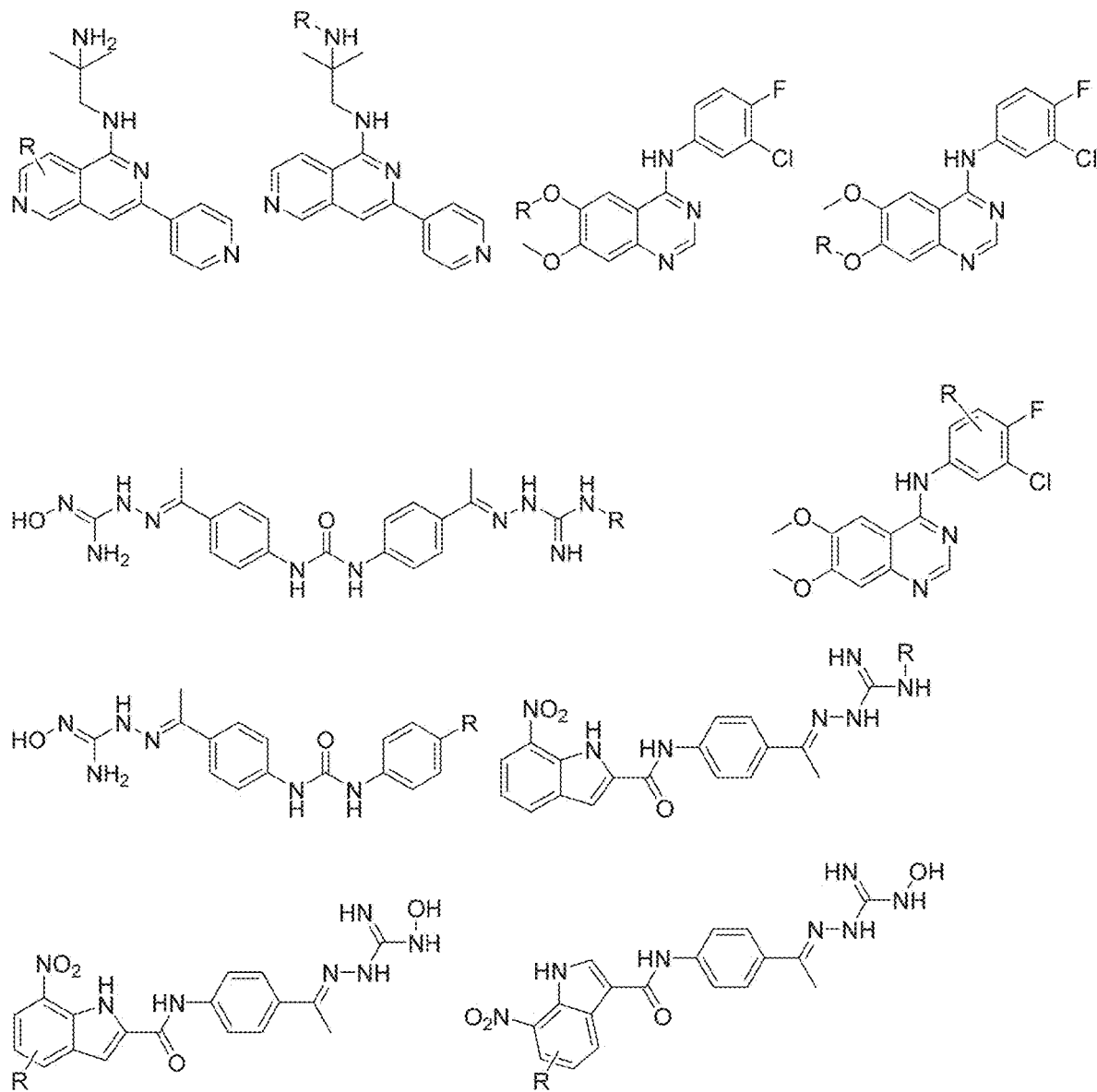
Figure 1P:
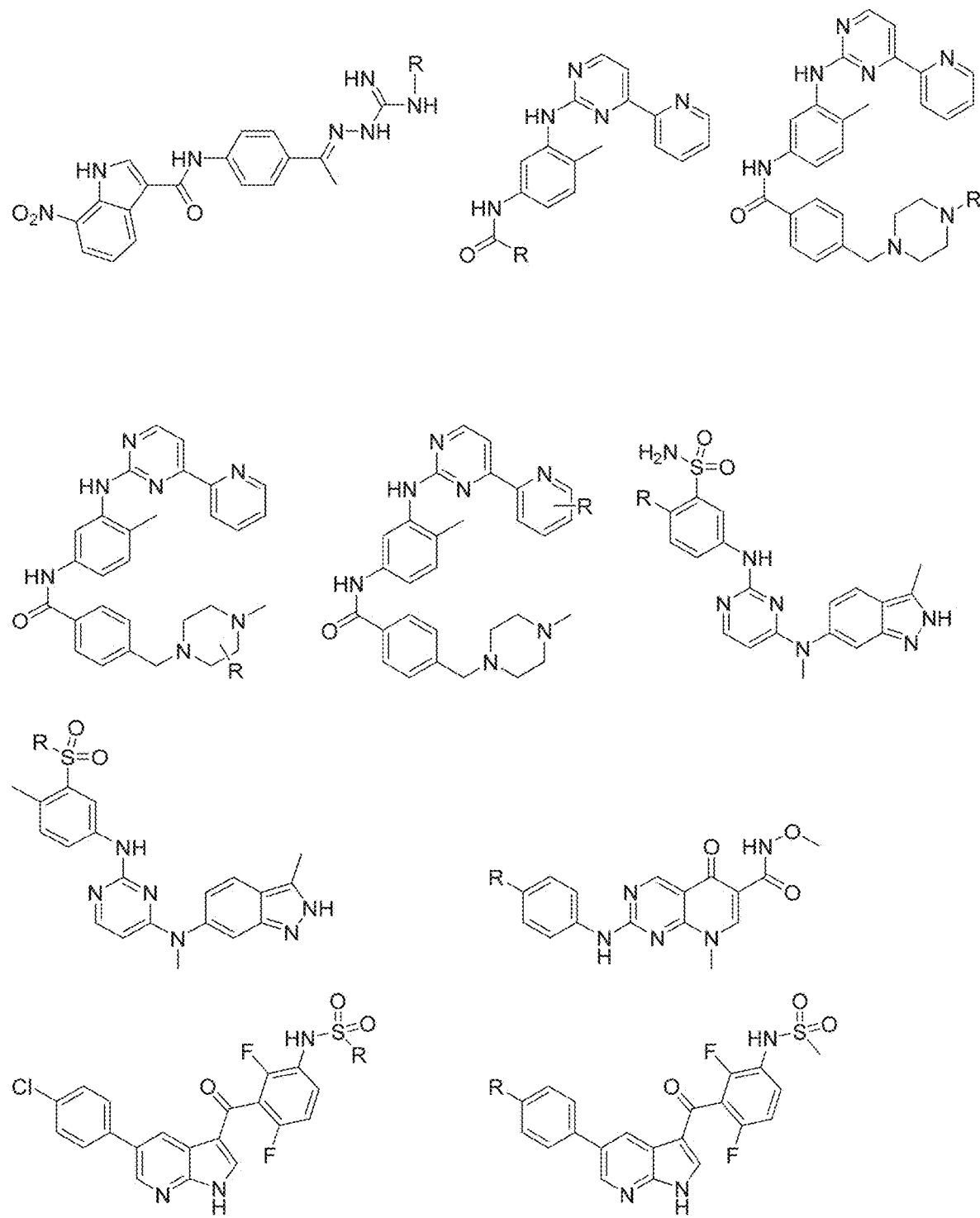
Figure 1Q:
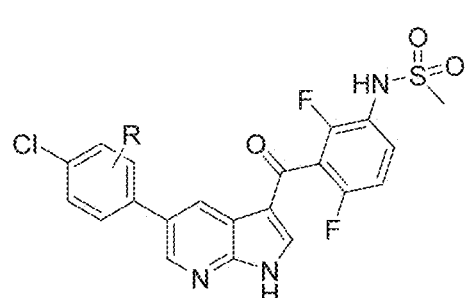
Figure 1Q:
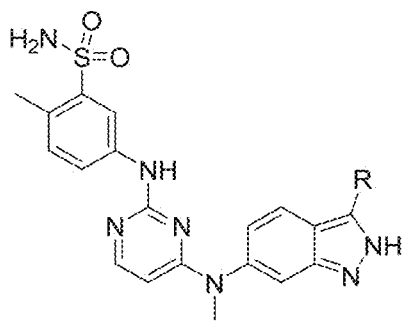
Figure 1R:
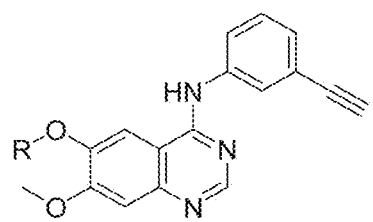
Figure 1R:
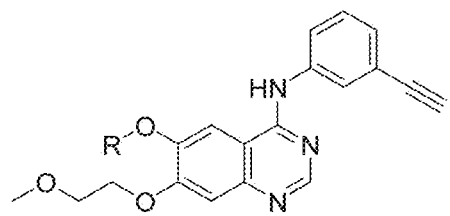
Figure 1R:
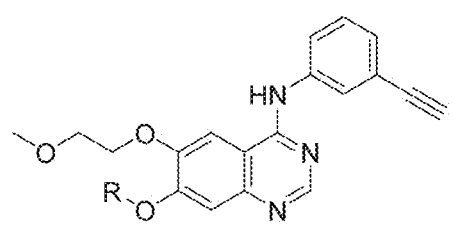
Figure 1R:
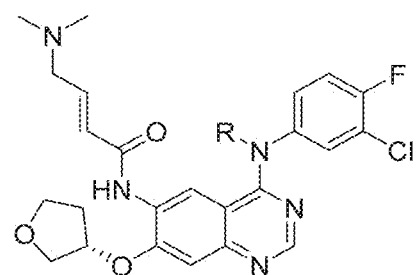
Figure 1R:
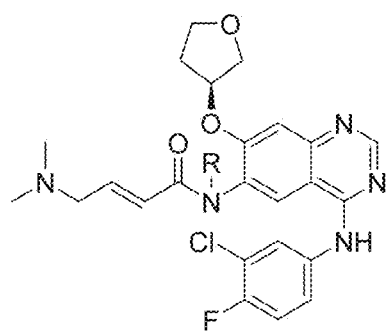
Figure 1R:
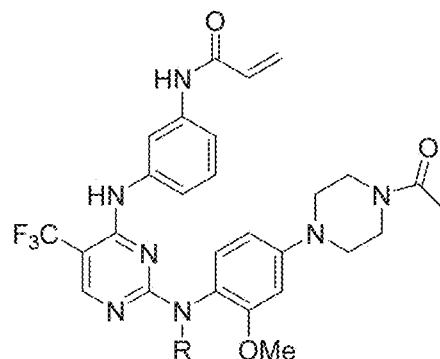
Figure 1S:
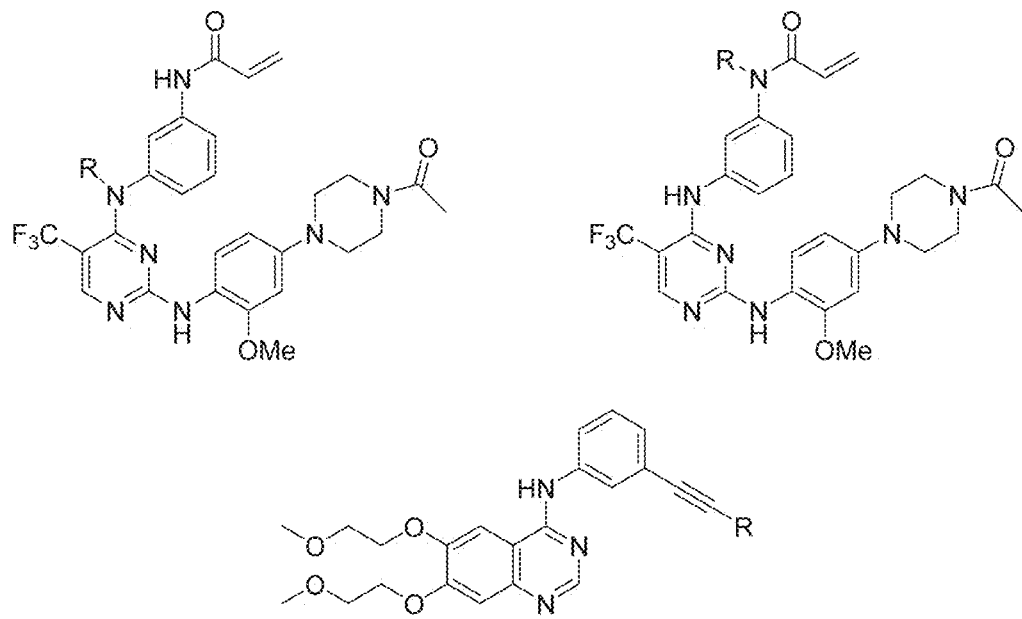
Figure 1T:
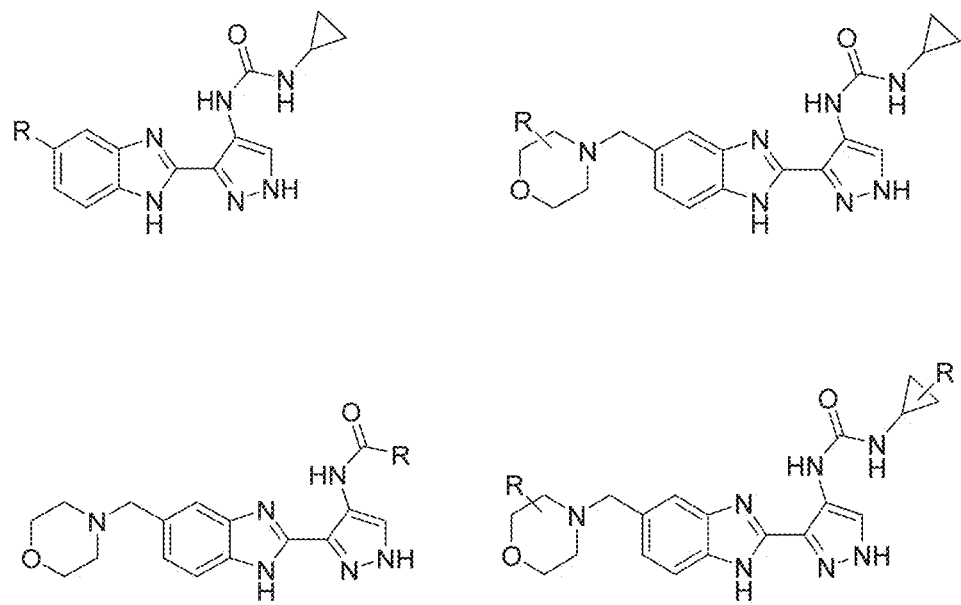
Figure 1U:
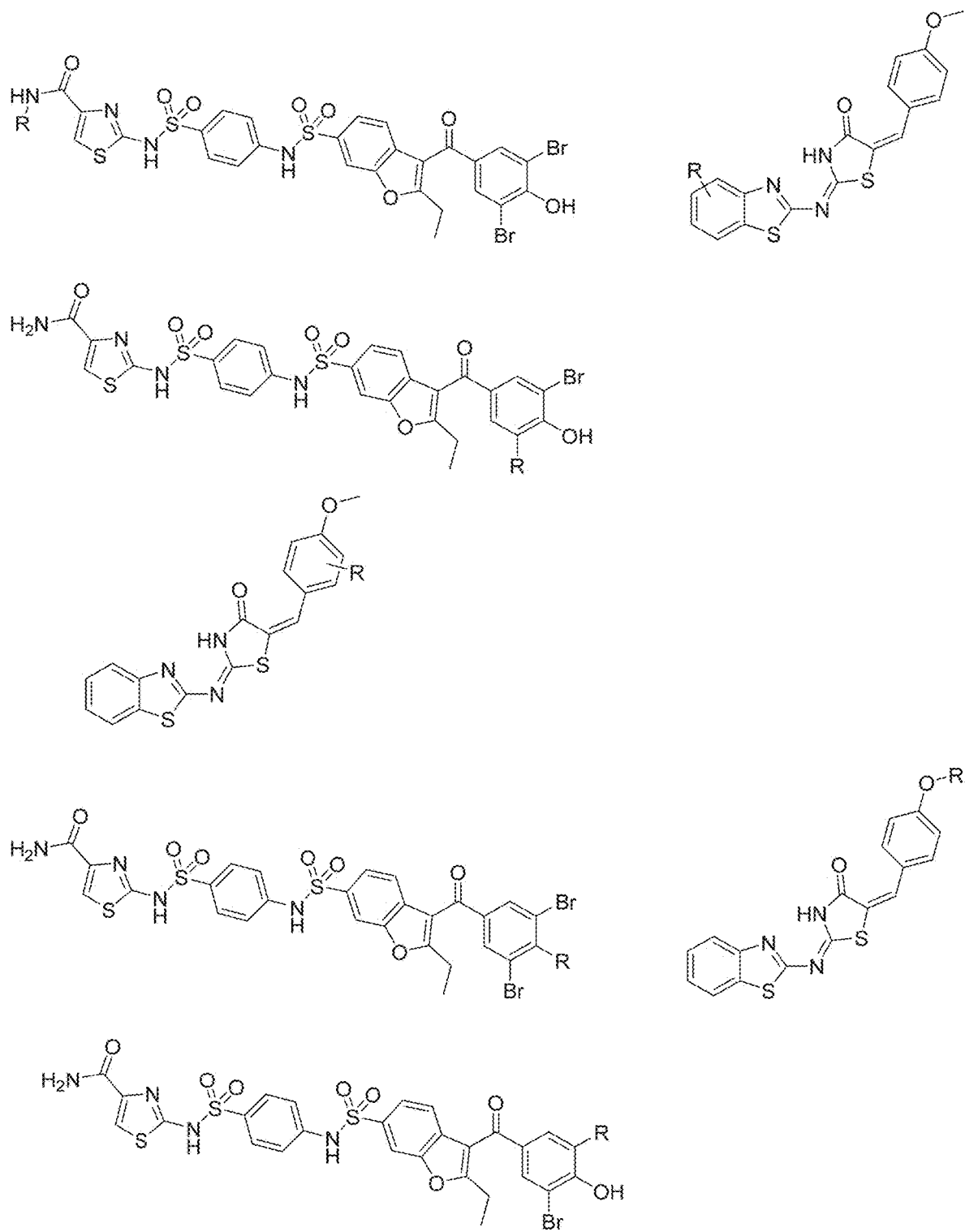
Figure 1V:
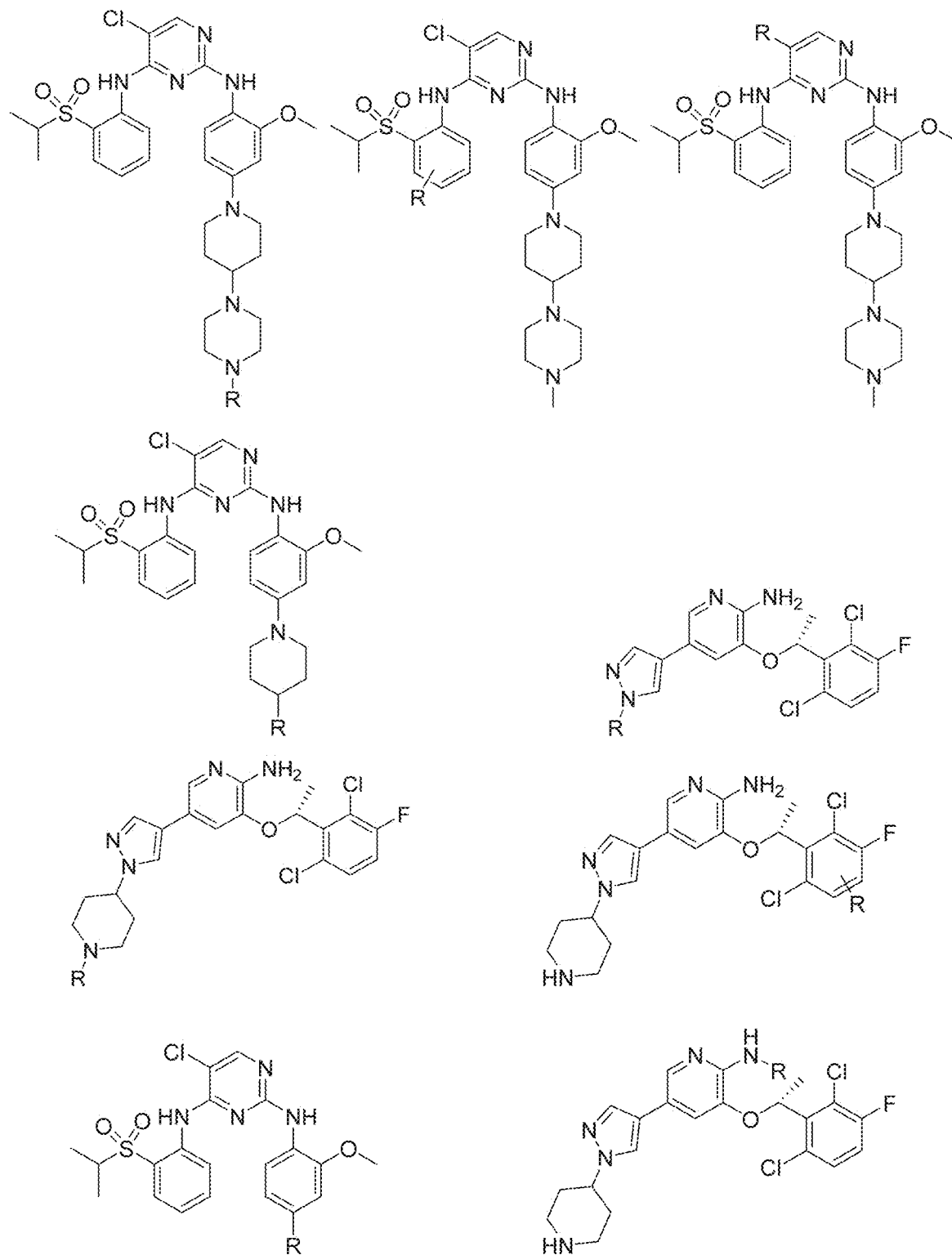
Figure 1W:
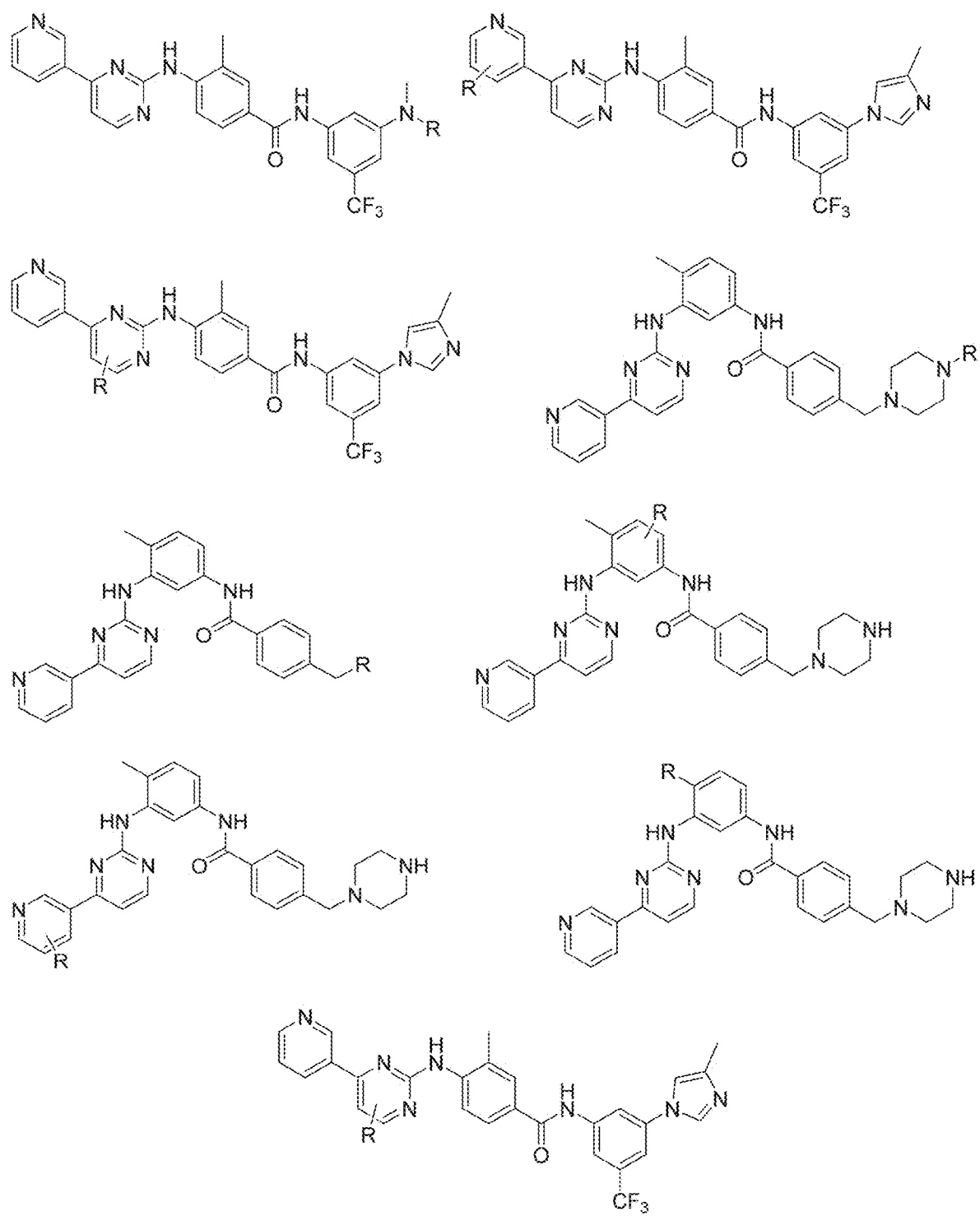
Figure 1X:
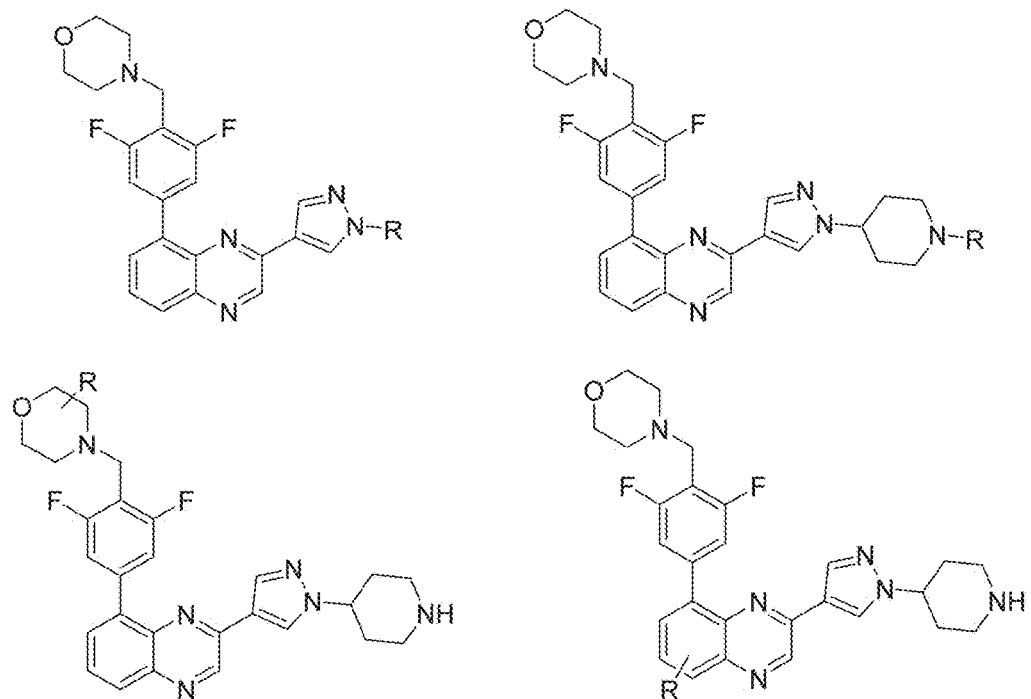
Figure 1Y:
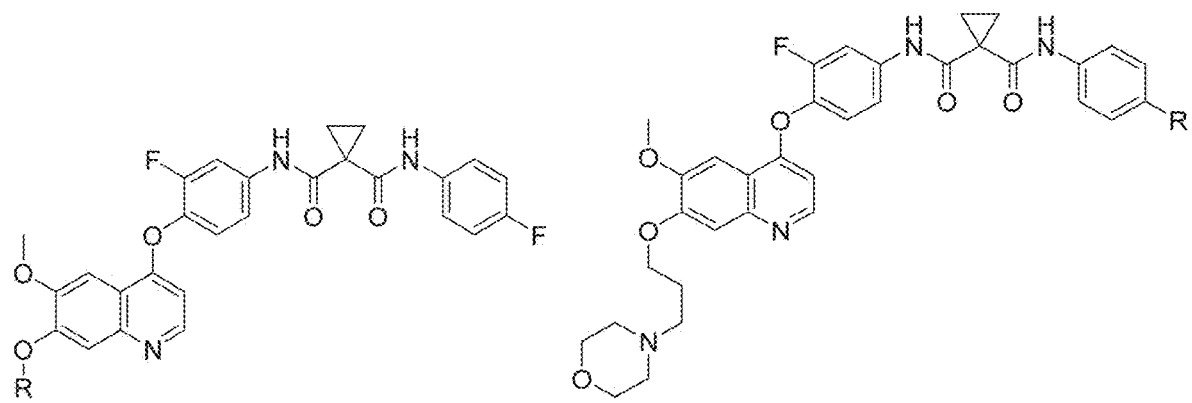
Figure 1Z:
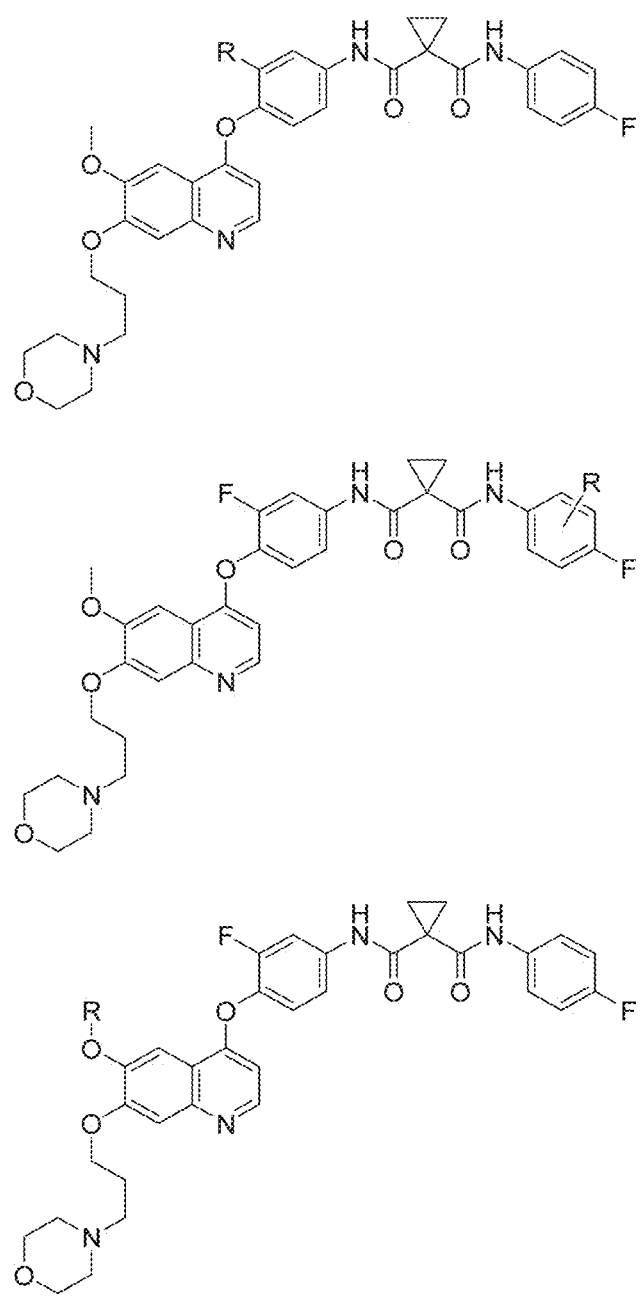
Figure 1A:
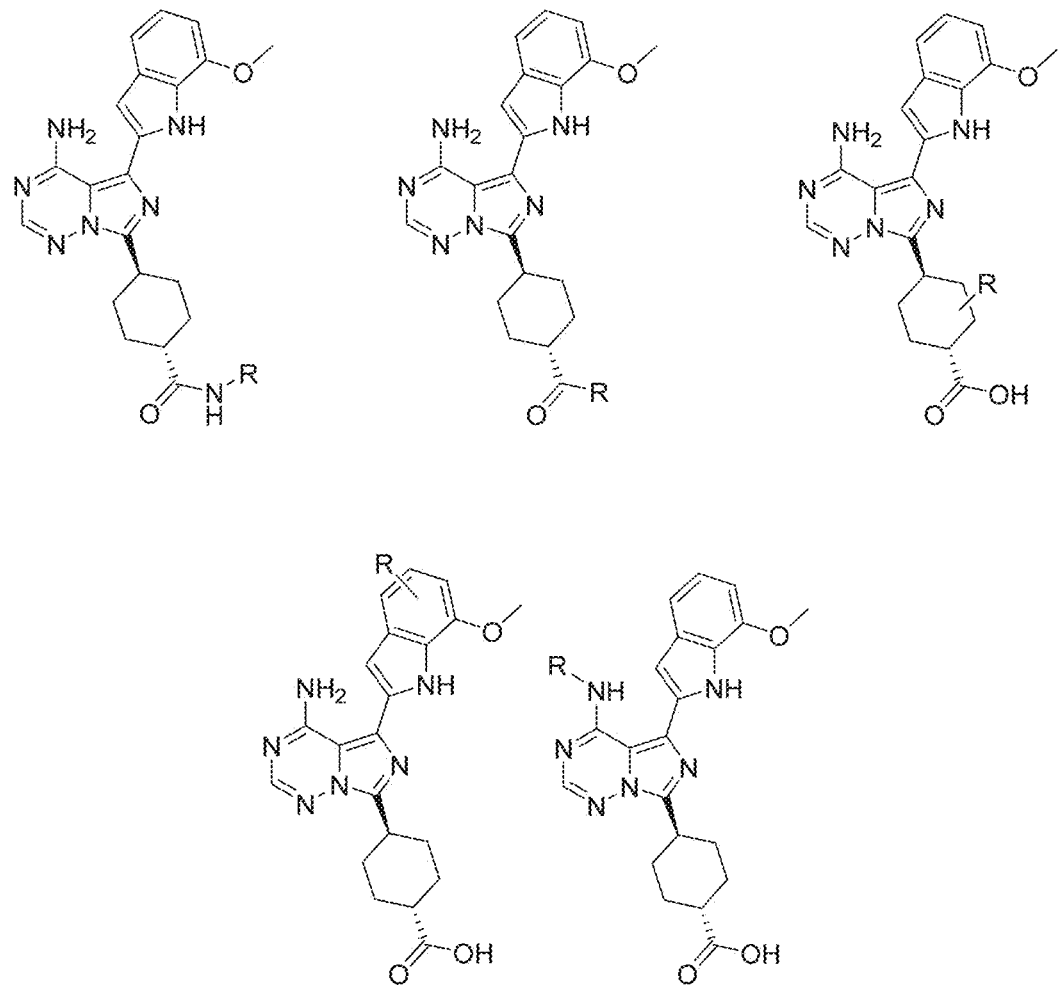
Figure 1B:
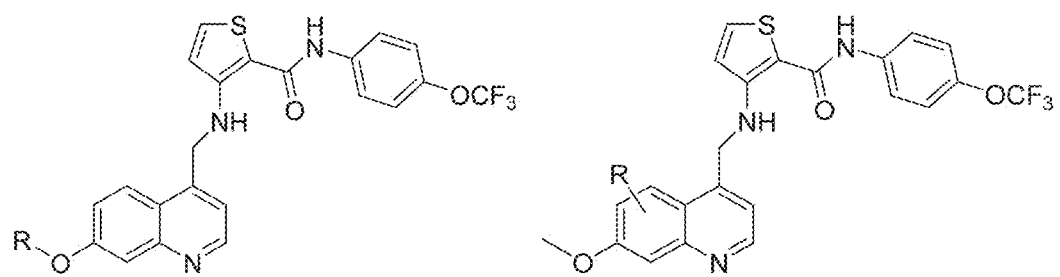
Figure 1C:
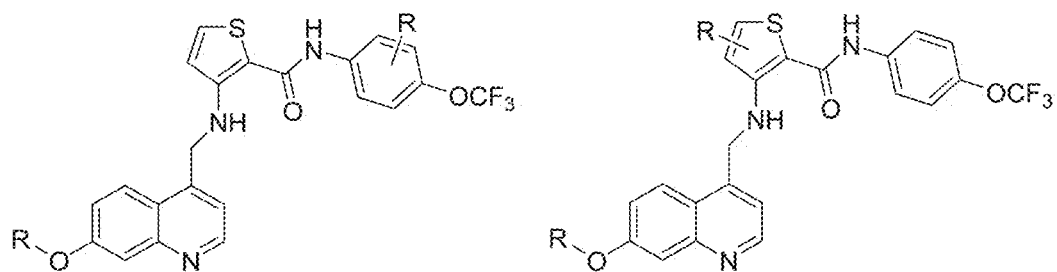
Figure 1D:
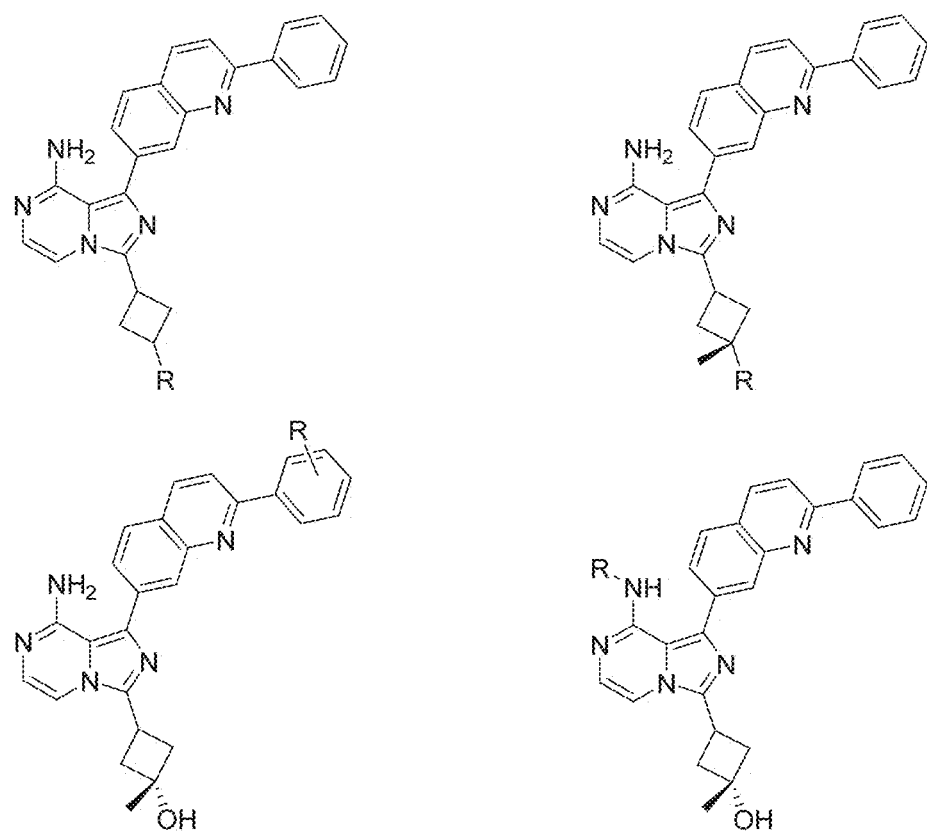
Figure 1E:
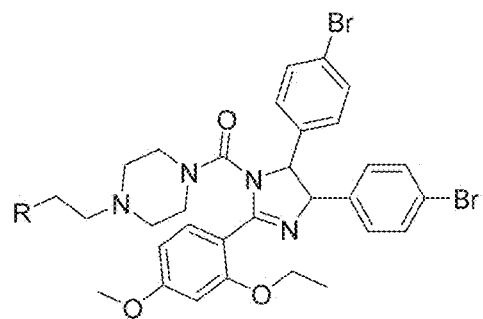
Figure 1E:
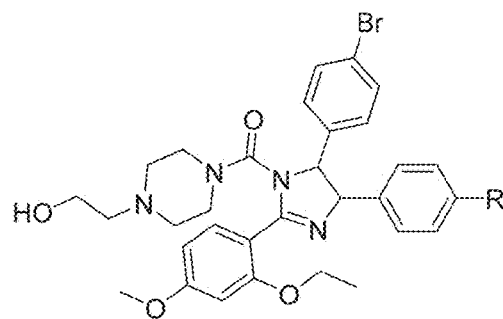
Figure 1E:
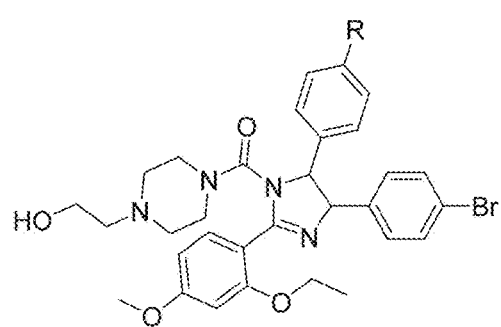
Figure 1E:
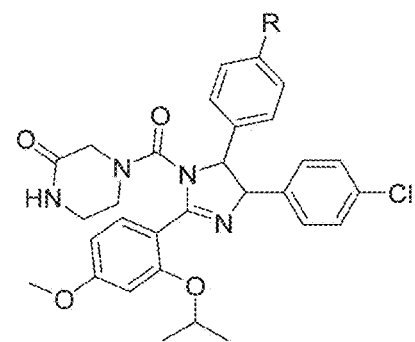
Figure 1E:
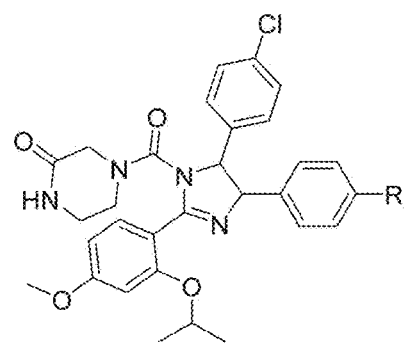
Figure 1E:
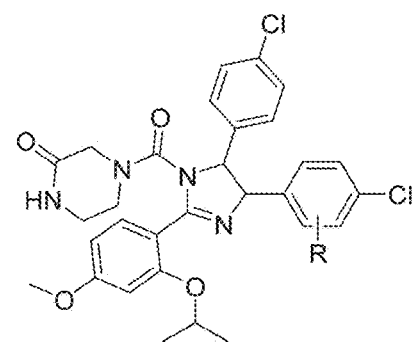
Figure 1E:
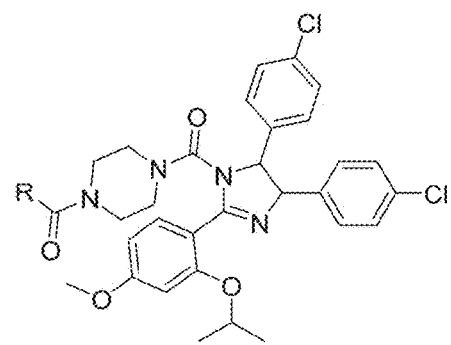
Figure 1E:
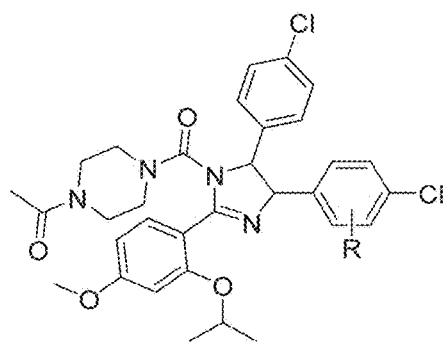
Figure 1F:
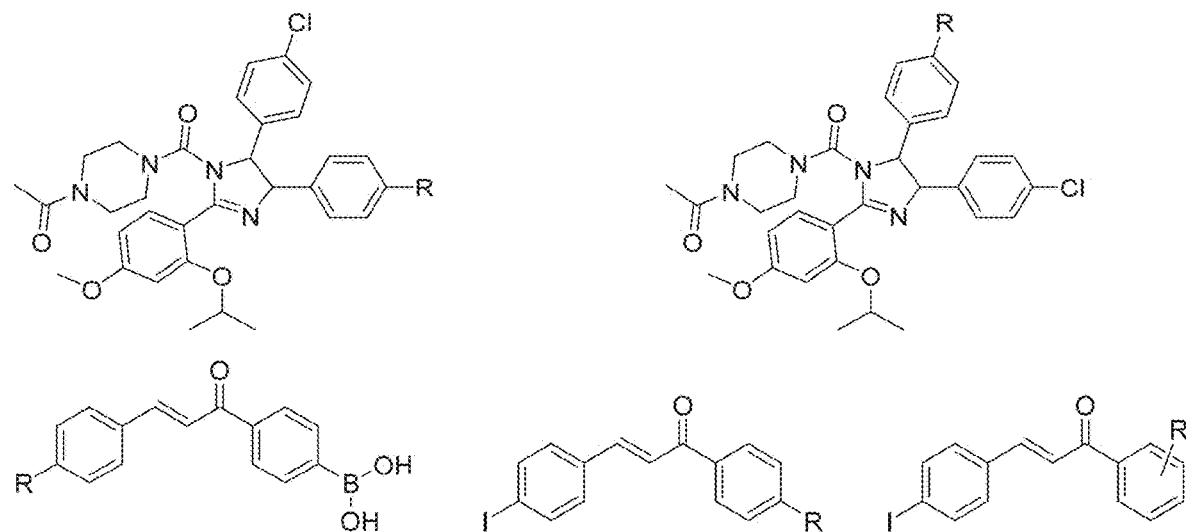
Figure 1G:
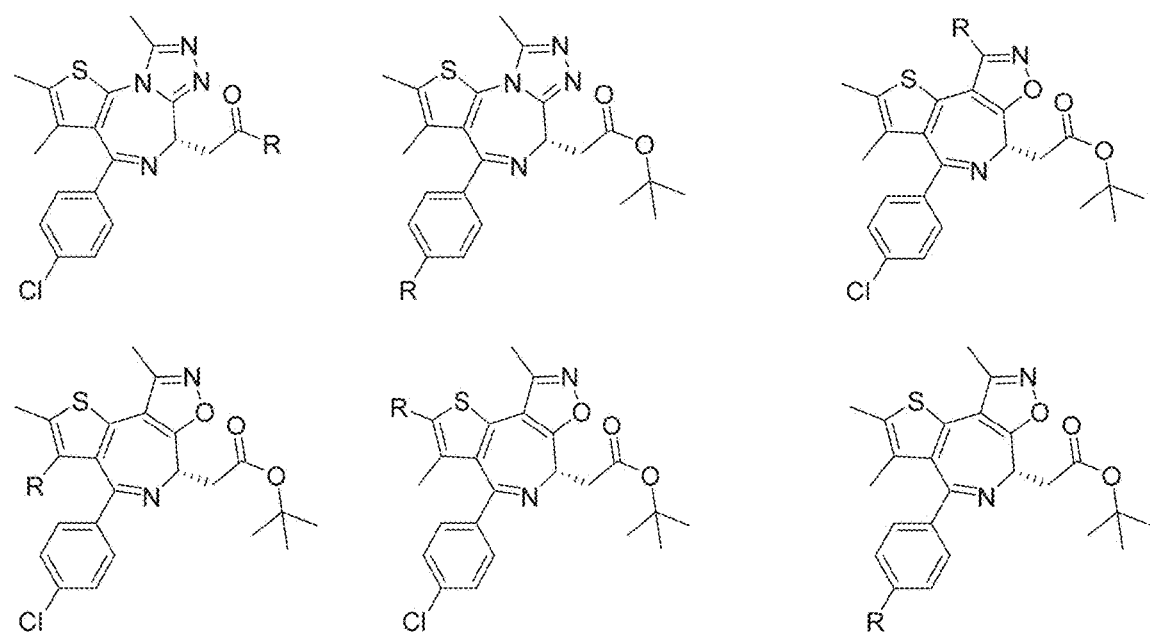
Figure 1H:
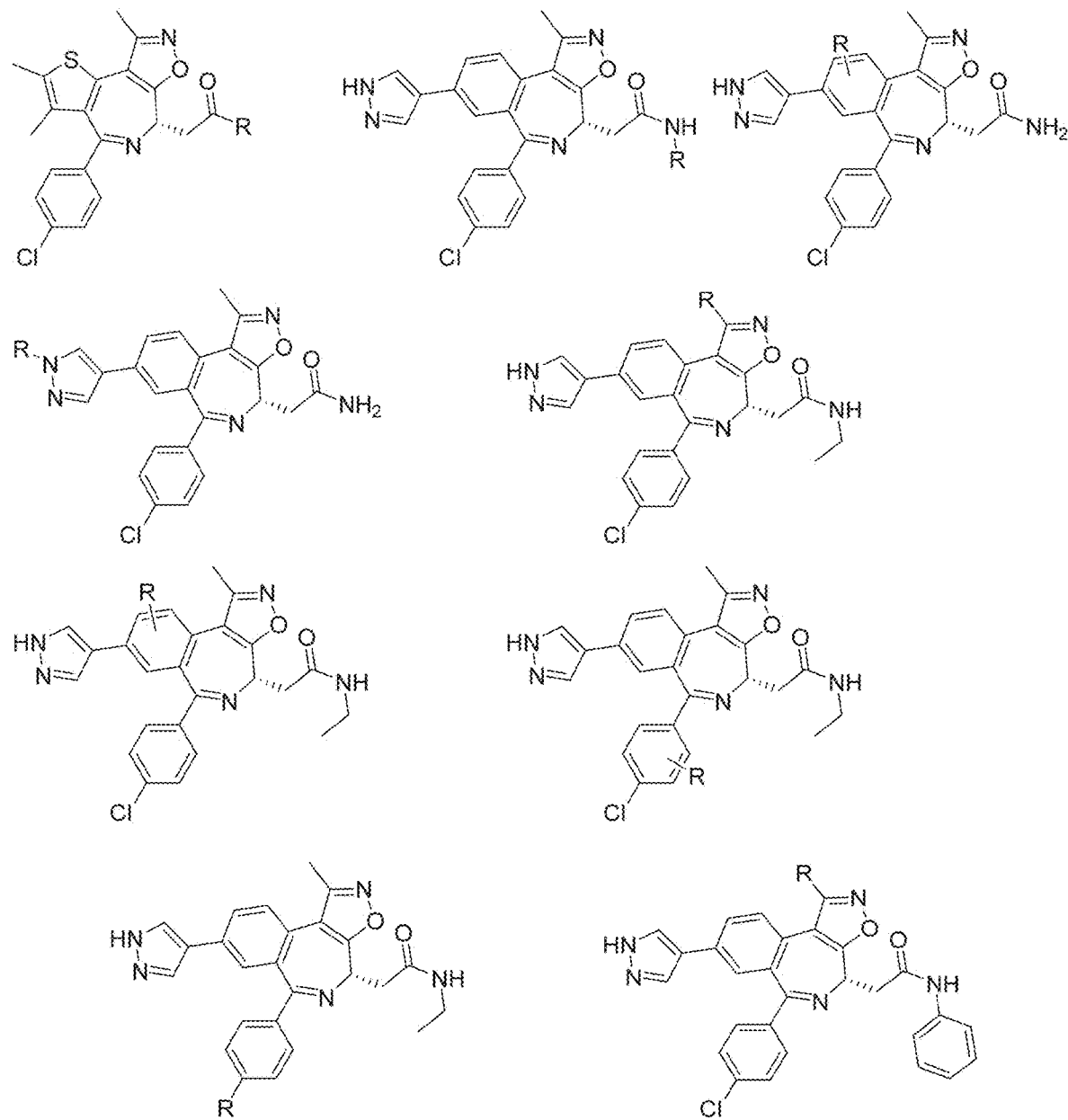
Figure 1I:
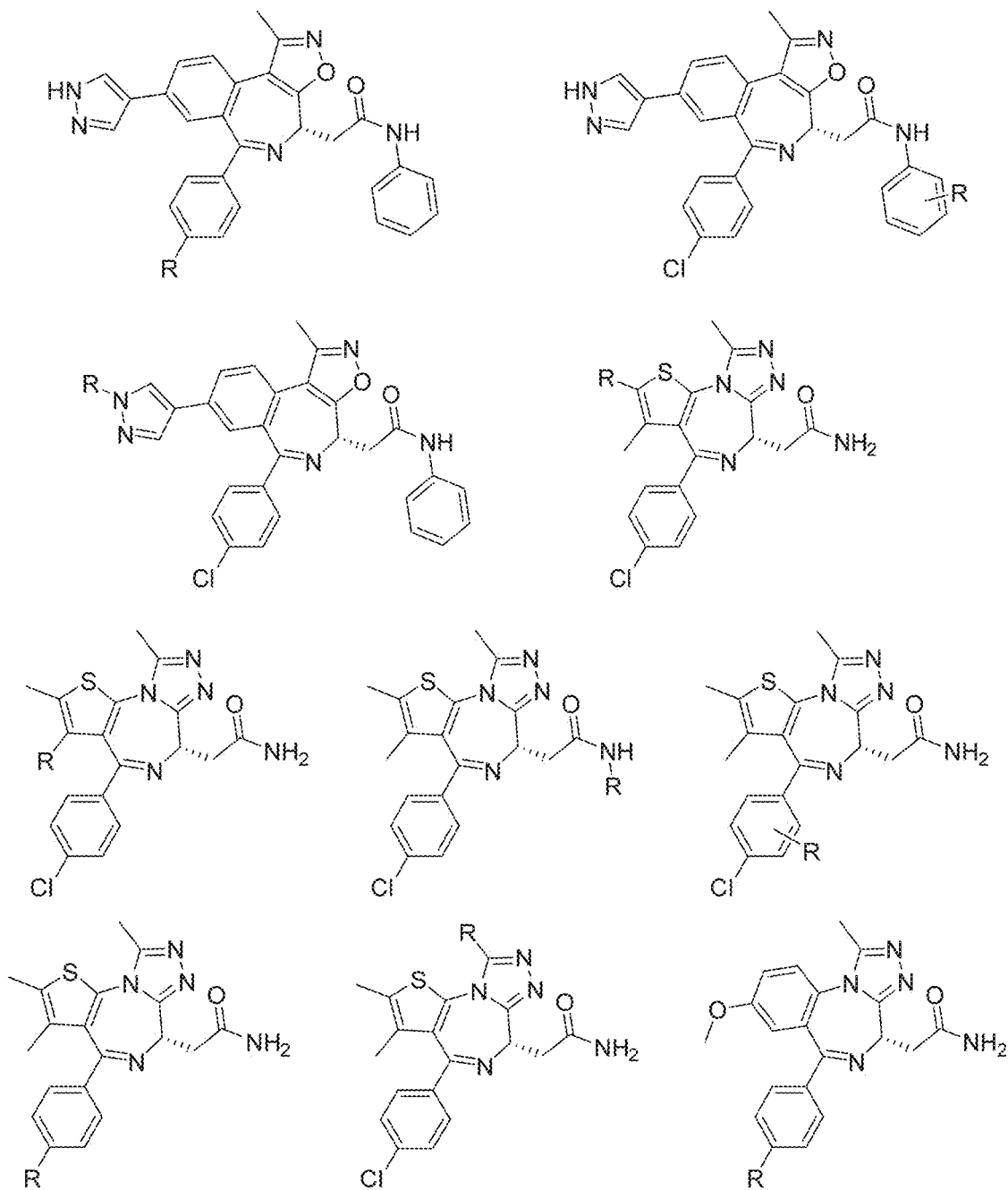
Figure 1J:
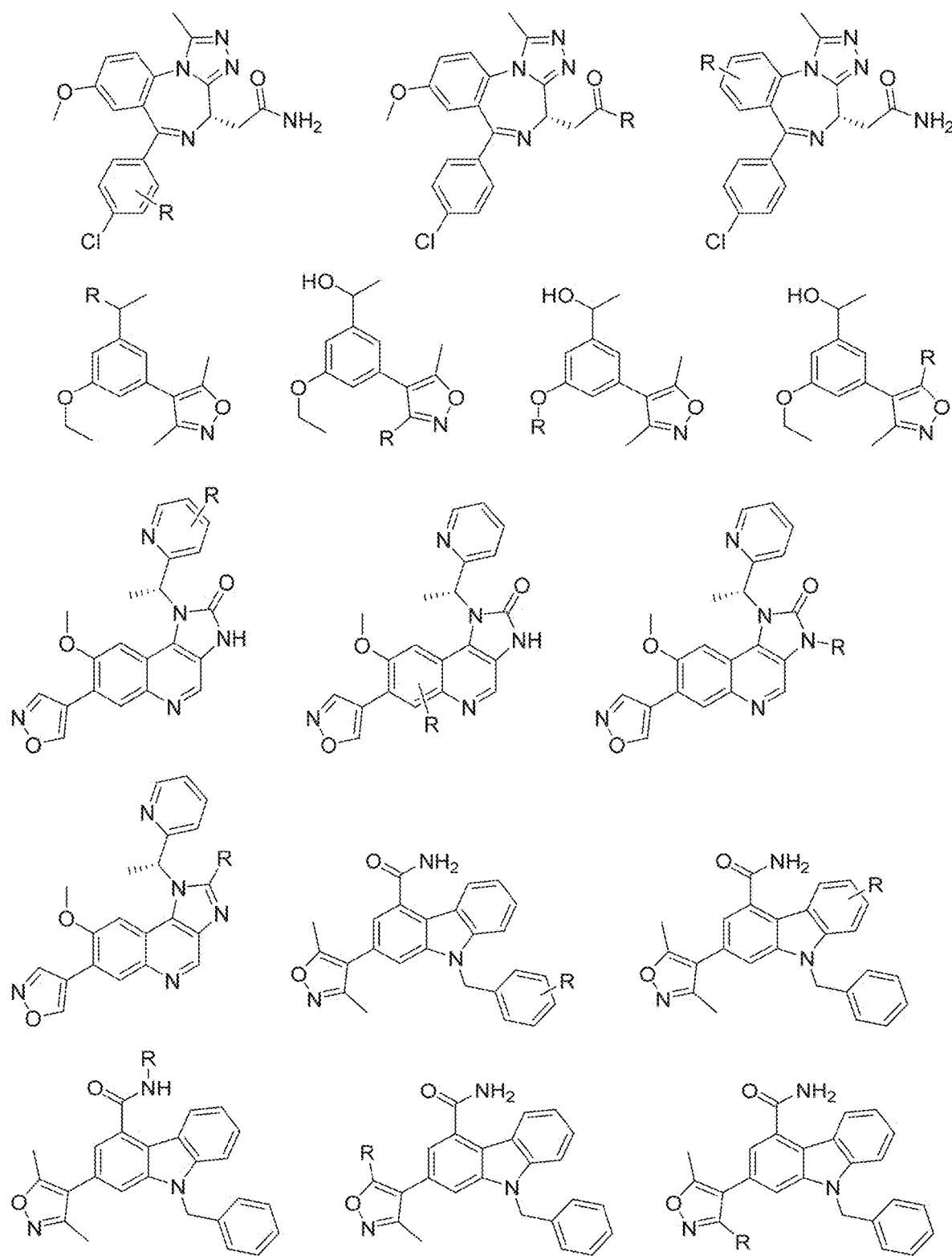
Figure 1K:
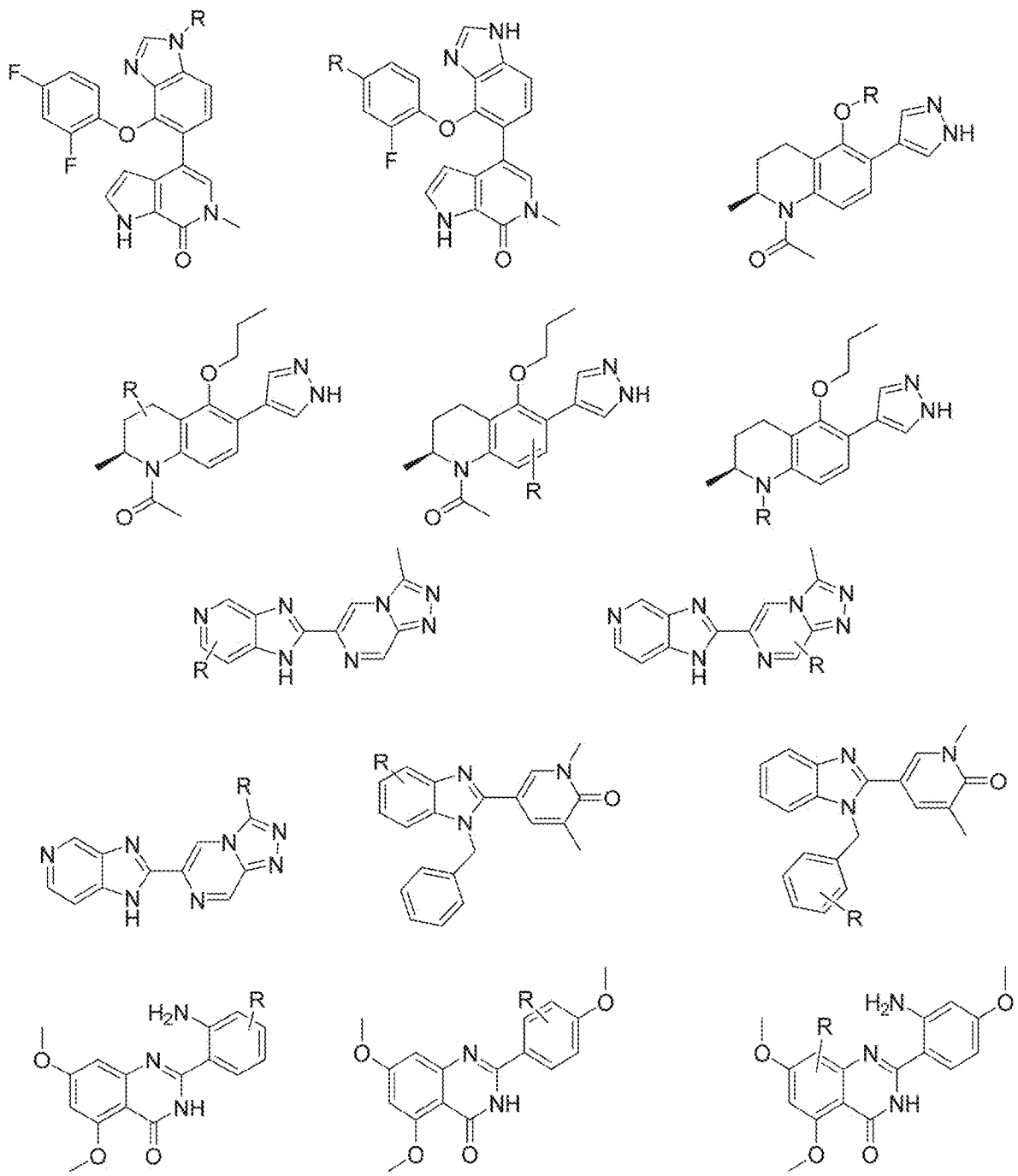
Figure 1L:
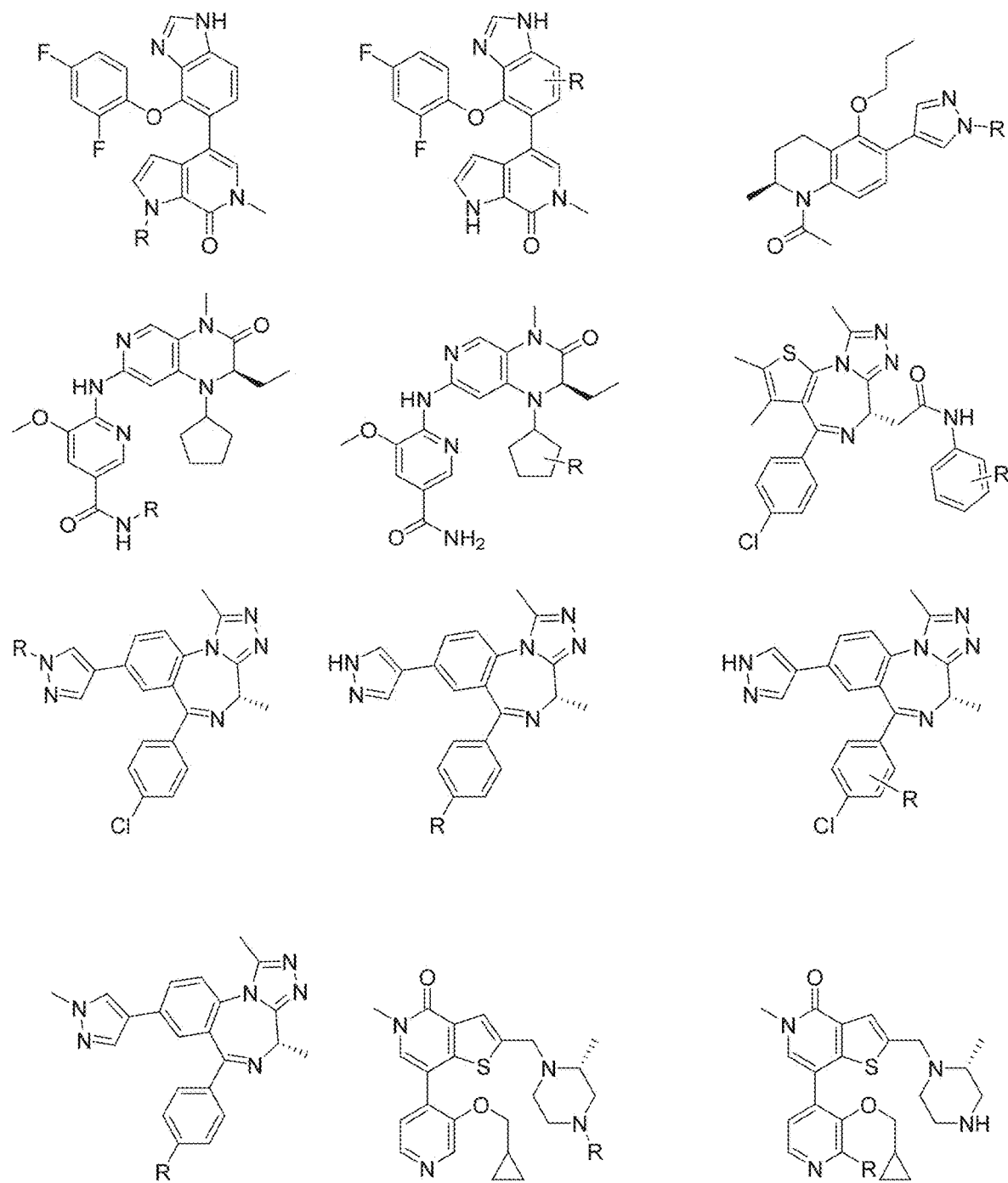
Figure 1M:
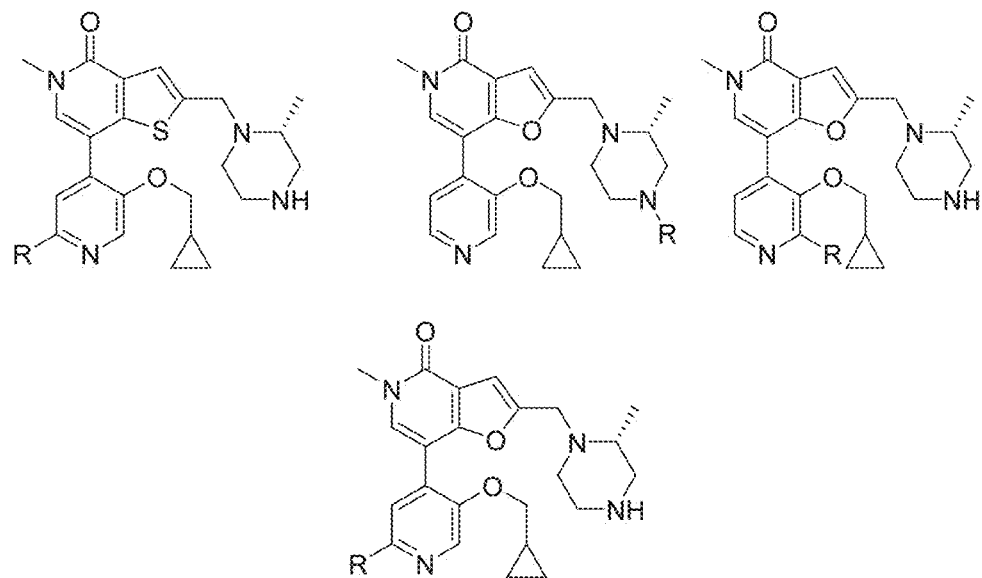
Figure 1N:
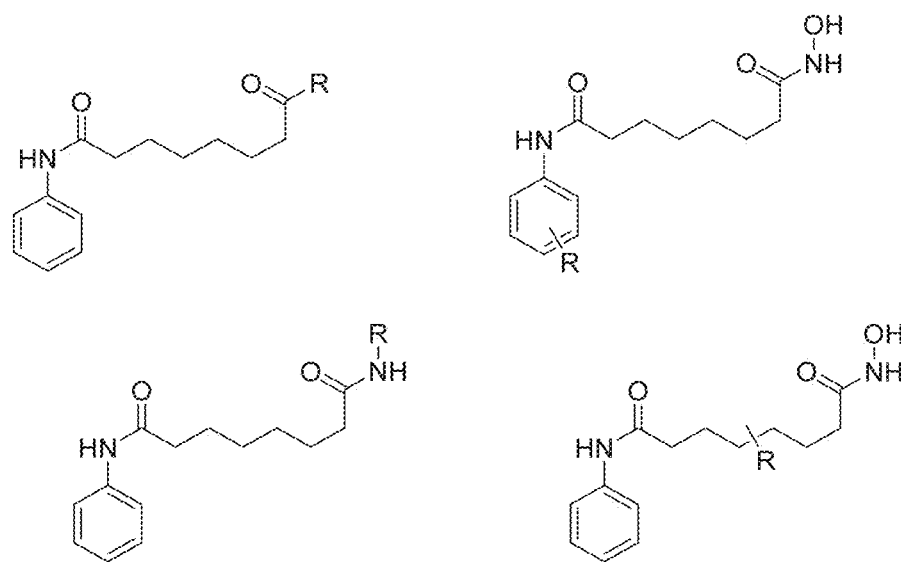
Figure 1O:
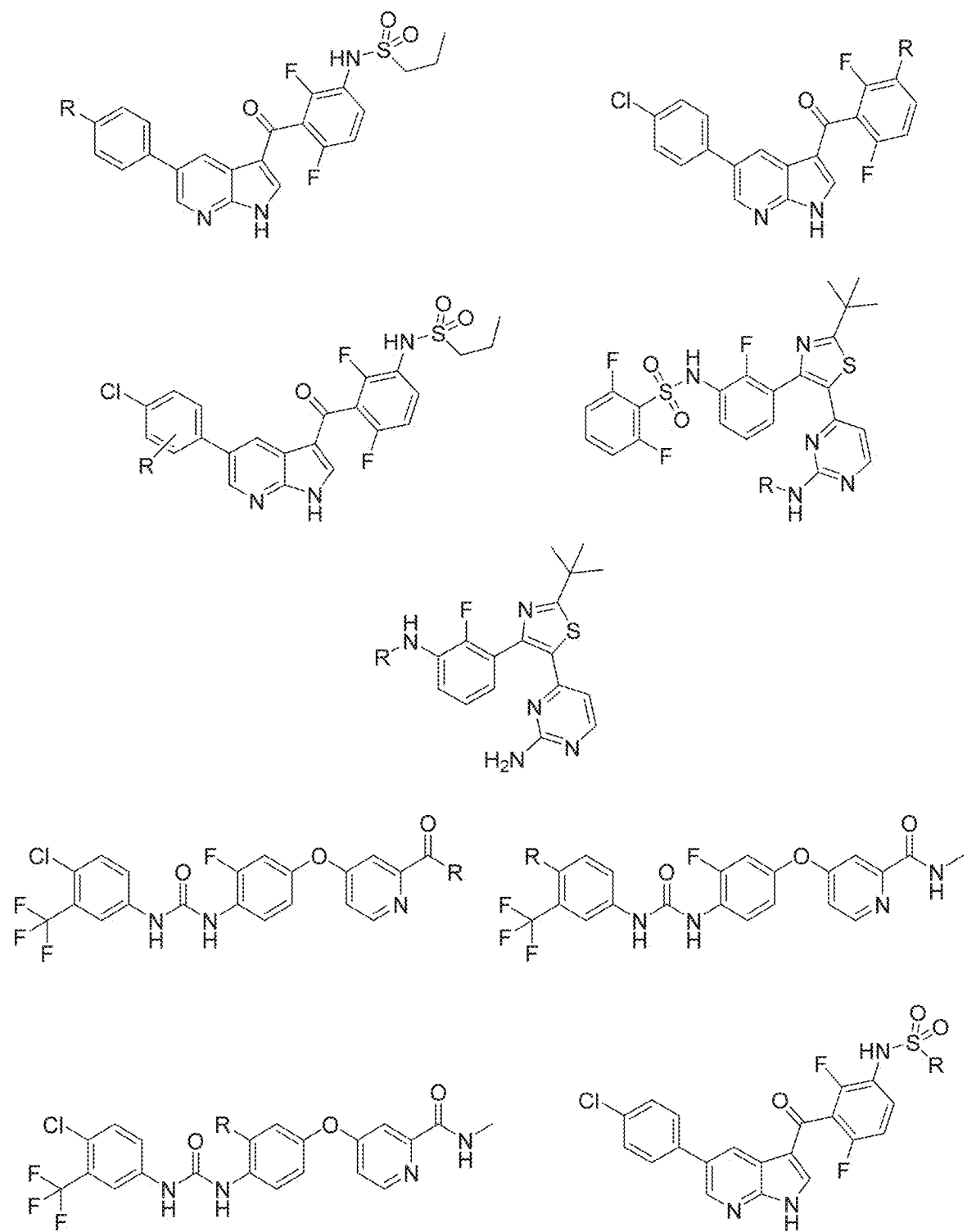
Figure 1P:
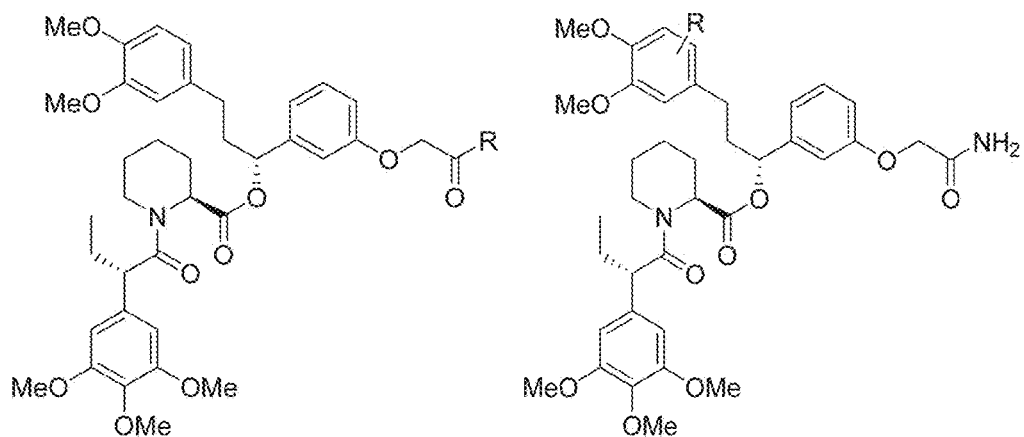
Figure 1P:
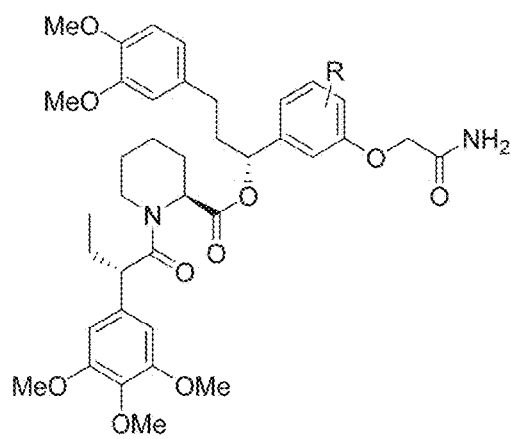
Figure 1Q:
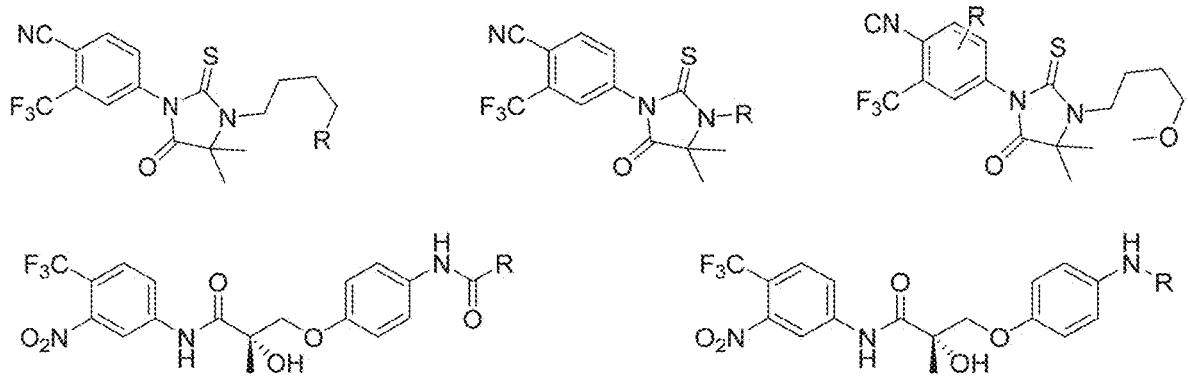
Figure 1R:
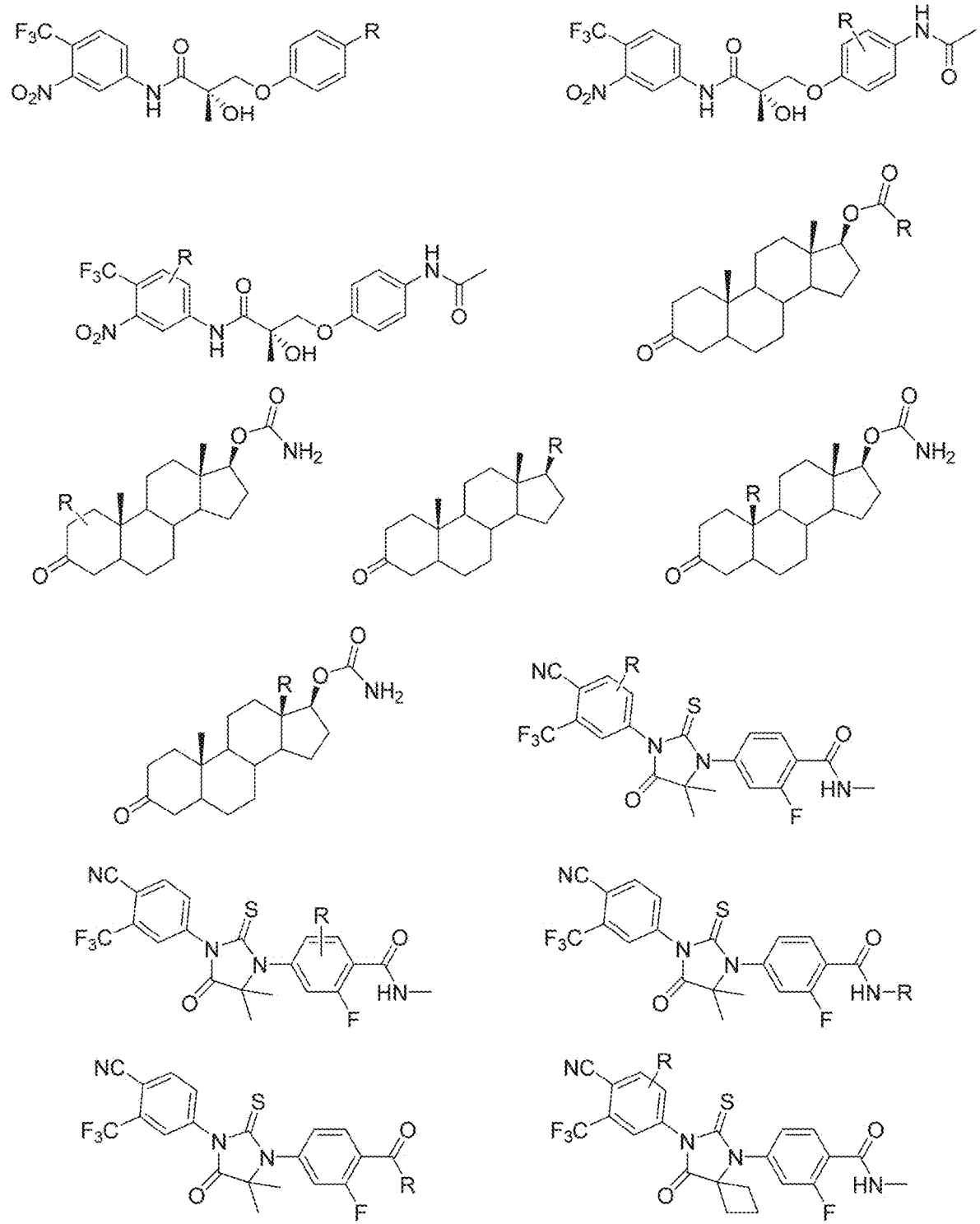
Figure 1S:
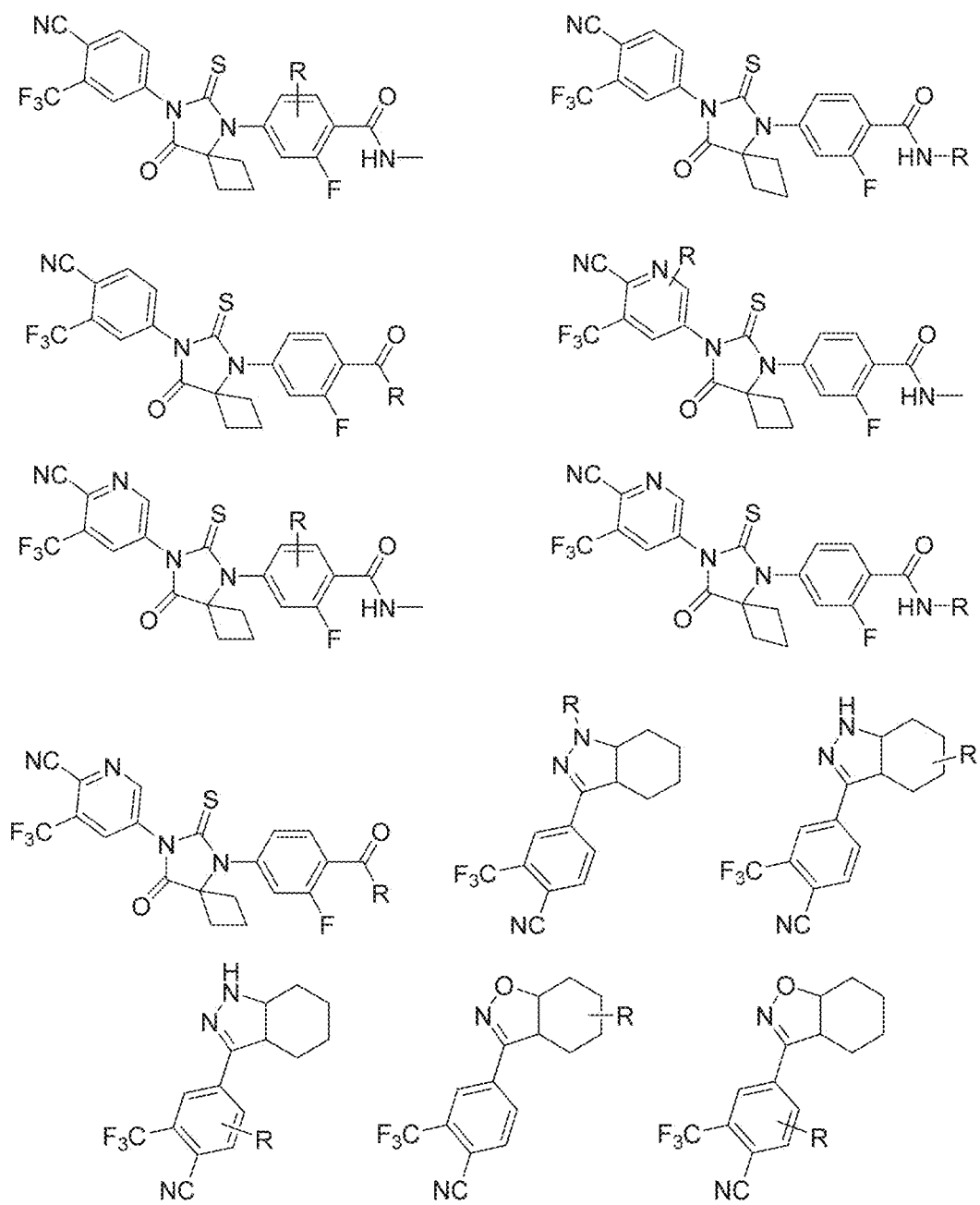
Figure 1T:
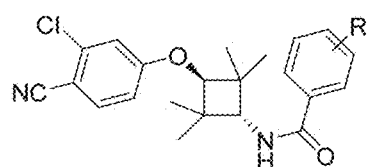
Figure 1T:
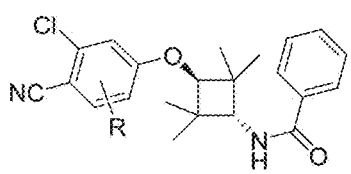
Figure 1U:
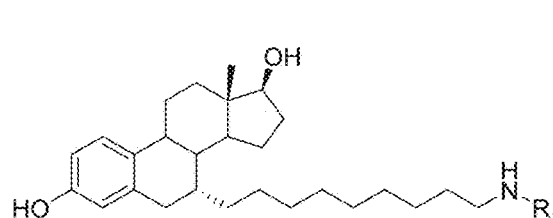
Figure 1U:
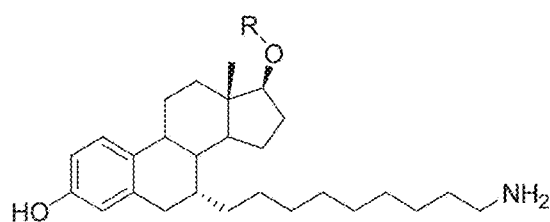
Figure 1U:
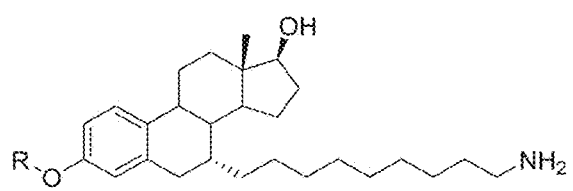
Figure 1U:
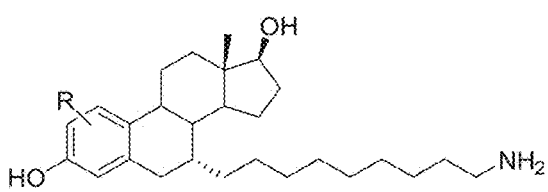
Figure 1V:
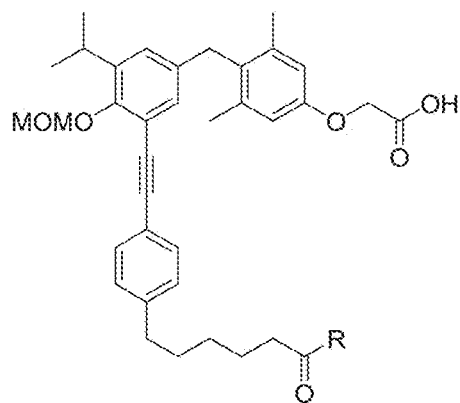
Figure 1V:
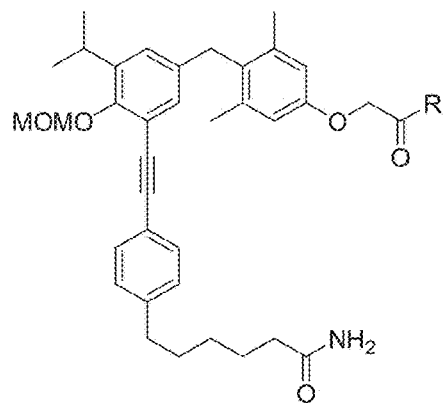
Figure 1W:
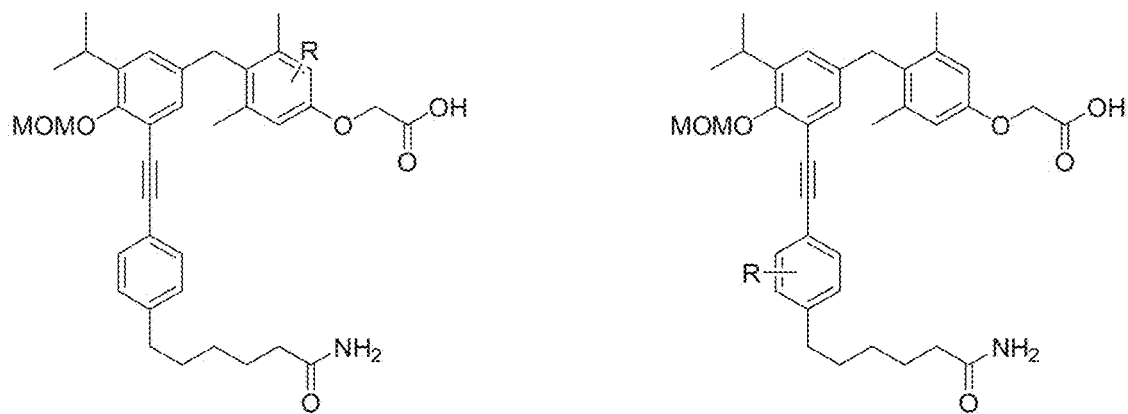
Figure 1X:
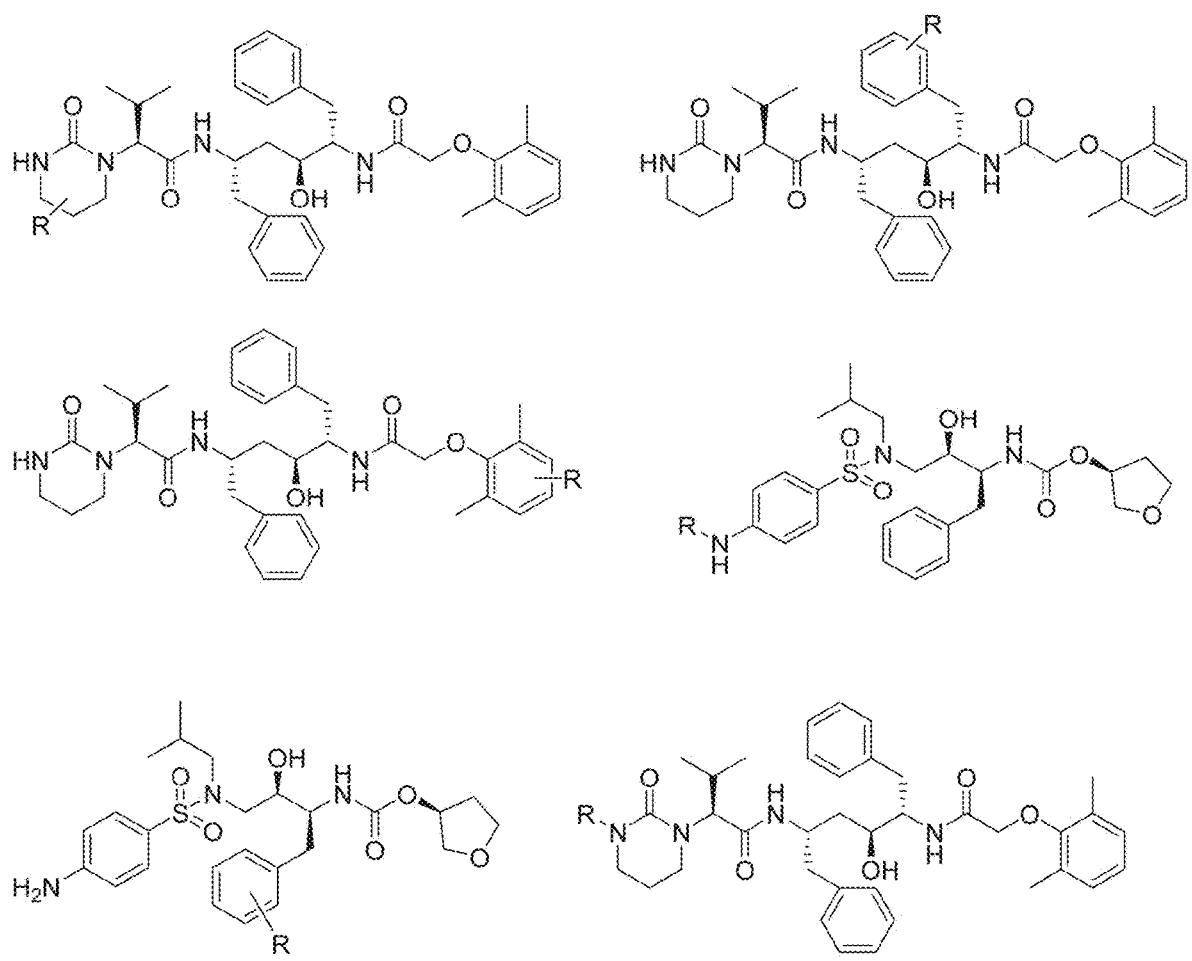
Figure 1Y:
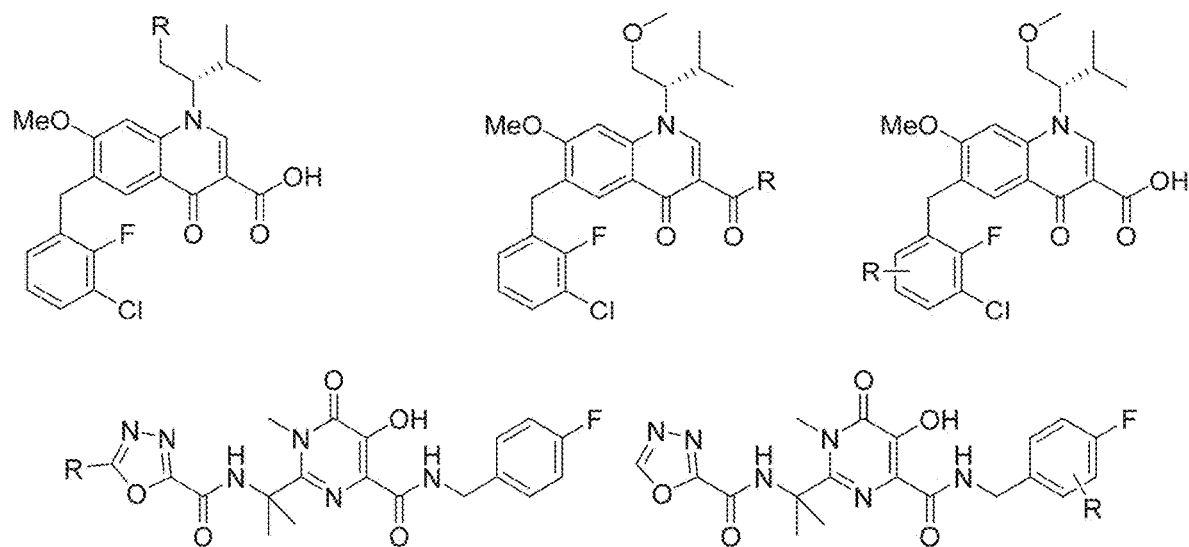
Figure 1Z:
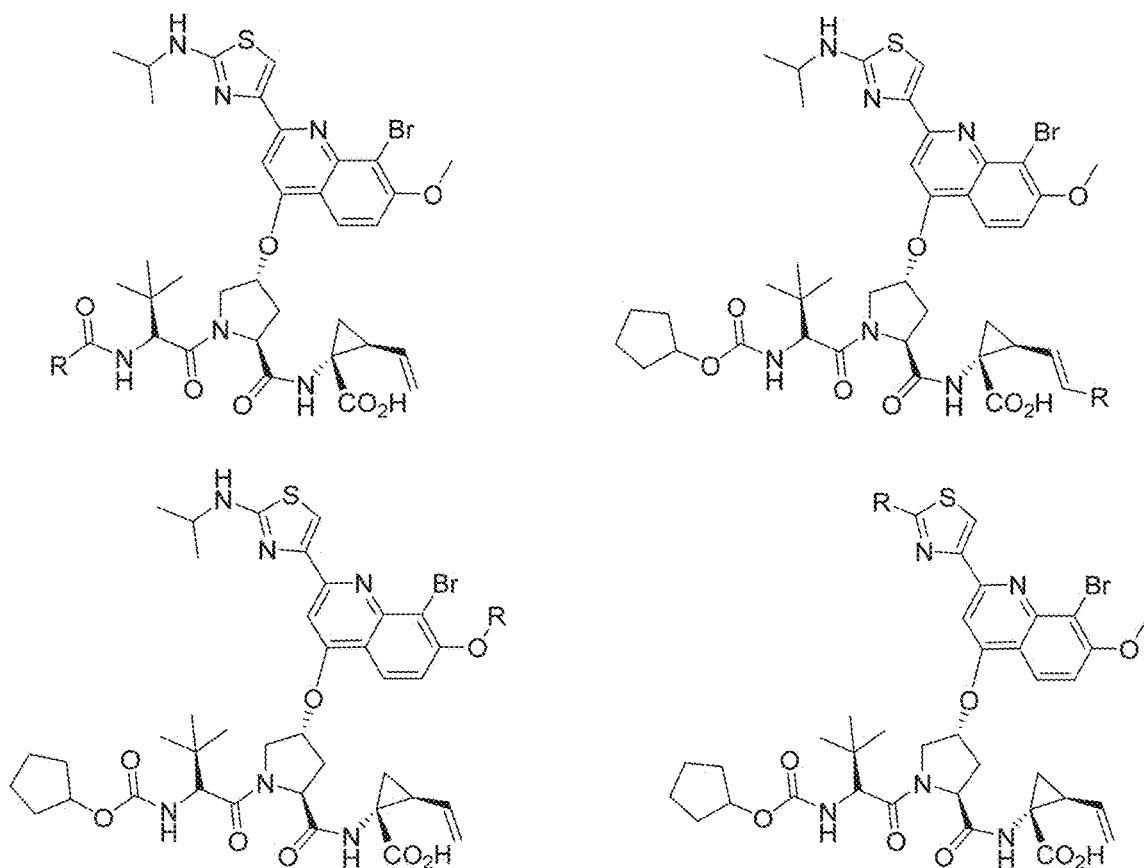
Figure 2A:
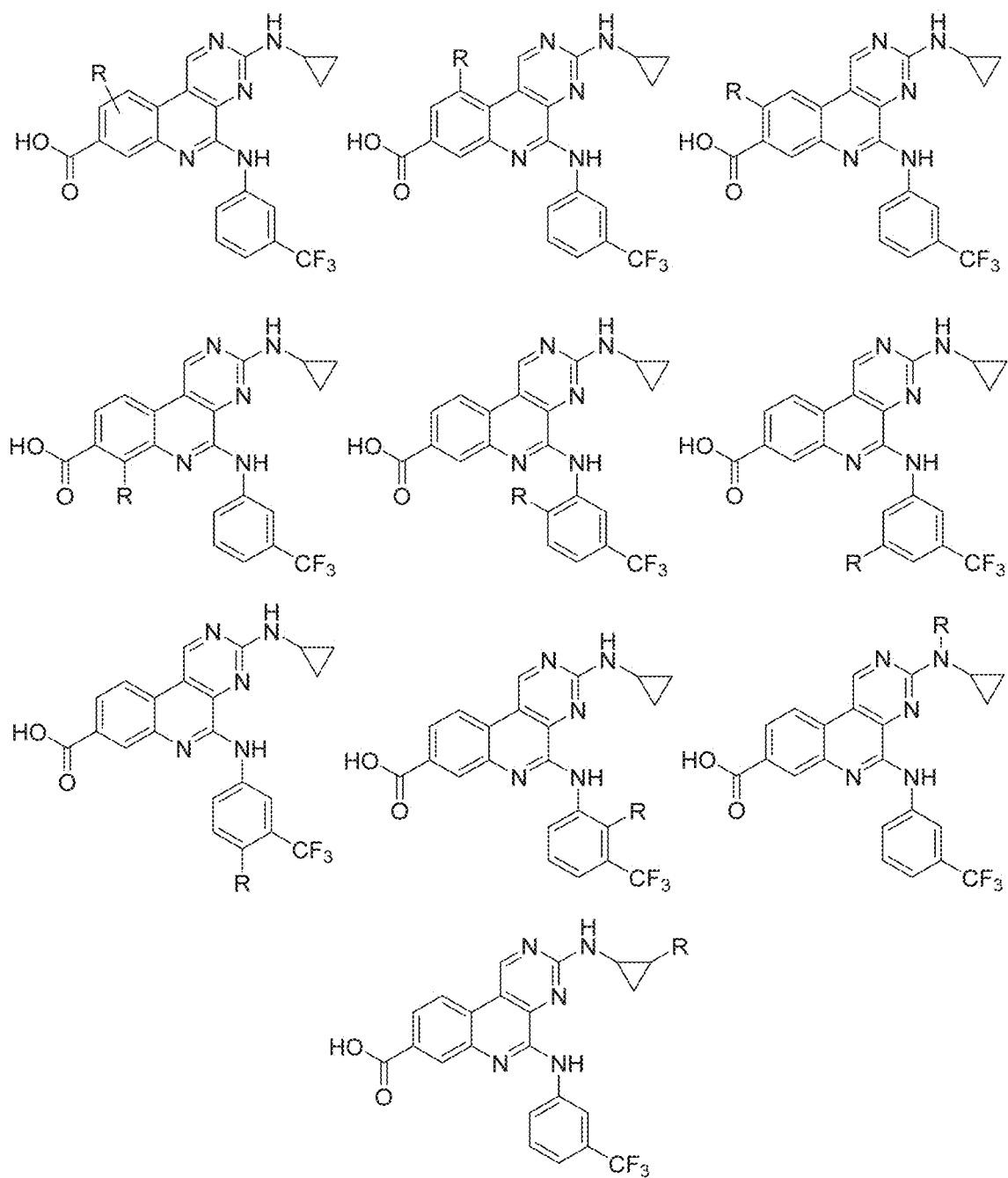
FIG. 2A presents examples of the kinase inhibitor Targeting Ligands U09-CX-5279 (derivatized) wherein R is the point at which the Linker is attached.
Figure 2B:
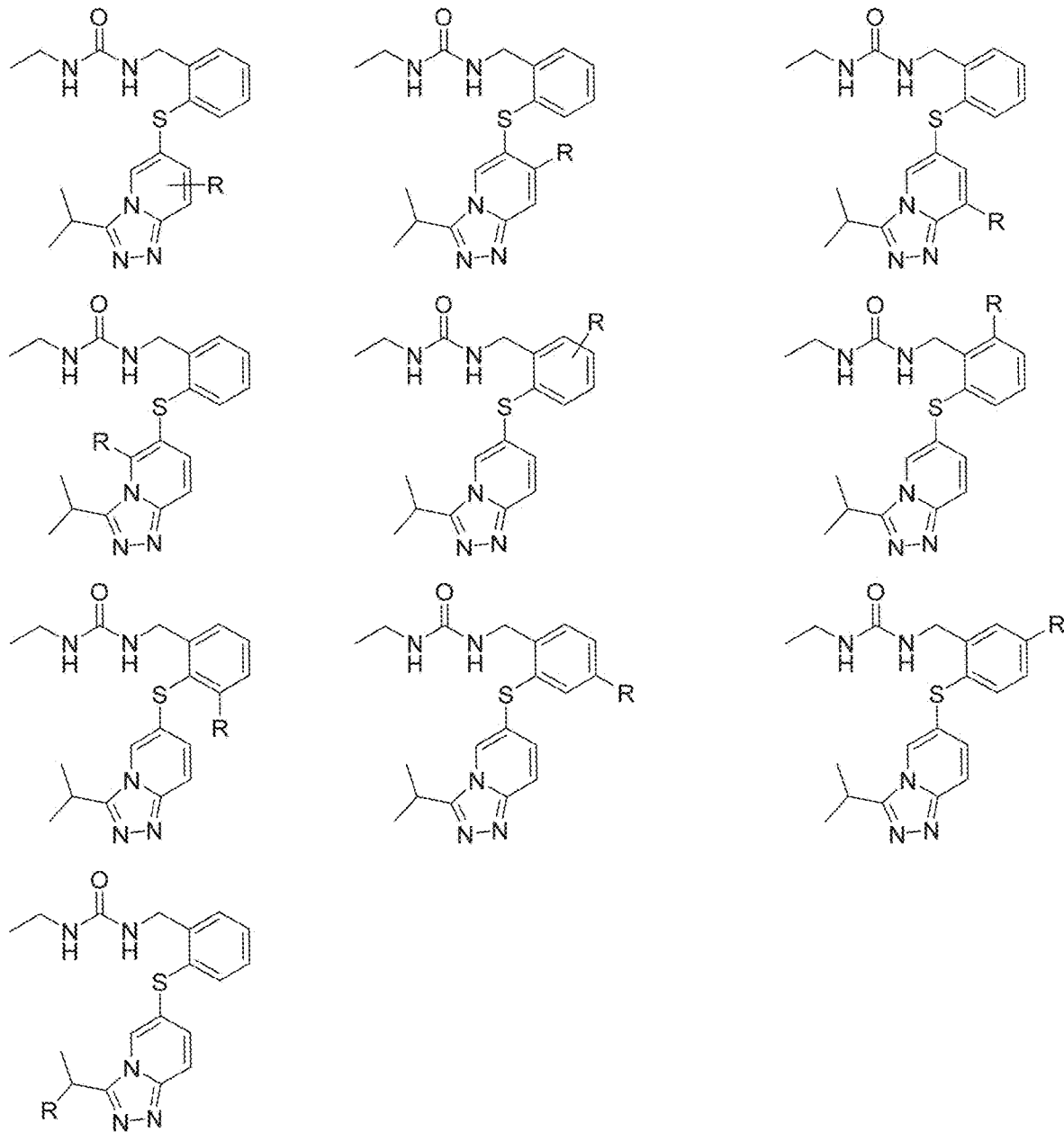
FIG. 2B-2C present examples of kinase inhibitor Targeting Ligands, including the kinase inhibitor compounds Y1W and Y1X (derivatized) wherein R is the point at which the Linker is attached. For additional examples and related ligands, see, the kinase inhibitors identified in Millan et al. "Design and Synthesis of Inhaled P38 Inhibitors for the Treatment of Chronic Obstructive Pulmonary Disease" *J. Med. Chem.*, 54: 7797 (2011).
Figure 2C:
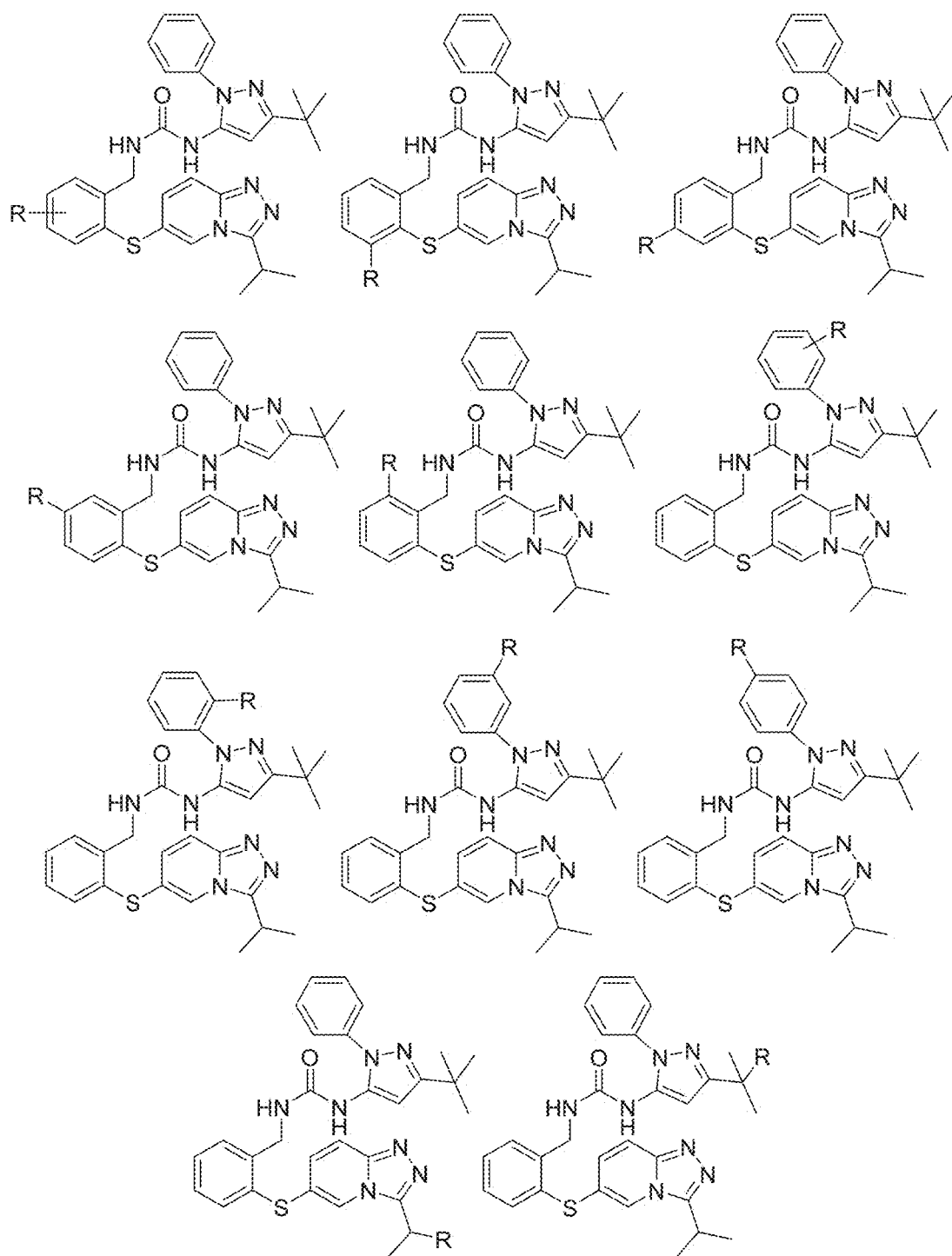
Figure 2D:
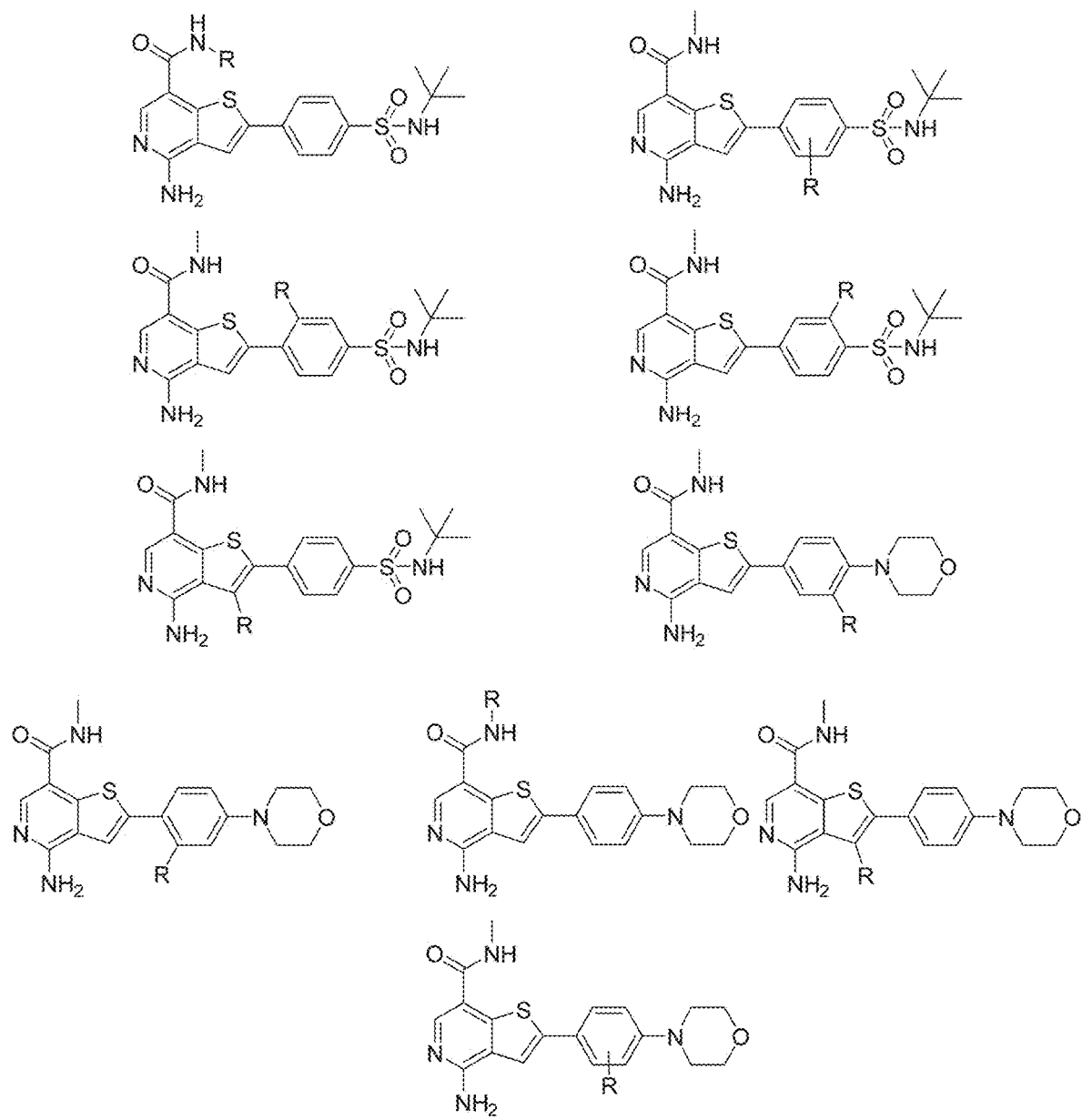
FIG. 2D presents examples of kinase inhibitor Targeting Ligands, including the kinase inhibitor compounds 6TP and 0TP (derivatized) wherein R is the point at which the Linker is attached. For additional examples and related ligands, see, the kinase inhibitors identified in Schenkel et al. "Discovery of Potent and Highly Selective Thienopyridine Janus Kinase 2 Inhibitors" *J. Med. Chem.*, 54 (24): 8440-8450 (2011).
Figure 2E:
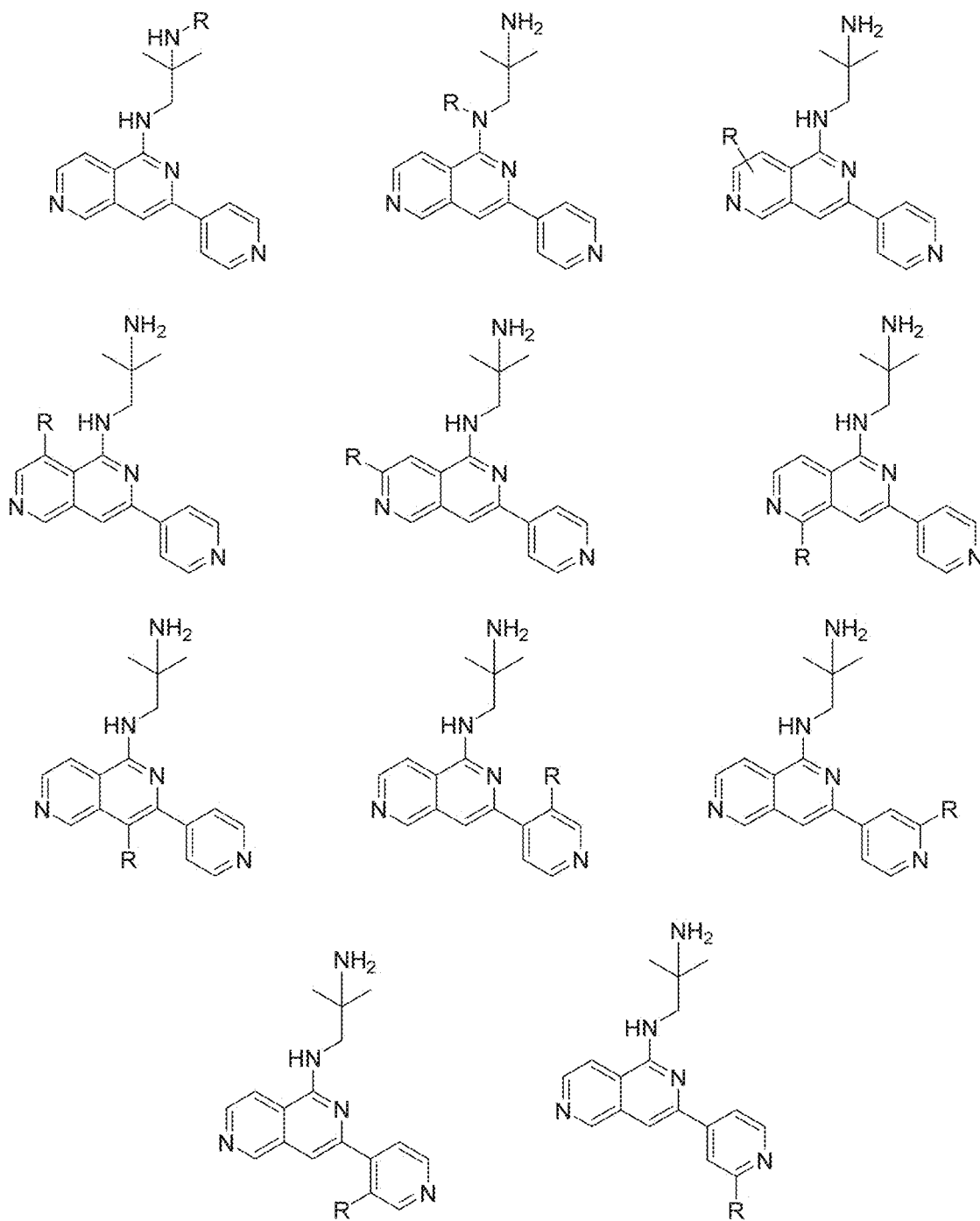
FIG. 2E presents examples of kinase inhibitor Targeting Ligands, including the kinase inhibitor compound 07U wherein R is the point at which the Linker is attached. For additional examples and related ligands, see, the kinase inhibitors identified in Van Eis et al. "2 6-Naphthyridines as potent and selective inhibitors of the novel protein kinase C isozymes" *Biorg. Med. Chem. Lett.*, 21(24): 7367-72 (2011).
Figure 2F:
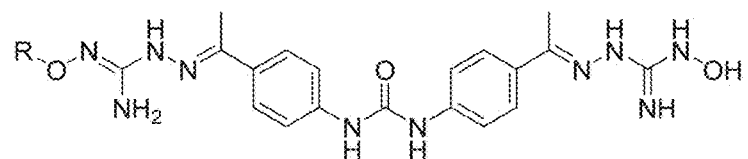
FIG. 2F presents examples of kinase inhibitor Targeting Ligands, including the kinase inhibitor compound YCF, wherein R is the point at which the Linker is attached. For additional examples and related ligands, see, the kinase inhibitors identified in Lountos et al. "Structural Characterization of Inhibitor Complexes with Checkpoint Kinase 2 (Chk2) a Drug Target for Cancer Therapy" *J. Struct. Biol.*, 176: 292 (2011).
Figure 2F:
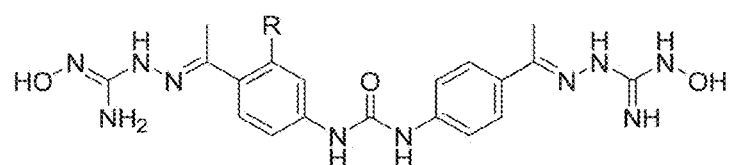
Figure 2F:
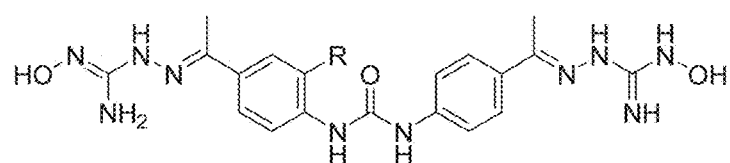
Figure 2G:
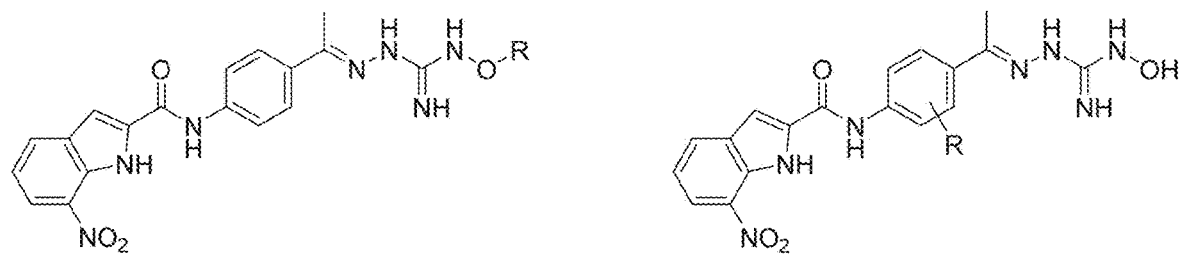
FIG. 2G-2H present examples of kinase inhibitor Targeting Ligands, including the kinase inhibitors XK9 and NXP (derivatized) wherein R is the point at which the Linker is attached. For additional examples and related ligands, see, the kinase inhibitors identified in Lountos et al. "Structural Characterization of Inhibitor Complexes with Checkpoint Kinase 2 (Chk2) a Drug Target for Cancer Therapy" *J. Struct. Biol.*, 176: 292 (2011).
Figure 2G:
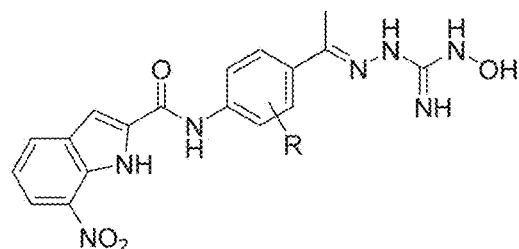
Figure 2G:
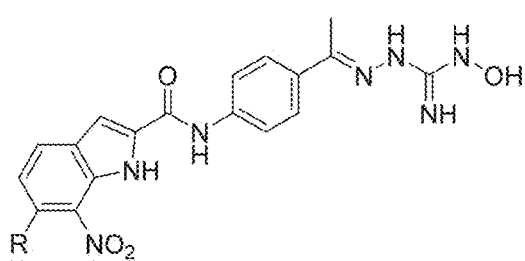
Figure 2G:
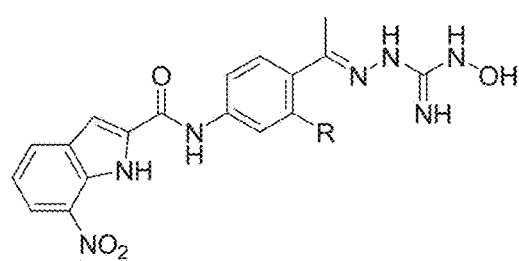
Figure 2G:
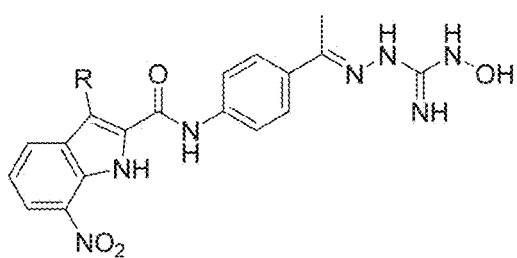
Figure 2G:
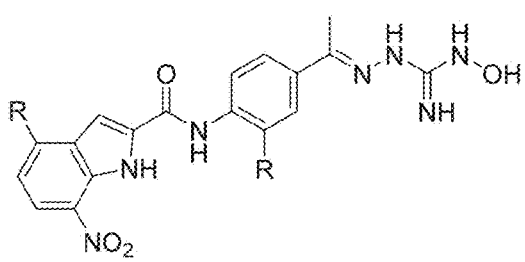
Figure 2H:
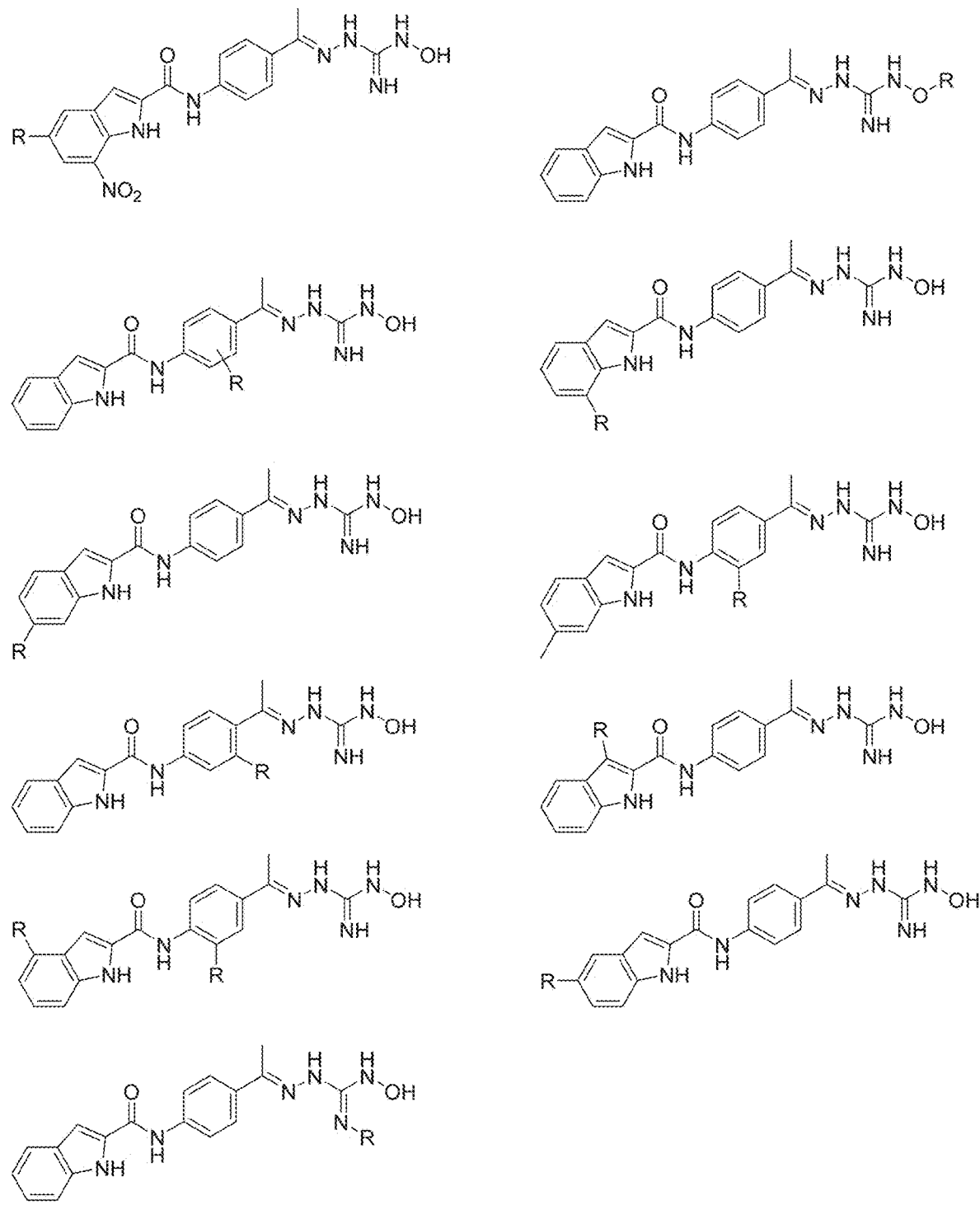
Figure 2I:
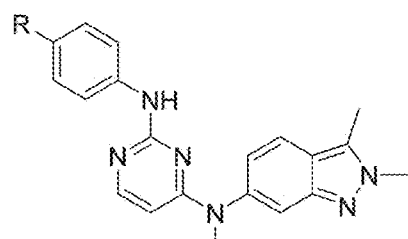
FIG. 2I-2J present examples of kinase inhibitor Targeting Ligands wherein R is the point at which the Linker r is attached.
Figure 2I:
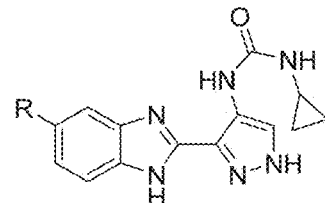
Figure 2I:
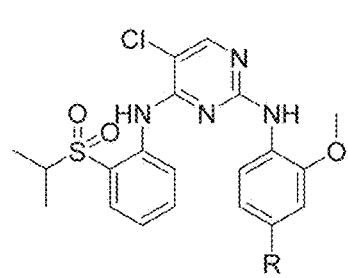
Figure 2I:
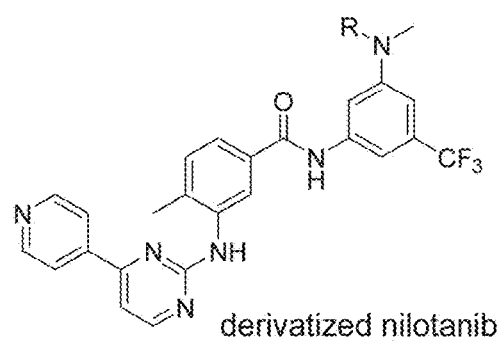
Figure 2I:
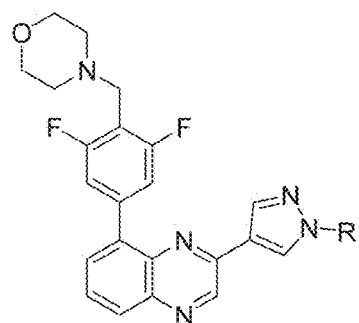
Figure 2I:
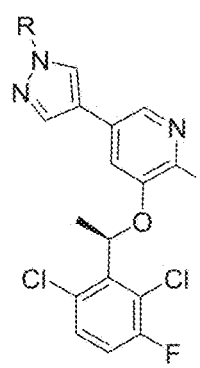
Figure 2I:
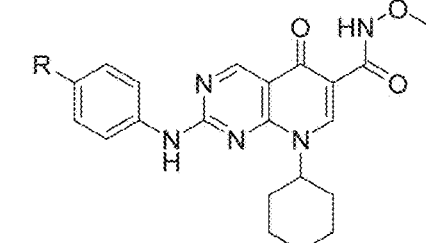
Figure 2I:
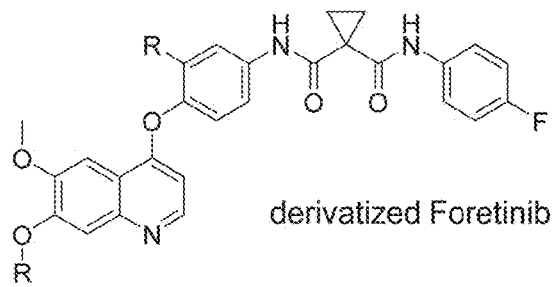
Figure 2I:
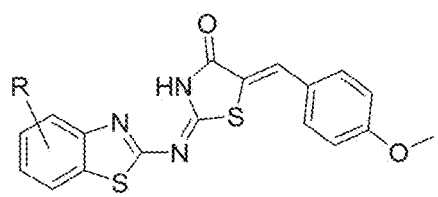
Figure 2J:
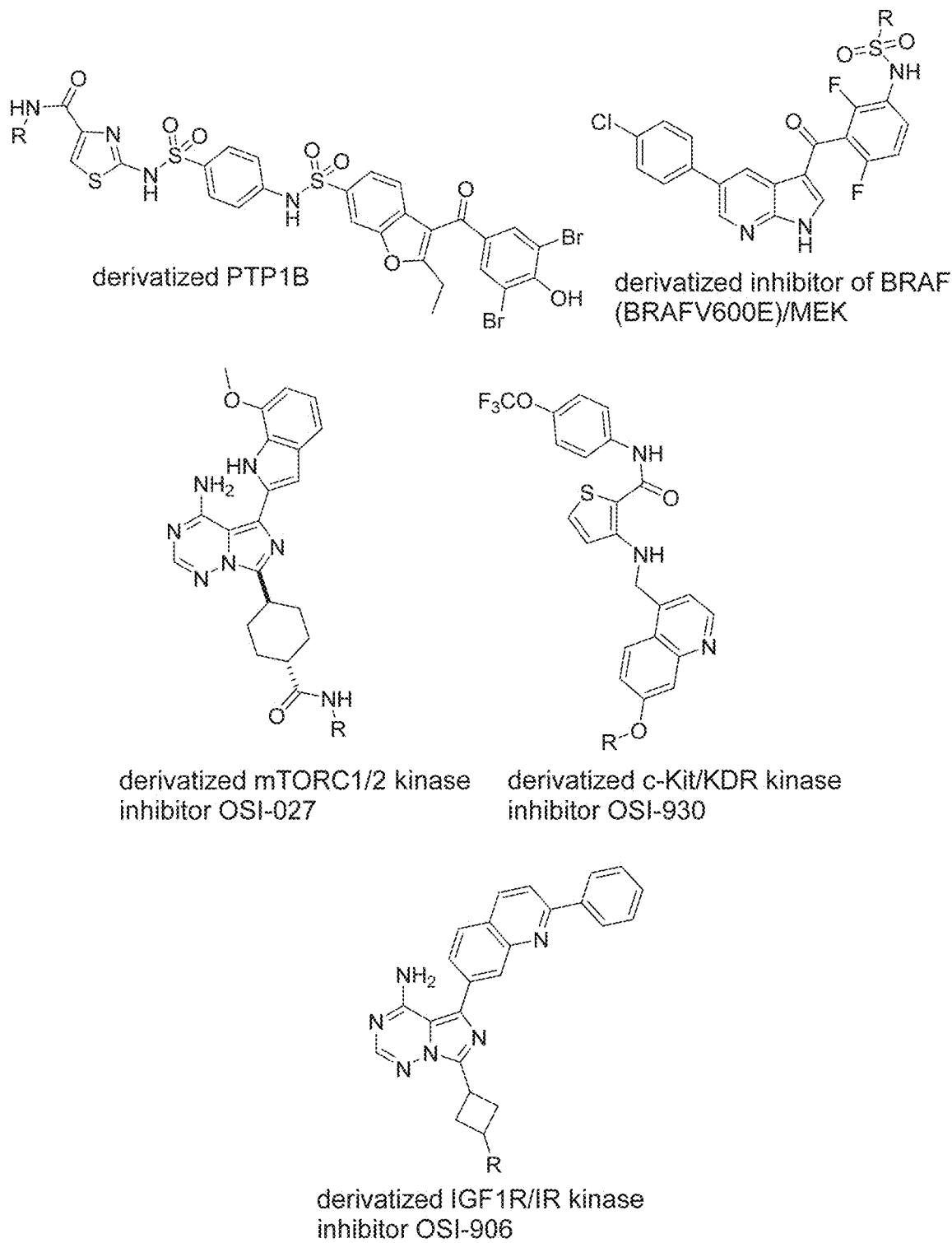
Figure 2K:
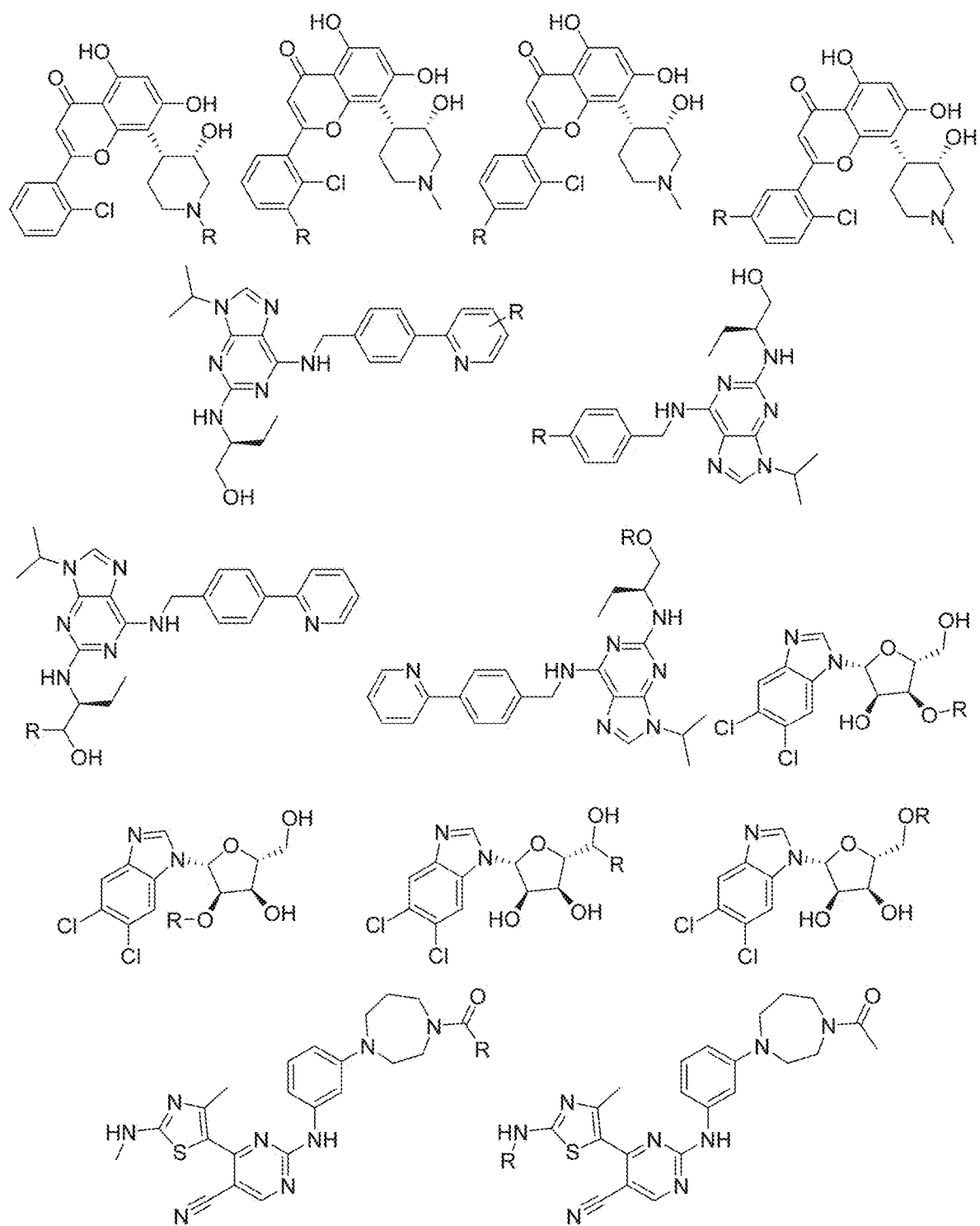
FIG. 2K-2M present examples of Cyclin Dependent Kinase 9 (CDK9) Targeting Ligands wherein R is the point at which the Linker is attached. For additional examples and related ligands, see, Baumli et al. "The structure of P-TEFb (CDK9/cyclin Ti) its complex with flavopiridol and regulation by phosphorylation." *Embo J.*, 27: 1907-1918 (2008); Bettayeb et al. "CDK Inhibitors Roscovitine and CR8 Trigger Mcl-1 Down-Regulation and Apoptotic Cell Death in Neuroblastoma Cells." *Genes Cancer*, 1: 369-380 (2010); Baumli et al. "Halogen bonds form the basis for selective P-TEFb inhibition by DRB." *Chem. Biol.* 17: 931-936 (2010); Hole et al. "Comparative Structural and Functional Studies of 4-(Thiazol-5-Yl)-2-(Phenylamino)Pyrimidine-5-Carbonitrile Cdk9 Inhibitors Suggest the Basis for Isotype Selectivity." *J. Med. Chem.* 56: 660 (2013); Lücking et al. "Identification of the potent and highly selective PTEFb inhibitor BAY 1251152 for the treatment of cancer—From p.o. to i.v. application via scaffold hops." Lücking et al. U. AACR Annual Meeting, Apr. 1-5, 2017 Washington, D.C. USA.
Figure 2L:
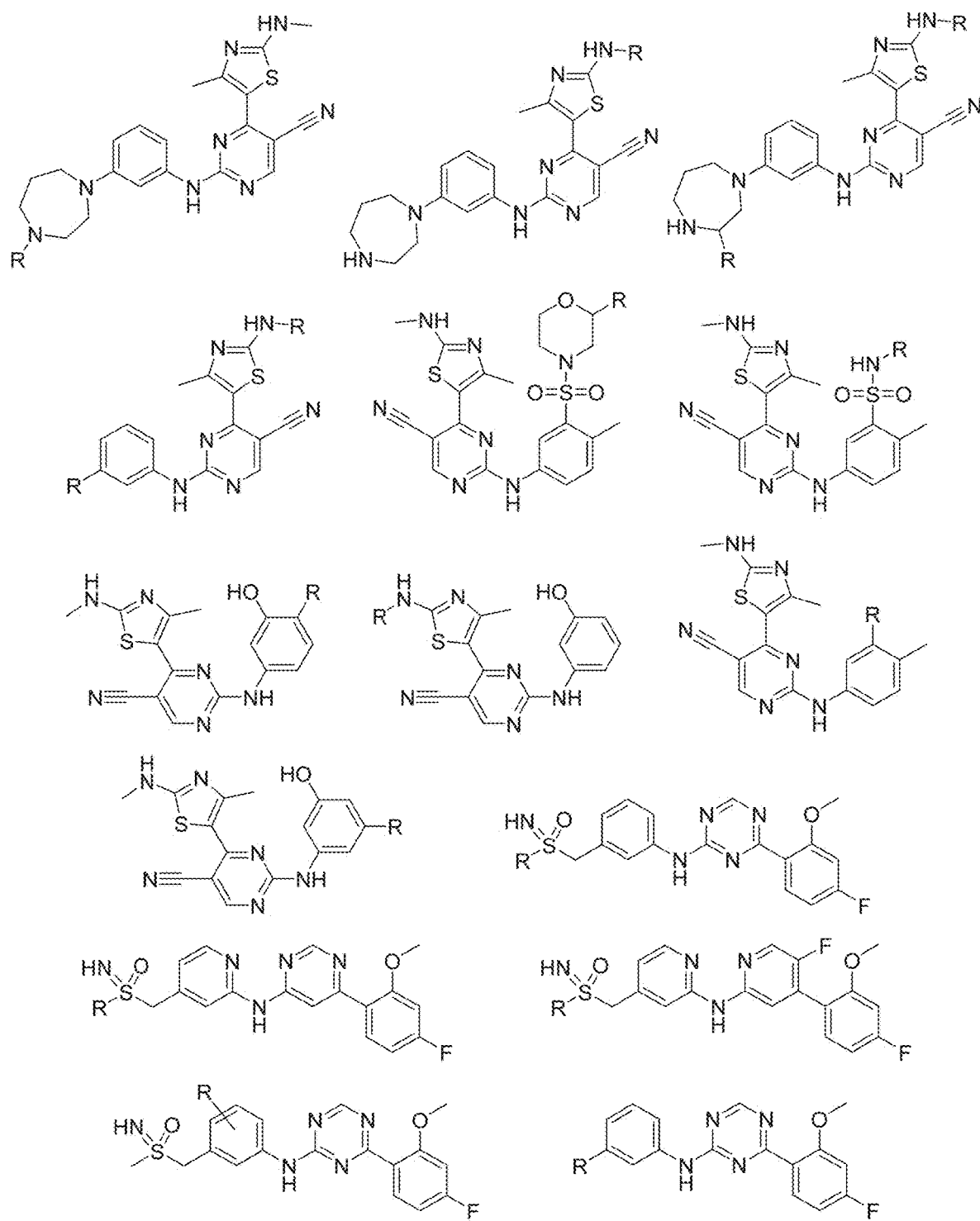
Figure 2M:
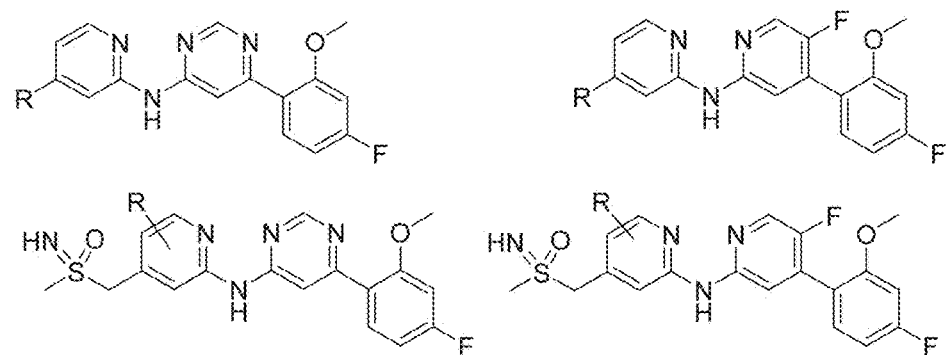
Figure 2N:
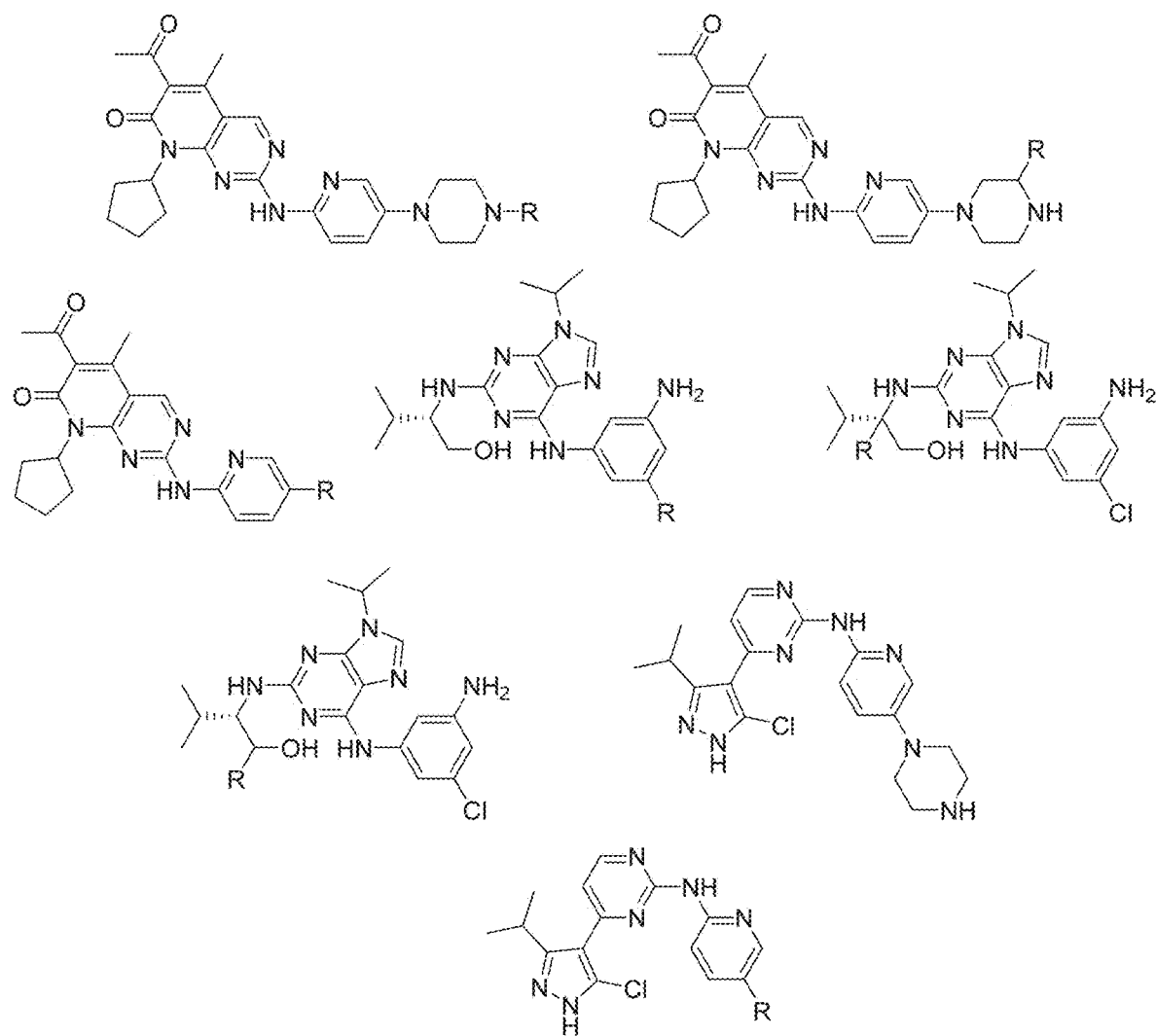
FIG. 2N-2P present examples of Cyclin Dependent Kinase 4/6 (CDK4/6) Targeting Ligands wherein R is the point at which the Linker is attached. For additional examples and related ligands, see, Lu H.; Schulze-Gahmen U.; "Toward understanding the structural basis of cyclin-dependent kinase 6 specific inhibition." *J. Med. Chem.*, 49: 3826-3831 (2006); 4-(Pyrazol-4-yl)-pyrimidines as selective inhibitors of cyclin-dependent kinase 4/6. Cho et al. (2010) *J. Med. Chem.* 53: 7938-7957; Cho Y. S. et al. "Fragment-Based Discovery of 7-Azabenzimidazoles as Potent Highly Selective and Orally Active CDK4/6 Inhibitors." *ACS Med Chem Lett* 3: 445-449 (2012); Li Z. et al. "Discovery of AMG 925 a FLT3 and CDK4 dual kinase inhibitor with preferential affinity for the activated state of FLT3." *J. Med. Chem.* 57: 3430-3449 (2014); Chen P. et al. "Spectrum and Degree of CDK Drug Interactions Predicts Clinical Performance." *Mol. Cancer Ther.* 15: 2273-2281 (2016).
Figure 2O:
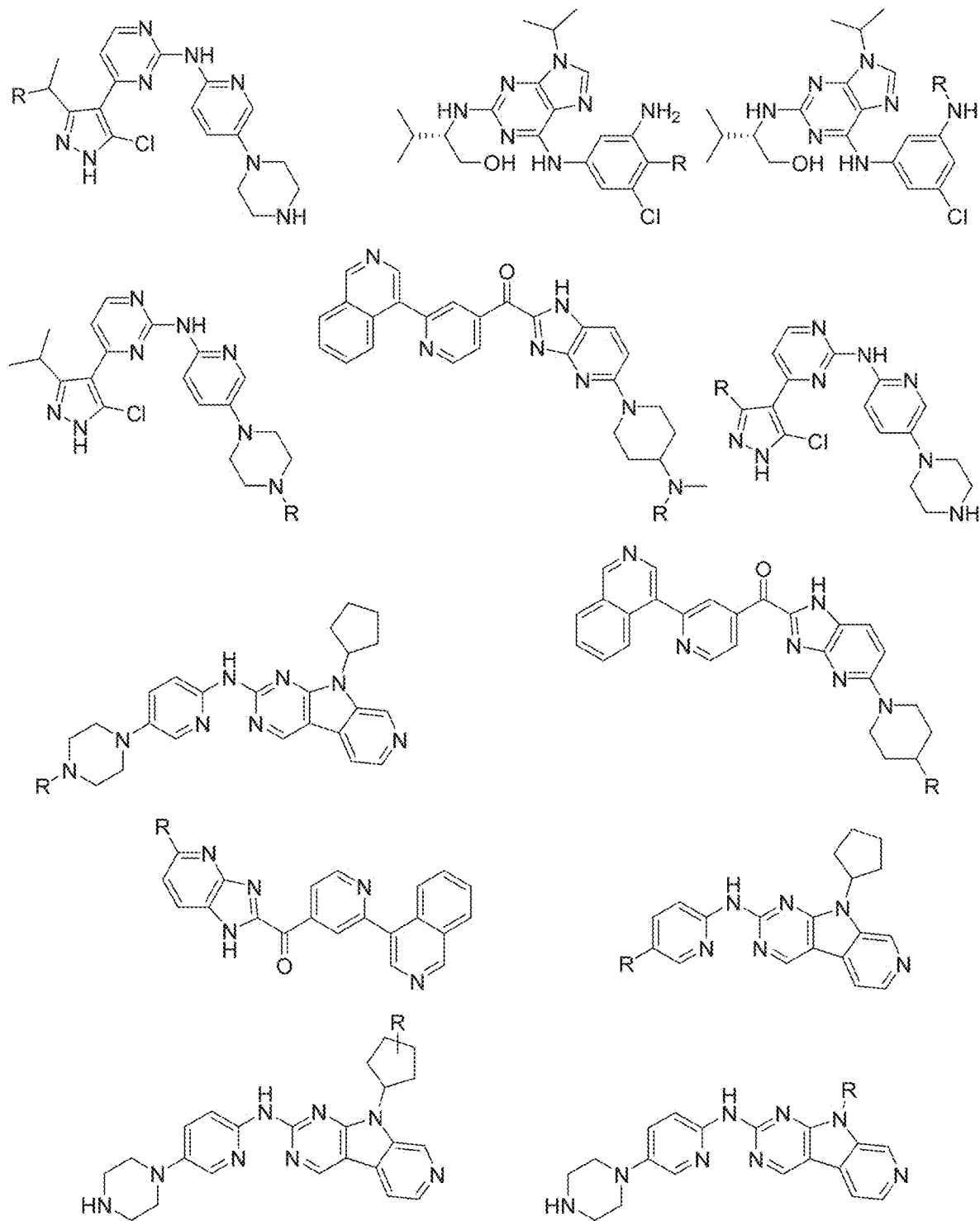
Figure 2P:
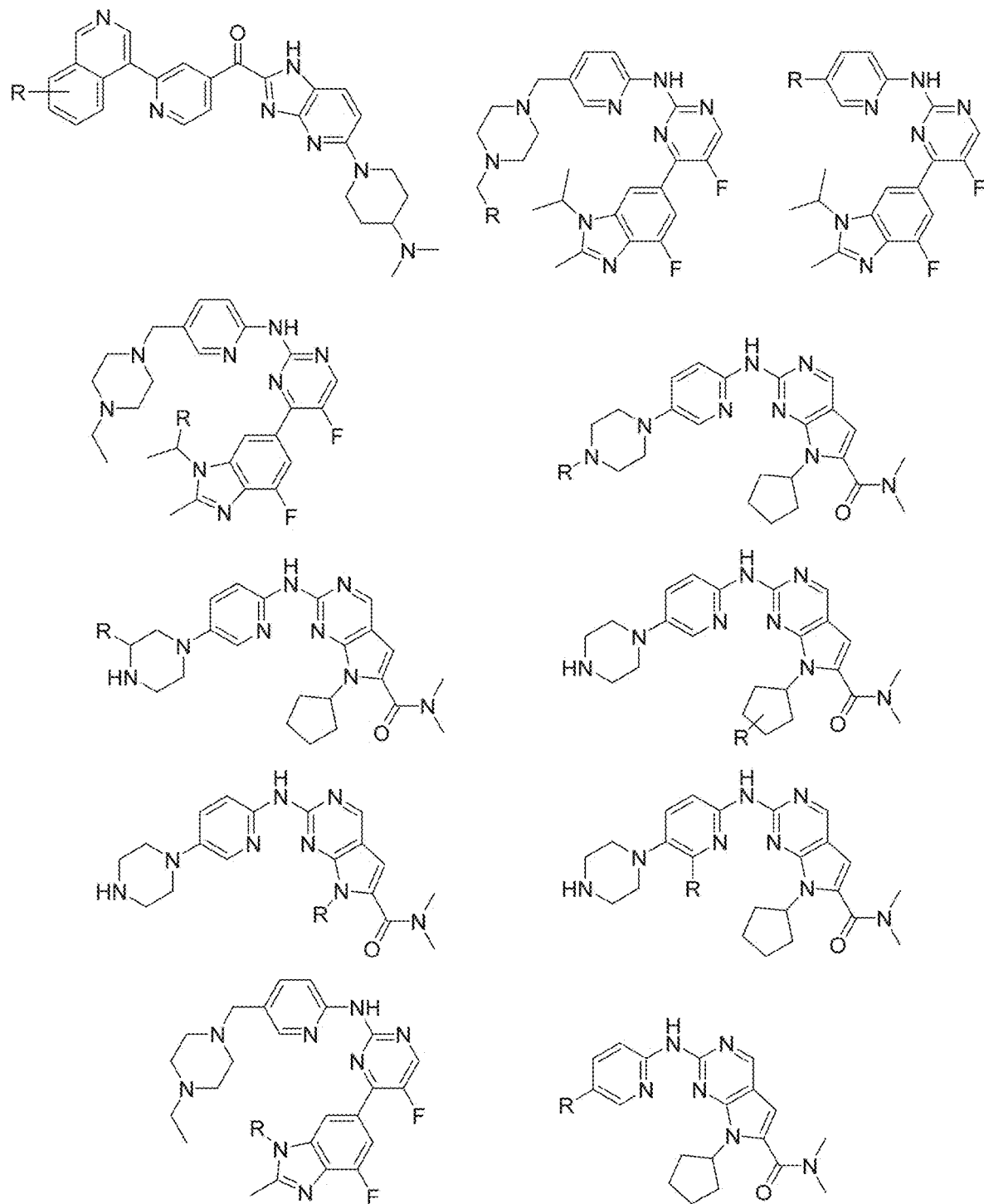
Figure 2Q:
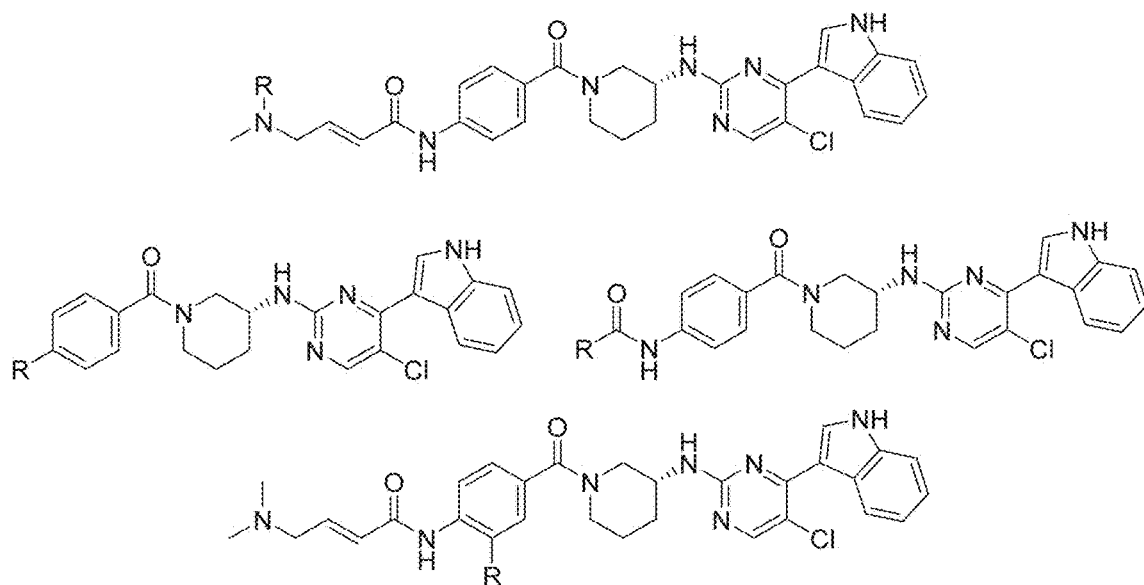
FIG. 2Q presents examples of Cyclin Dependent Kinase 12 and/or Cyclin Dependent Kinase 13 Targeting Ligands wherein R is the point at which the Linker is attached. For additional examples and related ligands, see, Zhang T. et al. "Covalent Targeting of Remote Cysteine Residues to Develop Cdk12 and Cdk13 Inhibitors." *Nat. Chem. Biol.* 12: 876 (2016).
Figure 2R:
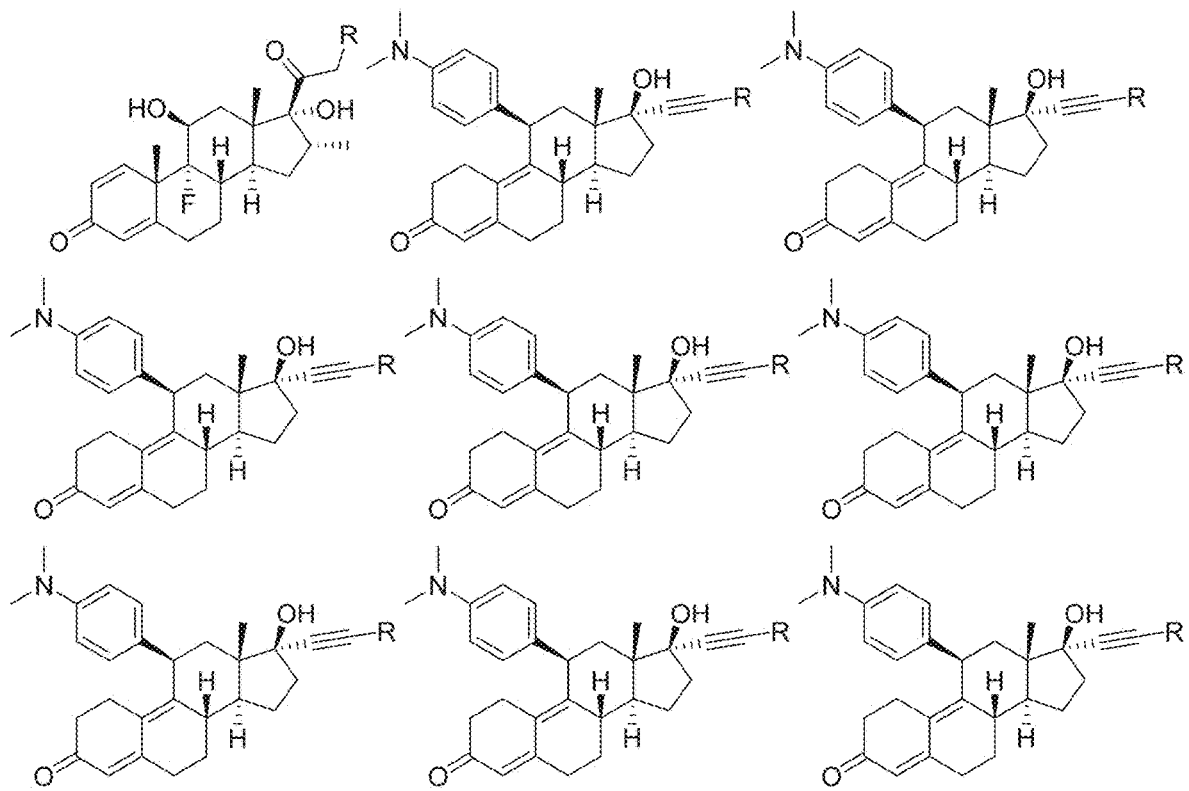
FIG. 2R-2S present examples of Glucocorticoid Receptor Targeting Ligands wherein R is the point at which the Linker is attached.
Figure 2S:
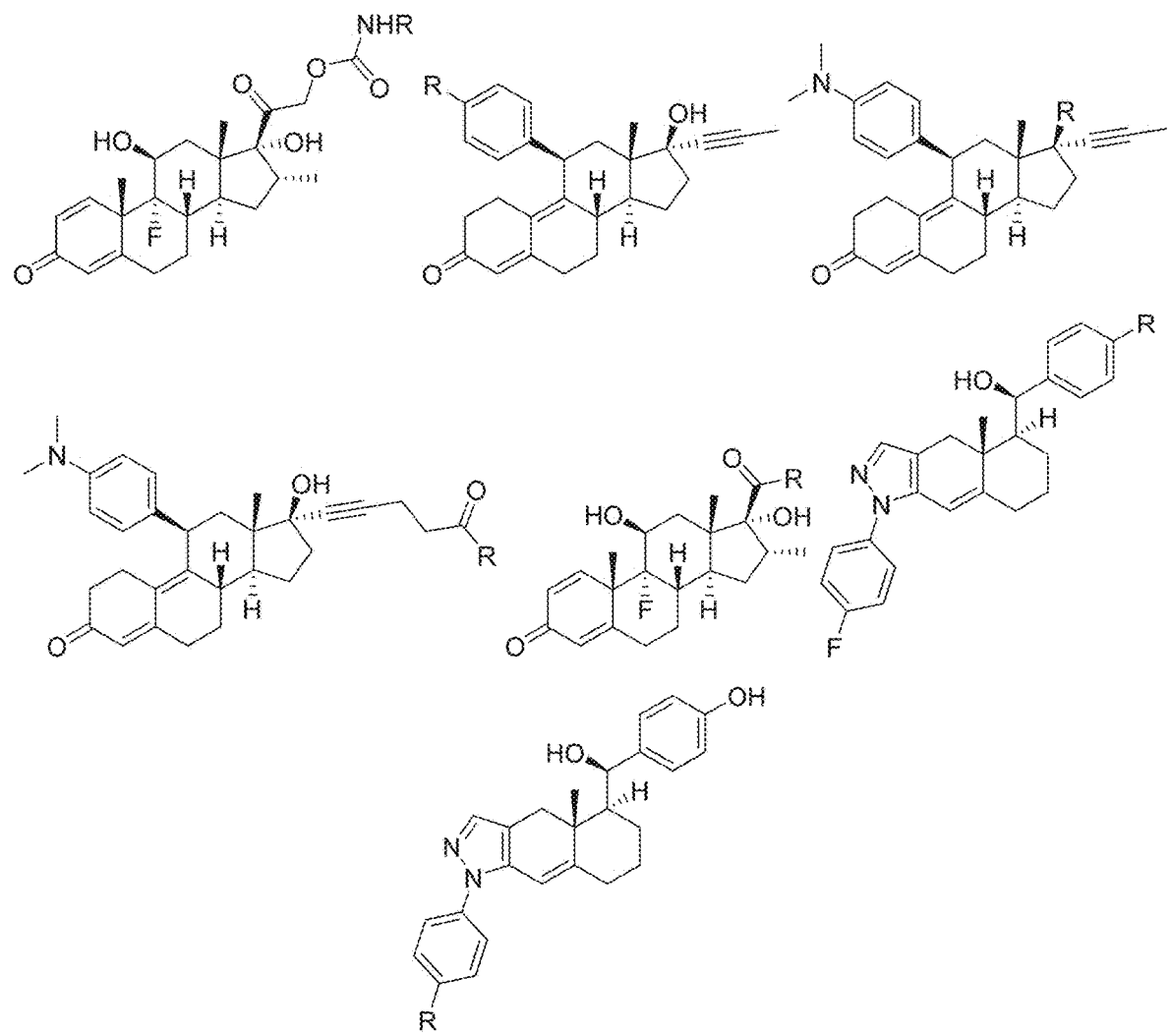
Figure 2T:
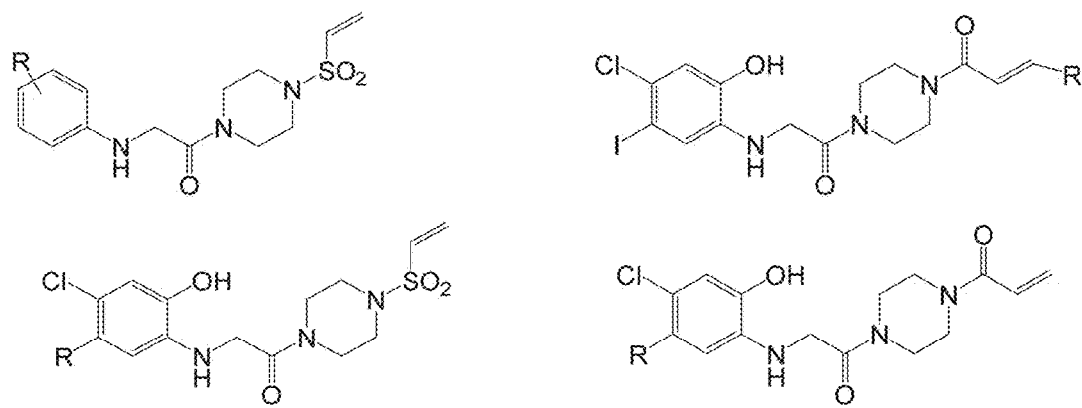
FIG. 2T-2U present examples of RasG12C Targeting Ligands wherein R is the point at which the Linker is attached.
Figure 2U:
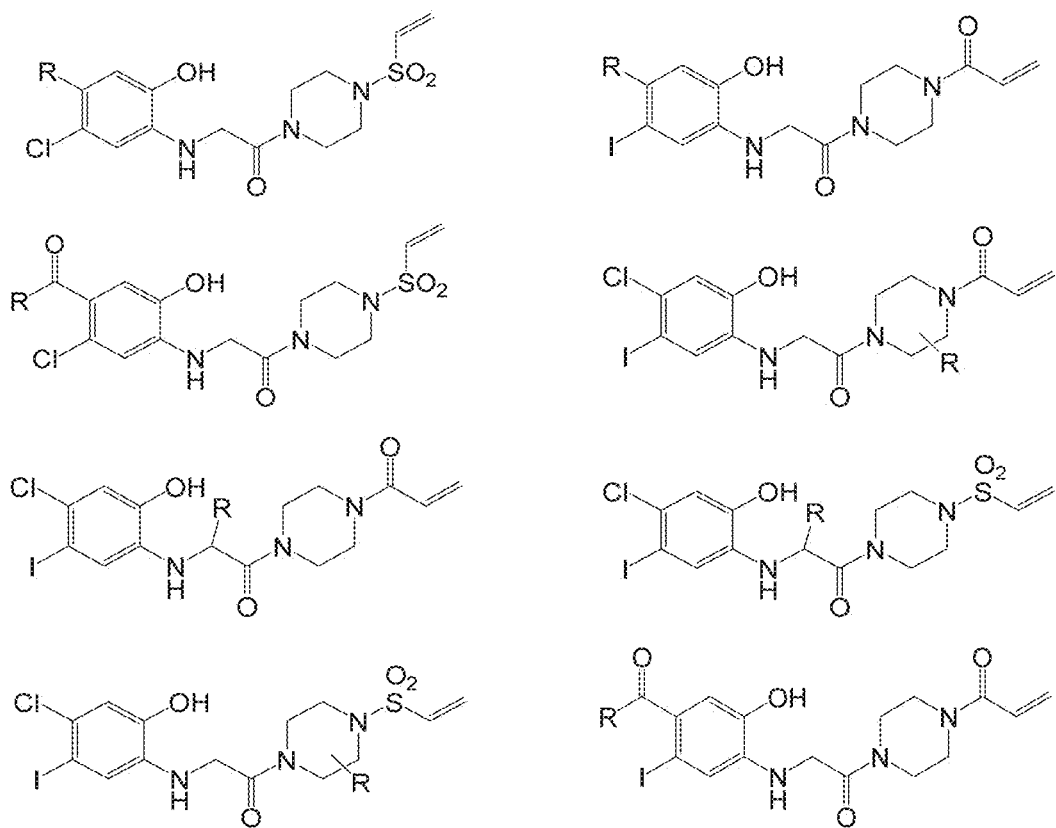
Figure 2V:
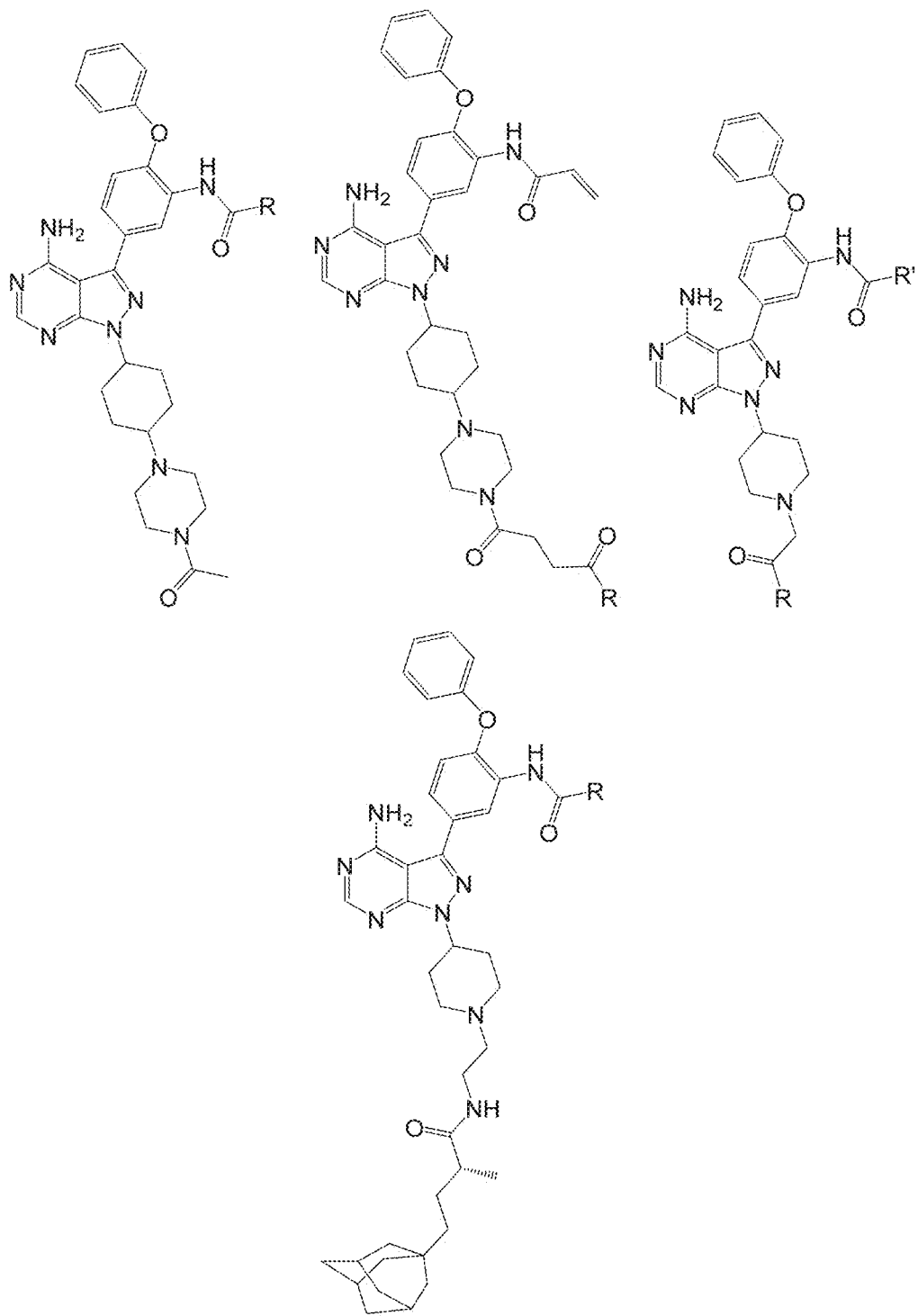
FIG. 2V presents examples of Her3 Targeting Ligands wherein R is the point at which the Linker is attached and R' is
Figure 2W:
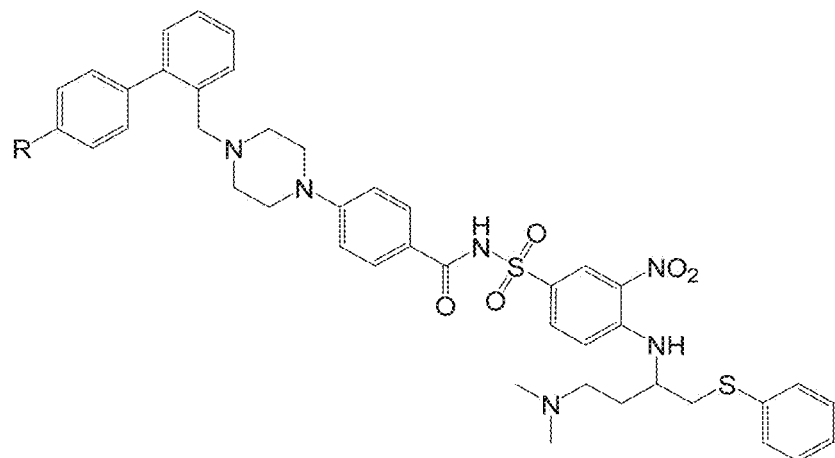
Figure 2W:
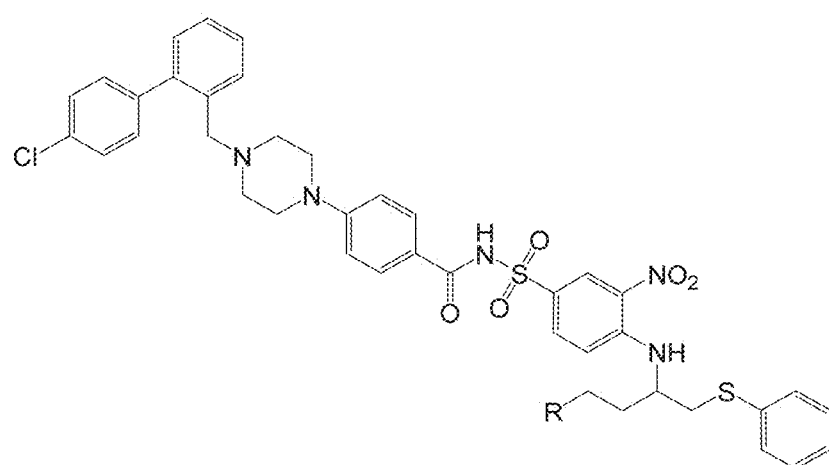

FIG. 2W presents examples of Bcl-2 or Bcl-XL Targeting Ligands wherein R is the point at which the Linker is attached.

Figure 2X:
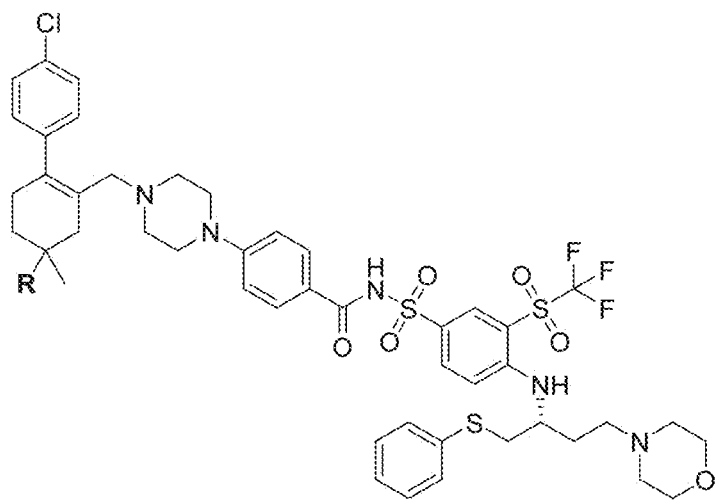
Figure 2X:
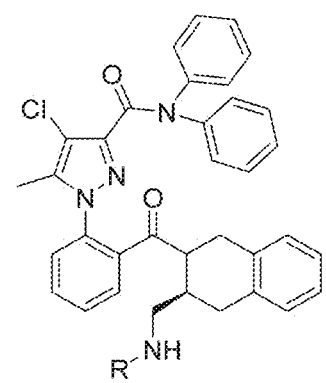

FIG. 2X-2NN present examples of BCL2 Targeting Ligands wherein R is the point at which the Linker is attached. For additional examples and related ligands, see, Toure B. B. et al. "The role of the acidity of N-heteroaryl sulfonamides as inhibitors of bcl-2 family protein-protein interactions." *ACS Med Chem Lett*, 4: 186-190 (2013); Porter J. e.t al. "Tetrahydroisoquinoline Amide Substituted Phenyl Pyrazoles as Selective Bcl-2 Inhibitors" *Bioorg. Med. Chem. Lett.* 19: 230 (2009); Souers A. J. et al. "ABT-199 a potent and selective BCL-2 inhibitor achieves antitumor activity while sparing platelets." *Nature Med.* 19: 202-208 (2013); Angelo Aguilar et al. "A Potent and Highly Efficacious Bcl-2/Bcl-xL Inhibitor" *J Med Chem.* 56(7): 3048-3067 (2013); Longchuan Bai et al. "BM-1197: A Novel and Specific Bcl-2/Bcl-xL Inhibitor Inducing Complete and Long-Lasting Tumor Regression In Vivo" *PLoS ONE* 9(6): e99404; Fariba Ne'matil et al. "Targeting Bcl-2/

Bcl-XL Induces Antitumor Activity in Uveal Melanoma Patient-Derived Xenografts" *PLoS ONE* 9(1): e80836; WO2015011396 titled "Novel derivatives of indole and pyrrole method for the production thereof and pharmaceutical compositions containing same"; WO2008060569A1 titled "Compounds and methods for inhibiting the interaction of Bcl proteins with binding partners"; "Inhibitors of the anti-apoptotic Bcl-2 proteins: a patent review" *Expert Opin. Ther. Patents* 22(1):2008 (2012); and, Porter et al. "Tetrahydroisoquinoline amide substituted phenyl pyrazoles as selective Bcl-2 inhibitors" *Bioorg Med Chem Lett.,* 19(1): 230-3 (2009).

FIG. 2OO-2UU present examples of BCL-XL Targeting Ligands wherein R is the point at which the Linker is attached. For additional examples and related ligands, see, Zhi-Fu Tao et al. "Discovery of a Potent and Selective BCL-XL Inhibitor with in Vivo Activity" *ACS Med. Chem. Lett.,* 5: 1088-1093 (2014); Joel D. Leverson et al. "Exploiting selective BCL-2 family inhibitors to dissect cell survival dependencies and define improved strategies for cancer therapy" *Science Translational Medicine,* 7:279ra40 (2015); and, the crystal structure PDB 3ZK6 (Guillaume Lessene et al. "Structure-guided design of a selective BCL-XL inhibitor" *Nature Chemical Biology* 9: 390-397 (2013))

FIG. 2VV presents examples of PPAR-gamma Targeting Ligands wherein R is the point at which the Linker is attached.

FIG. 2WW-2YY present examples of EGFR Targeting Ligands that target the EGFR L858R mutant, including erlotinib, gefitnib, afatinib, neratinib, and dacomitinib, wherein R is the point at which the Linker is attached.

Figure 2Y:
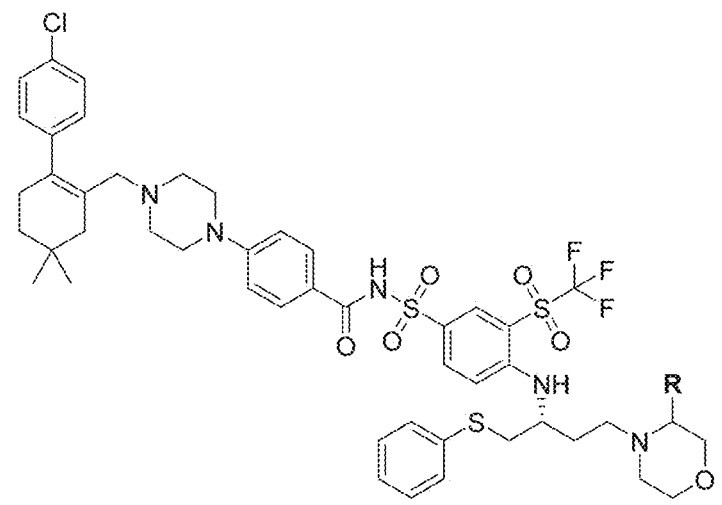
Figure 2Y:
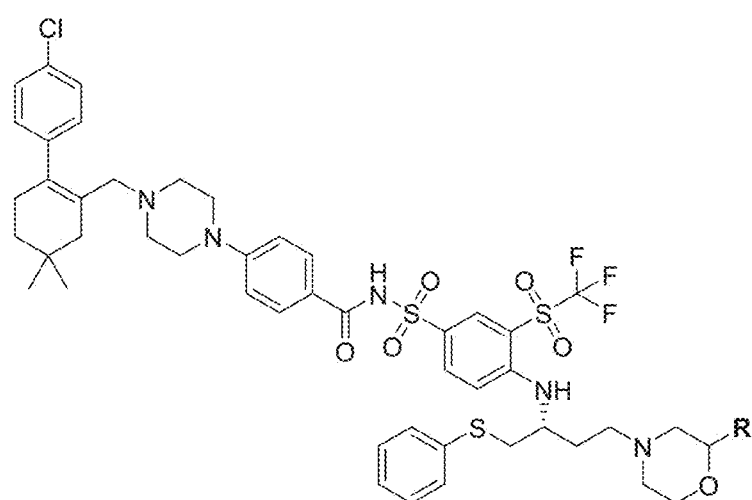
Figure 2Y:
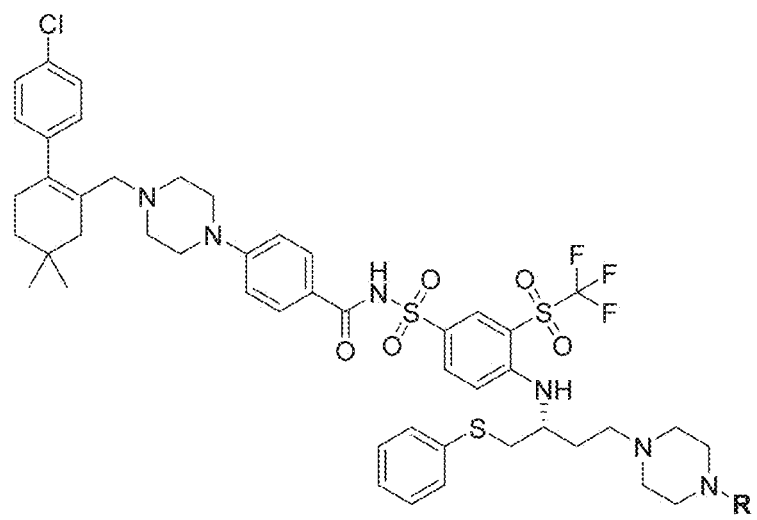
Figure 2Z:
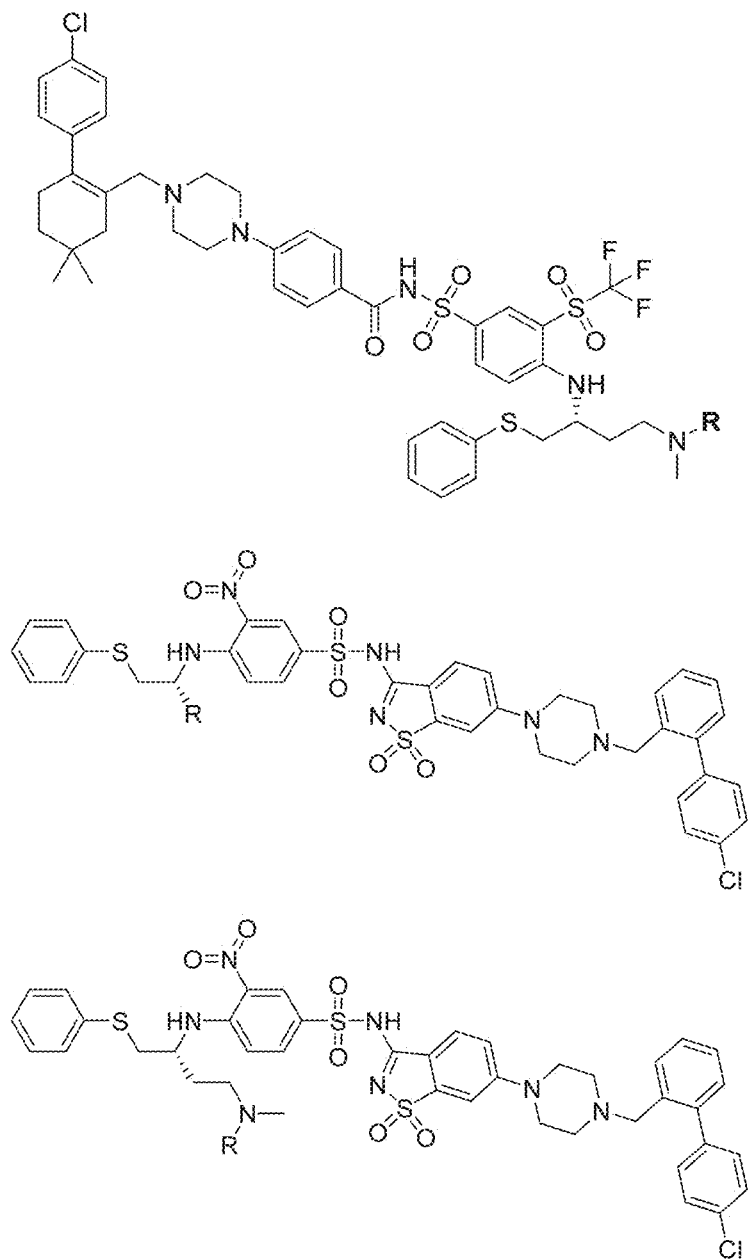
Figure 2A:
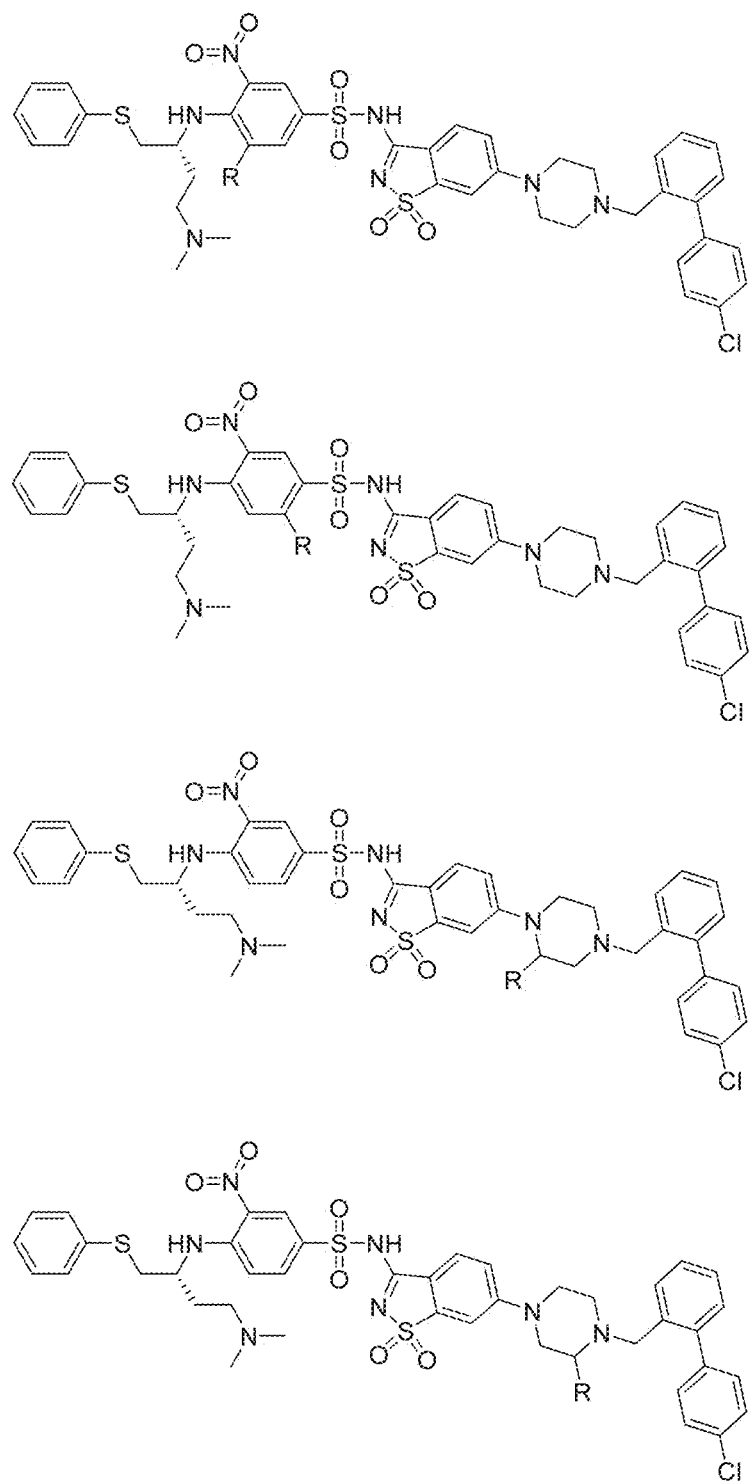
Figure 2B:
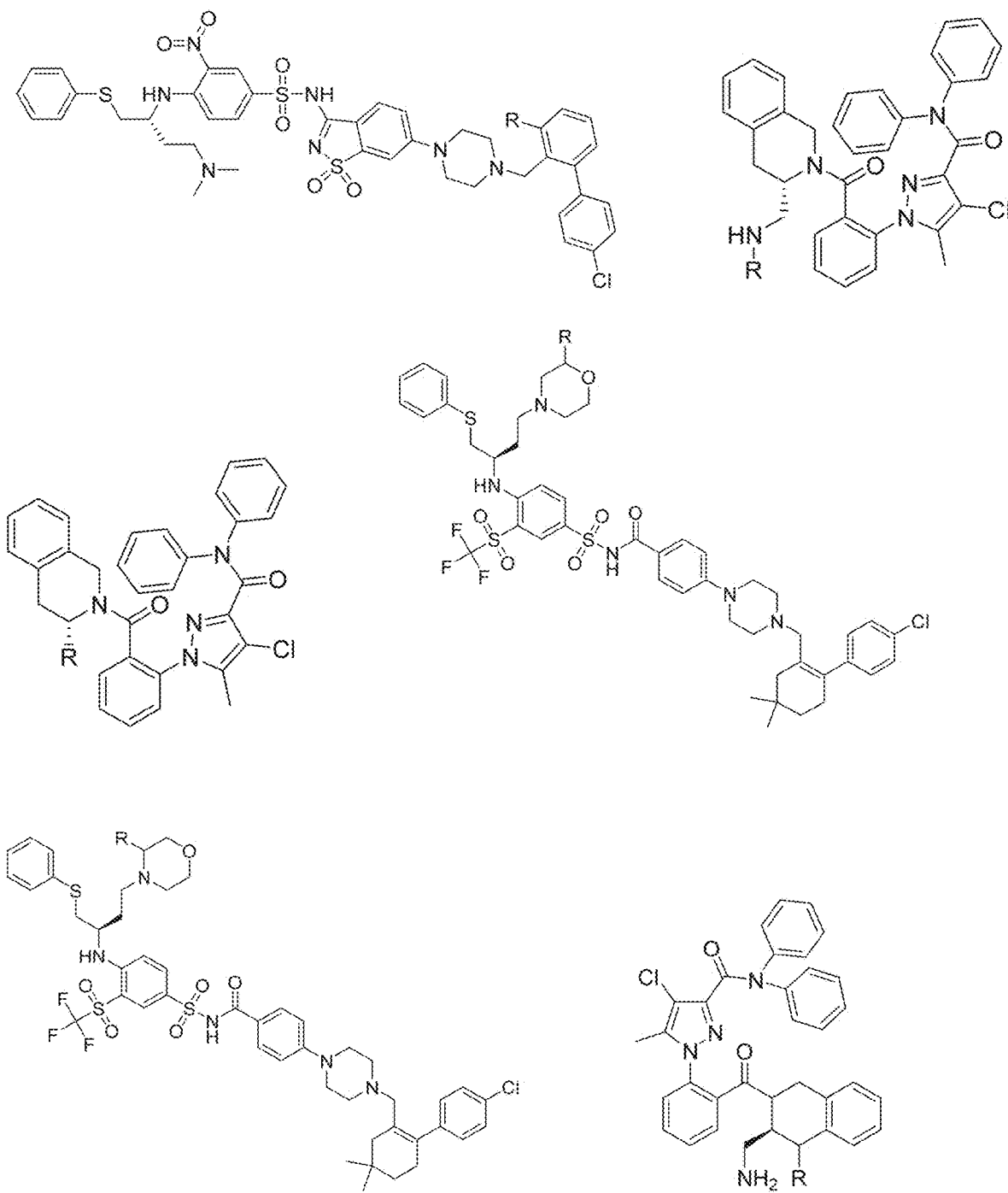
Figure 2C:
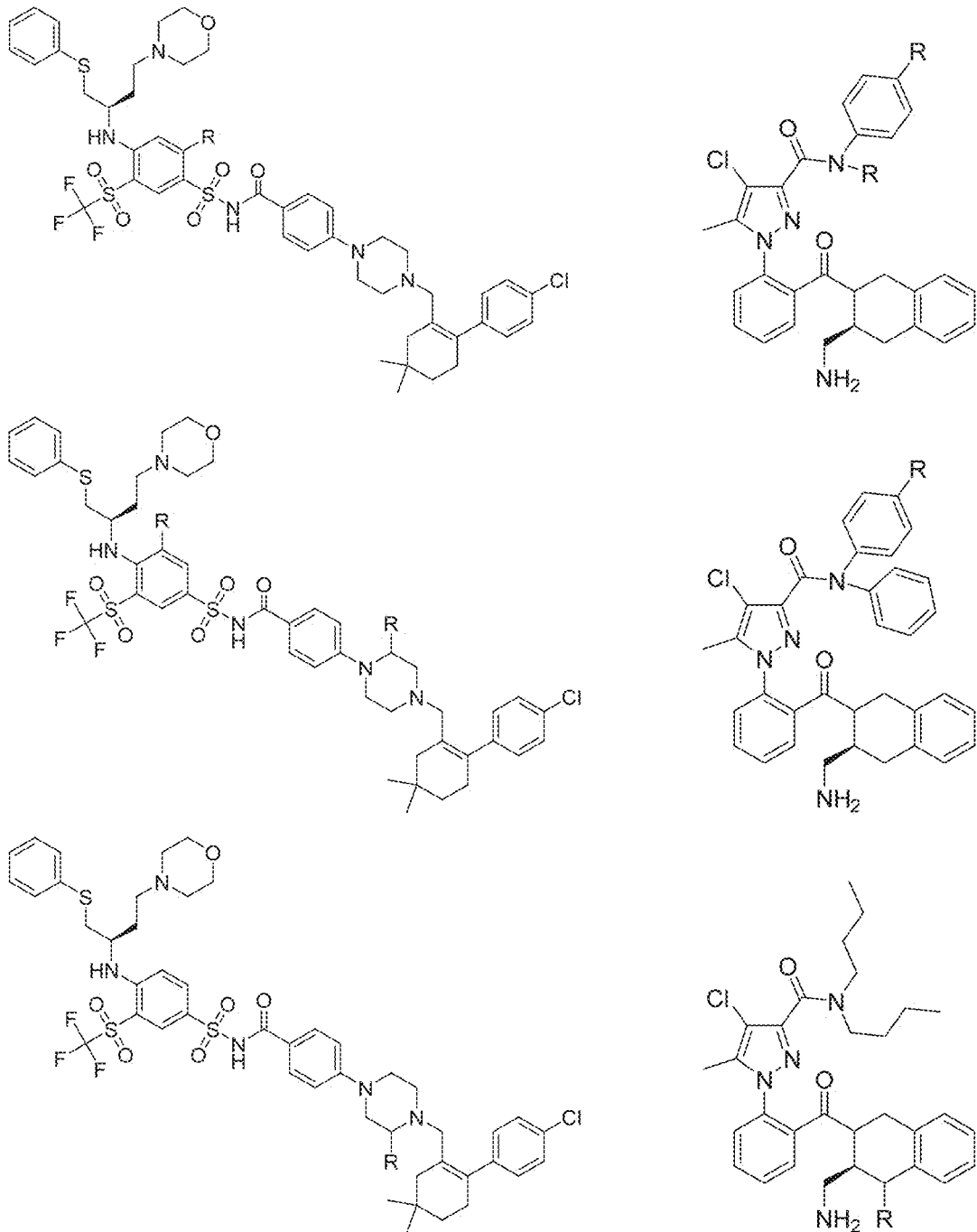
Figure 2D:
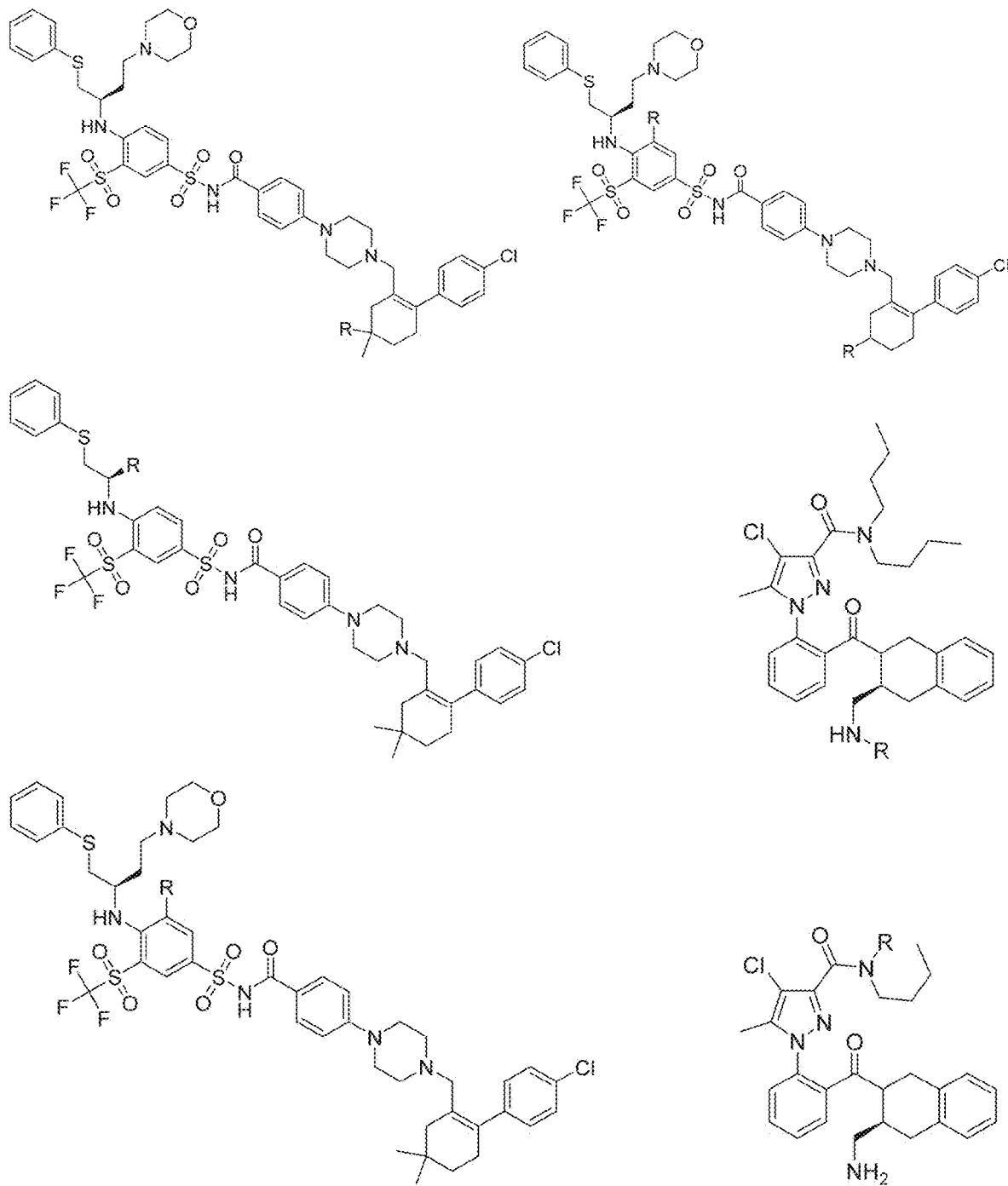
Figure 2E:
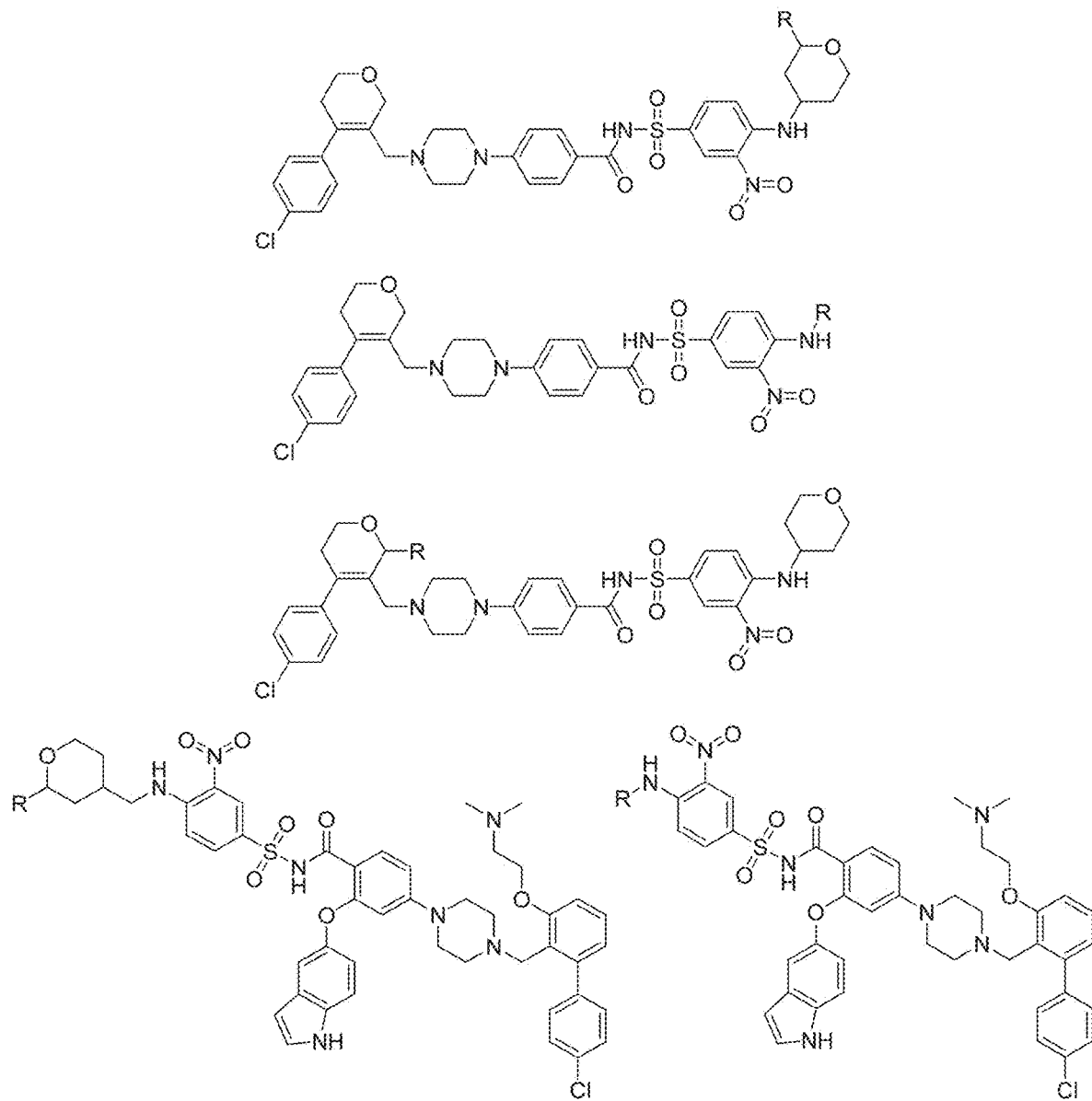
Figure 2F:
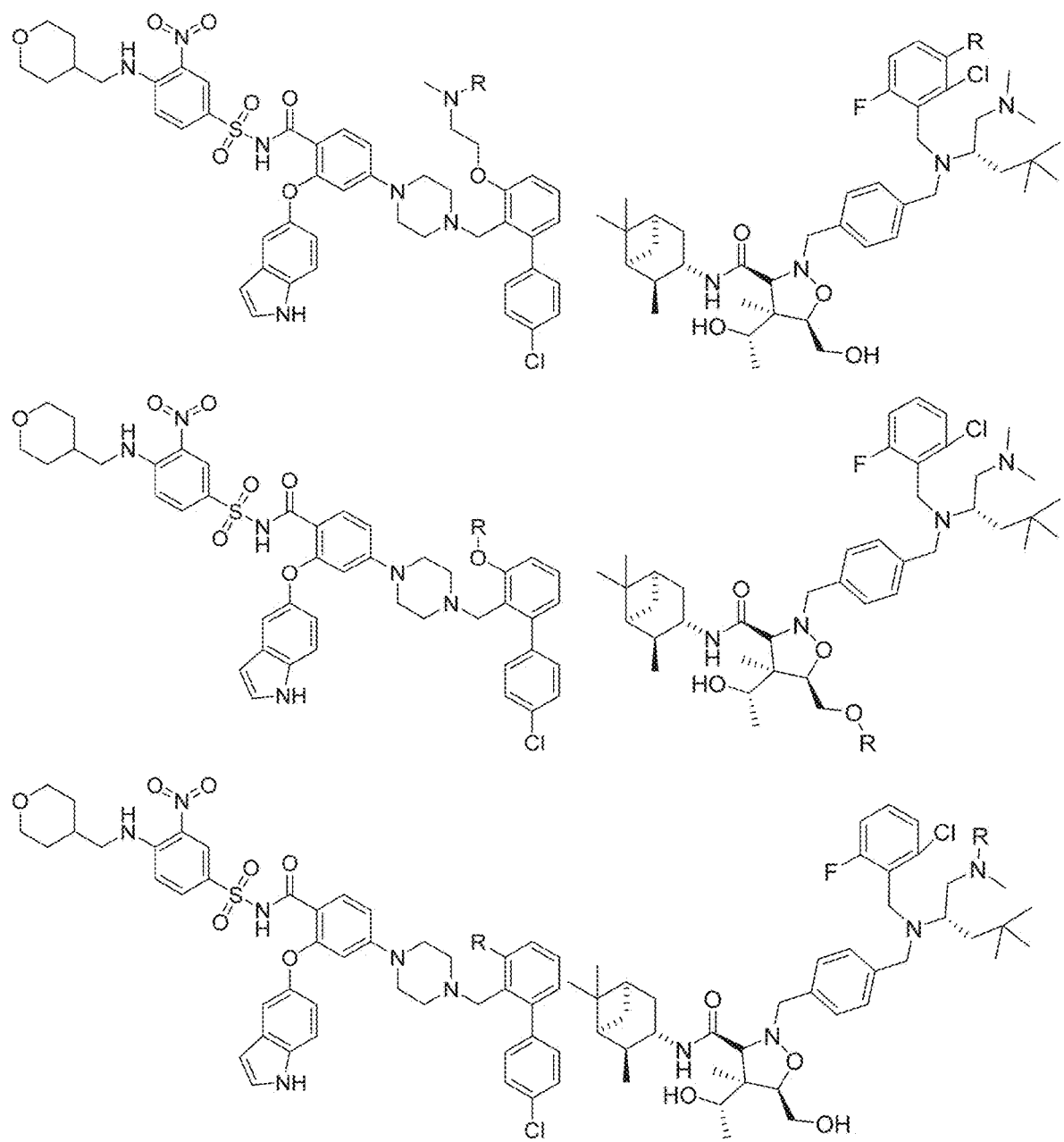
Figure 2G:
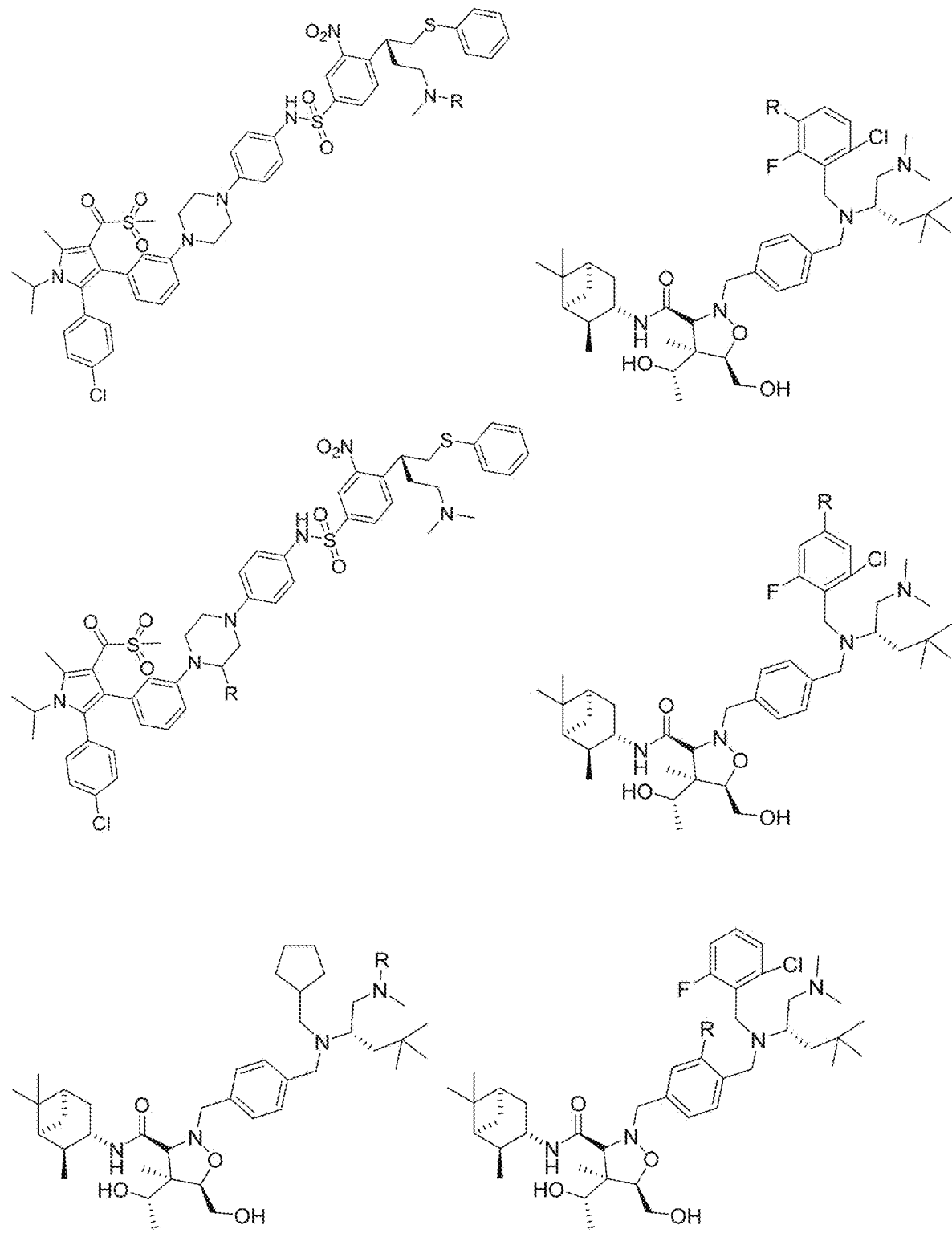
Figure 2H:
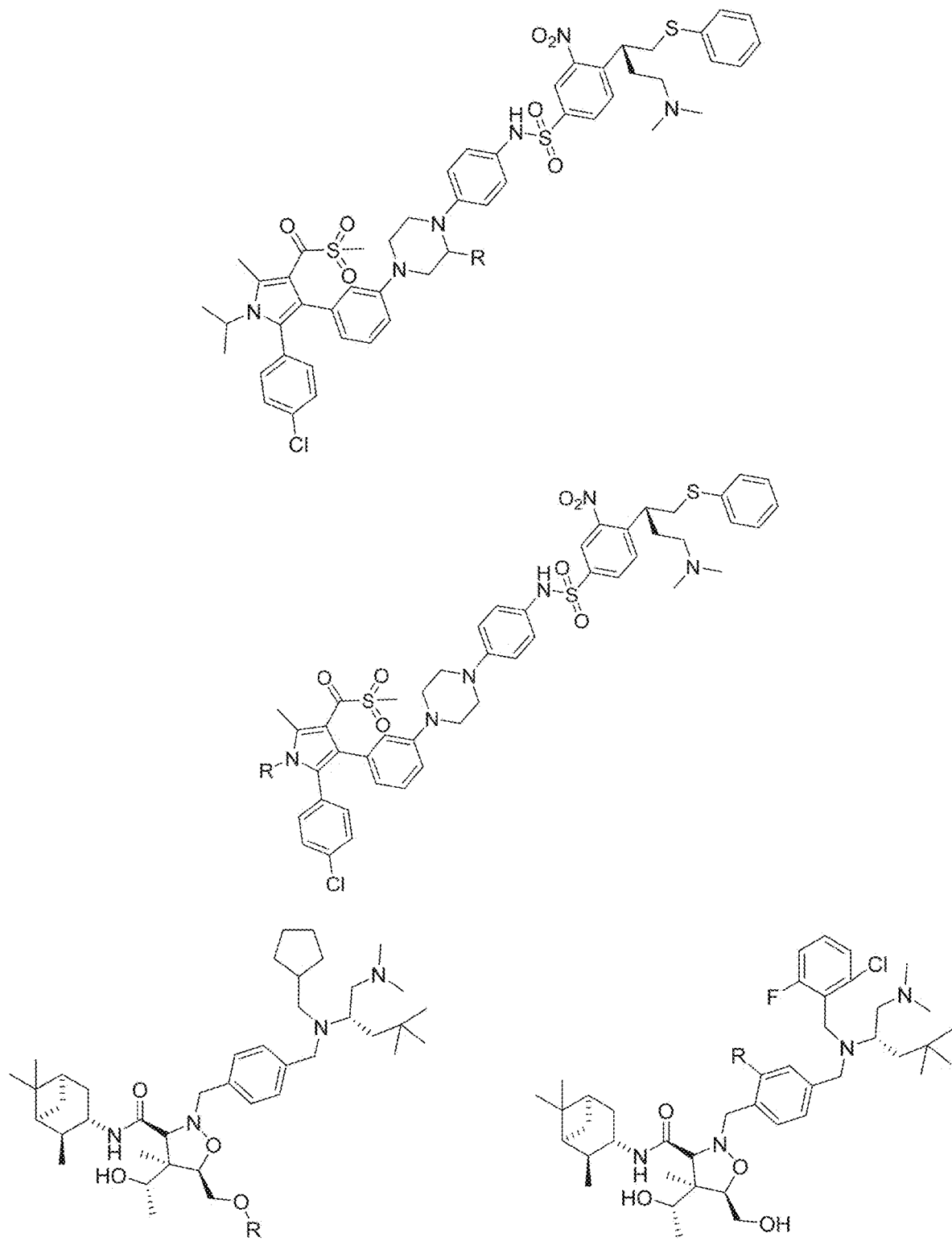
Figure 2I:
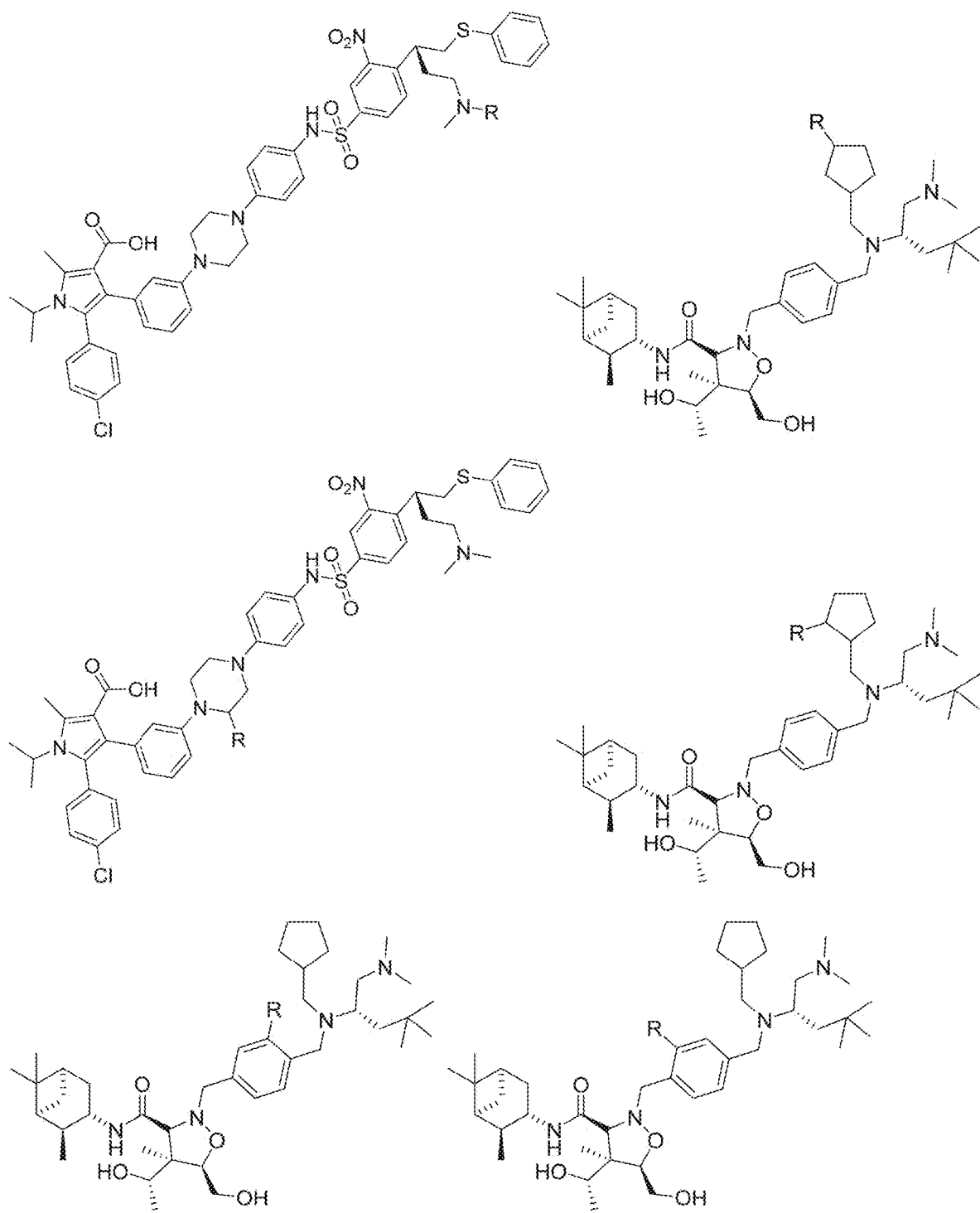
Figure 2J:
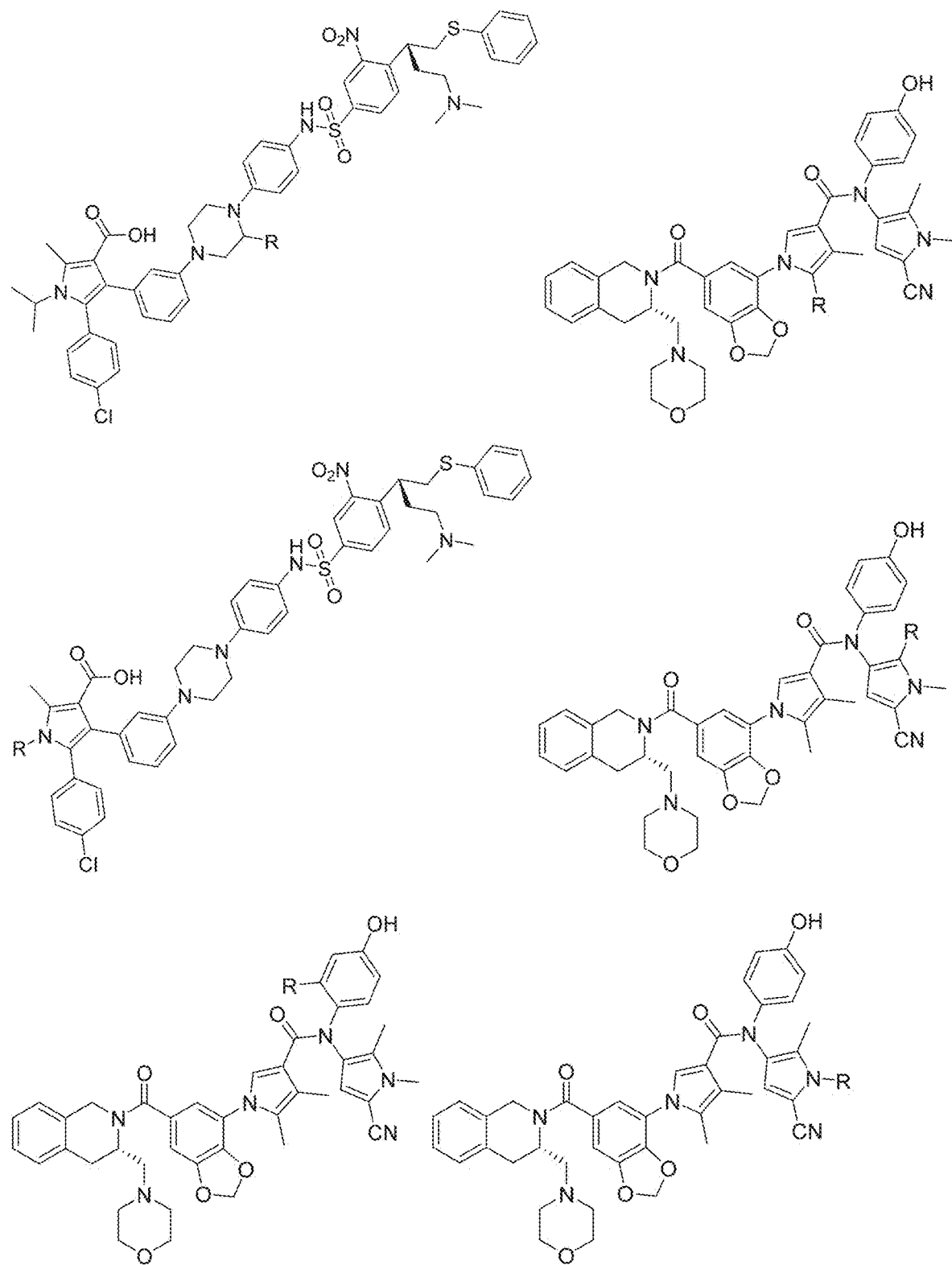
Figure 2K:
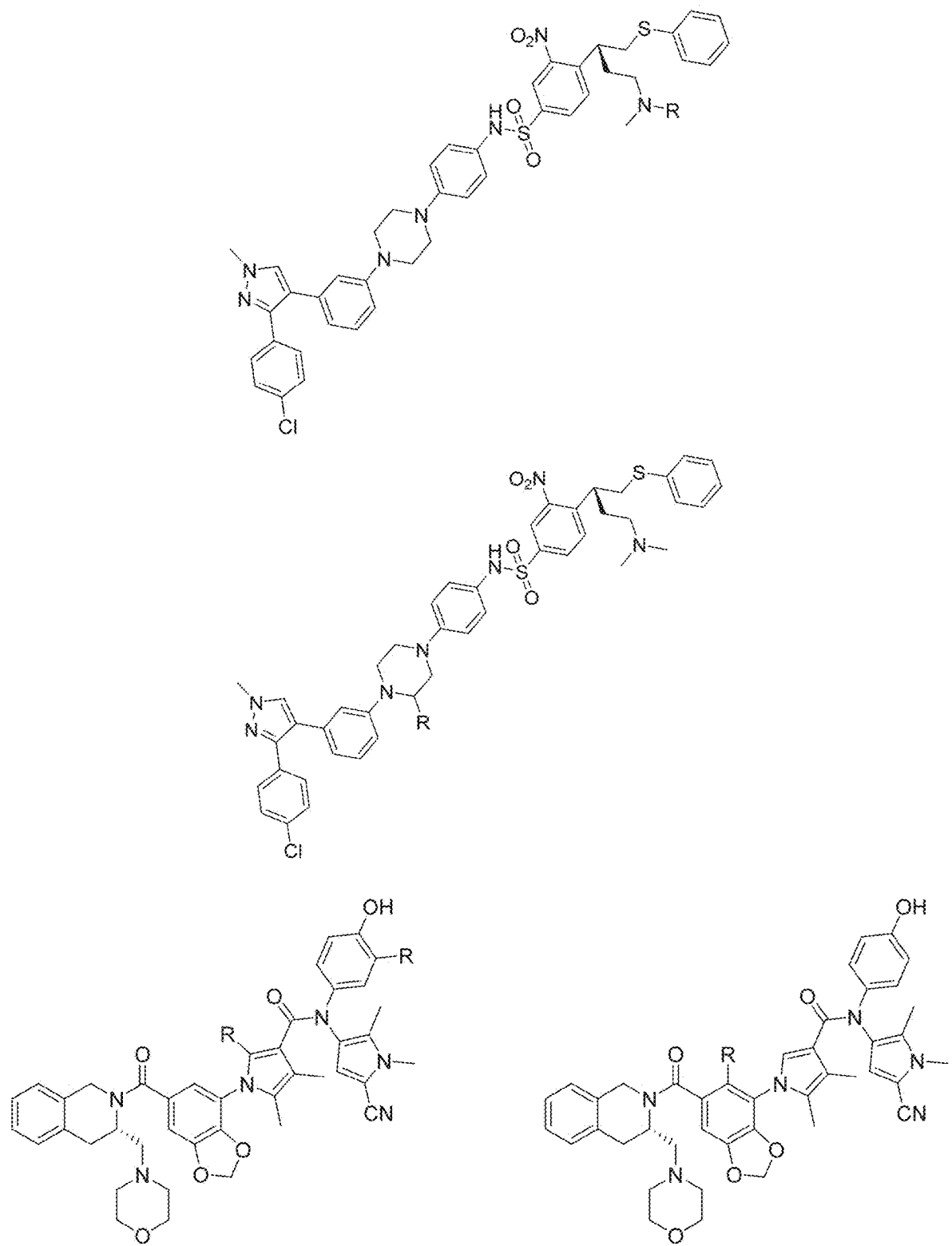
Figure 2L:
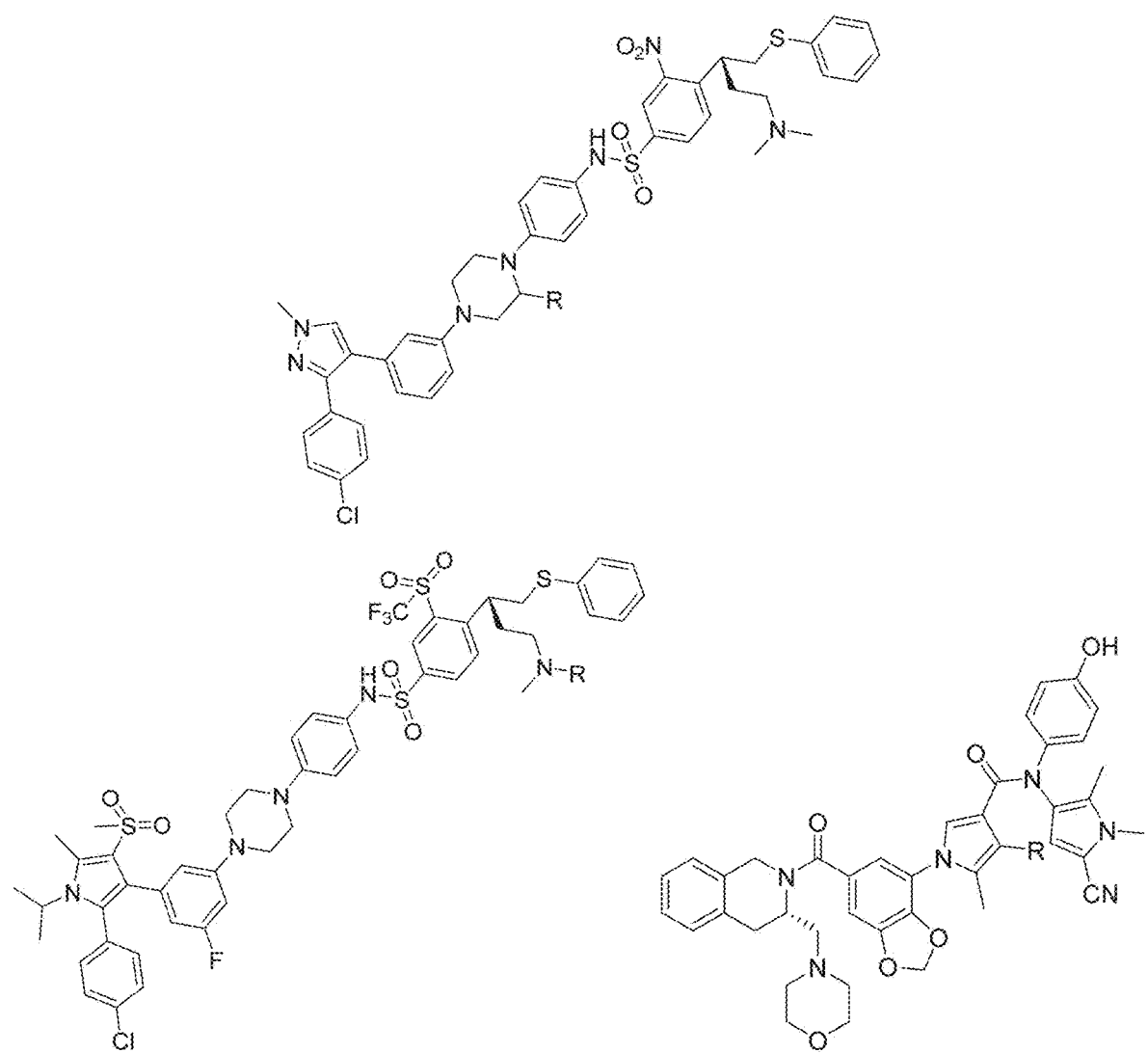
Figure 2M:
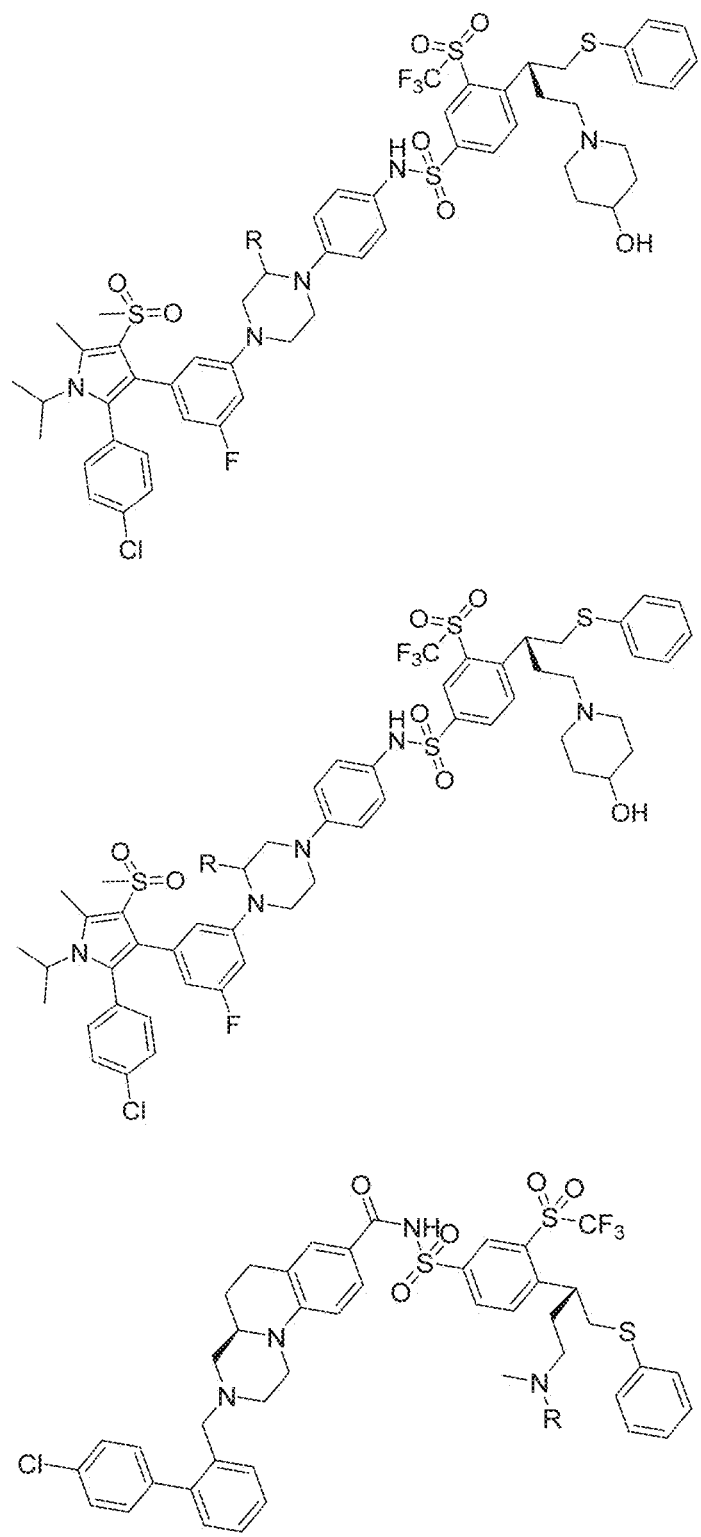
Figure 2N:
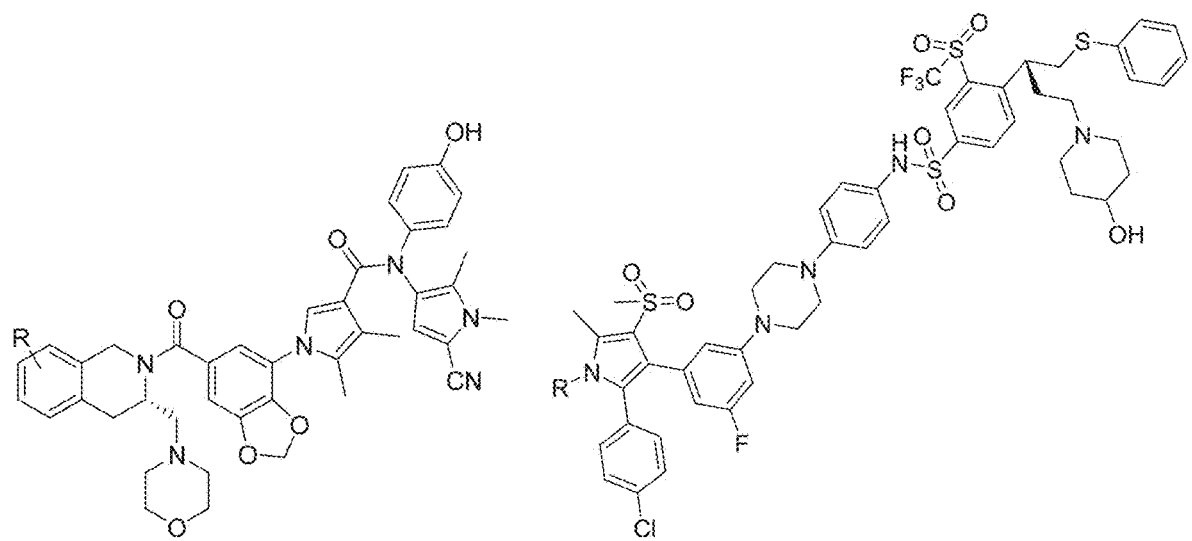
Figure 2O:
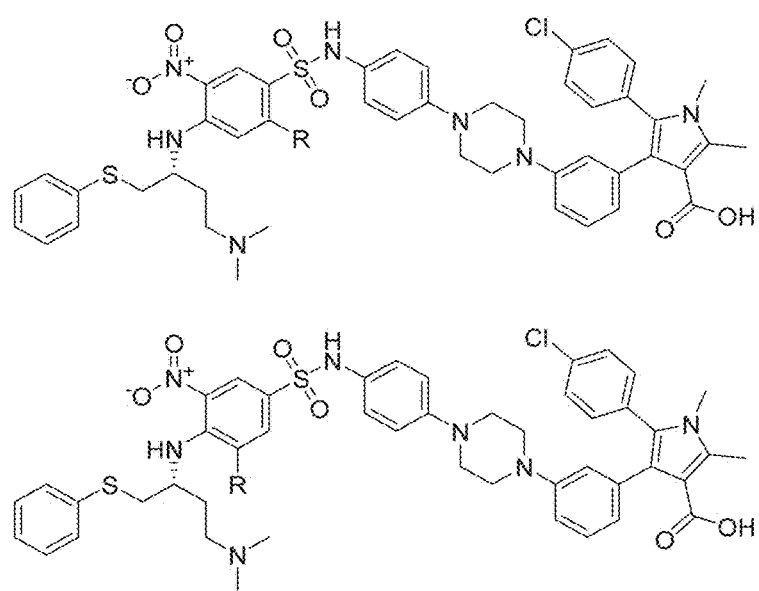
Figure 2P:
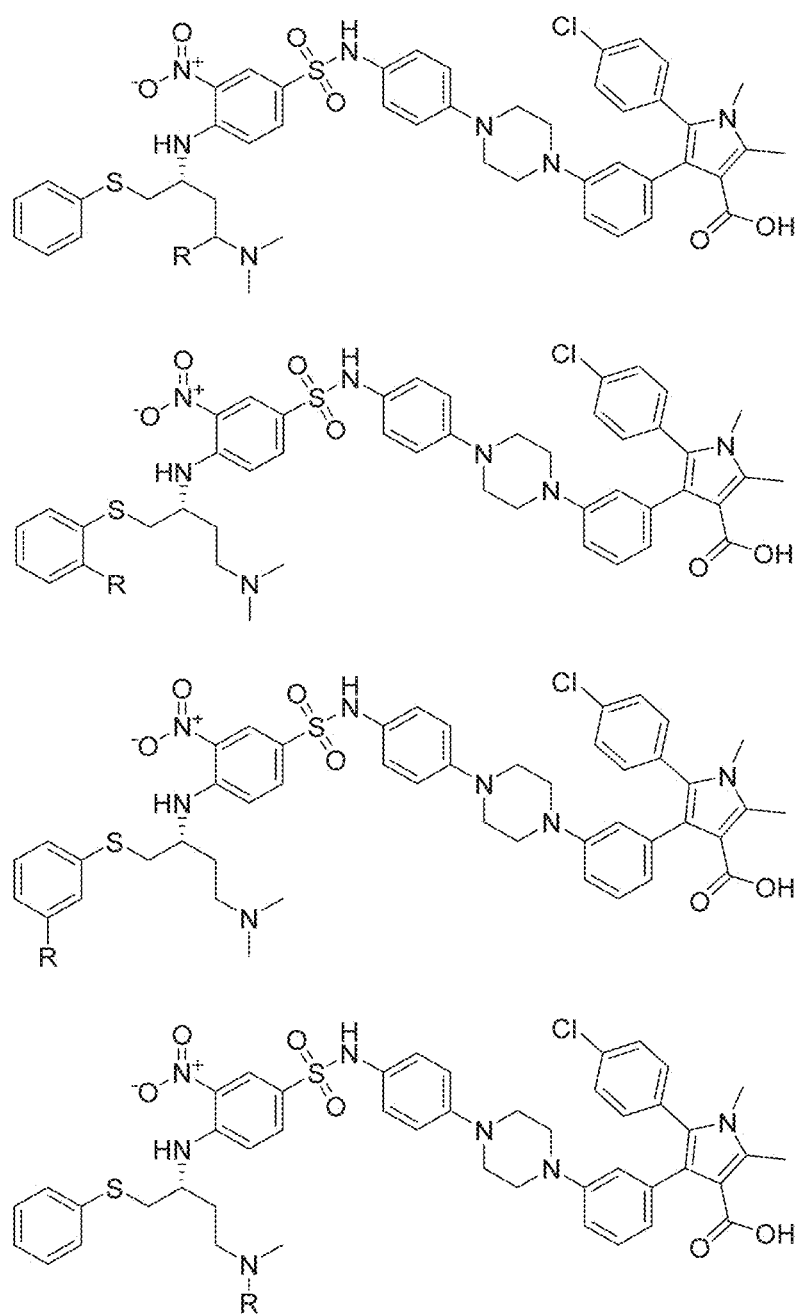
Figure 2Q:
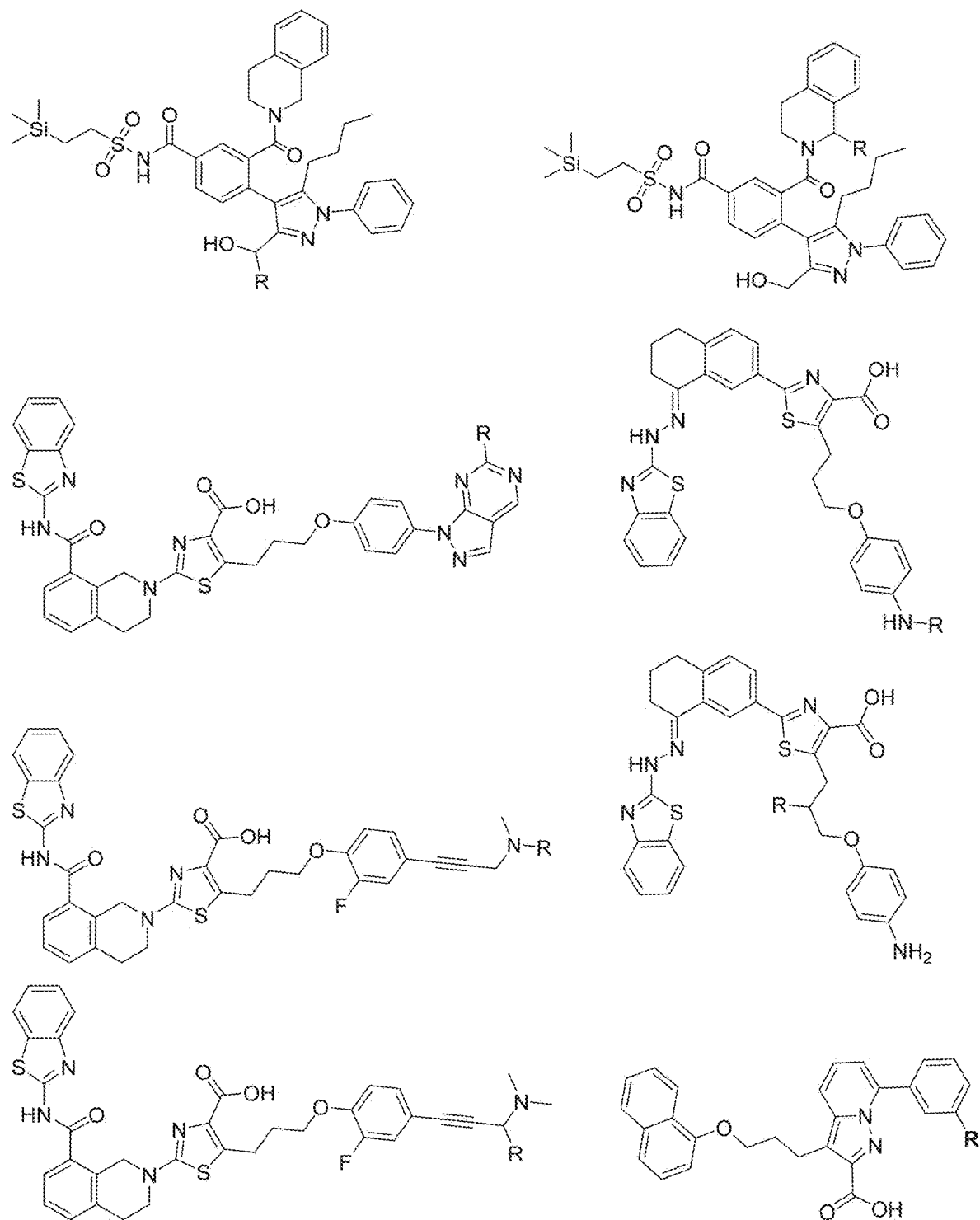
Figure 2R:
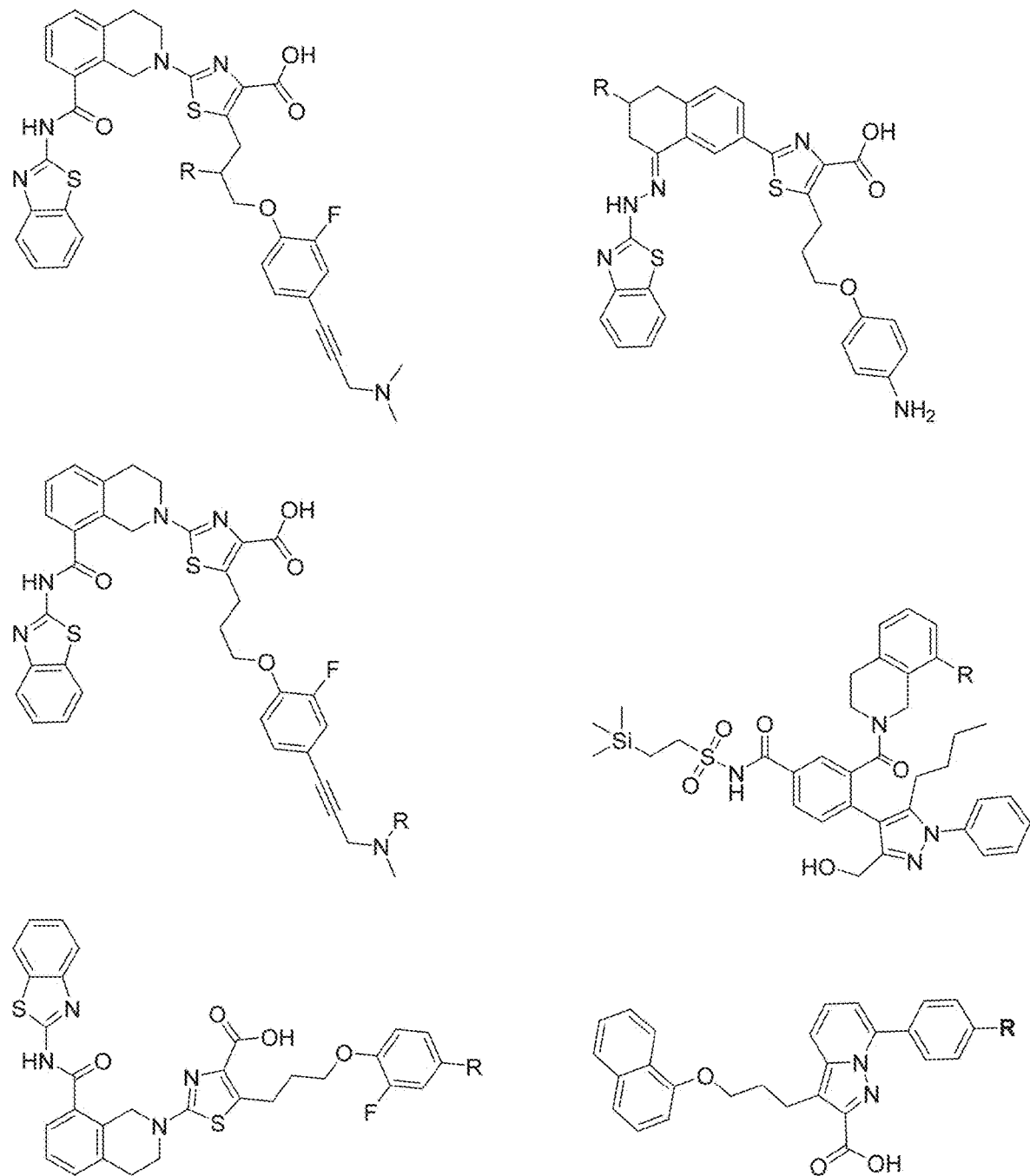
Figure 2S:
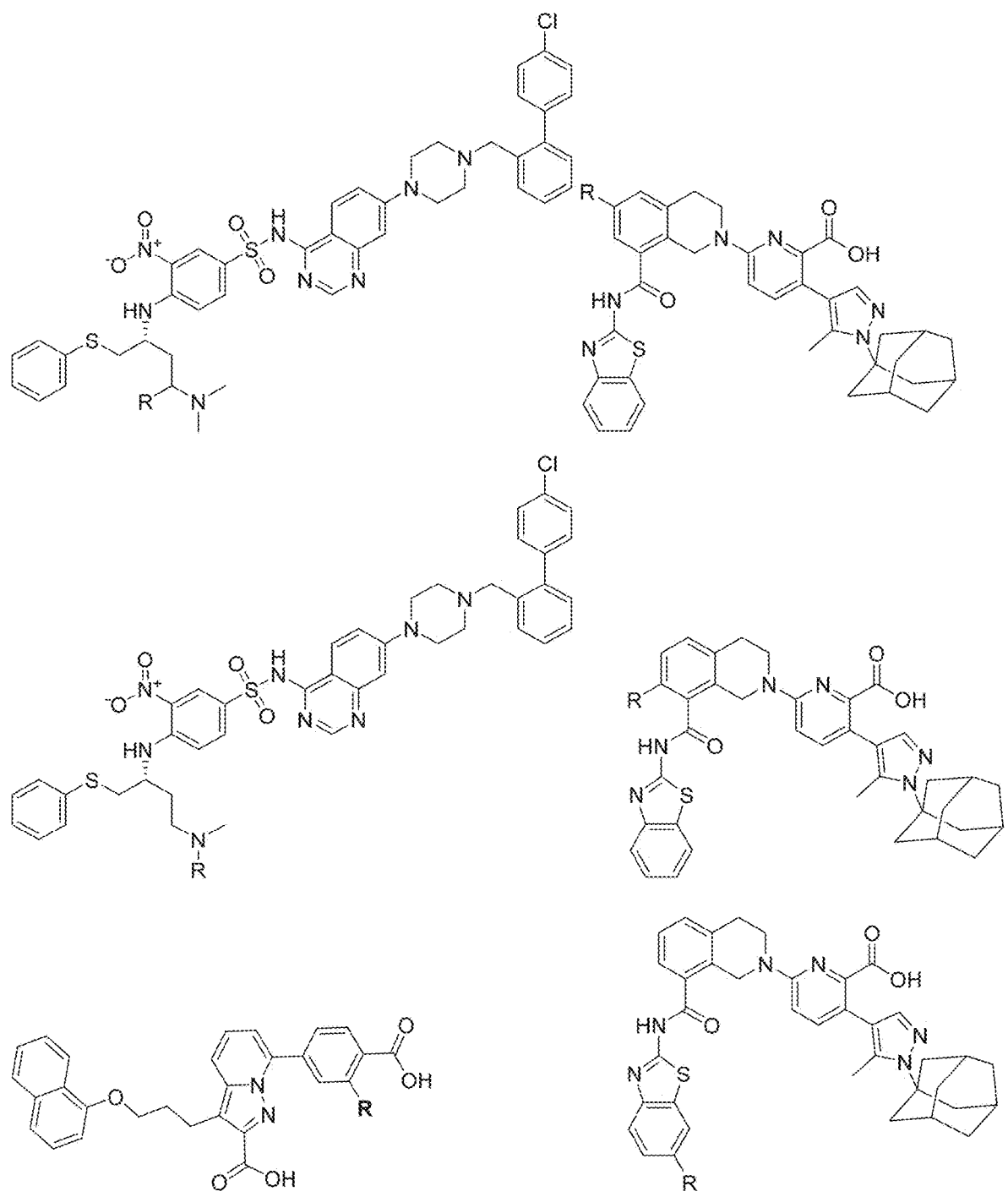
Figure 2T:
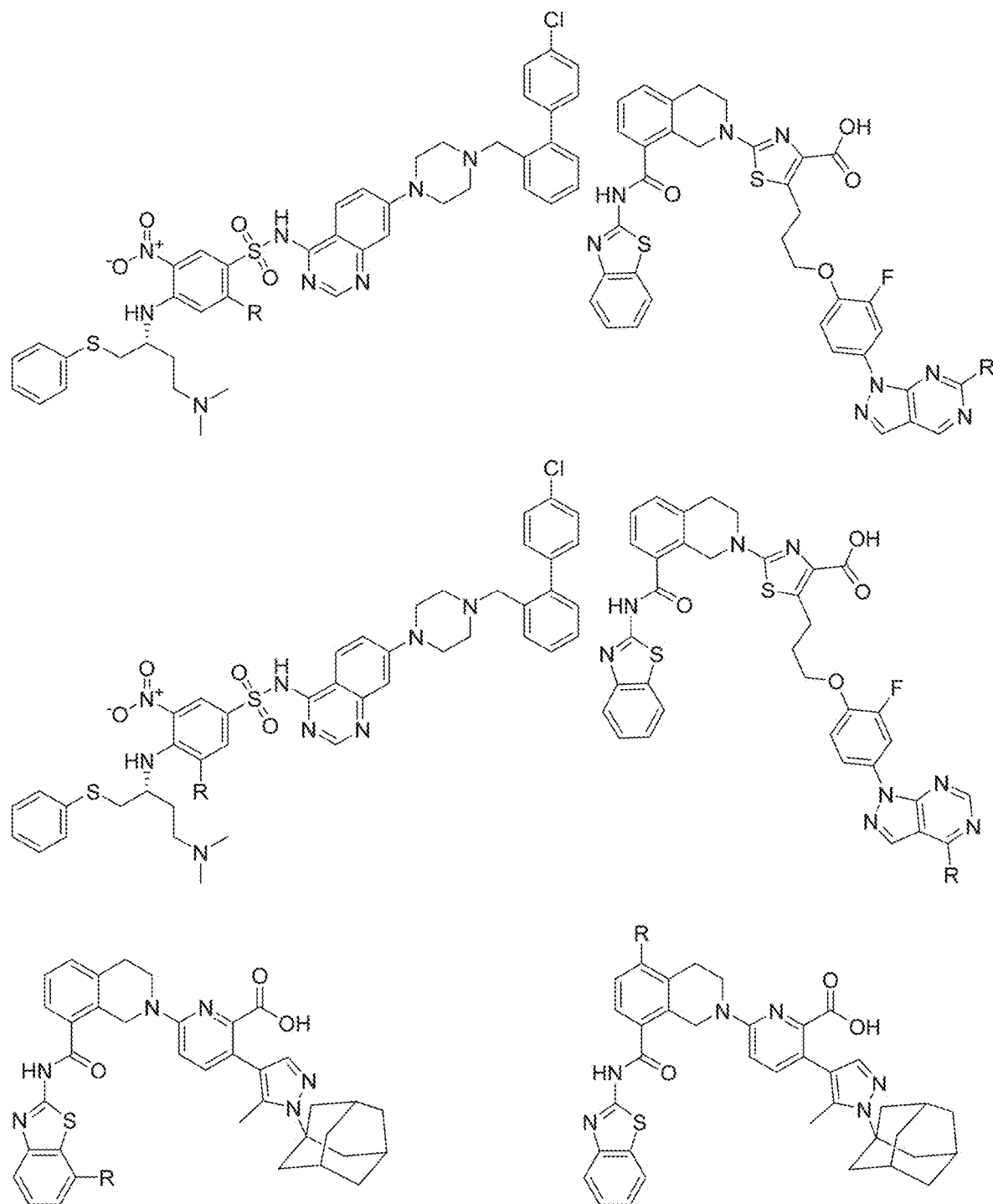
Figure 2U:
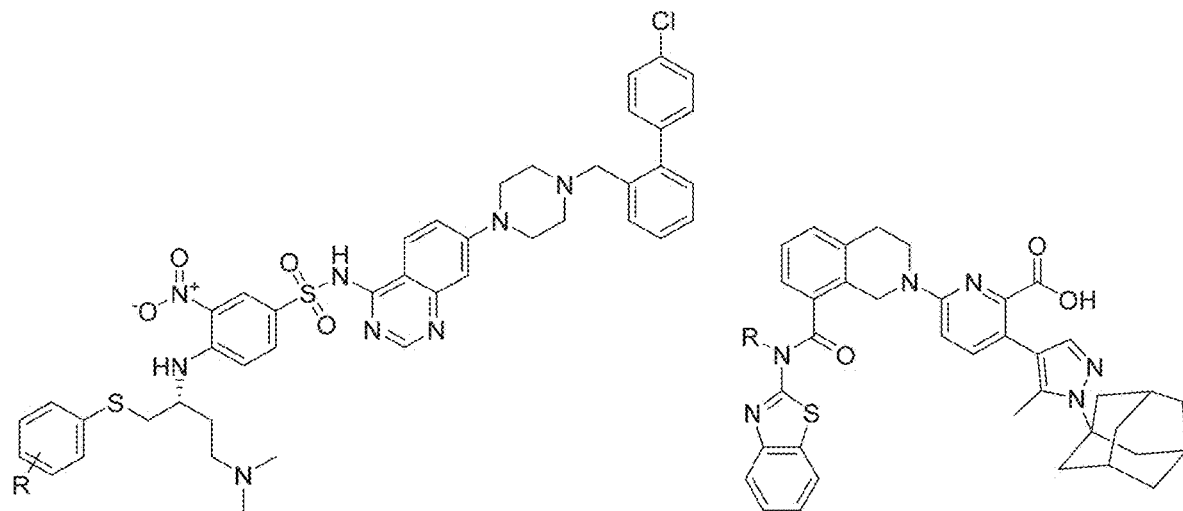
Figure 2U:
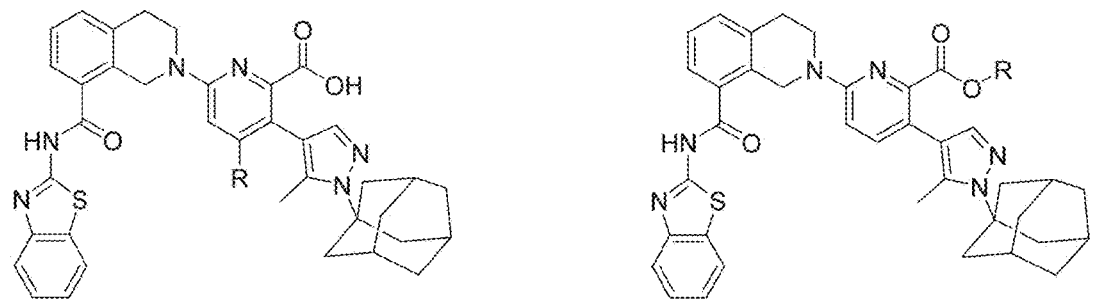
Figure 2V:
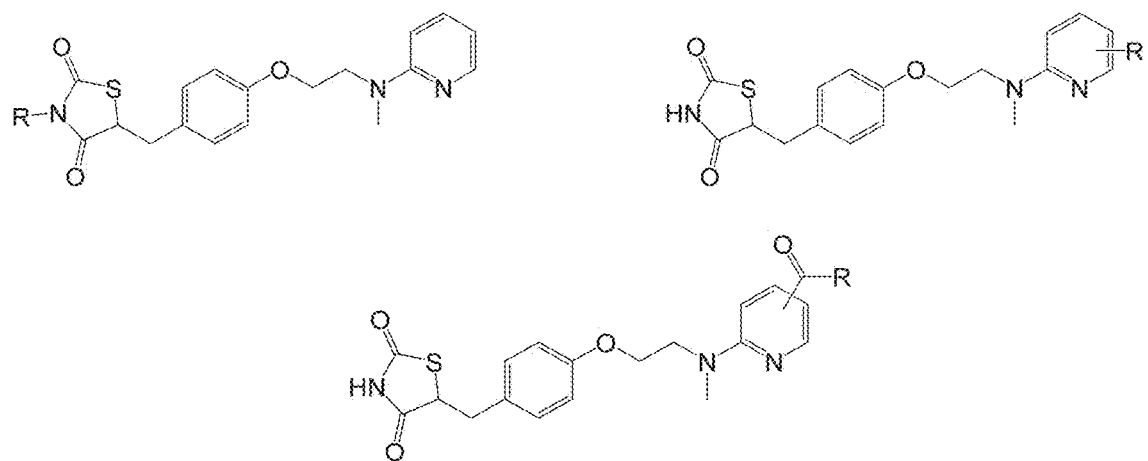
Figure 2W:
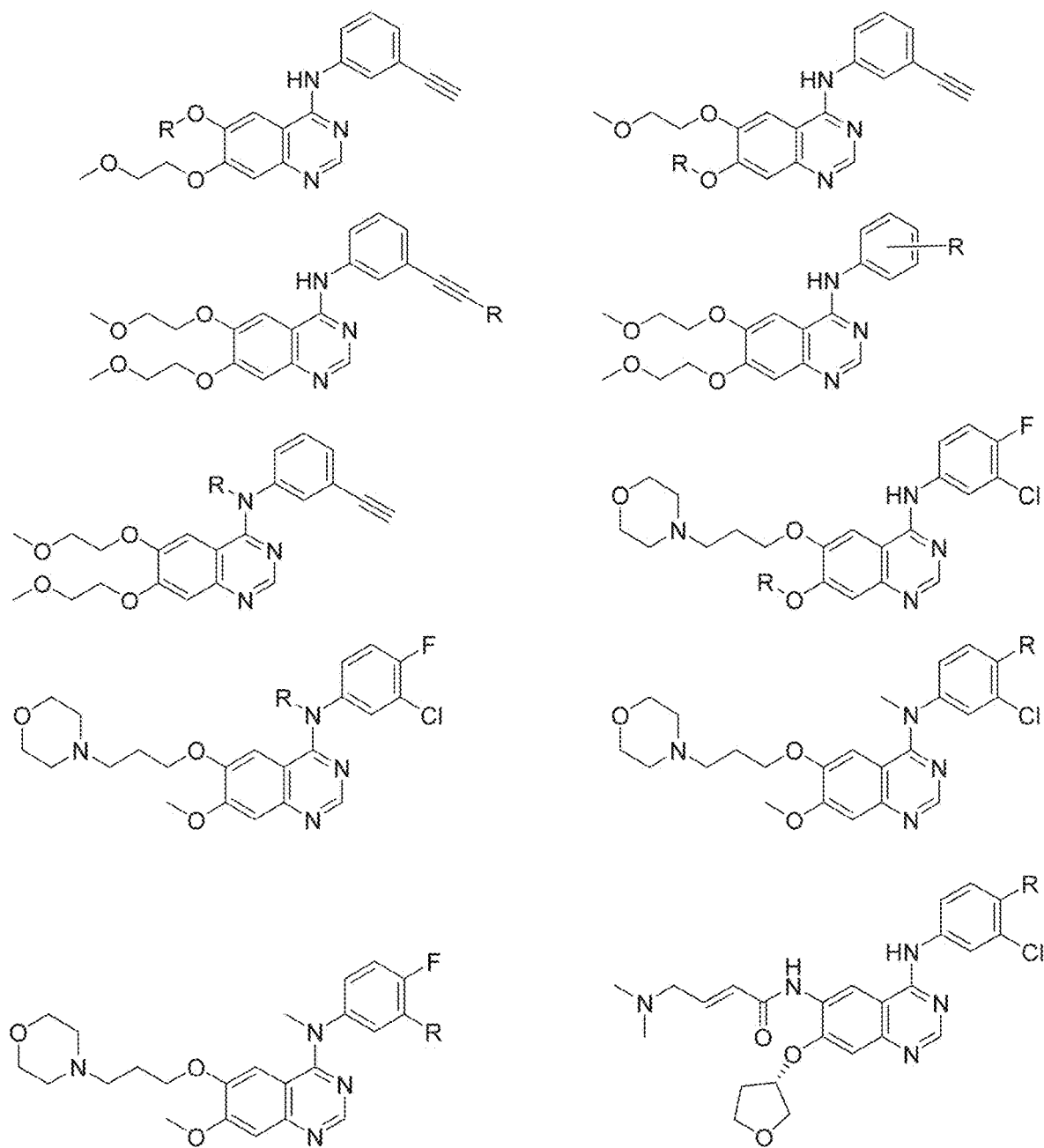
Figure 2X:
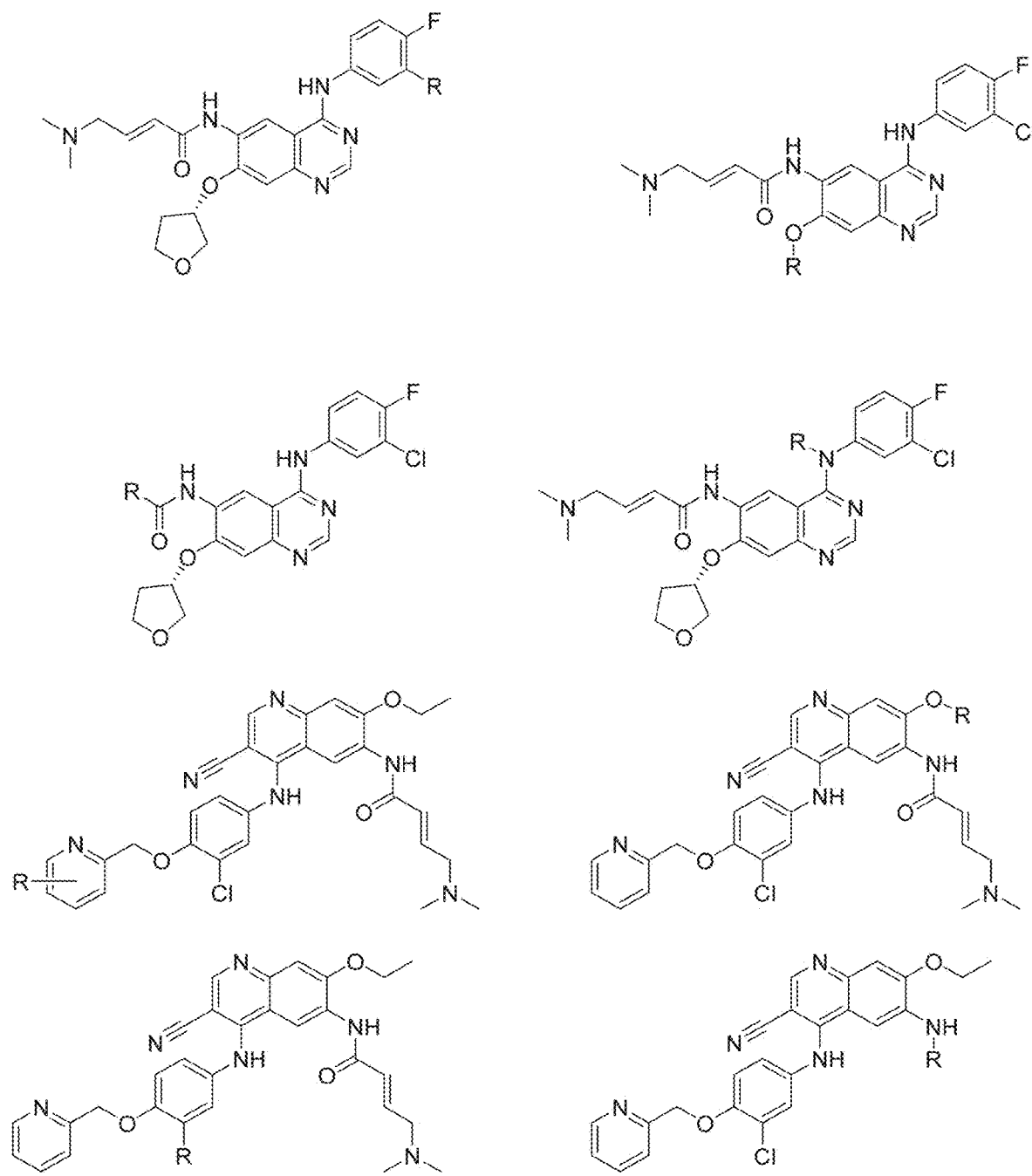
Figure 2Y:
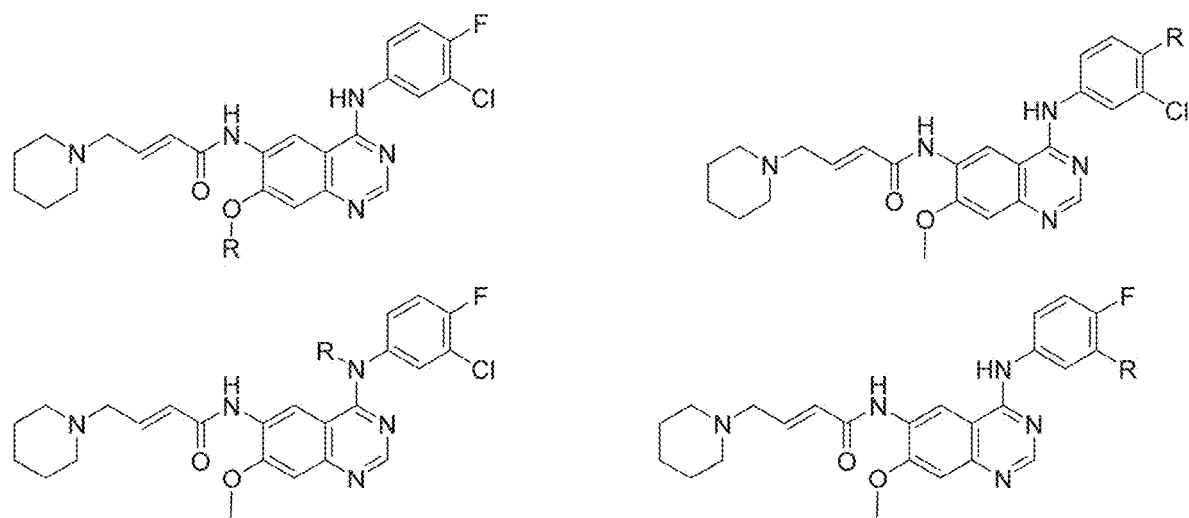
Figure 2Z:
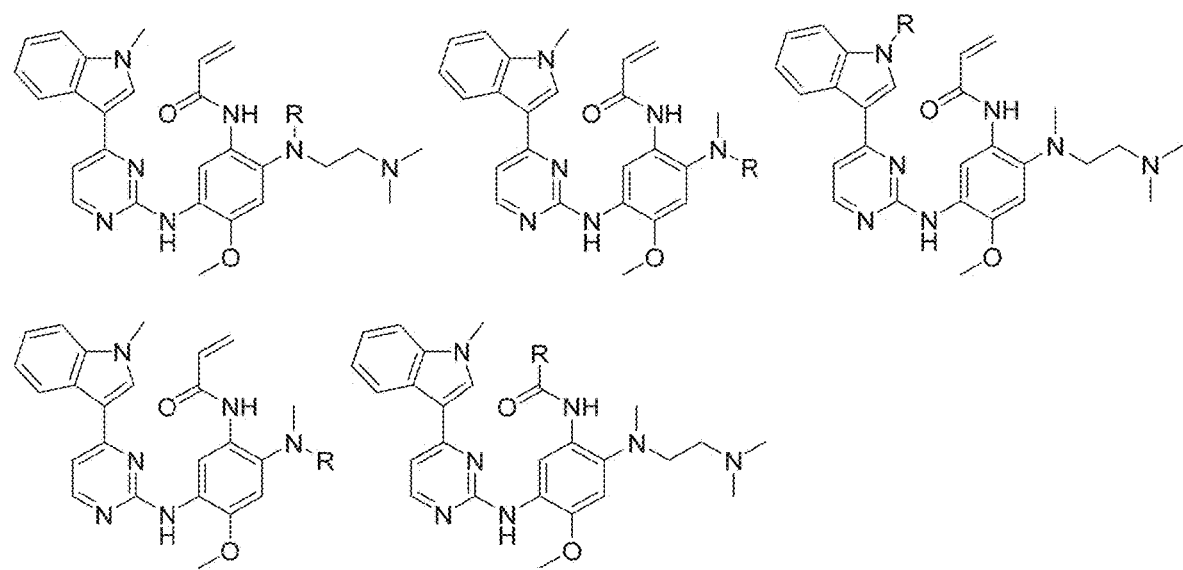

FIG. 2ZZ-2FFF present examples of EGFR Targeting Ligands that target the EGFR T790M mutant, including osimertinib, rociletinib, olmutinib, naquotinib, nazartinib, PF-06747775, Icotinib, Neratinib Avitinib, Tarloxotinib, PF-0645998, Tesevatinib, Transtinib, WZ-3146, WZ8040, and CNX-2006, wherein R is the point at which the Linker is attached.

FIG. 2GGG presents examples of EGFR Targeting Ligands that target the EGFR C797S mutant, including EAI045, wherein R is the point at which the Linker is attached.

FIG. 2HHH presents examples of BCR-ABL Targeting Ligands that target the BCR-ABL T315I mutantm including Nilotinib and Dasatinib, wherein R is the point at which the Linker is attached. See for example, the crystal structure PDB 3CS9.

FIG. 2III presents examples of Targeting Ligands that target BCR-ABL, including Nilotinib, Dasatinib Ponatinib and Bosutinib, wherein R is the point at which the Linker is attached.

FIG. 2JJJ-2KKK present examples of ALK Targeting Ligands that target the ALK L1196M mutant including Ceritinib, wherein R is the point at which the Linker is attached. See for example, the crystal structure PDB 4MKC.

FIG. 2LLL presents examples of JAK2 Targeting Ligands that target the JAK2V617F mutant, including Ruxolitinib, wherein R is the point at which the Linker is attached.

FIG. 2MMM presents examples of BRAF Targeting Ligands that target the BRAF V600E mutant including Vemurafenib, wherein R is the point at which the Linker is attached. For additional examples and related ligands, see, the crystal structure PBD 3OG7.

FIG. 2NNN presents examples of BRAF Targeting Ligands, including Dabrafenib, wherein R is the point at which the Linker is attached.

FIG. 2OOO presents examples of LRRK2 Targeting Ligands that target the LRRK2 R1441C mutant wherein R is the point at which the Linker is attached.

FIG. 2PPP presents examples of LRRK2 Targeting Ligands that target the LRRK2 G2019S mutant wherein R is the point at which the Linker is attached.

FIG. 2QQQ presents examples of LRRK2 Targeting Ligands that target the LRRK2 I2020T mutant wherein R is the point at which the Linker is attached.

FIG. 2RRR-2TTT present examples of PDGFRα Targeting Ligands that target the PDGFRα T674I mutant, including AG-1478, CHEMBL94431, Dovitinib, erlotinib, gefitinib, imatinib, Janex 1, Pazopanib, PD153035, Sorafenib, Sunitinib, and WHI-P180, wherein R is the point at which the Linker is attached.

FIG. 2UUU presents examples of RET Targeting Ligands that target the RET G691S mutant, including tozasertib, wherein R is the point at which the Linker is attached.

FIG. 2VVV presents examples of RET Targeting Ligands that target the RET R749T mutant, including tozasertib, wherein R is the point at which the Linker is attached.

FIG. 2WWW presents examples of RET Targeting Ligands that target the RET E762Q mutant, including tozasertib, wherein R is the point at which the Linker is attached.

FIG. 2XXX presents examples of RET Targeting Ligands that target the RET Y791F mutant, including tozasertib, wherein R is the point at which the Linker is attached.

FIG. 2YYY presents examples of RET Targeting Ligands that target the RET V804M mutant, including tozasertib, wherein R is the point at which the Linker is attached.

FIG. 2ZZZ presents examples of RET Targeting Ligands that target the RET M918T mutant, including tozasertib, wherein R is the point at which the Linker is attached.

FIG. 2AAAA presents examples of Fatty Acid Binding Protein Targeting Ligands wherein R is the point at which the Linker is attached.

FIG. 2BBBB presents examples of 5-Lipoxygenase Activating Protein (FLAP) Targeting Ligands wherein R is the point at which the Linker is attached.

FIG. 2CCCC presents examples of Kringle Domain V 4BVV Targeting Ligands wherein R is the point at which the Linker is attached.

FIG. 2DDDD presents examples of Lactoylglutathione Lyase Targeting Ligands wherein R is the point at which the Linker is attached.

FIG. 2EEEE-2FFFF present examples of mPGES-1 Targeting Ligands wherein R is the point at which the Linker is attached.

FIG. 2GGGG-2JJJJ present examples of Factor Xa Targeting Ligands wherein R is the point at which the Linker is attached. For additional examples and related ligands, see, Maignan S. et al. "Crystal structures of human factor Xa complexed with potent inhibitors." *J. Med. Chem.* 43: 3226-3232 (2000); Matsusue T. et al. "Factor Xa Specific Inhibitor that Induces the Novel Binding Model in Complex with Human Fxa." (to be published); the crystal structures PDB 1iqh, 1iqi, 1iqk, and 1iqm; Adler M. et al. "Crystal Structures of Two Potent Nonamidine Inhibitors Bound to Factor Xa." *Biochemistry* 41: 15514-15523 (2002); Roehrig S. et al. "Discovery of the Novel Antithrombotic Agent 5-Chloro-N-({(5S)-2-Oxo-3-[4-(3-Oxomorpholin-4-Yl)Phenyl]-1 3-Oxazolidin-5-Y1}Methyl)Thiophene-2-Carboxamide (Bay 59-7939): An Oral Direct Factor Xa Inhibitor." *J. Med. Chem.* 48: 5900 (2005); Anselm L. et al. "Discovery of a Factor Xa Inhibitor (3R 4R)-1-(2 2-Difluoro-Ethyl)-Pyrrolidine-3 4-Dicarboxylic Acid 3-[(5-Chloro-Pyridin-2-Yl)-Amide] 4-{[2-Fluoro-4-(2-Oxo-2H-Pyridin-1-Yl)-Phenyl]-

Amide} as a Clinical Candidate." *Bioorg. Med. Chem.* 20: 5313 (2010); and, Pinto D. J. et al. "Discovery of 1-(4-Methoxyphenyl)-7-oxo-6-(4-(2-oxopiperidin-1-yl)phenyl)-4 5 6 7-tetrahydro-1H-pyrazolo[3 4-c]pyridine-3-carboxamide (Apixaban BMS-562247) a Highly Potent Selective Efficacious and Orally Bioavailable Inhibitor of Blood Coagulation Factor Xa." *J. Med. Chem.* 50: 5339-5356 (2007).

FIG. 2KKKK presents examples of Kallikrein 7 Targeting Ligands wherein R is the point at which the Linker is attached. For additional examples and related ligands, see, Maibaum J. et al. "Small-molecule factor D inhibitors targeting the alternative complement pathway." *Nat. Chem. Biol.* 12: 1105-1110 (2016).

FIG. 2LLLL-2MMMM present examples of Cathepsin K Targeting Ligands wherein R is the point at which the Linker is attached. For additional examples and related ligands, see, Rankovic Z. et al. "Design and optimization of a series of novel 2-cyano-pyrimidines as cathepsin K inhibitors" *Bioorg. Med. Chem. Lett.* 20: 1524-1527 (2010); and, Cai J. et al. "Trifluoromethylphenyl as P2 for ketoamide-based cathepsin S inhibitors." *Bioorg. Med. Chem. Lett.* 20: 6890-6894 (2010).

FIG. 2NNNN presents examples of Cathepsin L Targeting Ligands wherein R is the point at which the Linker is attached. For additional examples and related ligands, see, Kuhn B. et al. "Prospective Evaluation of Free Energy Calculations for the Prioritization of Cathepsin L Inhibitors." *J. Med. Chem.* 60: 2485-2497 (2017).

FIG. 2OOOO presents examples of Cathepsin S Targeting Ligands wherein R is the point at which the Linker is attached. For additional examples and related ligands, see, Jadhav P. K. et al. "Discovery of Cathepsin S Inhibitor LY3000328 for the Treatment of Abdominal Aortic Aneurysm" *ACS Med. Chem. Lett.* 5: 1138-1142." (2014).

FIG. 2PPPP-2SSSS present examples of MTH1 Targeting Ligands wherein R is the point at which the Linker is attached. For additional examples and related ligands, see, Kettle J. G. et al. "Potent and Selective Inhibitors of Mth1 Probe its Role in Cancer Cell Survival." *J. Med. Chem.* 59: 2346 (2016); Huber K. V. M. et al. "Stereospecific Targeting of Mth1 by (S)-Crizotinib as an Anticancer Strategy." *Nature* 508: 222 (2014); Gad H. et al. "MTH1 inhibition eradicates cancer by preventing sanitation of the dNTP pool." *Nature* 508: 215-221 (2014); Nissink J. W. M. et al. "Mth1 Substrate Recognition—an Example of Specific Promiscuity." *Plos One* 11: 51154 (2016); and, Manuel Ellermann et al. "Novel class of potent and selective inhibitors efface MTH1 as broad-spectrum cancer target." AACR National Meeting Abstract 5226, 2017.

FIG. 2TTTT-2ZZZZ present examples of MDM2 and/or MDM4 Targeting Ligands wherein R is the point at which the Linker is attached. For additional examples and related ligands, see, Popowicz G. M. et al. "Structures of low molecular weight inhibitors bound to MDMX and MDM2 reveal new approaches for p53-MDMX/MDM2 antagonist drug discovery." *Cell Cycle,* 9 (2010); Miyazaki M. et al. "Synthesis and evaluation of novel orally active p53-MDM2 interaction inhibitors." *Bioorg. Med. Chem.* 21: 4319-4331 (2013); Miyazaki M. et al. "Discovery of DS-5272 as a promising candidate: A potent and orally active p53-MDM2 interaction inhibitor." *Bioorg Med Chem.* 23: 2360-7 (2015); Holzer P. et al. "Discovery of a Dihydroisoquinolinone Derivative (NVP-CGM097): A Highly Potent and Selective MDM2 Inhibitor Undergoing Phase 1 Clinical Trials in p53 wt Tumors." *J. Med. Chem.* 58: 6348-6358 (2015); Gonzalez-Lopez de Turiso F. et al. "Rational Design and Binding Mode Duality of MDM2-p53 Inhibitors." *J. Med. Chem.* 56: 4053-4070 (2013); Gessier F. et al. "Discovery of dihydroisoquinolinone derivatives as novel inhibitors of the p53-MDM2 interaction with a distinct binding mode." *Bioorg. Med. Chem. Lett.* 25: 3621-3625 (2015); Fry D. C. et al. "Deconstruction of a nutlin: dissecting the binding determinants of a potent protein-protein interaction inhibitor." *ACS Med Chem Lett* 4: 660-665 (2013); Ding Q. et al. "Discovery of RG7388 a Potent and Selective p53-MDM2 Inhibitor in Clinical Development." *J. Med. Chem.* 56: 5979-5983 (2013); Wang S. et al. "SAR405838: an optimized inhibitor of MDM2-p53 interaction that induces complete and durable tumor regression." *Cancer Res.* 74: 5855-5865 (2014); Rew Y. et al. "Discovery of AM-7209 a Potent and Selective 4-Amidobenzoic Acid Inhibitor of the MDM2-p53 Interaction." *J. Med. Chem.* 57: 10499-10511 (2014); Bogen S. L. et al. "Discovery of Novel 3 3-Disubstituted Piperidines as Orally Bioavailable Potent and Efficacious HDM2-p53 Inhibitors." *ACS Med. Chem. Lett.* 7: 324-329 (2016); and, Sun D. et al. "Discovery of AMG 232 a Potent Selective and Orally Bioavailable MDM2-p53 Inhibitor in Clinical Development." *J. Med. Chem.* 57: 1454-1472 (2014).

FIG. 2AAAAA-2EEEEE present examples of PARP1, PARP2, and/or PARP3 Targeting Ligands wherein R is the point at which the Linker is attached. For additional examples and related ligands, see, Iwashita A. et al. "Discovery of quinazolinone and quinoxaline derivatives as potent and selective poly(ADP-ribose) polymerase-1/2 inhibitors." *Febs Lett.* 579: 1389-1393 (2005); the crystal structure PDB 2RCW (PARP complexed with A861695, Park C. H.); the crystal structure PDB 2RD6 (PARP complexed with A861696, Park C. H.); the crystal structure PDB 3GN7; Miyashiro J. et al. "Synthesis and SAR of novel tricyclic quinoxalinone inhibitors of poly(ADP-ribose)polymerase-1 (PARP-1)" *Bioorg. Med. Chem. Lett.* 19: 4050-4054 (2009); Gandhi V. B. et al. "Discovery and SAR of substituted 3-oxoisoindoline-4-carboxamides as potent inhibitors of poly(ADP-ribose) polymerase (PARP) for the treatment of cancer." *Bioorg. Med. Chem. Lett.* 20: 1023-1026 (2010); Penning T. D. et al. "Optimization of phenyl-substituted benzimidazole carboxamide poly(ADP-ribose) polymerase inhibitors: identification of (S)-2-(2-fluoro-4-(pyrrolidin-2-yl)phenyl)-1H-benzimidazole-4-carboxamide (A-966492) a highly potent and efficacious inhibitor." *J. Med. Chem.* 53: 3142-3153 (2010); Ye N. et al. "Design, Synthesis, and Biological Evaluation of a Series of Benzo [de][1 7]naphthyridin-7(8H)-ones Bearing a Functionalized Longer Chain Appendage as Novel PARP1 Inhibitors." *J. Med. Chem.* 56: 2885-2903 (2013); Patel M. R. et al. "Discovery and Structure-Activity Relationship of Novel 2 3-Dihydrobenzofuran-7-carboxamide and 2 3-Dihydrobenzofuran-3(2H)-one-7-carboxamide Derivatives as Poly (ADP-ribose)polymerase-1 Inhibitors." *J. Med. Chem.* 57: 5579-5601 (2014); Thorsell A. G. et al. "Structural Basis for Potency and Promiscuity in Poly(ADP-ribose) Polymerase (PARP) and Tankyrase Inhibitors." *J. Med. Chem.* 60:1262-1271 (2012); the crystal structure PDB 4RV6 ("Human ARTD1 (PARP1) catalytic domain in complex with inhibitor Rucaparib", Karlberg T. et al.); Papeo G. M. E. et al. "Discovery of 2-[1-(4 4-Difluorocyclohexyl)Piperidin-4-Y1]-6-Fluoro-3-Oxo-2 3-Dihydro-1H-Isoindole-4-Carboxamide (Nms-P118): A Potent Orally Available and Highly Selective Parp-1 Inhibitor for Cancer Therapy." *J. Med. Chem.* 58: 6875 (2015); Kinoshita T. et al. "Inhibitor-induced structural change of the active site of human poly (ADP-ribose) polymerase." *Febs Lett.* 556: 43-46 (2004);

and, Gangloff A. R. et al. "Discovery of novel benzo[b][1 4]oxazin-3(4H)-ones as poly(ADP-ribose)polymerase inhibitors." *Bioorg. Med. Chem. Lett.* 23: 4501-4505 (2013).

FIG. 2FFFFF-2GGGGG present examples of PARP14 Targeting Ligands wherein R is the point at which the Linker is attached.

FIG. 2HHHHH presents examples of PARP15 Targeting Ligands wherein R is the point at which the Linker is attached.

FIG. 2IIIII presents examples of PDZ domain Targeting Ligands wherein R is the point at which the Linker(s) are attached.

FIG. 2JJJJJ presents examples of Phospholipase A2 domain Targeting Ligands wherein R is the point at which the Linker is attached.

FIG. 2KKKKK presents examples of Protein S100-A7 2WOS Targeting Ligands wherein R is the point at which the Linker is attached.

FIG. 2LLLLL-2MMMMM present examples of Saposin-B Targeting Ligands wherein R is the point at which the Linker is attached.

FIG. 2NNNNN-2OOOOO present examples of Sec7 Targeting Ligands wherein R is the point at which the Linker is attached.

FIG. 2PPPPP-2QQQQQ present examples of SH2 domain of pp60 Src Targeting Ligands wherein R is the point at which the Linker is attached.

FIG. 2RRRRR presents examples of Tank1 Targeting Ligands wherein R is the point at which the Linker is attached.

FIG. 2SSSSS presents examples of Ubc9 SUMO E2 ligase SF6D Targeting Ligands wherein R is the point at which the Linker is attached.

FIG. 2TTTTT presents examples of Src Targenting Ligands, including AP23464, wherein R is the point at which the Linker is attached.

FIG. 2UUUUU-2XXXXX present examples of Src-AS1 and/or Src AS2 Targeting Ligands wherein R is the point at which the Linker is attached.

FIG. 2YYYYY presents examples of JAK3 Targeting Ligands, including Tofacitinib, wherein R is the point at which the Linker is attached.

FIG. 2ZZZZZ presents examples of ABL Targeting Ligands, including Tofacitinib and Ponatinib, wherein R is the point at which the Linker is attached.

Figure 3B:
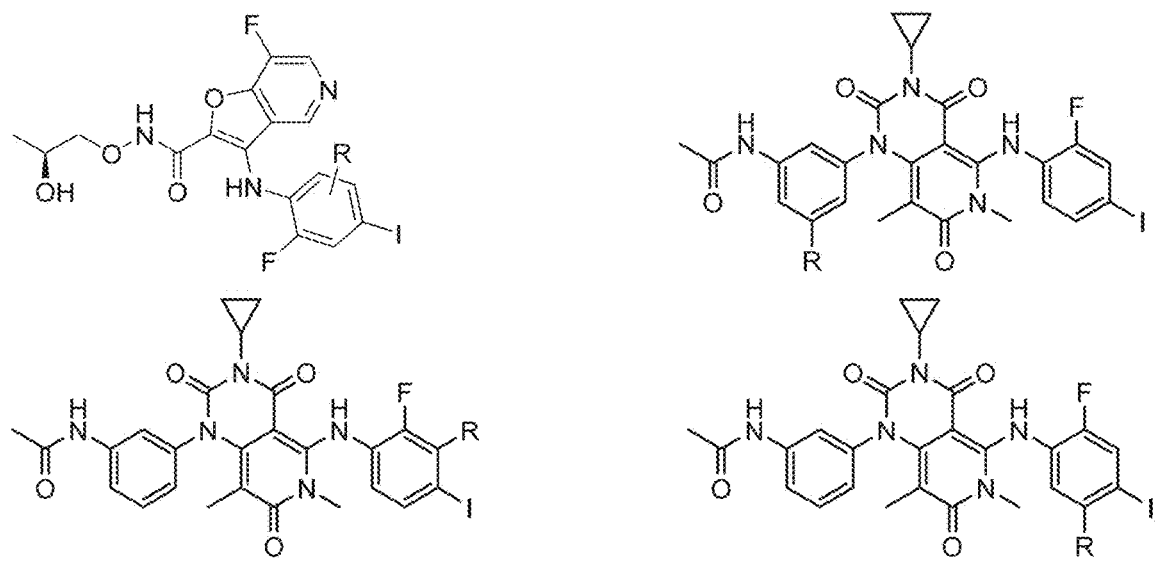
Figure 3C:
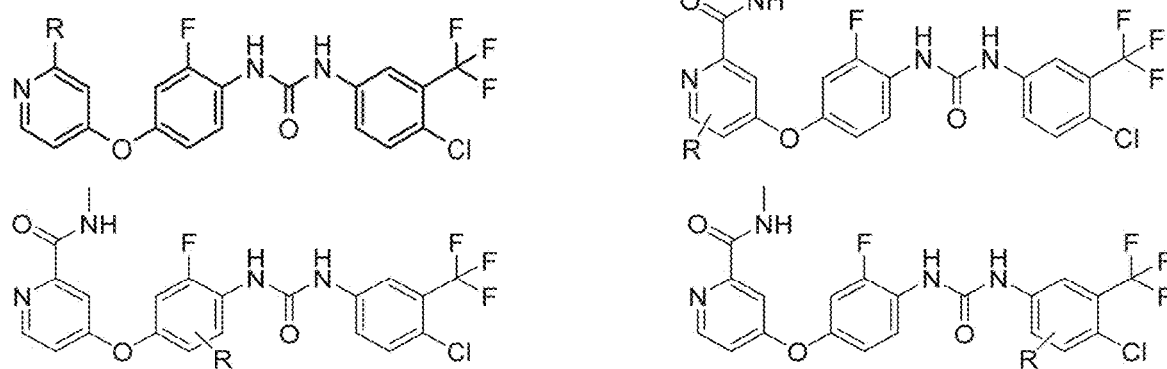
Figure 3D:
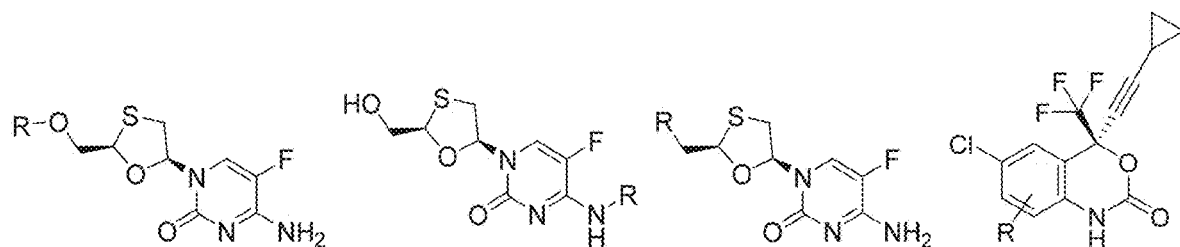
Figure 3E:
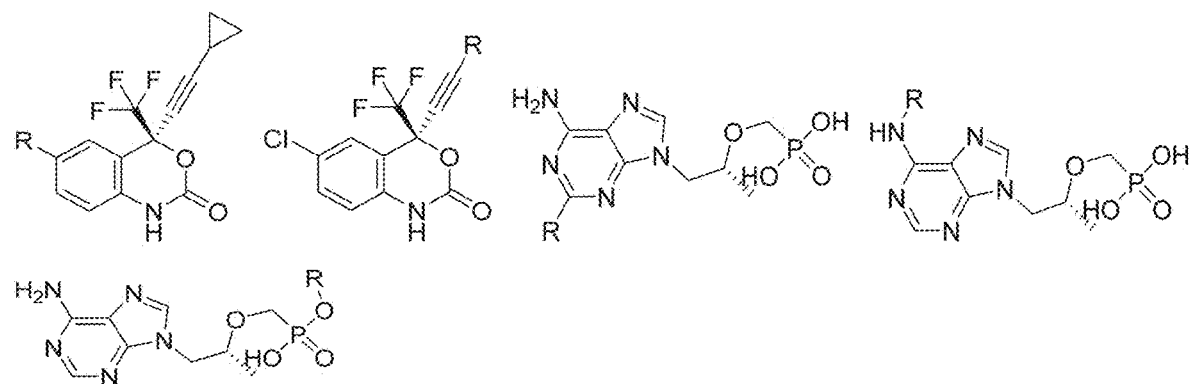
Figure 3F:
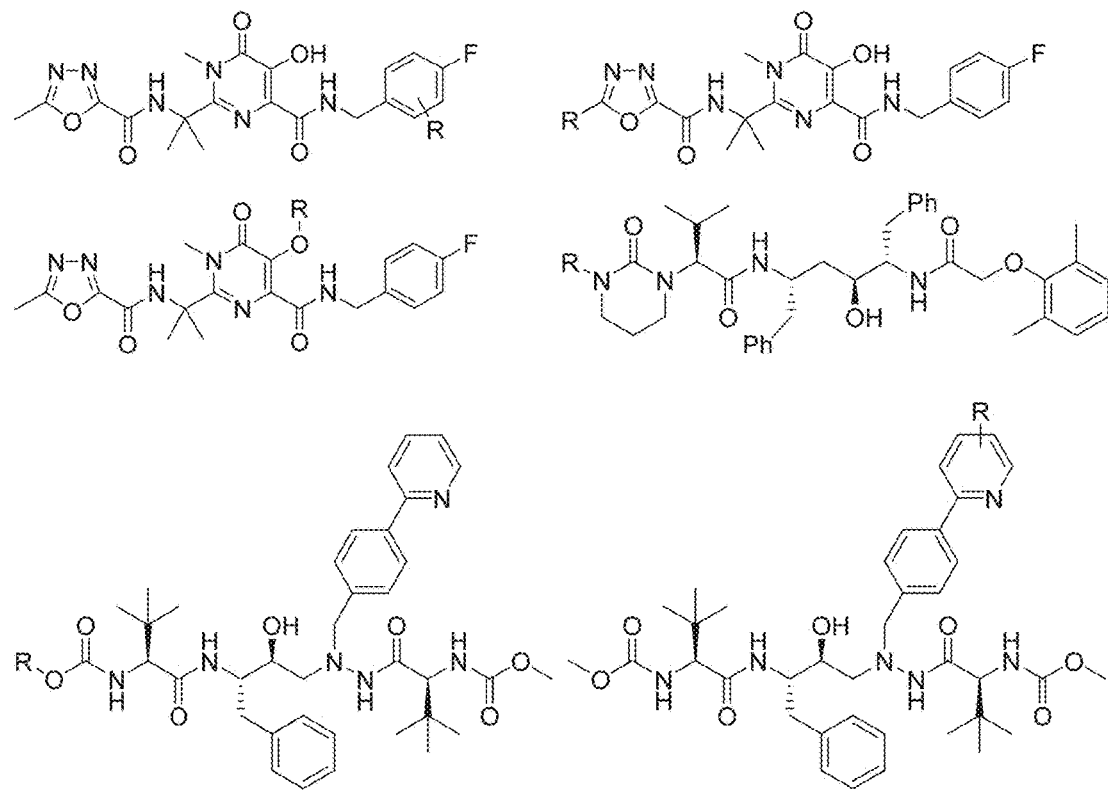
Figure 3G:
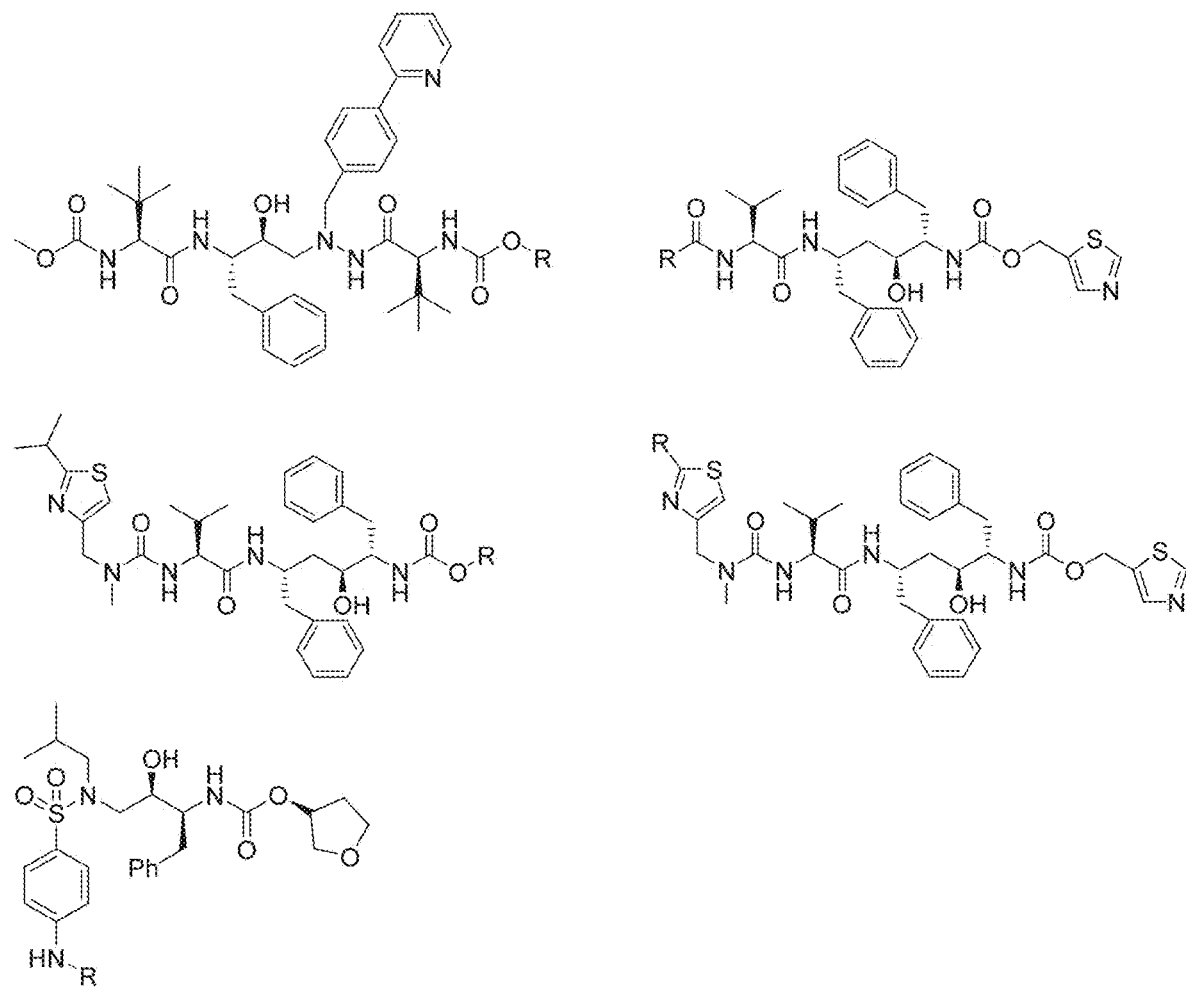
Figure 3H:
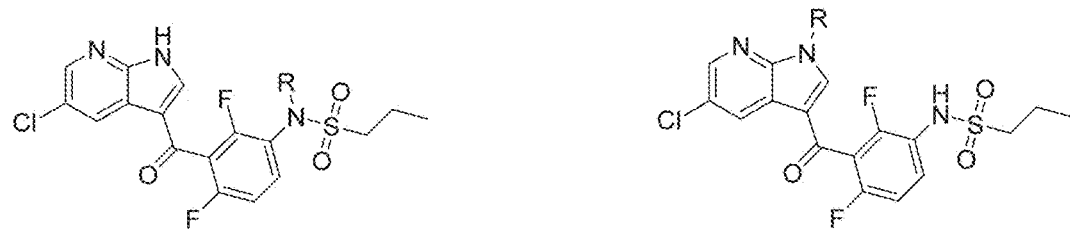
Figure 3I:
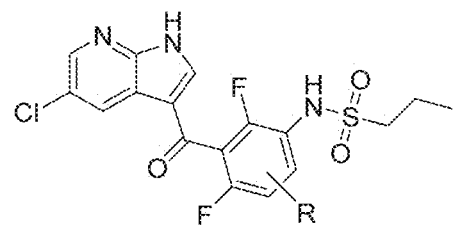
Figure 3I:
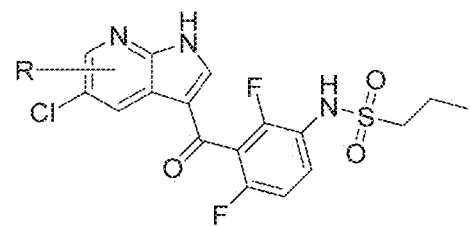
Figure 3J:
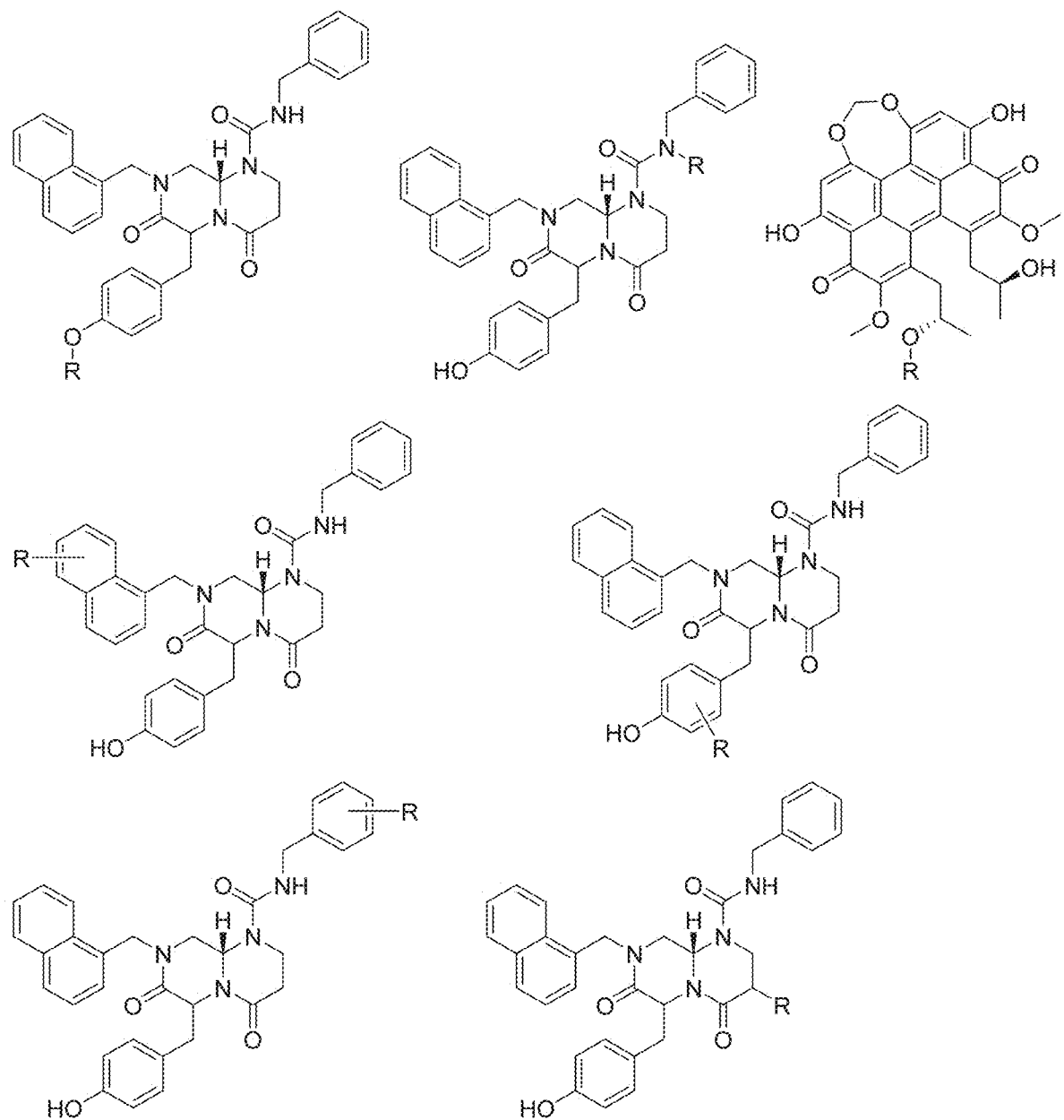
Figure 3K:
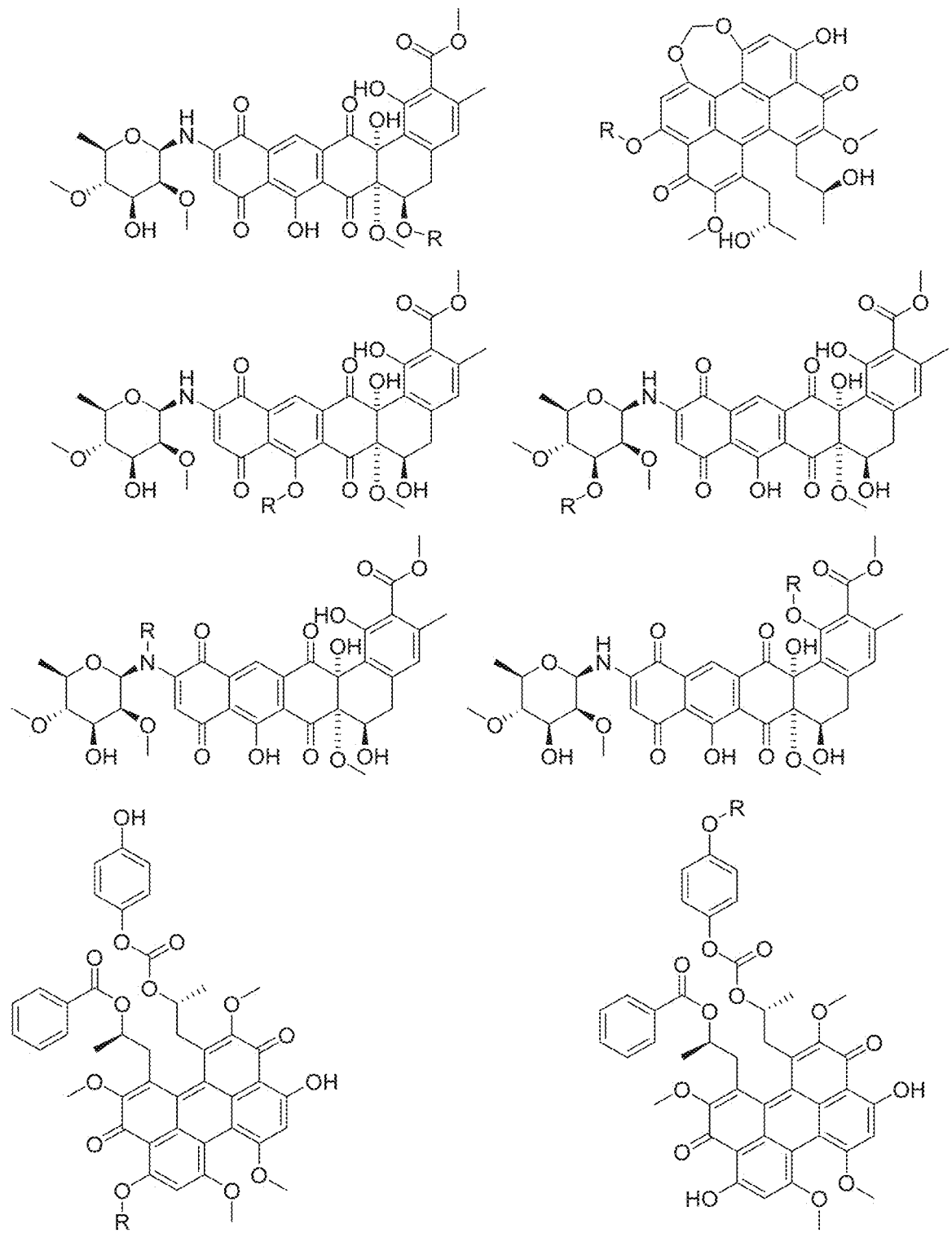
Figure 3L:
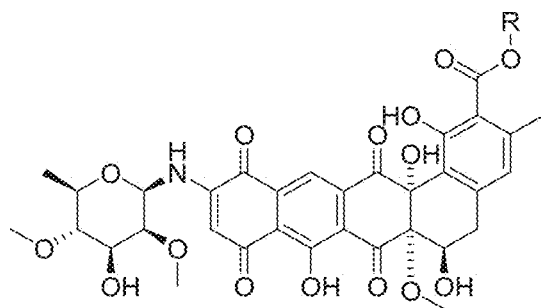
Figure 3M:
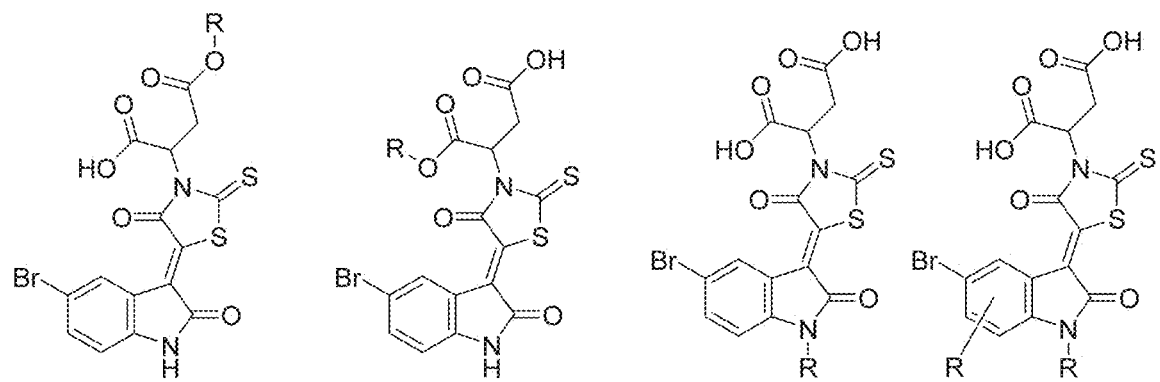
Figure 3N:
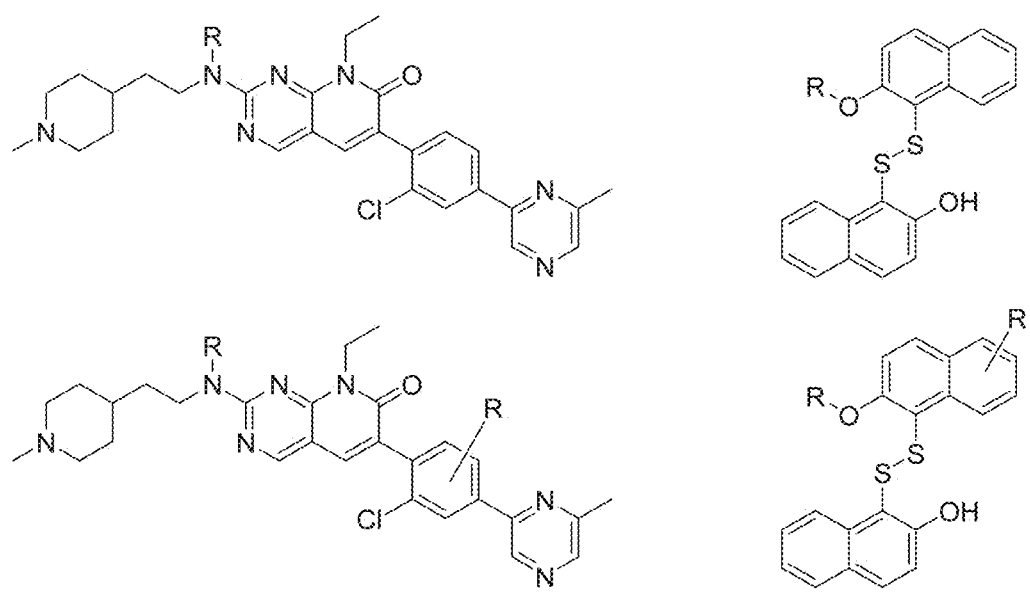
Figure 3O:
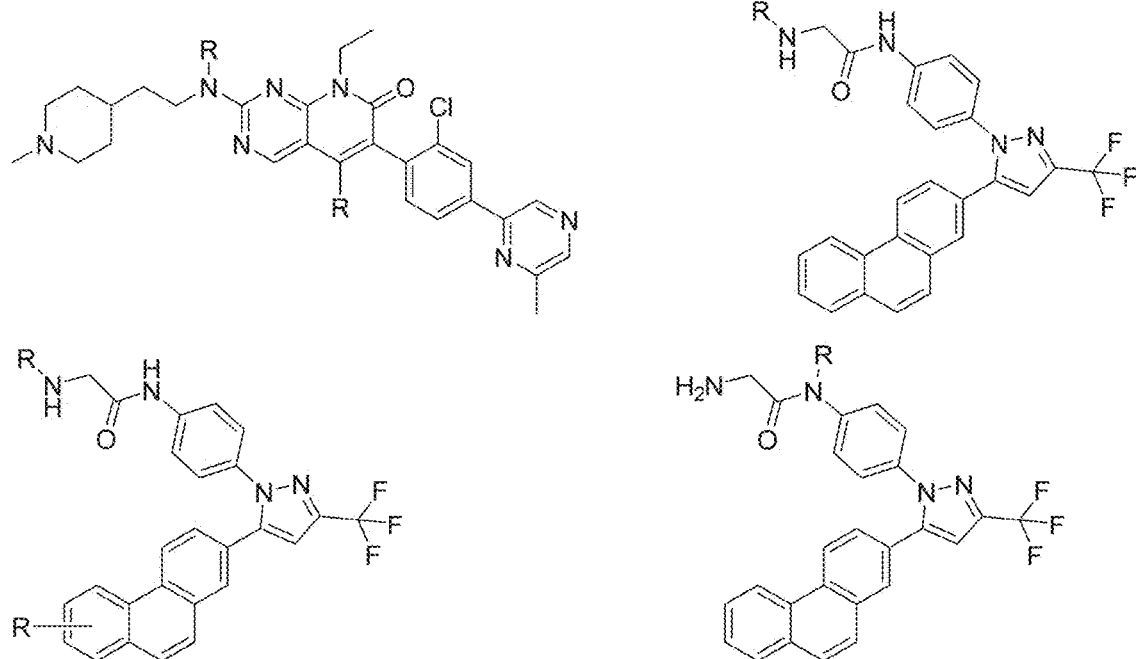
Figure 3P:
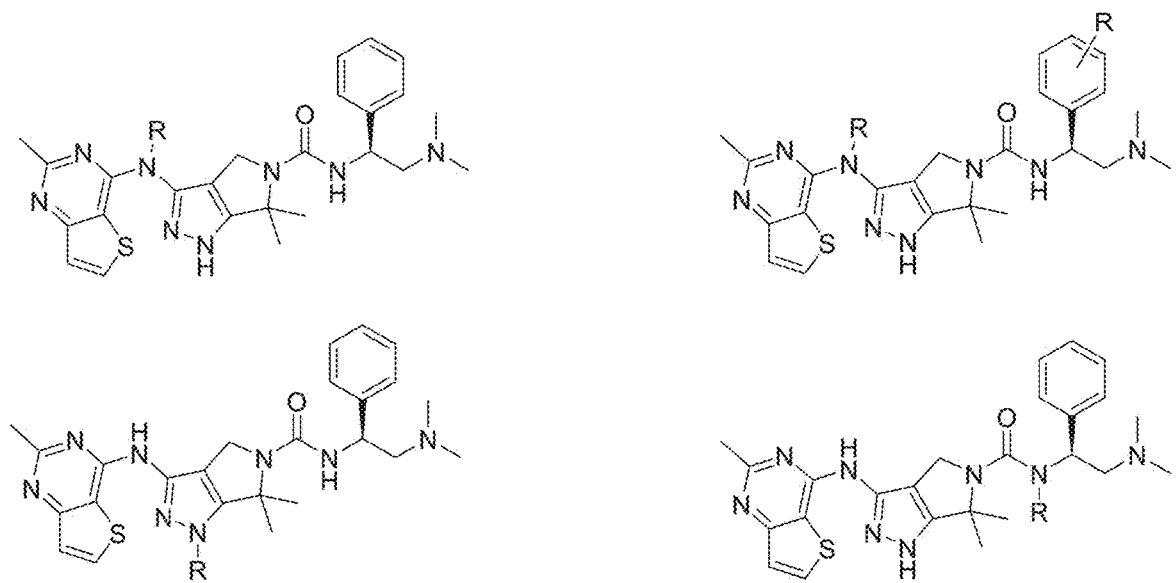
Figure 3Q:
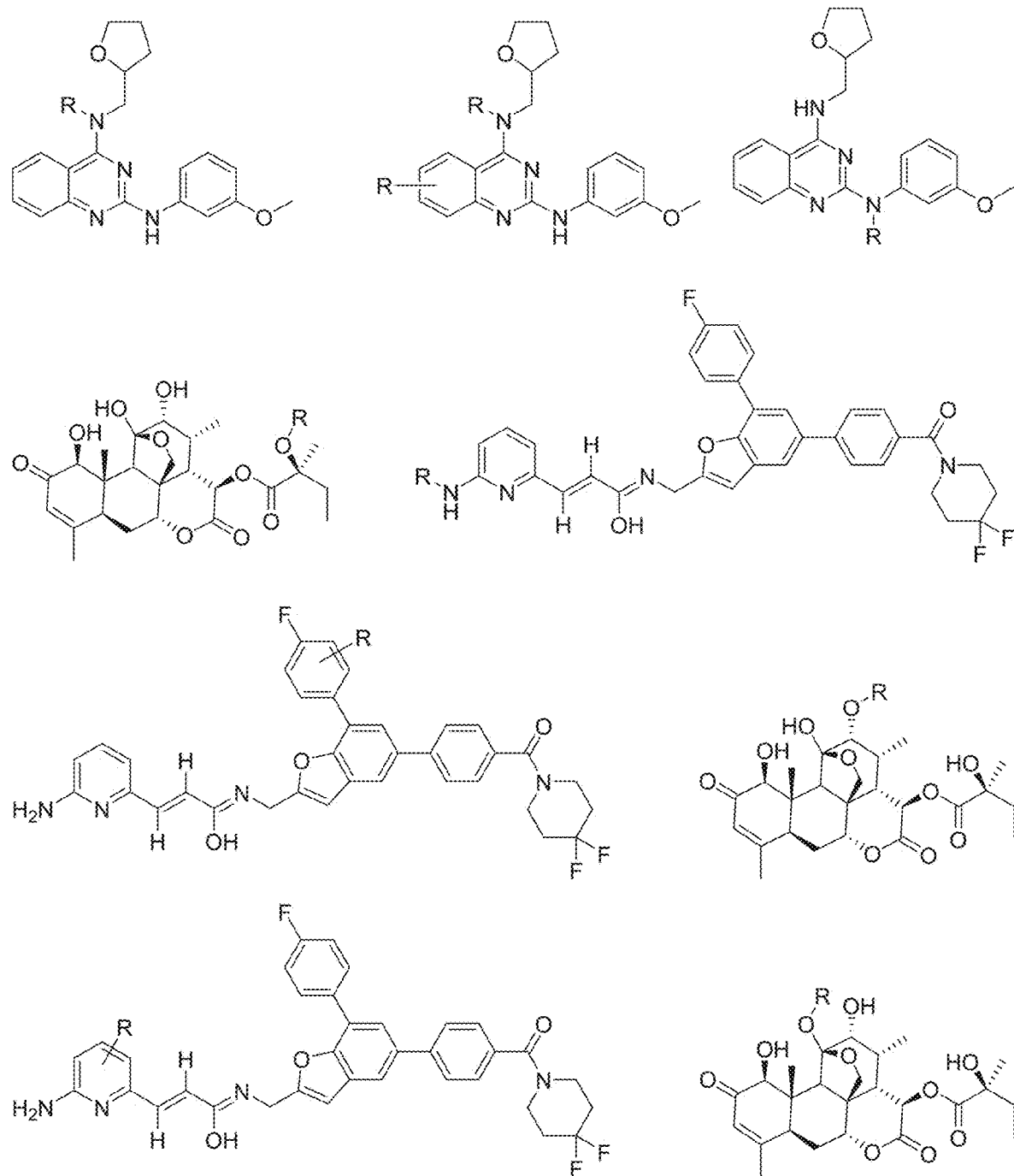
Figure 3R:
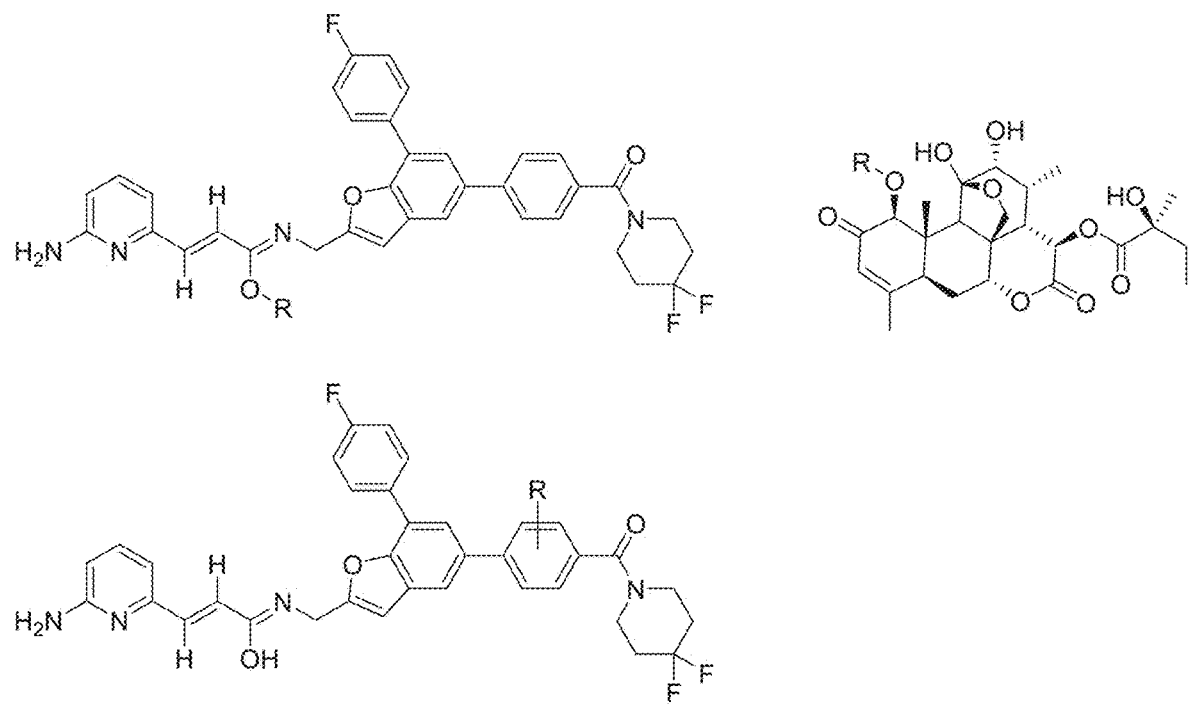
Figure 3S:
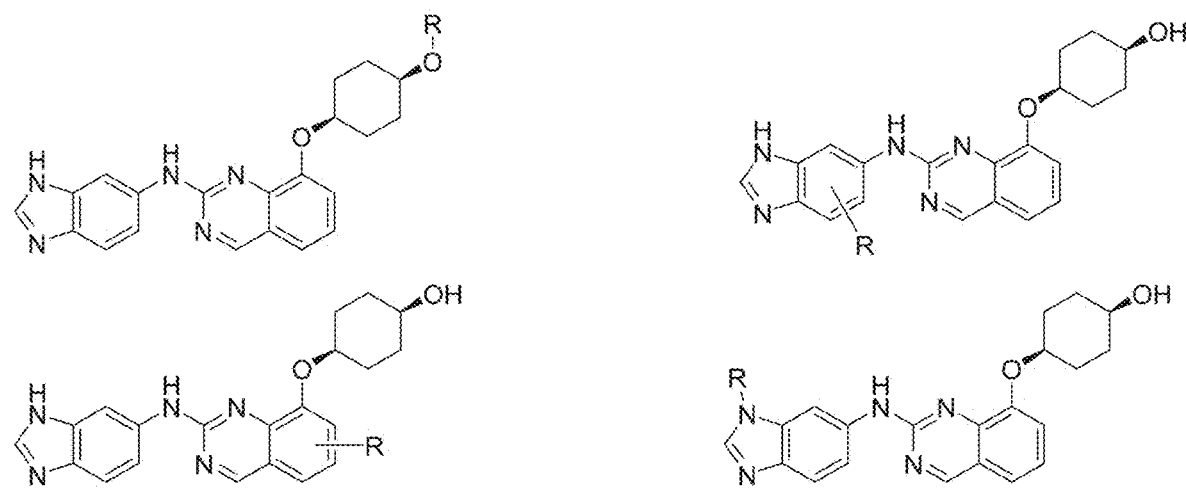
Figure 3T:
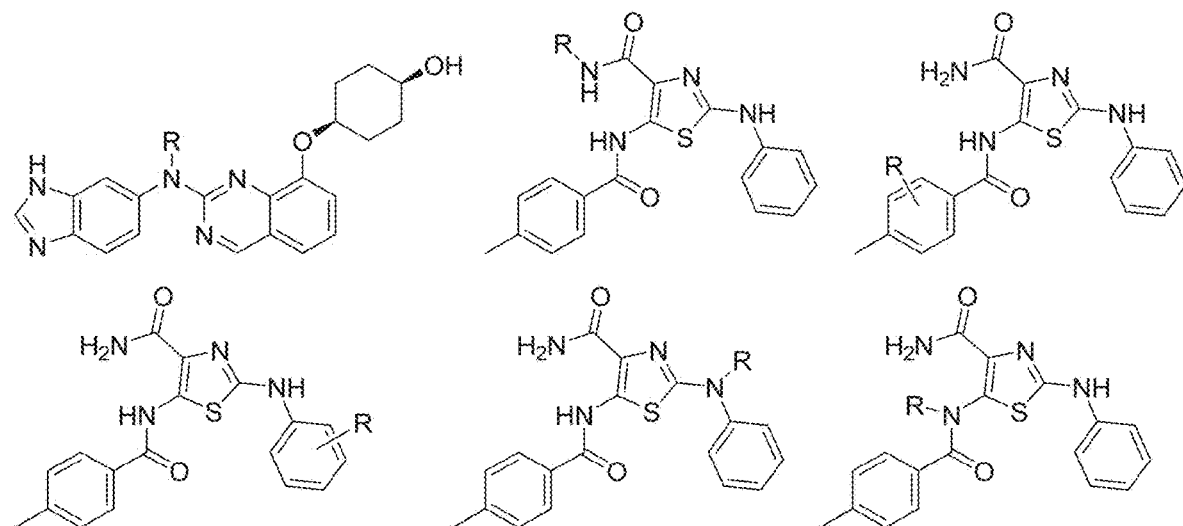
Figure 3U:
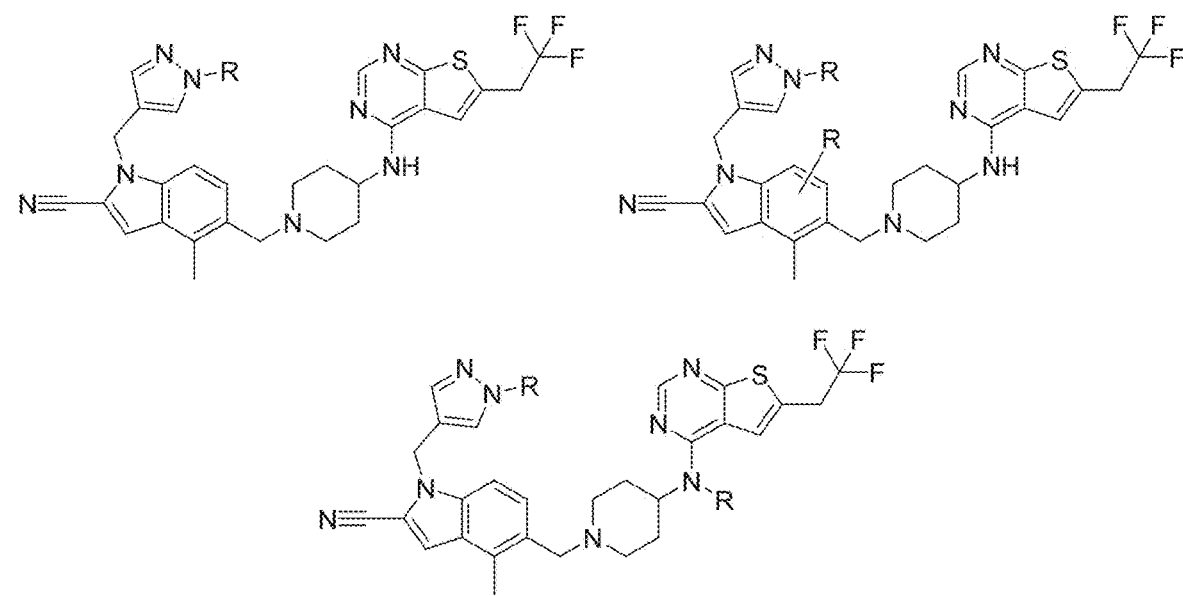
Figure 3V:
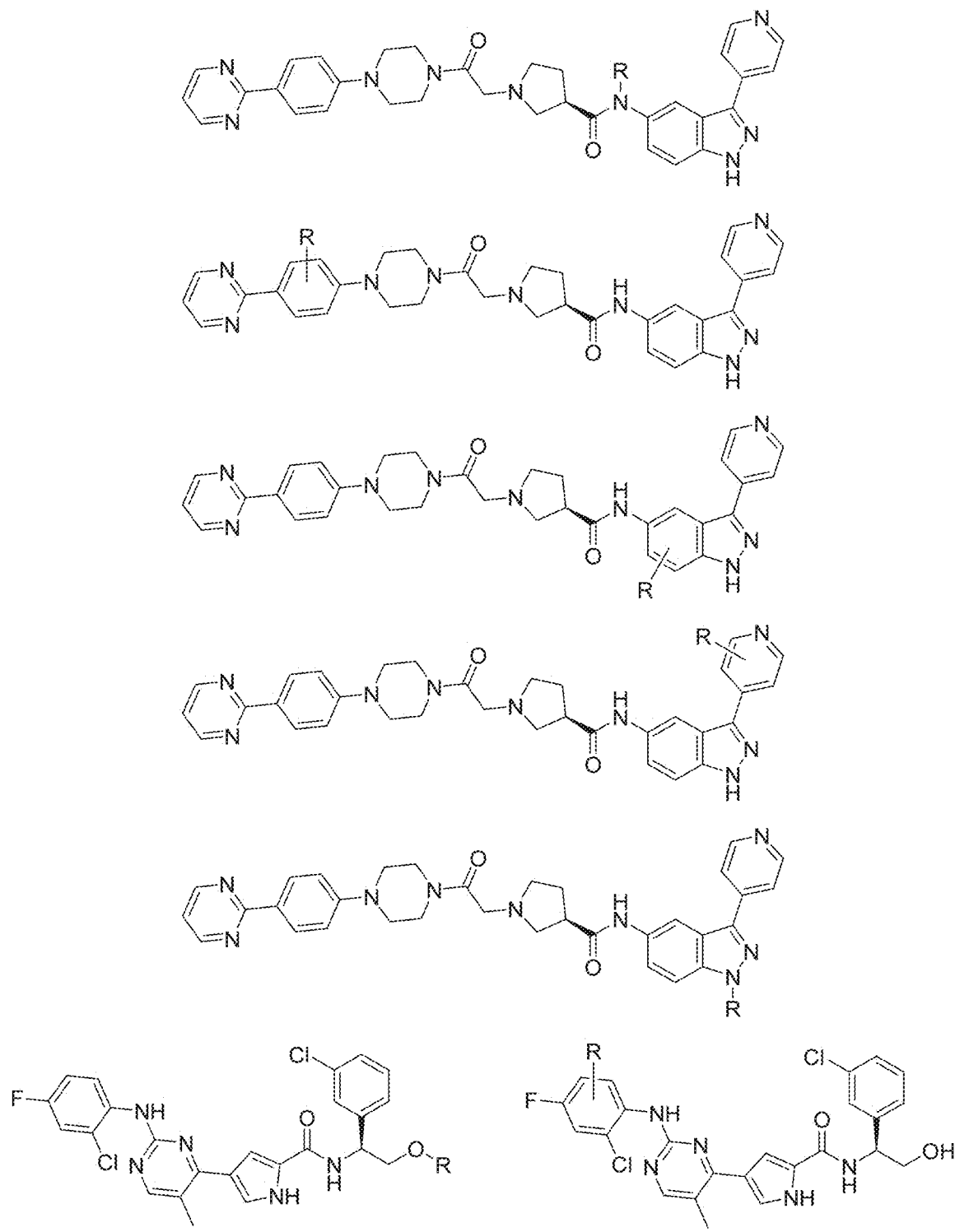
Figure 3W:
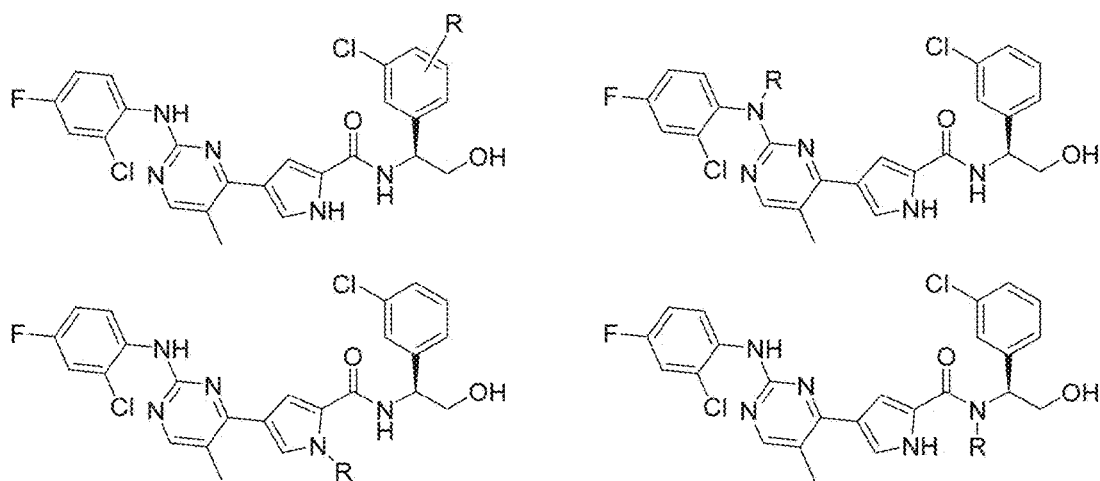
Figure 3X:
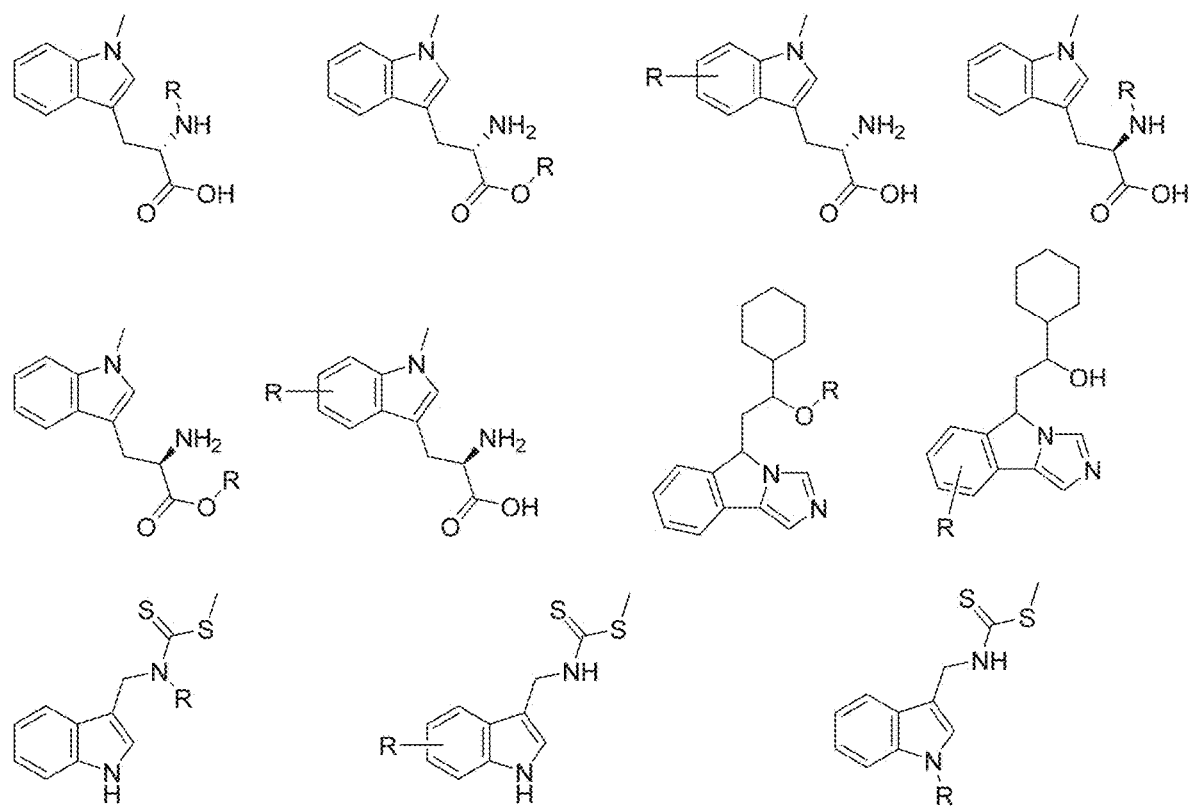
Figure 3Y:
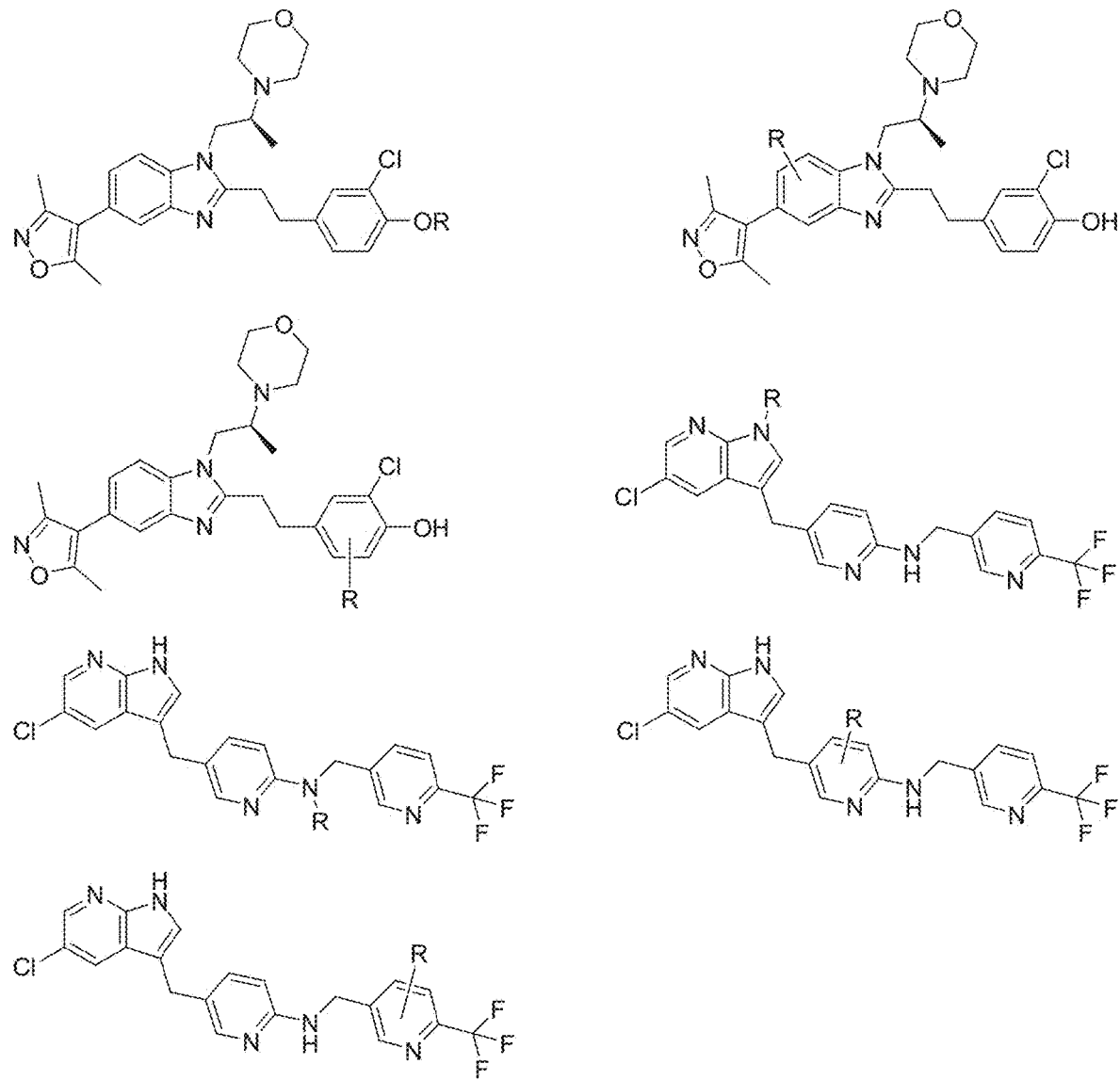
Figure 3Z:
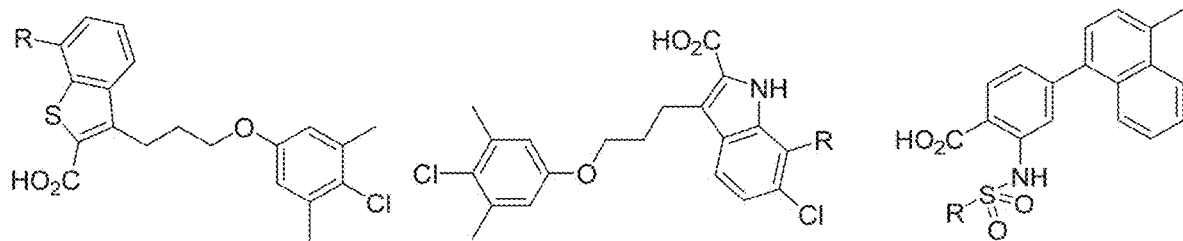
Figure 3A:
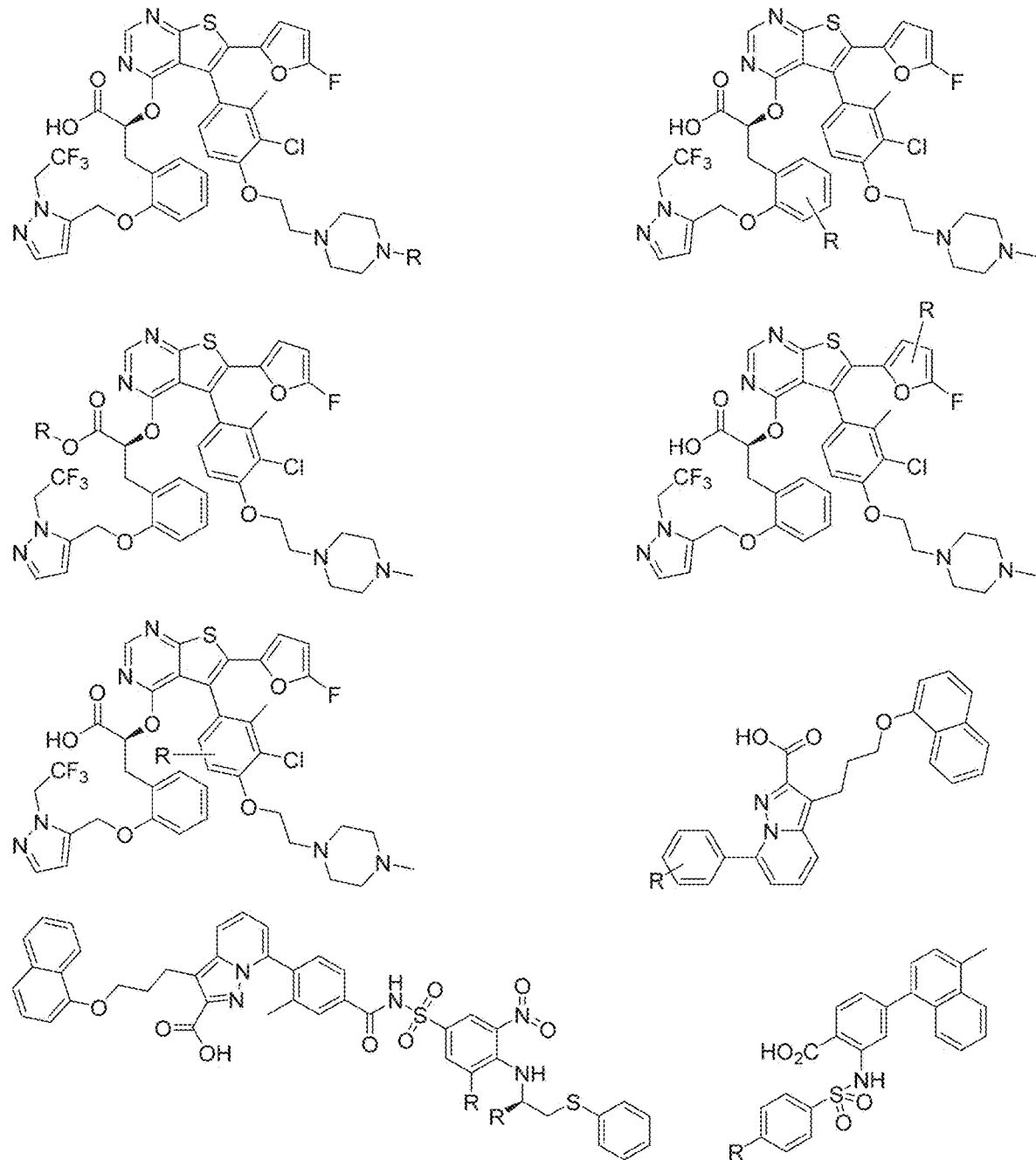
Figure 3B:
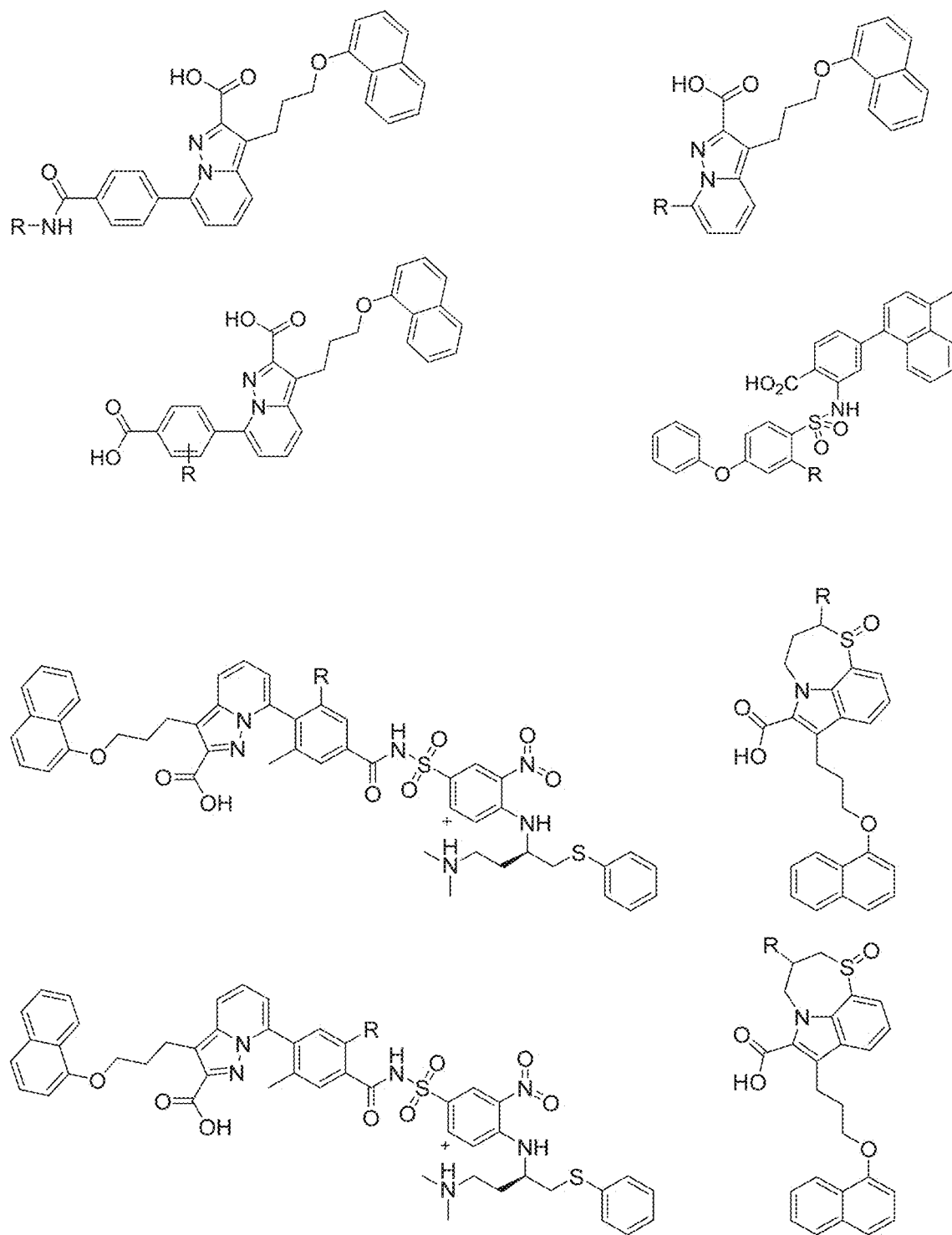
Figure 3C:
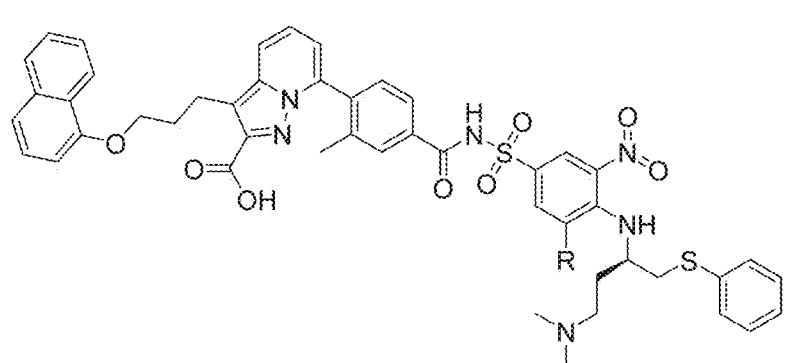
Figure 3C:
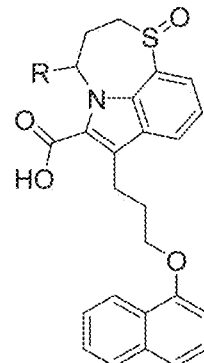
Figure 3C:
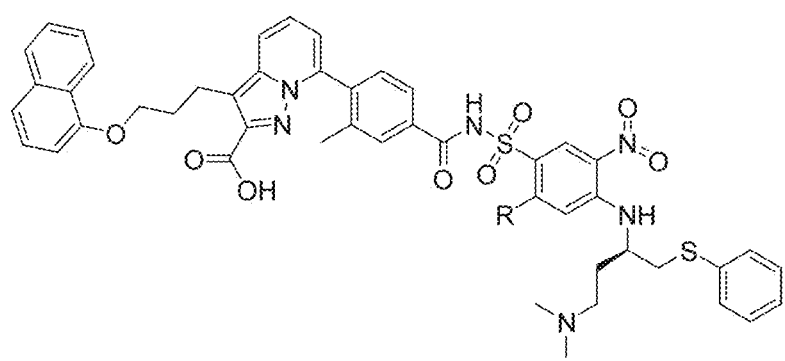
Figure 3C:
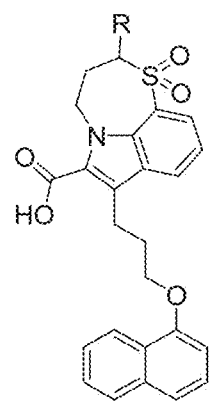
Figure 3C:
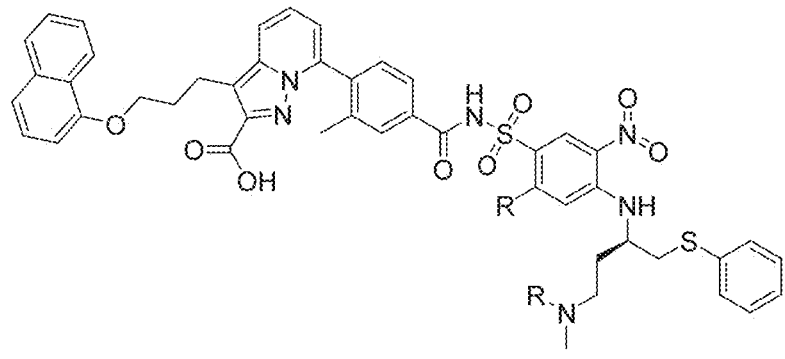
Figure 3C:
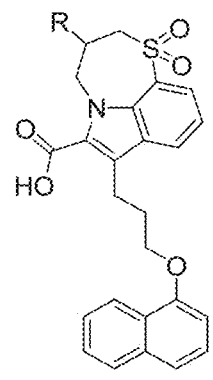
Figure 3C:
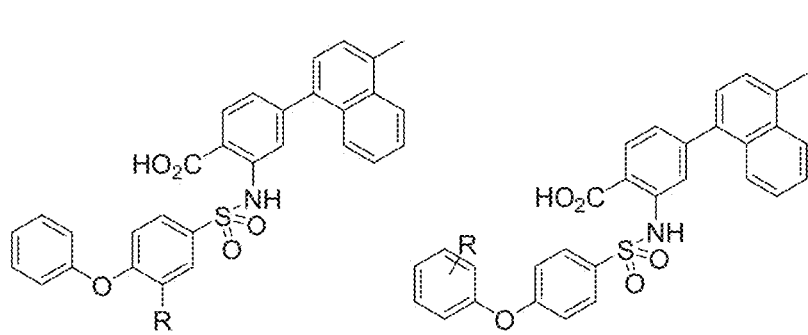
Figure 3C:
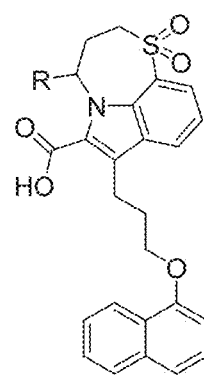
Figure 3D:
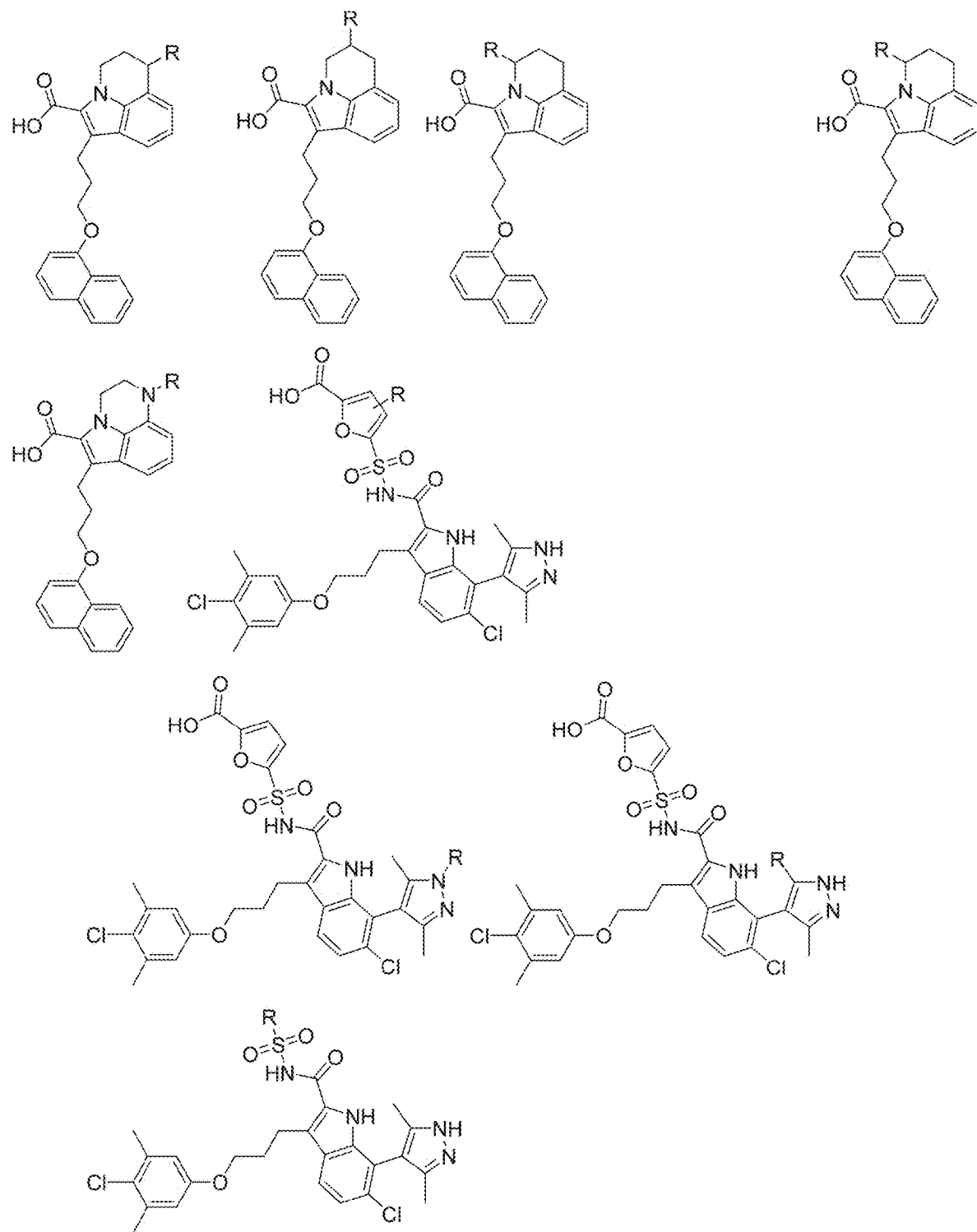
Figure 3E:
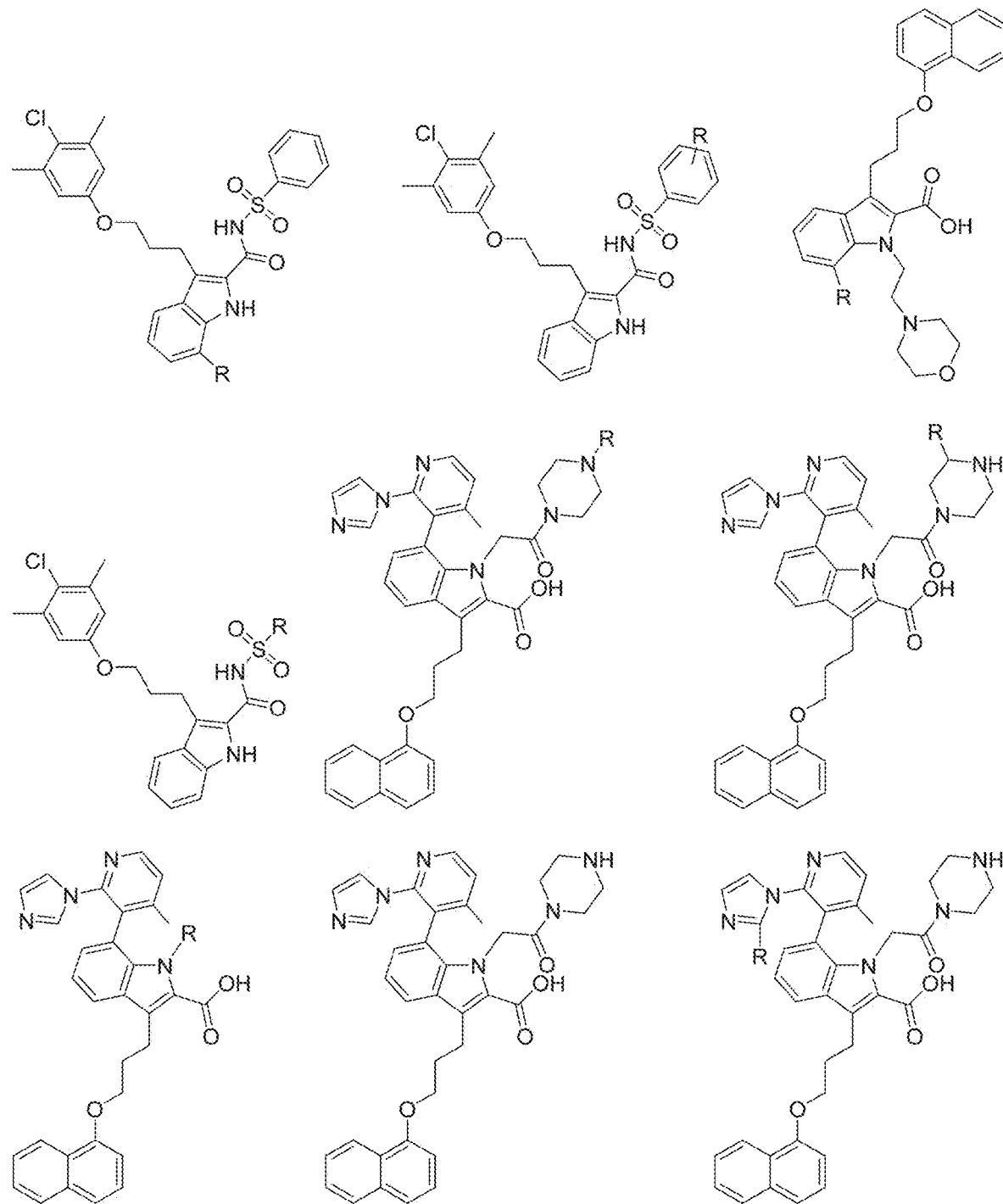
Figure 3F:
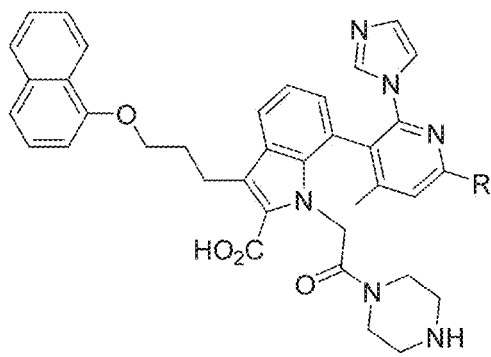
Figure 3F:
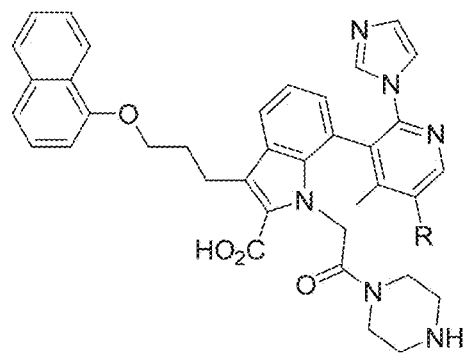
Figure 3F:
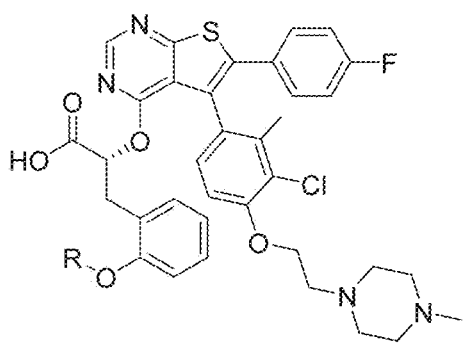
Figure 3F:
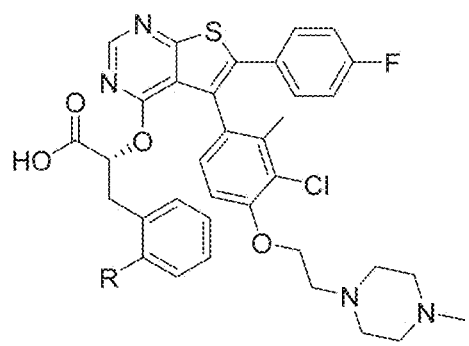
Figure 3F:
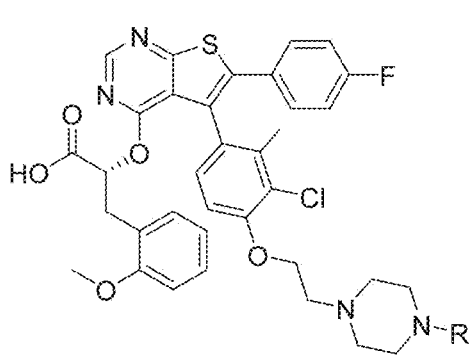
Figure 3F:
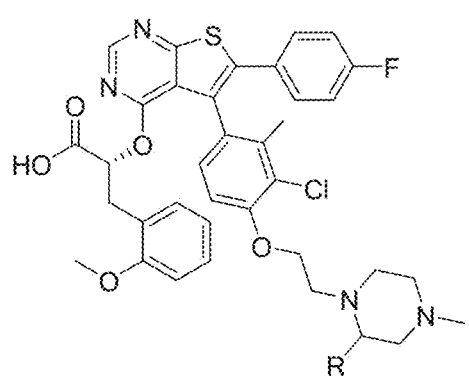
Figure 3F:
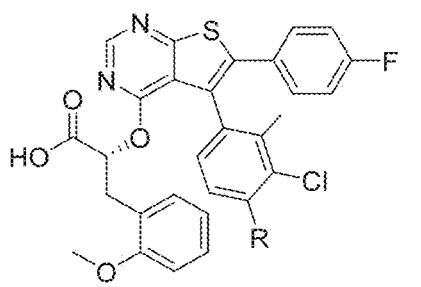
Figure 3F:
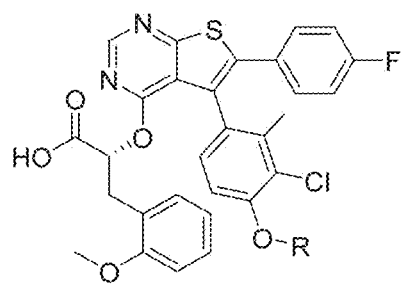
Figure 3G:
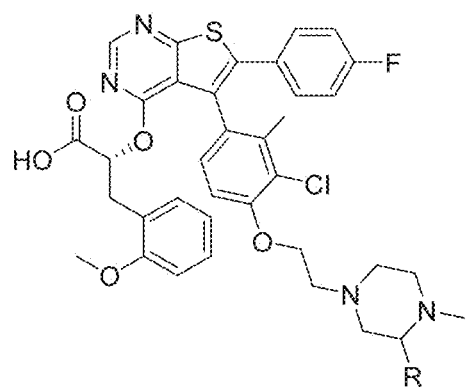
Figure 3G:
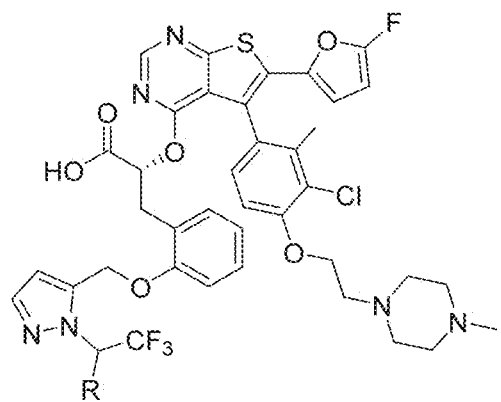
Figure 3G:
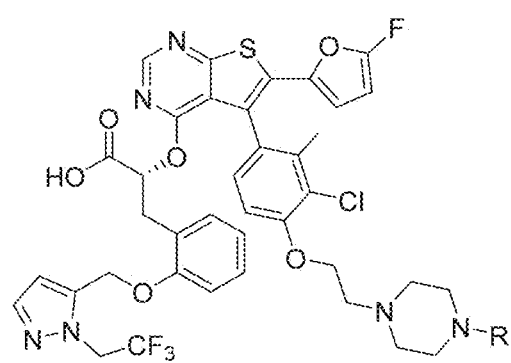
Figure 3G:
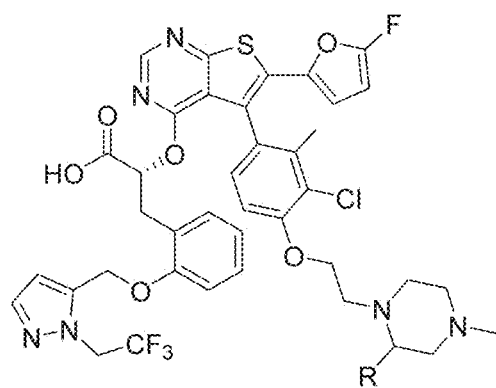
Figure 3G:
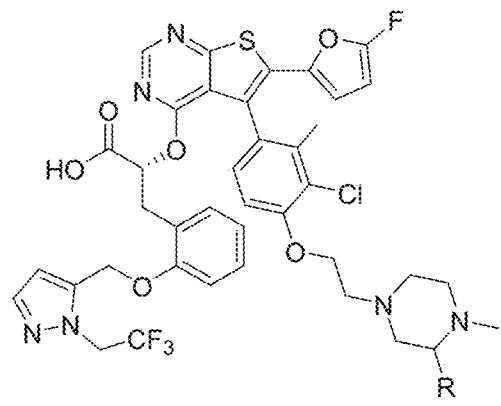
Figure 3G:
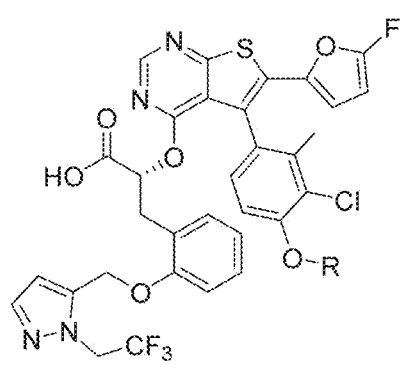
Figure 3H:
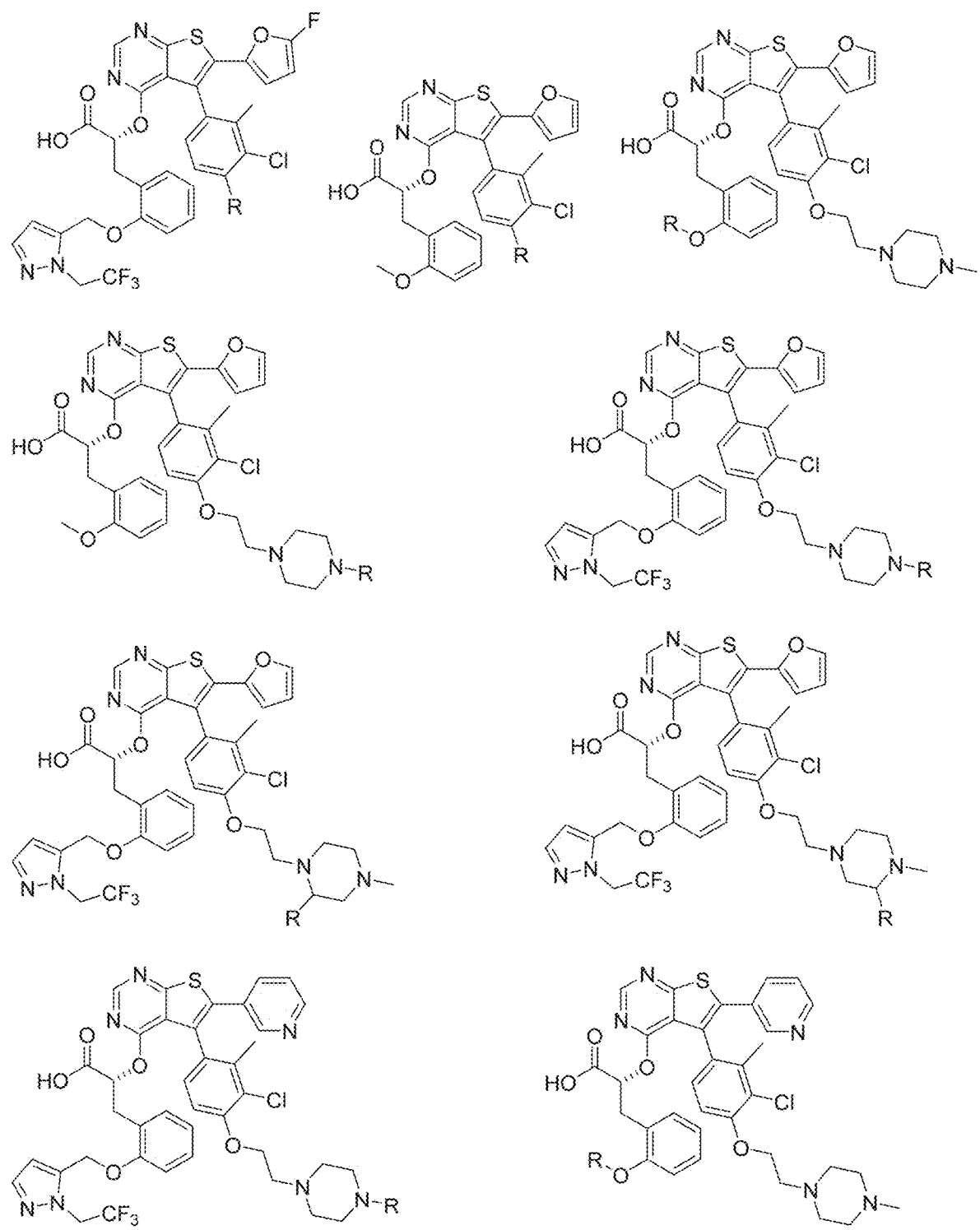
Figure 3I:
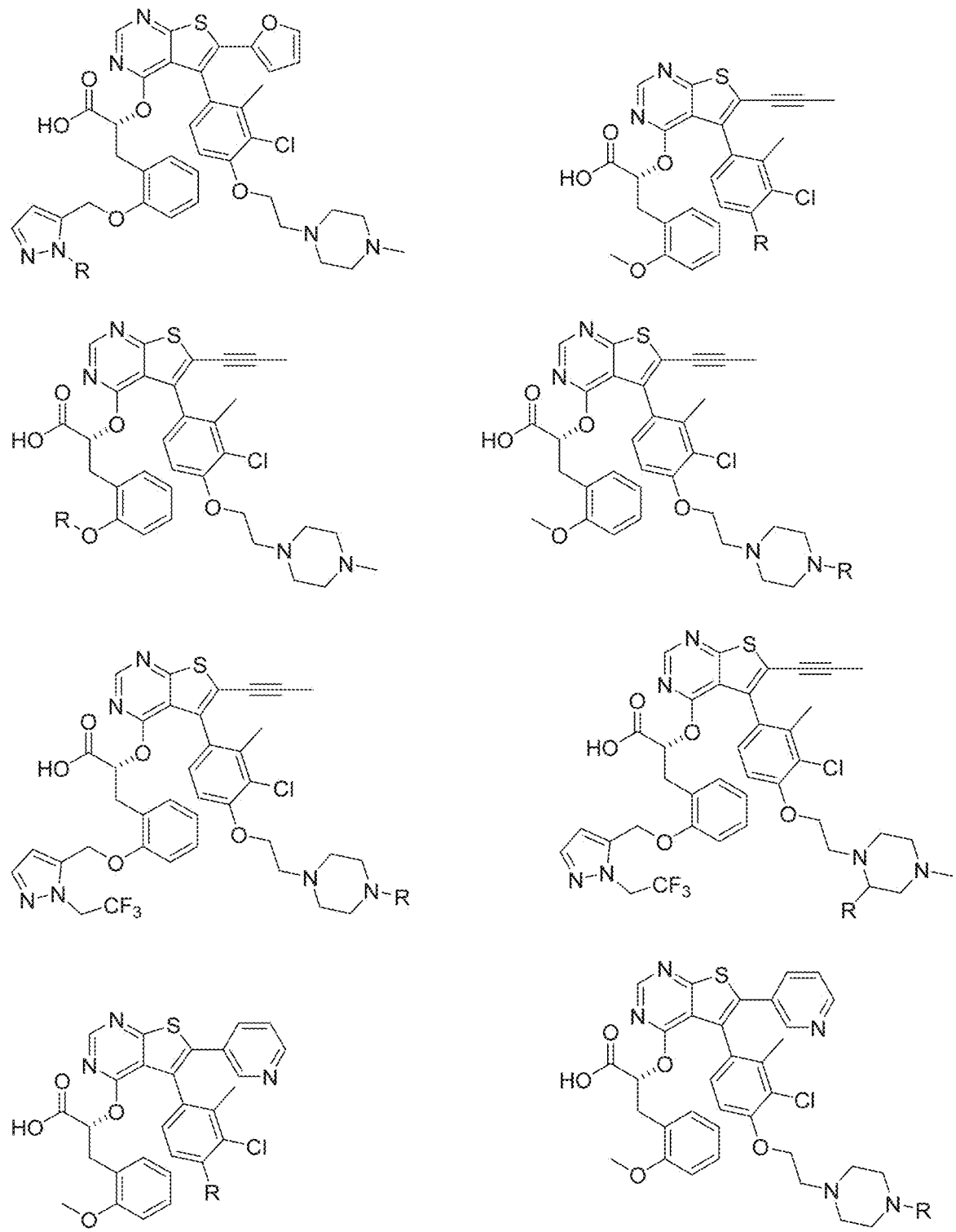
Figure 3J:
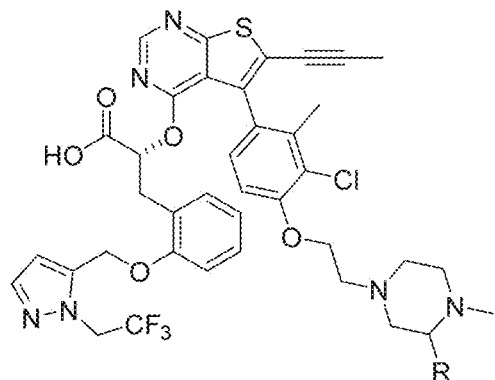
Figure 3J:
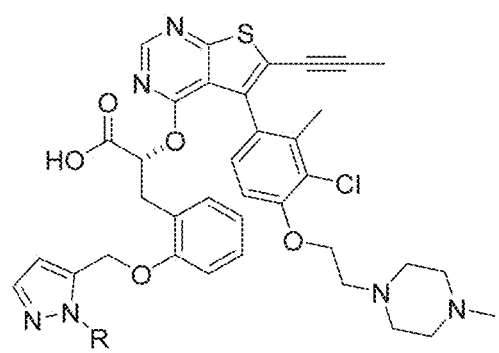
Figure 3J:
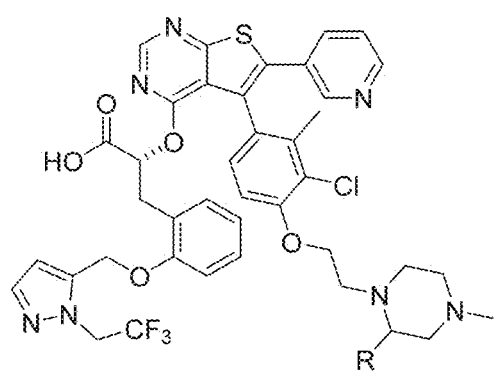
Figure 3J:
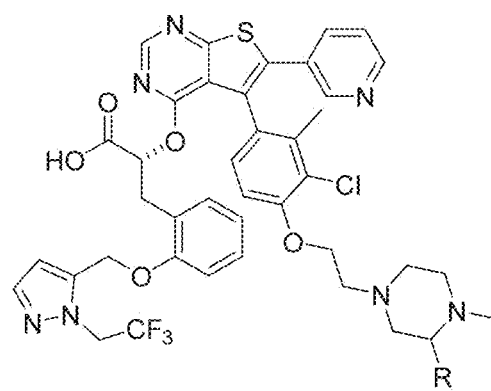
Figure 3J:
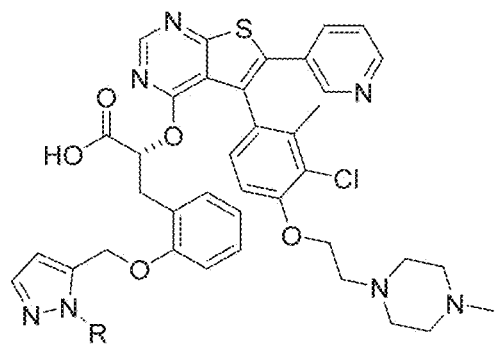
Figure 3J:
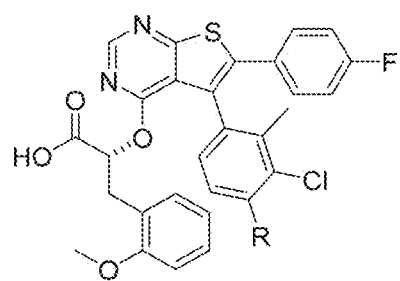
Figure 3J:
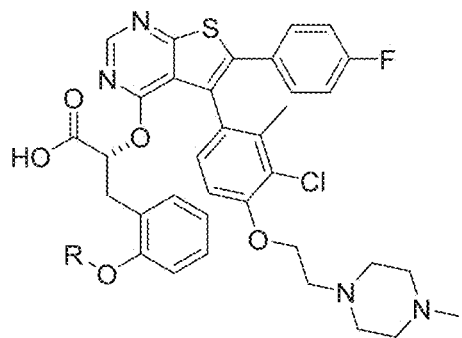
Figure 3J:
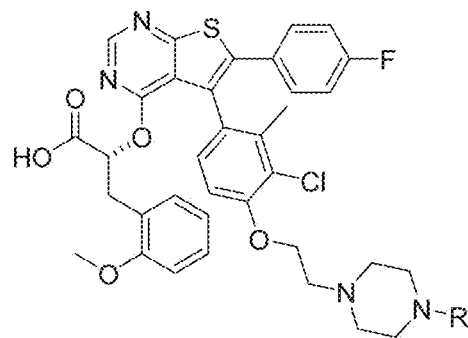
Figure 3K:
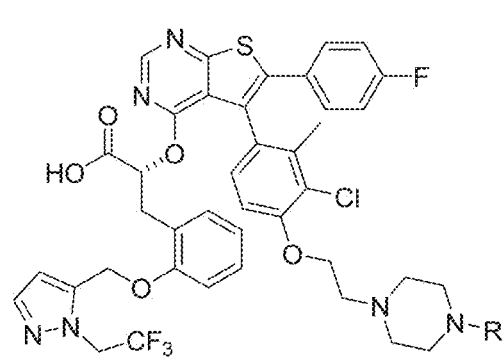
Figure 3K:
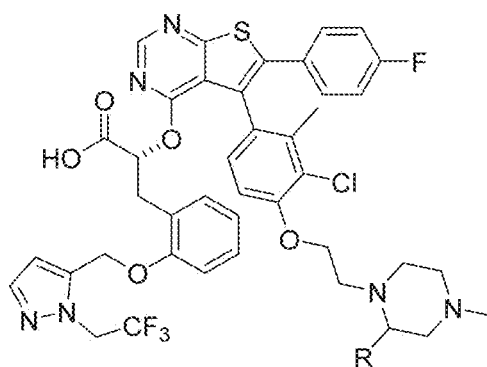
Figure 3K:
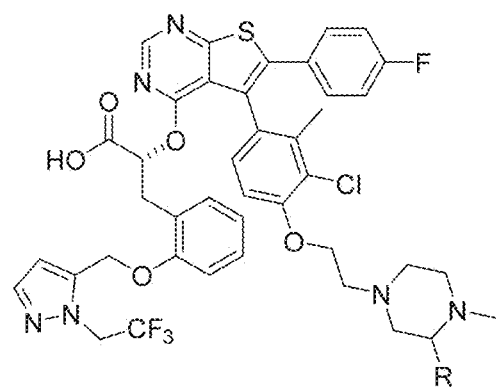
Figure 3K:
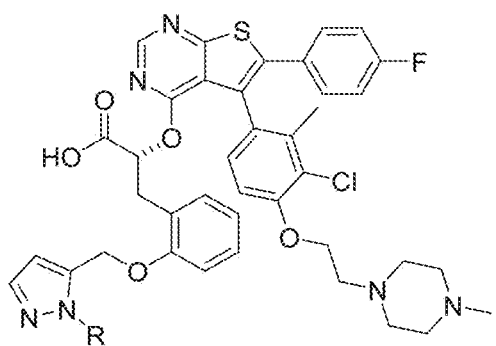
Figure 3K:
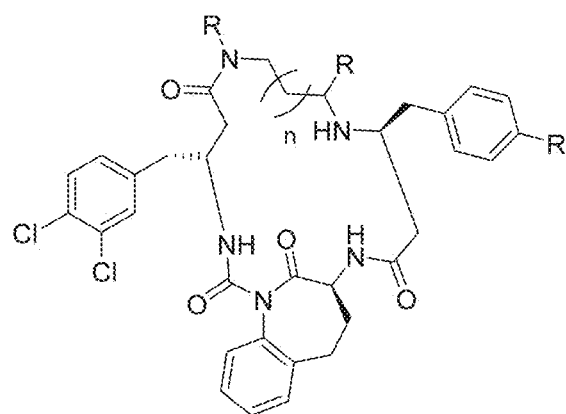
Figure 3K:
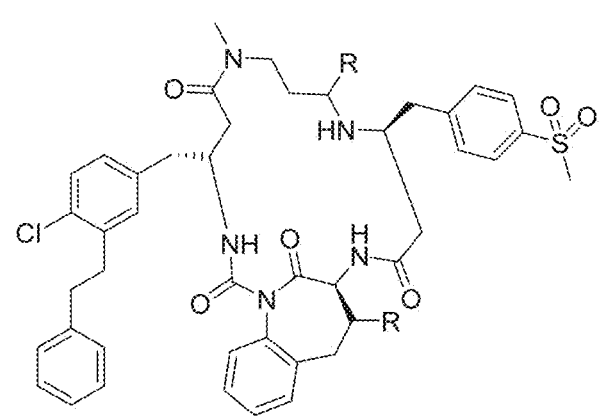
Figure 3L:
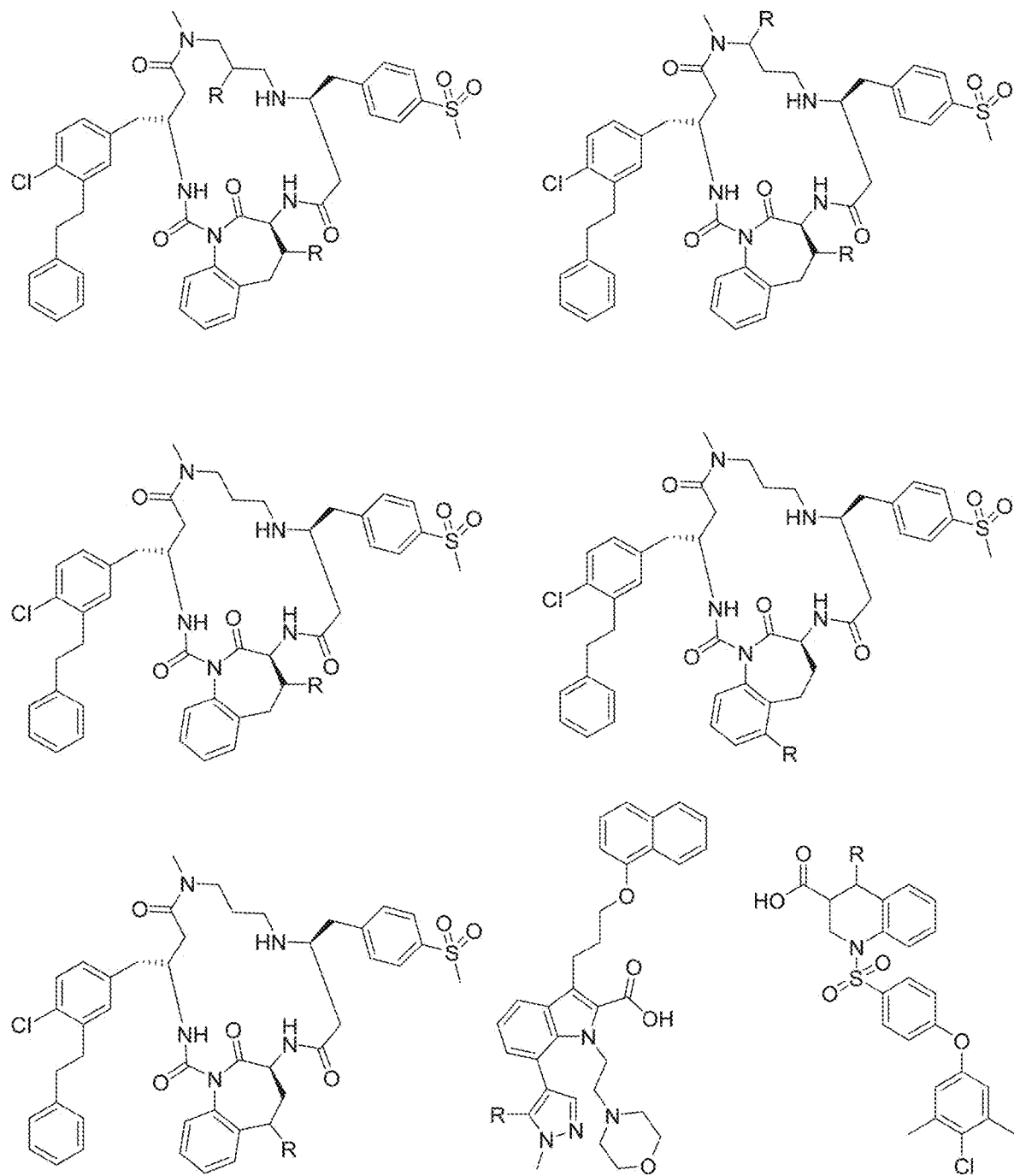
Figure 3M:
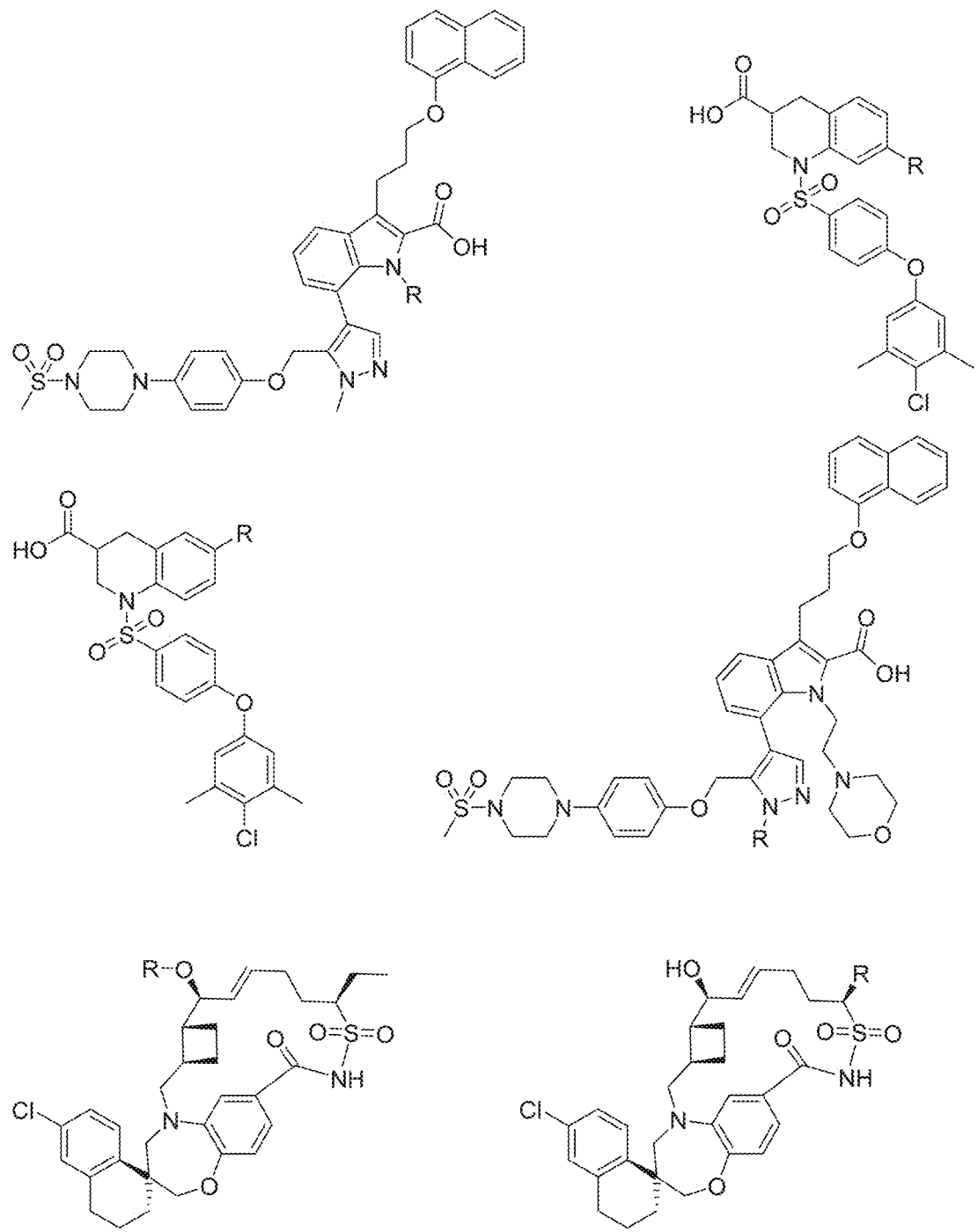
Figure 3N:

Figure 3N:

Figure 3N:

Figure 3N:
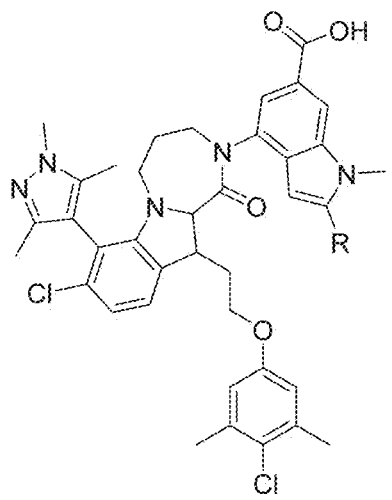
Figure 3N:
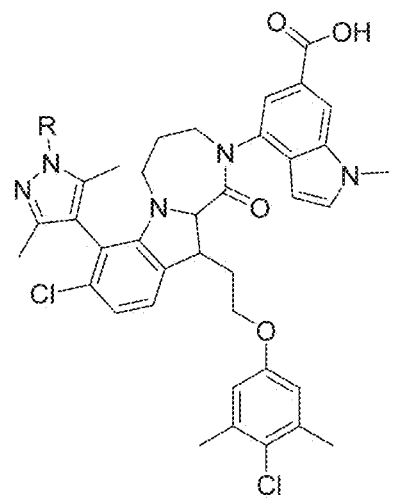
Figure 3N:
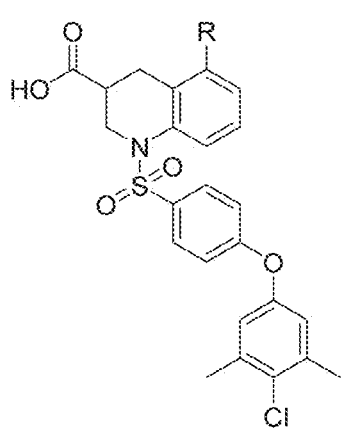
Figure 3O:
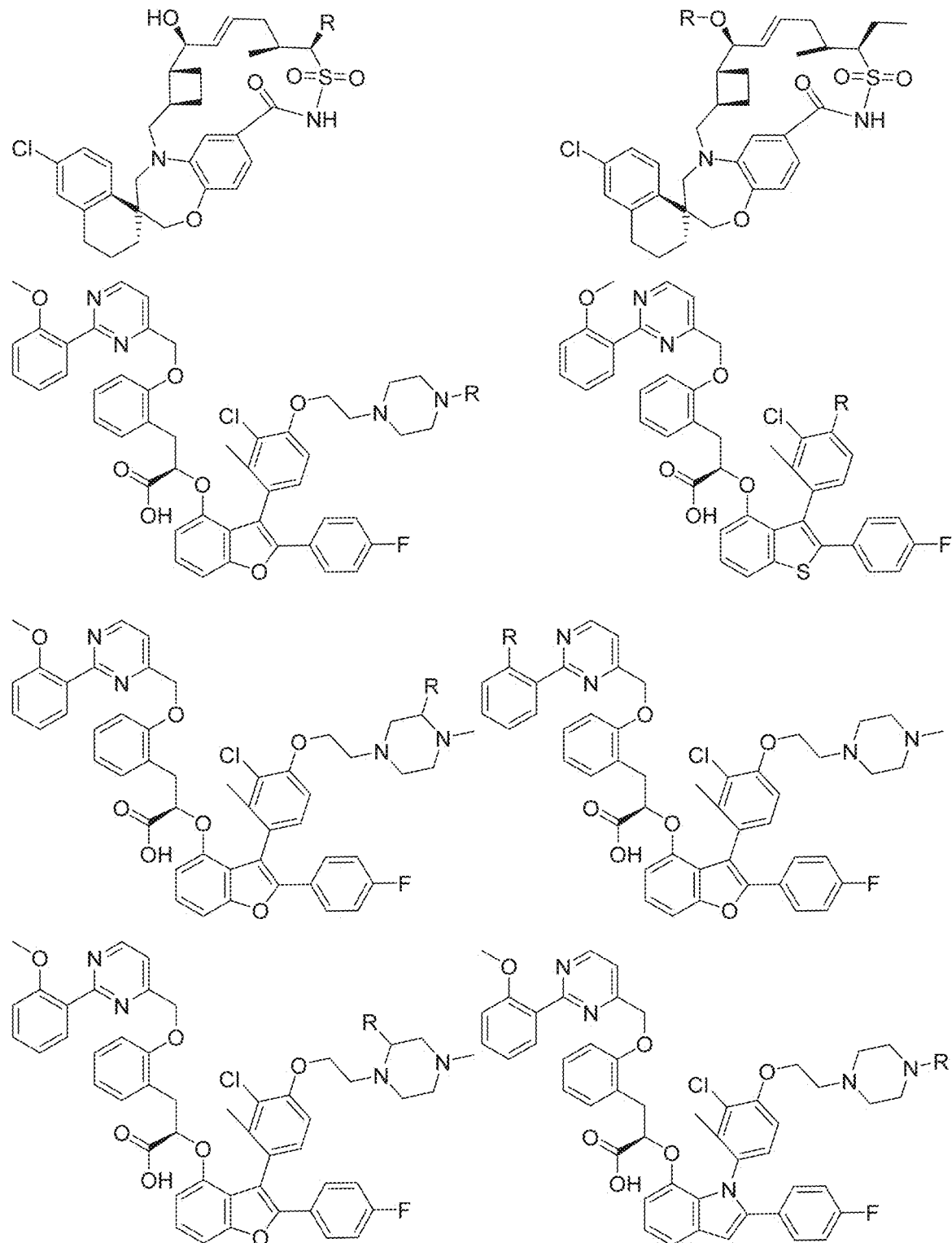
Figure 3P:
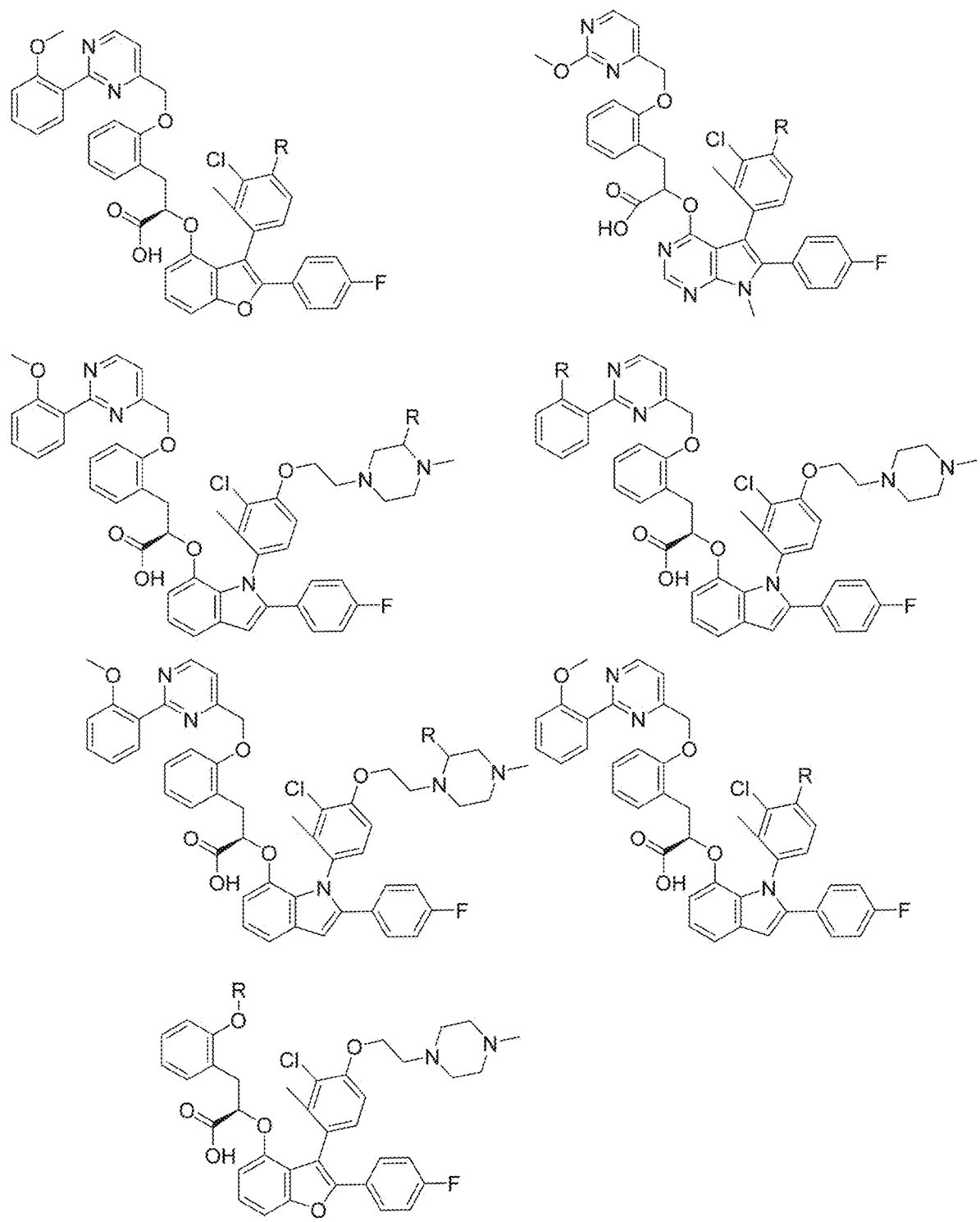
Figure 3Q:
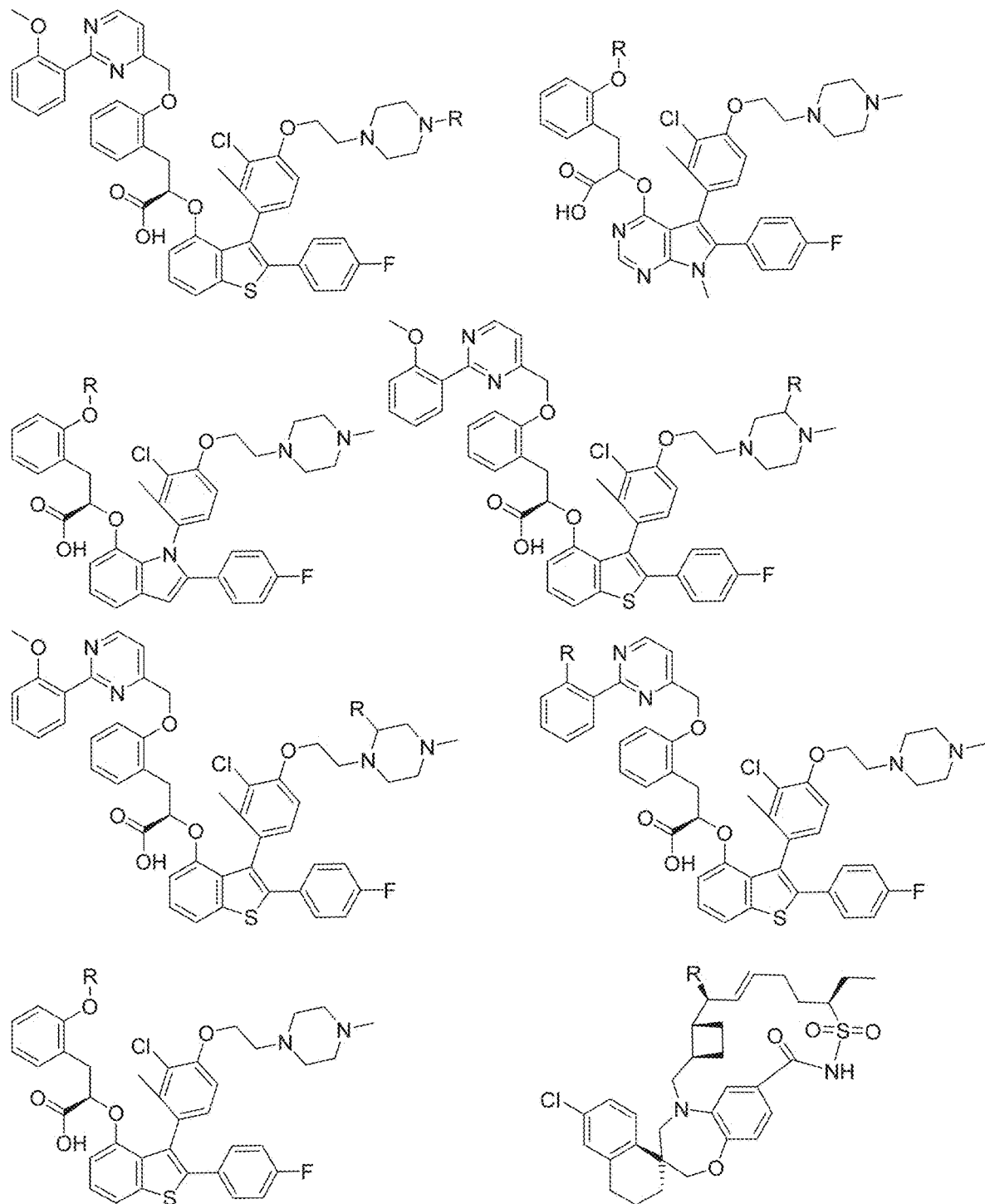
Figure 3R:
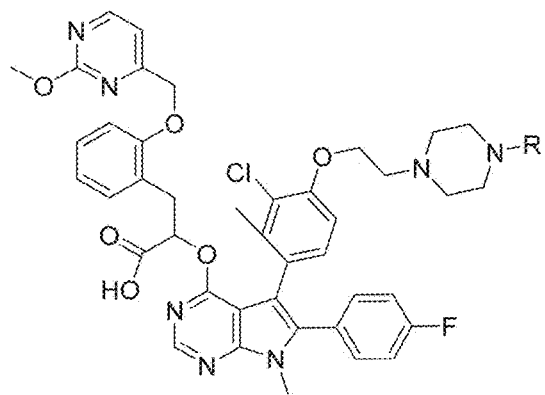
Figure 3R:
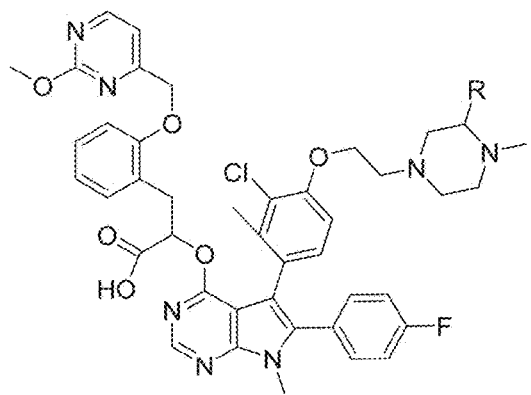
Figure 3R:
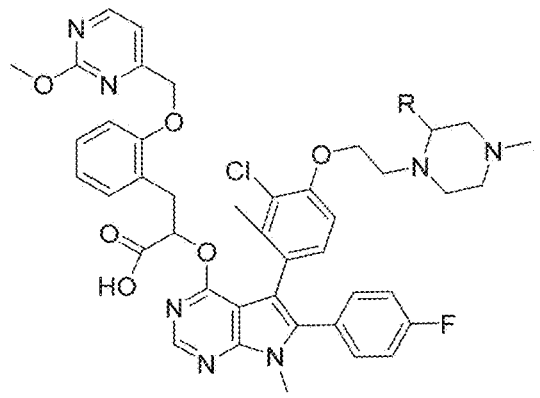
Figure 3R:
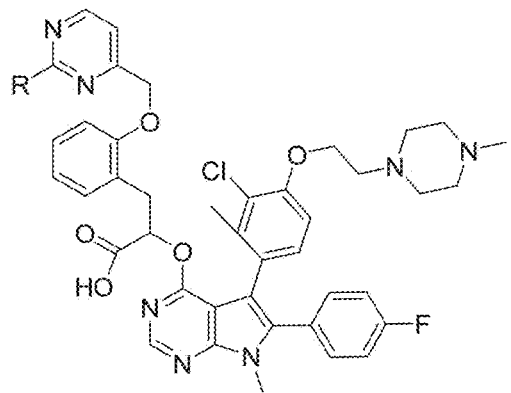
Figure 3R:
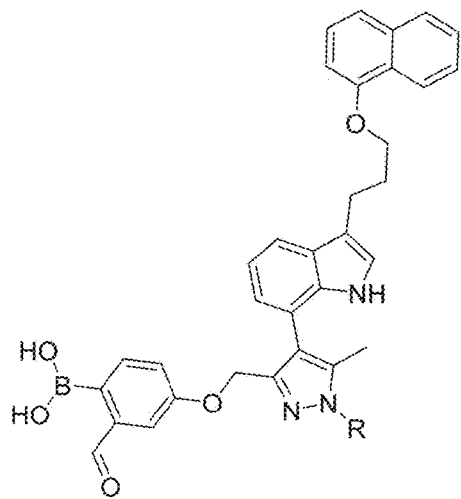
Figure 3R:
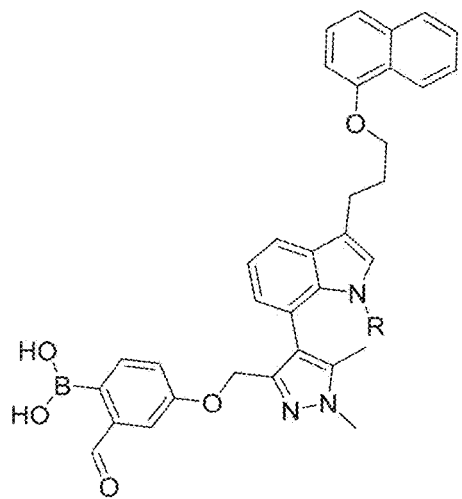
Figure 3S:
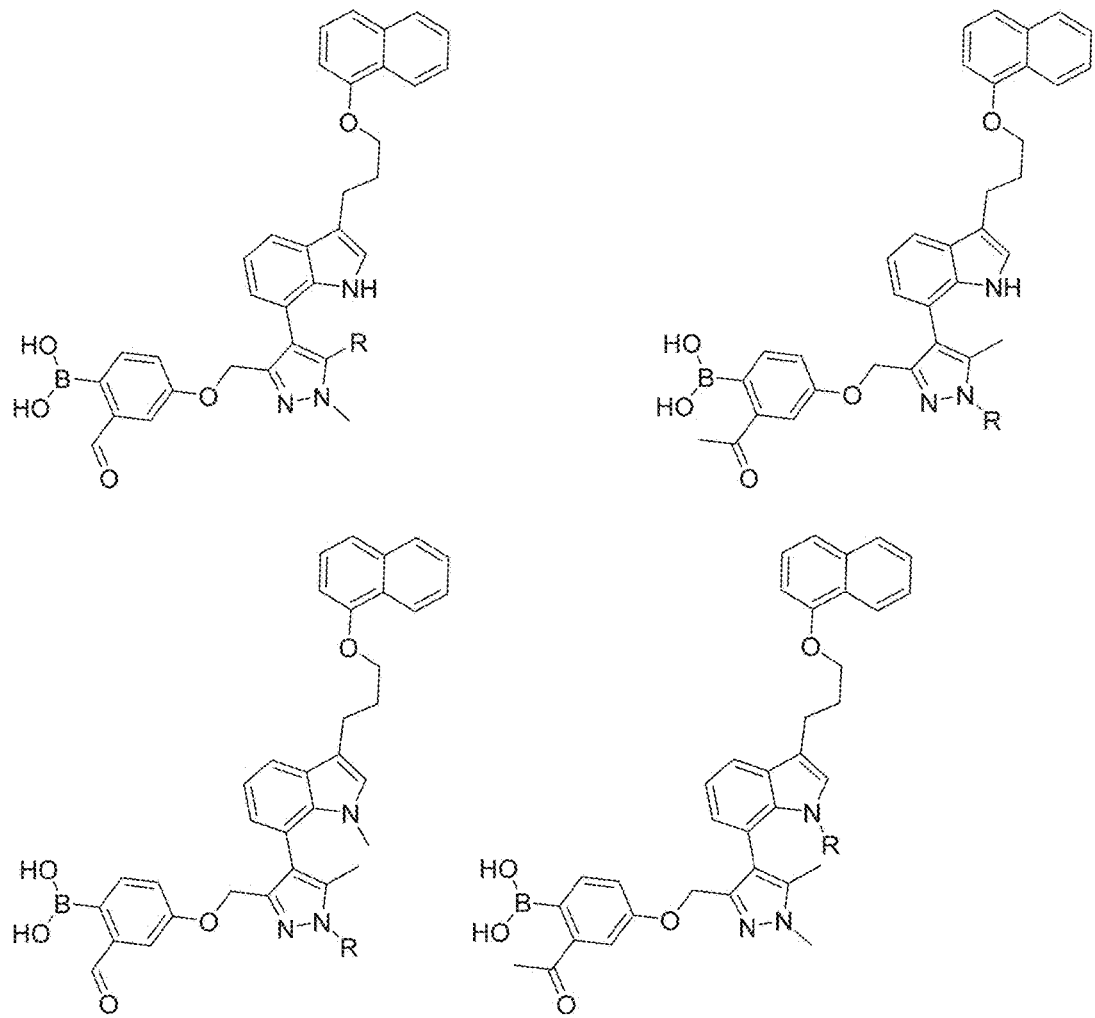
Figure 3T:

Figure 3U:
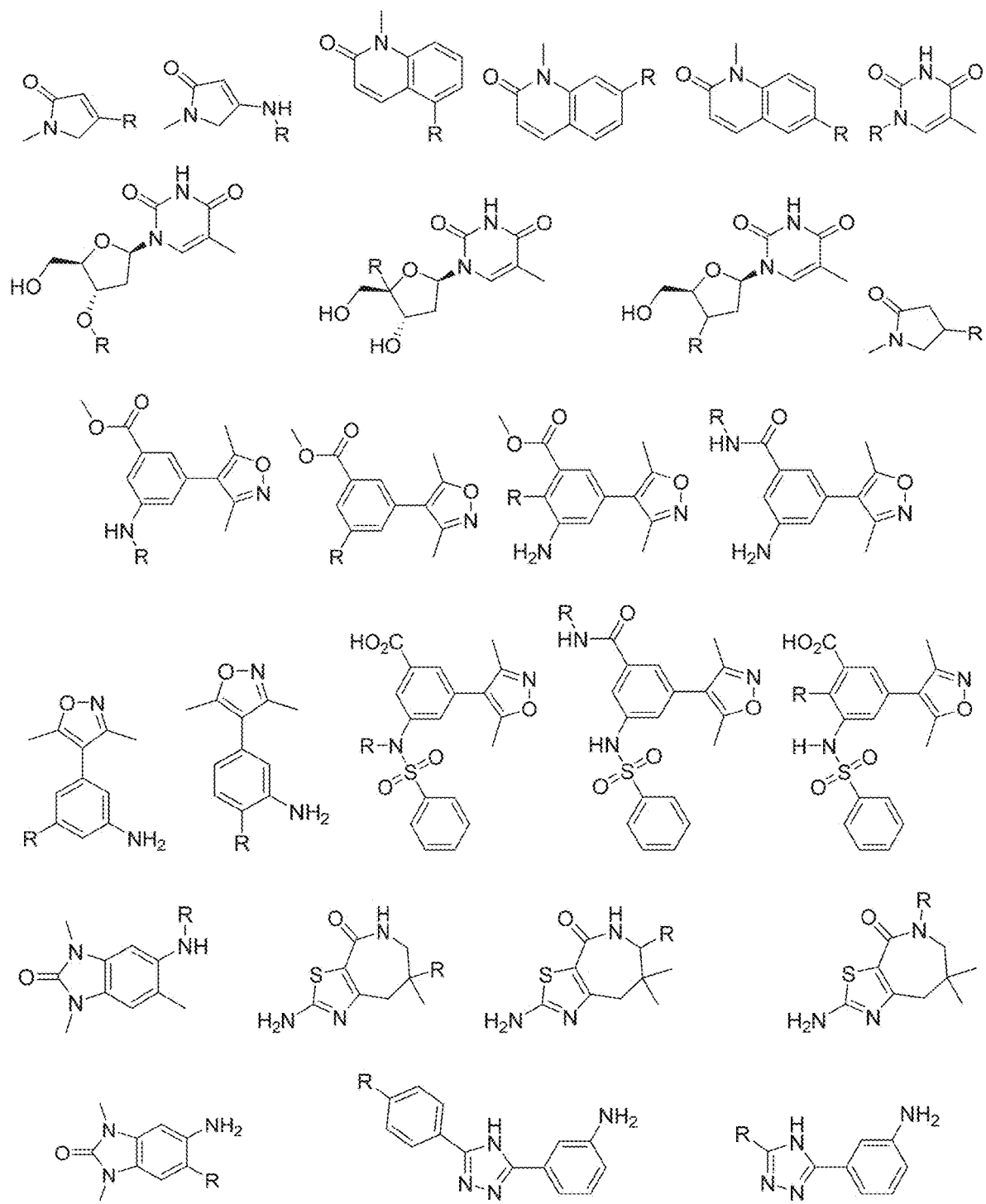
Figure 3V:
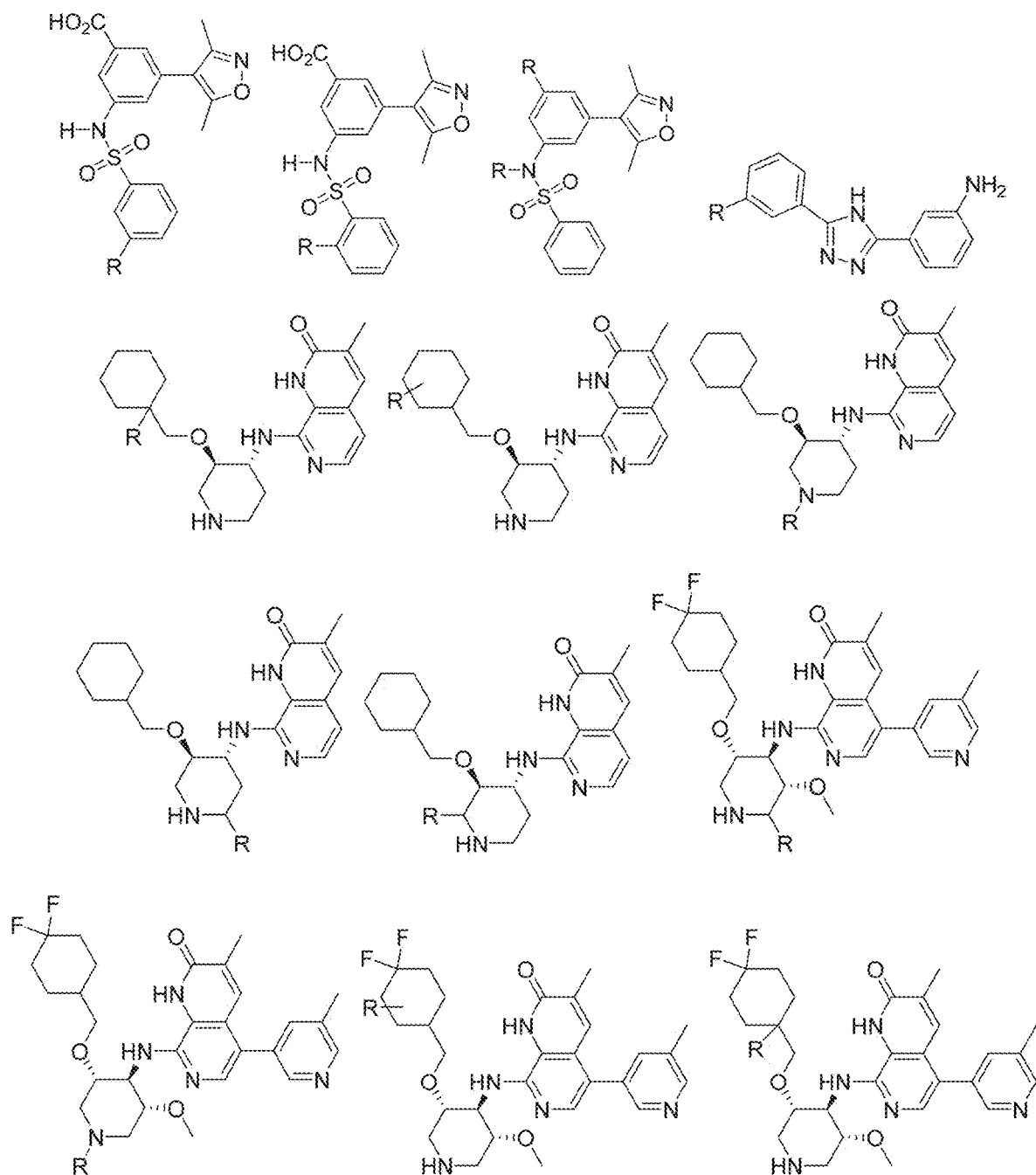
Figure 3W:
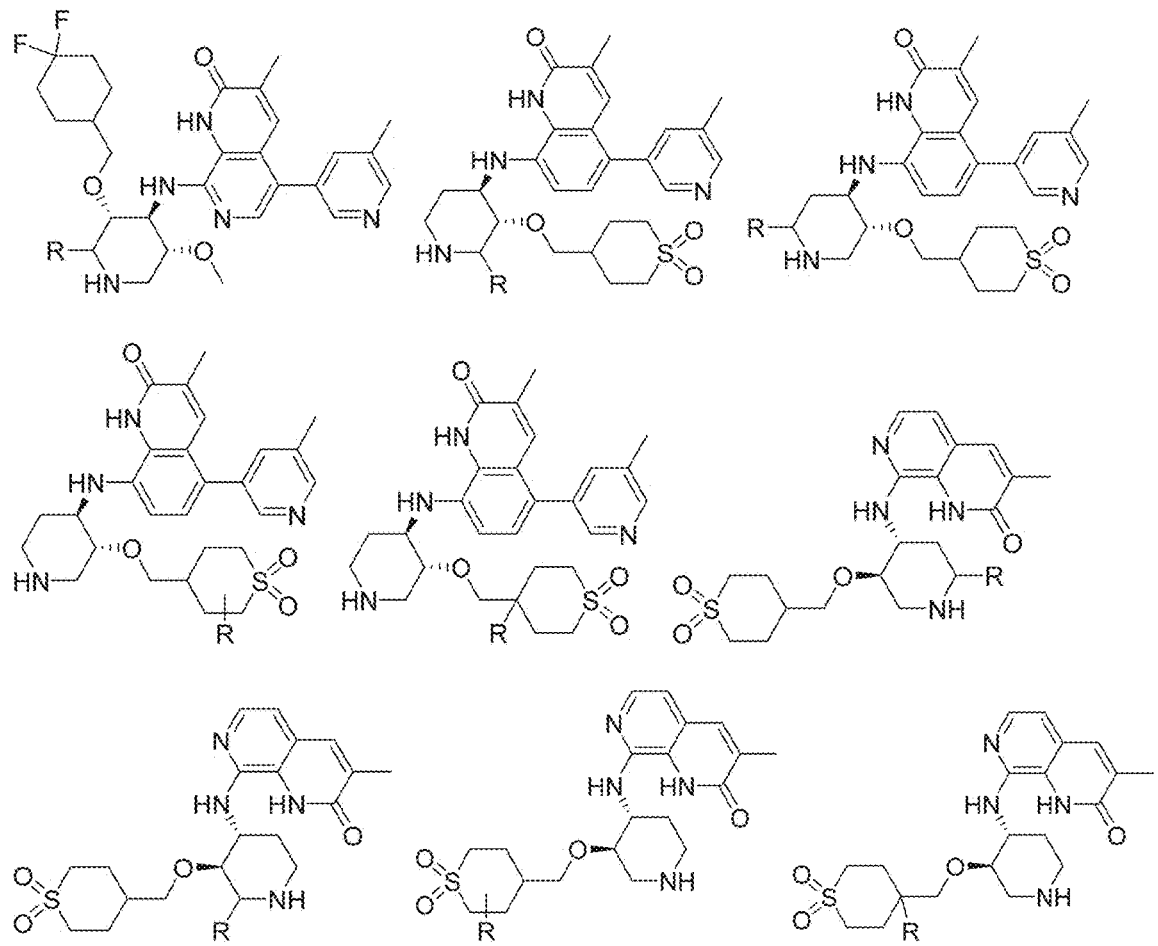
Figure 3X:
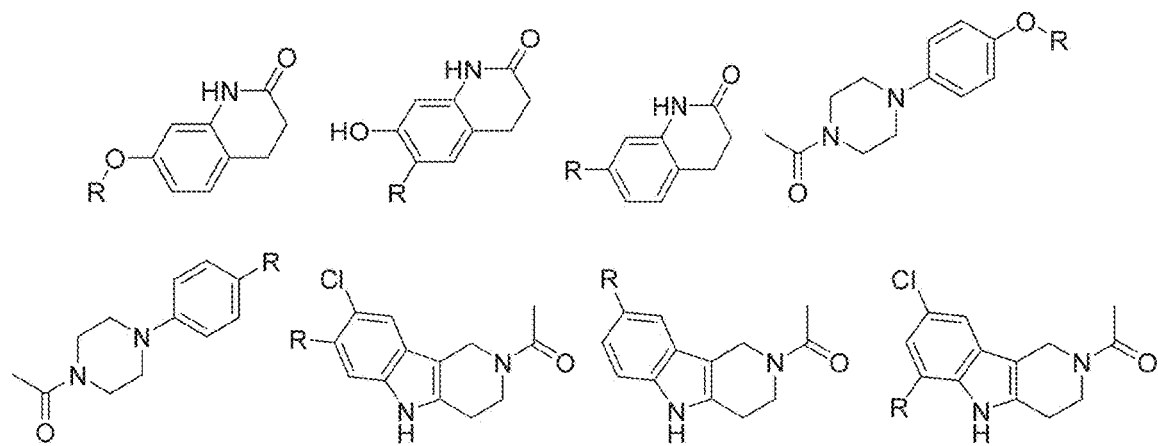
Figure 3Y:
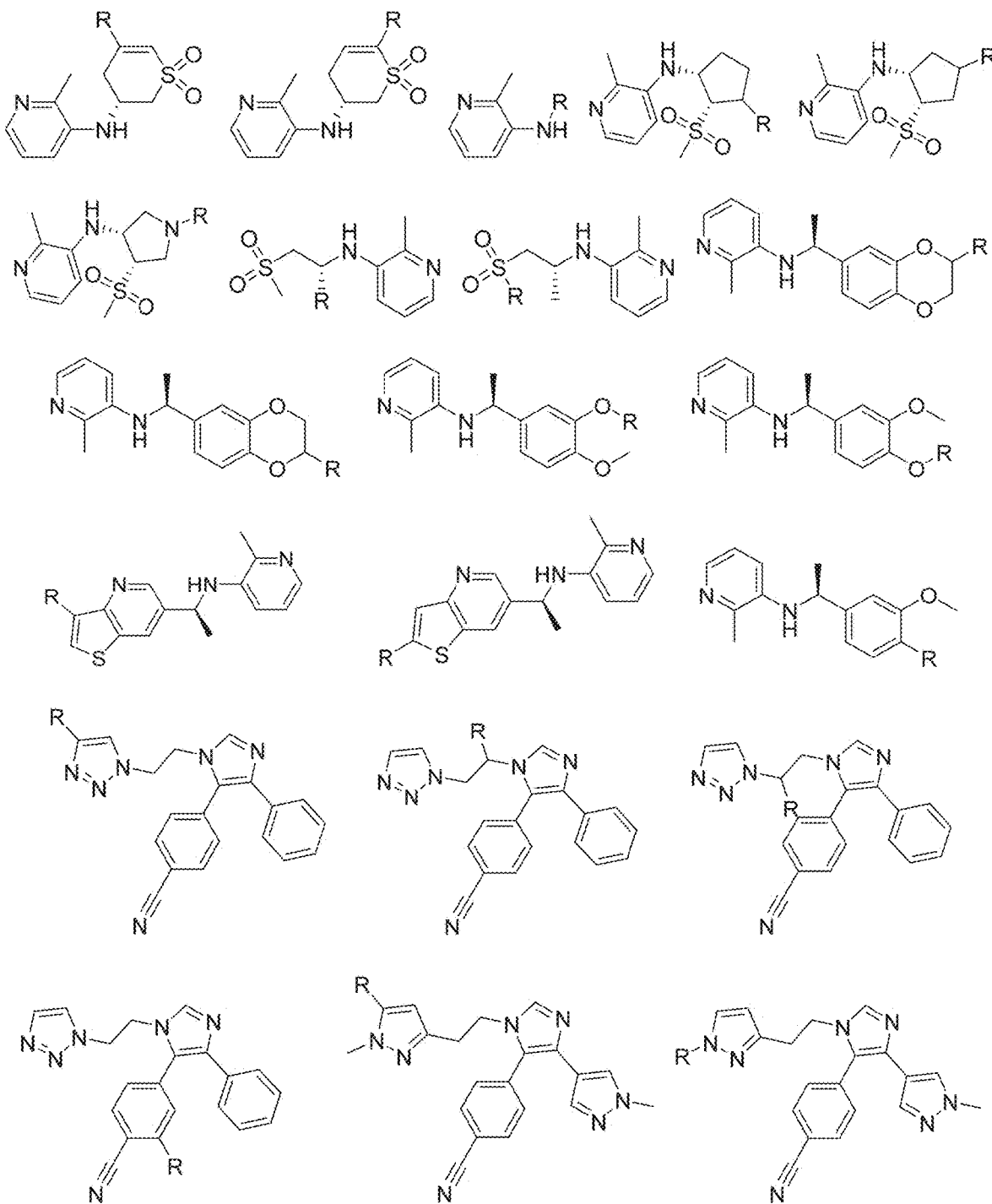
Figure 3Z:
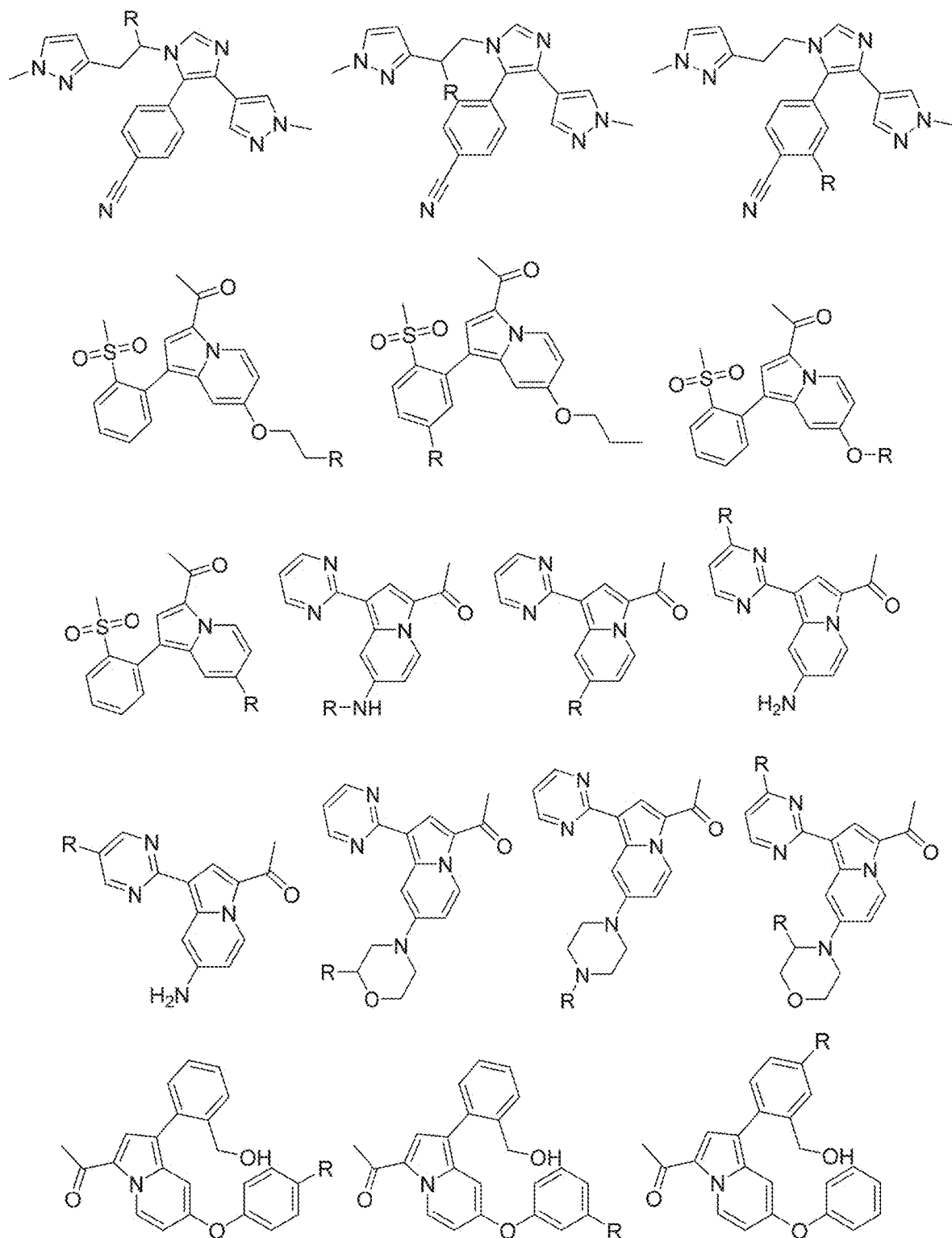

FIG. 3A-3B present examples of MEK1 Targeting Ligands, including PD318088, Trametinib and G-573, wherein R is the point at which the Linker is attached.

FIG. 3C presents examples of KIT Targeting Ligands, including Regorafenib, wherein R is the point at which the Linker is attached.

FIG. 3D-3E present examples of HIV Reverse Transcriptase Targeting Ligands, including Efavirenz, Tenofovir, Emtricitabine, Ritonavir, Raltegravir, and Atazanavir, wherein R is the point at which the Linker is attached.

FIG. 3F-3G present examples of HIV Protease Targeting Ligands, including Ritonavir, Raltegravir, and Atazanavir, wherein R is the point at which the Linker is attached.

FIG. 3H-3I present examples of KSR1 Targeting Ligands wherein R is the point at which the Linker is attached.

FIG. 3J-3L present examples of CNNTB1 Targeting Ligands wherein R is the point at which the Linker is attached.

FIG. 3M presents examples of BCL6 Targeting Ligands wherein R is the point at which the Linker is attached.

FIG. 3N-3O present examples of PAK1 Targeting Ligands wherein R is the point at which the Linker is attached.

FIG. 3P-3R present examples of PAK4 Targeting Ligands wherein R is the point at which the Linker is attached.

FIG. 3S-3T present examples of TNIK Targeting Ligands wherein R is the point at which the Linker is attached.

FIG. 3U presents examples of MEN1 Targeting Ligands wherein R is the point at which the Linker is attached.

FIG. 3V-3W present examples of ERK1 Targeting Ligands wherein R is the point at which the Linker is attached.

FIG. 3X presents examples of IDO1 Targeting Ligands wherein R is the point at which the Linker is attached.

FIG. 3Y presents examples of CBP Targeting Ligands wherein R is the point at which the Linker is attached.

FIG. 3Z-3SS present examples of MCL1 Targeting Ligands wherein R is the point at which the Linker is attached. For additional examples and related ligands, see, Tanaka Y. et al "Discovery of potent Mcl-1/Bcl-xL dual inhibitors by using a hybridization strategy based on structural analysis of target proteins." *J. Med. Chem.* 56: 9635-9645 (2013); Friberg A. et al. "Discovery of potent myeloid cell leukemia 1 (Mcl-1) inhibitors using fragment-based methods and structure-based design." *J. Med. Chem.* 56: 15-30 (2013); Petros A. M. et al "Fragment-based discovery of potent inhibitors of the anti-apoptotic MCL-1 protein." *Bioorg. Med. Chem. Lett.* 24: 1484-1488 (2014); Burke J. P. et al. "Discovery of tricyclic indoles that potently inhibit mcl-1 using fragment-based methods and structure-based design." *J. Med. Chem.* 58: 3794-3805 (2015); Pelz N. F. et al. "Discovery of 2-Indole-acylsulfonamide Myeloid Cell Leukemia 1 (Mcl-1) Inhibitors Using Fragment-Based Methods." *J. Med. Chem.* 59: 2054-2066 (2016); Clifton M. C. et al. "A Maltose-Binding Protein Fusion Construct Yields a Robust Crystallography Platform for MCL1." *Plos One* 10: e0125010-e0125010 (2015); Kotschy A et al. "The MCL1 inhibitor S63845 is tolerable and effective in diverse cancer models. *Nature* 538:477-482 (2016); EP 2886545 A1 titled "New thienopyrimidine derivatives a process for their preparation and pharmaceutical compositions containing them"; Jeffrey W. Johannes et al. "Structure Based Design of Non-Natural Peptidic Macrocyclic Mcl-1 Inhibitors" *ACS Med. Chem. Lett.* (2017); DOI: 10.1021/acsmedchemlett.6b00464; Bruncko M. et al. "Structure-Guided Design of a Series of MCL-1 Inhibitors with High Affinity and Selectivity." *J. Med. Chem.* 58: 2180-2194 (2015); Taekyu Lee et al. "Discovery and biological characterization of potent myeloid cell leukemia-1 inhibitors." *FEBS Letters* 591: 240-251 (2017); Chen L. et al. "Structure-Based Design of 3-Carboxy-Substituted 1 2 3 4-Tetrahydroquinolines as Inhibitors of Myeloid Cell Leukemia-1 (Mcl-1)." *Org. Biomol. Chem.* 14:5505-5510 (2016); US 2016/0068545 titled "Tetrahydronaphthalene derivatives that inhibit mcl-1 protein"; WO 2016207217 A1 titled "Preparation of new bicyclic derivatives as pro-apoptotic agents"; Gizem Akgay et al. "Inhibition of Mcl-1 through covalent modification of a noncatalytic lysine side chain" *Nature Chemical Biology* 12: 931-936 (2016).

FIG. 3TT presents examples of ASH1L Targeting Ligands wherein R is the point at which the Linker is attached. See for example, the crystal structure PDB 4YNM ("Human ASH1L SET domain in complex with S-adenosyl methionine (SAM)" Rogawski D. S. et al.)

FIG. 3UU-3WW present examples of ATAD2 Targeting Ligands wherein R is the point at which the Linker is attached. For additional examples and related ligands, see, Chaikuad A. et al. "Structure-based approaches towards identification of fragments for the low-druggability ATAD2 bromodomain" *Med Chem Comm* 5: 1843-1848 (2014);

Poncet-Montange G. et al. "Observed bromodomain flexibility reveals histone peptide- and small molecule ligand-compatible forms of ATAD2." *Biochem. J.* 466: 337-346 (2015); Harner M. J. et al. "Fragment-Based Screening of the Bromodomain of ATAD2." *J. Med. Chem.* 57: 9687-9692 (2014); Demont E. H. et al. "Fragment-Based Discovery of Low-Micromolar Atad2 Bromodomain Inhibitors." *J. Med. Chem.* 58: 5649 (2015); and, Bamborough P. et al. "Structure-Based Optimization of Naphthyridones into Potent Atad2 Bromodomain Inhibitors." *J. Med. Chem.* 58: 6151 (2015).

FIG. 3XX-3AAA present examples of BAZ2A and BAZ2B Targeting Ligands wherein R is the point at which the Linker is attached. For additional examples and related ligands, see, the crystal structure PDB 4CUU ("Human Baz2B in Complex with Fragment-6 N09645" Bradley A. et al.); the crystal structure PDB 5CUA ("Second Bromodomain of Bromodomain Adjacent to Zinc Finger Domain Protein 2B (BAZ2B) in complex with 1-Acetyl-4-(4-hydroxyphenyl)piperazine". Bradley A. et al.); Ferguson F. M. et al. "Targeting low-druggability bromodomains: fragment based screening and inhibitor design against the BAZ2B bromodomain." *J. Med. Chem.* 56: 10183-10187 (2013); Marchand J. R. et al. "Derivatives of 3-Amino-2-methylpyridine as BAZ2B Bromodomain Ligands: In Silico Discovery and in Crystallo Validation." *J. Med. Chem.* 59: 9919-9927 (2016); Drouin L. et al. "Structure Enabled Design of BAZ2-ICR A Chemical Probe Targeting the Bromodomains of BAZ2A and BAZ2B." *J. Med. Chem.* 58: 2553-2559 (2015); Chen P. et al. "Discovery and characterization of GSK2801 a selective chemical probe for the bromodomains BAZ2A and BAZ2B." *J. Med. Chem.* 59:1410-1424 (2016).

FIG. 3BBB presents examples of BRD1 Targeting Ligands wherein R is the point at which the Linker is attached. For additional examples and related ligands, see, the crystal structure PDB 5AME ("the Crystal Structure of the Bromodomain of Human Surface Epitope Engineered Brd1A in Complex with 3D Consortium Fragment 4-Acetyl-Piperazin-2-One Pearce", N. M. et al.); the crystal structure PDB 5AMF ("Crystal Structure of the Bromodomain of Human Surface Epitope Engineered Brd1A in Complex with 3D Consortium Fragment Ethyl 4 5 6 7-Tetrahydro-1H-Indazole-5-Carboxylate", Pearce N. M. et al.); the crystal structure PDB 5FG6 ("the Crystal structure of the bromodomain of human BRD1 (BRPF2) in complex with OF-1 chemical probe.", Tallant C. et al.); Filippakopoulos P. et al. "Histone recognition and large-scale structural analysis of the human bromodomain family." *Cell*, 149: 214-231 (2012).

FIG. 3CCC-3EEE present examples of BRD2 Bromodomain 1 Targeting Ligands wherein R is the point at which the Linker is attached. For additional examples and related ligands, see, the crystal structure PDB 2ydw; the crystal structure PDB 2yek; the crystal structure PDB 4a9h; the crystal structure PDB 4a9f; the crystal structure PDB 4a9i; the crystal structure PDB 4a9m; the crystal structure PDB 4akn; the crystal structure PDB 4alg, and the crystal structure PDB 4uyf.

FIG. 3FFF-3HHH present examples of BRD2 Bromodomain 2 Targeting Ligands wherein R is the point at which the Linker is attached. For additional examples and related ligands, see, the crystal structure PDB 3oni; Filippakopoulos P. et al. "Selective Inhibition of BET Bromodomains." *Nature* 468: 1067-1073 (2010); the crystal structure PDB 4j1p; McLure K. G. et al. "RVX-208: an Inducer of ApoA-I in Humans is a BET Bromodomain Antagonist." *Plos One* 8: e83190-e83190 (2013); Baud M. G. et al. "Chemical biology. A bump-and-hole approach to engineer controlled selectivity of BET bromodomain chemical probes" *Science* 346: 638-641 (2014); Baud M. G. et al. "New Synthetic Routes to Triazolo-benzodiazepine Analogues: Expanding the Scope of the Bump-and-Hole Approach for Selective Bromo and Extra-Terminal (BET) Bromodomain Inhibition" *J. Med. Chem.* 59: 1492-1500 (2016); Gosmini R. et al. "The Discovery of I-Bet726 (Gsk1324726A) a Potent Tetrahydroquinoline Apoa1 Up-Regulator and Selective Bet Bromodomain Inhibitor" *J. Med. Chem.* 57: 8111 (2014); the crystal structure PDB 5EK9 ("Crystal structure of the second bromodomain of human BRD2 in complex with a hydroquinolinone inhibitor", Tallant C. et al); the crystal structure PDB 5BT5; the crystal structure PDB 5dfd; Baud M. G. et al. "New Synthetic Routes to Triazolo-benzodiazepine Analogues: Expanding the Scope of the Bump-and-Hole Approach for Selective Bromo and Extra-Terminal (BET) Bromodomain Inhibition" *J. Med. Chem.* 59: 1492-1500 (2016).

FIG. 3III-3JJJ present examples of BRD4 Bromodomain 1 Targeting Ligands wherein R is the point at which the Linker is attached. For additional examples and related ligands, see, the crystal structure PDB 5WUU and the crystal structure PDB 5F5Z.

FIG. 3KKK-3LLL present examples of BRD4 Bromodomain 2 Targeting Ligands wherein R is the point at which the Linker is attached. For additional examples and related ligands, see, Chung C. W. et al. "Discovery and Characterization of Small Molecule Inhibitors of the Bet Family Bromodomains" *J. Med. Chem.* 54: 3827 (2011) and Ran X. et al. "Structure-Based Design of gamma-Carboline Analogues as Potent and Specific BET Bromodomain Inhibitors" *J. Med. Chem.* 58: 4927-4939 (2015).

FIG. 3MMM presents examples of BRDT Targeting Ligands wherein R is the point at which the Linker is attached. For additional examples and related ligands, see, the crystal structure PDB 4flp and the crystal structure PDB 4kcx.

FIG. 3NNN-3QQQ present examples of BRD9 Targeting Ligands wherein R is the point at which the Linker is attached. For additional examples and related ligands, see, the crystal structure PDB 4nqn; the crystal structure PDB 4uit; the crystal structure PDB 4uiu; the crystal structure PDB 4uiv; the crystal structure PDB 4z6h; the crystal structure PDB 4z6i; the crystal structure PDB 5e9v; the crystal structure PDB 5eu1; the crystal structure PDB 5f1h; and, the crystal structure PDB 5fp2.

FIG. 3RRR presents examples of SMARCA4 PB1 and/or SMARCA2 Targeting Ligands wherein R is the point at which the Linker is attached, A is N or CH, and m is 0 1 2 3 4 5 6 7 or 8.

FIG. 3SSS-3XXX present examples of additional Bromodomain Targeting Ligands wherein R is the point at which the Linker is attached. For additional examples and related ligands, see, Hewings et al. "3 5-Dimethylisoxazoles Act as Acetyl-lysine Bromodomain Ligands." *J. Med. Chem.* 54 6761-6770 (2011); Dawson et al. "Inhibition of BET Recruitment to Chromatin as an Effective Treatment for MLL-fusion Leukemia." *Nature*, 478, 529-533 (2011); US 2015/0256700; US 2015/0148342; WO 2015/074064; WO 2015/067770; WO 2015/022332; WO 2015/015318; and, WO 2015/011084.

FIG. 3YYY presents examples of PB1 Targeting Ligands wherein R is the point at which the Linker is attached. For additional examples and related ligands, see, the crystal structure PDB 3mb4; the crystal structure PDB 4q0n; and, the crystal structure PDB 5fh6.

FIG. 3ZZZ presents examples of SMARCA4 Targeting Ligands wherein R is the point at which the Linker is attached. For additional examples and related ligands, see, the crystal structure 3uvd and the crystal structure 5dkd.

FIG. 3AAAA presents examples of SMARCA2 Targeting Ligands wherein R is the point at which the Linker is attached. For additional examples and related ligands, see, the crystal structure 5dkc and the crystal structure 5dkh.

FIG. 3BBBB presents examples of TRIM24 (TIF1a) and/or BRPF1 Targeting Ligands wherein R is the point at which the Linker is attached and m is 0 1 2 3 4 5 6 7 or 8.

FIG. 3CCCC presents examples of TRIM24 (TIF1a) Targeting Ligands wherein R is the point at which the Linker is attached. For additional examples and related ligands, see, Palmer W. S. et al. "Structure-Guided Design of IACS-9571: a Selective High-Affinity Dual TRIM24-BRPF1 Bromodomain Inhibitor." *J. Med. Chem.* 59: 1440-1454 (2016).

FIG. 3DDDD-3FFFF present examples of BRPF1 Targeting Ligands wherein R is the point at which the Linker is attached. For additional examples and related ligands, see, the crystal structure PDB 4uye; the crystal structure PDB 5c7n; the crystal structure PDB 5c87; the crystal structure PDB 5c89; the crystal structure PDB 5d7x; the crystal structure PDB 5dya; the crystal structure PDB 5epr; the crystal structure PDB 5eq1; the crystal structure PDB 5etb; the crystal structure PDB 5ev9; the crystal structure PDB 5eva; the crystal structure PDB 5ewv; the crystal structure PDB 5eww; the crystal structure PDB 5ffy; the crystal structure PDB 5fg5; and, the crystal structure PDB 5g4r.

FIG. 3GGGG presents examples of CECR2 Targeting Ligands wherein R is the point at which the Linker is attached. For additional examples and related ligands, see, Moustakim M. et al. *Med. Chem. Comm.* 7:2246-2264 (2016) and Crawford T. et al. *Journal of Med. Chem.* 59; 5391-5402 (2016).

FIG. 3HHHH-3OOOO present examples of CREBBP Targeting Ligands wherein R is the point at which the Linker is attached, A is N or CH, and m is 0 1 2 3 4 5 6 7 or 8. For additional examples and related ligands, see, the crystal structure PDB 3p1d; the crystal structure PDB 3svh; the crystal structure PDB 4nr4; the crystal structure PDB 4nr5; the crystal structure PDB 4ts8; the crystal structure PDB 4nr6; the crystal structure PDB 4nr7; the crystal structure PDB 4nyw; the crystal structure PDB 4nyx; the crystal structure PDB 4tqn; the crystal structure PDB 5cgp; the crystal structure PDB 5dbm; the crystal structure PDB 5ep7; the crystal structure PDB 5i83; the crystal structure PDB 5i86; the crystal structure PDB 5i89; the crystal structure PDB 5i8g; the crystal structure PDB 5j0d; the crystal structure PDB 5ktu; the crystal structure PDB 5ktw; the crystal structure PDB 5ktx; the crystal structure PDB 5tb6.

FIG. 3PPPP presents examples of EP300 Targeting Ligands wherein R is the point at which the Linker is attached. For additional examples and related ligands, see, the crystal structure PDB 5BT3.

FIG. 3QQQQ presents examples of PCAF Targeting Ligands wherein R is the point at which the Linker is attached. See for example, M. Ghizzoni et al. *Bioorg. Med. Chem.* 18: 5826-5834 (2010).

FIG. 3RRRR presents examples of PHIP Targeting Ligands wherein R is the point at which the Linker is attached. For additional examples and related ligands, see, *Mol Cancer Ther.* 7(9): 2621-2632 (2008).

FIG. 3SSSS presents examples of TAF1 and TAF1L Targeting Ligands wherein R is the point at which the Linker is attached. For additional examples and related ligands, see, Picaud S. et al. *Sci Adv* 2: e1600760-e1600760 (2016).

FIG. 3TTTT presents examples of Histone Deacetylase 2 (HDAC2) Targeting Ligands wherein R is the point at which the Linker is attached. For additional examples and related ligands, see, Lauffer B. E. *J. Biol. Chem.* 288: 26926-26943 (2013); Wagner F. F. *Bioorg. Med. Chem.* 24: 4008-4015 (2016); Bressi J. C. *Bioorg. Med. Chem. Lett.* 20: 3142-3145 (2010); and, Lauffer B. E. *J. Biol. Chem.* 288: 26926-26943 (2013).

FIG. 3UUUU-3VVVV present examples of Histone Deacetylase 4 (HDAC4) Targeting Ligands wherein R is the point at which the Linker is attached. For additional examples and related ligands, see, Burli R. W. *J. Med. Chem.* 56: 9934 (2013); Luckhurst C. A. *ACS Med. Chem. Lett.* 7: 34 (2016); Bottomley M. J. *J. Biol. Chem.* 283: 26694-26704 (2008).

FIG. 3WWWW presents examples of Histone Deaceytlase 6 Targeting Ligands wherein R is the point at which the Linker is attached. For additional examples and related ligands, see, Harding R. J. (to be published); Hai Y. *Nat. Chem. Biol.* 12: 741-747, (2016); and, Miyake Y. *Nat. Chem. Biol.* 12: 748 (2016).

FIG. 3XXXX-3YYYY presents examples of Histone Deacetylase 7 Targeting Ligands wherein R is the point at which the Linker is attached. For additional examples and related ligands, see, Lobera M. *Nat. Chem. Biol.* 9: 319 (2013) and Schuetz A. *J. Biol. Chem.* 283: 11355-11363 (2008).

FIG. 3ZZZZ-3DDDDD present examples of Histone Deacetylase 8 Targeting Ligands wherein R is the point at which the Linker is attached. For additional examples and related ligands, see, Whitehead L. Biol. *Med. Chem.* 19: 4626-4634 (2011); Tabackman A. A. *J. Struct. Biol.* 195: 373-378 (2016); Dowling D. P. *Biochemistry* 47, 13554-13563 (2008); Somoza J. R. *Biochemistry* 12, 1325-1334 (2004); Decroos C. *Biochemistry* 54: 2126-2135 (2015); Vannini A. *Proc. Natl Acad. Sci.* 101: 15064 (2004); Vannini A. *EMBO Rep.* 8: 879 (2007); the crystal structure PDB 5BWZ; Decroos A. *ACS Chem. Biol.* 9: 2157-2164 (2014); Somoza J. R. *Biochemistry* 12: 1325-1334 (2004); Decroos C. *Biochemistry* 54: 6501-6513 (2015); Decroos A. *ACS Chem. Biol.* 9: 2157-2164 (2014); and, Dowling D. P. *Biochemistry* 47: 13554-13563 (2008).

FIG. 3EEEEE presents examples of Histone Acetyltransferase (KAT2B) Targeting Ligands wherein R is the point at which the Linker is attached. For additional examples and related ligands, see, Chaikuad A. *J. Med. Chem.* 59: 1648-1653 (2016); the crystal structure PDB 1ZS5; and, Zeng L. *J. Am. Chem. Soc.* 127: 2376-2377 (2005).

FIG. 3FFFFF-3GGGGG present examples of Histone Acetyltransferase (KAT2A) Targeting Ligands wherein R is the point at which the Linker is attached. For additional examples and related ligands, see, Ringel A. E. *Acta Crystallogr. D. Struct. Biol.* 72: 841-848 (2016).

FIG. 3HHHHH presents examples of Histone Acetyltransferase Type B Catalytic Unit (HAT1) Targeting Ligands wherein R is the point at which the Linker is attached. For additional examples and related ligands, see, the crystal structure PDB 2POW.

FIG. 3IIIII presents examples of Cyclic AMP-dependent Transcription Factor (ATF2) Targeting Ligands wherein R is the point at which the Linker is attached.

FIG. 3JJJJJ presents examples of Histone Acetyltransferase (KAT5) Targeting Ligands wherein R is the point at which the Linker is attached.

FIG. 3KKKKK-3MMMMM present examples of Lysine-specific histone demethylase 1A (KDM1A) Targeting Ligands wherein R is the point at which the Linker is attached. For additional examples and related ligands, see, Mimasu S. *Biochemistry* 49: 6494-6503 (2010); Sartori L. *J. Med. Chem.* 60:1673-1693 (2017); and, Vianello P. *J. Med. Chem.* 60: 1693-1715 (2017).

FIG. 3NNNNN presents examples of HDAC6 Zn Finger Domain Targeting Ligands wherein R is the point at which the Linker is attached.

FIG. 3OOOOO-3PPPPP present examples of general Lysine Methyltransferase Targeting Ligands wherein R is the point at which the Linker is attached.

FIG. 3QQQQQ-3TTTTT present examples of DOT1L Targeting Ligands wherein R is the point at which the Linker is attached, A is N or CH, and m is 0 1 2 3 4 5 6 7 or 8. For additional examples and related ligands, see, the crystal structure PDB 5MVS ("Dot1L in complex with adenosine and inhibitor CPD1" Be C. et al.); the crystal structure PDB 5MW4 ("Dot1L in complex inhibitor CPD7" Be C. et al.); the crystal structure PDB 5DRT ("Dot1L in complex inhibitor CPD2" Be C. et al.); Be C. et al. *ACS Med. Lett.* 8: 338-343 (2017); the crystal structure PDB 5JUW "(Dot1L in complex with SS148" Yu W. et al. Structural Genomics Consortium).

FIG. 3UUUUU presents examples of EHMT1 Targeting Ligands wherein R is the point at which the Linker is attached. For additional examples and related ligands, see, the crystal structure PDB 5TUZ ("EHMT1 in complex with inhibitor MS0124", Babault N. et al.).

FIG. 3VVVVV presents examples of EHMT2 Targeting Ligands wherein R is the point at which the Linker is attached. For additional examples and related ligands, see, the crystal structure PDB 5TUY ("EHMT2 in complex with inhibitor MS0124", Babault N. et al.); the PDB crystal structure 5TTF ("EHMT2 in complex with inhibitor MS012", Dong A. et al.); the PDB crystal structure 3RJW (Dong A. et al., Structural Genomics Consortium); the PDB crystal structure 3K5K; Liu F. et al. *J. Med. Chem.* 52: 7950-7953 (2009); and, the PDB crystal structure 4NVQ ("EHMT2 in complex with inhibitor A-366" Sweis R. F. et al.).

FIG. 3WWWWW presents examples of SETD2 Targeting Ligands wherein R is the point at which the Linker is attached. For additional examples and related ligands, see, the PDB crystal structure 5LSY ("SETD2 in complex with cyproheptadine", Tisi D. et al.); Tisi D. et al. *ACS Chem. Biol.* 11: 3093-3105 (2016); the crystal structures PDB 5LSS, 5LSX, 5LSZ, 5LT6, 5LT7, and 5LT8; the PDB crystal structure 4FMU; and, Zheng W. et al. *J. Am. Chem. Soc.* 134: 18004-18014 (2012).

FIG. 3XXXXX-3YYYYY present examples of SETD7 Targeting Ligands wherein R is the point at which the Linker is attached. For additional examples and related ligands, see, the PDB crystal structure 5AYF ("SETD7 in complex with cyproheptadine." Niwa H. et al.); the PDB crystal structure 4JLG ("SETD7 in complex with (R)-PFI-2", Dong A. et al.); the PDB crystal structure 4JDS (Dong A. et. al Structural Genomics Consortium); the PDB crystal structure 4E47 (Walker J. R. et al. Structural Genomics Consortium; the PDB crystal structure 3VUZ ("SETD7 in complex with AAM-1." Niwa H. et al.); the PDB crystal structure 3VVO; and, Niwa H et al. *Acta Crystallogr. Sect. D* 69: 595-602 (2013).

FIG. 3ZZZZZ presents examples of SETD8 Targeting Ligands wherein R is the point at which the Linker is attached. For additional examples and related ligands, see, the PDB crystal structure 5TH7 ("SETD8 in complex with MS453", Yu W. et al.) and the PDB crystal structure 5T5G (Yu W et. al.; to be published).

Figure 4B:
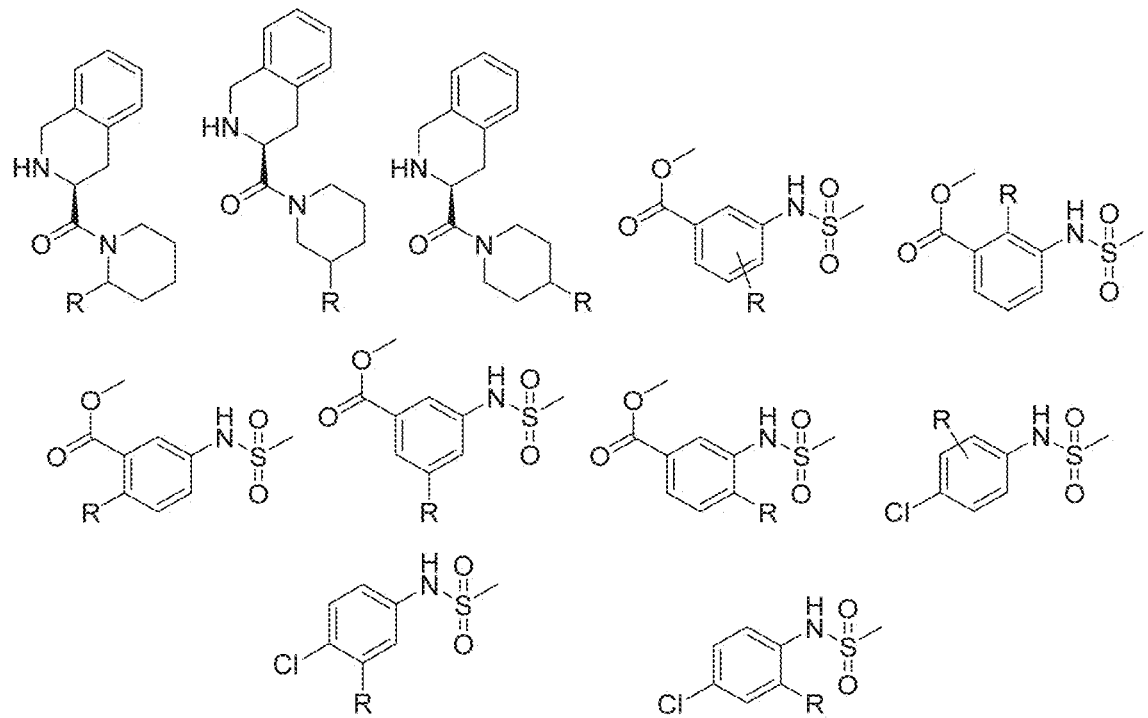
Figure 4C:
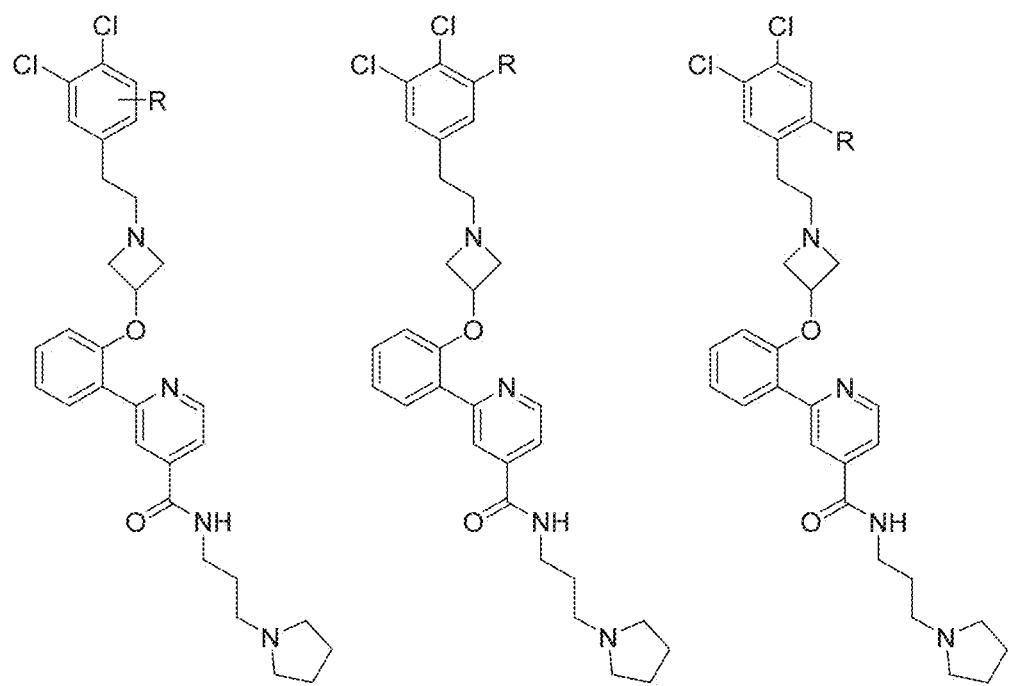
Figure 4D:
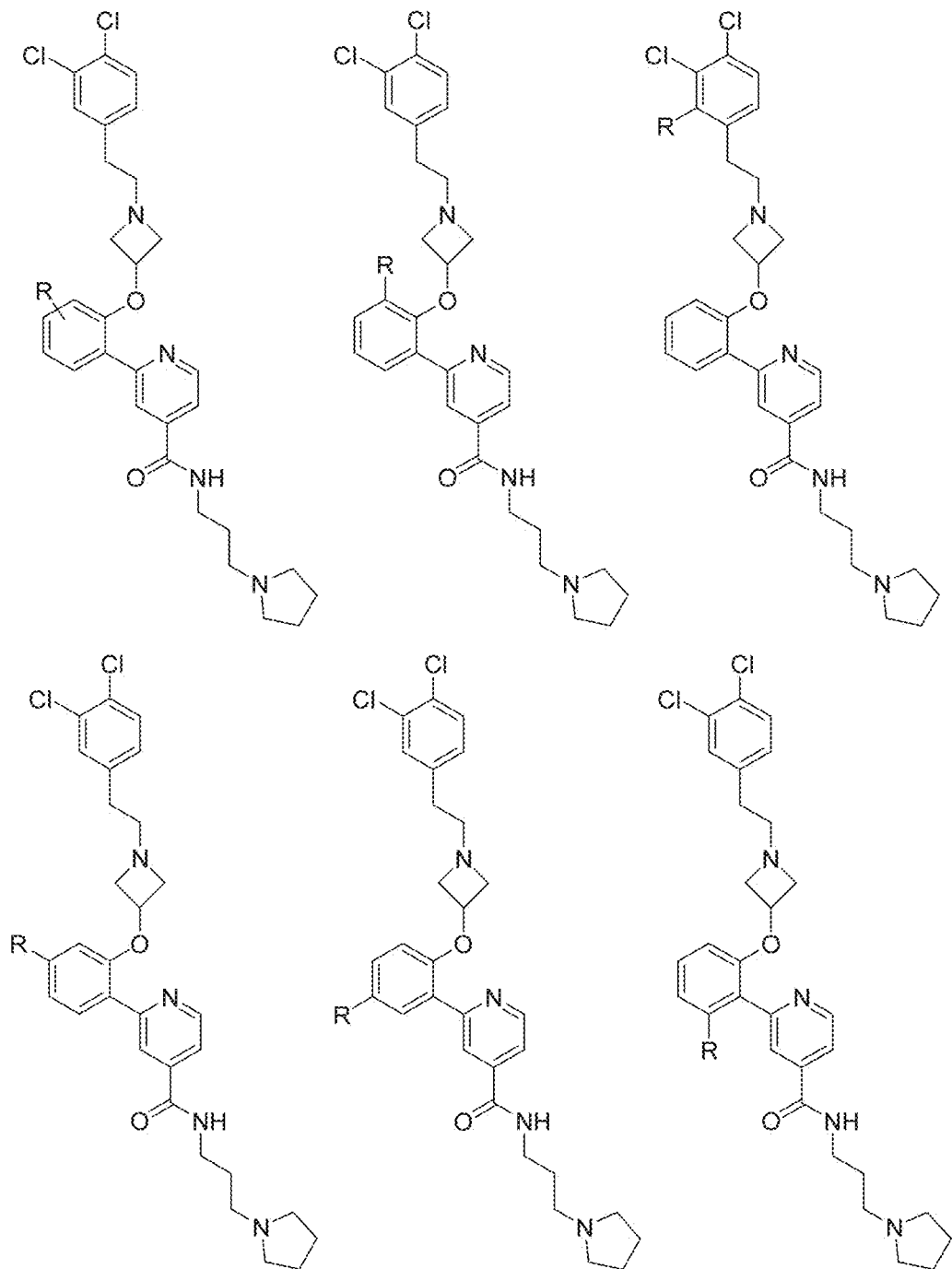
Figure 4E:
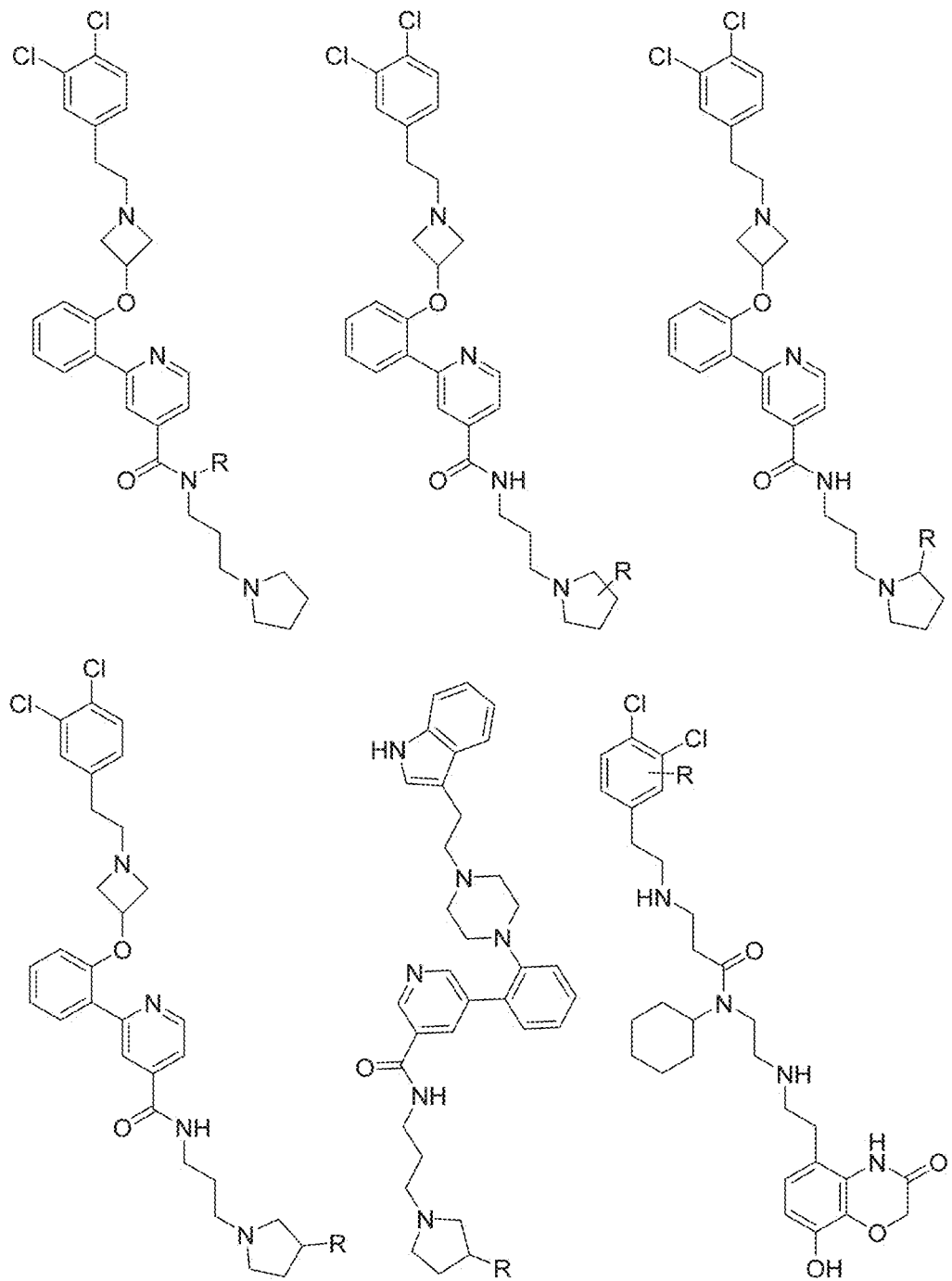
Figure 4F:
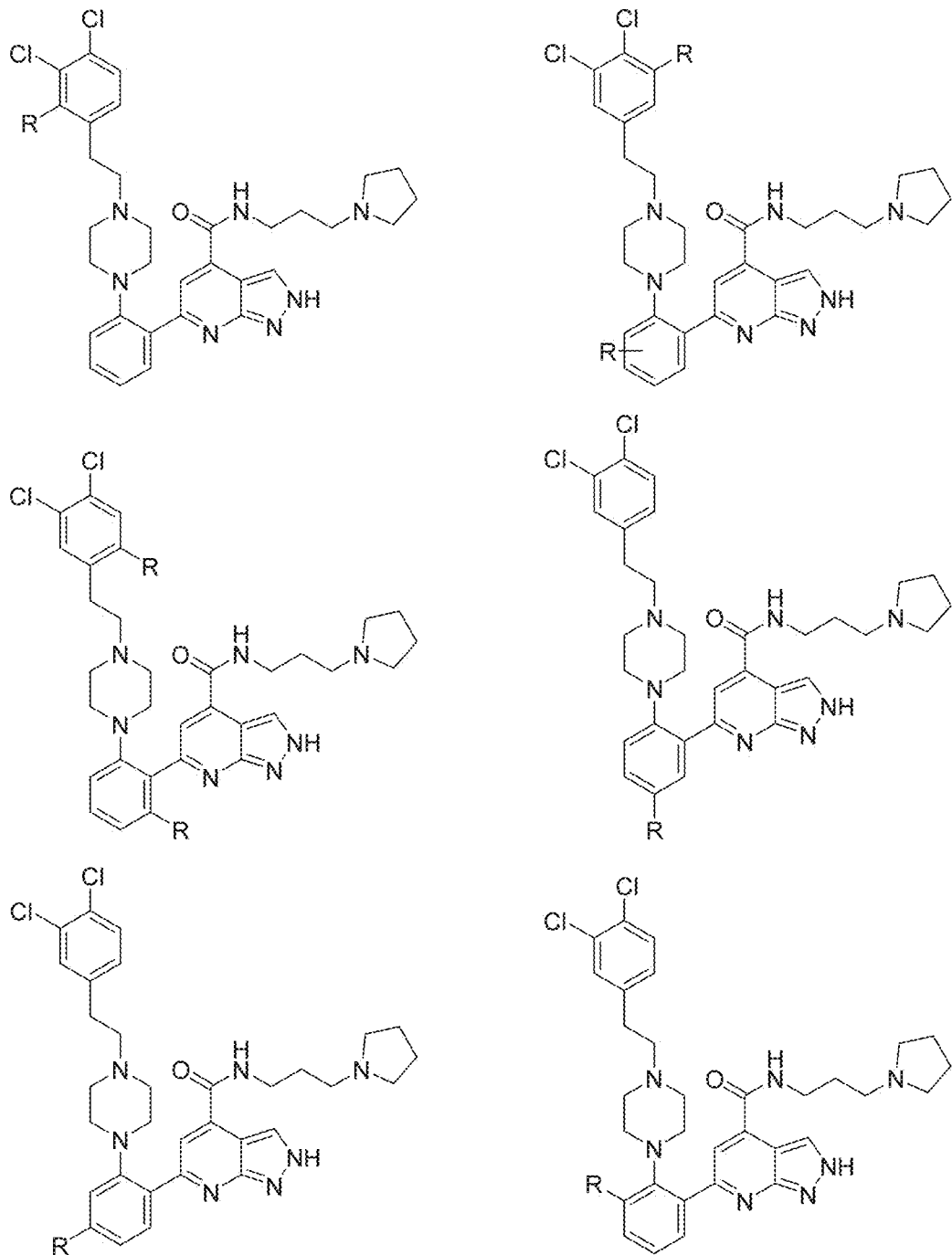
Figure 4G:
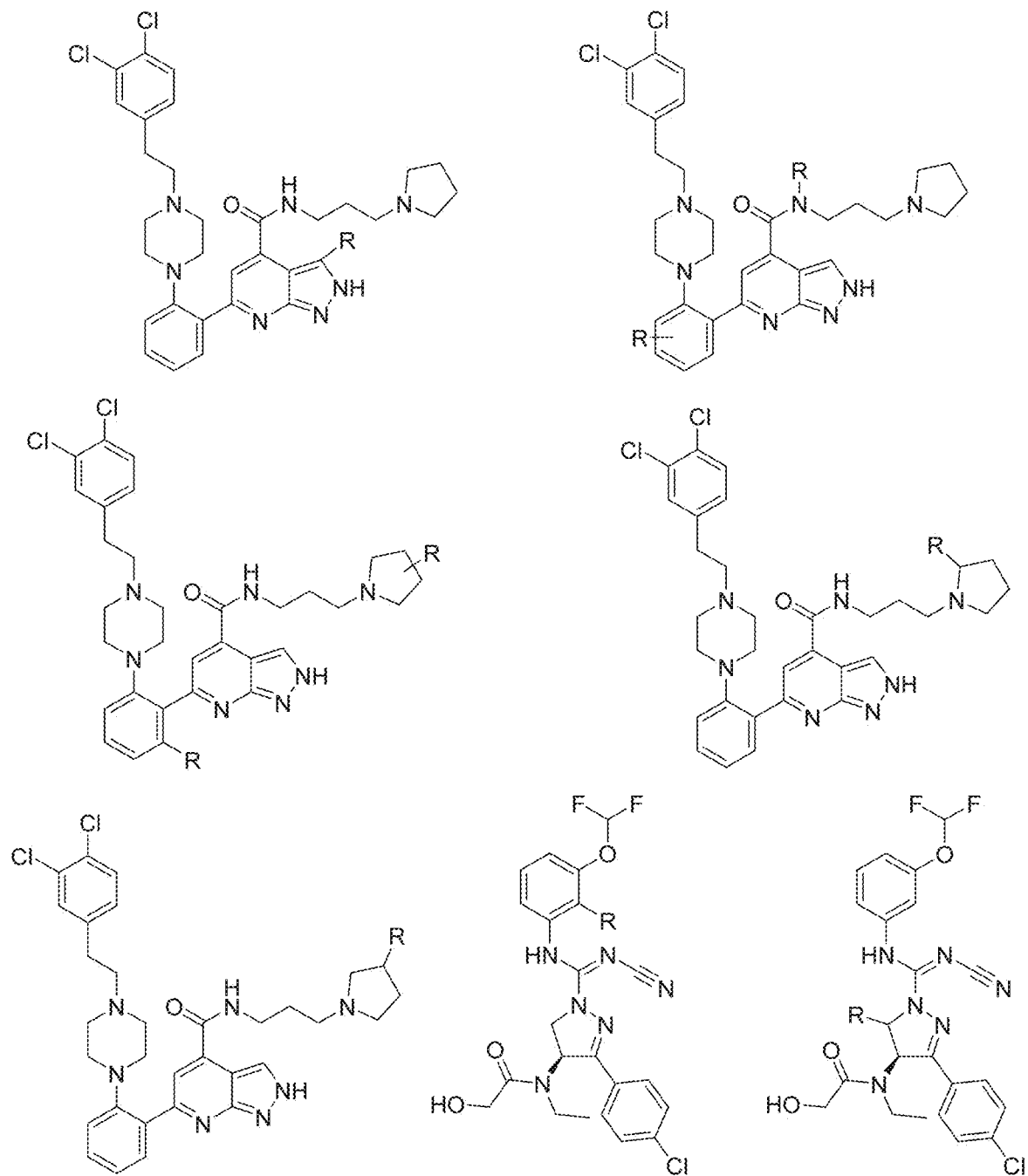
Figure 4H:
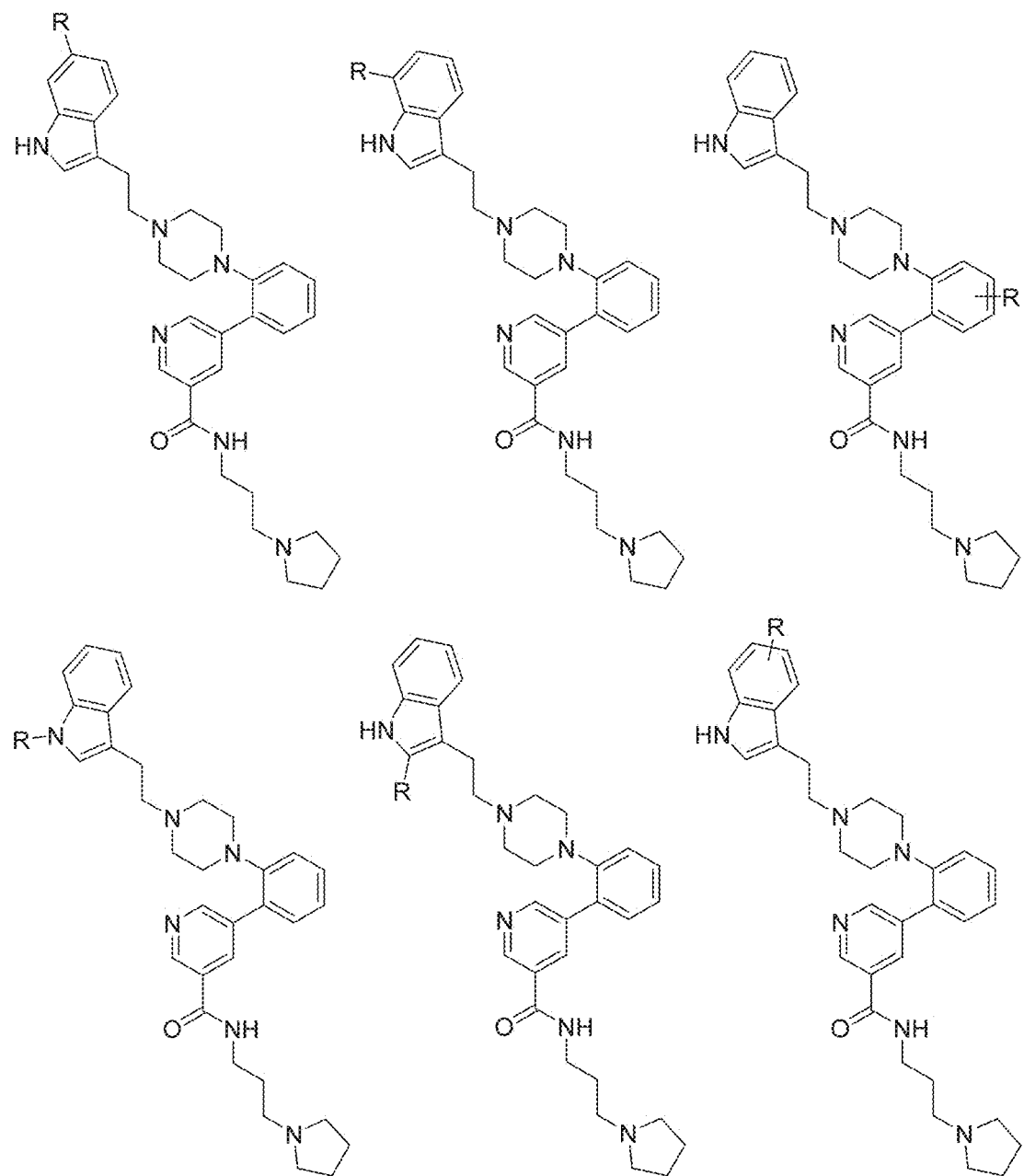
Figure 4I:
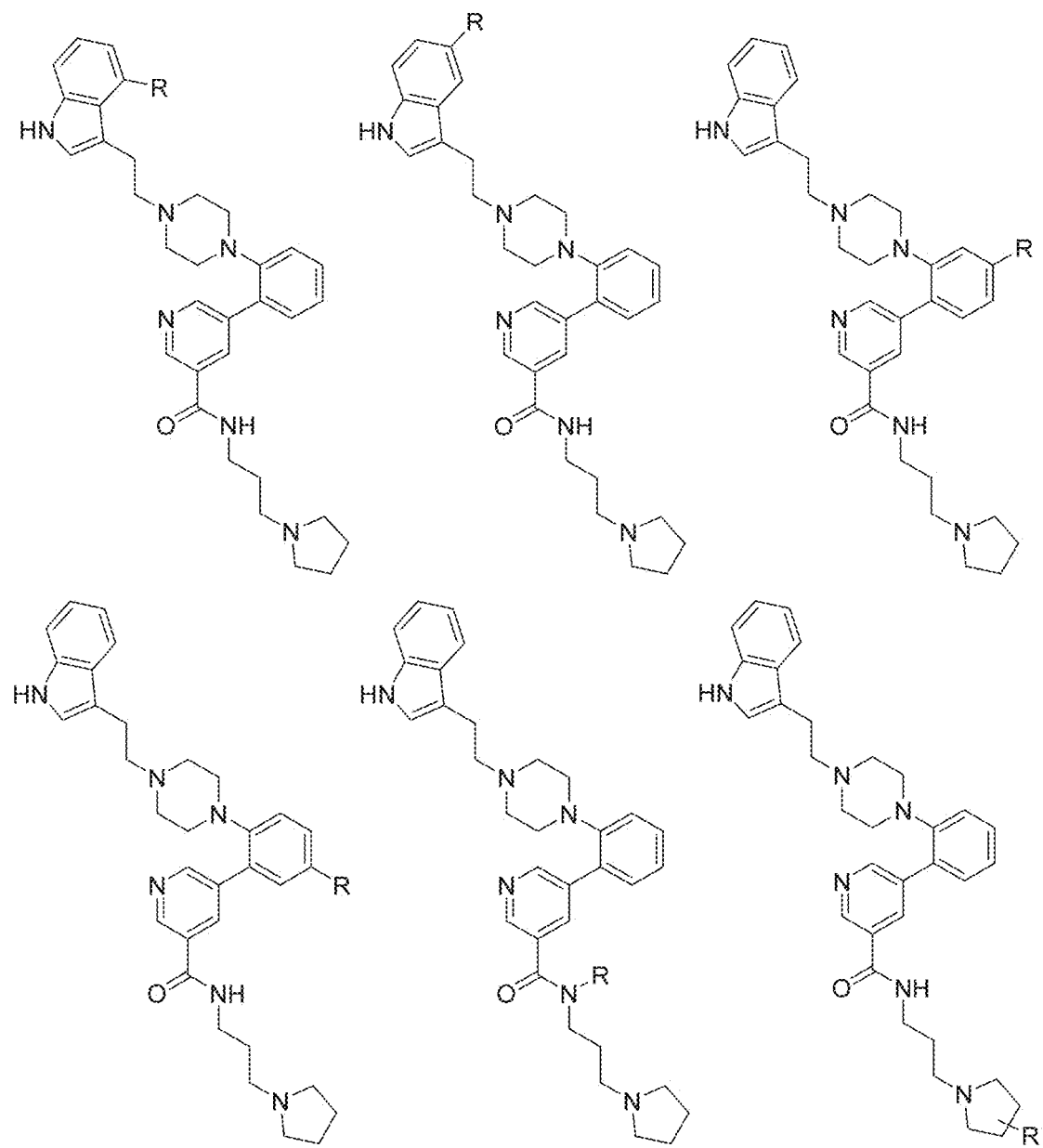
Figure 4J:
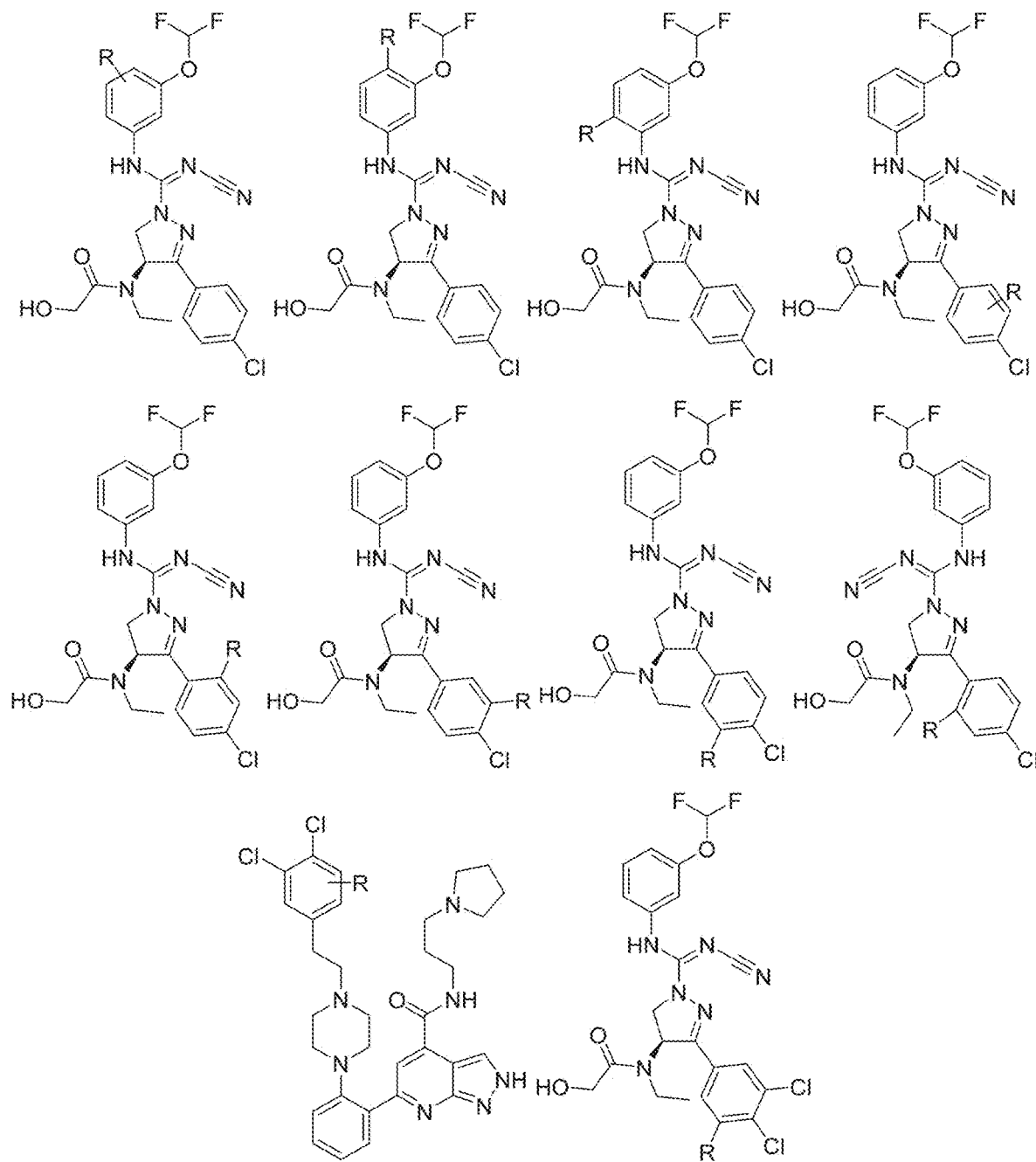
Figure 4K:
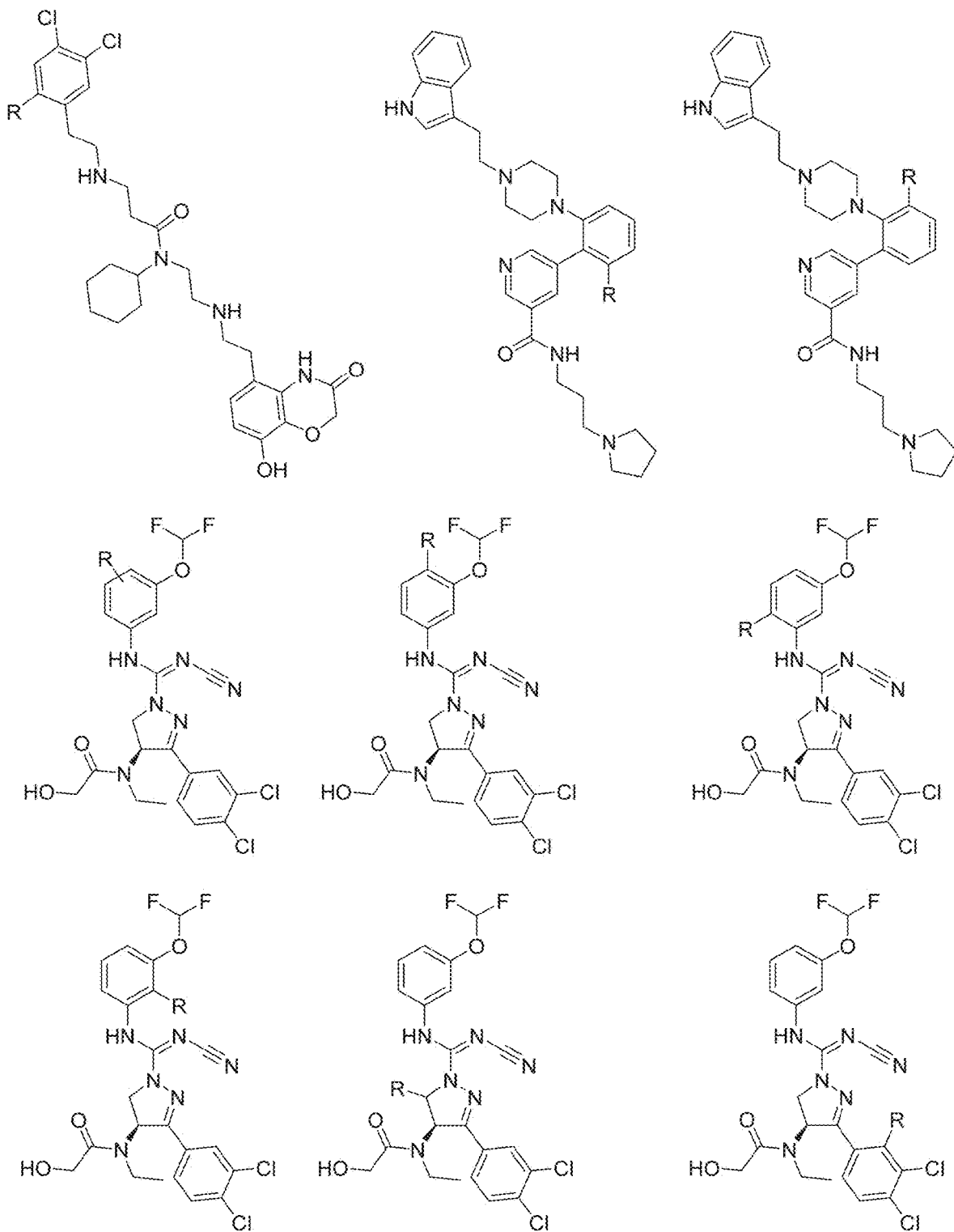
Figure 4L:
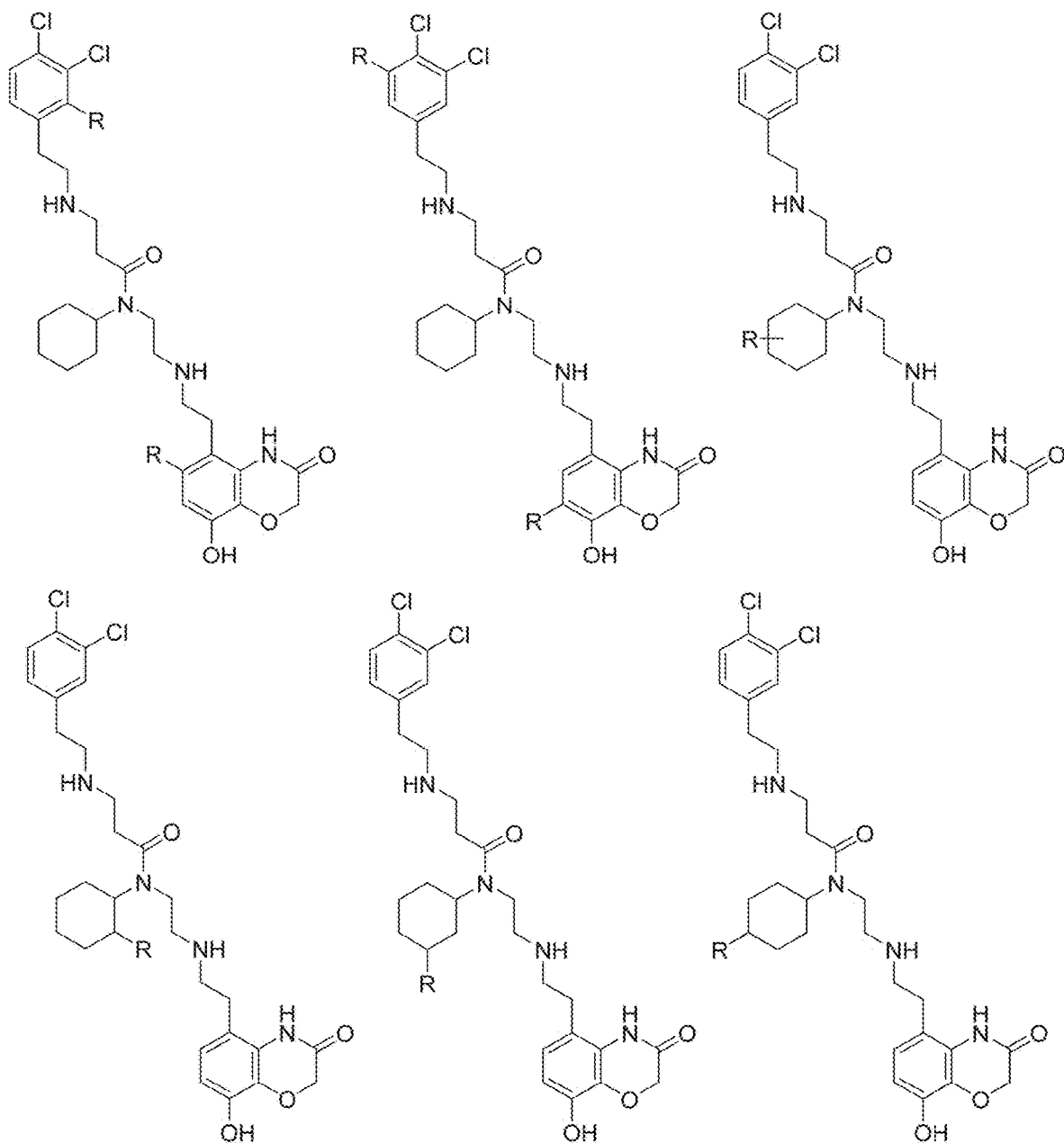
Figure 4M:
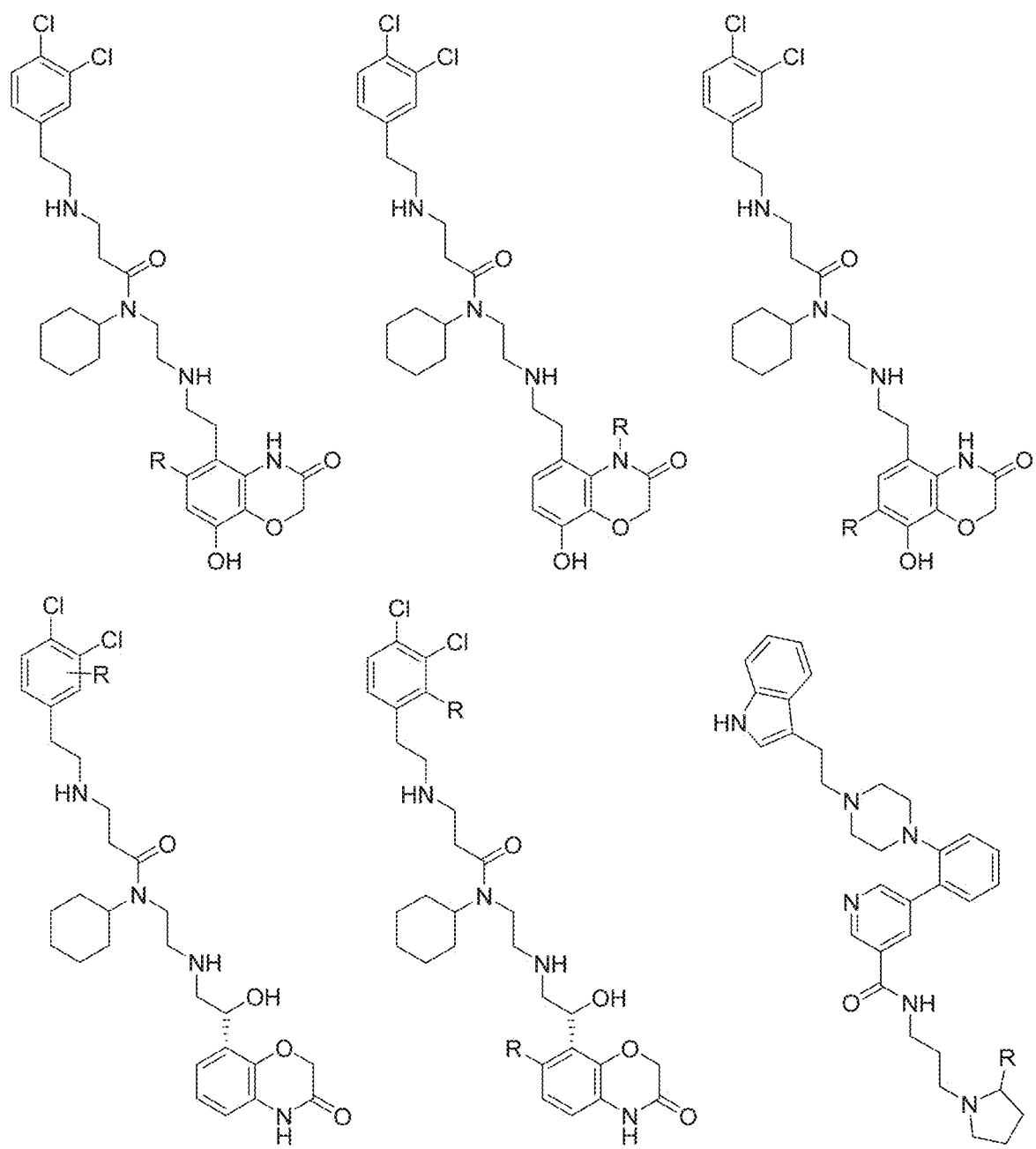
Figure 4N:
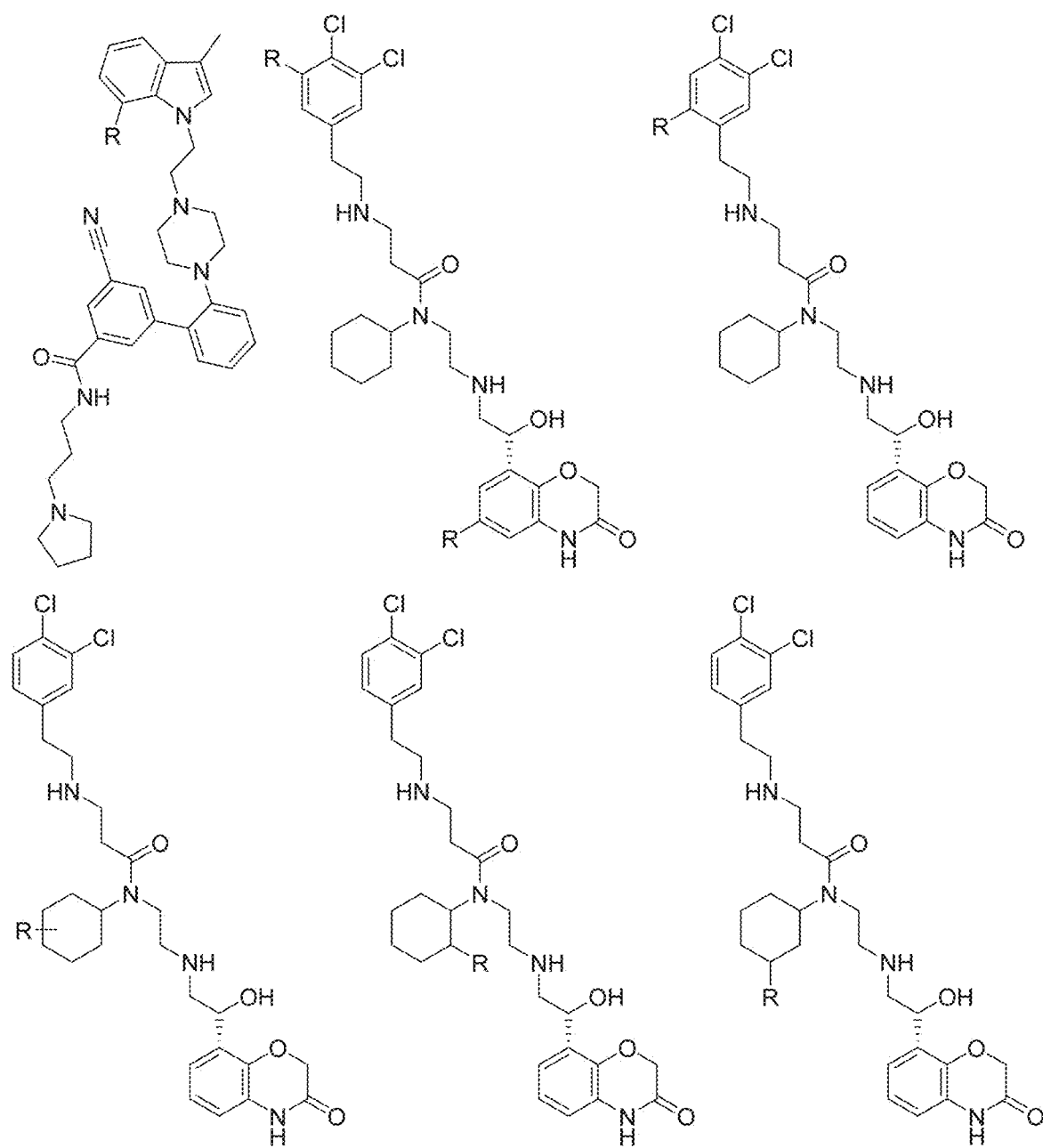
Figure 4O:
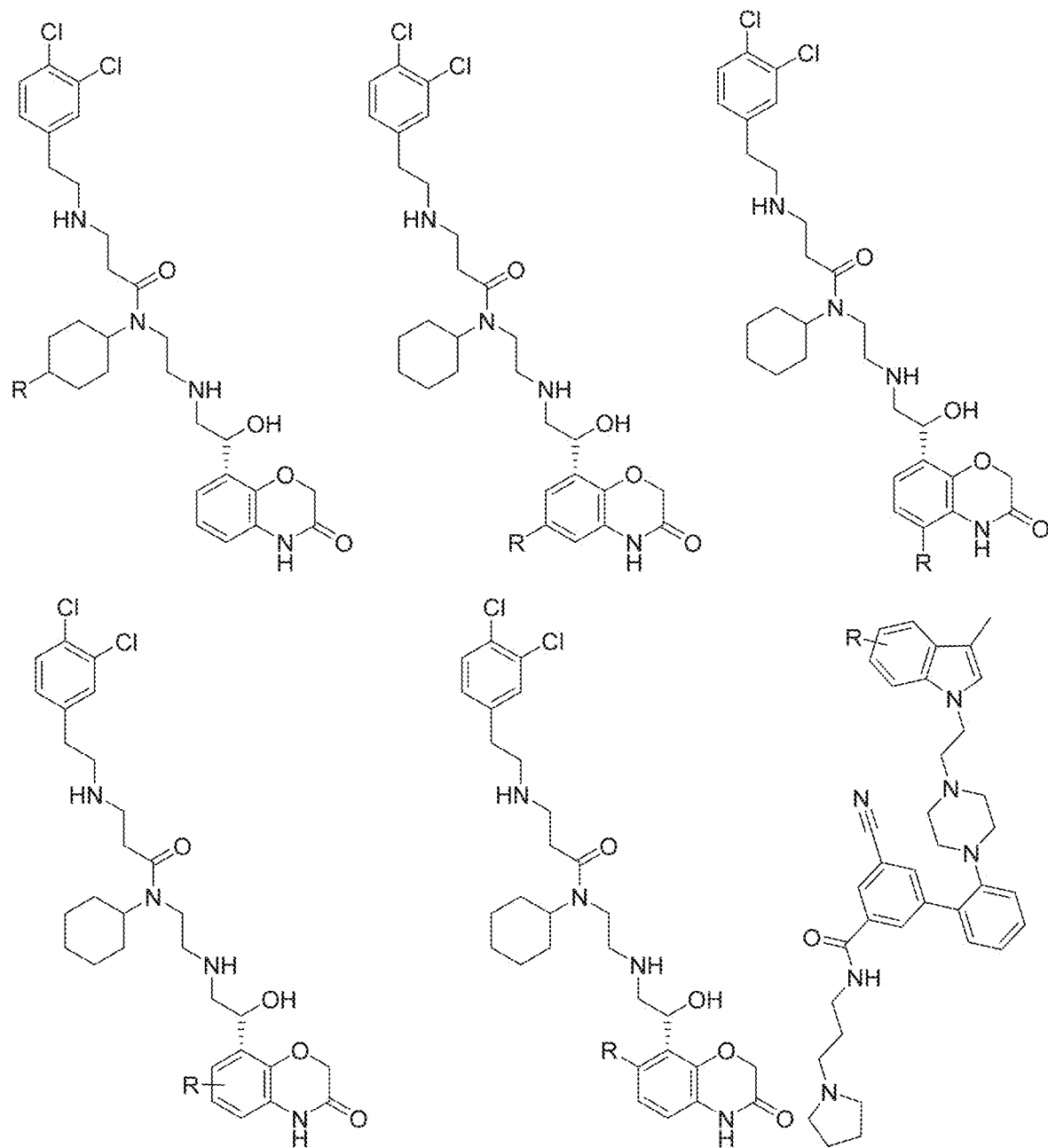
Figure 4P:
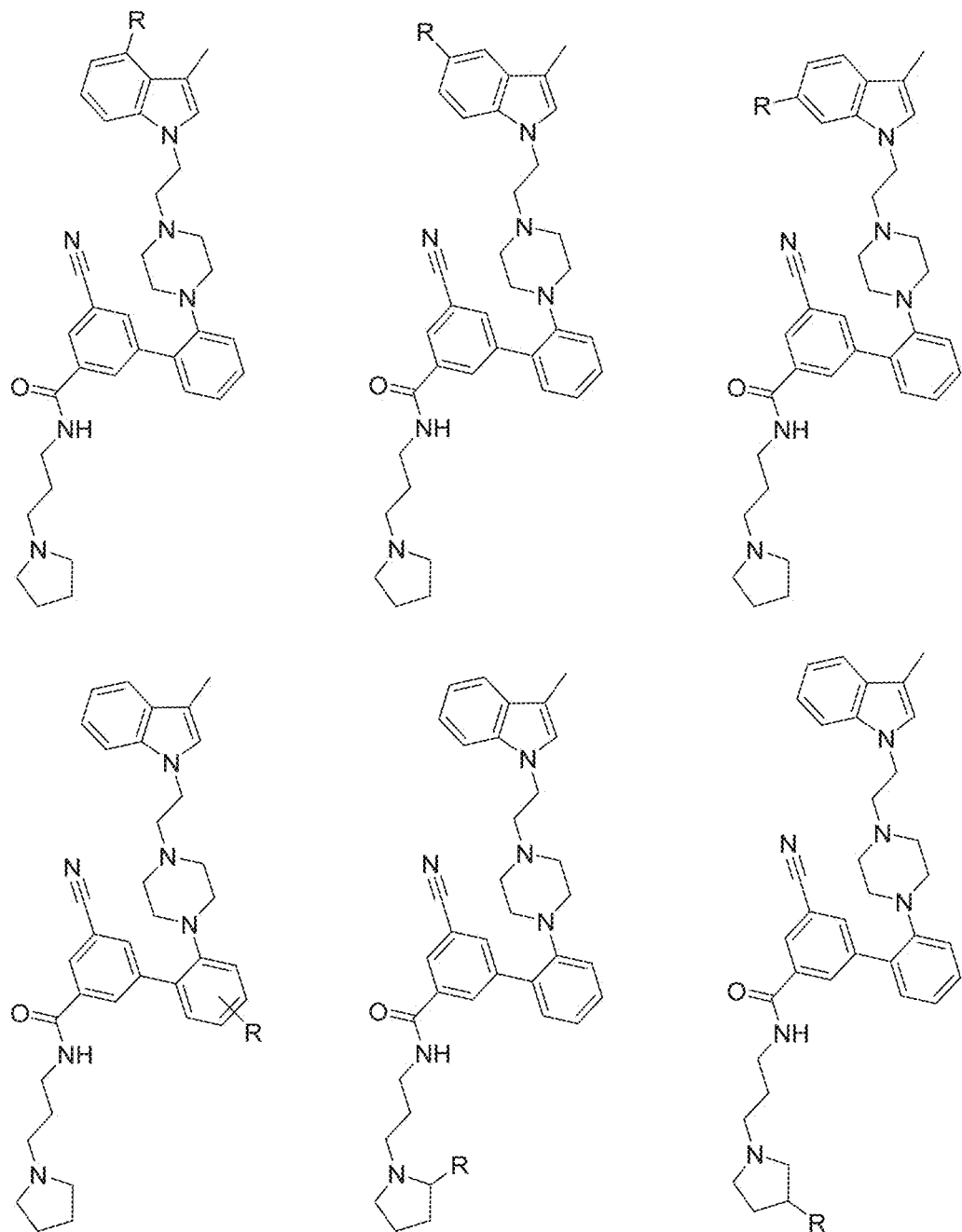
Figure 4Q:
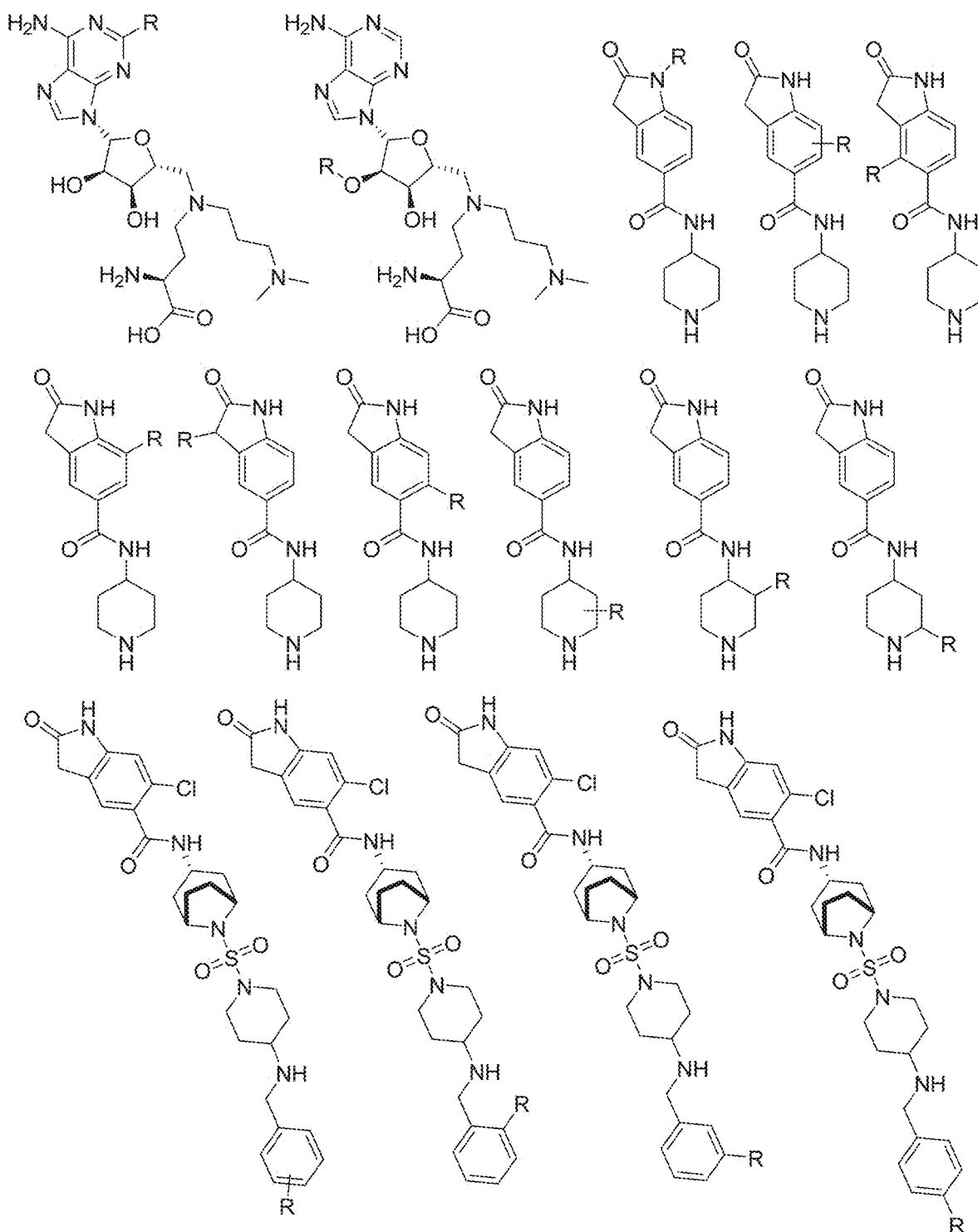
Figure 4R:
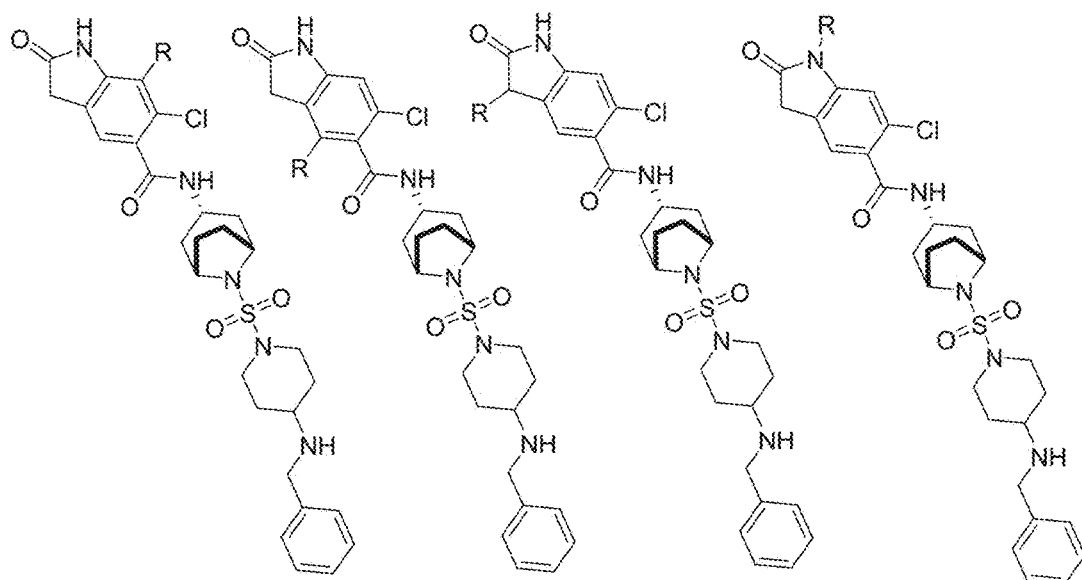
Figure 4S:
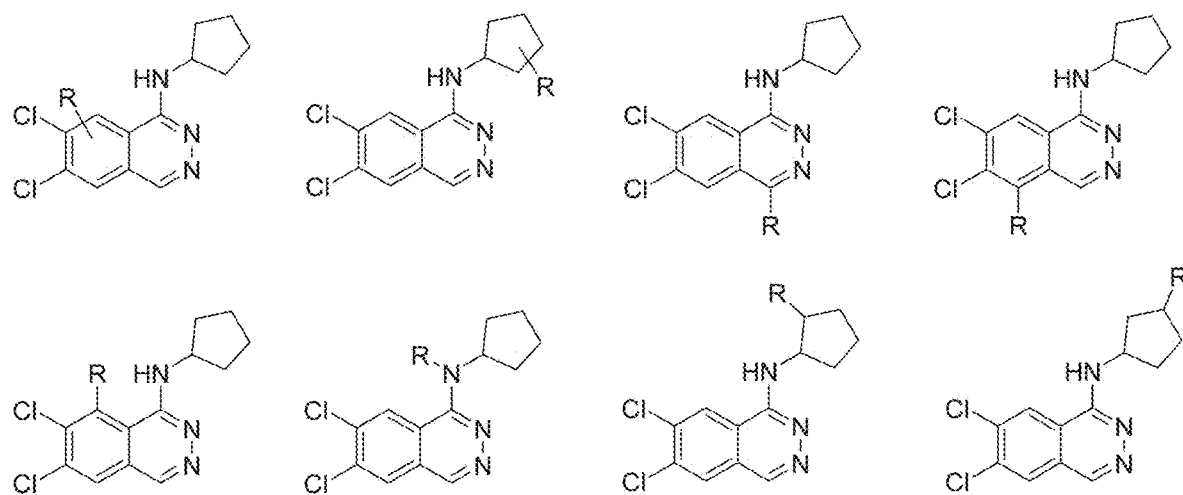
Figure 4T:
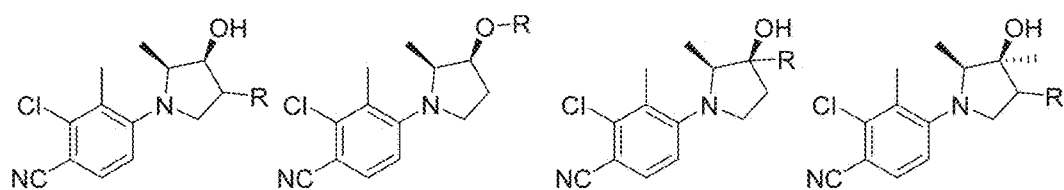
Figure 4U:
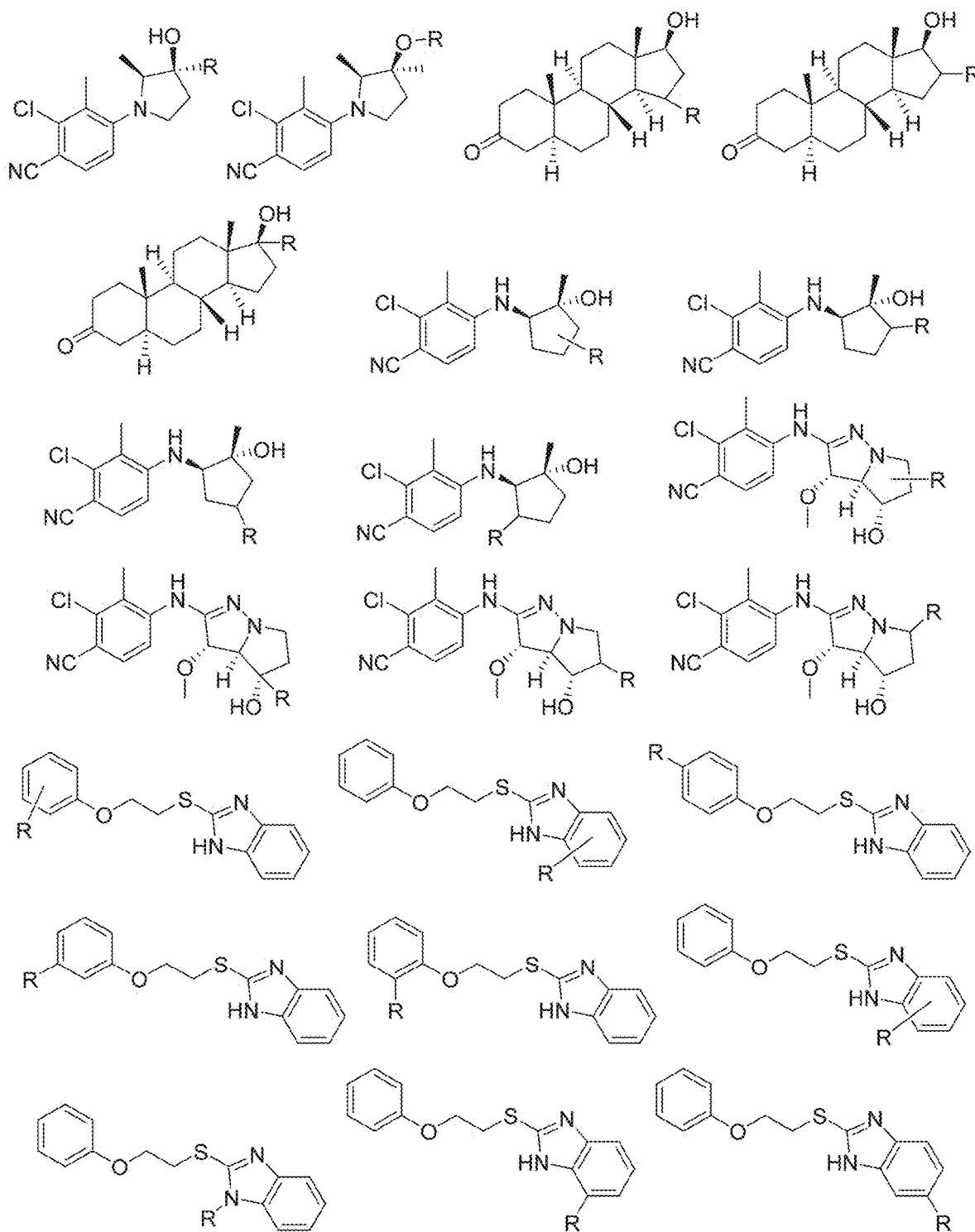
Figure 4V:
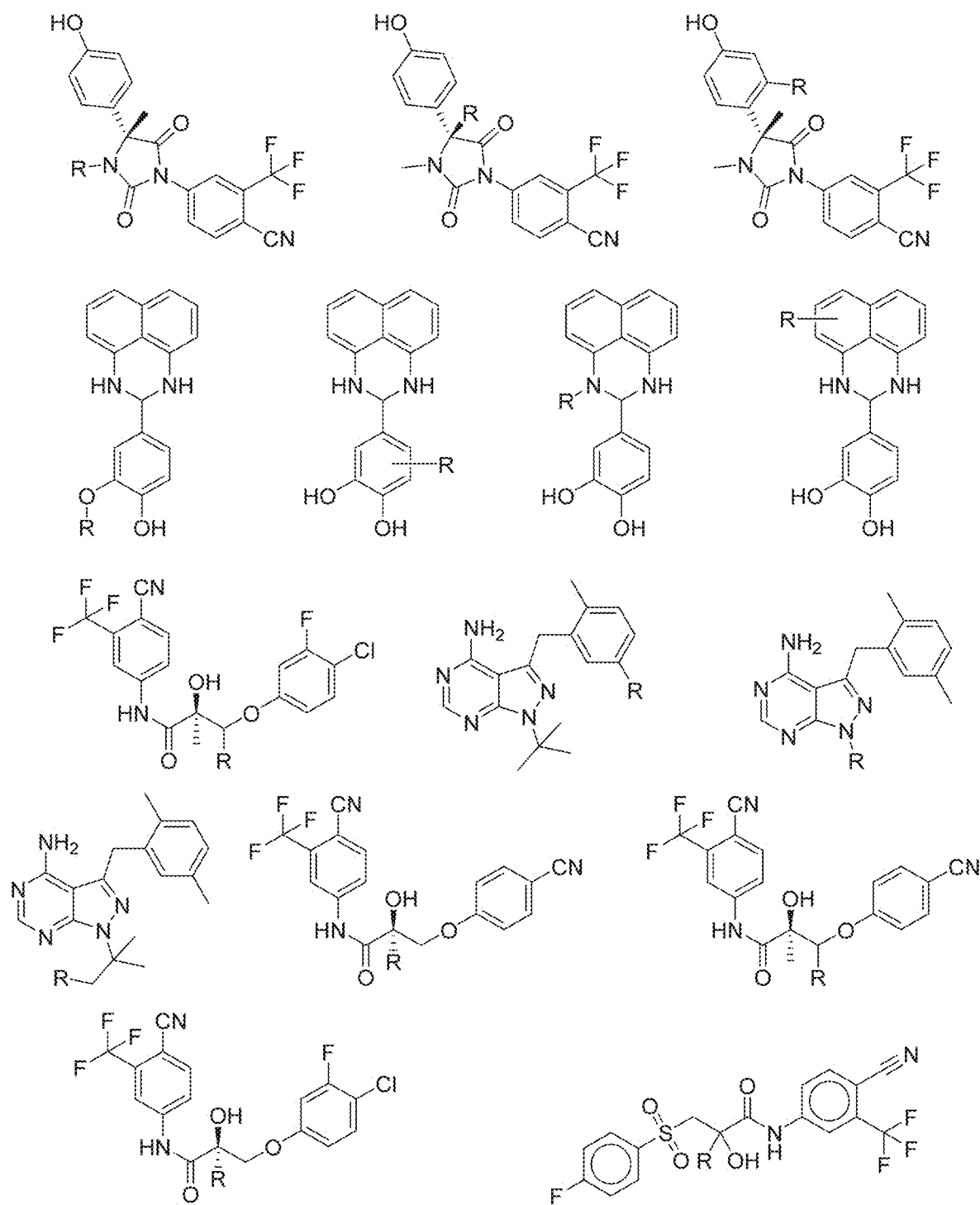
Figure 4W:
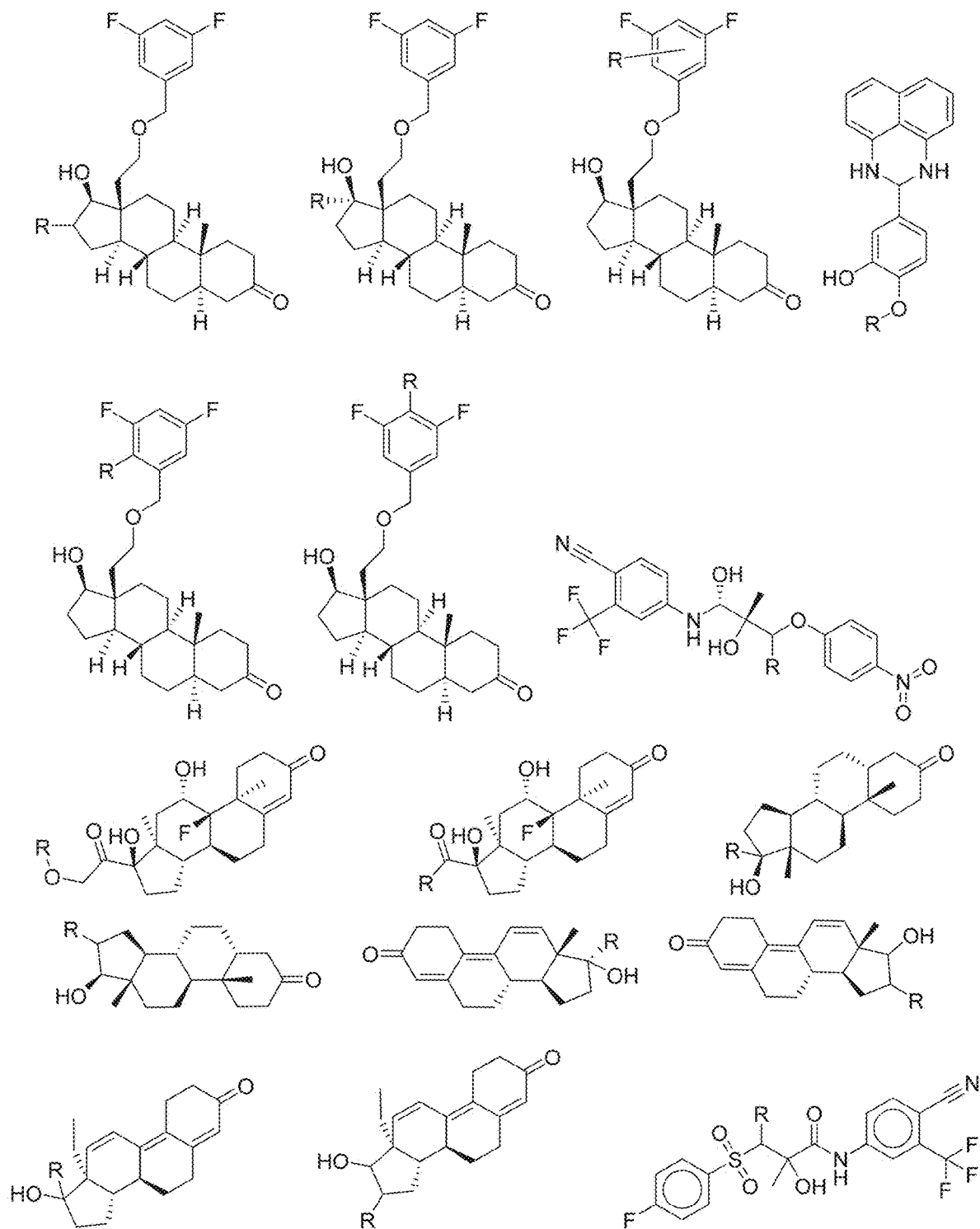
Figure 4X:
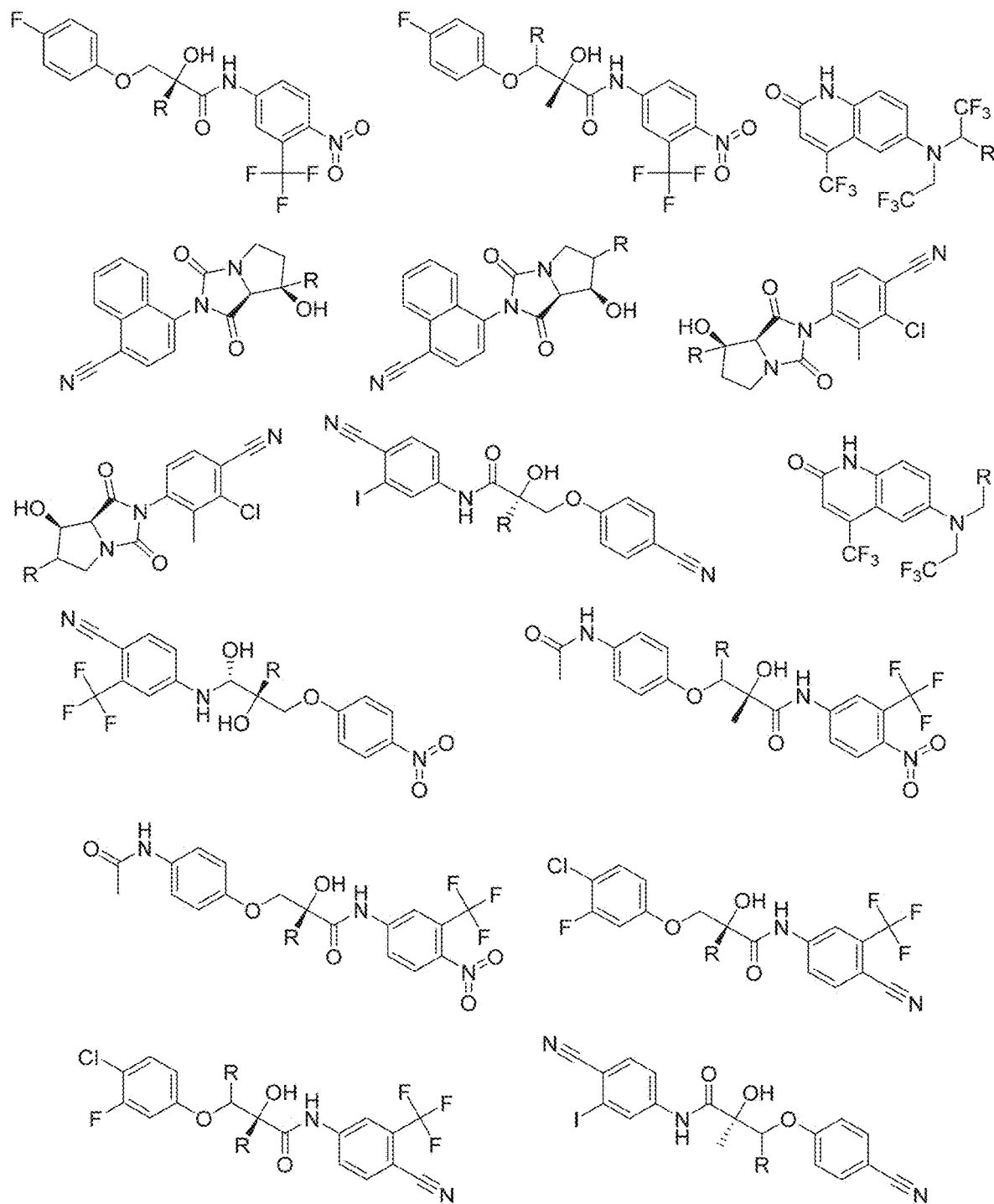
Figure 4Y:
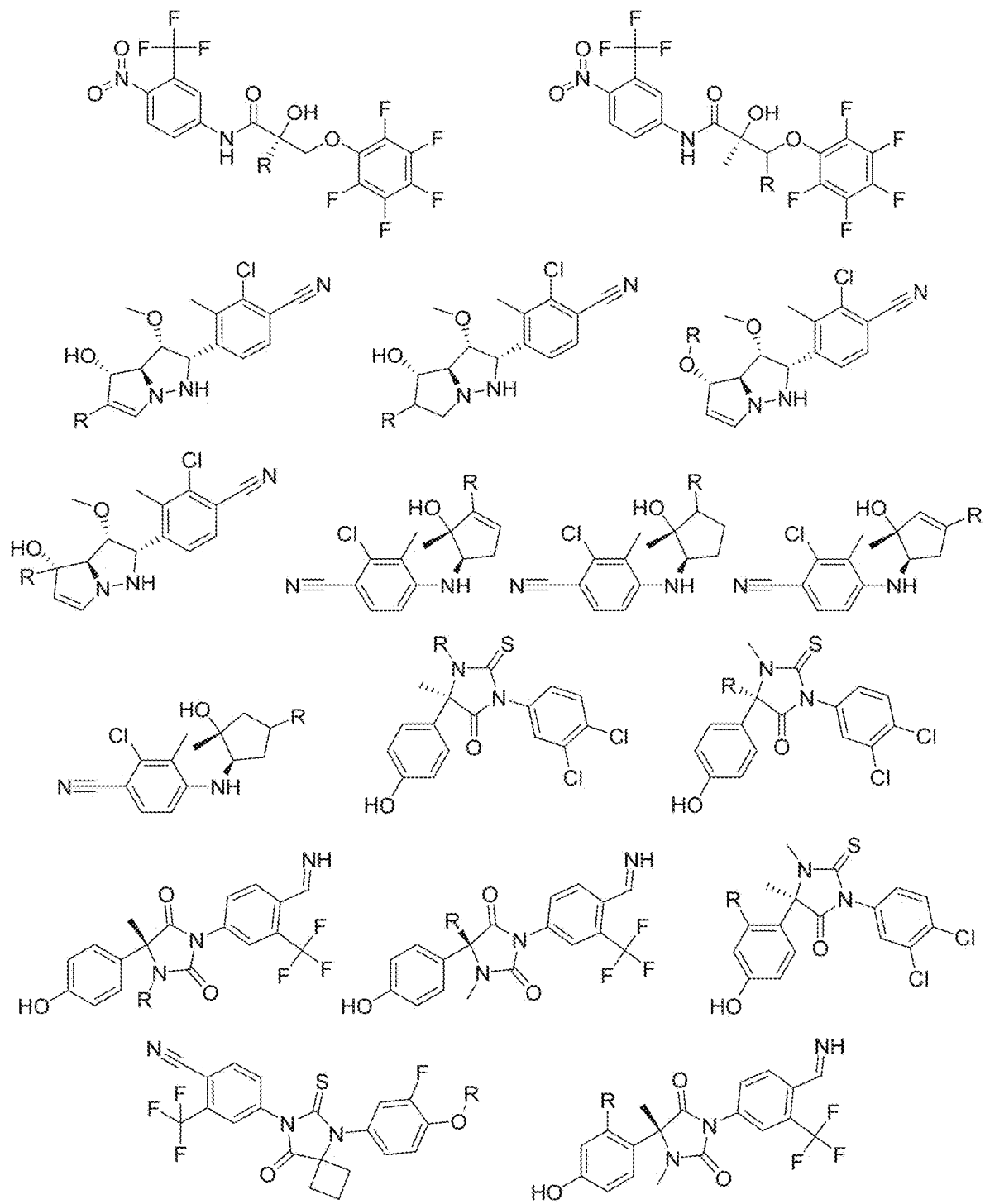
Figure 4Z:
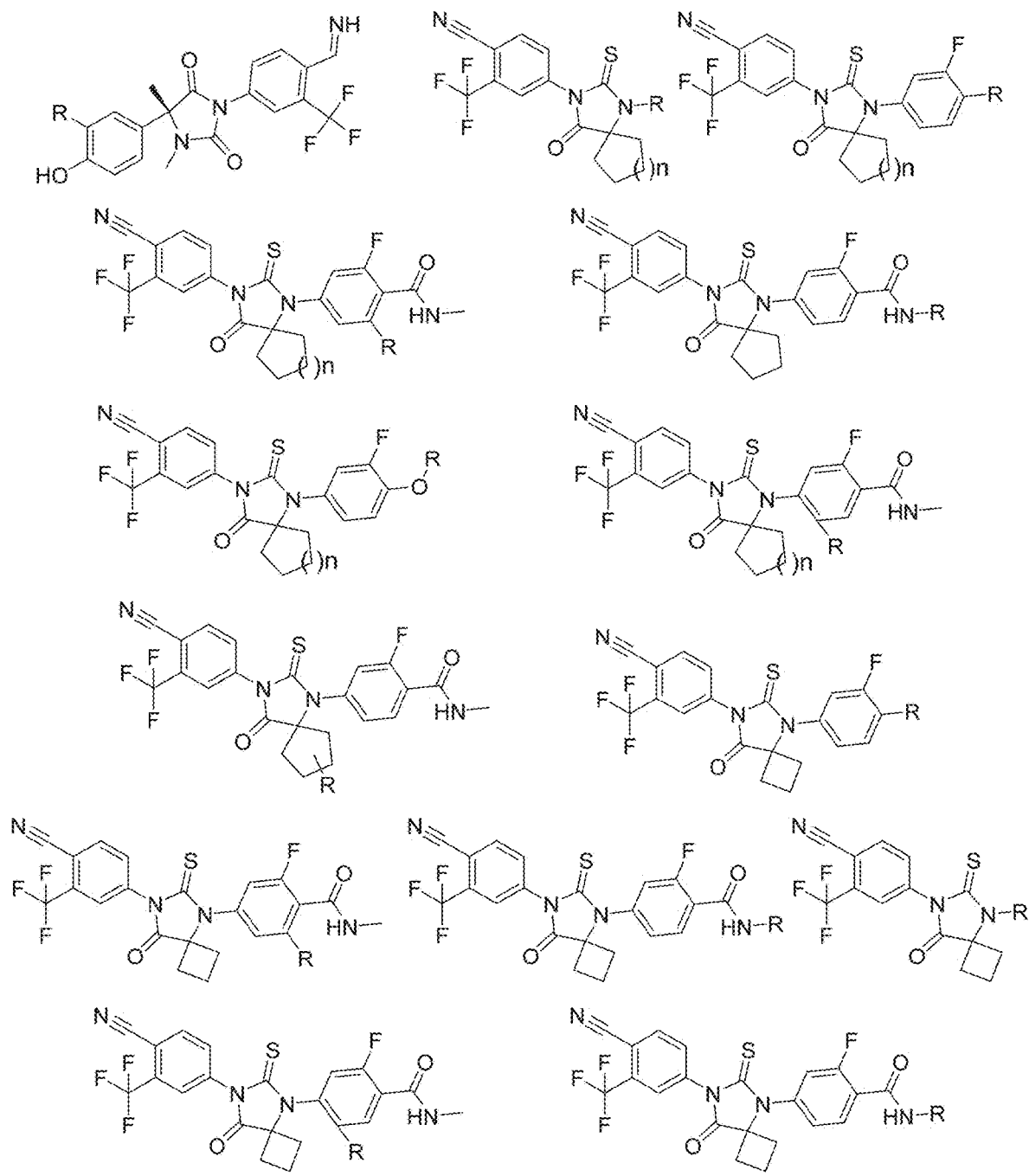
Figure 4A:
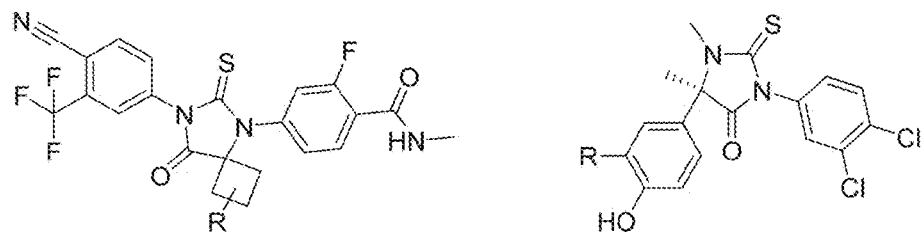
Figure 4B:
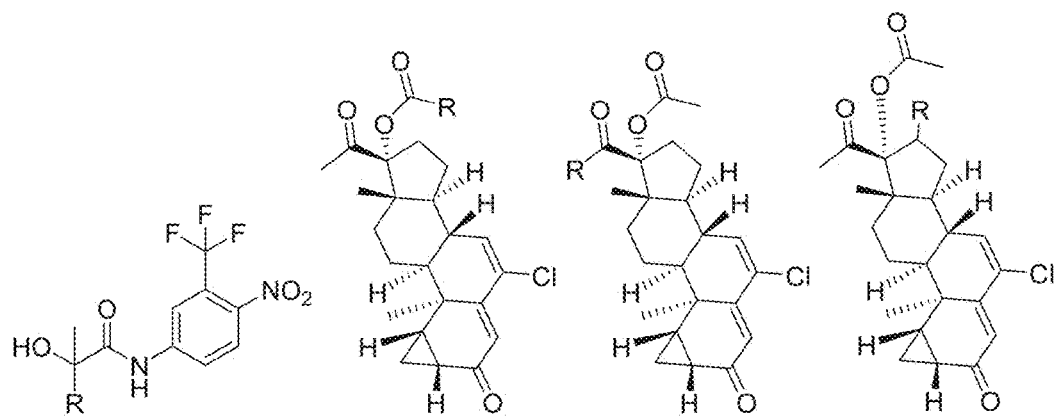
Figure 4C:
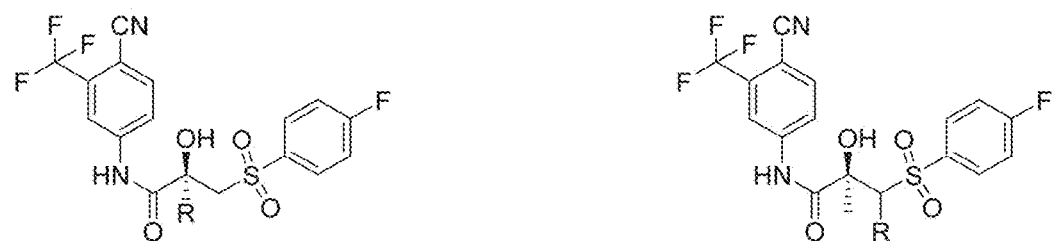
Figure 4D:
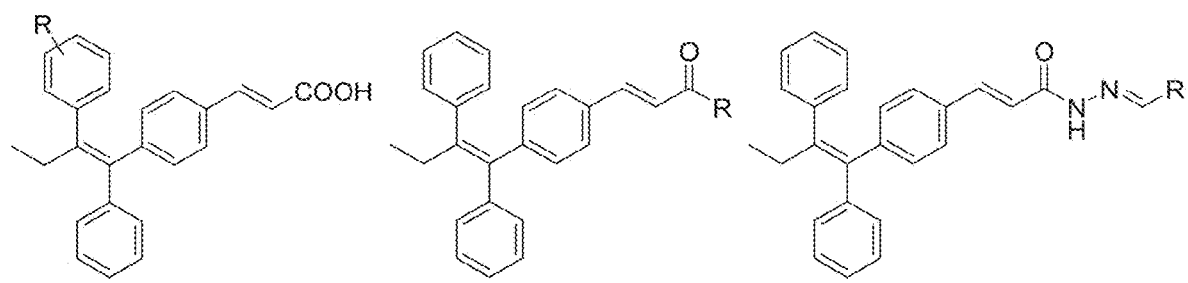
Figure 4E:
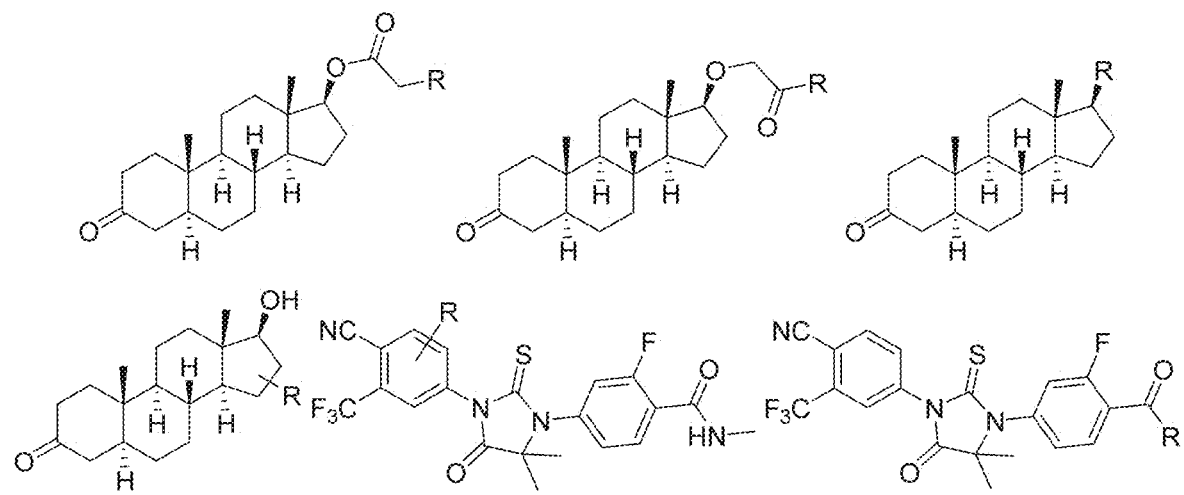

FIG. 4A-4B present examples of SETDB1 Targeting Ligands wherein R is the point at which the Linker is attached. For additional examples and related ligands, see, the PDB crystal structure 5KE2 ("SETDB1 in complex with inhibitor XST06472A", Iqbal A. et al.); the PDB crystal structure 5KE3 ("SETDB1 in complex with fragment MRT0181a", Iqbal A. et al.); the PDB crystal structure 5KH6 ("SETDB1 in complex with fragment methyl 3-(methylsulfonylamino)benzoate", Walker J. R. et al. Structural Genomics Consortium); and, the PDB crystal structure 5KCO ("SETDB1 in complex with [N]-(4-chlorophenyl)methanesulfonamide", Walker J. R. et al.)

FIG. 4C-4P present examples of SMYD2 Targeting Ligands wherein R is the point at which the Linker is attached. For additional examples and related ligands, see, the PDB crystal structure 5KJK ("SMYD2 in complex with inhibitor AZ13450370", Cowen S. D. et al.); the PDB crystal structure 5KJM ("SMYD2 in complex with AZ931", Cowen S. D. et al.); the PDB crystal structure 5KJN ("SMYD2 in complex with AZ506", Cowen S. D. et al.); the PDB crystal structure 5ARF ("SMYD2 in complex with N-[3-(4-chlorophenyl)-1-{N'-cyano-N-[3-(difluoromethoxy)phenyl]carbamimidoyl}-4 5-dihydro-1H-pyrazol-4-YL]-N-ethyl-2-hydroxyacetamide", Eggert E. et al.); the PDB crystal structure 5ARG ("SMYD2 in complex with BAY598", Eggert E. et al.); the PDB crystal structure 4YND ("SMYD2 in complex with A-893", Sweis R. F. et al.); the PDB crystal structure 4WUY ("SMYD2 in complex with LLY-507", Nguyen H. et al.); and, the PDB crystal structure 3S7B ("N-cyclohexyl-N~3~-[2-(3 4-dichlorophenyl)ethyl]-N-(2-{[2-(5-hydroxy-3-oxo-3 4-dihydro-2H-1 4-benzoxazin-8-yl)ethyl]amino}ethyl)-beta-alaninamide", Ferguson A. D. et al.).

FIG. 4Q-4R present examples of SMYD3 Targeting Ligands wherein R is the point at which the Linker is attached. For additional examples and related ligands, see, the crystal structure 5H17 ("SMYD3 in complex with 5'-{[(3S)-3-amino-3-carboxypropyl][3-(dimethylamino)propyl]amino}-5'-deoxyadenosine", Van Aller G. S. et al.); the crystal structure 5CCL ("SMYD3 in complex with oxindole compound", Mitchell L. H. et al.); and, the crystal structure 5CCM ("Crystal structure of SMYD3 with SAM and EPZ030456").

FIG. 4S presents examples of SUV4-20H1 Targeting Ligands wherein R is the point at which the Linker is attached. For additional examples and related ligands, see, the PDB crystal structure 5CPR ("SUV4-20H1 in complex with inhibitor A-196", Bromberg K. D. et al.).

FIG. 4T-4AA present examples of Wild Type Androgen Receptor Targeting Ligands wherein R is the point at which the Linker is attached. For additional examples and related ligands, see, the PDB crystal structures 5T8E and 5T8J ("Androgen Receptor in complex with 4-(pyrrolidin-1-yl) benzonitrile derivatives", Asano M. et al.); Asano M. et al. *Bioorg. Med. Chem. Lett.* 27: 1897-1901 (2017); the PDB crystal structure 5JJM ("Androgen Receptor", Nadal M. et al.); the PDB crystal structure 5CJ6 ("Androgen Receptor in complex with 2-Chloro-4-[[(1R 2R)-2-hydroxy-2-methyl-cyclopentyl]amino]-3-methyl-benzonitrile derivatives", Saeed A. et al.); the PDB crystal structure 4QL8 ("Androgen Receptor in complex with 3-alkoxy-pyrrolo[1 2-b]pyrazolines derivatives", Ullrich T. et al.); the PDB crystal structure 4HLW ("Androgen Receptor Binding Function 3 (BF3) Site of the Human Androgen Receptor through Virtual Screening", Munuganti R. S. et al.); the PDB crystal structure 3V49

("Androgen Receptor lbd with activator peptide and sarm inhibitor 1", Nique F. et al.); Nique F. et al. *J. Med. Chem.* 55: 8225-8235 (2012); the PDB crystal structure 2YHD ("Androgen Receptor in complex with AF2 small molecule inhibitor", Axerio-Cilies P. et al.); the PDB crystal structure 3RLJ ("Androgen Receptor ligand binding domain in complex with SARM S-22", Bohl C. E. et al.); Bohl C. E. et al. *J. Med. Chem.* 54: 3973-3976 (2011); the PDB crystal structure 3B5R ("Androgen Receptor ligand binding domain in complex with SARM C-31", Bohl C. E. et al.); Bohl C. E. et al. *Bioorg. Med. Chem. Lett.* 18: 5567-5570 (2008); the PDB crystal structure 2PIP ("Androgen Receptor ligand binding domain in complex with small molecule", Estebanez-Perpina E. et al.); Estebanez-Perpina. E. *Proc. Natl. Acad. Sci.* 104:16074-16079 (2007); the PDB crystal structure 2PNU ("Androgen Receptor ligand binding domain in complex with EM5744", Cantin L. et al.); and, the PDB crystal structure 2HVC ("Androgen Receptor ligand binding domain in complex with LGD2226", Wang F. et al.). For additional related ligands, see, Matias P. M. et al. "Structural Basis for the Glucocorticoid Response in a Mutant Human Androgen Receptor (Ar(Ccr)) Derived from an Androgen-Independent Prostate Cancer." *J. Med. Chem.* 45: 1439 (2002); Sack J. S. et al. "Crystallographic structures of the ligand-binding domains of the androgen receptor and its T877A mutant complexed with the natural agonist dihydrotestosterone." *Proc. Natl. Acad. Sci.* 98: 4904-4909 (2001); He B. et al. "Structural basis for androgen receptor interdomain and coactivator interactions suggests a transition in nuclear receptor activation function dominance." *Mol. Cell* 16: 425-438 (2004); Pereira de Jesus-Tran K. "Comparison of crystal structures of human androgen receptor ligand-binding domain complexed with various agonists reveals molecular determinants responsible for binding affinity." *Protein Sci.* 15: 987-999 (2006); Bohl C. E. et al. "Structural Basis for Accommodation of Nonsteroidal Ligands in the Androgen Receptor." *Mol Pharmacol.* 63(1): 211-23 (2003); Sun C. et al. "Discovery of potent orally-active and muscle-selective androgen receptor modulators based on an N-aryl-hydroxybicyclohydantoin scaffold." *J. Med. Chem.* 49: 7596-7599 (2006); Nirschl A. A. et al. "N-aryl-oxazolidin-2-imine muscle selective androgen receptor modulators enhance potency through pharmacophore reorientation." *J. Med. Chem.* 52: 2794-2798 (2009); Bohl C. E. et al. "Effect of B-ring substitution pattern on binding mode of propionamide selective androgen receptor modulators." *Bioorg. Med. Chem. Lett.* 18: 5567-5570 (2008); Ullrich T. et al. "3-alkoxy-pyrrolo[1 2-b]pyrazolines as selective androgen receptor modulators with ideal physicochemical properties for transdermal administration." *J. Med. Chem.* 57: 7396-7411 (2014); Saeed A. et al. "2-Chloro-4-[[(1R 2R)-2-hydroxy-2-methyl-cyclopentyl] amino]-3-methyl-benzonitrile: A Transdermal Selective Androgen Receptor Modulator (SARM) for Muscle Atrophy." *J. Med. Chem.* 59: 750-755 (2016); Nique et al. "Discovery of diarylhydantoins as new selective androgen receptor modulators." *J. Med. Chem.* 55: 8225-8235 (2012); and, Michael E. Jung et al. "Structure-Activity Relationship for Thiohydantoin Androgen Receptor Antagonists for Castration-Resistant Prostate Cancer (CRPC)." *J. Med. Chem.* 53: 2779-2796 (2010).

FIG. 4BB presents examples of Mutant T877A Androgen Receptor Targeting Ligands wherein R is the point at which the Linker is attached. For additional examples and related ligands, see, the PDB crystal structure 4OGH ('Androgen Receptor T877A-AR-LBD", Hsu C. L. et al.) and the PDB crystal structure 2OZ7 ("Androgen Receptor T877A-AR-LBD", Bohl C. E. et al.).

FIG. 4CC presents examples of Mutant W741L Androgen Receptor Targeting Ligands wherein R is the point at which the Linker is attached. For additional examples and related ligands, see, the PDB crystal structure 4OJB ("Androgen Receptor T877A-AR-LBD", Hsu C. L. et al.).

FIG. 4DD-4EE presents examples of Estrogen and/or Androgen Targeting Ligands wherein R is the point at which the Linker is attached.

Figure 5A:
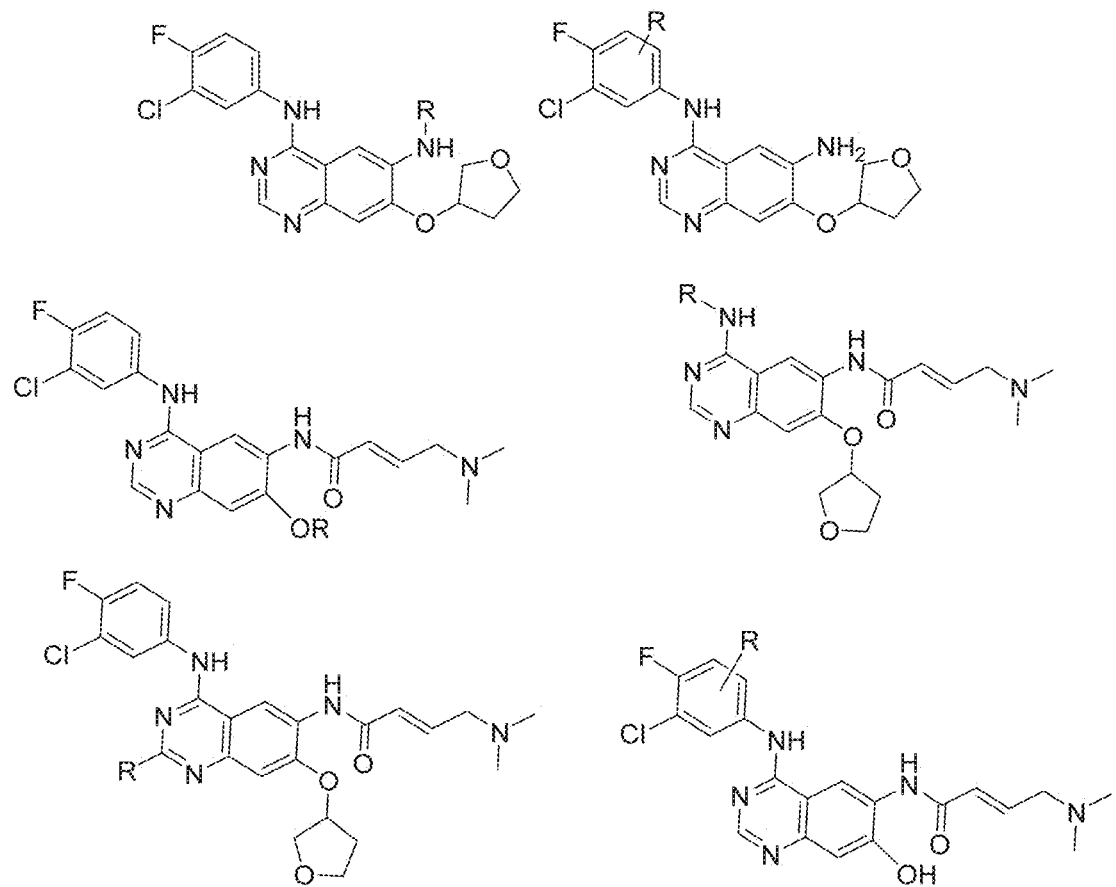

FIG. 5A presents examples of Afatinib, a Targeting Ligands for the EGFR and ErbB2/4 receptors. R is the point at which the Linker is attached.

Figure 5B:
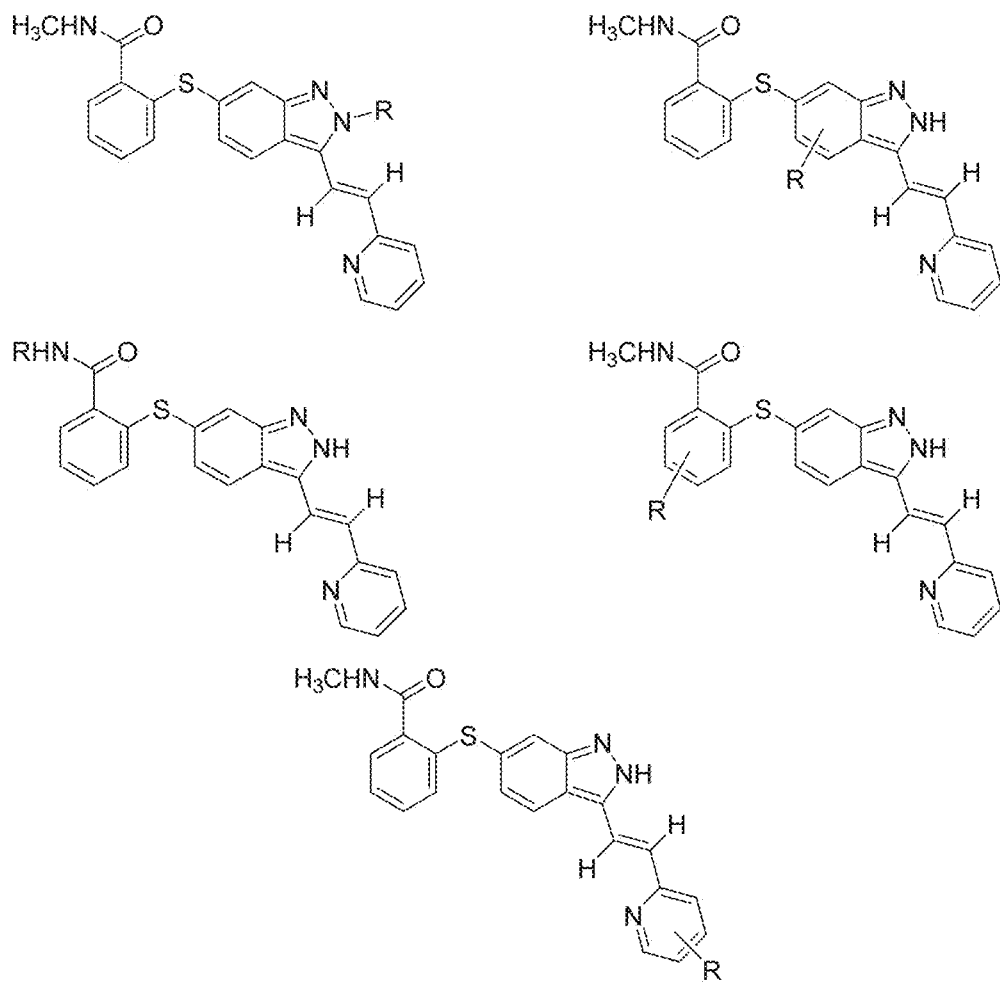

FIG. 5B presents examples of Axitinib, a Targeting Ligands for the VEGFR1/2/3, PDGFRβ, and Kit receptors. R is the point at which the Linker is attached.

Figure 5C:
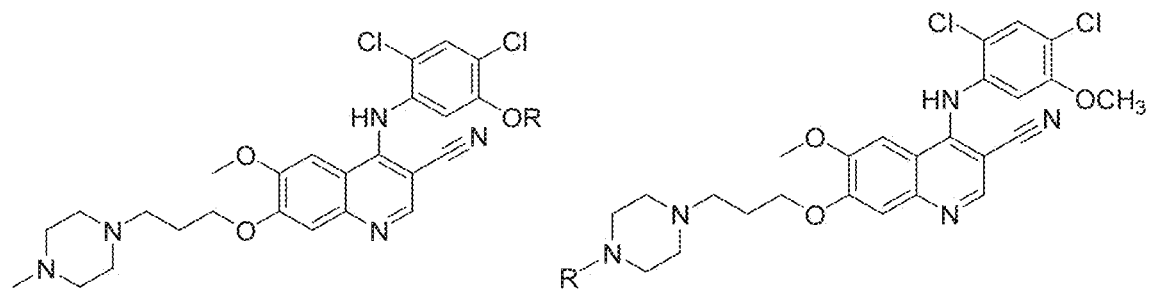
Figure 5D:
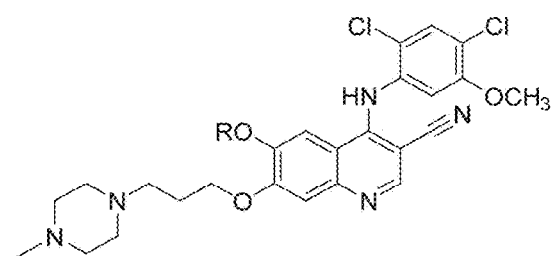

FIG. 5C-5D present examples of Bosutinib, a Targeting Ligands for the BCR-Abl, Src, Lyn and Hck receptors. R is the point at which the Linker is attached.

Figure 5E:
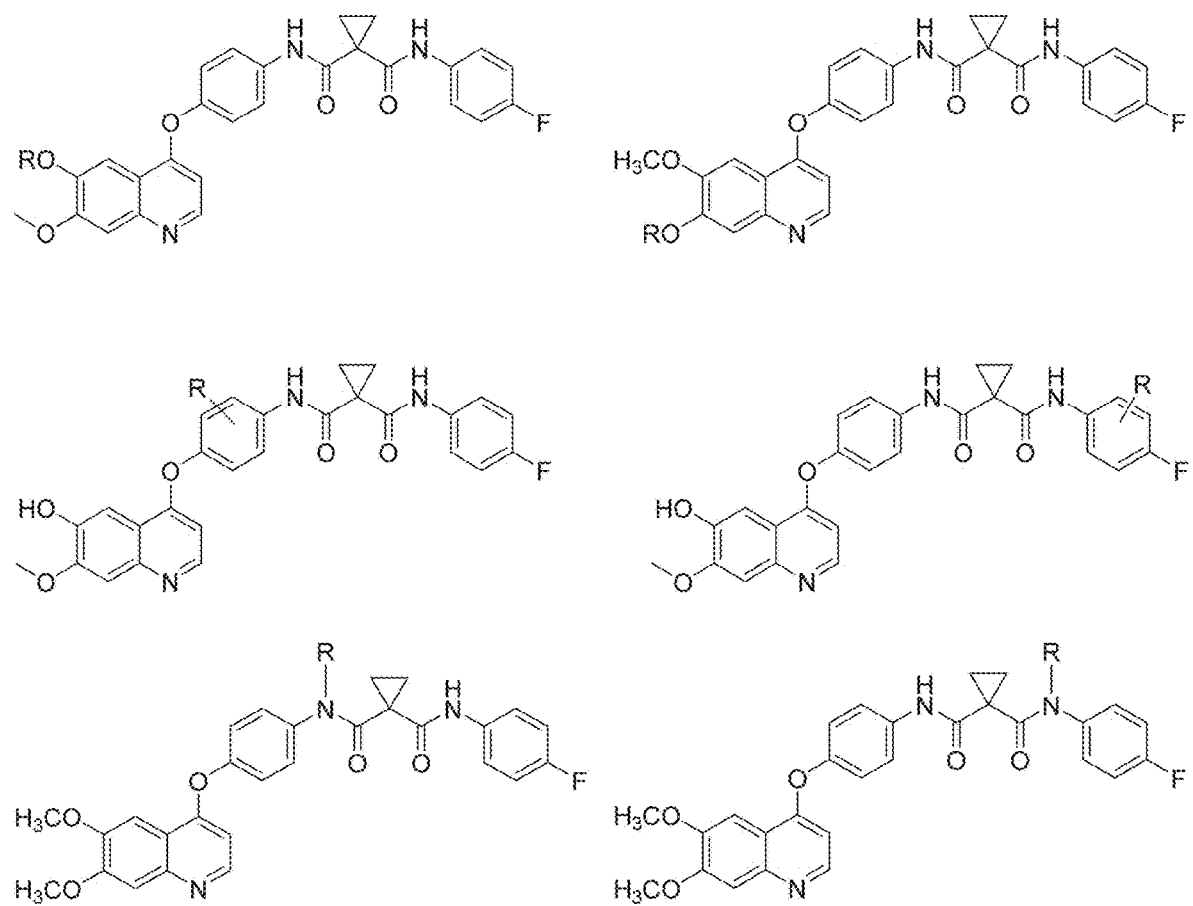

FIG. 5E presents examples of Cabozantinib, a Targeting Ligands for the RET, c-Met, VEGFR1/2/3, Kit, TrkB, Flt3, Axl, and Tie 2 receptors. R is the point at which the Linker is attached.

Figure 5F:
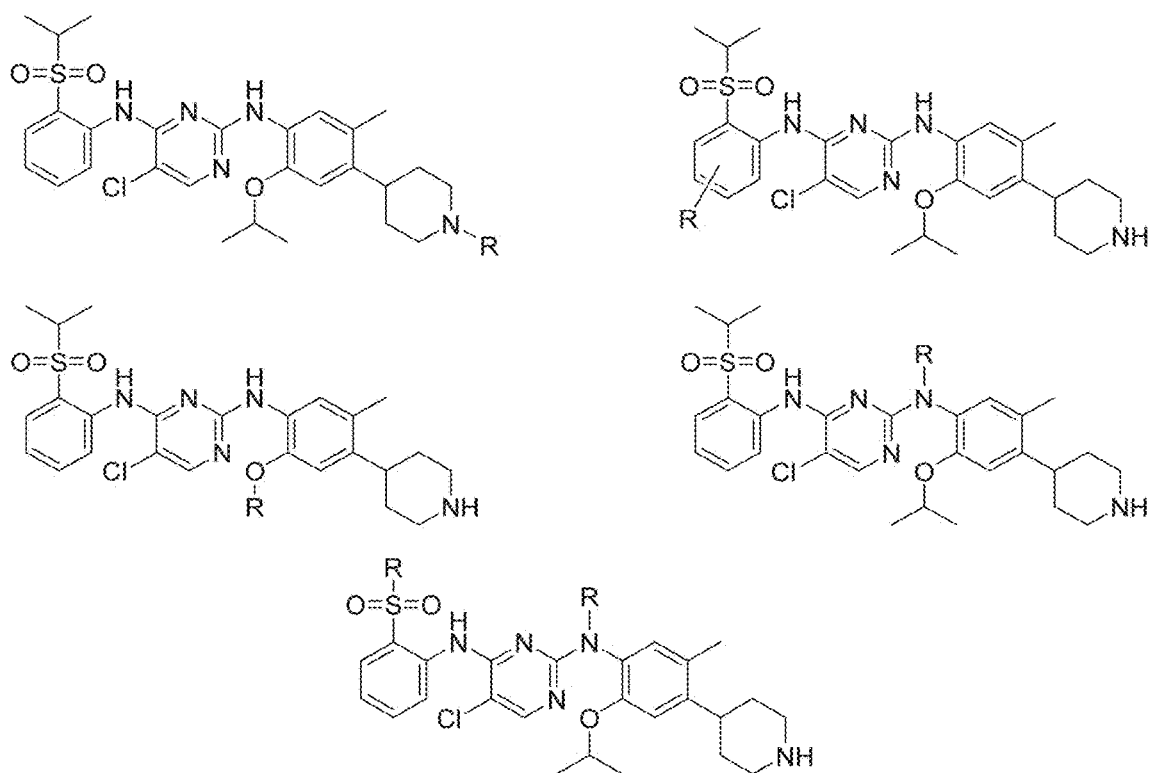

FIG. 5F presents examples of Ceritinib, a Targeting Ligands for the ALK, IGF-1R, InsR, and ROS1 receptors. R is the point at which the Linker is attached.

Figure 5G:
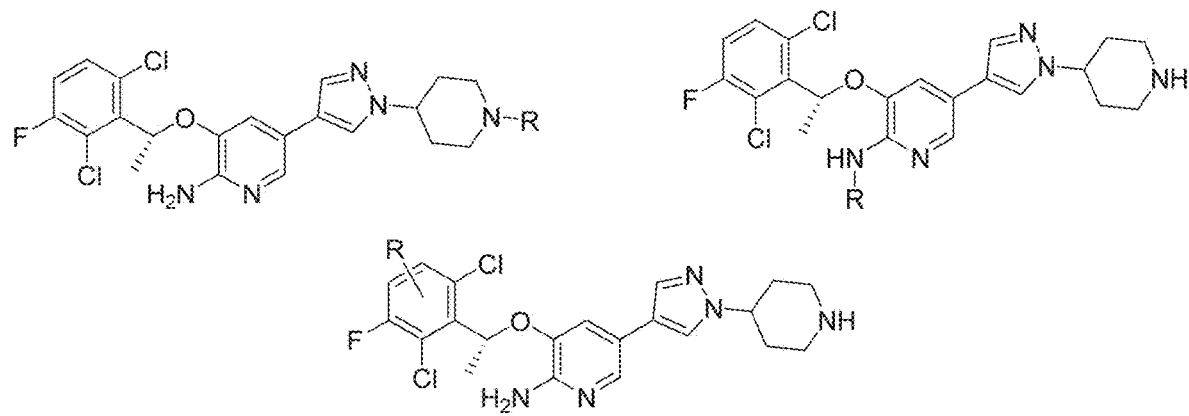

FIG. 5G presents examples of Crizotinib, a Targeting Ligands for the ALK, c-Met, HGFR, ROS1, and MST1R receptors. R is the point at which the Linker is attached.

Figure 5H:
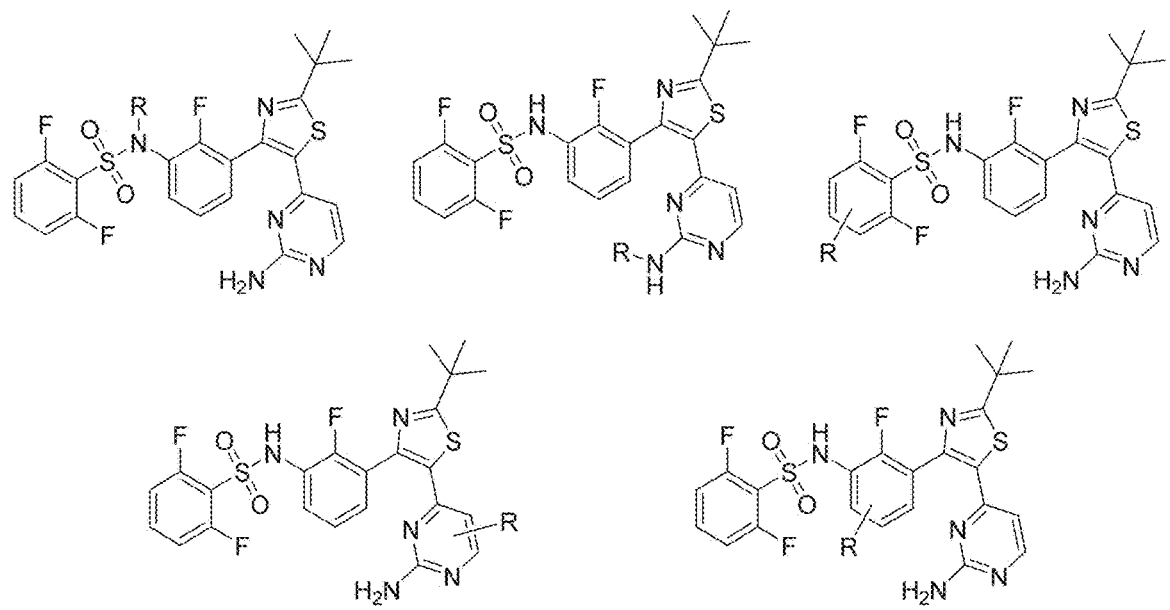

FIG. 5H presents examples of Dabrafenib, a Targeting Ligands for the B-Raf receptor. R is the point at which the Linker is attached.

Figure 5I:
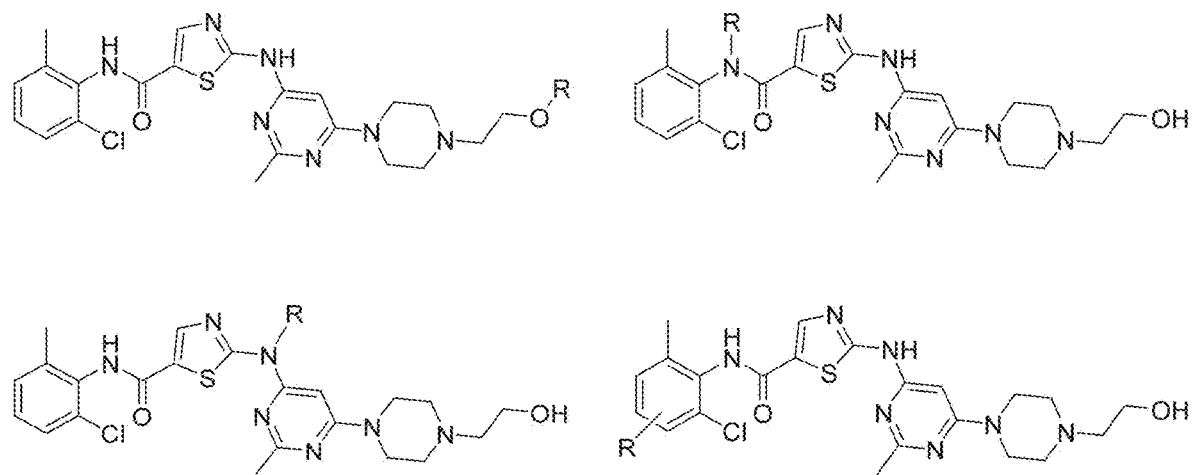

FIG. 5I presents examples of Dasatinib, a Targeting Ligands for the BCR-Abl, Src, Lck, Lyn, Yes, Fyn, Kit, EphA2, and PDGFRβ receptors. R is the point at which the Linker is attached.

Figure 5J:
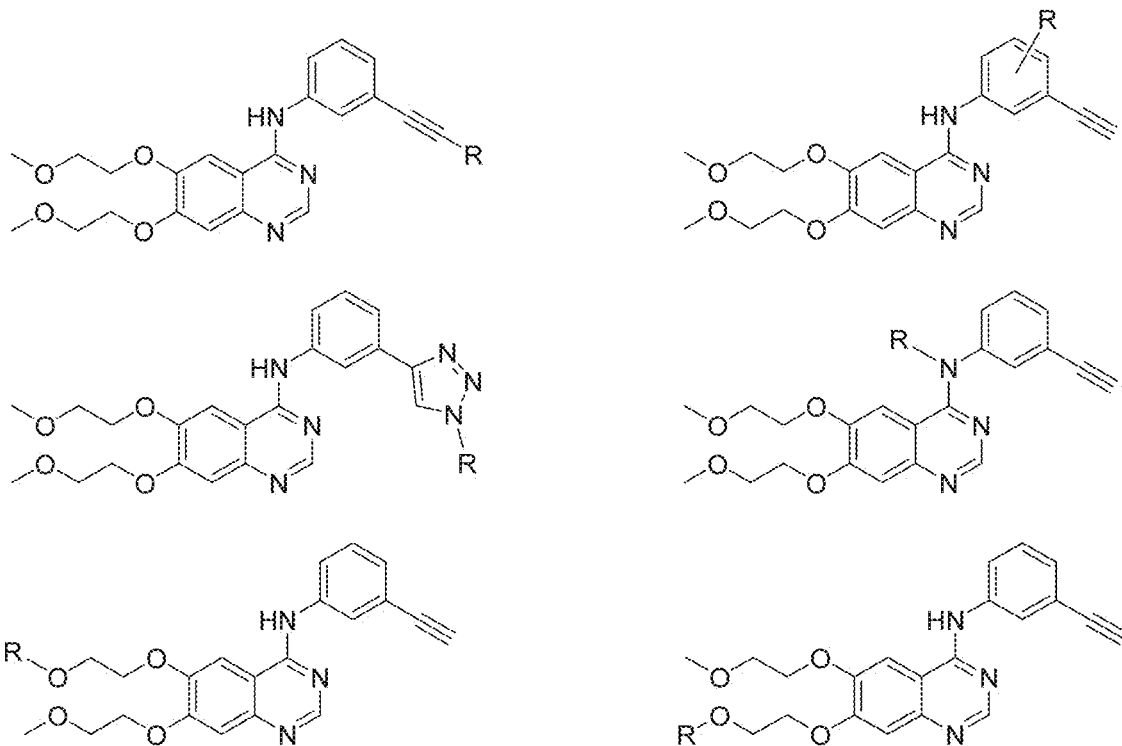

FIG. 5J presents examples of Erlotinib, a Targeting Ligands for the EGFR receptor. R is the point at which the Linker is attached.

Figure 5K:
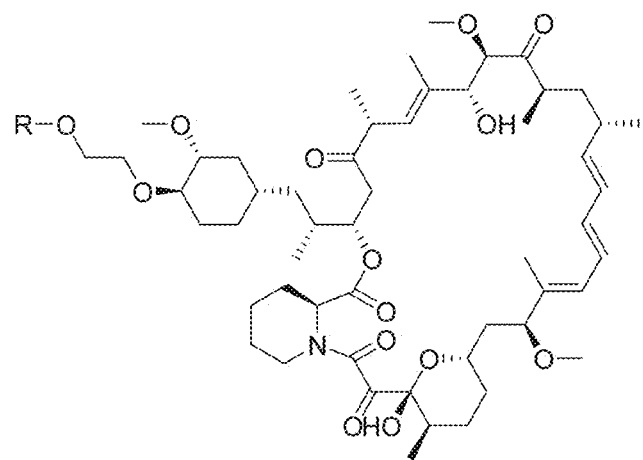
Figure 5L:
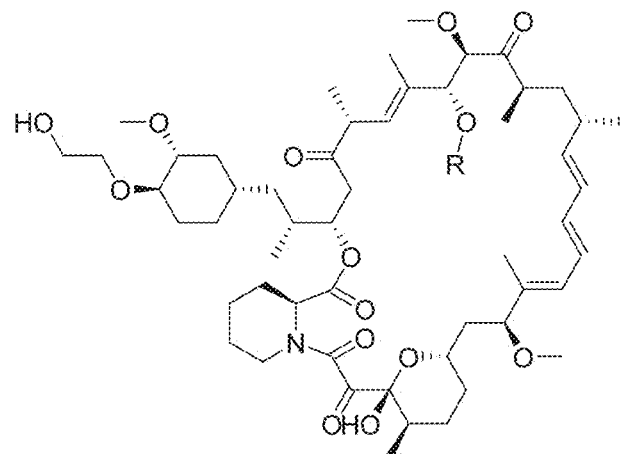
Figure 5L:
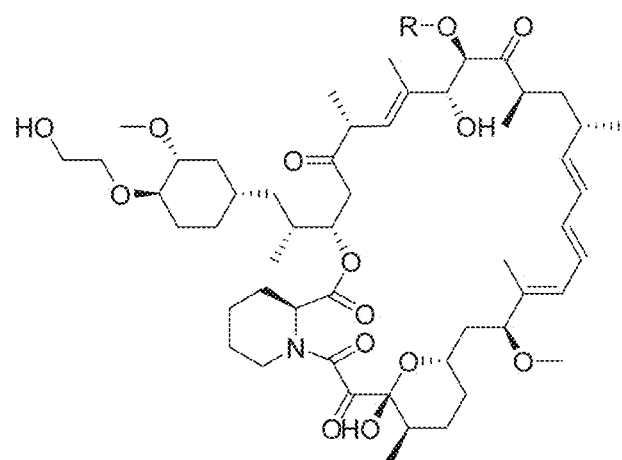
Figure 5L:
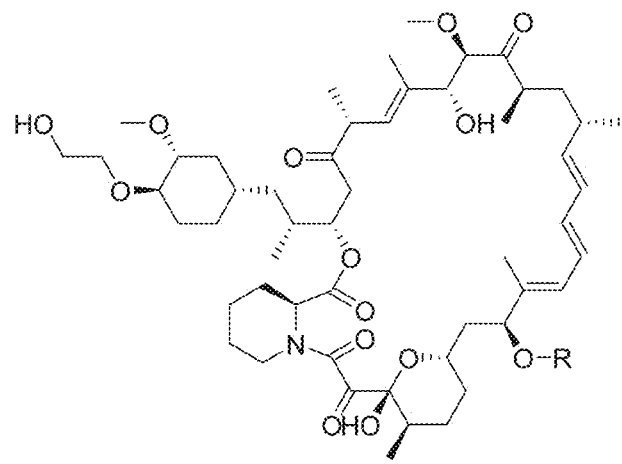
Figure 5M:
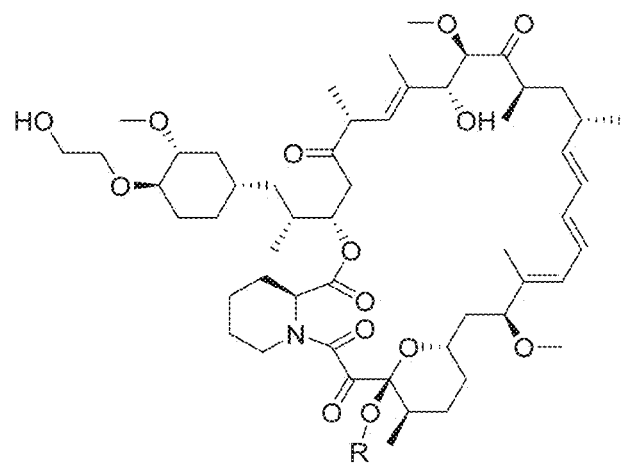
Figure 5M:
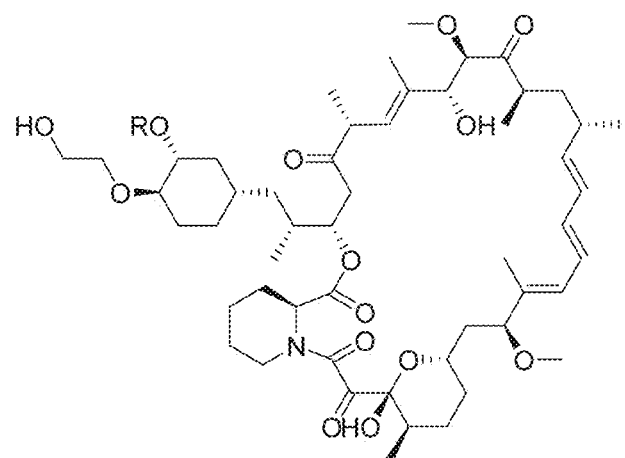

FIG. 5K-5M presents examples of Everolimus, a Targeting Ligands for the HER2 breast cancer receptor, the PNET receptor, the RCC receptors, the RAML receptor, and the SEGA receptor. R is the point at which the Linker is attached.

Figure 5N:
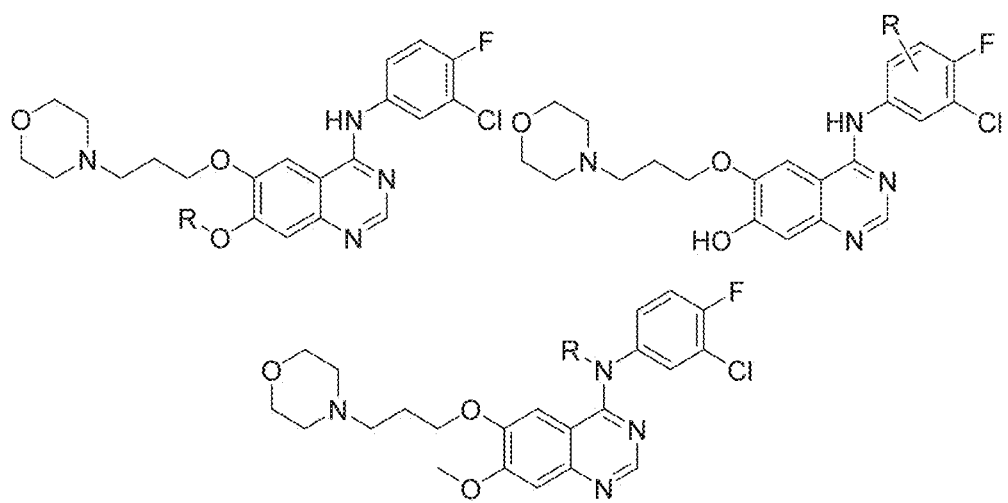

FIG. 5N presents examples of Gefitinib, a Targeting Ligands for the EGFR and PDGFR receptors. R is the point at which the Linker is attached.

Figure 5O:
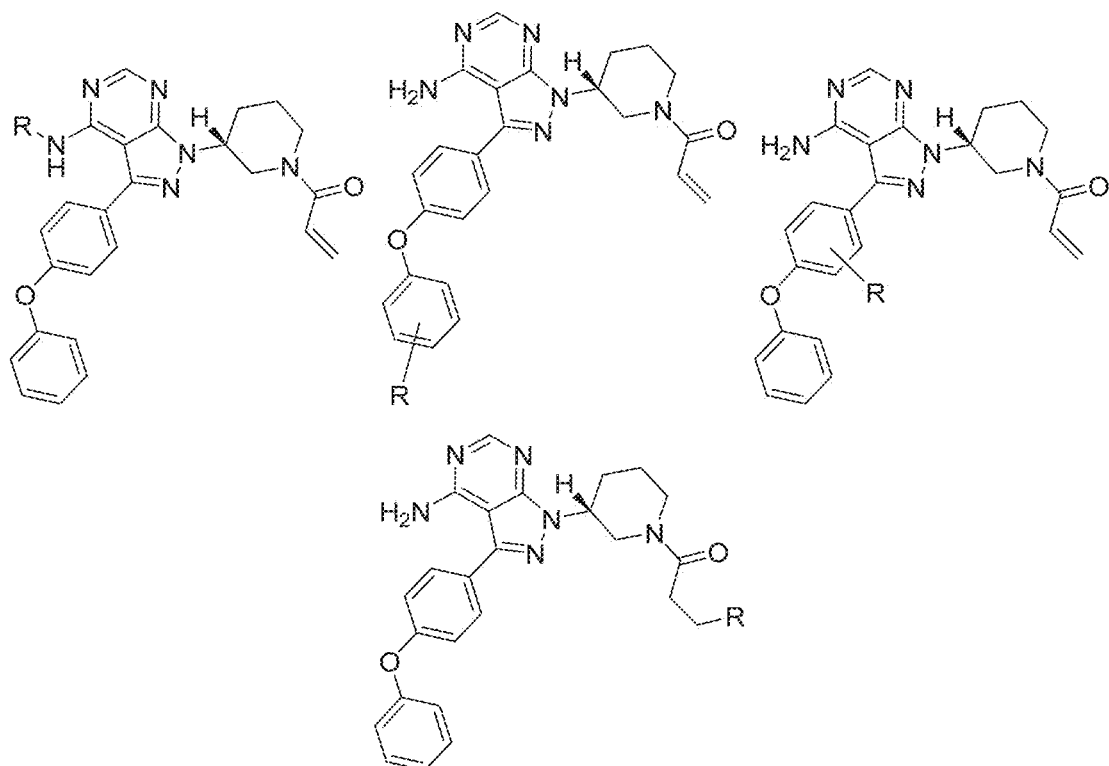

FIG. 5O presents examples of Ibrutinib, a Targeting Ligands for the BTK receptor. R is the point at which the Linker is attached.

Figure 5P:
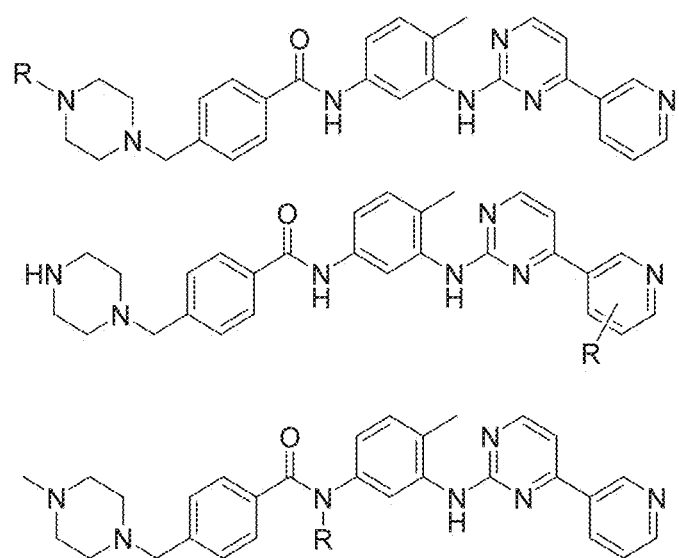
Figure 5Q:
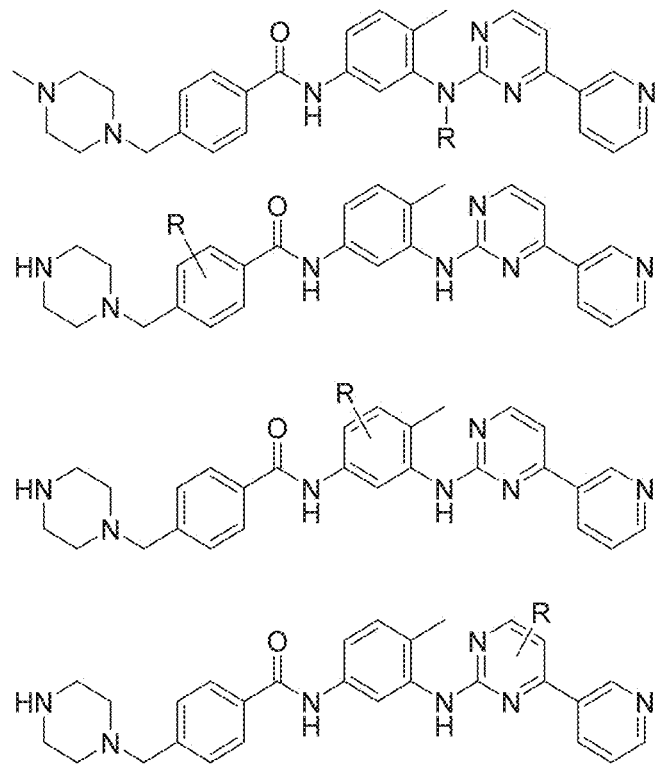

FIG. 5P-5Q present examples of Imatinib, a Targeting Ligands for the BCR-Abl, Kit, and PDGFR receptors. R is the point at which the Linker is attached.

Figure 5R:
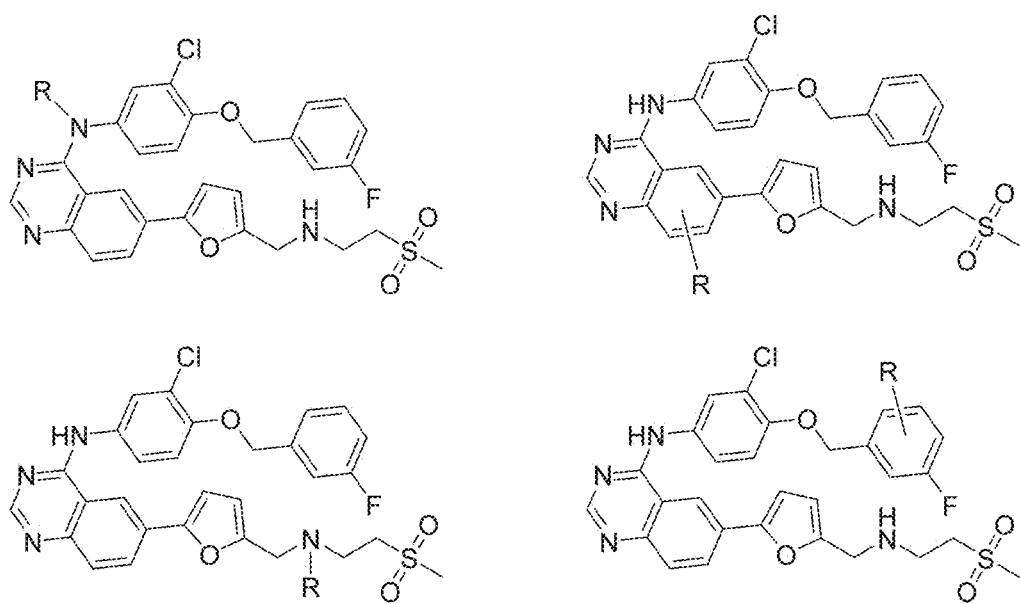
Figure 5S:
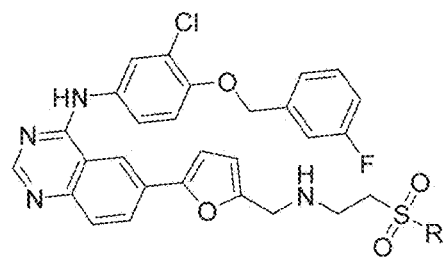

FIG. 5R-5S present examples of Lapatinib, a Targeting Ligands for the EGFR and ErbB2 receptors. R is the point at which the Linker is attached.

Figure 5T:
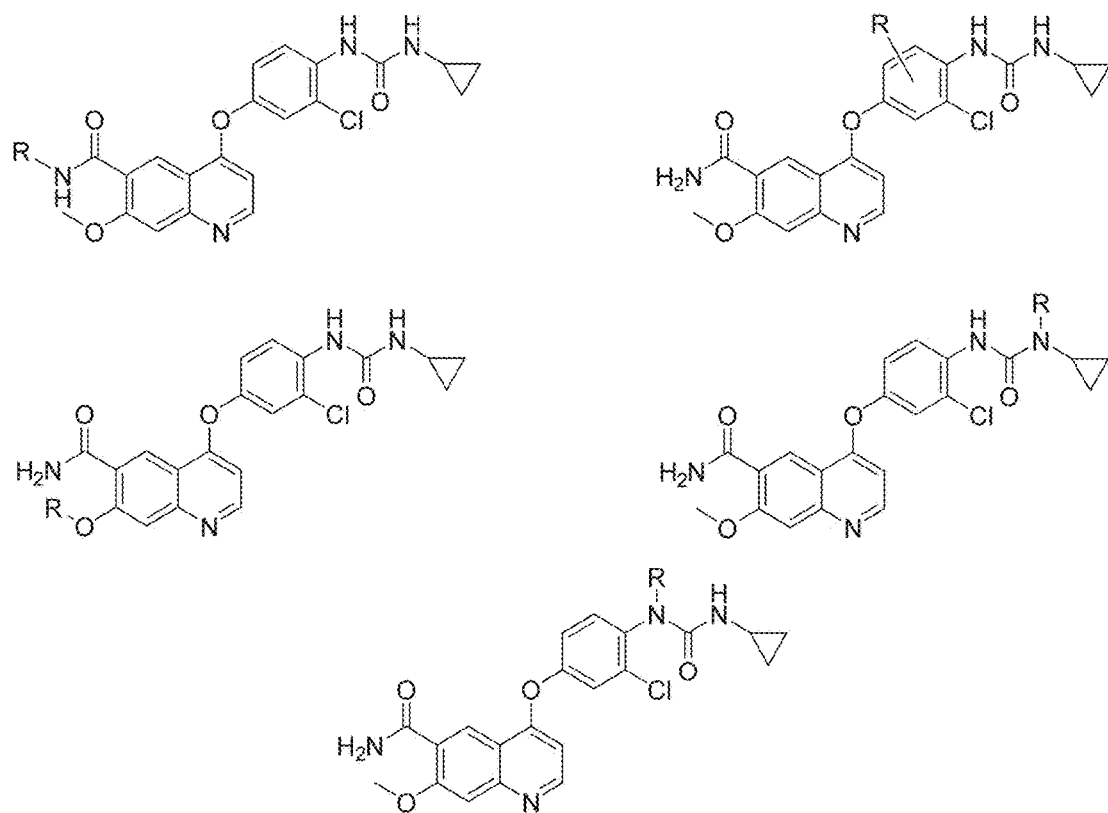

FIG. 5T presents examples of Lenvatinib, a Targeting Ligands for the VEGFR1/2/3, FGFR1/2/3/4, PDGFRα, Kit, and RET receptors. R is the point at which the Linker is attached.

Figure 5U:
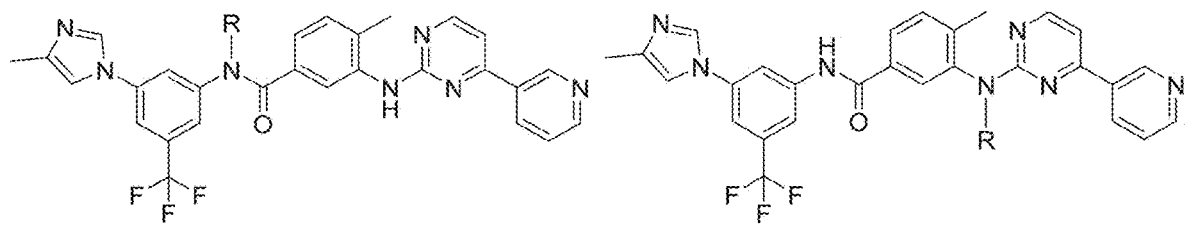
Figure 5V:
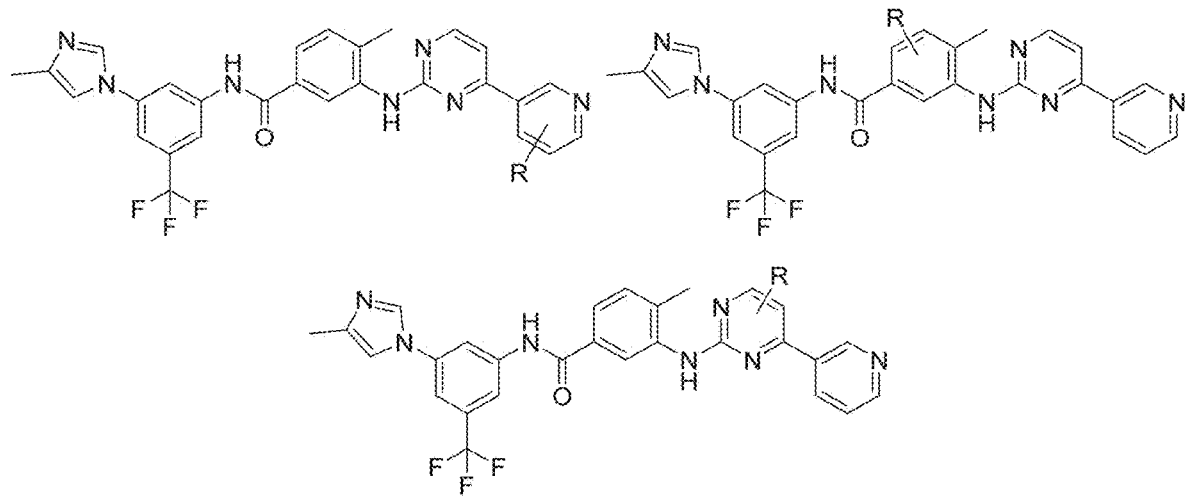

FIG. 5U-5V a present examples of Nilotinib, a Targeting Ligands for the BCR-Abl, PDGRF, and DDR1 receptors. R is the point at which the Linker is attached.

Figure 5W:
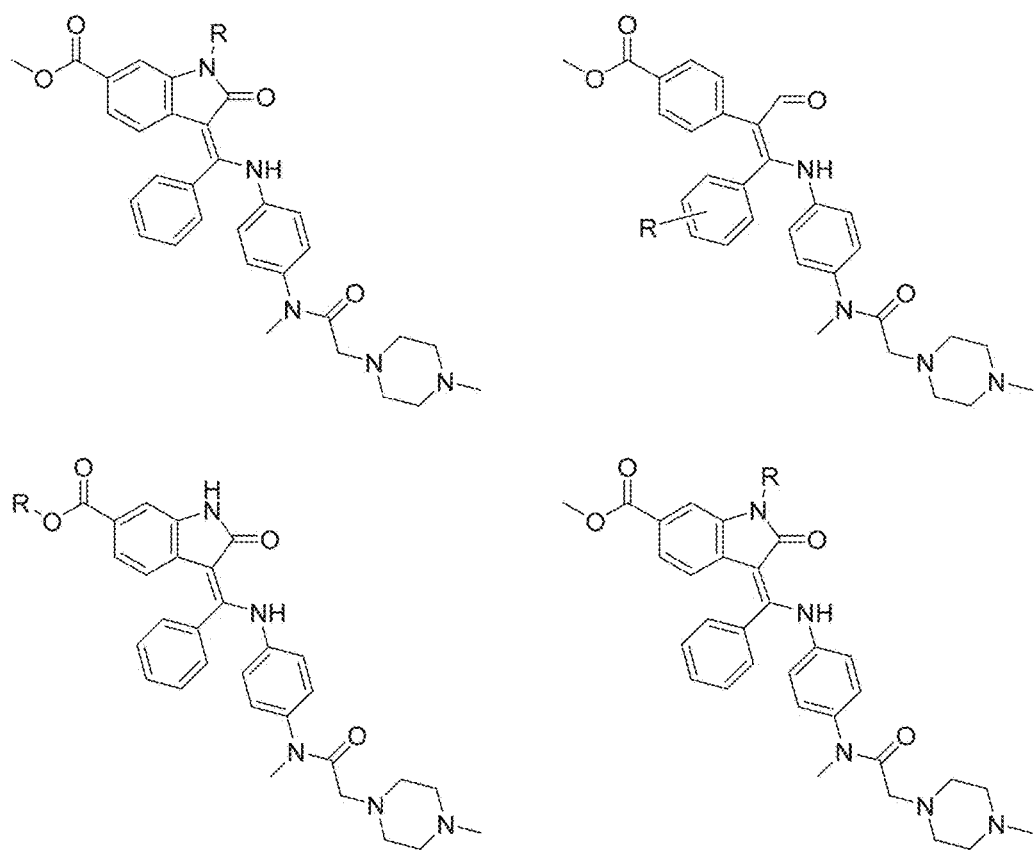
Figure 5X:
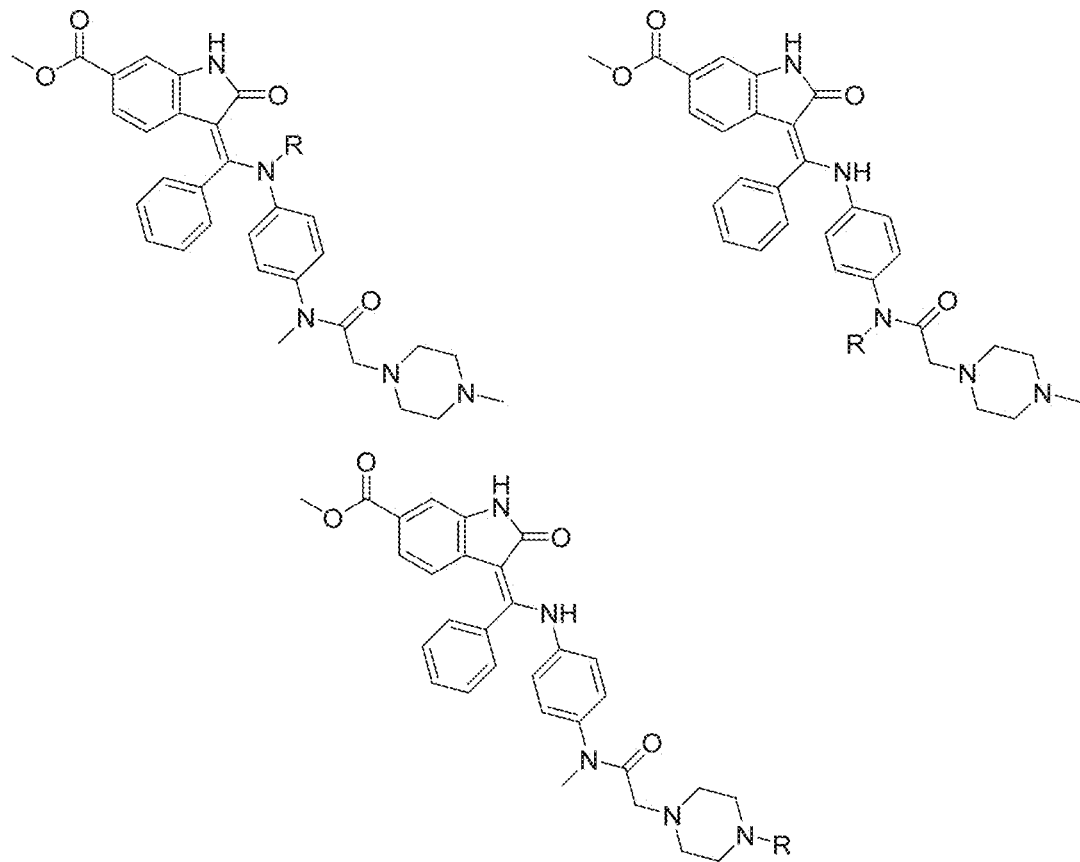

FIG. 5W-5X present examples of Nintedanib, a Targeting Ligands for the FGFR1/2/3, Flt3, Lck, PDGFRα/β, and VEGFR1/2/3 receptors. R is the point at which the Linker is attached.

Figure 5Y:
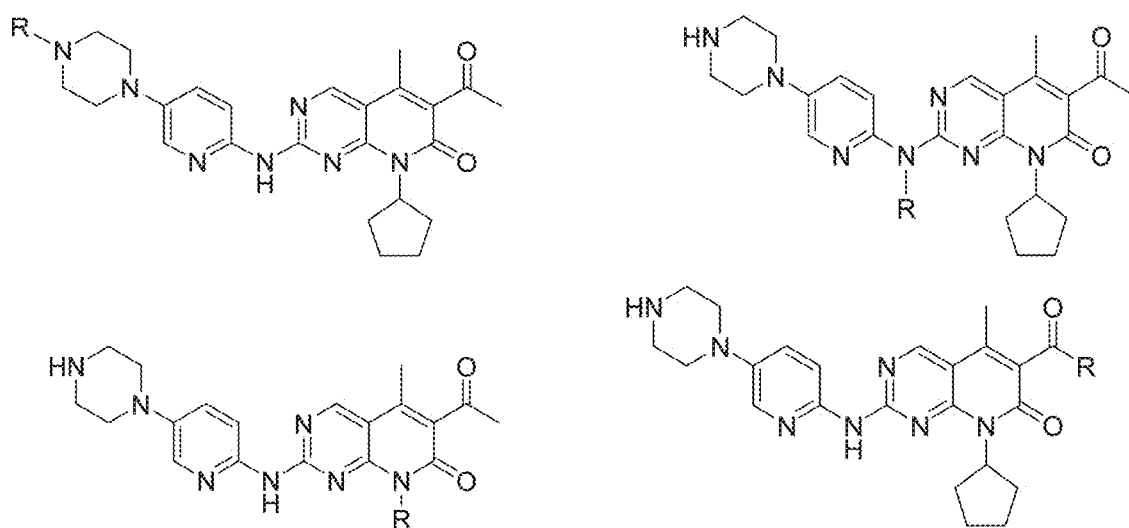
Figure 5Z:
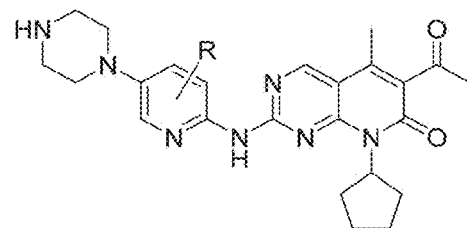
Figure 5A:
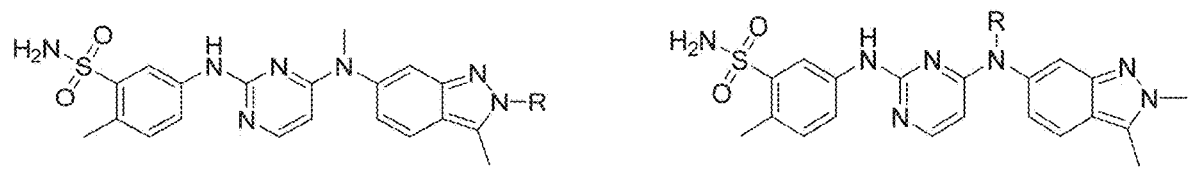
Figure 5A:
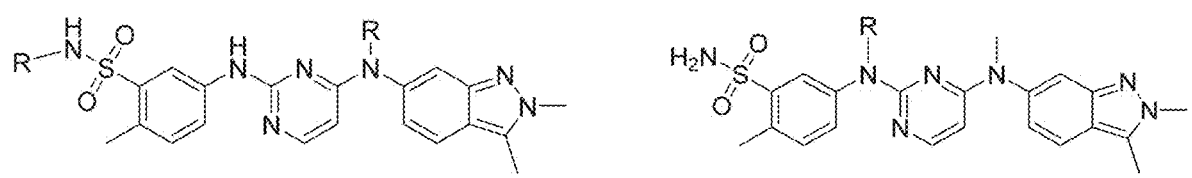
Figure 5A:
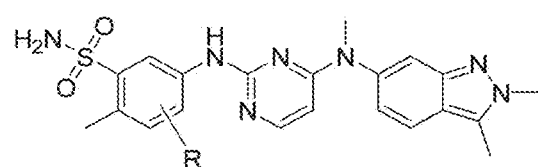
Figure 5B:
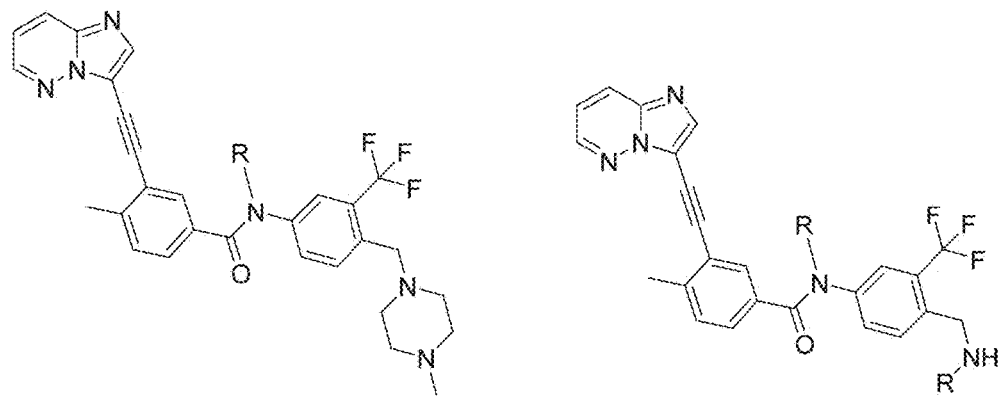
Figure 5C:
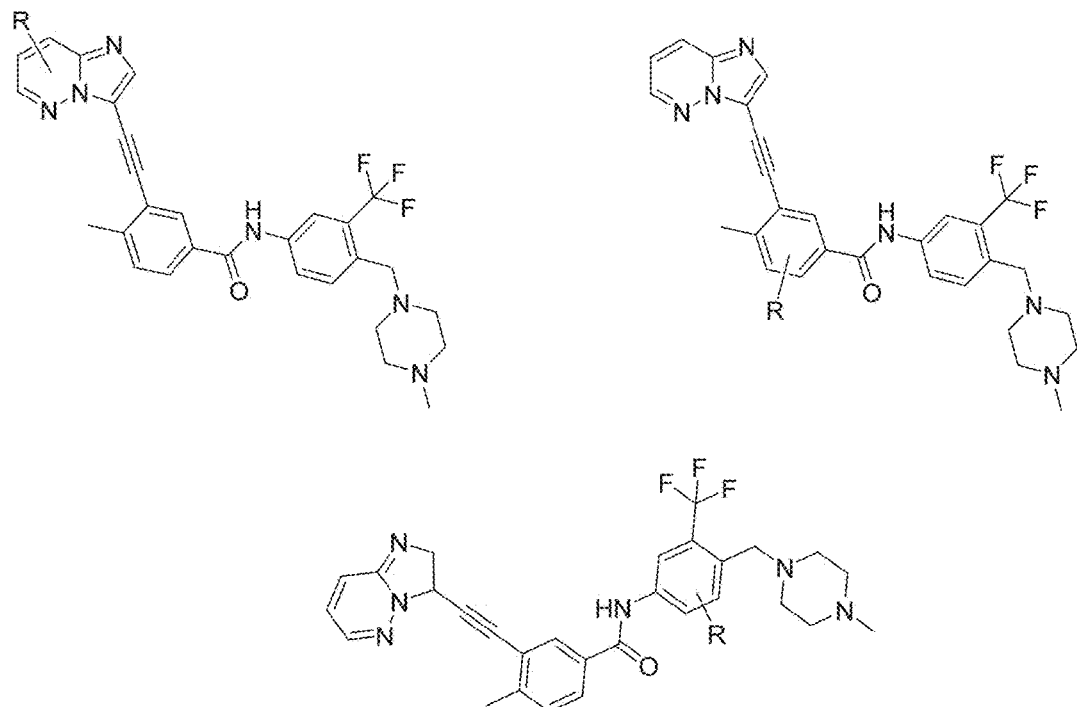
Figure 5D:
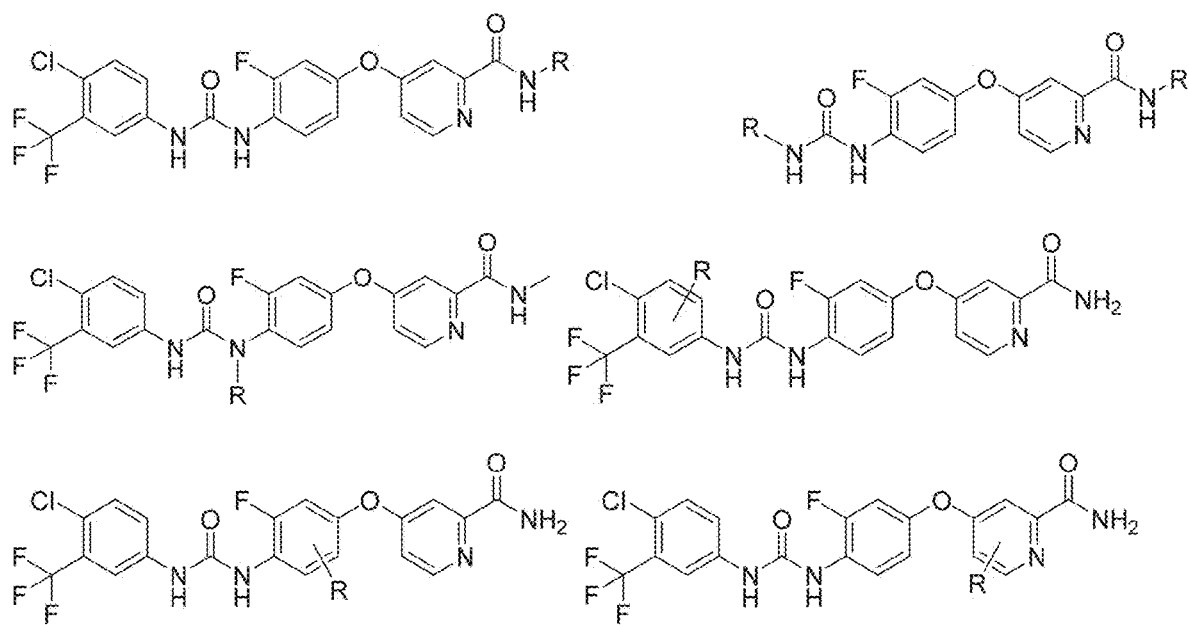
Figure 5E:
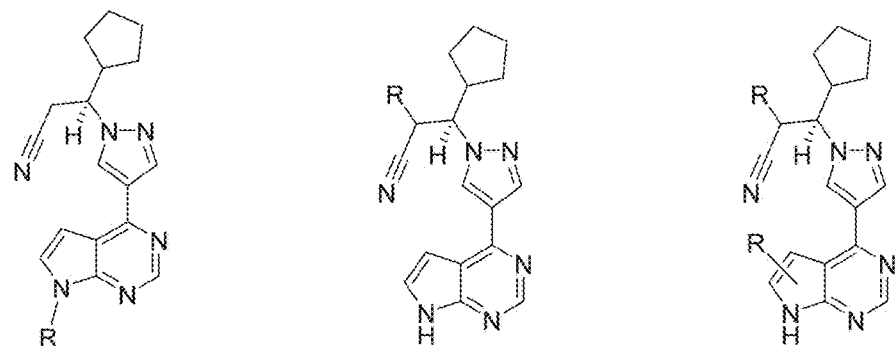
Figure 5F:
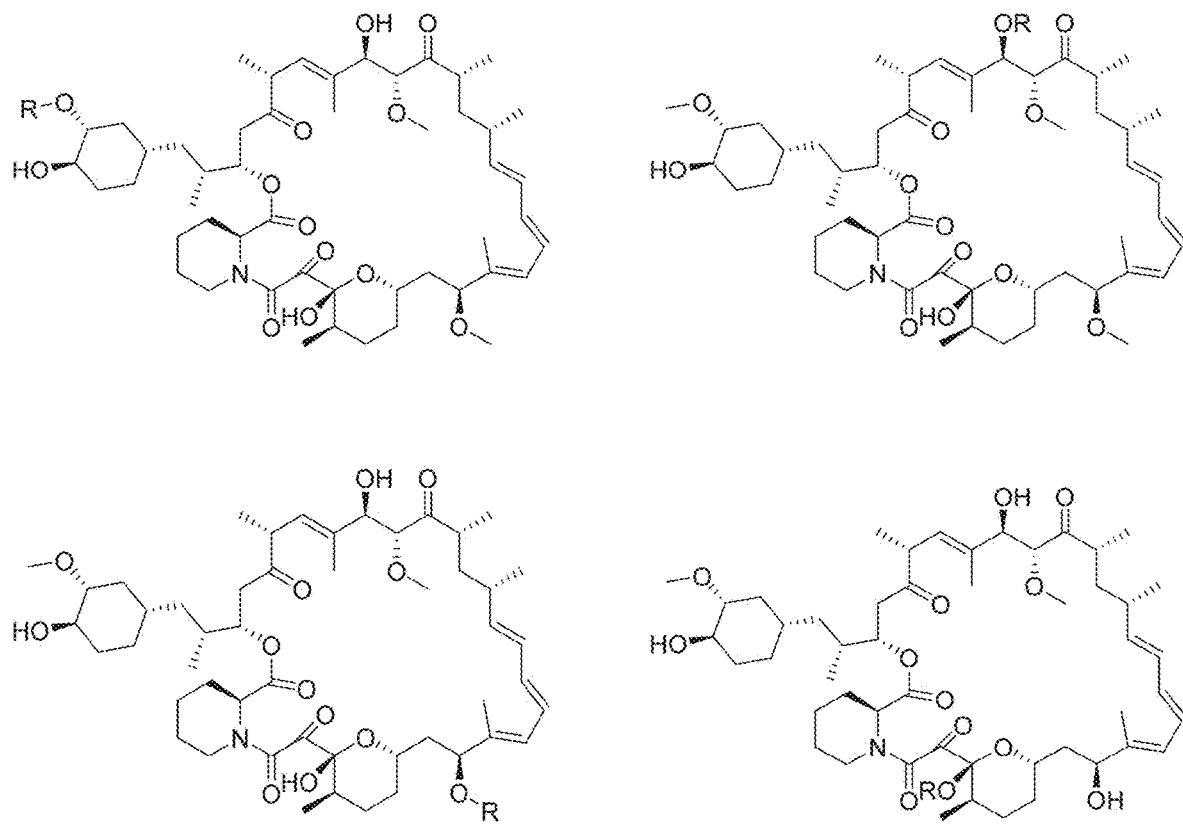
Figure 5G:
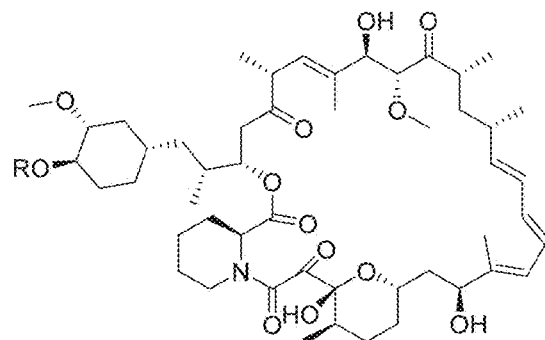
Figure 5H:
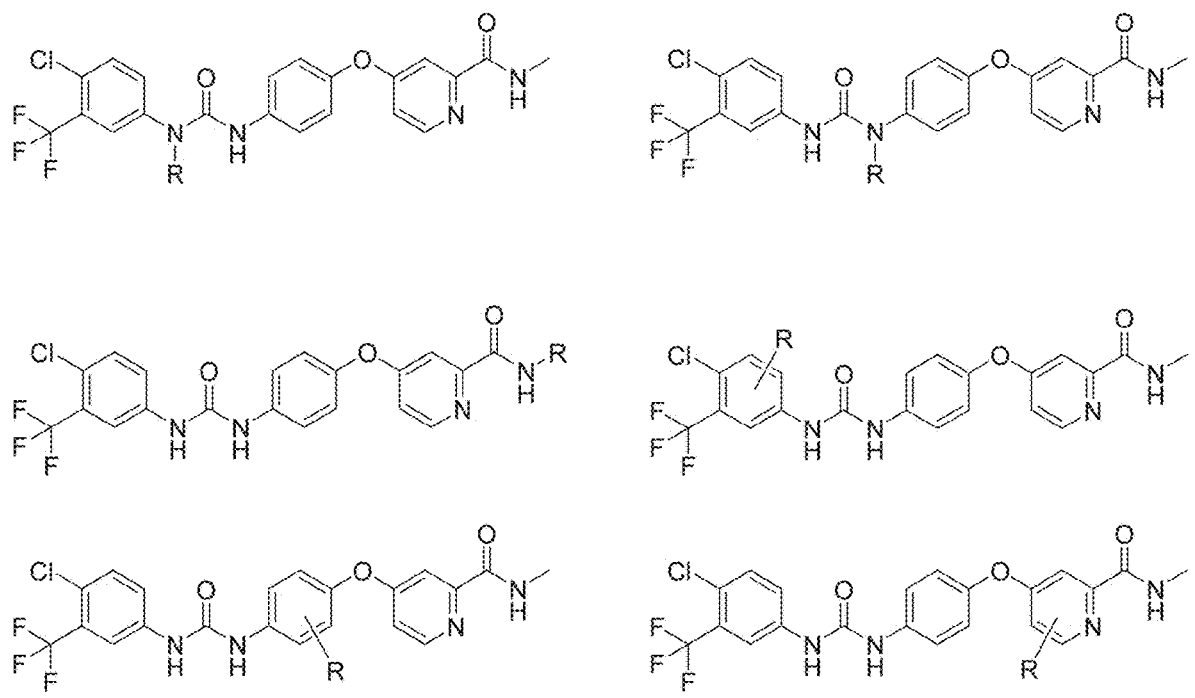
Figure 5I:
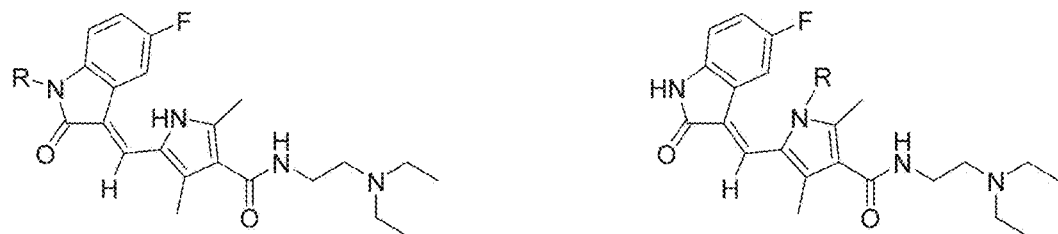
Figure 5J:
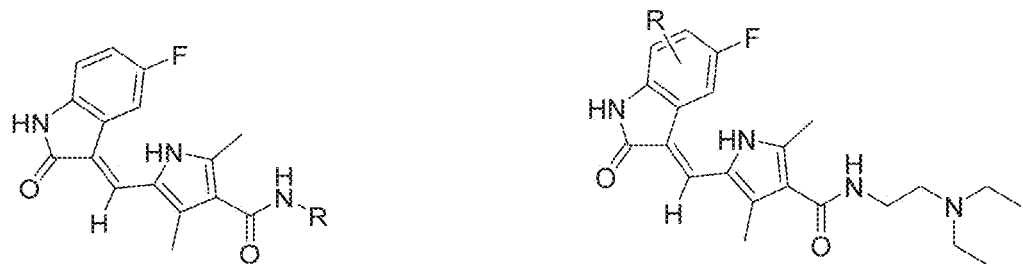
Figure 5K:
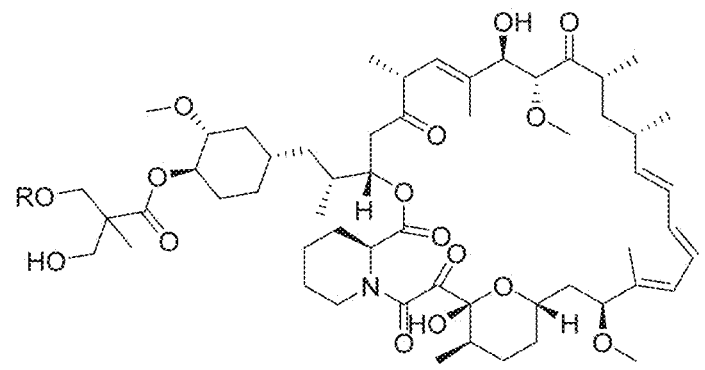
Figure 5K:
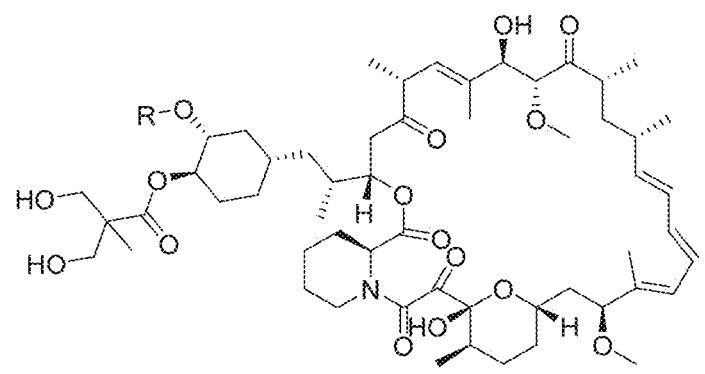
Figure 5L:
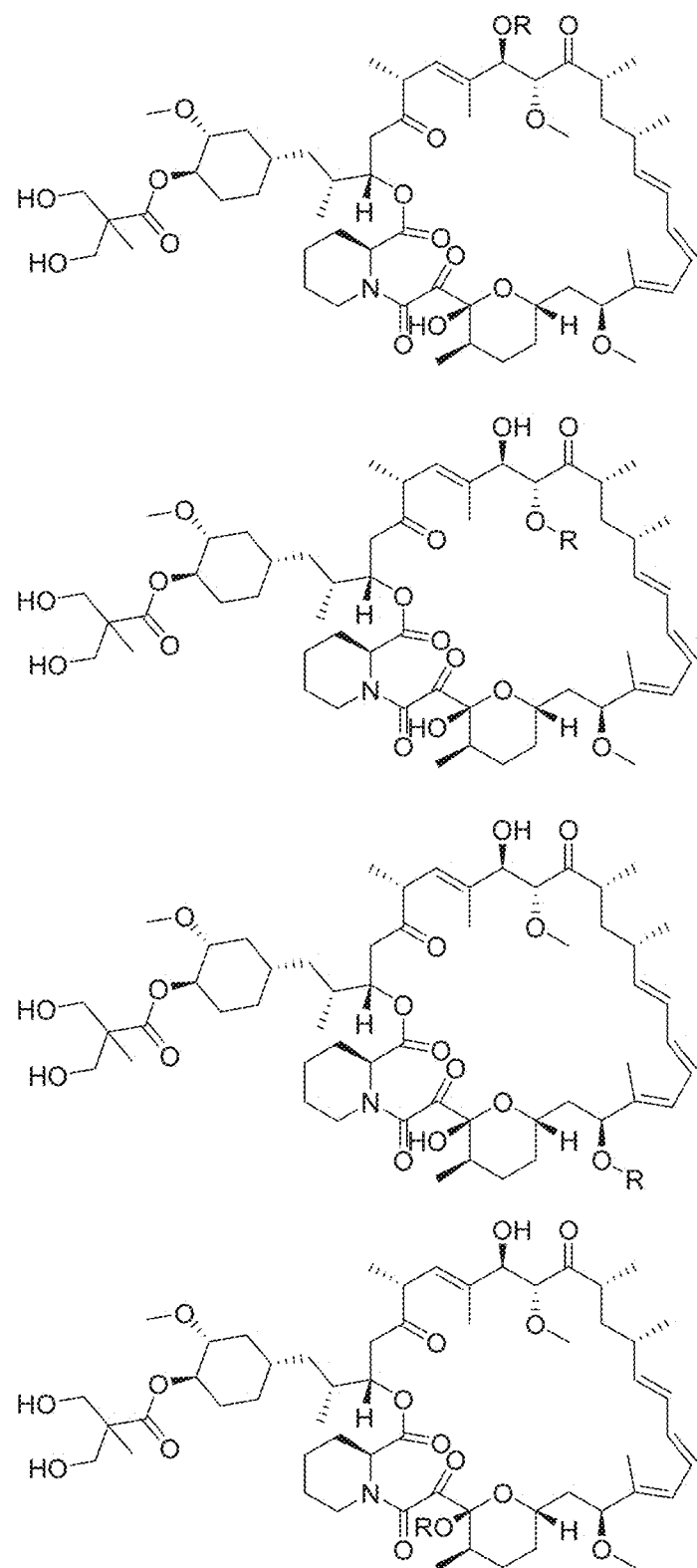
Figure 5M:
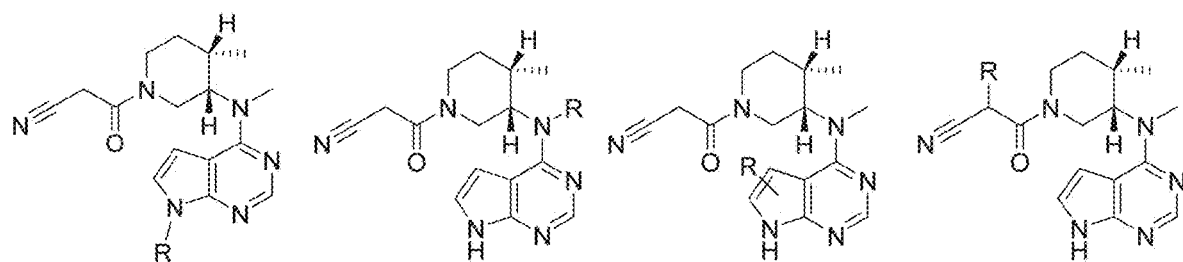
Figure 5N:
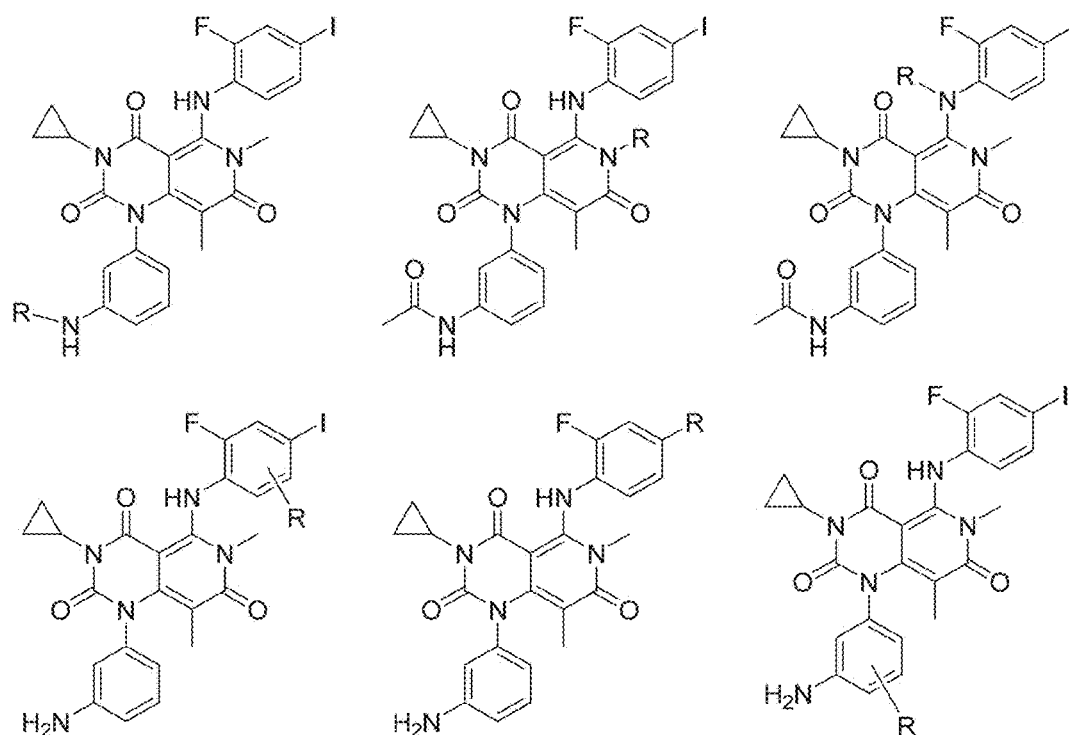
Figure 5O:
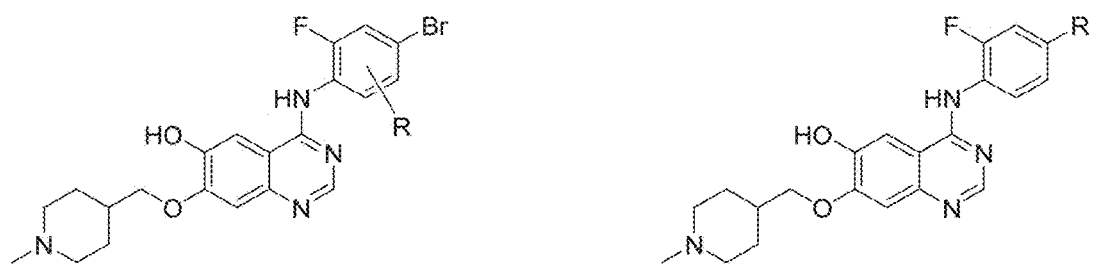
Figure 5P:
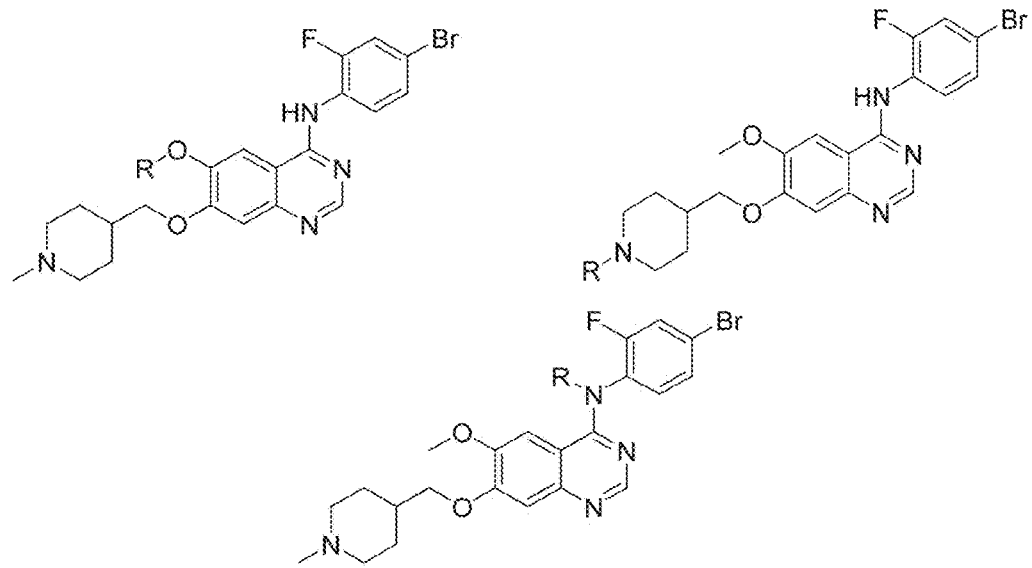
Figure 5Q:
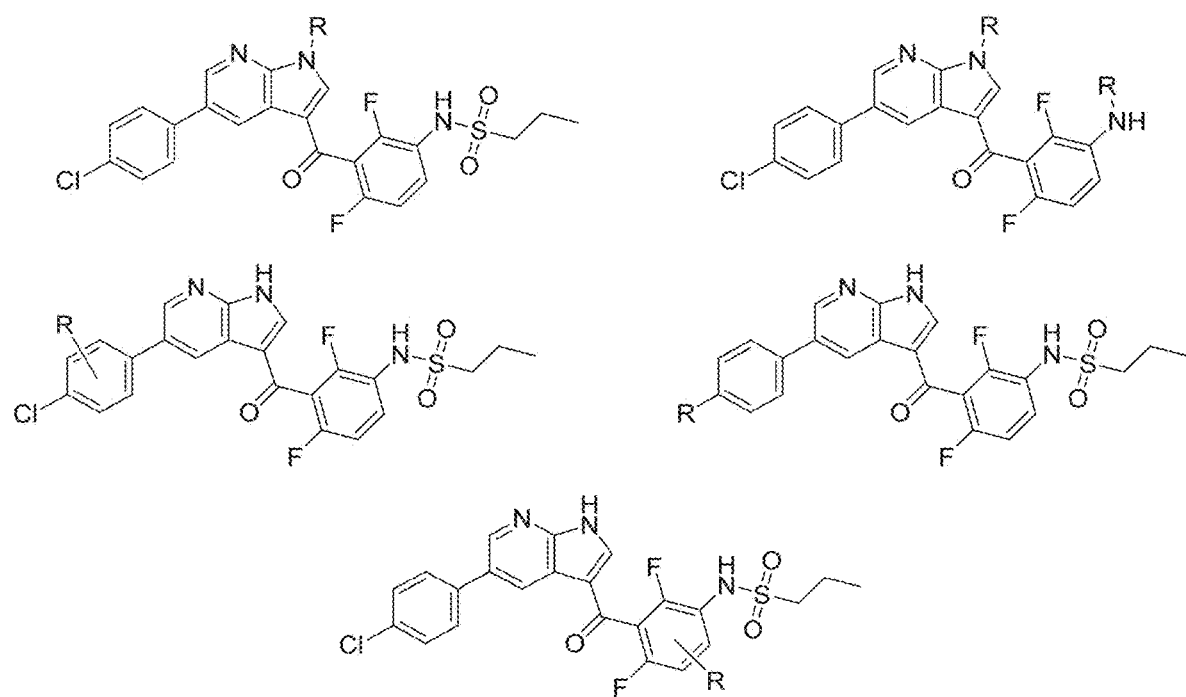
Figure 5R:
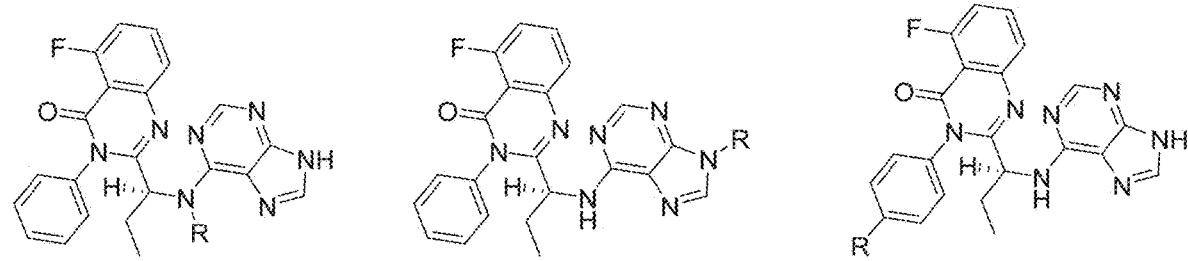
Figure 5S:
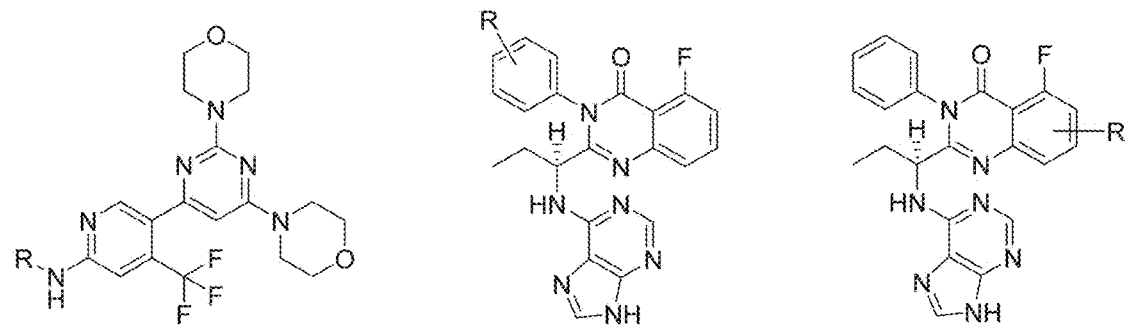
Figure 5T:
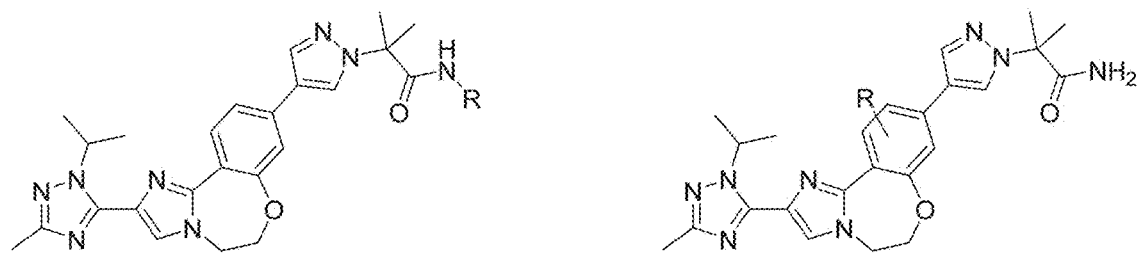
Figure 5U:
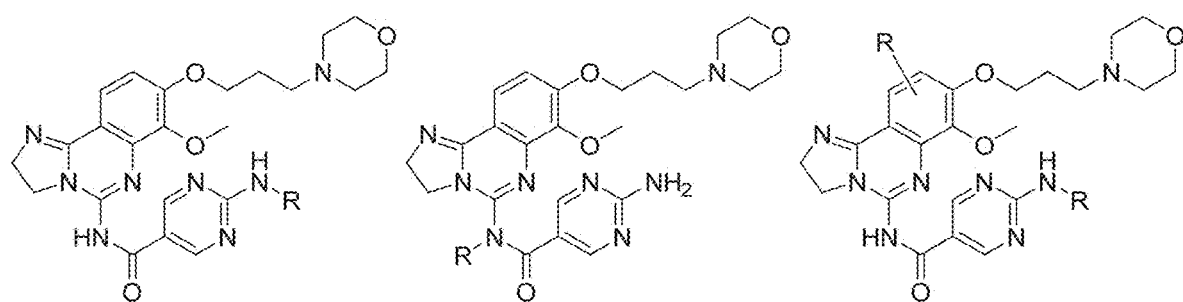
Figure 5V:
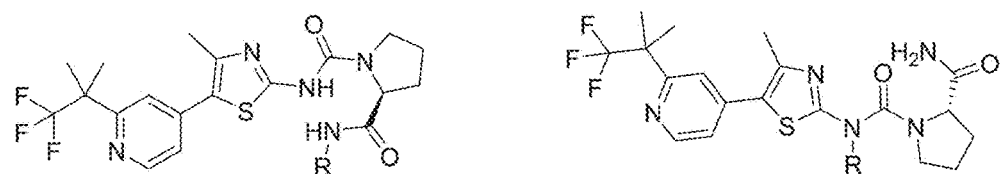
Figure 5W:
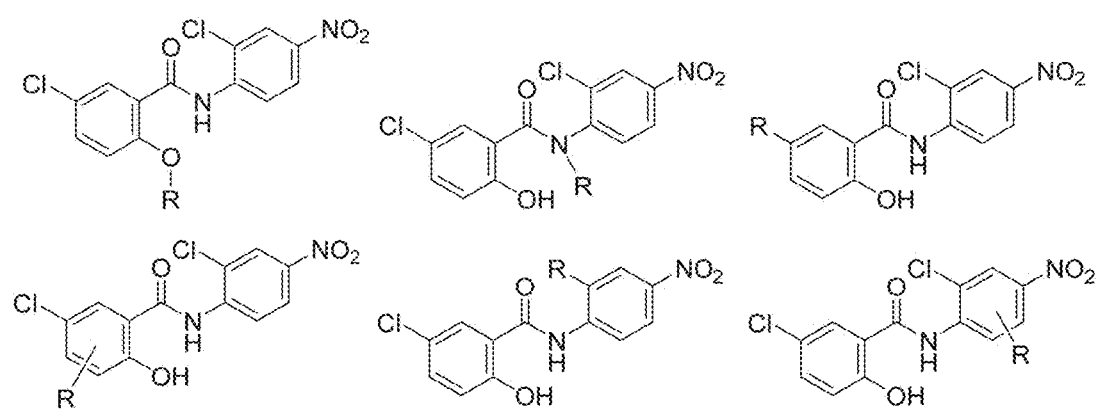

FIG. 5Y-5Z present examples of Palbociclib, a Targeting Ligands for the CDK4/6 receptor. R is the point at which the Linker is attached.

FIG. 5AA presents examples of Pazopanib, a Targeting Ligands for the VEGFR1/2/3, PDGFRα/β, FGFR1/3, Kit, Lck, Fms, and Itk receptors. R is the point at which the Linker is attached.

FIG. 5BB-5CC present examples of Ponatinib, a Targeting Ligands for the BCR-Abl, T315I VEGFR, PDGFR, FGFR, EphR, Src family kinases, Kit, RET, Tie2, and Flt3 receptors. R is the point at which the Linker is attached.

FIG. 5DD presents examples of Regorafenib, a Targeting Ligands for the VEGFR1/2/3, BCR-Abl, B-Raf, B-Raf (V600E), Kit, PDGFRα/β, RET, FGFR1/2, Tie2, and Eph2A. R is the point at which the Linker is attached.

FIG. 5EE presents examples of Ruxolitinib, a Targeting Ligands for the JAK1/2 receptors. R is the point at which the Linker is attached.

FIG. 5FF-5GG present examples of Sirolimus, a Targeting Ligands for the FKBP12/mTOR receptors. R is the point at which the Linker is attached.

FIG. 5HH presents examples of Sorafenib, a Targeting Ligands for the B-Raf, CDK8, Kit, Flt3, RET, VEGFR1/2/3, and PDGFR receptors. R is the point at which the Linker is attached.

FIG. 5II-5JJ present examples of Sunitinib, a Targeting Ligands for PDGFRα/β, VEGFR1/2/3, Kit, Flt3, CSF-1R, RET. R is the point at which the Linker is attached.

FIG. 5KK-5LL present examples of Temsirolimus, a Targeting Ligands FKBP12/mTOR. R is the point at which the Linker is attached.

FIG. 5MM presents examples of Tofacitinib, a Targeting Ligands for JAK3 receptors. R is the point at which the Linker is attached.

FIG. 5NN presents examples of Trametinib, a Targeting Ligands for the MEK1/2 receptors. R is the point at which the Linker is attached.

FIG. 5OO-5PP present examples of Vandetanib, a Targeting Ligands for the EGFR, VEGFR, RET, Tie2, Brk, and EphR. R is the point at which the Linker is attached.

FIG. 5QQ presents examples of Vemurafenib, a Targeting Ligands for the A/B/C-Raf, KSR1, and B-Raf (V600E) receptors. R is the point at which the Linker is attached.

FIG. 5RR presents examples of Idelasib, a Targeting Ligands for the PI3Ka receptor. R is the point at which the Linker is attached.

FIG. 5SS presents examples of Buparlisib, a Targeting Ligands for the PI3Ka receptor. R is the point at which the Linker is attached.

FIG. 5TT presents examples of Taselisib, a Targeting Ligands for the PI3Ka receptor. R is the point at which the Linker is attached.

FIG. 5UU presents examples of Copanlisib, a Targeting Ligands for the PI3Ka. R is the point at which the Linker is attached.

FIG. 5VV presents examples of Alpelisib, a Targeting Ligands for the PI3Ka. R is the point at which the Linker is attached.

FIG. 5WW presents examples of Niclosamide, a Targeting Ligands for the CNNTB1. R is the point at which the Linker is attached.

Figure 6A:
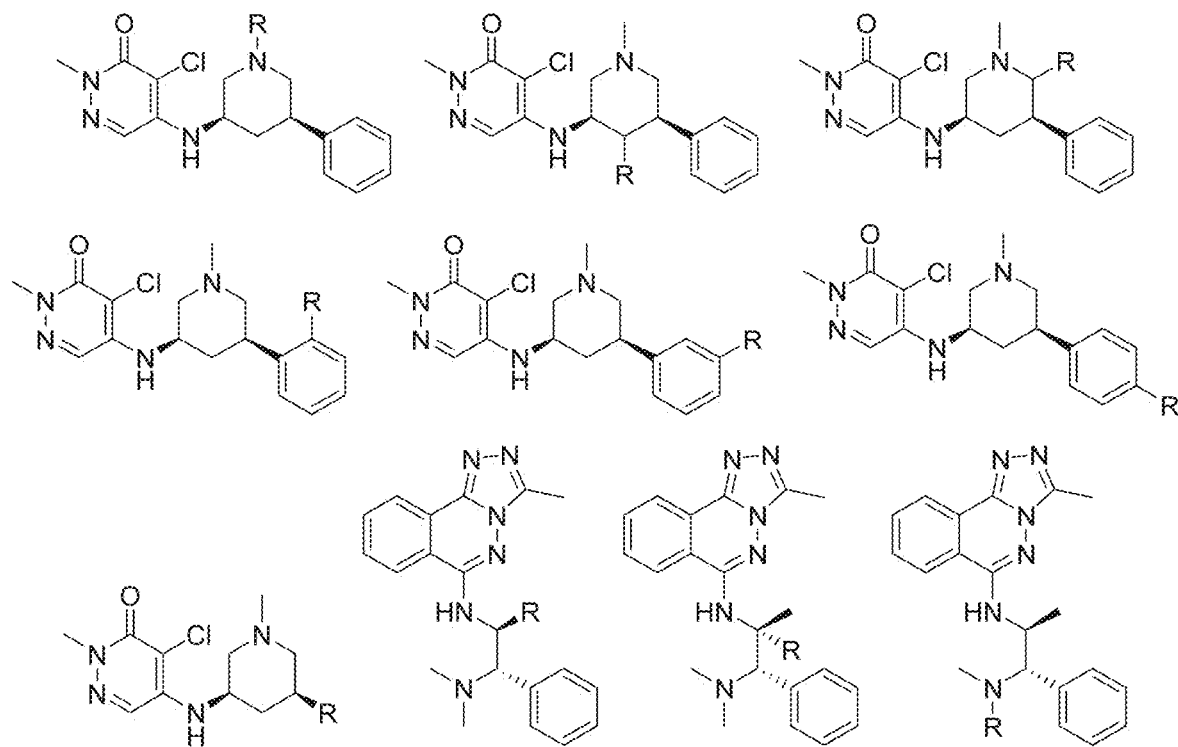
Figure 6B:
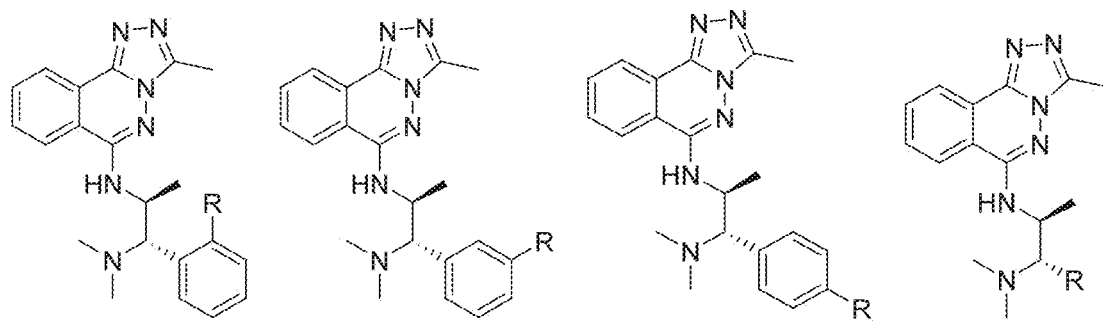

FIG. 6A-6B present examples of the BRD4 Bromodomains of PCAF and GCN5 receptors 1 Targeting Ligands wherein R is the point at which the Linker is attached. For additional examples and related ligands, see, the PDB crystal structure 5tpx ("Discovery of a PCAF Bromodomain Chemical Probe"); Moustakim, M., et al. *Angew. Chem. Int. Ed. Engl.* 56: 827 (2017); the PDB crystal structure 5mlj ("Discovery of a Potent, Cell Penetrant, and Selective p300/CBP-Associated Factor (PCAF)/General Control Nonderepressible 5 (GCN5) Bromodomain Chemical Probe"); and, Humphreys, P. G. et al. *J. Med. Chem.* 60: 695 (2017).

Figure 6C:
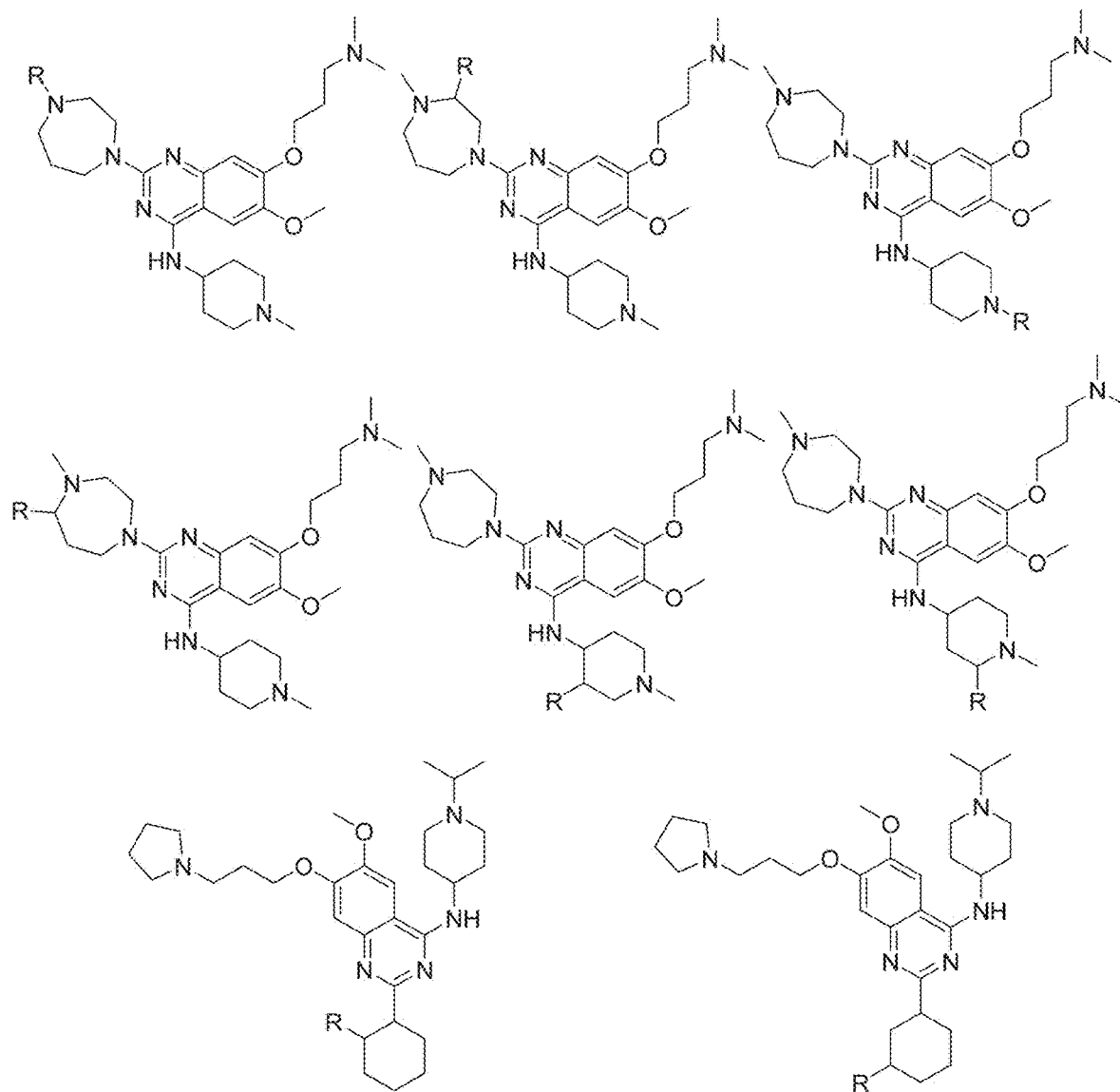
Figure 6D:
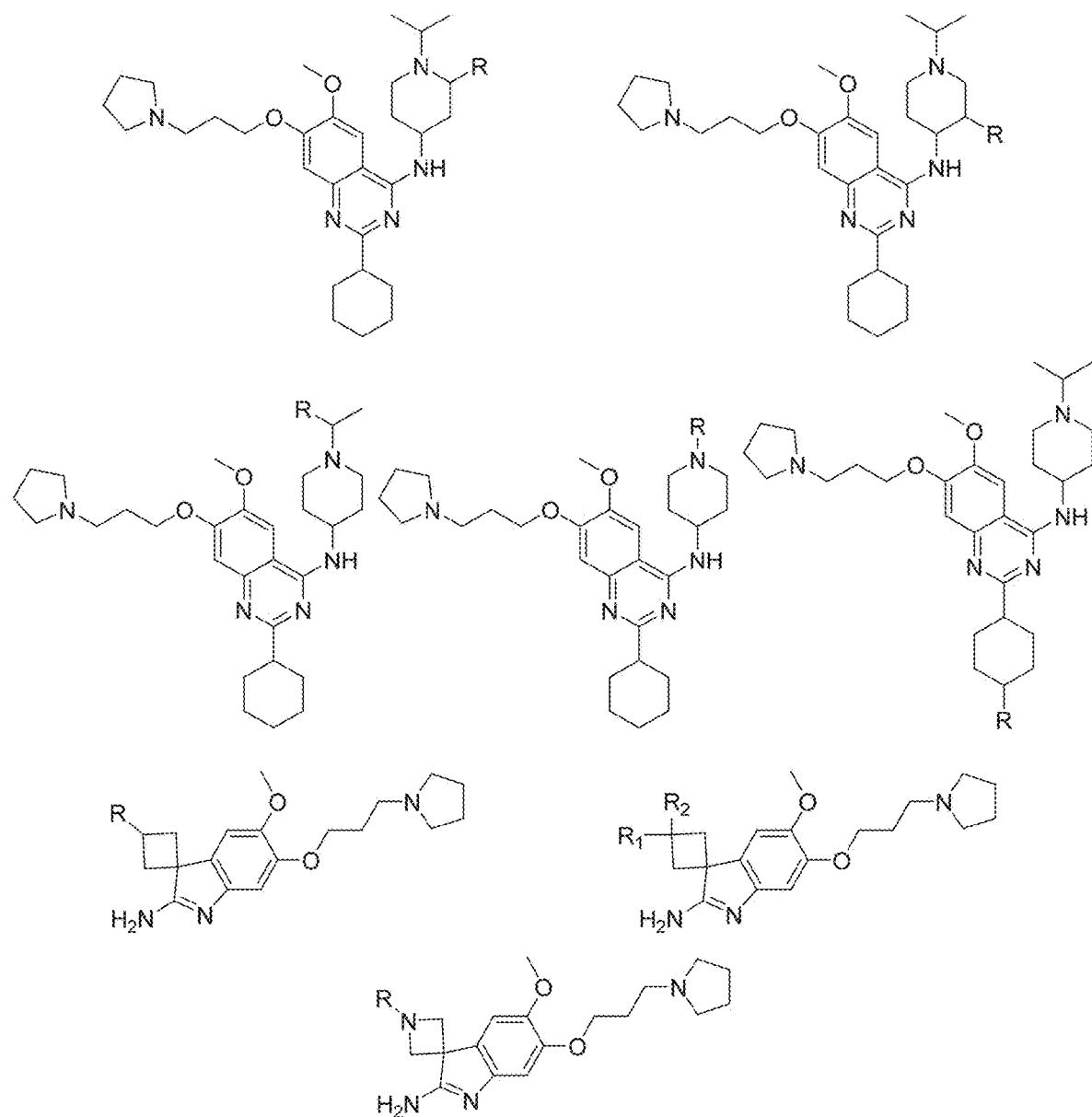

FIG. 6C-6D present examples of G9a (EHMT2) Targeting Ligands wherein R is the point at which the Linker is attached. For additional examples and related ligands, see, the PDB crystal structure 3k5k; ("Discovery of a 2,4-diamino-7-aminoalkoxyquinazoline as a potent and selective inhibitor of histone lysine methyltransferase G9a"); Liu, F. et al. *J. Med. Chem.* 52: 7950 (2009); the PDB crystal structure 3rjw ("A chemical probe selectively inhibits G9a and GLP methyltransferase activity in cells"); Vedadi, M. et al. *Nat. Chem. Biol.* 7: 566 (2011); the PDB crystal structure 4nvq ("Discovery and development of potent and selective inhibitors of histone methyltransferase g9a"); and, Sweis, R. F. et al. *ACS Med Chem Lett* 5: 205 (2014).

Figure 6E:
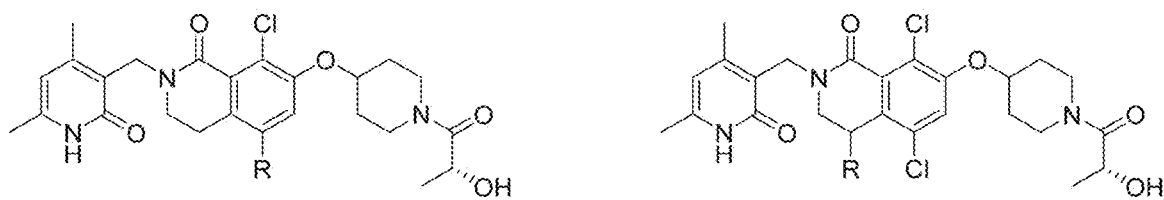
Figure 6F:
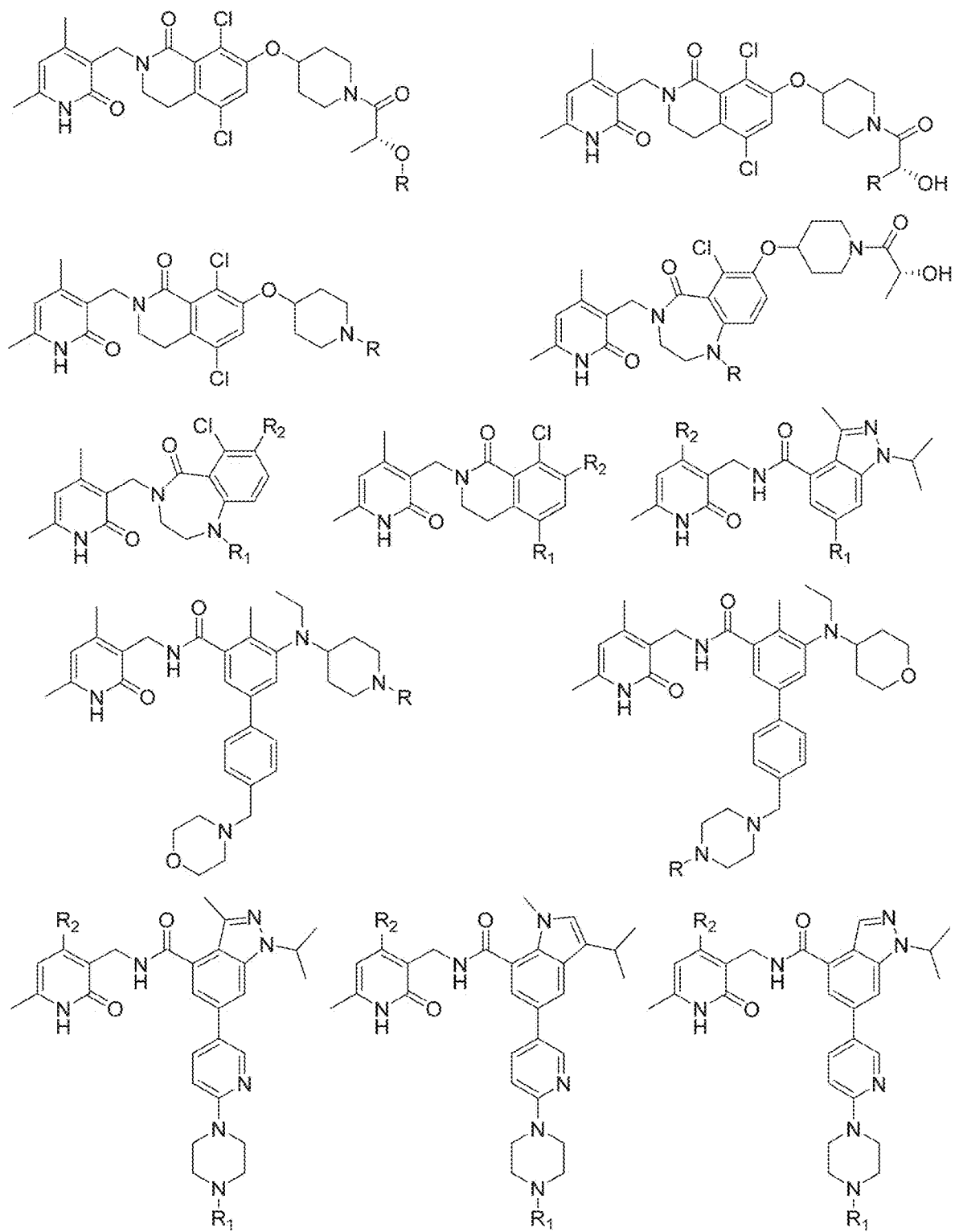
Figure 6G:
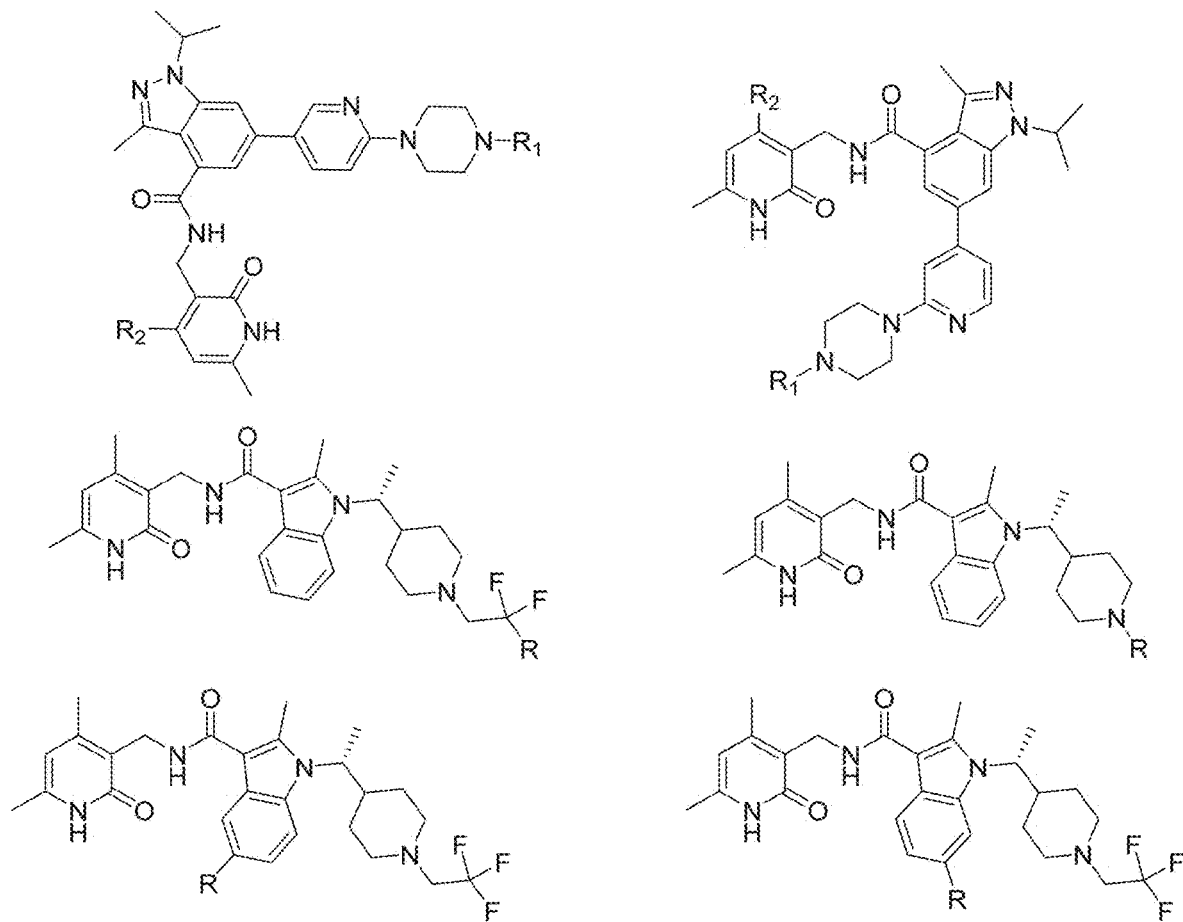

FIG. 6E-6G present examples of EZH2 Targeting Ligands wherein R is the point at which the Linker is attached. For additional examples and related ligands, see, the PDB crystal structure 5ij8 ("Polycomb repressive complex 2 structure with inhibitor reveals a mechanism of activation and drug resistance"); Brooun, A. et al. *Nat Commun* 7: 11384 (2016); the PDB crystal structure 51s6 ("Identification of (R)—N-((4-Methoxy-6-methyl-2-oxo-1,2-dihydropyridin-3-yl) methyl)-2-methyl-1-(1-(1-(2,2,2-trifluoroethyl)piperidin-4-yl)ethyl)-1H-indole-3-carboxamide (CPI-1205), a Potent and Selective Inhibitor of Histone Methyltransferase EZH2, Suitable for Phase I Clinical Trials for B-Cell Lymphomas"); Vaswani, R. G. et al. *J. Med. Chem.* 59: 9928 (2016); and, the PDB crystal structures 5ij8 and 51s6.

Figure 6H:
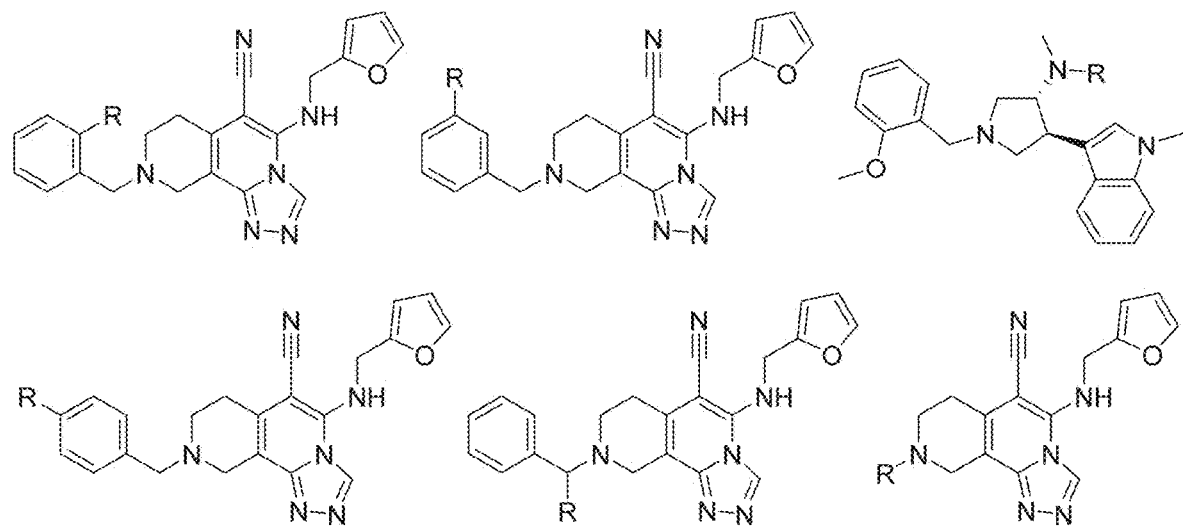
Figure 6I:
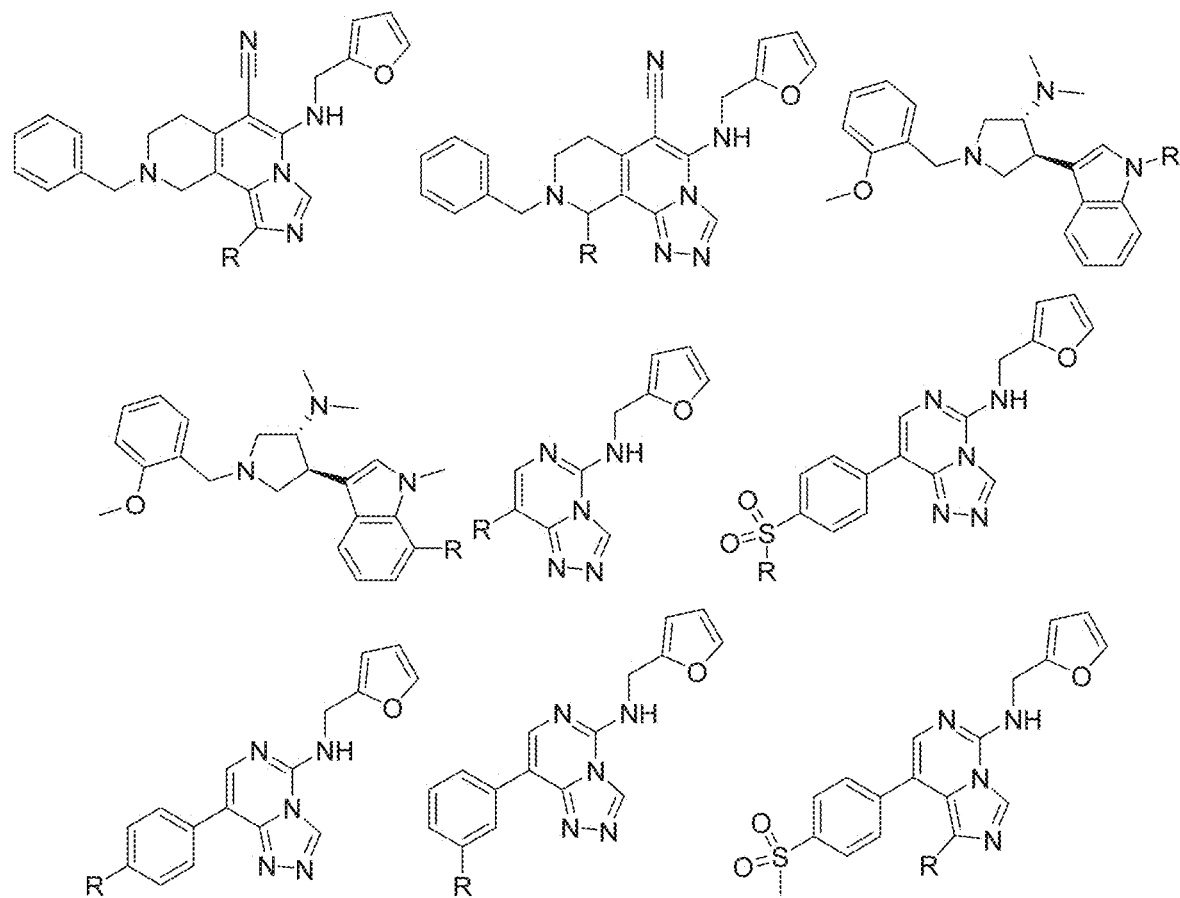

FIG. 6H-6I present examples of EED Targeting Ligands wherein R is the point at which the Linker is attached. For additional examples and related ligands, see, the PDB crystal structures 5h15 and 5h19 ("Discovery and Molecular Basis of a Diverse Set of Polycomb Repressive Complex 2 Inhibitors Recognition by EED"); Li, L. et al. *PLoS ONE* 12: e0169855 (2017); and, the PDB crystal structure 5h19.

Figure 6J:
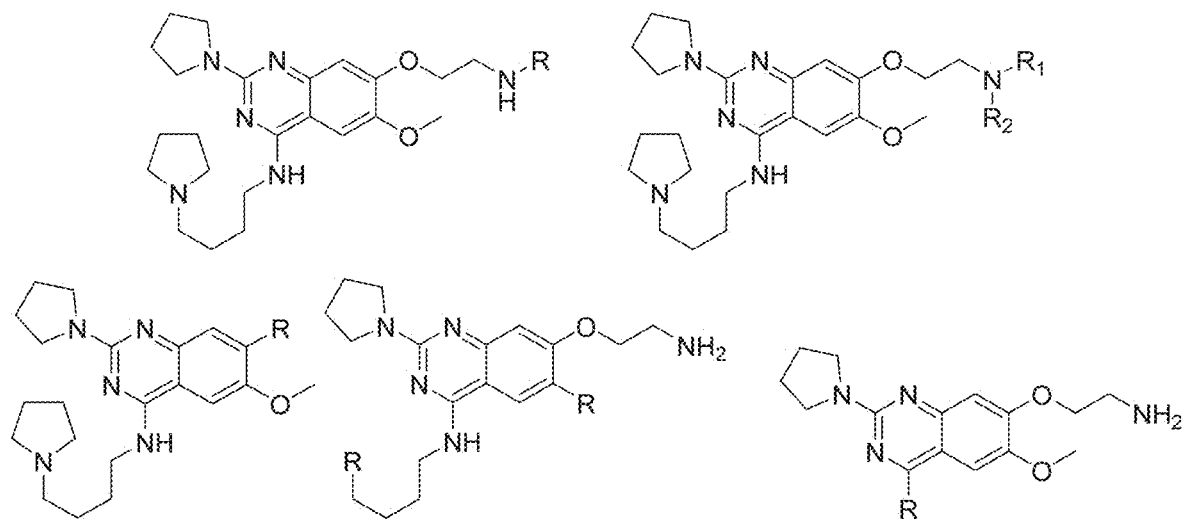

FIG. 6J presents examples of KMT5A (SETD8) Targeting Ligands wherein R is the point at which the Linker is attached. See for example, the PDB crystal structure 5t5g.

Figure 6K:
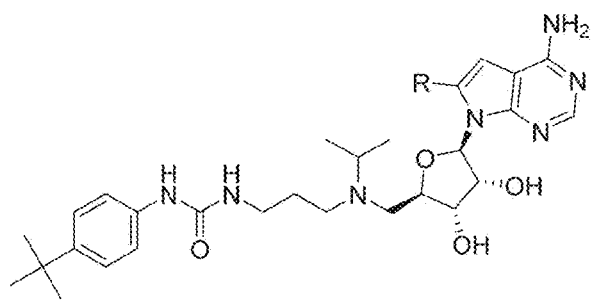
Figure 6K:
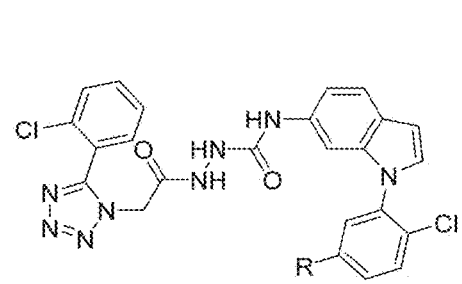
Figure 6K:
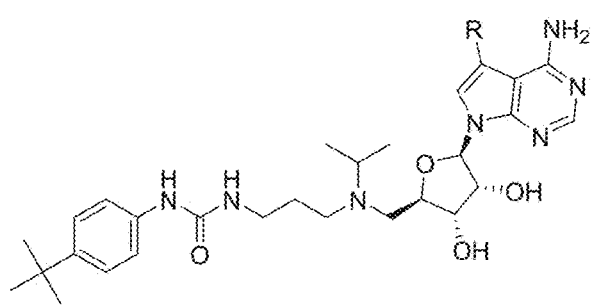
Figure 6K:
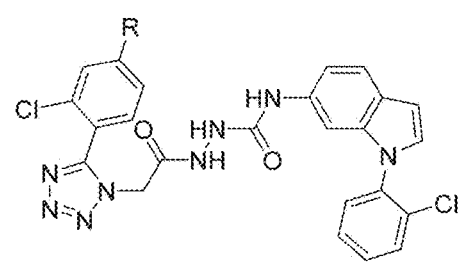
Figure 6K:
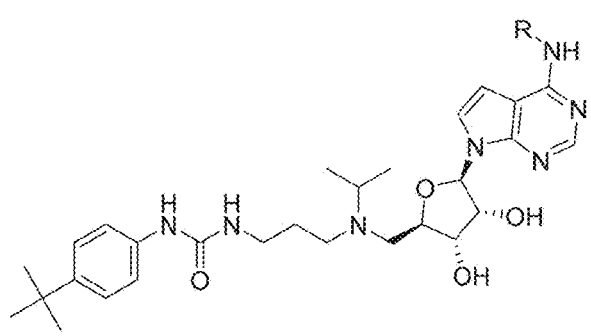
Figure 6K:
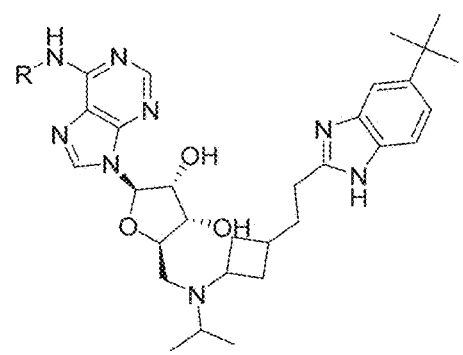
Figure 6K:
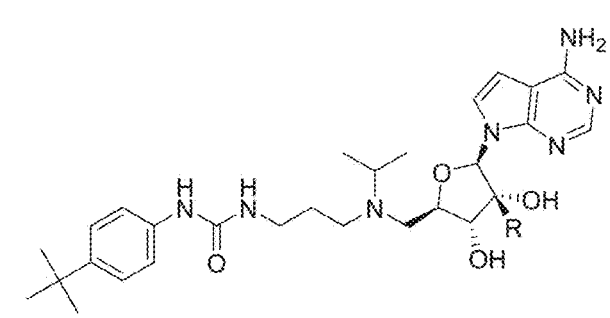
Figure 6K:
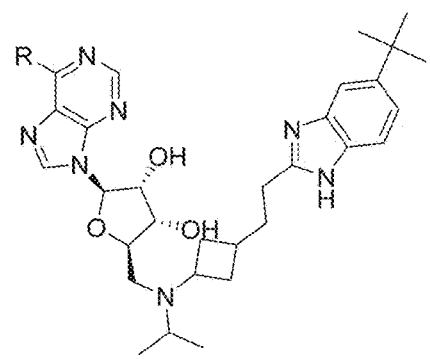
Figure 6L:
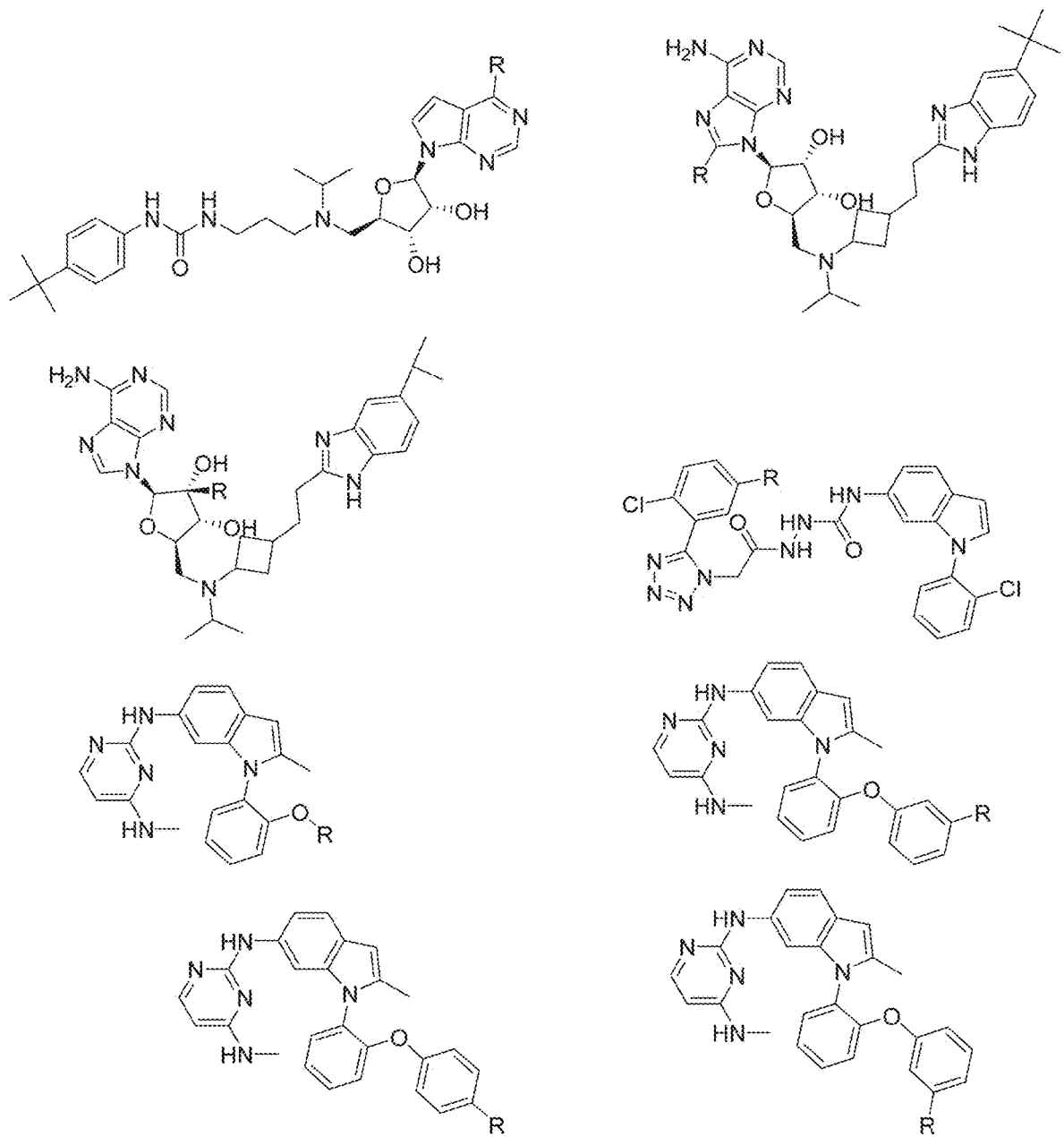

FIG. 6K-6L present examples of DOT1L Targeting Ligands wherein R is the point at which the Linker is attached. For additional examples and related ligands, see, the PDB crystal structure 4eki ("Conformational adaptation drives potent, selective and durable inhibition of the human protein methyltransferase DOT1L"); Basavapathruni, A. et al. *Chem. Biol. Drug Des.* 80: 971 (2012); the PDB crystal structure 4hra ("Potent inhibition of DOT1L as treatment of MLL-fusion leukemia"); Daigle, S. R. et al. *Blood* 122: 1017 (2013); the PDB crystal structure 5dry ("Discovery of Novel Dot1L Inhibitors through a Structure-Based Fragmentation Approach") Chen, C. et al. *ACS Med. Chem. Lett.* 7: 735 (2016); the PDB crystal structure 5dt2 ("Discovery of Novel Dot1L Inhibitors through a Structure-Based Fragmentation Approach"); and, Chen, C. et al. *ACS Med. Chem. Lett.* 7: 735 (2016).

Figure 6M:
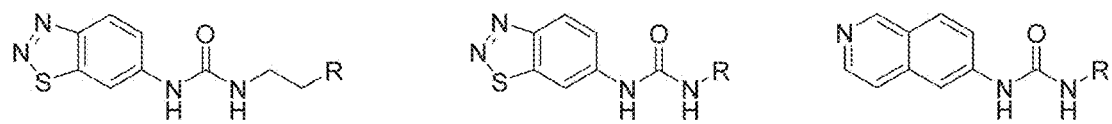
Figure 6N:
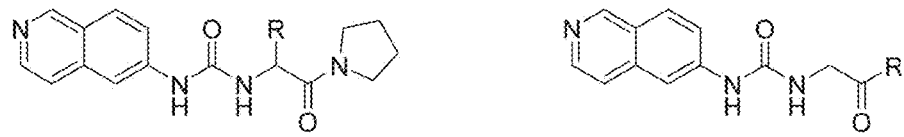

FIG. 6M-6N present examples of PRMT3 Targeting Ligands wherein R is the point at which the Linker is attached. For additional examples and related ligands, see, the PDB crystal structure 3smq ("An allosteric inhibitor of protein arginine methyltransferase 3"); Siarheyeva, A. et al.

*Structure* 20: 1425 (2012); PDB crystal structure 4ryl ("A Potent, Selective and Cell-Active Allosteric Inhibitor of Protein Arginine Methyltransferase 3 (PRMT3)"); and Kaniskan, H. U. et al. *Angew. Chem. Int. Ed. Engl.* 54: 5166 (2015).

Figure 6O:
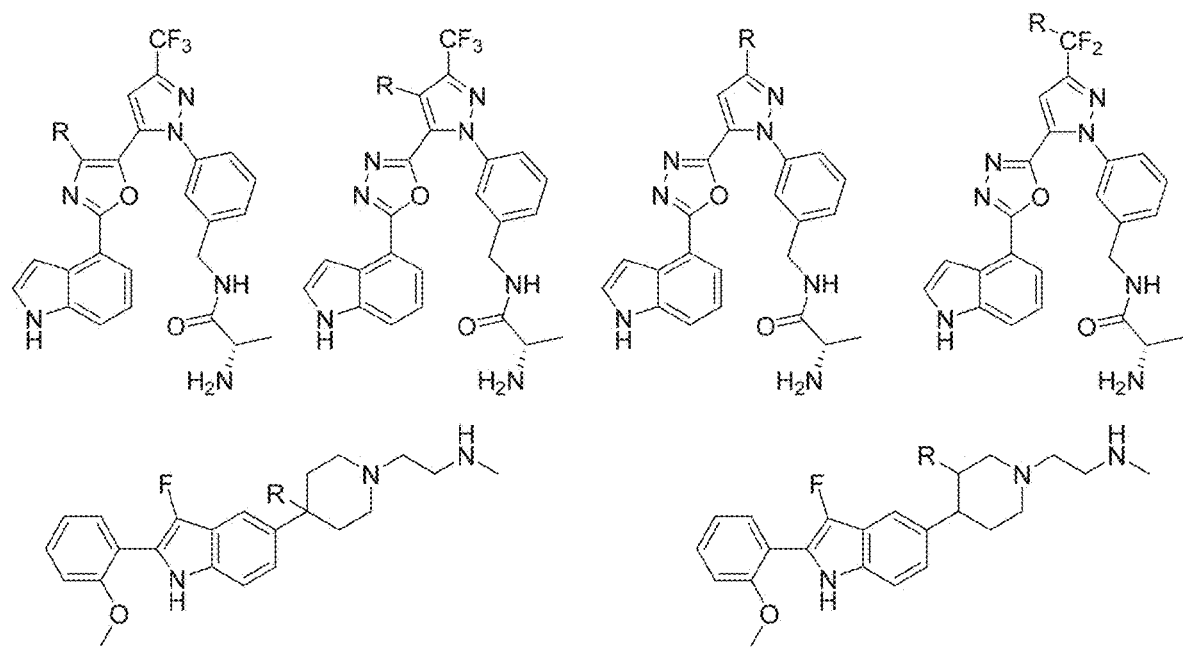

FIG. 6O presents examples of CARM1 (PRMT4) Targeting Ligands wherein R is the point at which the Linker is attached. For additional examples and related ligands, see, the PDB crystal structures 2ylx and 2ylw and related ligands described in "Structural Basis for Carm1 Inhibition by Indole and Pyrazole Inhibitors." Sack, J. S. et al. *Biochem. J.* 436: 331 (2011).

Figure 6P:
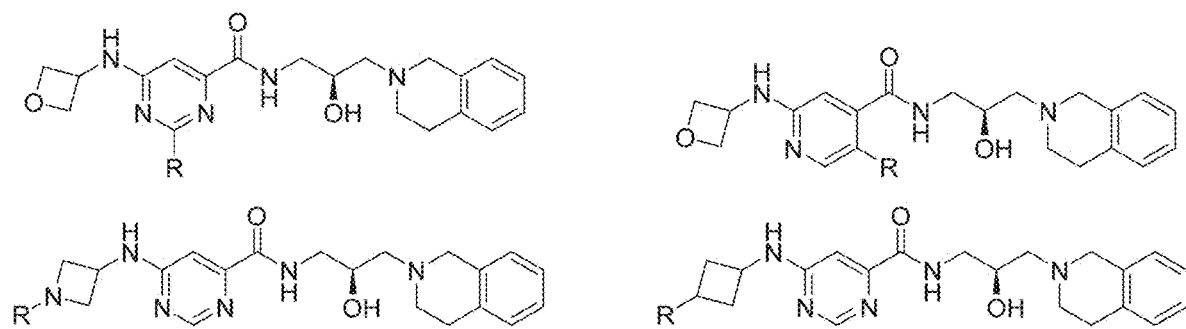

FIG. 6P presents examples of PRMT5 Targeting Ligands wherein R is the point at which the Linker is attached. For additional examples and related ligands, see, the PDB crystal structure 4x61 and related ligands described in "A selective inhibitor of PRMT5 with in vivo and in vitro potency in MCL models". Chan-Penebre, E. *Nat. Chem. Biol.* 11: 432 (2015).

Figure 6Q:
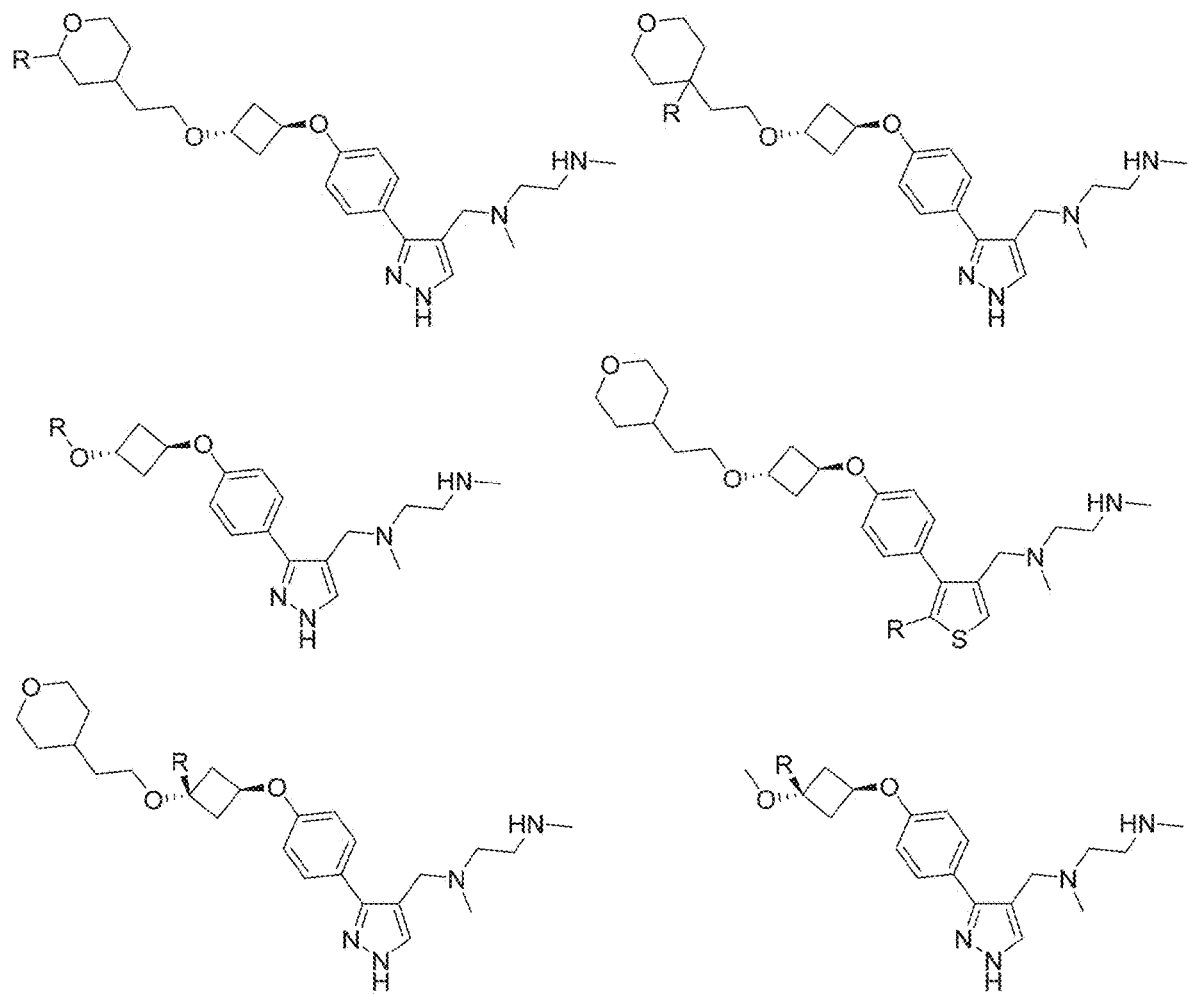

FIG. 6Q presents examples of PRMT6 Targeting Ligands wherein R is the point at which the Linker is attached. For additional examples and related ligands, see, the PDB crystal structure 4y30 and related ligands described in "Aryl Pyrazoles as Potent Inhibitors of Arginine Methyltransferases: Identification of the First PRMT6 Tool Compound". Mitchell, L. H. et al. *ACS Med. Chem. Lett.* 6: 655 (2015).

Figure 6R:
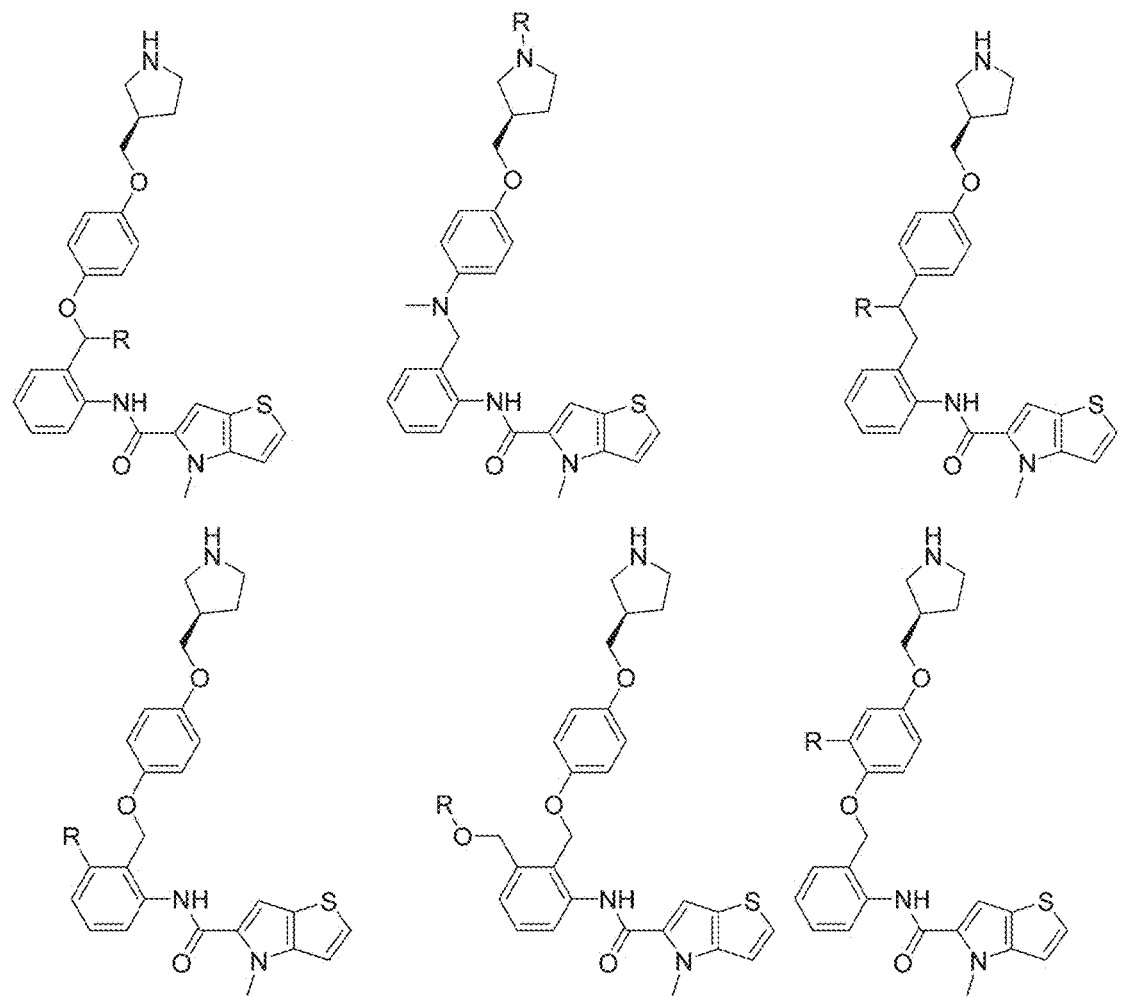

FIG. 6R presents examples of LSD1 (KDM1A) Targeting Ligands wherein R is the point at which the Linker is attached. For additional examples and related ligands, see, the PDB crystal structure 5lgu and related ligands described in "Thieno[3,2-b]pyrrole-5-carboxamides as New Reversible Inhibitors of Histone Lysine Demethylase KDM1A/LSD1. Part 2: Structure-Based Drug Design and Structure-Activity Relationship". Vianello, P. et al. *J. Med. Chem.* 60: 1693 (2017).

Figure 6S:
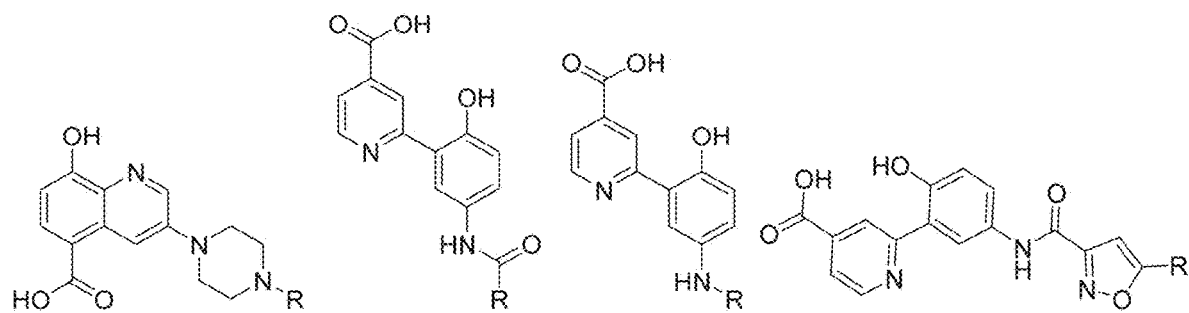
Figure 6T:
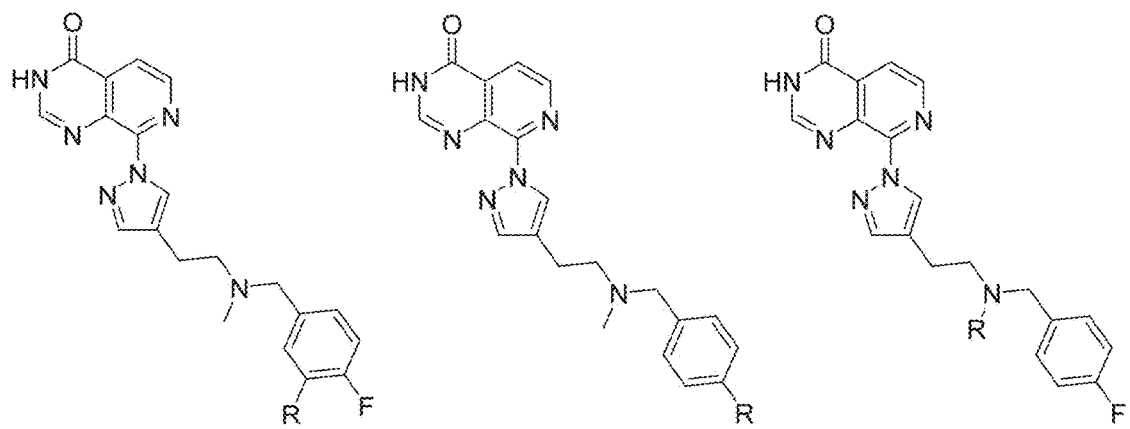

FIG. 6S-6T present examples of KDM4 Targeting Ligands wherein R is the point at which the Linker is attached. For additional examples and related ligands, see, the PDB crystal structure 3rvh; the PDB crystal structure 5a7p and related ligands described in "Docking and Linking of Fragments to Discover Jumonji Histone Demethylase Inhibitors." Korczynska, M., et al. *J. Med. Chem.* 59: 1580 (2016); and, the PDB crystal structure 3f3c and related ligands described in "8-Substituted Pyrido[3,4-d]pyrimidin-4(3H)-one Derivatives As Potent, Cell Permeable, KDM4 (JMJD2) and KDM5 (JARID1) Histone Lysine Demethylase Inhibitors." Bavetsias, V. et al. *J. Med. Chem.* 59: 1388 (2016).

Figure 6U:
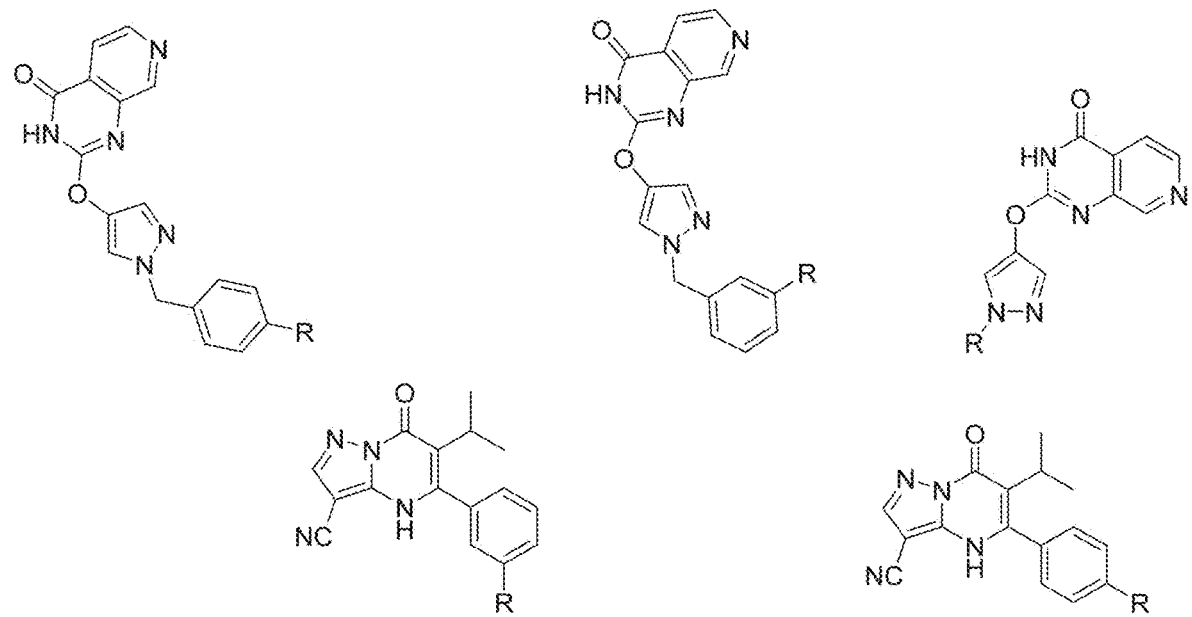

FIG. 6U presents examples of KDM5 Targeting Ligands wherein R is the point at which the Linker is attached. For additional examples and related ligands, see, the PDB crystal structure 3fun and related ligands described in "Structural Analysis of Human Kdm5B Guides Histone Demethylase Inhibitor Development". Johansson, C. et al. *Nat. Chem. Biol.* 12: 539 (2016) and the PDB crystal structure 5ceh and related ligands described in "An inhibitor of KDM5 demethylases reduces survival of drug-tolerant cancer cells". Vinogradova, M. et al. *Nat. Chem. Biol.* 12: 531 (2016).

Figure 6V:
Figure 6W:
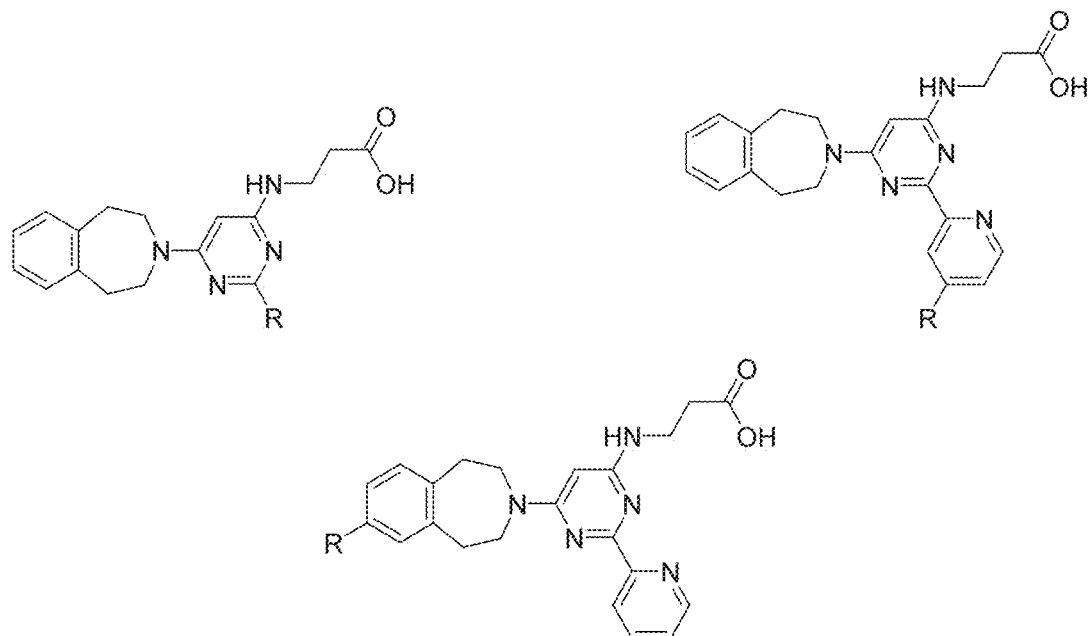

FIG. 6V-6W present examples of KDM6 Targeting Ligands wherein R is the point at which the Linker is attached. For additional examples and related ligands, see, the PDB crystal structure 4ask and related ligands described in "A Selective Jumonji H3K27 Demethylase Inhibitor Modulates the Proinflammatory Macrophage Response". Kruidenier, L. et al. *Nature* 488: 404 (2012).

Figure 6X:
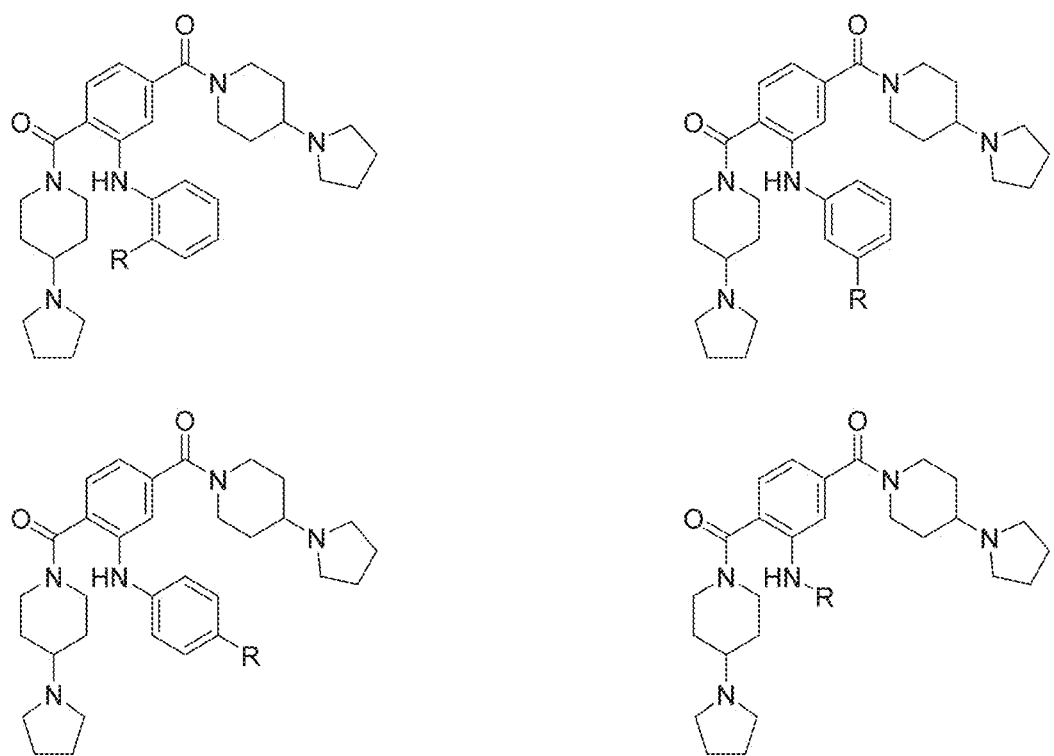

FIG. 6X presents examples of L3MBTL3 targeting ligands wherein R is the point at which the Linker is attached. See for example, the PDB crystal structure 4fl6.

Figure 6Y:
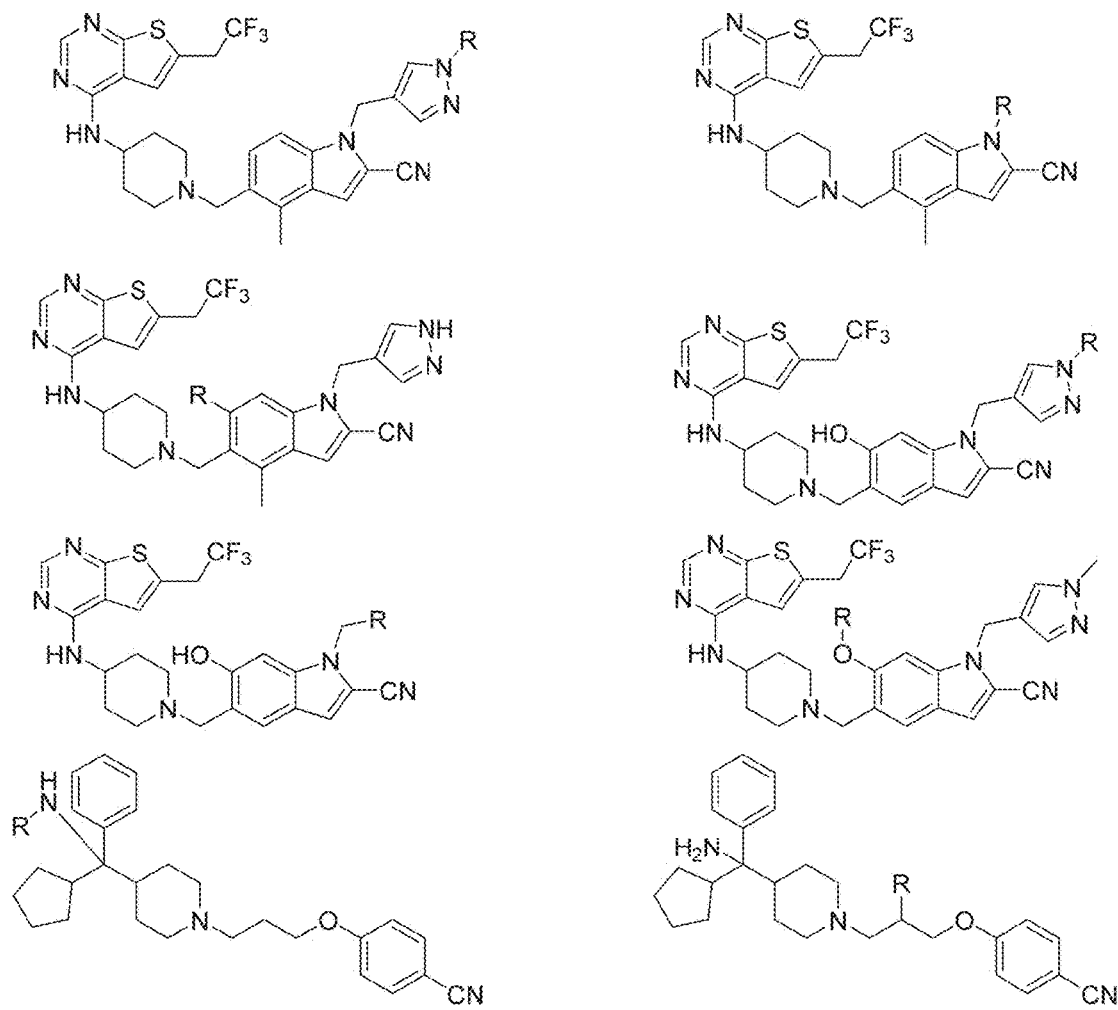

FIG. 6Y presents examples of Menin Targeting Ligands wherein R is the point at which the Linker is attached. For additional examples and related ligands, see, the PDB crystal structure 4x5y and related ligands described in "Pharmacologic Inhibition of the Menin-MLL Interaction Blocks Progression of MLL Leukemia In Vivo" Borkin, D. et al. *Cancer Cell* 27: 589 (2015) and the PDB crystal structure 4og8 and related ligands described in "High-Affinity Small-Molecule Inhibitors of the Menin-Mixed Lineage Leukemia (MLL) Interaction Closely Mimic a Natural Protein-Protein Interaction" He, S. et al. *J. Med. Chem.* 57: 1543 (2014).

Figure 6Z:
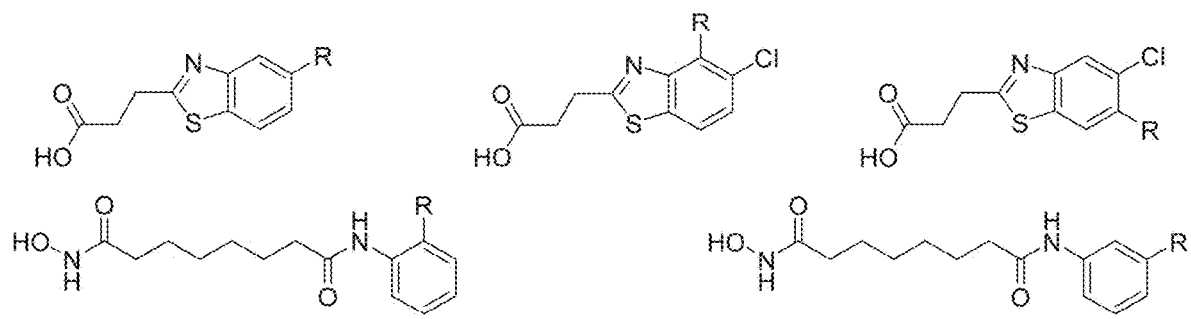
Figure 6A:
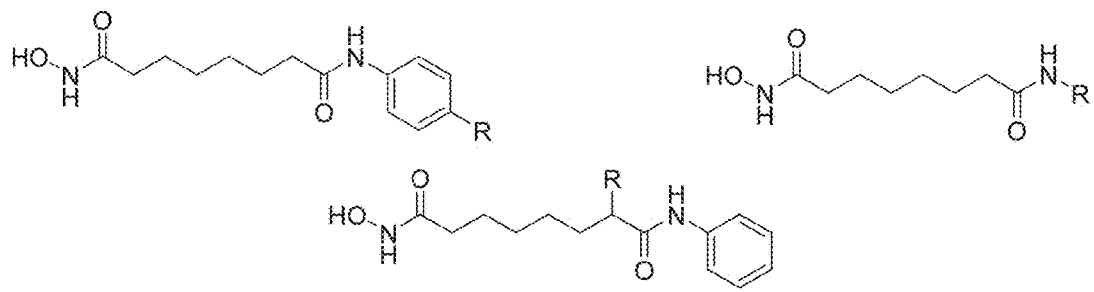
Figure 6B:
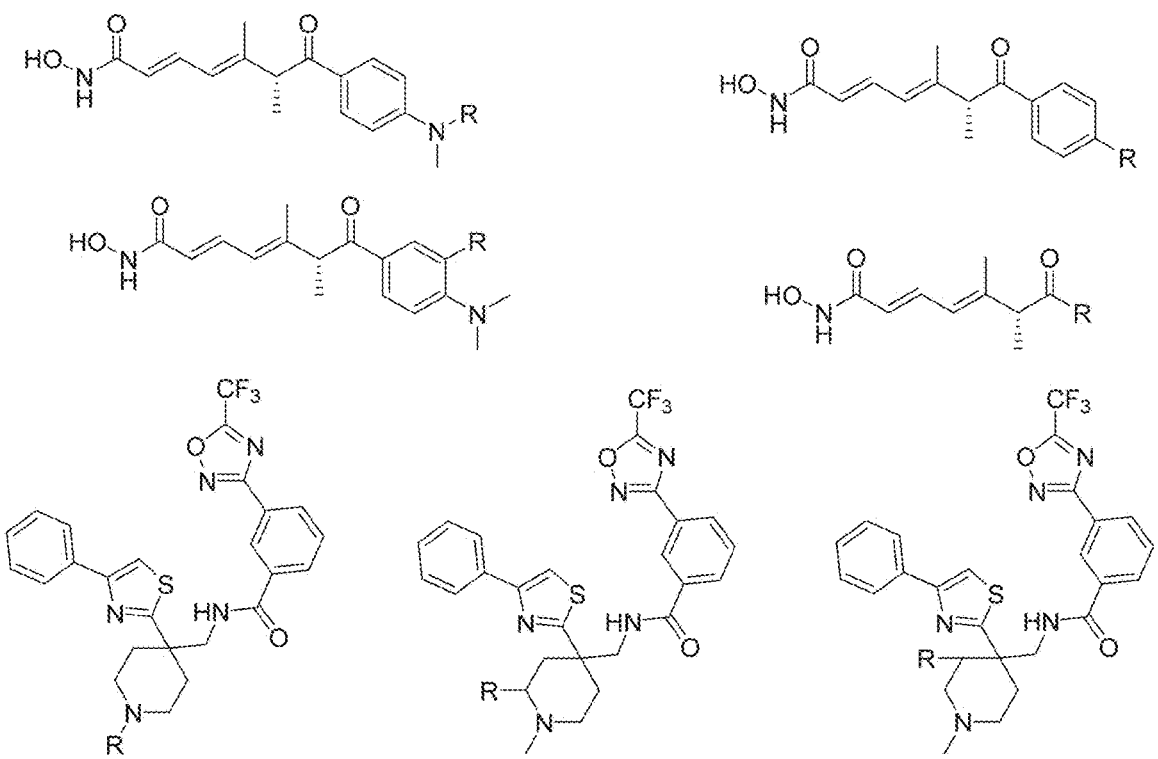

FIG. 6Z-6AA present examples of HDAC6 Targeting Ligands wherein R is the point at which the Linker is attached. See for example, the PDB crystal structures 5kh3 and 5eei.

FIG. 6BB presents examples of HDAC7 Targeting Ligands wherein R is the point at which the Linker is attached. For additional examples and related ligands, see, the PDB crystal structure 3c10 and related ligands described in "Human HDAC7 harbors a class IIa histone deacetylase-specific zinc binding motif and cryptic deacetylase activity." Schuetz, A. et al. *J. Biol. Chem.* 283: 11355 (2008) and the PDB crystal structure PDB 3zns and related ligands described in "Selective Class Iia Histone Deacetylase Inhibition Via a Non-Chelating Zinc Binding Group". Lobera, M. et al. *Nat. Chem. Biol.* 9: 319 (2013).

Figure 7A:
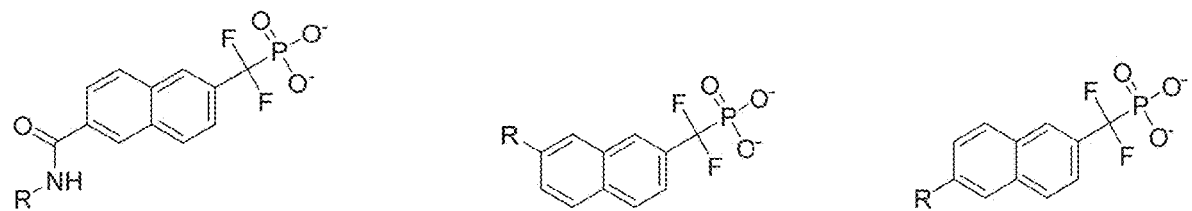
Figure 7B:
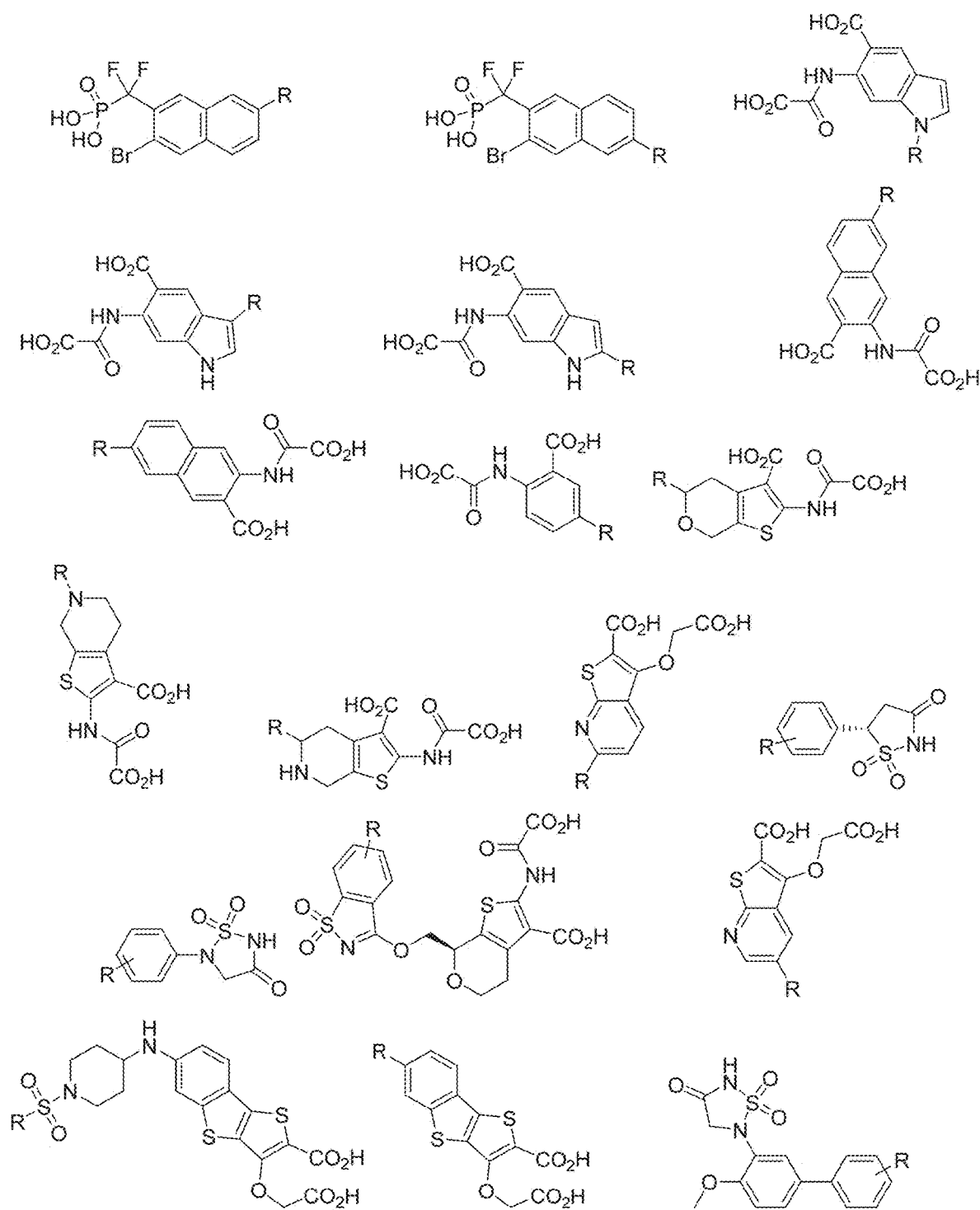
Figure 7C:
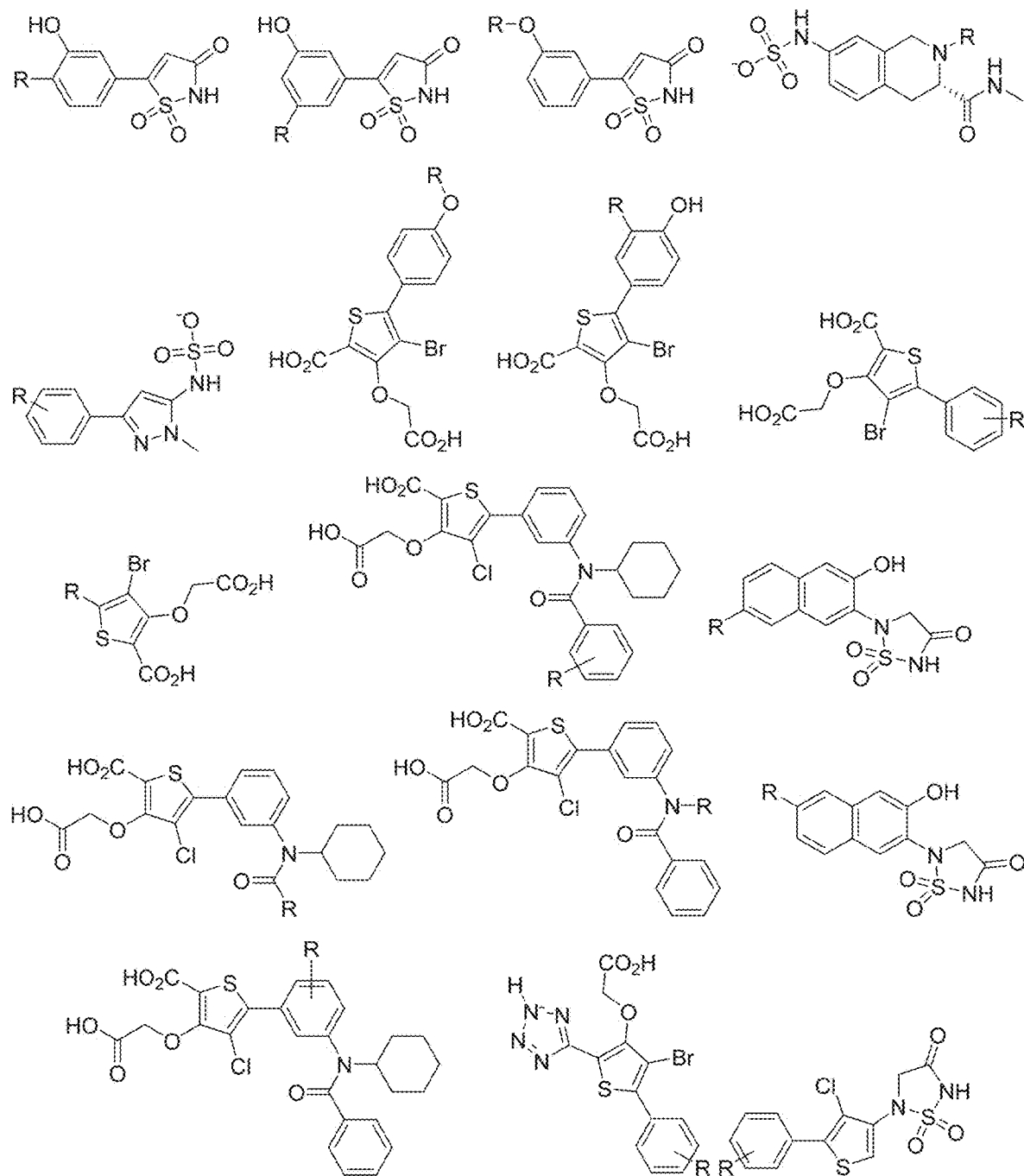

FIG. 7A-7C present examples of Protein Tyrosine Phosphatase, Non-Receptor Type 1, PTP1B Targeting Ligands wherein R is the point at which the Linker is attached. For additional examples and related ligands, see, the PDB crystal structure 1bzj described in "Structural basis for inhibition of the protein tyrosine phosphatase 1B by phosphotyrosine peptide mimetics" Groves, M. R. et al. *Biochemistry* 37: 17773-17783 (1998); the PDB crystal structure 3cwe described in "Discovery of [(3-bromo-7-cyano-2-naphthyl)(difluoro)methyl]phosphonic acid, a potent and orally active small molecule PTP1B inhibitor". Han Y, *Bioorg Med Chem Lett.* 18:3200-5 (2008); the PDB crystal structures 2azr and 2b07 described in "Bicyclic and tricyclic thiophenes as protein tyrosine phosphatase 1B inhibitors." Moretto, A. F. et al. *Bioorg. Med. Chem.* 14: 2162-2177 (2006); the PDB crystal structures PDB 2bgd, 2bge, 2cm7, 2cm8, 2cma, 2cmb, 2cmc described in ""Structure-Based Design of Protein Tyrosine Phosphatase-1B Inhibitors". Black, E. et al. *Bioorg. Med. Chem. Lett.* 15: 2503 (2005) and "Structural Basis for Inhibition of Protein-Tyrosine Phosphatase 1B by Isothiazolidinone Heterocyclic Phosphonate Mimetics." Ala, P. J. et al. *J. Biol. Chem.* 281: 32784 (2006); the PDB crystal structures 2f6t and 2f6w described in "1,2,3,4-Tetrahydroisoquinolinyl sulfamic acids as phosphatase PTP1B inhibitors". Klopfenstein, S. R. et al. *Bioorg. Med. Chem. Lett.* 16: 1574-1578 (2006); the PDB crystal structures 2h4g, 2h4k, 2hbl described in ""Monocyclic thiophenes as protein tyrosine phosphatase 1B inhibitors: Capturing interactions with Asp48." Wan, Z. K. et al. *Bioorg. Med. Chem. Lett.* 16: 4941-4945 (2006); the PDB crystal structures 2zn7 described in "Structure-based optimization of protein tyrosine phosphatase-1 B inhibitors: capturing interactions with arginine 24". Wan, Z. K. et al. *Chem Med Chem.* 3:1525-9 (2008); the PDB crystal structure 2nt7, 2nta described in "Probing acid replacements of thiophene PTP1B inhibitors." Wan, Z. K. et al. *Bioorg. Med. Chem. Lett.* 17: 2913-2920 (2007); and, WO 2008148744 A1 assigned to Novartis AG titled "Thiadiazole derivatives as antidiabetic agents". See also, the PDB crystal structures 1c84, 1c84, 1c85, 1c86, 1c88, 1l8g and described in ""2-(oxalylamino)-benzoic acid is a general, competitive inhibitor of protein-tyrosine phosphatases". Andersen, H. S. et al. *J. Biol. Chem.* 275: 7101-7108 (2000); "Structure-based design of a low molecular weight, nonphosphorus, nonpeptide, and highly selective inhibitor of protein-tyrosine phosphatase 1B." Iversen, L. F. et al. *J. Biol. Chem.* 275: 10300-10307 (2000); and, "Steric hindrance as a basis for structure-based design of selective inhibitors of protein-tyrosine phosphatases". Iversen, L. F. et al. *Biochemistry* 40: 14812-14820 (2001).

Figure 7D:
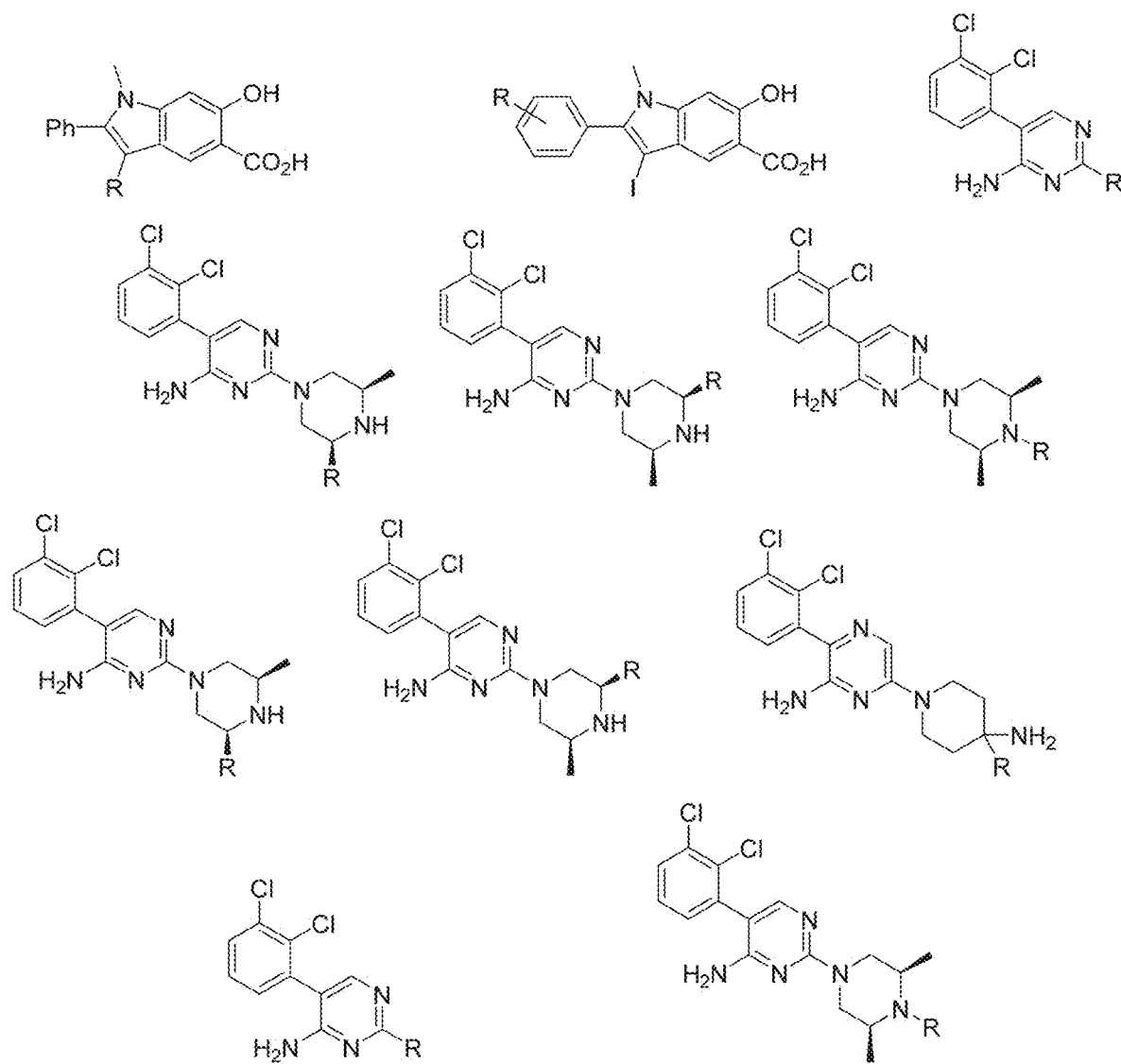

FIG. 7D presents examples of Tyrosine-protein phosphatase non-receptor type 11, SHP2 Targeting Ligands wherein R is the point at which the Linker is attached. For additional examples and related ligands, see, the crystal structures PDB 4pvg and 3o5x and described in "Salicylic acid based small molecule inhibitor for the oncogenic Src homology-2 domain containing protein tyrosine phosphatase-2 (SHP2)." Zhang, X. et al. *J. Med. Chem.* 53: 2482-2493 (2010); and, the crystal structure PDB 5ehr and related ligands described in "Allosteric Inhibition of SHP2: Identification of a Potent, Selective, and Orally Efficacious Phosphatase Inhibitor." Garcia Fortanet, J. et al. *J. Med. Chem.* 59: 7773-7782 (2016). Also, see the crystal structure PDB 5ehr described in "Allosteric Inhibition of SHP2: Identification of a Potent, Selective, and Orally Efficacious Phosphatase Inhibitor." Garcia Fortanet, J. et al. *J. Med. Chem.* 59: 7773-7782 (2016) and "Allosteric inhibition of SHP2 phosphatase inhibits cancers driven by receptor tyrosine kinases." Chen, Y. P. et al. *Nature* 535: 148-152 (2016).

Figure 7E:
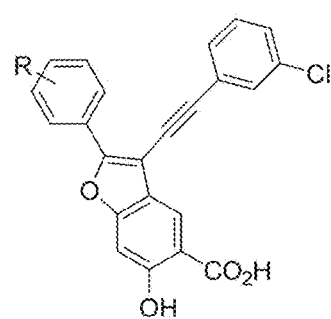
Figure 7E:
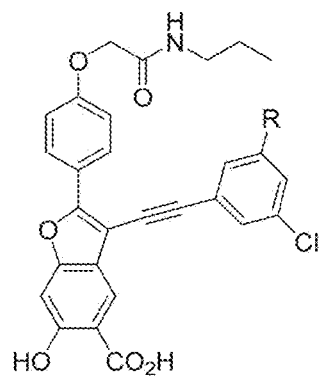
Figure 7E:
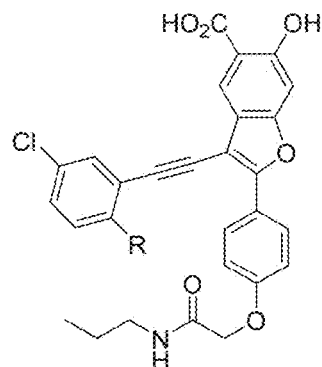
Figure 7E:
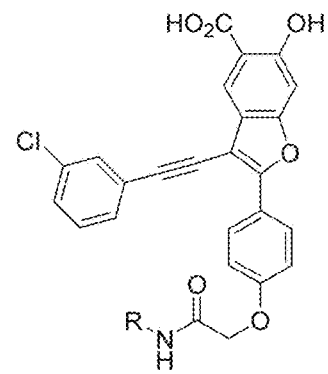

FIG. 7E presents examples of Tyrosine-protein phosphatase non-receptor type 22 Targeting Ligands wherein R is the point at which the Linker is attached. For additional examples and related ligands, see the crystal structure PDB 4j 51 described in "A Potent and Selective Small-Molecule Inhibitor for the Lymphoid-Specific Tyrosine Phosphatase (LYP), a Target Associated with Autoimmune Diseases." He, Y. et al. *J. Med. Chem.* 56: 4990-5008 (2013).

Figure 7F:
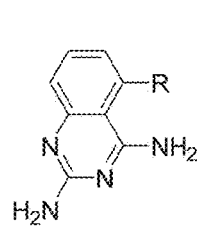
Figure 7F:
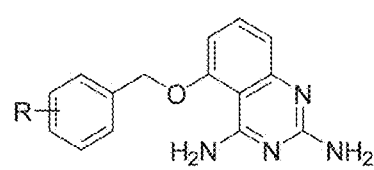
Figure 7F:
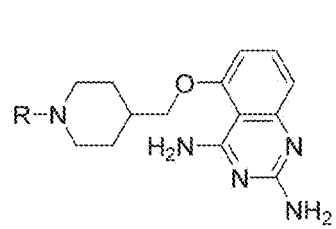
Figure 7F:
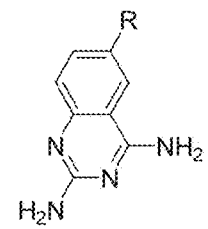

FIG. 7F presents examples of Scavenger mRNA-decapping enzyme DcpS Targeting Ligands wherein R is the point at which the Linker is attached. For additional examples and related ligands, see, the crystal structures PDB 3b17, 3b19, 3bla, 4qde, 4qdv, 4qeb and related ligands described in "DcpS as a therapeutic target for spinal muscular atrophy." Singh, J. et al. *ACS Chem. Biol.* 3: 711-722 (2008).

Figure 8A:
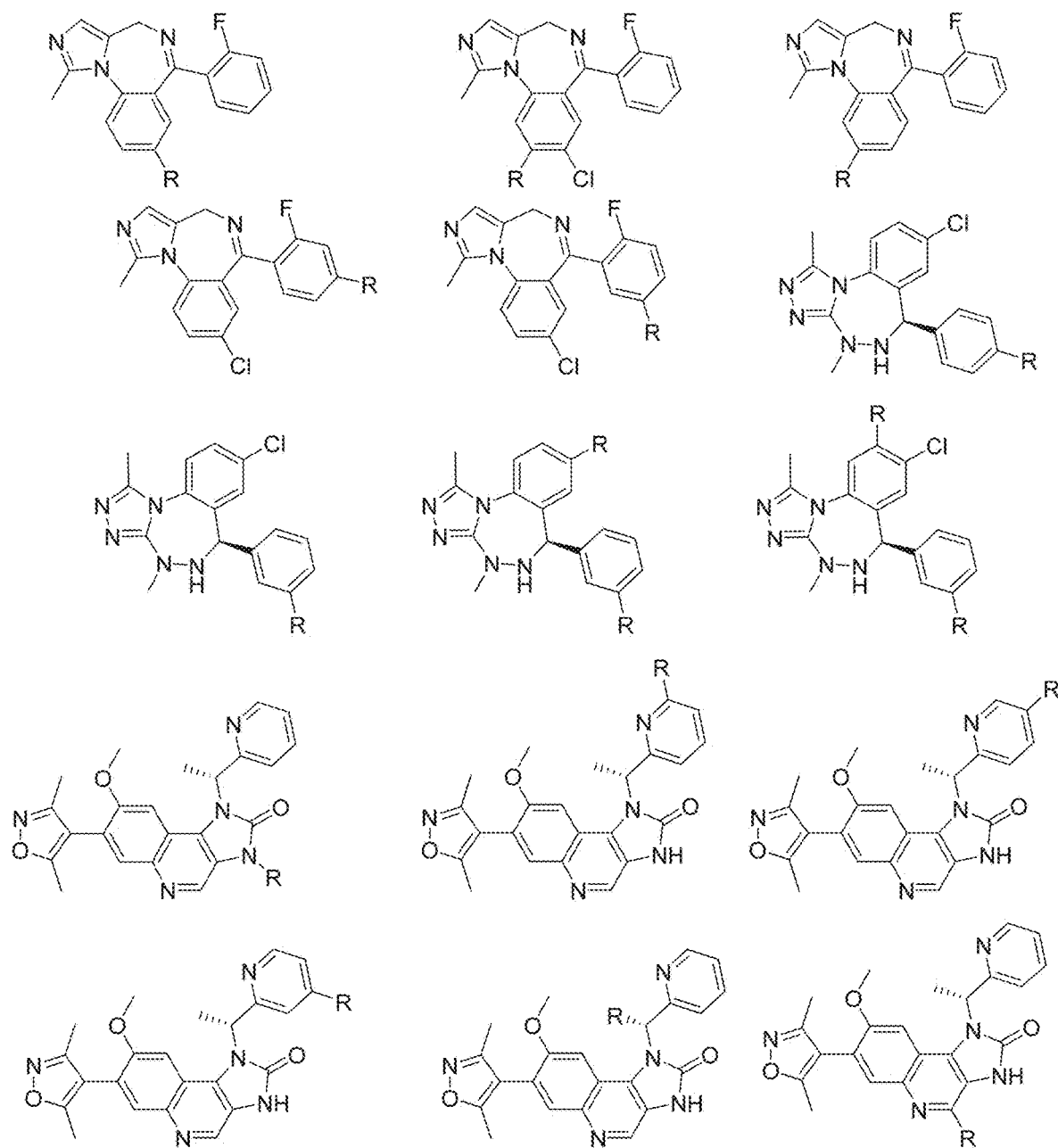
Figure 8B:
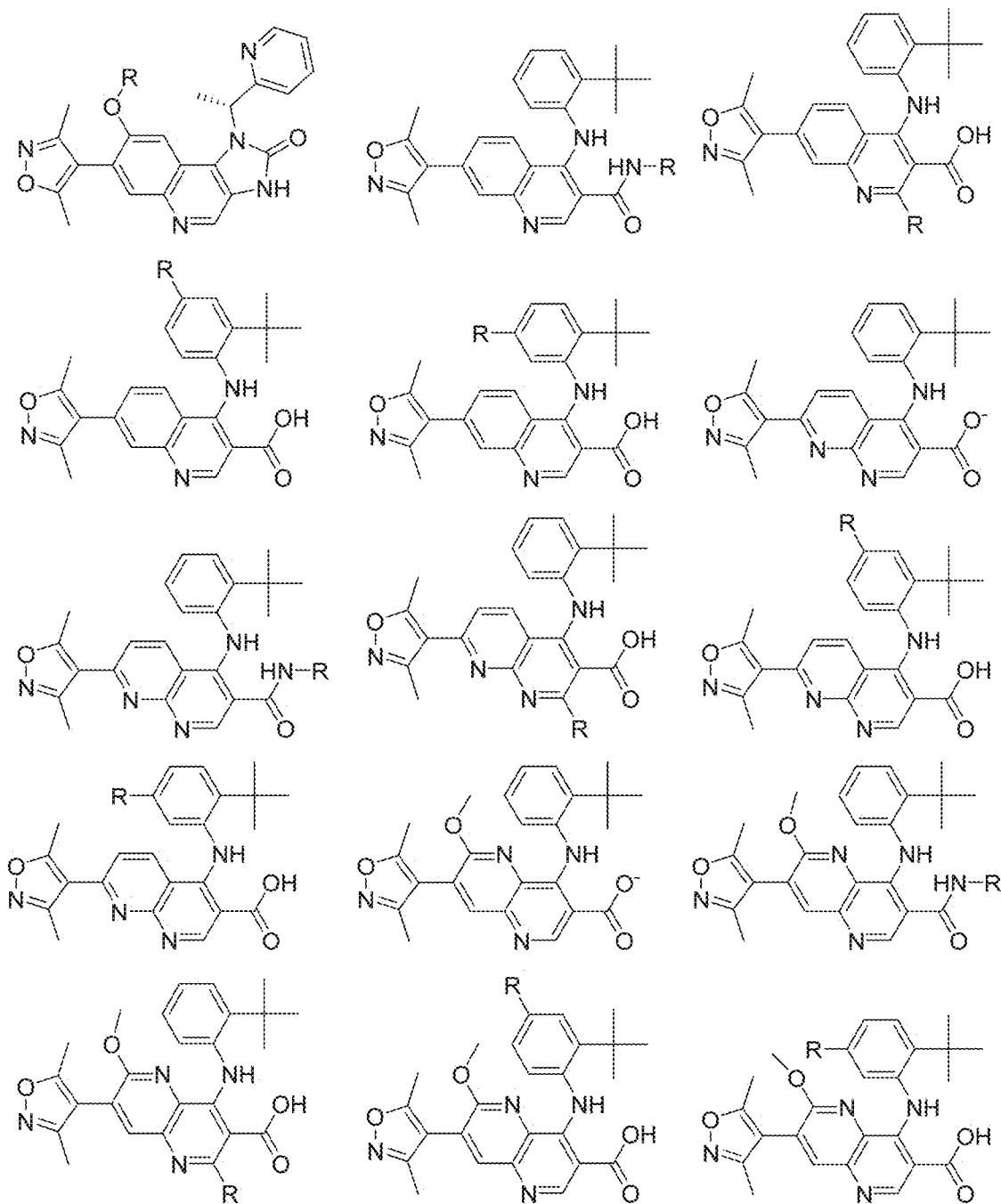
Figure 8C:
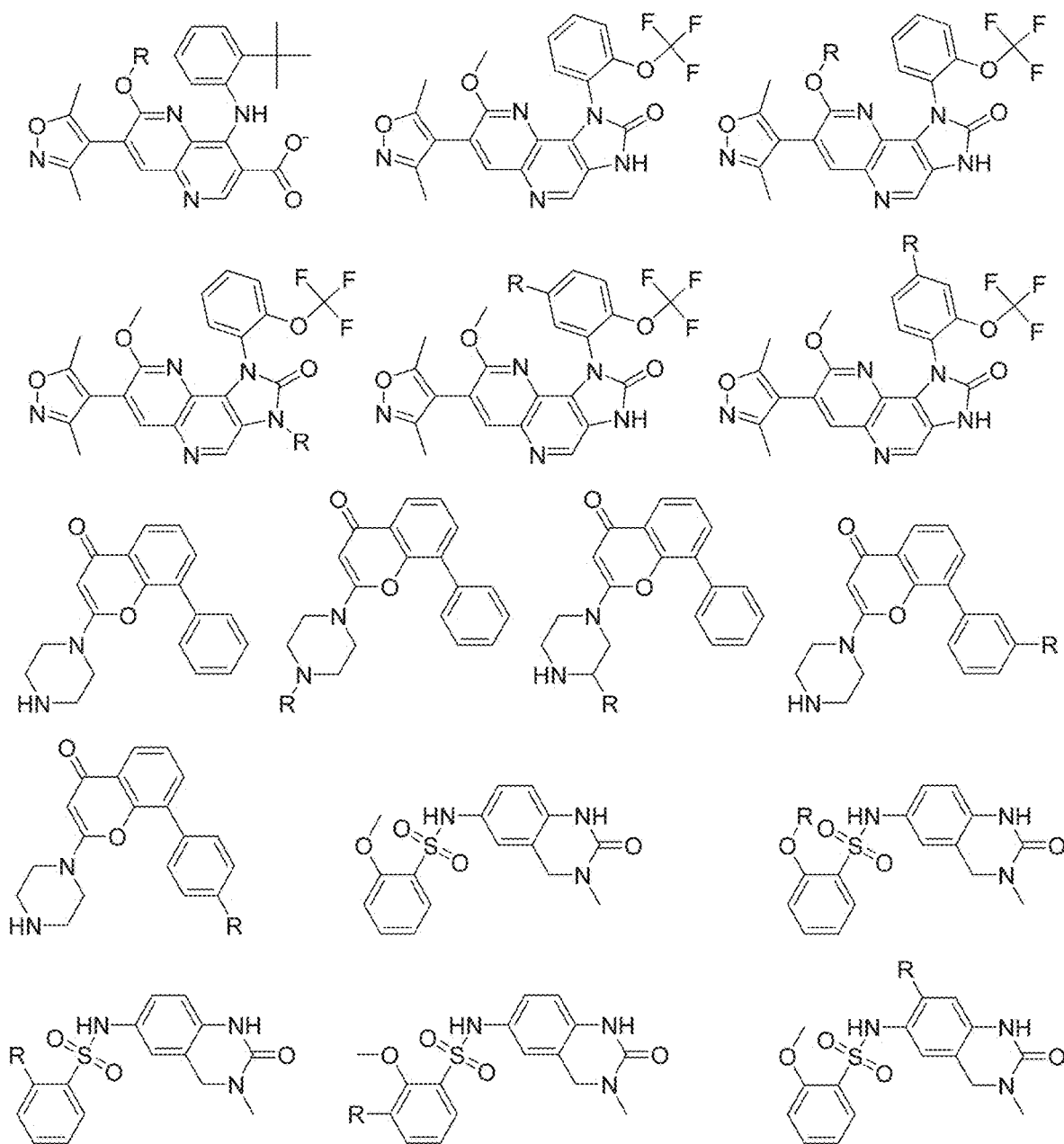
Figure 8D:
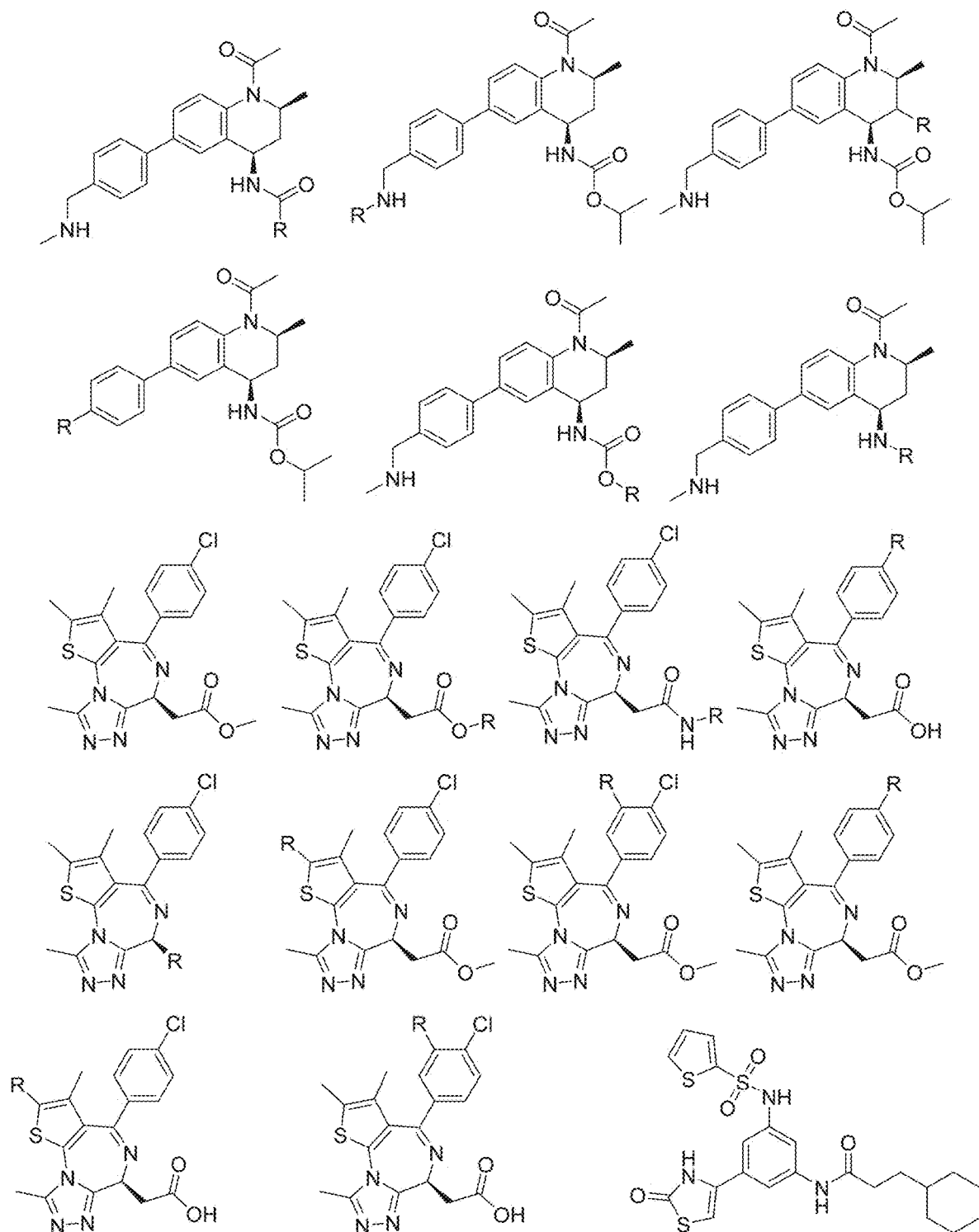
Figure 8E:
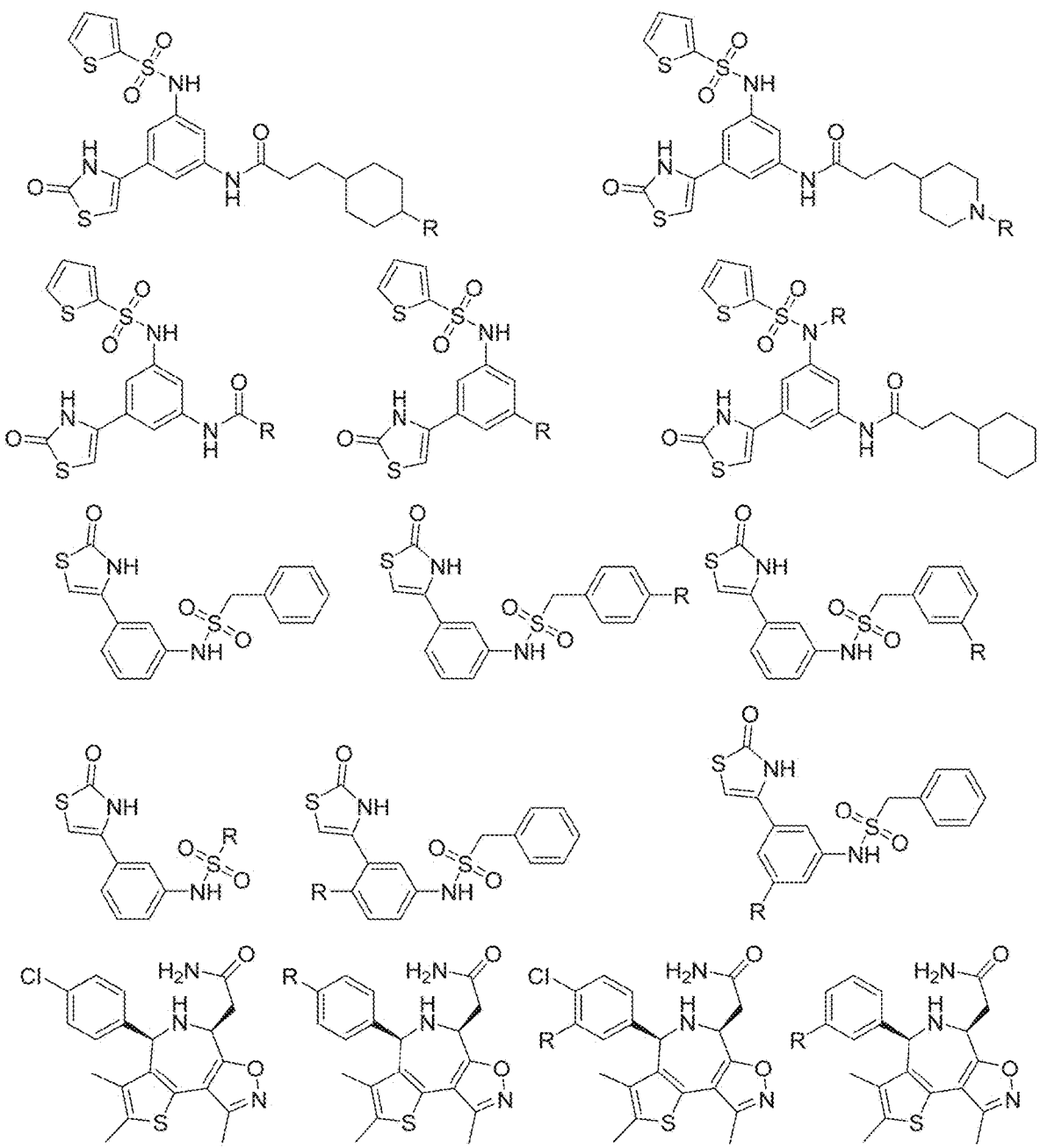
Figure 8F:
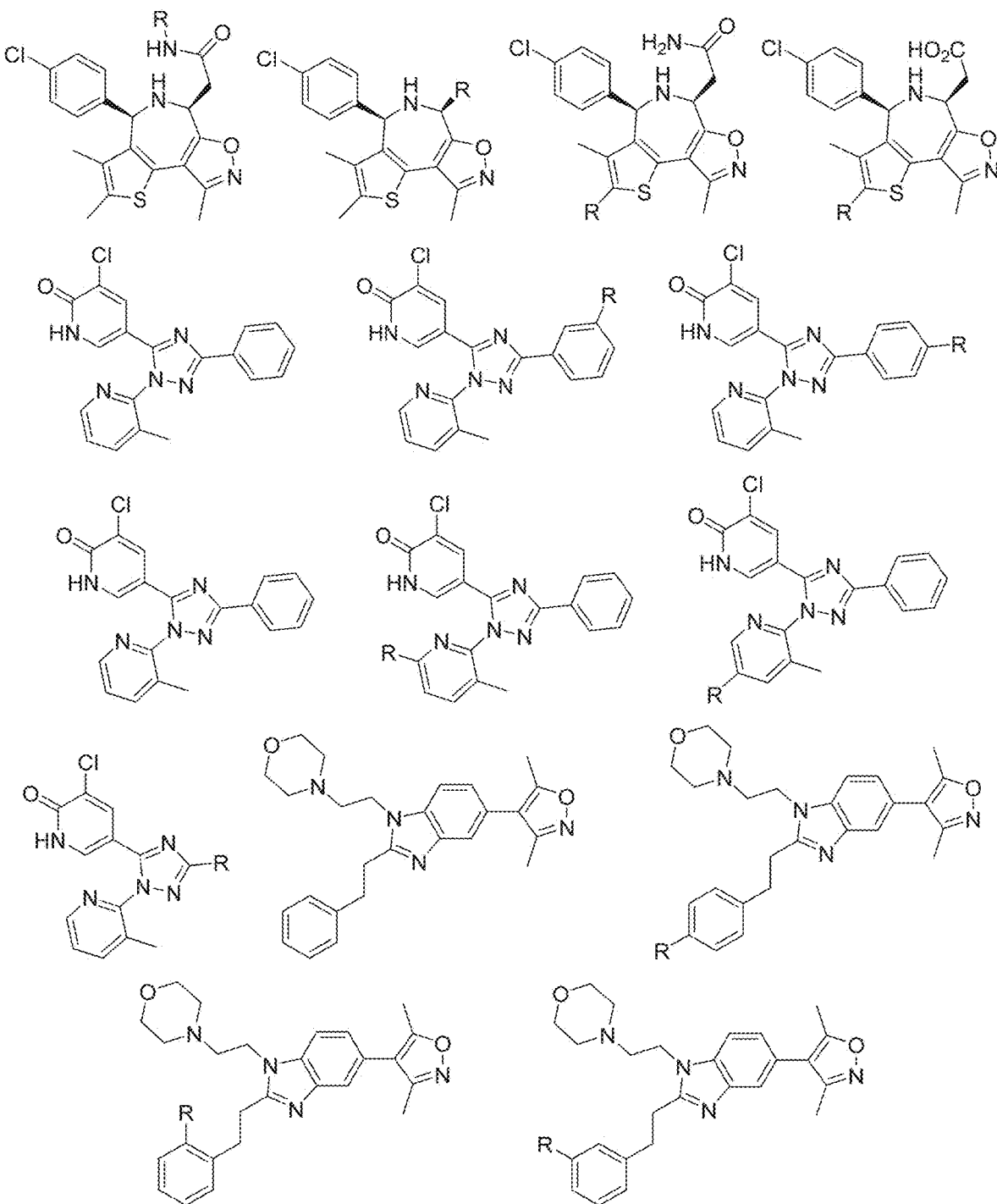
Figure 8G:
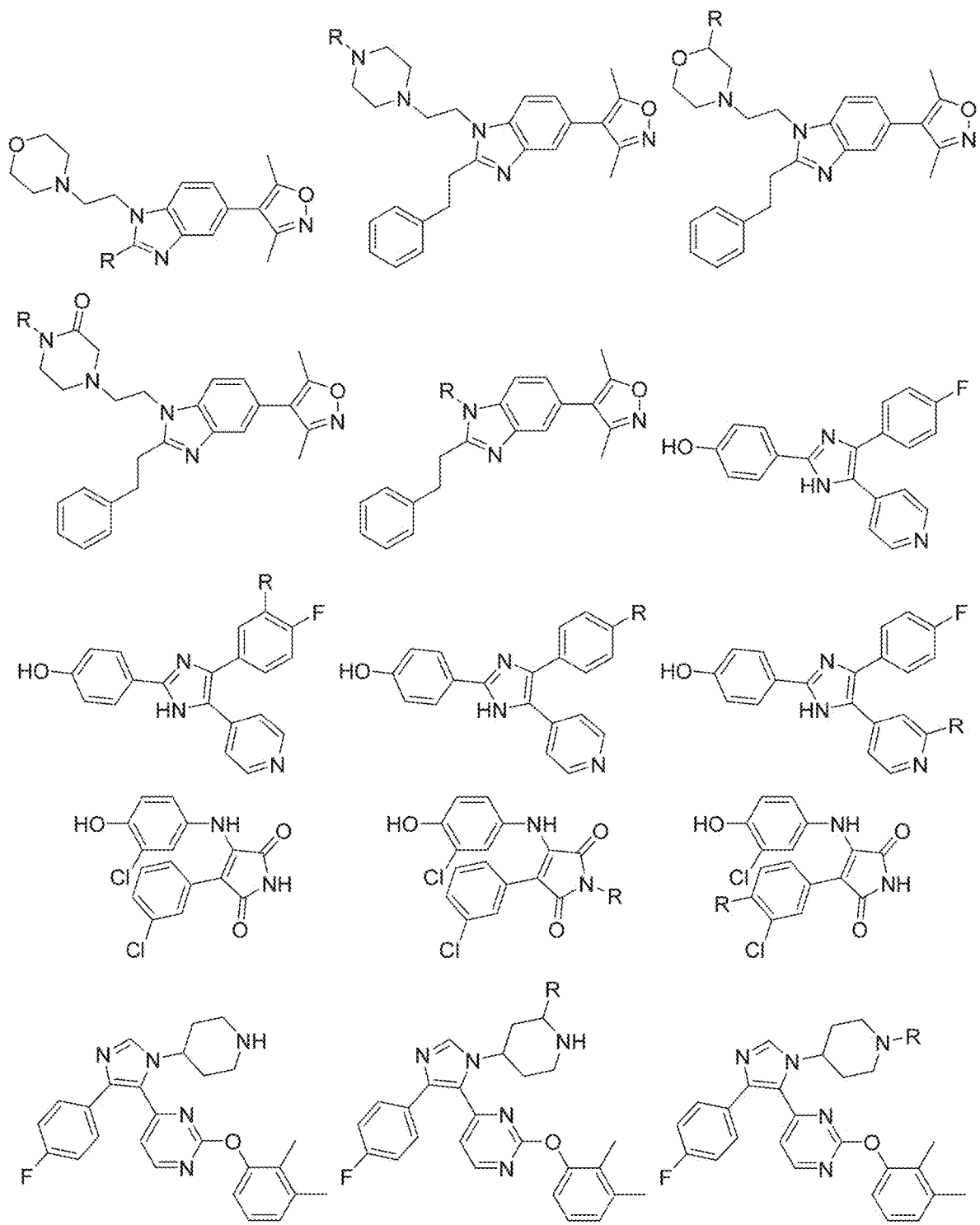
Figure 8H:
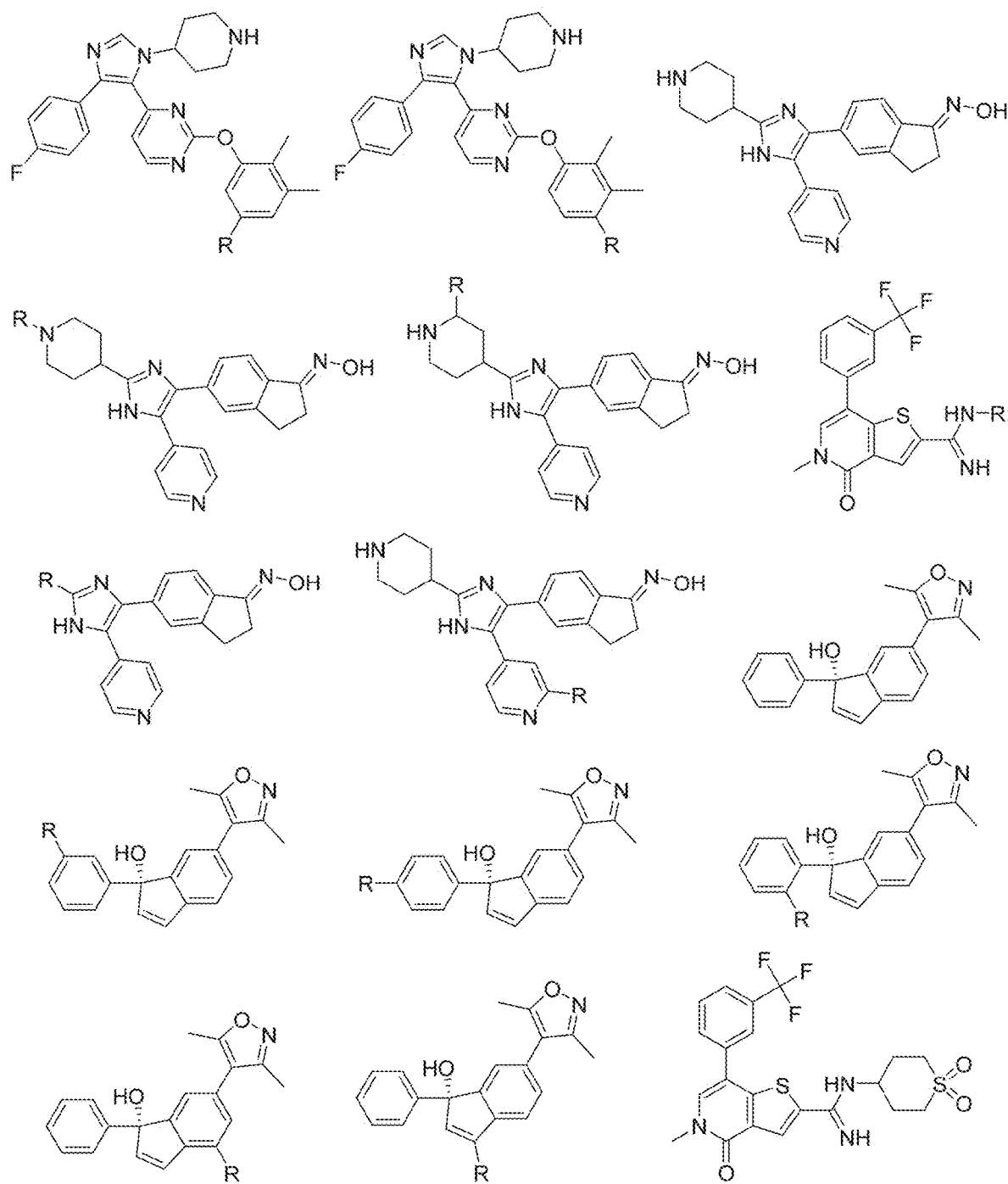
Figure 8I:
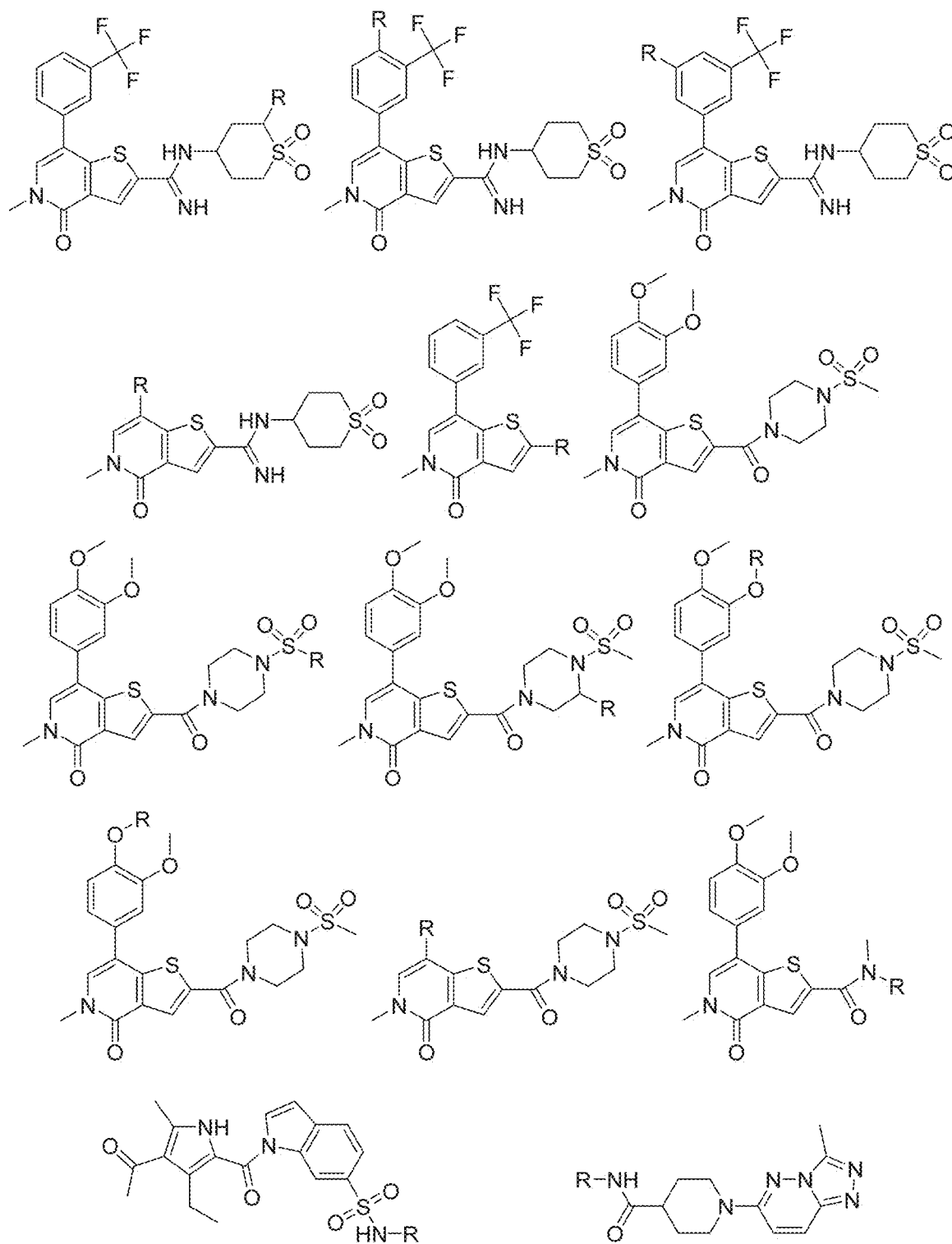
Figure 8J:
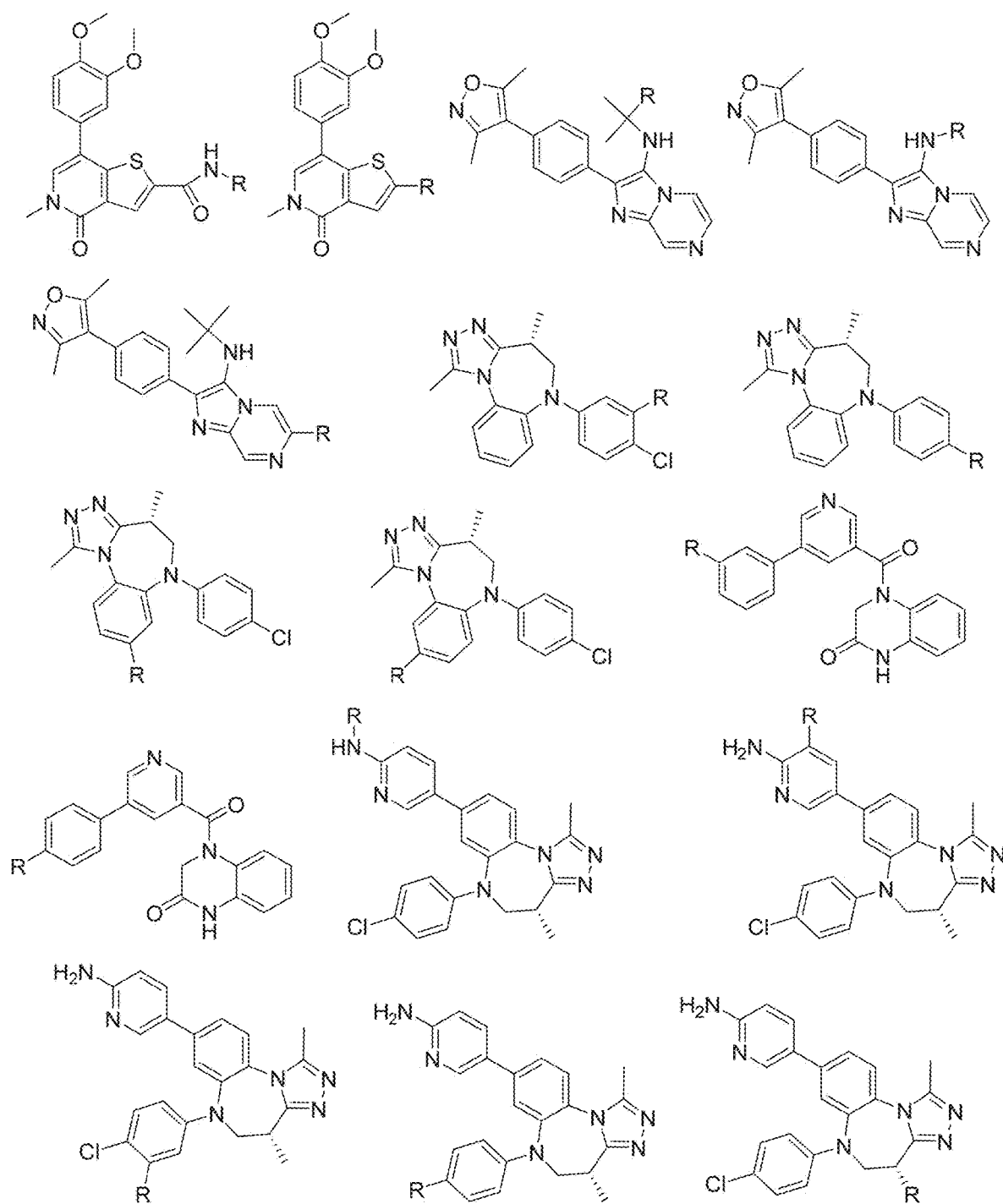
Figure 8K:
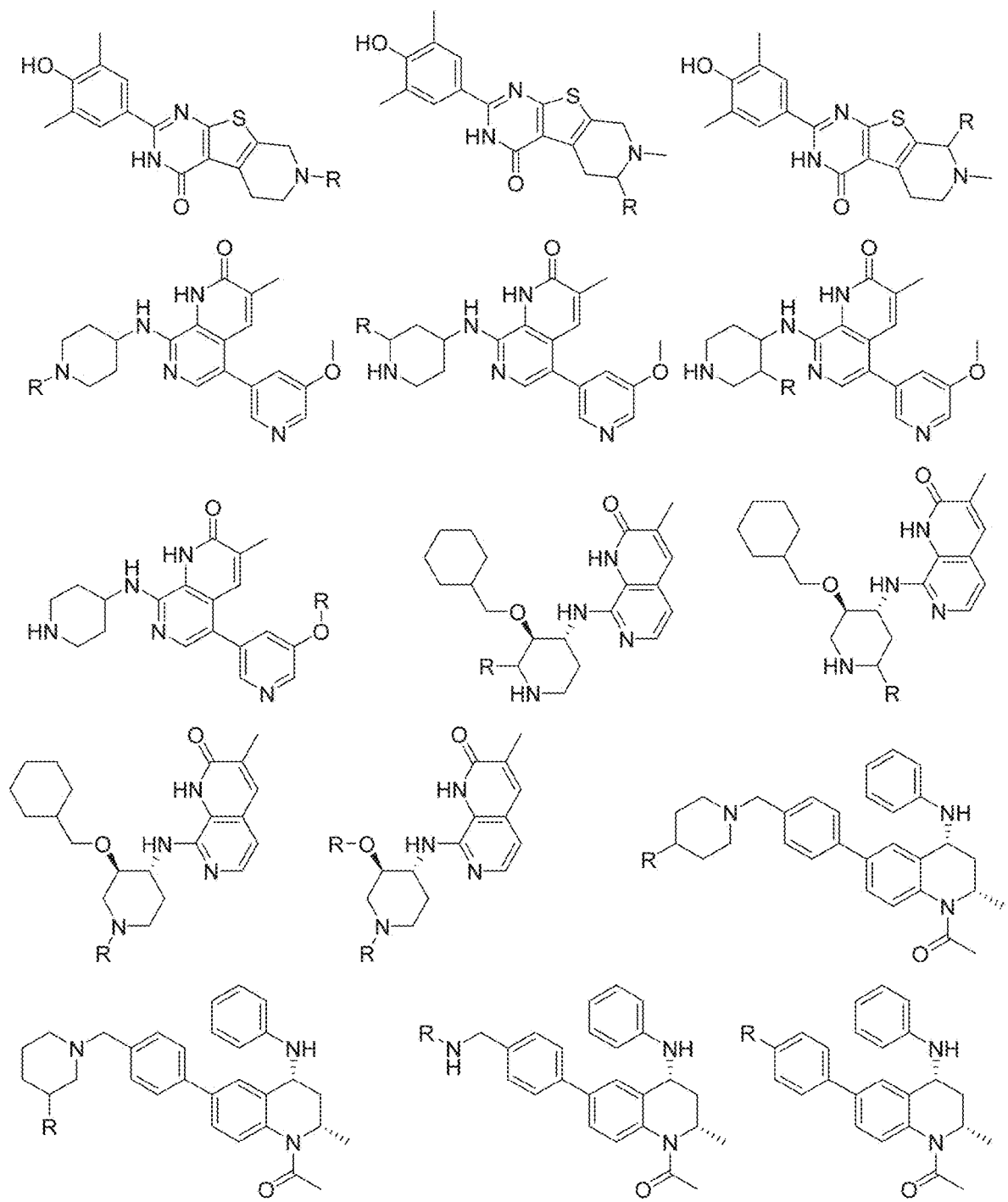
Figure 8L:
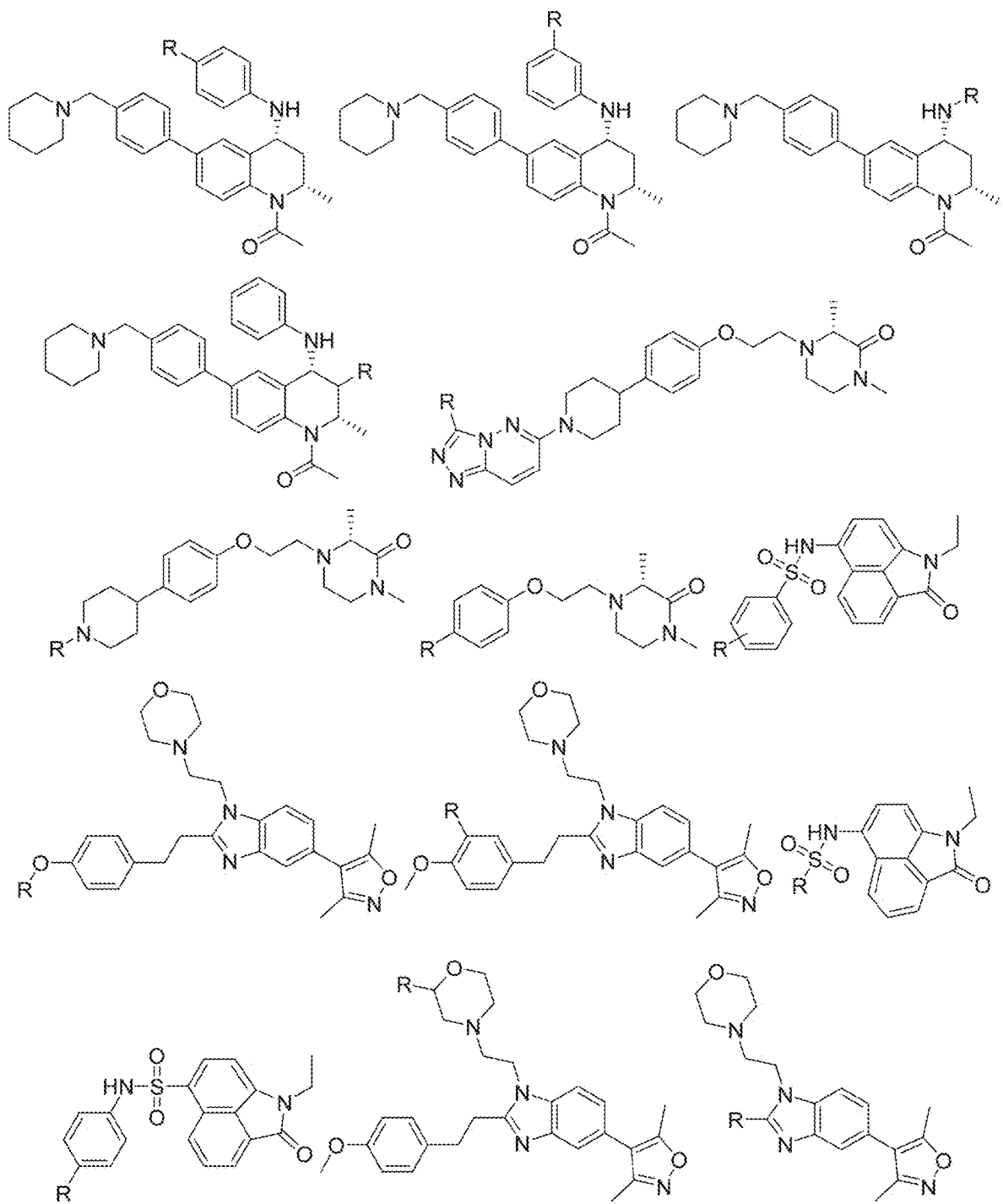
Figure 8M:
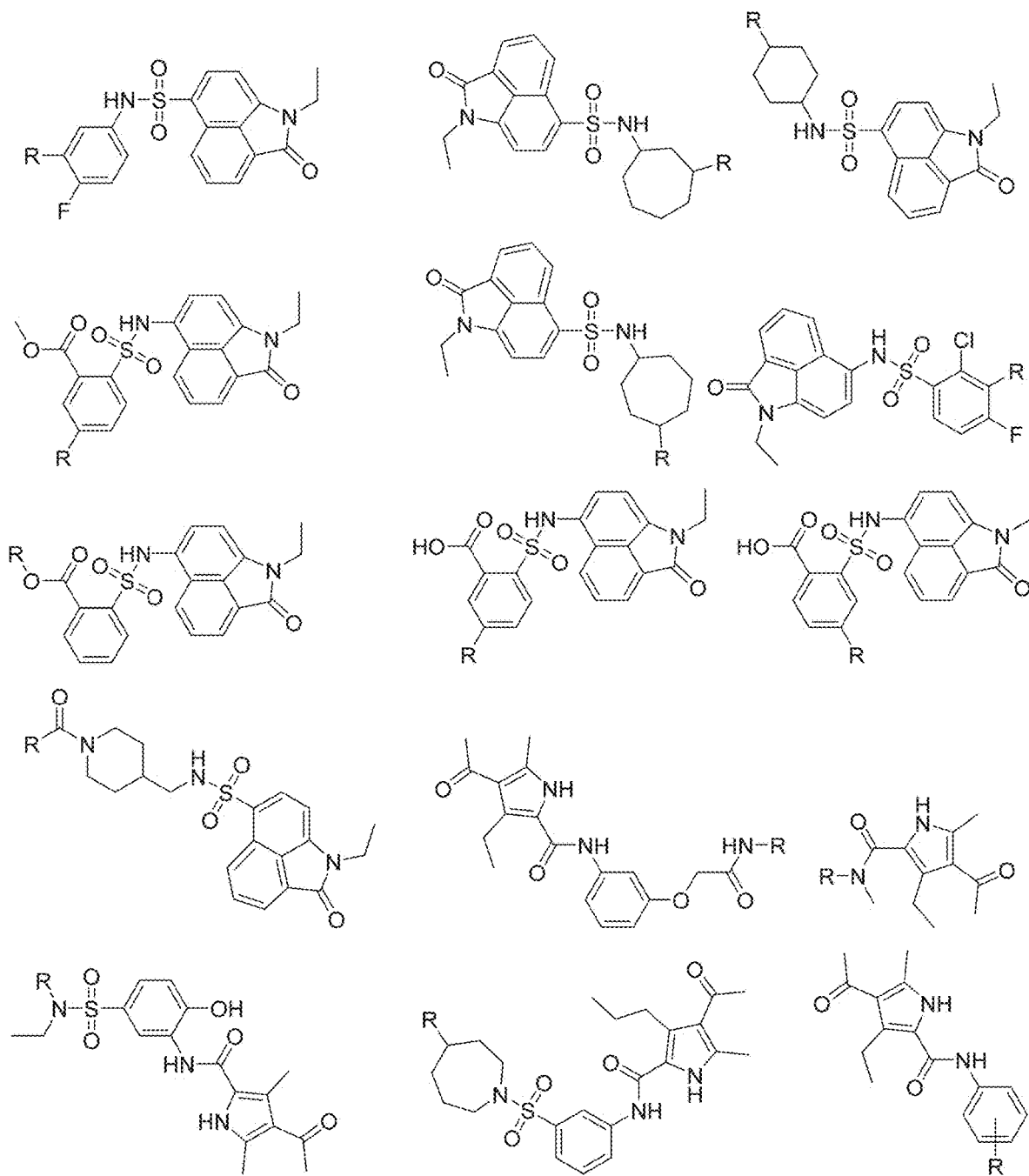
Figure 8N:
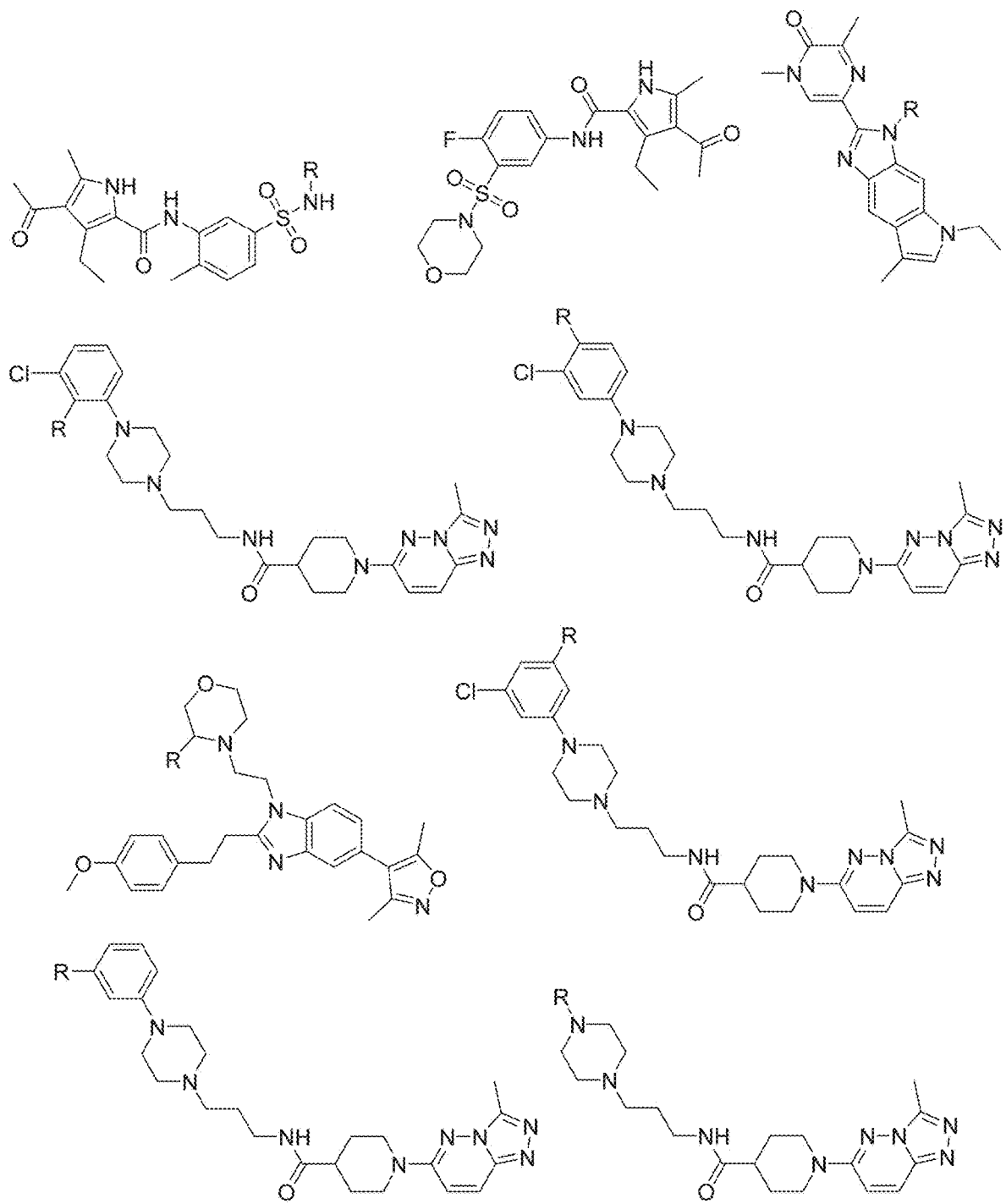
Figure 8O:
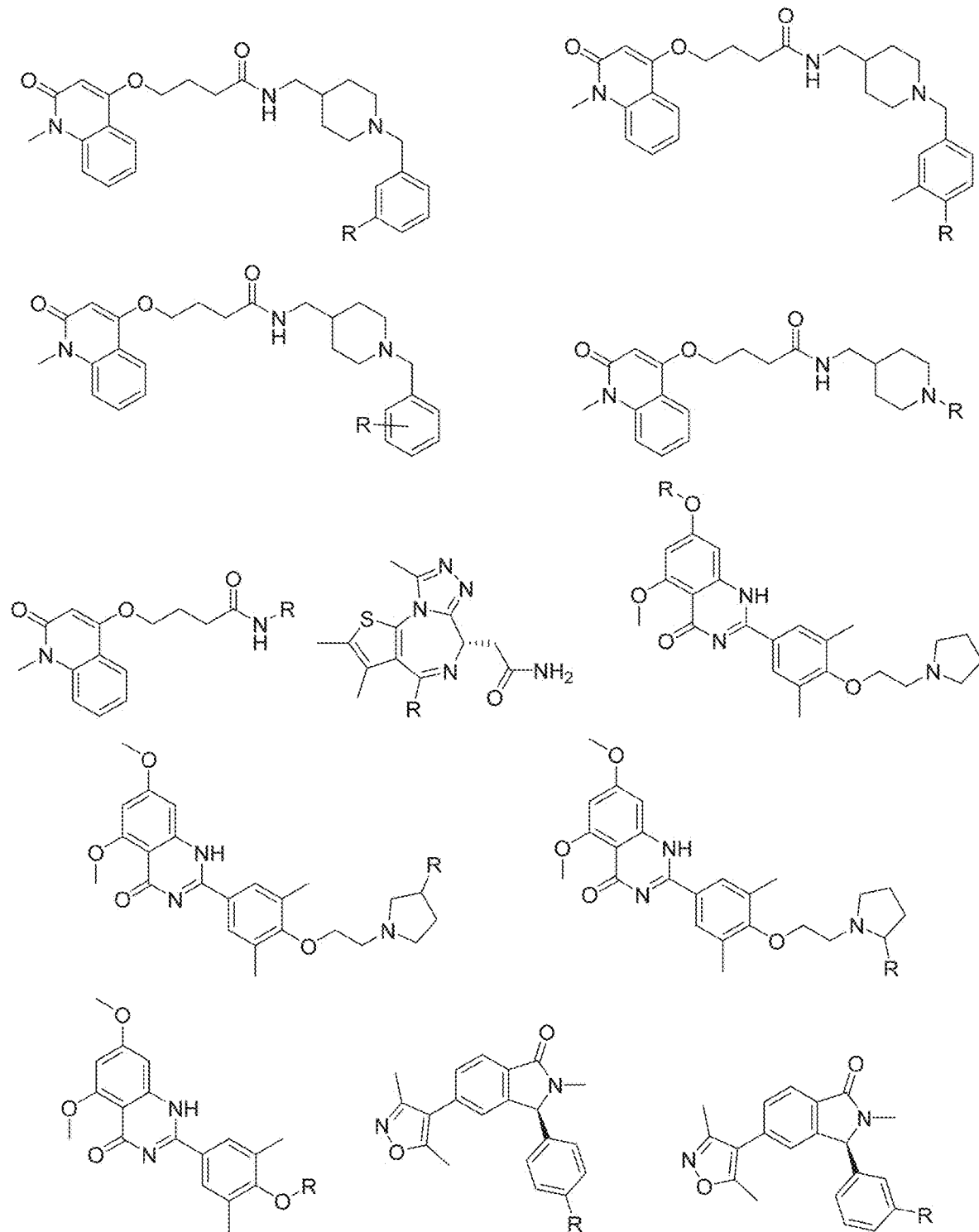
Figure 8P:
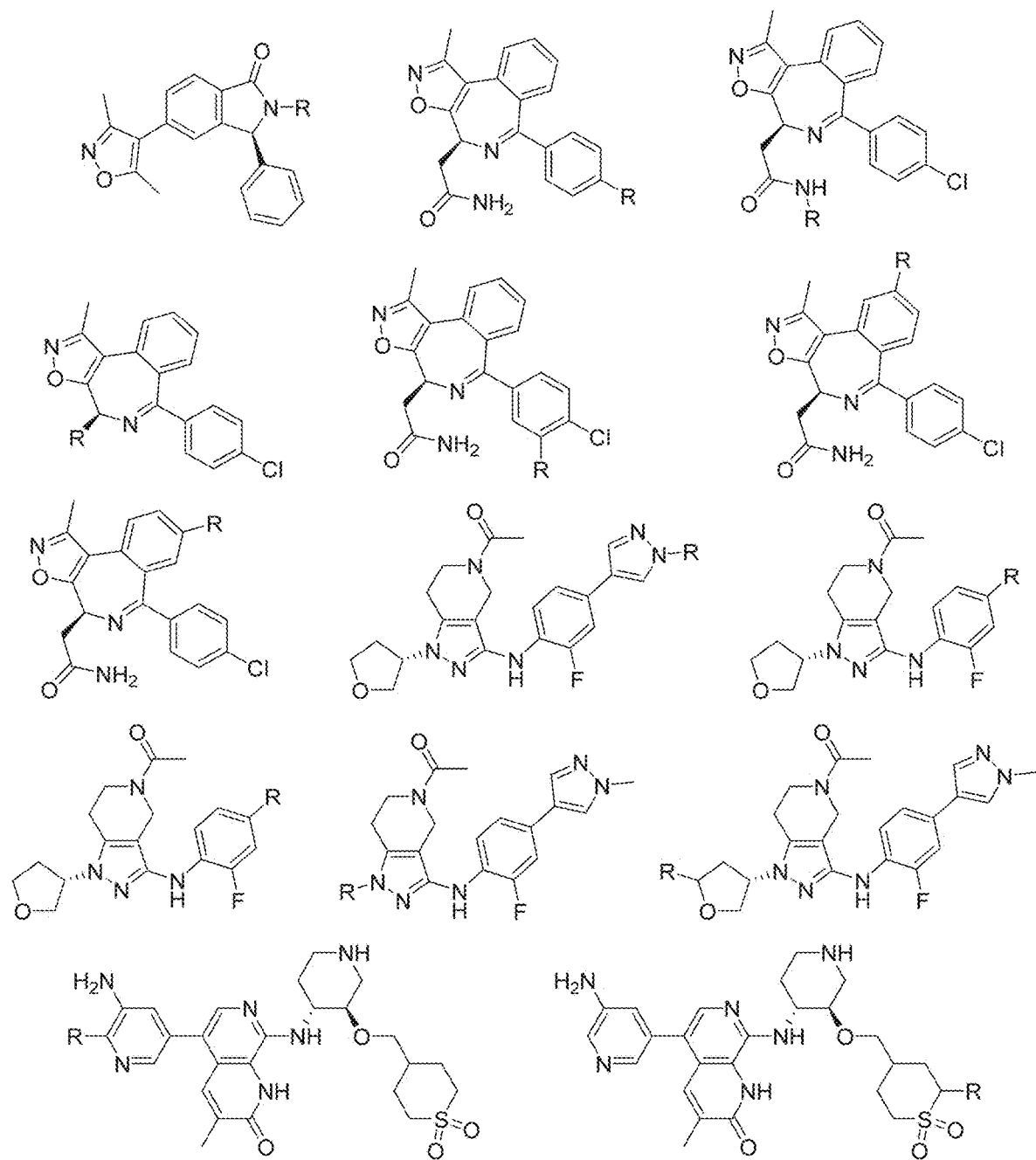
Figure 8Q:
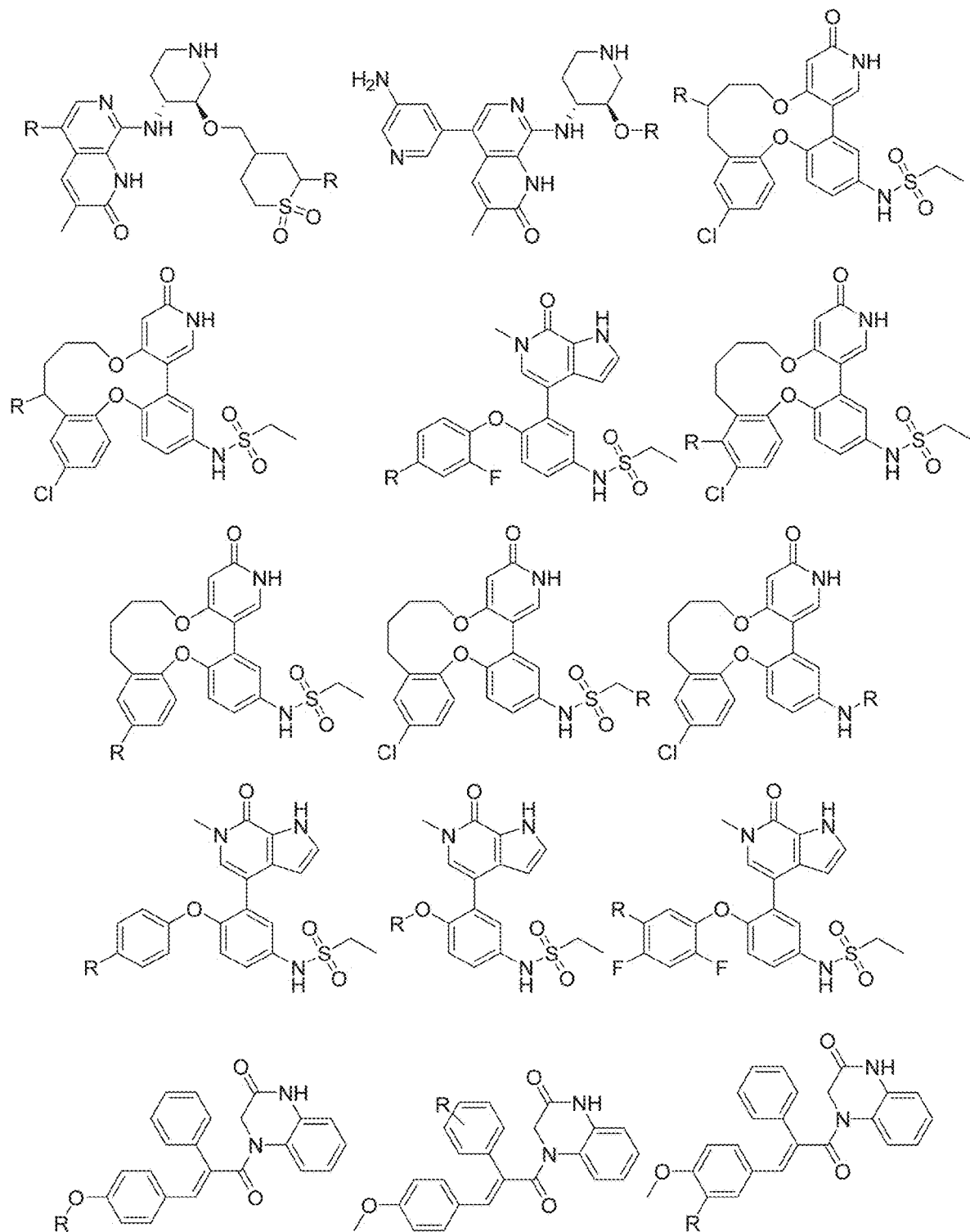
Figure 8R:
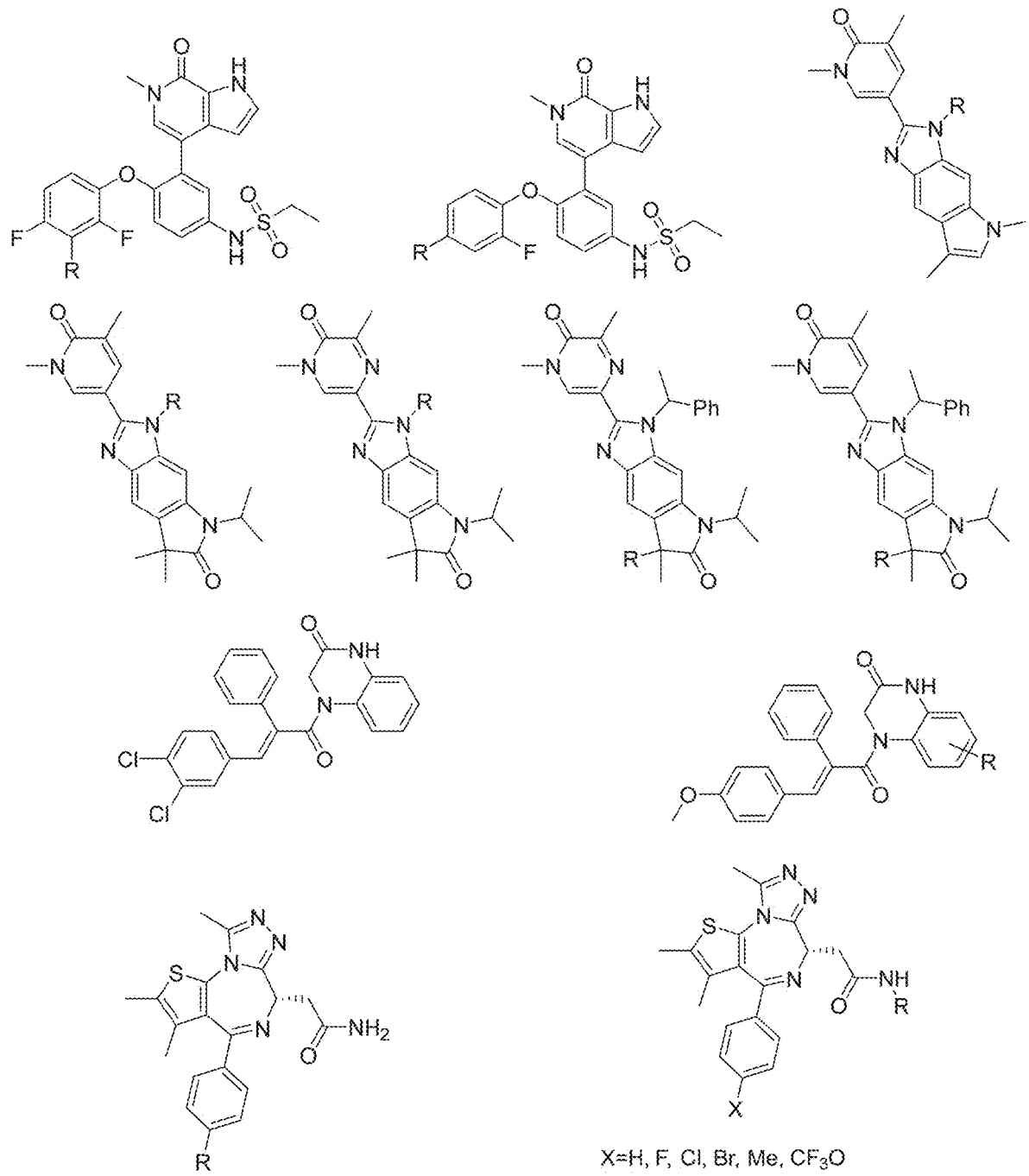
Figure 8S:
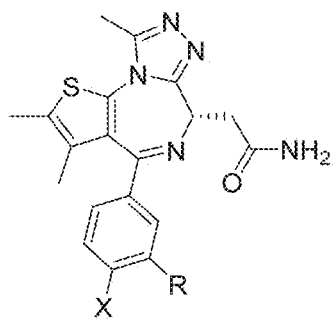
Figure 8S:
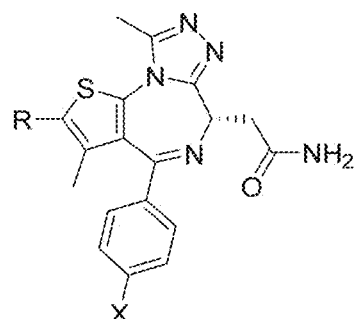

FIG. 8A-8S present examples of BRD4 Bromodomain 1 Targeting Ligands wherein R is the point at which the Linker is attached. For additional examples and related ligands, see, the crystal structures PDB 3u5k and 3u5l and related ligands in Filippakopoulos, P. et al. "Benzodiazepines and benzotriazepines as protein interaction inhibitors targeting bromodomains of the BET family", *Bioorg. Med. Chem.* 20: 1878-1886 (2012); the crystal structure PDB 3u5l; the crystal structure PDB 3zyu and related ligands described in Dawson, M. A. et al. "Inhibition of Bet Recruitment to Chromatin as an Effective Treatment for M11-Fusion Leukaemia." *Nature* 478: 529 (2011); the crystal structure PDB 4bwl and related ligands described in Mirguet, O. et al. "Naphthyridines as Novel Bet Family Bromodomain Inhibitors." *Chemmedchem* 9: 589 (2014); the crystal structure PDB 4cfl and related ligands described in Dittmann, A. et al. "The Commonly Used Pi3-Kinase Probe Ly294002 is an Inhibitor of Bet Bromodomains" *ACS Chem. Biol.* 9: 495 (2014); the crystal structure PDB 4e96 and related ligands described in Fish, P. V. et al. "Identification of a chemical probe for bromo and extra C-terminal bromodomain inhibition through optimization of a fragment-derived hit." *J. Med. Chem.* 55: 9831-9837 (2012); the crystal structure PDB 4clb and related ligands described in Atkinson, S. J. et al. "The Structure Based Design of Dual Hdac/Bet Inhibitors as Novel Epigenetic Probes." *Medchemcomm* 5: 342 (2014); the crystal structure PDB 4f3i and related ligands described in Zhang, G. et al. "Down-regulation of NF-{kappa}B Transcriptional Activity in HIV-associated Kidney Disease by BRD4 Inhibition." *J. Biol. Chem.* 287: 28840-28851 (2012); the crystal structure PDB 4hxl and related ligands described in Zhao, L. "Fragment-Based Drug Discovery of 2-Thiazolidinones as Inhibitors of the Histone Reader BRD4 Bromodomain." *J. Med. Chem.* 56: 3833-3851 (2013); the crystal structure PDB 4hxs and related ligands described in Zhao, L. et al. "Fragment-Based Drug Discovery of 2-Thiazolidinones as Inhibitors of the Histone Reader BRD4 Bromodomain." *J. Med. Chem.* 56: 3833-3851 (2013); the crystal structure PDB 4lrg and related ligands described in Gehling, V. S. et al. "Discovery, Design, and Optimization of Isoxazole Azepine BET Inhibitors." *ACS Med Chem Lett* 4: 835-840 (2013); the crystal structure PDB 4mep and related ligands described in Vidler, L. R. "Discovery of Novel Small-Molecule Inhibitors of BRD4 Using Structure-Based Virtual Screening." et al. *J. Med. Chem.* 56: 8073-8088 (2013); the crystal structures PDB 4nr8 and PDB 4c77 and related ligands described in Ember, S. W. et al. "Acetyl-lysine Binding Site of Bromodomain-Containing Protein 4 (BRD4) Interacts with Diverse Kinase Inhibitors". *ACS Chem. Biol.* 9: 1160-1171 (2014); the crystal structure PDB 4o7a and related ligands described in Ember, S. W. et al. "Acetyl-lysine Binding Site of Bromodomain-Containing Protein 4 (BRD4) Interacts with Diverse Kinase Inhibitors." *ACS Chem. Biol.* 9: 1160-1171 (2014); the crystal structure PDB 4o7b and related ligands described in "Acetyl-lysine Binding Site of Bromodomain-Containing Protein 4 (BRD4) Interacts with Diverse Kinase Inhibitors." Ember, S. W. et al. (2014) *ACS Chem. Biol.* 9: 1160-1171; the crystal structure PDB 4o7c and related ligands described in Ember, S. W. et al. "Acetyl-lysine Binding Site of Bromodomain-Containing Protein 4 (BRD4) Interacts with Diverse Kinase Inhibitors". *ACS Chem. Biol.* 9: 1160-1171 (2014); the crystal structure PDB 4gpj; the crystal structure PDB 4uix and related ligands described in Theodoulou, N. H. et al. "The Discovery of I-Brd9, a Selective Cell Active Chemical Probe for Bromodomain Containing Protein 9 Inhibition". *J. Med. Chem.* 59: 1425 (2016); the crystal structure PDB 4uiz and related ligands described in Theodoulou, N. H., et al. "The Discovery of I-Brd9, a Selective Cell Active Chemical Probe for Bromodomain Containing Protein 9 Inhibition". *J. Med. Chem.* 59: 1425 (2016); the crystal structure PDB 4wiv and related ligands described in McKeown, M. R. et al. "Biased multicomponent reactions to develop novel bromodomain inhibitors." *J. Med. Chem.* 57: 9019-9027 (2014); the crystal structure PDB 4x2i and related ligands described in Taylor, A. M. et al. "Discovery of Benzotriazolo[4,3-d][1,4]diazepines as Orally Active Inhibitors of BET Bromodomains." *ACS Med. Chem. Lett.* 7: 145-150 (2016); the crystal structure PDB 4yh3; And related ligands described in Duffy, B. C. "Discovery of a new chemical series of BRD4(1) inhibitors using protein-ligand docking and structure-guided design." *Bioorg. Med. Chem. Lett.* 25: 2818-2823 (2015); the crystal structure PDB 4yh4 and related ligands described in Duffy, B. C. "Discovery of a new chemical series of BRD4(1) inhibitors using protein-ligand docking and structure-guided design." *Bioorg. Med. Chem. Lett.* 25: 2818-2823 (2015); the crystal structure PDB 4zlq and related ligands described in Taylor, A. M. "Discovery of Benzotriazolo[4,3-d][1,4]diazepines as Orally Active Inhibitors of BET Bromodomains." *ACS Med. Chem. Lett.* 7: 145-150 (2016); the crystal structure PDB 4zwl; the crystal structure PDB 5a5s and related ligands described in Demont, E. H. "Fragment-Based Discovery of Low-Micromolar Atad2 Bromodomain Inhibitors. *J. Med. Chem.* 58: 5649 (2015); the crystal structure PDB 5a85 and related ligands described in Bamborough, P. "Structure-Based Optimization of Naphthyridones Into Potent Atad2 Bromodomain Inhibitors" *J. Med. Chem.* 58: 6151 (2015); the crystal structure PDB 5acy and related ligands described in Sullivan, J. M. "Autism-Like Syndrome is Induced by Pharmacological Suppression of Bet Proteins in Young Mice." *J. Exp. Med.* 212: 1771 (2015); the crystal structure PDB 5ad2 and related ligands described in Waring, M. J. et al. "Potent and Selective Bivalent Inhibitors of Bet Bromodomains". *Nat. Chem. Biol.* 12: 1097 (2016); the crystal structure PDB 5cfw and related ligands described in Chekler, E. L. et al. "Transcriptional Profiling of a Selective CREB Binding Protein Bromodomain Inhibitor Highlights Therapeutic Opportunities." *Chem. Biol.* 22: 1588-1596 (2015); the crystal structure PDB 5cqt and related ligands described in Xue, X. et al. "Discovery of Benzo[cd]indol-2(1H)-ones as Potent and Specific BET Bromodomain Inhibitors: Structure-Based Virtual Screening, Optimization, and Biological Evaluation". *J. Med. Chem.* 59: 1565-1579 (2016); the crystal structure PDB 5d3r and related ligands described in Hugle, M. et al. "4-Acyl Pyrrole Derivatives Yield Novel Vectors for Designing Inhibitors of the Acetyl-Lysine Recognition Site of BRD4(1)". *J. Med. Chem.* 59: 1518-1530 (2016); the crystal structure PDB 5dlx and related ligands described in Milhas, S. et al. "Protein-Protein Interaction Inhibition (2P2I)-Oriented Chemical Library Accelerates Hit Discovery." (2016) *ACS Chem. Biol.* 11: 2140-2148; the crystal structure PDB 5dlz and related ligands described in Milhas, S. et al. "Protein-Protein Interaction Inhibition (2P2I)-Oriented Chemical Library Accelerates Hit Discovery." *ACS Chem. Biol.* 11: 2140-2148 (2016); the crystal structure PDB 5dw2 and related ligands described in Kharenko, O. A. et al. "RVX-297—a novel BD2 selective inhibitor of BET bromodomains." *Biochem. Biophys. Res. Commun.* 477: 62-67 (2016); the crystal structure PDB 5dlx; the crystal structure PDB 5his and related ligands described in Albrecht, B. K. et al. "Identification of a Benzoisoxazoloazepine Inhibitor (CPI-0610) of the Bromodomain and Extra-Terminal (BET) Family as a Candidate for Human Clinical Trials." *J. Med. Chem.* 59: 1330-1339 (2016); the crystal structure PDB 5ku3 and related ligands described in Crawford, T. D. et al. "Discovery of a Potent and Selective in Vivo Probe (GNE-272) for the Bromodomains of CBP/EP300". *J. Med. Chem.* 59: 10549-10563 (2016); the crystal structure PDB 5lj2 and related ligands described in Bamborough, P. et al. "A Chemical Probe for the ATAD2 Bromodomain." *Angew. Chem. Int. Ed. Engl.* 55: 11382-11386 (2016); the crystal structure PDB 5dlx and related ligands described in Wang, L. "Fragment-based, structure-enabled discovery of novel pyridones and pyridone macrocycles as potent bromodomain and extra-terminal domain (BET) family bromodomain inhibitors". *J. Med. Chem.* 10.1021/acs.jmedchem.7b00017 (2017); WO 2015169962 A1 titled "Benzimidazole derivatives as BRD4 inhibitors and their preparation and use for the treatment of cancer" assigned to Boehringer Ingelheim International GmbH, Germany; and, WO 2011143669 A2 titled "Azolodiazepine derivatives and their preparation, compositions and methods for treating neoplasia, inflammatory disease and other disorders" assigned to Dana-Farber Cancer Institute, Inc, USA.

Figure 8T:
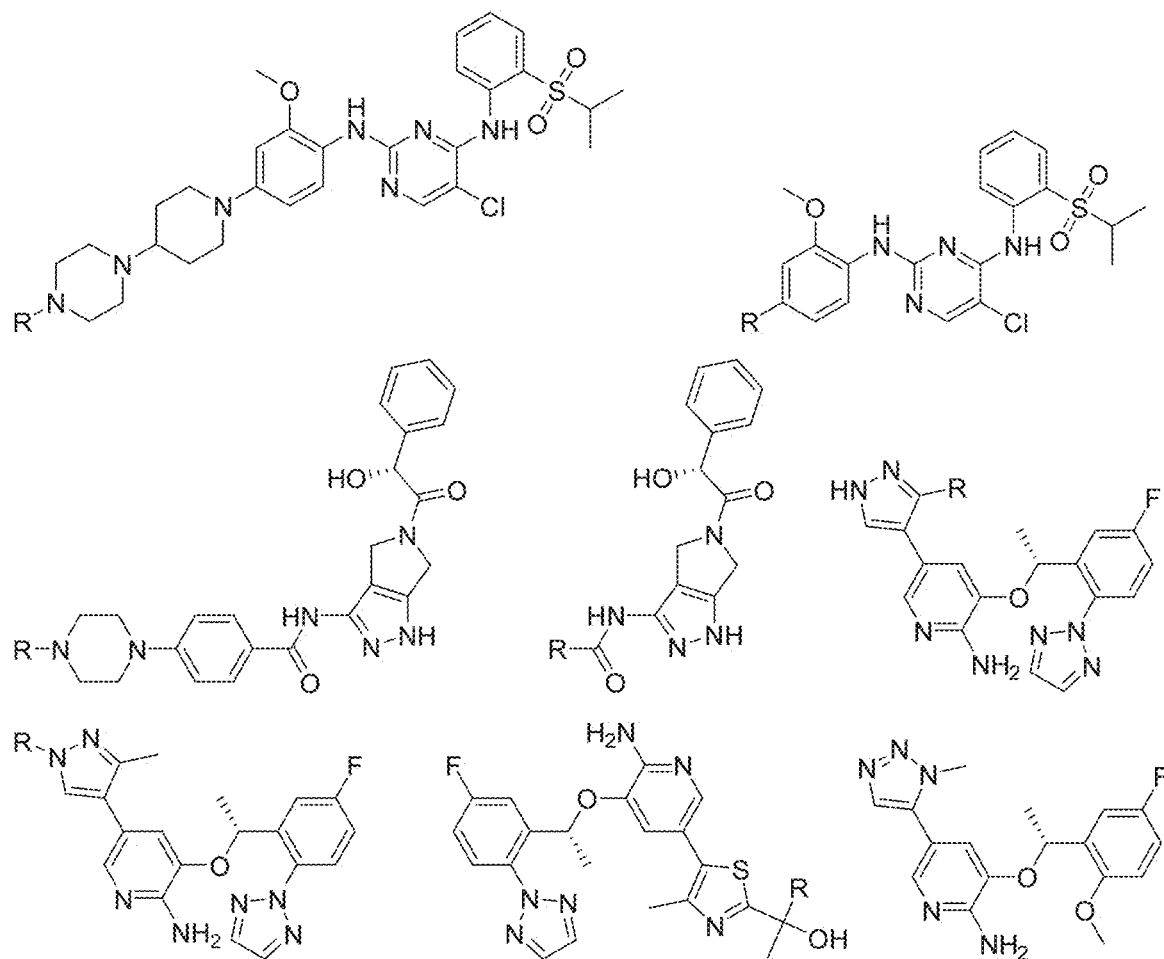
Figure 8U:
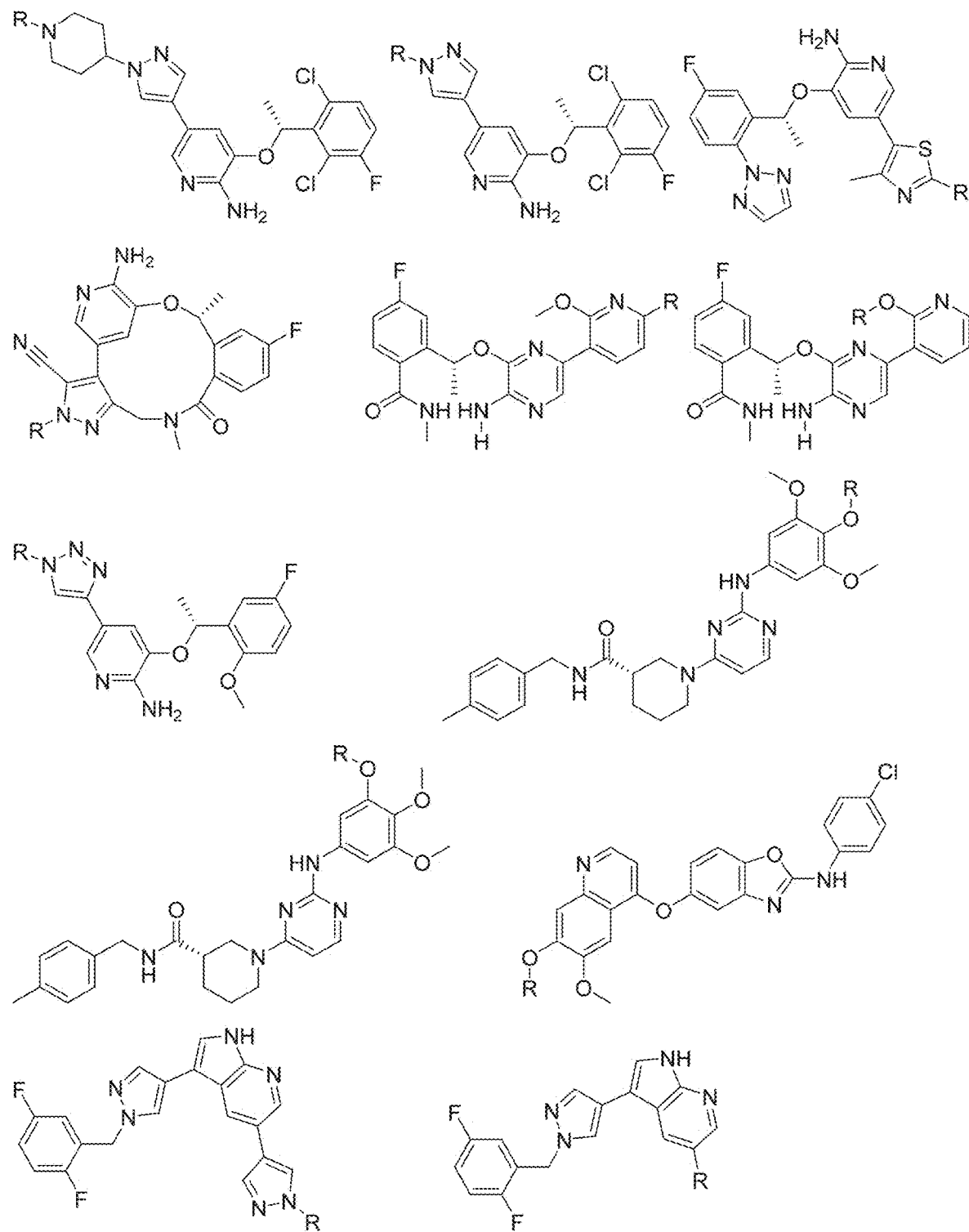
Figure 8V:
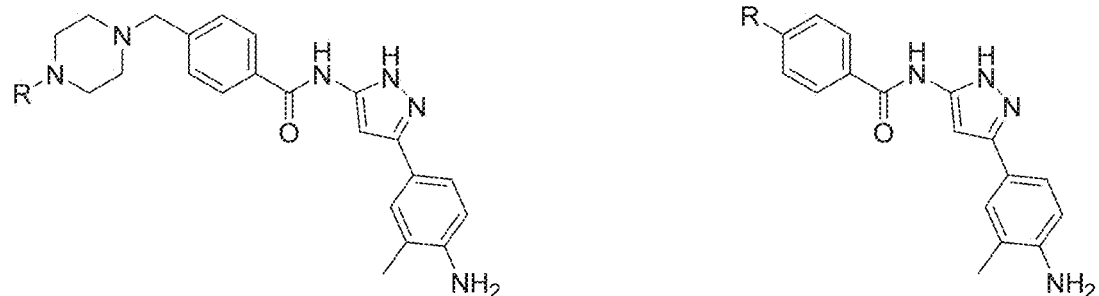

FIG. 8T-8V present examples of ALK Targeting Ligands wherein R is the point at which the Linker is attached. For additional examples and related ligands, see, the crystal structures PDB 2xb7 and 2xba and related ligands described in Bossi, R. T. et al. "Crystal Structures of Anaplastic Lymphoma Kinase in Complex with ATP Competitive Inhibitors" *Biochemistry* 49: 6813-6825 (2010); the crystal structures PDB 2yfx, 4ccb, 4ccu, amd 4cd0 snd related ligands described in Huang, Q. et al. "Design of Potent and Selective Inhibitors to Overcome Clinical Anaplastic Lymphoma Kinase Mutations Resistant to Crizotinib." *J. Med. Chem.* 57: 1170 (2014); the crystal structures PDB, 4cli, 4cmo, and 4cnh and related ligands described in Johnson, T. W. et al. "Discovery of (10R)-7-Amino-12-Fluoro-2,10,16-Trimethyl-15-Oxo-10,15,16,17-Tetrahydro-2H-8,4-(Metheno)Pyrazolo[4,3-H][2,5,11]Benzoxadiazacyclotetradecine-3-Carbonitrile (Pf-06463922), a Macrocyclic Inhibitor of Alk/Ros1 with Pre-Clinical Brain Exposure and Broad Spectrum Potency Against Alk-Resistant Mutations." *J. Med. Chem.* 57: 4720 (2014); the crystal structure PDB 4fny and related ligands described in Epstein, L. F. et al. "The R1275Q Neuroblastoma Mutant and Certain ATP-competitive Inhibitors Stabilize Alternative Activation Loop Conformations of Anaplastic Lymphoma Kinase." *J. Biol. Chem.* 287: 37447-37457 (2012). the crystal structure PDB 4dce and related ligands described in Bryan, M. C. et al "Rapid development of piperidine carboxamides as potent and selective anaplastic lymphoma kinase inhibitors." *J. Med. Chem.* 55: 1698-1705 (2012); the crystal structure PDB 4joa and related ligands described in Gummadi, V. R. et al. "Discovery of 7-azaindole based anaplastic lymphoma kinase (ALK) inhibitors: wild type and mutant (L1196M) active compounds with unique binding mode." (2013) *Bioorg. Med. Chem. Lett.* 23: 4911-4918; and, the crystal structure PDB 5iui and related ligands described in Tu, C. H. et al. "Pyrazolylamine Derivatives Reveal the Conformational Switching between Type I and Type II Binding Modes of Anaplastic Lymphoma Kinase (ALK)." *J. Med. Chem.* 59: 3906-3919 (2016).

Figure 8W:
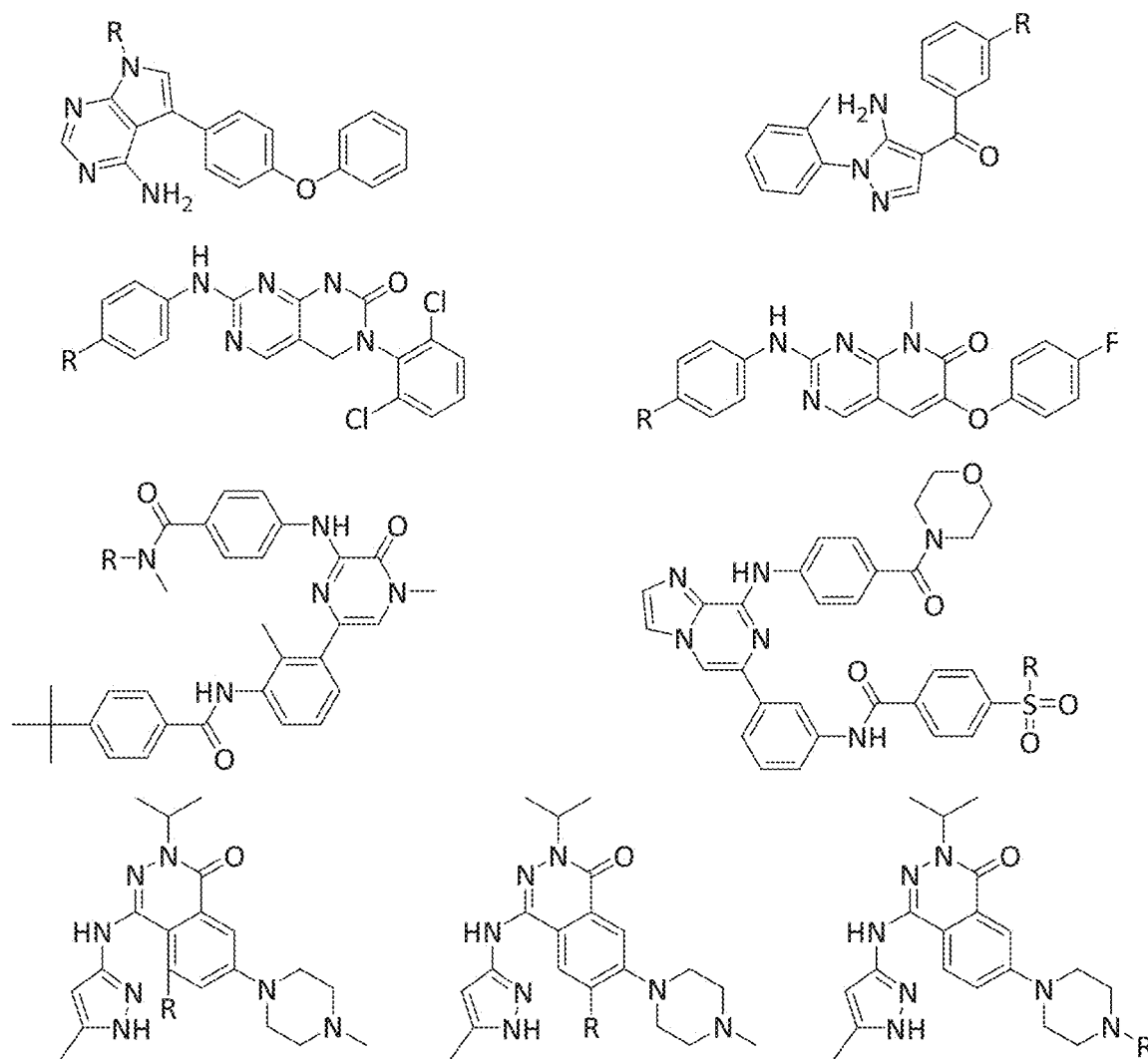
Figure 8X:
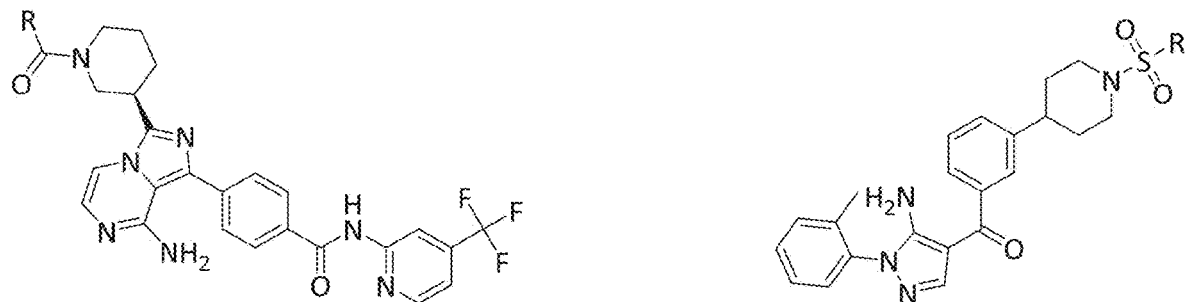

FIG. 8W-8X present examples of BTK Targeting Ligands wherein R is the point at which the Linker is attached. For additional examples and related ligands, see, the crystal structure PDB 3gen, 3piz and related ligands described in Marcotte, D. J. et al. "Structures of human Bruton's tyrosine kinase in active and inactive conformations suggest a mechanism of activation for TEC family kinases." *Protein Sci.* 19: 429-439 (2010) and Kuglstatter, A. et al. "Insights into the conformational flexibility of Bruton's tyrosine kinase from multiple ligand complex structures" *Protein Sci.* 20: 428-436" (2011); the crystal structure PDB 3ocs, 4ot6 and related ligands described in Lou, Y. et al. "Structure-Based Drug Design of RN486, a Potent and Selective Bruton's Tyrosine Kinase (BTK) Inhibitor, for the Treatment of Rheumatoid Arthritis" *J. Med. Chem.* 58: 512-516 (2015); the crystal structures PDB 5fbn and 5fbo and related ligands described in Liu, J. et al. "Discovery of 8-Amino-imidazo[1,5-a]pyrazines as Reversible BTK Inhibitors for the Treatment of Rheumatoid Arthritis." *ACS Med. Chem. Lett.* 7: 198-203 (2016); the crystal structure PDB 3pix and related ligands described in Kuglstatter, A. et al. "Insights into the conformational flexibility of Bruton's tyrosine kinase from multiple ligand complex structures." *Protein Sci.* 20: 428-436 (2011); and, the crystal structure PDB 3pij and related ligands described in Bujacz, A. et al. "Crystal structures of the apo form of beta-fructofuranosidase from *Bifidobacterium longum* and its complex with fructose." *Febs J.* 278: 1728-1744 (2011).

Figure 8Y:
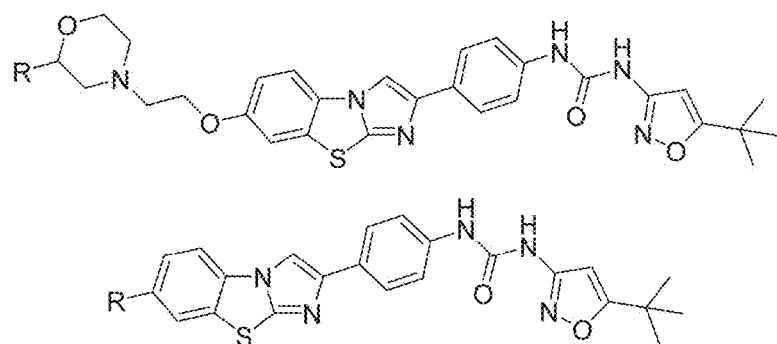

FIG. 8Y presents examples of FLT3 Targeting Ligands wherein R is the point at which the Linker is attached. For additional examples and related ligands, see, the crystal structures PDB 4xuf and 4rt7 and related ligands described in Zorn, J. A. et al. "Crystal Structure of the FLT3 Kinase Domain Bound to the Inhibitor Quizartinib (AC220)". *Plos One* 10: e0121177-e0121177 (2015).

Figure 8Z:
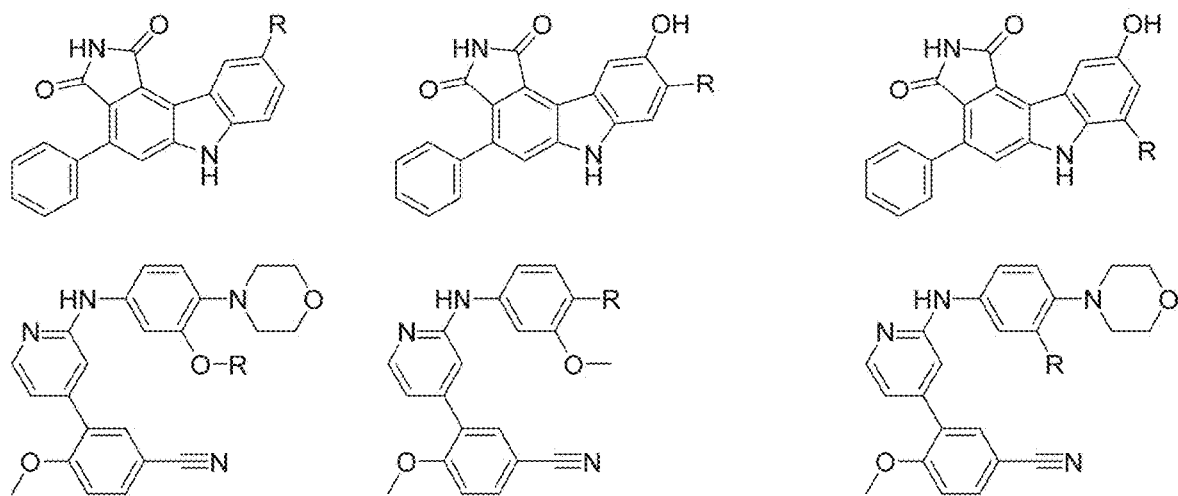
Figure 8A:
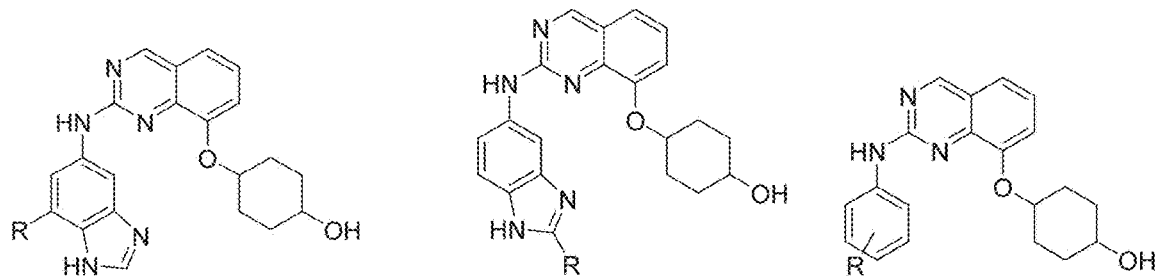
Figure 8B:
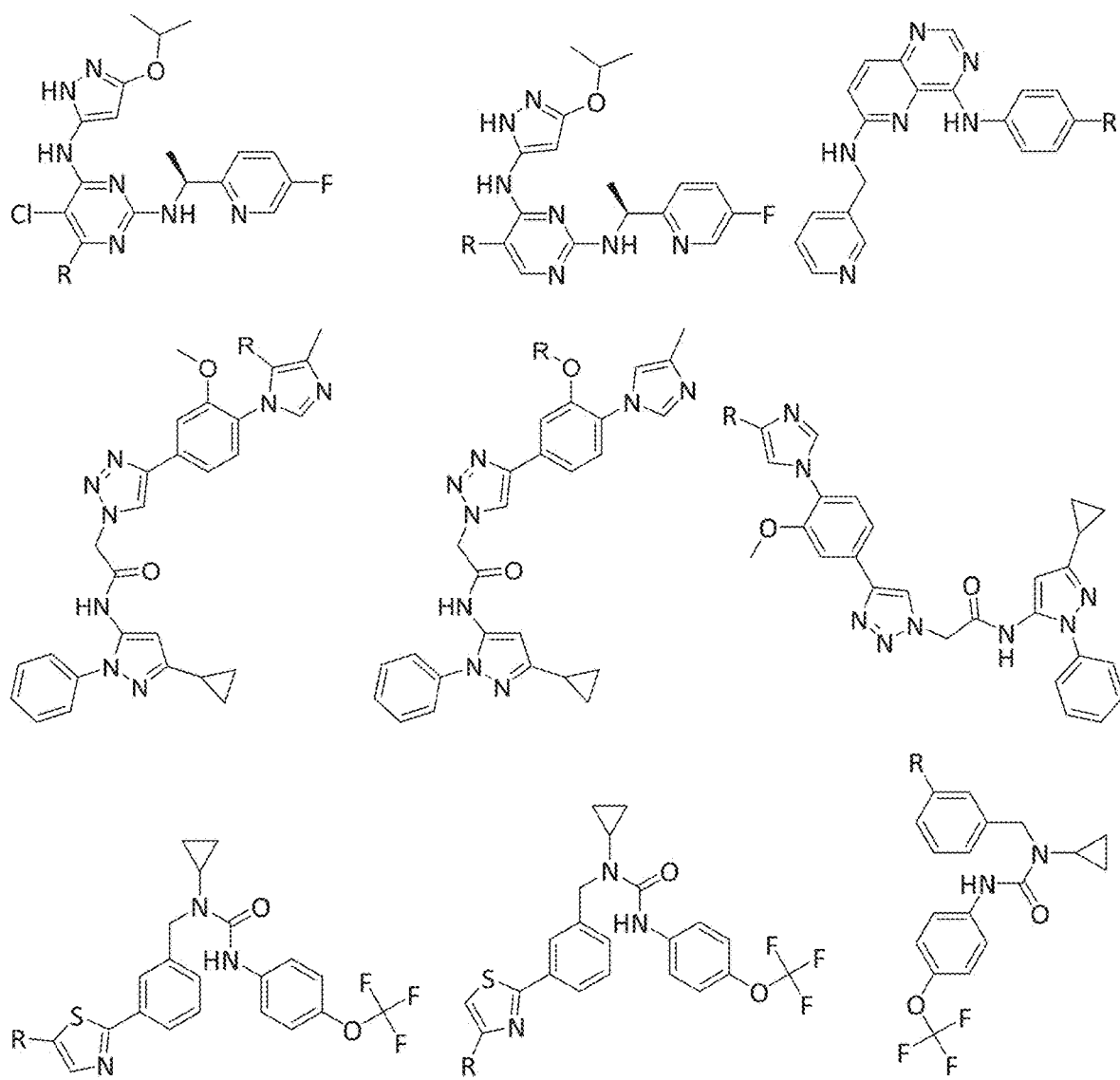
Figure 8C:
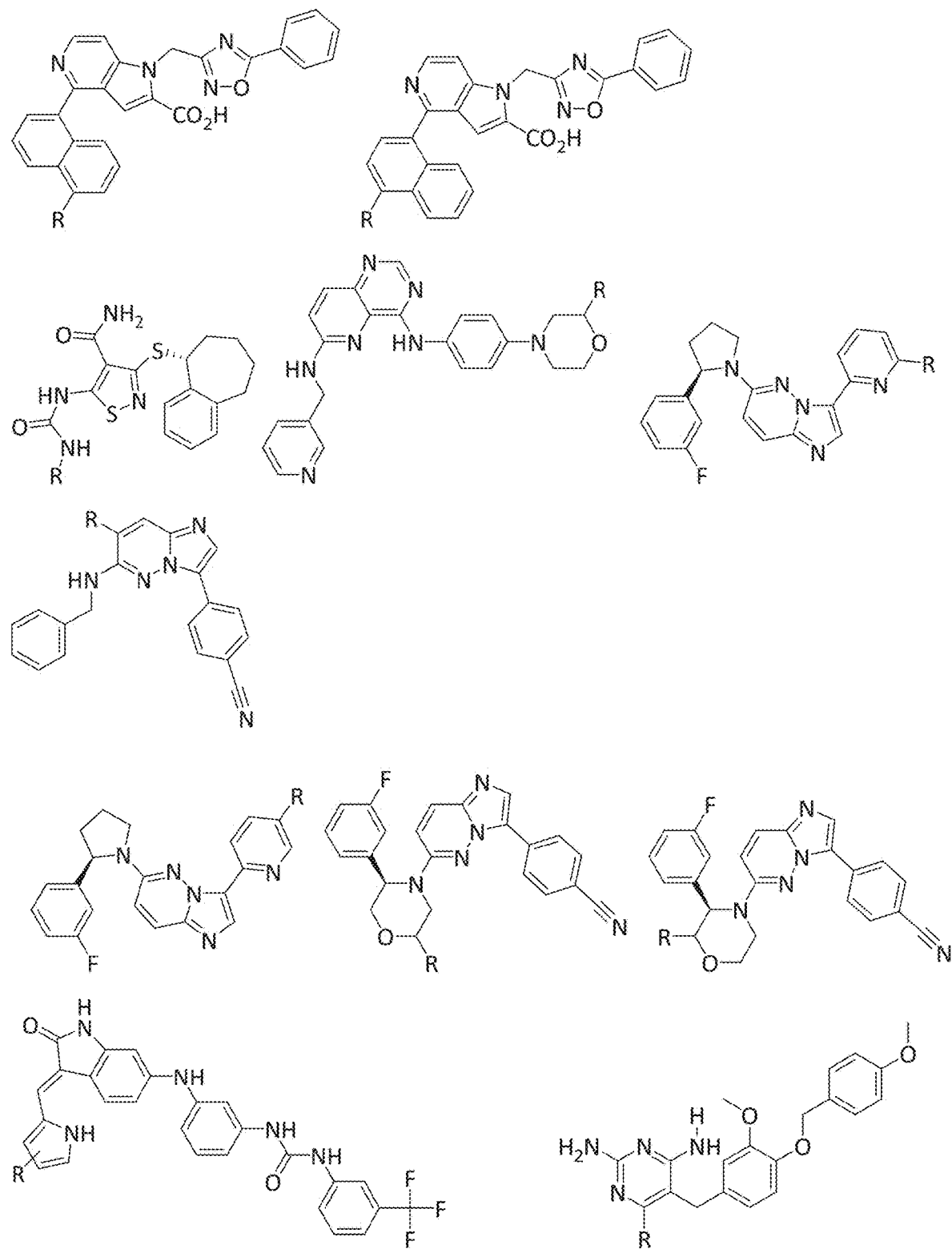
Figure 8D:
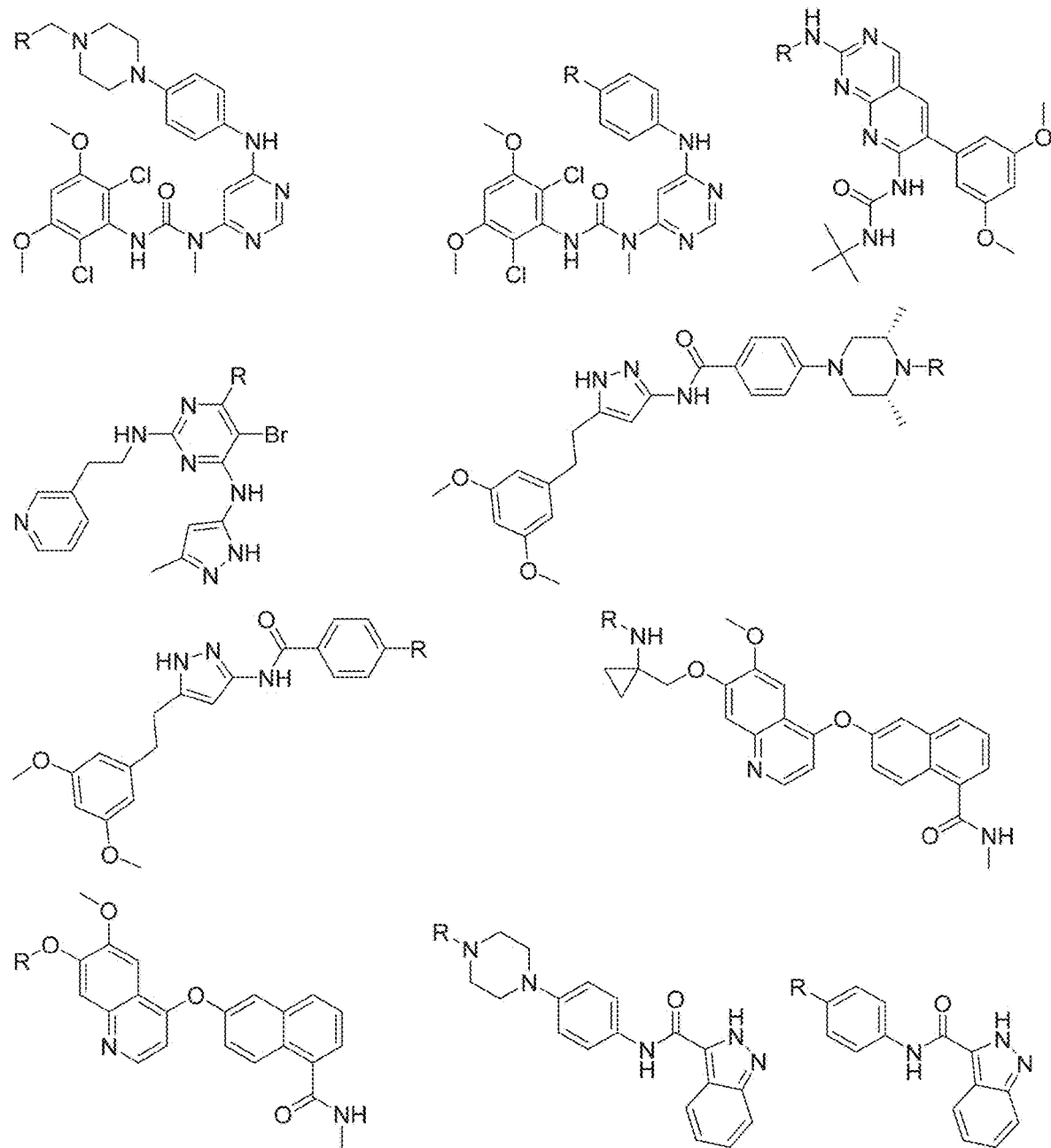
Figure 8E:
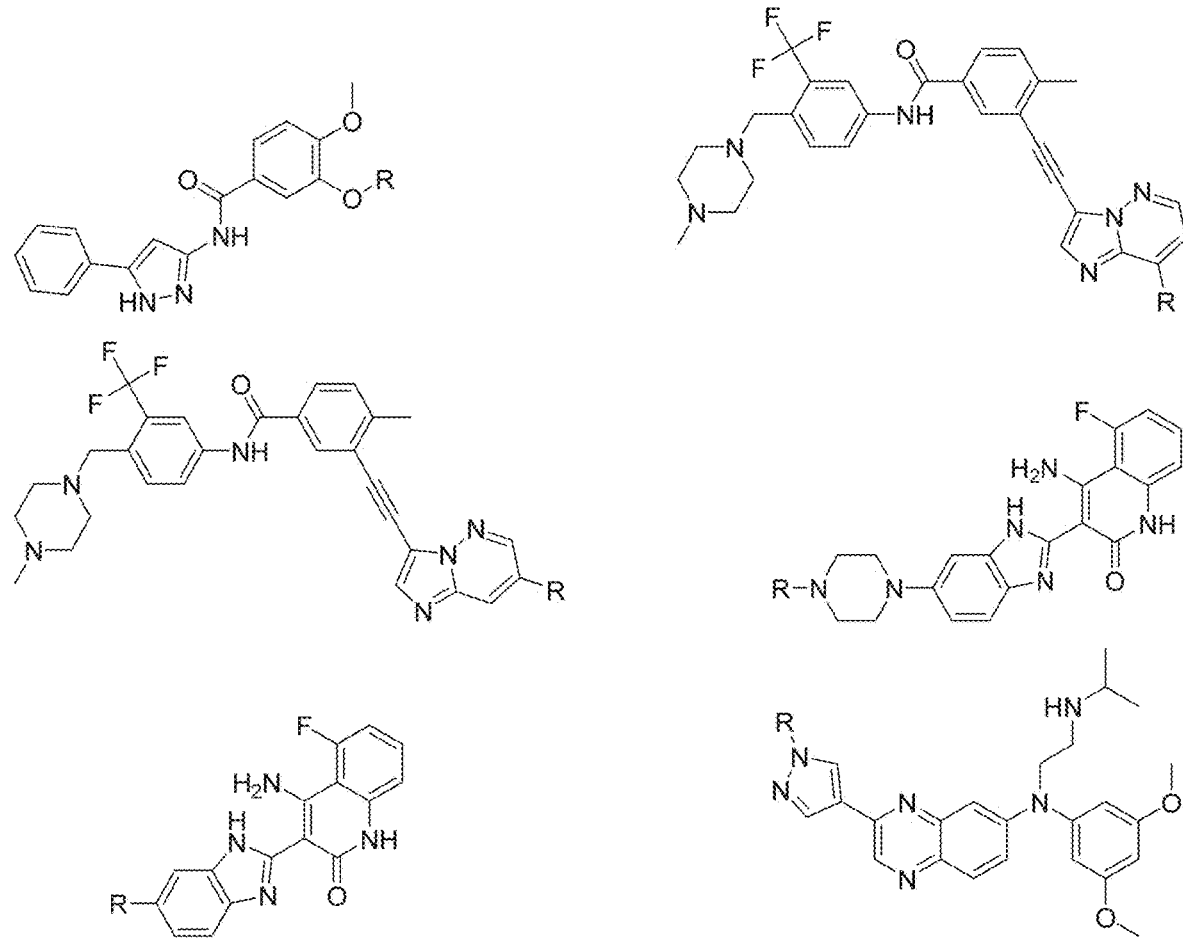
Figure 8F:
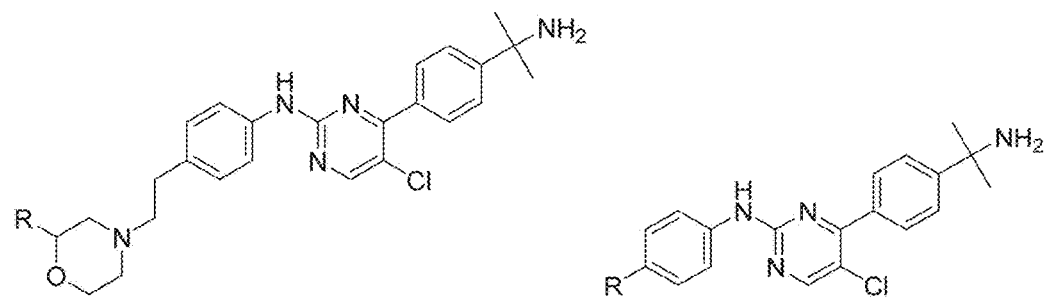
Figure 8G:
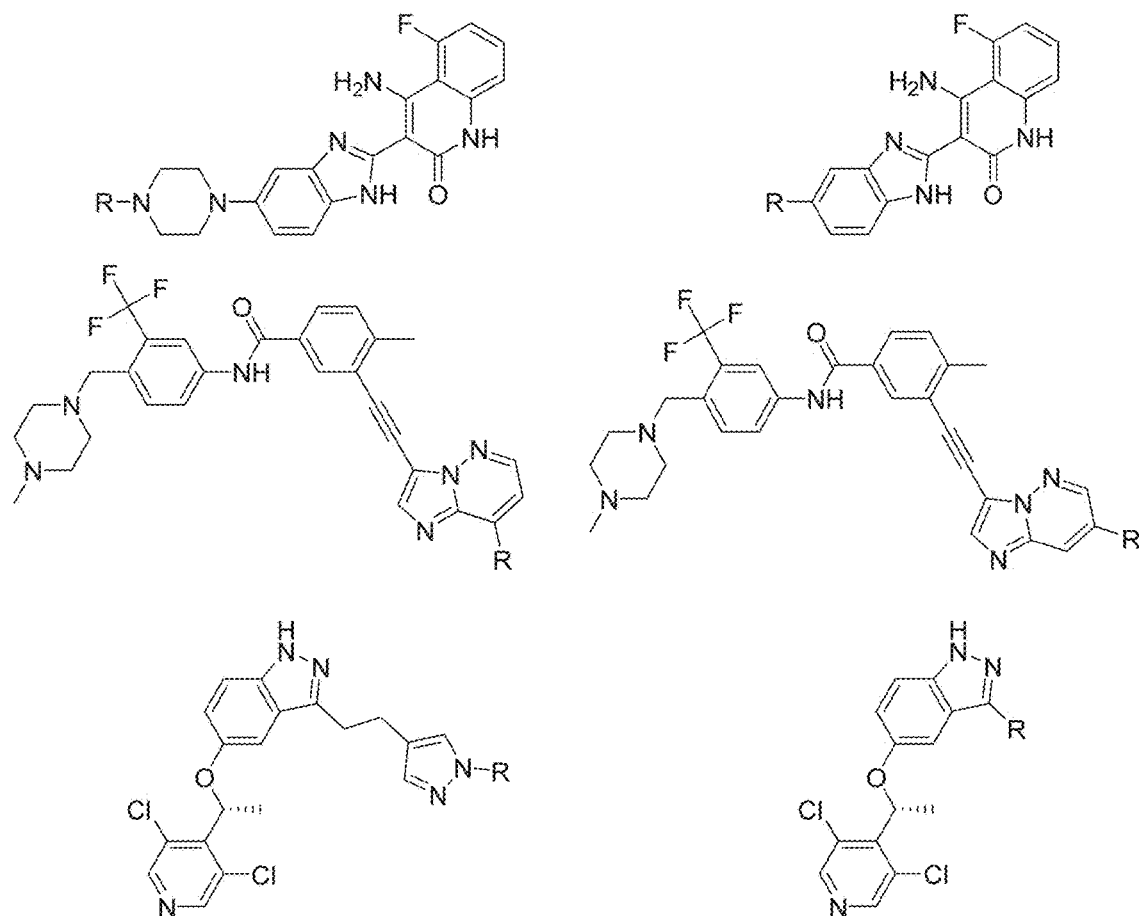
Figure 8H:
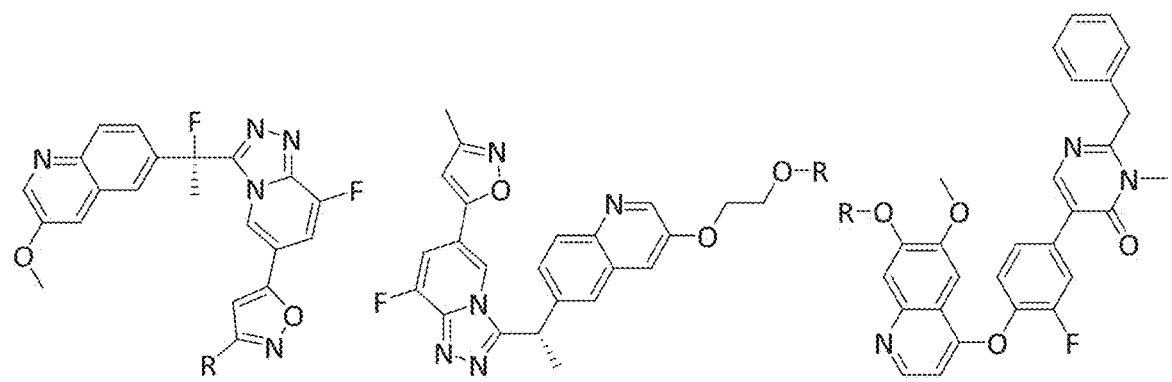
Figure 8I:
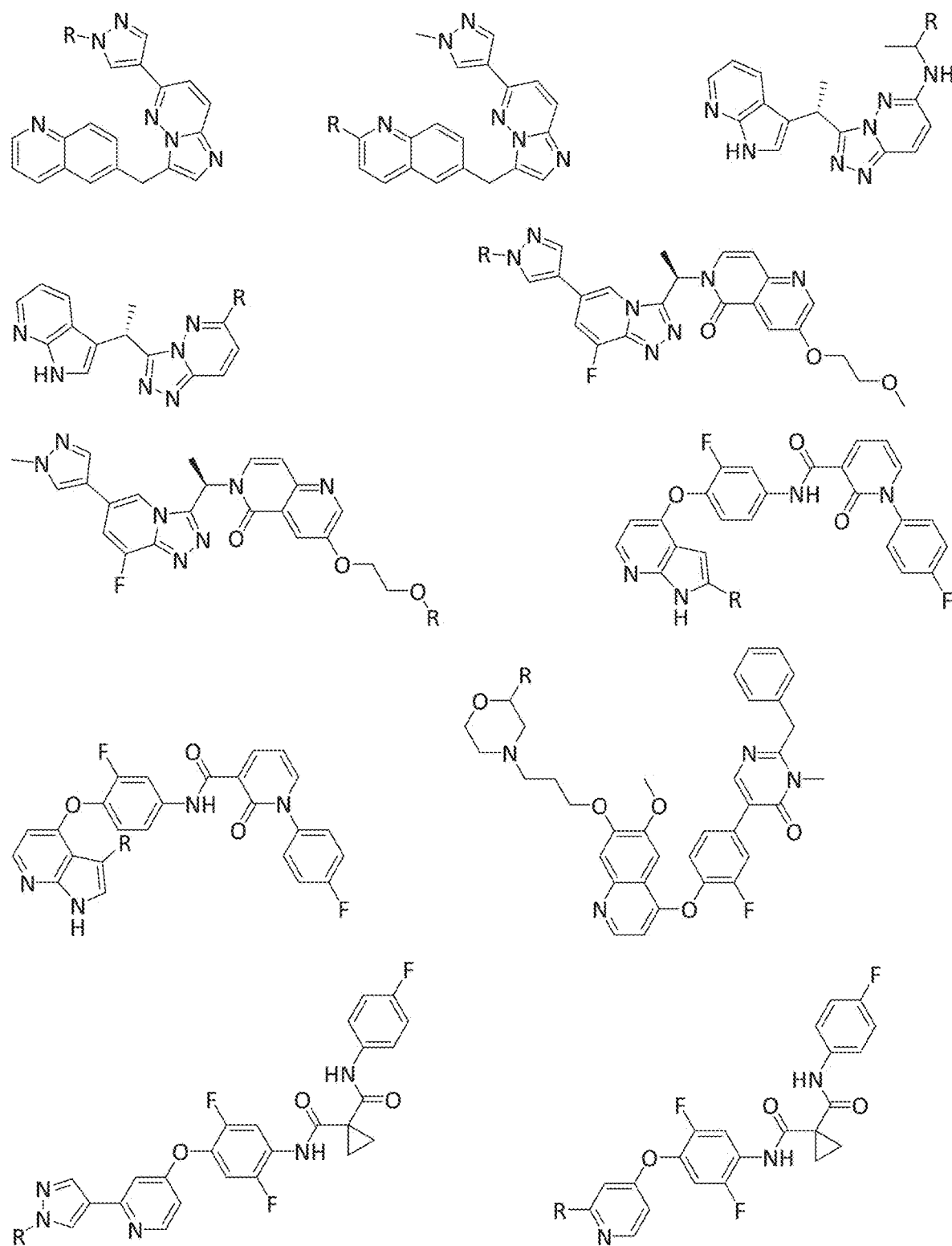
Figure 8J:
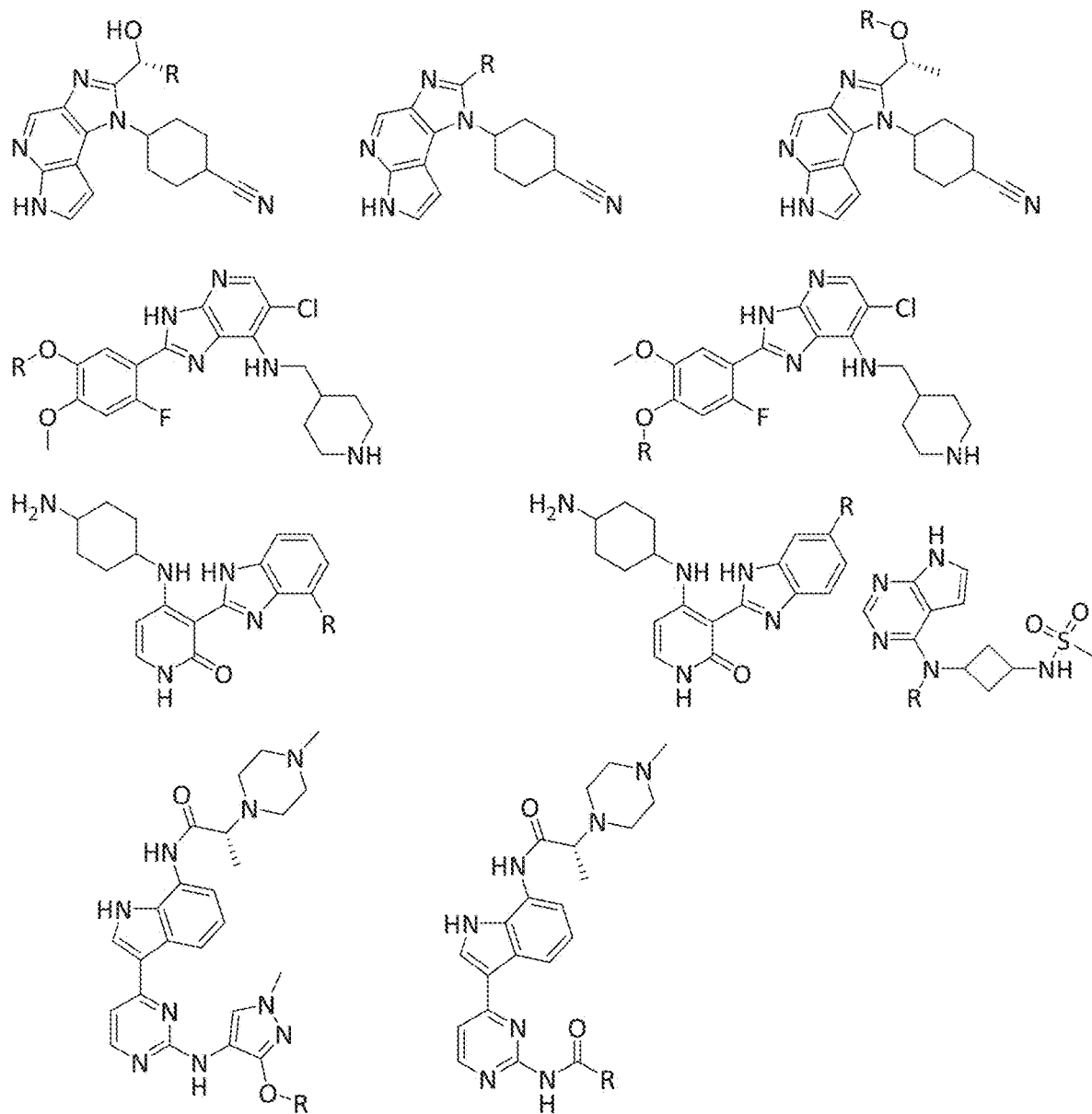
Figure 8K:
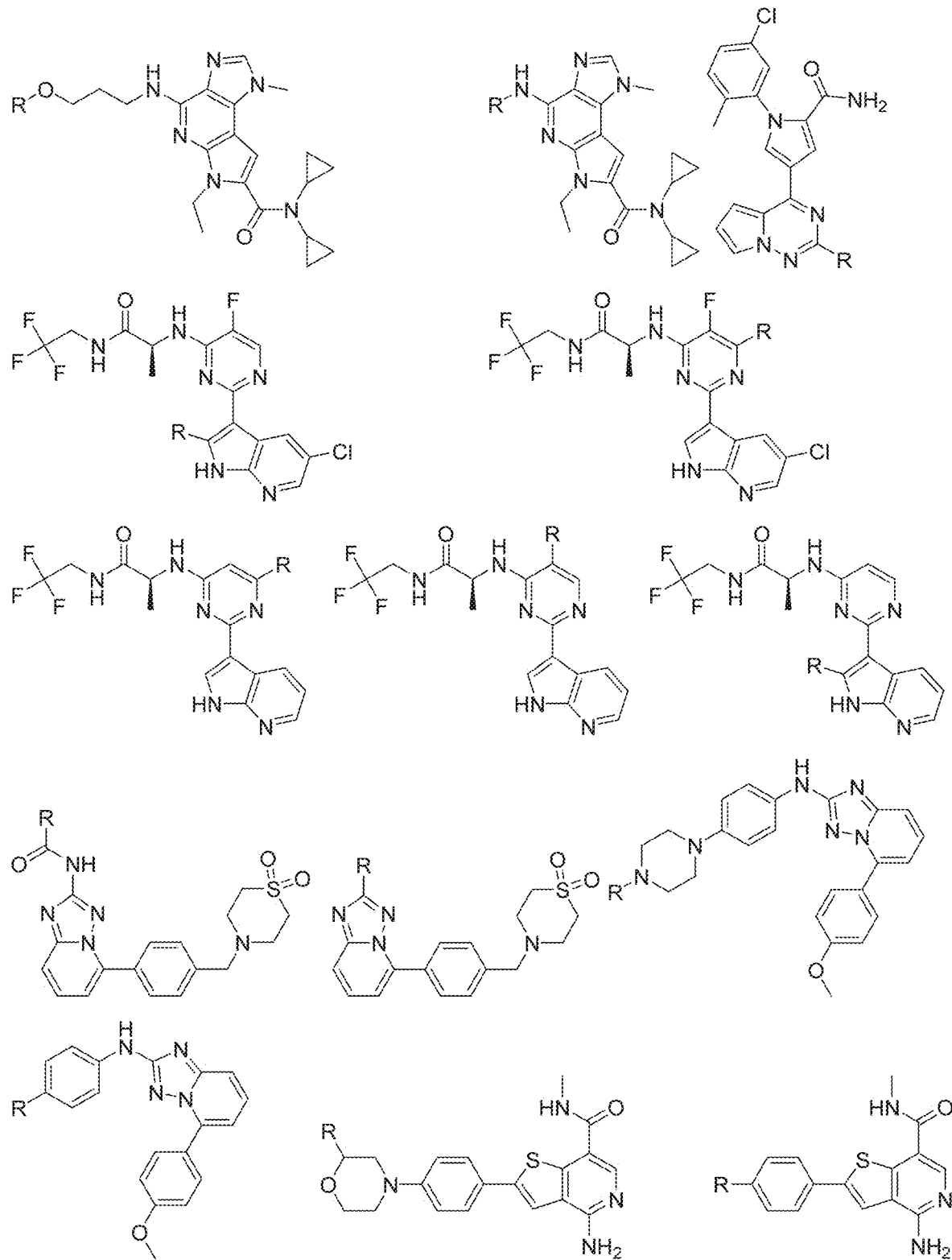
Figure 8L:
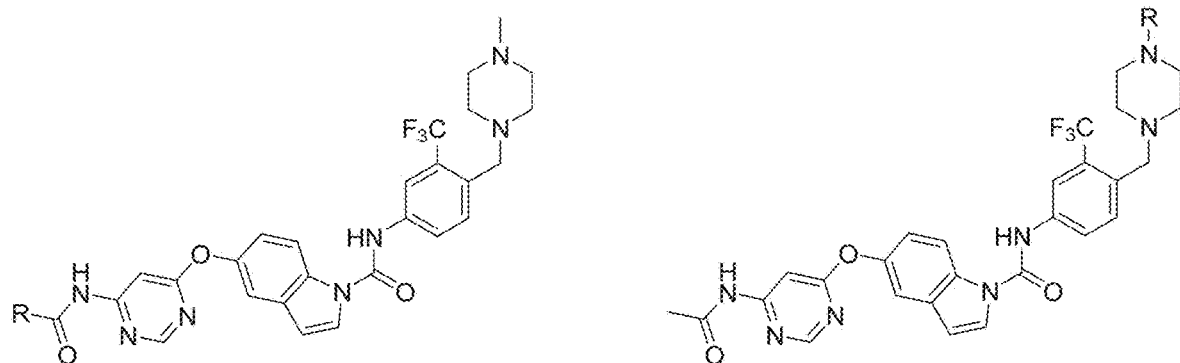
Figure 8M:
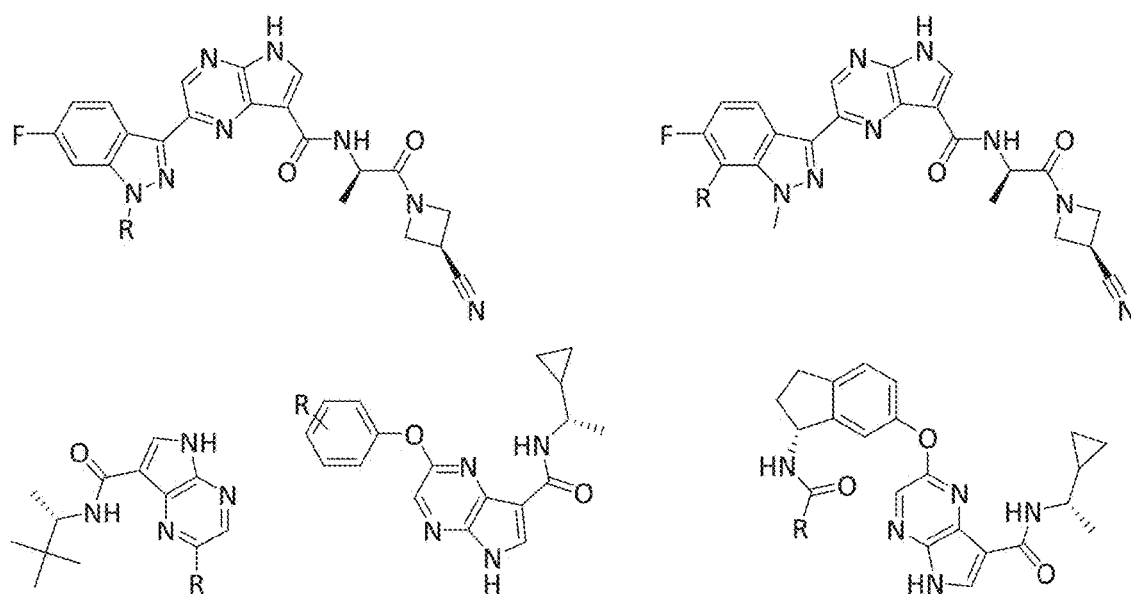
Figure 8N:
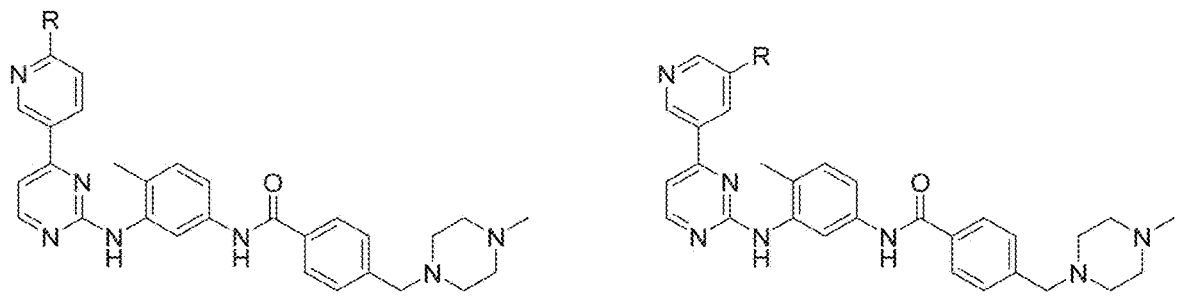
Figure 8O:
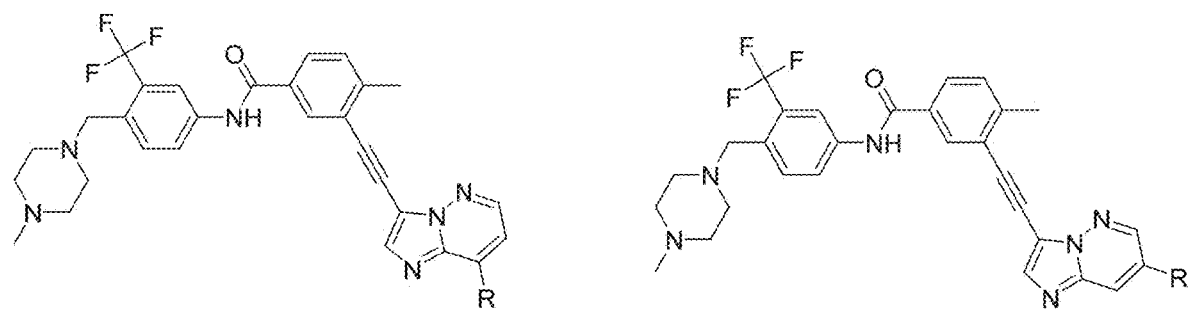
Figure 8P:
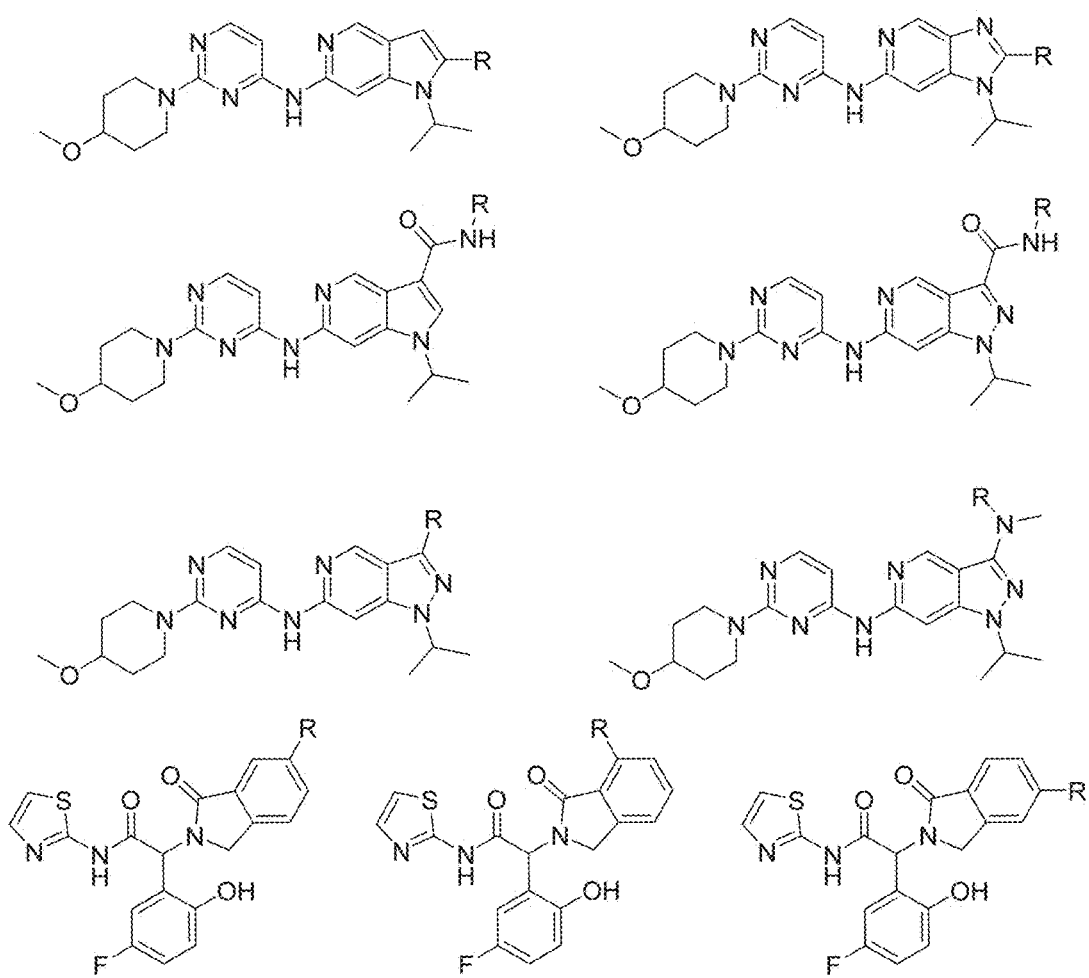
Figure 8Q:
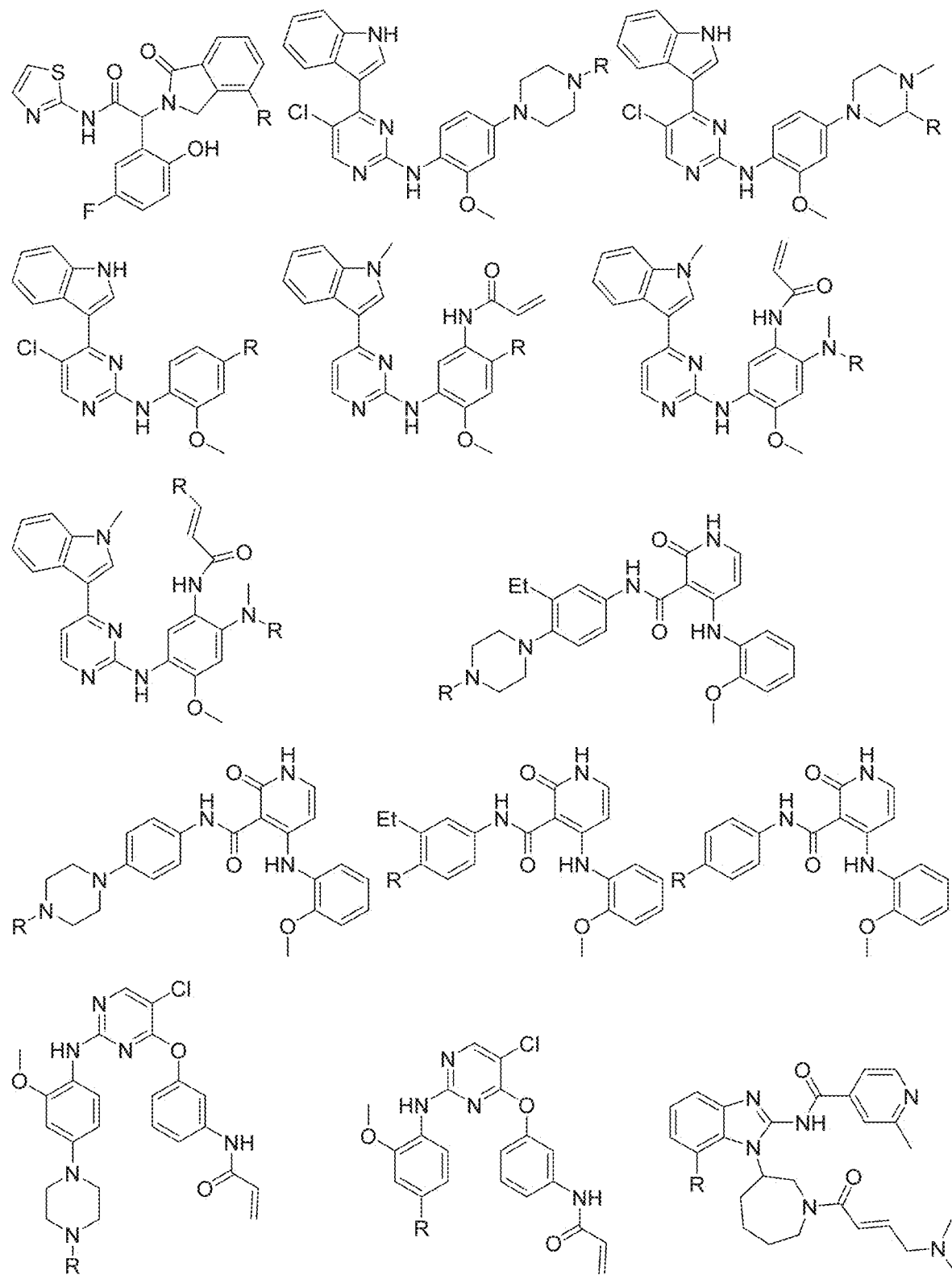
Figure 8R:
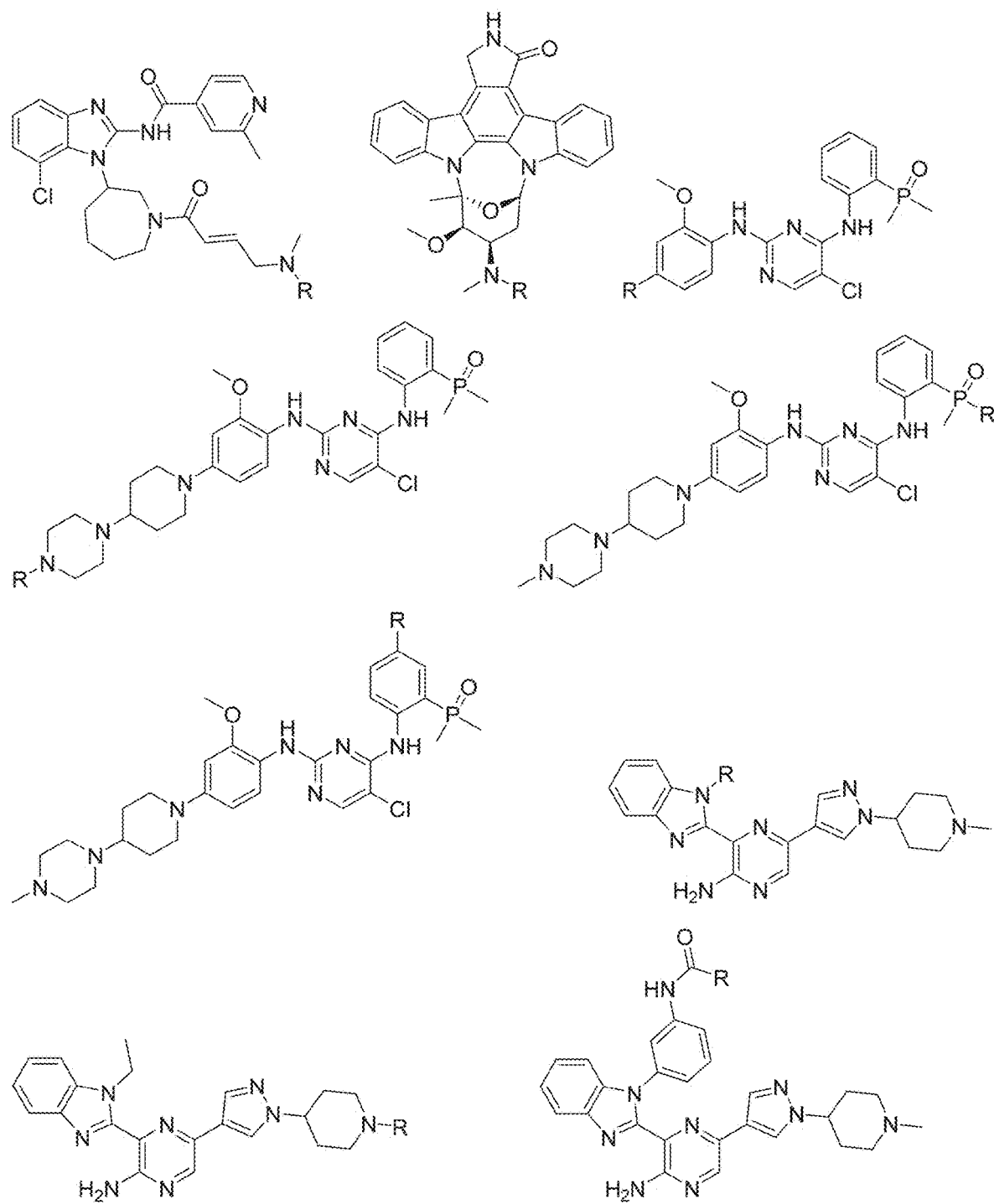
Figure 8S:
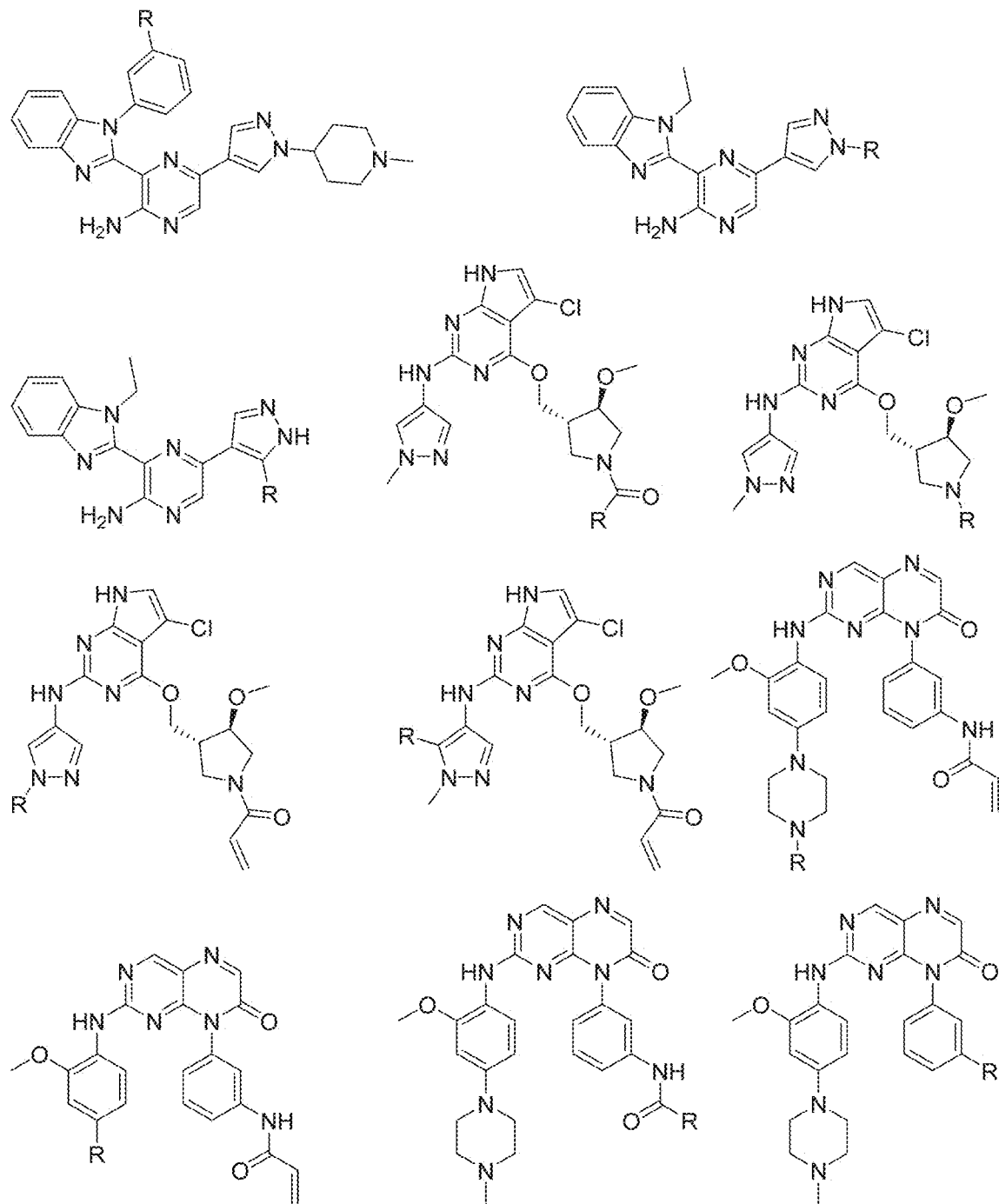
Figure 8T:
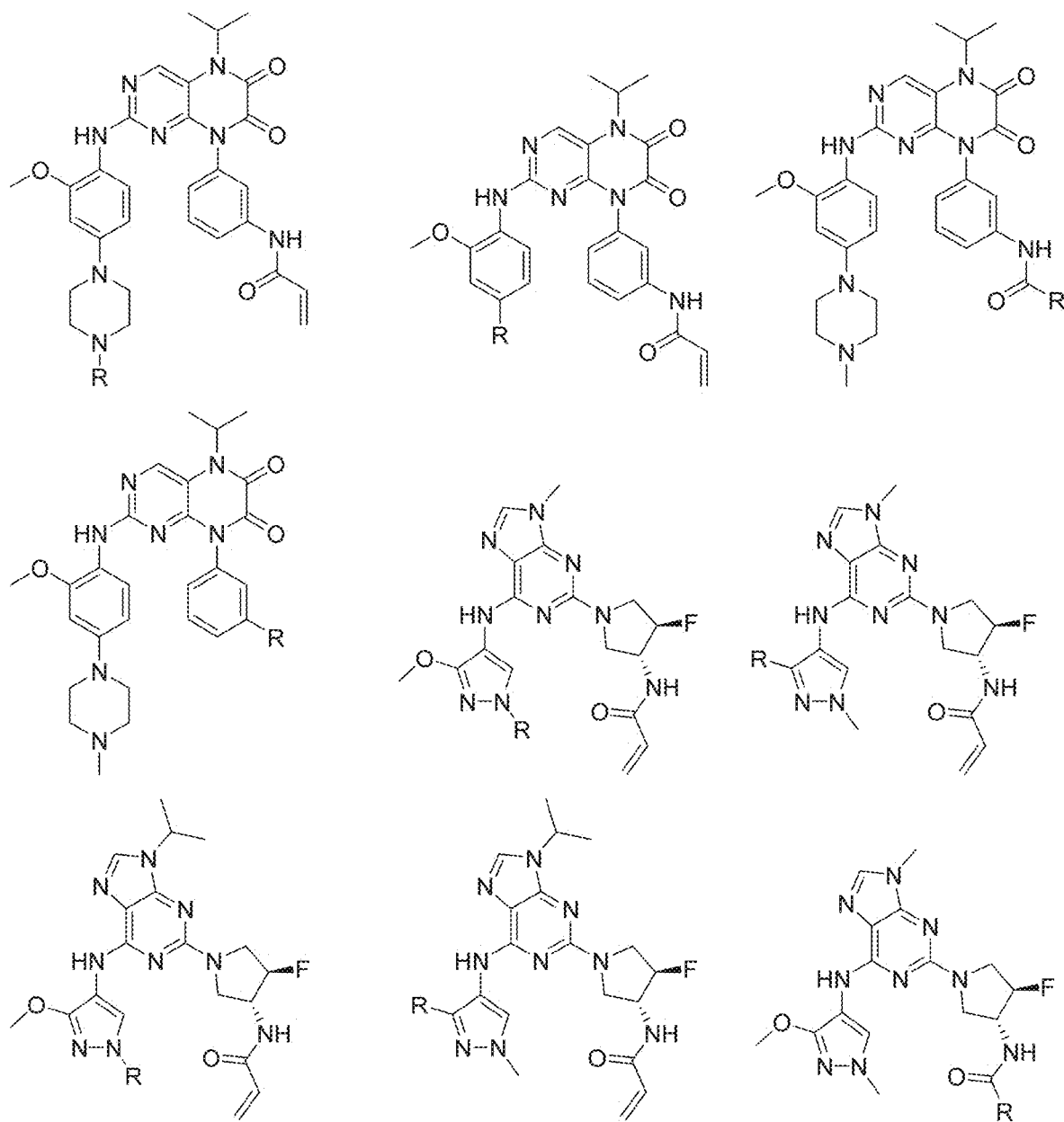
Figure 8U:
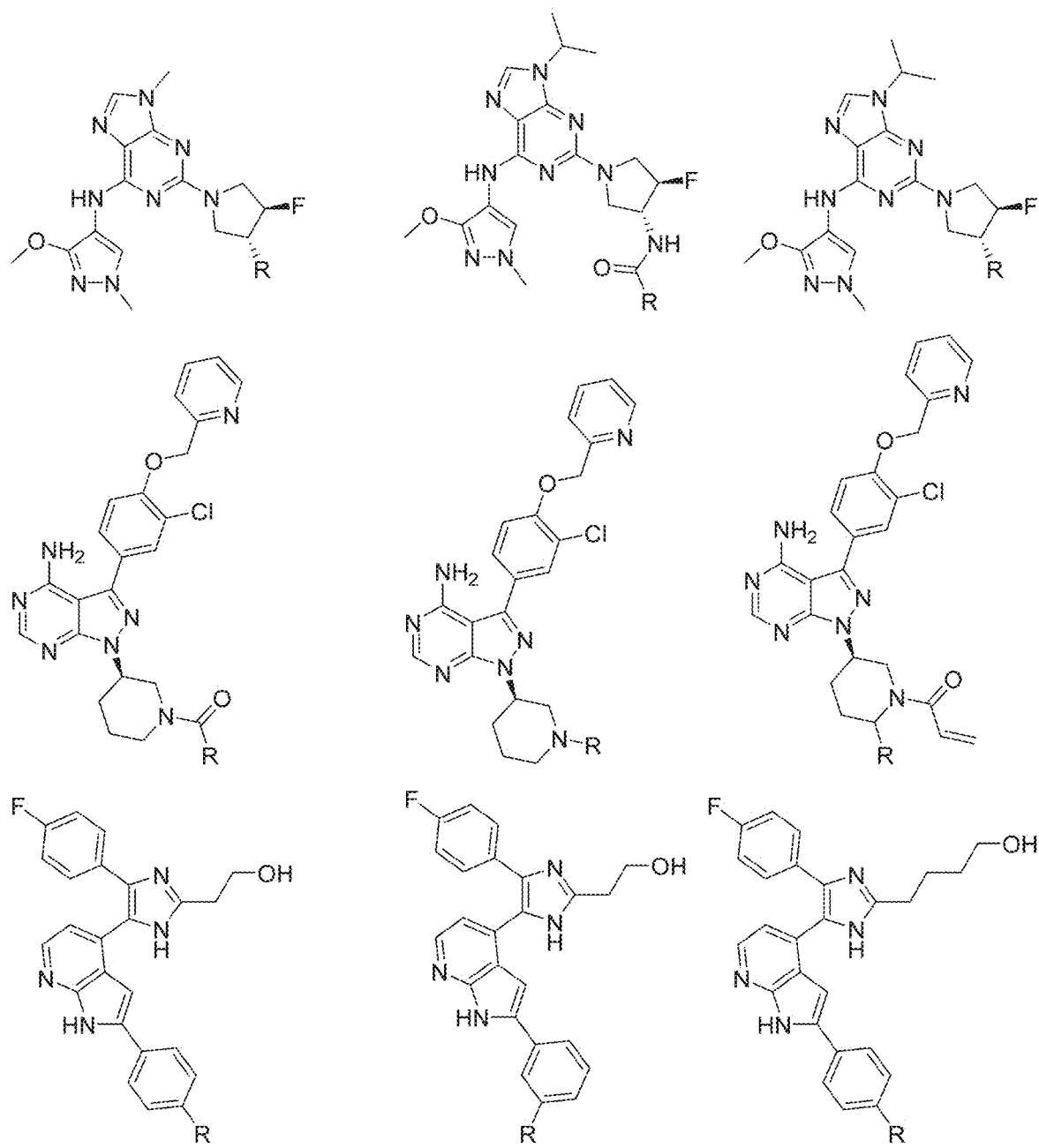
Figure 8V:
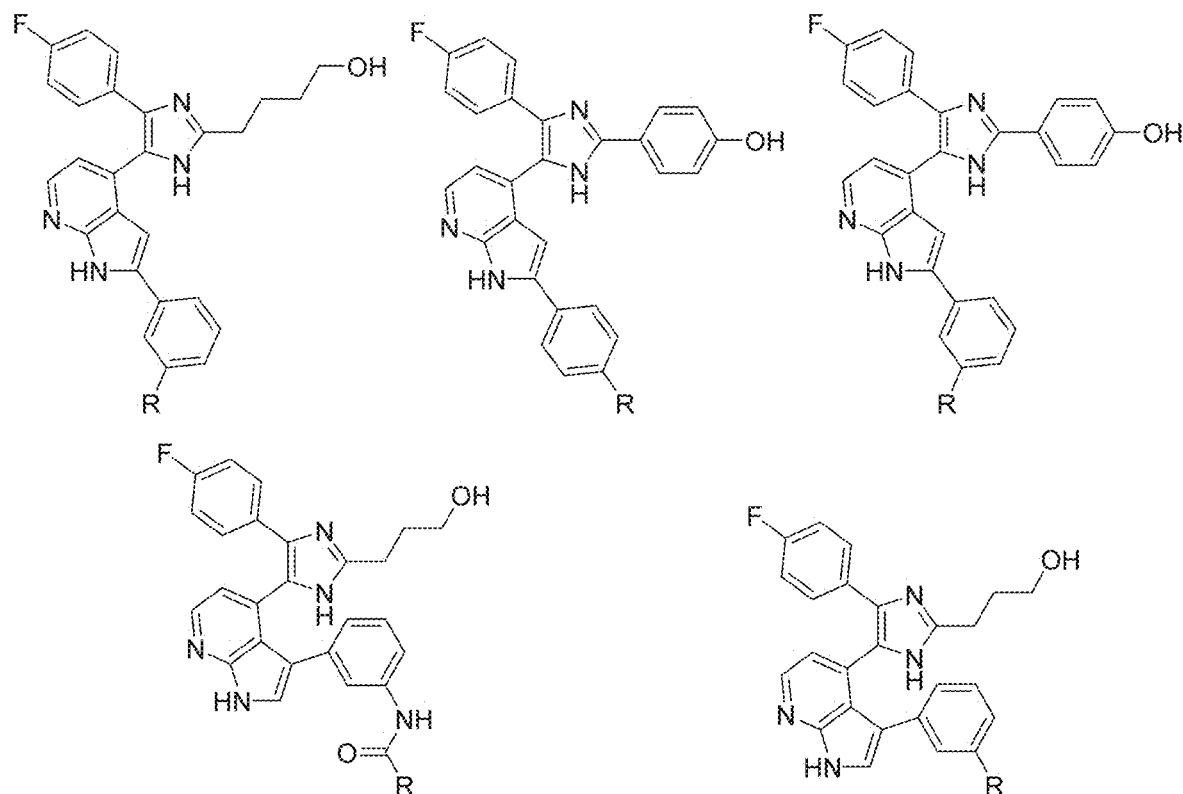
Figure 8W:
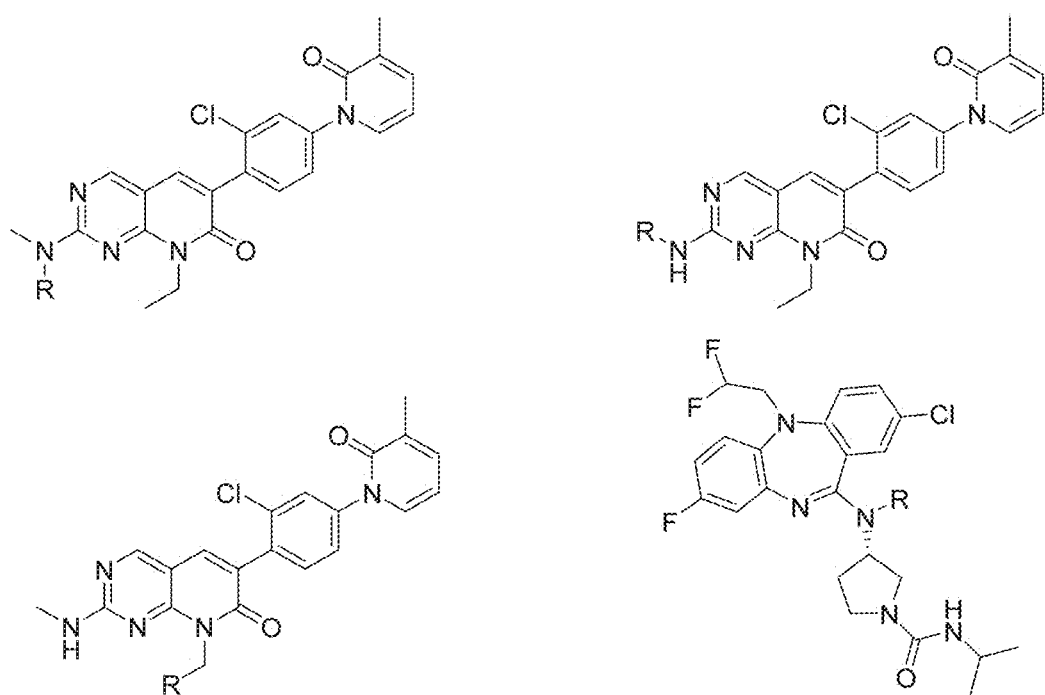
Figure 8X:
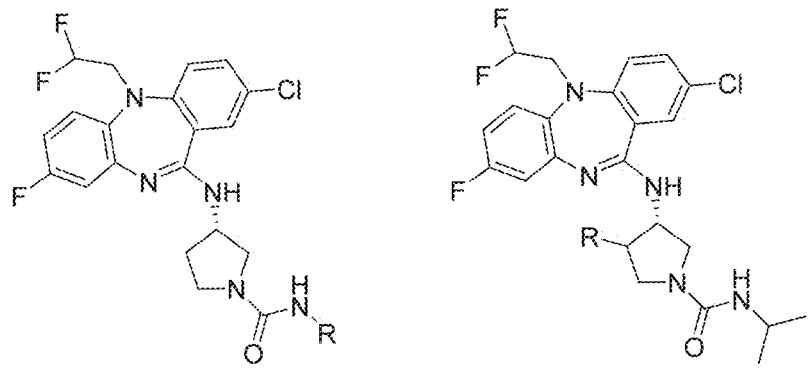
Figure 8Y:
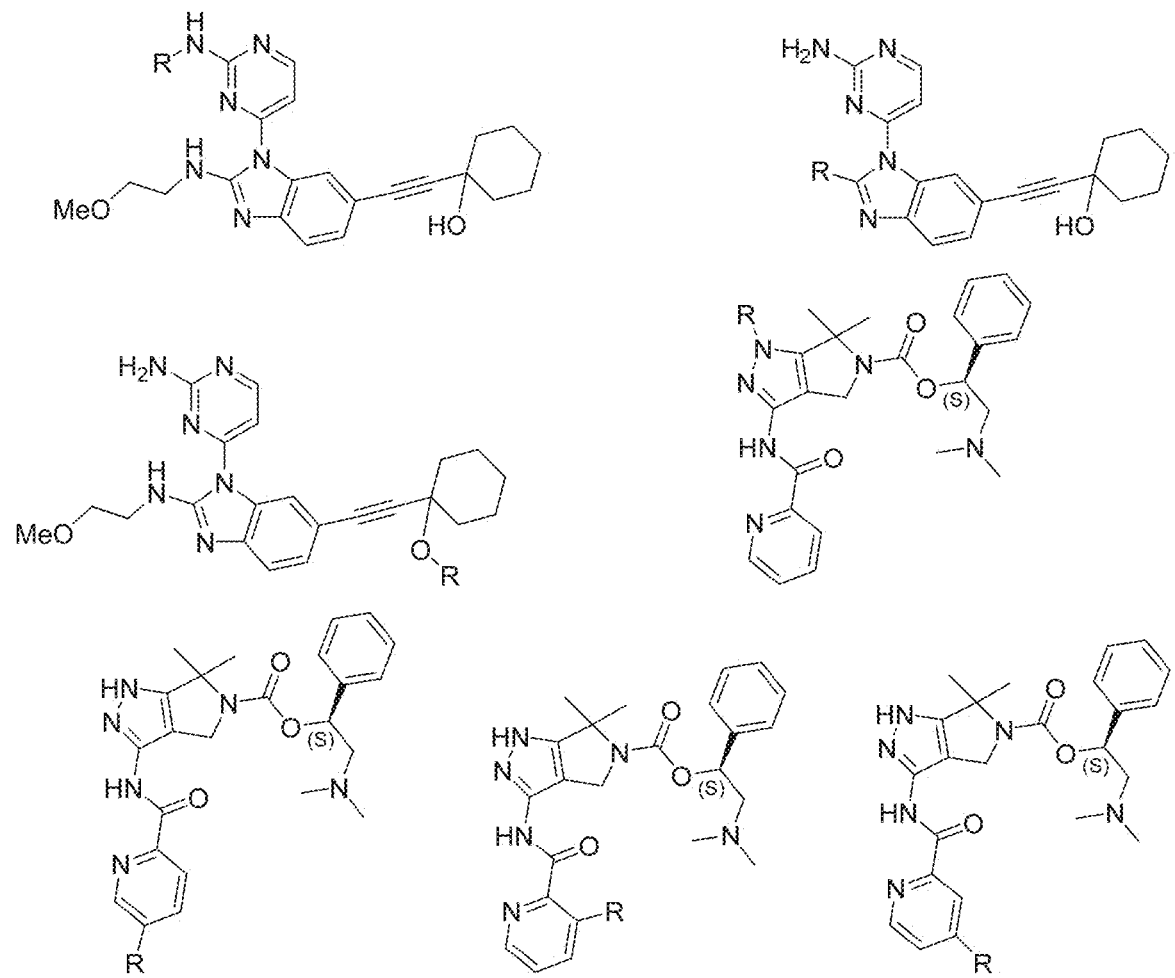
Figure 8Z:
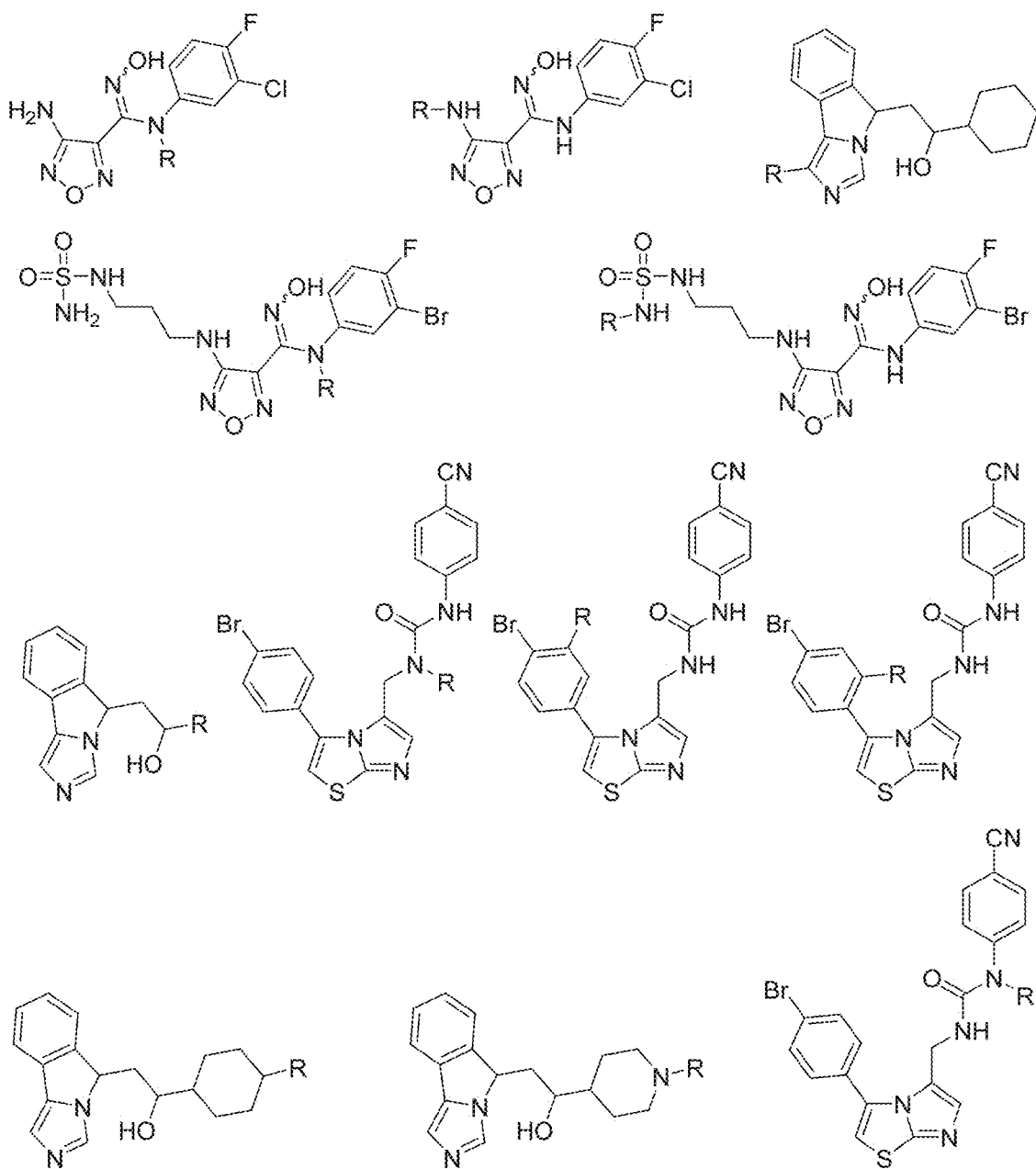

FIG. 8Z-8AA present examples of TNIK Targeting Ligands wherein R is the point at which the Linker is attached. For additional examples and related ligands, see, the crystal structure PDB 2x7f; the crystal structures PDB 5ax9 and 5d7a; and, related ligands described in Masuda, M. et al. "TNIK inhibition abrogates colorectal cancer stemness." *Nat Commun* 7: 12586-12586 (2016).

FIG. 8BB-8CC present examples of NTRK1, NTRK2, and NTRK3 Targeting Ligands wherein R is the point at which the Linker is attached. For additional examples and related ligands, see, the crystal structure PDB 4aoj and related ligands described in Wang, T. et al. "Discovery of Disubstituted Imidazo[4,5-B]Pyridines and Purines as Potent Trka Inhibitors." *ACS Med. Chem. Lett.* 3: 705 (2012); the crystal structures PDB 4pmm, 4pmp, 4pms and 4pmt and related ligands described in Stachel, S. J. et al. "Maximizing diversity from a kinase screen: identification of novel and selective pan-Trk inhibitors for chronic pain." *J. Med. Chem.* 57: 5800-5816 (2014); the crystal structures PDB 4yps and 4yne snd related ligands described in Choi, H. S. et al. "(R)-2-Phenylpyrrolidine Substituted Imidazopyridazines: A New Class of Potent and Selective Pan-TRK Inhibitors." *ACS Med. Chem. Lett.* 6: 562-567 (2015); the crystal structures PDB 4at5 and 4at3 and related ligands described in Bertrand, T. et al. "The Crystal Structures of Trka and Trkb Suggest Key Regions for Achieving Selective Inhibition." *J. Mol. Biol.* 423: 439 (2012); and, the crystal structures PDB 3v5q and 4ymj and related ligands described in Albaugh, P. et al. "Discovery of GNF-5837, a selective TRK Inhibitor with efficacy in rodent cancer tumor models." *ACS Med. Chem. Lett.* 3: 140-145 (2012) and Choi, H. S. et al. "(R)-2-Phenylpyrrolidine Substitute Imidazopyridazines: a New Class of Potent and Selective Pan-TRK Inhibitors." *ACS Med Chem Lett* 6: 562-567 (2015).

FIG. 8DD-8EE present examples of FGFR1 Targeting Ligands wherein R is the point at which the Linker is attached. For additional examples and related ligands, see, the crystal structures PDB 3tto and 2fgi and related ligands described in Brison, Y. et al. "Functional and structural characterization of alpha-(1-2) branching sucrase derived from DSR-E glucansucrase." *J. Biol. Chem.* 287: 7915-7924 (2012) and Mohammadi, M. et al. "Crystal structure of an angiogenesis inhibitor bound to the FGF receptor tyrosine kinase domain." *EMBO J.* 17: 5896-5904 (1998); the crystal structure PDB 4fb3; the crystal structure PDB 4rwk and related ligands described in Harrison, C. et al. "Polyomavirus large T antigen binds symmetrical repeats at the viral origin in an asymmetrical manner." *J. Virol.* 87: 13751-13759 (2013); the crystal structure PDB 4rwl and related ligands described in Sohl, C. D. et al. "Illuminating the Molecular Mechanisms of Tyrosine Kinase Inhibitor Resistance for the FGFR1 Gatekeeper Mutation: The Achilles' Heel of Targeted Therapy." *ACS Chem. Biol.* 10: 1319-1329 (2015); the crystal structure PDB 4uwc; the crystal structure PDB 4v01 and related ligands described in Tucker, J. A. et al. "Structural Insights Into Fgfr Kinase Isoform Selectivity: Diverse Binding Modes of Azd4547 and Ponatinib in Complex with Fgfr1 and Fgfr4." *Structure* 22: 1764 (2014); the crystal structure PDB 5a46 and related ligands described in Klein, T. et al. "Structural and Dynamic Insights Into the Energetics of Activation Loop Rearrangement in Fgfr1 Kinase." *Nat. Commun.* 6: 7877 (2015); and, the crystal structure PDB 5ew8 and related ligands described in Patani, H. et al. "Landscape of activating cancer mutations in FGFR kinases and their differential responses to inhibitors in clinical use." *Oncotarget* 7: 24252-24268 (2016).

FIG. 8FF presents examples of FGFR2 Targeting Ligands wherein R is the point at which the Linker is attached. For additional examples and related ligands, see, the crystal structure PDB 2pvf and related ligands described in Chen, H. et al. "A molecular brake in the kinase hinge region regulates the activity of receptor tyrosine kinases." *Mol. Cell* 27: 717-730 (2007).

FIG. 8GG presents examples of FGFR4 Targeting Ligands wherein R is the point at which the Linker is attached. For additional examples and related ligands, see, the crystal structure PDB 4tyi and related ligands described in Lesca, E. et al. "Structural analysis of the human fibroblast growth factor receptor 4 kinase." *J. Mol. Biol.* 426: 3744-3756 (2014).

FIG. 8HH-8II present examples of MET Targeting Ligands wherein R is the point at which the Linker is attached. For additional examples and related ligands, see, the crystal structures PDB 3qti and 3zcl; the crystal structures PDB 4xmo, 4xyf, and 3zcl and related ligands described in Peterson, E. A. et al. "Discovery of Potent and Selective 8-Fluorotriazolopyridine c-Met Inhibitors." *J. Med. Chem.* 58: 2417-2430 (2015) and Cui, J. J. et al. "Lessons from (S)-6-(1-(6-(1-Methyl-1H-Pyrazol-4-Yl)-[1, 2, 4]Triazolo[4,3-B]Pyridazin-3-Yl)Ethyl)Quinoline (Pf-04254644), an Inhibitor of Receptor Tyrosine Kinase C-met with High Protein Kinase Selectivity But Broad Phosphodiesterase Family Inhibition Leading to Myocardial Degeneration in Rats." *J. Med. Chem.* 56: 6651 (2013); the crystal structure PDB 5eyd and related ligands described in Boezio, A. A. et al. "Discovery of (R)-6-(1-(8-Fluoro-6-(1-methyl-1H-pyrazol-4-yl)-[1,2,4]triazolo[4,3-a]pyridin-3-yl)ethyl)-3-(2-methoxyethoxy)-1,6-naphthyridin-5 (6H)-one (AMG 337), a Potent and Selective Inhibitor of MET with High Unbound Target Coverage and Robust In Vivo Antitumor Activity." *J. Med. Chem.* 59: 2328-2342 (2016); the crystal structure PDB 3ce3 and related ligands described in Kim, K. S. et al. "Discovery of pyrrolopyridine-pyridone based inhibitors of Met kinase: synthesis, X-ray crystallographic analysis, and biological activities." *J. Med. Chem.* 51: 5330-5341 (2008); the crystal structure PDB 2rfn and related ligands described in Bellon, S. F. et al. "c-Met inhibitors with novel binding mode show activity against several hereditary papillary renal cell carcinoma-related mutations." *J. Biol. Chem.* 283: 2675-2683 (2008); and, the crystal structure PDB 5dg5 and related ligands described in Smith, B. D. et al "Altiratinib Inhibits Tumor Growth, Invasion, Angiogenesis, and Microenvironment-Mediated Drug Resistance via Balanced Inhibition of MET, TIE2, and VEGFR2.". *Mol. Cancer Ther.* 14: 2023-2034 (2015).

FIG. 8JJ presents examples of JAK1 Targeting Ligands wherein R is the point at which the Linker is attached. For additional examples and related ligands, see, the crystal structure PDB 4ivd and related ligands described in Zak, M. et al. "Identification of C-2 Hydroxyethyl Imidazopyrrolopyridines as Potent JAK1 Inhibitors with Favorable Physicochemical Properties and High Selectivity over JAK2." *J. Med. Chem.* 56: 4764-4785 (2013); the crystal structure PDB 5ele and related ligands described in Vasbinder, M. M. et al. "Identification of azabenzimidazoles as potent JAK1 selective inhibitors." *Bioorg. Med. Chem. Lett.* 26: 60-67 (2016); the crystal structure PDB 5hx8 and related ligands described in Simov, V., et al. "Structure-based design and development of (benz)imidazole pyridones as JAK1-selective kinase inhibitors." *Bioorg. Med. Chem. Lett.* 26: 1803-1808 (2016); the crystal structure PDB 5hx8 and related ligands described in Caspers, N. L. et al. "Development of a high-throughput crystal structure-determination platform for JAK1 using a novel metal-chelator soaking system". *Acta Crystallogr.* Sect. F 72: 840-845 (2016); and, Kettle, J. G. "Discovery of the JAK1 selective kinase inhibitor AZD4205", AACR National Meeting, April 2017.

FIG. 8KK-8LL present examples of JAK2 Targeting Ligands wherein R is the point at which the Linker is attached. For additional examples and related ligands, see, the crystal structure PDB 3ugc and related ligands described in Andraos, R. et al. "Modulation of activation-loop phosphorylation by JAK inhibitors is binding mode dependent." *Cancer Discov* 2: 512-523 (2012); the crystal structures PDB 5cf4, 5cf5, 5cf6 and 5cf8 and related ligands described in Hart, A. C. et al. "Structure-Based Design of Selective Janus Kinase 2 Imidazo[4,5-d]pyrrolo[2,3-b]pyridine Inhibitors." *ACS Med. Chem. Lett.* 6: 845-849 (2015); the crystal structure PDB 5aep and related ligands described in Brasca, M. G. et al "Novel Pyrrole Carboxamide Inhibitors of Jak2 as Potential Treatment of Myeloproliferative Disorders" *Bioorg. Med. Chem.* 23: 2387 (2015); the crystal structures PDB 4ytf, 4yth and 4yti and related ligands described in Farmer, L. J. et al. "Discovery of VX-509 (Decernotinib): A Potent and Selective Janus Kinase 3 Inhibitor for the Treatment of Autoimmune Diseases." *J. Med. Chem.* 58: 7195-7216 (2015); the crystal structure PDB 4ytf, 4yth, 4yti and related ligands described in Menet, C. J. et al. "Triazolopyridines as Selective JAK1 Inhibitors: From Hit Identification to GLPG0634." *J. Med. Chem.* 57: 9323-9342 (2014); the crystal structure PDB 4ji9 and related ligands described in Siu, M. et al. "2-Amino-[1,2,4]triazolo[1,5-a]pyridines as JAK2 inhibitors." *Bioorg. Med. Chem. Lett.* 23: 5014-5021 (2013); and, the crystal structures PDB 3io7 and 3iok and related ligands described in Schenkel, L. B. et al. "Discovery of potent and highly selective thienopyridine janus kinase 2 inhibitors." *J. Med. Chem.* 54: 8440-8450 (2011).

FIG. 8MM presents examples of JAK3 Targeting Ligands wherein R is the point at which the Linker is attached. For additional examples and related ligands, see, the crystal structure PDB 3zc6 and related ligands described in Lynch, S. M. et al. "Strategic Use of Conformational Bias and Structure Based Design to Identify Potent Jak3 Inhibitors with Improved Selectivity Against the Jak Family and the Kinome." *Bioorg. Med. Chem. Lett.* 23: 2793 (2013); and, the crystal structures PDB 4hvd, 4i6q, and 3zep and related ligands described in Soth, M. et al. "3-Amido Pyrrolopyrazine JAK Kinase Inhibitors: Development of a JAK3 vs JAK1 Selective Inhibitor and Evaluation in Cellular and in Vivo Models." *J. Med. Chem.* 56: 345-356 (2013) and Jaime-Figueroa, S. et al. "Discovery of a series of novel 5H-pyrrolo[2,3-b]pyrazine-2-phenyl ethers, as potent JAK3 kinase inhibitors." *Bioorg. Med. Chem. Lett.* 23: 2522-2526 (2013).

FIG. 8NN-8OO present examples of KIT Targeting Ligands wherein R is the point at which the Linker is attached. For additional examples and related ligands, see, the crystal structure PDB 1t46 and related ligands described in Mol, C. D. et al. "Structural basis for the autoinhibition and STI-571 inhibition of c-Kit tyrosine kinase." *J. Biol. Chem.* 279: 31655-31663 (2004); and, the crystal structure PDB 4uOi and related ligands described in Garner, A. P. et al. "Ponatinib Inhibits Polyclonal Drug-Resistant KIT Oncoproteins and Shows Therapeutic Potential in Heavily Pretreated Gastrointestinal Stromal Tumor (GIST) Patients." *Clin. Cancer Res.* 20: 5745-5755 (2014).

FIG. 8PP-8VV present examples of EGFR Targeting Ligands wherein R is the point at which the Linker is attached. For additional examples and related ligands, see, the crystal structures PDB 5hcy, 4rj4, and 5cav; Heald, R., "Noncovalent Mutant Selective Epidermal Growth Factor Receptor Inhibitors: A Lead Optimization Case Study", *J. Med. Chem.* 58, 8877-8895 (2015); Hanano, E. J., "Discovery of Selective and Noncovalent Diaminopyrimidine-Based Inhibitors of Epidermal Growth Factor Receptor Containing the T790M Resistance Mutation." *J. Med. Chem.*, 57, 10176-10191 (2014); Chan, B. K. et al. "Discovery of a Noncovalent, Mutant-Selective Epidermal Growth Factor Receptor Inhibitor" *J. Med. Chem.* 59, 9080 (2016); the crystal structure PDB 5d41 and related ligands described in Jia, Y. et al., "Overcoming EGFR(T790M) and EGFR (C797S) resistance with mutant-selective allosteric inhibitors" *Nature* 534, 129 (2016); Ward, R. A. "Structure- and reactivity-based development of covalent inhibitors of the activating and gatekeeper mutant forms of the epidermal growth factor receptor (EGFR)" *J. Med. Chem.* 56, 7025-7048 (2013); the crystal structure PDB 4zau and related ligands described in "Discovery of a Potent and Selective EGFR Inhibitor (AZD9291) of Both Sensitizing and T790M Resistance Mutations That Spares the Wild Type Form of the Receptor" *J. Med. Chem.*, 57 (20), 8249-8267 (2014); the crystal structure PDB 5em7 and related ligands described in Bryan, M. C. et al. "Pyridones as Highly Selective, Noncovalent Inhibitors of T790M Double Mutants of EGFR" *ACS Med. Chem. Lett.*, 7 (1), 100-104 (2016); the crystal structure PDB 3IKA and related ligands described in Zhou, W. et al. "Novel mutant-selective EGFR kinase inhibitors against EGFR T790M" *Nature* 462(7276), 1070-1074 (2009); the crystal structure see PDB 5feq and related ligands described in Lelais, G., J. "Discovery of (R,E)-N-(7-Chloro-1-(1-[4-(dimethylamino)but-2-enoyl]azepan-3-yl)-1H-benzo[d]imidazol-2-yl)-2-methylisonicotinamide (EGF816), a Novel, Potent, and WT Sparing Covalent Inhibitor of Oncogenic (L858R, ex19del) and Resistant (T790M) EGFR Mutants for the Treatment of EGFR Mutant Non-Small-Cell Lung Cancers" *Med. Chem.*, 59 (14), 6671-6689 (2016); Lee, H.-J. "Noncovalent Wild-type-Sparing Inhibitors of EGFR T790M" *Cancer Discov.* 3(2): 168-181 (2013); the crystal structure PDB 5j7h and related ligands described in Huang, W-S. et al. "Discovery of Brigatinib (AP26113), a Phosphine Oxide-Containing, Potent, Orally Active Inhibitor of Anaplastic Lymphoma Kinase." *J. Med. Chem.* 59: 4948-4964 (2016); the crystal structure PDB 4v0g and related ligands described in Hennessy, E. J. et al. "Utilization of Structure-Based Design to Identify Novel, Irreversible Inhibitors of EGFR Harboring the T790M Mutation." *ACS. Med. Chem. Lett.* 7: 514-519 (2016); the crystal structure PDB 5hg7 and related ligands described in Cheng, H. "Discovery of 1-{(3R,4R)-3-[({5-Chloro-2-[(1-methyl-1H-pyrazol-4-yl)amino]-7H-pyrrolo[2,3-d]pyrimidin-4-yl}oxy)methyl]-4-methoxypyrrolidin-1-yl}prop-2-en-1-one (PF-06459988), a Potent, WT Sparing, Irreversible Inhibitor of T790M-Containing EGFR Mutants." *J. Med. Chem.* 59: 2005-2024 (2016); Hao, Y. "Discovery and Structural Optimization of N5-Substituted 6,7-Dioxo-6,7-dihydropteridines as Potent and Selective Epidermal Growth Factor Receptor (EGFR) Inhibitors against L858R/T790M Resistance Mutation." *J. Med. Chem.* 59: 7111-7124 (2016); the crystal structure PDB 5ug8, 5ug9, and 5ugc and related ligands described in Planken, S. "Discovery of N-((3R,4R)-

4-Fluoro-1-(6-((3-methoxy-1-methyl-1H-pyrazol-4-yl) amino)-9-methyl-9H-purin-2-yl)pyrrolidine-3-yl)acrylamide (PF-06747775) through Structure-Based Drug Design: A High Affinity Irreversible Inhibitor Targeting Oncogenic EGFR Mutants with Selectivity over Wild-Type EGFR." *J. Med. Chem.* 60: 3002-3019 (2017); the crystal structure PDB 5gnk and related ligands described in Wang, A. "Discovery of (R)-1-(3-(4-Amino-3-(3-chloro-4-(pyridin-2-ylmethoxy)phenyl)-1H-pyrazolo[3,4-d]pyrimidin-1-yl)piperidin-1-yl)prop-2-en-1-one (CHMFL-EGFR-202) as a Novel Irreversible EGFR Mutant Kinase Inhibitor with a Distinct Binding Mode." *J. Med. Chem.* 60: 2944-2962 (2017); and, Juchum, M. "Trisubstituted imidazoles with a rigidized hinge binding motif act as single digit nM inhibitors of clinically relevant EGFR L858R/T790M and L858R/T790M/C797S mutants: An example of target hopping." *J. Med. Chem.* DOI: 10.1021/acs.jmedchem.7b00178 (2017).

FIG. 8WW-8XX present examples of PAK1 Targeting Ligands wherein R is the point at which the Linker is attached. For additional examples and related ligands, see, Rudolph, J. et al. "Chemically Diverse Group I p21-Activated Kinase (PAK) Inhibitors Impart Acute Cardiovascular Toxicity with a Narrow Therapeutic Window." *J. Med. Chem.* 59, 5520-5541 (2016) and Karpov A S, et al. *ACS Med Chem Lett.* 22; 6(7):776-81 (2015).

FIG. 8YY presents examples of PAK4 Targeting Ligands wherein R is the point at which the Linker is attached. For additional examples and related ligands, see, Staben S T, et al. *J Med Chem.* 13; 57(3):1033-45 (2014) and Guo, C. et al. "Discovery of pyrroloaminopyrazoles as novel PAK inhibitors" *J. Med. Chem.* 55, 4728-4739 (2012).

FIG. 8ZZ-8AAA present examples of IDO Targeting Ligands wherein R is the point at which the Linker is attached. For additional examples and related ligands, see, Yue, E. W.; et al. "Discovery of potent competitive inhibitors of indoleamine 2,3-dioxygenase with in vivo pharmacodynamic activity and efficacy in a mouse melanoma model." *J. Med. Chem.* 52, 7364-7367 (2009); Tojo, S.; et al. "Crystal structures and structure, and activity relationships of imidazothiazole derivatives as IDO1 inhibitors." *ACS Med. Chem. Lett.* 5, 1119-1123 (2014); Mautino, M. R. et al. "NLG919, a novel indoleamine-2,3-dioxygenase (IDO)-pathway inhibitor drug candidate for cancer therapy" Abstract 491, AACR 104th Annual Meeting 2013; Apr. 6-10, 2013; Washington, D.C.; and, WO2012142237 titled "Fused imidazole derivatives useful as IDO inhibitors".

FIG. 8BBB-8EEE present examples of ERK1 and ERK2 Targeting Ligands wherein R is the point at which the Linker is attached. For additional examples and related ligands, see, the crystal structures PDB 5K4I and 5K4J and related ligands described in Blake, J. F. et al. "Discovery of (S)-1-(1-(4-Chloro-3-fluorophenyl)-2-hydroxyethyl)-4-(2-((1-methyl-1H-pyrazol-5-yl)amino)pyrimidin-4-yl)pyridin-2 (1H)-one (GDC-0994), an Extracellular Signal-Regulated Kinase 1/2 (ERK1/2) Inhibitor in Early Clinical Development" *J. Med. Chem.* 59: 5650-5660 (2016); the crystal structure PDB 5BVF and related ligands described in Bagdanoff, J. T. et al. "Tetrahydropyrrolo-diazepenones as inhibitors of ERK2 kinase" *Bioorg. Med. Chem. Lett.* 25, 3788-3792 (2015); the crystal structure PDB 4QYY and related ligands described in Deng, Y. et al. "Discovery of Novel, Dual Mechanism ERK Inhibitors by Affinity Selection Screening of an Inactive Kinase" *J. Med. Chem.* 57: 8817-8826 (2014); the crystal structures PDB 5HD4 and 5HD7 and the related ligands described in Jha, S. et al. "Dissecting Therapeutic Resistance to ERK Inhibition" *Mol. Cancer Ther.* 15: 548-559 (2016); the crystal structure PDB 4XJ0 and related ligands described in Ren, L. et al. "Discovery of highly potent, selective, and efficacious small molecule inhibitors of ERK1/2." *J. Med. Chem.* 58: 1976-1991 (2015); the crystal structures PDB 4ZZM, 4ZZN, 4ZZO and related ligands described in Ward, R. A. et al. "Structure-Guided Design of Highly Selective and Potent Covalent Inhibitors of Erk1/2." *J. Med. Chem.* 58: 4790 (2015); Burrows, F. et al. "KO-947, a potent ERK inhibitor with robust preclinical single agent activity in MAPK pathway dysregulated tumors" Poster #5168, AACR National Meeting 2017; Bhagwat, S. V. et al. "Discovery of LY3214996, a selective and novel ERK1/2 inhibitor with potent antitumor activities in cancer models with MAPK pathway alterations." AACR National Meeting 2017; the crystal structures PDB 3FHR and 3FXH and related ligands described in Cheng, R. et al. "High-resolution crystal structure of human Mapkap kinase 3 in complex with a high affinity ligand" *Protein Sci.* 19: 168-173 (2010); the crystal structures PDB 5NGU, 5NHF, 5NHH, 5NHJ, 5NHL, 5NHO, 5NHP, and 5NHV and related ligands described in Ward, R. A. et al. "Structure-Guided Discovery of Potent and Selective Inhibitors of ERK1/2 from a Modestly Active and Promiscuous Chemical Start Point." *J. Med. Chem.* 60, 3438-3450 (2017); and, the crystal structures PDB 3 SHE and 3R1N and related ligands described in Oubrie, A. et al. "Novel ATP competitive MK2 inhibitors with potent biochemical and cell-based activity throughout the series." *Bioorg. Med. Chem. Lett.* 22: 613-618 (2012).

FIG. 8FFF-8III present examples of ABL1 Targeting Ligands wherein R is the point at which the Linker is attached. For additional examples and related ligands, see, the crystal structure PDB 1fpu and 2e2b and related ligands described in Schindler, T., et al. "Structural mechanism for STI-571 inhibition of abelson tyrosine kinase", *Science* 289: 1938-1942 (2000); and Horio, T. et al. "Structural factors contributing to the Abl/Lyn dual inhibitory activity of 3-substituted benzamide derivatives", *Bioorg. Med. Chem. Lett.* 17: 2712-2717 (2007); the crystal structures PDB 2hzn and 2hiw and related ligands described in Cowan-Jacob, S. W. et al. "Structural biology contributions to the discovery of drugs to treat chronic myelogenous leukaemia", *Acta Crystallog. Sect. D* 63: 80-93 (2007) and Okram, B. et al. "A general strategy for creating", *Chem. Biol.* 13: 779-786 (2006); the crystal structure PDB 3cs9 and related ligands described in Weisberg, E. et al. "Characterization of AMN107, a selective inhibitor of native and mutant Bcr-Abl", *Cancer Cell* 7: 129-14 (2005); the crystal structure PDB 3ik3 and related ligands described in O'Hare, T. et al. "AP24534, a pan-BCR-ABL inhibitor for chronic myeloid leukemia, potently inhibits the T315I mutant and overcomes mutation-based resistance", *Cancer Cell* 16: 401-412 (2009); the crystal structure PDB 3mss and related ligands described in Jahnke, W. et al. "Binding or bending: distinction of allosteric Abl kinase agonists from antagonists by an NMR-based conformational assay", *J. Am. Chem. Soc.* 132: 7043-7048 (2010); the crystal structure PDB 3oy3 and related ligands described in Zhou, T. et al. "Structural Mechanism of the Pan-BCR-ABL Inhibitor Ponatinib (AP24534): Lessons for Overcoming Kinase Inhibitor Resistance", *Chem. Biol. Drug Des.* 77: 1-11 (2011); the crystal structures PDB 3qri and 3qrk and related ligands described in Chan, W. W. et al. "Conformational Control Inhibition of the BCR-ABL1 Tyrosine Kinase, Including the Gatekeeper T315I Mutant, by the Switch-Control Inhibitor DCC-2036", *Cancer Cell* 19: 556-568 (2011); the crystal structure PDB 5hu9 and 2f4j and related ligands described in Liu, F. et al. "Discovery and characterization of a novel potent type II native and mutant BCR-ABL inhibitor (CHMFL-074) for Chronic Myeloid Leukemia (CML)", *Oncotarget* 7: 45562-45574 (2016) and Young, M. A. et al. "Structure of the kinase domain of an imatinib-resistant Abl mutant in complex with the Aurora kinase inhibitor VX-680*", Cancer Res.* 66: 1007-1014 (2006); the crystal structure PDB 2gqg and 2qoh and related ligands described in Tokarski, J. S. et al. "The Structure of Dasatinib (BMS-354825) Bound to Activated ABL Kinase Domain Elucidates Its Inhibitory Activity against Imatinib-Resistant ABL Mutants", *Cancer Res.* 66: 5790-5797 (2006); and Zhou, T. et al. "Crystal Structure of the T315I Mutant of Abl Kinase", *Chem. Biol. Drug Des.* 70: 171-181 (2007); the crystal structure PDB 2gqg and 2qoh and related ligands described in Tokarski, J. S. et al. "The Structure of Dasatinib (BMS-354825) Bound to Activated ABL Kinase Domain Elucidates Its Inhibitory Activity against Imatinib-Resistant ABL Mutants", *Cancer Res.* 66: 5790-5797 (2006) and Zhou, T. et al. "Crystal Structure of the T315I Mutant of Abl Kinase", *Chem. Biol. Drug Des.* 70: 171-181 (2007); the crystal structure PDB 2gqg and 2qoh and related ligands described in Tokarski, J. S. et al. "The Structure of Dasatinib (BMS-354825) Bound to Activated ABL Kinase Domain Elucidates Its Inhibitory Activity against Imatinib-Resistant ABL Mutants", *Cancer Res.* 66: 5790-5797 (2006) and Zhou, T. et al. "Crystal Structure of the T315I Mutant of Abl Kinase", *Chem. Biol. Drug Des.* 70: 171-181(2007); the crystal structures PDB 3dk3 and 3dk8 and related ligands described in Berkholz, D. S. et al. "Catalytic cycle of human glutathione reductase near 1 A resolution" *J. Mol. Biol.* 382: 371-384 (2008); the crystal structure PDB 3ue4 and related ligands described in Levinson, N. M. et al. "Structural and spectroscopic analysis of the kinase inhibitor bosutinib and an isomer of bosutinib binding to the abl tyrosine kinase domain", *Plos One* 7: e29828-e29828 (2012); the crystal structure PDB 4cy8 and related ligands described in Jensen, C. N. et al. "Structures of the Apo and Fad-Bound Forms of 2-Hydroxybiphenyl 3-Monooxygenase (Hbpa) Locate Activity Hotspots Identified by Using Directed Evolution", *Chembiochem* 16: 968 (2015); the crystal structure PDB 2hz0 and related ligands described in Cowan-Jacob, S. W. et al. "Structural biology contributions to the discovery of drugs to treat chronic myelogenous leukaemia", *Acta Crystallogr D Biol Crystallogr.* 63(Pt 1):80-93 (2007); the crystal structure PDB 3pyy and related ligands described in Yang, J. et al. "Discovery and Characterization of a Cell-Permeable, Small-Molecule c-Abl Kinase Activator that Binds to the Myristoyl Binding Site", *Chem. Biol.* 18: 177-186 (2011); and, the crystal structure PDB 5k5v and related ligands described in Kim, M. K., et al. "Structural basis for dual specificity of yeast N-terminal amidase in the N-end rule pathway", *Proc. Natl. Acad. Sci. U.S.A.* 113: 12438-12443 (2016).

FIG. 8JJJ presents examples of ABL2 Targeting Ligands wherein R is the point at which the Linker is attached. For additional examples and related ligands, see, the crystal structure PDB 2xyn and related ligands described in Salah, E. et al. "Crystal Structures of Abl-Related Gene (Abl2) in Complex with Imatinib, Tozasertib (Vx-680), and a Type I Inhibitor of the Triazole Carbothioamide Class", *J. Med. Chem.* 54: 2359 (2011); the crystal structure PDB 4xli and related ligands described in Ha, B. H. et al. "Structure of the ABL2/ARG kinase in complex with dasatinib" *Acta Crystallogr. Sect. F* 71: 443-448 (2015); and the crystal structure PDB 3gvu and related ligands described in Salah, E. et al. "The crystal structure of human ABL2 in complex with Gleevec", to be published.

FIG. 8KKK-8MMM present examples of AKT1 Targeting Ligands wherein R is the point at which the Linker is attached. For additional examples and related ligands, see, Lippa, B. et al. "Synthesis and structure based optimization of novel Akt inhibitors *Bioorg. Med. Chem. Lett.* 18: 3359-3363 (2008); Freeman-Cook, K. D. et al. "Design of selective, ATP-competitive inhibitors of Akt", *J. Med. Chem.* 53: 4615-4622 (2010); Blake, J. F. et al "Discovery of pyrrolopyrimidine inhibitors of Akt", *Bioorg. Med. Chem. Lett.* 20: 5607-5612 (2010); Kallan, N. C. et al. "Discovery and SAR of spirochromane Akt inhibitors", *Bioorg. Med. Chem. Lett.* 21: 2410-2414 (2011); Lin, K "An ATP-Site On-Off Switch That Restricts Phosphatase Accessibility of Akt", *Sci. Signal.* 5: ra37-ra37 (2012); Addie, M. et al. "Discovery of 4-Amino-N-[(1S)-1-(4-chlorophenyl)-3-hydroxypropyl]-1-(7H-pyrrolo[2,3-d]pyrimidin-4-yl)piperidine-4-carboxamide (AZD5363), an Orally Bioavailable, Potent Inhibitor of Akt Kinases", *J. Med. Chem.* 56: 2059-2073 (2013); Wu, W. I., et al. "Crystal structure of human AKT1 with an allosteric inhibitor reveals a new mode of kinase inhibition. *Plos One* 5: 12913-12913 (2010); Ashwell, M. A. et al. "Discovery and optimization of a series of 3-(3-phenyl-3H-imidazo[4,5-b]pyridin-2-yl)pyridin-2-amines: orally bioavailable, selective, and potent ATP-independent Akt inhibitors", *J. Med. Chem.* 55: 5291-5310 (2012); and, Lapierre, J. M. et al. "Discovery of 3-(3-(4-(1-Aminocyclobutyl)phenyl)-5-phenyl-3H-imidazo[4,5-b]pyridin-2-yl)pyridin-2-amine (ARQ 092): An Orally Bioavailable, Selective, and Potent Allosteric AKT Inhibitor", *J. Med. Chem.* 59: 6455-6469 (2016).

FIG. 8NNN-8OOO present examples of AKT2 Targeting Ligands wherein R is the point at which the Linker is attached. For additional examples and related ligands, see, the crystal structured PDB 2jdo and 2jdr and related ligands described in Davies, T. G. et al. "A Structural Comparison of Inhibitor Binding to Pkb, Pka and Pka-Pkb Chimera", *J. Mol. Biol.* 367: 882 (2007); the crystal structure PDB 2uw9 and related ligands described in Saxty, G. et al "Identification of Inhibitors of Protein Kinase B Using Fragment-Based Lead Discovery", *J. Med. Chem.* 50: 2293-2296 (2007); the crystal structure PDB 2x39 and 2xh5 and related ligands described in Mchardy, T. et al. "Discovery of 4-Amino-1-(7H-Pyrrolo[2,3-D]Pyrimidin-4-Yl)Piperidine-4-Carboxamides as Selective, Orally Active Inhibitors of Protein Kinase B (Akt)", *J. Med. Chem.* 53: 2239d (2010); the crystal structure PDB 3d03 and related ligands described in Hadler, K. S. et al. "Substrate-promoted formation of a catalytically competent binuclear center and regulation of reactivity in a glycerophosphodiesterase from *Enterobacter aerogenes*', *J. Am. Chem. Soc.* 130: 14129-14138 (2008); and, the crystal structures PDB 3e87, 3e8d and 3e88 and related ligands described in Rouse, M. B. et al. "Aminofurazans as potent inhibitors of AKT kinase" *Bioorg. Med. Chem. Lett.* 19: 1508-1511 (2009).

FIG. 8PPP presents examples of BMX Targeting Ligands wherein R is the point at which the Linker is attached. For additional examples and related ligands, see, the crystal structures PDB 3sxr and 3sxr and related ligands described in Muckelbauer, J. et al. "X-ray crystal structure of bone marrow kinase in the x chromosome: a Tec family kinase", *Chem. Biol. Drug Des.* 78: 739-748 (2011).

FIG. 8QQQ-8SSS present examples of CSF1R Targeting Ligands wherein R is the point at which the Linker is attached. For additional examples and related ligands, see, the crystal structures PDB 2i0v and 2i1m and related ligands described in Schubert, C. et al. "Crystal structure of the tyrosine kinase domain of colony-stimulating factor-1 receptor (cFMS) in complex with two inhibitors", *J. Biol. Chem.*

282: 4094-4101 (2007); the crystal structure PDB 3bea and related ligands described in Huang, H. et al. "Design and synthesis of a pyrido[2,3-d]pyrimidin-5-one class of anti-inflammatory FMS inhibitors", *Bioorg. Med. Chem. Lett.* 18: 2355-2361 (2008); the crystal structure PDB 3dpk and related ligands described in M. T., McKay, D. B. Overgaard, "Structure of the Elastase of *Pseudomonas aeruginosa* Complexed with Phosphoramidon", to be published; the crystal structures PDB 3krj and 3krl and related ligands described in Illig, C. R. et al. "Optimization of a Potent Class of Arylamide Colony-Stimulating Factor-1 Receptor Inhibitors Leading to Anti-inflammatory Clinical Candidate 4-Cyano-N-[2-(1-cyclohexen-1-yl)-4-[1-[(dimethylamino)acetyl]-4-piperidinyl]phenyl]-1H-imidazole-2-carboxamide (JNJ-28312141", *J. Med. Chem.* 54: 7860-7883 (2011); the crystal structure PDB 4r7h and related ligands described in Tap, W. D. et al. "Structure-Guided Blockade of CSF1R Kinase in Tenosynovial Giant-Cell Tumor, *N Engl J Med* 373: 428-437 (2015); the crystal structure PDB 3lcd and 3lcoa and related ligands described in Meyers, M. J. et al. "Structure-based drug design enables conversion of a DFG-in binding CSF-1R kinase inhibitor to a DFG-out binding mod", *Bioorg. Med. Chem. Lett.* 20: 1543-1547 (2010); the crystal structure PDB 4hw7 and related ligands described in Zhang, C. et al. "Design and pharmacology of a highly specific dual FMS and KIT kinase inhibitor", *Proc. Natl. Acad. Sci. USA* 110: 5689-5694 (2013); and, the crystal structure PDB 4r7i and related ligands described in Tap, W. D. et al. "Structure-Guided Blockade of CSF1R Kinase in Tenosynovial Giant-Cell Tumor", *N Engl J Med* 373: 428-437 (2015).

FIG. 8TTT presents examples of CSK Targeting Ligands wherein R is the point at which the Linker is attached. For additional examples and related ligands, see, Levinson, N. M. et al. "Structural basis for the recognition of c-Src by its inactivator Csk", *Cell* 134: 124-134 (2008).

FIG. 8UUU-8YYY present examples of DDR1 Targeting Ligands wherein R is the point at which the Linker is attached. For additional examples and related ligands, see, the crystal structures PDB 3zos and 4bkj and related ligands described in Canning, P. et al. "Structural Mechanisms Determining Inhibition of the Collagen Receptor Ddr1 by Selective and Multi-Targeted Type II Kinase Inhibitors", *J. Mol. Biol.* 426: 2457 (2014); the crystal structure PDB 4ckr and related ligands described in Kim, H. et al. "Discovery of a Potent and Selective Ddr1 Receptor Tyrosine Kinase Inhibitor", *ACS Chem. Biol.* 8: 2145 (2013); the crystal structure PDB 5bvk, 5bvn and 5bvw and related ligands described in Murray, C. W et al. "Fragment-Based Discovery of Potent and Selective DDR1/2 Inhibitors", *ACS Med. Chem. Lett.* 6: 798-803 (2015); the crystal structure PDB 5fdp and related ligands described in Wang, Z. et al. "Structure-Based Design of Tetrahydroisoquinoline-7-carboxamides as Selective Discoidin Domain Receptor 1 (DDR1) Inhibitors", *J. Med. Chem.* 59: 5911-5916 (2016); and, the crystal structure PDB 5fdx and related ligands described in Bartual, S. G. et al. "Structure of DDR1 receptor tyrosine kinase in complex with D2164 inhibitor at 2.65 Angstroms resolution", to be published.

FIG. 8ZZZ-8CCCC present examples of EPHA2 Targeting Ligands wherein R is the point at which the Linker is attached. For additional examples and related ligands, see, the crystal structures PDB 5i9x, 5i9y, 5ia0 and 5ia1 and related ligands described in Heinzlmeir, S. et al. "Chemical Proteomics and Structural Biology Define EPHA2 Inhibition by Clinical Kinase Drug", *ACS Chem. Biol.* 11: 3400-3411 (2016); the crystal structure PDB 5i9z and related ligands described in Heinzlmeir, S. et al. "Crystal Structure of Ephrin A2 (EphA2) Receptor Protein Kinase with danusertib (PHA739358)", *ACS Chem Biol* 11 3400-3411 (2016); and, the crystal structures PDB 5ia2, 5ia3, 5ia4, and 5ia5 and related ligands described in Heinzlmeir, S. et al. "Chemical Proteomics and Structural Biology Define EPHA2 Inhibition by Clinical Kinase Drug", *ACS Chem. Biol.* 11: 3400-3411 (2016).

FIG. 8DDDD-8FFFF present examples of EPHA3 Targeting Ligands wherein R is the point at which the Linker is attached. For additional examples and related ligands, see, the crystal structure PDB 4g2f and related ligands described in Zhao, H. et al. "Discovery of a novel chemotype of tyrosine kinase inhibitors by fragment-based docking and molecular dynamics", *ACS Med. Chem. Lett.* 3: 834-838 (2012); the crystal structure PDB 4gk2 and 4gk3 and related ligands described in Lafleur, K. et al. "Optimization of Inhibitors of the Tyrosine Kinase EphB4. 2. Cellular Potency Improvement and Binding Mode Validation by X-ray Crystallography", *J. Med. Chem.* 56: 84-96 (2013); the crystal structure PDB 4gk3 and related ligands described in Lafleur, K. et al. "Optimization of Inhibitors of the Tyrosine Kinase EphB4. 2. Cellular Potency Improvement and Binding Mode Validation by X-ray Crystallography", *J. Med. Chem.* 56: 84-96 (2013); the crystal structure PDB 4p4c and 4p5q and related ligands described in Unzue, A. et al. "Pyrrolo[3,2-b]quinoxaline Derivatives as Types I½ and II Eph Tyrosine Kinase Inhibitors: Structure-Based Design, Synthesis, and in Vivo Validation", *J. Med. Chem.* 57: 6834-6844 (2014); the crystal structure PDB 4p5z and related ligands described in Unzue, A. et al. "Pyrrolo[3,2-b]quinoxaline Derivatives as Types I½ and II Eph Tyrosine Kinase Inhibitors: Structure-Based Design, Synthesis, and in Vivo Validation", *J. Med. Chem.* 57: 6834-6844 (2014); the crystal structure PDB 4twn and related ligands described in Dong, J. et al. "Structural Analysis of the Binding of Type I, I½, and II Inhibitors to Eph Tyrosine Kinases", *ACS Med. Chem. Lett.* 6: 79-83 (2015); the crystal structure PDB 3dzq and related ligands described in Walker, J. R. "Kinase Domain of Human Ephrin Type-A Receptor 3 (Epha3) in Complex with ALW-II-38-3", to be published.

FIG. 8GGGG presents examples of EPHA4 Targeting Ligands wherein R is the point at which the Linker is attached. For additional examples and related ligands, see, the crystal structure PDB 2y60 and related ligands described in Clifton, I. J. et al. "The Crystal Structure of Isopenicillin N Synthase with Delta((L)-Alpha-Aminoadipoyl)-(L)-Cysteinyl-(D)-Methionine Reveals Thioether Coordination to Iron", *Arch. Biochem. Biophys.* 516: 103 (2011) and the crystal structure PDB 2xyu and related ligands described in Van Linden, O. P et al. "Fragment Based Lead Discovery of Small Molecule Inhibitors for the Epha4 Receptor Tyrosine Kinase", *Eur. J. Med. Chem.* 47: 493 (2012).

FIG. 8HHHH presents examples of EPHA7 Targeting Ligands wherein R is the point at which the Linker is attached. For additional examples and related ligands, see, the crystal structure PDB 3dko and related ligands described in Walker, J. R. et al. "Kinase domain of human ephrin type-a receptor 7 (epha7) in complex with ALW-II-49-7", to be published.

FIG. 8IIII-8LLLL presents examples of EPHB4 Targeting Ligands wherein R is the point at which the Linker is attached. For additional examples and related ligands, see, the crystal structure PDB 2vx1 and related ligands described in Bardelle, C. et al. "Inhibitors of the Tyrosine Kinase Ephb4. *Part 2:* Structure-Based Discovery and Optimisation of 3,5-Bis Substituted Anilinopyrimidines", *Bioorg. Med.*

Chem. Lett. 18: 5717(2008); the crystal structure PDB 2x9f and related ligands described in Bardelle, C. et al. "Inhibitors of the Tyrosine Kinase Ephb4. Part 3: Identification of Non-Benzodioxole-Based Kinase Inhibitors", *Bioorg. Med. Chem. Lett.* 20: 6242-6245 (2010); the crystal structure PDB 2xvd and related ligands described in Barlaam, B. et al. "Inhibitors of the Tyrosine Kinase Ephb4. Part 4: Discovery and Optimization of a Benzylic Alcohol Series", *Bioorg. Med. Chem. Lett.* 21: 2207 (2011); the crystal structure PDB 3zew and related ligands described in Overman, R. C. et al. "Completing the Structural Family Portrait of the Human Ephb Tyrosine Kinase Domains", *Protein Sci.* 23: 627 (2014); the crystal structure PDB 4aw5 and related ligands described in Kim, M. H. et al. "The Design, Synthesis, and Biological Evaluation of Potent Receptor Tyrosine Kinase Inhibitors", *Bioorg. Med. Chem. Lett.* 22: 4979 (2012); the crystal structure PDB 4bb4 and related ligands described in Vasbinder, M. M. et al. "Discovery and Optimization of a Novel Series of Potent Mutant B-Raf V600E Selective Kinase Inhibitors" *J. Med. Chem.* 56: 1996.", (2013); the crystal structures PDB 2vwu, 2vwv and 2vww and related ligands described in Bardelle, C. et al "Inhibitors of the Tyrosine Kinase Ephb4. Part 1: Structure-Based Design and Optimization of a Series of 2,4-Bis-Anilinopyrimidines", *Bioorg. Med. Chem. Lett.* 18: 2776-2780 (2008); the crystal structures PDB 2vwx, 2vwy, and 2vwz and related ligands described in Bardelle, C. et al. "Inhibitors of the Tyrosine Kinase Ephb4. Part 2: Structure-Based Discovery and Optimisation of 3,5-Bis Substituted Anilinopyrimidines", *Bioorg. Med. Chem. Lett.* 18: 5717 (2008); and, the crystal structure PDB 2vxo and related ligands described in Welin, M. et al. "Substrate Specificity and Oligomerization of Human Gmp Synthetas", *J. Mol. Biol.* 425: 4323 (2013).

FIG. 8MMMM presents examples of ERBB2 Targeting Ligands wherein R is the point at which the Linker is attached. For additional examples and related ligands, see, the crystal structure and related ligands described in Aertgeerts, K. et al "Structural Analysis of the Mechanism of Inhibition and Allosteric Activation of the Kinase Domain of HER2 Protein", *J. Biol. Chem.* 286: 18756-18765 (2011) and the crystal structure and related ligands described in Ishikawa, T. et al. "Design and Synthesis of Novel Human Epidermal Growth Factor Receptor 2 (HER2)/Epidermal Growth Factor Receptor (EGFR) Dual Inhibitors Bearing a Pyrrolo[3,2-d]pyrimidine Scaffold" *J. Med. Chem.* 54: 8030-8050 (2011).

FIG. 8NNNN presents examples of ERBB3 Targeting Ligands wherein R is the point at which the Linker is attached. For additional examples and related ligands, see, Littlefield, P. et al. "An ATP-Competitive Inhibitor Modulates the Allosteric Function of the HER3 Pseudokinase", *Chem. Biol.* 21: 453-458 (2014).

FIG. 8OOOO presents examples ERBB4 Targeting Ligands wherein R is the point at which the Linker is attached. For additional examples and related ligands, see, Qiu, C. et al. "Mechanism of Activation and Inhibition of the HER4/ErbB4 Kinase", *Structure* 16: 460-467 (2008) and Wood, E. R. et al. "6-Ethynylthieno[3,2-d]- and 6-ethynylthieno[2,3-d]pyrimidin-4-anilines as tunable covalent modifiers of ErbB kinases", *Proc. Natl. Acad. Sci. Usa* 105: 2773-2778 (2008).

FIG. 8PPPP-8QQQQ present examples of FES Targeting Ligands wherein R is the point at which the Linker is attached. For additional examples and related ligands, see, Filippakopoulos, P. et al "Structural Coupling of SH2-Kinase Domains Links Fes and Abl Substrate Recognition and Kinase Activation." *Cell* 134: 793-803 (2008) and Hellwig, S. et al. "Small-Molecule Inhibitors of the c-Fes Protein-Tyrosine Kinase", *Chem. Biol.* 19: 529-540 (2012).

FIG. 8RRRR presents examples of FYN Targeting Ligands wherein R is the point at which the Linker is attached. For additional examples and related ligands, see, Kinoshita, T. et. al. "Structure of human Fyn kinase domain complexed with staurosporine", *Biochem. Biophys. Res. Commun.* 346: 840-844 (2006).

FIG. 8SSSS-8VVVV present examples of GSG2 (Haspin) Targeting Ligands wherein R is the point at which the Linker is attached. For additional examples and related ligands, see, the crystal structures PDB 3e7v, PDB 3f2n, 3fmd and related ligands described in Filippakopoulos, P. et al. "Crystal Structure of Human Haspin with a pyrazolo-pyrimidine ligand", to be published; the crystal structure PDB 3iq7 and related ligands described in Eswaran, J. et al. "Structure and functional characterization of the atypical human kinase haspin", *Proc. Natl. Acad. Sci. USA* 106: 20198-20203 (2009); and, the crystal structure PDB 4qtc and related ligands described in Chaikuad, A. et al. "A unique inhibitor binding site in ERK1/2 is associated with slow binding kinetics", *Nat. Chem. Biol.* 10: 853-860 (2014).

FIG. 8WWWW-8AAAAA present examples of HCK Targeting Ligands wherein R is the point at which the Linker is attached. For additional examples and related ligands, see, the crystal structure PDB 1qcf and related ligands described in Schindler, T. et al. "Crystal structure of Hck in complex with a Src family-selective tyrosine kinase inhibitor", *Mol. Cell* 3: 639-648 (1999); the crystal structure PDB 2c0i and 2c0t and related ligands described in Burchat, A. et al. "Discovery of A-770041, a Src-Family Selective Orally Active Lck Inhibitor that Prevents Organ Allograft Rejection", *Bioorg. Med. Chem. Lett.* 16: 118 (2006); the crystal structure PDB 2hk5 and related ligands described in Sabat, M. et al. "The development of 2-benzimidazole substituted pyrimidine based inhibitors of lymphocyte specific kinase (Lck)", *Bioorg. Med. Chem. Lett.* 16: 5973-5977 (2006); the crystal structures PDB 3vry, 3vs3, 3vs6, and 3vs7 and related ligands described in Saito, Y. et al. "A Pyrrolo-Pyrimidine Derivative Targets Human Primary AML Stem Cells in Vivo", *Sci Transl Med* 5: 181ra52-181ra52 (2013); and, the crystal structure PDB 4lud and related ligands described in Parker, L. J. et al "Kinase crystal identification and ATP-competitive inhibitor screening using the fluorescent ligand SKF86002", *Acta Crystallogr., Sect. D* 70: 392-404 (2014).

FIG. 8BBBBB-8FFFFF present examples of IGF1R Targeting Ligands wherein R is the point at which the Linker is attached. For additional examples and related ligands, see, the crystal structure PDB 2oj9 and related ligands described in Velaparthi, U. et al. "Discovery and initial SAR of 3-(1H-benzo[d]imidazol-2-yl)pyridin-2(1H)-ones as inhibitors of insulin-like growth factor 1-receptor (IGF-1R)", *Bioorg. Med. Chem. Lett.* 17: 2317-2321 (2007); the crystal structure PDB 3i81 and related ligands described in Wittman, M. D. et al. "Discovery of a 2,4-disubstituted pyrrolo [1,2-f][1,2,4]triazine inhibitor (BMS-754807) of insulin-like growth factor receptor (IGF-1R) kinase in clinical development.", *J. Med. Chem.* 52: 7360-7363 (2009); the crystal structure PDB 3nw5 and related ligands described in Sampognaro, A. J. et al. "Proline isosteres in a series of 2,4-disubstituted pyrrolo[1,2-f][1,2,4]triazine inhibitors of IGF-1R kinase and IR kinase", *Bioorg. Med. Chem. Lett.* 20: 5027-5030 (2010); the crystal structure PDB 3qqu and related ligands described in Buchanan, J. L. et al. "Discovery of 2,4-bis-arylamino-1,3-pyrimidines as insulin-like growth factor-1 receptor (IGF-1R) inhibitors", *Bioorg. Med.*

*Chem. Lett.* 21: 2394-2399 (2011); the crystal structure PDB 4d2r and related ligands described in Kettle, J. G. et al. "Discovery and Optimization of a Novel Series of Dyrk1B Kinase Inhibitors to Explore a Mek Resistance Hypothesis". *J. Med. Chem.* 58: 2834 (2015); the crystal structure PDB 3fxq and related ligands described in Monferrer, D. et al. "Structural studies on the full-length LysR-type regulator TsaR from *Comamonas testosteroni* T-2 reveal a novel open conformation of the tetrameric LTTR fold", *Mol. Microbiol.* 75: 1199-1214 (2010); the crystal structure PDB 5fxs and related ligands described in Degorce, S. et al. "Discovery of Azd9362, a Potent Selective Orally Bioavailable and Efficacious Novel Inhibitor of Igf-R1", to be published; the crystal structure PDB 2zm3 and related ligands described in Mayer, S. C. et al. "Lead identification to generate isoquinolinedione inhibitors of insulin-like growth factor receptor (IGF-1R) for potential use in cancer treatment", *Bioorg. Med. Chem. Lett.* 18: 3641-3645 (2008); the crystal structure PDB 3f5p and related ligands described in "Lead identification to generate 3-cyanoquinoline inhibitors of insulin-like growth factor receptor (IGF-1R) for potential use in cancer treatment" *Bioorg. Med. Chem. Lett.* 19: 62-66 (2009); the crystal structure PDB 3lvp and related ligands described in Nemecek, C. et al. "Design of Potent IGF1-R Inhibitors Related to Bis-azaindoles" *Chem. Biol. Drug Des.* 76: 100-106 (2010); the crystal structure PDB 3o23 and related ligands described in Lesuisse, D. et al. "Discovery of the first non-ATP competitive IGF-1R kinase inhibitors: Advantages in comparison with competitive inhibitors", *Bioorg. Med. Chem. Lett.* 21: 2224-2228 (2011); the crystal structure PDB 3d94 and related ligands described in Wu, J. et al. "Small-molecule inhibition and activation-loop trans-phosphorylation of the IGF1 receptor", *Embo J.* 27: 1985-1994 (2008); and, the crystal structure PDB 5hzn and related ligands described in Stauffer, F. et al. "Identification of a 5-[3-phenyl-(2-cyclic-ether)-methylether]-4-aminopyrrolo[2,3-d]pyrimidine series of IGF-1R inhibitors", *Bioorg. Med. Chem. Lett.* 26: 2065-2067 (2016).

FIG. 8GGGGG-8JJJJJ present examples of INSR Targeting Ligands wherein R is the point at which the Linker is attached. For additional examples and related ligands, see, the crystal structure PDB 2z8c and related ligands described in Katayama, N. et al. "Identification of a key element for hydrogen-bonding patterns between protein kinases and their inhibitors", *Proteins* 73: 795-801 (2008); the crystal structure PDB 3ekk and related ligands described in Chamberlain, S. D. et al. "Discovery of 4,6-bis-anilino-1H-pyrrolo[2,3-d]pyrimidines: Potent inhibitors of the IGF-1R receptor tyrosine kinase", (2009) *Bioorg. Med. Chem. Lett.* 19: 469-473; the crystal structure PDB 3ekn and related ligands described in Chamberlain, S. D. et al. "Optimization of 4,6-bis-anilino-1H-pyrrolo[2,3-d]pyrimidine IGF-1R tyrosine kinase inhibitors towards JNK selectivity", *Bioorg. Med. Chem. Lett.* 19: 360-364 (2009); the crystal structure PDB 5els and related ligands described in Sanderson, M. P. et al. "BI 885578, a Novel IGF1R/INSR Tyrosine Kinase Inhibitor with Pharmacokinetic Properties That Dissociate Antitumor Efficacy and Perturbation of Glucose Homeostasis" *Mol. Cancer Ther.* 14: 2762-2772", (2015); the crystal structure PDB 3eta and related ligands described in Patnaik, S. et al. "Discovery of 3,5-disubstituted-1H-pyrrolo[2,3-b]pyridines as potent inhibitors of the insulin-like growth factor-1 receptor (IGF-1R) tyrosine kinase", *Bioorg. Med. Chem. Lett.* 19: 3136-3140 (2009); the crystal structure PDB 5hhw and related ligands described in Stauffer, F. et al. "Identification of a 5-[3-phenyl-(2-cyclic-ether)-methylether]-4-aminopyrrolo[2,3-d]pyrimidine series of IGF-1R inhibitors", *Bioorg. Med. Chem. Lett.* 26: 2065-2067 (2016); and, the crystal structure PDB 4ibm and related ligands described in Anastassiadis, T. et al. "A highly selective dual insulin receptor (IR)/insulin-like growth factor 1 receptor (IGF-1R) inhibitor derived from an extracellular signal-regulated kinase (ERK) inhibitor", *J. Biol. Chem.* 288: 28068-28077 (2013).

FIG. 8KKKKK-8PPPPP present examples of HBV Targeting Ligands wherein R is the point at which the Linker is attached, Y is methyl or isopropyl, and X is N or C. For additional examples and related ligands, see, Weber, O.; et al. "Inhibition of human hepatitis B virus (HBV) by a novel non-nucleosidic compound in a transgenic mouse model." *Antiviral Res.* 54, 69-78 (2002); Deres, K.; et al. "Inhibition of hepatitis B virus replication by drug-induced depletion of nucleocapsids." *Science,* 299, 893-896 (2003); Stray, S. J.; Zlotnick, A. "BAY 41-4109 has multiple effects on Hepatitis B virus capsid assembly." *J. Mol. Recognit.* 19, 542-548 (2006); Stray, S. J.; et al. "heteroaryldihydropyrimidine activates and can misdirect hepatitis B virus capsid assembly." *Proc. Natl. Acad. Sci. U.S.A.*, 102, 8138-8143 (2005); Guan, H.; et al. "The novel compound Z060228 inhibits assembly of the HBV capsid." *Life Sci.* 133, 1-7 (2015); Wang, X. Y.; et al. "In vitro inhibition of HBV replication by a novel compound, GLS4, and its efficacy against adefovir-dipivoxil-resistant HBV mutations." *Antiviral Ther.* 17, 793-803 (2012); Klumpp, K.; et al. "High-resolution crystal structure of a hepatitis B virus replication inhibitor bound to the viral core protein." 112, 15196-15201 (2015); Qiu, Z.; et al. "Design and synthesis of orally bioavailable 4-methyl heteroaryldihydropyrimidine based hepatitis B virus (HBV) capsid inhibitors." *J. Med. Chem.* 59, 7651-7666 (2016); Zhu, X.; et al. "2,4-Diaryl-4,6,7,8-tetrahydroquinazolin-5(1H)-one derivatives as anti-HBV agents targeting at capsid assembly." *Bioorg. Med. Chem. Lett.* 20, 299-301 (2010); Campagna, M. R.; et al. "Sulfamoylbenzamide derivatives inhibit the assembly of hepatitis B virus nucleocapsids." *J. Virol.* 87, 6931-6942 (2013); Campagna, M. R.; et al. "Sulfamoylbenzamide derivatives inhibit the assembly of hepatitis B virus nucleocapsids." *J. Virol.* 87, 6931-6942 (2013); WO 2013096744 A1 titled "Hepatitis B antivial agents"; WO 2015138895 titled "Hepatitis B core protein allosteric modulators"; Wang, Y. J.; et al. "A novel pyridazinone derivative inhibits hepatitis B virus replication by inducing genome-free capsid formation." *Antimicrob. Agents Chemother.* 59, 7061-7072 (2015); WO 2014033167 titled "Fused bicyclic sulfamoyl derivatives for the treatment of hepatitis"; U.S. 20150132258 titled "Azepane derivatives and methods of treating hepatitis B infections"; and, WO 2015057945 "Hepatitis B viral assembly effector".

Figure 9:
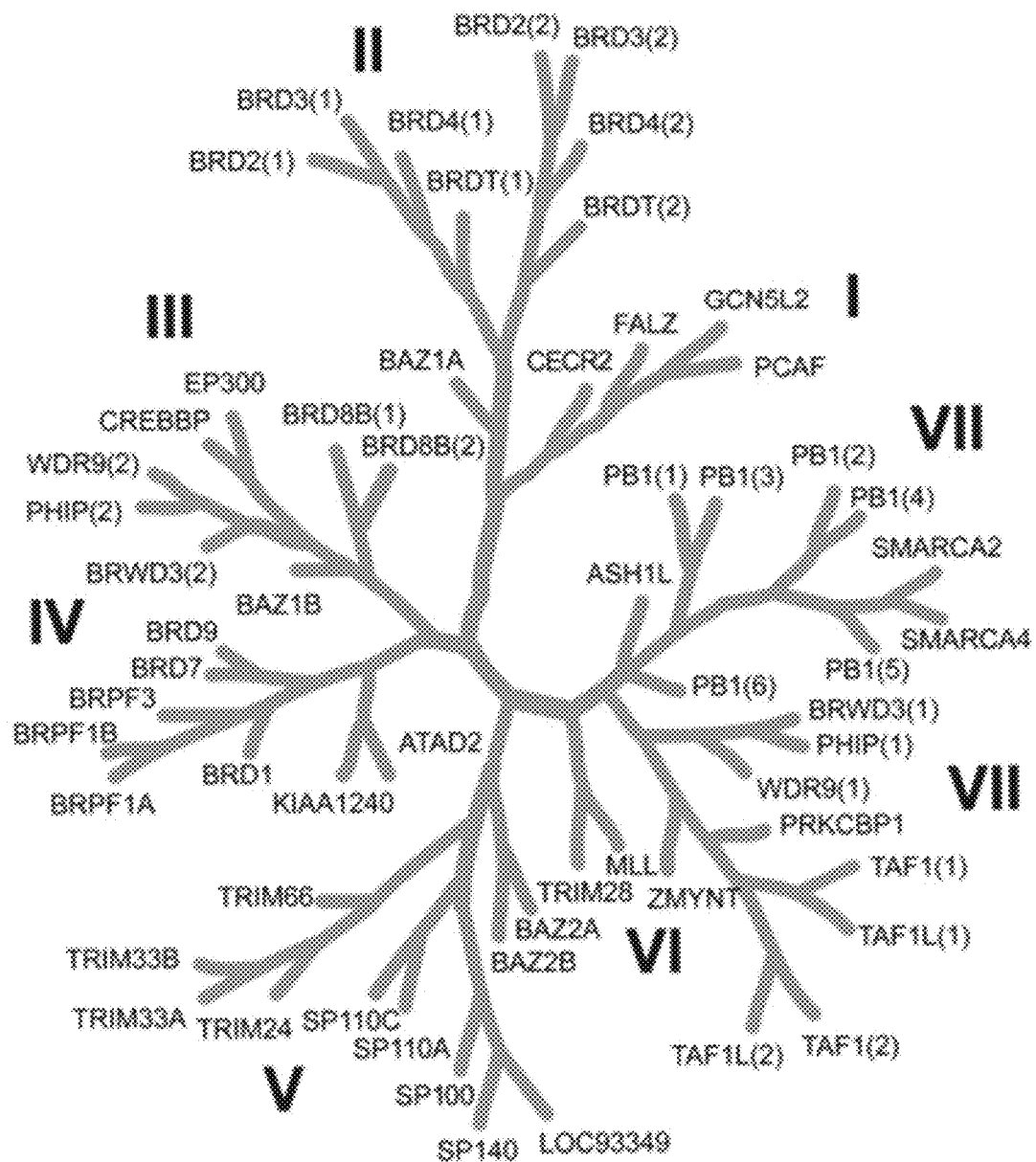

FIG. 9 is a dendrogram of the human bromodomain family of proteins organized into eight subfamilies, which are involved in epigenetic signaling and chromatin biology. Any of the proteins of the bromodomain family in FIG. 9 can be selected as a Target Protein according to the present invention.

DETAILED DESCRIPTION

I. Definitions

Compounds are described using standard nomenclature. Unless defined otherwise, all technical and scientific terms used herein have the same meaning as is commonly understood by one of skill in the art to which this invention belongs.

The compounds in any of the Formulas described herein may be in the form of a racemate, enantiomer, mixture of enantiomers, diastereomer, mixture of diastereomers, tautomer, N-oxide, isomer; such as rotamer, as if each is specifically described unless specifically excluded by context.

The terms "a" and "an" do not denote a limitation of quantity, but rather denote the presence of at least one of the referenced item. The term "or" means "and/or". Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of examples, or exemplary language (e.g., "such as"), is intended merely to better illustrate the invention and does not pose a limitation on the scope of the invention unless otherwise claimed.

The present invention includes compounds of Formula I, Formula II, Formula III, and Formula IV with at least one desired isotopic substitution of an atom, at an amount above the natural abundance of the isotope, i.e., enriched. Isotopes are atoms having the same atomic number but different mass numbers, i.e., the same number of protons but a different number of neutrons.

Examples of isotopes that can be incorporated into compounds of the invention include isotopes of hydrogen, carbon, nitrogen, oxygen, phosphorous, fluorine, chlorine and iodine such as $^2H$, $^3H$, $^{11}C$, $^{13}C$, $^{14}C$, $^{15}N$, $^{18}F$ $^{31}P$, $^{32}P$, $^{35}S$, $^{36}Cl$, and $^{125}I$ respectively. In one non-limiting embodiment, isotopically labelled compounds can be used in metabolic studies (with, for example $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

Isotopic substitutions, for example deuterium substitutions, can be partial or complete. Partial deuterium substitution means that at least one hydrogen is substituted with deuterium. In certain embodiments, the isotope is 90, 95 or 99% or more enriched in an isotope at any location of interest. In one non-limiting embodiment, deuterium is 90, 95 or 99% enriched at a desired location.

In one non-limiting embodiment, the substitution of a hydrogen atom for a deuterium atom can be provided in any compound of Formula I, Formula II, Formula III, Formula IV, Formula V or Formula VI. In one non-limiting embodiment, the substitution of a hydrogen atom for a deuterium atom occurs within one or more groups selected from any of the variables described herein, Linker, and Targeting Ligand. For example, when any of the groups are, or contain for example through substitution, methyl, ethyl, or methoxy, the alkyl residue may be deuterated (in non-limiting embodiments, $CDH_2$, $CD_2H$, $CD_3$, $CH_2CD_3$, $CD_2CD_3$, $CHDCH_2D$, $CH_2CD_3$, $CHDCHD_2$, $OCDH_2$, $OCD_2H$, or $OCD_3$ etc.). In certain other embodiments, when two substituents are combined to form a cycle the unsubstituted carbons may be deuterated.

The compound of the present invention may form a solvate with a solvent (including water). Therefore, in one non-limiting embodiment, the invention includes a solvated form of the compound. The term "solvate" refers to a molecular complex of a compound of the present invention (including a salt thereof) with one or more solvent molecules. Non-limiting examples of solvents are water, ethanol, isopropanol, dimethyl sulfoxide, acetone and other common organic solvents. The term "hydrate" refers to a molecular complex comprising a compound of the invention and water. Pharmaceutically acceptable solvates in accordance with the invention include those wherein the solvent may be isotopically substituted, e.g. $D_2O$, d6-acetone, d6-DMSO. A solvate can be in a liquid or solid form.

A dash ("-") that is not between two letters or symbols is used to indicate a point of attachment for a substituent. For example, —(C=O)NH$_2$ is attached through carbon of the carbonyl (C=O) group.

"Alkyl" is a branched or straight chain saturated aliphatic hydrocarbon group. In one non-limiting embodiment, the alkyl group contains from 1 to about 12 carbon atoms, more generally from 1 to about 6 carbon atoms or from 1 to about 4 carbon atoms. In one non-limiting embodiment, the alkyl contains from 1 to about 8 carbon atoms. In certain embodiments, the alkyl is $C_1$-$C_2$, $C_1$-$C_3$, $C_1$-$C_4$, $C_1$-$C_5$, or $C_1$-$C_6$. The specified ranges as used herein indicate an alkyl group having each member of the range described as an independent species. For example, the term $C_1$-$C_6$ alkyl as used herein indicates a straight or branched alkyl group having from 1, 2, 3, 4, 5, or 6 carbon atoms and is intended to mean that each of these is described as an independent species and therefore each subset is considered separately disclosed. For example, the term $C_1$-$C_4$ alkyl as used herein indicates a straight or branched alkyl group having from 1, 2, 3, or 4 carbon atoms and is intended to mean that each of these is described as an independent species. Examples of alkyl include, but are not limited to, methyl, ethyl, n-propyl, isopropyl, n-butyl, isobutyl, sec-butyl, t-butyl, n-pentyl, isopentyl, tert-pentyl, neopentyl, n-hexyl, 2-methylpentane, 3-methylpentane, 2,2-dimethylbutane, and 2,3-dimethylbutane. In an alternative embodiment, the alkyl group is optionally substituted. The term "alkyl" also encompasses cycloalkyl or carbocyclic groups. For example, when a term is used that includes "alk" then "cycloalkyl" or "carbocyclic" can be considered part of the definition, unless unambiguously excluded by the context. For example and without limitation, the terms alkyl, alkoxy, haloalkyl, etc. can all be considered to include the cyclic forms of alkyl, unless unambiguously excluded by context.

"Alkenyl" is a linear or branched aliphatic hydrocarbon groups having one or more carbon-carbon double bonds that may occur at a stable point along the chain. The specified ranges as used herein indicate an alkenyl group having each member of the range described as an independent species, as described above for the alkyl moiety. Examples of alkenyl radicals include, but are not limited to ethenyl, propenyl, allyl, propenyl, butenyl and 4-methylbutenyl. The term "alkenyl" also embodies "cis" and "trans" alkenyl geometry, or alternatively, "E" and "Z" alkenyl geometry. In an alternative embodiment, the alkenyl group is optionally substituted. The term "Alkenyl" also encompasses cycloalkyl or carbocyclic groups possessing at least one point of unsaturation.

"Alkynyl" is a branched or straight chain aliphatic hydrocarbon group having one or more carbon-carbon triple bonds that may occur at any stable point along the chain. The specified ranges as used herein indicate an alkynyl group having each member of the range described as an independent species, as described above for the alkyl moiety. Examples of alkynyl include, but are not limited to, ethynyl, propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl. In an alternative embodiment, the alkynyl group is optionally substituted. The term "Alkynyl" also encompasses cycloalkyl or carbocyclic groups possessing at least one triple bond.

"Alkylene" is a bivalent saturated hydrocarbon. Alkylenes, for example, can be a 1, 2, 3, 4, 5, 6, 7 to 8 carbon moiety, 1 to 6 carbon moiety, or an indicated number of carbon atoms, for example $C_1$-$C_2$alkylene, $C_1$-$C_3$alkylene, $C_1$-$C_4$alkylene, $C_1$-$C_5$alkylene, or $C_1$-$C_6$alkylene.

"Alkenylene" is a bivalent hydrocarbon having at least one carbon-carbon double bond. Alkenylenes, for example, can be a 2 to 8 carbon moiety, 2 to 6 carbon moiety, or an indicated number of carbon atoms, for example $C_2$-$C_4$alkenylene.

"Alkynylene" is a bivalent hydrocarbon having at least one carbon-carbon triple bond. Alkynylenes, for example, can be a 2 to 8 carbon moiety, 2 to 6 carbon moiety, or an indicated number of carbon atoms, for example $C_2$-$C_4$alkynylene.

"Halo" and "Halogen" refers to fluorine, chlorine, bromine or iodine.

"Haloalkyl" is a branched or straight-chain alkyl groups substituted with 1 or more halo atoms described above, up to the maximum allowable number of halogen atoms. Examples of haloalkyl groups include, but are not limited to, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perhaloalkyl" means an alkyl group having all hydrogen atoms replaced with halogen atoms. Examples include but are not limited to, trifluoromethyl and pentafluoroethyl.

"Chain" indicates a linear chain to which all other chains, long or short or both, may be regarded as being pendant. Where two or more chains could equally be considered to be the main chain, "chain" refers to the one which leads to the simplest representation of the molecule.

"Haloalkoxy" indicates a haloalkyl group as defined herein attached through an oxygen bridge (oxygen of an alcohol radical).

"Heterocycloalkyl" is an alkyl group as defined herein substituted with a heterocyclo group as defined herein.

"Arylalkyl" is an alkyl group as defined herein substituted with an aryl group as defined herein.

"Heteroarylalkyl" is an alkyl group as defined herein substituted with a heteroaryl group as defined herein.

As used herein, "aryl" refers to a radical of a monocyclic or polycyclic (e.g., bicyclic or tricyclic) 4n+2 aromatic ring system (e.g., having 6, 10, or 14 it electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. The one or more fused carbocyclyl or heterocyclyl groups can be 4 to 7 or 5 to 7-membered saturated or partially unsaturated carbocyclyl or heterocyclyl groups that optionally contain 1, 2, or 3 heteroatoms independently selected from nitrogen, oxygen, phosphorus, sulfur, silicon and boron, to form, for example, a 3,4-methylenedioxyphenyl group. In one non-limiting embodiment, aryl groups are pendant. An example of a pendant ring is a phenyl group substituted with a phenyl group. In an alternative embodiment, the aryl group is optionally substituted as described above. In certain embodiments, the aryl group is an unsubstituted $C_{6-14}$ aryl. In certain embodiments, the aryl group is a substituted $C_{6-14}$ aryl. An aryl group may be optionally substituted with one or more functional groups that include but are not limited to, halo, hydroxy, nitro, amino, cyano, haloalkyl, aryl, heteroaryl, and heterocyclo.

The term "heterocyclyl" (or "heterocyclo") includes saturated, and partially saturated heteroatom-containing ring radicals, where the heteroatoms may be selected from nitrogen, sulfur and oxygen. Heterocyclic rings comprise monocyclic 3-8 membered rings, as well as 5-16 membered bicyclic ring systems (which can include bridged fused and spiro-fused bicyclic ring systems). It does not include rings containing —O—O—, —O—S— or —S—S— portions. Said "heterocyclyl" group may be optionally substituted, for example, with 1, 2, 3, 4 or more substituents that include but are not limited to, hydroxyl, Boc, halo, haloalkyl, cyano, alkyl, aralkyl, oxo, alkoxy, and amino. Examples of saturated heterocyclo groups include saturated 3- to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include but are not limited to, dihydrothienyl, dihydropyranyl, dihydrofuryl, and dihydrothiazolyl. Examples of partially saturated and saturated heterocyclo groups include but are not limited to, pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9, 9a-hexahydro-1H-3-aza-fluorenyl, 5,6,7-trihydro-1,2,4-triazolo[3,4-a]isoquinolyl, 3,4-dihydro-2H-benzo[1,4] oxazinyl, benzo[1,4]dioxanyl, 2,3-dihydro-1H-1λ-benzo[d] isothiazol-6-yl, dihydropyranyl, dihydrofuryl and dihydrothiazolyl.

Heterocyclo groups also include radicals where heterocyclic radicals are fused/condensed with aryl or heteroaryl radicals: such as unsaturated condensed heterocyclic group containing 1 to 5 nitrogen atoms, for example, indoline, isoindoline, unsaturated condensed heterocyclic group containing 1 to 2 oxygen atoms and 1 to 3 nitrogen atoms, unsaturated condensed heterocyclic group containing 1 to 2 sulfur atoms and 1 to 3 nitrogen atoms, and saturated, partially unsaturated and unsaturated condensed heterocyclic group containing 1 to 2 oxygen or sulfur atoms.

The term "heteroaryl" denotes aryl ring systems that contain one or more heteroatoms selected from O, N and S, wherein the ring nitrogen and sulfur atom(s) are optionally oxidized, and nitrogen atom(s) are optionally quarternized. Examples include but are not limited to, unsaturated 5 to 6 membered heteromonocyclyl groups containing 1 to 4 nitrogen atoms, such as pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, IH-1,2,3-triazolyl, 2H-1,2,3-triazolyl]; unsaturated 5- to 6-membered heteromonocyclic groups containing an oxygen atom, for example, pyranyl, 2-furyl, 3-furyl, etc.; unsaturated 5 to 6-membered heteromonocyclic groups containing a sulfur atom, for example, 2-thienyl, 3-thienyl, etc.; unsaturated 5- to 6-membered heteromonocyclic groups containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic groups containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl].

The term "optionally substituted" denotes the substitution of a group herein by a moiety including, but not limited to, $C_1$-$C_{10}$ alkyl, $C_2$-$C_{10}$ alkenyl, $C_2$-$C_{10}$ alkynyl, $C_3$-$C_{12}$ cycloalkyl, $C_3$-$C_{12}$ cycloalkenyl, $C_1$-$C_{12}$ heterocycloalkyl, $C_3$-$C_{12}$ heterocycloalkenyl, $C_1$-$C_{10}$ alkoxy, aryl, aryloxy, heteroaryl, heteroaryloxy, amino, $C_1$-$C_{10}$ alkylamino, $C_1$-$C_{10}$ dialkylamino, arylamino, diarylamino, $C_1$-$C_{10}$ alkylsulfonamino, arylsulfonamino, $C_1$-$C_{10}$ alkylimino, arylimino, $C_1$-$C_{10}$ alkylsulfonimino, arylsulfonimino, hydroxyl, halo, thio, $C_1$-$C_{10}$ alkylthio, arylthio, $C_1$-$C_{10}$ alkylsulfonyl, arylsulfonyl, acylamino, aminoacyl, aminothioacyl, amidino, guanidine, ureido, cyano, nitro, azido, acyl, thioacyl, acyloxy, carboxyl, and carboxylic ester.

In one alternative embodiment any suitable group may be present on a "substituted" or "optionally substituted" position if indicated that forms a stable molecule and meets the desired purpose of the invention and includes, but is not limited to, e.g., halogen (which can independently be F, Cl, Br or I); cyano; hydroxyl; nitro; azido; alkanoyl (such as a $C_2$-$C_6$ alkanoyl group); carboxamide; alkyl, cycloalkyl, alkenyl, alkynyl, alkoxy, aryloxy such as phenoxy; thioalkyl including those having one or more thioether linkages; alkylsulfinyl; alkylsulfonyl groups including those having one or more sulfonyl linkages; aminoalkyl groups including groups having more than one N atoms; aryl (e.g., phenyl, biphenyl, naphthyl, or the like, each ring either substituted or unsubstituted); arylalkyl having for example, 1 to 3 separate or fused rings and from 6 to about 14 or 18 ring carbon atoms, with benzyl being an exemplary arylalkyl group; arylalkoxy, for example, having 1 to 3 separate or fused rings with benzyloxy being an exemplary arylalkoxy group; or a saturated or partially unsaturated heterocycle having 1 to 3 separate or fused rings with one or more N, O or S atoms, or a heteroaryl having 1 to 3 separate or fused rings with one or more N, O or S atoms, e.g. coumarinyl, quinolinyl, isoquinolinyl, quinazolinyl, pyridyl, pyrazinyl, pyrimidinyl, furanyl, pyrrolyl, thienyl, thiazolyl, triazinyl, oxazolyl, isoxazolyl, imidazolyl, indolyl, benzofuranyl, benzothiazolyl, tetrahydrofuranyl, tetrahydropyranyl, piperidinyl, morpholinyl, piperazinyl, and pyrrolidinyl. Such groups may be further substituted, e.g. with hydroxy, alkyl, alkoxy, halogen and amino. In certain embodiments "optionally substituted" includes one or more substituents independently selected from halogen, hydroxyl, amino, cyano, —CHO, —COOH, —CONH$_2$, alkyl including $C_1$-$C_6$alkyl, alkenyl including $C_2$-$C_6$alkenyl, alkynyl including $C_2$-$C_6$alkynyl, —$C_1$-$C_6$alkoxy, alkanoyl including $C_2$-$C_6$alkanoyl, $C_1$-$C_6$alkylester, (mono- and di-$C_1$-$C_6$alkylamino)$C_0$-$C_2$alkyl, haloalkyl including $C_1$-$C_6$haloalkyl, hydoxy$C_1$-$C_6$alkyl, ester, carbamate, urea, sulfonamide, —$C_1$-$C_6$alkyl(heterocyclo), $C_1$-$C_6$alkyl(heteroaryl), —$C_1$-$C_6$alkyl($C_3$-$C_7$cycloalkyl), O—$C_1$-$C_6$alkyl ($C_3$-$C_7$cycloalkyl), B(OH)$_2$, phosphate, phosphonate and haloalkoxy including $C_1$-$C_6$haloalkoxy.

"Aliphatic" refers to a saturated or unsaturated, straight, branched, or cyclic hydrocarbon. "Aliphatic" is intended herein to include, but is not limited to, alkyl, alkenyl, alkynyl, cycloalkyl, cycloalkenyl, and cycloalkynyl moieties, and thus incorporates each of these definitions. In one embodiment, "aliphatic" is used to indicate those aliphatic groups having 1-20 carbon atoms. The aliphatic chain can be, for example, mono-unsaturated, di-unsaturated, tri-unsaturated, or polyunsaturated, or alkynyl. Unsaturated aliphatic groups can be in a cis or trans configuration. In one embodiment, the aliphatic group contains from 1 to about 12 carbon atoms, more generally from 1 to about 6 carbon atoms or from 1 to about 4 carbon atoms. In one embodiment, the aliphatic group contains from 1 to about 8 carbon atoms. In certain embodiments, the aliphatic group is $C_1$-$C_2$, $C_1$-$C_3$, $C_1$-$C_4$, $C_1$-$C_5$ or $C_1$-$C_6$. The specified ranges as used herein indicate an aliphatic group having each member of the range described as an independent species. For example, the term $C_1$-$C_6$ aliphatic as used herein indicates a straight or branched alkyl, alkenyl, or alkynyl group having from 1, 2, 3, 4, 5, or 6 carbon atoms and is intended to mean that each of these is described as an independent species. For example, the term $C_1$-$C_4$ aliphatic as used herein indicates a straight or branched alkyl, alkenyl, or alkynyl group having from 1, 2, 3, or 4 carbon atoms and is intended to mean that each of these is described as an independent species. In one embodiment, the aliphatic group is substituted with one or more functional groups that results in the formation of a stable moiety.

The term "heteroaliphatic" refers to an aliphatic moiety that contains at least one heteroatom in the chain, for example, an amine, carbonyl, carboxy, oxo, thio, phosphate, phosphonate, nitrogen, phosphorus, silicon, or boron atoms in place of a carbon atom. In one embodiment, the only heteroatom is nitrogen. In one embodiment, the only heteroatom is oxygen. In one embodiment, the only heteroatom is sulfur. "Heteroaliphatic" is intended herein to include, but is not limited to, heteroalkyl, heteroalkenyl, heteroalkynyl, heterocycloalkyl, heterocycloalkenyl, and heterocycloalkynyl moieties. In one embodiment, "heteroaliphatic" is used to indicate a heteroaliphatic group (cyclic, acyclic, substituted, unsubstituted, branched or unbranched) having 1-20 carbon atoms. In one embodiment, the heteroaliphatic group is optionally substituted in a manner that results in the formation of a stable moiety. Nonlimiting examples of heteroaliphatic moieties are polyethylene glycol, polyalkylene glycol, amide, polyamide, polylactide, polyglycolide, thioether, ether, alkyl-heterocycle-alkyl, —O-alkyl-O-alkyl, alkyl-O-haloalkyl, etc.

A "dosage form" means a unit of administration of an active agent. Examples of dosage forms include tablets, capsules, injections, suspensions, liquids, emulsions, implants, particles, spheres, creams, ointments, suppositories, inhalable forms, transdermal forms, buccal, sublingual, topical, gel, mucosal, and the like. A "dosage form" can also include an implant, for example an optical implant.

An "effective amount" as used herein, means an amount which provides a therapeutic or prophylactic benefit.

As used herein "endogenous" refers to any material from or produced inside an organism, cell, tissue or system.

As used herein, the term "exogenous" refers to any material introduced from or produced outside an organism, cell, tissue or system.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

"Parenteral" administration of an immunogenic composition includes, e.g., subcutaneous (s.c.), intravenous (i.v.), intramuscular (i.m.), or intrasternal injection, or infusion techniques.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

To "treat" a disease as the term is used herein, means to reduce the frequency or severity of at least one sign or symptom of a disease or disorder experienced by a subject.

Ranges: throughout this disclosure, various aspects of the invention can be presented in a range format. It should be understood that the description in range format is merely for convenience and should not be construed as a limitation on the scope of the invention. The description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

As used herein, "pharmaceutical compositions" are compositions comprising at least one active agent, and at least one other substance, such as a carrier. "Pharmaceutical combinations" are combinations of at least two active agents which may be combined in a single dosage form or provided together in separate dosage forms with instructions that the active agents are to be used together to treat any disorder described herein.

As used herein, "pharmaceutically acceptable salt" is a derivative of the disclosed compound in which the parent compound is modified by making inorganic and organic, non-toxic, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are typical, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like, or using a different acid that produces the same counterion. Lists of additional suitable salts may be found, e.g., in *Remington's Pharmaceutical Sciences*, 17th ed., Mack Publishing Company, Easton, Pa., p. 1418 (1985).

The term "carrier" applied to pharmaceutical compositions/combinations of the invention refers to a diluent, excipient, or vehicle with which an active compound is provided.

A "pharmaceutically acceptable excipient" means an excipient that is useful in preparing a pharmaceutical composition/combination that is generally safe, non-toxic and neither biologically nor otherwise inappropriate for administration to a host, typically a human. In one embodiment, an excipient is used that is acceptable for veterinary use.

A "patient" or "host" or "subject" is a human or non-human animal in need of treatment or prevention of any of the disorders as specifically described herein, for example that is modulated by a natural (wild-type) or modified (non-wild type) protein that can be degraded according to the present invention, resulting in a therapeutic effect. Typically, the host is a human. A "host" may alternatively refer to for example, a mammal, primate (e.g., human), cow, sheep, goat, horse, dog, cat, rabbit, rat, mice, fish, bird and the like.

A "therapeutically effective amount" of a pharmaceutical composition/combination of this invention means an amount effective, when administered to a host, to provide a therapeutic benefit such as an amelioration of symptoms or reduction or diminution of the disease itself.

II. Compounds

In one aspect of the present invention a compound of Formula I or Formula II is provided:

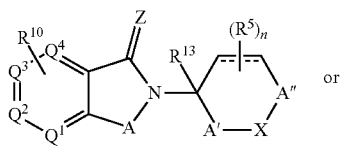
(I)

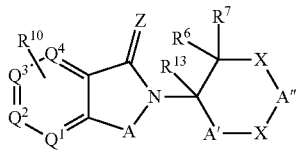
(II)

or a pharmaceutically acceptable salt, N-oxide, isotopic derivative, prodrug, optionally in a pharmaceutically acceptable carrier to form a pharmaceutically acceptable composition;

wherein:

the variables are as defined above, wherein in certain embodiments the compound has at least one of: a, b, c, d, e, f, g, h, i, j, k, l, or m:

a. n is 1 or 2;
b. at least one of $R^1$, $R^2$, $R^3$, or $R^4$ is alkyl;
c. $R^1$ and $R^2$ form a 4, 5, or 6 membered spiroheterocycle or 3, 4, 5, or 6 membered spirocarbocycle;
d. $R^3$ and $R^4$ form a 4, 5, or 6 membered spiroheterocycle or 3, 4, 5, or 6 membered spirocarbocycle;
e. $R^6$ and $R^7$ form a 4, 5, or 6 membered spiroheterocycle or 3, 4, 5, or 6 membered spirocarbocycle;
f. $R^8$ and $R^9$ form a 4, 5, or 6 membered spiroheterocycle or 3, 4, 5, or 6 membered spirocarbocycle;
g. $R^1$ and $R^3$ form a 1 or 2 carbon bridged ring;
h. $R^1$ and $R^{13}$ form a 3, 4, 5, or 6 carbon fused ring;
i. $R^4$ and $R^{13}$ form a 1 or 2 carbon bridged ring;
j. A is $SO_2$, S(O), P(O)Oalkyl, P(O)NHalkyl, P(O)N(alkyl)$_2$, P(O)alkyl, P(O)OH, or P(O)NH$_2$;
k. A' is $SO_2$, S(O), P(O)Oalkyl, P(O)NHalkyl, P(O)N(alkyl)$_2$, P(O)alkyl, P(O)OH, or P(O)NH$_2$
l. A" is $SO_2$, S(O), P(O)Oalkyl, P(O)NHalkyl, P(O)N(alkyl)$_2$, P(O)alkyl, P(O)OH, or P(O)NH$_2$; or
m. X is O, or S.

Non-limiting examples of compounds of Formula I include:

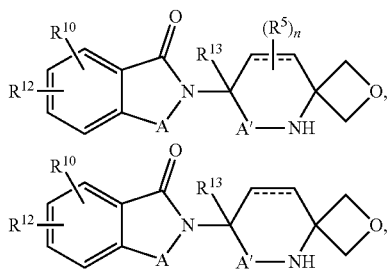

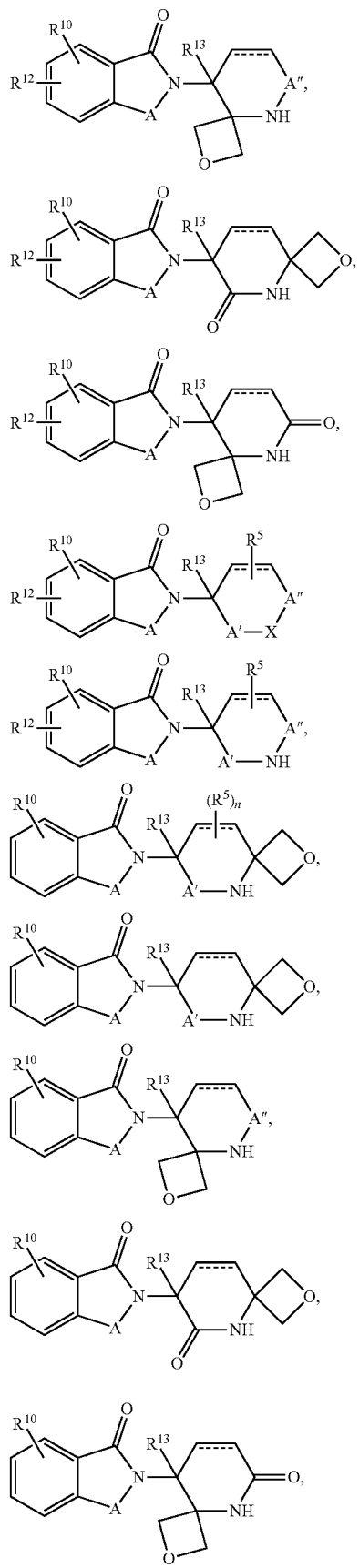

-continued
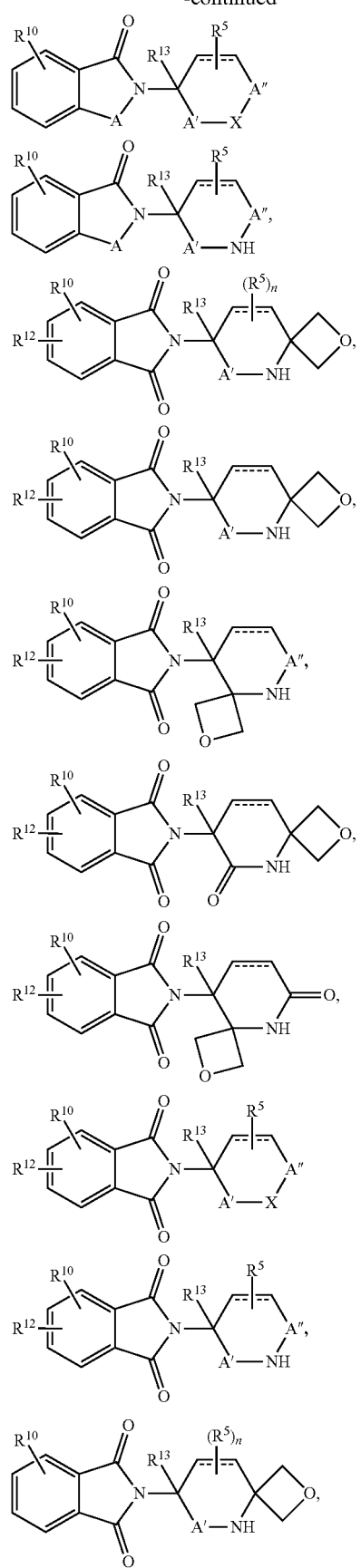
-continued
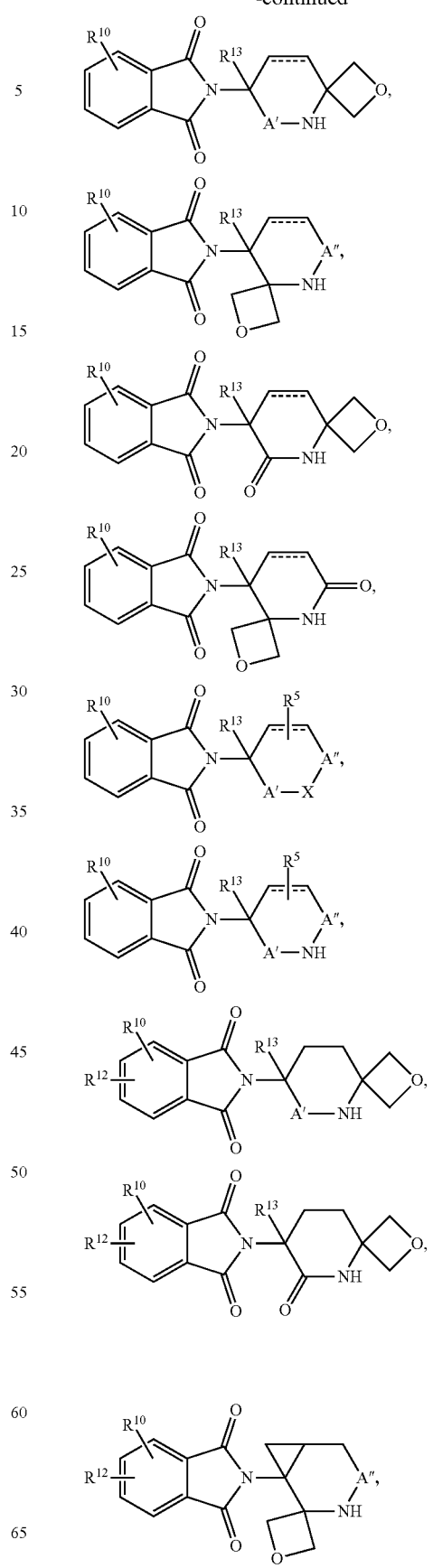

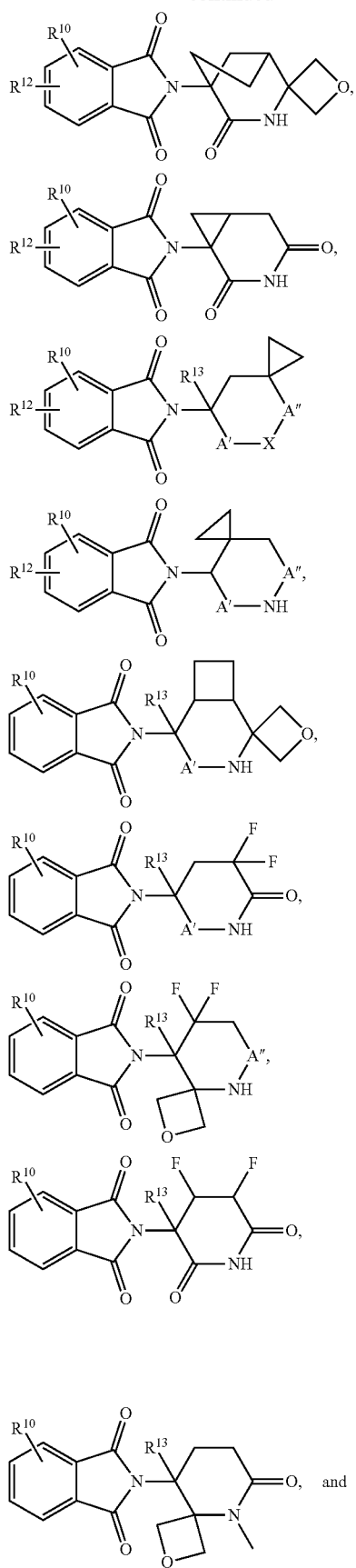
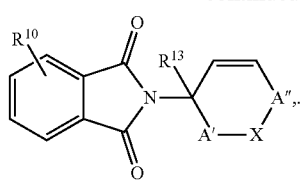
Additional non-limiting examples of compounds of Formula I include:
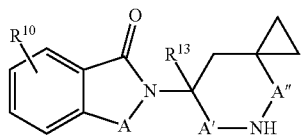
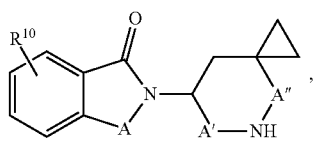
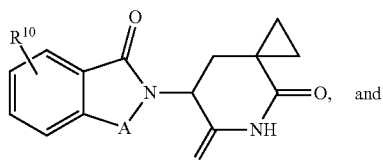
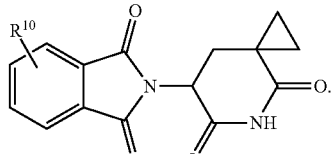
In one embodiment of the present invention
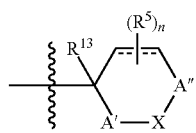
is selected from:
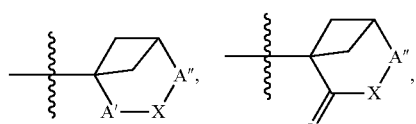
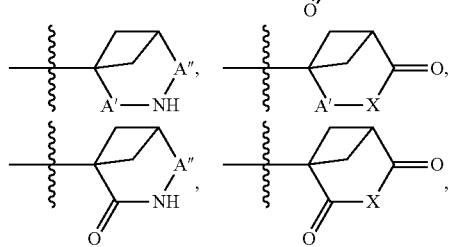

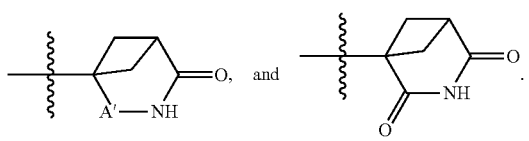
In an additional embodiment the Degronimer of Formula I is selected from:
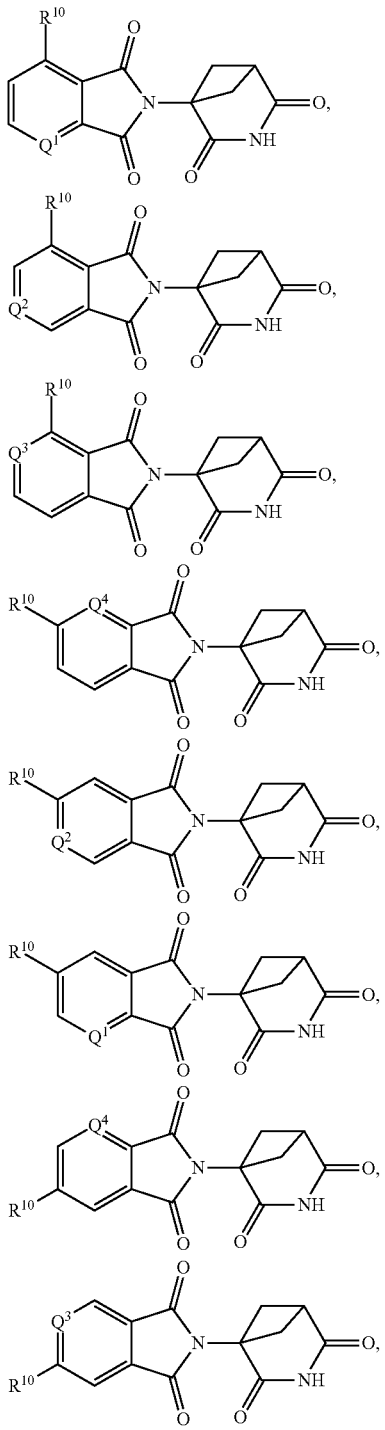
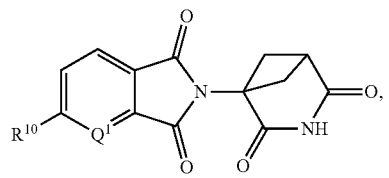
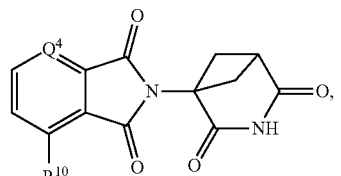
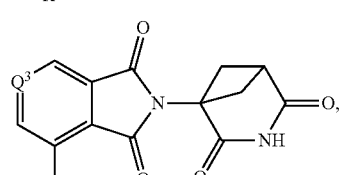
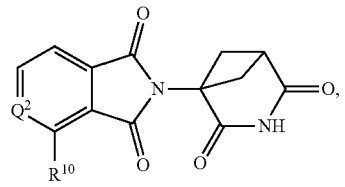
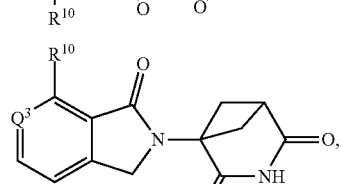
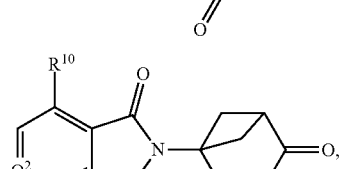
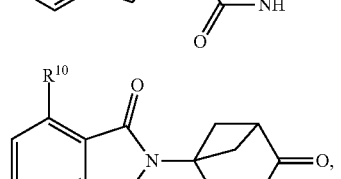
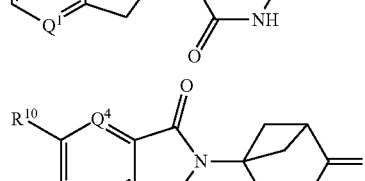
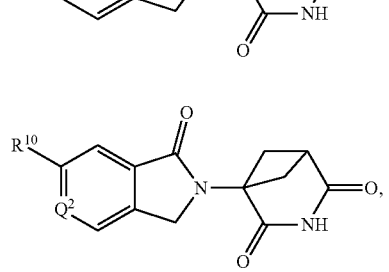

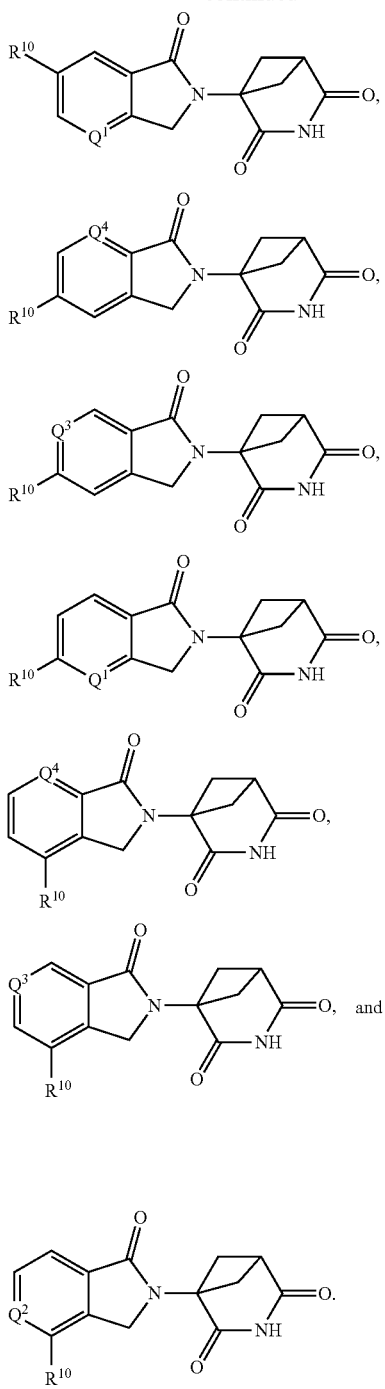
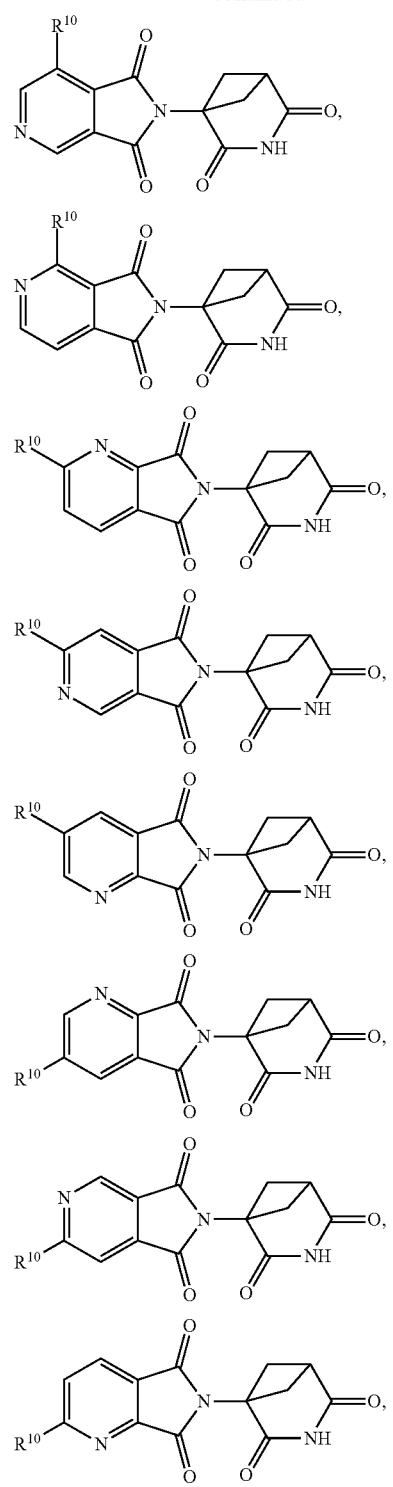
In an additional embodiment the Degronimer of Formula I is selected from:
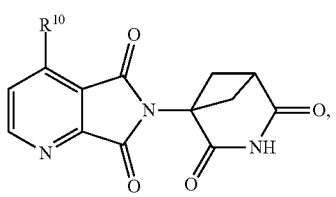

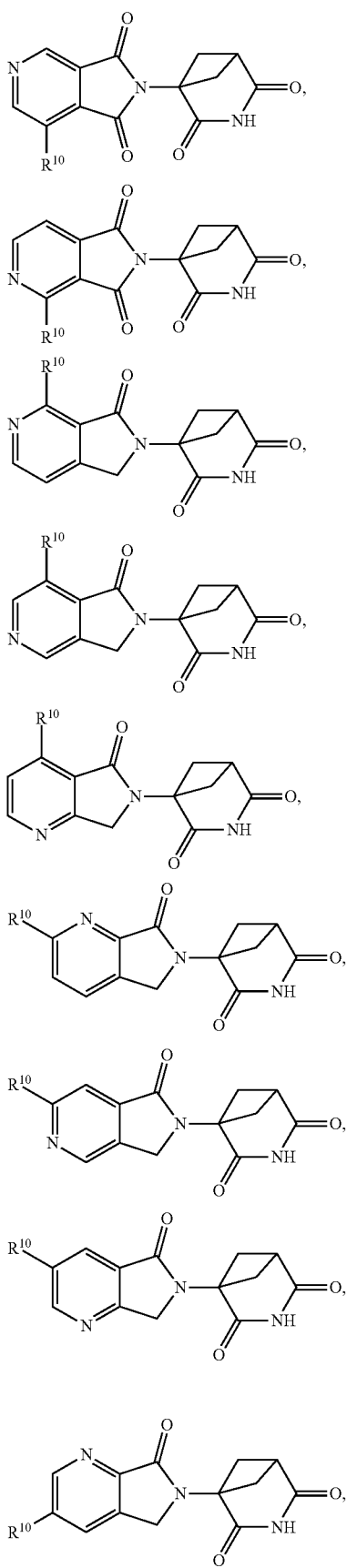
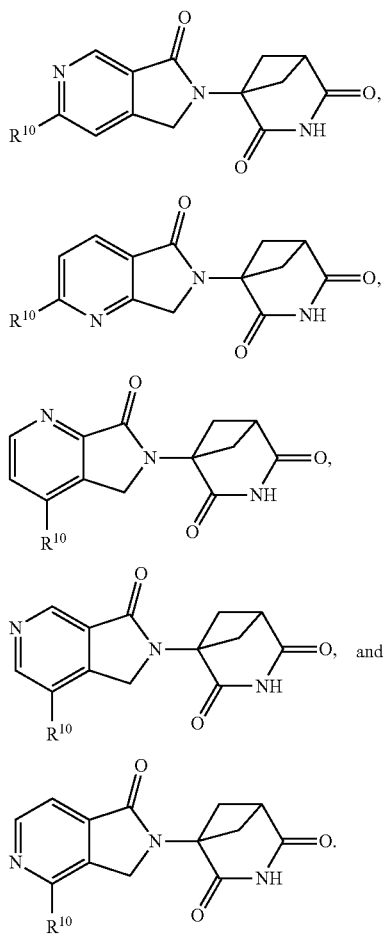
In an additional embodiment the Degronimer of Formula I is selected from:
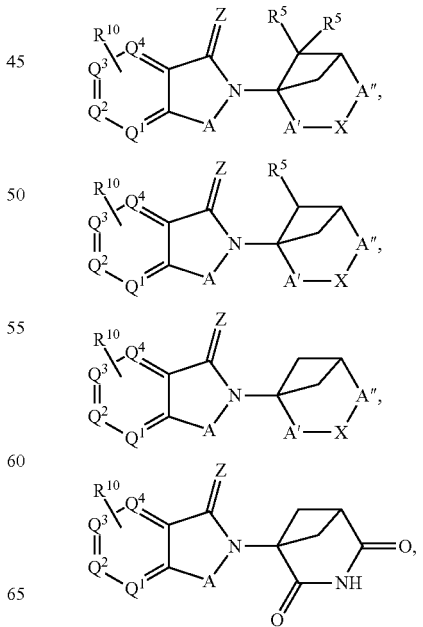

-continued
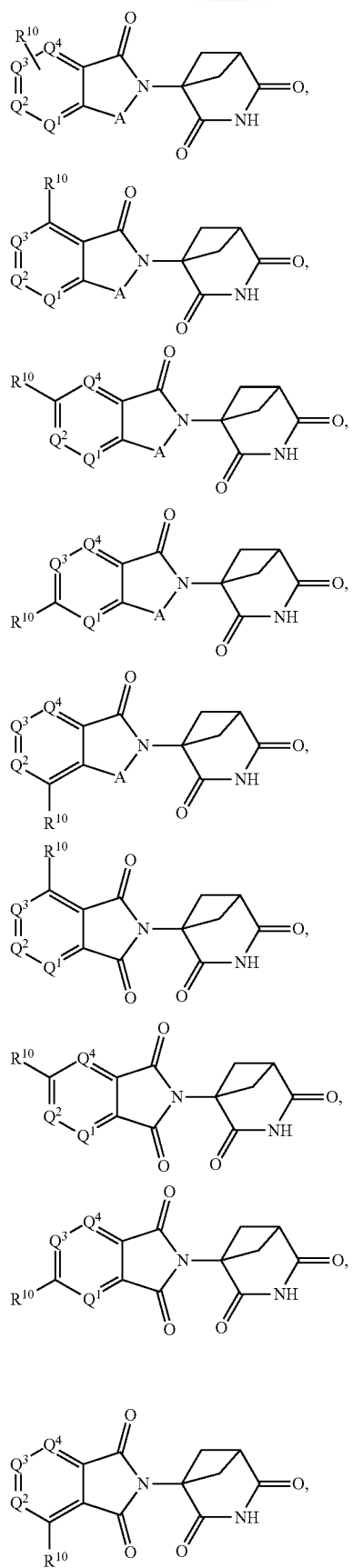
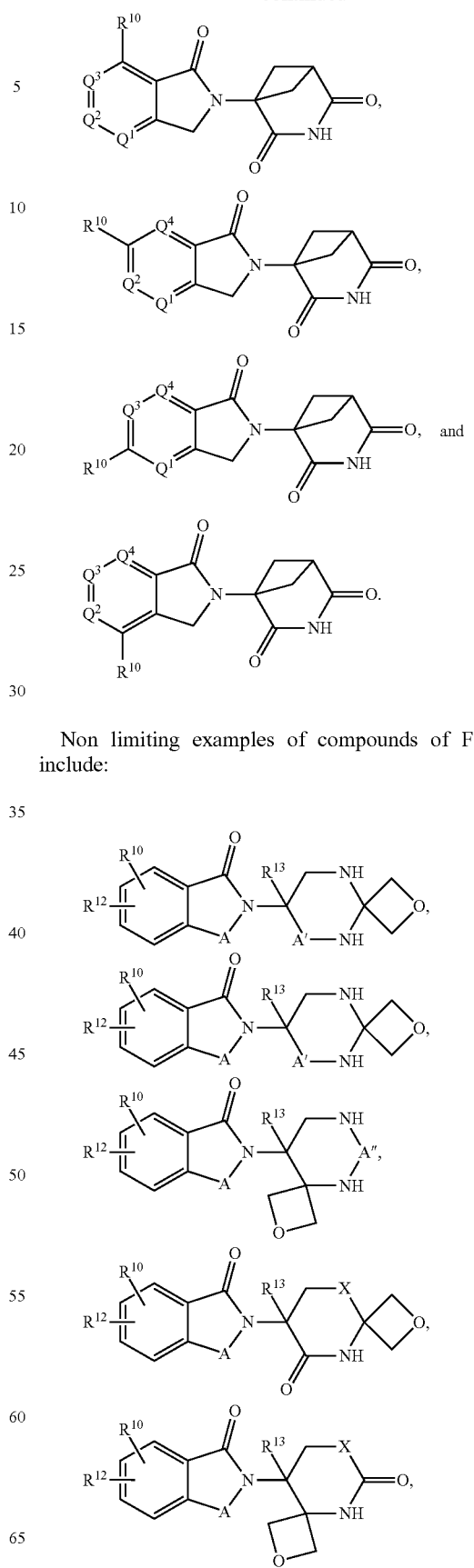
Non limiting examples of compounds of Formula II include:

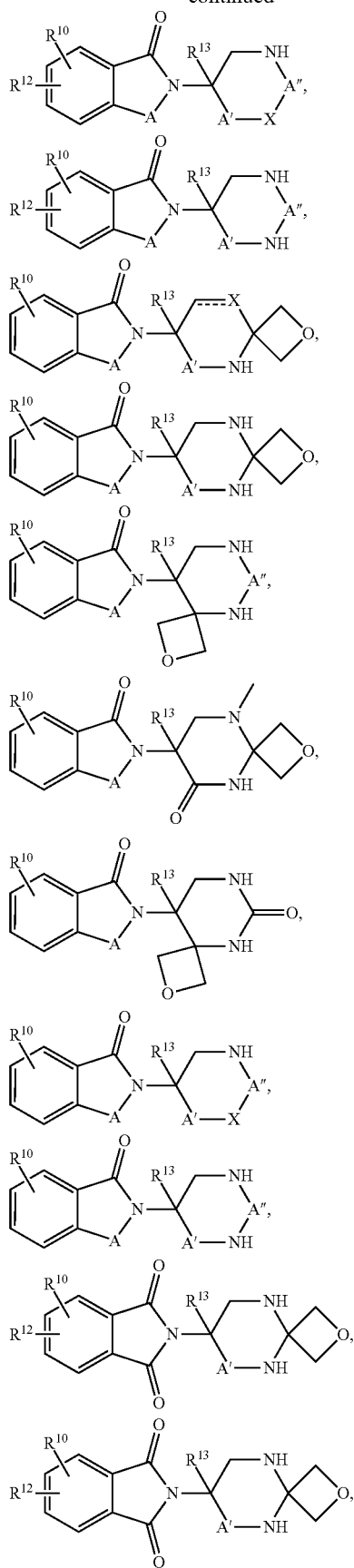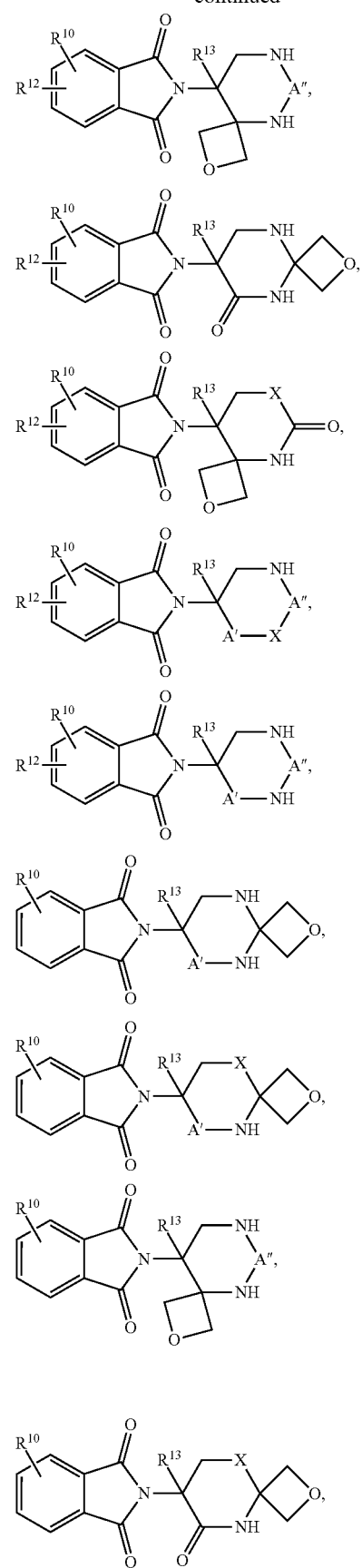

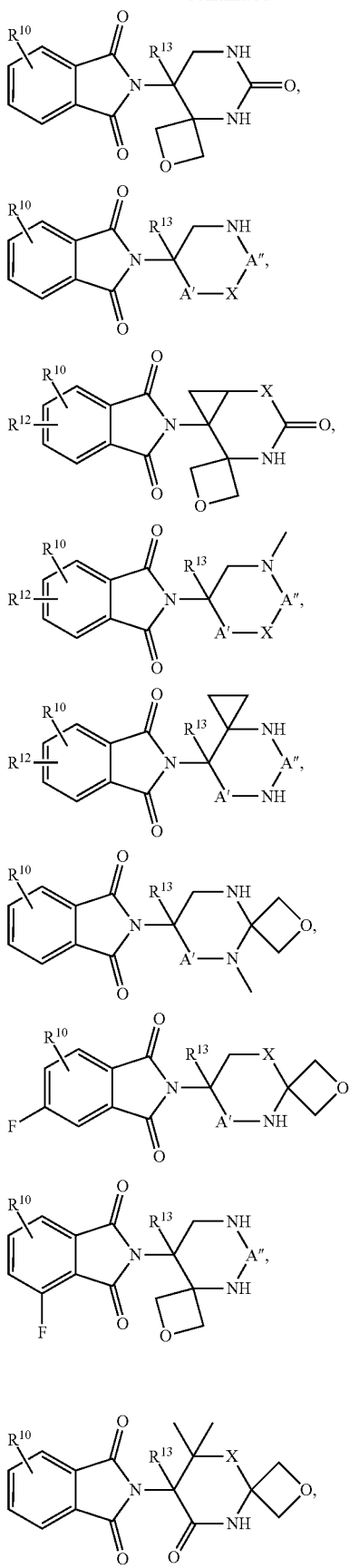
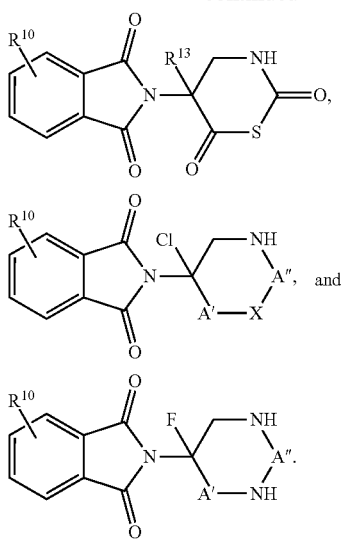

In another aspect of the present invention a compound of Formula III is provided:

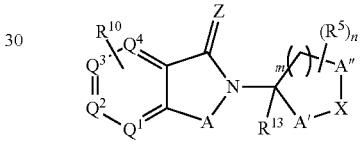

(III)

or a pharmaceutically acceptable salt, N-oxide, isotopic derivative, prodrug, optionally in a pharmaceutically acceptable carrier to form a pharmaceutically acceptable composition thereof, wherein the variables are as defined herein.

Non limiting examples of compounds of Formula III include:

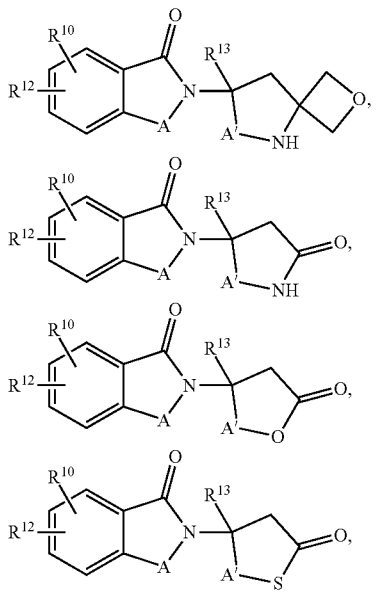

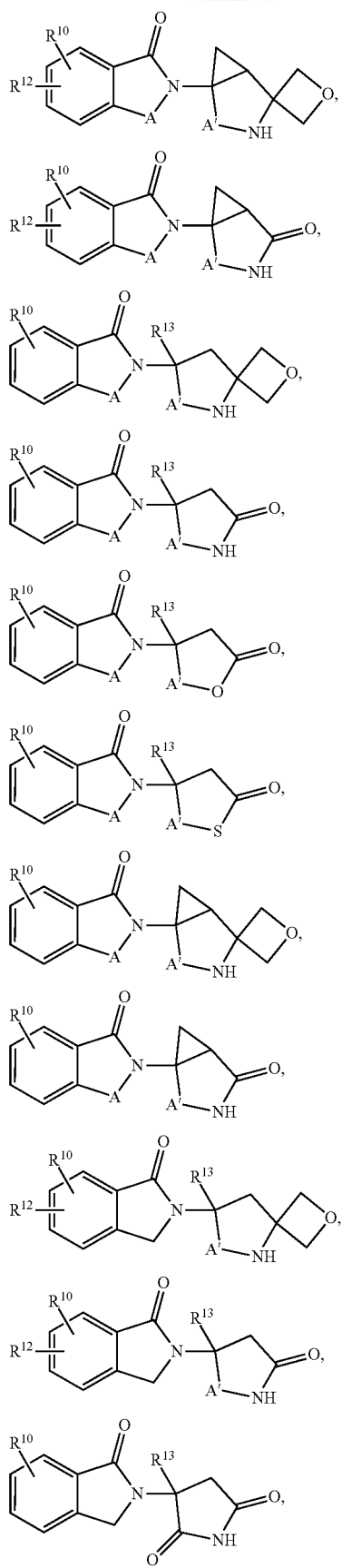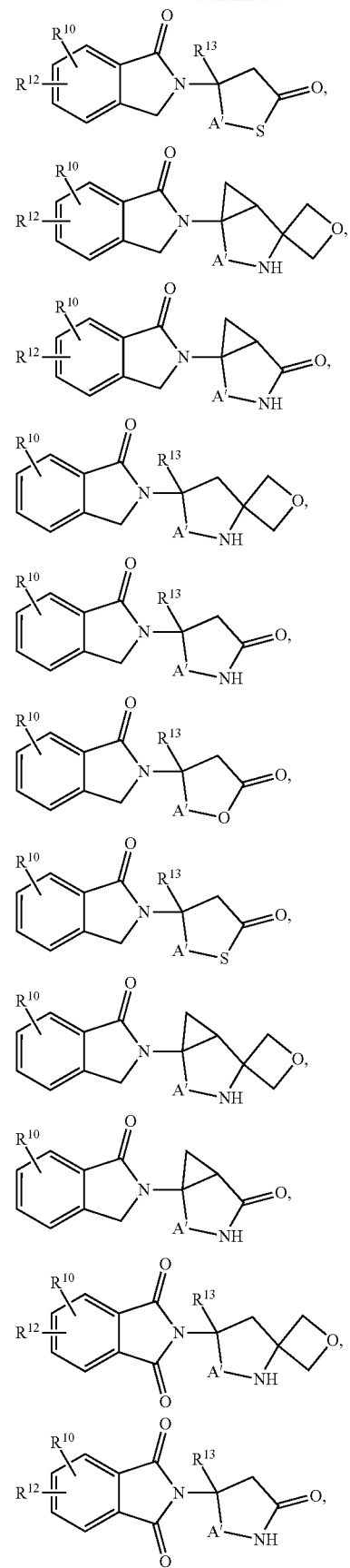

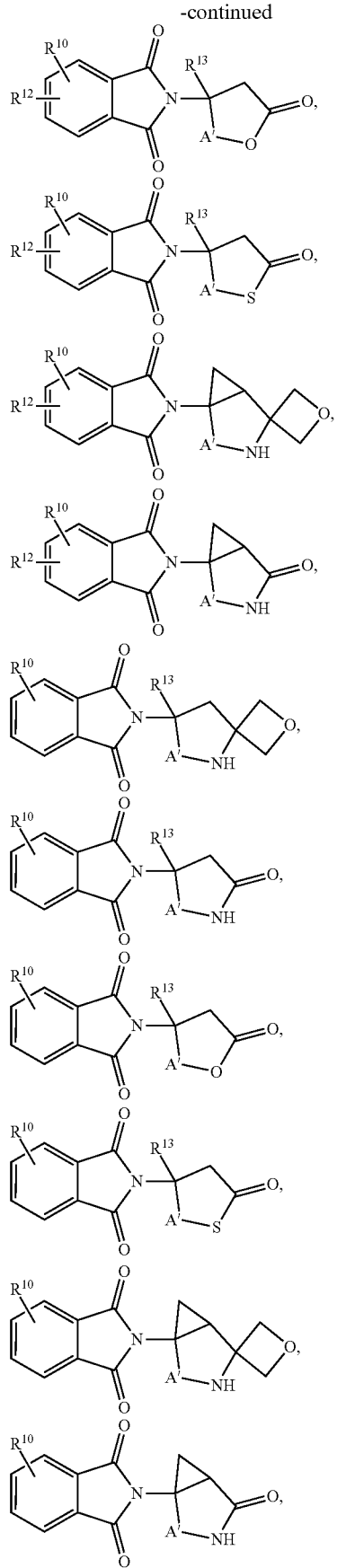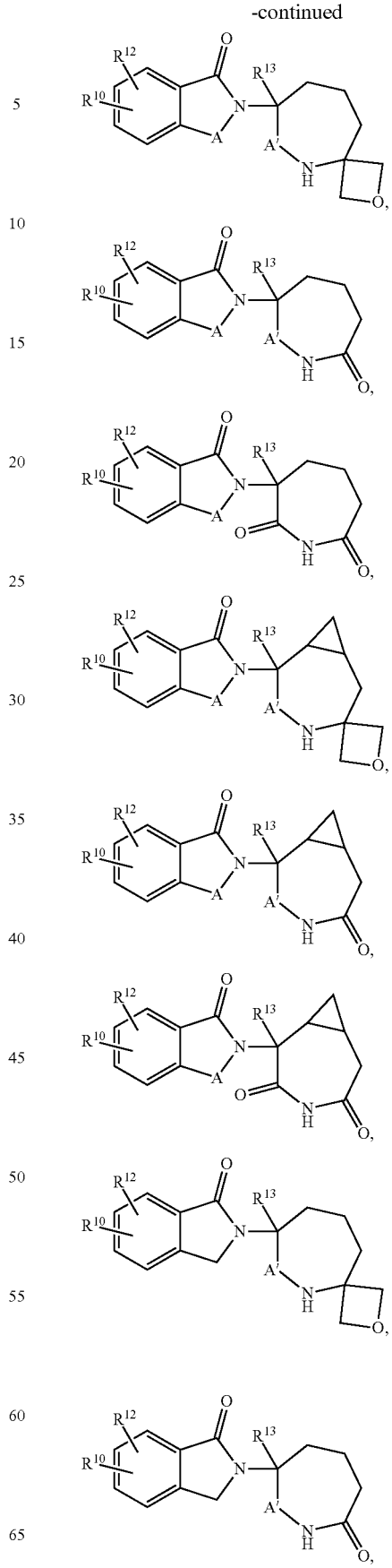

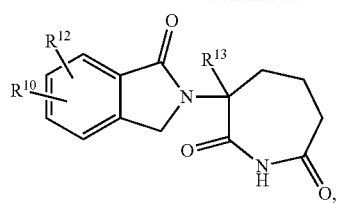
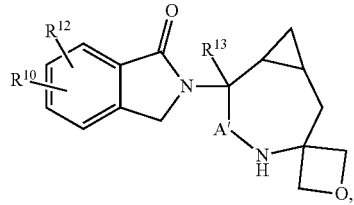
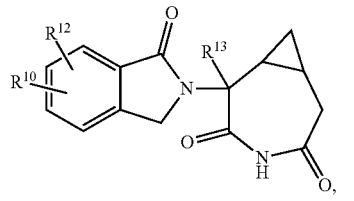
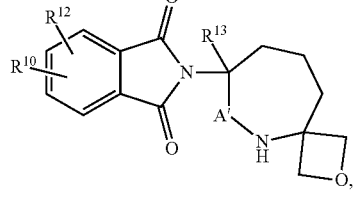
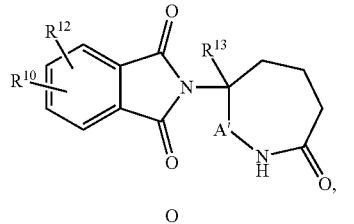
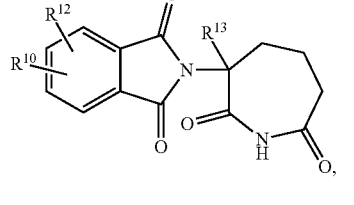
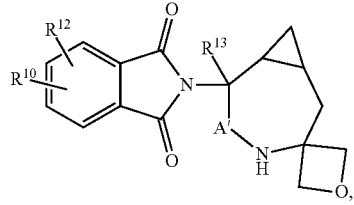
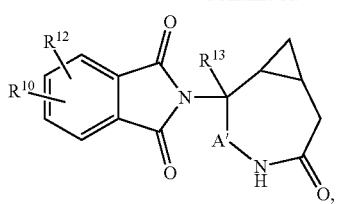
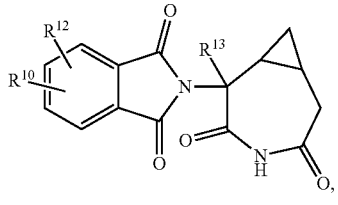
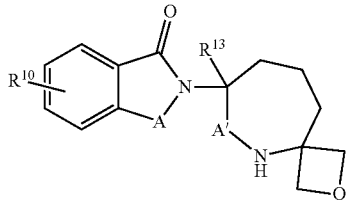
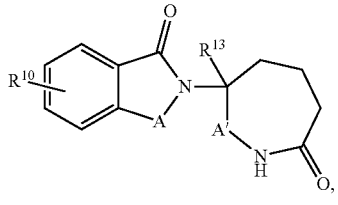
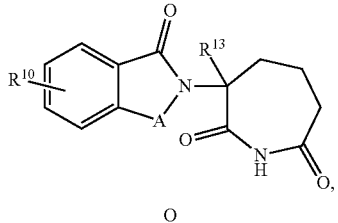
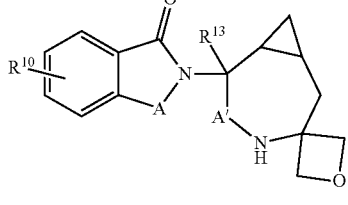
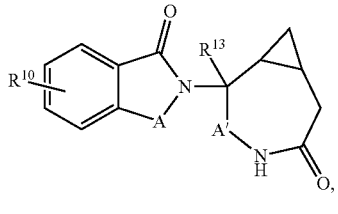
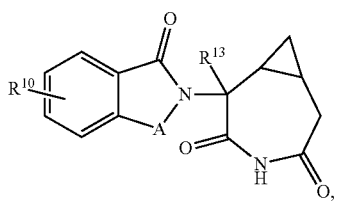

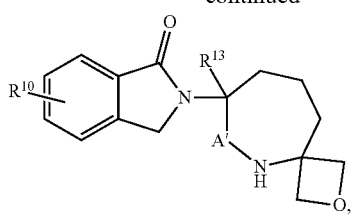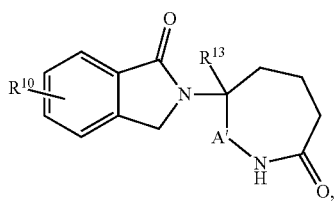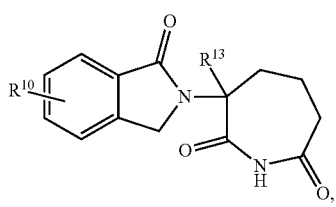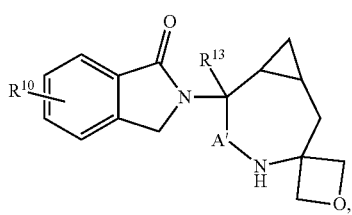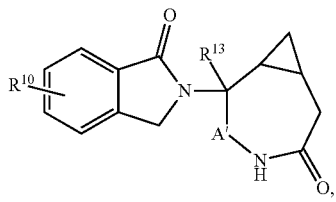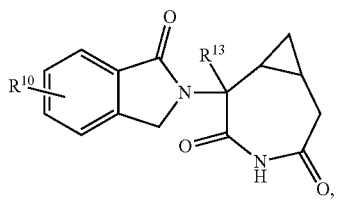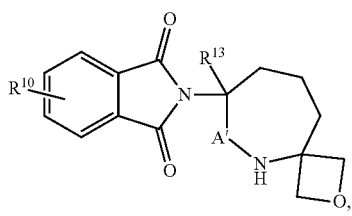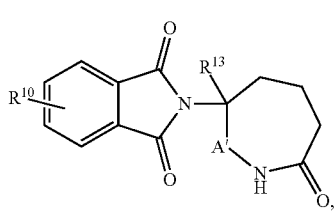
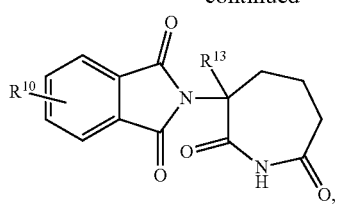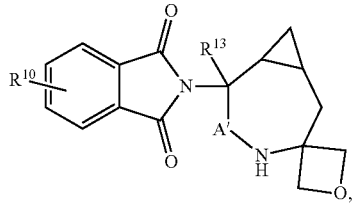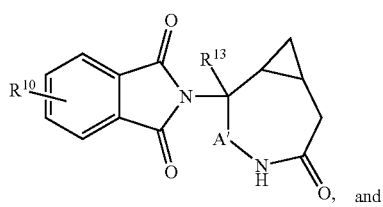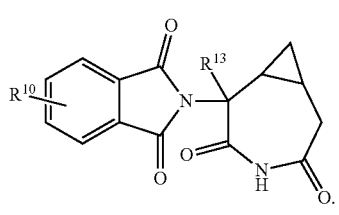
Additional non limiting examples of compounds of Formula III include:
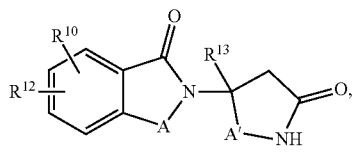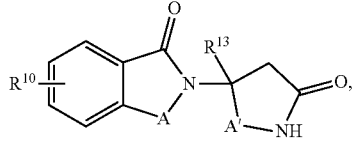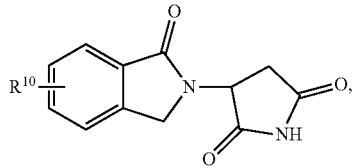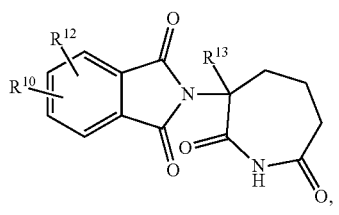

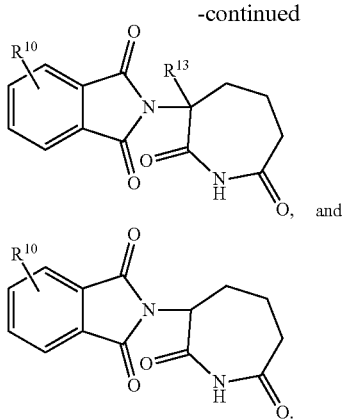

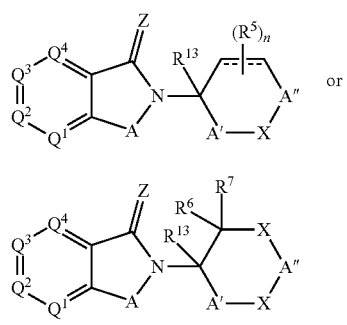

In another aspect of the present invention a compound of Formula IV or Formula V is provided:

(IV)

(V)

or a pharmaceutically acceptable salt, N-oxide, isotopic derivative, prodrug, optionally in a pharmaceutically acceptable carrier to form a pharmaceutically acceptable composition;

wherein:

the variables are as defined above and wherein in certain embodiments, a, b, c, d, e, f, g, h, i, or j is required:

a. $R^1$ and $R^2$ form a 4, 5, or 6 membered spiroheterocycle or 3, 4, 5, or 6 membered spirocarbocycle;
b. $R^3$ and $R^4$ form a 4, 5, or 6 membered spiroheterocycle or 3, 4, 5, or 6 membered spirocarbocycle;
c. $R^6$ and $R^7$ form a 4, 5, or 6 membered spiroheterocycle or 3, 4, 5, or 6 membered spirocarbocycle;
d. $R^8$ and $R^9$ form a 4, 5, or 6 membered spiroheterocycle or 3, 4, 5, or 6 membered spirocarbocycle;
e. $R^1$ and $R^3$ form a 1 or 2 carbon bridged ring;
f. $R^1$ and $R^{13}$ form a 3, 4, 5, or 6 membered fused ring;
g. $R^4$ and $R^{13}$ form a 1 or 2 carbon bridged ring;
h. A is P(O)Oalkyl, P(O)NHalkyl, P(O)N(alkyl)$_2$, P(O)alkyl, P(O)OH, or P(O)NH$_2$;
i. A' is SO$_2$, S(O), P(O)Oalkyl, P(O)NHalkyl, P(O)N(alkyl)$_2$, P(O)alkyl, P(O)OH, or P(O)NH$_2$; or
j. A" is SO$_2$, S(O), P(O)Oalkyl, P(O)NHalkyl, P(O)N(alkyl)$_2$, P(O)alkyl, P(O)OH, or P(O)NH$_2$.

Non limiting examples of compounds of Formula IV include:

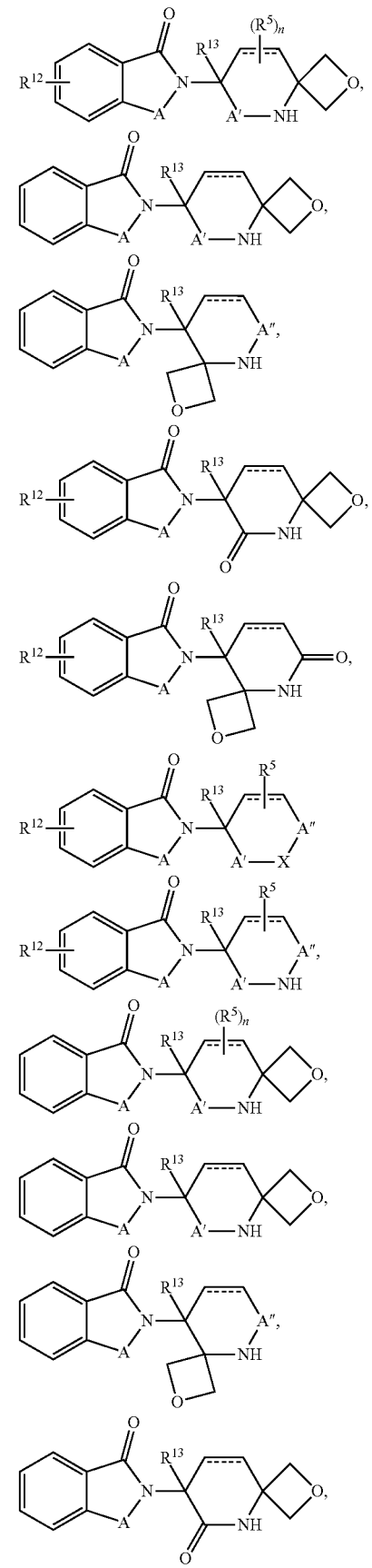

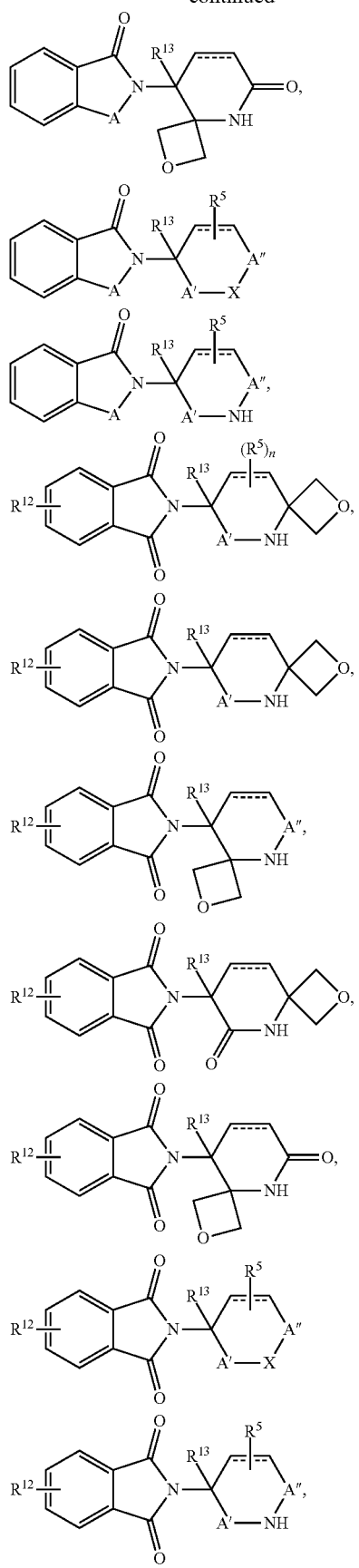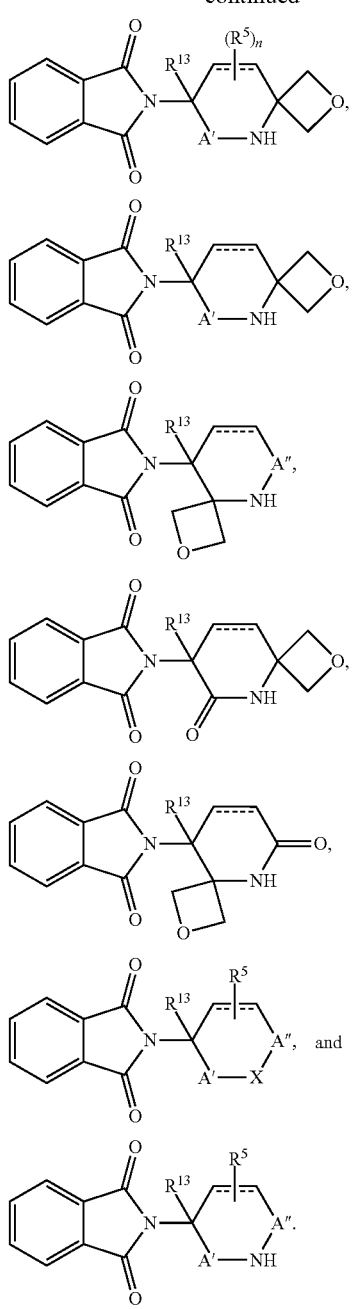
Additional non-limiting examples of compounds of Formula IV include:
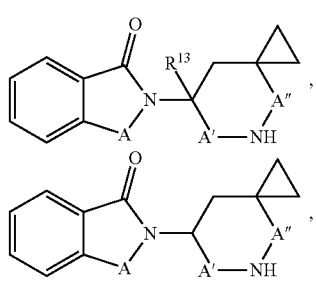

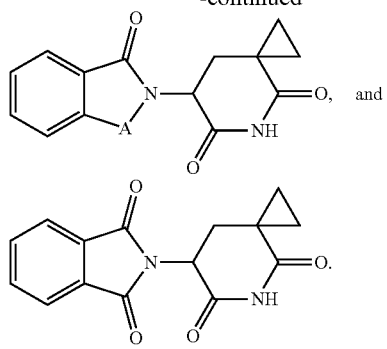
In an additional embodiment the Degronimer of Formula IV is selected from:
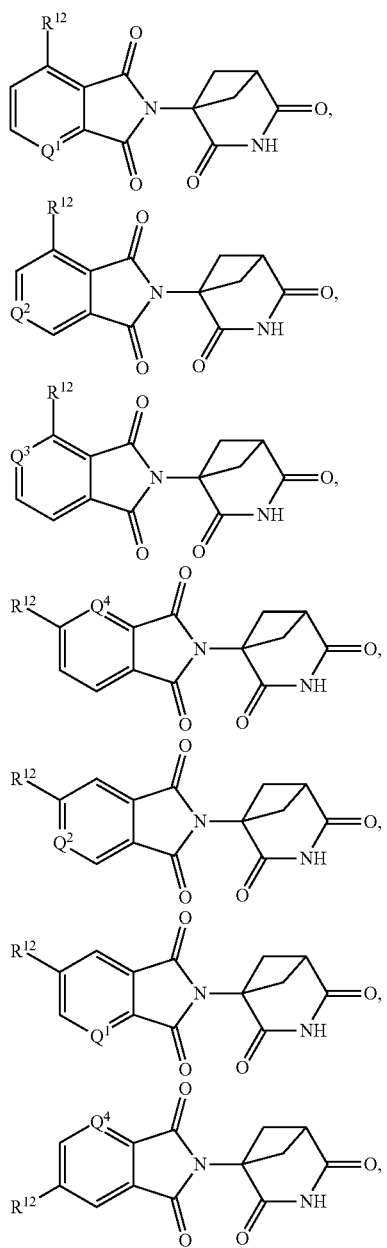
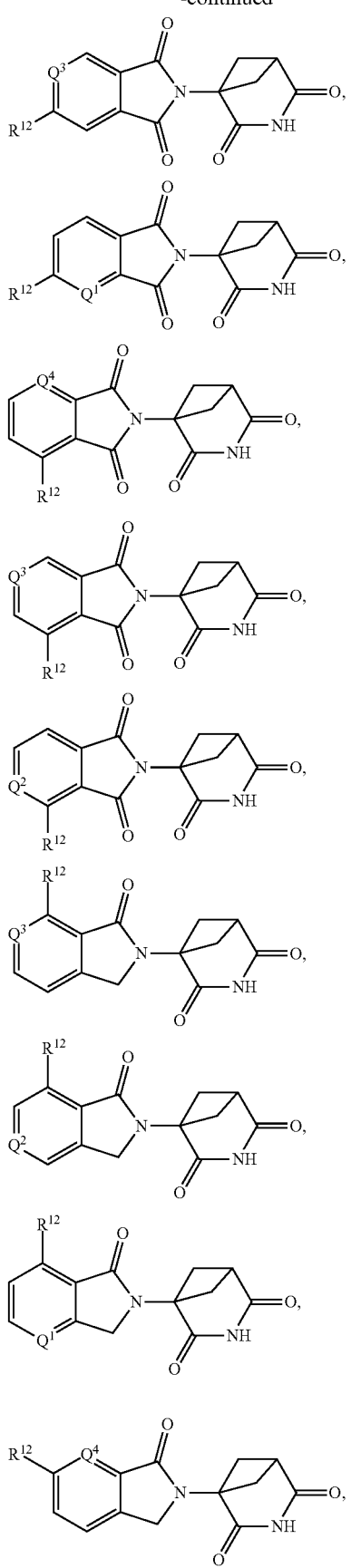

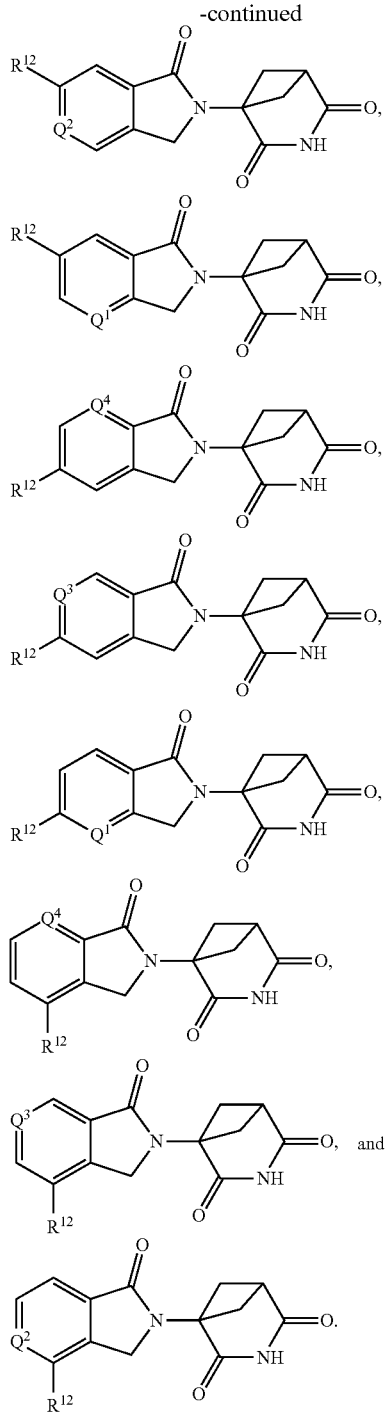
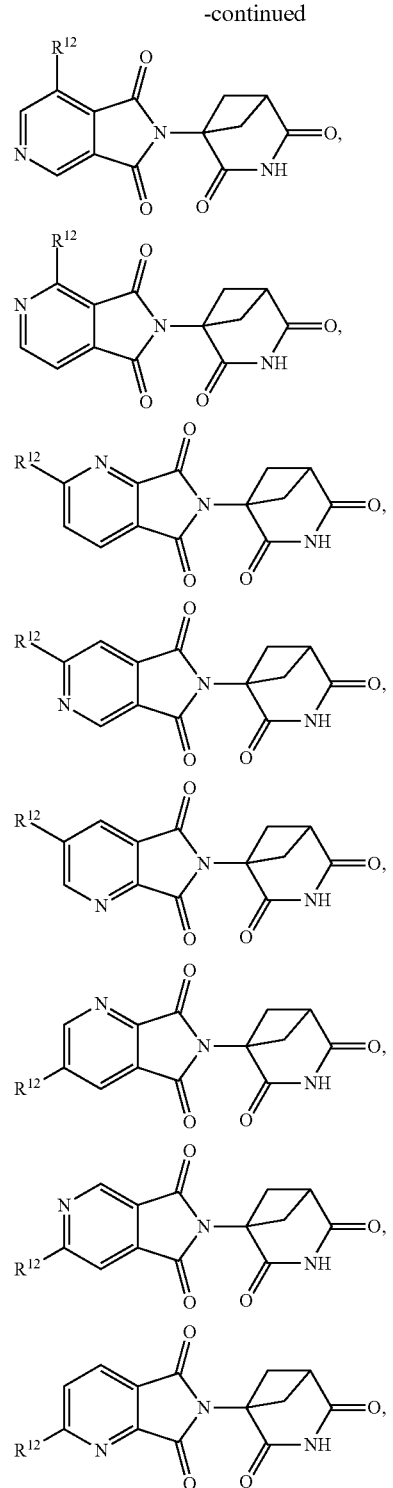
In an additional embodiment the Degronimer of Formula IV is selected from:
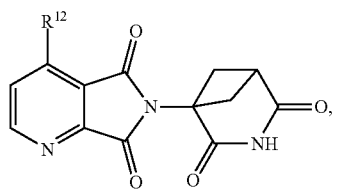
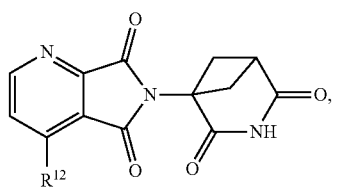

95
-continued
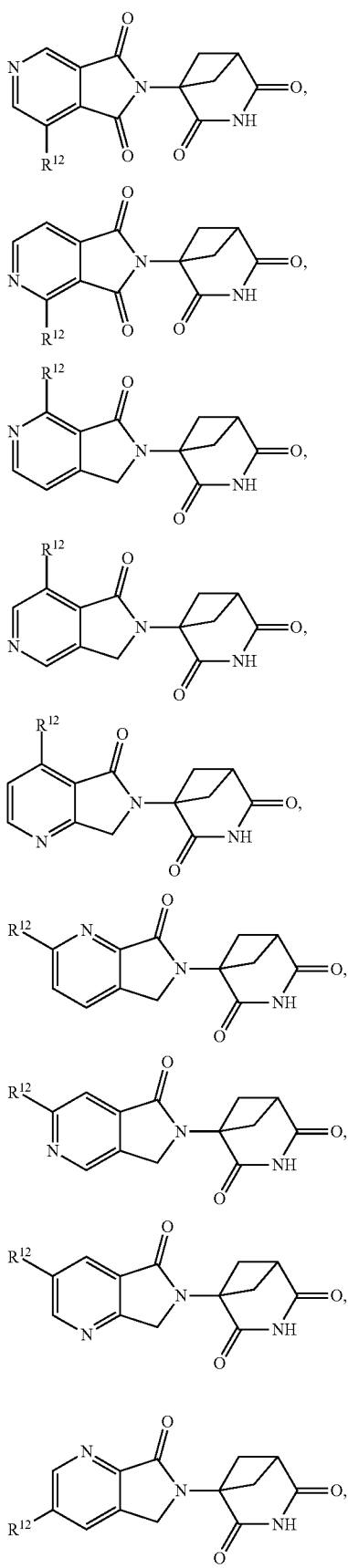
96
-continued
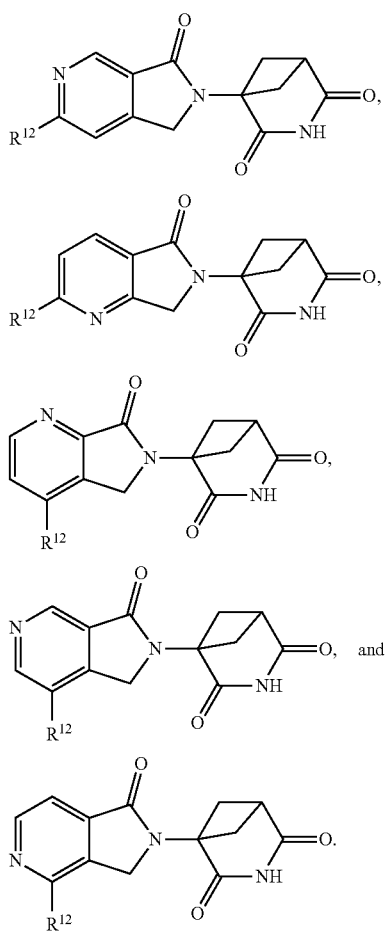
In an additional embodiment the Degronimer of Formula IV is selected from:
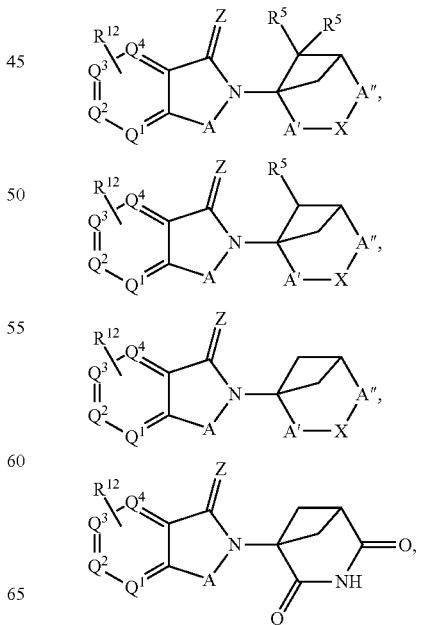

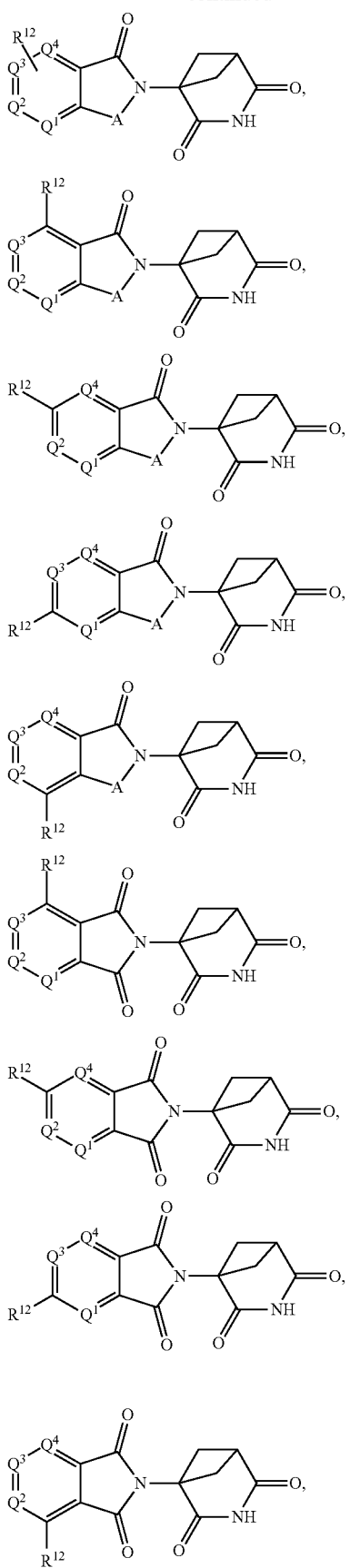
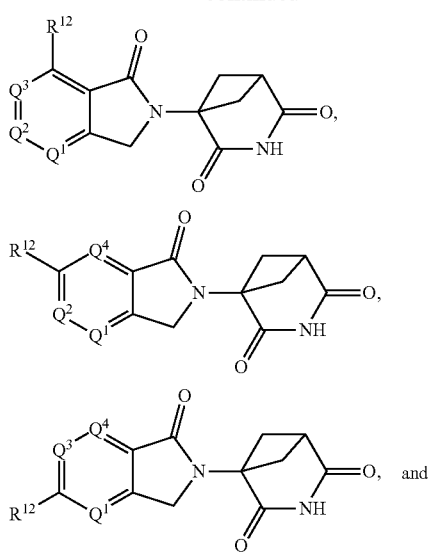
Non-limiting examples of compounds of Formula V include:
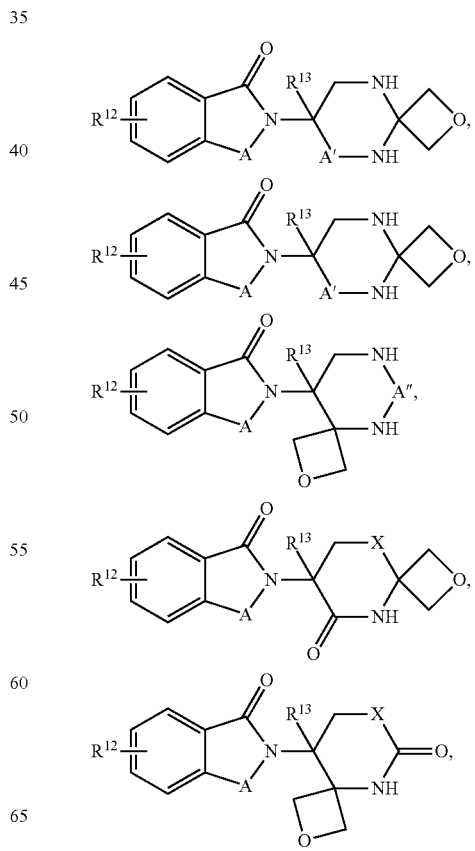

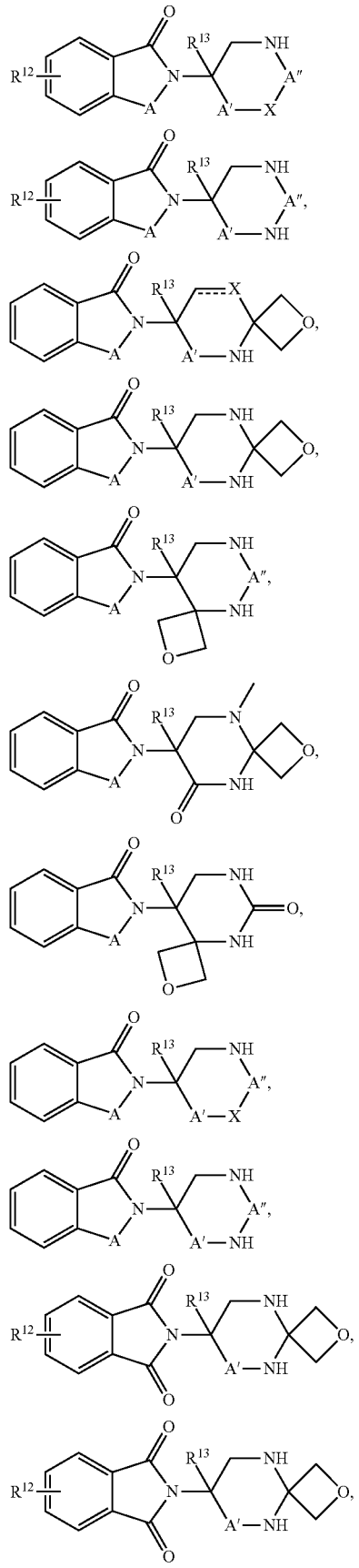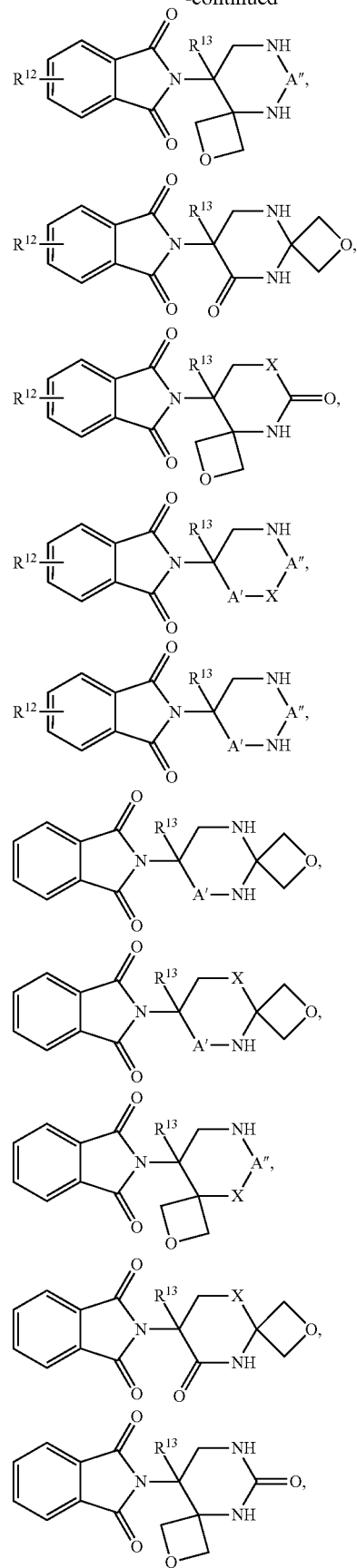

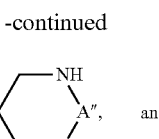
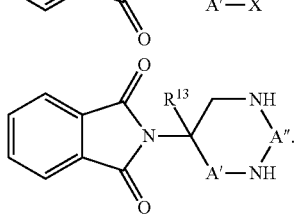

In another aspect of the present invention a compound of Formula VI is provided:

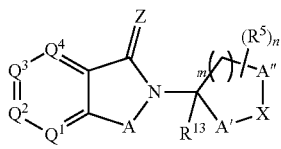

or a pharmaceutically acceptable salt, N-oxide, isotopic derivative, prodrug, optionally in a pharmaceutically acceptable carrier to form a pharmaceutically acceptable composition;
wherein:
A is $CR^8R^9$, C=O, C=S, C=$CH_2$, $SO_2$, S(O), P(O)Oalkyl, P(O)NHalkyl, P(O)N(alkyl)$_2$, P(O)alkyl, P(O)OH, P(O)NH$_2$;
A' is $CR^1R^2$, C=O, C=S, C=$CH_2$, $SO_2$, S(O), P(O)Oalkyl, P(O)NHalkyl, P(O)N(alkyl)$_2$, P(O)alkyl, P(O)OH, P(O)NH$_2$;
A" is $CR^3R^4$, C=O, C=S, C=$CH_2$, $SO_2$, S(O), P(O)Oalkyl, P(O)NHalkyl, P(O)N(alkyl)$_2$, P(O)alkyl, P(O)OH, P(O)NH$_2$;
X is independently NH, $NR^{11}$, $CH_2$, $CHR^{12}$, $C(R^{12})_2$, O, or S;
n is 0, 1, 2, 3, 4, or 5;
m is 1 or 3;
⎓⎓⎓ is a single or double bond;
$R^1$, $R^2$, $R^3$, $R^4$, $R^6$, $R^7$, $R^8$, $R^9$, and $R^{13}$ are independently selected from hydrogen, alkyl, hydroxyl, alkoxy, amine, —NHalkyl, —Nalkyl$_2$
or $R^1$ and $R^2$ form a 3-, 4-, 5-, or 6-membered spirocarbocycle, or a 4-, 5-, or 6-membered spiroheterocycle comprising 1 or 2 heteroatoms selected from N and O;
or $R^3$ and $R^4$ form a 3-, 4-, 5-, or 6-membered spirocarbocycle, or a 4-, 5-, or 6-membered spiroheterocycle comprising 1 or 2 heteroatoms selected from N and O;
or $R^6$ and $R^7$ form a 3-, 4-, 5-, or 6-membered spirocarbocycle, or a 4-, 5-, or 6-membered spiroheterocycle comprising 1 or 2 heteroatoms selected from N and O;
or $R^8$ and $R^9$ form a 3-, 4-, 5-, or 6-membered spirocarbocycle, or a 4-, 5-, or 6-membered spiroheterocycle comprising 1 or 2 heteroatoms selected from N and O;
or $R^1$ and $R^3$ form a 1 or 2 carbon bridged ring;
or $R^1$ and $R^7$ form a 1 or 2 carbon bridged ring;
or $R^3$ and $R^7$ form a 1 or 2 carbon bridged ring;
or $R^{13}$ and $R^1$ form a 3, 4, 5, or 6 carbon fused ring;
or $R^{13}$ and $R^4$ form a 1 or 2 carbon bridged ring;
or $R^{13}$ and $R^5$ form a 3, 4, 5, or 6 carbon fused ring wherein $R^5$ is on the carbon alpha to $R^{13}$ or a 1, 2, 3, or 4 carbon bridged ring wherein $R^5$ is not on the carbon alpha to $R^{13}$;
in a typical embodiment $W^1$ is C=O;
in another typical embodiment $W^2$ is C=O;
in another typical embodiment both $W^1$ and $W^2$ are C=O and X is NH;
$R^5$ is selected at each instance from: alkyl, alkene, alkyne, halogen, hydroxyl, alkoxy, azide, amino, —NHalkyl, —N(alkyl)$_2$, —NHSO$_2$alkyl, —N(alkyl)SO$_2$alkyl, —NHSO$_2$aryl, —N(alkyl)SO$_2$aryl, —NHSO$_2$alkenyl, —N(alkyl)SO$_2$alkenyl, —NHSO$_2$alkynyl, —N(alkyl)SO$_2$alkynyl, and haloalkyl;
or two $R^5$ substituents together with the carbon atom(s) to which they are bound can form a 3, 4, 5 or 6 membered ring;
$Q^1$, $Q^2$, $Q^3$, and $Q^4$ are independently selected from CH, $CR^{12}$, and N;
no more than three of $Q^1$, $Q^2$, $Q^3$, and $Q^4$ are N;
$R^{11}$ is independently selected from alkyl, alkenyl, alkynyl, C(O)H, —C(O)OH, —C(O)alkyl, —C(O)Oalkyl;
$R^{12}$ is independently selected from alkyl, alkenyl, alkynyl, halogen, hydroxyl, alkoxy, azide, amino, —C(O)H, —C(O)OH, —C(O)alkyl, —C(O)Oalkyl, —NHalkyl, —N(alkyl)$_2$, —NHSO$_2$alkyl, —N(alkyl)SO$_2$alkyl, —NHSO$_2$aryl, —N(alkyl)SO$_2$aryl, —NHSO$_2$alkenyl, —N(alkyl)SO$_2$alkenyl, —NHSO$_2$alkynyl, —N(alkyl)SO$_2$alkynyl, cyano, nitro, nitroso, —SH, —Salkyl, and haloalkyl;
wherein a, b, c, d, e, f, g, h, i, j, k, l, or m is required:
a. m is 3 and n is not 0;
b. $R^1$ and $R^2$ form a spirocycle;
c. $R^3$ and $R^4$ form a spirocycle;
d. $R^6$ and $R^7$ form a spirocycle;
e. $R^8$ and $R^9$ form a spirocycle;
f. $R^1$ and $R^3$ form a 1 or 2 carbon bridged ring;
g. $R^1$ and $R^{13}$ form a 3, 4, 5, or 6 carbon fused ring;
h. $R^4$ and $R^{13}$ form a 1 or 2 carbon bridged ring;
i. $R^{13}$ and $R^5$ form a 3, 4, 5, or 6 carbon fused ring;
j. $R^{13}$ and $R^5$ form a 1 or 2 carbon bridged ring;
k. A is $SO_2$, S(O), P(O)Oalkyl, P(O)NHalkyl, P(O)N(alkyl)$_2$, P(O)alkyl, P(O)OH, or P(O)NH$_2$;
l. A' is $SO_2$, S(O), P(O)Oalkyl, P(O)NHalkyl, P(O)N(alkyl)$_2$, P(O)alkyl, P(O)OH, or P(O)NH$_2$; or
m. A" is $SO_2$, S(O), P(O)Oalkyl, P(O)NHalkyl, P(O)N(alkyl)$_2$, P(O)alkyl, P(O)OH, or P(O)NH$_2$.

Non limiting examples of compounds of Formula VI include:

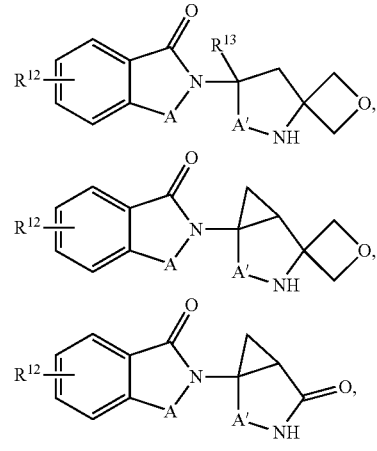

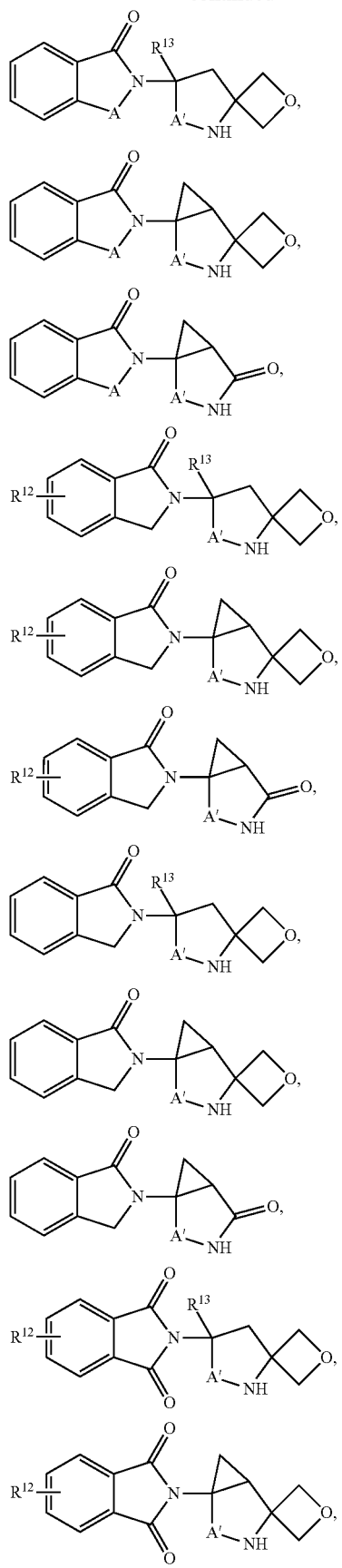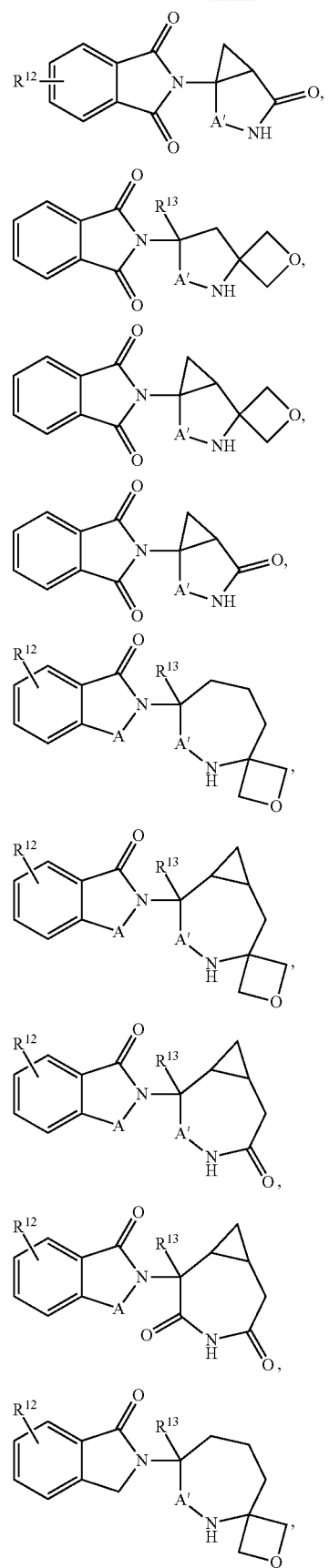

-continued
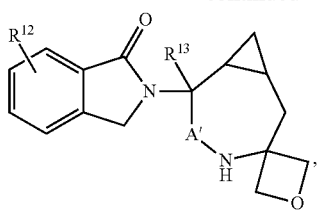
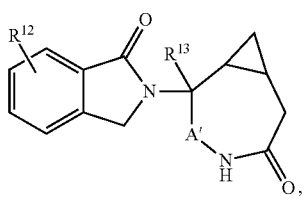
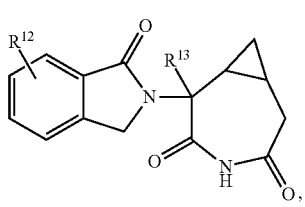
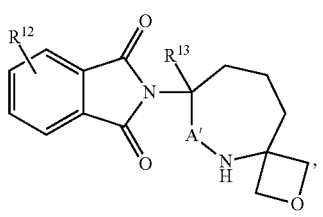
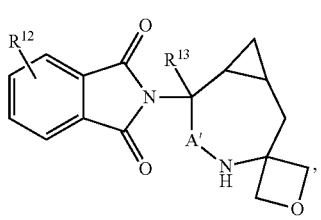
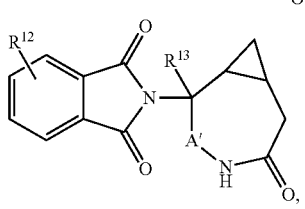
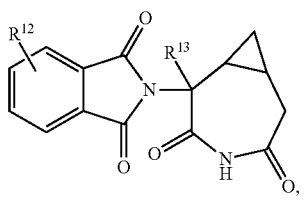
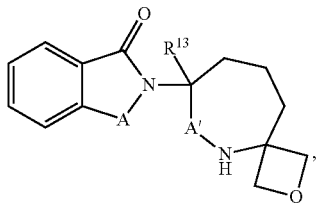
-continued
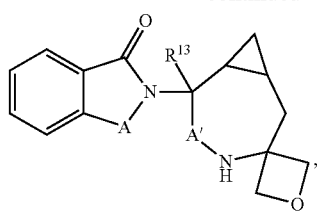
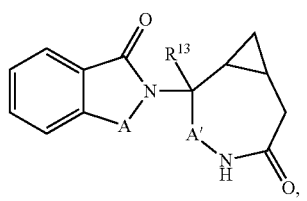
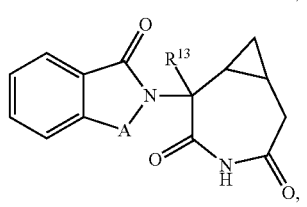
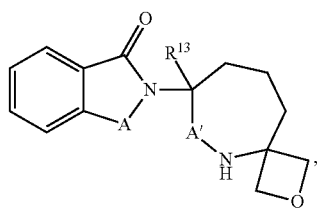
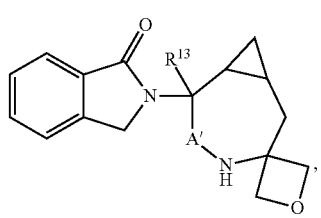
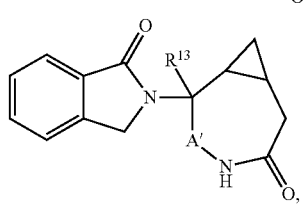
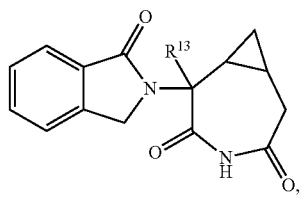
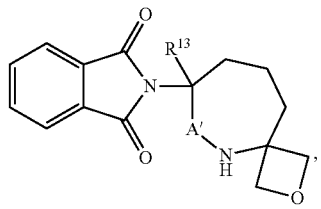

-continued
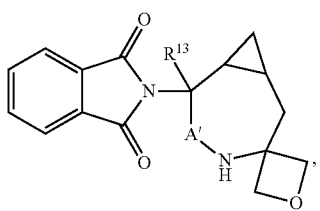
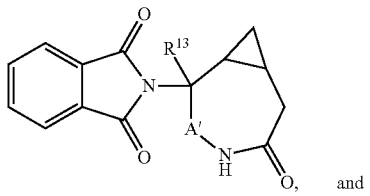
and
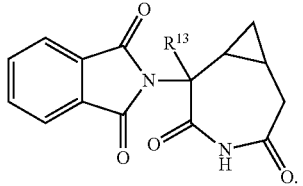
Additional non limiting examples of compounds of Formula VI include:
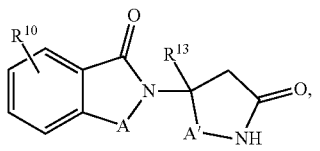
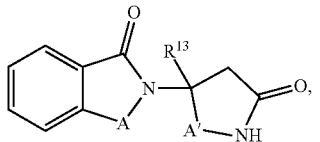
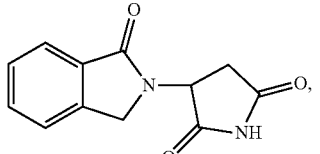
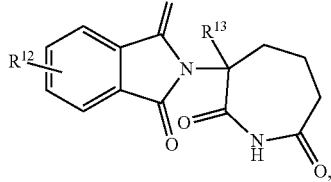
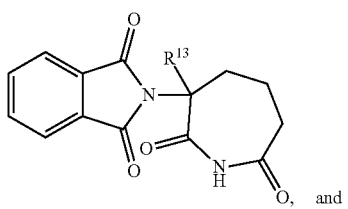
and
-continued
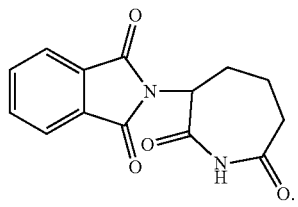
In one embodiment the
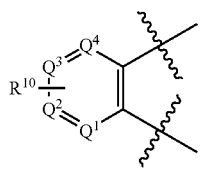
moiety of the Formulas above is selected from:
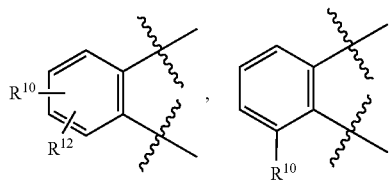
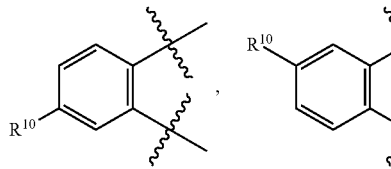
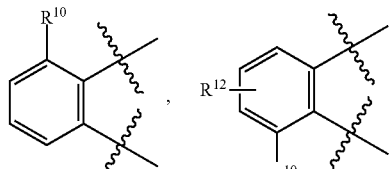
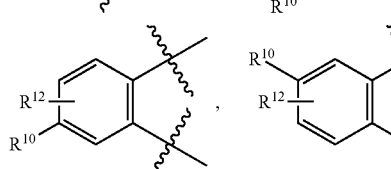
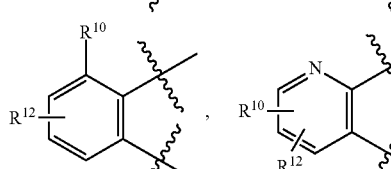
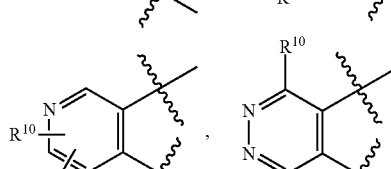
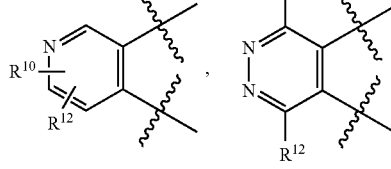

-continued

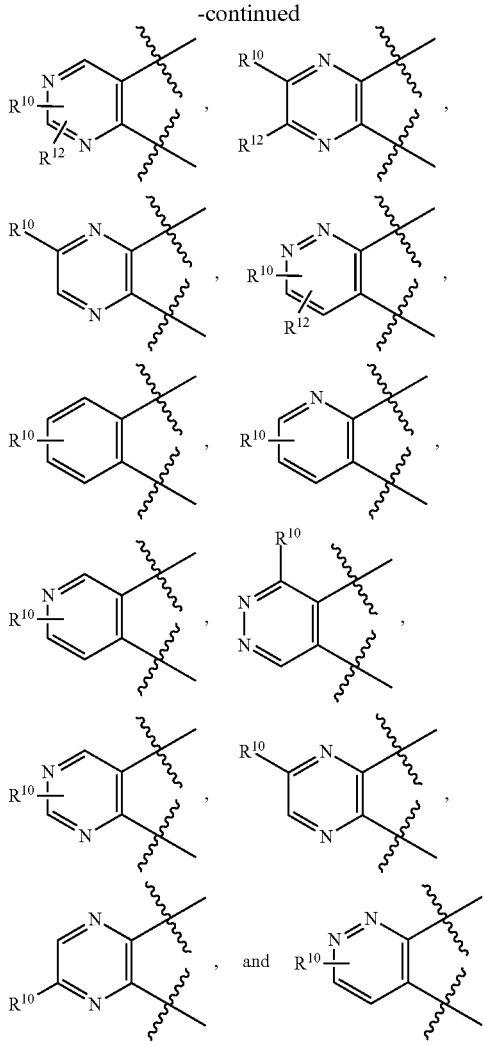

In one embodiment, a Linker is bonded to a heterocyclic Degron and a Targeting Ligand and the resulting molecule has a stable shelf life for at least 2 months, 3 months, 6 months or 1 year as part of a pharmaceutically acceptable dosage form, and itself is pharmaceutically acceptable.

Linker

A Linker is included in the Degronimers of Formula I, II, and III. Linker is a bond or a chemically stable group that attaches a Degron to a Targeting Ligand.

Any of the Linkers described herein can be used in either direction, i.e., either the left end is linked to the Degron and the right end to the Target Linker, or the left end is linked to the Target Linker and the right end is linked to the Degron. According to the invention, any desired linker can be used as long as the resulting compound has a stable shelf life for at least 2 months, 3 months, 6 months or 1 year as part of a pharmaceutically acceptable dosage form, and itself is pharmaceutically acceptable.

In a typical embodiment, the Linker has a chain of 2 to 14, 15, 16, 17, 18 or 20 or more carbon atoms of which one or more carbons can be replaced by a heteroatom such as O, N, S, or P. In certain embodiments the chain has 2, 3, 4, 5, 6, 7, 8, 9, 10, 11, 12, 13, 14, 15, 16, 17, 18, 19 or 20 contiguous atoms in the chain. For example, the chain may include 1 or more ethylene glycol units that can be contiguous, partially contiguous or non-contiguous (for example, 2, 3, 4, 5, 6, 7, 8, 9, 10, 11 or 12 ethylene glycol units). In certain embodiments the chain has at least 1, 2, 3, 4, 5, 6, 7, or 8 contiguous chains which can have branches which can be independently alkyl, heteroalkyl, aryl, heteroaryl, alkenyl, or alkynyl, aliphatic, heteroaliphatic, cycloalkyl or heterocyclic substituents.

In other embodiments, the linker can include or be comprised of one or more of ethylene glycol, propylene glycol, lactic acid and/or glycolic acid. In general, propylene glycol adds hydrophobicity, while propylene glycol adds hydrophilicity. Lactic acid segments tend to have a longer half-life than glycolic acid segments. Block and random lactic acid-co-glycolic acid moieties, as well as ethylene glycol and propylene glycol, are known in the art to be pharmaceutically acceptable and can be modified or arranged to obtain the desired half-life and hydrophilicity. In certain aspects, these units can be flanked or interspersed with other moieties, such as aliphatic, including alkyl, heteroaliphatic, aryl, heteroaryl, heterocyclic, cycloalkyl, etc., as desired to achieve the appropriate drug properties.

In one embodiment, the Linker is a moiety selected from Formula LI, Formula LII, Formula LIII, Formula LIV, Formula LV, Formula LVI, and Formula LVII:

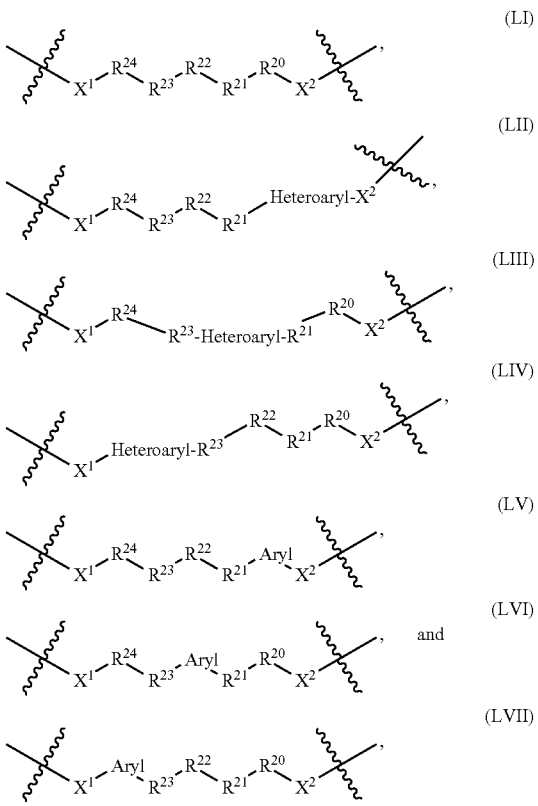

wherein:

$X^1$ and $X^2$ are independently selected from bond, NH, $NR^{25}$, $CH_2$, $CHR^{25}$, $C(R^{25})_2$, O, and S;

$R^{20}$, $R^{21}$, $R^{22}$, $R^{23}$, and $R^{24}$ are independently selected from bond, alkyl, —C(O)— —C(O)O—, —OC(O)—, —C(O)alkyl, —C(O)Oalkyl, —C(S)—, —SO$_2$—, —S(O)—, —C(S)—, —C(O)NH—, —NHC(O)—, —N(alkyl)C(O)—, —C(O)N(alkyl)-, —O—, —S—, —NH—, —N(alkyl)-, —CH(—O—$R^{26}$)—, —CH(—NH$R^{25}$)—, —CH(—NH$_2$)—, —CH(—N$R^{25}_2$)—, —C(—O—$R^{26}$)alkyl-, —C(—NH$R^{25}$)alkyl-, —C(—NH$_2$)alkyl-, —C(—N$R^{25}_2$)alkyl-, —C($R^4R^4$)—, -alkyl($R^{27}$)-alkyl ($R^{28}$)—, —C($R^{27}R^{28}$)—, —P(O)(O$R^{26}$)O—, —P(O)(O$R^{26}$)—, —NHC(O)NH—, —N($R^{25}$)C(O)N($R^{25}$)—, —N(H)C(O)N($R^{25}$)—, polyethylene glycol, poly(lactic-co-glycolic acid), alkene, haloalkyl, alkoxy, and alkyne;

or $R^{20}$, $R^{21}$, $R^{22}$, $R^{23}$, and $R^{24}$ can in addition to those above be independently selected from heteroarylalkyl, aryl, arylalkyl, heterocycle, aliphatic, heteroaliphatic, heteroaryl, polypropylene glycol, lactic acid, glycolic acid, carbocycle, or —O—(CH$_2$)$_{1-12}$—O—, —NH—(CH$_2$)$_{1-12}$—NH—, —NH—(CH$_2$)$_{1-12}$—O—, or —O—(CH$_2$)$_{1-12}$—NH—, —S—(CH$_2$)$_{1-12}$—O—, —O—(CH$_2$)$_{1-12}$—S—, —S—(CH$_2$)$_{1-12}$—S—, —S—(CH$_2$)$_{1-12}$—NH—, —NH—(CH$_2$)$_{1-12}$—S—, (and wherein the 1-12 can be independently 1, 2, 3, 4, 5, 6, 7, 8, 9, 10, 11 or 12, and wherein one or more of the CH$_2$ or NH can be modified by substitution of a H for a methyl, ethyl, cyclopropyl, F (if on carbon), etc, as described herein), and optionally, a heteroatom, heteroalkyl, aryl, heteroaryl or cycloaliphatic group is interspersed in the chain). Certain nonlimiting examples include —O—CH(CH$_3$)—CH(CH$_3$)CH—O—, —O—CH$_2$—CH(CH$_3$)CH—O—, —O—CH(CH$_3$)—CH$_2$CH—O—, etc.

each of which $R^{20}$, $R^{21}$, $R^{22}$, $R^{23}$, and $R^{24}$ is optionally substituted with one or more substituents selected from $R^{101}$ or alternatively as described in Section 1. Definitions;

$R^{25}$ is selected at each instance from: alkyl, —C(O)H, —C(O)OH, —C(O)alkyl, —C(O)Oalkyl, alkenyl, or alkynyl or alternatively can be aliphatic, heteroaliphatic, aryl, heteroaryl or heterocyclic;

$R^{26}$ is hydrogen, alkyl, silane, arylalkyl, heteroarylalkyl, alkene, and alkyne; or in addition to these can also be selected from aryl, heteroaryl, heterocyclic, aliphatic and heteroaliphatic;

$R^{27}$ and $R^{28}$ are independently selected from hydrogen, alkyl, amine, or together with the carbon atom to which they are attached, form C(O), C(S), C=CH$_2$, a C$_3$-C$_6$ spirocarbocycle, or a 4-, 5-, or 6-membered spiroheterocycle comprising 1 or 2 heteroatoms selected from N and O, or form a 1 or 2 carbon bridged ring;

$R^4$ is independently selected from hydrogen, alkyl, hydroxyl, alkoxy, amine, —NH(aliphatic, including alkyl), —Nalkyl$_2$;

$R^{101}$ is independently selected at each occurrence from hydrogen, alkyl, alkene, alkyne, haloalkyl, alkoxy, hydroxyl, aryl, heteroaryl, heterocycle, arylalkyl, heteroarylalkyl, heterocycloalkyl, aryloxy, heteroaryloxy, CN, —COOalkyl, COOH, NO$_2$, F, Cl, Br, I, CF$_3$, NH$_2$, NHalkyl, N(alkyl)$_2$, aliphatic, heteroaliphatic; and in addition to these can also be selected from aliphatic and heteroaliphatic.

In an additional embodiment, the Linker is a moiety selected from Formula LVIII, LIX, and LX:

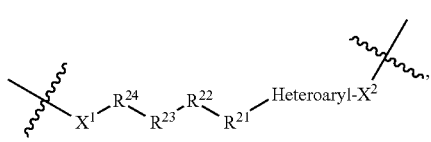
(LVIII)

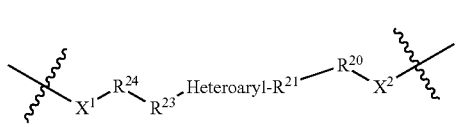
(LIX)
and

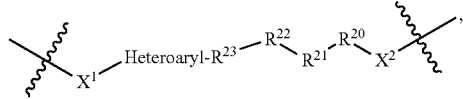
(LX)

wherein each variable is as it is defined in Formula LI. In alternative embodiments of LVIII, LIX and LX, a carbocyclic ring is used in place of the heterocycle.

The following are non-limiting examples of Linkers that can be used in this invention. Based on this elaboration, those of skill in the art will understand how to use the full breadth of Linkers that will accomplish the goal of the invention.

As certain non-limiting examples, Formula LI, Formula LII, Formula LIII, Formula LIV, Formula LV, Formula LVI, or Formula LVII include:

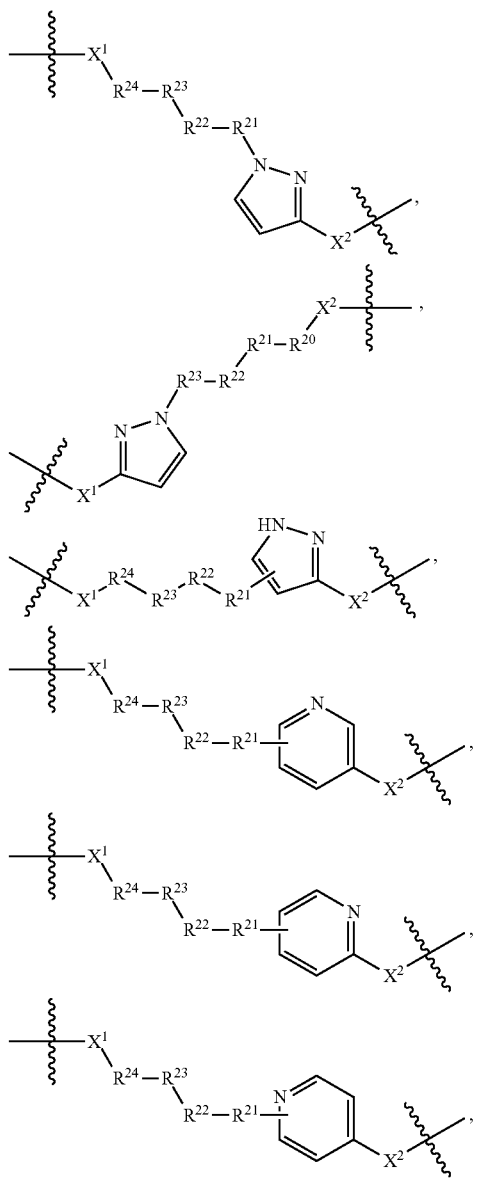

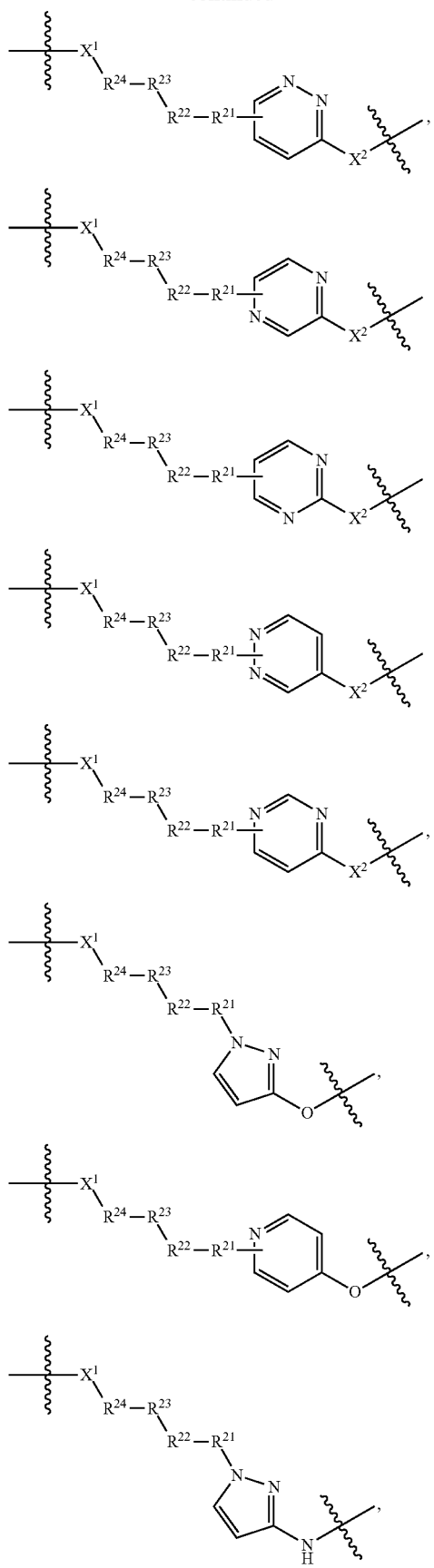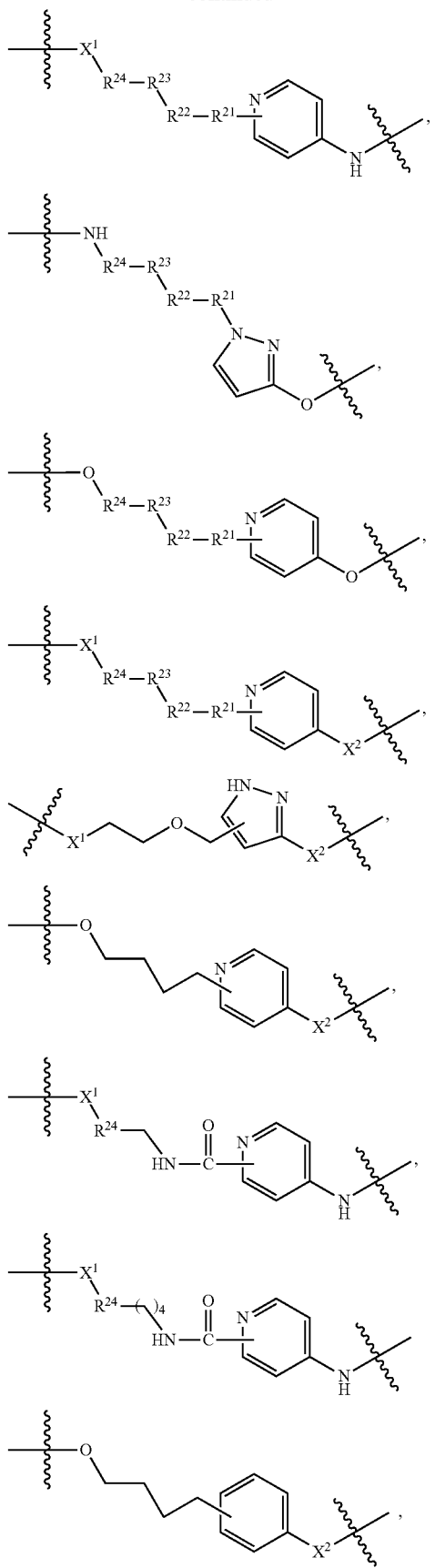

115
-continued
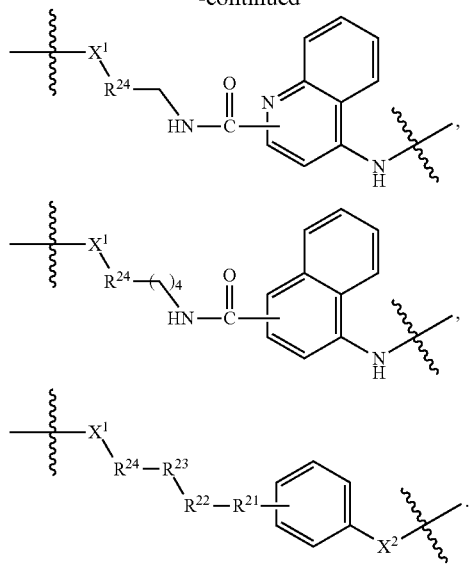
In an additional embodiment Linker is selected from:
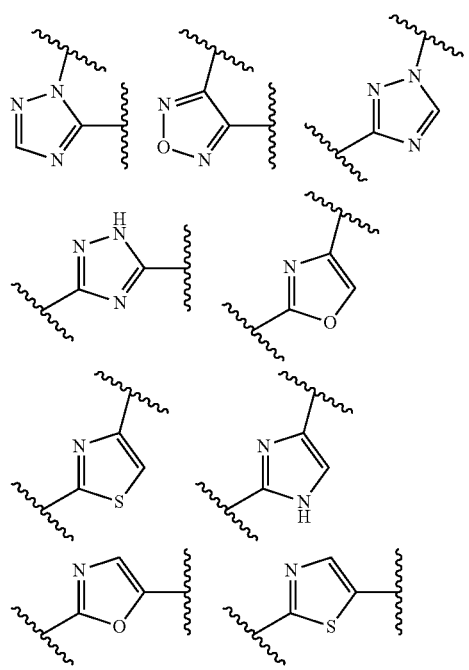
In an additional embodiment Linker is selected from:
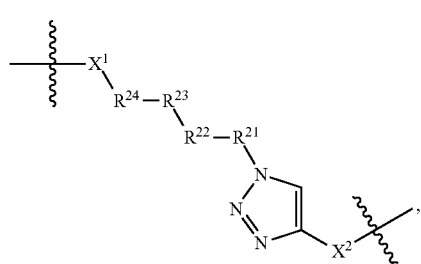
116
-continued
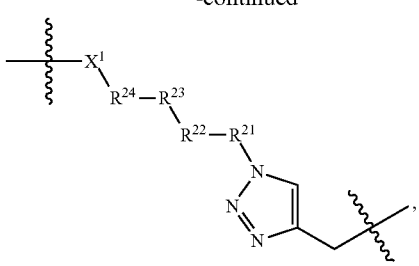
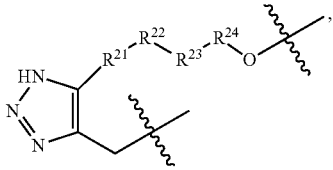
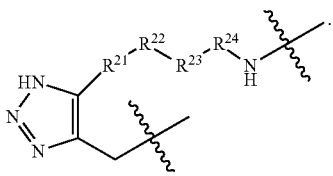
In one embodiment $X^1$ is attached to the Targeting Ligand. In another embodiment $X^2$ is attached to the Targeting Ligand.
Non-limiting examples of moieties of $R^{20}$, $R^{21}$, $R^{22}$, $R^{23}$, and $R^{24}$ include:

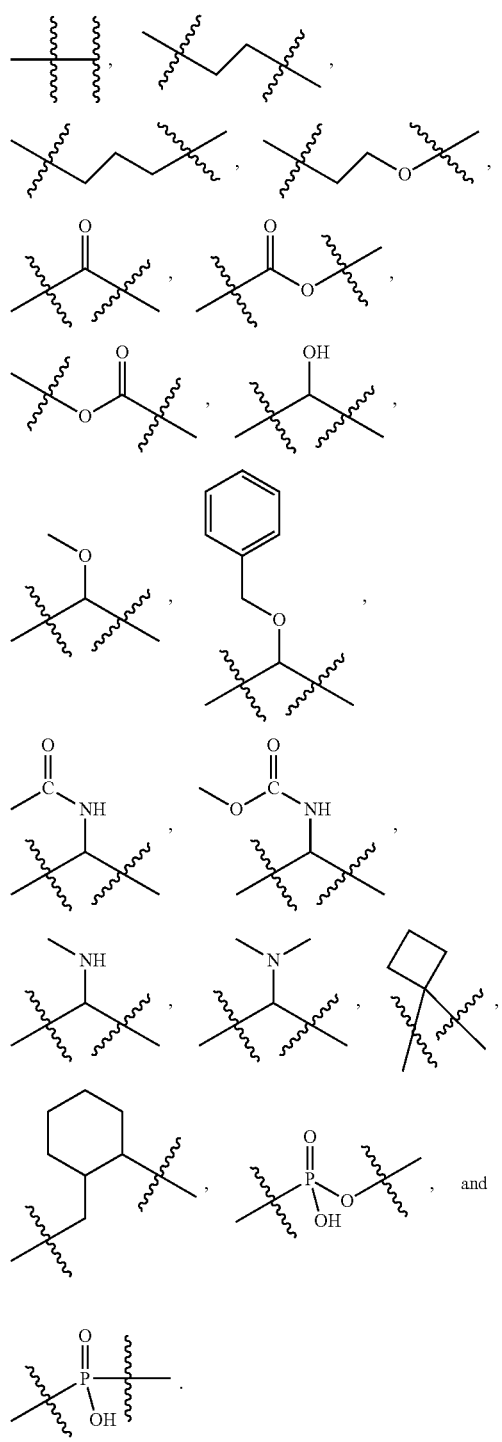
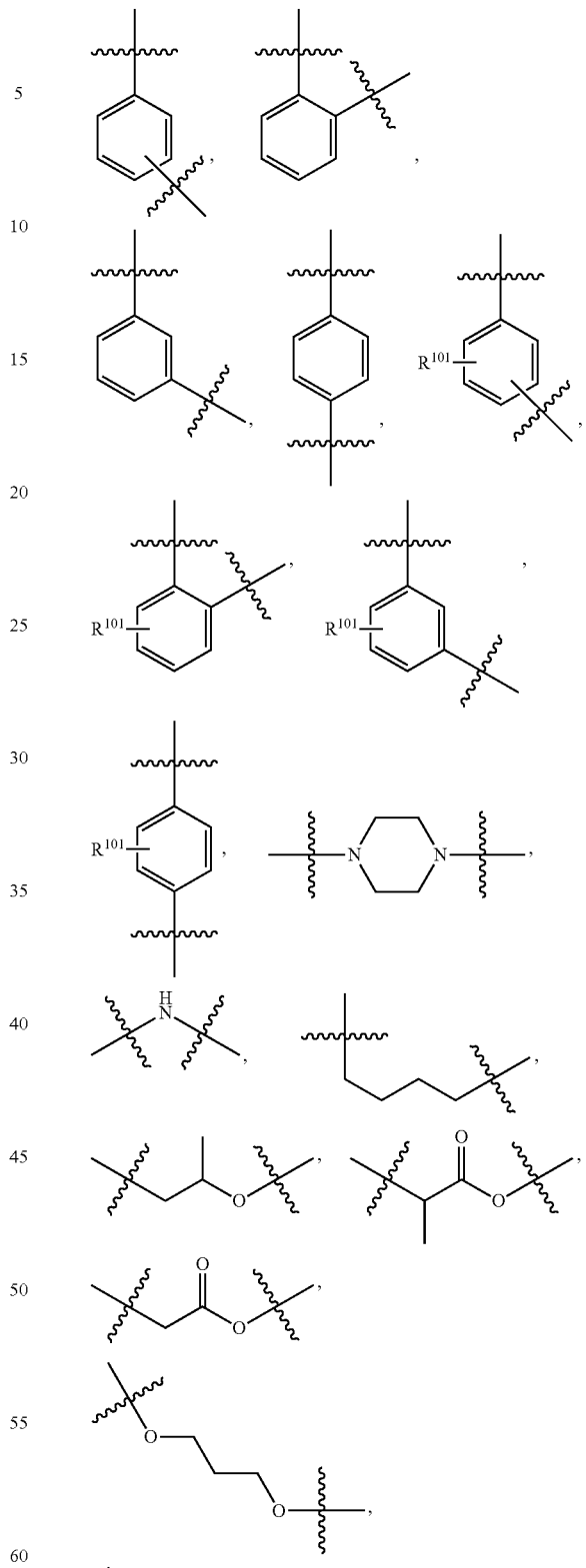
Additional non-limiting examples of moieties of $R^{20}$, $R^{21}$, $R^{22}$, $R^{23}$, and $R^{24}$ include:
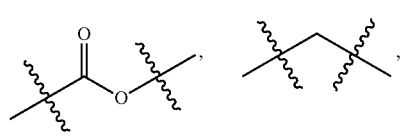
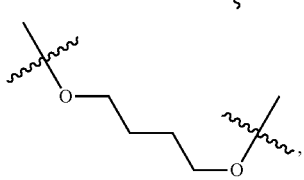

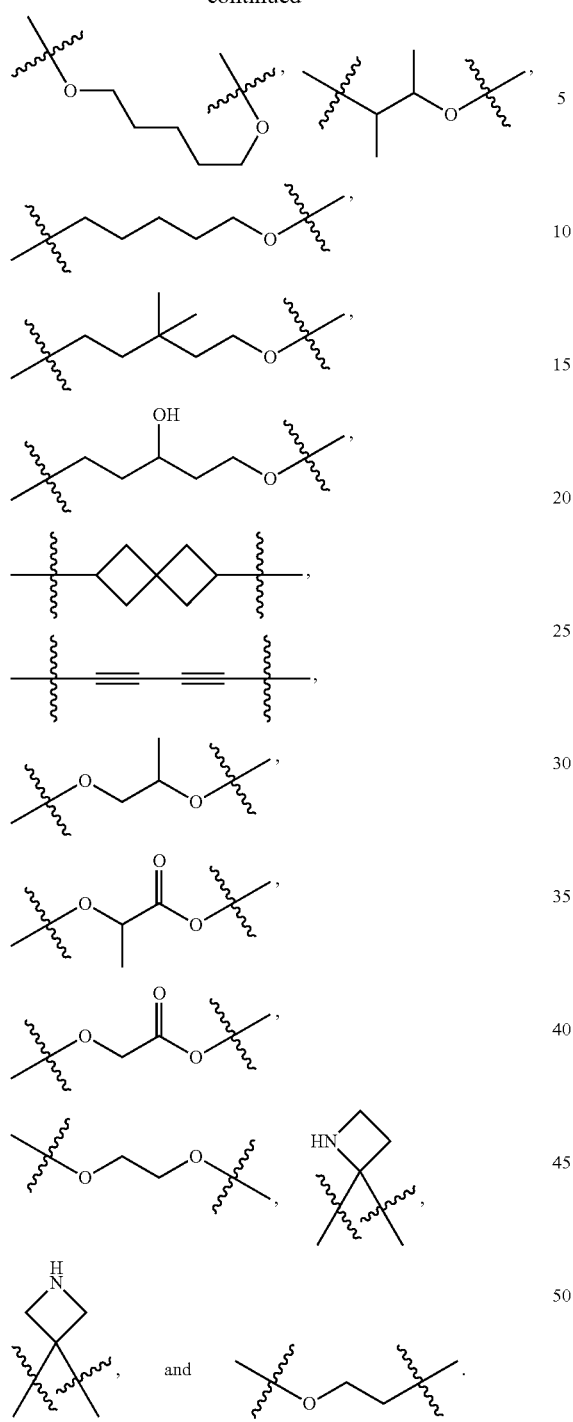
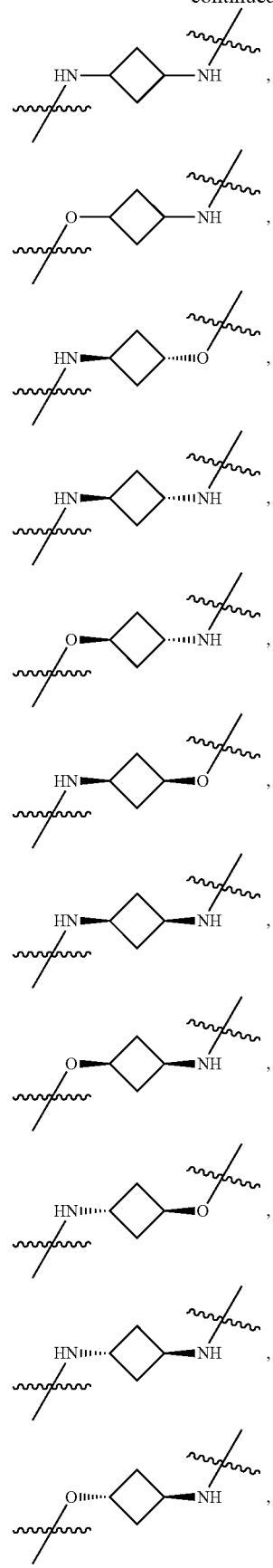
Additional non-limiting examples of moieties of $R^{20}$, $R^{21}$, $R^{22}$, $R^{23}$, and $R^{24}$ include:
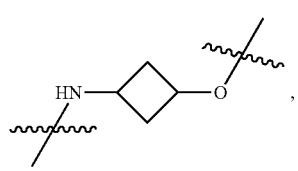

-continued

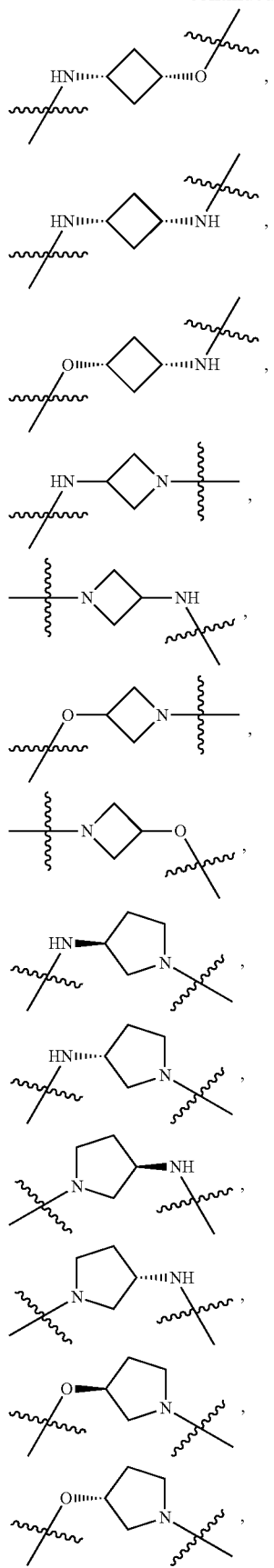

-continued

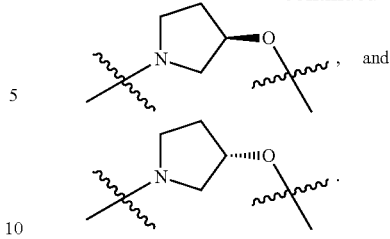

Additional non-limiting examples of moieties of $R^{20}$, $R^{21}$, $R^{22}$, $R^{23}$, and $R^{24}$ include:

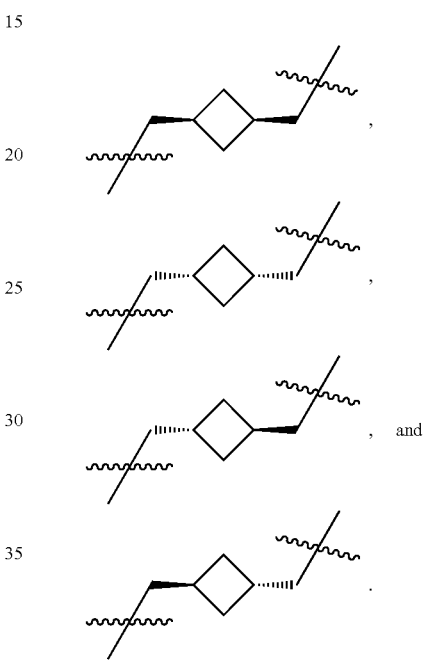

Additional non-limiting examples of moieties of $R^{20}$, $R^{21}$, $R^{22}$, $R^{23}$, and $R^{24}$ include:

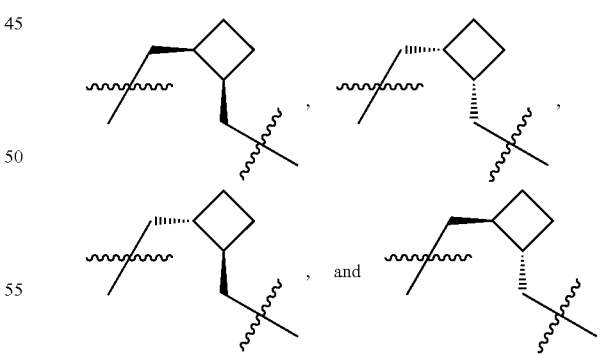

In additional embodiments, the Linker group is an optionally substituted (poly)ethylene glycol having at least 1, at least 2, at least 3, at least 4, at least 5, at least 6, at least 7, at least 8, at least 9, at least 10, ethylene glycol units, or optionally substituted alkyl groups interspersed with optionally substituted, O, N, S, P or Si atoms. In certain embodiments, the Linker is flanked, substituted, or interspersed with an aryl, phenyl, benzyl, alkyl, alkylene, or heterocycle group. In certain embodiments, the Linker may be asymmetric or symmetrical. In some embodiments, the Linker is a substituted or unsubstituted polyethylene glycol group ranging in size from about 1 to about 12 ethylene glycol units, between 1 and about 10 ethylene glycol units, about 2 about 6 ethylene glycol units, between about 2 and 5 ethylene glycol units, between about 2 and 4 ethylene glycol units. In any of the embodiments of the compounds described herein, the Linker group may be any suitable moiety as described herein.

In additional embodiments, the Linker is selected from:
—NR$^{61}$(CH$_2$)$_{n1}$-(lower alkyl)-, —NR$^{61}$(CH$_2$)$_{n1}$-(lower alkoxyl)-,
—NR$^{61}$(CH$_2$)$_{n1}$-(lower alkoxyl)-OCH$_2$—, —NR$^{61}$(CH$_2$)$_{n1}$-(lower alkoxyl)-(lower alkyl)-OCH$_2$—,
—NR$^{61}$(CH$_2$)$_{n1}$-(cycloalkyl)-(lower alkyl)-OCH$_2$—,
—NR$^{61}$(CH$_2$)$_{n1}$-(heterocycloalkyl)-,
—NR$^{61}$(CH$_2$CH$_2$O)$_{n1}$-(lower alkyl)-O—CH$_2$—, —NR$^{61}$(CH$_2$CH$_2$O)$_{n1}$-(heterocycloalkyl)-O—CH$_2$—,
—NR$^{61}$(CH$_2$CH$_2$O)$_{n1}$-Aryl-O—CH$_2$—, —NR$^{61}$(CH$_2$CH$_2$O)$_{n1}$-(heteroaryl)-O—CH$_2$—,
—NR$^{61}$(CH$_2$CH$_2$O)$_{n1}$-(cycloalkyl)-O-(heteroaryl)-O—CH$_2$—,
—NR$^{61}$(CH$_2$CH$_2$O)$_{n1}$-(cycloalkyl)-O-Aryl-O—CH$_2$—,
—NR$^{61}$(CH$_2$CH$_2$O)$_{n1}$-(lower alkyl)-NH-Aryl-O—CH$_2$—,
—NR$^{61}$(CH$_2$CH$_2$O)$_{n1}$-(lower alkyl)-O-Aryl-CH$_2$,
—NR$^{61}$(CH$_2$CH$_2$O)$_{n1}$-cycloalkyl-O-Aryl-, —NR$^{61}$(CH$_2$CH$_2$O)$_{n1}$-cycloalkyl-O-heteroaryl-,
—NR$^{61}$(CH$_2$CH$_2$)$_{n1}$-(cycloalkyl)-O-(heterocycle)-CH$_2$,
—NR$^{61}$(CH$_2$CH$_2$)$_{n1}$-(heterocycle)-(heterocycle)-CH$_2$, and
—NR$^{61}$-(heterocycle)-CH$_2$;
wherein n1 is 0, 1, 2, 3, 4, 5, 6, 7, 8, 9, or 10; and
R$^{61}$ is H, methyl, or ethyl.

In additional embodiments, the Linker is selected from:
—N(R$^{61}$)—(CH$_2$)$_{m1}$—O(CH$_2$)$_{n2}$—O(CH$_2$)$_{o1}$—O(CH$_2$)$_{p1}$—O(CH$_2$)$_{q1}$—O(CH$_2$)$_{r1}$—OCH$_2$—,
—O—(CH$_2$)$_{m1}$—O(CH$_2$)$_{n2}$—O(CH$_2$)$_{o1}$—O(CH$_2$)$_{p1}$—O(CH$_2$)$_{q1}$—O(CH$_2$)$_{r1}$—OCH$_2$—,
—O—(CH$_2$)$_{m1}$—O(CH$_2$)$_{n2}$—O(CH$_2$)$_{o1}$—O(CH$_2$)$_{p1}$—O(CH$_2$)$_{q1}$—O(CH$_2$)$_{r1}$—O—;
—N(R$^{61}$)—(CH$_2$)$_{m1}$—O(CH$_2$)$_{n2}$—O(CH$_2$)$_{o1}$—O(CH$_2$)$_{p1}$—O(CH$_2$)$_{q1}$—O(CH$_2$)$_{r1}$—O—;
—(CH$_2$)$_{m1}$—O(CH$_2$)$_{n2}$—O(CH$_2$)$_{o1}$—O(CH$_2$)$_{p1}$—O(CH$_2$)$_{q1}$—O(CH$_2$)$_{r1}$—O—;
—(CH$_2$)$_{m1}$—O(CH$_2$)$_{n2}$—O(CH$_2$)$_{o1}$—O(CH$_2$)$_{p1}$—O(CH$_2$)$_{q1}$—O(CH$_2$)$_{r1}$—OCH$_2$—;
—O(CH$_2$)$_{m1}$O(CH$_2$)$_{n2}$O(CH$_2$)$_{p1}$O(CH$_2$)$_{q1}$OCH$_2$—;
—O(CH$_2$)$_{m1}$O(CH$_2$)$_{n2}$O(CH$_2$)$_{p1}$O(CH$_2$)$_{q1}$OCH$_2$—;
wherein
m1, n2, o1, p1, q1, and r1 are independently 1, 2, 3, 4, or 5; and
R$^{61}$ is H, methyl, or ethyl.

In additional embodiments, the Linker is selected from:

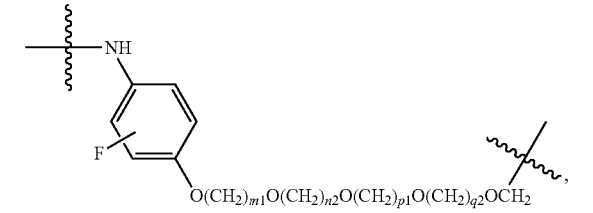

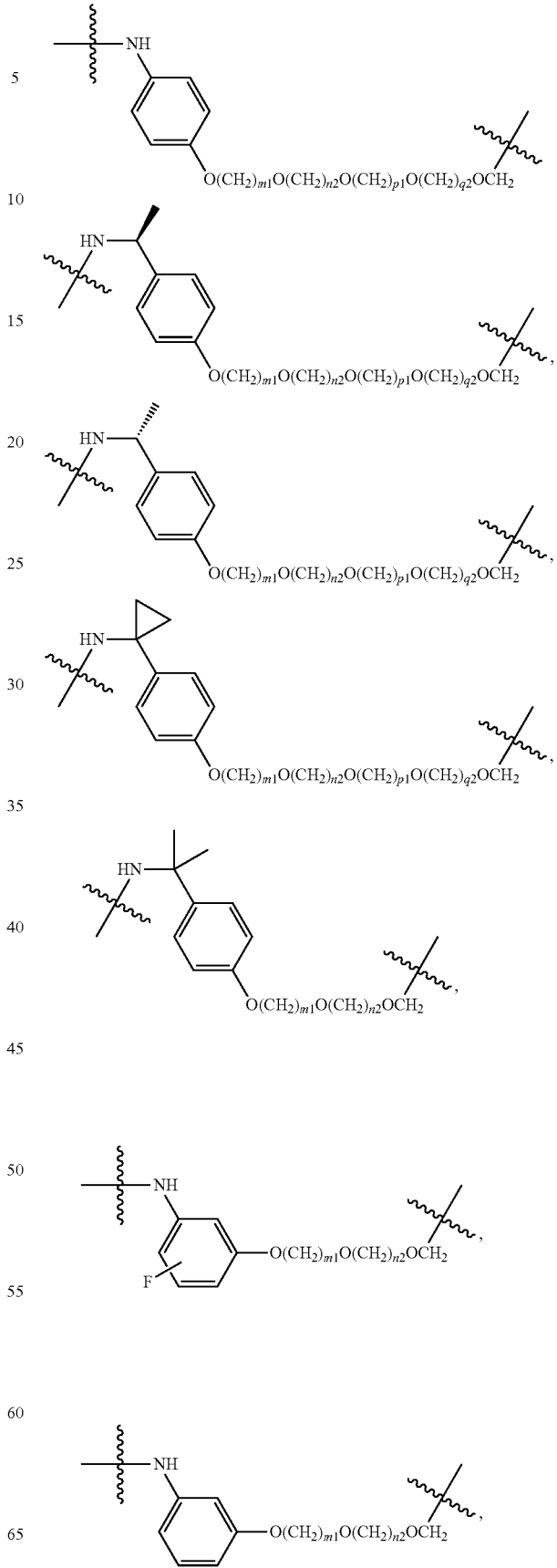

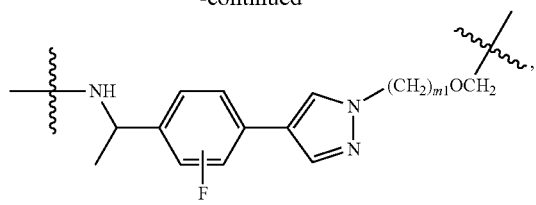
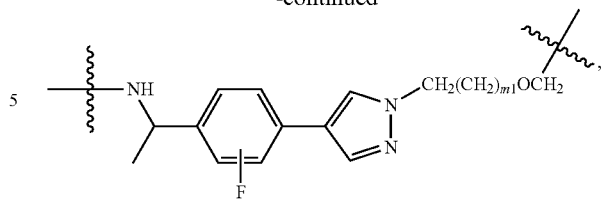
m1, n2, o1, p1, q2, and r1 are independently 1, 2, 3, 4, or 5.
In additional embodiments, the Linker is selected from:
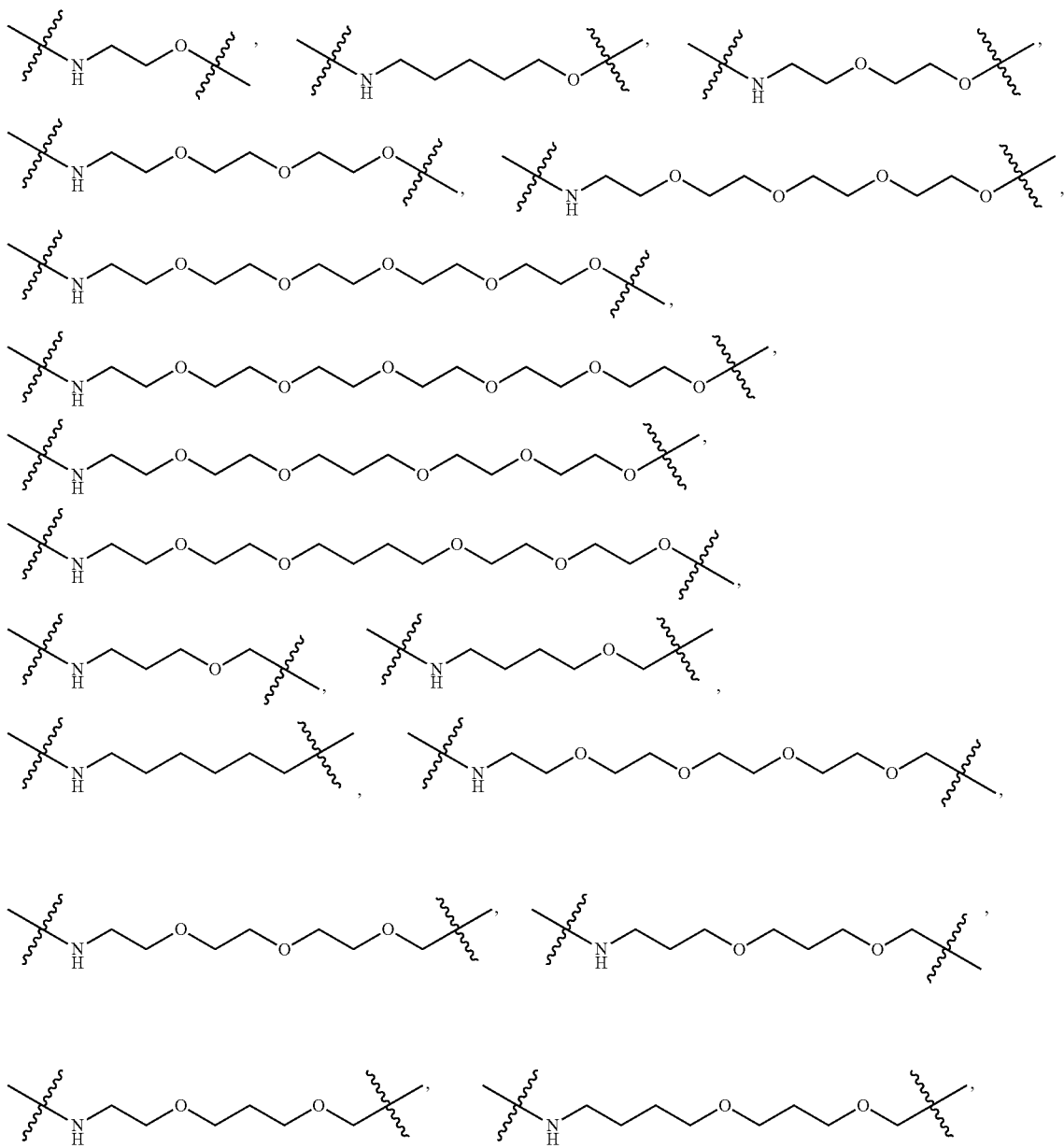

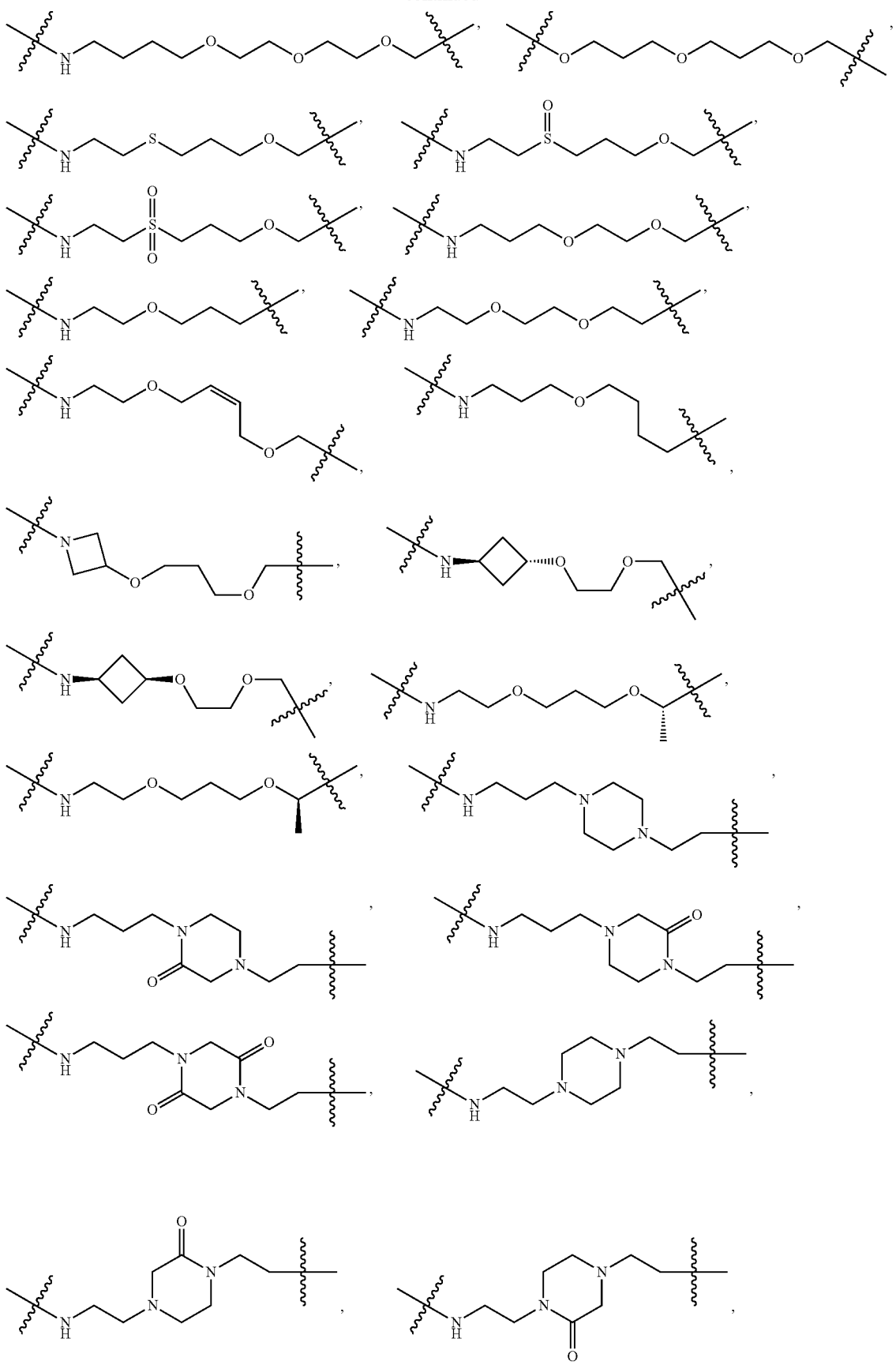

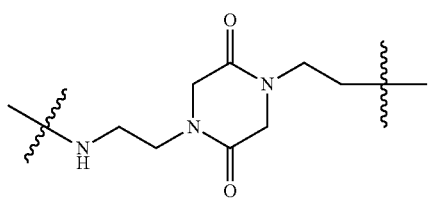
In additional embodiments, the Linker is selected from:
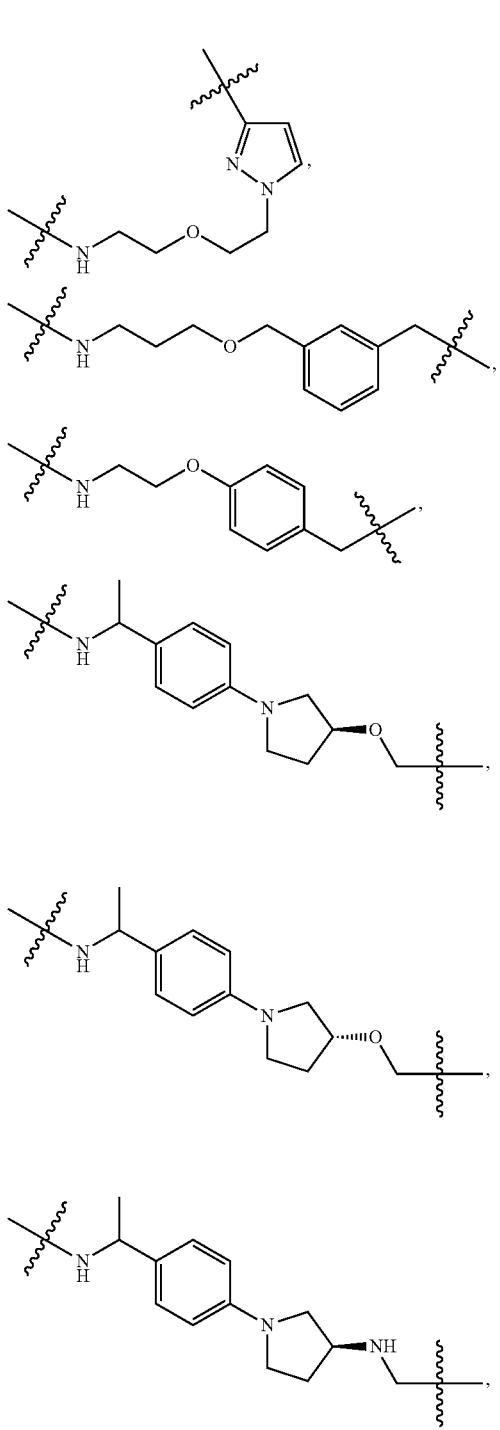
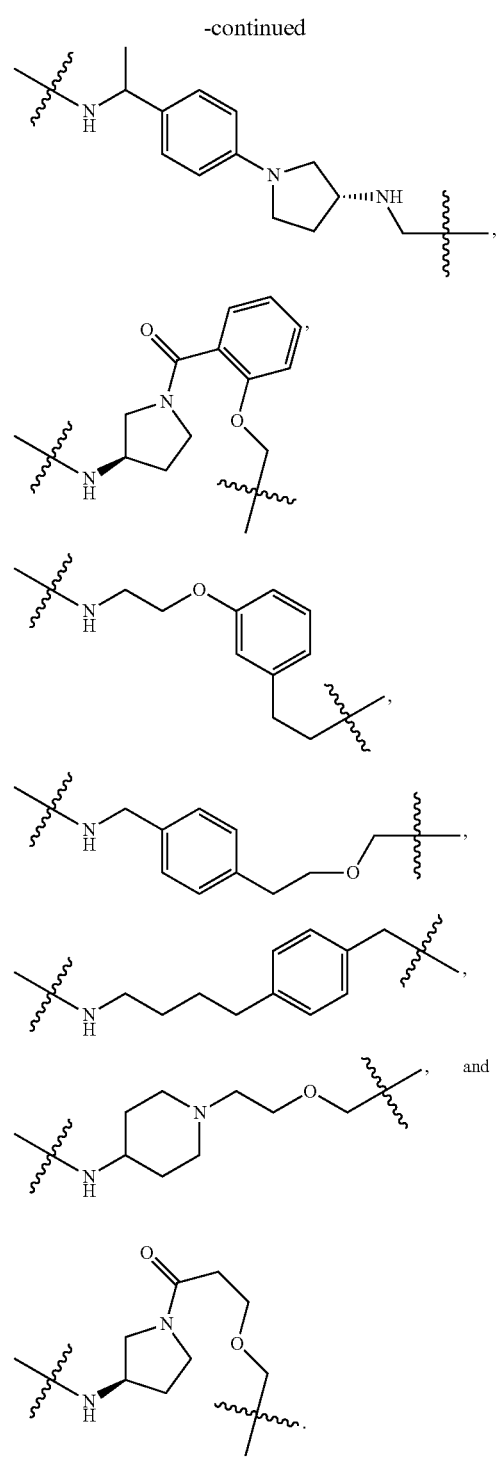

In additional embodiments, the Linker is selected from:
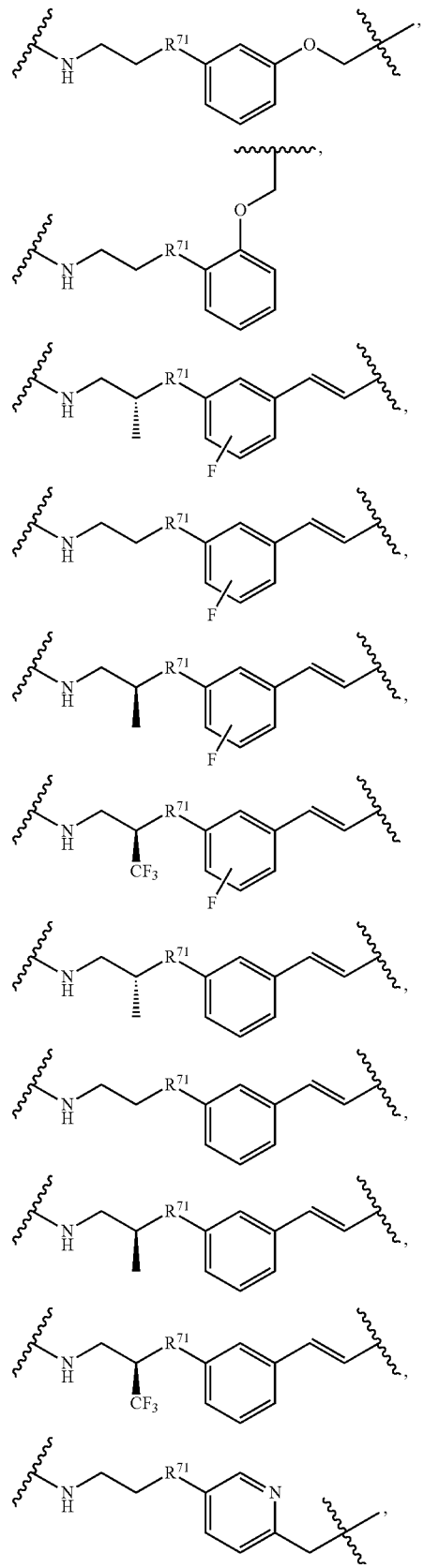
-continued
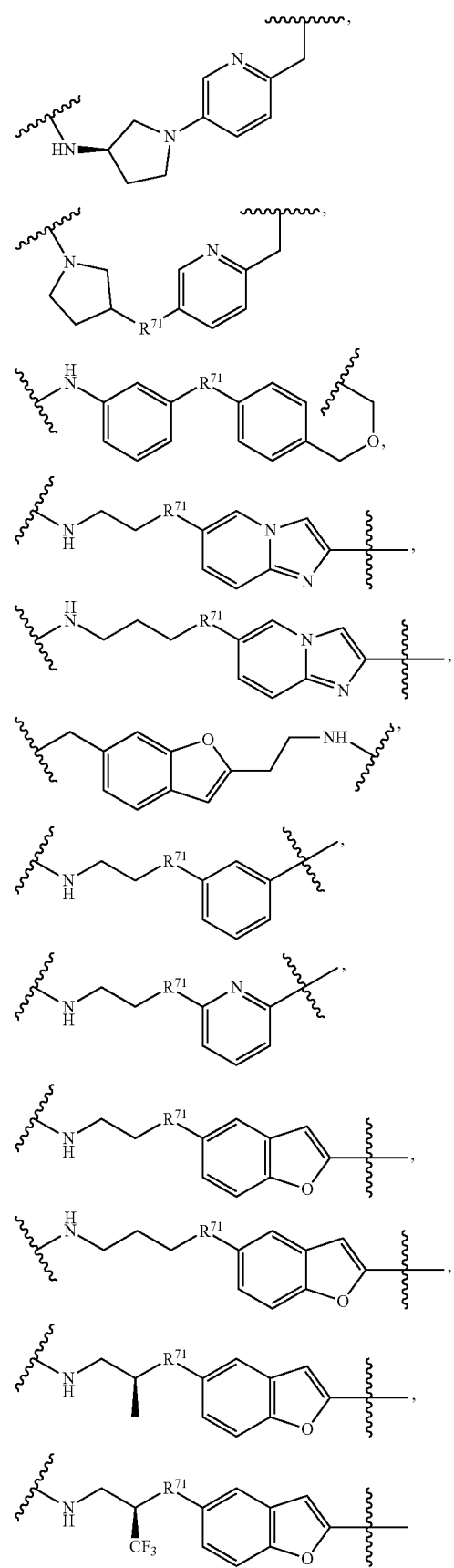

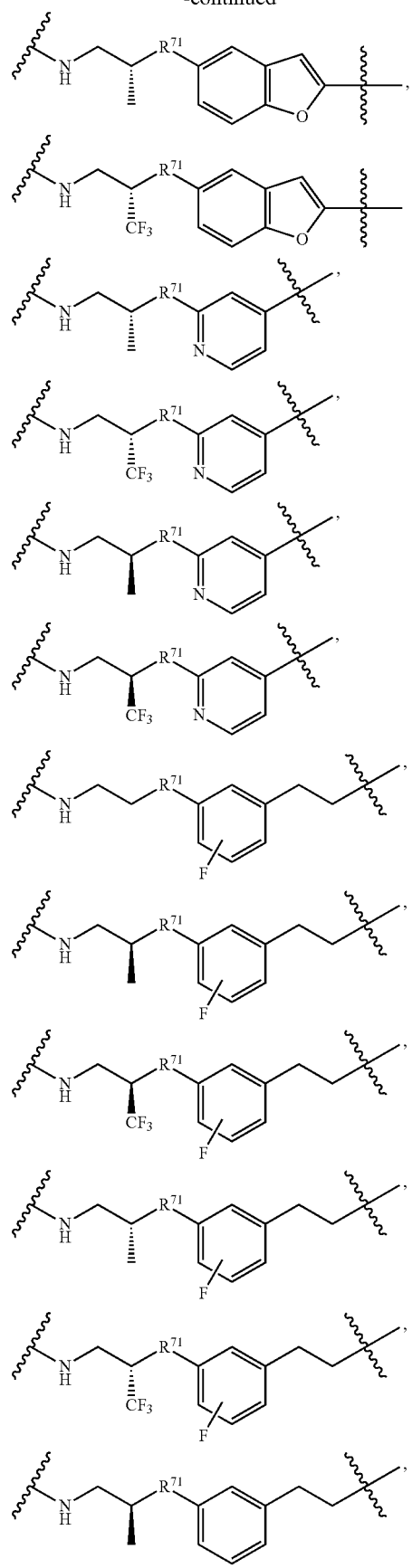
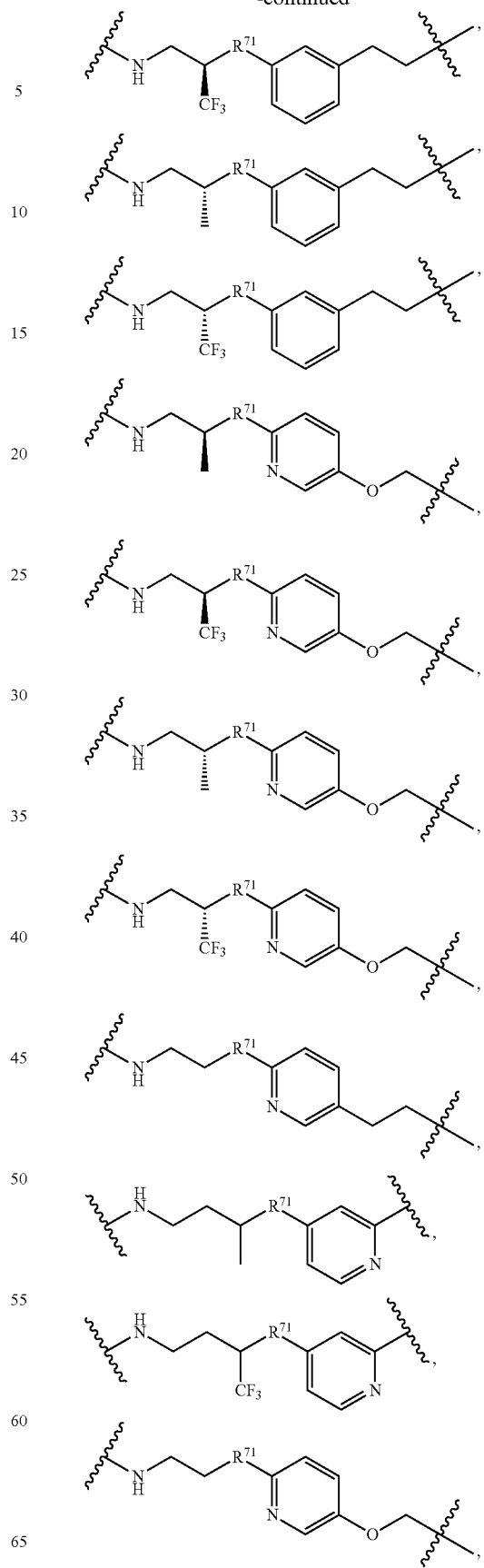

-continued
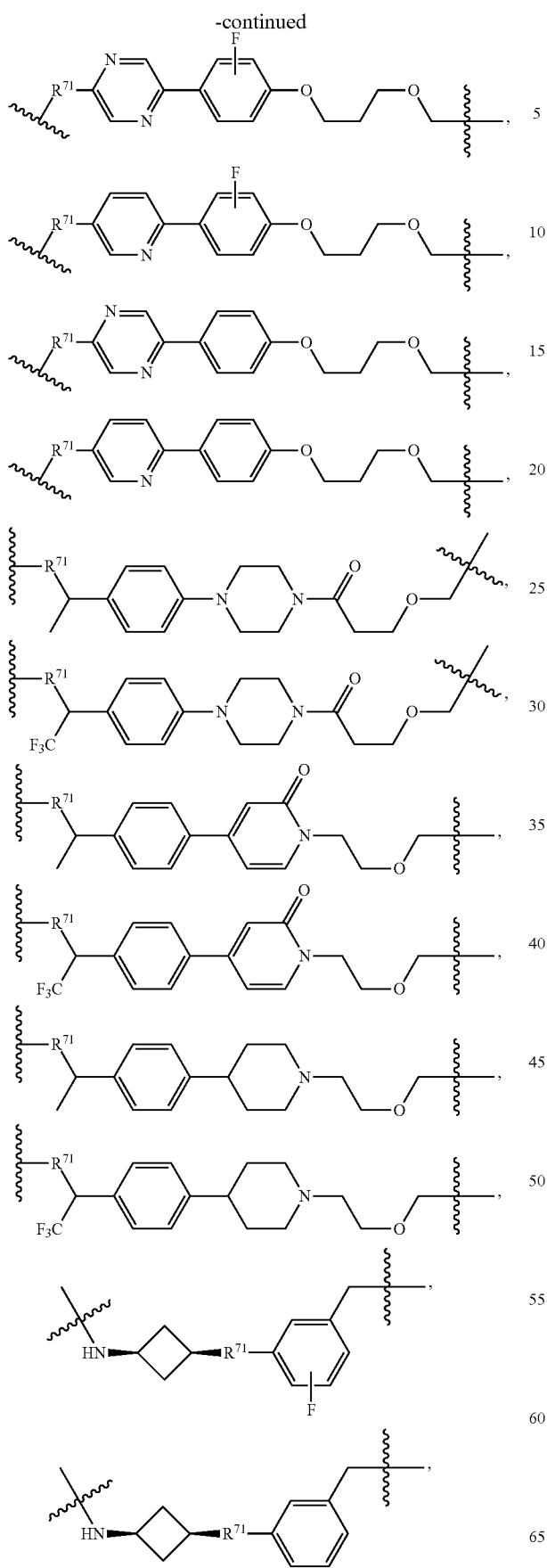
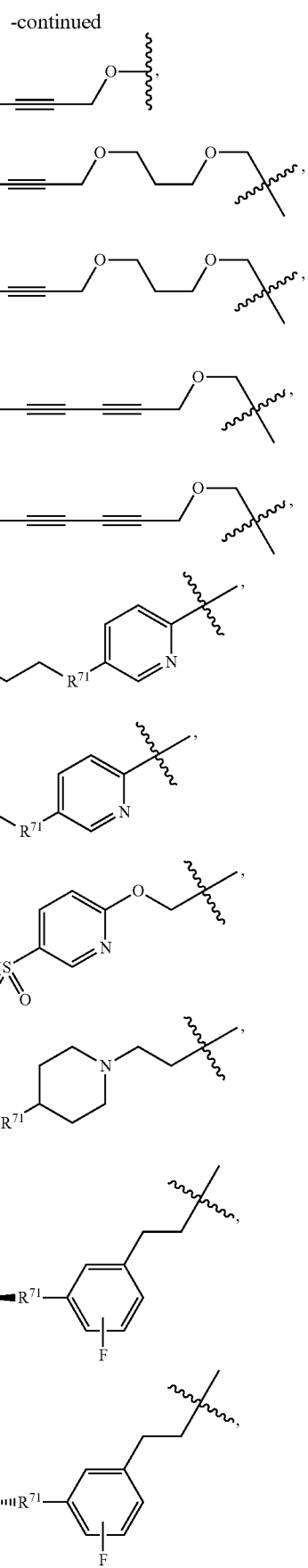

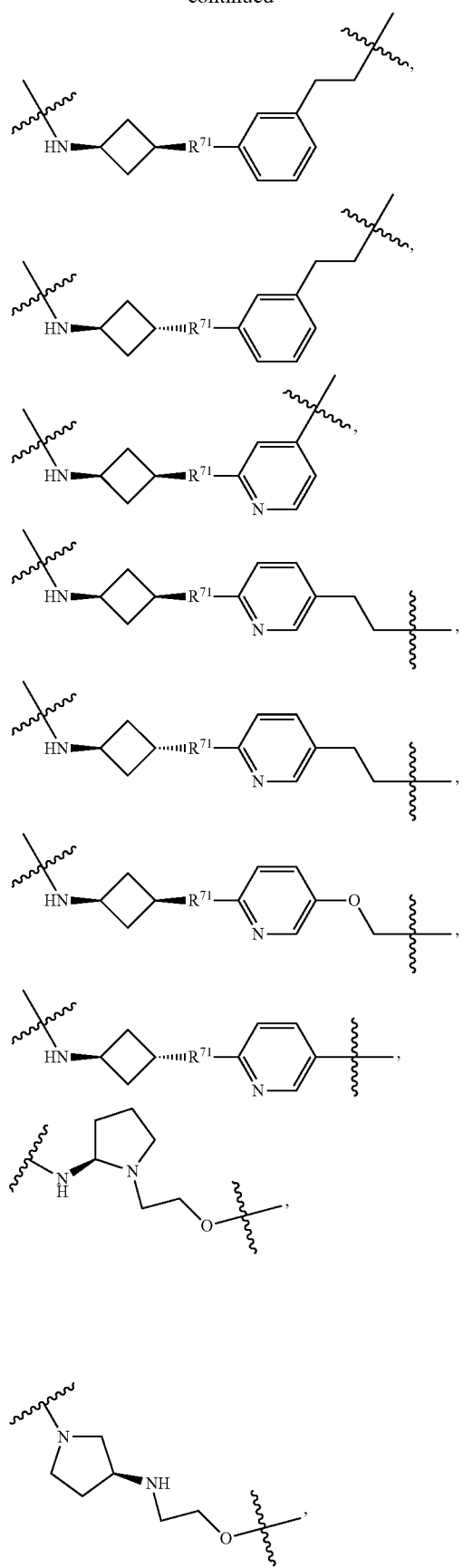
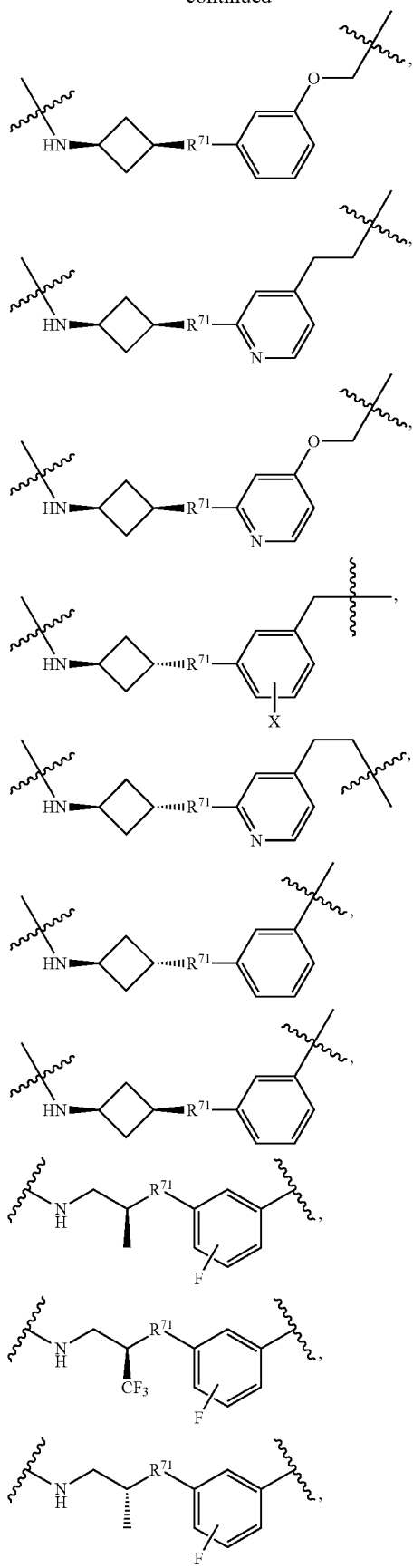

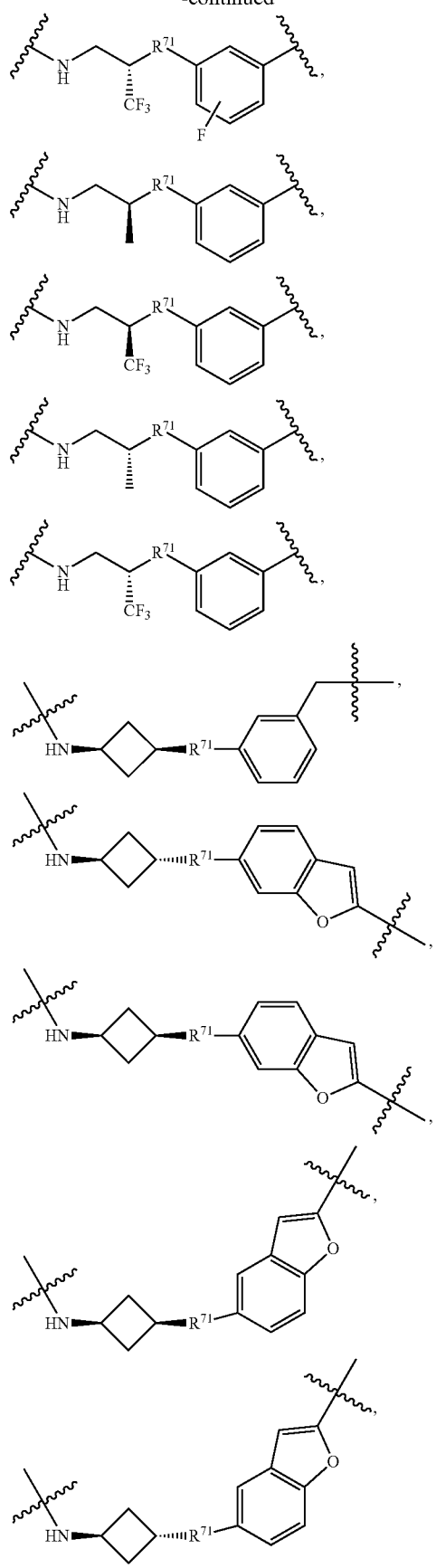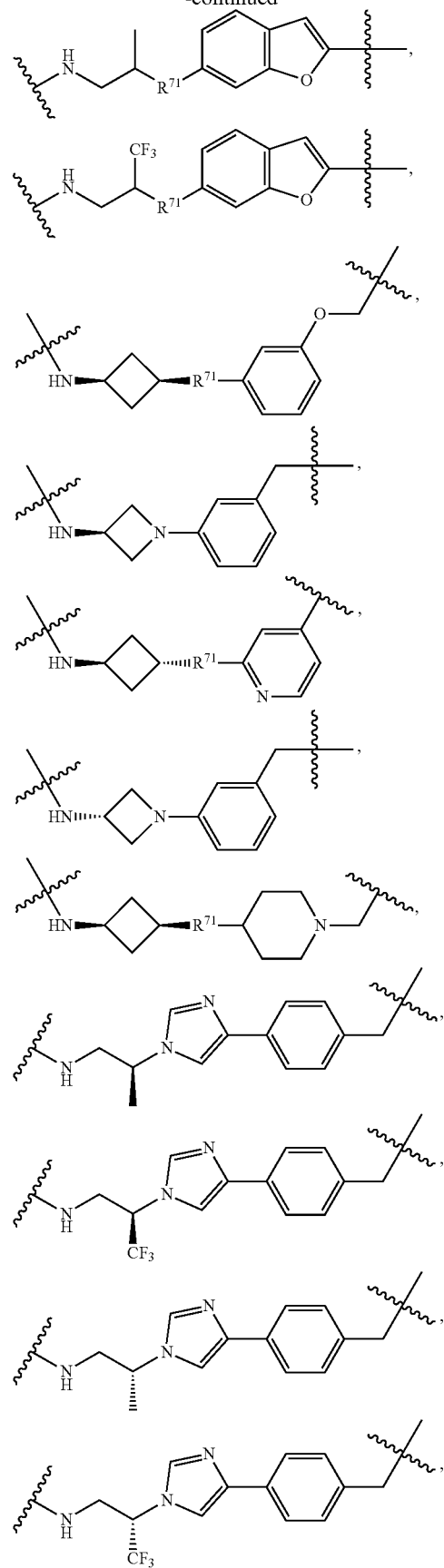

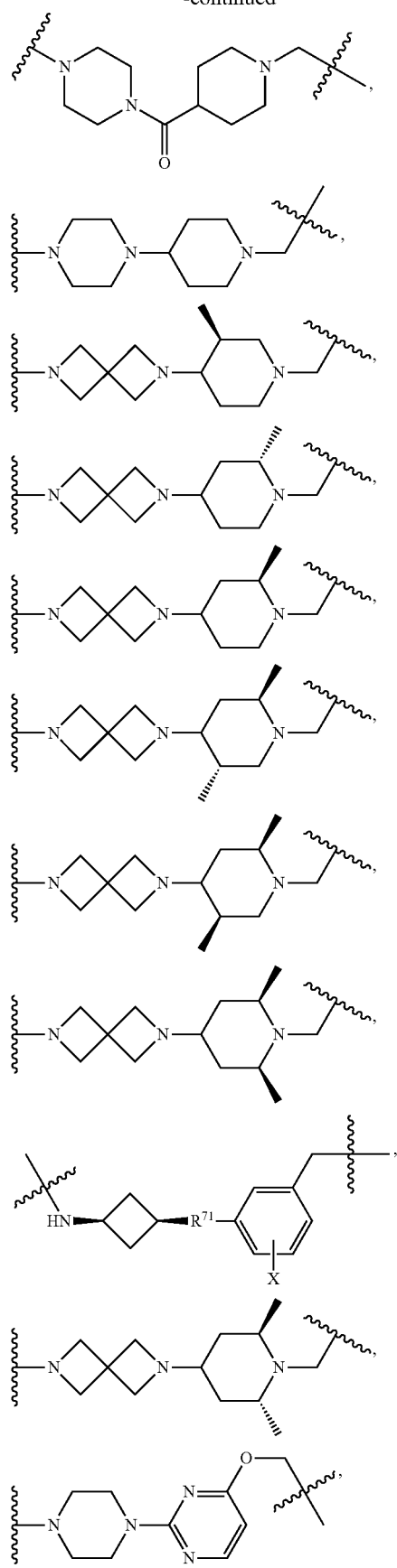
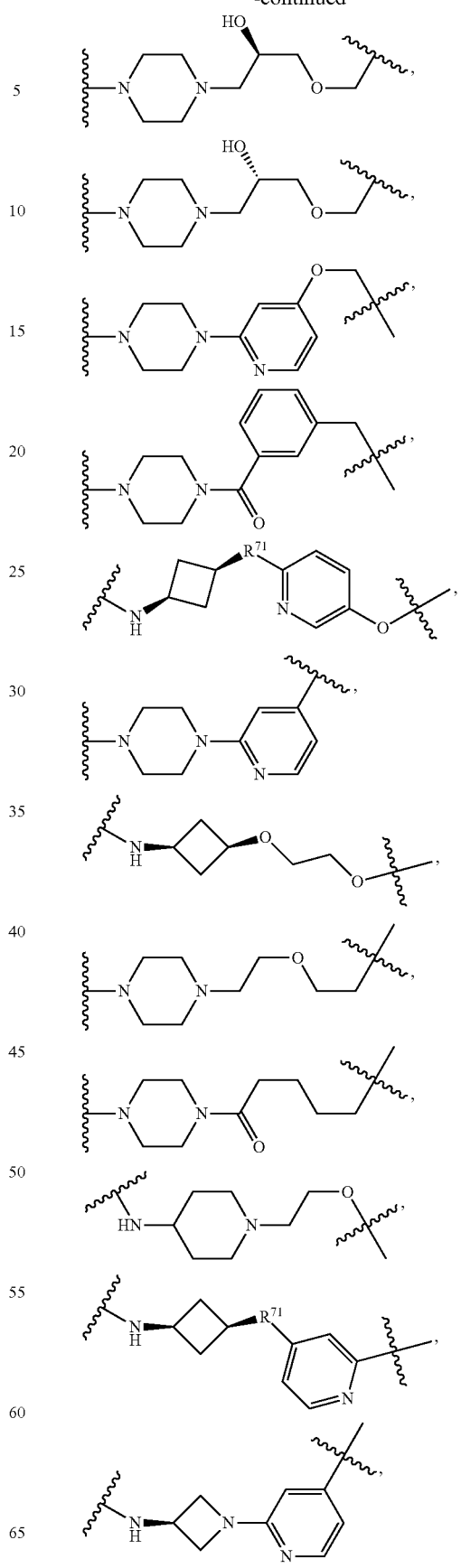

143
-continued
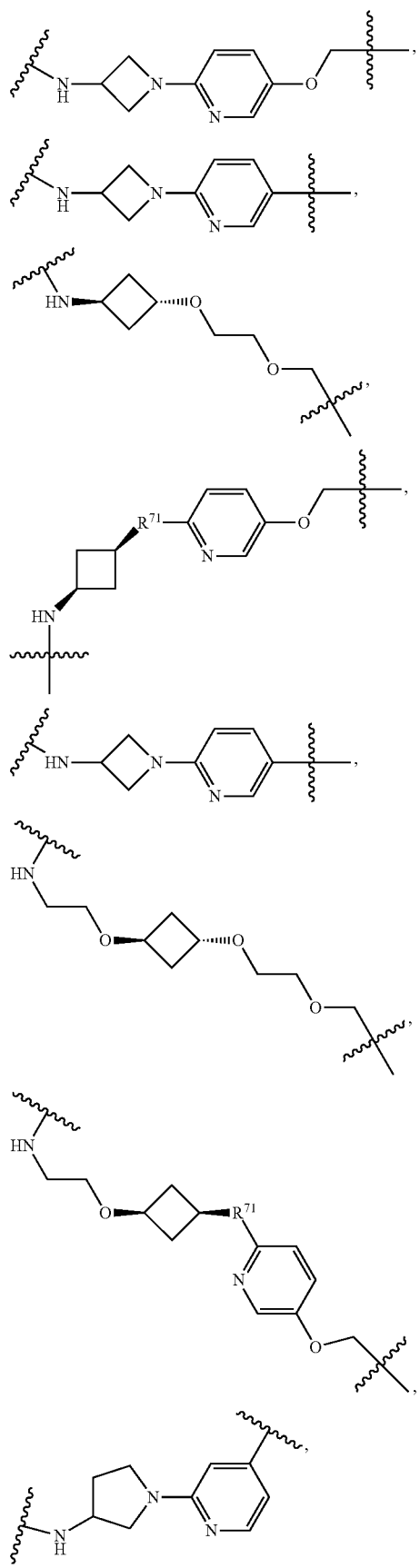
144
-continued
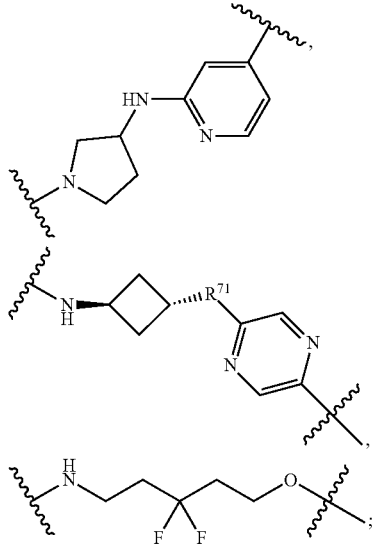
wherein R[71] is —O—, —NH, Nalkyl, heteroaliphatic, aliphatic or —NMe.
In additional embodiments, the Linker is selected from:
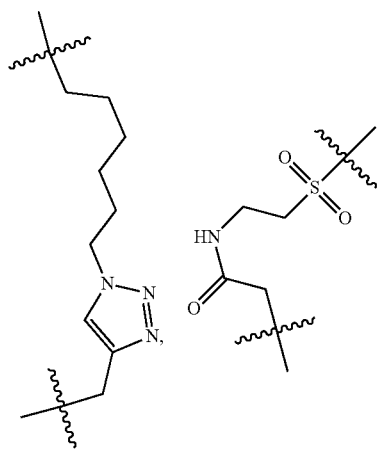
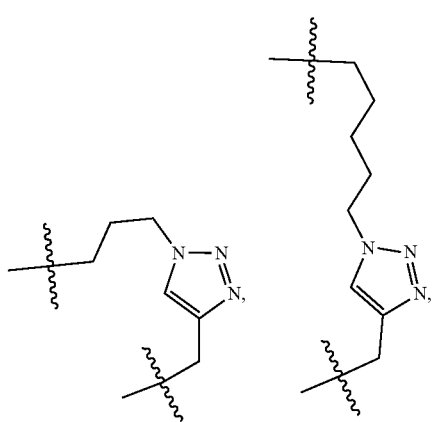

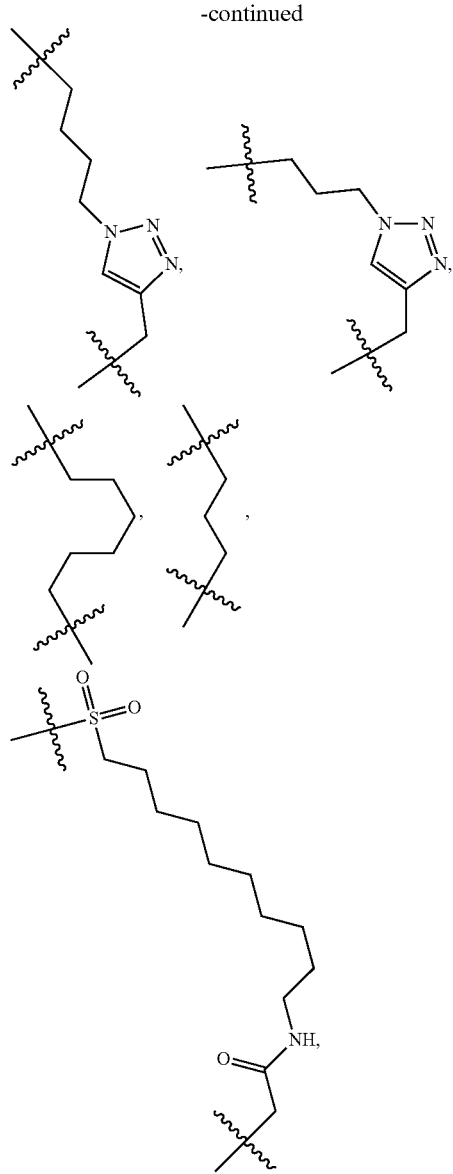
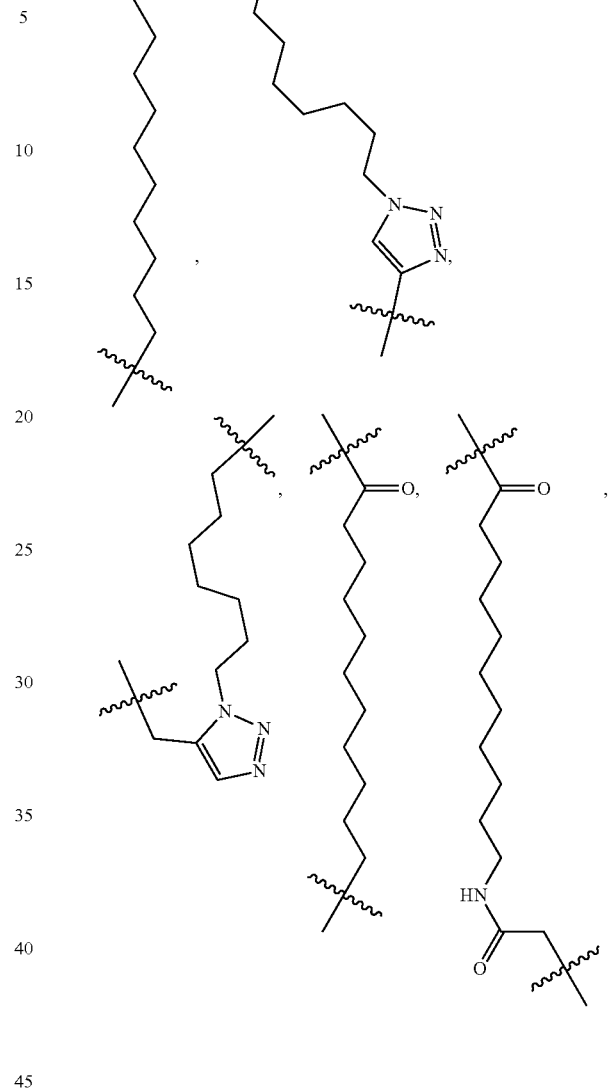
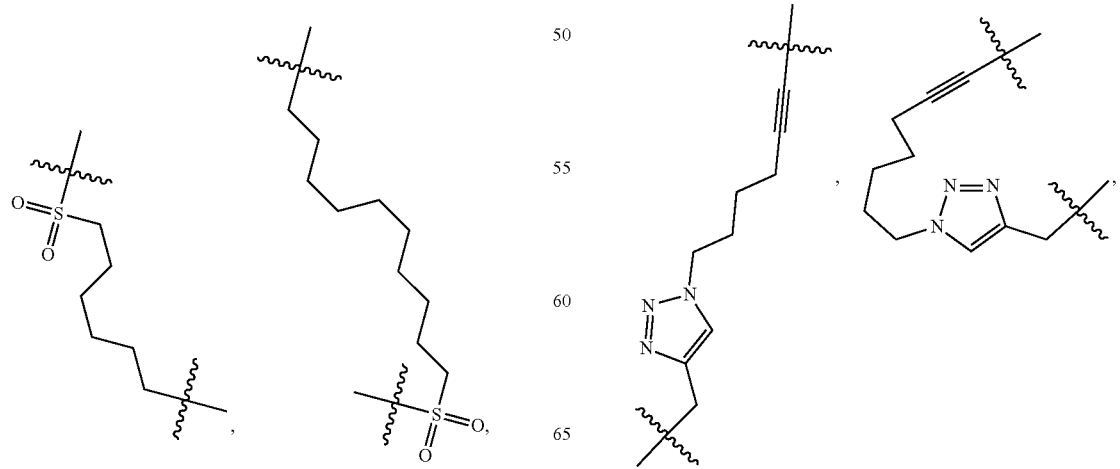

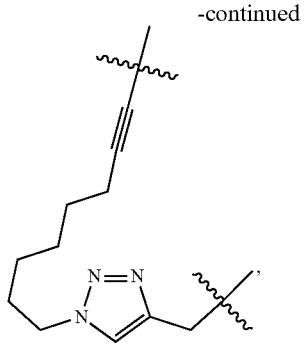
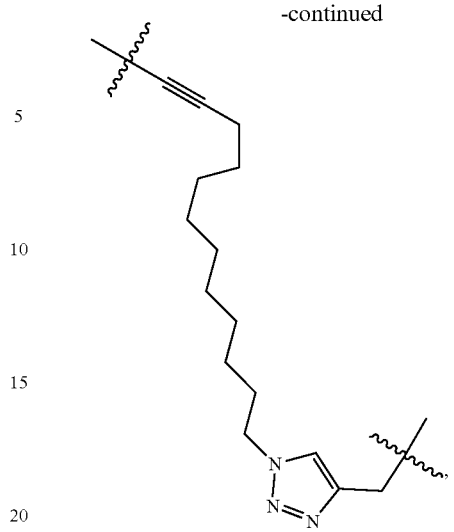
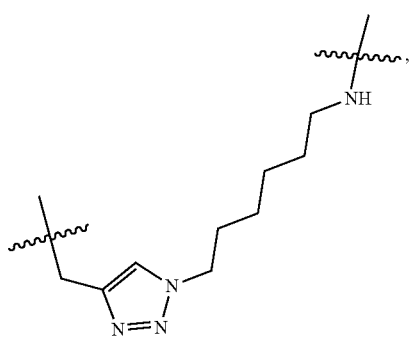
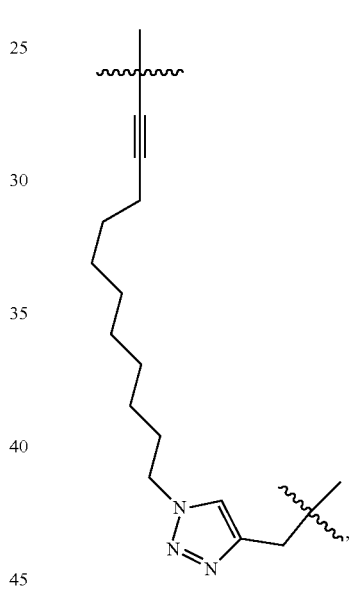
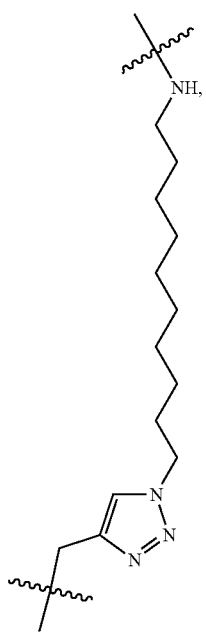
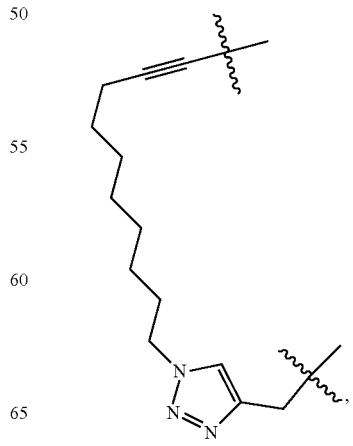

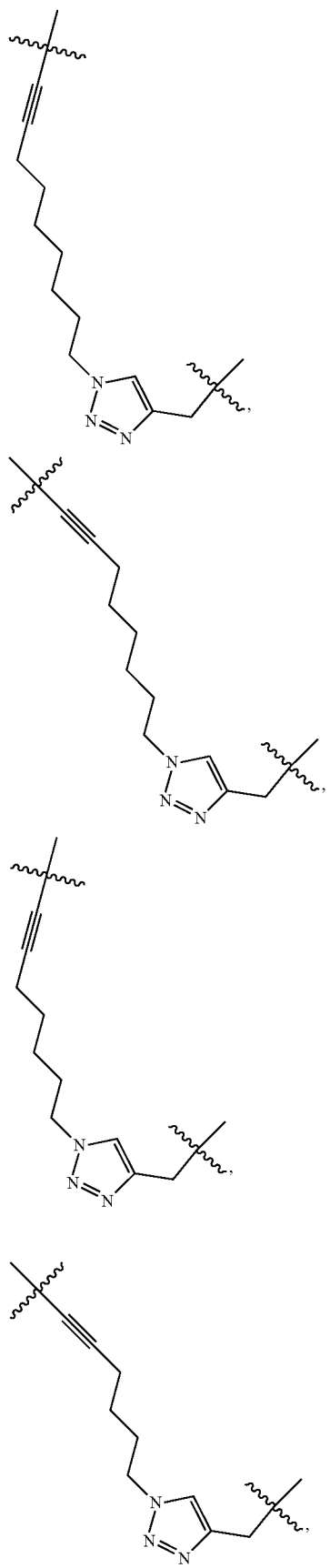
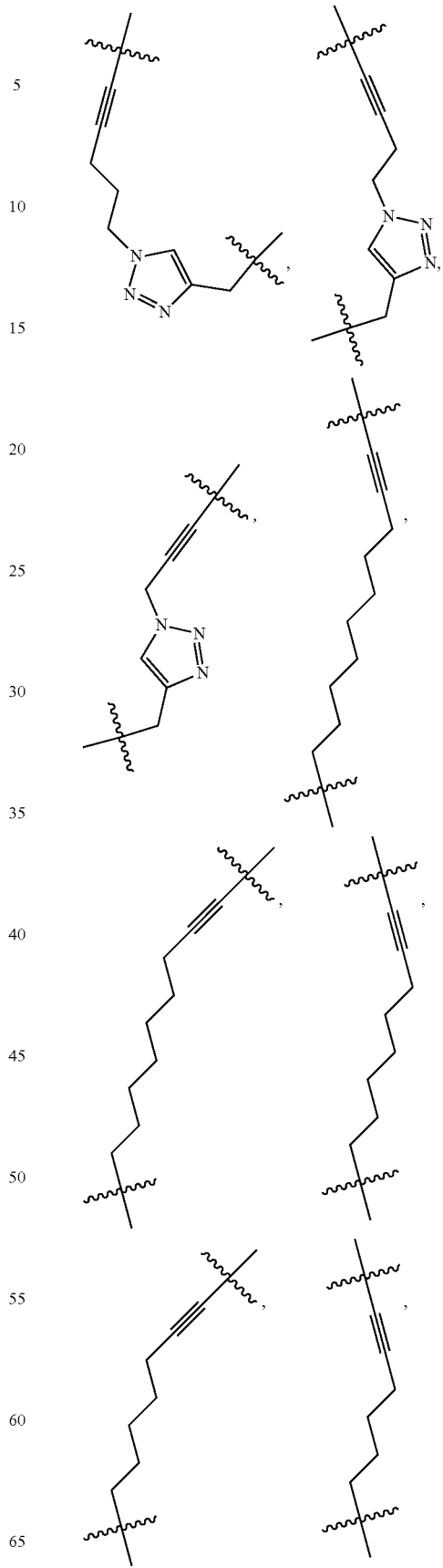

151
-continued
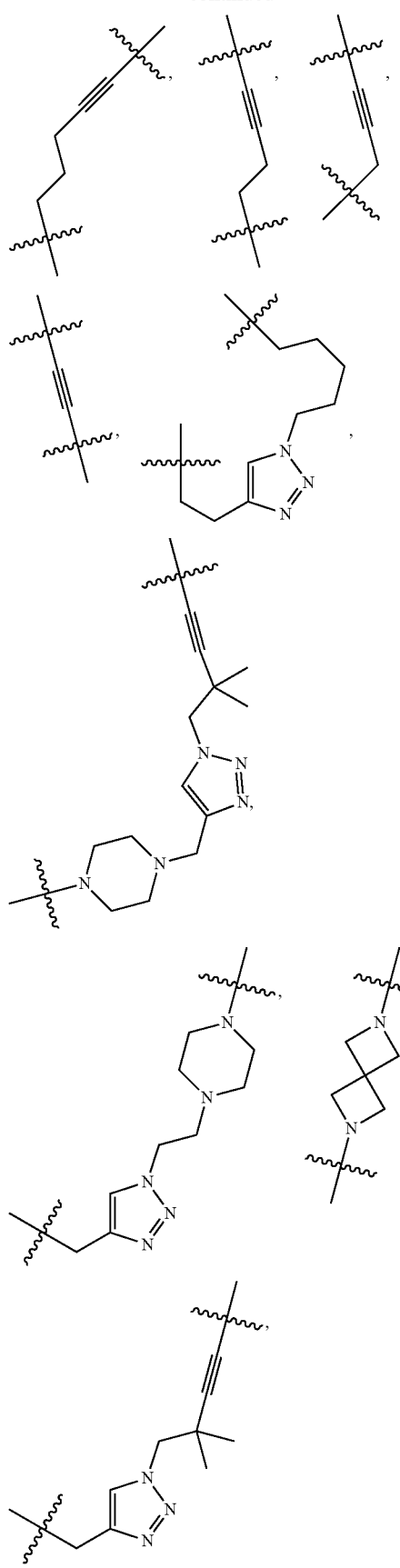
152
-continued
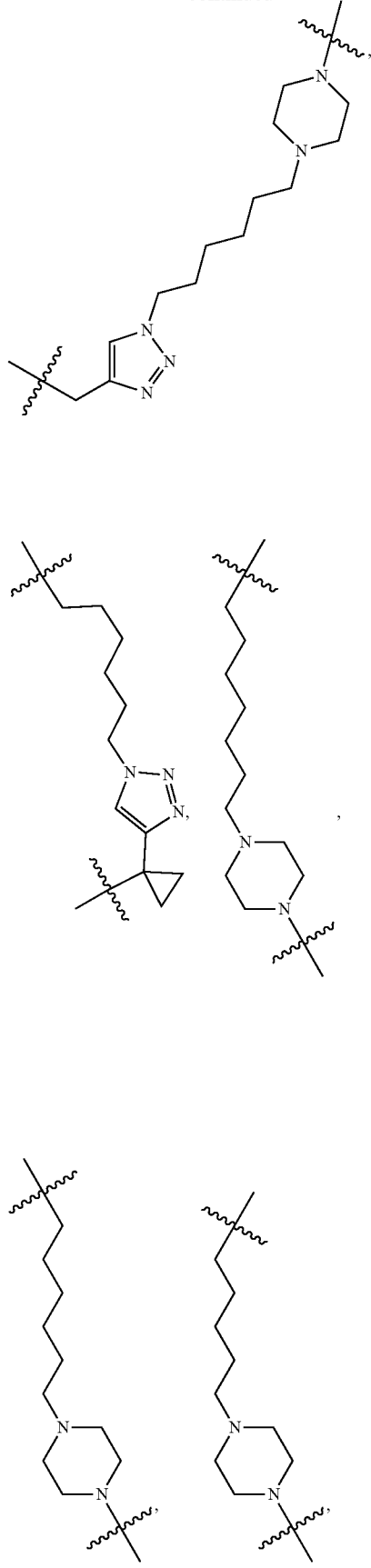

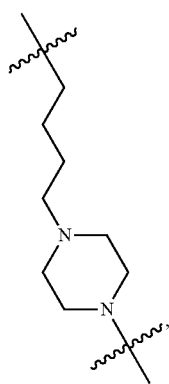
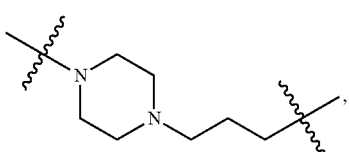
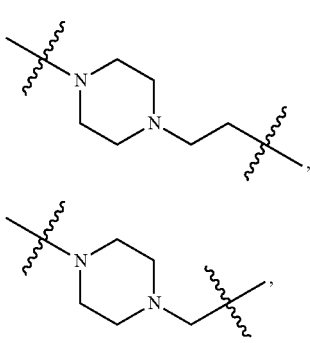
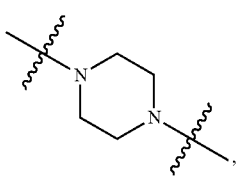
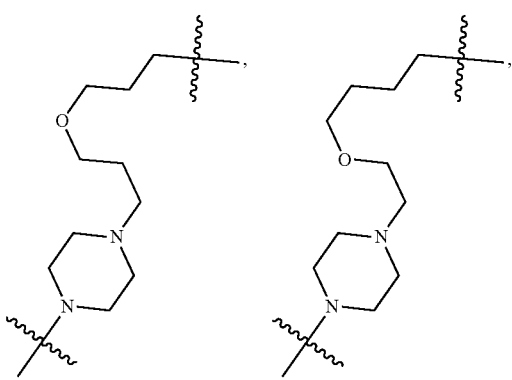
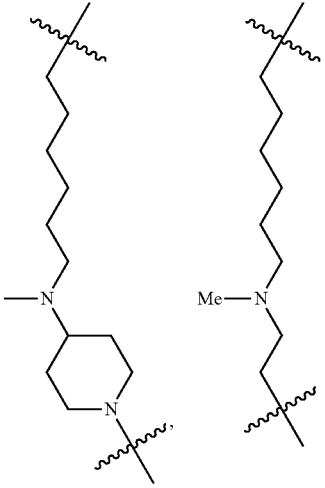
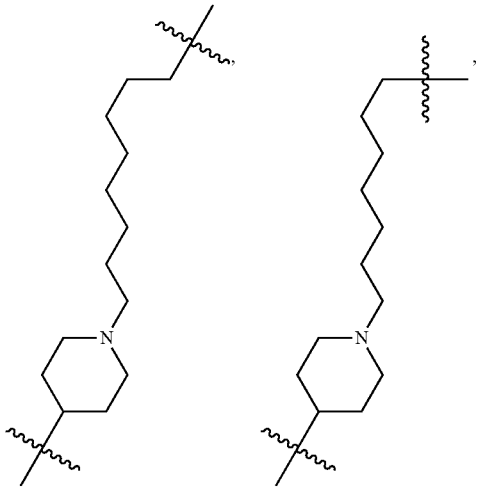
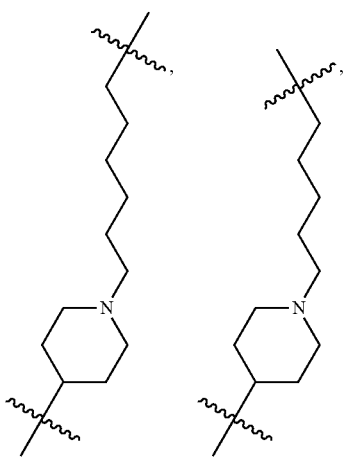

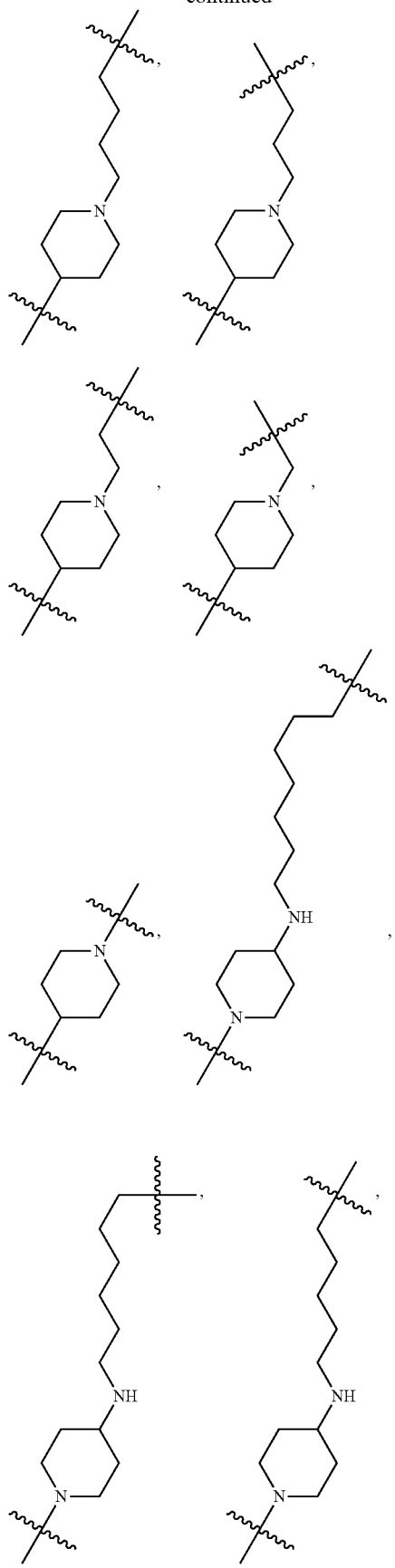
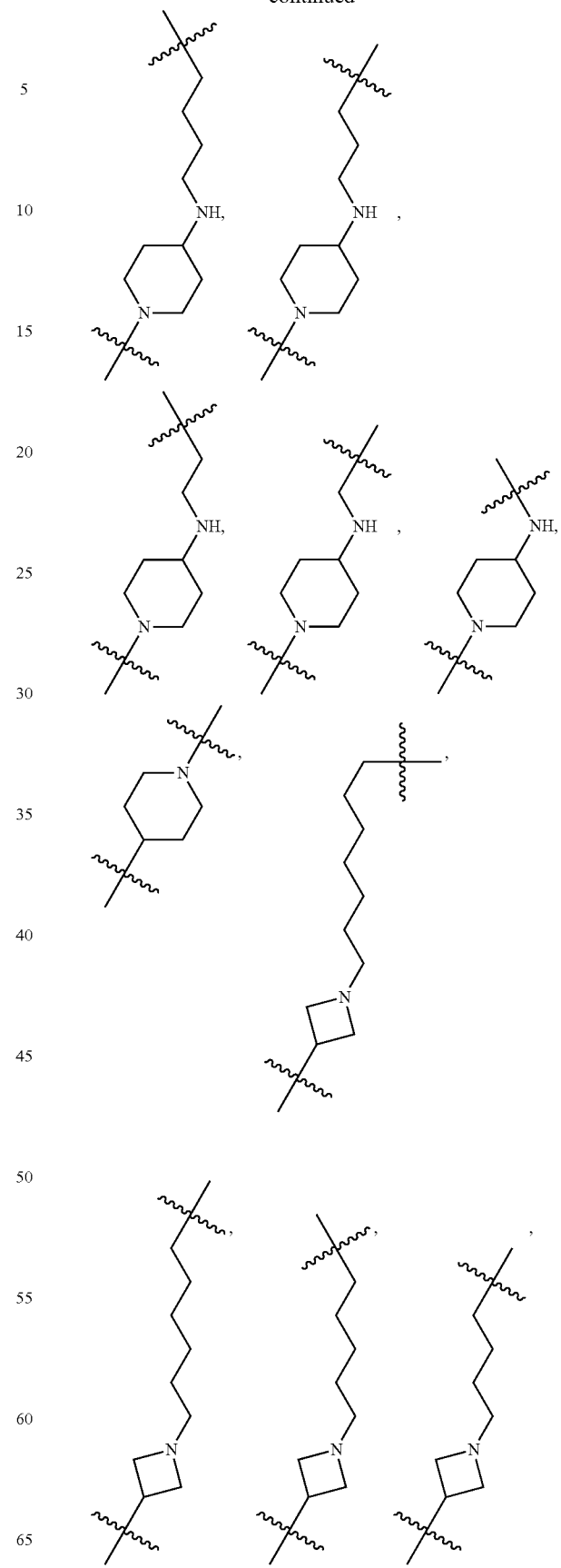

157
-continued
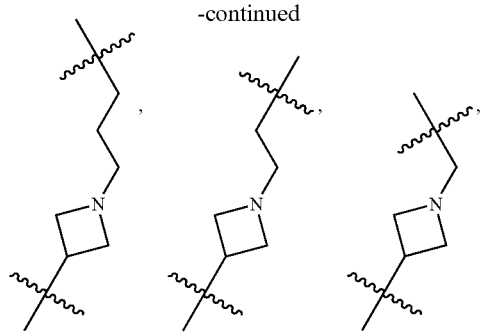
158
-continued
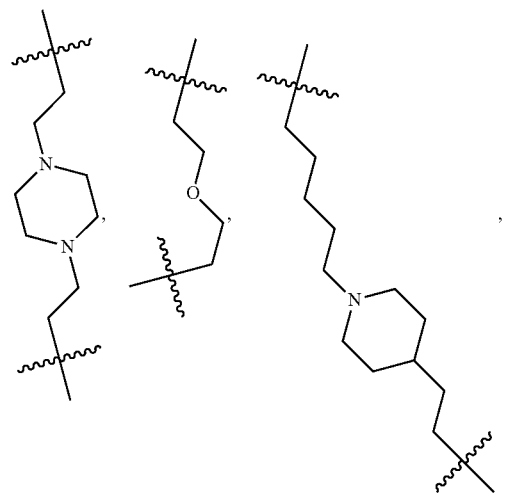
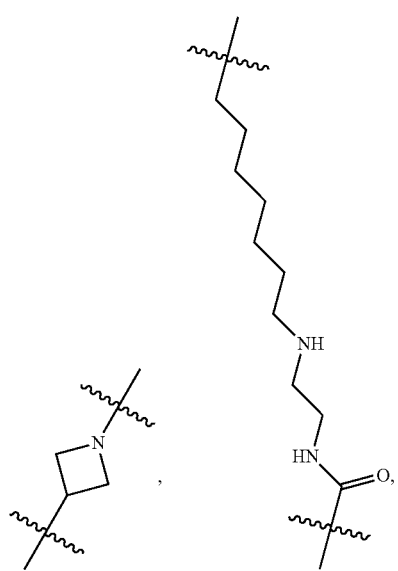
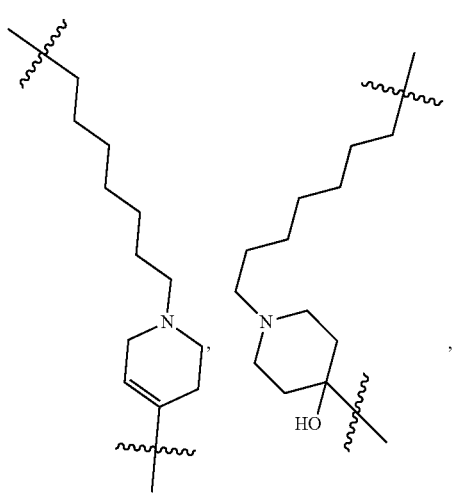
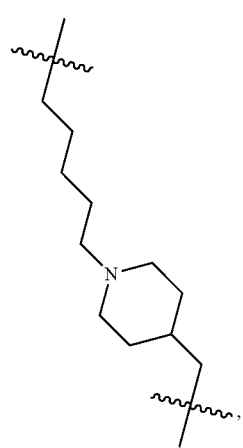

159
-continued
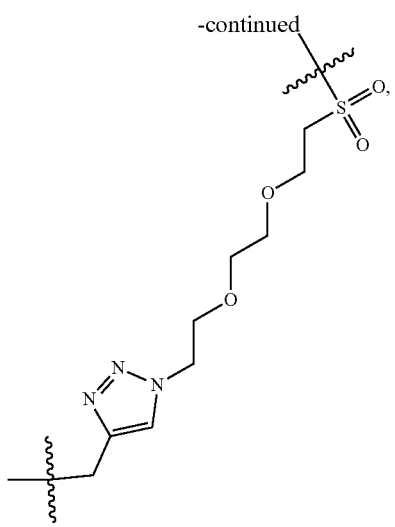
160
-continued
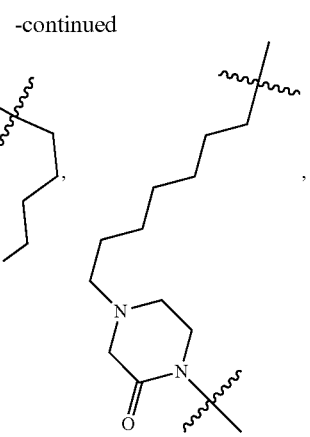
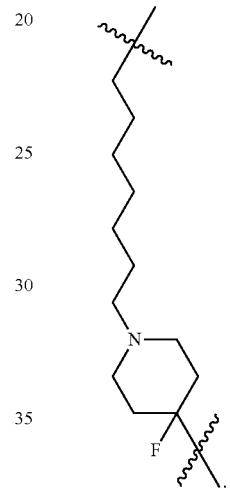
In additional embodiments, the Linker is selected from:
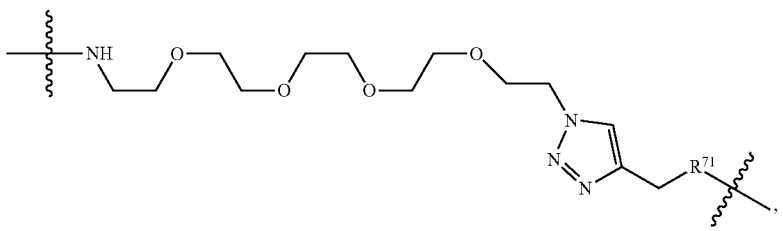
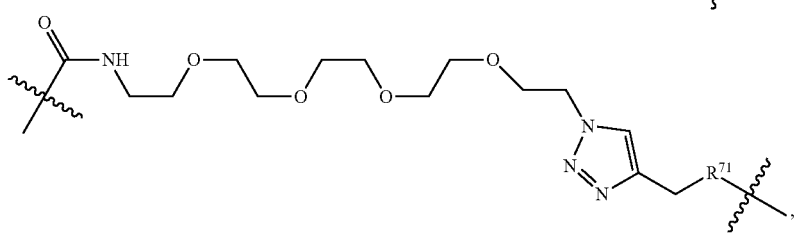
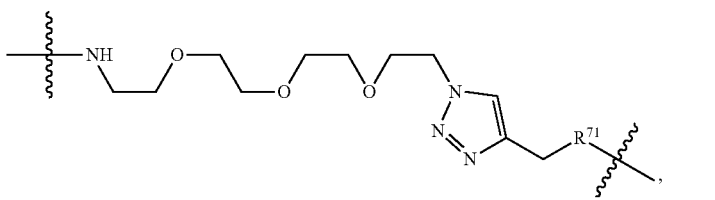

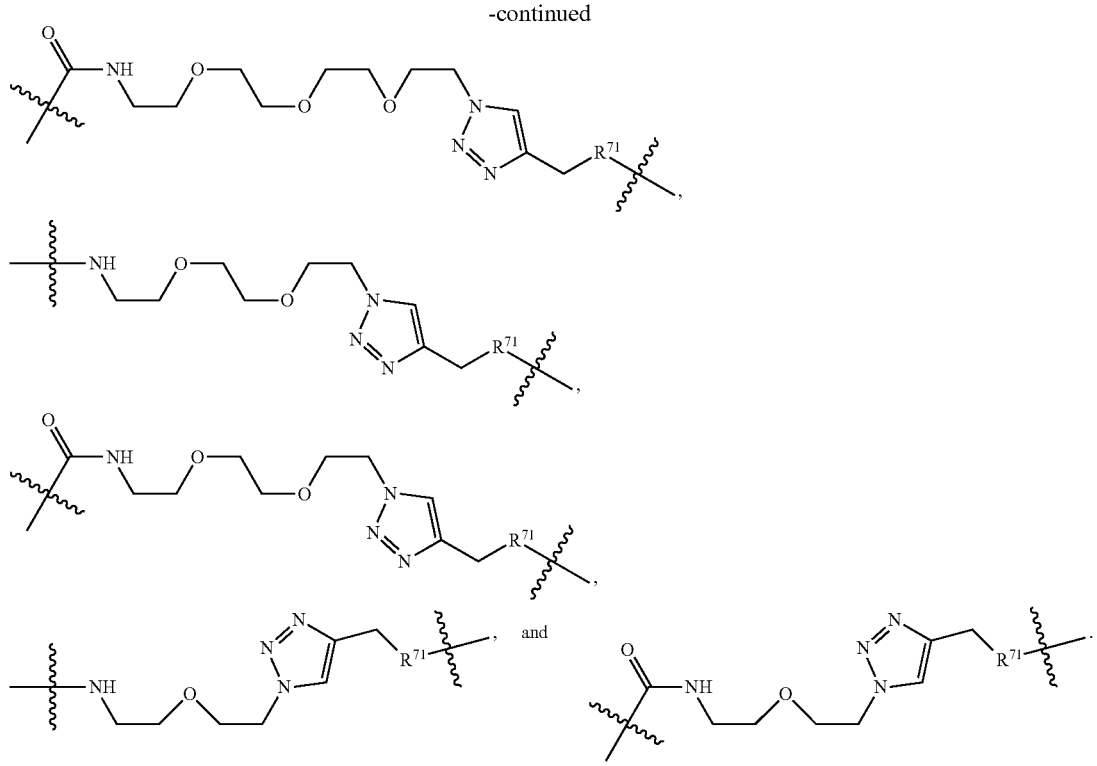
In additional embodiments, the Linker is selected from:
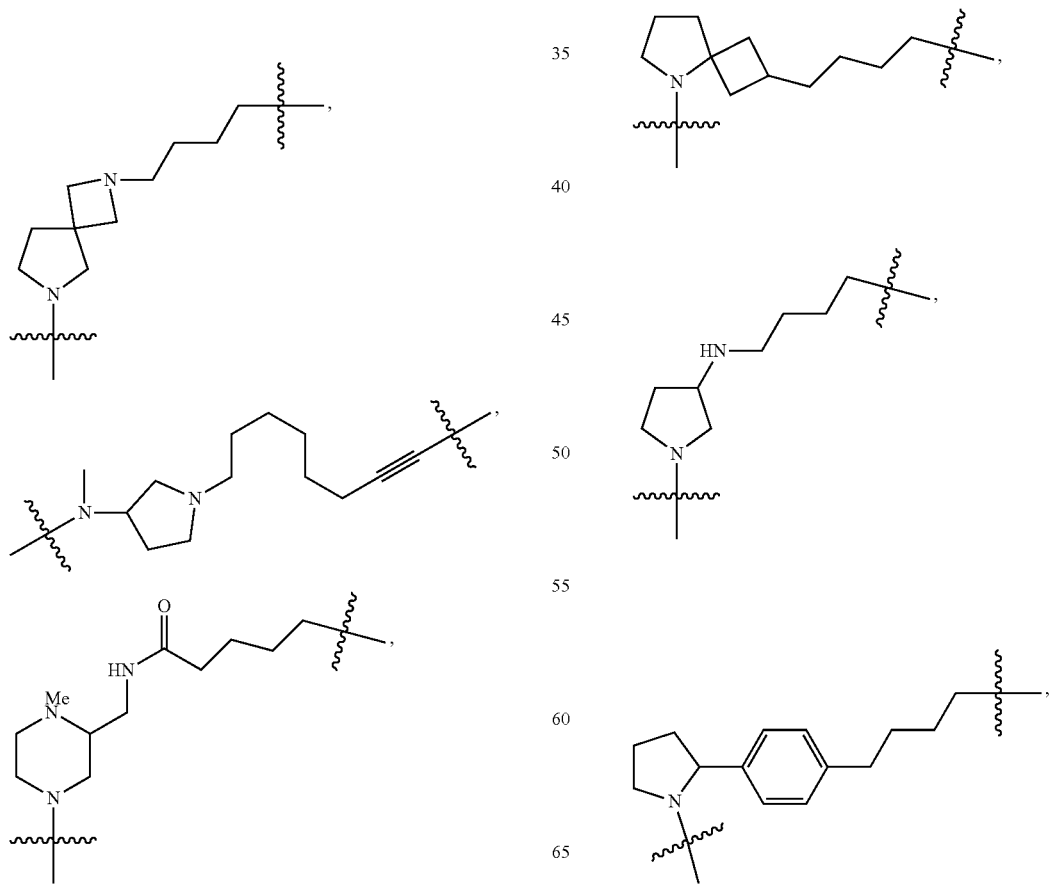

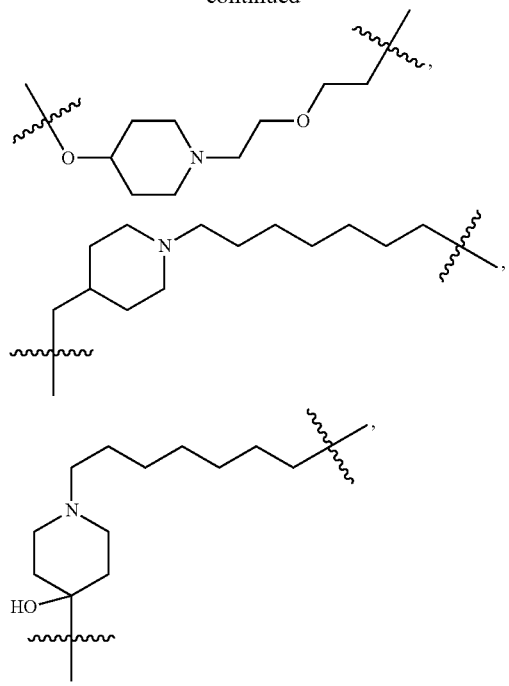
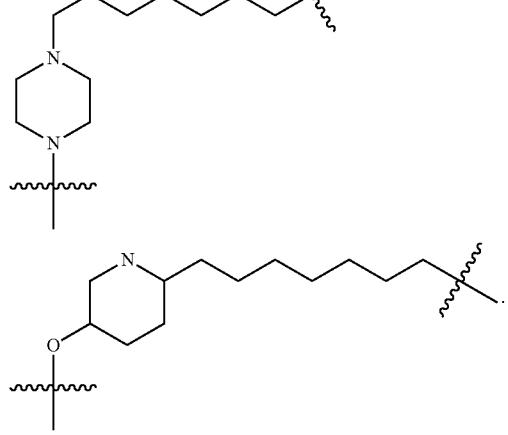
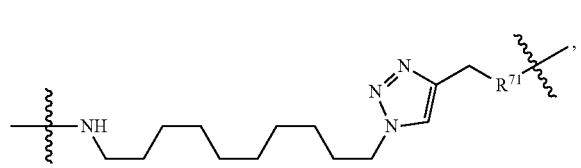
In additional embodiments, the Linker is selected from:
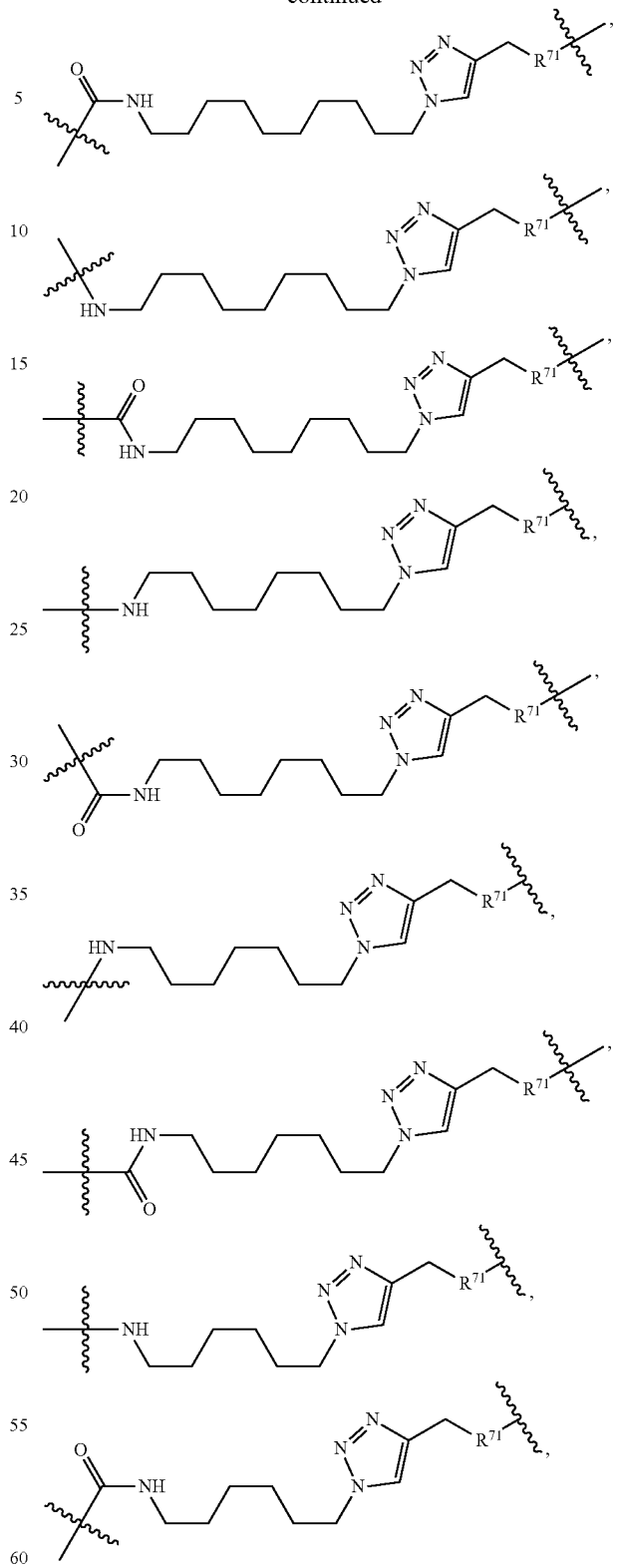

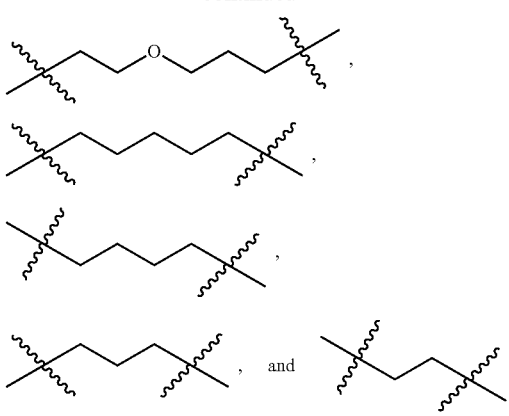
In additional embodiments, the Linker is selected from:
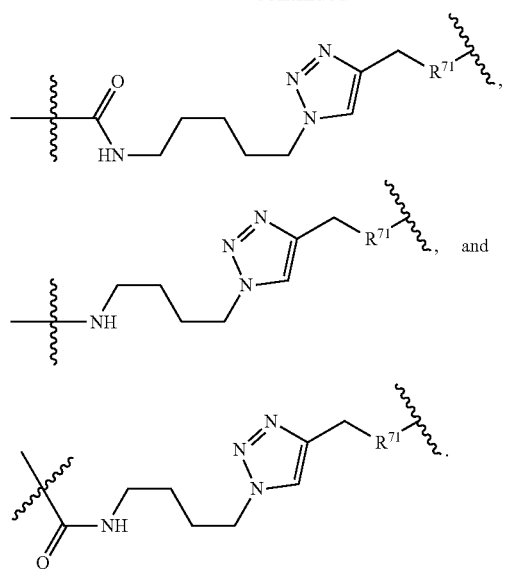
In additional embodiments, the Linker is selected from:
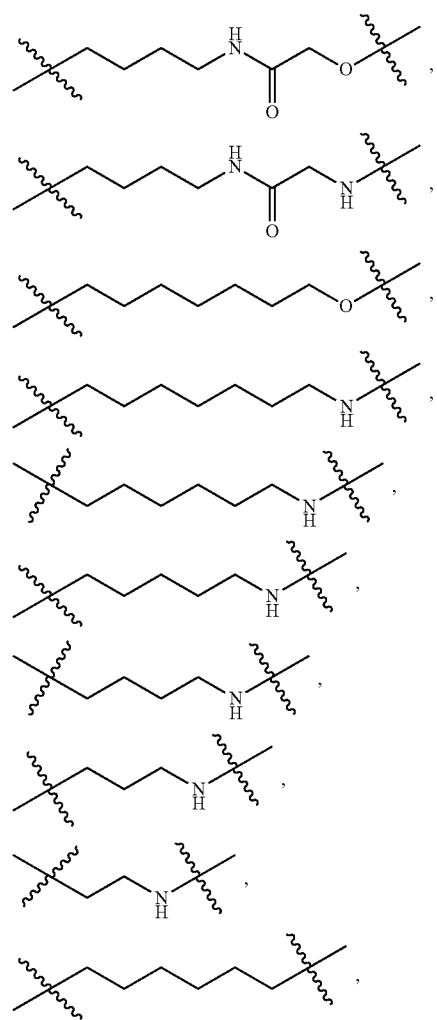
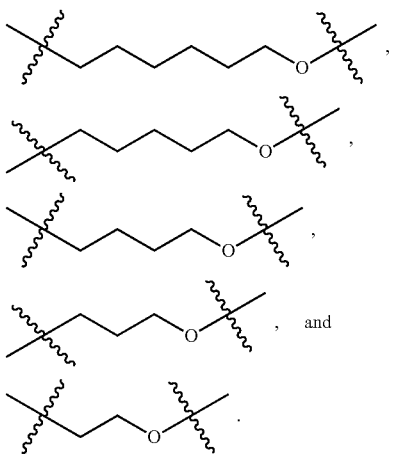
In certain embodiments, the Linker is selected from:
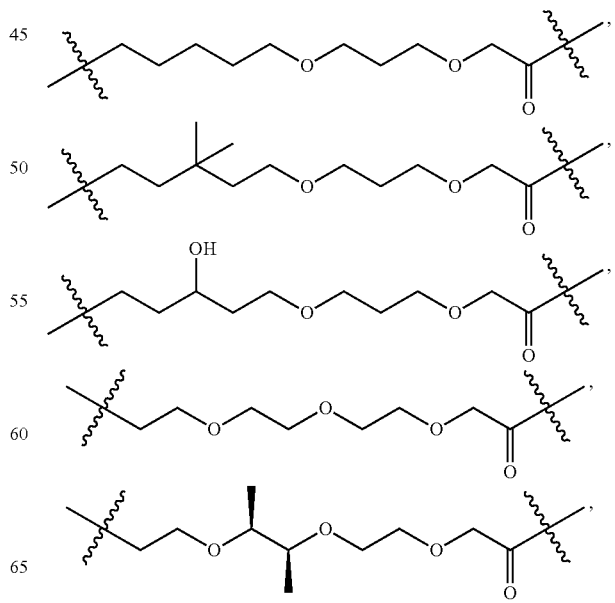

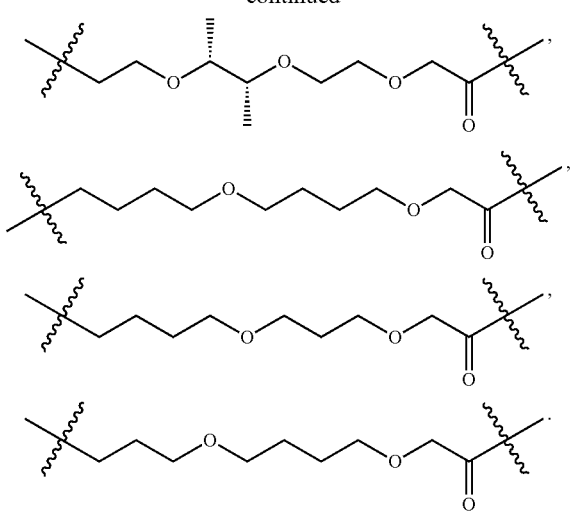
In certain embodiments the Linker is selected from:
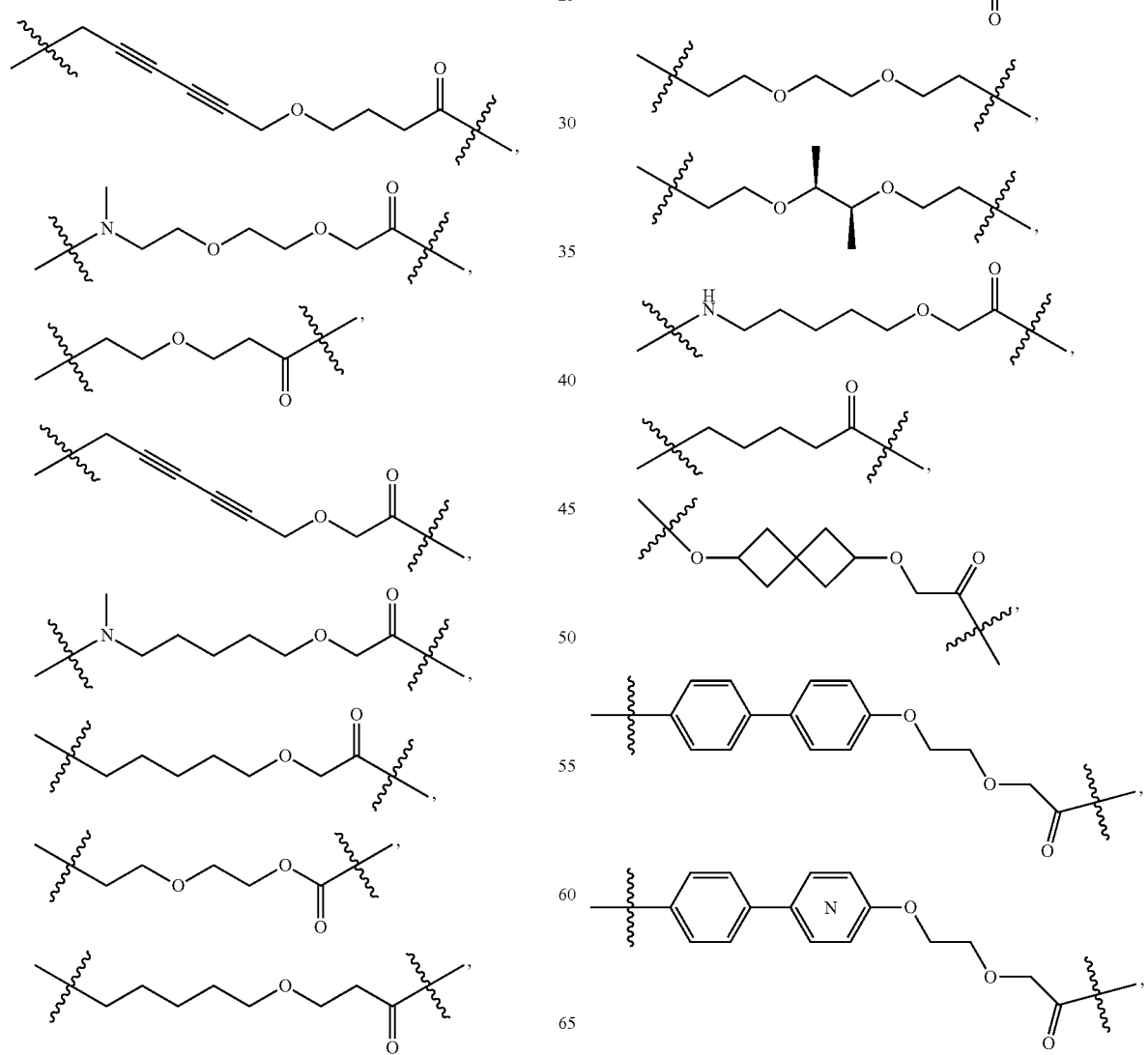

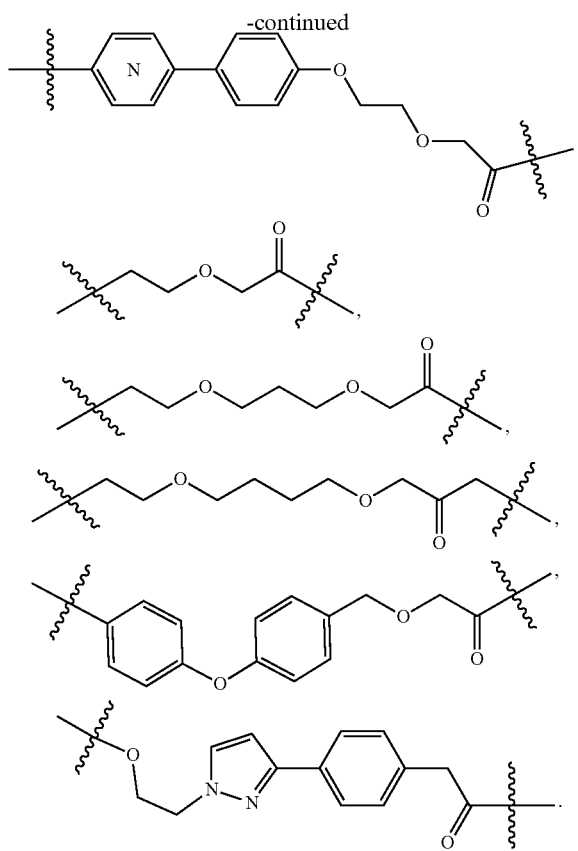
In the above structures
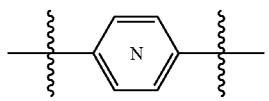
represents
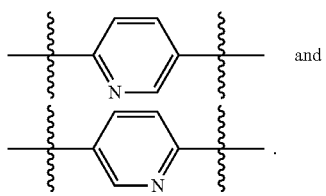 and
In certain embodiments, Linker can be a 4-24 carbon atom linear chains, wherein one or more the carbon atoms in the linear chain can be replaced or substituted with oxygen, nitrogen, amide, fluorinated carbon, etc., such as the following:
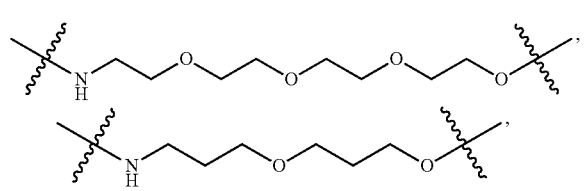
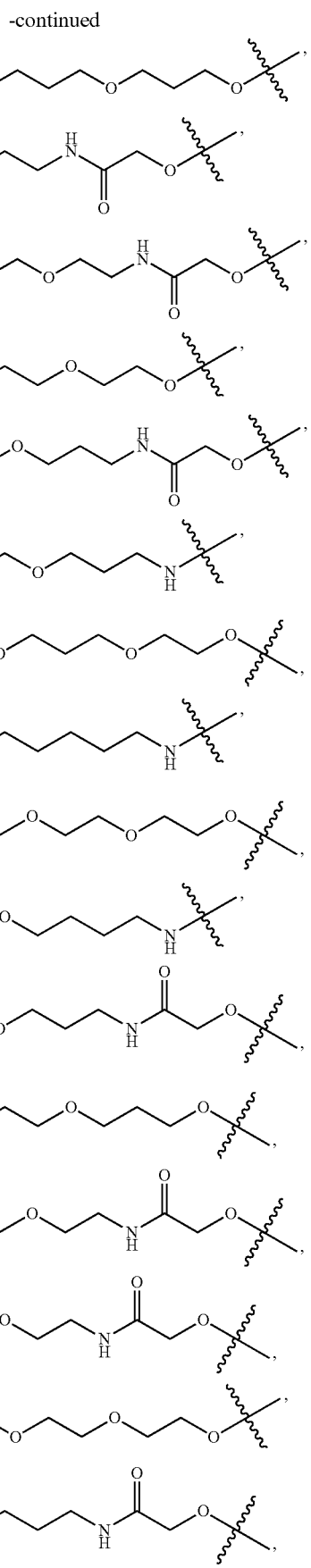
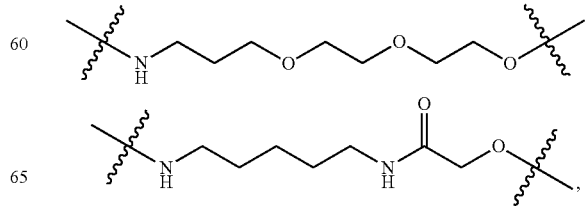

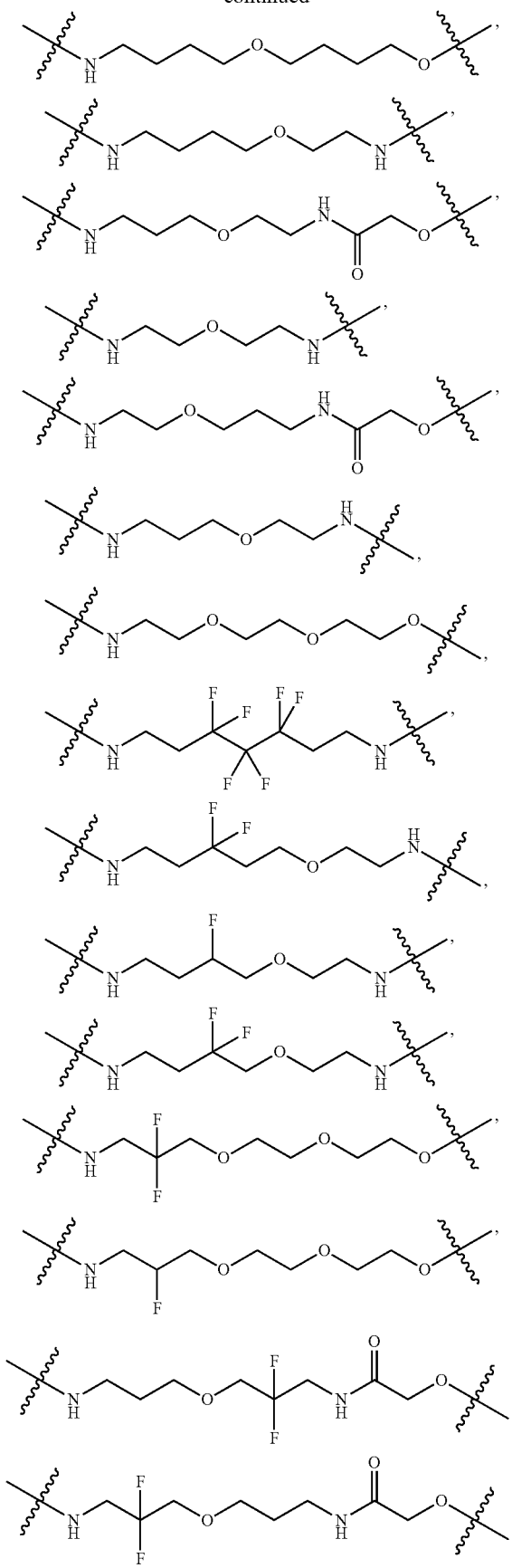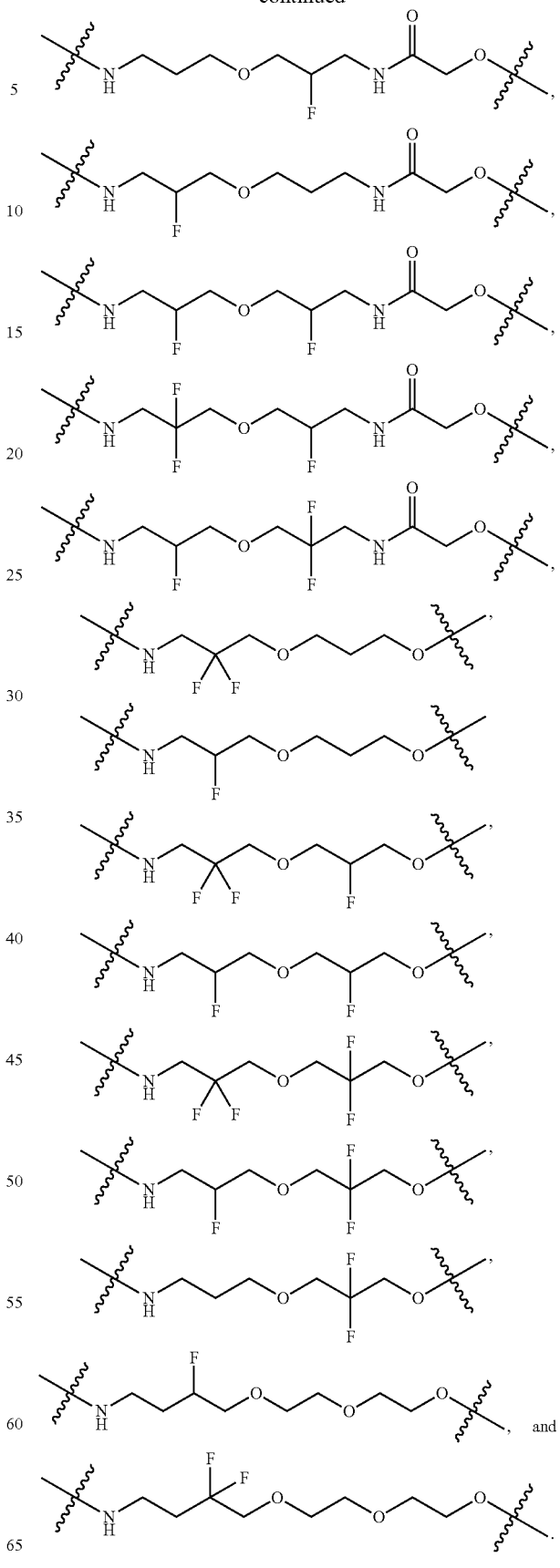

In certain embodiments, Linker can be a nonlinear chain, and can be, or include, aliphatic or aromatic or heteroaromatic cyclic moieties.

In certain embodiments, the Linker may include contiguous, partially contiguous or non-contiguous ethylene glycol unit groups ranging in size from about 1 to about 12 ethylene glycol units, between 1 and about 10 ethylene glycol units, about 2 about 6 ethylene glycol units, between about 2 and 5 ethylene glycol units, between about 2 and 4 ethylene glycol units, for example, 1, 2, 3, 4, 6, 6, 7, 8, 9, 10, 11 or 12 ethylene glycol units.

In certain embodiments, the Linker may have 1, 2, 3, 4, 5, 6, 7, 8, 9, 10, 11, 12, 13, 14, or 15 fluorine substituents. In another embodiment the Linker is perfluorinated. In yet another embodiment the Linker is a partially or fully fluorinated poly ether. Nonlimiting examples of fluorinated Linkers include:

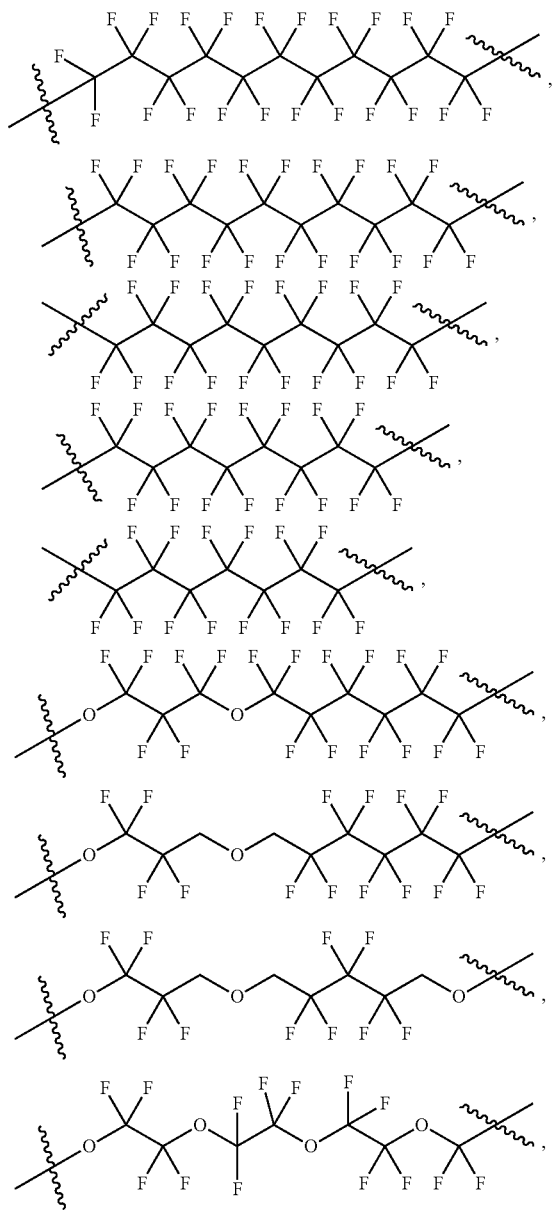

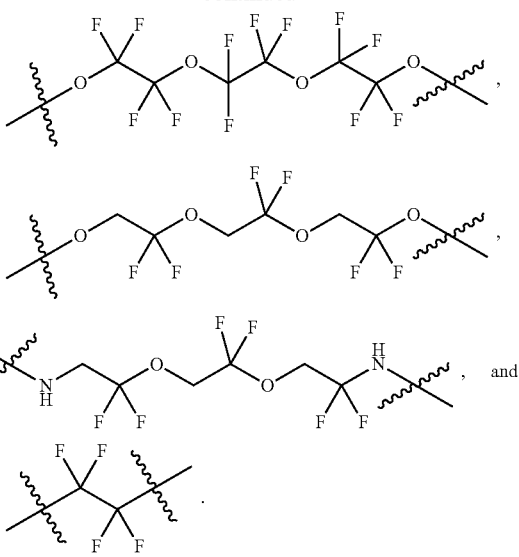

In certain embodiments, where the Target Ligand binds more than one protein (i.e., is not completely selective), selectivity may be enhanced by varying Linker length where the ligand binds some of its targets in different binding pockets, e.g., deeper or shallower binding pockets than others. Therefore, the length can be adjusted as desired.

In certain embodiments, the present application provides Degron-Linker (DL) having the following structure:

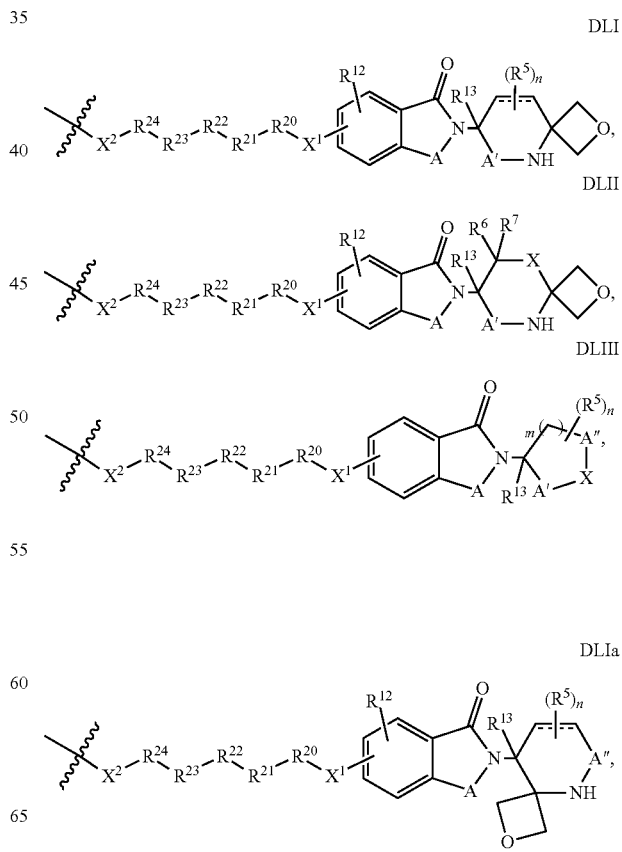

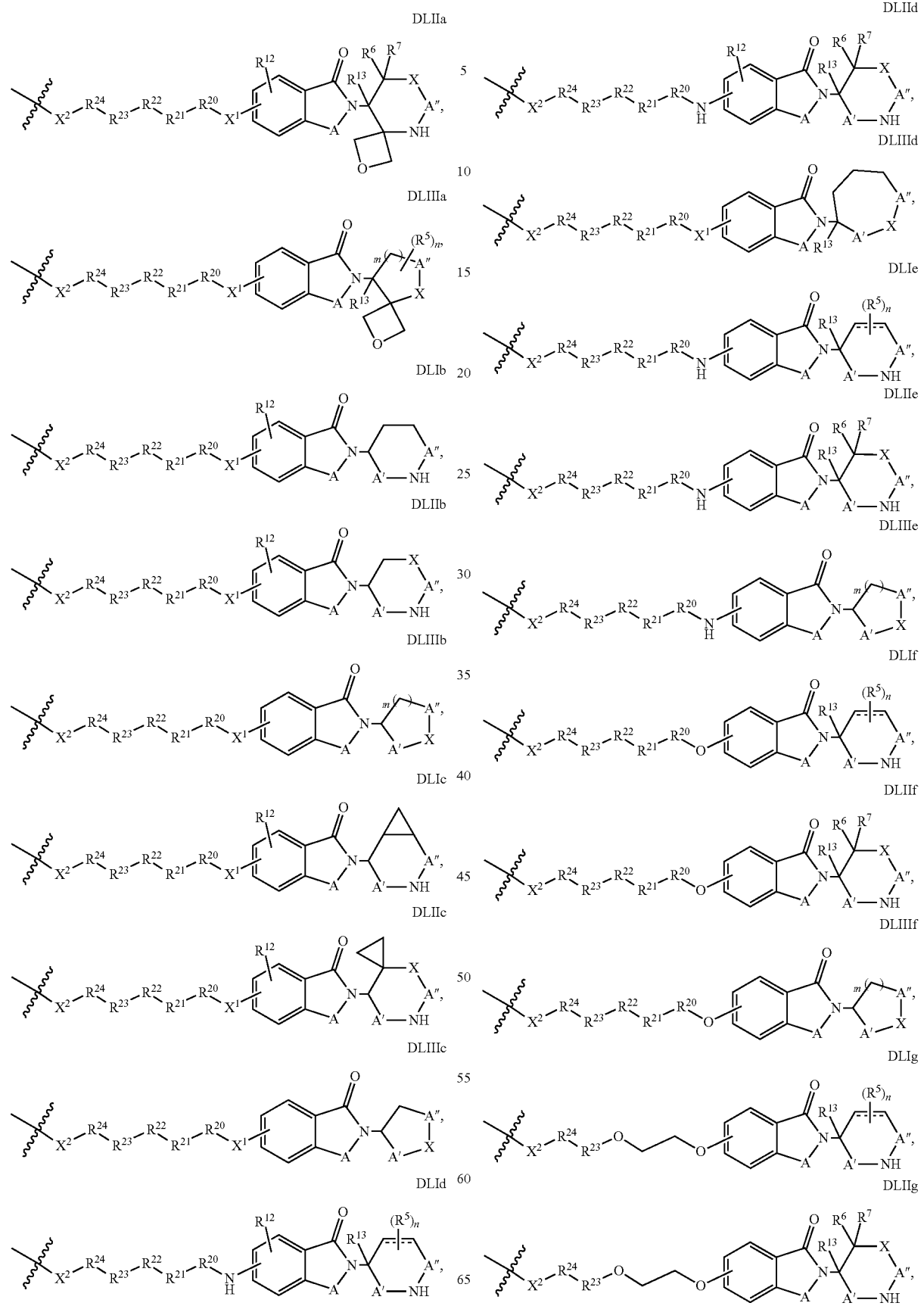

DLIIIg

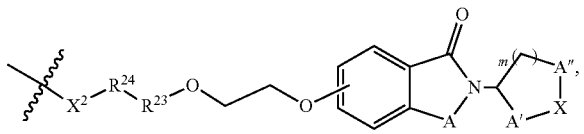

In an alternative embodiment, the present application provides Degron-Linker (DL) having the following structure:

DLIh

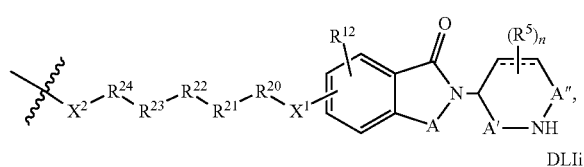

DLIi

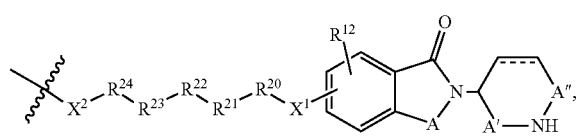

DLIj

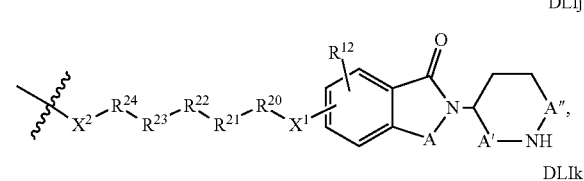

DLIk

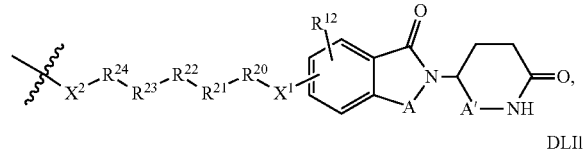

DLIl

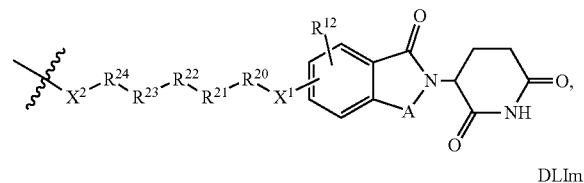

DLIm

DLIn

DLIo

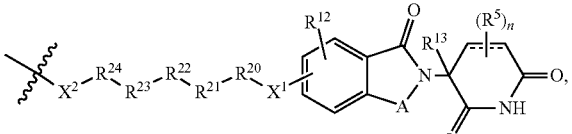

DLIp

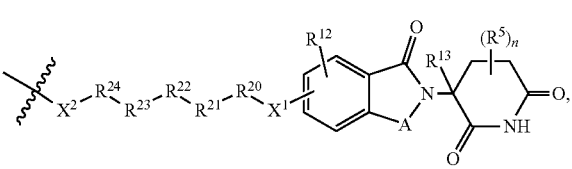

DLIq wherein each of the variables is as described above in Formula I, Formula II, Formula III, and Formula LI; and a Targeting Ligand is covalently bonded to the DL through the

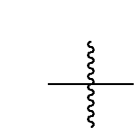

next to $X^2$.

Target Proteins

Degradation of cellular proteins is required for cell homeostasis and normal cell function, such as proliferation, differentiation and cell death. When this system becomes dysfunctional or does not identify and abate abnormal protein behavior in vivo, a disease state can arise in a host, such as a human. A large range of proteins can cause, modulate or amplify diseases in vivo, as well known to those skilled in the art, published in literature and patent filings as well as presented in scientific presentations.

Therefore, in one embodiment, a selected Degronimer of the present invention can be administered in vivo in an effective amount to a host in need thereof to degrade a selected protein that mediates a disorder to be treated. The selected Target Protein may modulate a disorder in a human via a mechanism of action such as modification of a biological pathway, pathogenic signaling or modulation of a signal cascade or cellular entry. In one embodiment, the Target Protein is a protein that is not druggable in the classic sense in that it does not have a binding pocket or an active site that can be inhibited or otherwise bound, and cannot be easily allosterically controlled. In another embodiment, the Target Protein is a protein that is druggable in the classic sense, yet for therapeutic purposes, degradation of the protein is preferred to inhibition.

The Target Protein is recruited with a Targeting Ligand for the Target Protein. Typically the Degron binds the Target Protein in a non-covalent fashion. In an alternative embodiment, the Target Protein is covalently bound to the Degron in a manner that can be irreversible or reversible.

In one embodiment, the selected Target Protein is expressed from a gene that has undergone an amplification, translocation, deletion, or inversion event which causes or is caused by a medical disorder. In certain aspects, the selected Target Protein has been post-translationally modified by one, or a combination, of phosphorylation, acetylation, acylation including propionylation and crotylation, N-linked glycosylation, amidation, hydroxylation, methylation and polymethylation, O-linked glycosylation, pyrogultamoylation, myristoylation, farnesylation, geranylgeranylation, ubiquitination, sumoylation, or sulfation which causes or is caused by a medical disorder.

As contemplated herein, the present invention includes an Degronimer with a Targeting Ligand that binds to a Target Protein of interest. The Target Protein is any amino acid sequence to which an Degronimer can be bound which by degradation thereof, causes a beneficial therapeutic effect in vivo. In one embodiment, the Target Protein is a non-endogenous peptide such as that from a pathogen or toxin. In another embodiment, the Target Protein can be an endogenous protein that mediates a disorder. The endogenous protein can be either the normal form of the protein or an aberrant form. For example, the Target Protein can be a mutant protein found in cancer cells, or a protein, for example, where a partial, or full, gain-of-function or loss-of-function is encoded by nucleotide polymorphisms. In some embodiments, the Degronimer targets the aberrant form of the protein and not the normal form of the protein. In another embodiment, the Target Protein can mediate an inflammatory disorder or an immune disorder, including an auto-immune disorder.

In one embodiment, the Target Protein is a non-endogenous protein from a virus, as non-limiting examples, HIV, HBV, HCV, RSV, HPV, CMV, flavivirus, pestivirus, coronavirus, noroviridae, etc. In one embodiment, the Target Protein is a non-endogenous protein from a bacteria, which may be for example, a gram positive bacteria, gram negative bacteria or other, and can be a drug-resistant form of bacteria. In one embodiment, the Target Protein is a non-endogenous protein from a fungus. In one embodiment, the Target Protein is a non-endogenous protein from a prion. In one embodiment, the Target Protein is a protein derived from a eukaryotic pathogen, for example a protist, helminth, etc.

In one aspect, the Target Protein mediates chromatin structure and function. The Target Protein may mediate an epigenetic action such as DNA methylation or covalent modification of histones. An example is histone deacetylase (HDAC 1, 2, 3, 4, 5, 6, 7, 8, 9, 10 or 11). Alternatively, the Target Protein may be a bromodomain, which are readers of lysine acetylation (for example, BRD1, 2, 3, 4, 5, 6, 7, 8, 9 and T. FIG. 9 is a dendogram of the proteins of the bromodomain family, which, for example, can act as Target Proteins according to the present invention.

Other nonlimiting examples of Target Proteins are a structural protein, receptor, enzyme, cell surface protein, a protein involved in apoptotic signaling, aromatase, helicase, mediator of a metabolic process (anabolism or catabolism), antioxidant, protease, kinase, oxidoreductase, transferase, hydrolase, lyase, isomerase, ligase, enzyme regulator, signal transducer, structural molecule, binding activity (protein, lipid carbohydrate), cell motility protein, membrane fusion protein, cell communication mediator, regulator of biological processes, behavioral protein, cell adhesion protein, protein involved in cell death, protein involved in transport (including protein transporter activity, nuclear transport, ion transporter, channel transporter, carrier activity, permease, secretase or secretion mediator, electron transporter, chaperone regulator, nucleic acid binding, transcription regulator, extracellular organization and biogenesis regulator, and translation regulator).

In one embodiment, the Target Protein is a modulator of a signaling cascade related to a known disease state. In another embodiment, the Target Protein mediates a disorder by a mechanism different from modulating a signaling cascade. Any protein in a eukaryotic system or a microbial system, including a virus, bacteria or fungus, as otherwise described herein, are targets for proteasomal degradation using the present invention. The Target Protein may be a eukaryotic protein, and in some embodiments, a human protein.

In one embodiment, the Target Protein is RXR, DHFR, Hsp90, a kinase, HDM2, MDM2, BET bromodomain-containing protein, HDAC, IDH1, Mcl-1, human lysine methyltransferase, a nuclear hormone receptor, aryl hydrocarbon receptor (AHR), RAS, RAF, FLT, SMARC, KSR, NF2L, CTNB, CBLB, BCL.

In one embodiment, a bromodomain containing protein has histone acetyl transferase activity.

In one embodiment, the bromodomain containing protein is BRD2, BRD3, BRD4, BRDT or ASH1L.

In one embodiment, the bromodomain containing protein is a non-BET protein.

In one embodiment, the non-BET protein is BRD7 or BRD9.

In one embodiment, the FLT is not FLT 3. In one embodiment, the RAS is not RASK. In one embodiment, the RAF is not RAF1. In one embodiment, the SMARC is not SMARC2. In one embodiment, the KSR is not KSR1. In one embodiment, the NF2L is not NF2L2. In one embodiment, the CTNB is not CTNB1. In one embodiment, the BCL is not BCL6.

In one embodiment, the Target Protein is selected from: EGFR, FLT3, RAF1, SMRCA2, KSR1, NF2L2, CTNB1, CBLB, BCL6, and RASK.

In another embodiment, the Target Protein is not selected from: EGFR, FLT3, RAF1, SMRCA2, KSR1, NF2L2, CTNB1, CBLB, BCL6, and RASK.

In one embodiment, the Targeting Ligand is an EGFR ligand, a FLT3 ligand, a RAF1 ligand, a SMRCA2 ligand, a KSR1 ligand, a NF2L2 ligand, a CTNB1 ligand, a CBLB ligand, a BCL6 ligand, or a RASK ligand.

In one embodiment, the Targeting Ligand is not a EGFR ligand, a FLT3 ligand, a RAF1 ligand, a SMRCA2 ligand, a KSR1 ligand, a NF2L2 ligand, a CTNB1 ligand, a CBLB ligand, a BCL6 ligand, or a RASK ligand.

The present invention may be used to treat a wide range of disease states and/or conditions, including any disease state and/or condition in which a protein is dysregulated and where a patient would benefit from the degradation of proteins.

For example, a Target Protein can be selected that is a known target for a human therapeutic, and the therapeutic can be used as the Targeting Ligand when incorporated into the Degronimer according to the present invention. These include proteins which may be used to restore function in a polygenic disease, including for example B7.1 and B7, TINFR1m, TNFR2, NADPH oxidase, BclIBax and other partners in the apoptosis pathway, C5a receptor, HMG-CoA reductase, PDE V phosphodiesterase type, PDE IV phosphodiesterase type 4, PDE I, PDE II, PDE III, squalene cyclase inhibitor, CXCR1, CXCR2, nitric oxide (NO) synthase, cyclo-oxygenase 1, cyclo-oxygenase 2, 5HT receptors, dopamine receptors, G Proteins, e.g., Gq, histamine receptors, 5-lipoxygenase, tryptase serine protease, thymidylate synthase, purine nucleoside phosphorylase, GAPDH trypanosomal, glycogen phosphorylase, Carbonic anhydrase, chemokine receptors, JAW STAT, RXR and similar, HIV 1 protease, HIV 1 integrase, influenza, neuraminidase, hepatitis B reverse transcriptase, sodium channel, multi drug resistance (MDR), protein P-glycoprotein (and MRP), tyrosine kinases, CD23, CD124, tyrosine kinase p56 lck, CD4, CD5, IL-2 receptor, IL-1 receptor, TNF-alphaR, ICAM1, Cat+ channels, VCAM, VLA-4 integrin, selectins, CD40/CD40L, neurokinins and receptors, inosine monophosphate dehydrogenase, p38 MAP Kinase, Ras/Raf/MER/ERK pathway, interleukin-1 converting enzyme, caspase, HCV, NS3 protease, HCV NS3 RNA helicase, glycinamide ribonucleotide formyl transferase, rhinovirus 3C protease, herpes simplex virus-1 (HSV-I), protease, cytomegalovirus (CMV) protease, poly (ADP-ribose) polymerase, cyclin dependent kinases, vascular endothelial growth factor, oxytocin receptor, microsomal transfer protein inhibitor, bile acid transport inhibitor, 5 alpha reductase inhibitors, angiotensin 11, glycine receptor, noradrenaline reuptake receptor, endothelin receptors, neuropeptide Y and receptor, estrogen receptors, androgen receptors, adenosine receptors, adenosine kinase and AMP deaminase, purinergic receptors (P2Y1, P2Y2, P2Y4, P2Y6, P2X1-7), farnesyltransferases, geranylgeranyl transferase, TrkA a receptor for NGF, beta-amyloid, tyrosine kinase Flk-IIKDR, vitronectin receptor, integrin receptor, Her-2/neu, telomerase inhibition, cytosolic phospholipaseA2 and EGF receptor tyrosine kinase. Additional protein targets include, for example, ecdysone 20-monooxygenase, ion channel of the GABA gated chloride channel, acetylcholinesterase, voltage-sensitive sodium channel protein, calcium release channel, and chloride channels. Still further Target Proteins include Acetyl-CoA carboxylase, adenylosuccinate synthetase, protoporphyrinogen oxidase, and enolpyruvylshikimate-phosphate synthase.

In certain embodiments, the Target Protein is derived from a kinase to which the Targeting Ligand is capable of binding or binds including, but not limited to, a tyrosine kinase (e.g., AATK, ABL, ABL2, ALK, AXL, BLK, BMX, BTK, CSF1R, CSK, DDR1, DDR2, EGFR, EPHA1, EPHA2, EPHA3, EPHA4, EPHA5, EPHA6, EPHA7, EPHA8, EPHA10, EPHB1, EPHB2, EPHB3, EPHB4, EPHB6, ERBB2, ERBB3, ERBB4, FER, FES, FGFR1, FGFR2, FGFR3, FGFR4, FGR, FLT1, FLT3, FLT4, FRK, FYN, GSG2, HCK, IGF1R, ILK, INSR, INSRR, IRAK4, ITK, JAK1, JAK2, JAK3, KDR, KIT, KSR1, LCK, LMTK2, LMTK3, LTK, LYN, MATK, MERTK, MET, MLTK, MST1R, MUSK, NPR1, NTRK1, NTRK2, NTRK3, PDGFRA, PDGFRB, PLK4, PTK2, PTK2B, PTK6, PTK7, RET, ROR1, ROR2, ROS1, RYK, SGK493, SRC, SRMS, STYK1, SYK, TEC, TEK, TEX14, TIE1, TNK1, TNK2, TNNI3K, TXK, TYK2, TYRO3, YES1, or ZAP70).

In certain embodiments, the Target Protein is derived from a kinase to which the Targeting Ligand is capable of binding or binds including, but not limited to, a serine/threonine kinase (e.g., casein kinase 2, protein kinase A, protein kinase B, protein kinase C, Raf kinases, CaM kinases, AKT1, AKT2, AKT3, ALK1, ALK2, ALK3, ALK4, Aurora A, Aurora B, Aurora C, CHK1, CHK2, CLK1, CLK2, CLK3, DAPK1, DAPK2, DAPK3, DMPK, ERK1, ERK2, ERK5, GCK, GSK3, HIPK, KHS1, LKB1, LOK, MAPKAPK2, MAPKAPK, MNK1, MSSK1, MST1, MST2, MST4, NDR, NEK2, NEK3, NEK6, NEK7, NEK9, NEK11, PAK1, PAK2, PAK3, PAK4, PAK5, PAK6, PIM1, PIM2, PLK1, RIP2, RIP5, RSK1, RSK2, SGK2, SGK3, SIK1, STK33, TAO1, TAO2, TGF-beta, TLK2, TSSK1, TSSK2, ULK1, or ULK2).

In certain embodiments, the Target Protein is derived from a kinase to which the Targeting Ligand is capable of binding or binds including, but not limited to a cyclin dependent kinase for example CDK1, CDK2, CDK3, CDK4, CDK5, CDK6, CDK7, CDK8, CDK9, CDK10, CDK11, CDK12, or CDK13.

In certain embodiments, the Target Protein is derived from a kinase to which the Targeting Ligand is capable of binding or binds including, but not limited to a leucine-rich repeat kinase (e.g., LRRK2).

In certain embodiments, the Target Protein is derived from a kinase to which the Targeting Ligand is capable of binding or binds including, but not limited to a lipid kinase (e.g., PIK3CA, PIK3CB) or a sphingosine kinase (e.g. S1P).

In certain embodiments, the Target Protein is derived from a BET bromodomain-containing protein to which the Targeting Ligand is capable of binding or binds including, but not limited to, ASH1L, ATAD2, BAZ1A, BAZ1B, BAZ2A, BAZ2B, BRD1, BRD2, BRD3, BRD4, BRD5, BRD6, BRD7, BRD8, BRD9, BRD10, BRDT, BRPF1, BRPF3, BRWD3, CECR2, CREBBP, EP300, FALZ, GCN5L2, KIAA1240, LOC93349, MLL, PB1, PCAF, PHIP, PRKCBP1, SMARCA2, SMARCA4, SP100, SP110, SP140, TAF1, TAF1L, TIF1a, TRIM28, TRIM33, TRIM66, WDR9, ZMYND11, and MLL4. In certain embodiments, a BET bromodomain-containing protein is BRD4.

In certain embodiments, the Target Protein is derived from a nuclear protein to which the Targeting Ligand is capable of binding or binds including, but not limited to, BRD2, BRD3, BRD4, Antennapedia Homeodomain Protein, BRCA1, BRCA2, CCAAT-Enhanced-Binding Proteins, histones, Polycomb-group proteins, High Mobility Group Proteins, Telomere Binding Proteins, FANCA, FANCD2, FANCE, FANCF, hepatocyte nuclear factors, Mad2, NF-kappa B, Nuclear Receptor Coactivators, CREB-binding protein, p55, p107, p130, Rb proteins, p53, c-fos, c-jun, c-mdm2, c-myc, and c-rel.

In one embodiment, the Target Protein is a protein, or a precursor, variant (e.g., a splice variant), mutant (e.g., substitution, deletion, duplication, insertion, insertion/deletion, extension, etc.), homolog, chimeric. polymorph, isoform, modification (e.g., post-translationally modified through glycosylation, phosphorylation, proteolysis, etc.), or recombinant thereof.

In certain embodiments, the Target Protein is a member of the Retinoid X Receptor (RXR) family and the disorder treated is a neuropsychiatric or neurodegenerative disorder. In certain embodiments, the Target Protein is a member of the Retinoid X Receptor (RXR) family and the disorder treated is schizophrenia.

In certain embodiments, the Target Protein is dihydrofolate reductase (DHFR) and the disorder treated is cancer. In certain embodiments, the Target Protein is dihydrofolate reductase (DHFR) and the disorder treated is microbial.

In certain embodiments, the Target Protein is dihydrofolate reductase from *Bacillus anthracis* (BaDHFR) and the disorder treated is anthrax.

In certain embodiments, the Target Protein is Heat Shock Protein 90 (HSP90) and the disorder treated is cancer.

In certain embodiments, the Target Protein is a kinase or phosphatase and the disorder treated is cancer.

In certain embodiments, the Target Protein is HDM2 and or MDM2 and the disorder treated is cancer.

In certain embodiments, the Target Protein is a BET bromodomain containing protein and the disorder treated is cancer.

In certain embodiments, the Target Protein is a lysine methyltransferase and the disorder treated is cancer.

In certain embodiments, the Target Protein belongs to the RAF family and the disorder treated is cancer.

In certain embodiments, the Target Protein belongs to the FKBP family and the disorder treated is an autoimmune disorder. In certain embodiments, the Target Protein belongs to the FKBP family and the disorder treated is organ rejection. In certain embodiments, the Target Protein belongs to the FKBP family and the compound is given prophylactically to prevent organ failure.

In certain embodiments, the Target Protein is an androgen receptor and the disorder treated is cancer.

In certain embodiments, the Target Protein is an estrogen receptor and the disorder treated is cancer.

In certain embodiments, the Target Protein is a viral protein and the disorder treated is a viral infection. In certain embodiments, the Target Protein is a viral protein and the disorder treated is HIV, HPV, or HCV.

In certain embodiments, the Target Protein is an AP-1 or AP-2 transcription factor and the disorder treated is cancer.

In certain embodiments, the Target Protein is a HIV protease and the disorder treated is a HIV infection. In certain embodiments, the Target Protein is a HIV integrase and the disorder treated is a HIV infection. In certain embodiments, the Target Protein is a HCV protease and the disorder treated is a HCV infection. In certain embodiments, the treatment is prophylactic and the Target Protein is a viral protein.

In certain embodiments, the Target Protein is a member of the histone deacetylase (HDAC) family and the disorder is a neurodegenerative disorder. In certain embodiments, the Target Protein is a member of the histone deacetylase (HDAC) family and the disorder is Huntingon's, Parkinson's, Kennedy disease, amyotropic lateral sclerosis, Rubinstein-Taybi syndrome, or stroke.

In certain embodiments, the Target Protein as referred to herein is named by the gene that expresses it. The person skilled in the art will recognize that when a gene is referred to as a Target Protein, the protein encoded by the gene is the Target Protein. For example, ligands for the protein SMCA2 which is encoded by SMRCA2 are referred to as SMRCA2 Targeting Ligands.

FIG. 9 is a dendrogram of the human bromodomain family of proteins organized into eight subfamilies, which are involved in epigenetic signaling and chromatin biology. Any of the proteins of the bromodomain family in FIG. 9 can be selected as a Target Protein according to the present invention.

Targeting Ligands

In certain aspects, the Targeting Ligand is a ligand which covalently or non-covalently binds to a Target Protein which has been selected for proteasomal degradation by the selected Degronimer. FIGS. 1A-8JJJJJ describe targeting ligands for a number of proteins wherein R is the point of attachment for the linker. While specific targeting ligands are exemplified in the figures, additional ligands and examples can be found in the references cited in the brief description of figures or are generally known in the art.

In one embodiment, the Targeting Ligand binds to an endogenous protein which has been selected for degradation as a means to achieve a therapeutic effect on the host. Illustrative Targeting Ligands include: RXR ligands, DHFR ligands, Hsp90 inhibitors, kinase inhibitors, HDM2 and MDM2 inhibitors, compounds targeting Human BET bromodomain-containing proteins, HDAC inhibitors, ligands of MerTK, ligands of IDH1, ligands of Mcl-1, ligands of SMRCA2, ligands of EGFR, ligands of RAF, ligands of cRAF, human lysine methyltransferase inhibitors, angiogenesis inhibitors, nuclear hormone receptor compounds, immunosuppressive compounds, and compounds targeting the aryl hydrocarbon receptor (AHR), among numerous others. Targeting Ligands also considered to include their pharmaceutically acceptable salts, prodrugs and isotopic derivatives.

In certain aspects, the Targeting Ligand binds to a dehalogenase enzyme in a patient or subject or in a diagnostic assay and is a haloalkane (preferably a $C_1$-$C_{10}$ alkyl group which is substituted with at least one halo group, preferably a halo group at the distal end of the alkyl group (i.e., away from the Linker). In still other embodiments, the Targeting Ligand is a haloalkyl group, wherein said alkyl group generally ranges in size from about 1 or 2 carbons to about 12 carbons in length, often about 2 to 10 carbons in length, often about 3 carbons to about 8 carbons in length, more often about 4 carbons to about 6 carbons in length. The haloalkyl groups are generally linear alkyl groups (although branched-chain alkyl groups may also be used) and are end-capped with at least one halogen group, preferably a single halogen group, often a single chloride group. Haloalkyl PT, groups for use in the present invention are preferably represented by the chemical structure —$(CH_2)_v$-Halo where v is any integer from 2 to about 12, often about 3 to about 8, more often about 4 to about 6. Halo may be any halogen, but is preferably $C_1$ or Br, more often $C_1$.

In certain embodiments, the Targeting Ligand is a retinoid X receptor (RXR) agonist or antagonist. Non-limiting examples include retinol, retinoic acid, bexarotene, docosahexenoic acid, compounds disclosed in WO 9929324, the publication by Canan Koch et al. (J. Med. Chem. 1996, 39, 3229-3234) titled "Identification of the First Retinoid X Receptor Homodimer Antagonist", WO 9712853, EP 0947496A1, WO 2016002968, and analogs thereof.

In certain embodiments, the Targeting Ligand is a DHFR agonist or antagonist. Non-limiting examples include folic acid, methotrexate, 8,10-dideazatetrahydrofolate compounds disclosed by Tian et al. (Chem. Biol. Drug Des. 2016, 87, 444-454) titled "Synthesis, Antifolate and Anticancer Activities of N5-Substituted 8,10-Dideazatetrahydrofolate Analogues", compounds prepared by Kaur et al. (Biorg. Med. Chem. Lett. 2016, 26, 1936-1940) titled "Rational Modification of the Lead Molecule: Enhancement in the Anticancer and Dihydrofolate Reductase Inhibitory Activity", WO 2016022890, compounds disclosed by Zhang et al. (Int. J. Antimicrob. Agents 46, 174-182) titled "New Small-Molecule Inhibitors of Dihydrofolate Reductase Inhibit *Streptococcus mutans*", modified trimethoprim analogs developed by Singh et al. (J. Med. Chem. 2012, 55, 6381-6390) titled "Mechanism Inspired Development of Rationally Designed Dihydrofolate Reductase Inhibitors as Anticancer Agents", WO20111153310, and analogs thereof.

In certain embodiments, the Targeting Ligand derived from estrogen, an estrogen analog, SERM (selective estrogen receptor modulator), a SERD (selective estrogen receptor degrader), a complete estrogen receptor degrader, or another form of partial or complete estrogen antagonist or agonist. Examples are the partial anti-estrogens raloxifene and tamoxifen and the complete antiestrogen fulvestrant. Non-limiting examples of anti-estrogen compounds are provided in WO 2014/19176 assigned to Astra Zeneca, WO2013/090921, WO 2014/203129, WO 2014/203132, and US2013/0178445 assigned to Olema Pharmaceuticals, and U.S. Pat. Nos. 9,078,871, 8,853,423, and 8,703,810, as well as US 2015/0005286, WO 2014/205136, and WO 2014/205138. Additional non-limiting examples of anti-estrogen compounds include: SERMS such as anordrin, bazedoxifene, broparestriol, chlorotrianisene, clomiphene citrate, cyclofenil, lasofoxifene, ormeloxifene, raloxifene, tamoxifen, toremifene, and fulvestrant; aromatase inhibitors such as aminoglutethimide, testolactone, anastrozole, exemestane, fadrozole, formestane, and letrozole; and antigonadotropins such as leuprorelin, cetrorelix, allylestrenol, chloromadinone acetate, cyproterone acetate, delmadinone acetate, dydrogesterone, medroxyprogesterone acetate, megestrol acetate, nomegestrol acetate, norethisterone acetate, progesterone, and spironolactone. Other estrogenic ligands that can be used according to the present invention are described in U.S. Pat. Nos. 4,418,068; 5,478,847; 5,393,763; and 5,457,117, WO2011/156518, U.S. Pat. Nos. 8,455,534 and 8,299,112, 9,078,871; 8,853,423; 8,703,810; US 2015/0005286; and WO 2014/205138, US2016/0175289, US2015/0258080, WO 2014/191726, WO 2012/084711; WO 2002/013802; WO 2002/004418; WO 2002/003992; WO 2002/003991; WO 2002/003990; WO 2002/003989; WO 2002/003988; WO 2002/003986; WO 2002/003977; WO 2002/003976; WO 2002/003975; WO 2006/078834; U.S. Pat. No. 6,821,989; US 2002/0128276; U.S. Pat. No. 6,777,424; US 2002/0016340; U.S. Pat. Nos. 6,326,392; 6,756,401; US 2002/0013327; U.S. Pat. Nos. 6,512,002; 6,632,834; US 2001/0056099; U.S. Pat. Nos. 6,583,170; 6,479,535; WO 1999/024027; U.S. Pat. No. 6,005,102; EP 0802184; U.S. Pat. Nos. 5,998,402; 5,780,497, 5,880,137, WO 2012/048058 and WO 2007/087684.

In certain embodiments, the Targeting Ligand is a HSP90 inhibitor identified in Vallee et al. (*J. Med. Chem.* 2011, 54, 7206-7219) titled "Tricyclic Series of Heat Shock Protein 90 (Hsp90) Inhibitors Part I: Discovery of Tricyclic Imidazo [4,5-C]Pyridines as Potent Inhibitors of the Hsp90 Molecular Chaperone", including YKB (N-[4-(3H-imidazo[4,5-C] Pyridin-2-yl)-9H-Fluoren-9-yl]-succinamide), a HSP90 inhibitors (modified) identified in Brough et al. (*J. Med. Chem.* 2008, 51, 196-218) titled "4,5-Diarylisoxazole Hsp90 Chaperone Inhibitors: Potential Therapeutic Agents for the Treatment of Cancer", including compound 2GJ (5-[2,4-dihydroxy-5-(1-methylethyl)phenyl]-n-ethyl-4-[4-(morpholin-4-ylmethyl)phenyl]isoxazole-3-carboxamide), the HSP90 inhibitor geldanamycin ((4E,6Z,8S,9S,10E,12S,13R,14S,16R)-13-hydroxy-8,14,19-trimethoxy-4,10,12,16-tetramethyl-3,20,22-trioxo-2-azabicyclo[16.3.1] (derivatized) or any of its derivatives (e.g. 17-alkylamino-17-desmethoxygeldanamycin ("17-AAG") or 17-(2-dimethylaminoethyl)amino-17-desmethoxygeldanamycin ("17-DMAG")), or a HSP90 inhibitor (modified) identified in Wright et al. (*Chem. Biol.* 2004, 11, 775-785) titled "Structure-Activity Relationships in Purine-Based Inhibitor Binding to Hsp90 Isoforms", including the HSP90 inhibitor PU3. Other non-limiting examples of Hsp90 Targeting Ligands include SNX5422 currently in phase I clinical trials Reddy et al. (*Clin. Lymphoma Myeloma Leuk.* 2013, 13, 385-391) titled "Phase I Trial of the Hsp90 Inhibitor Pf-04929113 (Snx5422) in Adult Patients with Recurrent, Refractory Hematologic Malignancies", or NVP-AUY922 whose anti-cancer activity was assessed by Jensen et al. (*Breast Cancer Research: BCR* 2008, 10, R33-R33) titled "Nvp-Auy922: A Small Molecule Hsp90 Inhibitor with Potent Antitumor Activity in Preclinical Breast Cancer Models".

In certain embodiments, the Targeting Ligand is a kinase inhibitor identified in Millan et al. (*J. Med. Chem.* 2011, 54, 7797-7814) titled "Design and Synthesis of Inhaled P38 Inhibitors for the Treatment of Chronic Obstructive Pulmonary Disease", including the kinase inhibitors Y1W and Y1X, a kinase inhibitor identified in Schenkel et al. (*J. Med. Chem.* 2011, 54, 8440-8450) titled "Discovery of Potent and Highly Selective Thienopyridine Janus Kinase 2 Inhibitors", including the compounds 6TP and 0TP, a kinase inhibitor identified in van Eis et al. (*Biorg. Med. Chem. Lett.* 2011, 21, 7367-7372) titled "2,6-Naphthyridines as Potent and Selective Inhibitors of the Novel Protein Kinase C Isozymes", including the kinase inhibitors 07U and YCF identified in Lountos et al. (*J. Struct. Biol.* 2011, 176, 292-301) titled "Structural Characterization of Inhibitor Complexes with Checkpoint Kinase 2 (Chk2), a Drug Target for Cancer Therapy", including the kinase inhibitors XK9 and NXP, afatinib, fostamatinib, gefitinib, lenvatinib, vandetanib, Gleevec, pazopanib, AT-9283, TAE684, nilotanib, NVP-BSK805, crizotinib, JNJ FMS, foretinib, OSI-027, OSI-930, or OSI-906.

In certain embodiments, the Targeting Ligand is a HDM2/MDM2 inhibitor identified in Vassilev et al. (*Science* 2004, 303, 844-848) titled "In Vivo Activation of the P53 Pathway by Small-Molecule Antagonists of Mdm2", and Schneekloth et al. (*Bioorg. Med. Chem. Lett.* 2008, 18, 5904-5908) titled "Targeted Intracellular Protein Degradation Induced by a Small Molecule: En Route to Chemical Proteomics", including the compounds nutlin-3, nutlin-2, and nutlin-1.

In certain embodiments, the Targeting Ligand is a Human BET Bromodomain Targeting Ligand identified in Filippakopoulos et al. (*Nature* 2010, 468, 1067-1073) titled "Selective Inhibition of Bet Bromodomains" such as JQ1; a ligand identified in Nicodeme et al. (*Nature* 2010, 468, 1119-1123) titled "Suppression of Inflammation by a Synthetic Histone Mimic"; Chung et al. (*J. Med. Chem.* 2011, 54, 3827-3838) titled "Discovery and Characterization of Small Molecule Inhibitors of the Bet Family Bromodomains"; a compound disclosed in Hewings et al. (*J. Med. Chem.* 2011, 54, 6761-6770) titled "3,5-Dimethylisoxazoles Act as Acetyl-Lysine-Mimetic Bromodomain Ligands"; a ligand identified in Dawson et al. (*Nature* 2011, 478, 529-533) titled "Inhibition of Bet Recruitment to Chromatin as an Effective Treatment for MLL-Fusion Leukaemia"; or a ligand identified in the following patent applications US 2015/0256700, US 2015/0148342, WO 2015/074064, WO 2015/067770, WO 2015/022332, WO 2015/015318, and WO 2015/011084.

In certain embodiments, the Targeting Ligand is a HDAC Targeting Ligand identified in Finnin et al. (*Nature* 1999, 401, 188-193) titled "Structures of a Histone Deacetylase Homologue Bound to the Tsa and Saha Inhibitors", or a ligand identified as Formula (I) in PCT WO0222577.

In certain embodiments, the Targeting Ligand is a Human Lysine Methyltransferase ligand identified in Chang et al. (*Nat Struct Mol Biol* 2009, 16, 312-317) titled "Structural Basis for G9a-Like Protein Lysine Methyltransferase Inhibition by Bix-01294", a ligand identified in Liu et al. (*J Med Chem* 2009, 52, 7950-7953) titled "Discovery of a 2,4-Diamino-7-Aminoalkoxyquinazoline as a Potent and Selective Inhibitor of Histone Lysine Methyltransferase G9a", azacitidine, decitabine, or an analog thereof.

In certain embodiments, the Targeting Ligand is an angiogenesis inhibitor. Non-limiting examples of angiogenesis inhibitors include: GA-1, estradiol, testosterone, ovalicin, fumagillin, and analogs thereof.

In certain embodiments, the Targeting Ligand is an immunosuppressive compound. Non-limiting examples of immunosuppressive compounds include: AP21998, hydrocortisone, prednisone, prednisolone, methylprednisolone, beclometasone dipropionate, methotrexate, ciclosporin, tacrolimus, actinomycin, and analogues thereof.

In certain embodiments, the Targeting Ligand is an Aryl Hydrocarbon Receptor (AHR) ligand. Non-limiting examples of AHR ligands include: apigenin, SR1, LGC006, and analogues thereof.

In certain embodiments, the Targeting Ligand is a MerTK or Mer Targeting ligand. Non-limiting examples of MerTK Targeting Ligands are included in WO2013/177168 and WO2014/085225, both titled "Pyrimidine Compounds for the Treatment of Cancer" filed by Wang, et al.

In certain embodiments, the Targeting Ligand is an EGFR ligand. In certain embodiments the Targeting Ligand is an EGRF ligand selected from Afatinib, Dacomitinib, Neratinib, Poziotinib, and Canertinib, or derivatives thereof.

In certain embodiments, the Targeting Ligand is a FLT3 Ligand. In certain embodiments, the Targeting Ligand is a FLT3 ligand selected from Tandutinib, Lestaurtinib, Sorafenib, Midostaurin, Quizartinib, and Crenolanib.

In certain embodiments, the Targeting Ligand is a RAF inhibitor. In certain embodiments the Targeting Ligand is a RAF inhibitor selected from Dabrafenib, Regorafenib, and Vemurafenib. In certain embodiments the Targeting Ligand is a cRAF inhibitor.

In some embodiments, the Targeting Ligand is an Ubc9 SUMO E2 ligase 5F6D Targeting Ligand including but not limited to those described in "Insights Into the Allosteric Inhibition of the SUMO E2 Enzyme Ubc9." by Hewitt, W. M., et. al. (2016) Angew. Chem. Int. Ed. Engl. 55: 5703-5707

In another embodiment, the Targeting Ligand is a Tank1 Targeting Ligand including but not limited to those described in "Structure of human tankyrase 1 in complex with small-molecule inhibitors PJ34 and XAV939." Kirby, C. A., Cheung, A., Fazal, A., Shultz, M. D., Stams, T, (2012) Acta Crystallogr., Sect. F 68: 115-118; and "Structure-Efficiency Relationship of [1,2,4]Triazol-3-ylamines as Novel Nicotinamide Isosteres that Inhibit Tankyrases." Shultz, M. D., et al. (2013) J. Med. Chem. 56: 7049-7059.

In another embodiment, the Targeting Ligand is a SH2 domain of pp60 Src Targeting Ligand including but not limited to those described in "Requirements for Specific Binding of Low Affinity Inhibitor Fragments to the SH2 Domain of pp60Src Are Identical to Those for High Affinity Binding of Full Length Inhibitors," Gudrun Lange, et al., J. Med. Chem. 2003, 46, 5184-5195.

In another embodiment, the Targeting Ligand is a Sec7 domain Targeting Ligand including but not limited to those described in "The Lysosomal Protein Saposin B Binds Chloroquine," Huta, B. P., et al., (2016) Chemmedchem 11: 277.

In another embodiment, the Targeting Ligand is a Saposin-B Targeting Ligand including but not limited to those described in "The structure of cytomegalovirus immune modulator UL 141 highlights structural Ig-fold versatility for receptor binding" I. Nemcovicova and D. M. Zajonc Acta Cryst. (2014). D70, 851-862.

In another embodiment, the Targeting Ligand is a Protein S100-A7 2OWS Targeting Ligand including but not limited to those described in "2WOS STRUCTURE OF HUMAN S100A7 IN COMPLEX WITH 2,6 ANS" DOI: 10.2210/pdb2wos/pdb; and "Identification and Characterization of Binding Sites on S100A7, a Participant in Cancer and Inflammation Pathways." Leon, R., Murray, et al., (2009) Biochemistry 48: 10591-10600.

In another embodiment, the Targeting Ligand is a Phospholipase A2 Targeting Ligand including but not limited to those described in "Structure-based design of the first potent and selective inhibitor of human non-pancreatic secretory phospholipase A2" Schevitz, R. W., et al., Nat. Struct. Biol. 1995, 2, 458-465.

In another embodiment, the Targeting Ligand is a PHIP Targeting Ligand including but not limited to those described in "A Poised Fragment Library Enables Rapid Synthetic Expansion Yielding the First Reported Inhibitors of PHIP(2), an Atypical Bromodomain" Krojer, T.; et al. Chem. Sci. 2016, 7, 2322-2330.

In another embodiment, the Targeting Ligand is a PDZ Targeting Ligand including but not limited to those described in "Discovery of Low-Molecular-Weight Ligands for the AF6 PDZ Domain" Mangesh Joshi, et al. Angew. Chem. Int. Ed. 2006, 45, 3790-3795.

In another embodiment, the Targeting Ligand is a PARP15 Targeting Ligand including but not limited to those described in "Structural Basis for Lack of ADP-ribosyltransferase Activity in Poly(ADP-ribose) Polymerase-13/Zinc Finger Antiviral Protein." Karlberg, T., et al., (2015) J. Biol. Chem. 290: 7336-7344.

In another embodiment, the Targeting Ligand is a PARP14 Targeting Ligand including but not limited to those described in "Discovery of Ligands for ADP-Ribosyltransferases via Docking-Based Virtual Screening." Andersson, C. D., et al., (2012) J. Med. Chem. 55: 7706-7718; "Family-wide chemical profiling and structural analysis of PARP and tankyrase inhibitors." Wahlberg, E., et al. (2012) Nat. Biotechnol. 30: 283-288; "Discovery of Ligands for ADP-Ribosyltransferases via Docking-Based Virtual Screening." Andersson, C. D., et al. (2012) J. Med. Chem. 55: 7706-7718.

In another embodiment, the Targeting Ligand is a MTH1 Targeting Ligand including but not limited to those described in "MTH1 inhibition eradicates cancer by preventing sanitation of the dNTP pool" Helge Gad, et. al. Nature, 2014, 508, 215-221.

In another embodiment, the Targeting Ligand is a mPGES-1 Targeting Ligand including but not limited to those described in "Crystal Structures of mPGES-1 Inhibitor Complexes Form a Basis for the Rational Design of Potent Analgesic and Anti-Inflammatory Therapeutics." Luz, J. G., et al., (2015) J. Med. Chem. 58: 4727-4737.

In another embodiment, the Targeting Ligand is a FLAP-5-lipoxygenase-activating protein Targeting Ligand including but not limited to those described in "Crystal structure of inhibitor-bound human 5-lipoxygenase-activating protein," Ferguson, A. D., McKeever, B. M., Xu, S., Wisniewski, D., Miller, D. K., Yamin, T. T., Spencer, R. H., Chu, L., Ujjainwalla, F., Cunningham, B. R., Evans, J. F., Becker, J. W. (2007) Science 317: 510-512.

In another embodiment, the Targeting Ligand is a FA Binding Protein Targeting Ligand including but not limited to those described in "A Real-World Perspective on Molecular Design." Kuhn, B.; et al. J. Med. Chem. 2016, 59, 4087-4102.

In another embodiment, the Targeting Ligand is a BCL2 Targeting Ligand including but not limited to those described in "ABT-199, a potent and selective BCL-2 inhibitor, achieves antitumor activity while sparing platelets." Souers, A. J., et al. (2013) NAT. MED. (N.Y.) 19: 202-208.

In another embodiment, the Targeting Ligand is a NF2L2 Targeting Ligand.

In another embodiment, the Targeting Ligand is a CTNNB1 Targeting Ligand.

In another embodiment, the Targeting Ligand is a CBLB Targeting Ligand.

In another embodiment, the Targeting Ligand is a BCL6 Targeting Ligand.

In another embodiment, the Targeting Ligand is a RASK Targeting Ligand.

In another embodiment, the Targeting Ligand is a TNIK Targeting Ligand.

In another embodiment, the Targeting Ligand is a MEN1 Targeting Ligand.

In another embodiment, the Targeting Ligand is a PI3Ka Targeting Ligand.

In another embodiment, the Targeting Ligand is a IDO1 Targeting Ligand.

In another embodiment, the Targeting Ligand is a MCL1 Targeting Ligand.

In another embodiment, the Targeting Ligand is a PTPN2 Targeting Ligand.

In another embodiment, the Targeting Ligand is a HER2 Targeting Ligand.

In another embodiment, the Targeting Ligand is an EGFR Targeting Ligand. In one embodiment the Targeting Ligand is selected from erlotinib (Tarceva), gefitinib (Iressa), afatinib (Gilotrif), rociletinib (CO-1686), osimertinib (Tagrisso), olmutinib (Olita), naquotinib (ASP8273), nazartinib (EGF816), PF-06747775 (Pfizer), icotinib (BPI-2009), neratinib (HKI-272; PB272); avitinib (AC0010), EAI045, tarloxotinib (TH-4000; PR-610), PF-06459988 (Pfizer), tesevatinib (XL647; EXEL-7647; KD-019), transtinib, WZ-3146, WZ8040, CNX-2006, and dacomitinib (PF-00299804; Pfizer). The linker can be placed on these Targeting Ligands in any location that does not interfere with the Ligands binding to EGFR. Non-limiting examples of Linker binding locations are provided in the below tables. In one embodiment, the EGFR Targeting Ligand binds the L858R mutant of EGFR. In another embodiment, the EGFR Targeting Ligand binds the T790M mutant of EGFR. In another embodiment, the EGFR Targeting Ligand binds the C797G or C797S mutant of EGFR. In one embodiment, the EGFR Targeting Ligand is selected from erlotinib, gefitinib, afatinib, neratinib, and dacomitinib and binds the L858R mutant of EGFR. In another embodiment, the EGFR Targeting Ligand is selected from osimertinib, rociletinib, olmutinib, naquotinib, nazartinib, PF-06747775, Icotinib, Neratinib, Avitinib, Tarloxotinib, PF-0645998, Tesevatinib, Transtinib, WZ-3146, WZ8040, and CNX-2006 and binds the T790M mutant of EGFR. In another embodiment, the EGFR Targeting Ligand is EAI045 and binds the C797G or C797S mutant of EGFR.

In one embodiment, the protein target and Targeting Ligand pair are chosen by screening a library of ligands. Such a screening is exemplified in "Kinase Inhibitor Profiling Reveals Unexpected Opportunities to Inhibit Disease-Associated Mutant Kinases" by Duong-Ly et al.; Cell Reports 14, 772-781 Feb. 2, 2016.

In one embodiment, the protein target and Targeting Ligand pair are discovered by screening promiscuous kinase binding ligands for context-specific degradation. Non-limiting examples of targeting ligands are shown below and are found in "Optimized Chemical Proteomics Assay for Kinase Inhibitor Profiling" Guillaume Medard, Fiona Pachl, Benjamin Ruprecht, Susan Klaeger, Stephanie Heinzlmeir, Dominic Helm, Huichao Qiao, Xin Ku, Mathias Wilhelm, Thomas Kuehne, Zhixiang Wu, Antje Dittmann, Carsten Hopf, Karl Kramer, and Bernhard Kuster J. Proteome Res., 2015, 14(3), pp 1574-1586:

VI16743

CTx-0294885

Vandetanib

CTx-related

-continued
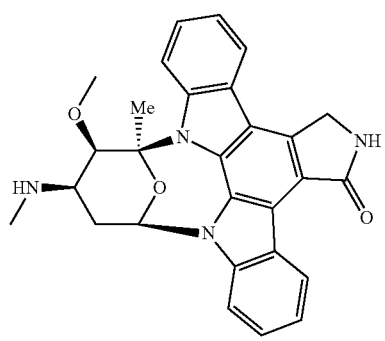
Staurosporine
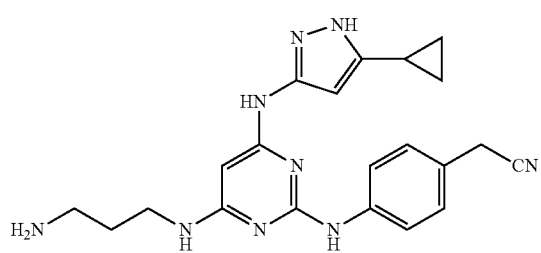
DOI: 10.1021/acschembio.5b00847
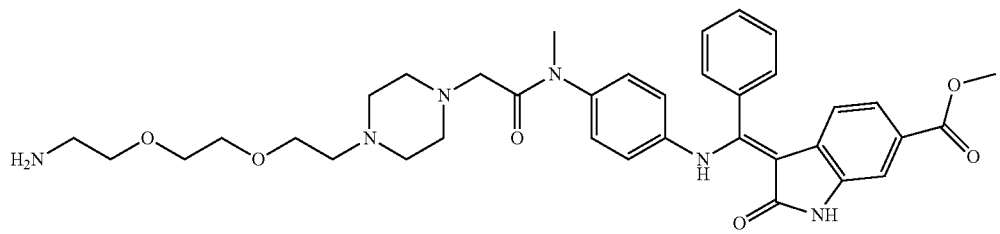
Nintedanib
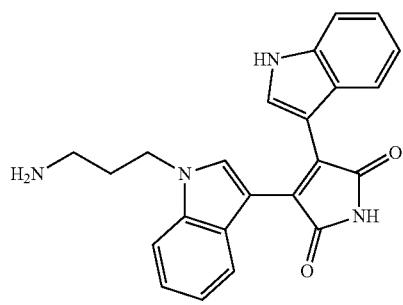
bisindolylmaleimide III
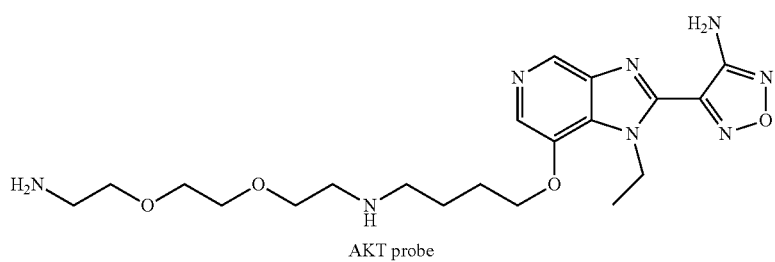
AKT probe
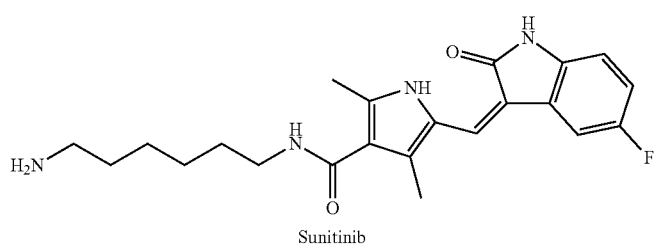
Sunitinib -continued
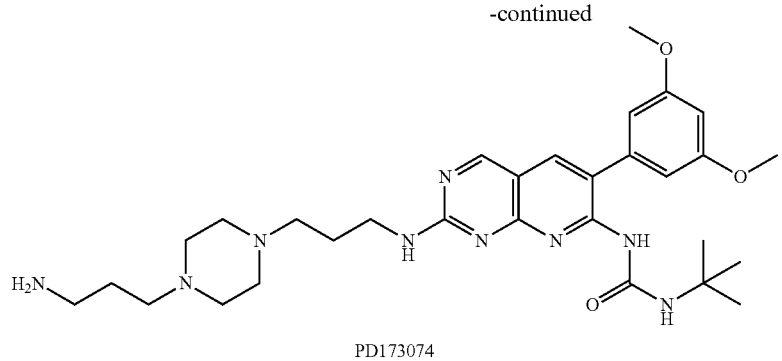
PD173074
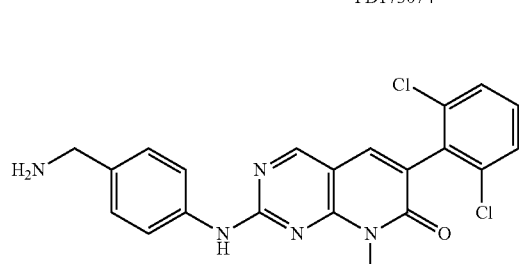
PD173955
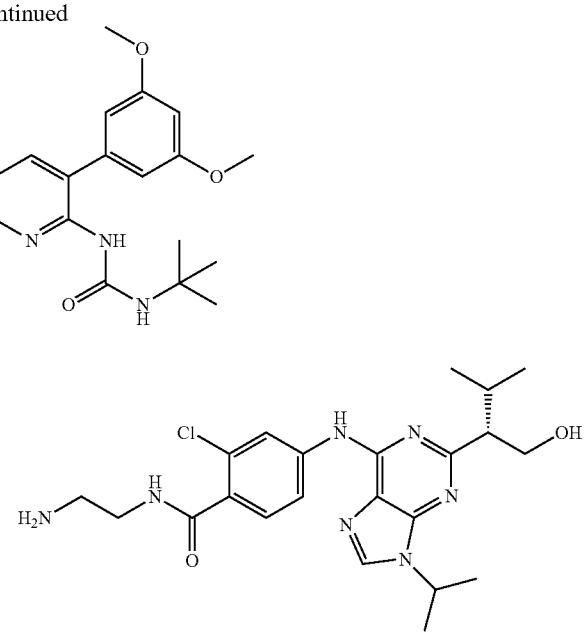
Purvalanol B
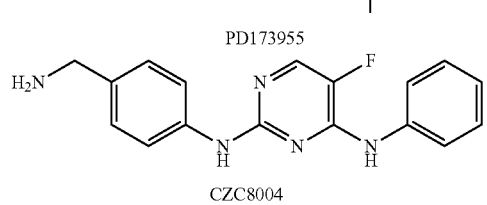
CZC8004
These ligands can be attached to linkers as shown below:
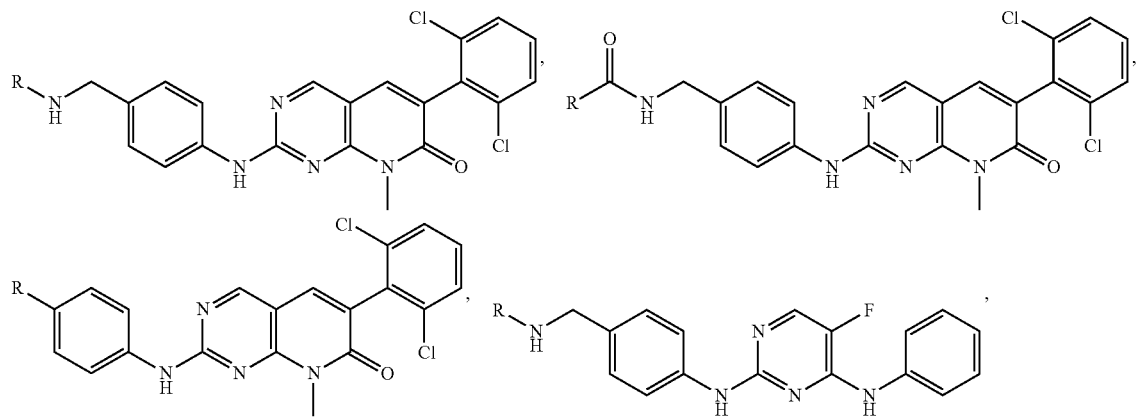
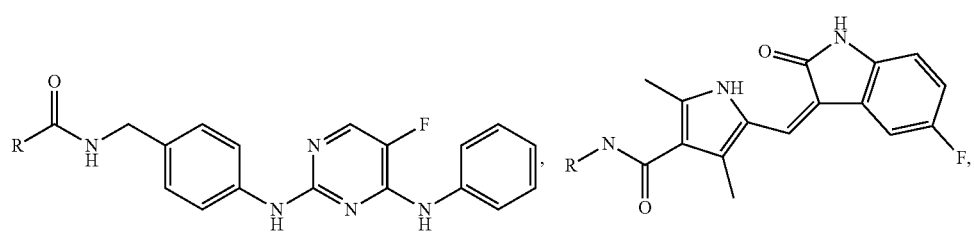

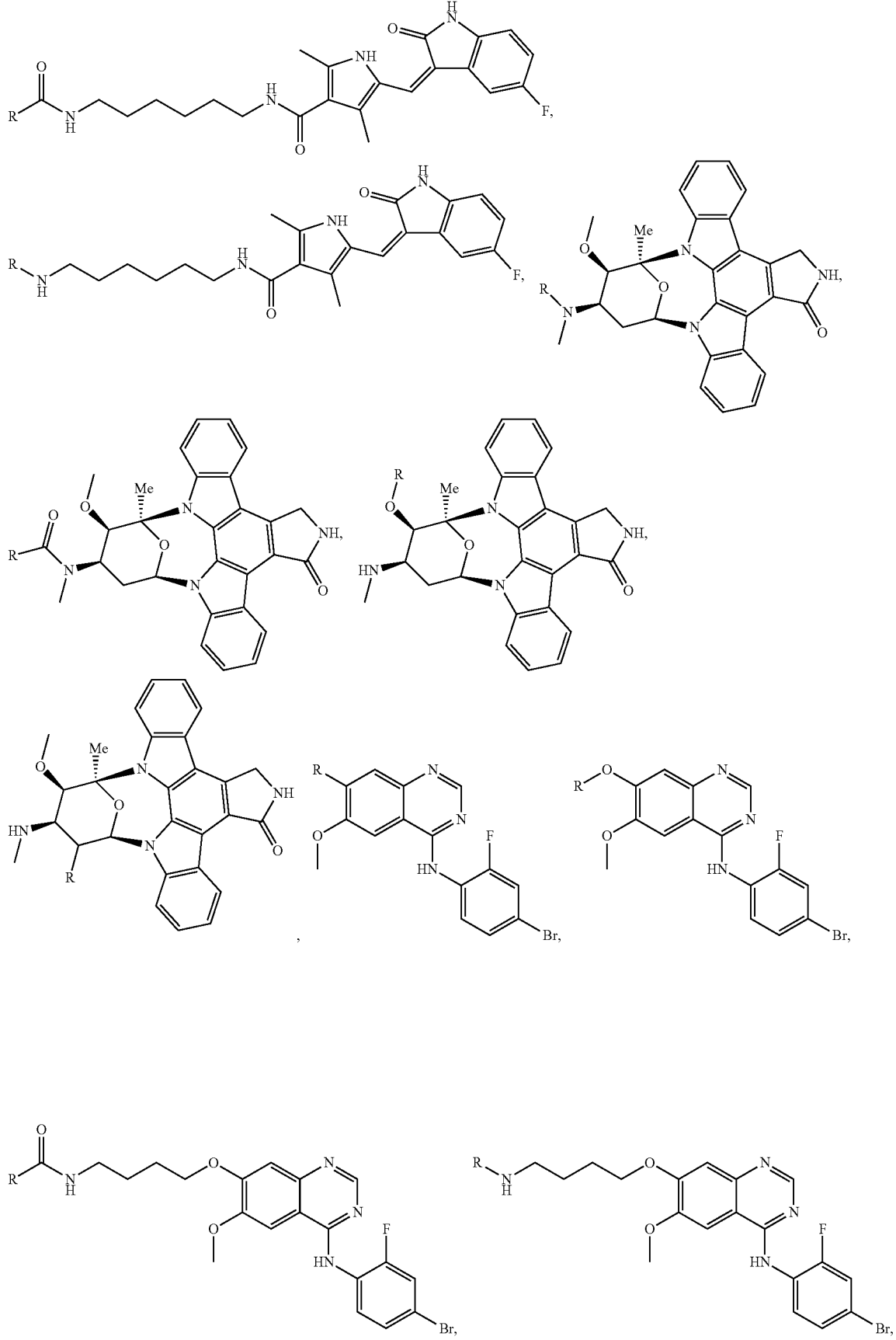

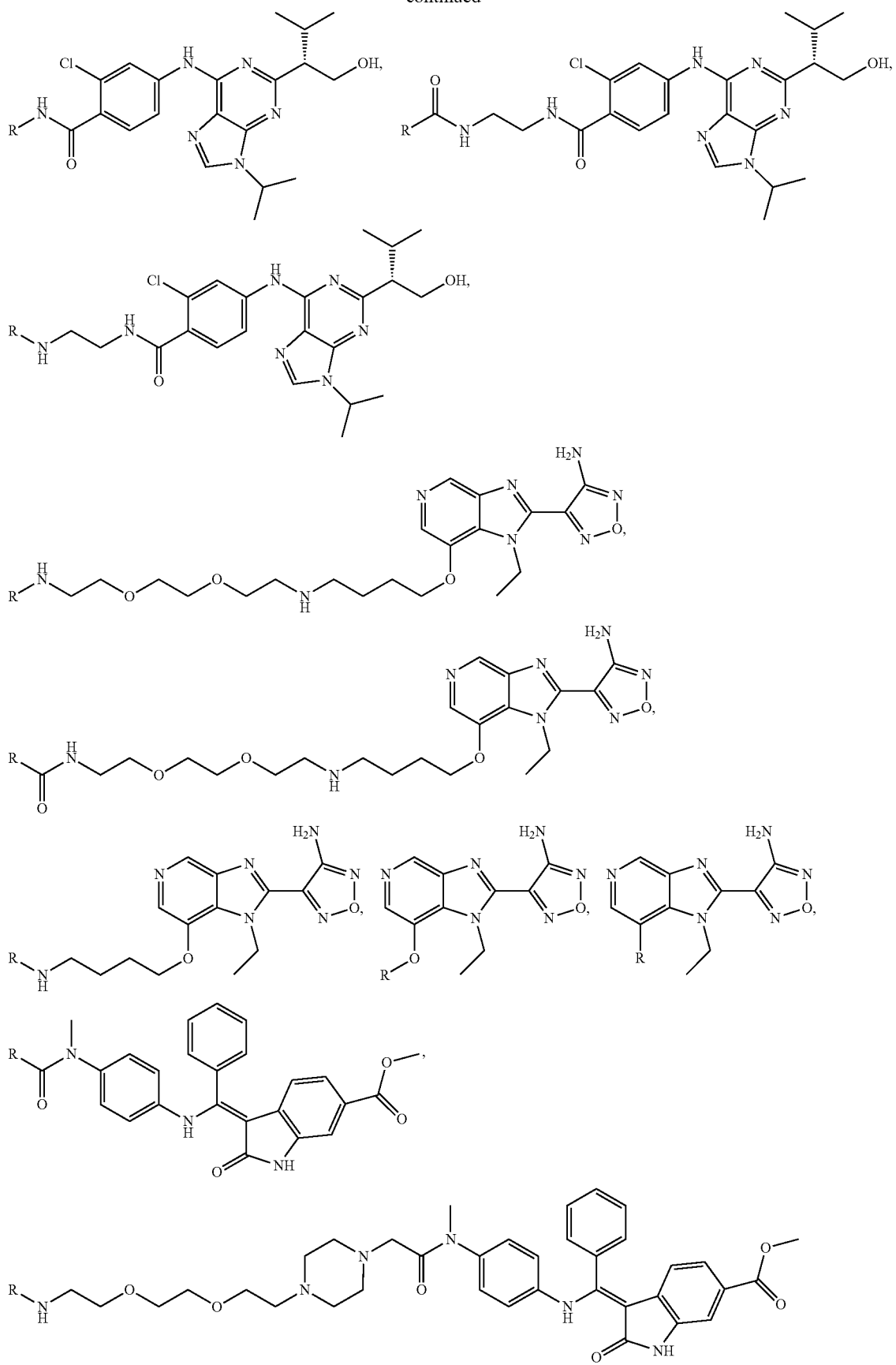

-continued
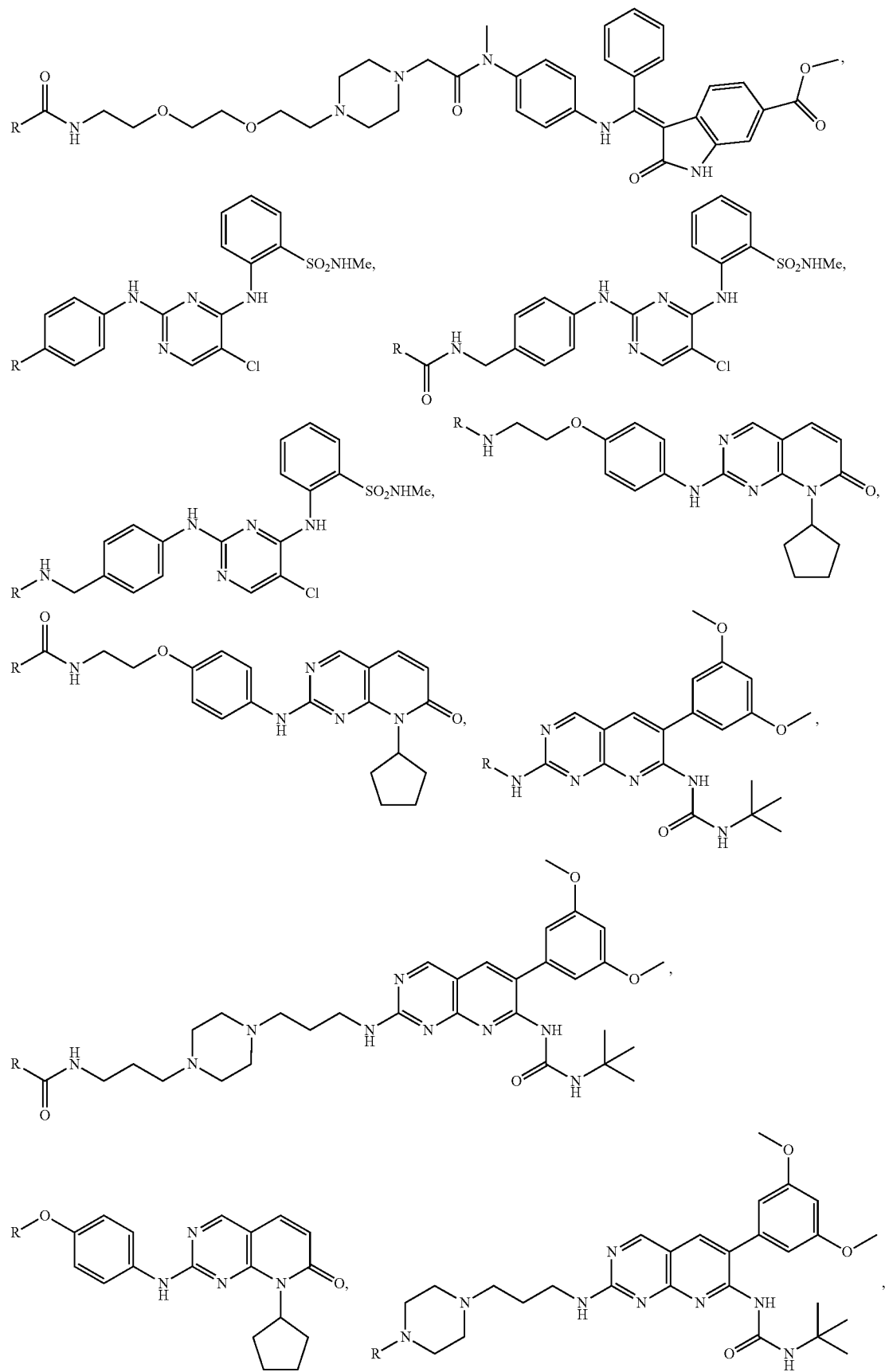

-continued
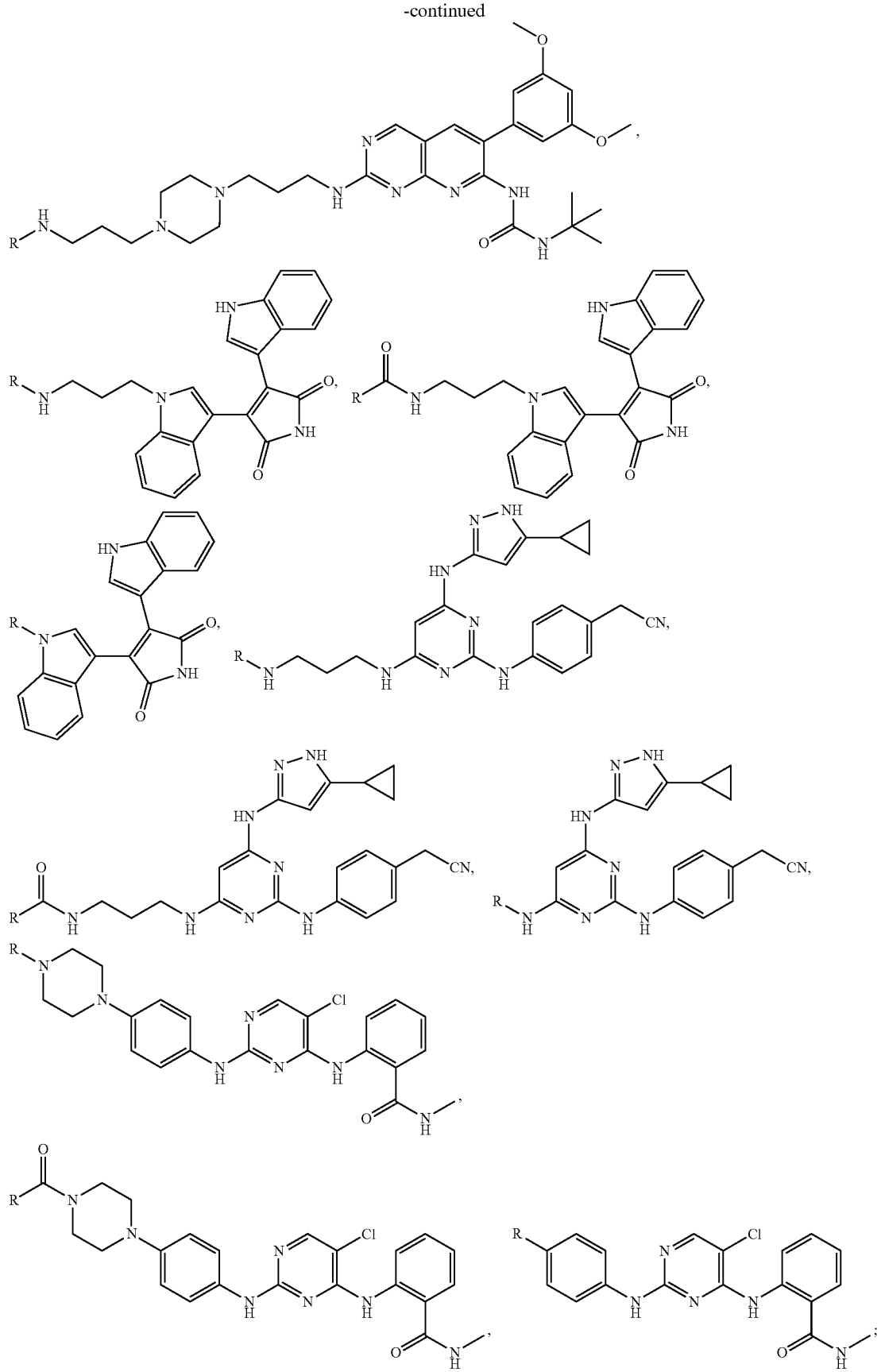

wherein:

R is the point at which the Linker is attached.

According to the present invention, the Targeting Ligand can be covalently bound to the Linker in any manner that achieves the desired results of the Degronimer for therapeutic use. In certain non-limiting embodiments, the Targeting Ligand is bound to the Linker with a functional group that does not adversely affect the binding of the Ligand to the Target Protein. The attachment points below are exemplary in nature and one of ordinary skill in the art would be able to determine different appropriate attachment points.

The non-limiting compounds described below exemplify some of the members of these types of small molecule Targeting Ligands. In the Tables below, R is the point at which the Linker is attached to the Targeting Ligand.

In certain embodiments, the Targeting Ligand is a compound of Formula TL-I:

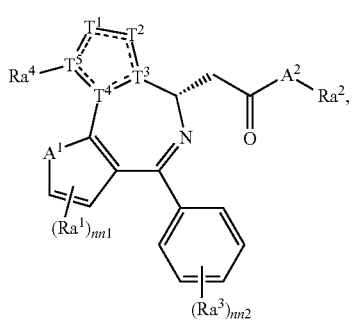

(TL-I)

or a pharmaceutically acceptable salt thereof, wherein:

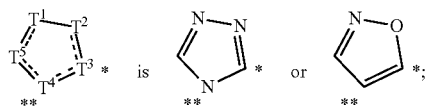

$A^1$ is S or C=C;
$A^2$ is $NRa^5$ or O;
nn1 is 0, 1, or 2;
each $Ra^1$ is independently $C_1$-$C_3$ alkyl, $(CH_2)_{0-3}$—CN, $(CH_2)_{0-3}$-halogen, $(CH_2)_{0-3}$—OH, $(CH_2)_{0-3}$—$C_1$-$C_3$ alkoxy, or R;
$Ra^2$ is H, $C_1$-$C_6$ alkyl, $(CH_2)_{0-3}$-heterocyclyl, $(CH_2)_{0-3}$-phenyl, or R, wherein the heterocyclyl comprises one saturated 5- or 6-membered ring and 1-2 heteroatoms selected from N, O, and S and is optionally substituted with $C_1$-$C_3$ alkyl and wherein the phenyl is optionally substituted with $C_1$-$C_3$ alkyl, CN, halogen, OH, $C_1$-$C_3$ alkoxy;
nn2 is 0, 1, 2, or 3;
each $Ra^3$ is independently $C_1$-$C_3$ alkyl, $(CH_2)_{0-3}$—CN, $(CH_2)_{0-3}$-halogen, or R;
$Ra^4$ is $C_1$-$C_3$ alkyl;
$Ra^5$ is H or $C_1$-$C_3$ alkyl; and
R is the point at which the Linker is attached.
wherein the compound of Formula TL-I is substituted with only one R.

In certain embodiments, the Targeting Ligand is a compound of Formula TL-VIII or Formula TL-IX:

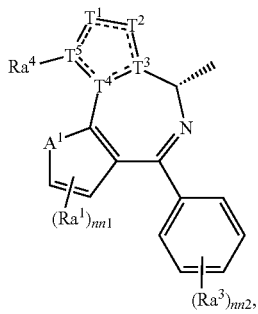

(TL-VIII)

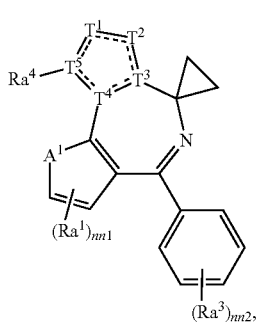

(TL-IX)

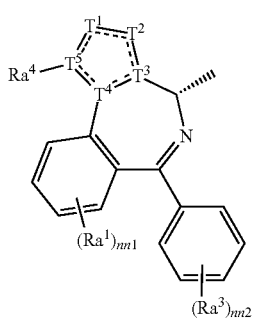

(TL-X)

or

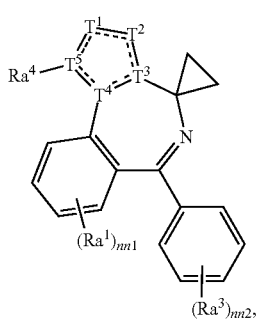

(TL-XI)

wherein the compound of Formula TL-VIII or TL-IX is substituted with only one R.

In certain embodiments,

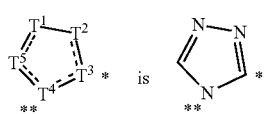

In certain embodiments,

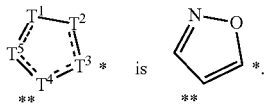 is

In certain embodiments, $A^1$ is S.
In certain embodiments, $A^1$ is C=C.
In certain embodiments, $A^2$ is $NRa^5$. In further embodiments, $Ra^5$ is H. In other embodiments, $Ra^5$ is $C_1$-$C_3$ alkyl (e.g., methyl, ethyl, propyl, or i-propyl). In further embodiments, $Ra^5$ is methyl.
In certain embodiments, $A^2$ is O.
In certain embodiments, nn1 is 0.
In certain embodiments, nn1 is 1.
In certain embodiments, nn1 is 2.
In certain embodiments, at least one $Ra^1$ is $C_1$-$C_3$ alkyl (e.g., methyl, ethyl, propyl, or i-propyl). In further embodiments, at least one $Ra^1$ is methyl. In further embodiments, two $Ra^1$ are methyl.
In certain embodiments, at least one $Ra^1$ is CN, $(CH_2)$—CN, $(CH_2)_2$—CN, or $(CH_2)_3$—CN. In further embodiments, at least one $Ra^1$ is $(CH_2)$—CN.
In certain embodiments, at least one $Ra^1$ is halogen (e.g., F, Cl, or Br), $(CH_2)$-halogen, $(CH_2)_2$-halogen, or $(CH_2)_3$-halogen. In further embodiments, at least one $Ra^1$ is Cl, $(CH_2)$—Cl, $(CH_2)_2$—Cl, or $(CH_2)_3$—Cl.
In certain embodiments, at least one $Ra^1$ is OH, $(CH_2)$—OH, $(CH_2)_2$—OH, or $(CH_2)_3$—OH.
In certain embodiments, at least one $Ra^1$ is $C_1$-$C_3$ alkoxy (e.g., methoxy, ethoxy, or propoxy), $(CH_2)$—$C_1$-$C_3$ alkoxy, $(CH_2)_2$—$C_1$-$C_3$ alkoxy, or $(CH_2)_3$—$C_1$-$C_3$ alkoxy. In certain embodiments, at least one $Ra^1$ is methoxy.
In further embodiments, $Ra^5$ is H. In other embodiments, $Ra^5$ is $C_1$-$C_3$ alkyl (e.g., methyl, ethyl, propyl, or i-propyl).
In further embodiments, $Ra^5$ is H. In other embodiments, $Ra^5$ is $C_1$-$C_3$ alkyl (e.g., methyl, ethyl, propyl, or i-propyl). In other embodiments, $Ra^5$ is methyl.
In certain embodiments, one $Ra^1$ is R.
In certain embodiments, $Ra^2$ is H.
In certain embodiments, $Ra^2$ is straight-chain $C_1$-$C_6$ or branched $C_3$-$C_6$ alkyl (e.g., methyl, ethyl, propyl, i-propyl, butyl, i-butyl, t-butyl, pentyl, or hexyl). In further embodiments, $Ra^2$ is methyl, ethyl, or t-butyl.
In certain embodiments, $Ra^2$ is heterocyclyl, $(CH_2)$-heterocyclyl, $(CH_2)_2$-heterocyclyl, or $(CH_2)_3$-heterocyclyl. In further embodiments, $Ra^2$ is $(CH_2)_3$-heterocyclyl. In further embodiments, the heterocyclyl is selected from pyrrolidinyl, pyrazolidinyl, imidazolidinyl, oxazolidinyl, isoxazolidinyl, thiazolidinyl, isothiazolidinyl, piperidinyl, piperazinyl, hexahydropyrimidinyl, morpholinyl, and thiomorpholinyl. In further embodiments, the heterocyclyl is piperazinyl.
In certain embodiments, the heterocyclyl is substituted with $C_1$-$C_3$ alkyl (e.g., methyl, ethyl, propyl, or i-propyl).
In certain embodiments, $Ra^2$ is phenyl, $(CH_2)$-phenyl, $(CH_2)_2$-phenyl, or $(CH_2)_3$-phenyl. In further embodiments, $Ra^2$ is phenyl.
In certain embodiments, the phenyl is substituted with $C_1$-$C_3$ alkyl (e.g., methyl, ethyl, propyl, or i-propyl). In certain embodiments, the phenyl is substituted with CN. In certain embodiments, the phenyl is substituted with halogen (e.g., F, Cl, or Br). In certain embodiments, the phenyl is substituted with OH. In certain embodiments, the phenyl is substituted with $C_1$-$C_3$ alkoxy (e.g., methoxy, ethoxy, or propoxy).
In certain embodiments, $Ra^2$ is R.
In certain embodiments, nn2 is 0.
In certain embodiments, nn2 is 1.
In certain embodiments, nn2 is 2.
In certain embodiments, nn2 is 3.
In certain embodiments, at least one $Ra^3$ is $C_1$-$C_3$ alkyl (e.g., methyl, ethyl, propyl, or i-propyl). In further embodiments, at least one $Ra^3$ is methyl.
In certain embodiments, at least one $Ra^3$ is CN, $(CH_2)$—CN, $(CH_2)_2$—CN, or $(CH_2)_3$—CN. In further embodiments, at least one $Ra^3$ is CN.
In certain embodiments, at least one $Ra^3$ is halogen (e.g., F, Cl, or Br), $(CH_2)$-halogen, $(CH_2)_2$-halogen, or $(CH_2)_3$-halogen. In further embodiments, at least one $Ra^3$ is Cl, $(CH_2)$—Cl, $(CH_2)_2$—Cl, or $(CH_2)_3$—Cl. In further embodiments, at least one $Ra^3$ is Cl.
In certain embodiments, one $Ra^3$ is R.
In further embodiments, $Ra^5$ is H. In other embodiments, $Ra^5$ is $C_1$-$C_3$ alkyl (e.g., methyl, ethyl, propyl, or i-propyl).
In certain embodiments, $Ra^4$ is $C_1$-$C_3$ alkyl (e.g., methyl, ethyl, propyl, or i-propyl). In further embodiments, $Ra^4$ is methyl.
In certain embodiments, $Ra^5$ is H.
In certain embodiments, $Ra^5$ is $C_1$-$C_3$ alkyl (e.g., methyl, ethyl, propyl, or i-propyl). In further embodiments, $Ra^5$ is methyl.
In certain embodiments,

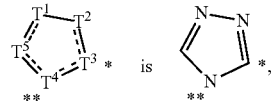

and $A^1$ is S.
In certain embodiments,

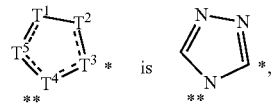

and $A^1$ is C=C.
In certain embodiments,

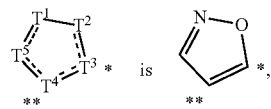

and $A^1$ is C=C.
In certain embodiments, $A^2$ is NH, and $Ra^2$ is $(CH_2)_{0-3}$-heterocyclyl. In further embodiments, $Ra^2$ is $(CH_2)_3$-heterocyclyl.
In certain embodiments, $A^2$ is NH, and $Ra^2$ is $(CH_2)_{0-3}$-phenyl. In further embodiments, $Ra^2$ is phenyl. In further embodiments, the phenyl is substituted with OH.
In certain embodiments, $A^2$ is NH, and $Ra^2$ is R.
In certain embodiments, $A^2$ is NH, and $Ra^2$ is H or $C_1$-$C_6$ alkyl. In further embodiments, $Ra^2$ is $C_1$-$C_4$ alkyl.
In certain embodiments, $A^2$ is O, and $Ra^2$ is H or $C_1$-$C_6$ alkyl. In further embodiments, $Ra^2$ is $C_1$-$C_4$ alkyl.

III. Methods of Treatment

The compound of Formulas I, II, III, IV, V and VI can be used in an effective amount to treat a host with any of the disorders described herein, including a human, in need thereof, optionally in a pharmaceutically acceptable carrier. In certain embodiments, the method comprises administering an effective amount of the active compound or its salt as described herein, optionally including a pharmaceutically acceptable excipient, carrier, adjuvant, i.e., a pharmaceutically acceptable composition, optionally in combination or alternation with another bioactive agent or combination of agents.

The compound of Formula I, II, and III or a pharmaceutically acceptable salt thereof as described herein can be used to degrade a Target Protein which is a mediator of the disorder affecting the patient, such as a human. The reduction in the Target Protein level afforded by the Formula I, II, or III Degronimers of the present invention provides treatment of the implicated disease state or condition, which is modulated through the Target Protein by lowering the level of that protein in the cell, e.g., cell of a patient. The term "disease state or condition" when used in connection with a Formula I, II or III is meant to refer to any disease state or condition wherein protein dysregulation occurs that involves the selected Target Protein and where degradation of such protein in a patient may provide beneficial therapy or relief of symptoms to a patient in need thereof. In certain instances, the disease state or condition may be cured.

The compounds of Formula I, II or III are useful as therapeutic agents when administered in an effective amount to a host, including a human, to treat a tumor, cancer (solid, non-solid, diffuse, hematological, etc), abnormal cellular proliferation, immune disorder, inflammatory disorder, blood disorder, a myelo- or lymphoproliferative disorder such as B- or T-cell lymphomas, multiple myeloma, breast cancer, prostate cancer, AML, ALL, ACL, lung cancer, pancreatic cancer, colon cancer, skin cancer, melanoma, Waldenstrom's macroglobulinemia, Wiskott-Aldrich syndrome, or a post-transplant lymphoproliferative disorder; an autoimmune disorder, for example, Lupus, Crohn's Disease, Addison disease, Celiac disease, dermatomyositis, Graves disease, thyroiditis, multiple sclerosis, pernicious anemia, reactive arthritis, or type I diabetes; a disease of cardiologic malfunction, including hypercholesterolemia; an infectious disease, including a viral and/or bacterial infection; an inflammatory condition, including asthma, chronic peptic ulcers, tuberculosis, rheumatoid arthritis, periodontitis, ulcerative colitis, or hepatitis.

The term "disease state or condition" when used in connection with a Formula IV, V and VI, for example, refers to any therapeutic indication which can be treated by decreasing the activity of cereblon or a cereblon-containing E3 Ligase, including but not limited to uses known for the cereblon binders thalidomide, pomalidomide or lenalidomide. The compounds of Formula IV, V or VI can increase, decrease or modify the action of cereblon via binding. Nonlimiting examples of uses for cereblon binders are multiple myeloma, a hematological disorder such as myelodysplastic syndrome, cancer, tumor, abnormal cellular proliferation, breast cancer, prostate cancer, AML, ALL, ACL, lung cancer, pancreatic cancer, colon cancer, skin cancer, melanoma, HIV/AIDS, HBV, HCV, hepatitis, Crohn's disease, sarcoidosis, graft-versus-host disease, rheumatoid arthritis, Behcet's disease, tuberculosis, and myelofibrosis. Other indications include a myelo- or lymphoproliferative disorder such as B- or T-cell lymphomas, Waldenstrom's macroglobulinemia, Wiskott-Aldrich syndrome, or a post-transplant lymphoproliferative disorder; an immune disorder, including autoimmune disorders for example as Lupus, Addison disease, Celiac disease, dermatomyositis, Graves disease, thyroiditis, multiple sclerosis, pernicious anemia, arthritis, and in particular rheumatoid arthritis, or type I diabetes; a disease of cardiologic malfunction, including hypercholesterolemia; an infectious disease, including viral and/or bacterial infection, as described generally herein; an inflammatory condition, including asthma, chronic peptic ulcers, tuberculosis, rheumatoid arthritis, periodontitis and ulcerative colitis.

In certain embodiments, the present invention provides the administration of an effective amount of a compound to treat a patient, for example, a human, having an infectious disease, wherein the therapy targets a Target Protein of the infectious agent or host (Formulas I, II, III), or acts via binding to cereblon or its E3 ligase (Formulas IV, V or VI) optionally in combination with another bioactive agent. The disease state or condition may be caused by a microbial agent or other exogenous agent such as a virus (as non-limiting examples, HIV, HBV, HCV, HSV, HPV, RSV, CMV, Ebola, Flavivirus, Pestivirus, Rotavirus, Influenza, Coronavirus, EBV, viral pneumonia, drug-resistant viruses, Bird flu, RNA virus, DNA virus, adenovirus, poxvirus, Picornavirus, Togavirus, Orthomyxovirus, Retrovirus or Hepadnovirus), bacteria (including but not limited to Gram-negative, Gram-positive, Atypical, *Staphylococcus, Streptococcus, E. coli, Salmonella, Helicobacter pylori*, meningitis, gonorrhea, Chlamydiaceae, Mycoplasmataceae, etc), fungus, protozoa, helminth, worms, prion, parasite, or other microbe.

In certain embodiments, the condition treated with a compound of the present invention is a disorder related to abnormal cellular proliferation. Abnormal cellular proliferation, notably hyperproliferation, can occur as a result of a wide variety of factors, including genetic mutation, infection, exposure to toxins, autoimmune disorders, and benign or malignant tumor induction.

There are a number of skin disorders associated with cellular hyperproliferation. Psoriasis, for example, is a benign disease of human skin generally characterized by plaques covered by thickened scales. The disease is caused by increased proliferation of epidermal cells of unknown cause. Chronic eczema is also associated with significant hyperproliferation of the epidermis. Other diseases caused by hyperproliferation of skin cells include atopic dermatitis, lichen planus, warts, pemphigus vulgaris, actinic keratosis, basal cell carcinoma and squamous cell carcinoma.

Other hyperproliferative cell disorders include blood vessel proliferation disorders, fibrotic disorders, autoimmune disorders, graft-versus-host rejection, tumors and cancers.

Blood vessel proliferative disorders include angiogenic and vasculogenic disorders. Proliferation of smooth muscle cells in the course of development of plaques in vascular tissue cause, for example, restenosis, retinopathies and atherosclerosis. Both cell migration and cell proliferation play a role in the formation of atherosclerotic lesions.

Fibrotic disorders are often due to the abnormal formation of an extracellular matrix. Examples of fibrotic disorders include hepatic cirrhosis and mesangial proliferative cell disorders. Hepatic cirrhosis is characterized by the increase in extracellular matrix constituents resulting in the formation of a hepatic scar. Hepatic cirrhosis can cause diseases such as cirrhosis of the liver. An increased extracellular matrix resulting in a hepatic scar can also be caused by viral infection such as hepatitis. Lipocytes appear to play a major role in hepatic cirrhosis.

Mesangial disorders are brought about by abnormal proliferation of mesangial cells. Mesangial hyperproliferative cell disorders include various human renal diseases, such as glomerulonephritis, diabetic nephropathy, malignant nephrosclerosis, thrombotic micro-angiopathy syndromes, transplant rejection, and glomerulopathies.

Another disease with a proliferative component is rheumatoid arthritis. Rheumatoid arthritis is generally considered an autoimmune disease that is thought to be associated with activity of autoreactive T cells, and to be caused by autoantibodies produced against collagen and IgE.

Other disorders that can include an abnormal cellular proliferative component include Bechet's syndrome, acute respiratory distress syndrome (ARDS), ischemic heart disease, post-dialysis syndrome, leukemia, acquired immune deficiency syndrome, vasculitis, lipid histiocytosis, septic shock and inflammation in general.

Cutaneous contact hypersensitivity and asthma are just two examples of immune responses that can be associated with significant morbidity. Others include atopic dermatitis, eczema, Sjogren's Syndrome, including keratoconjunctivitis sicca secondary to Sjogren's Syndrome, alopecia areata, allergic responses due to arthropod bite reactions, Crohn's disease, aphthous ulcer, iritis, conjunctivitis, keratoconjunctivitis, ulcerative colitis, cutaneous lupus erythematosus, scleroderma, vaginitis, proctitis, and drug eruptions. These conditions may result in any one or more of the following symptoms or signs: itching, swelling, redness, blisters, crusting, ulceration, pain, scaling, cracking, hair loss, scarring, or oozing of fluid involving the skin, eye, or mucosal membranes.

In atopic dermatitis, and eczema in general, immunologically mediated leukocyte infiltration (particularly infiltration of mononuclear cells, lymphocytes, neutrophils, and eosinophils) into the skin importantly contributes to the pathogenesis of these diseases. Chronic eczema also is associated with significant hyperproliferation of the epidermis. Immunologically mediated leukocyte infiltration also occurs at sites other than the skin, such as in the airways in asthma and in the tear producing gland of the eye in keratoconjunctivitis sicca.

In one non-limiting embodiment compounds of the present invention are used as topical agents in treating contact dermatitis, atopic dermatitis, eczematous dermatitis, psoriasis, Sjogren's Syndrome, including keratoconjunctivitis sicca secondary to Sjogren's Syndrome, alopecia areata, allergic responses due to arthropod bite reactions, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, and drug eruptions. The novel method may also be useful in reducing the infiltration of skin by malignant leukocytes in diseases such as mycosis fungoides. These compounds can also be used to treat an aqueous-deficient dry eye state (such as immune mediated keratoconjunctivitis) in a patient suffering therefrom, by administering the compound topically to the eye.

Disease states which may be treated according to the present invention include, for example, asthma, autoimmune diseases such as multiple sclerosis, various cancers, ciliopathies, cleft palate, diabetes, heart disease, hypertension, inflammatory bowel disease, mental retardation, mood disorder, obesity, refractive error, infertility, Angelman syndrome, Canavan disease, Coeliac disease, Charcot-Marie-Tooth disease, Cystic fibrosis, Duchenne muscular dystrophy, Haemochromatosis, Haemophilia, Klinefelter's syndrome, Neurofibromatosis, Phenylketonuria, Polycystic kidney disease, (PKD1) or 4 (PKD2) Prader-Willi syndrome, Sickle-cell disease, Tay-Sachs disease, Turner syndrome.

Further disease states or conditions which may be treated by the disclosed compounds according to the present invention include Alzheimer's disease, Amyotrophic lateral sclerosis (Lou Gehrig's disease), Anorexia nervosa, Anxiety disorder, Atherosclerosis, Attention deficit hyperactivity disorder, Autism, Bipolar disorder, Chronic fatigue syndrome, Chronic obstructive pulmonary disease, Crohn's disease, Coronary heart disease, Dementia, Depression, Diabetes mellitus type 1, Diabetes mellitus type 2, Epilepsy, Guillain-Barré syndrome, Irritable bowel syndrome, Lupus, Metabolic syndrome, Multiple sclerosis, Myocardial infarction, Obesity, Obsessive-compulsive disorder, Panic disorder, Parkinson's disease, Psoriasis, Rheumatoid arthritis, Sarcoidosis, Schizophrenia, Stroke, Thromboangiitis obliterans, Tourette syndrome, Vasculitis.

Still additional disease states or conditions which can be treated by the disclosed compounds according to the present invention include aceruloplasminemia, Achondrogenesis type II, achondroplasia, Acrocephaly, Gaucher disease type 2, acute intermittent porphyria, Canavan disease, Adenomatous Polyposis Coli, ALA dehydratase deficiency, adenylosuccinate lyase deficiency, Adrenogenital syndrome, Adrenoleukodystrophy, ALA-D porphyria, ALA dehydratase deficiency, Alkaptonuria, Alexander disease, Alkaptonuric ochronosis, alpha 1-antitrypsin deficiency, alpha-1 proteinase inhibitor, emphysema, amyotrophic lateral sclerosis Alström syndrome, Alexander disease, Amelogenesis imperfecta, ALA dehydratase deficiency, Anderson-Fabry disease, androgen insensitivity syndrome, Anemia Angiokeratoma Corporis Diffusum, Angiomatosis retinae (von Hippel-Lindau disease) Apert syndrome, Arachnodactyly (Marfan syndrome), Stickler syndrome, Arthrochalasis multiplex congenital (Ehlers-Danlos syndrome # arthrochalasia type) ataxia telangiectasia, Rett syndrome, primary pulmonary hypertension, Sandhoff disease, neurofibromatosis type II, Beare-Stevenson cutis gyrata syndrome, Mediterranean fever, familial, Benjamin syndrome, beta-thalassemia, Bilateral Acoustic Neurofibromatosis (neurofibromatosis type II), factor V Leiden thrombophilia, Bloch-Sulzberger syndrome (incontinentia pigmenti), Bloom syndrome, X-linked sideroblastic anemia, Bonnevie-Ullrich syndrome (Turner syndrome), Bourneville disease (tuberous sclerosis), prion disease, Birt-Hogg-Dubé syndrome, Brittle bone disease (osteogenesis imperfecta), Broad Thumb-Hallux syndrome (Rubinstein-Taybi syndrome), Bronze Diabetes/Bronzed Cirrhosis (hemochromatosis), Bulbospinal muscular atrophy (Kennedy's disease), Burger-Grutz syndrome (lipoprotein lipase deficiency), CGD Chronic granulomatous disorder, Campomelic dysplasia, biotinidase deficiency, Cardiomyopathy (Noonan syndrome), Cri du chat, CAVD (congenital absence of the vas deferens), Caylor cardiofacial syndrome (CBAVD), CEP (congenital erythropoietic porphyria), cystic fibrosis, congenital hypothyroidism, Chondrodystrophy syndrome (achondroplasia), otospondylomegaepiphyseal dysplasia, Lesch-Nyhan syndrome, galactosemia, Ehlers-Danlos syndrome, Thanatophoric dysplasia, Coffin-Lowry syndrome, Cockayne syndrome, (familial adenomatous polyposis), Congenital erythropoietic porphyria, Congenital heart disease, Methemoglobinemia/Congenital methaemoglobinaemia, achondroplasia, X-linked sideroblastic anemia, Connective tissue disease, Conotruncal anomaly face syndrome, Cooley's Anemia (beta-thalassemia), Copper storage disease (Wilson's disease), Copper transport disease (Menkes disease), hereditary coproporphyria, Cowden syndrome, Craniofacial dysarthrosis (Crouzon syndrome), Creutzfeldt-Jakob disease (prion disease), Cockayne syndrome, Cowden syndrome, Curschmann-Batten-Steinert syndrome (myotonic dystrophy), Beare-Stevenson cutis gyrata syndrome, primary hyperoxaluria, spondyloepimetaphyseal dysplasia (Strudwick type), muscular dystrophy, Duchenne and Becker types (DBMD), Usher syndrome, Degenerative nerve diseases including de Grouchy syndrome and Dejerine-Sottas syndrome, developmental disabilities, distal spinal muscular atrophy, type V, androgen insensitivity syndrome, Diffuse Globoid Body Sclerosis (Krabbe disease), Di George's syndrome, Dihydrotestosterone receptor deficiency, androgen insensitivity syndrome, Down syndrome, Dwarfism, erythropoietic protoporphyria Erythroid 5-aminolevulinate synthetase deficiency, Erythropoietic porphyria, erythropoietic protoporphyria, erythropoietic uroporphyria, Friedreich's ataxia-familial paroxysmal polyserositis, porphyria cutanea tarda, familial pressure sensitive neuropathy, primary pulmonary hypertension (PPH), Fibrocystic disease of the pancreas, fragile X syndrome, galactosemia, genetic brain disorders, Giant cell hepatitis (Neonatal hemochromatosis), Gronblad-Strandberg syndrome (pseudoxanthoma elasticum), Gunther disease (congenital erythropoietic porphyria), haemochromatosis, Hallgren syndrome, sickle cell anemia, hemophilia, hepatoerythropoietic porphyria (HEP), Hippel-Lindau disease (von Hippel-Lindau disease), Huntington's disease, Hutchinson-Gilford progeria syndrome (progeria), Hyperandrogenism, Hypochondroplasia, Hypochromic anemia, Immune system disorders, including X-linked severe combined immunodeficiency, Insley-Astley syndrome, Jackson-Weiss syndrome, Joubert syndrome, Lesch-Nyhan syndrome, Jackson-Weiss syndrome, Kidney diseases, including hyperoxaluria, Klinefelter's syndrome, Kniest dysplasia, Lacunar dementia, Langer-Saldino achondrogenesis, ataxia telangiectasia, Lynch syndrome, Lysyl-hydroxylase deficiency, Machado-Joseph disease, Metabolic disorders, including Kniest dysplasia, Marfan syndrome, Movement disorders, Mowat-Wilson syndrome, cystic fibrosis, Muenke syndrome, Multiple neurofibromatosis, Nance-Insley syndrome, Nance-Sweeney chondrodysplasia, Niemann-Pick disease, Noack syndrome (Pfeiffer syndrome), Osler-Weber-Rendu disease, Peutz-Jeghers syndrome, Polycystic kidney disease, polyostotic fibrous dysplasia (McCune-Albright syndrome), Peutz-Jeghers syndrome, Prader-Labhart-Willi syndrome, hemochromatosis, primary hyperuricemia syndrome (Lesch-Nyhan syndrome), primary pulmonary hypertension, primary senile degenerative dementia, prion disease, progeria (Hutchinson Gilford Progeria Syndrome), progressive chorea, chronic hereditary (Huntington) (Huntington's disease), progressive muscular atrophy, spinal muscular atrophy, propionic acidemia, protoporphyria, proximal myotonic dystrophy, pulmonary arterial hypertension, PXE (pseudoxanthoma elasticum), Rb (retinoblastoma), Recklinghausen disease (neurofibromatosis type I), Recurrent polyserositis, Retinal disorders, Retinoblastoma, Rett syndrome, RFALS type 3, Ricker syndrome, Riley-Day syndrome, Roussy-Levy syndrome, severe achondroplasia with developmental delay and acanthosis nigricans (SADDAN), Li-Fraumeni syndrome, sarcoma, breast, leukemia, and adrenal gland (SBLA) syndrome, sclerosis tuberose (tuberous sclerosis), SDAT, SED congenital (spondyloepiphyseal dysplasia congenita), SED Strudwick (spondyloepimetaphyseal dysplasia, Strudwick type), SEDc (spondyloepiphyseal dysplasia congenita) SEMD, Strudwick type (spondyloepimetaphyseal dysplasia, Strudwick type), Shprintzen syndrome, Skin pigmentation disorders, Smith-Lemli-Opitz syndrome, South-African genetic porphyria (variegate porphyria), infantile-onset ascending hereditary spastic paralysis, Speech and communication disorders, sphingolipidosis, Tay-Sachs disease, spinocerebellar ataxia, Stickler syndrome, stroke, androgen insensitivity syndrome, tetrahydrobiopterin deficiency, beta-thalassemia, Thyroid disease, Tomaculous neuropathy (hereditary neuropathy with liability to pressure palsies).

The term "neoplasia" or "cancer" is used throughout the specification to refer to the pathological process that results in the formation and growth of a cancerous or malignant neoplasm, i.e., abnormal tissue (solid) or cells (non-solid) that grow by cellular proliferation, often more rapidly than normal and continues to grow after the stimuli that initiated the new growth cease. Malignant neoplasms show partial or complete lack of structural organization and functional coordination with the normal tissue and most invade surrounding tissues, can metastasize to several sites, are likely to recur after attempted removal and may cause the death of the patient unless adequately treated. As used herein, the term neoplasia is used to describe all cancerous disease states and embraces or encompasses the pathological process associated with malignant hematogenous, ascitic and solid tumors. Exemplary cancers which may be treated by the present disclosed compounds either alone or in combination with at least one additional anti-cancer agent include squamous-cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor and teratocarcinomas. Additional cancers which may be treated using the disclosed compounds according to the present invention include, for example, acute granulocytic leukemia, acute lymphocytic leukemia (ALL), acute myelogenous leukemia (AML), adenocarcinoma, adenosarcoma, adrenal cancer, adrenocortical carcinoma, anal cancer, anaplastic astrocytoma, angiosarcoma, appendix cancer, astrocytoma, Basal cell carcinoma, B-Cell lymphoma, bile duct cancer, bladder cancer, bone cancer, bone marrow cancer, bowel cancer, brain cancer, brain stem glioma, breast cancer, triple (estrogen, progesterone and HER-2) negative breast cancer, double negative breast cancer (two of estrogen, progesterone and HER-2 are negative), single negative (one of estrogen, progesterone and HER-2 is negative), estrogen-receptor positive, HER2-negative breast cancer, estrogen receptor-negative breast cancer, estrogen receptor positive breast cancer, metastatic breast cancer, luminal A breast cancer, luminal B breast cancer, Her2-negative breast cancer, HER2-positive or negative breast cancer, progesterone receptor-negative breast cancer, progesterone receptor-positive breast cancer, recurrent breast cancer, carcinoid tumors, cervical cancer, cholangiocarcinoma, chondrosarcoma, chronic lymphocytic leukemia (CLL), chronic myelogenous leukemia (CML), colon cancer, colorectal cancer, craniopharyngioma, cutaneous lymphoma, cutaneous melanoma, diffuse astrocytoma, ductal carcinoma in situ (DCIS), endometrial cancer, ependymoma, epithelioid sarcoma, esophageal cancer, ewing sarcoma, extrahepatic bile duct cancer, eye cancer, fallopian tube cancer, fibrosarcoma, gallbladder cancer, gastric cancer, gastrointestinal cancer, gastrointestinal carcinoid cancer, gastrointestinal stromal tumors (GIST), germ cell tumor glioblastoma multiforme (GBM), glioma, hairy cell leukemia, head and neck cancer, hemangioendothelioma, Hodgkin lymphoma, hypopharyngeal cancer, infiltrating ductal carcinoma (IDC), infiltrating lobular carcinoma (ILC), inflammatory breast cancer (IBC), intestinal Cancer, intrahepatic bile duct cancer, invasive/infiltrating breast cancer, Islet cell cancer, jaw cancer, Kaposi sarcoma, kidney cancer, laryngeal cancer, leiomyosarcoma, leptomeningeal metastases, leukemia, lip cancer, liposarcoma, liver cancer, lobular carcinoma in situ, low-grade astrocytoma, lung cancer, lymph node cancer, lymphoma, male breast cancer, medullary carcinoma, medulloblastoma, melanoma, meningioma, Merkel cell carcinoma, mesenchymal chondrosarcoma, mesenchymous, mesothelioma metastatic breast cancer, metastatic melanoma metastatic squamous neck cancer, mixed gliomas, monodermal teratoma, mouth cancer mucinous carcinoma, mucosal melanoma, multiple myeloma, Mycosis Fungoides, myelodysplastic syndrome, nasal cavity cancer, nasopharyngeal cancer, neck cancer, neuroblastoma, neuroendocrine tumors (NETs), non-Hodgkin's lymphoma, non-small cell lung cancer (NSCLC), oat cell cancer, ocular cancer, ocular melanoma, oligodendroglioma, oral cancer, oral cavity cancer, oropharyngeal cancer, osteogenic sarcoma, osteosarcoma, ovarian cancer, ovarian epithelial cancer ovarian germ cell tumor, ovarian primary peritoneal carcinoma, ovarian sex cord stromal tumor, Paget's disease, pancreatic cancer, papillary carcinoma, paranasal sinus cancer, parathyroid cancer, pelvic cancer, penile cancer, peripheral nerve cancer, peritoneal cancer, pharyngeal cancer, pheochromocytoma, pilocytic astrocytoma, pineal region tumor, pineoblastoma, pituitary gland cancer, primary central nervous system (CNS) lymphoma, prostate cancer, rectal cancer, renal cell carcinoma, renal pelvis cancer, rhabdomyosarcoma, salivary gland cancer, soft tissue sarcoma, bone sarcoma, sarcoma, sinus cancer, skin cancer, small cell lung cancer (SCLC), small intestine cancer, spinal cancer, spinal column cancer, spinal cord cancer, squamous cell carcinoma, stomach cancer, synovial sarcoma, T-cell lymphoma, testicular cancer, throat cancer, thymoma/thymic carcinoma, thyroid cancer, tongue cancer, tonsil cancer, transitional cell cancer, tubal cancer, tubular carcinoma, undiagnosed cancer, ureteral cancer, urethral cancer, uterine adenocarcinoma, uterine cancer, uterine sarcoma, vaginal cancer, vulvar cancer, T-cell lineage acute lymphoblastic leukemia (T-ALL), T-cell lineage lymphoblastic lymphoma (T-LL), peripheral T-cell lymphoma, Adult T-cell leukemia, Pre-B ALL, Pre-B lymphomas, large B-cell lymphoma, Burkitts lymphoma, B-cell ALL, Philadelphia chromosome positive ALL, Philadelphia chromosome positive CML, juvenile myelomonocytic leukemia (JMML), acute promyelocytic leukemia (a subtype of AML), large granular lymphocytic leukemia, Adult T-cell chronic leukemia, diffuse large B cell lymphoma, follicular lymphoma; Mucosa-Associated Lymphatic Tissue lymphoma (MALT), small cell lymphocytic lymphoma, mediastinal large B cell lymphoma, nodal marginal zone B cell lymphoma (NMZL); splenic marginal zone lymphoma (SMZL); intravascular large B-cell lymphoma; primary effusion lymphoma; or lymphomatoid granulomatosis; B-cell prolymphocytic leukemia; splenic lymphoma/leukemia, unclassifiable, splenic diffuse red pulp small B-cell lymphoma; lymphoplasmacytic lymphoma; heavy chain diseases, for example, Alpha heavy chain disease, Gamma heavy chain disease, Mu heavy chain disease, plasma cell myeloma, solitary plasmacytoma of bone; extraosseous plasmacytoma; primary cutaneous follicle center lymphoma, T cell/histocyte rich large B-cell lymphoma, DLBCL associated with chronic inflammation; Epstein-Barr virus (EBV)+ DLBCL of the elderly; primary mediastinal (thymic) large B-cell lymphoma, primary cutaneous DLBCL, leg type, ALK+ large B-cell lymphoma, plasmablastic lymphoma; large B-cell lymphoma arising in HHV8-associated multicentric, Castleman disease; B-cell lymphoma, unclassifiable, with features intermediate between diffuse large B-cell lymphoma, or B-cell lymphoma, unclassifiable, with features intermediate between diffuse large B-cell lymphoma and classical Hodgkin lymphoma.

IV. Combination Therapy

The disclosed compounds of Formula I, II, III, IV, V and VI can be used in an effective amount alone or in combination with another compound of the present invention or another bioactive agent to treat a host such as a human with a disorder as described herein.

The term "bioactive agent" is used to describe an agent, other than the selected compound according to the present invention, which can be used in combination or alternation with a compound of the present invention to achieve a desired result of therapy. In one embodiment, the compound of the present invention and the bioactive agent are administered in a manner that they are active in vivo during overlapping time periods, for example, have time-period overlapping Cmax, Tmax, AUC or other pharmacokinetic parameter. In another embodiment, the compound of the present invention and the bioactive agent are administered to a host in need thereof that do not have overlapping pharmacokinetic parameter, however, one has a therapeutic impact on the therapeutic efficacy of the other.

In one aspect of this embodiment, the bioactive agent is an immune modulator, including but not limited to a checkpoint inhibitor, including as non-limiting examples, a PD-1 inhibitor, PD-L1 inhibitor, PD-L2 inhibitor, CTLA-4 inhibitor, LAG-3 inhibitor, TIM-3 inhibitor, V-domain Ig suppressor of T-cell activation (VISTA) inhibitors, small molecule, peptide, nucleotide, or other inhibitor. In certain aspects, the immune modulator is an antibody, such as a monoclonal antibody.

PD-1 inhibitors that blocks the interaction of PD-1 and PD-L1 by binding to the PD-1 receptor, and in turn inhibit immune suppression include, for example, nivolumab (Opdivo), pembrolizumab (Keytruda), pidilizumab, AMP-224 (AstraZeneca and MedImmune), PF-06801591 (Pfizer), MEDI0680 (AstraZeneca), PDR001 (Novartis), REGN2810 (Regeneron), SHR-12-1 (Jiangsu Hengrui Medicine Company and Incyte Corporation), TSR-042 (Tesaro), and the PD-L1/VISTA inhibitor CA-170 (Curis Inc.). PD-L1 inhibitors that block the interaction of PD-1 and PD-L1 by binding to the PD-L1 receptor, and in turn inhibits immune suppression, include for example, atezolizumab (Tecentriq), durvalumab (AstraZeneca and MedImmune), KN035 (Alphamab), and BMS-936559 (Bristol-Myers Squibb). CTLA-4 checkpoint inhibitors that bind to CTLA-4 and inhibits immune suppression include, but are not limited to, ipilimumab, tremelimumab (AstraZeneca and MedImmune), AGEN1884 and AGEN2041 (Agenus). LAG-3 checkpoint inhibitors, include, but are not limited to, BMS-986016 (Bristol-Myers Squibb), GSK2831781 (GlaxoSmithKline), IMP321 (Prima BioMed), LAG525 (Novartis), and the dual PD-1 and LAG-3 inhibitor MGD013 (MacroGenics). An example of a TIM-3 inhibitor is TSR-022 (Tesaro).

In yet another embodiment, one of the active compounds described herein can be administered in an effective amount for the treatment of abnormal tissue of the female reproductive system such as breast, ovarian, endometrial, or uterine cancer, in combination or alternation with an effective amount of an estrogen inhibitor including but not limited to a SERM (selective estrogen receptor modulator), a SERD (selective estrogen receptor degrader), a complete estrogen receptor degrader, or another form of partial or complete estrogen antagonist or agonist. Partial anti-estrogens like raloxifene and tamoxifen retain some estrogen-like effects, including an estrogen-like stimulation of uterine growth, and also, in some cases, an estrogen-like action during breast cancer progression which actually stimulates tumor growth. In contrast, fulvestrant, a complete anti-estrogen, is free of estrogen-like action on the uterus and is effective in tamoxifen-resistant tumors. Non-limiting examples of anti-estrogen compounds are provided in WO 2014/19176 assigned to Astra Zeneca, WO2013/090921, WO 2014/203129, WO 2014/203132, and US2013/0178445 assigned to Olema Pharmaceuticals, and U.S. Pat. Nos. 9,078,871, 8,853,423, and 8,703, 810, as well as US 2015/0005286, WO 2014/205136, and WO 2014/205138. Additional non-limiting examples of anti-estrogen compounds include: SERMS such as anordrin, bazedoxifene, broparestriol, chlorotrianisene, clomiphene citrate, cyclofenil, lasofoxifene, ormeloxifene, raloxifene, tamoxifen, toremifene, and fulvestratnt; aromatase inhibitors such as aminoglutethimide, testolactone, anastrozole, exemestane, fadrozole, formestane, and letrozole; and antigonadotropins such as leuprorelin, cetrorelix, allylestrenol, chloromadinone acetate, cyproterone acetate, delmadinone acetate, dydrogesterone, medroxyprogesterone acetate, megestrol acetate, nomegestrol acetate, norethisterone acetate, progesterone, and spironolactone. Other estrogenic ligands that can be used according to the present invention are described in U.S. Pat. Nos. 4,418,068; 5,478, 847; 5,393,763; and 5,457,117, WO2011/156518, U.S. Pat. Nos. 8,455,534 and 8,299,112, 9,078,871; 8,853,423; 8,703, 810; US 2015/0005286; and WO 2014/205138, US2016/0175289, US2015/0258080, WO 2014/191726, WO 2012/084711; WO 2002/013802; WO 2002/004418; WO 2002/003992; WO 2002/003991; WO 2002/003990; WO 2002/003989; WO 2002/003988; WO 2002/003986; WO 2002/003977; WO 2002/003976; WO 2002/003975; WO 2006/078834; U.S. Pat. No. 6,821,989; US 2002/0128276; U.S. Pat. No. 6,777,424; US 2002/0016340; U.S. Pat. Nos. 6,326, 392; 6,756,401; US 2002/0013327; U.S. Pat. Nos. 6,512, 002; 6,632,834; US 2001/0056099; U.S. Pat. Nos. 6,583, 170; 6,479,535; WO 1999/024027; U.S. Pat. No. 6,005,102; EP 0802184; U.S. Pat. Nos. 5,998,402; 5,780,497; 5,880, 137, WO 2012/048058 and WO 2007/087684.

In another embodiment, an active compounds described herein can be administered in an effective amount for the treatment of abnormal tissue of the male reproductive system such as prostate or testicular cancer, in combination or alternation with an effective amount of an androgen (such as testosterone) inhibitor including but not limited to a selective androgen receptor modulator, a selective androgen receptor degrader, a complete androgen receptor degrader, or another form of partial or complete androgen antagonist. In one embodiment, the prostate or testicular cancer is androgen-resistant. Non-limiting examples of anti-androgen compounds are provided in WO 2011/156518 and U.S. Pat. Nos. 8,455,534 and 8,299,112. Additional non-limiting examples of anti-androgen compounds include: enzalutamide, apalutamide, cyproterone acetate, chlormadinone acetate, spironolactone, canrenone, drospirenone, ketoconazole, topilutamide, abiraterone acetate, and cimetidine.

In one embodiment, the bioactive agent is an ALK inhibitor. Examples of ALK inhibitors include but are not limited to Crizotinib, Alectinib, ceritinib, TAE684 (NVP-TAE684), GSK1838705A, AZD3463, ASP3026, PF-06463922, entrectinib (RXDX-101), and AP26113.

In one embodiment, the bioactive agent is an EGFR inhibitor. Examples of EGFR inhibitors include erlotinib (Tarceva), gefitinib (Iressa), afatinib (Gilotrif), rociletinib (CO-1686), osimertinib (Tagrisso), olmutinib (Olita), naquotinib (ASP8273), nazartinib (EGF816), PF-06747775 (Pfizer), icotinib (BPI-2009), neratinib (HKI-272; PB272); avitinib (AC0010), EAI045, tarloxotinib (TH-4000; PR-610), PF-06459988 (Pfizer), tesevatinib (XL647; EXEL-7647; KD-019), transtinib, WZ-3146, WZ8040, CNX-2006, and dacomitinib (PF-00299804; Pfizer).

In one embodiment, the bioactive agent is an HER-2 inhibitor. Examples of HER-2 inhibitors include trastuzumab, lapatinib, ado-trastuzumab emtansine, and pertuzumab.

In one embodiment, the bioactive agent is a CD20 inhibitor. Examples of CD20 inhibitors include obinutuzumab, rituximab, fatumumab, ibritumomab, tositumomab, and ocrelizumab.

In one embodiment, the bioactive agent is a JAK3 inhibitor. Examples of JAK3 inhibitors include tasocitinib.

In one embodiment, the bioactive agent is a BCL-2 inhibitor. Examples of BCL-2 inhibitors include venetoclax, ABT-199 (4-[4-[[2-(4-Chlorophenyl)-4,4-dimethylcyclohex-1-en-1-yl]methyl]piperazin-1-yl]-N-[[3-nitro-4-[[(tetrahydro-2H-pyran-4-yl)methyl]amino]phenyl]sulfonyl]-2-[(1H-pyrrolo[2,3-b]pyridin-5-yl)oxy]benzamide), ABT-737 (4-[4-[[2-(4-chlorophenyl)phenyl]methyl]piperazin-1-yl]-N-[4-[[(2R)-4-(dimethylamino)-1-phenyl sulfanylbutan-2-yl] amino]-3-nitrophenyl]sulfonylbenzamide) (navitoclax), ABT-263 ((R)-4-(4-((4'-chloro-4,4-dimethyl-3,4,5,6-tetrahydro-[1,1'-biphenyl]-2-yl)methyl)piperazin-1-yl)-N-((4-((4-morpholino-1-(phenylthio)butan-2-yl)amino)-3((trifluoromethyl)sulfonyl)phenyl)sulfonyl)benzamide), GX15-070 (obatoclax mesylate, (2Z)-2-[(5Z)-5-[(3,5-dimethyl-1H-pyrrol-2-yl)methylidene]-4-methoxypyrrol-2-ylidene]indole; methanesulfonic acid))), 2-methoxy-antimycin A3, YC137 (4-(4,9-dioxo-4,9-dihydronaphtho[2,3-d]thiazol-2-ylamino)-phenyl ester), pogosin, ethyl 2-amino-6-bromo-4-(1-cyano-2-ethoxy-2-oxoethyl)-4H-chromene-3-carboxylate, Nilotinib-d3, TW-37 (N-[4-[[2-(1,1-Dimethylethyl)phenyl] sulfonyl]phenyl]-2,3,4-trihydroxy-5-[[2-(1-methylethyl) phenyl]methyl]benzamide), Apogossypolone (ApoG2), HA14-1, AT101, sabutoclax, gambogic acid, or G3139 (Oblimersen).

In one embodiment, the bioactive agent is a kinase inhibitor. In one embodiment, the kinase inhibitor is selected from a phosphoinositide 3-kinase (PI3K) inhibitor, a Bruton's tyrosine kinase (BTK) inhibitor, or a spleen tyrosine kinase (Syk) inhibitor, or a combination thereof.

Examples of PI3 kinase inhibitors include but are not limited to Wortmannin, demethoxyviridin, perifosine, idelalisib, Pictilisib, Palomid 529, ZSTK474, PWT33597, CUDC-907, and AEZS-136, duvelisib, GS-9820, BKM120, GDC-0032 (Taselisib) (2-[4-[2-(2-Isopropyl-5-methyl-1,2,4-triazol-3-yl)-5,6-dihydroimidazo[1,2-d][1,4]benzoxazepin-9-yl]pyrazol-1-yl]-2-methylpropanamide), MLN-1117 ((2R)-1-Phenoxy-2-butanyl hydrogen (S)-methylphosphonate; or Methyl(oxo) {[(2R)-1-phenoxy-2-butanyl]oxy}phosphonium)), BYL-719 ((2S)—N1-[4-Methyl-5-[2-(2,2,2-trifluoro-1,1-dimethylethyl)-4-pyridinyl]-2-thiazolyl]-1,2-pyrrolidinedicarboxamide), GSK2126458 (2,4-Difluoro-N-{2-(methyloxy)-5-[4-(4-pyridazinyl)-6-quinolinyl]-3-pyridinyl}benzenesulfonamide) (omipalisib), TGX-221 ((+)-7-Methyl-2-(morpholin-4-yl)-9-(1-phenylaminoethyl)-pyrido[1,2-a]-pyrimidin-4-one), GSK2636771 (2-Methyl-1-(2-methyl-3-(trifluoromethyl)benzyl)-6-morpholino-1H-benzo[d]imidazole-4-carboxylic acid dihydrochloride), KIN-193 ((R)-2-((l-(7-methyl-2-morpholino-4-oxo-4H-pyrido[1,2-a]pyrimidin-9-yl)ethyl)amino)benzoic acid), TGR-1202/RP5264, GS-9820 ((S)-1-(4-((2-(2-aminopyrimidin-5-yl)-7-methyl-4-mohydroxypropan-1-one), GS-1101 (5-fluoro-3-phenyl-2-([S)]-1-[9H-purin-6-ylamino]-propyl)-3H-quinazolin-4-one), AMG-319, GSK-2269557, SAR245409 (N-(4-(N-(3-((3,5-dimethoxyphenyl)amino)quinoxalin-2-yl)sulfamoyl)phenyl)-3-methoxy-4 methylbenzamide), BAY80-6946 (2-amino-N-(7-methoxy-8-(3-morpholinopropoxy)-2,3-dihydroimidazo[1,2-c]quinaz), AS 252424 (5-[1-[5-(4-Fluoro-2-hydroxy-phenyl)-furan-2-yl]-meth-(Z)-ylidene]-thiazolidine-2,4-dione), CZ 24832 (5-(2-amino-8-fluoro-[1,2,4]triazolo[1,5-a]pyridin-6-yl)-N-tert-butylpyridine-3-sulfonamide), Buparlisib (5-[2,6-Di(4-morpholinyl)-4-pyrimidinyl]-4-(trifluoromethyl)-2-pyridinamine), GDC-0941 (2-(1H-Indazol-4-yl)-6-[[4-(methyl sulfonyl)-1-piperazinyl]methyl]-4-(4-morpholinyl) thieno[3,2-d]pyrimidine), GDC-0980 ((S)-1-(4-((2-(2-aminopyrimidin-5-yl)-7-methyl-4-morpholinothieno[3,2-d] pyrimidin-6 yl)methyl)piperazin-1-yl)-2-hydroxypropan-1-one (also known as RG7422)), SF1126 ((8S,14S,17S)-14-(carboxymethyl)-8-(3-guanidinopropyl)-17-(hydroxymethyl)-3,6,9,12,15-pentaoxo-1-(4-(4-oxo-8-phenyl-4H-chromen-2-yl)morpholino-4-ium)-2-oxa-7,10,13,16-tetraazaoctadecan-18-oate), PF-05212384 (N-[4-[[4-(Dimethylamino)-1-piperidinyl]carbonyl]phenyl]-N'-[4-(4,6-di-4-morpholinyl-1,3,5-triazin-2-yl)phenyl]urea) (gedatolisib), LY3023414, BEZ235 (2-Methyl-2-{4-[3-methyl-2-oxo-8-(quinolin-3-yl)-2,3-dihydro-1H-imidazo[4,5-c]quinolin-1-yl]phenyl}propanenitrile) (dactolisib), XL-765 (N-(3-(N-(3-(3,5-dimethoxyphenylamino)quinoxalin-2-yl)sulfamoyl) phenyl)-3-methoxy-4-methylbenzamide), and GSK1059615 (5-[[4-(4-Pyridinyl)-6-quinolinyl]methylene]-2,4-thiazolidenedione), PX886 ([(3aR,6E,9S,9aR,10R,11aS)-6-[[bis(prop-2-enyl)amino]methylidene]-5-hydroxy-9-(methoxymethyl)-9a,11a-dimethyl-1,4,7-trioxo-2,3,3a,9,10,11-hexahydroindeno[4,5h]isochromen-10-yl] acetate (also known as sonolisib)), LY294002, AZD8186, PF-4989216, pilaralisib, GNE-317, PI-3065, PI-103, NU7441 (KU-57788), HS 173, VS-5584 (SB2343), CZC24832, TG100-115, A66, YM201636, CAY10505, PIK-75, PIK-93, AS-605240, BGT226 (NVP-BGT226), AZD6482, voxtalisib, alpelisib, IC-87114, TGI100713, CH5132799, PKI-402, copanlisib (BAY 80-6946), XL 147, PIK-90, PIK-293, PIK-294, 3-MA (3-methyladenine), AS-252424, AS-604850, apitolisib (GDC-0980; RG7422), and the structure described in WO2014/071109 having the formula:

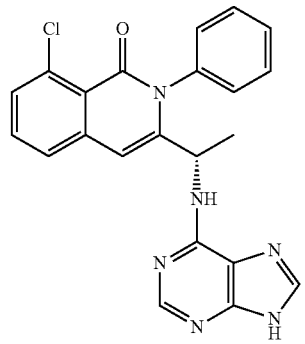

Compound 292

Examples of BTK inhibitors include ibrutinib (also known as PCI-32765)(Imbruvica™)(1-[(3R)-3-[4-amino-3-(4-phenoxy-phenyl)pyrazolo[3,4-d]pyrimidin-1-yl]piperidin-1-yl]prop-2-en-1-one), dianilinopyrimidine-based inhibitors such as AVL-101 and AVL-291/292 (N-(3-((5-fluoro-2-((4-(2-methoxyethoxy)phenyl)amino)pyrimidin-4-yl)amino)phenyl)acrylamide) (Avila Therapeutics) (see US Patent Publication No 2011/0117073, incorporated herein in its entirety), Dasatinib ([N-(2-chloro-6-methylphenyl)-2-(6-(4-(2-hydroxyethyl)piperazin-1-yl)-2-methylpyrimidin-4-ylamino)thiazole-5-carboxamide], LFM-A13 (alpha-cyano-beta-hydroxy-beta-methyl-N-(2,5-ibromophenyl) propenamide), GDC-0834 ([R—N-(3-(6-(4-(1,4-dimethyl-3-oxopiperazin-2-yl)phenylamino)-4-methyl-5-oxo-4,5-dihydropyrazin-2-yl)-2-methylphenyl)-4,5,6,7-tetrahydrobenzo[b]thiophene-2-carboxamide], CGI-560 4-(tert-butyl)-N-(3-(8-(phenylamino)imidazo[1,2-a]pyrazin-6-yl)phenyl) benzamide, CGI-1746 (4-(tert-butyl)-N-(2-methyl-3-(4-methyl-6-((4-(morpholine-4-carbonyl)phenyl)amino)-5-oxo-4,5-dihydropyrazin-2-yl)phenyl)benzamide), CNX-774 (4-(4-((4-((3-acrylamidophenyl)amino)-5-fluoropyrimidin-2-yl)amino)phenoxy)-N-methylpicolinamide), CTA056 (7-benzyl-1-(3-(piperidin-1-yl)propyl)-2-(4-(pyridin-4-yl) phenyl)-1H-imidazo[4,5-g]quinoxalin-6(5H)-one), GDC-0834 ((R)—N-(3-(6-((4-(1,4-dimethyl-3-oxopiperazin-2-yl) phenyl)amino)-4-methyl-5-oxo-4,5-dihydropyrazin-2-yl)-2-methylphenyl)-4,5,6,7-tetrahydrobenzo[b]thiophene-2-carboxamide), GDC-0837 ((R)—N-(3-(6-((4-(1,4-dimethyl-3-oxopiperazin-2-yl)phenyl)amino)-4-methyl-5-oxo-4,5-dihydropyrazin-2-yl)-2-methylphenyl)-4,5,6,7-tetrahydrobenzo[b]thiophene-2-carboxamide), HM-71224, ACP-196, ONO-4059 (Ono Pharmaceuticals), PRT062607 (4-((3-(2H-1,2,3-triazol-2-yl)phenyl)amino)-2-(((1R,2S)-2-aminocyclohexyl)amino)pyrimidine-5-carboxamide hydrochloride), QL-47 (1-(1-acryloylindolin-6-yl)-9-(1-methyl-1H-pyrazol-4-yl)benzo[h][1,6]naphthyridin-2(1H)-one), and RN486 (6-cyclopropyl-8-fluoro-2-(2-hydroxymethyl-3-{1-methyl-5-[5-(4-methyl-piperazin-1-yl)-pyridin-2-ylamino]-6-oxo-1,6-dihydro-pyridin-3-yl}-phenyl)-2H-isoquinolin-1-one), and other molecules capable of inhibiting BTK activity, for example those BTK inhibitors disclosed in Akinleye et ah, Journal of Hematology & Oncology, 2013, 6:59, the entirety of which is incorporated herein by reference.

Syk inhibitors include, for example, Cerdulatinib (4-(cyclopropylamino)-2-((4-(4-(ethylsulfonyl)piperazin-1-yl) phenyl)amino)pyrimidine-5-carboxamide), entospletinib (6-(1H-indazol-6-yl)-N-(4-morpholinophenyl)imidazo[1,2-a] pyrazin-8-amine), fostamatinib ([6-({5-Fluoro-2-[(3,4,5-trimethoxyphenyl)amino]-4-pyrimidinyl}amino)-2,2- dimethyl-3-oxo-2,3-dihydro-4H-pyrido[3,2-b][1,4]oxazin-4-yl]methyl dihydrogen phosphate), fostamatinib disodium salt (sodium (6-((5-fluoro-2-((3,4, 5-trimethoxyphenyl)amino)pyrimidin-4-yl)amino)-2,2-dimethyl-3-oxo-2H-pyrido[3,2-b][1,4]oxazin-4(3H)-yl)methyl phosphate), BAY 61-3606 (2-(7-(3,4-Dimethoxyphenyl)-imidazo[1,2-c]pyrimidin-5-ylamino)-nicotinamide HCl), RO9021 (6-[(1R,2S)-2-Amino-cyclohexylamino]-4-(5,6-dimethyl-pyridin-2-ylamino)-pyridazine-3-carboxylic acid amide), imatinib (Gleevac; 4-[(4-methylpiperazin-1-yl)methyl]-N-(4-methyl-3-{[4-(pyridin-3-yl)pyrimidin-2-yl]amino}phenyl)benzamide), staurosporine, GSK143 (2-(((3R,4R)-3-aminotetrahydro-2H-pyran-4-yl)amino)-4-(p-tolylamino)pyrimidine-5-carboxamide), PP2 (1-(tert-butyl)-3-(4-chlorophenyl)-1H-pyrazolo[3,4-d]pyrimidin-4-amine), PRT-060318 (2-(((1R,2S)-2-aminocyclohexyl)amino)-4-(m-tolylamino)pyrimidine-5-carboxamide), PRT-062607 (4-((3-(2H-1,2,3-triazol-2-yl)phenyl)amino)-2-(((1R,2S)-2-aminocyclohexyl)amino)pyrimidine-5-carboxamide hydrochloride), R112 (3,3'-((5-fluoropyrimidine-2,4-diyl)bis(azanediyl))diphenol), R348 (3-Ethyl-4-methylpyridine), R406 (6-((5-fluoro-2-((3,4, 5-trimethoxyphenyl)amino)pyrimidin-4-yl)amino)-2,2-dimethyl-2H-pyrido[3,2-b][1,4]oxazin-3 (4H)-one), piceatannol (3-Hydroxyresveratol), YM193306 (see Singh et al. Discovery and Development of Spleen Tyrosine Kinase (SYK) Inhibitors, J. Med. Chem. 2012, 55, 3614-3643), 7-azaindole, piceatannol, ER-27319 (see Singh et al. Discovery and Development of Spleen Tyrosine Kinase (SYK) Inhibitors, J. Med. Chem. 2012, 55, 3614-3643 incorporated in its entirety herein), Compound D (see Singh et al. Discovery and Development of Spleen Tyrosine Kinase (SYK) Inhibitors, J. Med. Chem. 2012, 55, 3614-3643 incorporated in its entirety herein), PRT060318 (see Singh et al. Discovery and Development of Spleen Tyrosine Kinase (SYK) Inhibitors, J. Med. Chem. 2012, 55, 3614-3643 incorporated in its entirety herein), luteolin (see Singh et al. Discovery and Development of Spleen Tyrosine Kinase (SYK) Inhibitors, J. Med. Chem. 2012, 55, 3614-3643 incorporated in its entirety herein), apigenin (see Singh et al. Discovery and Development of Spleen Tyrosine Kinase (SYK) Inhibitors, J. Med. Chem. 2012, 55, 3614-3643 incorporated in its entirety herein), quercetin (see Singh et al. Discovery and Development of Spleen Tyrosine Kinase (SYK) Inhibitors, J. Med. Chem. 2012, 55, 3614-3643 incorporated in its entirety herein), fisetin (see Singh et al. Discovery and Development of Spleen Tyrosine Kinase (SYK) Inhibitors, J. Med. Chem. 2012, 55, 3614-3643 incorporated in its entirety herein), myricetin (see Singh et al. Discovery and Development of Spleen Tyrosine Kinase (SYK) Inhibitors, J. Med. Chem. 2012, 55, 3614-3643 incorporated in its entirety herein), morin (see Singh et al. Discovery and Development of Spleen Tyrosine Kinase (SYK) Inhibitors, J. Med. Chem. 2012, 55, 3614-3643 incorporated in its entirety herein).

In one embodiment, the bioactive agent is a MEK inhibitor. MEK inhibitors are well known, and include, for example, trametinib/GSK1120212 (N-(3-{3-Cyclopropyl-5-[(2-fluoro-4-iodophenyl)amino]-6,8-dimethyl-2,4,7-trioxo-3,4,6,7-tetrahydropyrido[4,3-d]pyrimidin-1(2H-yl}phenyl) acetamide), selumetinib (6-(4-bromo-2-chloroanilino)-7-fluoro-N-(2-hydroxyethoxy)-3-methylbenzimidazole-5-carboxamide), pimasertib/AS703026/MSC 1935369 ((S)—N-(2,3-dihydroxypropyl)-3-((2-fluoro-4-iodophenyl)amino) isonicotinamide), XL-518/GDC-0973 (1-({3,4-difluoro-2-[(2-fluoro-4-iodophenyl)amino]phenyl}carbonyl)-3-[(2S)-piperidin-2-yl]azetidin-3-ol), refametinib/BAY869766/RDEA1 19 (N-(3,4-difluoro-2-(2-fluoro-4-iodophenylamino)-6-methoxyphenyl)-1-(2,3-dihydroxypropyl)cyclopropane-1-sulfonamide), PD-0325901 (N-[(2R)-2,3-Dihydroxypropoxy]-3,4-difluoro-2-[(2-fluoro-4-iodophenyl)amino]-benzamide), TAK733 ((R)-3-(2,3-Dihydroxypropyl)-6-fluoro-5-(2-fluoro-4-iodophenylamino)-8-methylpyrido[2,3-d]pyrimidine-4,7(3H, 8H)-dione), MEK162/ARRY438162 (5-[(4-Bromo-2-fluorophenyl)amino]-4-fluoro-N-(2-hydroxyethoxy)-1-methyl-1H-benzimidazole-6-carboxamide), R05126766 (3-[[3-Fluoro-2-(methyl sulfamoylamino)-4-pyridyl]methyl]-4-methyl-7-pyrimidin-2-yloxychromen-2-one), WX-554, R04987655/CH4987655 (3,4-difluoro-2-((2-fluoro-4-iodophenyl)amino)-N-(2-hydroxyethoxy)-5-((3-oxo-1,2-oxazinan-2yl)methyl)benzamide), or AZD8330 (2-((2-fluoro-4-iodophenyl)amino)-N-(2 hydroxyethoxy)-1,5-dimethyl-6-oxo-1,6-dihydropyridine-3-carboxamide), U0126-EtOH, PD184352 (CI-1040), GDC-0623, BI-847325, cobimetinib, PD98059, BIX 02189, BIX 02188, binimetinib, SL-327, TAK-733, PD318088.

In one embodiment, the bioactive agent is a Raf inhibitor. Raf inhibitors are known and include, for example, Vemurafinib (N-[3-[[5-(4-Chlorophenyl)-1H-pyrrolo[2,3-b]pyridin-3-yl]carbonyl]-2,4-difluorophenyl]-1-propanesulfonamide), sorafenib tosylate (4-[4-[[4-chloro-3-(trifluoromethyl)phenyl]carbamoylamino]phenoxy]-N-methylpyridine-2-carboxamide; 4-methylbenzenesulfonate), AZ628 (3-(2-cyanopropan-2-yl)-N-(4-methyl-3-(3-methyl-4-oxo-3,4-dihydroquinazolin-6-ylamino)phenyl)benzamide), NVP-BHG712 (4-methyl-3-(1-methyl-6-(pyridin-3-yl)-1H-pyrazolo[3,4-d]pyrimidin-4-ylamino)-N-(3-(trifluoromethyl) phenyl)benzamide), RAF-265 (1-methyl-5-[2-[5-(trifluoromethyl)-1H-imidazol-2-yl]pyridin-4-yl]oxy-N-[4-(trifluoromethyl)phenyl]benzimidazol-2-amine), 2-Bromoaldisine (2-Bromo-6,7-dihydro-1H,5H-pyrrolo[2,3-c]azepine-4,8-dione), Raf Kinase Inhibitor IV (2-chloro-5-(2-phenyl-5-(pyridin-4-yl)-1H-imidazol-4-yl)phenol), Sorafenib N-Oxide (4-[4-[[[[4-Chloro-3 (trifluoroMethyl)phenyl]aMino]carbonyl]aMino]phenoxy]-N-Methyl-2pyridinecarboxaMide 1-Oxide), PLX-4720, dabrafenib (GSK2118436), GDC-0879, RAF265, AZ 628, SB590885, ZM336372, GW5074, TAK-632, CEP-32496, LY3009120, and GX818 (Encorafenib).

In one embodiment, the bioactive agent is an AKT inhibitor, including but not limited to, MK-2206, GSK690693, Perifosine, (KRX-0401), GDC-0068, Triciribine, AZD5363, Honokiol, PF-04691502, and Miltefosine, a FLT-3 inhibitor, including but not limited to, P406, Dovitinib, Quizartinib (AC220), Amuvatinib (MP-470), Tandutinib (MLN518), ENMD-2076, and KW-2449, or a combination thereof.

In one embodiment, the bioactive agent is an mTOR inhibitor. Examples of mTOR inhibitors include but are not limited to rapamycin and its analogs, everolimus (Afinitor), temsirolimus, ridaforolimus, sirolimus, and deforolimus. Examples of MEK inhibitors include but are not limited to tametinib/GSK1120212 (N-(3-{3-Cyclopropyl-5-[(2-fluoro-4-iodophenyl)amino]-6,8-dimethyl-2,4,7-trioxo-3,4, 6,7-tetrahydropyrido[4,3-d]pyrimidin-1(2H-yl}phenyl)acetamide), selumetinob (6-(4-bromo-2-chloroanilino)-7-fluoro-N-(2-hydroxyethoxy)-3-methylbenzimidazole-5-carboxamide), pimasertib/AS703026/MSC1935369 ((S)—N-(2,3-dihydroxypropyl)-3-((2-fluoro-4-iodophenyl)amino) isonicotinamide), XL-518/GDC-0973 (1-({3,4-difluoro-2-[(2-fluoro-4-iodophenyl)amino]phenyl}carbonyl)-3-[(2S)-piperidin-2-yl]azetidin-3-ol) (cobimetinib), refametinib/BAY869766/RDEA119 (N-(3,4-difluoro-2-(2-fluoro-4-iodophenylamino)-6-methoxyphenyl)-1-(2,3-dihydroxypropyl)cyclopropane-1-sulfonamide), PD-0325901 (N-[(2R)-2, 3-Dihydroxypropoxy]-3,4-difluoro-2-[(2-fluoro-4-iodophenyl)amino]-benzamide), TAK733 ((R)-3-(2,3-Dihydroxypropyl)-6-fluoro-5-(2-fluoro-4-iodophenylamino)-8-methylpyrido[2,3 d]pyrimidine-4,7(3H,8H)-dione), MEK162/ARRY438162 (5-[(4-Bromo-2-fluorophenyl) amino]-4-fluoro-N-(2-hydroxyethoxy)-1-methyl-1H-benzimidazole-6 carboxamide), RO5126766 (3-[[3-Fluoro-2-(methylsulfamoylamino)-4-pyridyl]methyl]-4-methyl-7-pyrimidin-2-yloxychromen-2-one), WX-554, RO4987655/CH4987655 (3,4-difluoro-2-((2-fluoro-4-iodophenyl) amino)-N-(2-hydroxyethoxy)-5-((3-oxo-1,2-oxazinan-2 yl)methyl)benzamide), or AZD8330 (2-((2-fluoro-4-iodophenyl)amino)-N-(2-hydroxyethoxy)-1, 5-dimethyl-6-oxo-1,6-dihydropyridine-3-carboxamide).

In one embodiment, the bioactive agent is a RAS inhibitor. Examples of RAS inhibitors include but are not limited to Reolysin and siG12D LODER.

In one embodiment, the bioactive agent is a HSP inhibitor. HSP inhibitors include but are not limited to Geldanamycin or 17-N-Allylamino-17-demethoxygeldanamycin (17AAG), and Radicicol.

Additional bioactive compounds include, for example, everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an aurora kinase inhibitor, a PIK-1 modulator, an HDAC inhibitor, a c-MET inhibitor, a PARP inhibitor, a Cdk inhibitor, an IGFR-TK inhibitor, an anti-HGF antibody, a focal adhesion kinase inhibitor, a Map kinase kinase (mek) inhibitor, a VEGF trap antibody, pemetrexed, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdRiKRX-0402, lucanthone, LY317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES (diethyl stilbestrol), estradiol, estrogen, conjugated estrogen, bevacizumab, IMC-1C11, CHIR-258); 3-[5-(methylsulfonylpiperadinemethyl)-indolyl-quinolone, vatalanib, AG-013736, AVE-0005, goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, lonafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, Bacillus Calmette-Guerin (BCG) vaccine, adriamycin, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gleevec, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonist, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa and mixtures thereof.

In one embodiment, the bioactive agent is selected from, but are not limited to, Imatinib mesylate (Gleevac®), Dasatinib (Sprycel®), Nilotinib (Tasigna®), Bosutinib (Bosulif®), Trastuzumab (Herceptin®), trastuzumab-DM1, Pertuzumab (Perjeta™), Lapatinib (Tykerb®), Gefitinib (Iressa®), Erlotinib (Tarceva®), Cetuximab (Erbitux®), Panitumumab (Vectibix®), Vandetanib (Caprelsa®), Vemurafenib (Zelboraf®), Vorinostat (Zolinza®), Romidepsin (Istodax®), Bexarotene (Tagretin®), Alitretinoin (Panretin®), Tretinoin (Vesanoid®), Carfilizomib (Kyprolis™), Pralatrexate (Folotyn®), Bevacizumab (Avastin®), Ziv-aflibercept (Zaltrap®), Sorafenib (Nexavar®), Sunitinib (Sutent®), Pazopanib (Votrient®), Regorafenib (Stivarga®), and Cabozantinib (Cometriq™).

In certain aspects, the bioactive agent is an anti-inflammatory agent, a chemotherapeutic agent, a radiotherapeutic, an additional therapeutic agent, or an immunosuppressive agent.

Suitable chemotherapeutic bioactive agents include, but are not limited to, a radioactive molecule, a toxin, also referred to as cytotoxin or cytotoxic agent, which includes any agent that is detrimental to the viability of cells, and liposomes or other vesicles containing chemotherapeutic compounds. General anticancer pharmaceutical agents include: Vincristine (Oncovin®) or liposomal vincristine (Marqibo®), Daunorubicin (daunomycin or Cerubidine®) or doxorubicin (Adriamycin®), Cytarabine (cytosine arabinoside, ara-C, or Cytosar®), L-asparaginase (Elspar®) or PEG-L-asparaginase (pegaspargase or Oncaspar®), Etoposide (VP-16), Teniposide (Vumon®), 6-mercaptopurine (6-MP or Purinethol®), Methotrexate, Cyclophosphamide (Cytoxan®), Prednisone, Dexamethasone (Decadron), imatinib (Gleevec®), dasatinib (Sprycel®), nilotinib (Tasigna®), bosutinib (Bosulif®), and ponatinib (Iclusig™). Examples of additional suitable chemotherapeutic agents include but are not limited to 1-dehydrotestosterone, 5-fluorouracil decarbazine, 6-mercaptopurine, 6-thioguanine, actinomycin D, adriamycin, aldesleukin, an alkylating agent, allopurinol sodium, altretamine, amifostine, anastrozole, anthramycin (AMC)), an anti-mitotic agent, cis-dichlorodiamine platinum (II) (DDP) cisplatin), diamino dichloro platinum, anthracycline, an antibiotic, an antimetabolite, asparaginase, BCG live (intravesical), betamethasone sodium phosphate and betamethasone acetate, bicalutamide, bleomycin sulfate, busulfan, calcium leucouorin, calicheamicin, capecitabine, carboplatin, lomustine (CCNU), carmustine (BSNU), Chlorambucil, Cisplatin, Cladribine, Colchicin, conjugated estrogens, Cyclophosphamide, Cyclothosphamide, Cytarabine, Cytarabine, cytochalasin B, Cytoxan, Dacarbazine, Dactinomycin, dactinomycin (formerly actinomycin), daunirubicin HCL, daunorucbicin citrate, denileukin diftitox, Dexrazoxane, Dibromomannitol, dihydroxy anthracin dione, Docetaxel, dolasetron mesylate, doxorubicin HCL, dronabinol, *E. coli* L-asparaginase, emetine, epoetin-α, *Erwinia* L-asparaginase, esterified estrogens, estradiol, estramustine phosphate sodium, ethidium bromide, ethinyl estradiol, etidronate, etoposide citrororum factor, etoposide phosphate, filgrastim, floxuridine, fluconazole, fludarabine phosphate, fluorouracil, flutamide, folinic acid, gemcitabine HCL, glucocorticoids, goserelin acetate, gramicidin D, granisetron HCL, hydroxyurea, idarubicin HCL, ifosfamide, interferon α-2b, irinotecan HCL, letrozole, leucovorin calcium, leuprolide acetate, levamisole HCL, lidocaine, lomustine, maytansinoid, mechlorethamine HCL, medroxyprogesterone acetate, megestrol acetate, melphalan HCL, mercaptipurine, mesna, methotrexate, methyltestosterone, mithramycin, mitomycin C, mitotane, mitoxantrone, nilutamide, octreotide acetate, ondansetron HCL, paclitaxel, pamidronate disodium, pentostatin, pilocarpine HCL, plimycin, polifeprosan 20 with carmustine implant, porfimer sodium, procaine, procarbazine HCL, propranolol, rituximab, sargramostim, streptozotocin, tamoxifen, taxol, teniposide, tenoposide, testolactone, tetracaine, thioepa chlorambucil, thioguanine, thiotepa, topotecan HCL, toremifene citrate, trastuzumab, tretinoin, valrubicin, vinblastine sulfate, vincristine sulfate, and vinorelbine tartrate.

Additional therapeutic agents that can be administered in combination with a degronimer disclosed herein can include bevacizumab, sutinib, sorafenib, 2-methoxyestradiol or 2ME2, finasunate, vatalanib, vandetanib, aflibercept, volociximab, etaracizumab (MEDI-522), cilengitide, erlotinib, cetuximab, panitumumab, gefitinib, trastuzumab, dovitinib, figitumumab, atacicept, rituximab, alemtuzumab, aldesleukine, atlizumab, tocilizumab, temsirolimus, everolimus, lucatumumab, dacetuzumab, HLL1, huN901-DM1, atiprimod, natalizumab, bortezomib, carfilzomib, marizomib, tanespimycin, saquinavir mesylate, ritonavir, nelfinavir mesylate, indinavir sulfate, belinostat, panobinostat, mapatumumab, lexatumumab, dulanermin, ABT-737, oblimersen, plitidepsin, talmapimod, P276-00, enzastaurin, tipifarnib, perifosine, imatinib, dasatinib, lenalidomide, thalidomide, simvastatin, celecoxib, bazedoxifene, AZD4547, rilotumumab, oxaliplatin (Eloxatin), PD0332991, ribociclib (LEE011), amebaciclib (LY2835219), HDM201, fulvestrant (Faslodex), exemestane (Aromasin), PIM447, ruxolitinib (INC424), BGJ398, necitumumab, pemetrexed (Alimta), and ramucirumab (IMC-1121B).

In one aspect of the invention, the disclosed compound is administered in combination with an anti-infective agent, for example but not limited to an anti-HIV agent, anti-HCV agent, anti-HBV agent, or other anti-viral or anti-bacterial agent. In one embodiment, the anti-HIV agent can be, but is not limited to, for example, a nucleoside reverse transcriptase inhibitor (NRTI), other non-nucleoside reverse transcriptase inhibitor, protease inhibitor, fusion inhibitor, among others. Nucleoside/Nucleotide Reverse Transcriptase Inhibitors (NRTIs) include, but are not limited to, Abacavir or ABC (Ziagen), Didanosine or ddI (Videx), Emtricitabine or FTC (Emtriva), Lamivudine or 3TC (Epivir), ddC (zalcitabine), Stavudine or d4T (Zerit), Tenofovircor TDF (Viread), D-D4FC (Reverset), and Zidovudine or AZT or ZDV (Retrovir). Non-nucleoside Reverse Transcriptase Inhibitors (NNRTIs) include, but are not limited to, Delavirdine (Rescriptor), Efavirenz (Sustiva), Etravirine (Intelence), Nevirapine (Viramune), and Rilpivirine (Edurant). Anti-HIV Protease Inhibitors (PIs) include, but are not limited to, Atazanavir or ATV (Reyataz), Darunavir or DRV (Prezista), Fosamprenavir or FPV (Lexiva), Indinavir or IDV (Crixivan), Lopinavir+ritonavir, or LPV/r (Kaletra), Nelfinavir or NFV (Viracept), Ritonavir or RTV (Norvir), Saquinavir or SQV (Invirase), Tipranavir, or TPV (Aptivus), Cobicistat (Tybost), Atazanavir+cobicistat, or ATV/COBI (Evotaz), Darunavir+cobicistat, or DRV/COBI (Prezcobix). Anti-HIV Fusion Inhibitors include, but are not limited to, Enfuvirtide or ENF or T-20 (Fuzeon). Anti-HIV also include, but are not limited to, Maraviroc or MVC (Selzentry). Anti-HIV Integrase Inhibitors include, but are not limited to Dolutegravir (Tivicay), Elvitegravir (Vitekta), Raltegravir (Isentress). Anti-HIV combinations agents include Abacavir+Dolutegravir+lamivudine, or ABC/DTG/3TC (Triumeq), Abacavir+lamivudine or ABC/3TC (Epzicom), Abacavir+lamivudine+zidovudine, or ABC/3TC/ZDV (Trizivir), Efavirenz+emtricitabine+tenofovir or EFV/FTC/TDF (Atripla, Tribuss), elvitegravir, cobicistat, emtricitabine, tenofovir alafenamide or EVG/COBI/FTC/TAF or ECF/TAF (Genvoya; (Stribild), emtricitabine+rilpivirine+tenofovir or FTC/RPV/TAF (Odefsey); Emtricitabine+rilpivirine+tenofovir or FTC/RPV/TDF (Complera), Emtricitabine+tenofovir or TAF/FTC (Descovy), emtricitabine and tenofovir disoproxil fumarate (Truvada), and Lamivudine+zidovudine or 3TC/ZDV (Combivir). Other anti-HIV compounds include, but are not limited to Racivir, L-FddC, L-FD4C, SQVM (Saquinavir mesylate), IDV (Indinavir), SQV (Saquinavir), APV (Amprenavir), LPV (Lopinavir), fusion inhibitors such as T20, among others, fuseon and mixtures thereof, including anti-HIV compounds presently in clinical trials or in development.

Other anti-HIV agents which may be used in co-administration with the disclosed compounds according to the present invention. NNRTIs may be selected from the group consisting of nevirapine (BI-R6-587), delavirdine (U-90152S/T), efavirenz (DMP-266), UC-781 (N-[4-chloro-3-(3-methyl-2-butenyloxy)phenyl]-2methyl3-furancarbothiamide), etravirine (TMC125), Trovirdine (Ly300046.HCl), HI-236, HI-240, HI-280, HI-281, rilpivirine (TMC-278), MSC-127, HBY 097, DMP266, Baicalin (TJN-151) ADAM-II (Methyl 3',3'-dichloro-4',4"-dimethoxy-5',5"-bis(methoxycarbonyl)-6,6-diphenylhexenoate), Methyl 3-Bromo-5-(1-5-bromo-4-methoxy-3-(methoxycarbonyl)phenyl)hept-1-enyl)-2-methoxybenzoate (Alkenyl-diarylmethane analog, Adam analog), (5-chloro-3-(phenylsulfinyl)-2'-indolecarboxamide), AAP-BHAP (U-104489 or PNU-104489), Capravirine (AG-1549, S-1153), atevirdine (U-87201E), aurin tricarboxylic acid (SD-095345), 1-[(6-cyano-2-indolyl)carbonyl]-4-[3-(isopropylamino)-2-pyridinyl]piperazine, 1-[5-[[N-(methyl)methylsulfonylamino]-2-indolylcarbonyl-4-[3-(isopropylamino)-2-pyridinyl]piperazine, 1-[3-(Ethylamino)-2-[pyridinyl]-4-[(5-hydroxy-2-indolyl)carbonyl]piperazine, 1-[(6-Formyl-2-indolyl)carbonyl]-4-[3-(isopropylamino)-2-pyridinyl]piperazine, 1-[[5-(Methylsulfonyloxy)-2-indoyly)carbonyl]-4-[3-(isopropylamino)-2-pyridinyl]piperazine, U88204E, Bis(2-nitrophenyl)sulfone (NSC 633001), Calanolide A (NSC675451), Calanolide B, 6-Benzyl-5-methyl-2-(cyclohexyloxy)pyrimidin-4-one (DABO-546), DPC 961, E-EBU, E-EBU-dm, E-EPSeU, E-EPU, Foscarnet (Foscavir), HEPT (1-[(2-Hydroxyethoxy)methyl]-6-(phenylthio)thymine), HEPT-M (1-[(2-Hydroxyethoxy)methyl]-6-(3-methylphenyl)thio)thymine), HEPT-S (1-[(2-Hydroxyethoxy)methyl]-6-(phenylthio)-2-thiothymine), Inophyllum P, L-737,126, Michellamine A (NSC650898), Michellamine B (NSC649324), Michellamine F, 6-(3,5-Dimethylbenzyl)-1-[(2-hydroxyethoxy)methyl]-5-isopropyluracil, 6-(3,5-Dimethylbenzyl)-1-(ethyoxymethyl)-5-isopropyluracil, NPPS, E-BPTU (NSC 648400), Oltipraz (4-Methyl-5-(pyrazinyl)-3H-1,2-dithiole-3-thione), N-{2-(2-Chloro-6-fluorophenethyl]-N'-(2-thiazolyl)thiourea (PETT $C_1$, F derivative), N-{2-(2,6-Difluorophenethyl]-N'-[2-(5-bromopyridyl)]thiourea {PETT derivative), N-{2-(2,6-Difluorophenethyl]-N'-[2-(5-methylpyridyl]thiourea {PETT Pyridyl derivative), N-[2-(3-Fluorofuranyl)ethyl]-N'-[2-(5-chloropyridyl)]thiourea, N-[2-(2-Fluoro-6-ethoxyphenethyl)]-N'-[2-(5-bromopyridyl)]thiourea, N-(2-Phenethyl)-N'-(2-thiazolyl)thiourea (LY-73497), L-697,639, L-697,593, L-697,661, 342-(4,7-Difluorobenzoxazol-2-yl)ethyl}-5-ethyl-6-methyl (pypridin-2(1H)-thione (2-Pyridinone Derivative), 3-[[(2-Methoxy-5,6-dimethyl-3-pyridyl)methyl]amine]-5-ethyl-6-methyl(pypridin-2(1H)-thione, R82150, R82913, R87232, R88703, R89439 (Loviride), R90385, S-2720, Suramin Sodium, TBZ (Thiazolobenzimidazole, NSC 625487), Thiazoloisoindol-5-one, (+)(R)-9b-(3,5-Dimethylphenyl-2,3-dihydrothiazolo[2,3-a]isoindol-5 (9bH)-one, Tivirapine (R86183), UC-38 and UC-84, among others.

In one aspect of the invention, the disclosed compound when used to treat an HCV infection can be administered in combination with another anti-HCV agent. Anti-HCV agents are known in the art. To date, a number of fixed dose drug combinations have been approved for the treatment of HCV. Harvoni® (Gilead Sciences, Inc.) contains the NS5A inhibitor ledipasvir and the NS5B inhibitor sofosbuvir. Technivie™ (AbbVie, Inc.) is a fixed-dose combination containing ombitasvir, an NS5A inhibitor; paritaprevir, an NS3/4A protease inhibitor; and ritonavir, a CYP3A inhibitor. Daklinza™ (daclatasvir, Bristol-Myers Squibb) is a HCV NS5A inhibitor indicated for use with sofosbuvir for the treatment of chronic genotype 3 infection. Zepatier™ (Merck & Co.) has recently been approved for the treatment of chronic HCV genotypes 1 and 4. Zepatier™ is a fixed-dose combination product containing elbasvir, an HCV NS5A inhibitor, and grazoprevir, an HCV NS3/4A protease inhibitor. Zepatier™ is indicated with or without ribavirin. Epclusa® (Gilead Sciences, Inc.) is a fixed-dose combination tablet containing sofosbuvir and velpatasvir. Additional anti-HCV agents and combinations thereof include those described in U.S. Pat. Nos. 9,382,218; 9,321,753; 9,249,176; 9,233,974; 9,221,833; 9,211,315; 9,194,873; 9,186,369; 9,180,193; 9,156,823; 9,138,442; 9,133,170; 9,108,999; 9,090,559; 9,079,887; 9,073,943; 9,073,942; 9,056,090; 9,051,340; 9,034,863; 9,029,413; 9,011,938; 8,987,302; 8,945,584; 8,940,718; 8,927,484; 8,921,341; 8,884,030; 8,841,278; 8,822,430; 8,772,022; 8,765,722; 8,742,101; 8,741,946; 8,674,085; 8,673,288; 8,669,234; 8,663,648; 8,618,275; 8,580,252; 8,575,195; 8,575,135; 8,575,118; 8,569,302; 8,524,764; 8,513,298; 8,501,714; 8,404,651; 8,273,341; 8,257,699; 8,197,861; 8,158,677; 8,105,586; 8,093,353; 8,088,368; 7,897,565; 7,871,607; 7,846,431; 7,829,081; 7,829,077; 7,824,851; 7,572,621; and 7,326,536; patents assigned to Alios: U.S. Pat. Nos. 9,365,605; 9,346,848; 9,328,119; 9,278,990; 9,249,174; 9,243,022; 9,073,960; 9,012,427; 8,980,865; 8,895,723; 8,877,731; 8,871,737; 8,846,896 and 8,772,474; Achillion U.S. Pat. Nos. 9,273,082; 9,233,136; 9,227,952; 9,133,115; 9,125,904; 9,115,175; 9,085,607; 9,006,423; 8,946,422; 8,835,456; 8,809,313; 8,785,378; 8,614,180; 8,445,430; 8,435,984; 8,183,263; 8,173,636; 8,163,693; 8,138,346; 8,114,888; 8,106,209; 8,088,806; 8,044,204; 7,985,541; 7,906,619; 7,902,365; 7,767,706; 7,741,334; 7,718,671; 7,659,399; 7,476,686; 7,439,374; 7,365,068; 7,199,128; and 7,094,807; Cocrystal Pharma Inc. U.S. Pat. Nos. 9,181,227; 9,173,893; 9,040,479 and 8,771,665; Gilead Sciences U.S. Pat. Nos. 9,353,423; 9,346,841; 9,321,800; 9,296,782; 9,296,777; 9,284,342; 9,238,039; 9,216,996; 9,206,217; 9,161,934; 9,145,441; 9,139,604; 9,090,653; 9,090,642; 9,085,573; 9,062,092; 9,056,860; 9,045,520; 9,045,462; 9,029,534; 8,980,878; 8,969,588; 8,962,652; 8,957,046; 8,957,045; 8,946,238; 8,933,015; 8,927,741; 8,906,880; 8,889,159; 8,871,785; 8,841,275; 8,815,858; 8,809,330; 8,809,267; 8,809,266; 8,779,141; 8,765,710; 8,759,544; 8,759,510; 8,735,569; 8,735,372; 8,729,089; 8,722,677; 8,716,264; 8,716,263; 8,716,262; 8,697,861; 8,664,386; 8,642,756; 8,637,531; 8,633,309; 8,629,263; 8,618,076; 8,592,397; 8,580,765; 8,569,478; 8,563,530; 8,551,973; 8,536,187; 8,513,186; 8,513,184; 8,492,539; 8,486,938; 8,481,713; 8,476,225; 8,420,597; 8,415,322; 8,338,435; 8,334,270; 8,329,926; 8,329,727; 8,324,179; 8,283,442; 8,263,612; 8,232,278; 8,178,491; 8,173,621; 8,163,718; 8,143,394; patents assigned to Idenix, acquired by Merck, include U.S. Pat. Nos. 9,353,100; 9,309,275; 9,296,778; 9,284,307; 9,249,173; 9,243,025; 9,211,300; 9,187,515; 9,187,496, 9,109,001; 8,993,595; 8,951,985; 8,691,788; 8,680,071; 8,637,475; 8,507,460; 8,377,962; 8,362,068; 8,343,937; 8,299,038; 8,193, 372; 8,093,379; 7,951,789; 7,932,240; 7,902,202; 7,662,798; 7,635,689; 7,625,875; 7,608,600; 7,608,597; 7,582,618; 7,547,704; 7,456,155; 7,384,924; 7,365,057; 7,192,936; 7,169,766; 7,163,929; 7,157,441; 7,148,206; 7,138,376; 7,105,493; 6,914,054 and 6,812,219; patents assigned to Merck include U.S. Pat. Nos. 9,364,482; 9,339,541; 9,328,138; 9,265,773; 9,254,292; 9,243,002; 9,242,998; 9,242,988; 9,242,917; 9,238,604; 9,156,872; 9,150,603; 9,139,569; 9,120,818; 9,090,661; 9,073,825; 9,061,041; 8,987,195; 8,980,920; 8,927,569; 8,871,759; 8,828,930; 8,772,505; 8,715,638; 8,697,694; 8,637,449; 8,609,635; 8,557,848; 8,546,420; 8,541,434; 8,481,712; 8,470,834; 8,461,107; 8,404,845; 8,377,874; 8,377,873; 8,354,518; 8,349,869; 8,309,540; 8,278,322; 8,216,999; 8,148,349; 8,138,164; 8,080,654; 8,071,568; 7,973,040; 7,935,812; 7,915,400; 7,879,815; 7,879,797; 7,632,821; 7,569,374; 7,534,767; 7,470,664 and 7,329,732; patent application publication US 2013/0029904 to Boehringer Ingelheim GMBH and US 2014/0113958 to Stella Aps.

In one embodiment, the additional therapy is a monoclonal antibody (MAb). Some MAbs stimulate an immune response that destroys cancer cells. Similar to the antibodies produced naturally by B cells, these MAbs may "coat" the cancer cell surface, triggering its destruction by the immune system. For example, bevacizumab targets vascular endothelial growth factor (VEGF), a protein secreted by tumor cells and other cells in the tumor's microenvironment that promotes the development of tumor blood vessels. When bound to bevacizumab, VEGF cannot interact with its cellular receptor, preventing the signaling that leads to the growth of new blood vessels. Similarly, cetuximab and panitumumab target the epidermal growth factor receptor (EGFR), and trastuzumab targets the human epidermal growth factor receptor 2 (HER-2). MAbs that bind to cell surface growth factor receptors prevent the targeted receptors from sending their normal growth-promoting signals. They may also trigger apoptosis and activate the immune system to destroy tumor cells.

In one aspect of the present invention, the bioactive agent is an immunosuppressive agent. The immunosuppressive agent can be a calcineurin inhibitor, e.g. a cyclosporin or an ascomycin, e.g. Cyclosporin A (NEORAL®), FK506 (tacrolimus), pimecrolimus, a mTOR inhibitor, e.g. rapamycin or a derivative thereof, e.g. Sirolimus (RAPAMUNE®), Everolimus (Certican®), temsirolimus, zotarolimus, biolimus-7, biolimus-9, a rapalog, e.g. ridaforolimus, azathioprine, campath 1H, a S1P receptor modulator, e.g. fingolimod or an analogue thereof, an anti IL-8 antibody, mycophenolic acid or a salt thereof, e.g. sodium salt, or a prodrug thereof, e.g. Mycophenolate Mofetil (CELLCEPT®), OKT3 (ORTHOCLONE OKT3®), Prednisone, ATGAM®, THYMOGLOBULIN®, Brequinar Sodium, OKT4, T10B9.A-3A, 33B3.1, 15-deoxyspergualin, tresperimus, Leflunomide ARAVA®, CTLAI-Ig, anti-CD25, anti-IL2R, Basiliximab (SIMULECT®), Daclizumab (ZENAPAX®), mizorbine, methotrexate, dexamethasone, ISAtx-247, SDZ ASM 981 (pimecrolimus, Elidel®), CTLA4Ig (Abatacept), belatacept, LFA3Ig, etanercept (sold as Enbrel® by Immunex), adalimumab (Humira®), infliximab (Remicade®), an anti-LFA-1 antibody, natalizumab (Antegren®), Enlimomab, gavilimomab, antithymocyte immunoglobulin, siplizumab, Alefacept efalizumab, pentasa, mesalazine, asacol, codeine phosphate, benorylate, fenbufen, naprosyn, diclofenac, etodolac and indomethacin, aspirin and ibuprofen.

V. Pharmaceutical Compositions

The compounds of Formula I, II, III, VI, V and VI as disclosed herein can be administered as the neat chemical, but are more typically administered as a pharmaceutical composition, that includes an effective amount for a host, typically a human, in need of such treatment for any of the disorders described herein. Accordingly, the disclosure provides pharmaceutical compositions comprising an effective amount of the disclosed compound or pharmaceutically acceptable salt thereof together with at least one pharmaceutically acceptable carrier for any of the uses described herein. The pharmaceutical composition may contain the disclosed compound or salt as the only active agent, or, in an alternative embodiment, the disclosed compound and at least one additional active agent.

Compounds disclosed herein may be administered by any suitable route desired by the healthcare provider, including orally, topically, systemically, parenterally, by inhalation or spray, sublingually, via implant, including ocular implant, transdermally, via buccal administration, rectally, as an ophthalmic solution, injection, including ocular injection, intravenous, intra-arterial, intra-aortal, intracranial, subdermal, intraperitioneal, subcutaneous, transnasal, sublingual, or rectal or by other means, in dosage unit formulations containing conventional pharmaceutically acceptable carriers.

In general, the compositions of the disclosure will be administered in a therapeutically effective amount by the desired mode of administration. Suitable dosage ranges depend upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this application, to ascertain a therapeutically effective amount of the compositions of the disclosure for a given disease.

In certain embodiments the pharmaceutical composition is in a dosage form that contains from about 0.1 mg to about 2000 mg, from about 10, 25, 50 or 100 mg to about 1000 mg, from about 100 mg to about 800 mg, or from about 50 to 500, 75 to 500, or 200 mg to about 600 mg of the active compounds and optionally for example from about 0.1 mg to about 2000 mg, from about 10, 25, 50 or 100 mg to about 1000 mg, from about 50 to 500, 75 to 500, from about 100 mg to about 800 mg, or from about 200 mg to about 600 mg of an additional active agent in a unit dosage form. Examples are dosage forms with at least 0.1, 1, 5, 10, 25, 50, 100, 200, 250, 300, 400, 500, 600, 700, 750 or 800 mg of active compound, or its salt.

The therapeutically effective dosage of any active compound described herein will be determined by the health care practitioner depending on the condition, size and age of the patient as well as the route of delivery. In one non-limited embodiment, a dosage from about 0.1 to about 200 mg/kg, from about 0.01 mg/kg to about 250 mg/kg body weight, more preferably about 0.1 mg/kg to up to about 1, 2, 3, 4, 5, 6, 7, 8, 9, 10, 20 or 30 mg/kg, in at least one dose. In some embodiments, the dosage may be the amount of compound needed to provide a serum concentration of the active compound of up to about 10 nM, 50 nM, 100 nM, 200 nM, 300 nM, 400 nM, 500 nM, 600 nM, 700 nM, 800 nM, 900 nM, 1 µM, 5 µM, 10 µM, 20 µM, 30 µM, or 40 µM.

The pharmaceutical composition may be formulated as any pharmaceutically useful form, e.g., as an aerosol, a cream, a gel, a pill, an injection or infusion solution, a capsule, a tablet, a syrup, a transdermal patch, a subcutaneous patch, a dry powder, an inhalation formulation, in a medical device, suppository, buccal, or sublingual formulation, parenteral formulation, or an ophthalmic solution. Some dosage forms, such as tablets and capsules, are subdivided into suitably sized unit doses containing appropriate quantities of the active components, e.g., an effective amount to achieve the desired purpose.

"Pharmaceutically acceptable carriers" for therapeutic use are well known in the pharmaceutical art, and are described, for example, in Remington's Pharmaceutical Sciences, 18th Edition (Easton, Pa.: Mack Publishing Company, 1990). For example, sterile saline and phosphate-buffered saline at physiological pH can be used. Preservatives, stabilizers, dyes and even flavoring agents can be provided in the pharmaceutical composition. For example, sodium benzoate, sorbic acid and esters of p-hydroxybenzoic acid can be added as preservatives. Id. at 1449. In addition, antioxidants and suspending agents can be used. Id. Carriers include excipients must be of sufficiently high purity and sufficiently low toxicity to render them suitable for administration to the patient being treated. The carrier can be inert or it can possess pharmaceutical benefits of its own. The amount of carrier employed in conjunction with the disclosed compound is sufficient to provide a practical quantity of material for administration per unit dose of the compound, as described in more detail herein.

Classes of carriers include, but are not limited to binders, buffering agents, coloring agents, diluents, disintegrants, emulsifiers, flavorants, glidents, lubricants, preservatives, stabilizers, surfactants, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin; talc, and vegetable oils. Optional active agents may be included in a pharmaceutical composition, which do not substantially interfere with the activity of the disclosed compounds of the present invention.

Additionally, auxiliary substances, such as wetting or emulsifying agents, biological buffering substances, surfactants, and the like, can be present in such vehicles. A biological buffer can be any solution which is pharmacologically acceptable and which provides the formulation with the desired pH, i.e., a pH in the physiologically acceptable range. Examples of buffer solutions include saline, phosphate buffered saline, Tris buffered saline, Hank's buffered saline, and the like.

Depending on the intended mode of administration, the pharmaceutical compositions can be in the form of solid, semi-solid or liquid dosage forms, such as, for example, tablets, suppositories, pills, capsules, powders, liquids, suspensions, creams, ointments, lotions or the like, preferably in unit dosage form suitable for single administration of a precise dosage. The compositions will include an effective amount of the selected drug in combination with a pharmaceutically acceptable carrier and, in addition, can include other pharmaceutical agents, adjuvants, diluents, buffers, and the like.

Thus, the compositions of the disclosure can be administered as pharmaceutical formulations including those suitable for oral (including buccal and sub-lingual), rectal, nasal, topical, pulmonary, vaginal or parenteral (including intramuscular, intra-arterial, intrathecal, subcutaneous and intravenous) administration or in a form suitable for administration by inhalation or insufflation. The preferred manner of administration is intravenous or oral using a convenient daily dosage regimen which can be adjusted according to the degree of affliction.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, and the like, an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered can also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, and the like. Actual methods of preparing such dosage forms are known, or will be apparent, to those skilled in this art; for example, see Remington's Pharmaceutical Sciences, referenced above.

In yet another embodiment is the use of permeation enhancer excipients including polymers such as: polycations (chitosan and its quaternary ammonium derivatives, poly-L-arginine, aminated gelatin); polyanions (N-carboxymethyl chitosan, poly-acrylic acid); and, thiolated polymers (carboxymethyl cellulose-cysteine, polycarbophil-cysteine, chitosan-thiobutylamidine, chitosan-thioglycolic acid, chitosan-glutathione conjugates).

For oral administration, the composition will generally take the form of a tablet, capsule, a softgel capsule or can be an aqueous or nonaqueous solution, suspension or syrup. Tablets and capsules are preferred oral administration forms. Tablets and capsules for oral use can include one or more commonly used carriers such as lactose and corn starch. Lubricating agents, such as magnesium stearate, are also typically added. Typically, the compositions of the disclosure can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

When liquid suspensions are used, the active agent can be combined with any oral, non-toxic, pharmaceutically acceptable inert carrier such as ethanol, glycerol, water, and the like and with emulsifying and suspending agents. If desired, flavoring, coloring and/or sweetening agents can be added as well. Other optional components for incorporation into an oral formulation herein include, but are not limited to, preservatives, suspending agents, thickening agents, and the like.

Parenteral formulations can be prepared in conventional forms, either as liquid solutions or suspensions, solid forms suitable for solubilization or suspension in liquid prior to injection, or as emulsions. Preferably, sterile injectable suspensions are formulated according to techniques known in the art using suitable carriers, dispersing or wetting agents and suspending agents. The sterile injectable formulation can also be a sterile injectable solution or a suspension in a nontoxic parenterally acceptable diluent or solvent. Among the acceptable vehicles and solvents that can be employed are water, Ringer's solution and isotonic sodium chloride solution. In addition, sterile, fixed oils, fatty esters or polyols are conventionally employed as solvents or suspending media. In addition, parenteral administration can involve the use of a slow release or sustained release system such that a constant level of dosage is maintained.

Parenteral administration includes intraarticular, intravenous, intramuscular, intradermal, intraperitoneal, and subcutaneous routes, and include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Administration via certain parenteral routes can involve introducing the formulations of the disclosure into the body of a patient through a needle or a catheter, propelled by a sterile syringe or some other mechanical device such as an continuous infusion system. A formulation provided by the disclosure can be administered using a syringe, injector, pump, or any other device recognized in the art for parenteral administration.

Preferably, sterile injectable suspensions are formulated according to techniques known in the art using suitable carriers, dispersing or wetting agents and suspending agents. The sterile injectable formulation can also be a sterile injectable solution or a suspension in a nontoxic parenterally acceptable diluent or solvent. Among the acceptable vehicles and solvents that can be employed are water, Ringer's solution and isotonic sodium chloride solution. In addition, sterile, fixed oils, fatty esters or polyols are conventionally employed as solvents or suspending media. In addition, parenteral administration can involve the use of a slow release or sustained release system such that a constant level of dosage is maintained.

Preparations according to the disclosure for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms can also contain adjuvants such as preserving, wetting, emulsifying, and dispersing agents. They can be sterilized by, for example, filtration through a bacteria retaining filter, by incorporating sterilizing agents into the compositions, by irradiating the compositions, or by heating the compositions. They can also be manufactured using sterile water, or some other sterile injectable medium, immediately before use.

Sterile injectable solutions are prepared by incorporating one or more of the compounds of the disclosure in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. Thus, for example, a parenteral composition suitable for administration by injection is prepared by stirring 1.5% by weight of active ingredient in 10% by volume propylene glycol and water. The solution is made isotonic with sodium chloride and sterilized.

Formulations suitable for rectal administration are typically presented as unit dose suppositories. These may be prepared by admixing the active disclosed compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the active compound. In one embodiment, microneedle patches or devices are provided for delivery of drugs across or into biological tissue, particularly the skin. The microneedle patches or devices permit drug delivery at clinically relevant rates across or into skin or other tissue barriers, with minimal or no damage, pain, or irritation to the tissue.

Formulations suitable for administration to the lungs can be delivered by a wide range of passive breath driven and active power driven single/-multiple dose dry powder inhalers (DPI). The devices most commonly used for respiratory delivery include nebulizers, metered-dose inhalers, and dry powder inhalers. Several types of nebulizers are available, including jet nebulizers, ultrasonic nebulizers, and vibrating mesh nebulizers. Selection of a suitable lung delivery device depends on parameters, such as nature of the drug and its formulation, the site of action, and pathophysiology of the lung.

Additional non-limiting examples of drug delivery devices and methods include, for example, US20090203709 titled "Pharmaceutical Dosage Form For Oral Administration Of Tyrosine Kinase Inhibitor" (Abbott Laboratories); US20050009910 titled "Delivery of an active drug to the posterior part of the eye via subconjunctival or periocular delivery of a prodrug", US 20130071349 titled "Biodegradable polymers for lowering intraocular pressure", U.S. Pat. No. 8,481,069 titled "Tyrosine kinase microspheres", U.S. Pat. No. 8,465,778 titled "Method of making tyrosine kinase microspheres", U.S. Pat. No. 8,409,607 titled "Sustained release intraocular implants containing tyrosine kinase inhibitors and related methods", U.S. Pat. No. 8,512,738 and US 2014/0031408 titled "Biodegradable intravitreal tyrosine kinase implants", US 2014/0294986 titled "Microsphere Drug Delivery System for Sustained Intraocular Release", U.S. Pat. No. 8,911,768 titled "Methods For Treating Retinopathy With Extended Therapeutic Effect" (Allergan, Inc.); U.S. Pat. No. 6,495,164 titled "Preparation of injectable suspensions having improved injectability" (Alkermes Controlled Therapeutics, Inc.); WO 2014/047439 titled "Biodegradable Microcapsules Containing Filling Material" (Akina, Inc.); WO 2010/132664 titled "Compositions And Methods For Drug Delivery" (Baxter International Inc. Baxter Healthcare SA); US20120052041 titled "Polymeric nanoparticles with enhanced drug loading and methods of use thereof" (The Brigham and Women's Hospital, Inc.); US20140178475, US20140248358, and US20140249158 titled "Therapeutic Nanoparticles Comprising a Therapeutic Agent and Methods of Making and Using Same" (BIND Therapeutics, Inc.); U.S. Pat. No. 5,869,103 titled "Polymer microparticles for drug delivery" (Danbiosyst UK Ltd.); U.S. Pat. No. 8,628,801 titled "Pegylated Nanoparticles" (Universidad de Navarra); US2014/0107025 titled "Ocular drug delivery system" (Jade Therapeutics, LLC); U.S. Pat. No. 6,287,588 titled "Agent delivering system comprised of microparticle and biodegradable gel with an improved releasing profile and methods of use thereof", U.S. Pat. No. 6,589,549 titled "Bioactive agent delivering system comprised of microparticles within a biodegradable to improve release profiles" (Macromed, Inc.); U.S. Pat. Nos. 6,007,845 and 5,578,325 titled "Nanoparticles and microparticles of non-linear hydrophilic hydrophobic multiblock copolymers" (Massachusetts Institute of Technology); US20040234611, US20080305172, US20120269894, and US20130122064 titled "Ophthalmic depot formulations for periocular or subconjunctival administration (Novartis Ag); U.S. Pat. No. 6,413,539 titled "Block polymer" (Poly-Med, Inc.); US 20070071756 titled "Delivery of an agent to ameliorate inflammation" (Peyman); US 20080166411 titled "Injectable Depot Formulations And Methods For Providing Sustained Release Of Poorly Soluble Drugs Comprising Nanoparticles" (Pfizer, Inc.); U.S. Pat. No. 6,706,289 titled "Methods and compositions for enhanced delivery of bioactive molecules" (PR Pharmaceuticals, Inc.); and U.S. Pat. No. 8,663,674 titled "Microparticle containing matrices for drug delivery" (Surmodics).

VI. General Synthesis

Compounds of the present invention without stereocenters for convenience. One skilled in the art will recognize that pure enantiomers and diastereomers can be prepared by methods known in the art. Examples of methods to obtain optically active materials include at least the following.

i) physical separation of crystals—a technique whereby macroscopic crystals of the individual enantiomers are manually separated. This technique can be used if crystals of the separate enantiomers exist, i.e., the material is a conglomerate, and the crystals are visually distinct;

ii) simultaneous crystallization—a technique whereby the individual enantiomers are separately crystallized from a solution of the racemate, possible only if the latter is a conglomerate in the solid state;

iii) enzymatic resolutions—a technique whereby partial or complete separation of a racemate by virtue of differing rates of reaction for the enantiomers with an enzyme;

iv) enzymatic asymmetric synthesis—a synthetic technique whereby at least one step of the synthesis uses an enzymatic reaction to obtain an enantiomerically pure or enriched synthetic precursor of the desired enantiomer;

v) chemical asymmetric synthesis—a synthetic technique whereby the desired enantiomer is synthesized from an achiral precursor under conditions that produce asymmetry (i.e., chirality) in the product, which may be achieved using chiral catalysts or chiral auxiliaries;

vi) diastereomer separations—a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations—a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors—a synthetic technique whereby the desired enantiomer is obtained from non-chiral starting materials and where the stereochemical integrity is not or is only minimally compromised over the course of the synthesis;

x) chiral liquid chromatography—a technique whereby the enantiomers of a racemate are separated in a liquid mobile phase by virtue of their differing interactions with a stationary phase (including via chiral HPLC). The stationary phase can be made of chiral material or the mobile phase can contain an additional chiral material to provoke the differing interactions;

xi) chiral gas chromatography—a technique whereby the racemate is volatilized and enantiomers are separated by virtue of their differing interactions in the gaseous mobile phase with a column containing a fixed non-racemic chiral adsorbent phase;

xii) extraction with chiral solvents—a technique whereby the enantiomers are separated by virtue of preferential dissolution of one enantiomer into a particular chiral solvent;

xiii) transport across chiral membranes—a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane that allows only one enantiomer of the racemate to pass through.

xiv) simulated moving bed chromatography, is used in one embodiment. A wide variety of chiral stationary phases are commercially available.

The compounds described herein can be prepared by methods known by those skilled in the art. In one non-limiting example the disclosed compounds can be made by the following schemes.

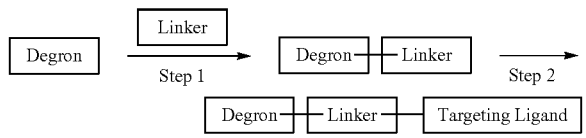

Scheme 1

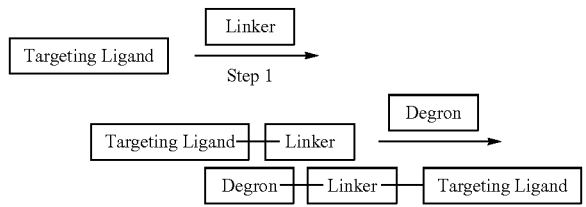

Scheme 2

As shown in Scheme 1 compounds for use in the present invention can be prepared by chemically combining a Degron and a Linker followed by subsequent addition of a Targeting Ligand. Similarly, in Scheme 2 compounds for use in the present invention are prepared by chemically combing a Targeting Ligand and Linker first, followed by subsequent addition of a Degron. As illustrated in the above and following schemes, compounds for use in the present invention can readily be synthesized by one skilled in the art in a variety of methods and chemical reactions.

Scheme 3

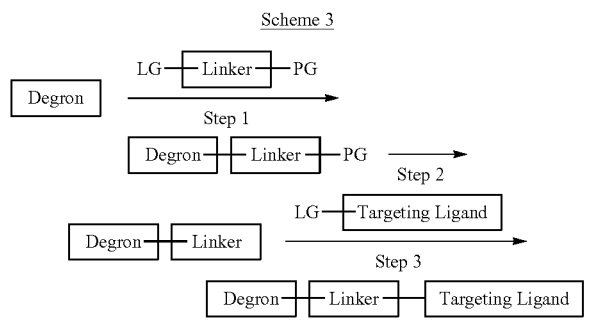

Scheme 3: In Step 1, a nucleophilic Degron displaces a leaving group on the Linker to make a Degron Linker fragment. In Step 2, the protecting group is removed by methods known in the art to free a nucleophilic site on the linker. In Step 3, the nucleophilic Degron Linker fragment displaces a leaving group on the Targeting Ligand to form a compound for use in the present invention. In an alternative embodiment Step 1 and/or Step 2 is accomplished by a coupling reaction instead of a nucleophilic attack.

Scheme 4

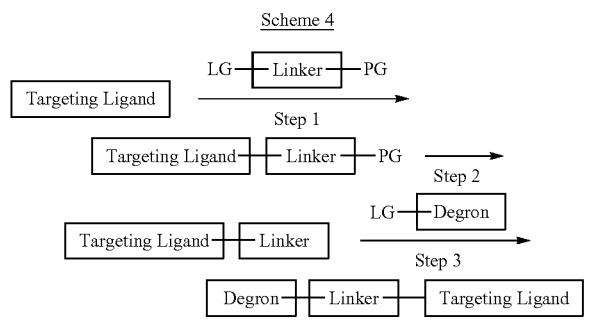

Scheme 4: In Step 1, a nucleophilic Targeting Ligand displaces a leaving group on the Linker to make a Targeting Ligand Linker fragment. In Step 2, the protecting group is removed by methods known in the art to free a nucleophilic site on the linker. In Step 3, the nucleophilic Targeting Ligand Linker fragment displaces a leaving group on the Degron to form a compound for use in the present invention. In an alternative embodiment Step 1 and/or Step 2 is accomplished by a coupling reaction instead of a nucleophilic attack.

Scheme 5

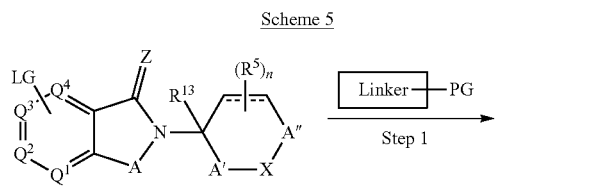

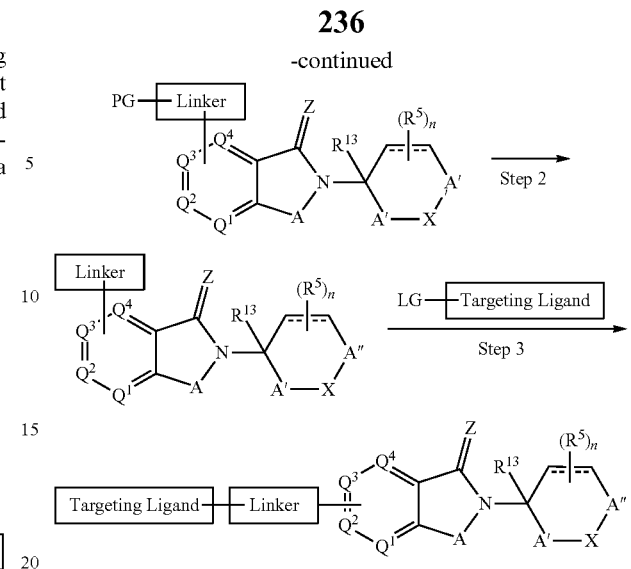

Scheme 6

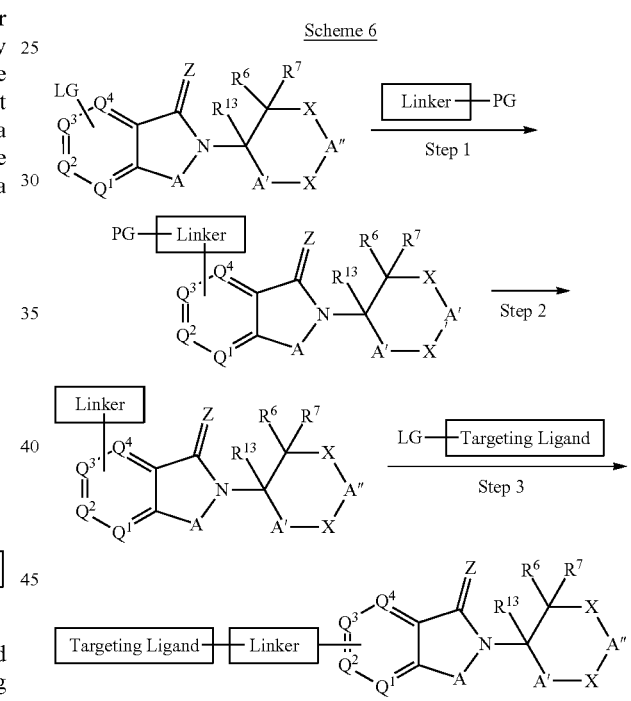

Scheme 7

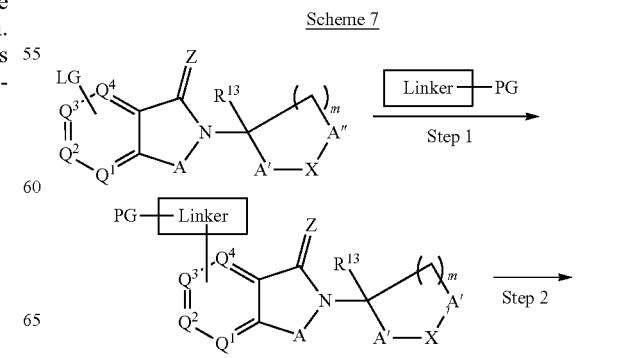

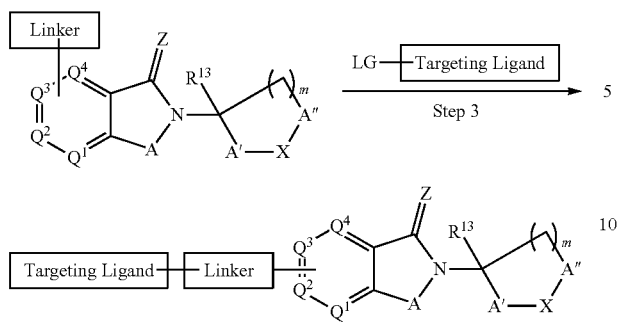

Scheme 5, Scheme 6, and Scheme 7: In Step 1, a nucleophilic Linker displaces a leaving group on the Degron to make a Degron Linker fragment. In Step 2, the protecting group is removed by methods known in the art to free a nucleophilic site on the linker. In Step 3, the nucleophilic Degron Linker fragment displaces a leaving group on the Targeting Ligand to form a compound of Formula I, Formula II, or Formula III. In an alternative embodiment Step 1 and/or Step 2 is accomplished by a coupling reaction instead of a nucleophilic attack.

VII. Synthesis of Representative Compounds

In the following Schemes, R is the point of attachment to the linker.

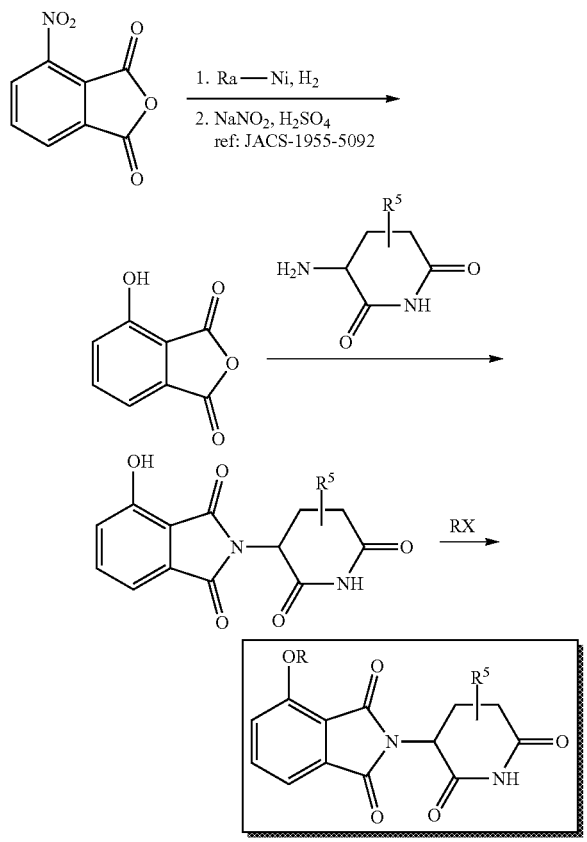

3-Hydroxyphthalic Anhydride

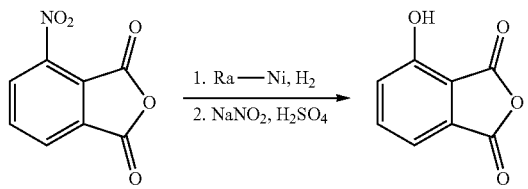

A solution of 3-nitrophthalic anhydride (1 equiv.) in acetone is subjected to catalytic reduction under hydrogen (60 psi) in the presence of Raney nickel and anhydrous magnesium sulfate. After 2-3 hours, the solution is warmed to 50° C., treated with Norite, filtered, and concentrated in vacuo at room temperature. The residue is treated with ethyl acetate, chilled and collected to give 3-aminophthalic anhydride. 15 N sulfuric acid is cooled to 0° C., 3-aminophthalic anhydride (1 equiv.) is added gradually with good stirring. After one hour, a solution of sodium nitrite (1 equiv.) in water is added slowly while maintaining the temperature below 5° C. After another 30 minutes, the mixture is warmed to 80° C. and maintained at this temperature until nitrogen evolution ceases. The now dark orange solution is diluted with water and extracted with ether. The organic layer is dried with sodium sulfate, filtered and shaken for two hours with finely powdered barium chloride to remove traces of sulfuric acid. The solution is filtered and concentrated and the resulting crude 3-hydroxyphthalic acid sublimes at about 160-180° C. (0.2 mm.) to give 3-hydroxyphthalic anhydride. (*J. Am. Chem. Soc.*, 1955, 77 (19), pp 5092-5095)

4-Hydroxythalidomide

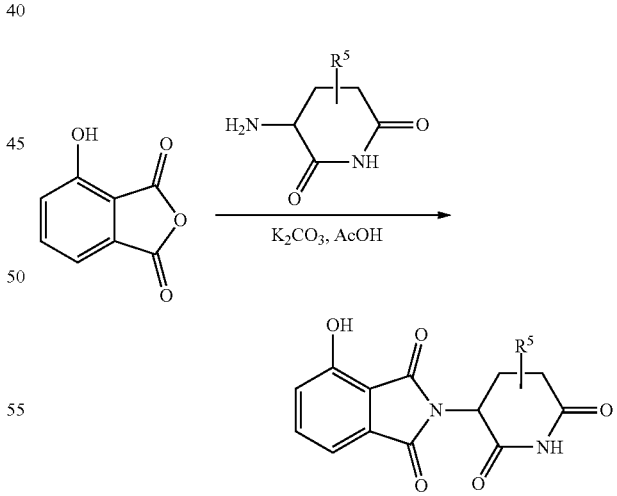

A mixture of 3-hydroxyphthalic anhydride (1 equiv.), 3-aminopiperidine-2,6-dione HCl salt (1 equiv.), and potassium acetate (2.5 equiv.) in acetic acid is stirred at 120° C. overnight. The dark mixture is cooled and filtered. The filter cake is dissolved in DCM and washed with saturated NaHCO$_3$ and brine. The organic layer is dried (Na$_2$SO$_4$) and concentrated to provide 4-hydroxythalidomide.

4-Alkoxythalidomide

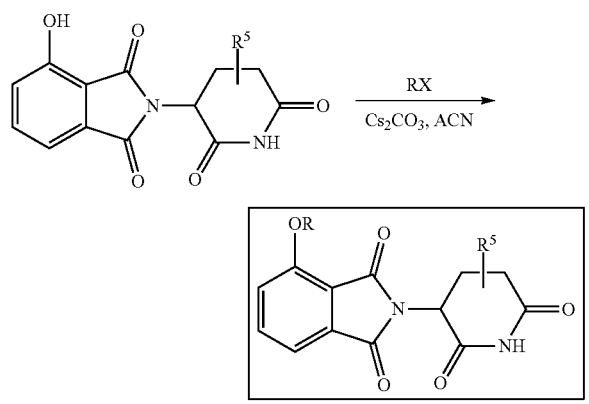

Alkyl halide (1 equiv.) is dissolved in MeCN. 4-hydroxythalidomide (1.1 equiv.) and cesium carbonate (2.75 equiv.) are added and the mixture is heated at 80° C. overnight. The mixture is cooled to room temperature and diluted water and extracted with chloroform and EtOAc. The combined organic layers are dried over sodium sulfate, filtered and concentrated. The crude is purified by column chromatography on silica gel to give 4-alkoxythalidomide. (*Science* 2015, 348 (6241), 1376-1381)

General Procedure to Prepare Pomalidomide Derivatives

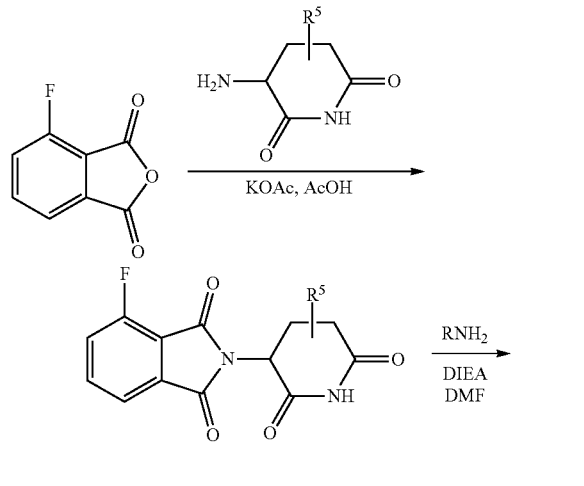

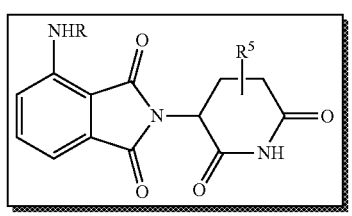

4-Fluorothalidomide

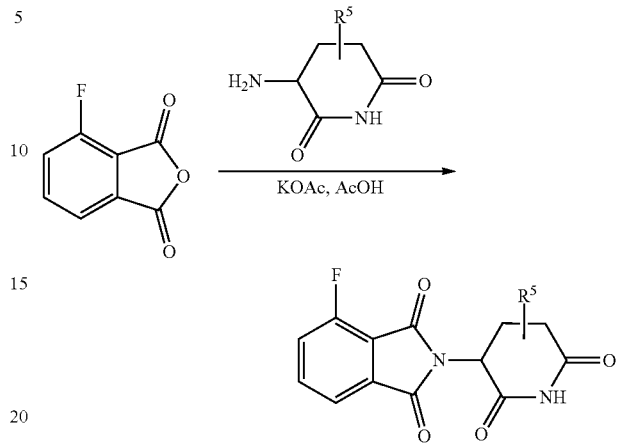

A mixture of 3-fluorophthalic anhydride (1 equiv.), 3-aminopiperidine-2,6-dione HCl salt (1 equiv.), and potassium acetate (2.5 equiv.) in acetic acid is stirred at 120° C. overnight. The dark mixture is cooled and filtered. The filter cake is dissolved in DCM and washed with saturated NaHCO$_3$ and brine. The organic layer is dried (Na$_2$SO$_4$) and concentrated to provide 4-fluorothalidomide.

Pomalidomide Analogs

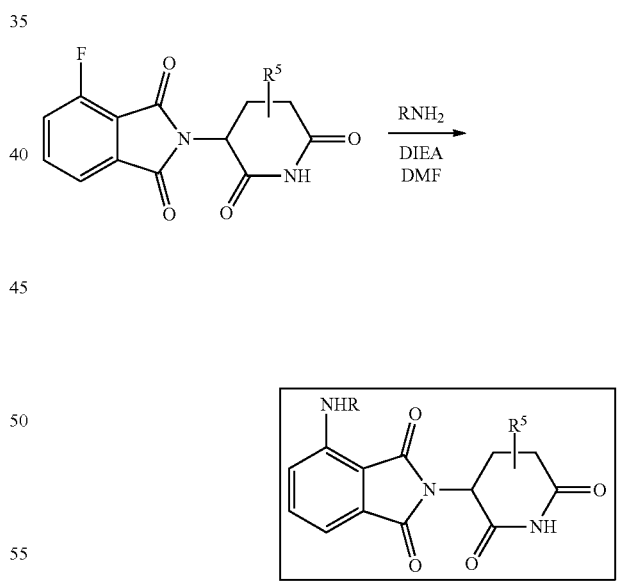

A mixture of amine (1 equiv.), 4-fluorothalidomide (1 equiv.) and DIEA (2 eq.) in dry DMF is stirred at 90° C. for 12 h. The mixture is cooled to room temperature, poured into water and extracted with ethyl acetate. The combined organic phases are washed with water and brine, dried over anhydrous sodium sulfate, and concentrated under reduced pressure. The crude residue is purified by column chromatography on silica gel to give pomalidomide analogs. (*Chem Biol.* 2015 Jun. 18; 22(6):755-63.)

General Procedure to Prepare Lenalidomide Derivatives

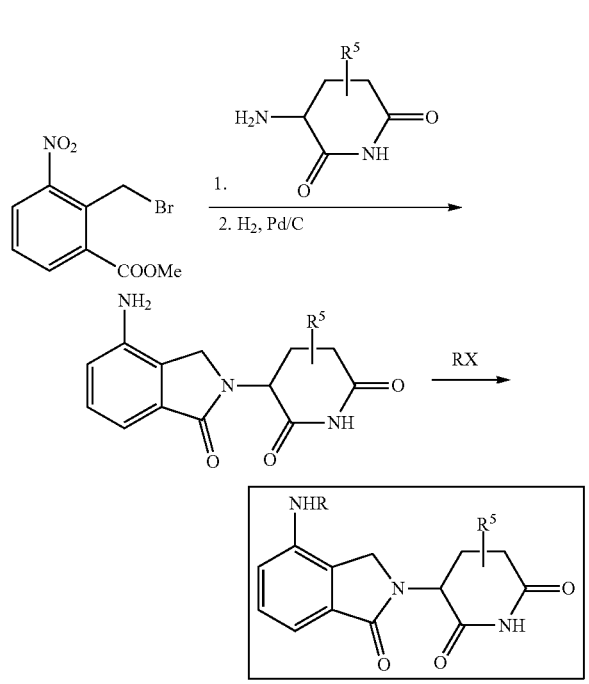

3-(7-Nitro-1-oxoisoindolin-2-yl)piperidine-2,6-dione

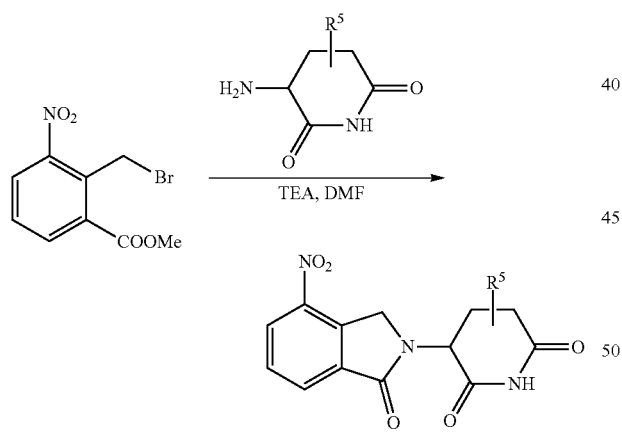

To a solution of α-aminoglutarimide (1.0 equiv.) and methyl 2-(bromomethyl)-3-nitrobenzoate (1.3 equiv) in DMF is added triethylamine (3.0 equiv), and the mixture is heated to 75° C. and stirred for 20 h. Then it is cooled to RT and poured into LiCl (5% in $H_2O$). It is extracted with EtOAc, and the combined organic phases are washed with LiCl (5% in $H_2O$) and saturated aqueous NaCl, dried ($Na_2SO_4$), filtered, and concentrated in vacuo. The crude is purified by column chromatography on silica gel to give 3-(7-nitro-1-oxoisoindolin-2-yl)piperidine-2,6-dione. (*Org. Lett.*, 2013, 15(17), pp 4312-4315)

Lenalidomide

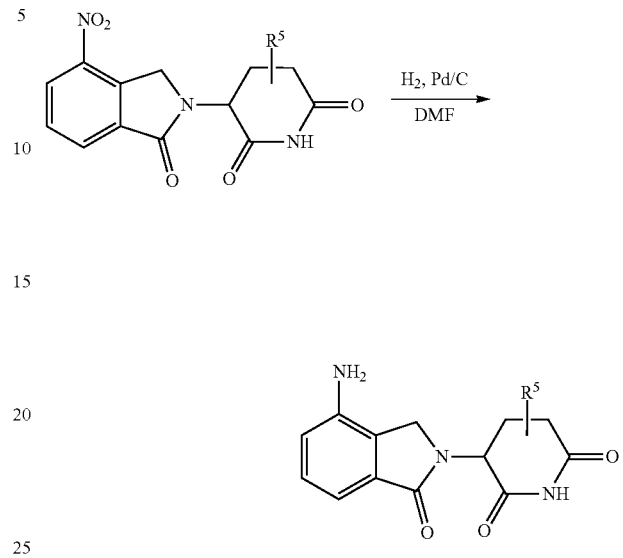

A mixture of 3-(7-nitro-1-oxoisoindolin-2-yl)piperidine-2,6-dione (1 equiv.) and palladium on activated carbon (10% wt) in THF is hydrogenated until the disappearance of the starting material. The mixture is filtered through Celite® and concentrated to give lenalidomide.

Lenalidomide Analogs

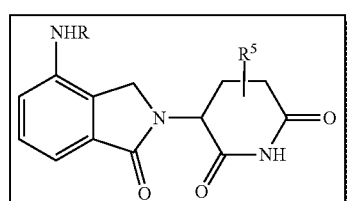

Alkyl halide (1 equiv.) is dissolved in DMF. Lenalidomide (1.1 equiv.) and potassium carbonate (2 equiv.) are added and the mixture is stirred at rt overnight. The mixture is diluted water and extracted with EtOAc. The combined organic layer is dried over sodium sulfate, filtered and concentrated. The crude is purified by column chromatography on silica gel to give lenalidomide analogs.

General Procedure to Prepare Boc-Protected Glutarimide

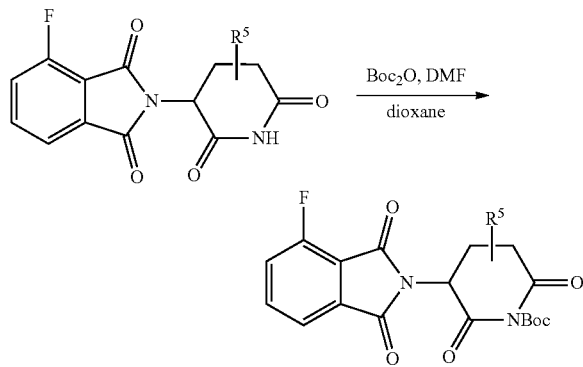

To a stirred solution of 4-fluorothalidomide (1.0 equiv.) in DMF is added potassium carbonate (2.0 equiv.). The resulting solution is cooled to 0-5° C. and Boc anhydride (3.0 equiv.) is added slowly as a solution in 1,4-dioxane (also cooled). The resulting mixture is stirred at 0° C. for 1 h and allowed to warm to room temperature overnight. Water is then added and the aqueous layer is extracted 2 times with DCM and concentrated. The residue is purified by column chromatography on silica gel to obtain N-Boc 4-fluorothalidomide. (WO 2014/147531 A2)

Thal/Pom/Len Analogs with Variation on the Phthalimide Moiety

General Procedure to Prepare O-Aryl Thalidomide

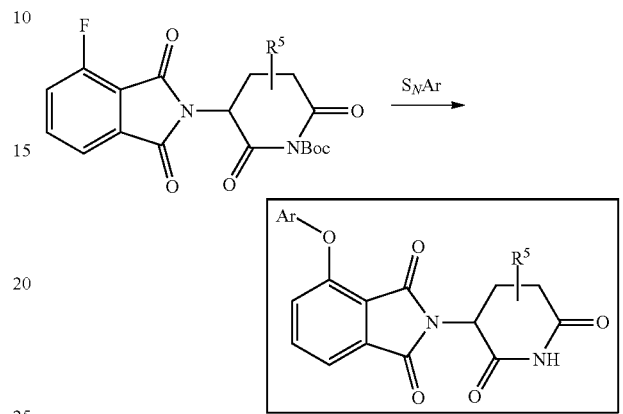

General Procedure Example 1: O-Pyrazole Thalidomide

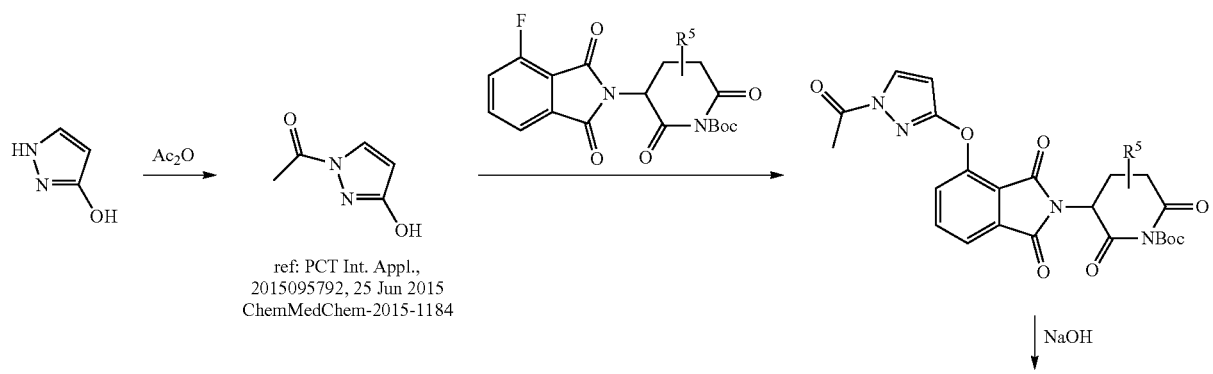

ref: PCT Int. Appl., 2015095792, 25 Jun 2015
ChemMedChem-2015-1184

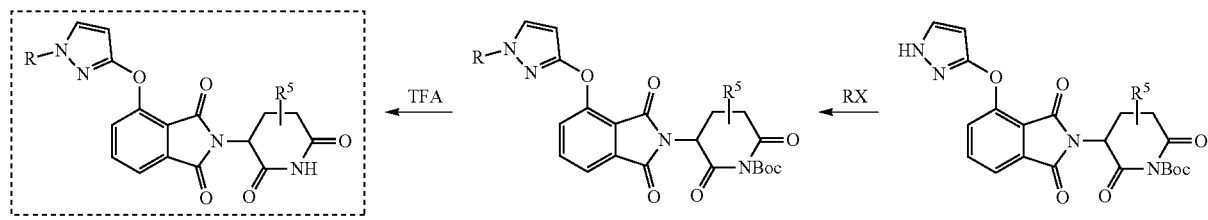

1-(3-Hydroxy-1H-pyrazol-1-yl)ethanone

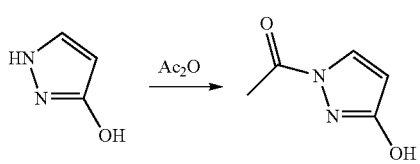

A solution of 3-hydroxy-1H-pyrazole (1 equiv.) in pyridine is heated to 95° C. A mixture consisting of acetic anhydride (1.05 equiv.) and pyridine is added over 20 min. After stirring at 95° C. for 2 h, all volatiles are removed in vacuo and Et$_2$O is added to the residue. The slurry is stirred overnight at rt. The solid was filtered off and washed with Et$_2$O to give the 1-(3-hydroxy-1H-pyrazol-1-yl)ethanone. (*Chem Med Chem* 2015, 10, 1184-1199)

tert-Butyl 3-(4-((1-acetyl-1H-pyrazol-3-yl)oxy)-1,3-dioxoisoindolin-2-yl)-2,6-dioxopiperidine-1-carboxylate

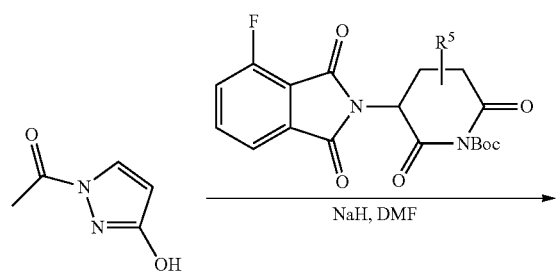

1-(3-Hydroxy-1H-pyrazol-1-yl)ethanone (1 equiv.) is dissolved in DMF. NaH (1.5 equiv.) is added slowly and stirred at rt for 30 min. 4-Fluorothalidomide (1 equiv.) is added and the solution is stirred at rt or 90° C. until the consumption of the starting materials. The reaction is quenched with methanol and extracted with EtOAc. The organic layer is washed with brine, dried (Na$_2$SO$_4$), and concentrated. The residue is purified by column chromatography on silica gel to give tert-butyl 3-(4-((1-acetyl-1H-pyrazol-3-yl)oxy)-1,3-dioxoisoindolin-2-yl)-2,6-dioxopiperidine-1-carboxylate. (PCT Int. Appl., 2015087234, 18 Jun. 2015)

tert-Butyl 3-(4-((1H-pyrazol-3-yl)oxy)-1,3-dioxoisoindolin-2-yl)-2,6-dioxopiperidine-1-carboxylate

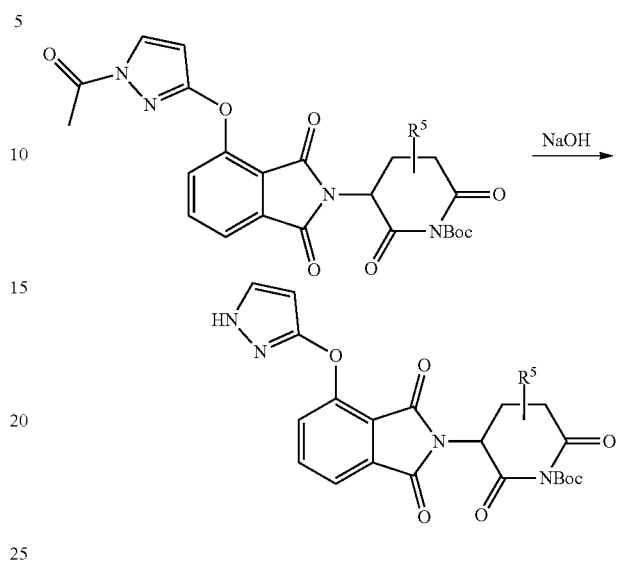

tert-Butyl 3-(4-((1-acetyl-1H-pyrazol-3-yl)oxy)-1,3-dioxoisoindolin-2-yl)-2,6-dioxopiperidine-1-carboxylate (1 equiv.) is dissolved in a mixture of MeOH/THF (2:3). 10% NaOH is added, and the solution is stirred at rt for 5 h. Then all the volatiles are removed in vacuo. The residue is diluted with EtOAc and water. The aqueous phase was extracted with EtOAc. The combined organic layers are washed with water and brine and dried (Na$_2$SO$_4$). Evaporation of all the volatiles gives tert-butyl 3-(4-((1H-pyrazol-3-yl)oxy)-1,3-dioxoisoindolin-2-yl)-2,6-dioxopiperidine-1-carboxylate. (PCT Int. Appl., 2015087234, 18 Jun. 2015)

tert-Butyl 3-(4-((1-alkyl-pyrazol-3-yl)oxy)-1,3-dioxoisoindolin-2-yl)-2,6-dioxopiperidine-1-carboxylate

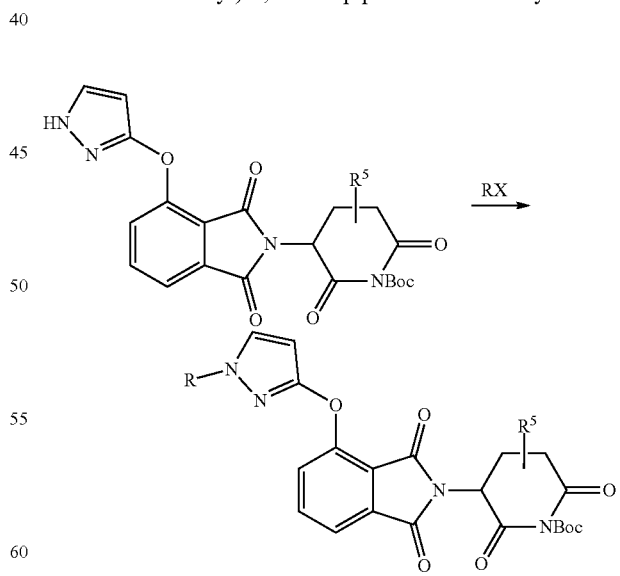

tert-Butyl 3-(4-((1H-pyrazol-3-yl)oxy)-1,3-dioxoisoindolin-2-yl)-2,6-dioxopiperidine-1-carboxylate (1 equiv.) is dissolved in DMF and K$_2$CO$_3$ (2 equiv.) is added, followed by alkyl halide (1.2 equiv.). The mixture is stirred at rt overnight. The reaction is poured into water and extracted with EtOAc. The organic layer is washed with water and brine, dried (Na$_2$SO$_4$), and concentrated. The residue is purified by column chromatography on silica gel to give tert-butyl 3-(4-((1-alkyl-pyrazol-3-yl)oxy)-1,3-dioxoisoindolin-2-yl)-2,6-dioxopiperidine-1-carboxylate.

4-((1-Alkyl-pyrazol-3-yl)oxy)-2-(2,6-dioxopiperidin-3-yl)isoindoline-1,3-dione

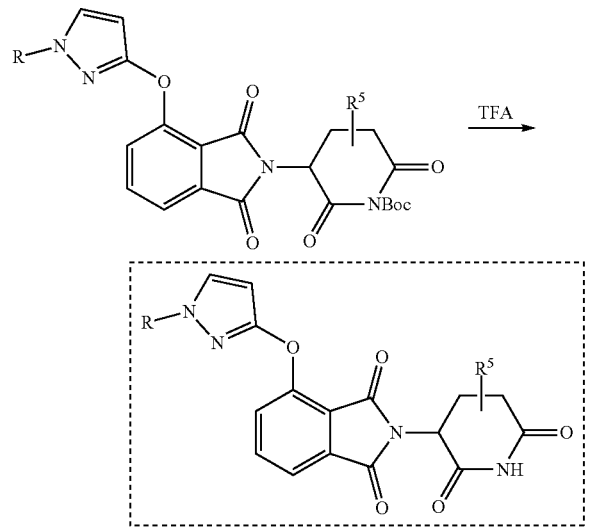

A solution of tert-butyl 3-(4-((1-alkyl-pyrazol-3-yl)oxy)-1,3-dioxoisoindolin-2-yl)-2,6-dioxopiperidine-1-carboxylate (1 equiv.) in TFA/DCM (1:1) is stirred at rt overnight. Solvent is evaporated and the residue is purified by column chromatography on silica gel to give 4-((1-alkyl-pyrazol-3-yl)oxy)-2-(2,6-dioxopiperidin-3-yl)isoindoline-1,3-dione.

General Procedure to Prepare N-Aryl Pomalidomide

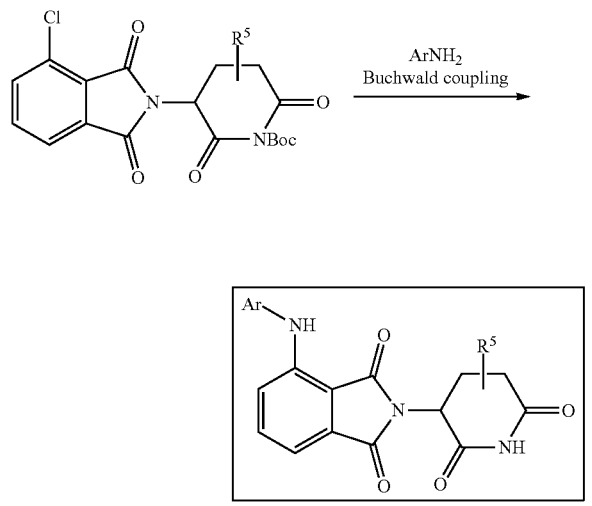

General Procedure Example 2: N-Pyrazole Pomalidomide

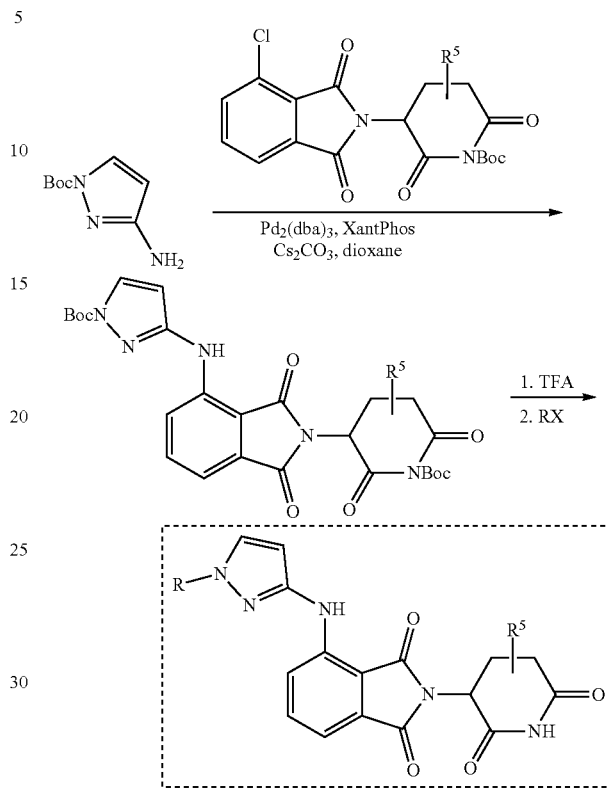

tert-Butyl 3-(4-((1-(tert-butoxycarbonyl)-1H-pyrazol-3-yl)amino)-1,3-dioxoisoindolin-2-yl)-2,6-dioxopiperidine-1-carboxylate

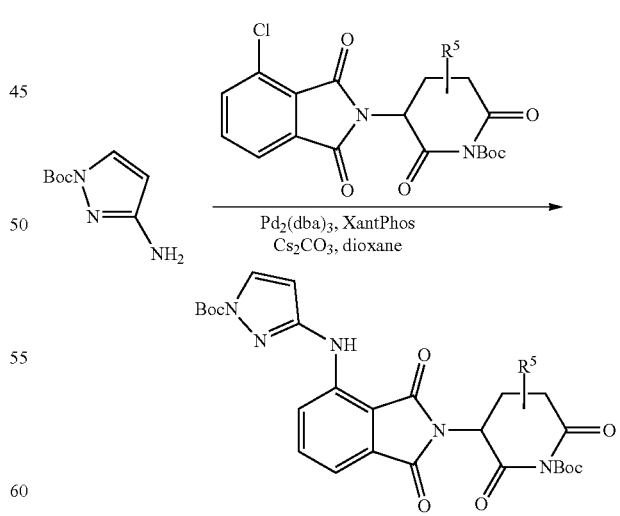

4-Chlorothalidomide (1 equiv.) and 3-amino-1-Boc-pyrazole (2 equiv.) are dissolved in dioxane. XantPhos (0.1 equiv.) and Cs$_2$CO$_3$ (2.5 equiv.) are added and the mixture is degassed with nitrogen. Pd$_2$(dba)$_3$ (0.05 equiv.) is added and the mixture is sealed and heated at 80° C. overnight. The reaction is poured into water and extracted with EtOAc. The organic layer is washed with water and brine, dried ($Na_2SO_4$), and concentrated. The residue is purified by column chromatography on silica gel to give tert-butyl 3-(4-((1-(tert-butoxycarbonyl)-1H-pyrazol-3-yl)amino)-1,3-dioxoisoindolin-2-yl)-2,6-dioxopiperidine-1-carboxylate.

4-((1H-Pyrazol-3-yl)amino)-2-(2,6-dioxopiperidin-3-yl)isoindoline-1,3-dione

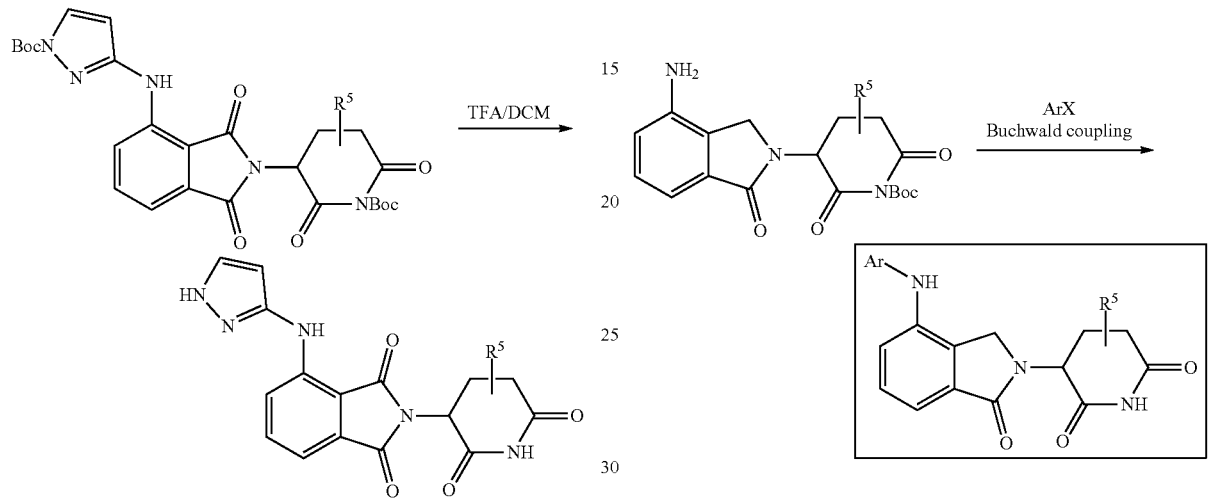

A solution of tert-butyl 3-(4-((1-(tert-butoxycarbonyl)-1H-pyrazol-3-yl)amino)-1,3-dioxoisoindolin-2-yl)-2,6-dioxopiperidine-1-carboxylate (1 equiv.) in TFA/DCM (1:1) is stirred at rt overnight. Solvent is evaporated and the residue is purified by column chromatography on silica gel to give 4-((1H-pyrazol-3-yl)amino)-2-(2,6-dioxopiperidin-3-yl)isoindoline-1,3-dione.

4-((1-Alkyl-pyrazol-3-yl)amino)-2-(2,6-dioxopiperidin-3-yl)isoindoline-1,3-dione 4-((1H-pyrazol-3-yl)amino)-2-(2,6-dioxopiperidin-3-yl)isoindoline-1,3-dione (1 equiv.) is dissolved in DMF and $K_2CO_3$ (1.2 equiv.) is added, followed by alkyl halide (1 equiv.). The mixture is stirred at rt overnight. The reaction is poured into water and extracted with EtOAc. The organic layer is washed with water and brine, dried ($Na_2SO_4$), and concentrated. The residue is purified by column chromatography on silica gel to give 4-((1-alkyl-pyrazol-3-yl)amino)-2-(2,6-dioxopiperidin-3-yl)isoindoline-1,3-dione.

General Procedure to Prepare N-Aryl Lenalidomide

General Procedure Example 3: N-Pyridyl Lenalidomide

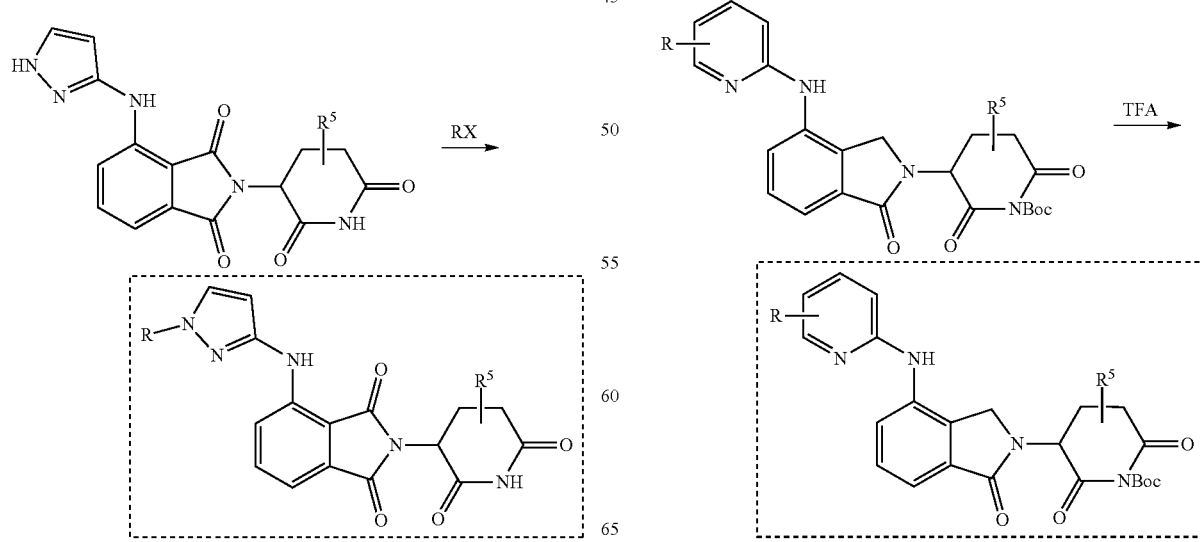

251
N-Pyridyl-Boc-Lenalidomide

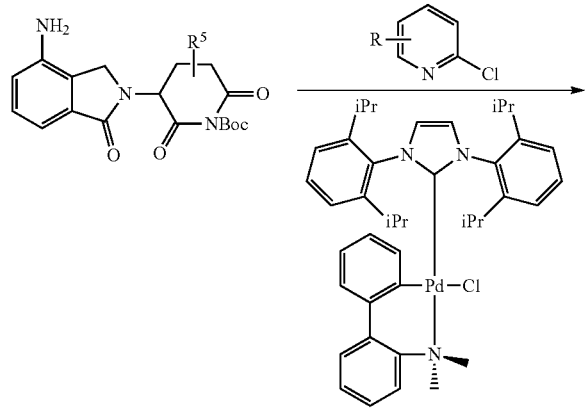

ref: OL-2003-1479

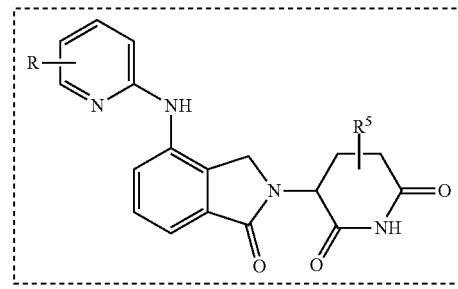

Under argon, substituted 2-chloropyridine (1 equiv.) and lenalidomide (1.1 equiv.) are loaded into oven-dried vials, followed by the addition of palladium catalyst (1 mol %), NaOtBu (1.1 equiv.) and dry dioxane. The reaction is run at 70° C. After consumption of reactants or no further conversion, the reaction is quenched with aqueous NH$_4$Cl solution and extracted with CH$_2$Cl$_2$. The organic layer is dried over Na$_2$SO$_4$ and concentrated. The residue is purified by column chromatography on silica gel to give N-pyridyl-Boc-lenalidomide. (*Org. Lett.* 2003, 5, 1479-1482)

N-Pyridyl-Lenalidomide

252

A solution of N-pyridyl-Boc-lenalidomide (1 equiv.) in TFA/DCM (1:1) is stirred at rt overnight. Solvent is evaporated and the residue is purified by column chromatography on silica gel to give N-pyridyl-lenalidomide.

General Procedure to Prepare O-Aryl Lenalidomide

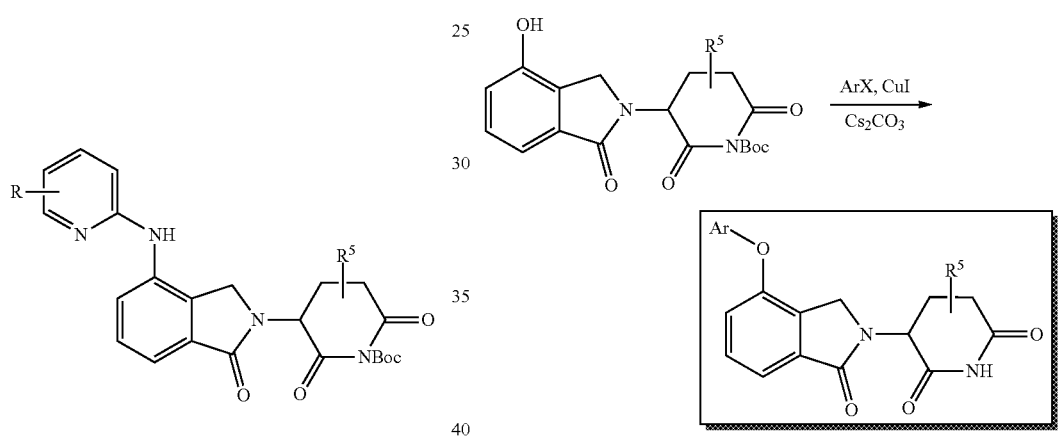

General Procedure Example 4:
O-Pyridyl-Lenalidomide

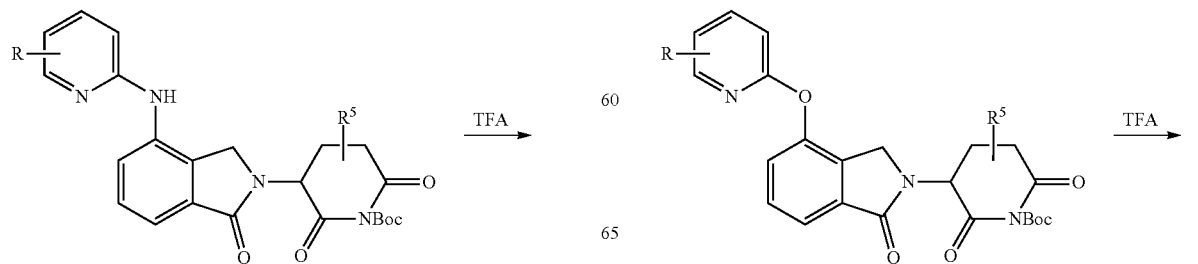

ref: Adv. Syn. Cat. 2011, 3403

-continued

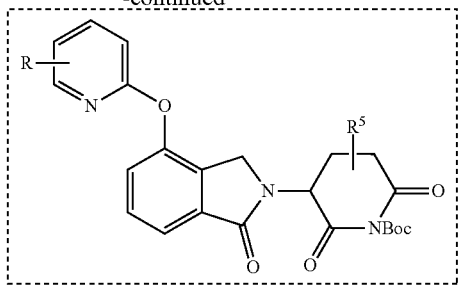

O-Pyridyl-Boc-Lenalidomide

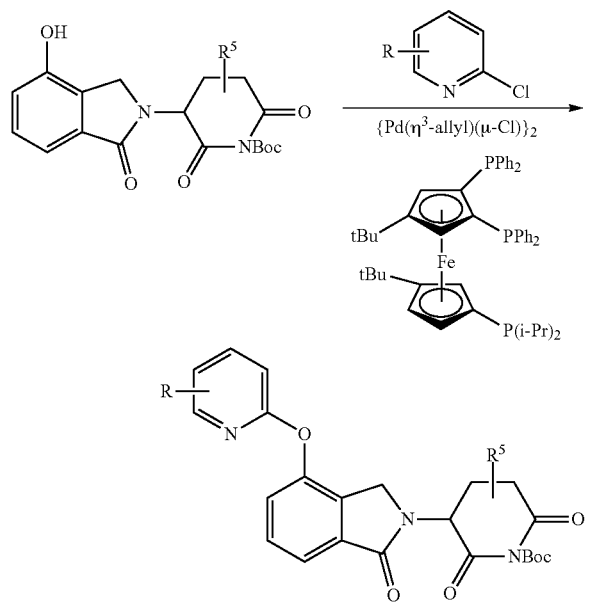

Substituted 2-chloropyridine (1 equiv.), 4-hydroxylenalidomide (1 equiv.), and $K_3PO_4$ (2 equiv.) are introduced under argon in a Schlenk tube, equipped with a magnetic stirring bar. The [{Pd($\eta^3$-allyl)($\mu$-Cl)}2]/ferrocenyl ligand (ratio 1:2, 0.2 mol % Pd) catalyst and toluene are added, and the Schlenk tube is purged several times with argon. The reaction is heated at 115° C. for 20 h. The solvent is removed and the residue is purified by column chromatography on silica gel to give O-pyridyl-Boc-lenalidomide. (*Adv. Synth. Catal.* 2011, 353, 3403-3414)

O-Pyridyl-Lenalidomide

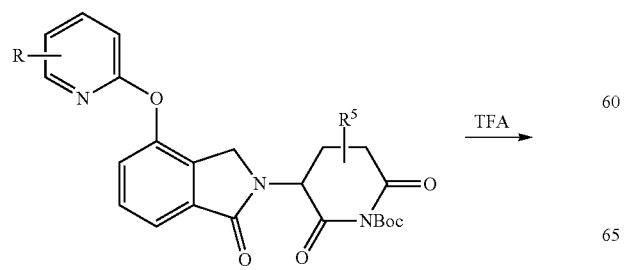

-continued

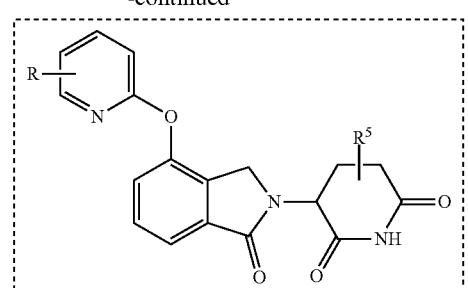

A solution of O-pyridyl-Boc-lenalidomide (1 equiv.) in TFA/DCM (1:1) is stirred at rt overnight. Solvent is evaporated and the residue is purified by column chromatography on silica gel to give O-pyridyl-lenalidomide.

5-Methylthalidomide Derivatives

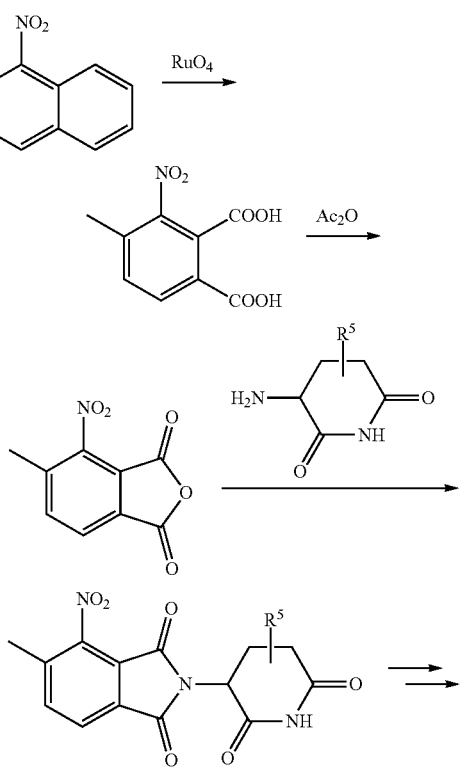

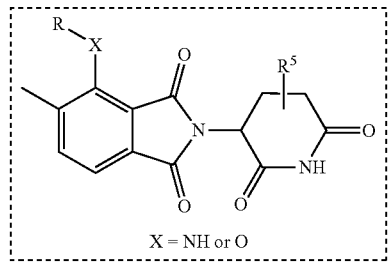

X = NH or O

255
4-Methyl-3-Nitrophthalic Anhydride

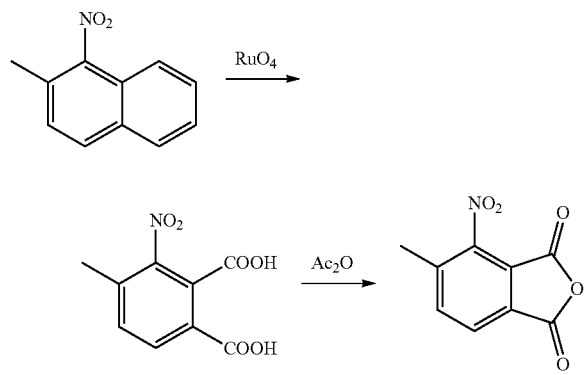

Oxidation of ruthenium dioxide to ruthenium tetraoxide is carried out with aqueous sodium hypochlorite (household bleach, 5.25% concentration). Into a 3-L, three-necked flask fitted with mechanical stirrer and air condenser are added carbon tetrachloride, RuO₂.H₂0, and bleach. The reaction is stirred until all the insoluble black ruthenium dioxide is converted into soluble yellow ruthenium tetraoxide. As the two-phase mixture is being stirred, 1-nitro-2-methylnaphthalene (1 equiv.) is added. The reaction is allowed to stir until the black color of the ruthenium dioxide begins to persist. More bleach is added and stirring is continued. The reaction is then allowed to stir for about 20 h. The aqueous phase is separated from the organic layer, concentrated, and extracted with diethyl ether. The ether layer is dried (Na₂SO₄) and concentrated. The residue is dissolved in ether and filtered, which leaves behind a large amount of extracted salts. The product in ether solution is again taken to complete dryness and dissolved in acetone. The acetone solution is concentrated and water is added to retain any remaining undesired salts. The 4-methyl-3-nitrophthalic acid product is allowed to precipitate from the acetone-water solution.

Excess acetic anhydride is added to 4-methyl-3-nitrophthalic acid. The mixture is heated at gentle reflux until the phthalic acid is completely dissolved. Reflux is continued for an additional 30 min. The reaction mixture is concentrated in vacuo, and the excess acetic anhydride is allowed to evaporate under a gentle stream of dry air to give 4-methyl-3-nitrophthalic anhydride. (*J. Agric. Food Chem.* 1991, 39, 554-559)

5-Methyl-4-nitrothalidomide

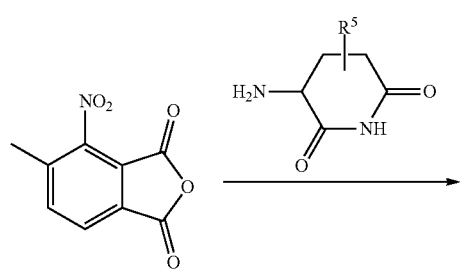

256

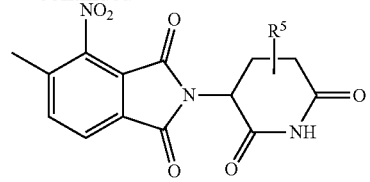

A mixture of 4-methyl-3-nitrophthalic anhydride (1 equiv.), 3-aminopiperidine-2,6-dione HCl salt (1 equiv.), and potassium acetate (2.5 equiv.) in acetic acid is stirred at 120° C. overnight. The dark mixture is cooled and filtered. The filter cake is dissolved in DCM and washed with saturated NaHCO₃ and brine. The organic layer is dried (Na₂SO₄) and concentrated to provide 5-methyl-4-nitrothalidomide.

5-Methylpomalidomide

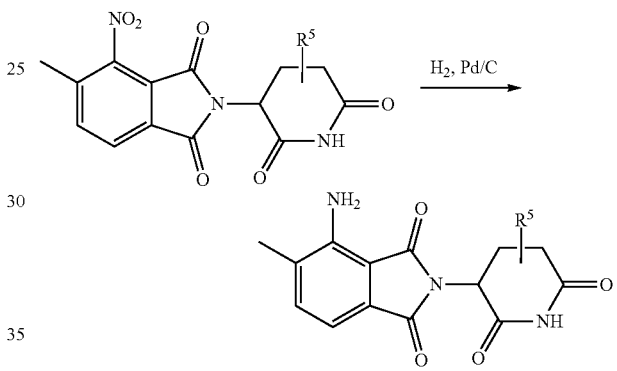

A mixture of 5-methyl-4-nitrothalidomide (1 equiv.) and palladium on activated carbon (10% wt) in THF is hydrogenated until the disappearance of the starting material. The mixture is filtered through Celite® and concentrated to give 5-methylpomalidomide.

General Procedure Example 5: N-Linked 5-Methylpomalidomide Derivatives

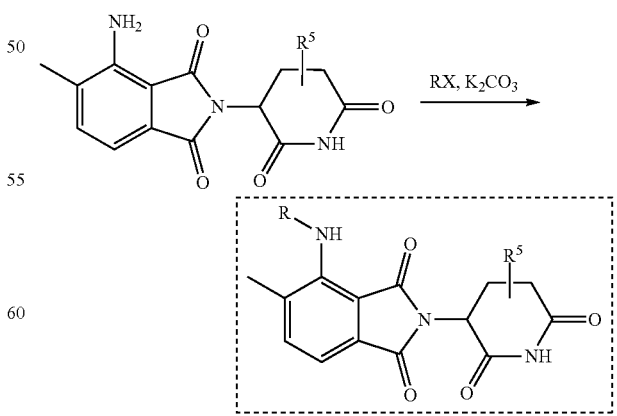

5-Methylpomalidomide (1 equiv.) is dissolved in DMF and K₂CO₃ (2 equiv.) is added, followed by alkyl halides (1.2 equiv.). The mixture is stirred at rt until the consumption of the starting material. The mixture is diluted with water and extracted with EtOAc. The organic layer is washed with brine, dried (Na$_2$SO$_4$), and concentrated. The residue is purified by column chromatography to give N-linked 5-methylpomalidomide derivatives.

General Procedure Example 6: O-Linked 5-Methylthalidomide Derivatives

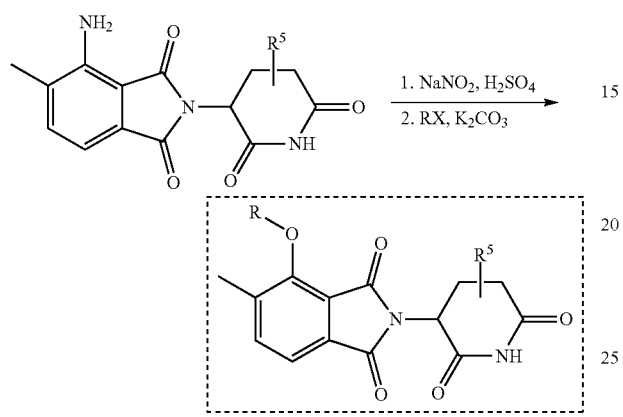

15 N Sulfuric acid is cooled to 0° C., 5-methylpomalidomide (1 equiv.) is added gradually with good stirring. After one hour, a solution of sodium nitrite (1 equiv.) in water is added slowly while maintaining the temperature below 5° C. After another 30 minutes, the mixture is warmed to 80° C. and maintained at this temperature until nitrogen evolution ceases. The now dark orange solution is diluted with water and extracted with ether. The organic layer is dried with sodium sulfate, filtered and shaken for two hours with finely powdered barium chloride to remove traces of sulfuric acid. The solution is filtered and concentrated and the residue is purified by column chromatography to give 5-methyl-4-hydroxythalidomide. (*J. Am. Chem. Soc.*, 1955, 77 (19), pp 5092-5095)

5-Methyl-4-hydroxythalidomide (1 equiv.) is dissolved in DMF and K$_2$CO$_3$ (2 equiv.) is added, followed by alkyl halides (1.2 equiv.). The mixture is stirred at rt until the consumption of the starting material. The mixture is diluted with water and extracted with EtOAc. The organic layer is washed with brine, dried (Na$_2$SO$_4$), and concentrated. The residue is purified by column chromatography to give O-linked 5-methylthalidomide derivatives.

6-Methylthalidomide Derivatives

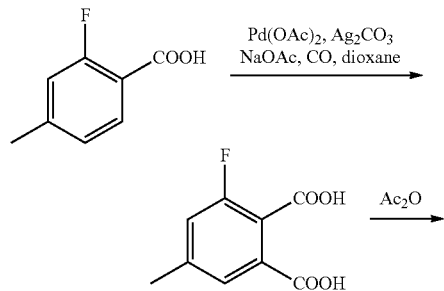

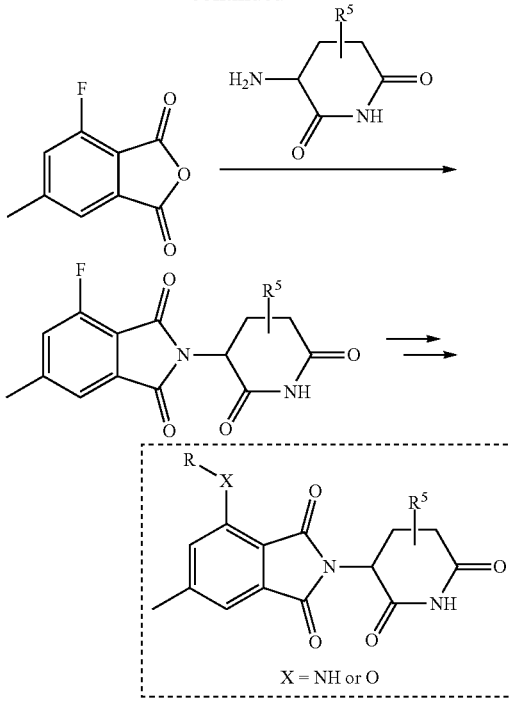

3-Fluoro-5-Methylphthalic Acid

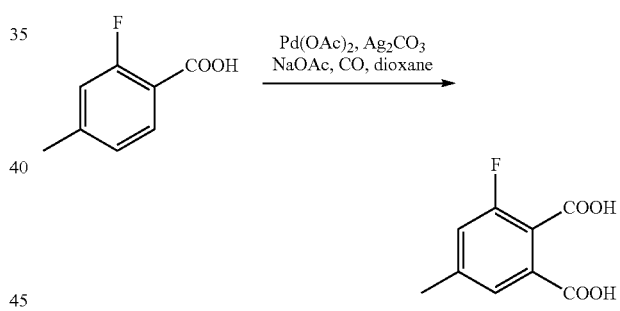

1,4-Dioxane is added to a mixture of Pd(OAc)$_2$ (10 mol %), 2-fluoro-4-methylbenzoic acid (1 equiv.), Ag$_2$CO$_3$ (2 equiv.) and NaOAc (2 equiv.) in a Schlenk tube containing a Hi-Vac valve. The Schlenk tube is degassed under high vacuum and filled with carbon monoxide at room temperature. The reaction mixture is heated at 130° C. with vigorous stirring. After 18-48 h, the reaction is cooled to room temperature, acidified with 2 N HCl and thoroughly extracted with ethyl acetate. The ethyl acetate fractions are combined, the solvent is removed in a rotary evaporator and the product is purified on a silica gel column to provide 3-fluoro-5-methylphthalic acid. (*J. Am. Chem. Soc.*, 2008, 130 (43), pp 14082-14083)

3-fluoro-5-methylphthalic Anhydride

Excess acetic anhydride is added to 3-fluoro-5-methylphthalic acid. The mixture is heated at gentle reflux until the phthalic acid is completely consumed. Reflux is continued for an additional 30 min. The reaction mixture is concentrated in vacuo, and the excess acetic anhydride is allowed to evaporate under a gentle stream of dry air to give 3-fluoro-5-methylphthalic anhydride. (*J. Agric. Food Chem.* 1991, 39, 554-559)

4-Fluoro-6-methylthalidomide

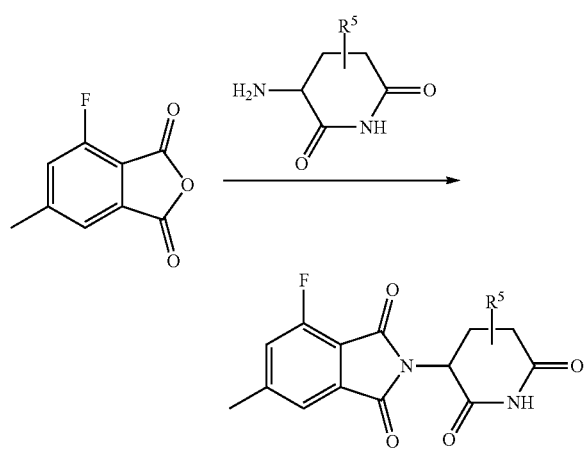

A mixture of 3-fluoro-5-methylphthalic anhydride (1 equiv.), 3-aminopiperidine-2,6-dione HCl salt (1 equiv.), and potassium acetate (2.5 equiv.) in acetic acid is stirred at 120° C. overnight. The dark mixture is cooled and filtered. The filter cake is dissolved in DCM and washed with saturated NaHCO₃ and brine. The organic layer is dried (Na₂SO₄) and concentrated to provide 4-fluoro-6-methylthalidomide.

General Procedure Example 7: N-Linked 6-Methylpomalidomide Derivatives

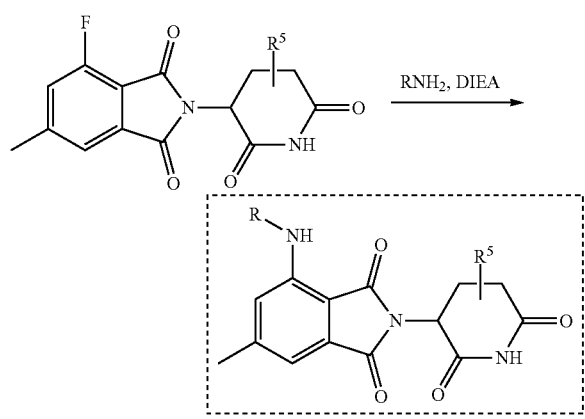

A mixture of 4-fluoro-6-methylthalidomide (1 equiv.), alkyl amine (1 equiv.) and DIEA (2 equiv.) in dry DMF is stirred at 90° C. for 12 h. The mixture is cooled to room temperature, poured into water and extracted with ethyl acetate. The combined organic phases are washed with water and brine, dried over anhydrous sodium sulfate, and concentrated under reduced pressure. The crude residue is purified by column chromatography on silica gel to provide N-linked 6-methylpomalidomide derivatives. (*Chem Biol.* 2015 Jun. 18; 22(6):755-63.)

General Procedure Example 8: O-Linked 6-methylthalidomide Derivatives

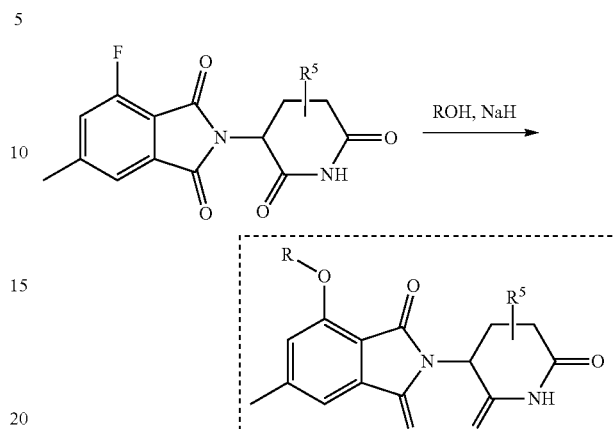

To a cooled solution of alcohol (1.2 equiv.) in DMF is added NaH (1.3 equiv.) and stirred at 0° C. for 30 min. 4-Fluoro-6-methylthalidomide (1 equiv.) was added and the mixture is heated at 80° C. overnight. The reaction is cooled and quenched with methanol. The mixture is poured into water and extracted with ethyl acetate. The combined organic phases are washed with water and brine, dried over anhydrous sodium sulfate, and concentrated under reduced pressure. The crude residue is purified by column chromatography on silica gel to provide O-linked 6-methylthalidomide derivatives.

7-Methylthalidomide Derivatives

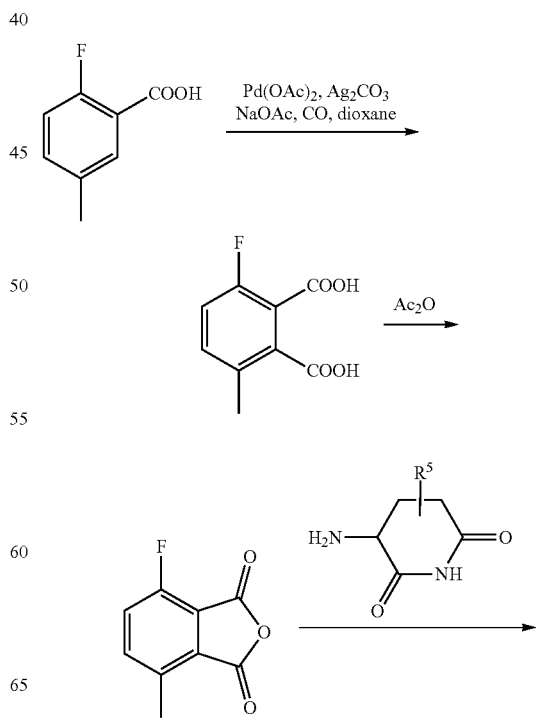

261
-continued

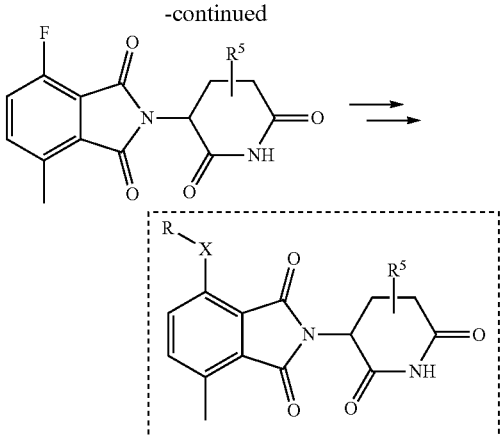

3-Fluoro-6-methylphthalic Acid

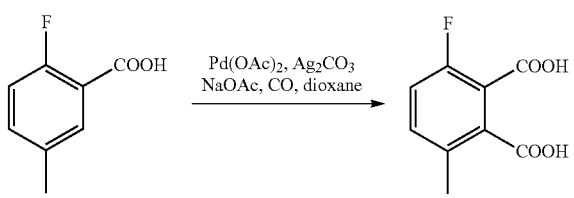

1,4-Dioxane is added to a mixture of Pd(OAc)₂ (10 mol %), 2-fluoro-5-methylbenzoic acid (1 equiv.), Ag₂CO₃ (2 equiv.) and NaOAc (2 equiv.) in a Schlenk tube containing a Hi-Vac valve. The Schlenk tube is degassed under high vacuum and filled with carbon monoxide at room temperature. The reaction mixture is heated at 130° C. with vigorous stirring. After 18-48 h, the reaction is cooled to room temperature, acidified with 2 N HCl and thoroughly extracted with ethyl acetate. The ethyl acetate fractions are combined, the solvent is removed in a rotary evaporator and the product is purified on a silica gel column to provide 3-fluoro-6-methylphthalic acid. (*J. Am. Chem. Soc.*, 2008, 130 (43), pp 14082-14083)

3-Fluoro-6-methylphthalic Anhydride

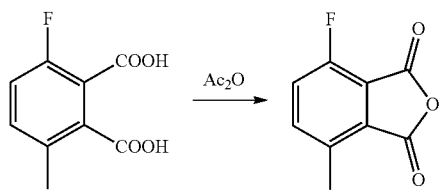

Excess acetic anhydride is added to 3-fluoro-6-methylphthalic acid. The mixture is heated at gentle reflux until the phthalic acid is completely consumed. Reflux is continued for an additional 30 min. The reaction mixture is concentrated in vacuo, and the excess acetic anhydride is allowed to evaporate under a gentle stream of dry air to give 3-fluoro-6-methylphthalic anhydride. (*J. Agric. Food Chem.* 1991, 39, 554-559)

262
4-Fluoro-7-methylthalidomide

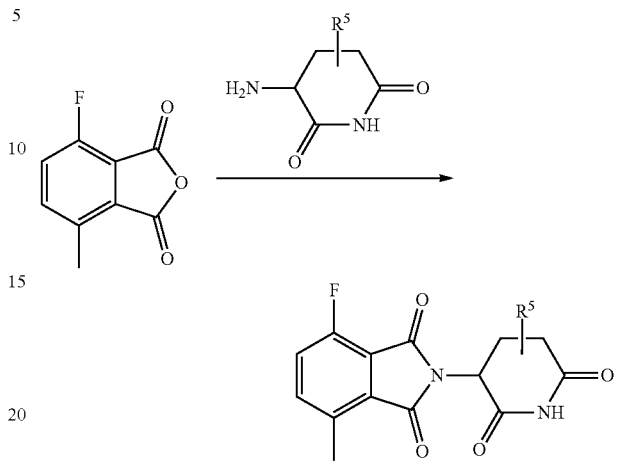

A mixture of 3-fluoro-6-methylphthalic anhydride (1 equiv.), 3-aminopiperidine-2,6-dione HCl salt (1 equiv.), and potassium acetate (2.5 equiv.) in acetic acid is stirred at 120° C. overnight. The dark mixture is cooled and filtered. The filter cake is dissolved in DCM and washed with saturated NaHCO₃ and brine. The organic layer is dried (Na₂SO₄) and concentrated to provide 4-fluoro-7-methylthalidomide.

General Procedure Example 9: N-Linked 7-methylpomalidomide Derivatives

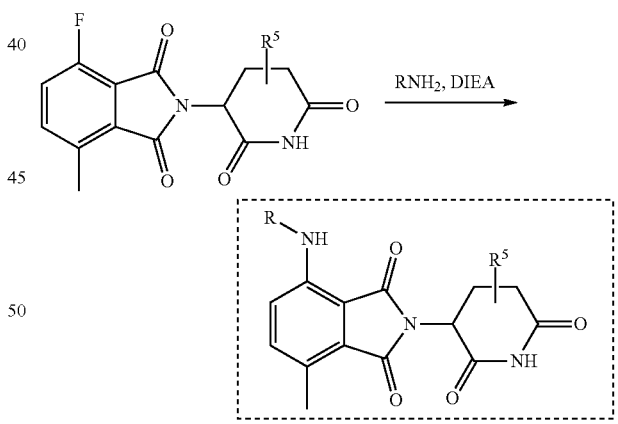

A mixture of 4-fluoro-7-methylthalidomide (1 equiv.), alkyl amine (1 equiv.) and DIEA (2 equiv.) in dry DMF is stirred at 90° C. for 12 h. The mixture is cooled to room temperature, poured into water and extracted with ethyl acetate. The combined organic phases are washed with water and brine, dried over anhydrous sodium sulfate, and concentrated under reduced pressure. The crude residue is purified by column chromatography on silica gel to provide N-linked 7-methylpomalidomide derivatives. (*Chem Biol.* 2015 Jun. 18; 22(6):755-63.)

General Procedure Example 10: O-Linked 7-methylthalidomide Derivatives

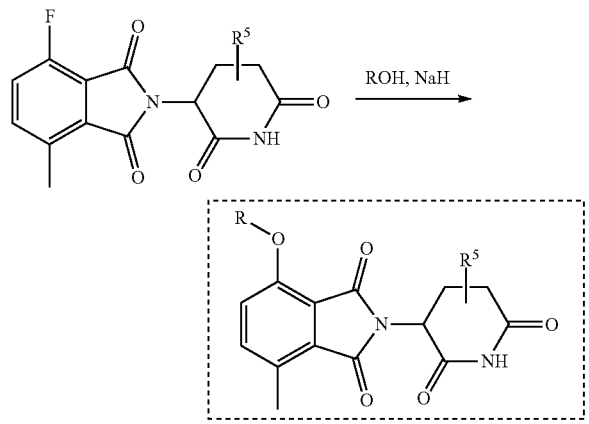

To a cooled solution of alcohol (1.2 equiv.) in DMF is added NaH (1.3 equiv.) and stirred at 0° C. for 30 min. 4-Fluoro-7-methylthalidomide (1 equiv.) was added and the mixture is heated at 80° C. overnight. The reaction is cooled and quenched with methanol. The mixture is poured into water and extracted with ethyl acetate. The combined organic phases are washed with water and brine, dried over anhydrous sodium sulfate, and concentrated under reduced pressure. The crude residue is purified by column chromatography on silica gel to provide O-linked 7-methylthalidomide derivatives.

5-Trifluoromethylthalidomide Derivatives

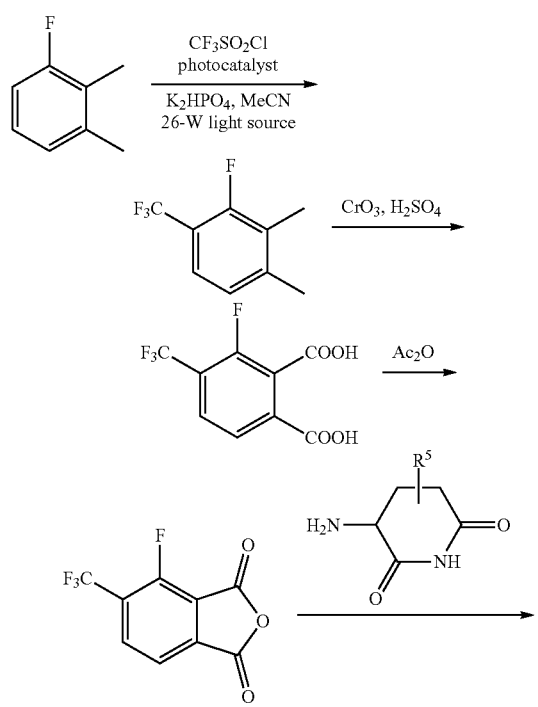

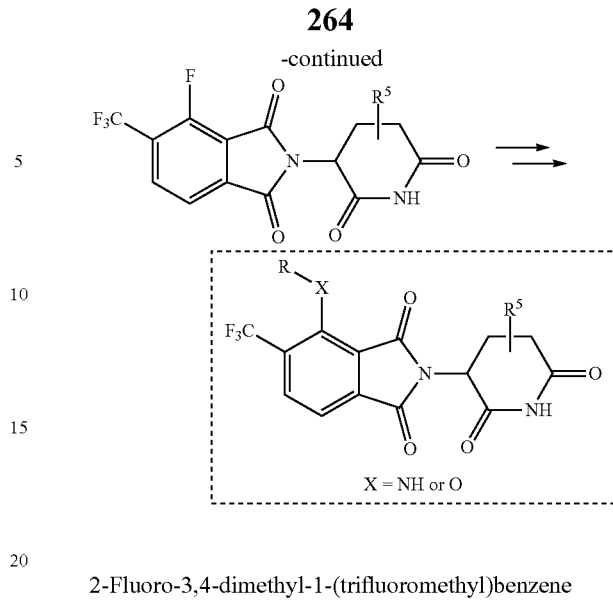

2-Fluoro-3,4-dimethyl-1-(trifluoromethyl)benzene

An oven-dried vial is equipped with Ru(phen)$_3$Cl$_2$ (1-2 mol %), dry K$_2$HPO$_4$ (3 equiv.), 1-fluoro-2,3-dimethylbenzene (1 equiv.) and MeCN (0.125 M), and degassed by alternating vacuum evacuation and argon backfill at −78° C. The triflyl chloride (1-4 equiv.) is then added and the solution is stirred at room temperature adjacent to a 26-W compact fluorescent light bulb. After 24 h, the reaction mixture is purified by column chromatography on silica gel to furnish 2-fluoro-3,4-dimethyl-1-(trifluoromethyl)benzene and 1-fluoro-2,3-dimethyl-4-(trifluoromethyl)benzene. The former one is taken to proceed to the next steps. (*Nature* 2011, 480, 224)

3-Fluoro-4-Trifluoromethylphthalic Acid

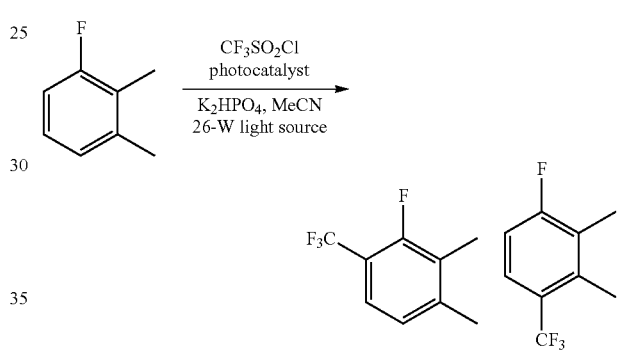

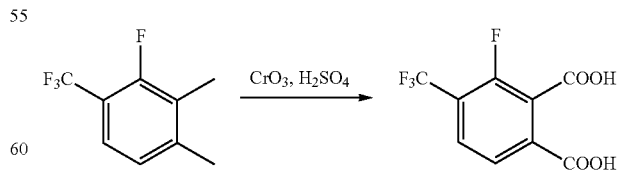

2-Fluoro-3,4-dimethyl-1-(trifluoromethyl)benzene (1 equiv.) is dissolved in acetic acid glacial (0.045 M). To this solution, sulfuric acid about 96% is added (1/5 volume of AcOH) and the mixture is cooled to approximately 15° C. in an ice bath, under stirring. Chromium(VI) trioxide (4.6 equiv.) is added stepwise within approximately 30 min. After the addition, the ice bath is removed and the mixture is allowed to warm to approximately room temperature and then is heated to about 35° C. for about 20 h. Further, the mixture is diluted approximately 1.5 fold with water and methanol is added cautiously in order to destroy the excess $CrO_3$. The aqueous mixture is extracted with ethyl acetate (3×) and the combined organic fractions are washed with water (2×) and dried over $Na_2SO_4$. After filtration, the solvent is evaporated completely under vacuum and the crude is recrystallized from toluene to provide 3-fluoro-4-trifluoromethylphthalic acid. (PCT Int. Appl., 2012061344, 10 May 2012)

3-Fluoro-4-trifluoromethylphthalic Anhydride

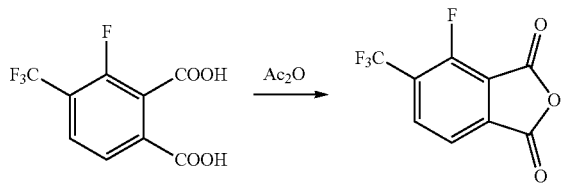 [SMILES: "Ac2O" ; O=C(O)c1ccc(C(F)(F)F)c(F)c1C(=O)O ; O=C1OC(=O)c2c1ccc(C(F)(F)F)c2F]

Excess acetic anhydride is added to 3-fluoro-4-trifluoromethylphthalic acid. The mixture is heated at gentle reflux until the phthalic acid is completely consumed. Reflux is continued for an additional 30 min. The reaction mixture is concentrated in vacuo, and the excess acetic anhydride is allowed to evaporate under a gentle stream of dry air to give 3-fluoro-4-trifluoromethylphthalic anhydride. (*J. Agric. Food Chem.* 1991, 39, 554-559)

4-Fluoro-5-trimethylfluorothalidomide

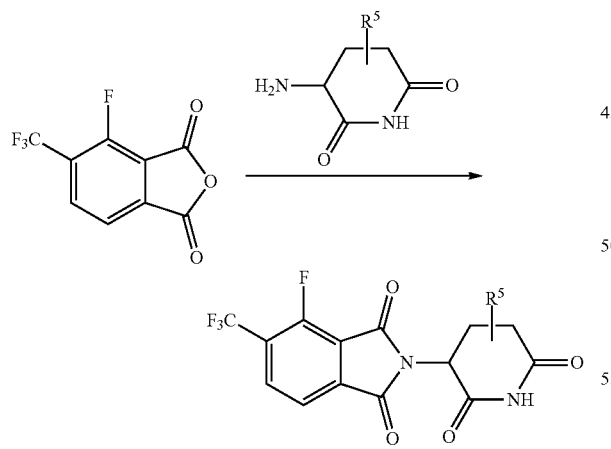

A mixture of 3-fluoro-4-trifluoromethylphthalic anhydride (1 equiv.), 3-aminopiperidine-2,6-dione HCl salt (1 equiv.), and potassium acetate (2.5 equiv.) in acetic acid is stirred at 120° C. overnight. The dark mixture is cooled and filtered. The filter cake is dissolved in DCM and washed with saturated $NaHCO_3$ and brine. The organic layer is dried ($Na_2SO_4$) and concentrated to provide 4-fluoro-5-trimethylfluorothalidomide.

General Procedure Example 11: N-Linked 5-trimethylfluoropomalidomide Derivatives

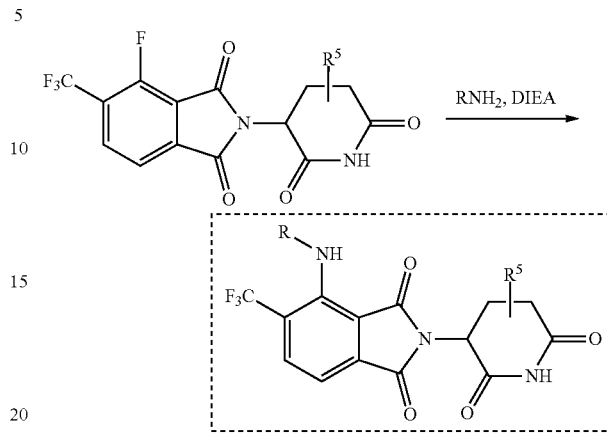

A mixture of 4-fluoro-5-trimethylfluorothalidomide (1 equiv.), alkyl amine (1 equiv.) and DIEA (2 equiv.) in dry DMF is stirred at 90° C. for 12 h. The mixture is cooled to room temperature, poured into water and extracted with ethyl acetate. The combined organic phases are washed with water and brine, dried over anhydrous sodium sulfate, and concentrated under reduced pressure. The crude residue is purified by column chromatography on silica gel to provide N-linked 5-trimethylfluoropomalidomide derivatives. (*Chem Biol.* 2015 Jun. 18; 22(6):755-63.)

General Procedure Example 12: O-Linked 5-trimethylfluorothalidomide Derivatives

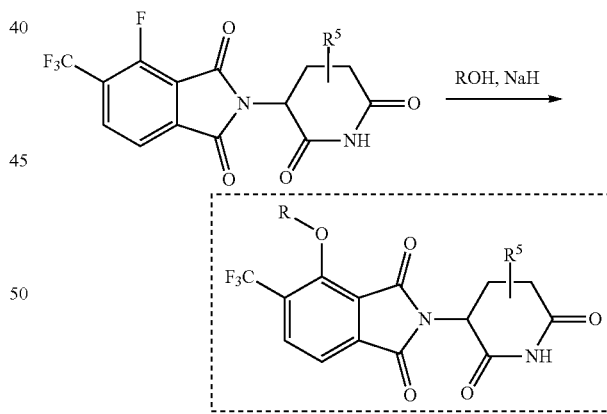

To a cooled solution of alcohol (1.2 equiv.) in DMF is added NaH (1.3 equiv.) and stirred at 0° C. for 30 min. 4-fluoro-5-trimethylfluorothalidomide (1 equiv.) was added and the mixture is heated at 80° C. overnight. The reaction is cooled and quenched with methanol. The mixture is poured into water and extracted with ethyl acetate. The combined organic phases are washed with water and brine, dried over anhydrous sodium sulfate, and concentrated under reduced pressure. The crude residue is purified by column chromatography on silica gel to provide O-linked 5-trimethylfluorothalidomide derivatives.

6-Trifluoromethylthalidomide Derivatives

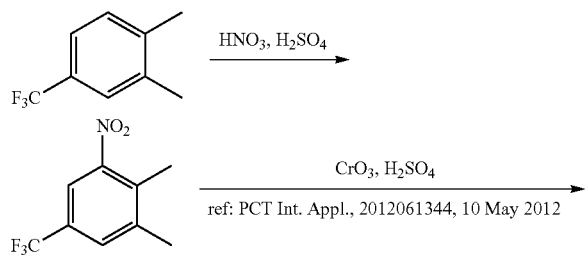

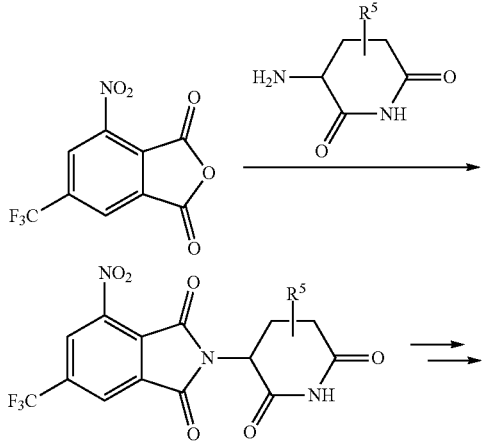

1,2-Dimethyl-3-nitro-5-(trifluoromethyl)benzene

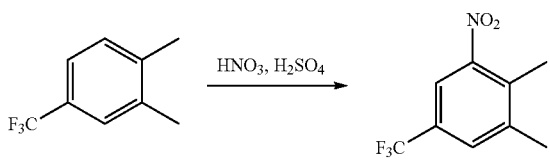

In particular, a mixture of sulfuric acid about 96% (42 equiv.) and fuming nitric acid (14 equiv.) is given under stirring to 1,2-dimethyl-4-(trifluoromethyl)benzene (1 equiv.) and heated to approximately 60° C. for about 3 h. After cooling to room temperature, the mixture is poured over crushed ice. The milky solution is then extracted with $CH_2Cl_2$ (2×). The combined organic fractions are washed with 3% $Na_2CO_3$ solution (2×) and then water (2×). The organic solution is dried over $Na_2SO_4$, filtered and evaporated in vacuo. The crude is purified by column chromatography on silica gel to give 1,2-dimethyl-3-nitro-5-(trifluoromethyl)benzene. (PCT Int. Appl., 2012061344, 10 May 2012)

3-Nitro-5-trifluoromethylphthalic Acid

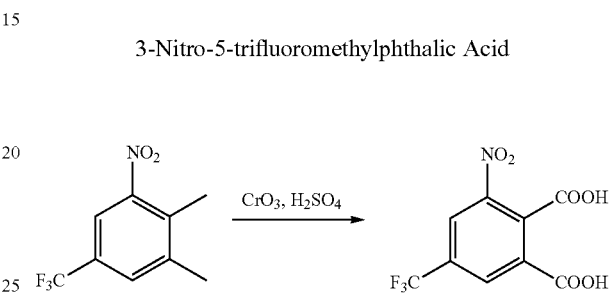

1,2-dimethyl-3-nitro-5-(trifluoromethyl)benzene (1 equiv.) is dissolved in acetic acid glacial (0.045 M). To this solution, sulfuric acid about 96% is added (1/5 volume of AcOH) and the mixture is cooled to approximately 15° C. in an ice bath, under stirring. Chromium(VI) trioxide (4.6 equiv.) is added stepwise within approximately 30 min. After the addition, the ice bath is removed and the mixture is allowed to warm to approximately room temperature and then is heated to about 35° C. for about 20 h. Further, the mixture is diluted approximately 1.5 fold with water and methanol is added cautiously in order to destroy the excess $CrO_3$. The aqueous mixture is extracted with ethyl acetate (3×) and the combined organic fractions are washed with water (2×) and dried over $Na_2SO_4$. After filtration, the solvent is evaporated completely under vacuum and the crude is recrystallized from toluene to provide 3-nitro-5-trifluoromethylphthalic acid. (PCT Int. Appl., 2012061344, 10 May 2012)

3-Nitro-5-trifluoromethylphthalic Anhydride

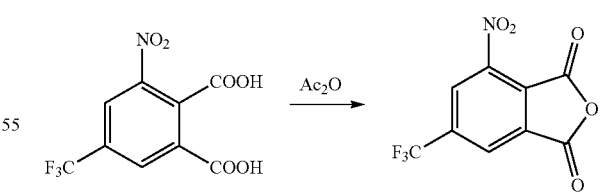

Excess acetic anhydride is added to 3-nitro-5-trifluoromethylphthalic acid. The mixture is heated at gentle reflux until the phthalic acid is completely consumed. Reflux is continued for an additional 30 min. The reaction mixture is concentrated in vacuo, and the excess acetic anhydride is allowed to evaporate under a gentle stream of dry air to give 3-nitro-5-trifluoromethylphthalic anhydride. (*J. Agric. Food Chem.* 1991, 39, 554-559)

4-Nitro-6-trimethylfluorothalidomide

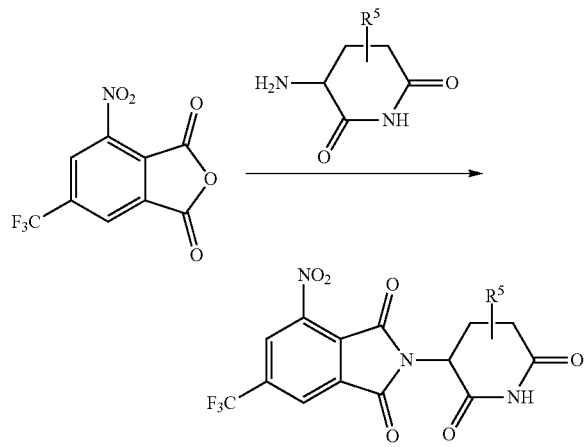

A mixture of 3-nitro-5-trifluoromethylphthalic anhydride (1 equiv.), 3-aminopiperidine-2,6-dione HCl salt (1 equiv.), and potassium acetate (2.5 equiv.) in acetic acid is stirred at 120° C. overnight. The dark mixture is cooled and filtered. The filter cake is dissolved in DCM and washed with saturated NaHCO$_3$ and brine. The organic layer is dried (Na$_2$SO$_4$) and concentrated to provide 4-nitro-6-trimethylfluorothalidomide.

4-Amino-6-trimethylfluorothalidomide

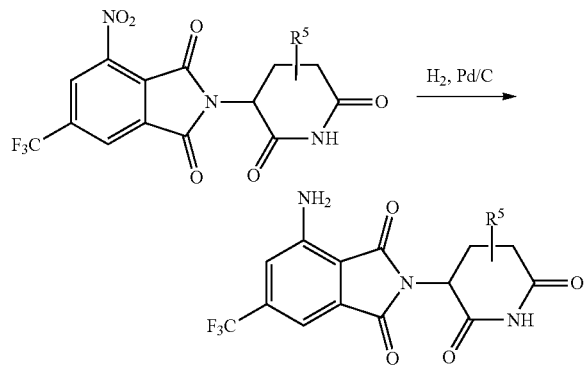

A mixture of 4-nitro-6-trimethylfluorothalidomide (1 equiv.) and palladium on activated carbon (10% wt) in THF is hydrogenated until the disappearance of the starting material. The mixture is filtered through Celite® and concentrated to give 4-amino-6-trimethylfluorothalidomide.

General Procedure Example 13: N-Linked 6-trimethylfluoropomalidomide Derivatives

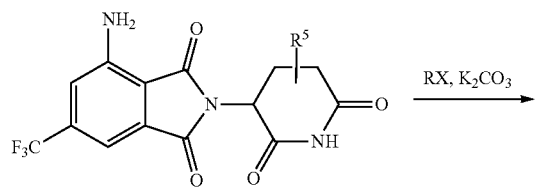

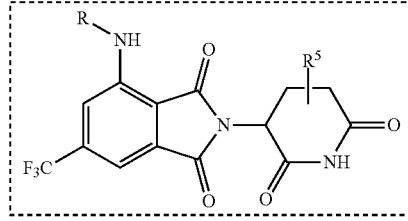

4-Amino-6-trimethylfluorothalidomide (1 equiv.) is dissolved in DMF and K$_2$CO$_3$ (2 equiv.) is added, followed by alkyl halides (1.2 equiv.). The mixture is stirred at rt until the consumption of the starting material. The mixture is diluted with water and extracted with EtOAc. The organic layer is washed with brine, dried (Na$_2$SO$_4$), and concentrated. The residue is purified by column chromatography to give N-linked 6-trimethylfluoropomalidomide derivatives.

General Procedure Example 14: O-Linked 6-trifluoromethylthalidomide Derivatives

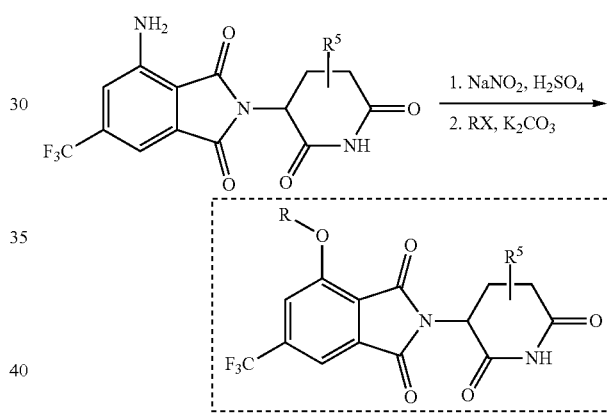

15 N Sulfuric acid is cooled to 0° C., 4-amino-6-trimethylfluorothalidomide (1 equiv.) is added gradually with good stirring. After one hour, a solution of sodium nitrite (1 equiv.) in water is added slowly while maintaining the temperature below 5° C. After another 30 minutes, the mixture is warmed to 80° C. and maintained at this temperature until nitrogen evolution ceases. The now dark orange solution is diluted with water and extracted with ether. The organic layer is dried with sodium sulfate, filtered and shaken for two hours with finely powdered barium chloride to remove traces of sulfuric acid. The solution is filtered and concentrated and the residue is purified by column chromatography to give 4-hydroxy-6-trimethylfluorothalidomide. (*J. Am. Chem. Soc.*, 1955, 77 (19), pp 5092-5095)

4-hydroxy-6-trimethylfluorothalidomide (1 equiv.) is dissolved in DMF and K$_2$CO$_3$ (2 equiv.) is added, followed by alkyl halides (1.2 equiv.). The mixture is stirred at rt until the consumption of the starting material. The mixture is diluted with water and extracted with EtOAc. The organic layer is washed with brine, dried (Na$_2$SO$_4$), and concentrated. The residue is purified by column chromatography to give O-linked 6-trifluoromethylthalidomide derivatives.

7-Trifluoromethylthalidomide Derivatives

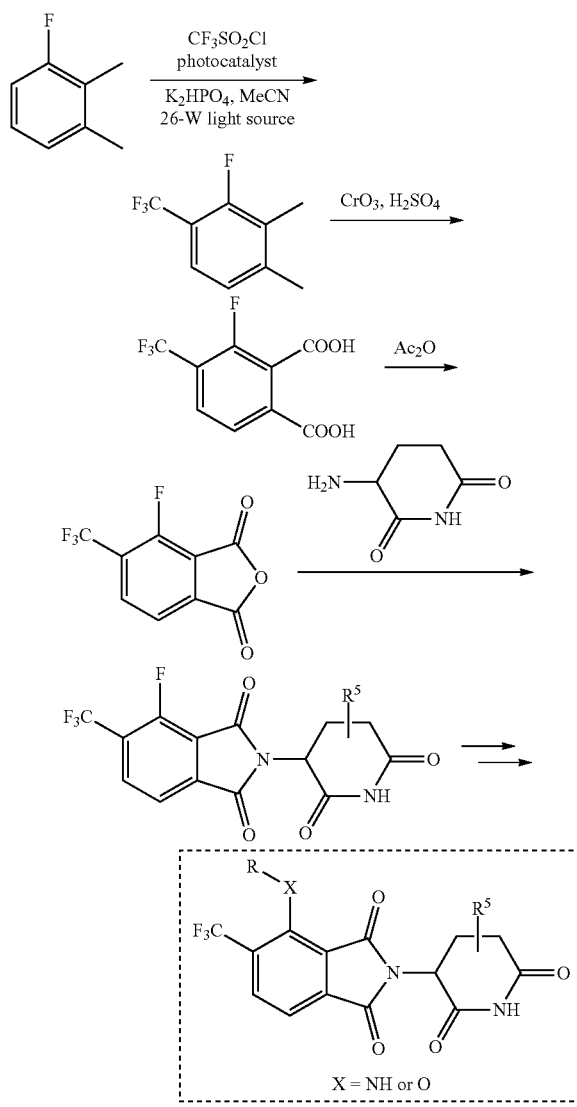

1-Fluoro-2,3-dimethyl-4-(trifluoromethyl)benzene

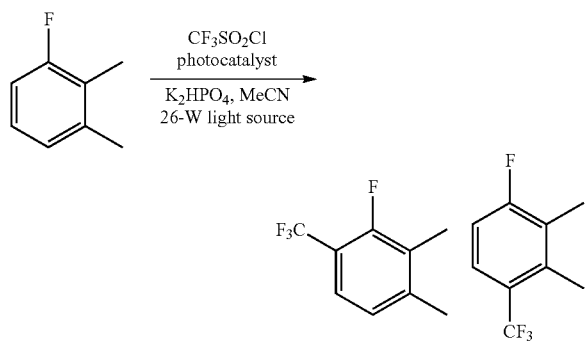

An oven-dried vial is equipped with Ru(phen)₃Cl₂ (1-2 mol %), dry K₂HPO₄ (3 equiv.), 1-fluoro-2,3-dimethylbenzene (1 equiv.) and MeCN (0.125 M), and degassed by alternating vacuum evacuation and argon backfill at −78° C. The triflyl chloride (1-4 equiv.) is then added and the solution is stirred at room temperature adjacent to a 26-W compact fluorescent light bulb. After 24 h, the reaction mixture is purified by column chromatography on silica gel to furnish 2-fluoro-3,4-dimethyl-1-(trifluoromethyl)benzene and 1-fluoro-2,3-dimethyl-4-(trifluoromethyl)benzene. The latter one is taken to proceed to the next steps. (*Nature* 2011, 480, 224)

3-Fluoro-6-trifluoromethylphthalic Acid

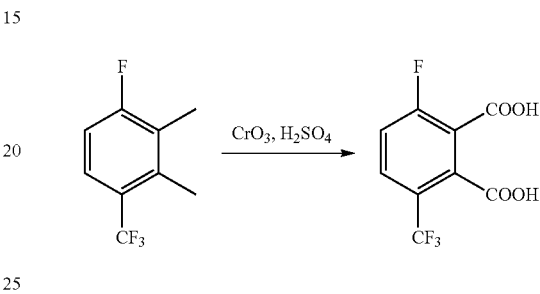

1-fluoro-2,3-dimethyl-4-(trifluoromethyl)benzene (1 equiv.) is dissolved in acetic acid glacial (0.045 M). To this solution, sulfuric acid about 96% is added (1/5 volume of AcOH) and the mixture is cooled to approximately 15° C. in an ice bath, under stirring. Chromium(VI) trioxide (4.6 equiv.) is added stepwise within approximately 30 min. After the addition, the ice bath is removed and the mixture is allowed to warm to approximately room temperature and then is heated to about 35° C. for about 20 h. Further, the mixture is diluted approximately 1.5 fold with water and methanol is added cautiously in order to destroy the excess CrO₃. The aqueous mixture is extracted with ethyl acetate (3×) and the combined organic fractions are washed with water (2×) and dried over Na₂SO₄. After filtration, the solvent is evaporated completely under vacuum and the crude is recrystallized from toluene to provide 3-fluoro-6-trifluoromethylphthalic acid. (PCT Int. Appl., 2012061344, 10 May 2012)

3-Fluoro-6-trifluoromethylphthalic Anhydride

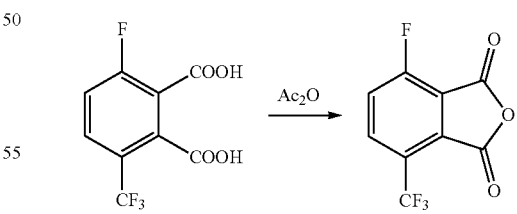

Excess acetic anhydride is added to 3-fluoro-6-trifluoromethylphthalic acid. The mixture is heated at gentle reflux until the phthalic acid is completely consumed. Reflux is continued for an additional 30 min. The reaction mixture is concentrated in vacuo, and the excess acetic anhydride is allowed to evaporate under a gentle stream of dry air to give 3-fluoro-6-trifluoromethylphthalic anhydride. (*J. Agric. Food Chem.* 1991, 39, 554-559)

4-Fluoro-7-trimethylfluorothalidomide

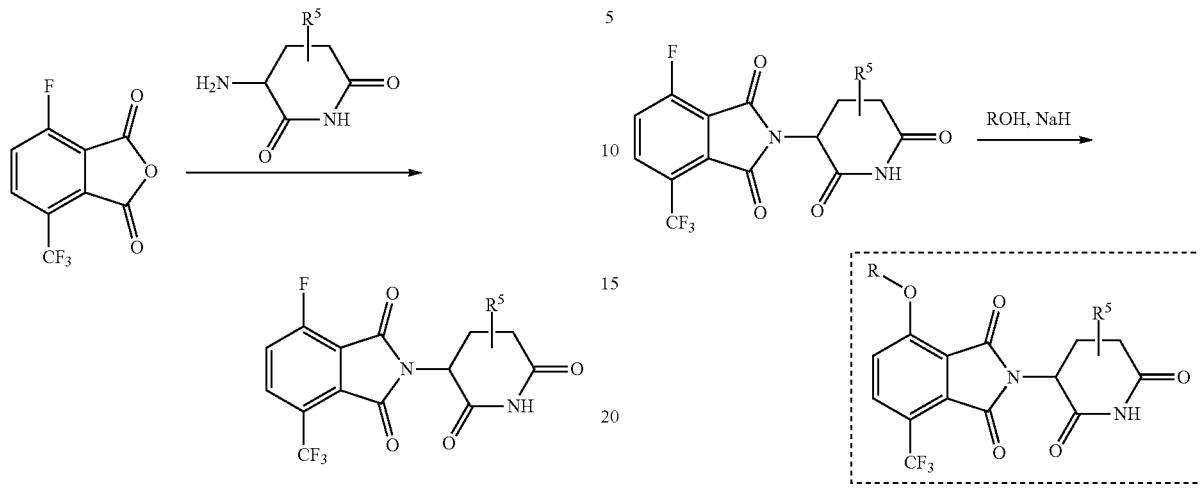

A mixture of 3-fluoro-6-trifluoromethylphthalic anhydride (1 equiv.), 3-aminopiperidine-2,6-dione HCl salt (1 equiv.), and potassium acetate (2.5 equiv.) in acetic acid is stirred at 120° C. overnight. The dark mixture is cooled and filtered. The filter cake is dissolved in DCM and washed with saturated $NaHCO_3$ and brine. The organic layer is dried ($Na_2SO_4$) and concentrated to provide 4-fluoro-7-trimethylfluorothalidomide.

General Procedure Example 15: N-Linked 7-trimethylfluoropomalidomide Derivatives

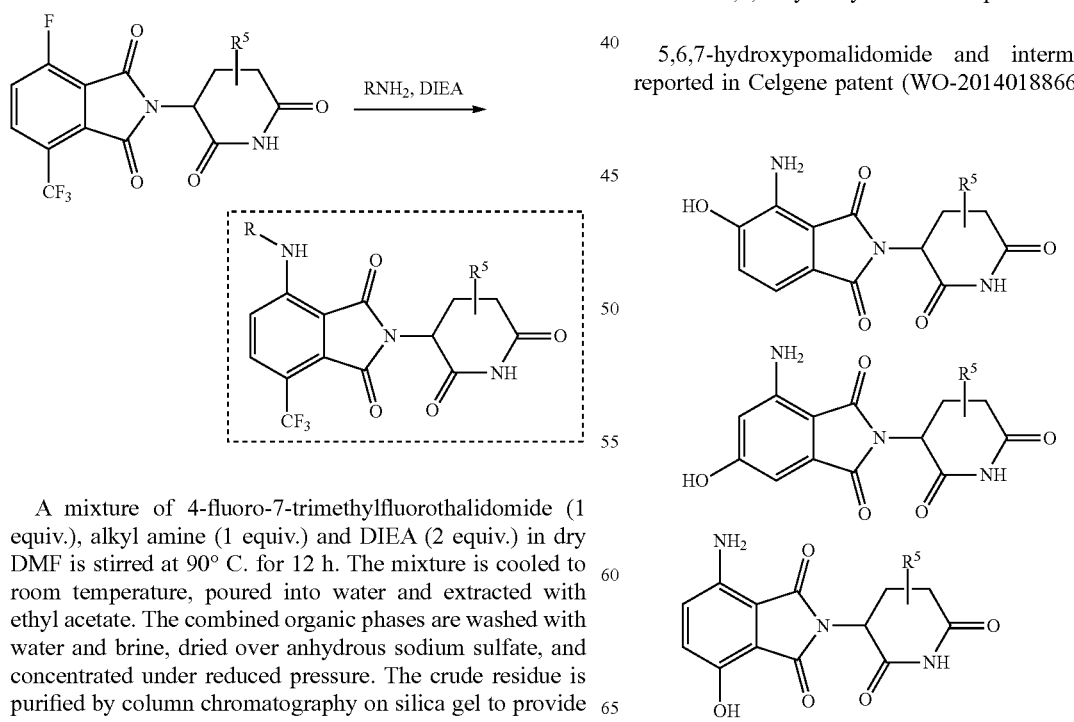

A mixture of 4-fluoro-7-trimethylfluorothalidomide (1 equiv.), alkyl amine (1 equiv.) and DIEA (2 equiv.) in dry DMF is stirred at 90° C. for 12 h. The mixture is cooled to room temperature, poured into water and extracted with ethyl acetate. The combined organic phases are washed with water and brine, dried over anhydrous sodium sulfate, and concentrated under reduced pressure. The crude residue is purified by column chromatography on silica gel to provide N-linked 7-trimethylfluoropomalidomide derivatives. (*Chem Biol.* 2015 Jun. 18; 22(6):755-63.)

General Procedure Example 16: O-Linked 7-trimethylfluorothalidomide Derivatives To a cooled solution of alcohol (1.2 equiv.) in DMF is added NaH (1.3 equiv.) and stirred at 0° C. for 30 min. 4-fluoro-7-trimethylfluorothalidomide (1 equiv.) was added and the mixture is heated at 80° C. overnight. The reaction is cooled and quenched with methanol. The mixture is poured into water and extracted with ethyl acetate. The combined organic phases are washed with water and brine, dried over anhydrous sodium sulfate, and concentrated under reduced pressure. The crude residue is purified by column chromatography on silica gel to provide O-linked 7-trimethylfluorothalidomide derivatives.

5,6,7-Hydroxythalidomide/pomalidomide 5,6,7-hydroxypomalidomide and intermediates were reported in Celgene patent (WO-2014018866-A1):

5,6,7-Alkoxythalidomide/pomalidomide
Starting materials are found in Celgene patent (WO-2014018866-A1)
N-Linked 5-alkoxypomalidomide
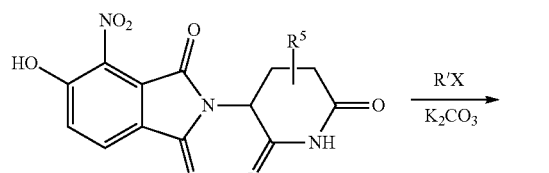
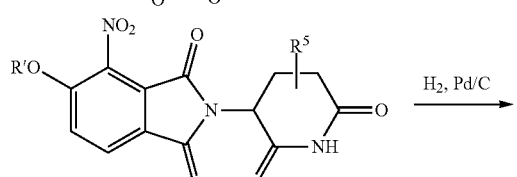
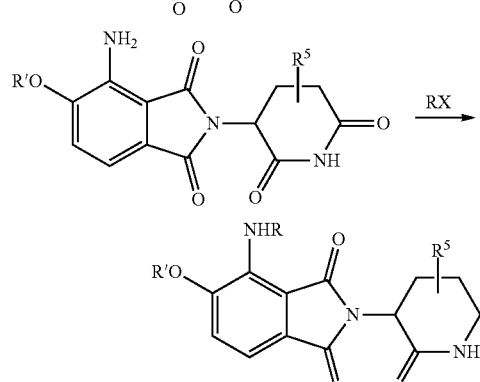
O-Linked 5-alkoxythalidomide
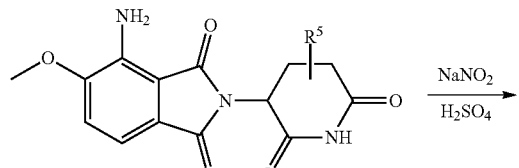
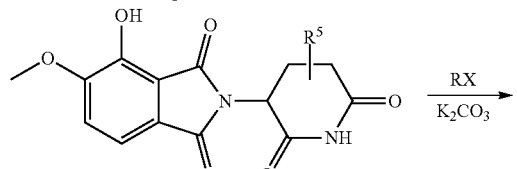
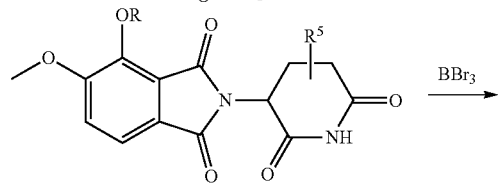
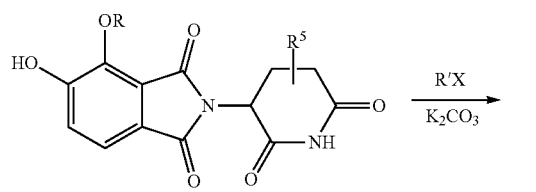
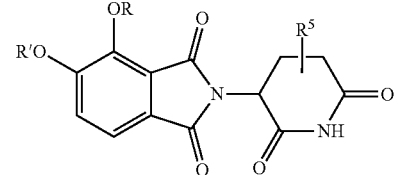
N-Linked 6-alkoxypomalidomide
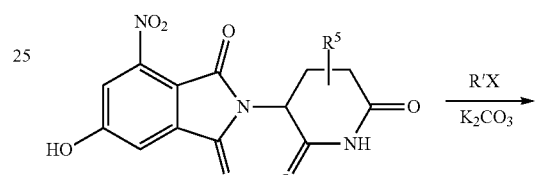
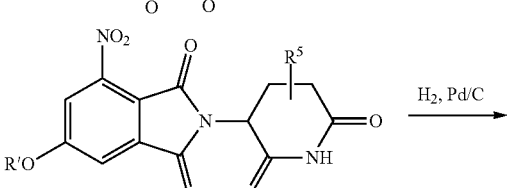
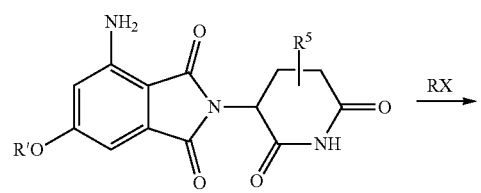
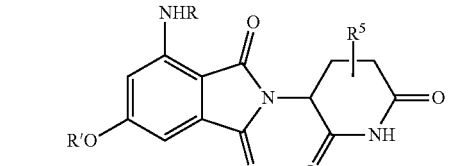
O-Linked 6-alkoxythalidomide
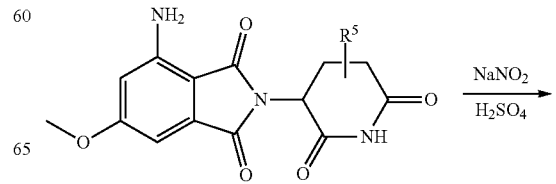

277
-continued
278
O-Linked 7-alkoxythalidomide
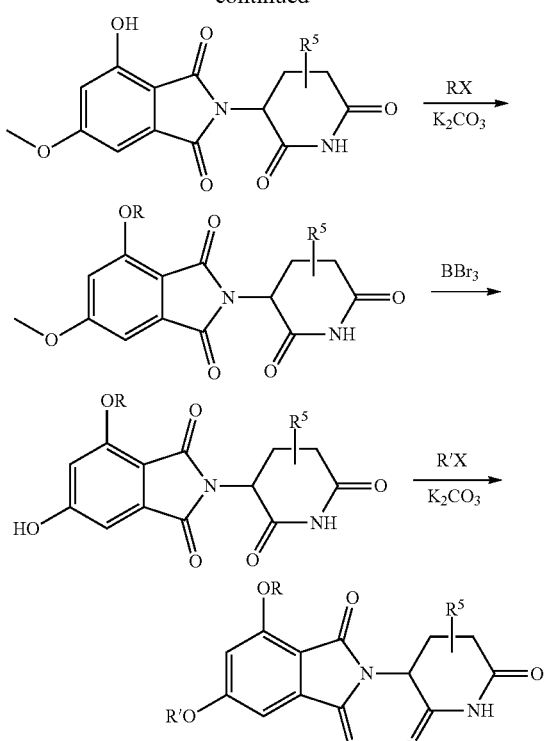
N-Linked 7-alkoxypomalidomide
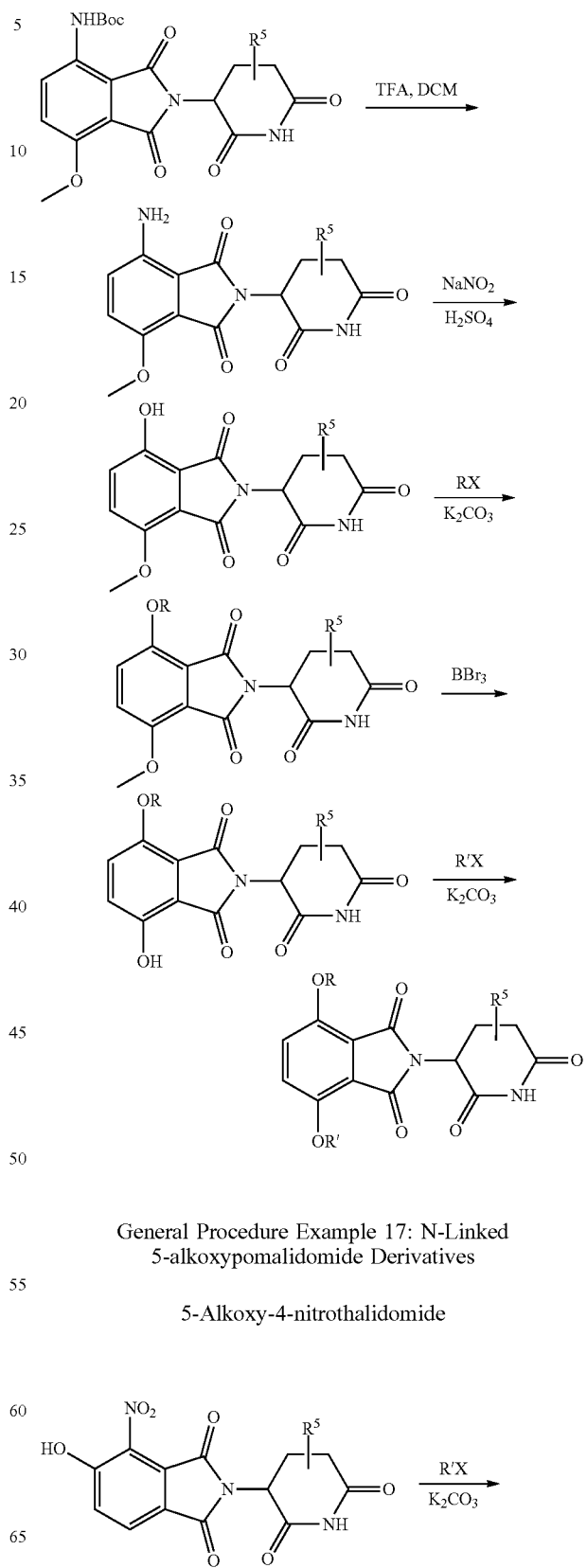
General Procedure Example 17: N-Linked
5-alkoxypomalidomide Derivatives
5-Alkoxy-4-nitrothalidomide

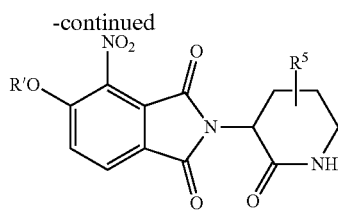

5-hydroxy-4-nitrothalidomide (1 equiv.) is dissolved in DMF and K$_2$CO$_3$ (2 equiv.) is added, followed by alkyl halides (1.2 equiv.). The mixture is stirred at rt until the consumption of the starting material. The mixture is diluted with water and extracted with EtOAc. The organic layer is washed with brine, dried (Na$_2$SO$_4$), and concentrated. The residue is purified by column chromatography to give 5-alkoxy-4-nitrothalidomide.

4-Amino-5-alkoxythalidomide

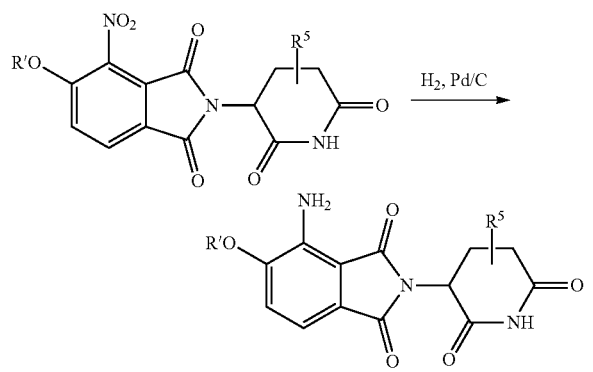

A mixture of 5-alkoxy-4-nitrothalidomide (1 equiv.) and palladium on activated carbon (10% wt) in THF is hydrogenated until the disappearance of the starting material. The mixture is filtered through Celite® and concentrated to give 4-amino-5-alkoxythalidomide.

N-Linked 5-alkoxypomalidomide Derivatives

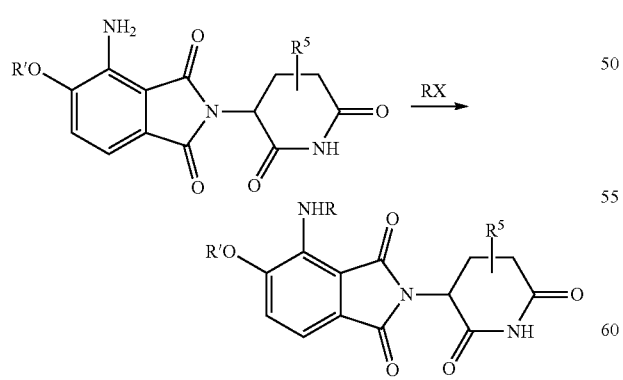

4-amino-5-alkoxythalidomide (1 equiv.) is dissolved in DMF and K$_2$CO$_3$ (2 equiv.) is added, followed by alkyl halides (1.2 equiv.). The mixture is stirred at rt until the consumption of the starting material. The mixture is diluted with water and extracted with EtOAc. The organic layer is washed with brine, dried (Na$_2$SO$_4$), and concentrated. The residue is purified by column chromatography to give N-linked 5-alkoxypomalidomide derivatives.

General Procedure Example 18: O-Linked 5-alkoxythalidomide Derivatives

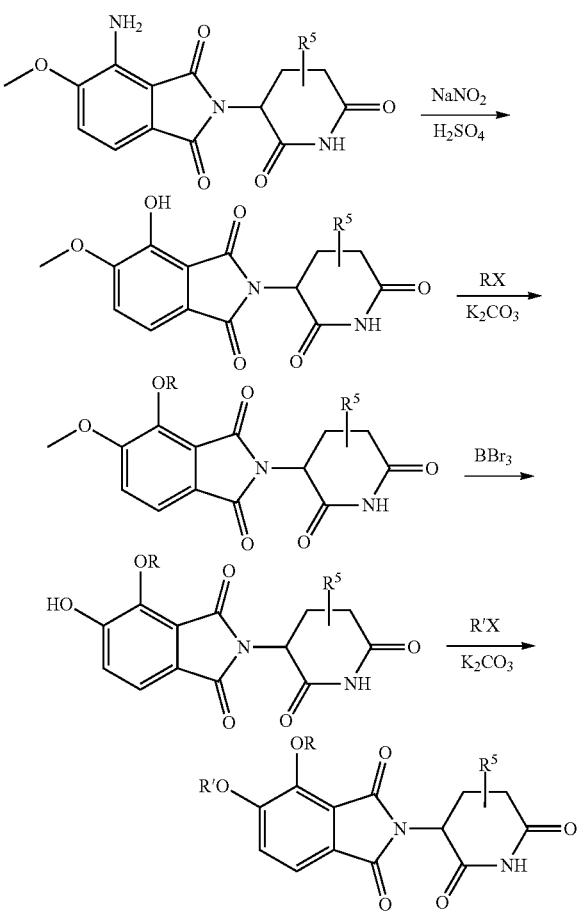

4-Hydroxy-5-methoxythalidomide

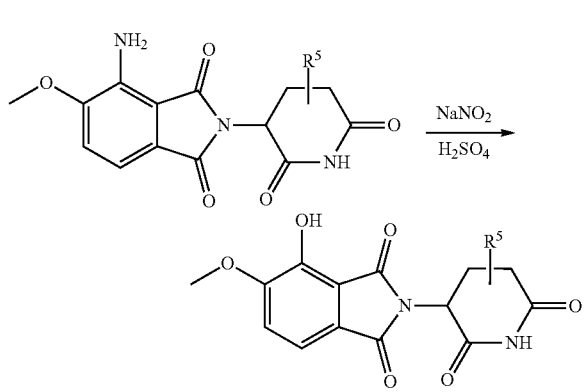

15 N Sulfuric acid is cooled to 0° C., 4-amino-5-methoxythalidomide (1 equiv.) is added gradually with good stirring. After one hour, a solution of sodium nitrite (1 equiv.) in water is added slowly while maintaining the temperature below 5° C. After another 30 minutes, the mixture is warmed to 80° C. and maintained at this temperature until nitrogen evolution ceases. The now dark orange solution is diluted with water and extracted with ether. The organic layer is dried with sodium sulfate, filtered and shaken for two hours with finely powdered barium chloride to remove traces of sulfuric acid. The solution is filtered and concentrated and the residue is purified by column chromatography to give 4-hydroxy-5-methoxythalidomide.

4-Alkoxy-5-methoxythalidomide

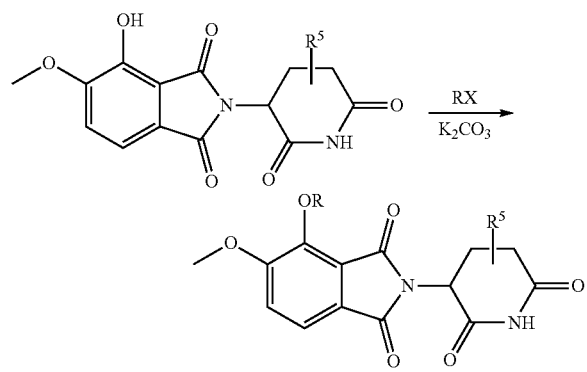

4-Hydroxy-5-methoxythalidomide (1 equiv.) is dissolved in DMF and K$_2$CO$_3$ (2 equiv.) is added, followed by alkyl halides (1.2 equiv.). The mixture is stirred at rt until the consumption of the starting material. The mixture is diluted with water and extracted with EtOAc. The organic layer is washed with brine, dried (Na$_2$SO$_4$), and concentrated. The residue is purified by column chromatography to give 4-alkoxy-5-methoxythalidomide.

4-Alkoxy-5-hydroxythalidomide

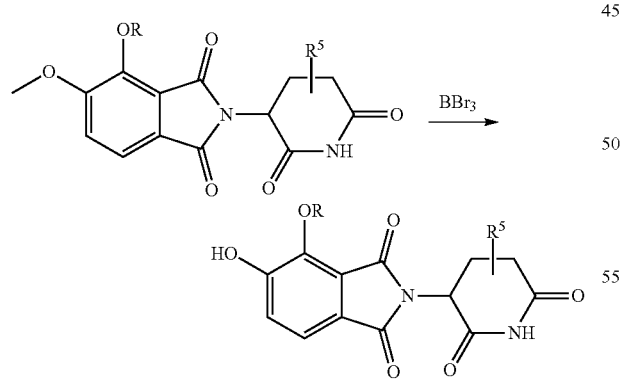

To a solution of 4-alkoxy-5-methoxythalidomide (1 equiv.) in DCM is added BBr$_3$ (10 equiv.). The mixture is stirred at rt for 12 h. The reaction is quenched by adding DCM and water. The organic layer is separated, dried over sodium sulfate, filtered, and concentrated. The residue is purified by column chromatography to give 4-alkoxy-5-hydroxythalidomide.

O-linked 5-alkoxythalidomide Derivatives

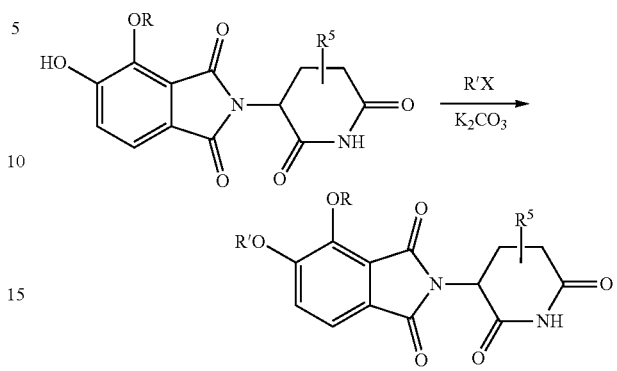

4-Alkoxy-5-hydroxythalidomide (1 equiv.) is dissolved in DMF and K$_2$CO$_3$ (2 equiv.) is added, followed by alkyl halides (1.2 equiv.). The mixture is stirred at rt until the consumption of the starting material. The mixture is diluted with water and extracted with EtOAc. The organic layer is washed with brine, dried (Na$_2$SO$_4$), and concentrated. The residue is purified by column chromatography to give O-linked 5-alkoxythalidomide derivatives.

Thal/Pom/Len Analogs with Variation on the Glutarimide Moiety

α-Fluoro, Methyl, Deutero-Substituted Thalidomide/Pomalidomide

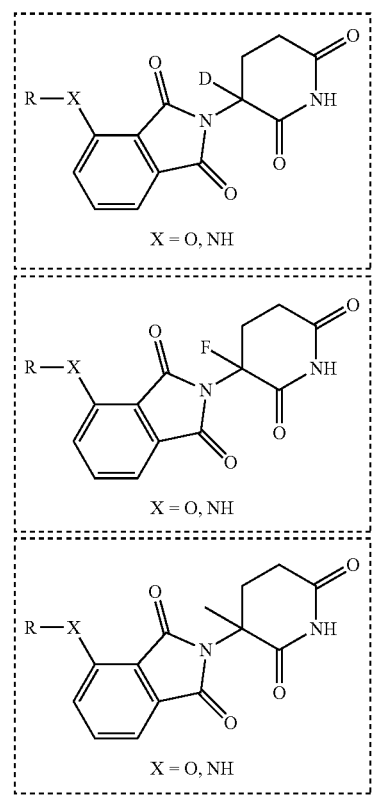

283
General Scheme

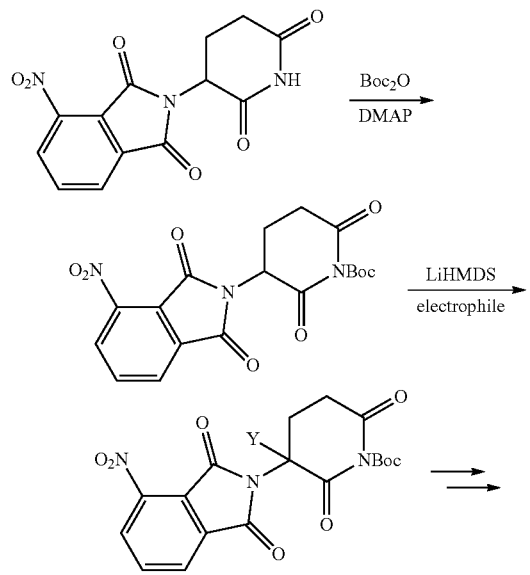

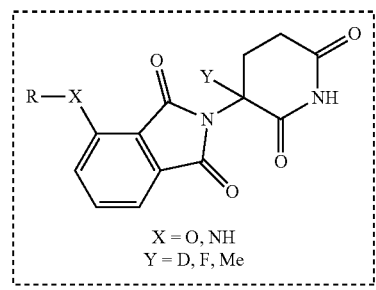

General Procedure Example 19: N-Linked α-D Pomalidomide Derivatives

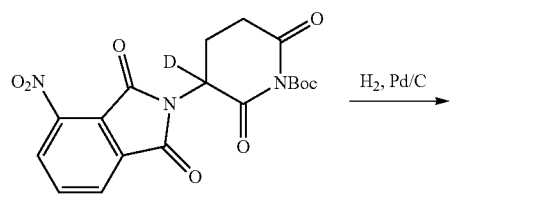

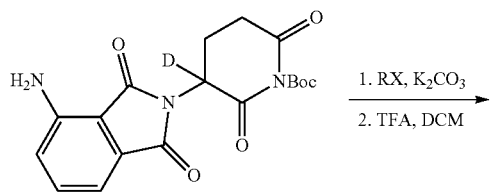

284

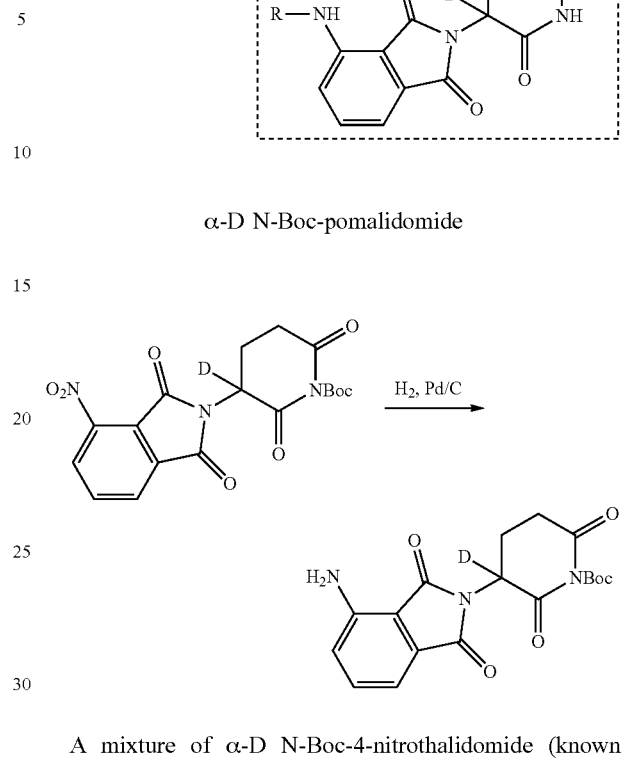

α-D N-Boc-pomalidomide

A mixture of α-D N-Boc-4-nitrothalidomide (known compound reported in BMCL, 2003, 13, 3415) (1 equiv.) and palladium on activated carbon (10% wt) in THF is hydrogenated until the disappearance of the starting material. The mixture is filtered through Celite® and concentrated to give α-D N-Boc-pomalidomide.

N-Linked α-D Pomalidomide Derivatives

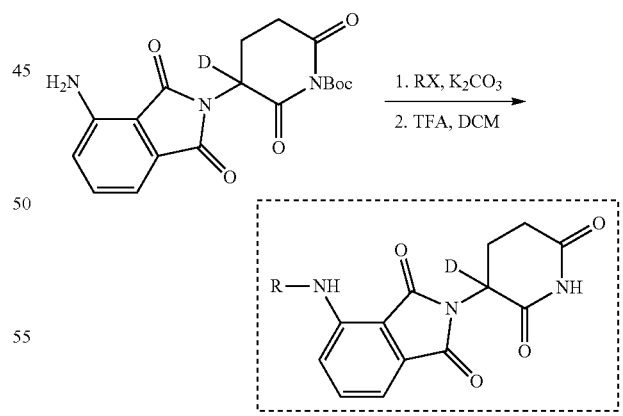

α-D N-Boc-pomalidomide (1 equiv.) is dissolved in DMF and $K_2CO_3$ (2 equiv.) is added, followed by alkyl halides (1.2 equiv.). The mixture is stirred at rt until the consumption of the starting material. The mixture is diluted with water and extracted with EtOAc. The organic layer is washed with brine, dried ($Na_2SO_4$), and concentrated. The residue is purified by column chromatography to give α-D N-Boc-pomalidomide derivatives.

A solution of α-D N-Boc-pomalidomide derivatives (1 equiv.) in TFA/DCM (1:1) is stirred at rt overnight. Solvent is evaporated and the residue is purified by column chromatography on silica gel to give N-linked α-D pomalidomide derivatives.

General Procedure Example 20: O-Linked α-D Thalidomide Derivatives

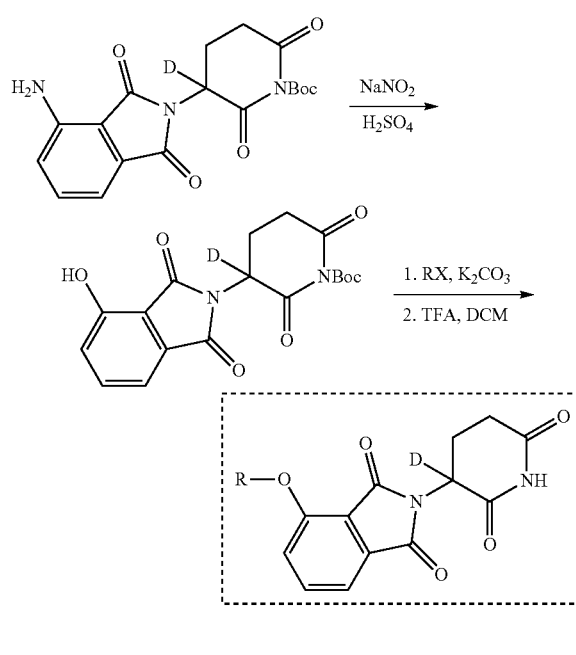

α-D N-Boc-4-hydroxythalidomide

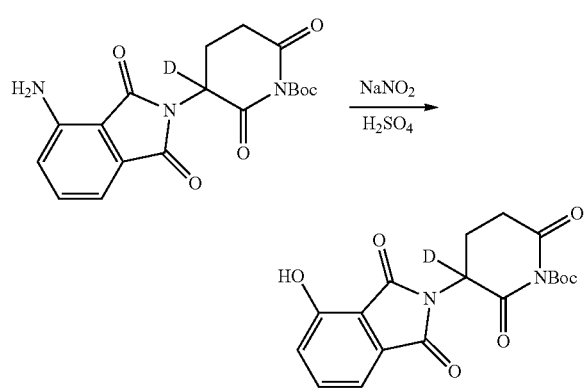

15 N Sulfuric acid is cooled to 0° C., α-D N-Boc-pomalidomide (1 equiv.) is added gradually with good stirring. After one hour, a solution of sodium nitrite (1 equiv.) in water is added slowly while maintaining the temperature below 5° C. After another 30 minutes, the mixture is warmed to 80° C. and maintained at this temperature until nitrogen evolution ceases. The now dark orange solution is diluted with water and extracted with ether. The organic layer is dried with sodium sulfate, filtered and shaken for two hours with finely powdered barium chloride to remove traces of sulfuric acid. The solution is filtered and concentrated and the residue is purified by column chromatography to give α-D N-Boc-4-hydroxythalidomide.

O-Linked α-D Thalidomide Derivatives

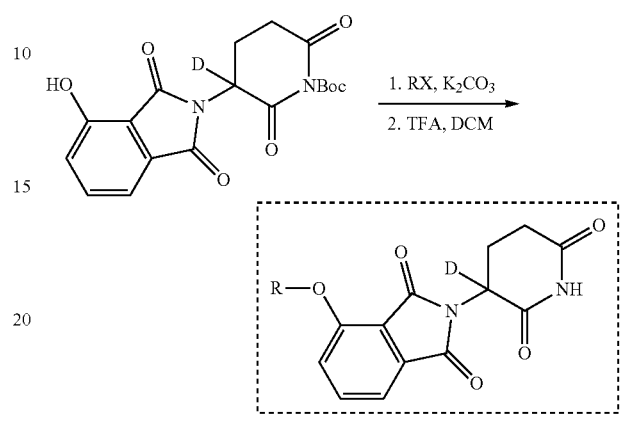

α-D N-Boc-4-hydroxythalidomide (1 equiv.) is dissolved in DMF and $K_2CO_3$ (2 equiv.) is added, followed by alkyl halides (1.2 equiv.). The mixture is stirred at rt until the consumption of the starting material. The mixture is diluted with water and extracted with EtOAc. The organic layer is washed with brine, dried ($Na_2SO_4$), and concentrated. The residue is purified by column chromatography to give α-D N-Boc-4-hydroxythalidomide derivatives.

A solution of α-D N-Boc-4-hydroxythalidomide derivatives (1 equiv.) in TFA/DCM (1:1) is stirred at rt overnight. Solvent is evaporated and the residue is purified by column chromatography on silica gel to give O-linked α-D thalidomide derivatives.

General Procedure Example 21: N-Linked α-F Pomalidomide Derivatives

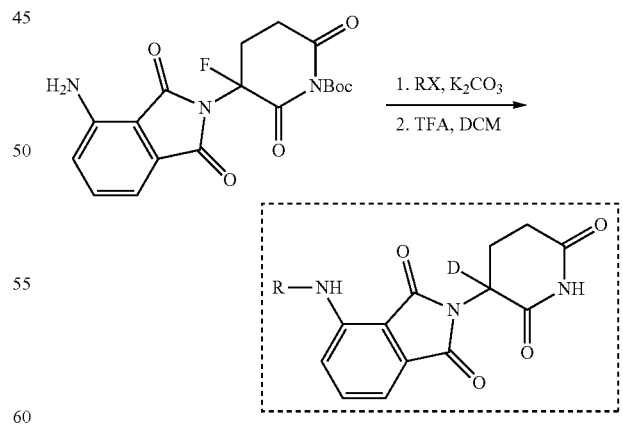

α-F N-Boc-pomalidomide (known compound reported in BMCL, 2003, 13, 3415) (1 equiv.) is dissolved in DMF and $K_2CO_3$ (2 equiv.) is added, followed by alkyl halides (1.2 equiv.). The mixture is stirred at rt until the consumption of the starting material. The mixture is diluted with water and extracted with EtOAc. The organic layer is washed with brine, dried (Na$_2$SO$_4$), and concentrated. The residue is purified by column chromatography to give α-F N-Boc-pomalidomide derivatives.

A solution of α-F N-Boc-pomalidomide derivatives (1 equiv.) in TFA/DCM (1:1) is stirred at rt overnight. Solvent is evaporated and the residue is purified by column chromatography on silica gel to give N-linked α-F pomalidomide derivatives.

General Procedure Example 22: O-Linked α-F Thalidomide Derivatives

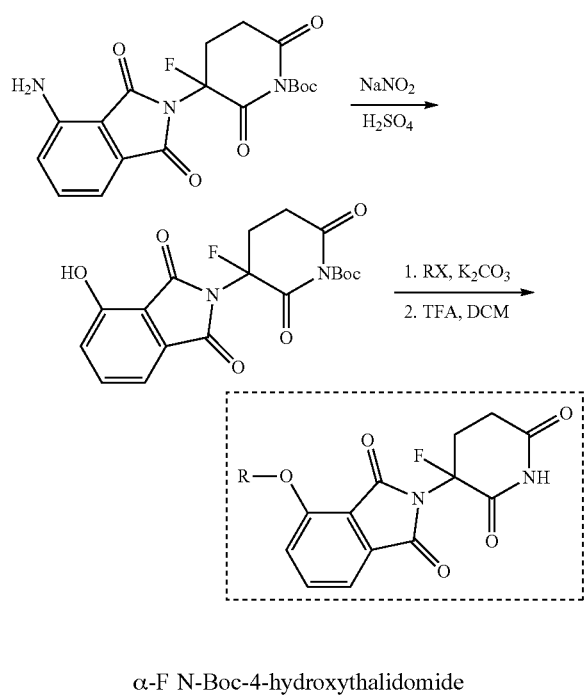

α-F N-Boc-4-hydroxythalidomide

15 N Sulfuric acid is cooled to 0° C., α-F N-Boc-pomalidomide (1 equiv.) is added gradually with good stirring. After one hour, a solution of sodium nitrite (1 equiv.) in water is added slowly while maintaining the temperature below 5° C. After another 30 minutes, the mixture is warmed to 80° C. and maintained at this temperature until nitrogen evolution ceases. The now dark orange solution is diluted with water and extracted with ether. The organic layer is dried with sodium sulfate, filtered and shaken for two hours with finely powdered barium chloride to remove traces of sulfuric acid. The solution is filtered and concentrated and the residue is purified by column chromatography to give α-F N-Boc-4-hydroxythalidomide.

O-Linked α-F Thalidomide Derivatives

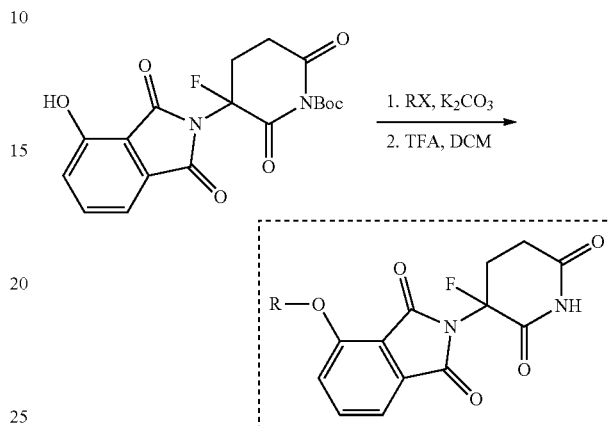

α-F N-Boc-4-Hydroxythalidomide (1 equiv.) is dissolved in DMF and K$_2$CO$_3$ (2 equiv.) is added, followed by alkyl halides (1.2 equiv.). The mixture is stirred at rt until the consumption of the starting material. The mixture is diluted with water and extracted with EtOAc. The organic layer is washed with brine, dried (Na$_2$SO$_4$), and concentrated. The residue is purified by column chromatography to give α-F N-Boc-4-hydroxythalidomide derivatives.

A solution of α-F N-Boc-4-hydroxythalidomide derivatives (1 equiv.) in TFA/DCM (1:1) is stirred at rt overnight. Solvent is evaporated and the residue is purified by column chromatography on silica gel to give O-linked α-F thalidomide derivatives.

General Procedure Example 23: N-Linked α-Methylpomalidomide Derivatives

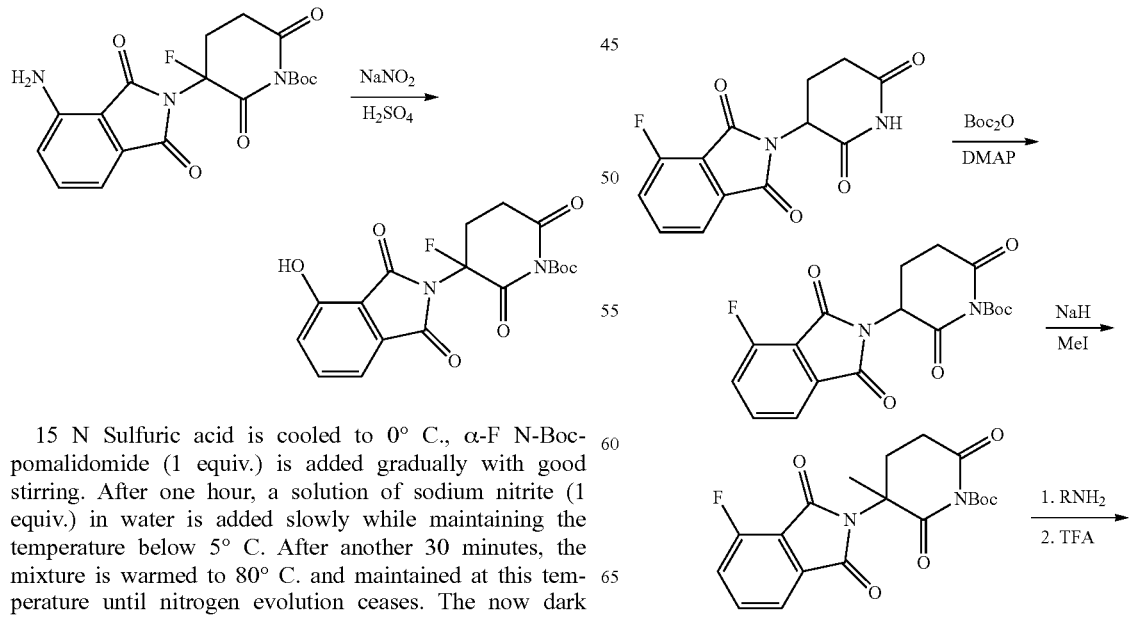

-continued

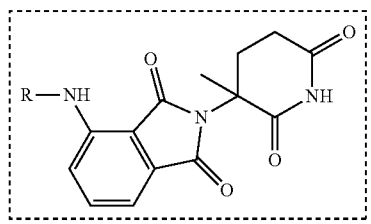

N-Boc 4-Fluorothalidomide

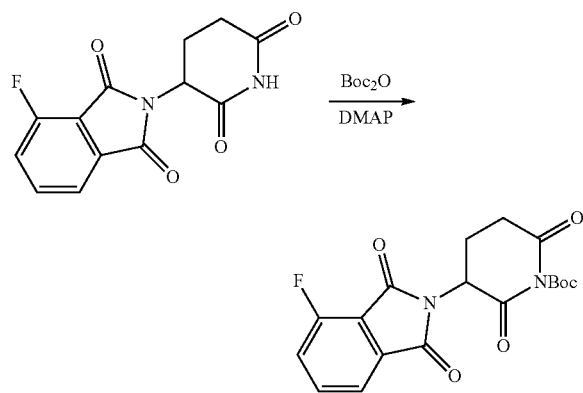

N-Boc 4-Fluoro-α-methylthalidomide

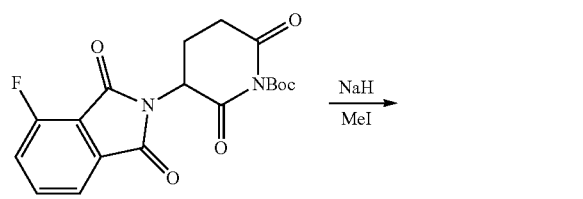

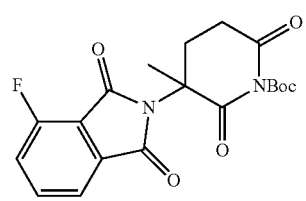

To a stirred solution of 4-fluorothalidomide (1.0 equiv.) in DMF is added potassium carbonate (2.0 equiv.). The resulting solution is cooled to 0-5° C. and Boc anhydride (3.0 equiv.) is added slowly as a solution in 1,4-dioxane (also cooled). The resulting mixture is stirred at 0° C. for 1 h and allowed to warm to room temperature overnight. Water is then added and the aqueous layer is extracted 2 times with DCM and concentrated. The residue is purified by column chromatography on silica gel to obtain N-Boc 4-fluorothalidomide.

To a solution of N-Boc 4-fluorothalidomide (1 equiv.) in DMF is added sodium hydride (2 equiv.) slowly at 0° C. The mixture is stirred at 0° C. for 30 min and methyl iodide (1.1 equiv.) is added dropwise. The mixture is stirred at rt until the consumption of the starting material and then quenched with methanol. The mixture is diluted with saturated NaHCO₃, extracted with EtOAc, dried (Na₂SO₄), and concentrated. The residue is purified by column chromatography on silica gel to obtain N-Boc 4-fluoro-α-methylthalidomide.

N-Linked α-methylpomalidomide Derivatives

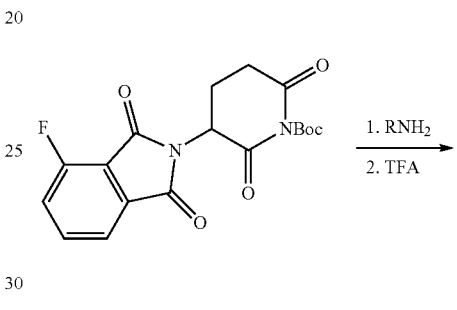

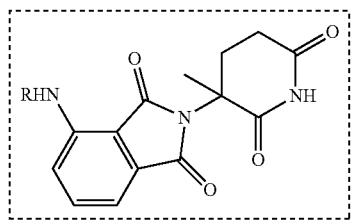

A mixture of N-Boc 4-fluoro-α-methylthalidomide (1 equiv.), alkyl amine (1 equiv.) and DIEA (2 equiv.) in dry DMF is stirred at 90° C. for 12 h. The mixture is cooled to room temperature, poured into water and extracted with ethyl acetate. The combined organic phases are washed with water and brine, dried over anhydrous sodium sulfate, and concentrated under reduced pressure. The crude residue is purified by column chromatography on silica gel to provide N-Boc α-methylpomalidomide derivatives. (ref: *Chem Biol.* 2015 Jun. 18; 22(6):755-63.) A solution of N-Boc α-methylpomalidomide derivatives (1 equiv.) in TFA/DCM (1:1) is stirred at rt overnight. Solvent is evaporated and the residue is purified by column chromatography on silica gel to give N-linked α-methylpomalidomide derivatives.

291
5′-Hydroxyl, Alkoxy, Amino, Sulfonamide Substituted Glutarimide
General Scheme
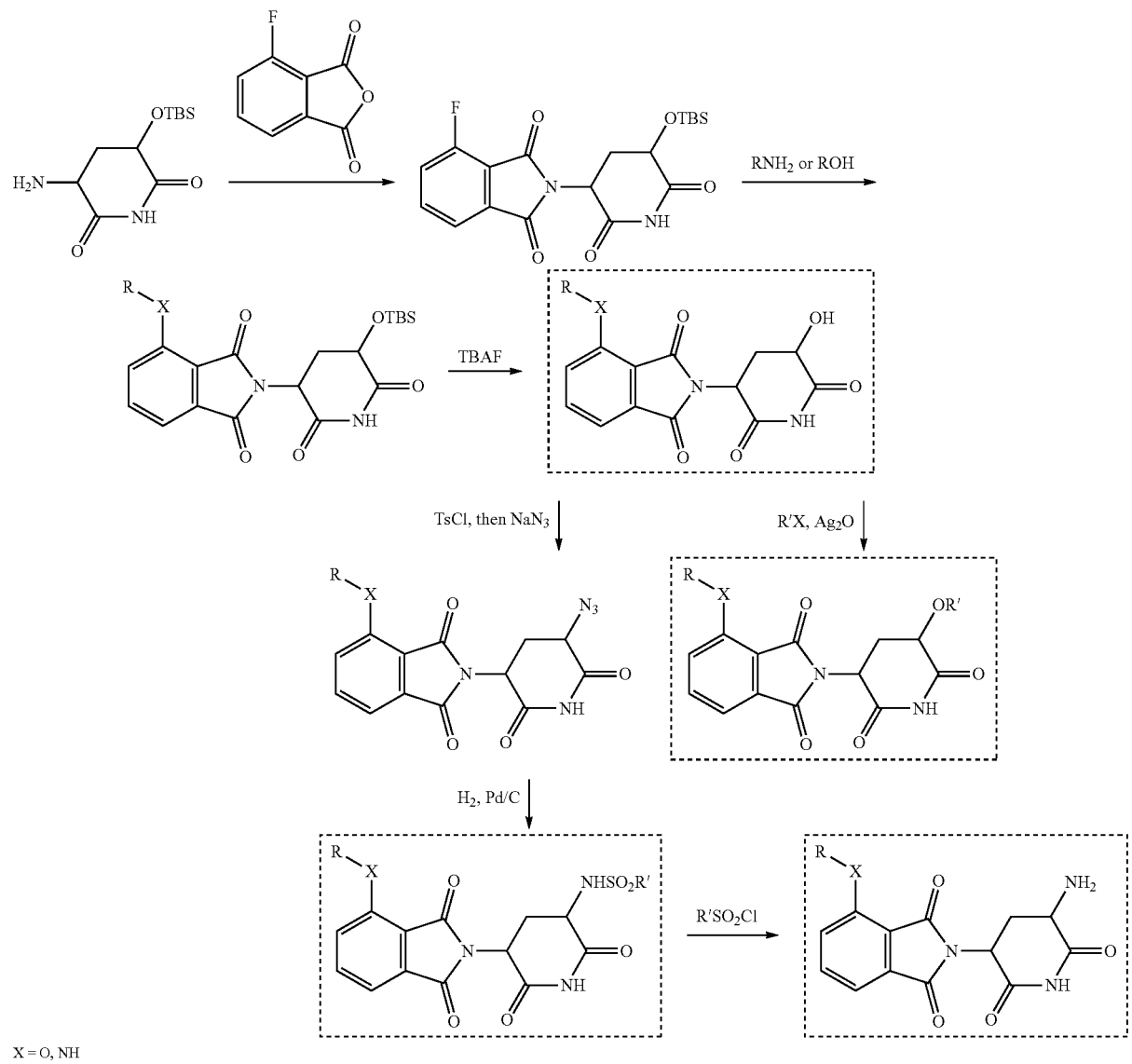
X = O, NH
General Procedure Example 24: 5′-Hydroxyl Substituted Pomalidomide Derivatives
5′-tert-Butyldimethylsilyloxy-4-fluorothalidomide
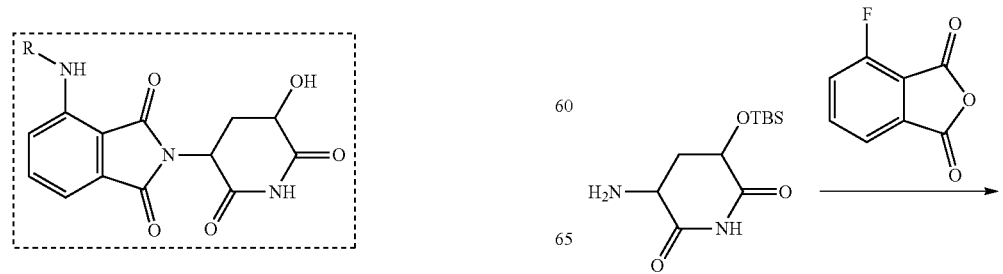

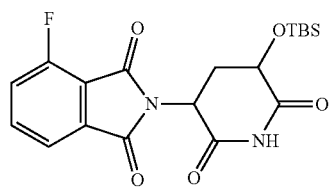

A mixture of 3-amino-5-((tert-butyldimethylsilyl)oxy)piperidine-2,6-dione (known compound reported in *Chem. Pharm. Bull.* 2006, 54, 1709) (1 equiv.), 3-aminopiperidine-2,6-dione HCl salt (1 equiv.), and potassium acetate (2.5 equiv.) in acetic acid is stirred at 120° C. overnight. The dark mixture is cooled and filtered. The filter cake is dissolved in DCM and washed with saturated NaHCO$_3$ and brine. The organic layer is dried (Na$_2$SO$_4$) and concentrated to provide 5'-tert-butyldimethylsilyloxy-4-fluorothalidomide.

5'-tert-Butyldimethylsilyloxy-pomalidomide Derivatives

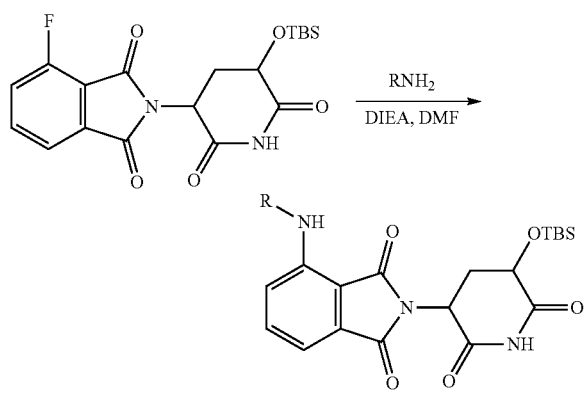

A mixture of alkyl amine (1 equiv.), 5'-tert-butyldimethylsilyloxy-4-fluorothalidomide (1 equiv.) and DIEA (2 equiv.) in dry DMF is stirred at 90° C. for 12 h. The mixture is cooled to room temperature, poured into water and extracted with ethyl acetate. The combined organic phases are washed with water and brine, dried over anhydrous sodium sulfate, and concentrated under reduced pressure. The crude residue is purified by column chromatography on silica gel to give 5'-tert-butyldimethylsilyloxy-pomalidomide derivatives. (*Chem Biol.* 2015 Jun. 18; 22(6):755-63.)

5'-Hydroxyl Pomalidomide Derivatives

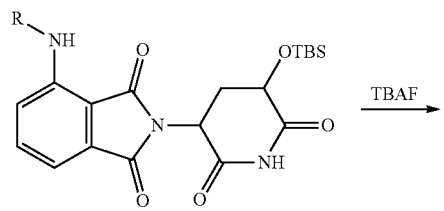

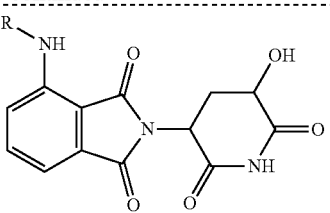

To a solution of 5'-tert-butyldimethylsilyloxy-pomalidomide derivatives (1 equiv.) in dry THF is added TBAF (1.1 equiv.) at 0° C., and the reaction mixture is stirred at 0° C. for 40 min, and then at room temperature for 2 h. CHCl$_3$ is added, and the mixture is washed with 0.5 M HCl and brine, dried over Na$_2$SO$_4$, filtered and concentrated. The crude product is purified by flash column chromatography on silica gel to provide 5'-hydroxyl pomalidomide derivatives. (*Chem. Pharm. Bull.* 2006, 54, 1709)

General Procedure Example 25: 5'-Alkoxy Substituted Pomalidomide Derivatives

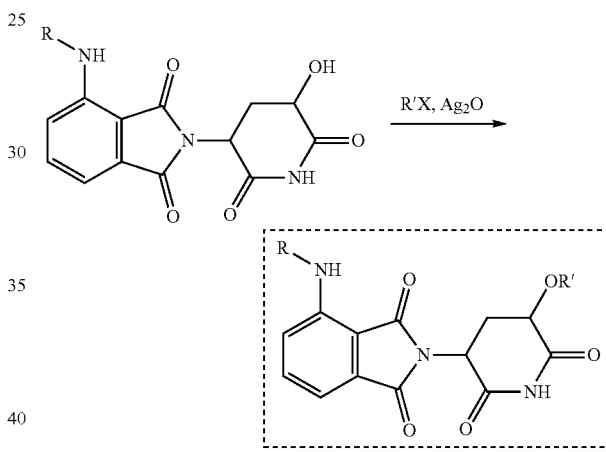

To a solution of 5'-hydroxyl pomalidomide derivatives (1 equiv.) and alkyl halide (2 eq.) in Et$_2$O (0.05 M) under a nitrogen atmosphere is added Ag$_2$O (2 equiv.) at room temperature. The resulting suspension is stirred at dark at room temperature for 16 h then filtered through a pad of Celite® using Et$_2$O as eluent. The residue is concentrated in vacuo and purified by column chromatography on silica gel to provide 5'-alkoxy pomalidomide derivatives. (*Org. Lett.* 2013, 15, 5878)

General Procedure Example 26: 5'-Amino Substituted Pomalidomide Derivatives

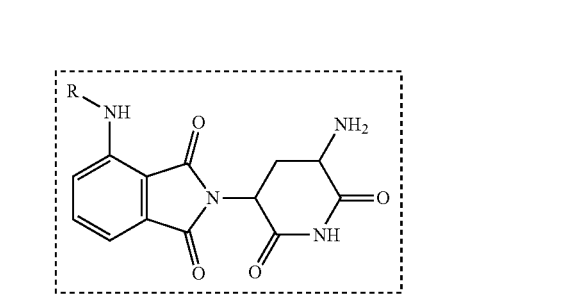

5'-Azido Pomalidomide Derivatives

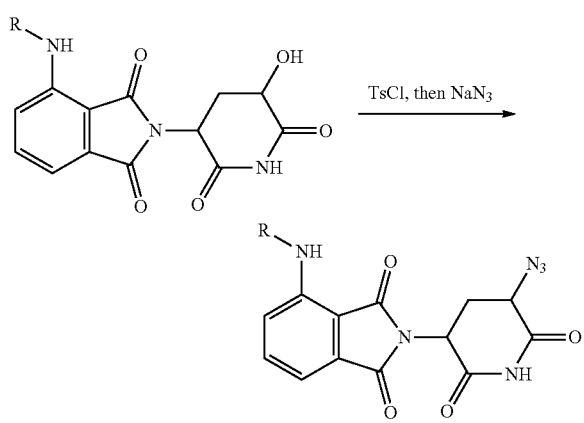

5'-Hydroxy pomalidomide derivatives (1 equiv.) is dissolved in anhydrous 1,4-dioxane under nitrogen. 1.4 M n-butyllithium hexane solution (5 equiv.) diluted with 1,4-dioxane is added, and stirred for 10 minutes at room temperature. A solution of p-toluene sulfonyl chloride in 1,4-dioxane is added and stirred for 1 hour. After reaction completion, it is quenched with aqueous ammonia chloride, and extracted with EtOAc. The organic layer is dried ($Na_2SO_4$) and concentrated to provide 5'-tosyloxy-pomalidomide derivatives, which are used in next reaction without further purification. (Jpn. Kokai Tokkyo Koho, 2009215195, 24 Sep. 2009)

To a stirred solution of 5'-tosyloxy-pomalidomide derivatives (1 equiv.) in anhydrous DMF at 70° C. under a N2 atmosphere is added $NaN_3$ (5 equiv.). The mixture is then allowed to stir at 70° C. for 6 h, and then quenched with cool $H_2O$ and extracted with EtOAc (2×). The combined organic extracts are washed with cool $H_2O$ and brine, dried ($Na_2SO_4$), and concentrated and purified by flash column chromatography on silica gel to provide 5'-azido pomalidomide derivatives. (*Synthesis* 2013, 45, 3383-3386)

5'-Amino Pomalidomide Derivatives

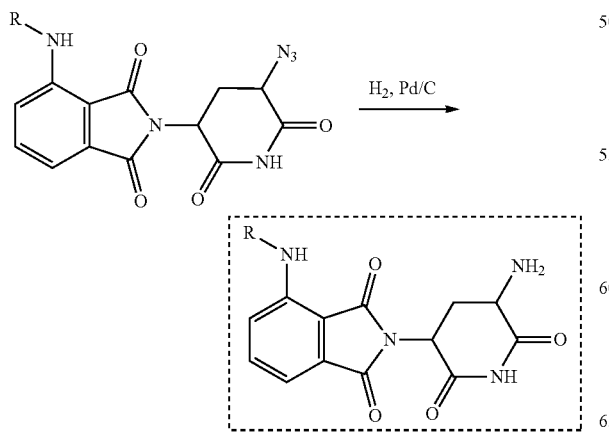

General Procedure Example 27: 5'-Sulfonamide Substituted Pomalidomide

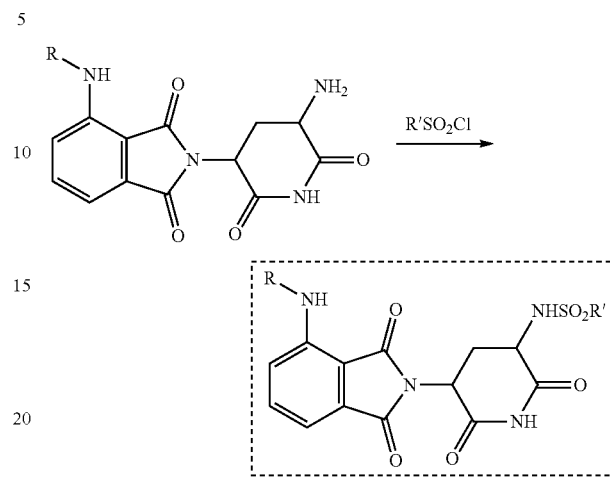

To a solution of 5'-amino pomalidomide derivatives (1 equiv.), triethylamine (2 equiv.) in chloroform is added sulfonyl chloride (1.1 equiv.). The reaction is stirred till the consumption of the starting material. The mixture is then extracted with EtOAc, washed with water and brine, dried ($Na_2SO_4$), and concentrated. The residue is purified by flash column chromatography on silica gel to give 5'-sulfonamide pomalidomide derivatives.

5',5'-Difluoro Substituted Glutarimide

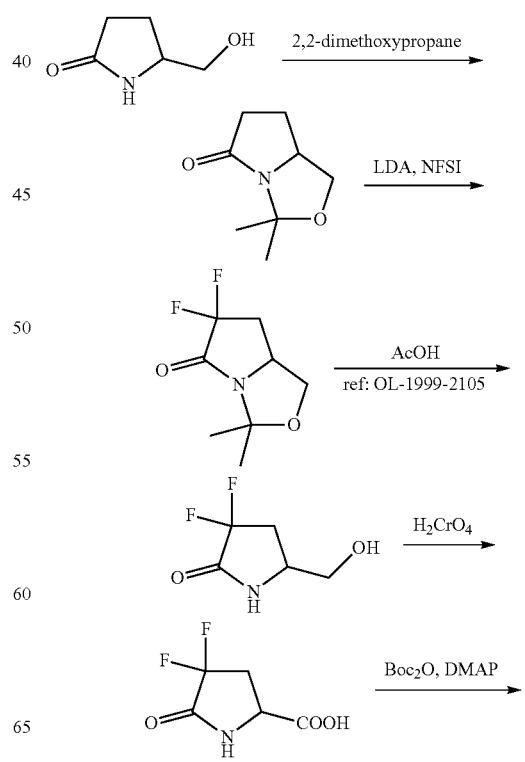

297
-continued

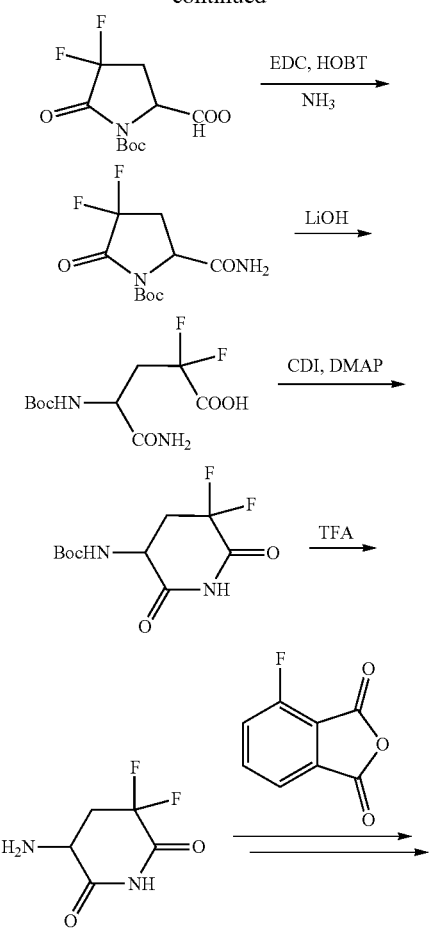

General Procedure Example 28: 5',5'-Difluoro Substituted Pomalidomide Derivatives

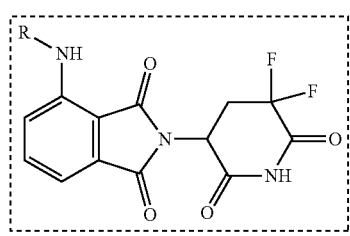

298

N-Boc-4,4-Difluoropyroglutamic Acid

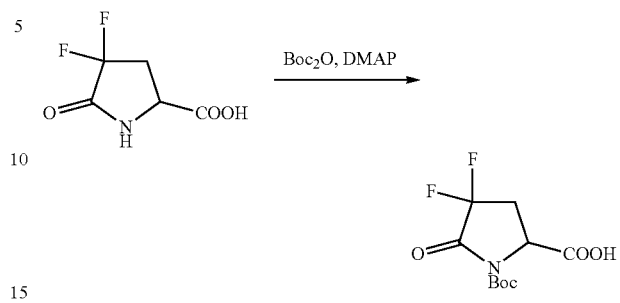

To a stirred solution of 4,4-difluoropyroglutamic acid (known compound reported in *Org. Lett.* 1999, 1, 2105) (1.0 equiv.) in DMF is added Boc anhydride (2.0 equiv.), followed by DMAP (0.1 equiv.). The resulting mixture is stirred at room temperature overnight. Water is then added and the aqueous layer is extracted 2 times with DCM and concentrated. The residue is purified by column chromatography on silica gel to obtain N-Boc-4,4-difluoropyroglutamic acid.

N-Boc-4,4-Difluoropyroglutamide

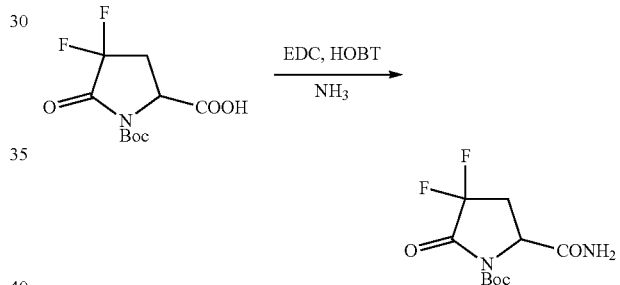

To a solution of N-Boc-4,4-difluoropyroglutamic acid (1 equiv.) in dry $CH_3CN$ is added EDCI.HCl (1.2 equiv.) and HOBT (1.2 equiv.) at 0° C. The mixture is stirred at room temperature for 6 h, then cooled to 0° C., and 28% aqueous ammonia (excess) is carefully added. Stirring is continued at 0° C. for 30 min and then at room temperature for 1 h. Insoluble material is removed by filtration, then the filtrate was concentrated and purified by flash column chromatography on silica gel to provide N-Boc-4,4-difluoropyroglutamide. (*Chem. Pharm. Bull.* 2006, 54, 1709)

3-N-Boc-Amino-5,5-difluoroglutarimide

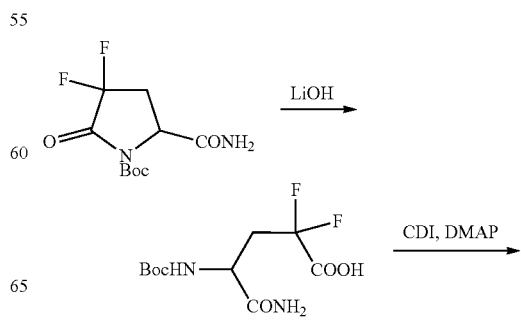

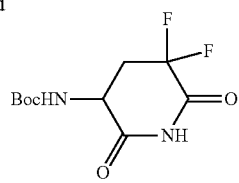

A solution of N-Boc-4,4-difluoropyroglutamide (1 equiv.) in dry THF is stirred at 0° C., and 1.0 M aqueous LiOH (3 equiv.) is carefully added. The reaction mixture is stirred at 0° C. for 3 h, then acidified by addition of 2.0 M aqueous HCl, and extracted 3 times with CHCl₃. The organic layer is washed with brine, dried over Na₂SO₄, filtered and concentrated to afford 5-amino-4-(N-Boc-amino)-2,2-difluoro-5-oxopentanoic acid, which is used directly for the next step without further purification.

To a solution of 5-amino-4-(N-Boc-amino)-2,2-difluoro-5-oxopentanoic acid (1 equiv.) in dry DCM is added CDI (1.15 equiv.), DMAP (0.1 equiv.), and DIPEA (2 equiv.) at 0° C. The mixture is stirred at room temperature for 5 d, then washed with 0.5 M aqueous HCl and brine, dried over Na₂SO₄, filtered and concentrated. The residue was purified by flash column chromatography on silica gel to provide 3-N-Boc-amino-5,5-difluoroglutarimide. (*Chem. Pharm. Bull.* 2006, 54, 1709)

3-Amino-5,5-difluoroglutarimide

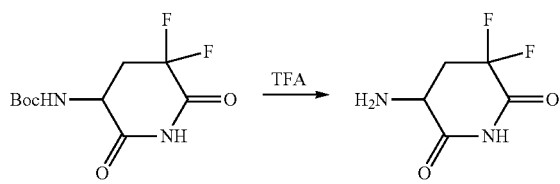 [SMILES: "TFA" ; CC(C)(C)OC(=O)NC1CC(F)(F)C(=O)NC1=O ; NC1CC(F)(F)C(=O)NC1=O]

A solution of 3-N-Boc-amino-5,5-difluoroglutarimide (1 equiv.) in TFA/DCM (1:1) is stirred at rt overnight. Solvent is evaporated and the residue is purified by column chromatography on silica gel to give 3-amino-5,5-difluoroglutarimide.

5',5'-Difluoro-4-fluorothalidomide

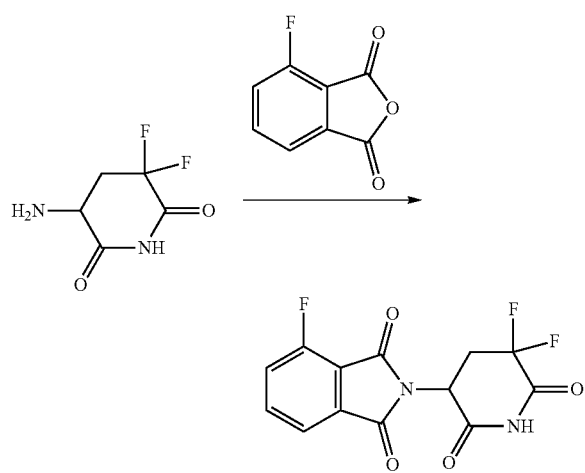

A mixture of 3-fluorophthalic anhydride (1 equiv.), 3-amino-5,5-difluoroglutarimide (1 equiv.), and potassium acetate (2.5 equiv.) in acetic acid is stirred at 120° C. overnight. The dark mixture is cooled and filtered. The filter cake is dissolved in DCM and washed with saturated NaHCO₃ and brine. The organic layer is dried (Na₂SO₄) and concentrated to provide 5',5'-difluoro-4-fluorothalidomide.

5',5'-Difluoro Pomalidomide Derivatives

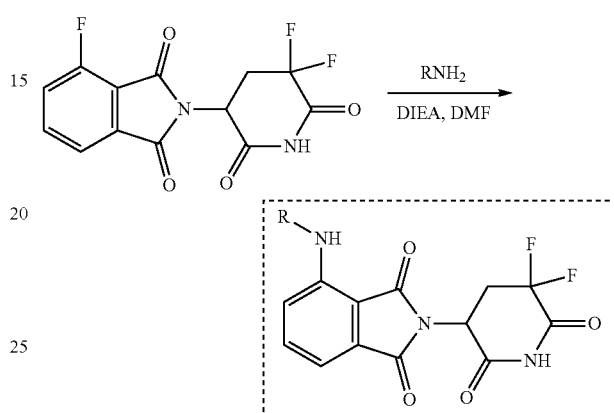

A mixture of alkyl amine (1 equiv.), 5',5'-difluoro-4-fluorothalidomide (1 equiv.) and DIEA (2 equiv.) in dry DMF is stirred at 90° C. for 12 h. The mixture is cooled to room temperature, poured into water and extracted with ethyl acetate. The combined organic phases are washed with water and brine, dried over anhydrous sodium sulfate, and concentrated under reduced pressure. The crude residue is purified by column chromatography on silica gel to give 5',5'-difluoro pomalidomide derivatives. (*Chem Biol.* 2015, 22, 755-763)

Oxetano Glutarimide

2'-Oxetanothalidomide/lenalidomide were reported by Erick M. Carreira (*Org. Lett.* 2013, 15, 4312)

OL-2013-4312

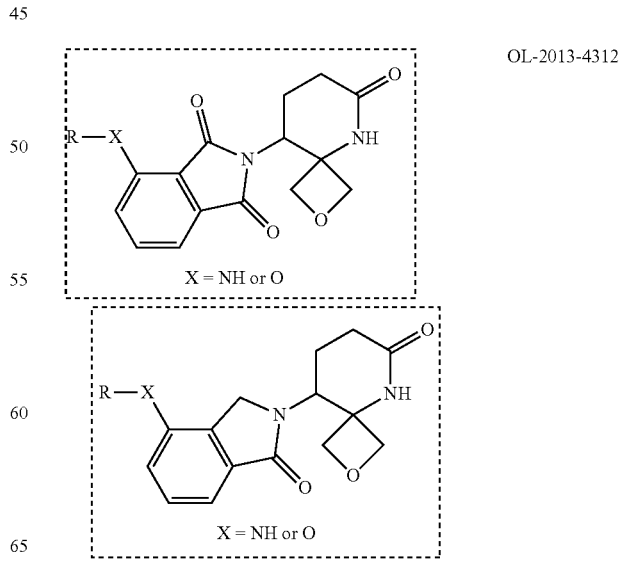

301
6'-Oxetanothalidomide/pomalidomide/lenalidomide
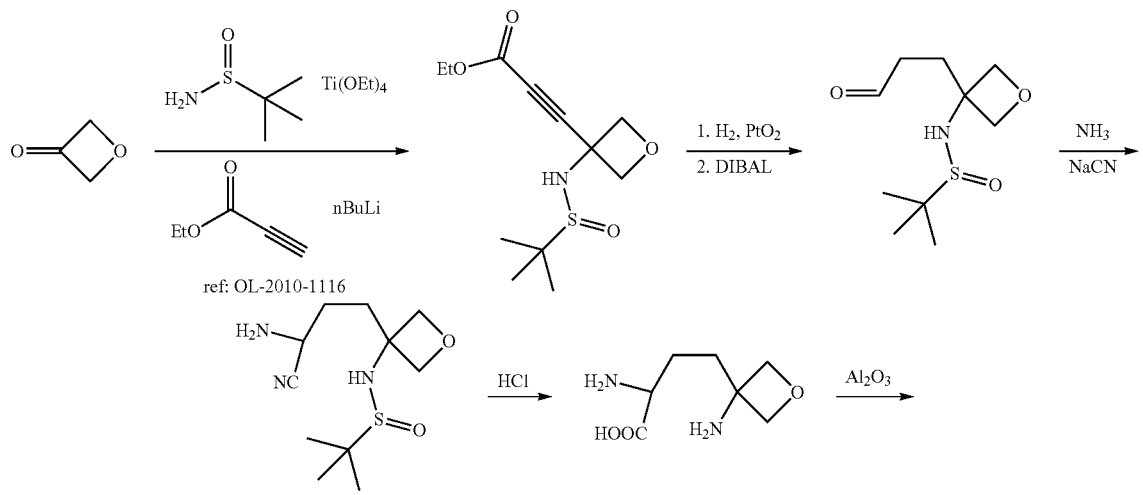
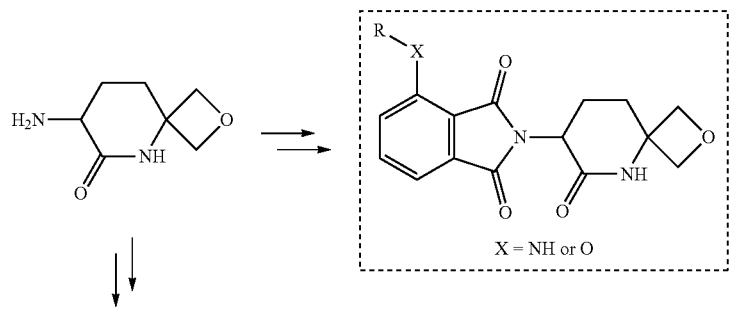
General Procedure Example 29:
6'-Oxetanopomalidomide
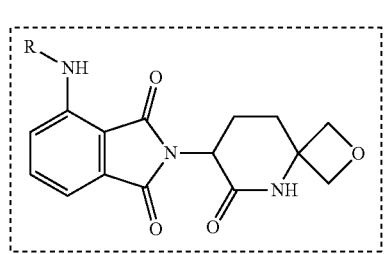
Ethyl 3-(3-((tert-butylsulfinyl)amino)oxetan-3-yl) propiolate
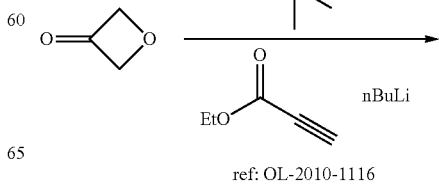

-continued

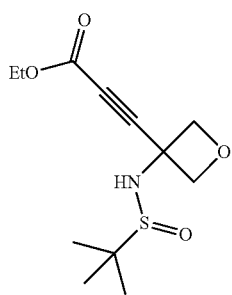

Known compound and procedure reported in *Org. Lett.* 2010, 12, 1116.

2-Methyl-N-(3-(3-oxopropyl)oxetan-3-yl)propane-2-sulfinamide

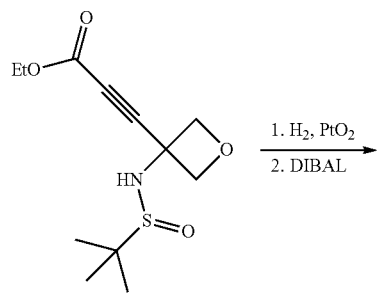

To a solution of ethyl 3-(3-((tert-butylsulfinyl)amino)oxetan-3-yl)propiolate (1 equiv.) in EtOAc is added PtO$_2$/C (0.1 wt equiv.). The reaction vessel is purged three times with hydrogen and heated under hydrogen until the consumption of starting material. Upon cooling to ambient temperature, the reaction mixture is filtered through Celite® and concentrated to give ethyl 3-(3-((tert-butylsulfinyl)amino)oxetan-3-yl)propanoate, which is used directly without further purifications.

The ester obtained above is dissolved in THF, and cooled to −78° C. DIBAL (1.0 equiv.) is added carefully while monitoring the conversion of the starting material. When considerable amount of aldehyde is formed, the reaction is quenched with saturated ammonium chloride, extracted with EtOAc, washed with brine, dried over sodium sulfate, and concentrated. The aldehyde is used directly or purified by column chromatography.

N-(3-(3-Amino-3-cyanopropyl)oxetan-3-yl)-2-methylpropane-2-sulfinamide

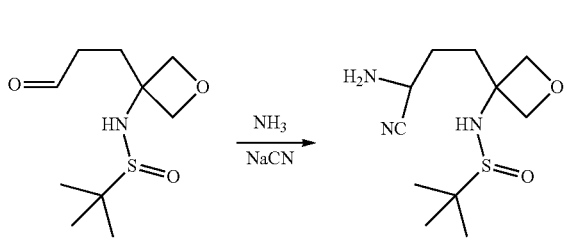

To a mixture of magnesium sulfate (0.5 equiv.), ammonium chloride (0.5 equiv.), and sodium cyanide (1 equiv.) is added 7 M ammonia in methanol (4 equiv.). The mixture is stirred and cooled to 0° C. After 10 min, the resulting suspension is added to aldehyde (1 equiv.). The mixture is stirring for 1 h at 0° C., then increased to RT and continued to react for 4 h. The solvent is then removed under reduced pressure while maintaining the internal temperature <30° C. until nearly all of the methanol and ammonia are removed. The resulting slurry of inorganic salts and the product is diluted with MTBE, stirred at RT for 30 min, and filtered. The inorganic wet cake is washed with MTBE, and the solvent is removed under reduced pressure to provide N-(3-(3-amino-3-cyanopropyl)oxetan-3-yl)-2-methylpropane-2-sulfinamide. (*ACS Med. Chem. Lett.* 2014, 5, 1152-1155).

2-Amino-4-(3-aminooxetan-3-yl)butanoic Acid

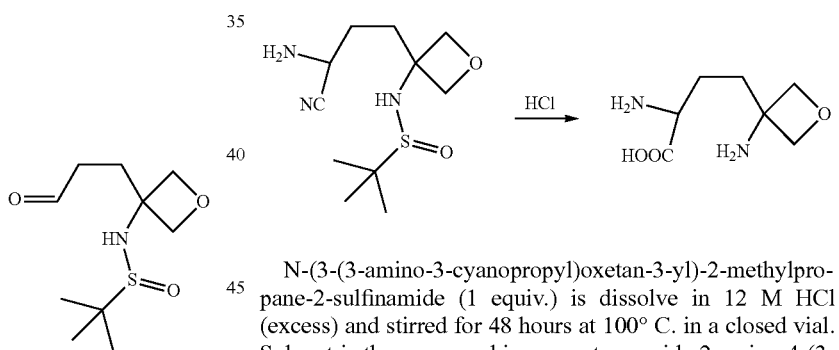

N-(3-(3-amino-3-cyanopropyl)oxetan-3-yl)-2-methylpropane-2-sulfinamide (1 equiv.) is dissolve in 12 M HCl (excess) and stirred for 48 hours at 100° C. in a closed vial. Solvent is then removed in vacuo to provide 2-amino-4-(3-aminooxetan-3-yl)butanoic acid. (*Angew. Chem. Int. Ed.* 2014, 53, 557)

7-Amino-2-oxa-5-azaspiro[3.5]nonan-6-one

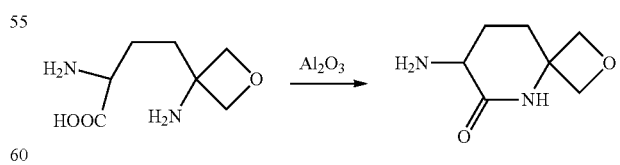

A mixture of 2-amino-4-(3-aminooxetan-3-yl)butanoic acid (1 equiv.), alumina (3 wt. equiv.) in toluene is heated under reflux for 1.5 h. The water produced during the reaction is collected in a Dean-Stark trap. The reaction mixture is allowed to cool and the alumina is filtered off and washed with 10% MeOH/CH$_2$Cl$_2$. The filtration is com-

4-Fluoro-6'-oxetano-thalidomide

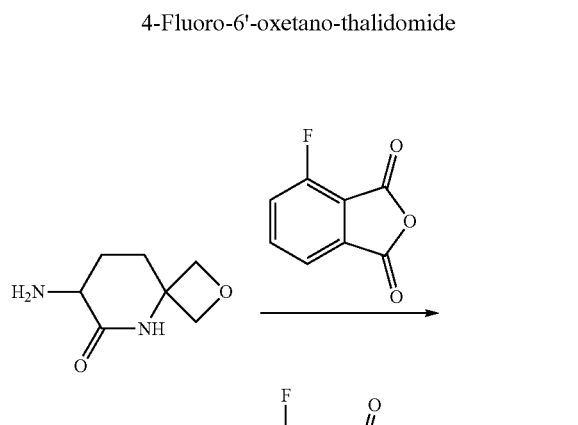

A mixture of 3-fluorophthalic anhydride (1 equiv.), 7-amino-2-oxa-5-azaspiro[3.5]nonan-6-one (1 equiv.), and potassium acetate (2.5 equiv.) in acetic acid is stirred at 120° C. overnight. The dark mixture is cooled and filtered. The filter cake is dissolved in DCM and washed with saturated NaHCO₃ and brine. The organic layer is dried (Na₂SO₄) and concentrated to provide 4-fluoro-6'-oxetano-thalidomide.

6'-Oxetano-pomalidomide Derivatives

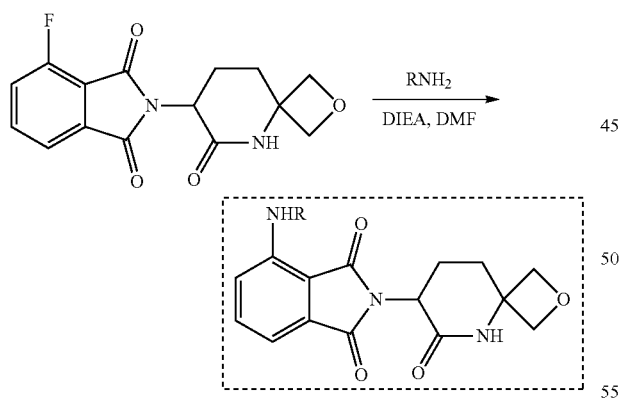

A mixture of alkyl amine (1 equiv.), 4-fluoro-6'-oxetano-thalidomide (1 equiv.) and DIEA (2 equiv.) in dry DMF is stirred at 90° C. for 12 h. The mixture is cooled to room temperature, poured into water and extracted with ethyl acetate. The combined organic phases are washed with water and brine, dried over anhydrous sodium sulfate, and concentrated under reduced pressure. The crude residue is purified by column chromatography on silica gel to give 6'-oxetano-pomalidomide derivatives. (*Chem Biol.* 2015, 22, 755-763)

6'-Sulfonyl Glutarimide

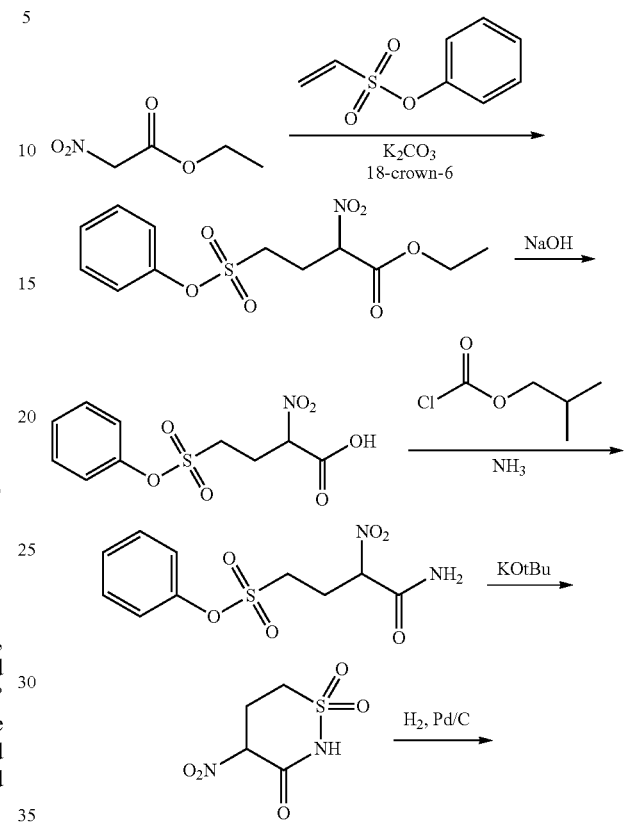

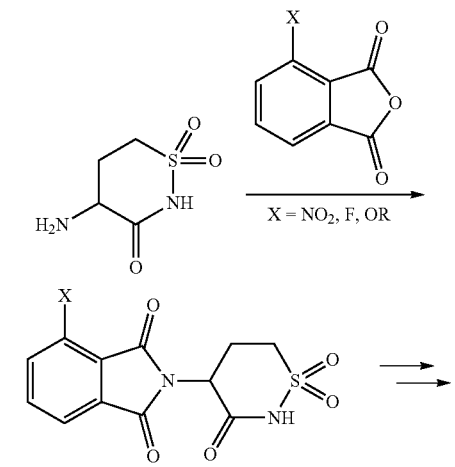

ref: PCT Int. Appl., 2000006537, 10 Feb 2000

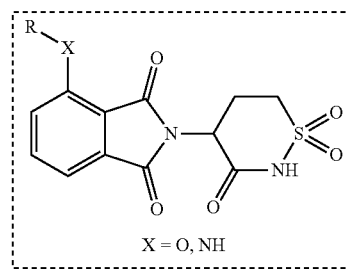

General Procedure Example 30: 6'-sulfonyl Pomalidomide Derivatives

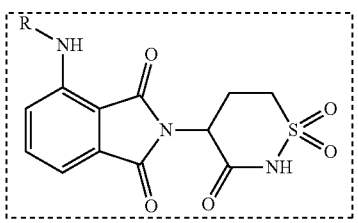

Ethyl 2-nitro-4-(phenoxysulfonyl)butanoate

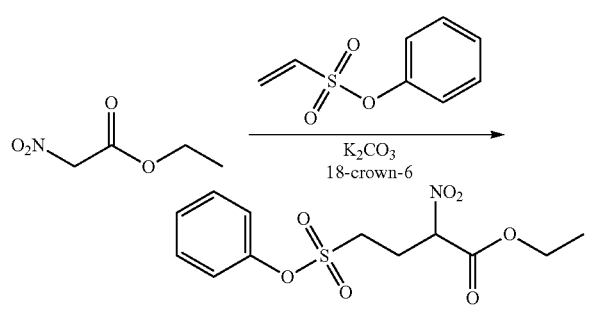

A mixture of ethyl 2-nitroacetate (2 equiv.), potassium carbonate (1 equiv.) and 18-crown-6 (0.5 equiv.) in toluene is heated to 90° C. and phenyl vinylsulfonate (1 equiv.) in toluene is added dropwise over one hour. The mixture is heated for 16 hours, cooled to ambient temperature and diluted with ethyl acetate. The mixture is washed with saturated brine. The organic layer is separated and the aqueous layer is extracted with ethyl acetate. The combined organic layers are dried ($Na_2SO_4$), filtered and concentrated in vacuo. The residue is purified by column chromatography on silica gel to give ethyl 2-nitro-4-(phenoxysulfonyl)butanoate. (PCT Int. Appl., 2000006537, 10 Feb. 2000)

2-Nitro-4-(phenoxysulfonyl)butanoic Acid

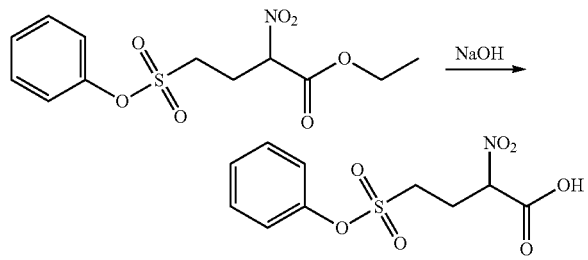

A mixture of 2-nitro-4-(phenoxysulfonyl)butanoate (1 equiv.), 1 M NaOH (excess) in methanol is stirred at rt for 2 h. The reaction is neutralized with 1 M HCl and concentrated to provide 2-nitro-4-(phenoxysulfonyl)butanoic acid.

Phenyl 4-amino-3-nitro-4-oxobutane-1-sulfonate

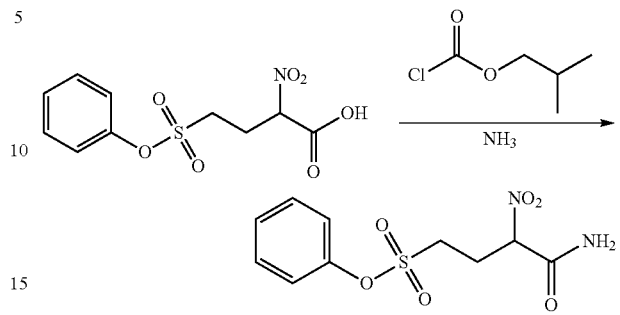

To a solution of 2-nitro-4-(phenoxysulfonyl)butanoic acid (1 equiv.) in dry $CH_3CN$ is added EDCI.HCl (1.2 equiv.) and HOBT (1.2 equiv.) at 0° C. The mixture is stirred at room temperature for 6 h, then cooled to 0° C., and 28% aqueous ammonia (excess) is carefully added. Stirring is continued at 0° C. for 30 min and then at room temperature for 1 h. Insoluble material is removed by filtration, then the filtrate was concentrated and purified by flash column chromatography on silica gel to provide phenyl 4-amino-3-nitro-4-oxobutane-1-sulfonate. (*Chem. Pharm. Bull.* 2006, 54, 1709)

4-Nitro-1,2-thiazinan-3-one 1,1-dioxide

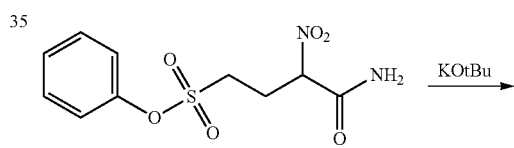

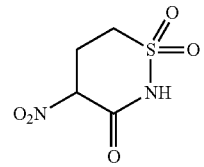

To a 0° C. solution of 1.0 M THF solution of potassium tert-butoxide (2 equiv.) in THF is added a solution of 4-amino-3-nitro-4-oxobutane-1-sulfonate (1 equiv.) in THF dropwise over 30 minutes. After stirring at 0° C. for 2 h, the cooling bath is removed and stirring continued for 30 minutes. The mixture is diluted with water and extracted two times with ethyl ether. The aqueous portion is acidified to pH 2 with 10% aqueous sodium bisulfate and extracted four times with 20 mL each of ethyl acetate. The combined ethyl acetate layers are dried ($Na_2SO_4$), filtered and concentrated in vacuo. The residue is purified by column chromatography on silica gel to give 4-nitro-1,2-thiazinan-3-one 1,1-dioxide. (PCT Int. Appl., 2000006537, 10 Feb. 2000)

309

4-Amino-1,2-thiazinan-3-one 1,1-dioxide

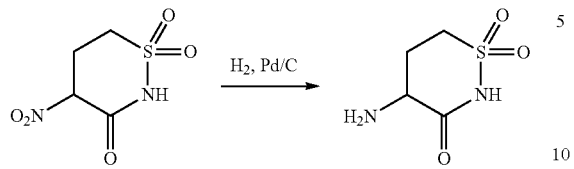

A mixture of 4-nitro-1,2-thiazinan-3-one 1,1-dioxide (1 equiv.) and palladium on activated carbon (10% wt) in THF is hydrogenated until the disappearance of the starting material. The mixture is filtered through Celite® and concentrated to give 4-amino-1,2-thiazinan-3-one 1,1-dioxide.

4-Fluoro-6'-sulfonyl-thalidomide

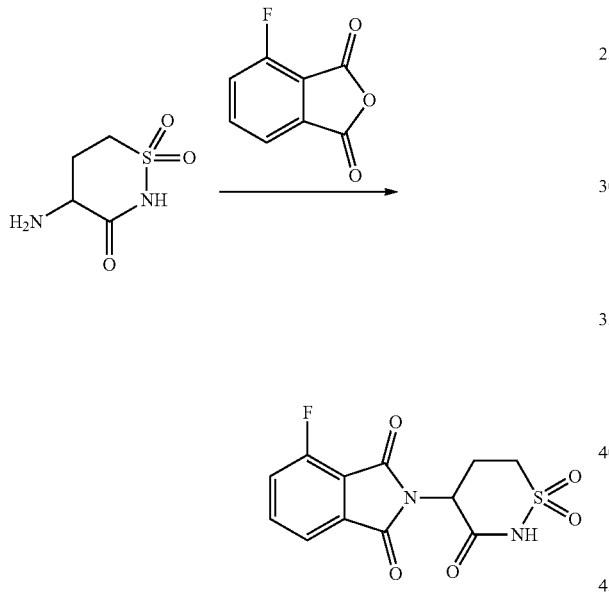

A mixture of 3-fluorophthalic anhydride (1 equiv.), 4-amino-1,2-thiazinan-3-one 1,1-dioxide (1 equiv.), and potassium acetate (2.5 equiv.) in acetic acid is stirred at 120° C. overnight. The dark mixture is cooled and filtered. The filter cake is dissolved in DCM and washed with saturated NaHCO$_3$ and brine. The organic layer is dried (Na$_2$SO$_4$) and concentrated to provide 4-fluoro-6'-sulfonyl-thalidomide.

6'-Sulfonyl Pomalidomide Derivatives

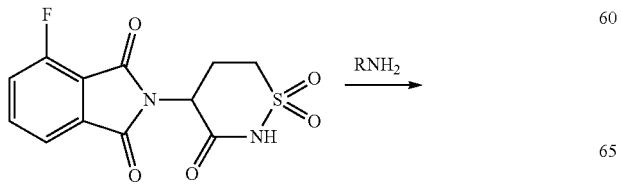

310

-continued

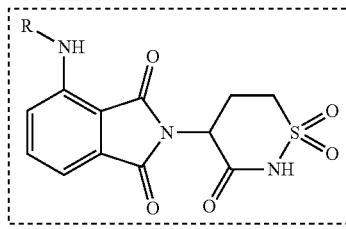

A mixture of alkyl amine (1 equiv.), 4-fluoro-6'-sulfonyl-thalidomide (1 equiv.) and DIEA (2 equiv.) in dry DMF is stirred at 90° C. for 12 h. The mixture is cooled to room temperature, poured into water and extracted with ethyl acetate. The combined organic phases are washed with water and brine, dried over anhydrous sodium sulfate, and concentrated under reduced pressure. The crude residue is purified by column chromatography on silica gel to give 6'-sulfonyl pomalidomide derivatives. (*Chem Biol.* 2015, 22, 755-763)

2'-Sulfonyl Glutarimide

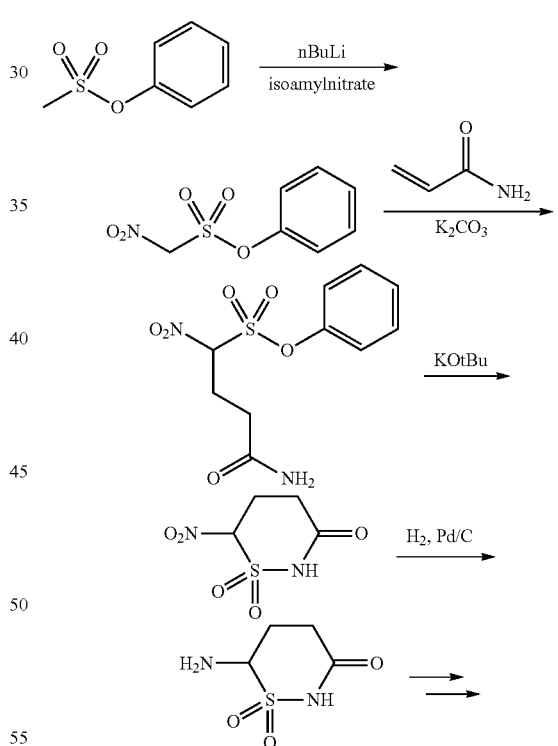

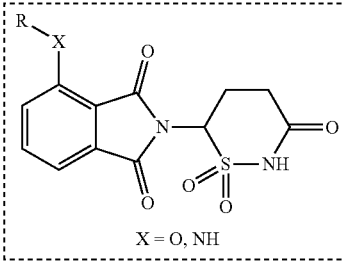

X = O, NH

General Procedure Example 31: 2'-Sulfonyl Pomalidomide Derivatives

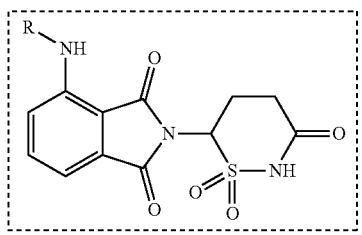

Phenyl Nitromethanesulfonate

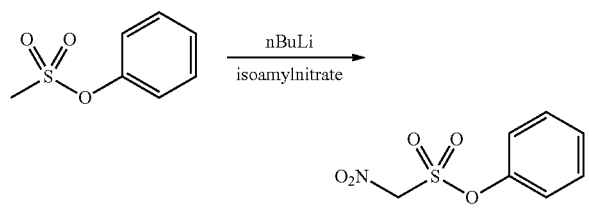

To a dry THF solution containing phenyl methanesulfonate (1 equiv.) at −10° C. under a nitrogen atmosphere is added dropwise 1.6 M n-BuLi in hexane (2.4 equiv.). The mixture is stirred for 10 min, and then cooled to −30° C. and isoamylnitrate (2.2 equiv.) is then added dropwise. After stirring for 4 h at the same temperature, the reaction is quenched with water, and the volatiles are evaporated in vacuo. 1 M NaOH (2 equiv.) is added to the reaction mixture and the mixture is washed with ethyl ether. The aqueous layer is acidified with acetic acid (pH=5), and extracted with CH$_2$Cl$_2$. The organic layer is washed with brine and dried over anhydrous Na$_2$SO$_4$, filtered, and concentrated. The residue is purified by column chromatography on silica gel to provide phenyl nitromethanesulfonate. (*Bioorg. Med. Chem.* 2000, 8, 2167-2173)

Phenyl 4-amino-1-nitro-4-oxobutane-1-sulfonate

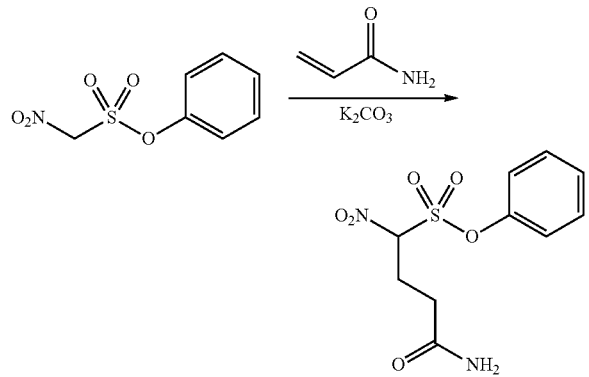

A mixture of phenyl nitromethanesulfonate (1 equiv.), potassium carbonate (1 equiv.) and 18-crown-6 (0.5 equiv.) in toluene is stirred and acrylamide (1 equiv.) is added dropwise. The mixture is stirred for 16 hours, and diluted with ethyl acetate. The mixture is washed with saturated brine. The organic layer is separated and the aqueous layer is extracted with ethyl acetate. The combined organic layers are dried (Na$_2$SO$_4$), filtered and concentrated in vacuo. The residue is purified by column chromatography on silica gel to give phenyl 4-amino-1-nitro-4-oxobutane-1-sulfonate.

6-Nitro-1,2-thiazinan-3-one 1,1-dioxide

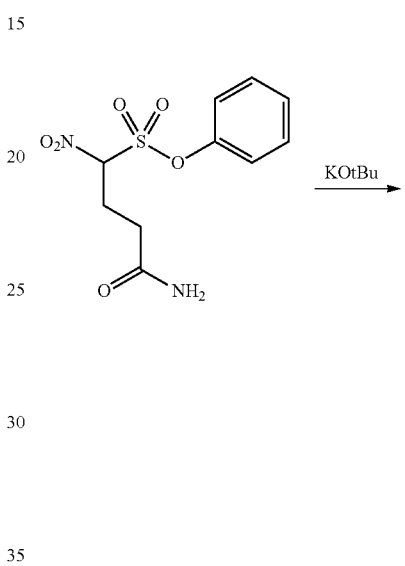

To a 0° C. solution of 1.0 M THF solution of potassium tert-butoxide (2 equiv.) in THF is added a solution of phenyl 4-amino-1-nitro-4-oxobutane-1-sulfonate (1 equiv.) in THF dropwise over 30 minutes. After stirring at 0° C. for 2 h, the cooling bath is removed and stirring continued for 30 minutes. The mixture is diluted with water and extracted two times with ethyl ether. The aqueous portion is acidified to pH 2 with 10% aqueous sodium bisulfate and extracted four times with 20 mL each of ethyl acetate. The combined ethyl acetate layers are dried (Na$_2$SO$_4$), filtered and concentrated in vacuo. The residue is purified by column chromatography on silica gel to give 6-nitro-1,2-thiazinan-3-one 1,1-dioxide. (PCT Int. Appl., 2000006537, 10 Feb. 2000)

6-Amino-1,2-thiazinan-3-one 1,1-dioxide

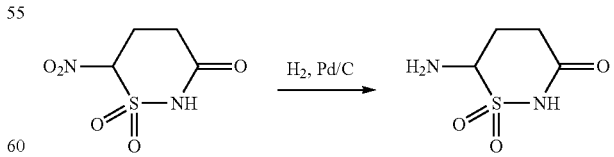

A mixture of 6-nitro-1,2-thiazinan-3-one 1,1-dioxide (1 equiv.) and palladium on activated carbon (10% wt) in THF is hydrogenated until the disappearance of the starting material. The mixture is filtered through Celite® and concentrated to give 6-amino-1,2-thiazinan-3-one 1,1-dioxide.

313
4-Fluoro-2'-sulfonyl-thalidomide

314
2'-Sulfonyl Pomalidomide Derivatives

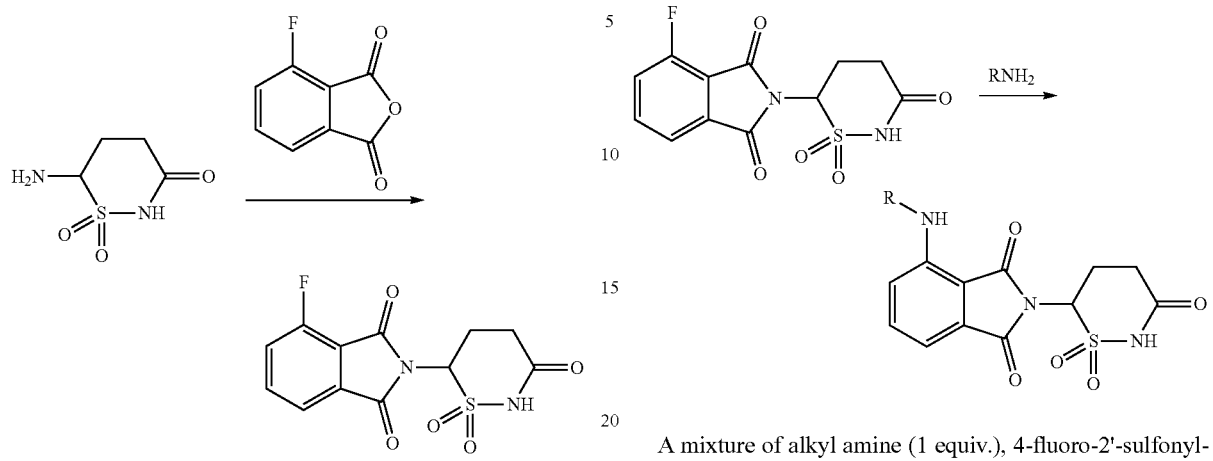

A mixture of 3-fluorophthalic anhydride (1 equiv.), 6-amino-1,2-thiazinan-3-one 1,1-dioxide (1 equiv.), and potassium acetate (2.5 equiv.) in acetic acid is stirred at 120° C. overnight. The dark mixture is cooled and filtered. The filter cake is dissolved in DCM and washed with saturated NaHCO$_3$ and brine. The organic layer is dried (Na$_2$SO$_4$) and concentrated to provide 4-fluoro-2'-sulfonyl-thalidomide.

A mixture of alkyl amine (1 equiv.), 4-fluoro-2'-sulfonyl-thalidomide (1 equiv.) and DIEA (2 equiv.) in dry DMF is stirred at 90° C. for 12 h. The mixture is cooled to room temperature, poured into water and extracted with ethyl acetate. The combined organic phases are washed with water and brine, dried over anhydrous sodium sulfate, and concentrated under reduced pressure. The crude residue is purified by column chromatography on silica gel to give 2'-sulfonyl pomalidomide derivatives. (*Chem Biol.* 2015, 22, 755-763)

Oxetano Sulfonamide Glutarimide Derivatives

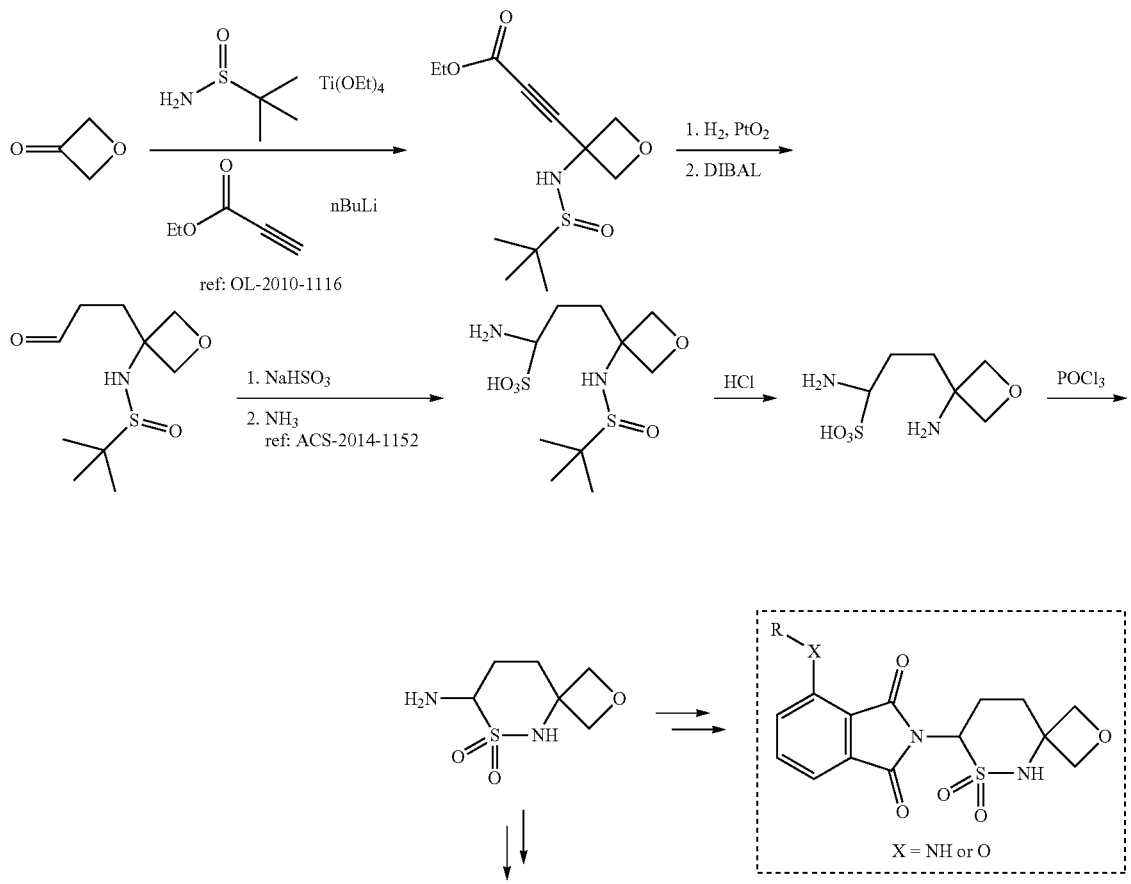

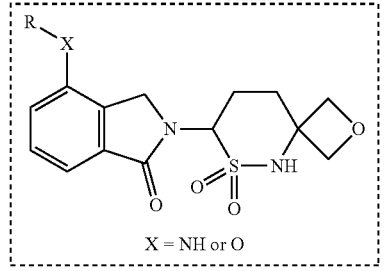

X = NH or O

General Procedure Example 32:
6'-Oxetano-2'-sulfonyl Pomalidomide Derivatives

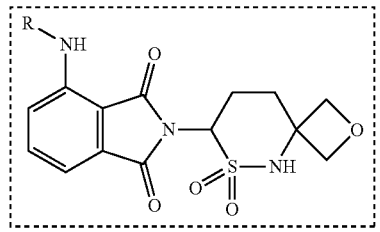

Sodium 1-amino-3-(3-((tert-butylsulfinyl)amino)
oxetan-3-yl)propane-1-sulfonate

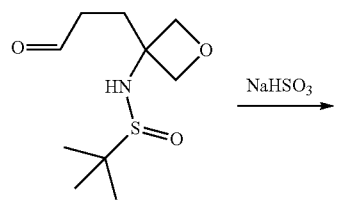

ref: ACS-2014-1152

A solution of sodium bisulfite (1 equiv.) in water is slowly added to the solution of 2-methyl-N-(3-(3-oxopropyl)oxetan-3-yl)propane-2-sulfinamide (preparation was mentioned above) (1 equiv.) in methanol. The mixture is stirred for 60 min at RT, and then the solvent is removed to provide sodium 3-(3-((tert-butylsulfinyl)amino)oxetan-3-yl)-1-hydroxypropane-1-sulfonate, which is used for the next step without further purification.

An aqueous solution of ammonia (30%, 1 equiv.) is added to a solution of sodium 3-(3-((tert-butylsulfinyl)amino)oxetan-3-yl)-1-hydroxypropane-1-sulfonate (1 equiv.) in MeOH:H$_2$O 1:1, and the mixture is stirred at room temperature. After 1 h, the reaction is concentrated to provide sodium 1-amino-3-(3-((tert-butylsulfinyl)amino)oxetan-3-yl)propane-1-sulfonate without further purification. (*ACS Med. Chem. Lett.* 2014, 5, 1152)

1-Amino-3-(3-aminooxetan-3-yl)propane-1-sulfonic Acid

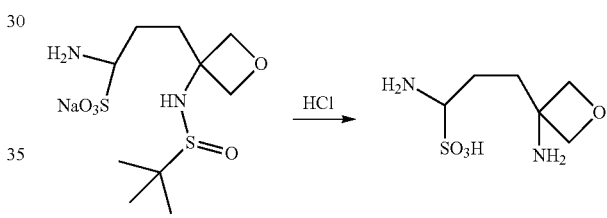

Sodium 1-amino-3-(3-((tert-butylsulfinyl)amino)oxetan-3-yl)propane-1-sulfonate (1 equiv.) is dissolve in 12 M HCl (excess) and stirred at rt until the consumption of the starting material. Solvent is then removed in vacuo to provide 1-amino-3-(3-aminooxetan-3-yl)propane-1-sulfonic acid.

7-Amino-2-oxa-6-thia-5-azaspiro[3.5]nonane 6,6-dioxide

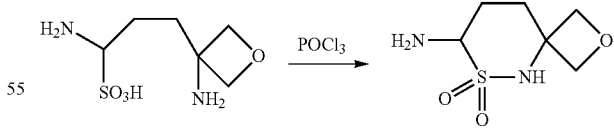

1-Amino-3-(3-aminooxetan-3-yl)propane-1-sulfonic acid (1 equiv.) is dissolved in POCl$_3$ (diluted) and stirred at 100° C. until the consumption of the starting material. Solvent is removed in vacuo and the residue is dissolved in DCM and washed carefully with saturated sodium carbonate, then brine. The organic layer is dried (Na$_2$SO$_4$), concentrated, and purified by column chromatography on silica gel to give 7-amino-2-oxa-6-thia-5-azaspiro[3.5]nonane 6,6-dioxide.

4-Fluoro-6'-oxetano-2'-sulfonyl-thalidomide

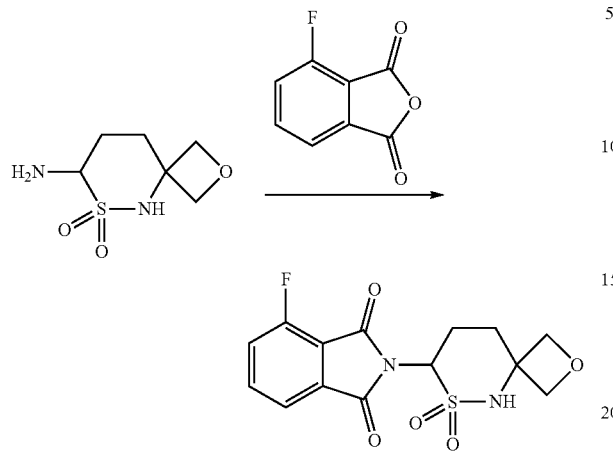

A mixture of 3-fluorophthalic anhydride (1 equiv.), 7-amino-2-oxa-6-thia-5-azaspiro[3.5]nonane 6,6-dioxide (1 equiv.), and potassium acetate (2.5 equiv.) in acetic acid is stirred at 120° C. overnight. The dark mixture is cooled and filtered. The filter cake is dissolved in DCM and washed with saturated NaHCO$_3$ and brine. The organic layer is dried (Na$_2$SO$_4$) and concentrated to provide 4-fluoro-6'-oxetano-2'-sulfonyl-thalidomide.

6'-Oxetano-2'-sulfonyl Pomalidomide Derivatives

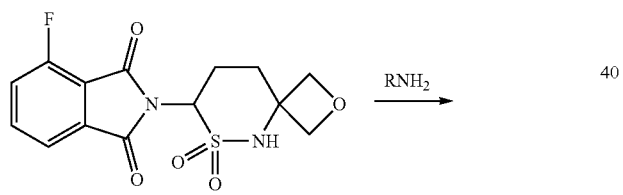

A mixture of alkyl amine (1 equiv.), 4-fluoro-6'-oxetano-2'-sulfonyl-thalidomide (1 equiv.) and DIEA (2 equiv.) in dry DMF is stirred at 90° C. for 12 h. The mixture is cooled to room temperature, poured into water and extracted with ethyl acetate. The combined organic phases are washed with water and brine, dried over anhydrous sodium sulfate, and concentrated under reduced pressure. The crude residue is purified by column chromatography on silica gel to give 6'-oxetano-2'-sulfonyl pomalidomide derivatives. (*Chem Biol.* 2015, 22, 755-763)

General Procedure Example 33:
2'-Oxetano-6'-sulfonyl Pomalidomide Derivatives

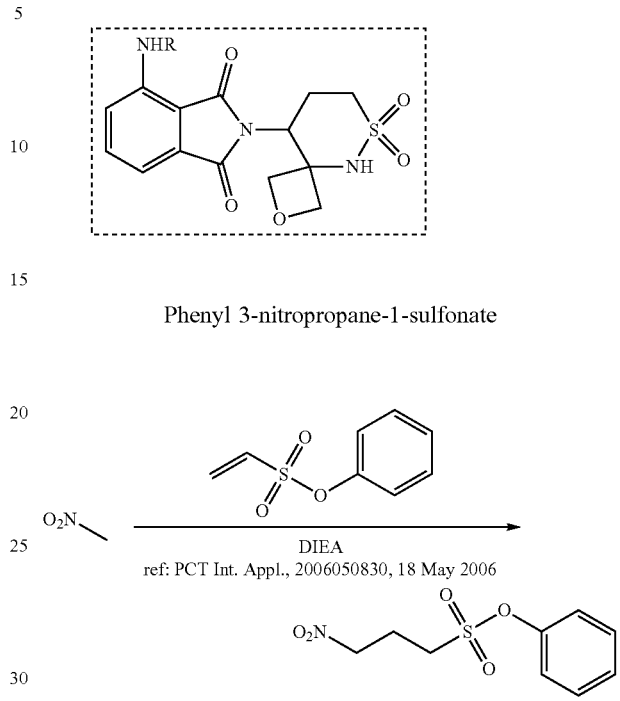

Phenyl 3-nitropropane-1-sulfonate

A mixture of phenyl ethenesulfonate (1 equiv.) and nitromethane (1 equiv.) is heated to 80° C. and, at 80° C., ethyldiisopropylamine (2 equiv.) is added dropwise. The mixture is stirred at 80° C. till the consumption of starting materials. Cooling to RT is followed by addition of a 2 M aqueous HCl solution and extraction 3 times with EtOAc. Drying over Na$_2$SO$_4$ and removal of the solvent in vacuo are followed by coevaporation 3 times with toluene to provide phenyl 3-nitropropane-1-sulfonate. (PCT Int. Appl., 2006050830, 18 May 2006)

Phenyl 3-nitro-3-(oxetan-3-ylidene)propane-1-sulfonate

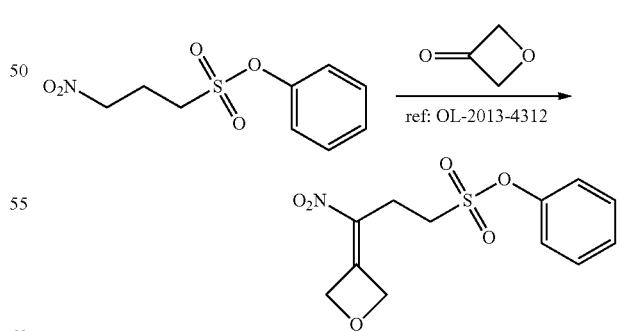

To phenyl 3-nitropropane-1-sulfonate (1.0 equiv.) is added oxetan-3-one (1.3 equiv.) and Et$_3$N (0.2 equiv.), and the mixture is stirred at RT for 75 min. Then it is dissolved in CH$_2$Cl$_2$ and the solution is cooled to −78° C. Et$_3$N (3.0 equiv.) is added followed by MsCl (2.5 equiv.), and the mixture is stirred at −78° C. for 30 min, when it is allowed to warm to −25° C. over ca. 45 min. After stirring at RT for 20 min, it is quenched with HCl (0.1 M in H₂O). The resulting mixture is diluted with CH₂Cl₂, and the phases are separated. The aqueous phase is extracted with CH₂Cl₂, and the combined organic layers are dried (Na₂SO₄), filtered, and concentrated in vacuo. Purification of the residue by column chromatography on silica gel provides phenyl 3-nitro-3-(oxetan-3-ylidene)propane-1-sulfonate. (*Org. Lett.* 2013, 15, 4312)

Phenyl 3-(3-((4-methoxybenzyl)amino)oxetan-3-yl)-3-nitropropane-1-sulfonate

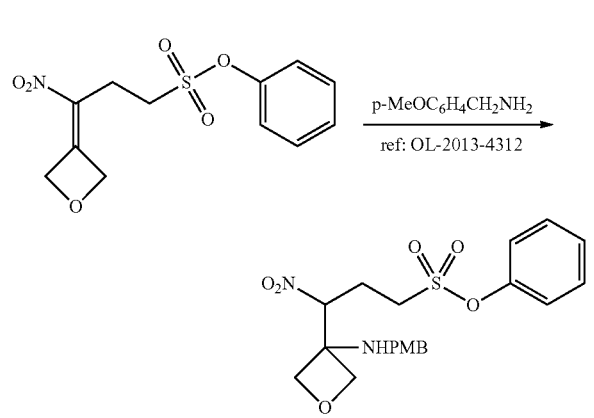

To a cooled (0° C.) solution of phenyl 3-nitro-3-(oxetan-3-ylidene)propane-1-sulfonate (1.0 equiv.) in THF is added 4-methoxybenzylamine (1.0 equiv.), and the mixture is stirred at 0° C. for 30 min. Then it is allowed to warm to RT and stirring is continued for another 10 min. At this point the mixture is concentrated in vacuo and the residue is purified by column chromatography on silica gel to provide phenyl 3-(3-((4-methoxybenzyl)amino)oxetan-3-yl)-3-nitropropane-1-sulfonate. (*Org. Lett.* 2013, 15, 4312)

Phenyl 3-(hydroxyimino)-3-(3-((4-methoxybenzyl)amino)oxetan-3-yl)propane-1-sulfonate

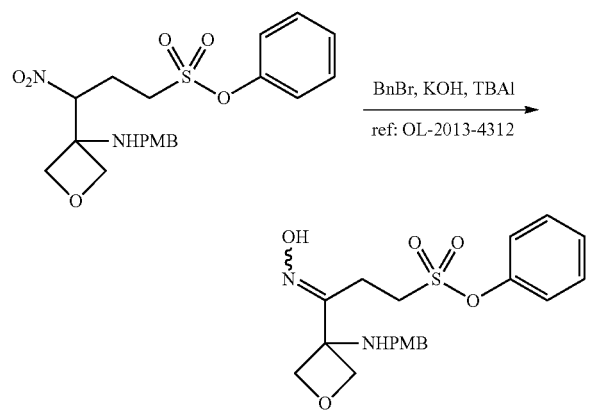

To a solution of phenyl 3-(3-((4-methoxybenzyl)amino)oxetan-3-yl)-3-nitropropane-1-sulfonate (1.0 equiv.) in THF is added at RT tetrabutylammonium iodide (0.05 equiv.), benzyl bromide (1.2 equiv.), and potassium hydroxide (1.2 equiv.). The mixture is stirred at RT for 3.5 h. Then it is diluted with Et₂O and washed with saturated aqueous NaCl. Then it is dried (Na₂SO₄), filtered, and concentrated in vacuo. The residue is purified by column chromatography on silica gel to provide phenyl 3-(hydroxyimino)-3-(3-((4-methoxybenzyl)amino)oxetan-3-yl)propane-1-sulfonate as a mixture of oxime isomers. (*Org. Lett.* 2013, 15, 4312)

9-(Hydroxyimino)-5-(4-methoxybenzyl)-2-oxa-6-thia-5-azaspiro[3.5]nonane 6,6-dioxide

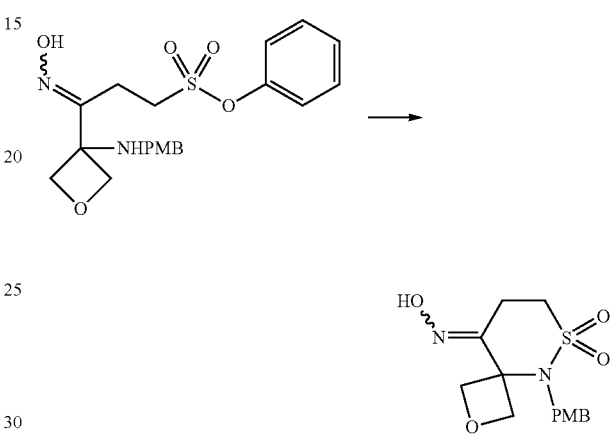

A solution of phenyl 3-(hydroxyimino)-3-(3-((4-methoxybenzyl)amino)oxetan-3-yl)propane-1-sulfonate (mixture of oxime isomers; 1.0 equiv.) in xylenes is heated to 140° C. and stirred at that temperature for 23 h. Then it is cooled to RT and concentrated in vacuo. The residue is purified by column chromatography on silica gel to provide 9-(hydroxyimino)-5-(4-methoxybenzyl)-2-oxa-6-thia-5-azaspiro[3.5]nonane 6,6-dioxide. (*Org. Lett.* 2013, 15, 4312)

9-Amino-5-(4-methoxybenzyl)-2-oxa-6-thia-5-azaspiro[3.5]nonane 6,6-dioxide

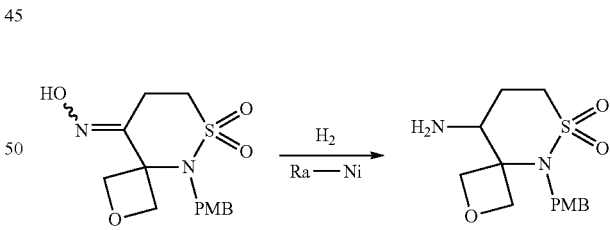

Raney-Ni (50% slurry in H₂O) is washed with EtOH (3×), then is added a solution of 9-(hydroxyimino)-5-(4-methoxybenzyl)-2-oxa-6-thia-5-azaspiro[3.5]nonane 6,6-dioxide (1.0 equiv.) in EtOH, and the mixture is diluted with EtOH. A hydrogen atmosphere (balloon) is built up, and the mixture is vigorously stirred at RT for 9 h. Then the atmosphere is changed to N2 and the mixture is filtered over Celite® and washed with MeOH. The filtrate is then concentrated in vacuo. The crude product is dissolved in CH₂Cl₂ and filtered again over Celite®. The filtrate is concentrated in vacuo to afford 9-amino-5-(4-methoxybenzyl)-2-oxa-6-thia-5-azaspiro[3.5]nonane 6,6-dioxide. (*Org. Lett.* 2013, 15, 4312)

4-Fluoro-2'-oxetano-6'-sulfonyl-thalidomide

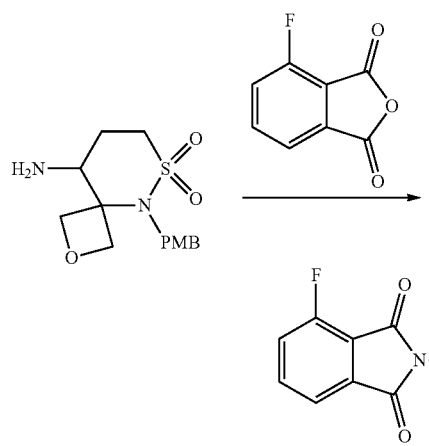

A mixture of 3-fluorophthalic anhydride (1 equiv.), 9-amino-5-(4-methoxybenzyl)-2-oxa-6-thia-5-azaspiro[3.5]nonane 6,6-dioxide (1 equiv.), and potassium acetate (2.5 equiv.) in acetic acid is stirred at 120° C. overnight. The dark mixture is cooled and filtered. The filter cake is dissolved in DCM and washed with saturated NaHCO$_3$ and brine. The organic layer is dried (Na$_2$SO$_4$) and concentrated to provide 4-fluoro-2'-oxetano-6'-sulfonyl-thalidomide.

2'-Oxetano-6'-sulfonyl Pomalidomide Derivatives

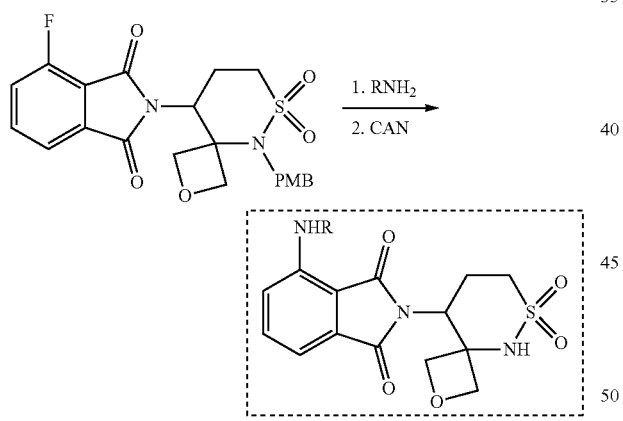

A mixture of alkyl amine (1 equiv.), 4-fluoro-2'-oxetano-6'-sulfonyl-thalidomide (1 equiv.) and DIEA (2 equiv.) in dry DMF is stirred at 90° C. for 12 h. The mixture is cooled to room temperature, poured into water and extracted with ethyl acetate. The combined organic phases are washed with water and brine, dried over anhydrous sodium sulfate, and concentrated under reduced pressure. (*Chem Biol.* 2015, 22, 755-763)

To a solution of the resulting residue (1.0 equiv) in CH$_3$CN, cooled to 0° C., is added a solution of CAN (3.0 equiv) in H$_2$O, and the yellow clear solution is stirred at 0° C. for 2 h. Then it is diluted with EtOAc and quenched with half saturated aqueous NaCl and diluted with EtOAc and H$_2$O. The phases are separated, and the aqueous phase is extracted with EtOAc (2×) and CH$_2$Cl$_2$ (2×). The combined organic phases are dried (Na$_2$SO$_4$), filtered, and concentrated in vacuo. The residue is purified by column chromatography on silica gel to provide 2'-oxetano-6'-sulfonyl pomalidomide derivatives. (*Org. Lett.* 2013, 15, 4312)

7-Membered Imides

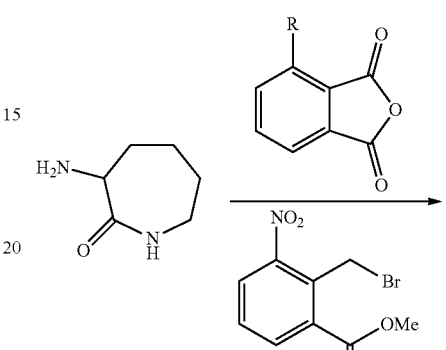

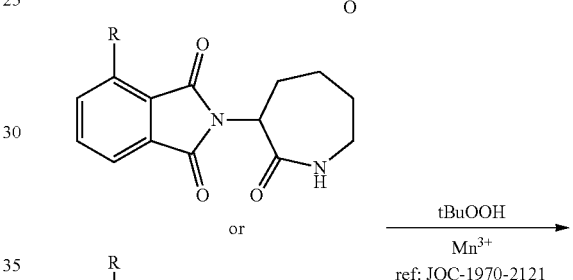

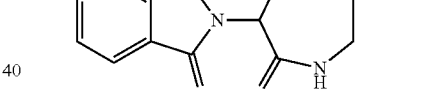

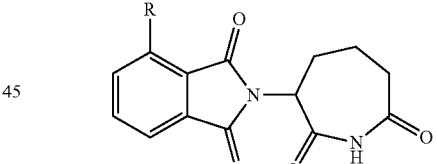

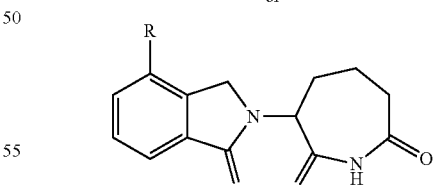

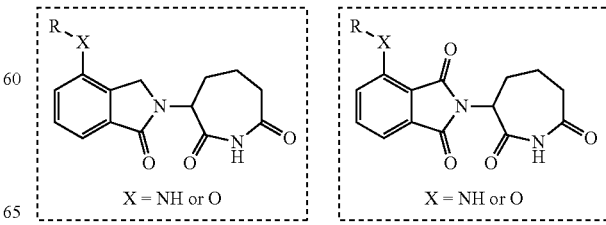

X = NH or O       X = NH or O

General Procedure Example 34: 7-Membered Pomalidomide Derivatives

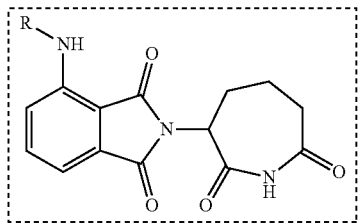

4-Fluoro-2-(2-oxoazepan-3-yl)isoindoline-1,3-dione

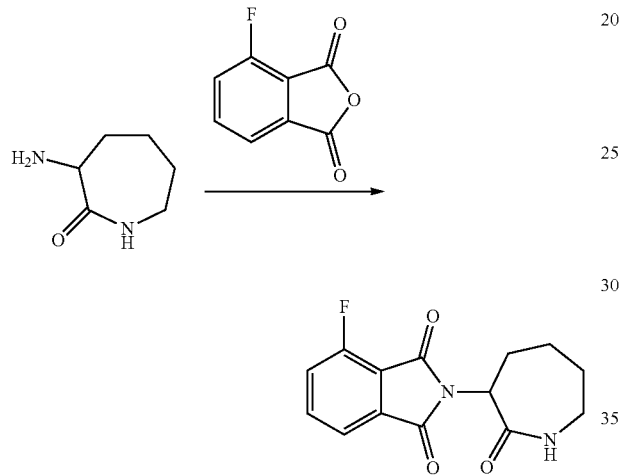

A mixture of 3-fluorophthalic anhydride (1 equiv.), 3-aminoazepan-2-one (1 equiv.), and potassium acetate (2.5 equiv.) in acetic acid is stirred at 120° C. overnight. The dark mixture is cooled and filtered. The filter cake is dissolved in DCM and washed with saturated NaHCO$_3$ and brine. The organic layer is dried (Na$_2$SO$_4$) and concentrated to provide 4-fluoro-2-(2-oxoazepan-3-yl)isoindoline-1,3-dione.

2-(2,7-Dioxoazepan-3-yl)-4-fluoroisoindoline-1,3-dione

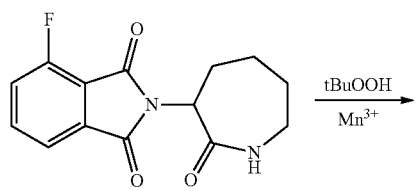

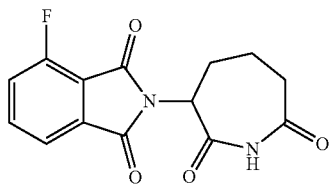

A solution of 4-fluoro-2-(2-oxoazepan-3-yl)isoindoline-1,3-dione (1 equiv.), manganic acetylacetonate (0.01 wt equiv.), and 68.8% t-butyl hydroperoxide (1.5 equiv.) is stirred at rt for 4 d. The mixture is concentrated and purified by column chromatography on silica gel to provide 2-(2,7-dioxoazepan-3-yl)-4-fluoroisoindoline-1,3-dione. (*J. Org. Chem.* 1970, 35, 2121)

7-Membered Pomalidomide Derivatives

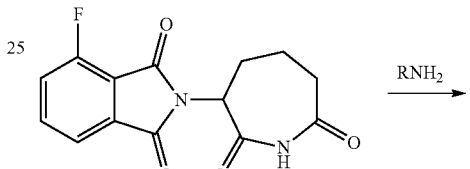

A mixture of alkyl amine (1 equiv.), 2-(2,7-dioxoazepan-3-yl)-4-fluoroisoindoline-1,3-dione (1 equiv.) and DIEA (2 equiv.) in dry DMF is stirred at 90° C. for 12 h. The mixture is cooled to room temperature, poured into water and extracted with ethyl acetate. The combined organic phases are washed with water and brine, dried over anhydrous sodium sulfate, and concentrated under reduced pressure. The crude residue is purified by column chromatography on silica gel to give 7-membered pomalidomide derivatives. (*Chem Biol.* 2015, 22, 755-763)

[3.1.0] System

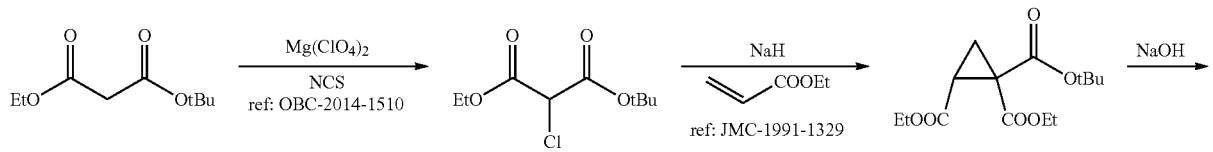

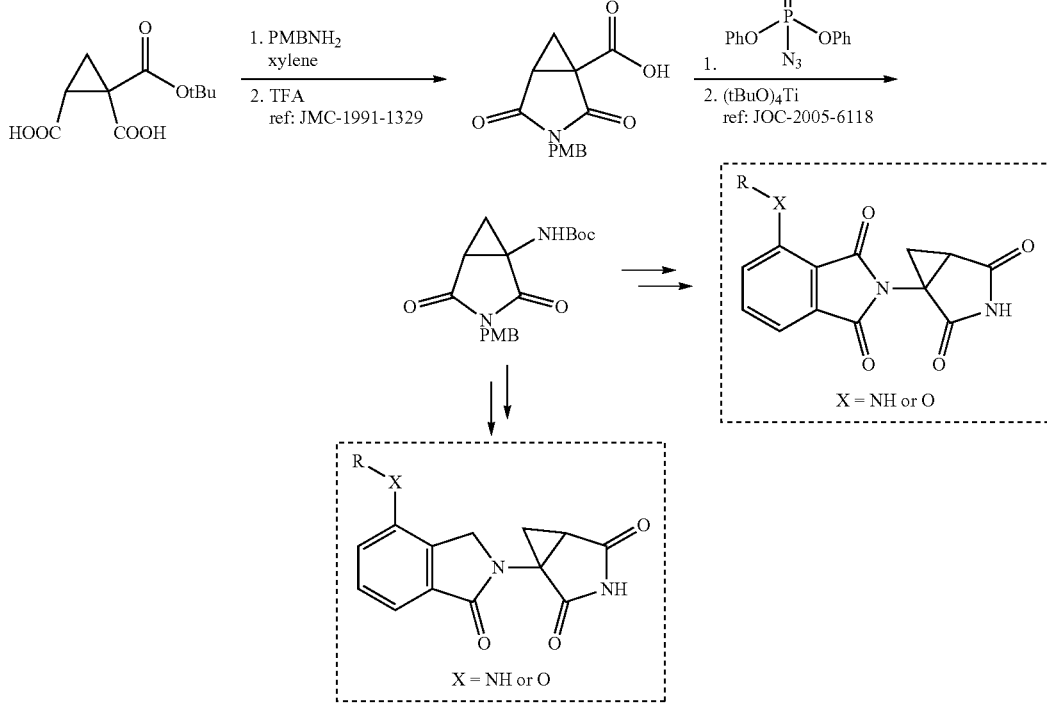

General Procedure Example 35: [3.1.0] Pomalidomide Derivatives

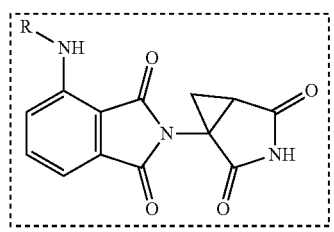

1-(tert-Butyl) 3-ethyl 2-chloromalonate

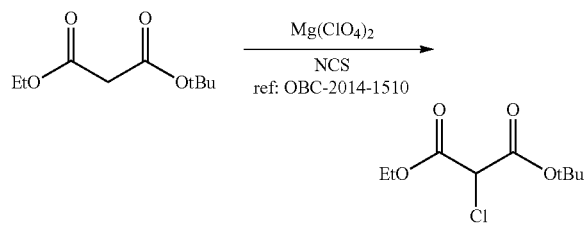

A solution of tert-butyl ethyl malonate (1 equiv.) in dry MeCN is added to N-chlorosuccinimide (1.2 equiv.) and magnesium perchlorate (0.3 equiv.). The reaction mixture is stirred for 4 hours. After the solvent is removed on a rotary evaporator, the mixture is diluted with EtOAc and washed with brine. The organic layers are dried with Na$_2$SO$_4$, and concentrated in vacuo. The residue is purified by column chromatography on silica gel to afford 1-(tert-butyl) 3-ethyl 2-chloromalonate. (*Org. Biomol. Chem.* 2014, 12, 1510)

1-(tert-Butyl) 1,2-diethyl cyclopropane-1,1,2-tricarboxylate

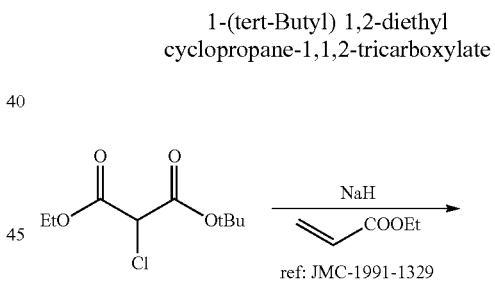

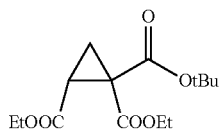

To a stirred slurry of NaH (60% in mineral oil, 1 equiv.) in anhydrous Et$_2$O is added 1-(tert-butyl) 3-ethyl 2-chloromalonate (1 equiv.) and ethyl acrylate (1 equiv.) during which the temperature is maintained between 25 and 30° C. The mixture is stirred at room temperature for 24 h, and then unreacted NaH is decomposed with methanol. H$_2$O is added, and the organic layer is separated, dried over Na$_2$SO$_4$, filtered, and concentrated. The residue is purified by column chromatography on silica gel to afford 1-(tert-butyl) 1,2-diethyl cyclopropane-1,1,2-tricarboxylate. (*J. Med. Chem.* 1981, 24, 481)

1-(tert-Butoxycarbonyl)cyclopropane-1,2-dicarboxylic Acid

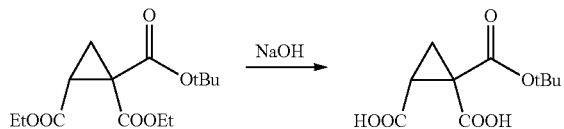 [SMILES: CCOC(=O)C1CC1(C(=O)OCC)C(=O)OC(C)(C)C ; "NaOH" ; CC(C)(C)OC(=O)C1(C(=O)O)CC1C(=O)O]

A mixture of 1-(tert-butyl) 1,2-diethyl cyclopropane-1,1,2-tricarboxylate (1 equiv.) and NaOH (2 equiv.) in 1:1 EtOH-H$_2$O is stirred at rt for 6 h and then is evaporated to one-half volume. The aqueous solution is extracted with Et$_2$O, chilled in ice, and then made acidic with 1 N HCl. Crystalline product is collected by filtration and is recrystallized to give the 1-(tert-butoxycarbonyl)cyclopropane-1,2-dicarboxylic acid.

3-(4-Methoxybenzyl)-2,4-dioxo-3-azabicyclo[3.1.0]hexane-1-carboxylic Acid

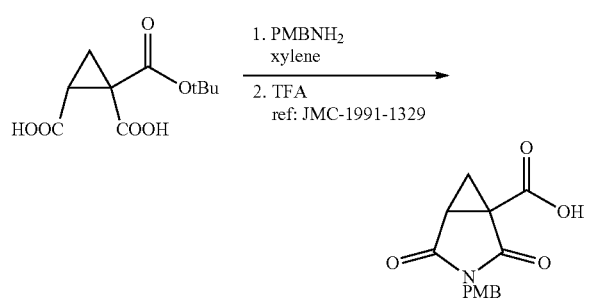

A solution of 1-(tert-butoxycarbonyl)cyclopropane-1,2-dicarboxylic acid (1 equiv.) in xylene (isomeric mixture) is boiled under a water trap for 5 h and cooled. To this solution of the intermediary anhydride formed during the reaction is added a solution of PMBNH$_2$ (1 equiv.) in xylene. The mixture is boiled for a further 15 h and evaporated to dryness. (*J. Med. Chem.* 1991, 34, 1333). The residue is dissolved in 1:1 TFA/DCM and stirred at rt for 2 h. Solvents are evaporated to provide 3-(4-methoxybenzyl)-2,4-dioxo-3-azabicyclo[3.1.0]hexane-1-carboxylic acid.

tert-Butyl (3-(4-methoxybenzyl)-2,4-dioxo-3-azabicyclo[3.1.0]hexan-1-yl)carbamate

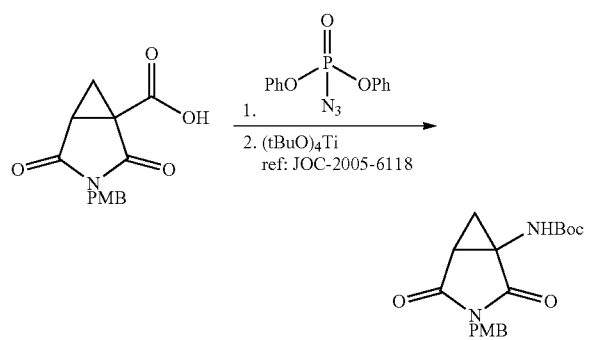

To a solution of 3-(4-methoxybenzyl)-2,4-dioxo-3-azabicyclo[3.1.0]hexane-1-carboxylic acid (1 equiv.) in toluene is added triethylamine (1.2 equiv.). Diphenylphosphoryl azide (1.1 equiv.) is added dropwise and the mixture is heated to reflux while stirring for 30 min. The mixture is then cooled to rt and quenched with saturated aqueous NH$_4$Cl. After separation of the two phases, the aqueous solution is extracted with Et$_2$O (3×) and the combined organic layers are washed with brine, dried with anhydrous Na$_2$SO$_4$ and concentrated in vacuo. The crude product is purified by flash chromatography on silica gel to afford isocyanate. (*J. Org. Chem.* 2005, 70, 6118) To a solution of the isocyanate (1.0 equiv. of 0.2 M in benzene) is added the t-butyl alcohol (1.5 equiv). Titanium tetratbutoxide (0.10 equiv.) is then added, and the mixture is stirred at 120° C. until completion. After quenching with saturated aqueous NH$_4$Cl and separating the two phases, the aqueous layer is extracted three times with CH$_2$Cl$_2$, and the combined organic layers are dried with anhydrous Na$_2$SO$_4$, and concentrated in vacuo. The residue is purified by flash chromatography on silica gel to afford tert-butyl (3-(4-methoxybenzyl)-2,4-dioxo-3-azabicyclo[3.1.0]hexan-1-yl)carbamate. (*J. Org. Chem.* 2005, 70, 6118)

1-Amino-3-(4-methoxybenzyl)-3-azabicyclo[3.1.0]hexane-2,4-dione

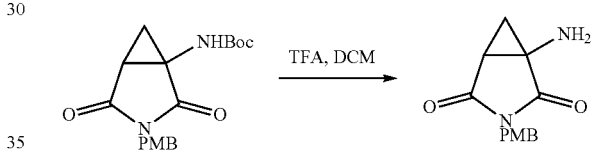

A solution of tert-butyl (3-(4-methoxybenzyl)-2,4-dioxo-3-azabicyclo[3.1.0]hexan-1-yl)carbamate (1 equiv.) in 1:1 TFA/DCM is stirred at rt for 2 h. Solvents are evaporated to provide 1-amino-3-(4-methoxybenzyl)-3-azabicyclo[3.1.0]hexane-2,4-dione.

2-(2,4-Dioxo-3-azabicyclo[3.1.0]hexan-1-yl)-4-fluoroisoindoline-1,3-dione

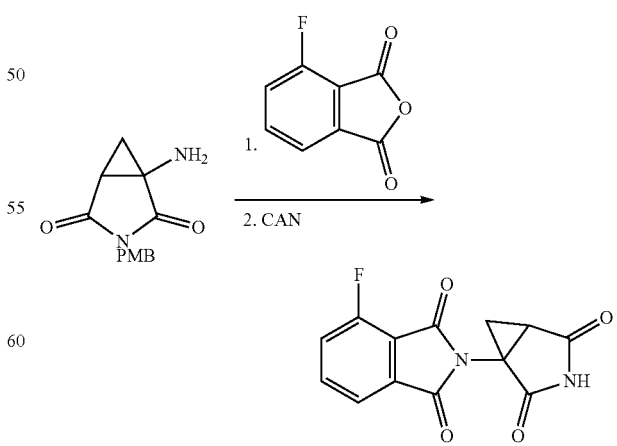

A mixture of 3-fluorophthalic anhydride (1 equiv.), 1-amino-3-(4-methoxybenzyl)-3-azabicyclo[3.1.0]hexane- 2,4-dione (1 equiv.), and potassium acetate (2.5 equiv.) in acetic acid is stirred at 120° C. overnight. The dark mixture is cooled and filtered. The filter cake is dissolved in DCM and washed with saturated NaHCO$_3$ and brine. The organic layer is dried (Na$_2$SO$_4$) and concentrated to provide 4-fluoro adduct.

To a solution of the resulting residue (1.0 equiv) in CH$_3$CN, cooled to 0° C., is added a solution of CAN (3.0 equiv) in H$_2$O, and the yellow clear solution is stirred at 0° C. for 2 h. Then it is diluted with EtOAc and quenched with half saturated aqueous NaCl and diluted with EtOAc and H$_2$O. The phases are separated, and the aqueous phase is extracted with EtOAc (2×) and CH$_2$Cl$_2$ (2×). The combined organic phases are dried (Na$_2$SO$_4$), filtered, and concentrated in vacuo. The residue is purified by column chromatography on silica gel to provide 2-(2,4-dioxo-3-azabicyclo [3.1.0]hexan-1-yl)-4-fluoroisoindoline-1,3-dione. (*Org. Lett.* 2013, 15, 4312)

[3.1.0] Pomalidomide Derivatives

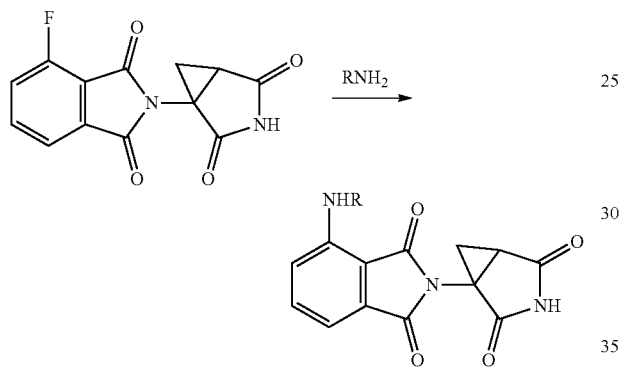

A mixture of alkyl amine (1 equiv.), 2-(2,4-dioxo-3-azabicyclo[3.1.0]hexan-1-yl)-4-fluoroisoindoline-1,3-dione (1 equiv.) and DIEA (2 equiv.) in dry DMF is stirred at 90° C. for 12 h. The mixture is cooled to room temperature, poured into water and extracted with ethyl acetate. The combined organic phases are washed with water and brine, dried over anhydrous sodium sulfate, and concentrated under reduced pressure. The crude residue is purified by column chromatography on silica gel to give [3.1.0] pomalidomide derivatives. (*Chem Biol.* 2015, 22, 755-763)

[4.1.0] System

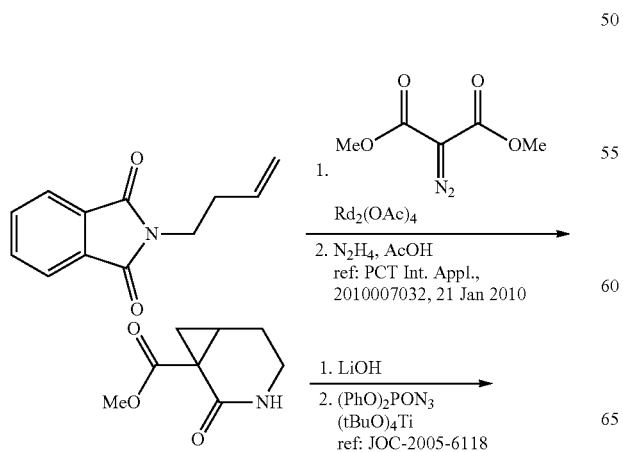

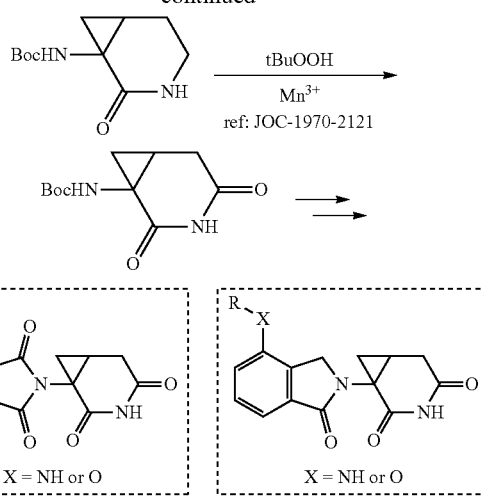

General Procedure Example 36: [4.1.0] Pomalidomide Derivatives

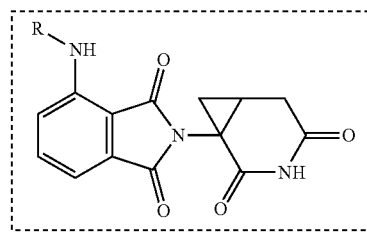

Methyl 2-oxo-3-azabicyclo[4.1.0]heptane-1-carboxylate

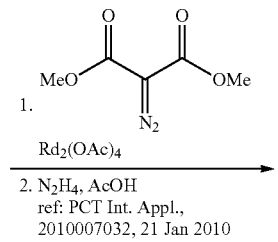

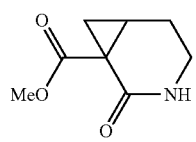

Known compound and procedure reported in PCT Int. Appl., 2010007032, 21 Jan. 2010.

331 tert-Butyl (2-oxo-3-azabicyclo[4.1.0]heptan-1-yl)carbamate

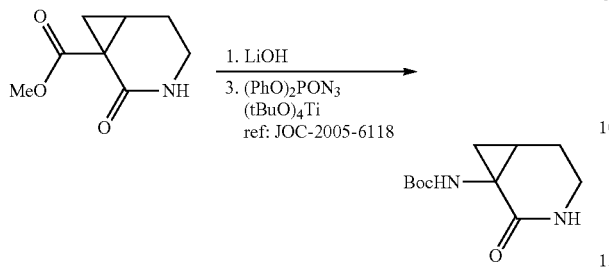

A mixture of methyl 2-oxo-3-azabicyclo[4.1.0]heptane-1-carboxylate (1 equiv.) and LiOH (2 equiv.) in 1:1 MeOH—H$_2$O is stirred at rt for 6 h and then is evaporated to one-half volume. The aqueous solution is extracted with Et$_2$O, chilled in ice, and then made acidic with 1 N HCl. Crystalline product is collected by filtration to give the 2-oxo-3-azabicyclo[4.1.0]heptane-1-carboxylic acid.

To a solution of 2-oxo-3-azabicyclo[4.1.0]heptane-1-carboxylic acid (1 equiv.) in toluene is added triethylamine (1.2 equiv.). Diphenylphosphoryl azide (1.1 equiv.) is added dropwise and the mixture is heated to reflux while stirring for 30 min. The mixture is then cooled to rt and quenched with saturated aqueous NH$_4$Cl. After separation of the two phases, the aqueous solution is extracted with Et$_2$O (3×) and the combined organic layers are washed with brine, dried with anhydrous Na$_2$SO$_4$ and concentrated in vacuo. The crude product is purified by flash chromatography on silica gel to afford isocyanate. (J. Org. Chem. 2005, 70, 6118)

To a solution of the isocyanate (1.0 equiv. of 0.2 M in benzene) is added the t-butyl alcohol (1.5 equiv). Titanium tetratbutoxide (0.10 equiv.) is then added, and the mixture is stirred at 120° C. until completion. After quenching with saturated aqueous NH$_4$Cl and separating the two phases, the aqueous layer is extracted three times with CH$_2$Cl$_2$, and the combined organic layers are dried with anhydrous Na$_2$SO$_4$, and concentrated in vacuo. The residue is purified by flash chromatography on silica gel to afford tert-butyl (2-oxo-3-azabicyclo[4.1.0]heptan-1-yl)carbamate. (J. Org. Chem. 2005, 70, 6118)

tert-Butyl (2,4-dioxo-3-azabicyclo[4.1.0]heptan-1-yl)carbamate

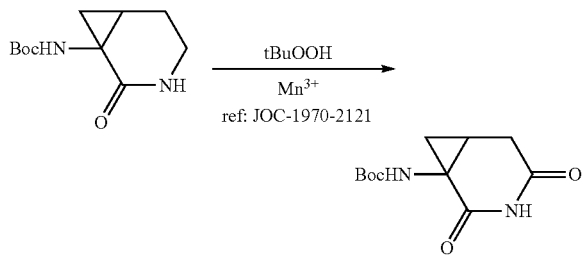

A solution of tert-butyl (2-oxo-3-azabicyclo[4.1.0]heptan-1-yl)carbamate (1 equiv.), manganic acetylacetonate (0.01 wt equiv.), and 68.8% t-butyl hydroperoxide (1.5 equiv.) is stirred at rt for 4 d. The mixture is concentrated and purified by column chromatography on silica gel to provide

332 tert-butyl (2,4-dioxo-3-azabicyclo[4.1.0]heptan-1-yl)carbamate. (J. Org. Chem. 1970, 35, 2121)

1-Amino-3-azabicyclo[4.1.0]heptane-2,4-dione

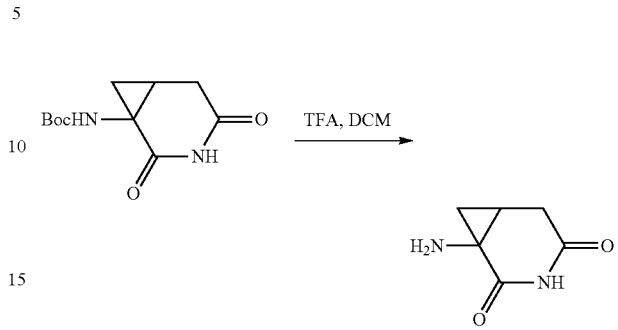

A solution of tert-butyl (2,4-dioxo-3-azabicyclo[4.1.0]heptan-1-yl)carbamate (1 equiv.) in 1:1 TFA/DCM is stirred at rt for 2 h. Solvents are evaporated to provide 1-amino-3-azabicyclo[4.1.0]heptane-2,4-dione.

2-(2,4-Dioxo-3-azabicyclo[4.1.0]heptan-1-yl)-4-fluoroisoindoline-1,3-dione

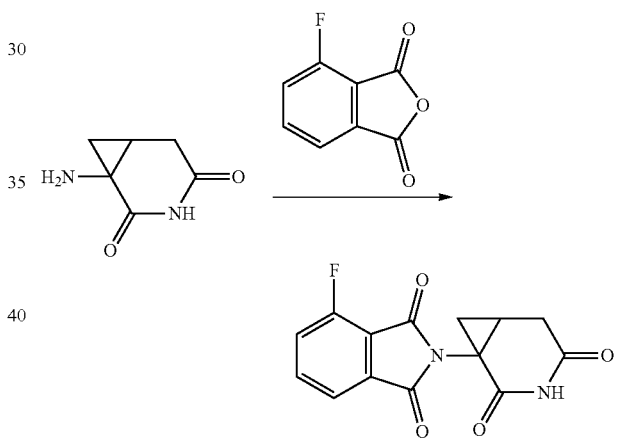

A mixture of 3-fluorophthalic anhydride (1 equiv.), 1-amino-3-azabicyclo[4.1.0]heptane-2,4-dione (1 equiv.), and potassium acetate (2.5 equiv.) in acetic acid is stirred at 120° C. overnight. The dark mixture is cooled and filtered. The filter cake is dissolved in DCM and washed with saturated NaHCO$_3$ and brine. The organic layer is dried (Na$_2$SO$_4$) and concentrated to provide 2-(2,4-dioxo-3-azabicyclo[4.1.0]heptan-1-yl)-4-fluoroisoindoline-1,3-dione.

[4.1.0] Pomalidomide Derivatives

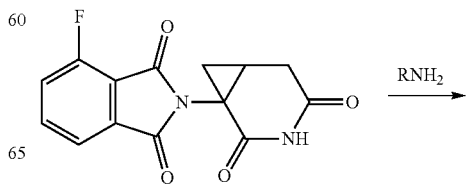

333

-continued

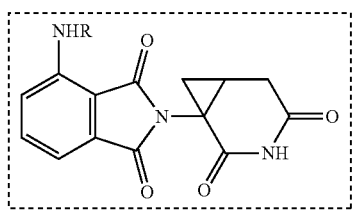

A mixture of alkyl amine (1 equiv.), 2-(2,4-dioxo-3-azabicyclo[4.1.0]heptan-1-yl)-4-fluoroisoindoline-1,3-dione (1 equiv.) and DIEA (2 equiv.) in dry DMF is stirred at 90° C. for 12 h. The mixture is cooled to room temperature, poured into water and extracted with ethyl acetate. The combined organic phases are washed with water and brine, dried over anhydrous sodium sulfate, and concentrated under reduced pressure. The crude residue is purified by column chromatography on silica gel to give [4.1.0] pomalidomide derivatives. (*Chem Biol.* 2015, 22, 755-763)

[3.1.1] System

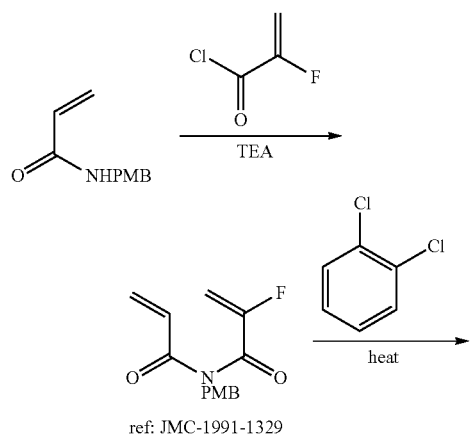

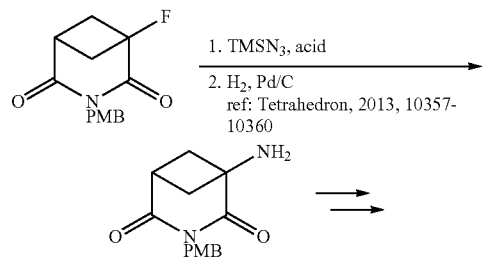

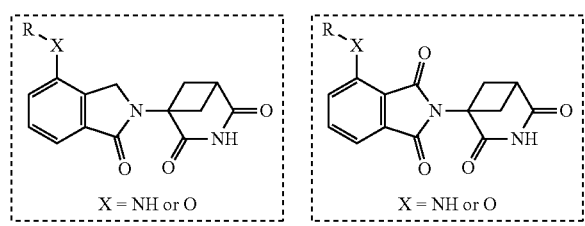

334

General Procedure Example 37: [3.1.1] Pomalidomide Derivatives

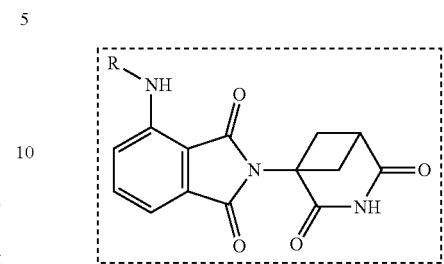

N-Acryloyl-2-fluoro-N-(4-methoxybenzyl)acrylamide

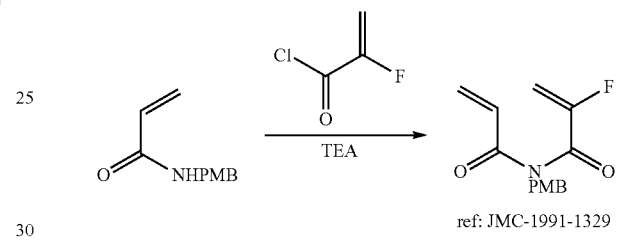

A solution of 2-fluoroacryloyl chloride (1 equiv.) is cooled to 0° C. and added dropwise to a precooled solution of N-(4-methoxybenzyl)acrylamide (1 equiv.) and triethylamine (2 equiv.) in methylene chloride. The mixture is stirred for 1.5 h at room temperature and evaporated to dryness. The residue is extracted with ether, the filtrate is evaporated. The crude residue is purified by column chromatography on silica gel to give N-acryloyl-2-fluoro-N-(4-methoxybenzyl)acrylamide. (*J. Med. Chem.* 1991, 34, 1333)

1-Fluoro-3-(4-methoxybenzyl)-3-azabicyclo[3.1.1]heptane-2,4-dione

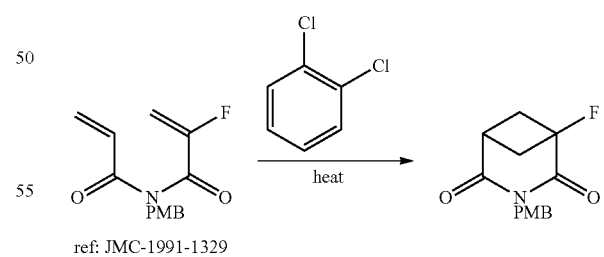

A solution of N-acryloyl-2-fluoro-N-(4-methoxybenzyl)acrylamide (1 equiv.) and 2,6-di-tert-butyl-p-cresionl (13.75 equiv.) in 1,2-dichlorbenzene is stirred at 170° C. for 1.5 h. After concentration by evaporation, the residue is purified by column chromatography on silica gel to give 1-fluoro-3-(4-methoxybenzyl)-3-azabicyclo[3.1.1]heptane-2,4-dione.

1-Amino-3-(4-methoxybenzyl)-3-azabicyclo[3.1.1]heptane-2,4-dione

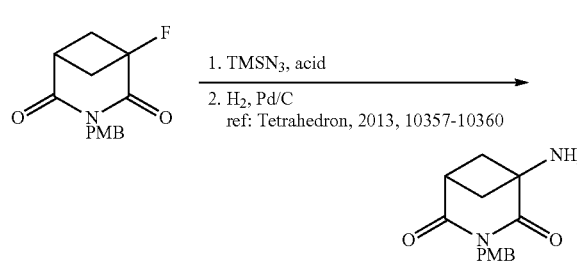

Under nitrogen atmosphere, a mixture of 1-fluoro-3-(4-methoxybenzyl)-3-azabicyclo[3.1.1]heptane-2,4-dione (1 equiv.), sodium azide (1.2 equiv.), and Al(OTf)$_3$ (0.3 equiv.) in dry CH$_2$Cl$_2$ is stirred under reflux for 12 h. The mixture is poured into water and extracted with CH$_2$Cl$_2$ (3×). The combined organic layers are dried over Na$_2$SO$_4$ and concentrated under reduced pressure. The residue is purified by column chromatography on silica gel to give 1-azido-3-(4-methoxybenzyl)-3-azabicyclo[3.1.1]heptane-2,4-dione.

The azide obtained above is dissolved in methanol and added palladium on activated carbon (10% wt). The mixture is hydrogenated until the consumption of the starting material. After filtration and concentration, the residue is purified by column chromatography on silica gel to give 1-amino-3-(4-methoxybenzyl)-3-azabicyclo[3.1.1]heptane-2,4-dione.

1-(4-Fluoro-1,3-dioxoisoindolin-2-yl)-3-(4-methoxybenzyl)-3-azabicyclo[3.1.1]heptane-2,4-dione

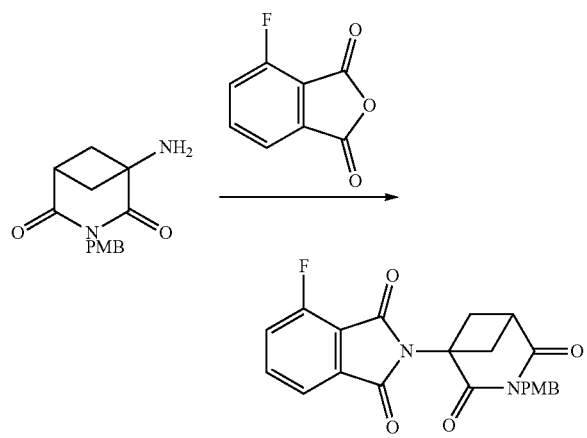

A mixture of 3-fluorophthalic anhydride (1 equiv.), 1-amino-3-(4-methoxybenzyl)-3-azabicyclo[3.1.1]heptane-2,4-dione (2.5 equiv.) in acetic acid is stirred at 120° C. overnight. The dark mixture is cooled and filtered. The filter cake is dissolved in DCM and washed with saturated NaHCO$_3$ and brine. The organic layer is dried (Na$_2$SO$_4$) and concentrated to provide 1-(4-fluoro-1,3-dioxoisoindolin-2-yl)-3-(4-methoxybenzyl)-3-azabicyclo[3.1.1]heptane-2,4-dione.

[3.1.1] Pomalidomide Derivatives

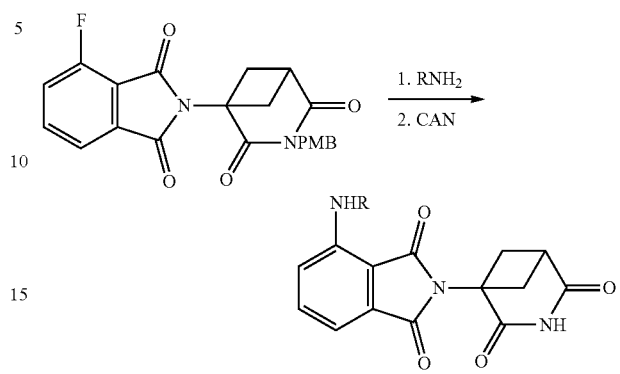

A mixture of alkyl amine (1 equiv.), 1-(4-fluoro-1,3-dioxoisoindolin-2-yl)-3-(4-methoxybenzyl)-3-azabicyclo[3.1.1]heptane-2,4-dione (1 equiv.) and DIEA (2 equiv.) in dry DMF is stirred at 90° C. for 12 h. The mixture is cooled to room temperature, poured into water and extracted with ethyl acetate. The combined organic phases are washed with water and brine, dried over anhydrous sodium sulfate, and concentrated under reduced pressure. (*Chem Biol.* 2015, 22, 755-763)

To a solution of the resulting residue (1.0 equiv) in CH$_3$CN, cooled to 0° C., is added a solution of CAN (3.0 equiv) in H$_2$O, and the yellow clear solution is stirred at 0° C. for 2 h. Then it is diluted with EtOAc and quenched with half saturated aqueous NaCl and diluted with EtOAc and H$_2$O. The phases are separated, and the aqueous phase is extracted with EtOAc (2×) and CH$_2$Cl$_2$ (2×). The combined organic phases are dried (Na$_2$SO$_4$), filtered, and concentrated in vacuo. The residue is purified by column chromatography on silica gel to provide [3.1.1] pomalidomide derivatives. (*Org. Lett.* 2013, 15, 4312)

[3.2.1] System

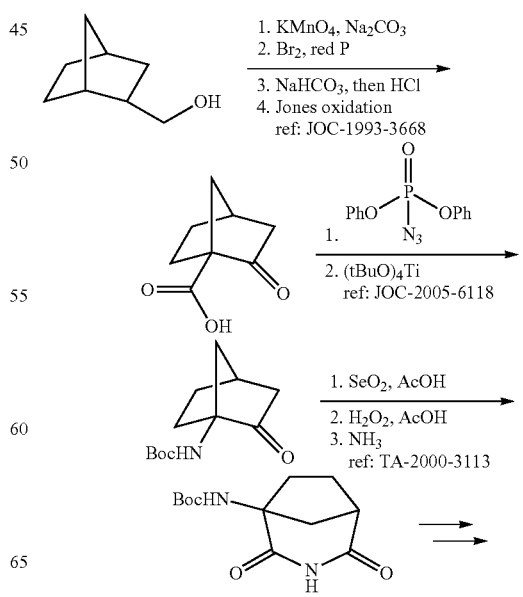

-continued

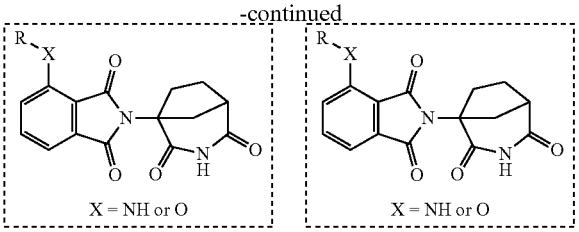

X = NH or O    X = NH or O

General Procedure Example 38: [3.2.1] Pomalidomide Derivatives

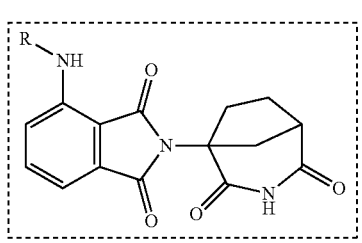

(1R,4S)-2-Oxobicyclo[2.2.1]heptane-1-carboxylic Acid

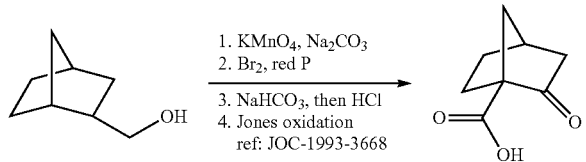

1. KMnO$_4$, Na$_2$CO$_3$
2. Br$_2$, red P
3. NaHCO$_3$, then HCl
4. Jones oxidation
ref: JOC-1993-3668

Known compound and procedure reported in *J. Org. Chem.* 1993, 58, 3668.

tert-Butyl ((1R,4S)-2-oxobicyclo[2.2.1]heptan-1-yl) carbamate

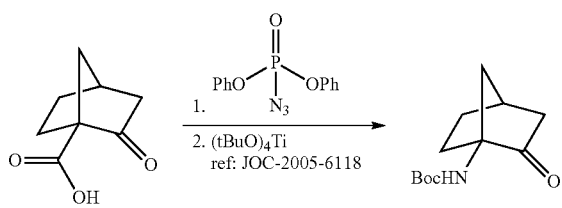

1. PhO-P(=O)(OPh)-N$_3$
2. (tBuO)$_4$Ti
ref: JOC-2005-6118

To a solution of (1R,4S)-2-oxobicyclo[2.2.1]heptane-1-carboxylic acid (1 equiv.) in toluene is added triethylamine (1.2 equiv.). Diphenylphosphoryl azide (1.1 equiv.) is added dropwise and the mixture is heated to reflux while stirring for 30 min. The mixture is then cooled to rt and quenched with saturated aqueous NH$_4$Cl. After separation of the two phases, the aqueous solution is extracted with Et$_2$O (3×) and the combined organic layers are washed with brine, dried with anhydrous Na$_2$SO$_4$ and concentrated in vacuo. The crude product is purified by flash chromatography on silica gel to afford isocyanate. (*J. Org. Chem.* 2005, 70, 6118)

To a solution of the isocyanate (1.0 equiv. of 0.2 M in benzene) is added the t-butyl alcohol (1.5 equiv). Titanium tetratbutoxide (0.10 equiv.) is then added, and the mixture is stirred at 120° C. until completion. After quenching with saturated aqueous NH$_4$Cl and separating the two phases, the aqueous layer is extracted three times with CH$_2$Cl$_2$, and the combined organic layers are dried with anhydrous Na$_2$SO$_4$, and concentrated in vacuo. The residue is purified by flash chromatography on silica gel to afford tert-butyl ((1R,4S)-2-oxobicyclo[2.2.1]heptan-1-yl)carbamate. (*J. Org. Chem.* 2005, 70, 6118)

tert-Butyl (2,4-dioxo-3-azabicyclo[3.2.1]octan-1-yl) carbamate

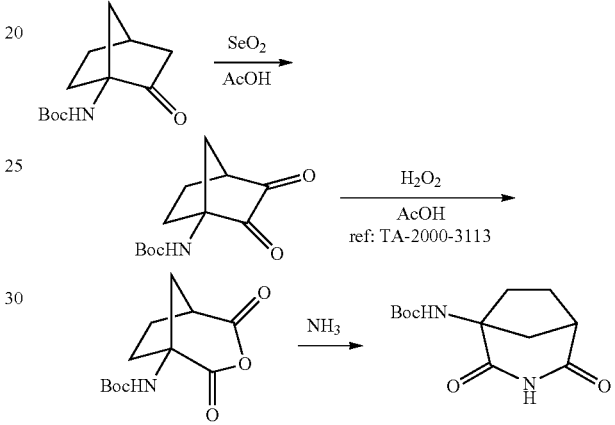

SeO$_2$ / AcOH

H$_2$O$_2$ / AcOH
ref: TA-2000-3113

NH$_3$ tert-Butyl ((1R,4S)-2-oxobicyclo[2.2.1]heptan-1-yl)carbamate (1 equiv.) is mixed with selenium dioxide (1.1 equiv.), dissolved in acetic acid and refluxed for 18 h. The reaction mixture is filtered, concentrated to smaller volume and 30% hydrogen peroxide (excess) is added. After cooling to 0° C. the reaction is filtered, dried and crystallized from toluene/hexane to provide anhydride. The resulting anhydride (1 equiv.) is dissolved in 25% aqueous ammonia (excess) and evaporated to dryness. The residue is heated at 180° C. for 0.5 h, dissolved in chloroform, decolorized with silica gel, filtered and the solvent is evaporated. The residue is purified by flash chromatography on silica gel to afford tert-butyl (2,4-dioxo-3-azabicyclo[3.2.1]octan-1-yl)carbamate. (*Tetrahedron: Asymmetry* 2000, 11, 3113-3122)

1-Amino-3-azabicyclo[3.2.1]octane-2,4-dione

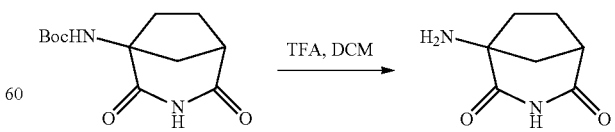

TFA, DCM

A solution of tert-butyl (2,4-dioxo-3-azabicyclo[3.2.1] octan-1-yl)carbamate (1 equiv.) in 1:1 TFA/DCM is stirred at rt for 2 h. Solvents are evaporated to provide 1-amino-3-azabicyclo[3.2.1]octane-2,4-dione.

339

2-(2,4-Dioxo-3-azabicyclo[3.2.1]octan-1-yl)-4-fluoroisoindoline-1,3-dione

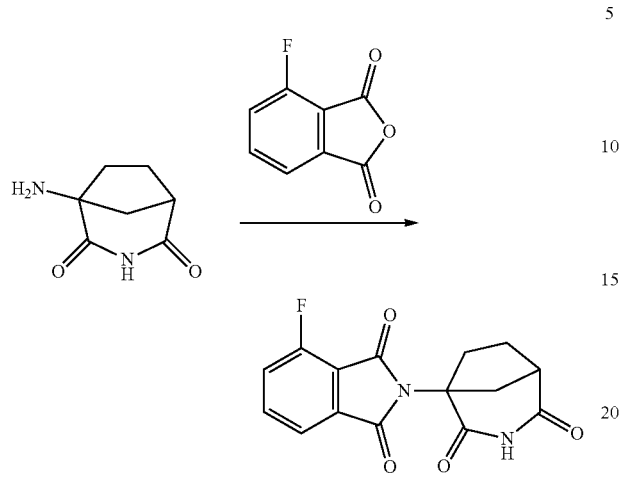

A mixture of 3-fluorophthalic anhydride (1 equiv.), 1-amino-3-azabicyclo[3.2.1]octane-2,4-dione (2.5 equiv.) in acetic acid is stirred at 120° C. overnight. The dark mixture is cooled and filtered. The filter cake is dissolved in DCM and washed with saturated NaHCO$_3$ and brine. The organic layer is dried (Na$_2$SO$_4$) and concentrated to provide 2-(2,4-dioxo-3-azabicyclo[3.2.1]octan-1-yl)-4-fluoroisoindoline-1,3-dione.

[3.2.1] Pomalidomide Derivatives

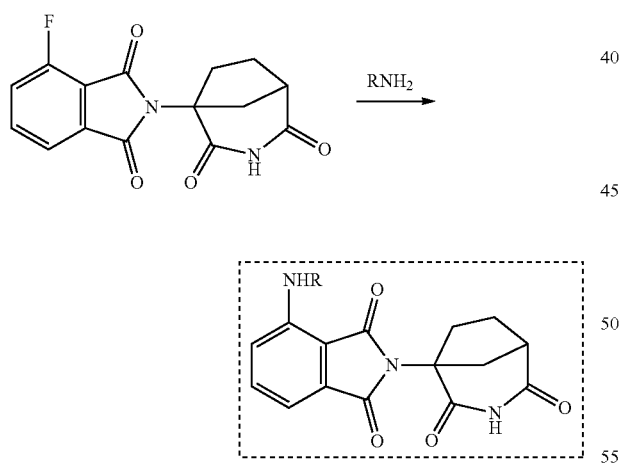

A mixture of alkyl amine (1 equiv.), 2-(2,4-dioxo-3-azabicyclo[3.2.1]octan-1-yl)-4-fluoroisoindoline-1,3-dione (1 equiv.) and DIEA (2 equiv.) in dry DMF is stirred at 90° C. for 12 h. The mixture is cooled to room temperature, poured into water and extracted with ethyl acetate. The combined organic phases are washed with water and brine, dried over anhydrous sodium sulfate, and concentrated under reduced pressure. The residue is purified by column chromatography on silica gel to give [3.2.1] pomalidomide derivatives. (*Chem Biol.* 2015, 22, 755-763)

340

4'-Spiroglutarimide

General Procedure Example 39: 4'-Spiro Pomalidomide Derivatives

4-Bromo-6-azaspiro[2.5]octane-5,7-dione

Bromine (1 equiv.) is added to a solution of 6-azaspiro[2.5]octane-5,7-dione (1 equiv.) in 1,1,2-trichloroethane at room temperature. The mixture is allowed to stir for 2 hours at 110° C. and then for 1 hour at room temperature. The reaction mixture is concentrated in vacuo and the resulting residue is purified by flash column chromatography on silica gel to provide 4-bromo-6-azaspiro[2.5]octane-5,7-dione. (PCT 5,7-dionet. Appl., 2013033901, 14 Mar. 2013)

4-Amino-6-azaspiro[2.5]octane-5,7-dione

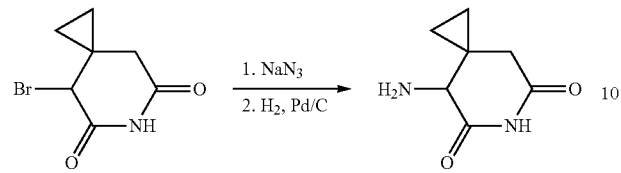

4-Bromo-6-azaspiro[2.5]octane-5,7-dione (1 equiv.) is dissolved in DMF and NaN₃ (3 equiv.) is added. The resulting mixture is heated at 50° C. for 3 h. Solvent is removed in vacuo and the crude azide is dried under vacuum. (U.S. Pat. Appl. Publ., 20040006062, 8 Jan. 2004) The crude azide is dissolved in methanol and palladium on activated carbon (10% wt) is added. The mixture is hydrogenated at rt until the consumption of starting material. The mixture is filtered, and concentrated. The residue is purified by flash column chromatography on silica gel to provide 4-amino-6-azaspiro[2.5]octane-5,7-dione.

2-(5,7-Dioxo-6-azaspiro[2.5]octan-4-yl)-4-fluor-oisoindoline-1,3-dione

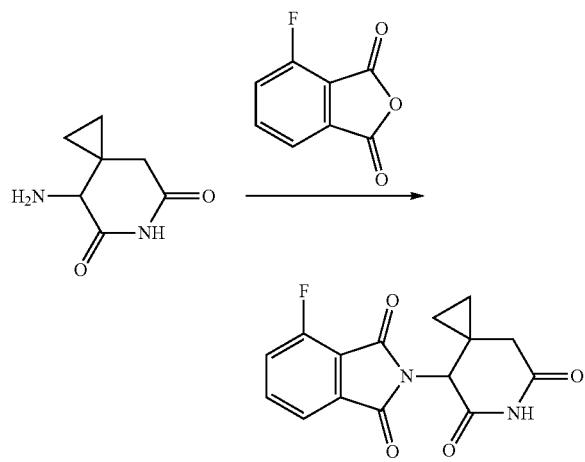

A mixture of 3-fluorophthalic anhydride (1 equiv.), 4-amino-6-azaspiro[2.5]octane-5,7-dione (2.5 equiv.) in acetic acid is stirred at 120° C. overnight. The dark mixture is cooled and filtered. The filter cake is dissolved in DCM and washed with saturated NaHCO₃ and brine. The organic layer is dried (Na₂SO₄) and concentrated to provide 2-(5,7-dioxo-6-azaspiro[2.5]octan-4-yl)-4-fluoroisoindoline-1,3-dione.

4'-Spiro Pomalidomide Derivatives

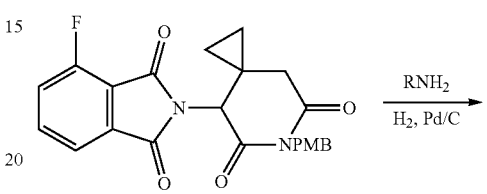

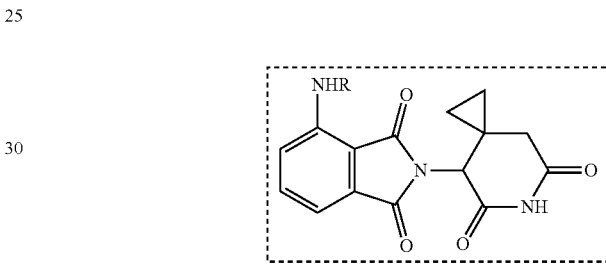

A mixture of alkyl amine (1 equiv.), 2-(5,7-dioxo-6-azaspiro[2.5]octan-4-yl)-4-fluoroisoindoline-1,3-dione (1 equiv.) and DIEA (2 equiv.) in dry DMF is stirred at 90° C. for 12 h. The mixture is cooled to room temperature, poured into water and extracted with ethyl acetate. The combined organic phases are washed with water and brine, dried over anhydrous sodium sulfate, and concentrated under reduced pressure. The residue is purified by column chromatography on silica gel to give 4'-spiro pomalidomide derivatives. (*Chem Biol.* 2015, 22, 755-763)

5'-Spiroglutarimide

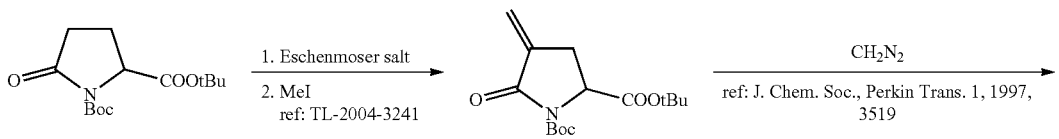

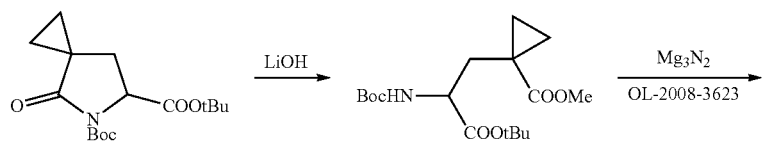

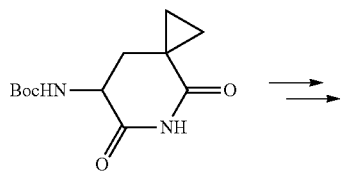

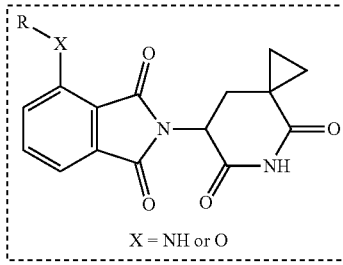

X = NH or O

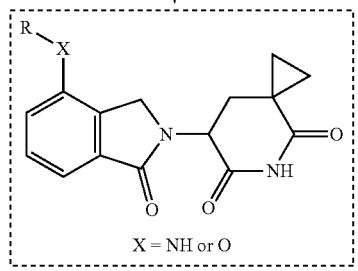

X = NH or O

General Procedure Example 40: 5'-spiro Pomalidomide Derivatives

Methyl 1-(3-(tert-butoxy)-2-((tert-butoxycarbonyl)amino)-3-oxopropyl)cyclopropane-1-carboxylate

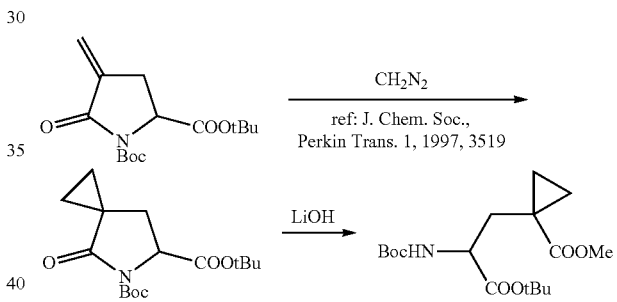

Known compound and procedures reported in *J. Chem. Soc., Perkin Trans.* 1, 1997, 3519.

2-Amino-3-(1-carbamoylcyclopropyl)propanoic Acid

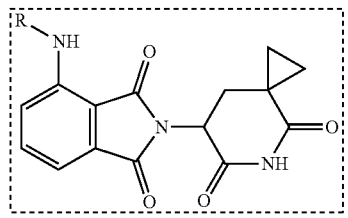

di-tert-Butyl 4-methylene-5-oxopyrrolidine-1,2-dicarboxylate

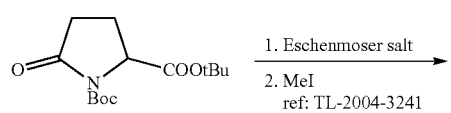

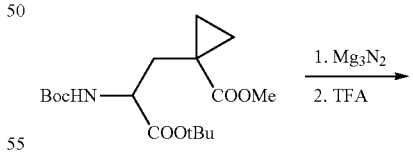

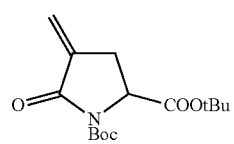

Known compound and procedure reported in *Tetrahedron Lett.* 2004, 45, 3241.

To a stirred solution of methyl 1-(3-(tert-butoxy)-2-((tert-butoxycarbonyl)amino)-3-oxopropyl)cyclopropane-1-carboxylate (1 equiv.) in methanol at 0° C. in a 2-5 mL microwave vial is added magnesium nitride (5 equiv.) in a single portion. The vial is sealed immediately and allowed to warm to room temperature in a water bath. After approximately 1 hour the reaction is heated at 80° C. for 24 h. The reaction is allowed to cool to room temperature and diluted with chloroform and water. The aqueous layer is neutralized with 3 N HCl and the organic layer is separated. The aqueous layer is further extracted with chloroform (2×) and the organic layers are combined, passed through a hydrophobic frit and concentrated in vacuo to afford crude carboxamide. (*Org. Lett.* 2008, 10, 3623)

The resulting carboxamide (1 equiv.) is dissolved in 1:1 TFA/DCM and stirred at rt for 2 h. Solvents are evaporated and the residue is purified by column chromatography on silica gel to provide 2-amino-3-(1-carbamoylcyclopropyl) propanoic acid.

7-Amino-5-azaspiro[2.5]octane-4,6-dione

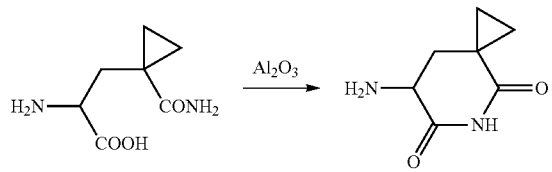

A mixture of 2-amino-3-(1-carbamoylcyclopropyl)propanoic acid (1 equiv.), alumina (3 wt. equiv.) in toluene is heated under reflux for 1.5 h. The water produced during the reaction is collected in a Dean-Stark trap. The reaction mixture is allowed to cool and the alumina is filtered off and washed with 10% MeOH/CH₂Cl₂. The filtration is combined and the solvent is removed under vacuum to provide 7-amino-5-azaspiro[2.5]octane-4,6-dione. (*Org. Biomol. Chem.* 2015, 13, 7624-7627)

2-(4,6-Dioxo-5-azaspiro[2.5]octan-7-yl)-4-fluoroisoindoline-1,3-dione

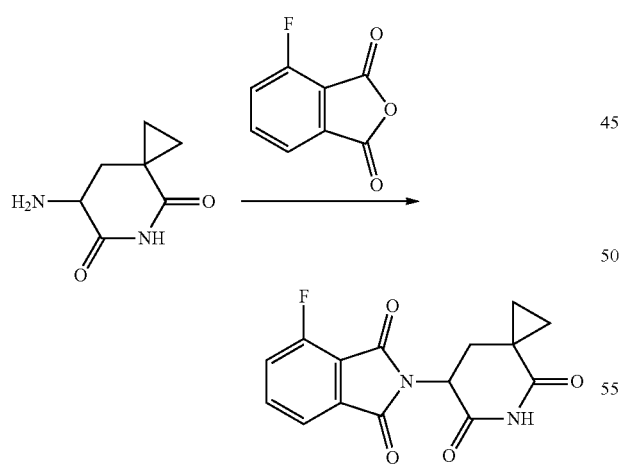

A mixture of 3-fluorophthalic anhydride (1 equiv.), 7-amino-5-azaspiro[2.5]octane-4,6-dione (2.5 equiv.) in acetic acid is stirred at 120° C. overnight. The dark mixture is cooled and filtered. The filter cake is dissolved in DCM and washed with saturated NaHCO₃ and brine. The organic layer is dried (Na₂SO₄) and concentrated to provide 2-(4,6-dioxo-5-azaspiro[2.5]octan-7-yl)-4-fluoroisoindoline-1,3-dione.

5'-Spiro Pomalidomide Derivatives

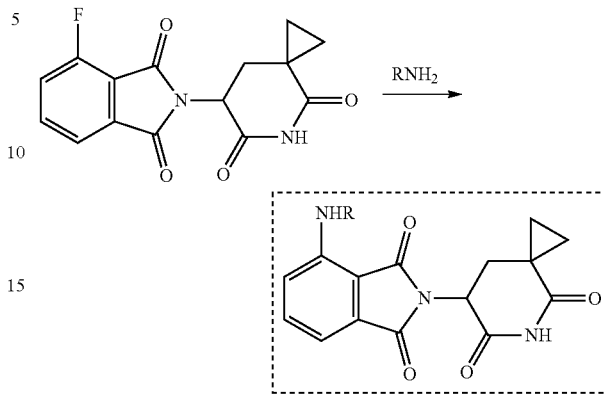

A mixture of alkyl amine (1 equiv.), 2-(4,6-dioxo-5-azaspiro[2.5]octan-7-yl)-4-fluoroisoindoline-1,3-dione (1 equiv.) and DIEA (2 equiv.) in dry DMF is stirred at 90° C. for 12 h. The mixture is cooled to room temperature, poured into water and extracted with ethyl acetate. The combined organic phases are washed with water and brine, dried over anhydrous sodium sulfate, and concentrated under reduced pressure. The residue is purified by column chromatography on silica gel to give 5'-spiro pomalidomide derivatives. (*Chem Biol.* 2015, 22, 755-763)

Intermediate Functionalization in Preparation for Linker Installation

General procedure to convert 4-fluoro-thalidomide to 4-bromo-thalidomide, which then be used to convert to various functional groups for linker installation.

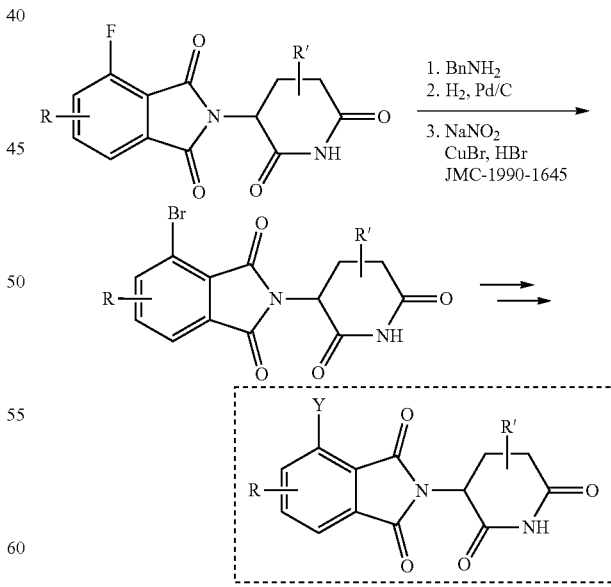

Y = OH, ethynyl, propargyloxy, COOH, CH₂OH, CHO, CH₂Br, CH₂N₃

General procedure to convert lenalidomide to 4-bromo-lenalidomide, which then be used to convert to various functional groups for linker installation.

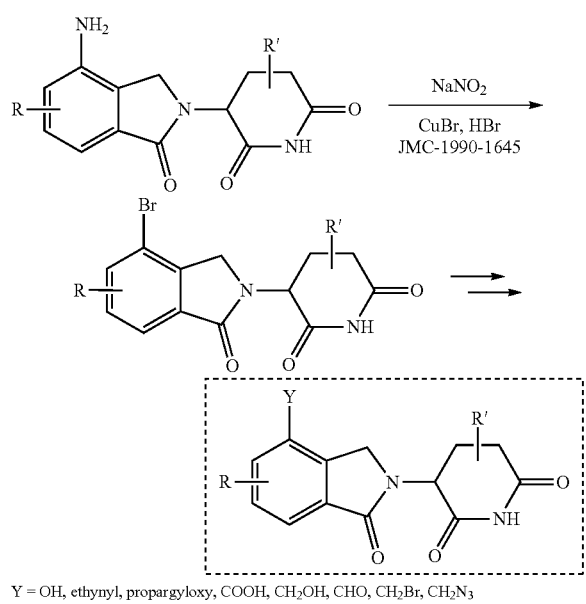

Y = OH, ethynyl, propargyloxy, COOH, CH₂OH, CHO, CH₂Br, CH₂N₃

General Procedure Example 41: N-Boc 5'-spiro-pomalidomide

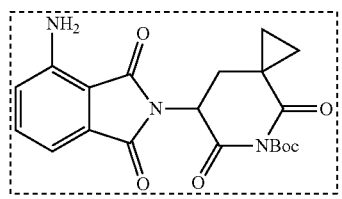 [SMILES: CC(C)(C)OC(=O)N1C(=O)C(N2C(=O)c3cccc(N)c3C2=O)CC2(CC2)C1=O]

N-Boc 4-Fluoro-5'-spiro-thalidomide

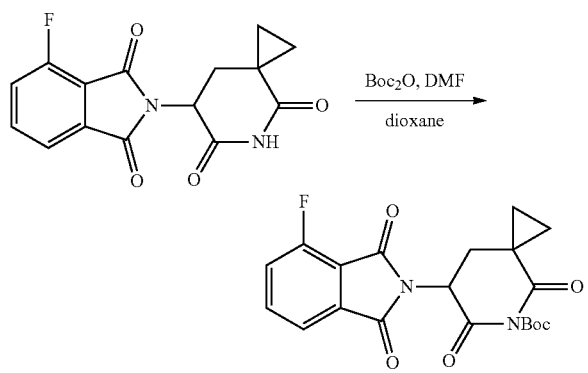

To a stirred solution of 4-fluoro-5'-spiro-thalidomide (1.0 equiv.) in DMF is added potassium carbonate (2.0 equiv.). The resulting solution is cooled to 0-5° C. and Boc anhydride (3.0 equiv.) is added slowly as a solution in 1,4-dioxane (also cooled). The resulting mixture is stirred at 0° C. for 1 h and allowed to warm to room temperature overnight. Water is then added and the aqueous layer is extracted 2 times with DCM and concentrated. The residue is purified by column chromatography on silica gel to obtain N-Boc 4-fluoro-5'-spiro-thalidomide. (WO 2014/147531 A2)

N-Boc 4-Benzylamino-5'-spiro-thalidomide

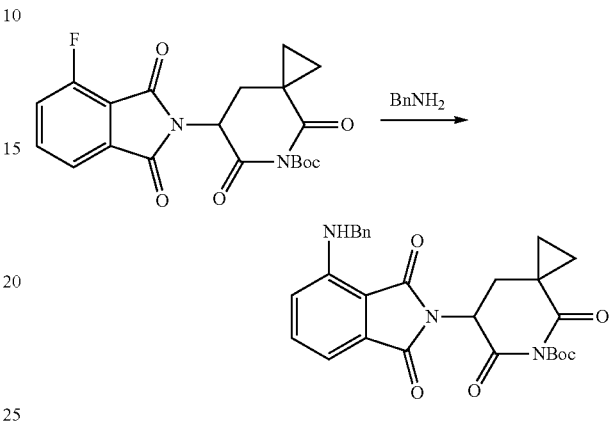

A mixture containing N-Boc 4-fluoro-5'-spiro-thalidomide (1 equiv.) and benzylamine (2 equiv.) in CH₃CN is stirred at room temperature until the consumption of the starting material. After concentration of the reaction mixture under reduced pressure, the residue is diluted with water and extracted with CHCl₃. The organic layer is dried and concentrated to dryness under reduced pressure. The residue is purified by flash column chromatography on silica gel to provide N-Boc 4-benzylamino-5'-spiro-thalidomide. (*J. Med. Chem.* 1990, 33, 1645)

N-Boc 4-Amino-5-spiro-thalidomide

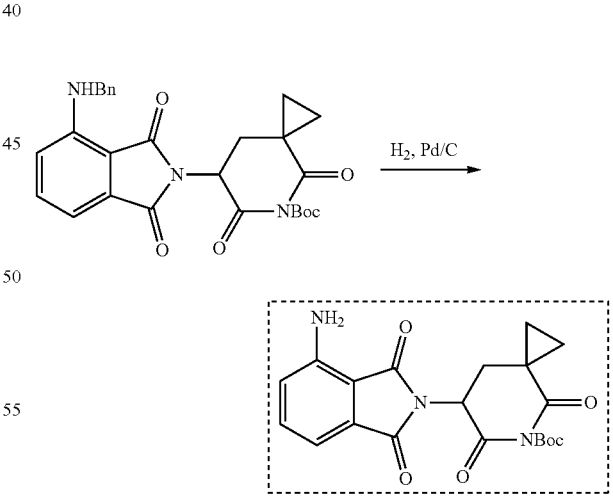

A mixture containing N-Boc 4-benzylamino-5'-spiro-thalidomide (1 equiv.) and 5% Pd/C (0.1 wt equiv.) in dioxane is hydrogenated at 50-55° C. until the required volume of H2 has been taken up. The reaction mixture is filtered to remove the catalyst. The filtrate is concentrated under reduced pressure to provide N-Boc 4-amino-5'-spiro-thalidomide. (*J. Med. Chem.* 1990, 33, 1645)

General Procedure Example 42: N-Boc 4-Bromo-5'-spiro-thalidomide

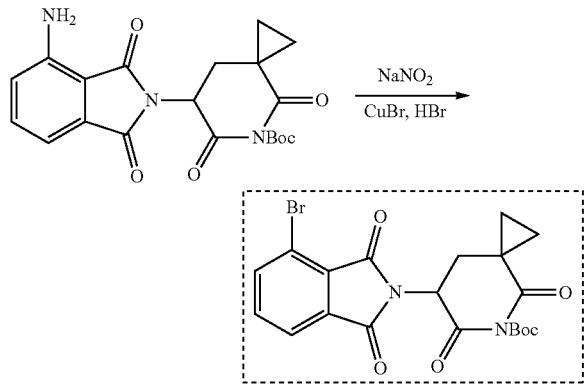

To a suspension of N-Boc 4-amino-5'-spiro-thalidomide (1 equiv.) in 20% HBr is added $NaNO_2$ (1.2 equiv.) under ice cooling. After stirring for 5 min, the reaction mixture is added to a solution of CuBr (1.5 equiv.) in 20% HBr. The reaction mixture is stirred at room temperature for 1 h. After neutralization with 20% NaOH, the solution is extracted with $CHCl_3$. The organic layer is dried and concentrated to dryness. The residue is purified by flash column chromatography on silica gel to provide N-Boc 4-bromo-5'-spiro-thalidomide. (*J. Med. Chem.* 1990, 33, 1645)

General Procedure Example 43: N-Boc 4-Hydroxyl-5'-spiro-thalidomide

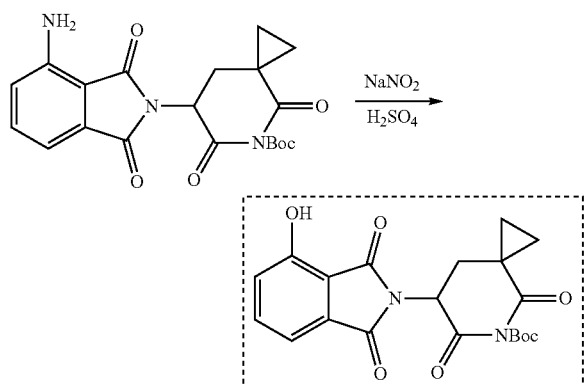

15 N Sulfuric acid is cooled to 0° C., N-Boc 4-bromo-5'-spiro-thalidomide (1 equiv.) is added gradually with good stirring. After one hour, a solution of sodium nitrite (1 equiv.) in water is added slowly while maintaining the temperature below 5° C. After another 30 minutes, the mixture is warmed to 80° C. and maintained at this temperature until nitrogen evolution ceases. The now dark orange solution is diluted with water and extracted with ether. The organic layer is dried with sodium sulfate, filtered and shaken for two hours with finely powdered barium chloride to remove traces of sulfuric acid. The solution is filtered and concentrated. The residue is purified by flash column chromatography on silica gel to provide N-Boc 4-hydroxyl-5'-spiro-thalidomide. (*J. Am. Chem. Soc.*, 1955, 77 (19), pp 5092-5095)

General Procedure Example 44: N-Boc 4-Ethynyl-5'-spiro-thalidomide

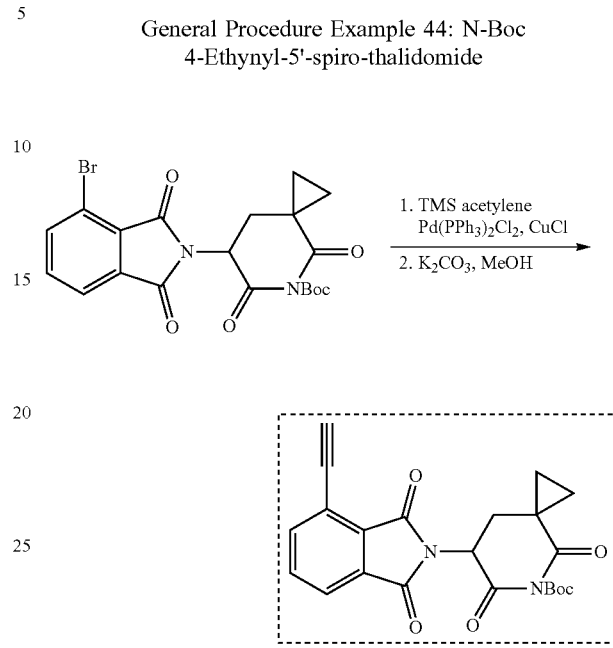

A reaction vessel is charged with bis(triphenylphosphine) palladium(II) chloride (2 mol %), copper(I) iodide (4 mol %) and N-Boc 4-bromo-5'-spiro-thalidomide (1 equiv.). The reaction atmosphere is cycled between nitrogen and vacuum 3 times then triethylamine (1.55 equiv.) and trimethylsilylacetylene (1.25 equiv.) are added and the reaction is mixed for 24 hours. When the starting materials are consumed, the reaction is diluted with ethyl acetate and filtered through a plug of Celite®. The filtrate is concentrated and the residue is purified by silica gel chromatography to provide N-Boc 4-trimethylsilylethynyl-5'-spiro-thalidomide. (*Org. Lett.* 2014, 16, 6302)

A reaction vessel is charged with N-Boc 4-trimethylsilylethynyl-5'-spiro-thalidomide (1 equiv.), potassium carbonate (4 equiv.) and MeOH. The reaction is mixed at ambient temperature for 8 hours then concentrated. The residue is diluted with water and ethyl acetate. The aqueous layer is extracted with ethyl acetate and the combined organic layer is dried over sodium sulfate, filtered and concentrated. The crude residue is purified by silica gel chromatography to provide N-Boc 4-ethynyl-5'-spiro-thalidomide.

General Procedure Example 45: N-Boc 4-Propargyloxy-5'-spiro-thalidomide

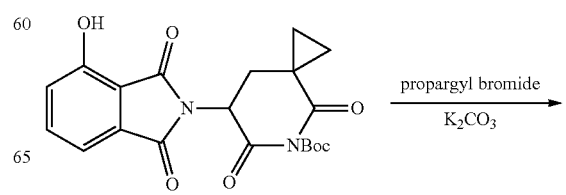

-continued

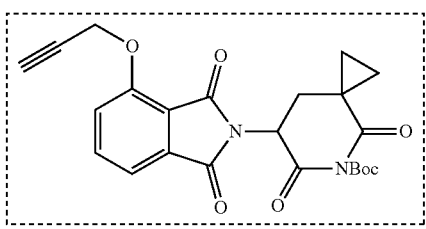

A reaction vessel is charged with N-Boc 4-hydroxyl-5'-spiro-thalidomide (1 equiv.) and acetone (0.25 M). To this solution is added sequentially potassium carbonate (4 equiv.) and propargyl bromide (1.2 equiv.). The reaction is refluxed overnight, cooled to ambient temperature, filtered through a medium frit, and concentrated. The crude residue is purified by silica gel chromatography to provide N-Boc 4-propargyloxy-5'-spiro-thalidomide. (*J. Med. Chem.* 2013, 56, 2828)

General Procedure Example 46: N-Boc 4-Carboxy-5'-spiro-thalidomide

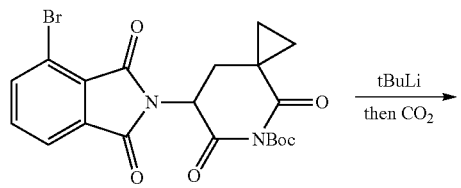

A flame-dried reaction vessel is charged with N-Boc 4-bromo-5'-spiro-thalidomide (1 equiv.) and the atmosphere is cycled between nitrogen and vacuum three times. Ether is added and the solution is cooled to −78° C. tert-Butyllithium (2 equiv.) is added dropwise and the reaction is mixed for 15 min then carbon dioxide gas is bubbled through the solution for 15 min. The reaction is warmed to ambient temperature allowing excess carbon dioxide gas to slowly evolve from solution. The reaction is quenched with 1 M aq. NaOH solution and washed with ether (2×). The pH of the aqueous layer is adjusted to 3 and extracted with ethyl acetate (3×). The combined organic layer is dried over sodium sulfate and concentrated to dryness with toluene (3×) to provide N-Boc 4-carboxy-5'-spiro-thalidomide.

General Procedure Example 47: N-Boc 4-Hydroxymethyl-5'-spiro-thalidomide

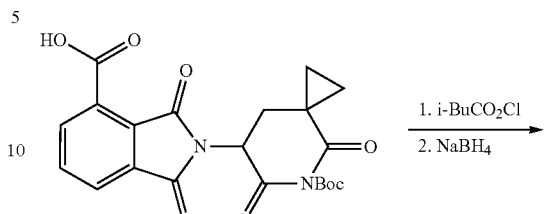

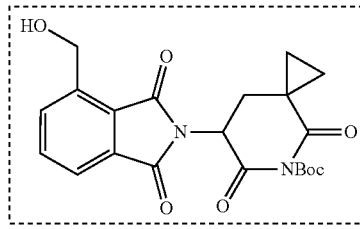

A reaction vessel is charged with N-Boc 4-carboxy-5'-spiro-thalidomide (1 equiv.), THF and cool to 0° C. Triethylamine (1.1 equiv.) and isobutylchloroformate (1.1 equiv.) are added and the reaction mixed ambient temperature for 1 hour. The reaction is filtered through a medium frit and cooled to 0° C. To the solution of mixed anhydride is added a solution of sodium borohydride (2 equiv.) in MeOH. Upon complete reduction to the corresponding benzylic alcohol, the reaction is concentrated then treated with ethyl acetate and 10% aq. HCl. The phases are separated and aqueous solution is extracted with ethyl acetate (3×). The combined organic layer is washed with 5% sodium bicarbonate solution, dried over sodium sulfate, and concentrated. The residue is purified by silica gel chromatography to provide N-Boc 4-hydroxymethyl-5'-spiro-thalidomide.

General Procedure Example 48: N-Boc 4-Formyl-5'-spiro-thalidomide

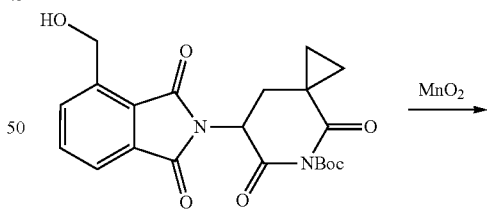

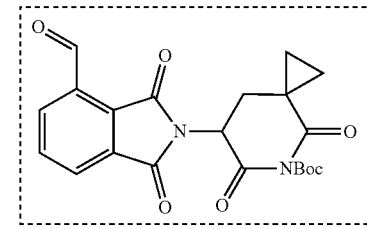

A reaction vessel is charged with N-Boc 4-hydroxymethyl-5'-spiro-thalidomide (1 equiv.) and manganese dioxide (10 equiv.) and DCM. The reaction is heated at reflux overnight then cooled to ambient temperature and filtered.

The filtrate is concentrated and purified by silica gel chromatography to provide N-Boc 4-formyl-5'-spiro-thalidomide.

General Procedure Example 49: N-Boc 4-Bromomethyl-5'-spiro-thalidomide

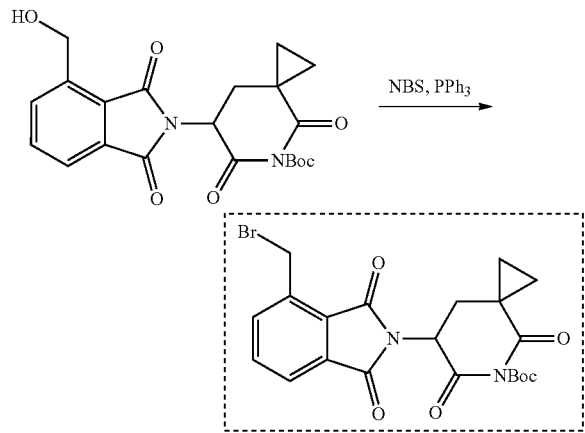

A reaction vessel is charged with N-Boc 4-hydroxymethyl-5'-spiro-thalidomide (1 equiv.) and DCM. The solution is cooled to 0° C. and N-bromosuccinimide (1.25 equiv.) and triphenylphosphine (1.25 equiv.) are then added. The reaction is mixed for 3 hours then concentrated. The crude residue is purified by silica gel chromatography to provide N-Boc 4-bromomethyl-5'-spiro-thalidomide. (*J. Med. Chem.* 2015, 58, 1215)

General Procedure Example 50: N-Boc 4-Azidomethyl-5'-spiro-thalidomide

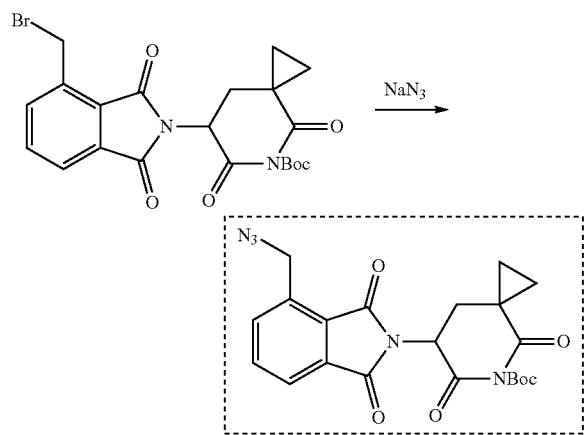

Sodium azide (3 equiv.) is added to a solution of N-Boc 4-bromomethyl-5'-spiro-thalidomide (1 equiv.) in water and acetone (1:3, 0.25 M). The reaction is heated at 60° C. for 6 hours. The reaction is cooled to ambient temperature and the solvent removed by rotary evaporation. The aqueous layer is extracted with DCM (3×) and the combined organic layer is dried over sodium sulfate and filtered. The filtrate is concentrated and the crude residue is purified by silica gel chromatography to provide N-Boc 4-azidomethyl-5'-spiro-thalidomide. (*Angew. Chem. Int. Ed.* 2014, 53, 10155)

Linker Installation

Linker Installation Example 1: tert-Butyl 7-(4-((8-hydroxyoctyl)oxy)-1,3-dioxoisoindolin-2-yl)-4,6-dioxo-5-azaspiro[2.5]octane-5-carboxylate

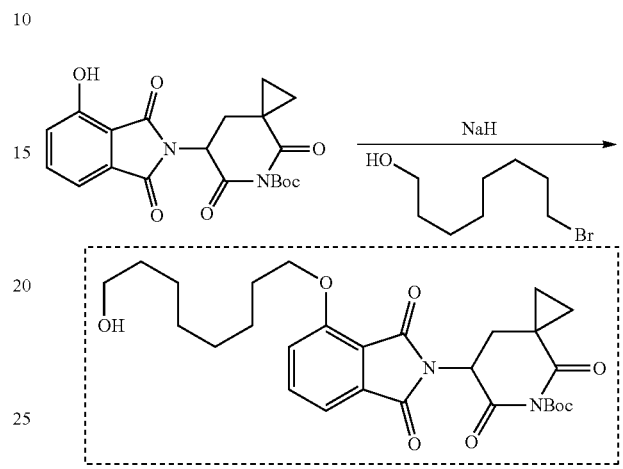

A reaction vessel is charged with N-Boc 4-hydroxyl-5'-spiro-thalidomide (1 equiv.) and DMF (0.3 M) then cooled to 0° C. Sodium hydride (60% dispersion in mineral oil, 1.1 equiv.) is added and the reaction is warmed to ambient temperature and mixed for 1 hour. The reaction is cooled to 0° C. then 8-bromooctan-1-ol (1.1 equiv.) is added and the reaction is mixed at ambient temperature overnight. DMF is removed by rotary evaporation and the residue is deposited onto silica gel and purified by silica gel chromatography to provide tert-butyl 7-(4-((8-hydroxyoctyl)oxy)-1,3-dioxoisoindolin-2-yl)-4,6-dioxo-5-azaspiro[2.5]octane-5-carboxylate.

Linker Installation Example 2: tert-Butyl 7-(4-(2-(2-(2-hydroxyethoxy)ethoxy)ethoxy)-1,3-dioxoisoindolin-2-yl)-4,6-dioxo-5-azaspiro[2.5]octane-5-carboxylate

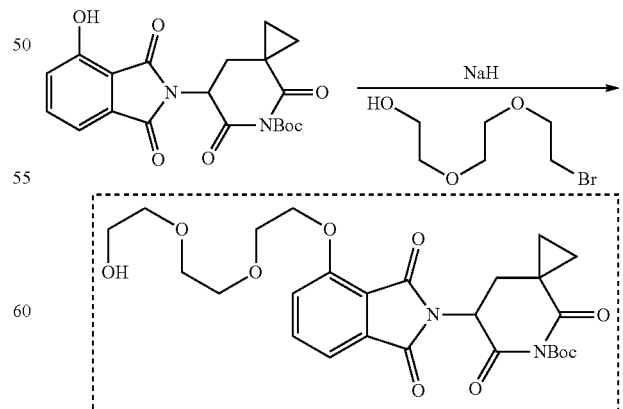

A reaction vessel is charged with N-Boc 4-hydroxyl-5'-spiro-thalidomide (1 equiv.) and DMF (0.3 M) then cooled to 0° C. Sodium hydride (60% dispersion in mineral oil, 1.1 equiv.) is added and the reaction is warmed to ambient temperature and mixed for 1 hour. The reaction is cooled to 0° C. then 2-(2-(2-bromoethoxy)ethoxy)ethan-1-ol (1.1 equiv.) is added and the reaction is mixed at ambient temperature overnight. DMF is removed by rotary evaporation and the residue is deposited onto silica gel and purified by silica gel chromatography to provide tert-butyl 7-(4-(2-(2-(2-hydroxyethoxy)ethoxy)ethoxy)-1,3-dioxoisoindolin-2-yl)-4,6-dioxo-5-azaspiro[2.5]octane-5-carboxylate.

Linker Installation Example 3: tert-Butyl 7-(4-((1-(3-hydroxypropyl)-1H-1,2,3-triazol-4-yl)methoxy)-1,3-dioxoisoindolin-2-yl)-4,6-dioxo-5-azaspiro[2.5]octane-5-carboxylate

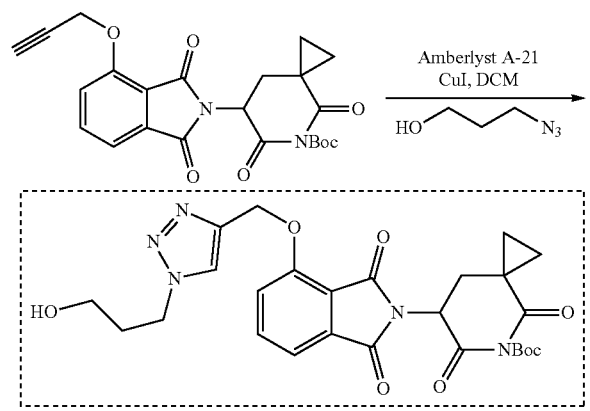

A reaction vessel is charged with the polymer supported catalyst (Amberlyst A-21, 1.23 mmol/g; CuI, 13 mol %). The azide (0.5 M in DCM, 1 equiv.) is added dropwise followed by a solution of N-Boc 4-propargyloxy-5'-spiro-thalidomide (0.5 M in DCM, 1 equiv.). The suspension is mixed for 12 hours at ambient temperature. The reaction solution is filtered through a frit and the polymer cake is washed is washed with DCM (2×). The combined filtrate is concentrated and the residue purified by silica gel chromatography to provide tert-butyl 7-(4-((1-(3-hydroxypropyl)-1H-1,2,3-triazol-4-yl)methoxy)-1,3-dioxoisoindolin-2-yl)-4,6-dioxo-5-azaspiro[2.5]octane-5-carboxylate. (*Org. Lett.* 2006, 8, 1689)

Linker Installation Example 4: tert-Butyl 7-(4-(2-((3,5-dihydroxy-3-methylpentyl)oxy)ethoxy)-1,3-dioxoisoindolin-2-yl)-4,6-dioxo-5-azaspiro[2.5]octane-5-carboxylate

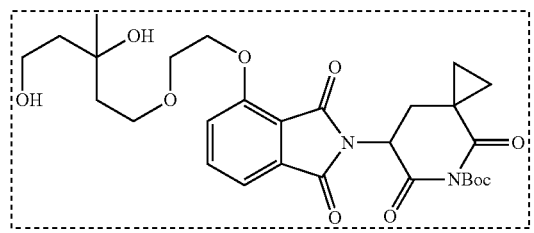 [SMILES: CC(O)(CCO)CCOCCOc1cccc2c1C(=O)N(C1CC3(CC3)C(=O)N(C(=O)OC(C)(C)C)C1=O)C2=O]

tert-Butyl 7-(4-(2-hydroxyethoxy)-1,3-dioxoisoindolin-2-yl)-4,6-dioxo-5-azaspiro[2.5]octane-5-carboxylate

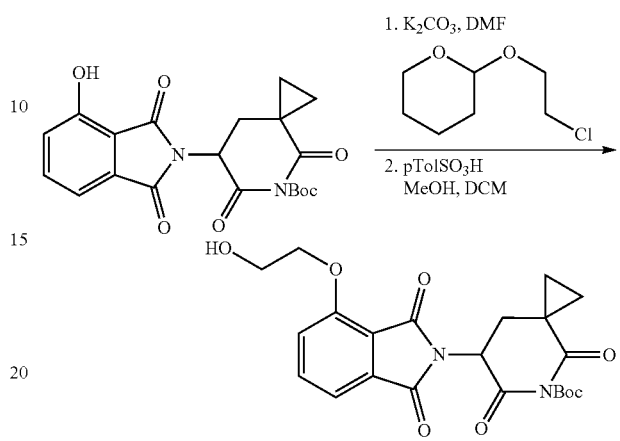

A reaction vessel is charged with N-Boc 4-hydroxyl-5'-spiro-thalidomide (1 equiv.), potassium carbonate (2 equiv.) and DMF (0.5 M). 2-(2-Chloroethoxy)tetrahydro-2H-pyran (1.1 equiv.) is added and the reaction is heated at 110° C. for 12 hours. The reaction is then cooled to ambient temperature and concentrated. The residue is taken up in water and ethyl acetate and the layers separated. The aqueous layer is extracted with ethyl acetate (2×). The combined organic layer is washed with brine, dried over sodium sulfate, filtered and concentrated. The crude residue is used directly in the following reaction.

A reaction vessel is charged with crude residue (1 equiv.), MeOH and DCM (1:1, 0.2 M). p-Toluenesulfonic acid (0.1 equiv.) is added and the reaction mixed at ambient temperature. Upon completion of the hydrolysis reaction, the volatiles are removed by rotary evaporation and the residue purified by silica gel chromatography to provide tert-butyl 7-(4-(2-hydroxyethoxy)-1,3-dioxoisoindolin-2-yl)-4,6-dioxo-5-azaspiro[2.5]octane-5-carboxylate.

tert-Butyl 7-(1,3-dioxo-4-(2-(2-oxopropoxy)ethoxy) isoindolin-2-yl)-4,6-dioxo-5-azaspiro[2.5]octane-5-carboxylate

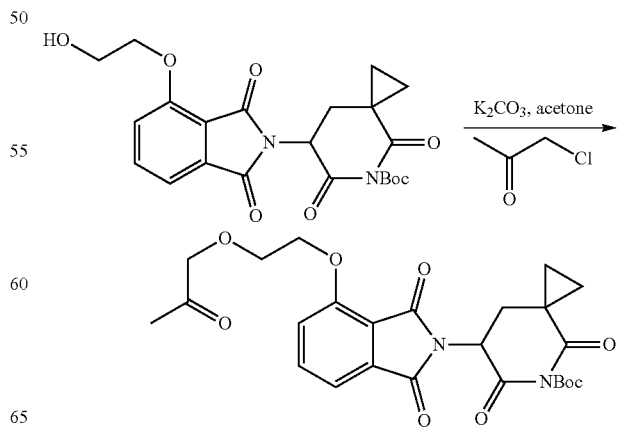

A reaction vessel is charged with tert-buty 7-(4-(2-hydroxyethoxy)-1,3-dioxosondolin-2-yl)-4,6-dioxo-5-azaspiro[2.5]octane-5-carboxylate (1 equiv.), potassium carbonate (1.2 equiv.) and acetone (0.1 M). Chloroacetone (1.2 equiv.) is then added and the reaction heated at reflux overnight. The reaction is cooled then concentrated and the crude residue partitioned between water and ethyl acetate. The layers were separated and the aqueous layer was extracted with ethyl acetate (2×). The combined organic layers are dried over sodium sulfate, filtered and concentrated.

The crude residue is purified by column chromatography to provide tert-butyl 7-(1,3-dioxo-4-(2-(2-oxopropoxy)ethoxy)isoindolin-2-yl)-4,6-dioxo-5-azaspiro[2.5]octane-5-carboxylate. (J. Med. Chem. 2007, 50(18), 4304)

tert-Butyl 7-(4-(2-((3,5-dihydroxy-3-methylpentyl)oxy)ethoxy)-1,3-dioxoisoindolin-2-yl)-4,6-dioxo-5-azaspiro[2.5]octane-5-carboxylate

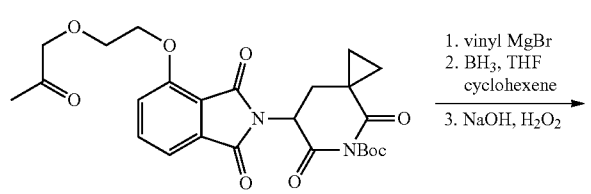

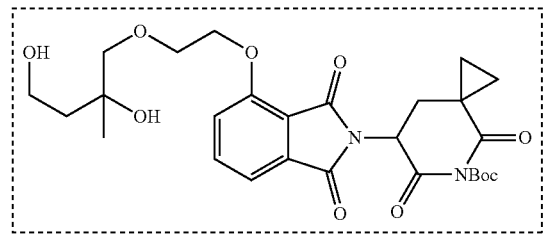

A reaction vessel is charged with tert-butyl 7-(1,3-dioxo-4-(2-(2-oxopropoxy)ethoxy)isoindolin-2-yl)-4,6-dioxo-5-azaspiro[2.5]octane-5-carboxylate (1 equiv.), and THF (0.2 M), purged with nitrogen and cooled to −78° C. Vinylmagnesium bromide (4 equiv.) is added dropwise and the reaction is warmed to 0° C. over 1 hour. The reaction is quenched with aq. 1% HCl solution and extracted with ethyl acetate (3×). The combined organic layer is washed with brine, dried over sodium sulfate, filtered and concentrated. The crude residue is purified by silica gel chromatography to provide tert-butyl 7-(4-(2-((2-hydroxy-2-methylbut-3-en-1-yl)oxy)ethoxy)-1,3-dioxoisoindolin-2-yl)-4,6-dioxo-5-azaspiro[2.5]octane-5-carboxylate.

Cyclohexene (4.2 equiv.) is added to a solution of $BH_3$·THF (1 M in THF, 2 equiv.) at 0° C. under argon. After stirring for 1 hour at 0° C., a solution of tert-butyl 7-(4-(2-((2-hydroxy-2-methylbut-3-en-1-yl)oxy)ethoxy)-1,3-dioxoisoindolin-2-yl)-4,6-dioxo-5-azaspiro[2.5]octane-5-carboxylate (1 equiv.) in THF (0.15 M) is added to the mixture at 0° C. After stirring for 2 hours at 0° C., 3 NNaOH (6 equiv.) and 30% $H_2O_2$ (33% volume of aq. NaOH solution addition) is added to the mixture. This solution is allowed to mix at ambient temperature for 30 min. The reaction is quenched with saturated aqueous $NH_4Cl$ (8 volumes) at 0° C., and the resulting mixture is extracted with ethyl acetate (3×). The combined extracts are washed with brine, dried over sodium sulfate, filtered, and concentrated under reduced pressure. The crude residue is purified by silica gel chromatography to provide tert-butyl 7-(4-(2-((3,5-dihydroxy-3-methylpentyl)oxy)ethoxy)-1,3-dioxoisoindolin-2-yl)-4,6-dioxo-5-azaspiro[2.5]octane-5-carboxylate. (Org. Lett. 2012, 14, 6374)

Linker Installation Example 5: tert-Butyl 7-(4-((6-chloro-4-hydroxy-4-methylhex-2-yn-1-yl)oxy)-1,3-dioxoisoindolin-2-yl)-4,6-dioxo-5-azaspiro[2.5]octane-5-carboxylate

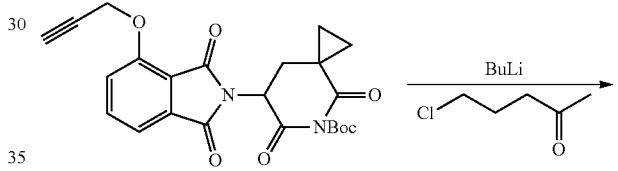

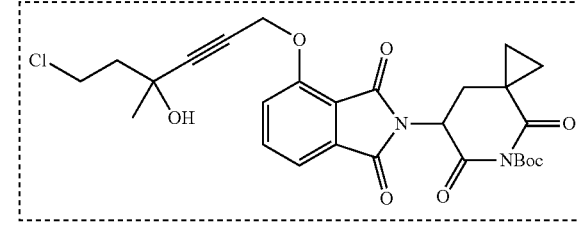

A reaction vessel is charged with N-Boc 4-propargyloxy-5'-spiro-thalidomide (1 equiv.) and the atmosphere cycled between nitrogen and vacuum three times. Anhydrous THF (0.1 M) is added and the reaction cooled to −78° C. Butyllithium (1.05 equiv.) is added and the reaction is mixed for 15 min. 5-Chloro-2-pentanone (1.1 equiv.) in THF (5 volumes) is then added and the reaction is warmed to ambient temperature and quenched with sat. aq. ammonium chloride solution. Ethyl acetate is added and the phases are separated. The aqueous layer is extracted with ethyl acetate (2×). The combined organic layers are washed with brine, dried over sodium sulfate, filtered and concentrated. The crude residue is purified by silica gel chromatography to provide tert-butyl 7-(4-((6-chloro-4-hydroxy-4-methylhex-2-yn-1-yl)oxy)-1,3-dioxoisoindolin-2-yl)-4,6-dioxo-5-azaspiro[2.5]octane-5-carboxylate.

Final Compounds

Glucocorticoid Receptor Targeting Ligand (8S,9R,10S,11S,13S,14S,16R,17R)—N-(8-((2-(4,6-Dioxo-5-azaspiro[2.5]octan-7-yl)-1,3-dioxoisoindolin-4-yl)oxy)octyl)-9-fluoro-11,17-dihydroxy-10,16-dimethyl-3-oxo-6,7,8,9,10,11,12,13,14,15,16,17-dodecahydro-3H-cyclopenta[a]phenanthrene-17-carboxamide

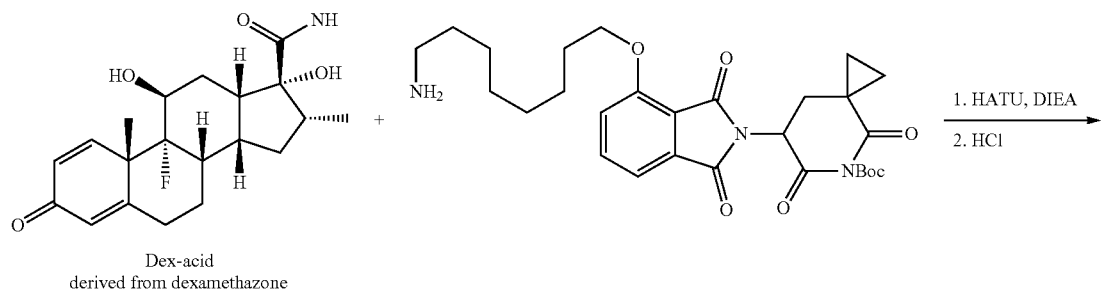

Dex-acid
derived from dexamethazone

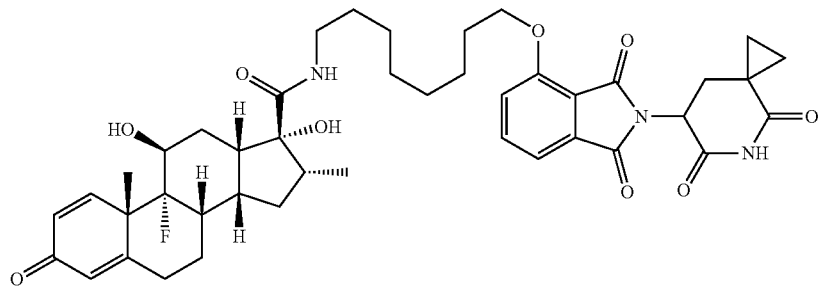

tert-Butyl 7-(4-((8-aminooctyl)oxy)-1,3-dioxoisoindolin-2-yl)-4,6-dioxo-5-azaspiro[2.5]octane-5-carboxylate (1 equiv.) is dissolved in DMF and added to a solution of Dex-acid (1 equiv.), DIPEA (3 equiv.). HATU (2 equiv.) is then added and the mixture is stirred for 24 hours. The mixture is then diluted with ethyl acetate and washed with saturated sodium bicarbonate solution, water, and then brine. The organic layer is dried over sodium sulfate and concentrated. The crude material is then dissolved in dioxane. HCl (4N in dioxane) is added and the solution stirred at room temperature for 12 hours. The solvent is then evaporated under reduced pressure and the crude product is purified by flash column chromatography on silica gel to provide (8 S,9R,10S,11S,13S,14S,16R,17R)—N-(8-((2-(4,6-dioxo-5-azaspiro[2.5]octan-7-yl)-1,3-dioxoisoindolin-4-yl)oxy)octyl)-9-fluoro-11,17-dihydroxy-10,16-dimethyl-3-oxo-6,7,8,9,10,11,12,13,14,15,16,17-dodecahydro-3H-cyclopenta[a]phenanthrene-17-carboxamide.

FKBP Targeting Ligand 2-(3-((3S)-5-(3,4-Dimethoxyphenyl)-1-(1-(3,3-dimethyl-2-oxopentanoyl)piperidin-2-yl)-1-oxopentan-3-yl)phenoxy)-N-(8-((2-(4,6-dioxo-5-azaspiro[2.5]octan-7-yl)-1,3-dioxoisoindolin-4-yl)oxy)octyl)acetamide

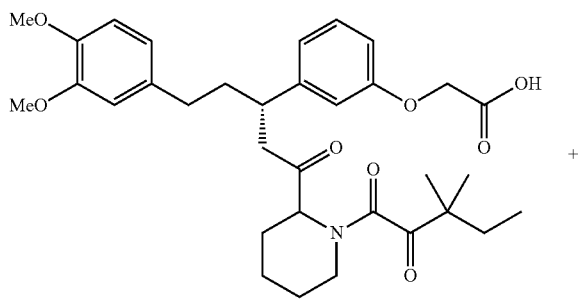

AP1479

-continued

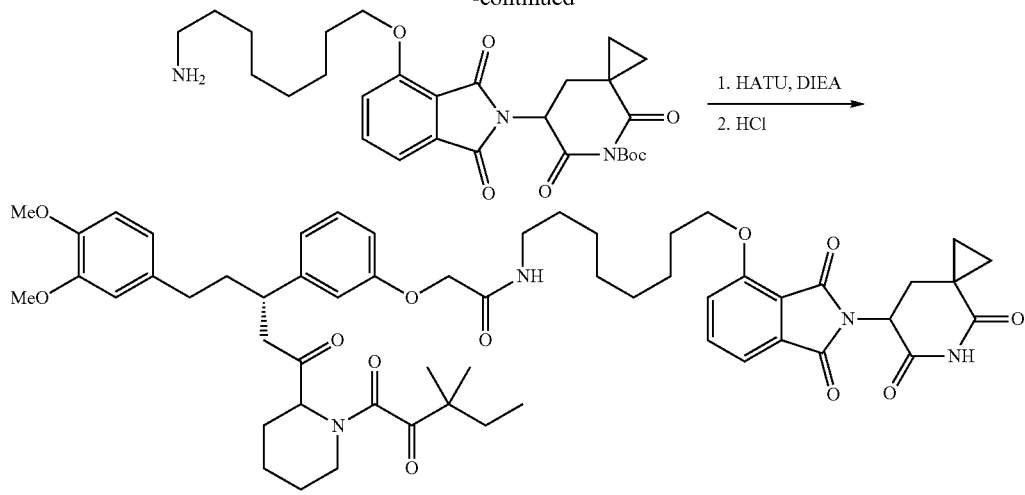

tert-Butyl 7-(4-((8-aminooctyl)oxy)-1,3-dioxoisoindolin-2-yl)-4,6-dioxo-5-azaspiro[2.5]octane-5-carboxylate (1 equiv.) is dissolved in DMF and added to a solution of AP1479 (1 equiv.), DIPEA (3 equiv.). HATU (1 equiv.) is then added and the mixture is stirred for 24 hours. The mixture is then diluted with ethyl acetate and washed with saturated sodium bicarbonate solution, water, and then brine. The organic layer is dried over sodium sulfate and concentrated. The crude material is then dissolved in dioxane. HCl (4N in dioxane) is added and the solution stirred at room temperature for 12 hours. The solvent is then evaporated under reduced pressure and the crude product is purified by flash column chromatography on silica gel to provide 2-(3-((3S)-5-(3,4-dimethoxyphenyl)-1-(1-(3,3-dimethyl-2-oxopentanoyl)piperidin-2-yl)-1-oxopentan-3-yl)phenoxy)-N-(8-((2-(4,6-dioxo-5-azaspiro[2.5]octan-7-yl)-1,3-dioxo-isoindolin-4-yl)oxy)octyl)acetamide.

BRD Targeting Ligand 2-((S)-4-(4-Chlorophenyl)-2,3,9-trimethyl-6H-thieno[3,2-f][1,2,4]triazolo[4,3-a][1,4]diazepin-6-yl)-N-(8-((2-(4,6-dioxo-5-azaspiro[2.2.5]octan-7-yl)-1,3-dioxoisoindolin-4-yl)oxy)octyl)acetamide

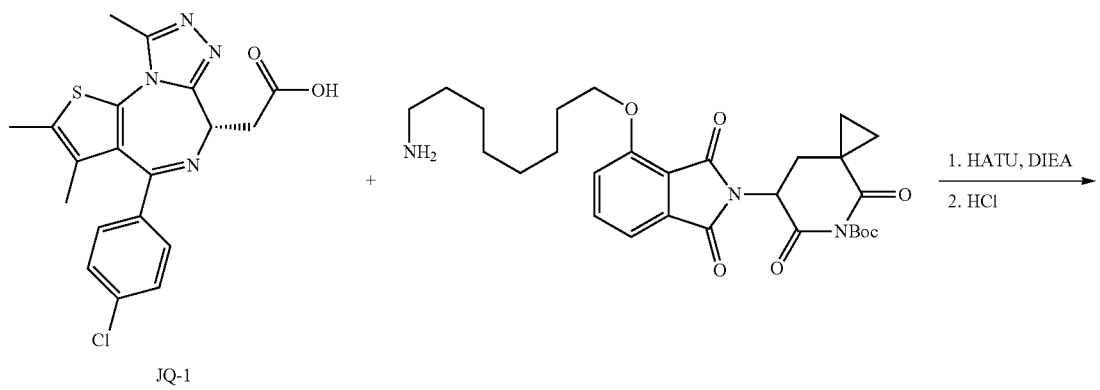

JQ-1

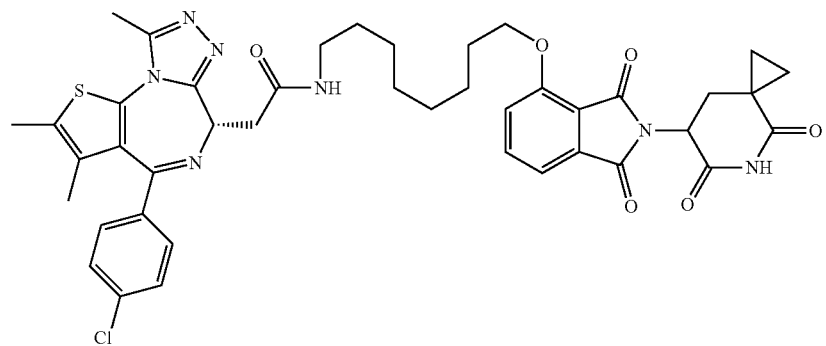

tert-Butyl 7-(4-((8-aminooctyl)oxy)-1,3-dioxoisoindolin-2-yl)-4,6-dioxo-5-azaspiro[2.5]octane-5-carboxylate (1 equiv.) is dissolved in DMF and added to a solution of JQ-1 (1 equiv.), DIPEA (3 equiv.). HATU (1 equiv.) is then added and the mixture is stirred for 24 hours. The mixture is then diluted with ethyl acetate and washed with saturated sodium bicarbonate solution, water, and then brine. The organic layer is dried over sodium sulfate and concentrated. The crude material is then dissolved in dioxane. HCl (4N in dioxane) is added and the solution stirred at room temperature for 12 hours. The solvent is then evaporated under reduced pressure and the crude product is purified by flash column chromatography on silica gel to provide 2-((S)-4-(4-chlorophenyl)-2,3,9-trimethyl-6H-thieno[3,2-f][1,2,4]triazolo[4,3-a][1,4]diazepin-6-yl)-N-(8-((2-(4,6-dioxo-5-azaspiro[2.5]octan-7-yl)-1,3-dioxoisoindolin-4-yl)oxy)octyl)acetamide.

ABL Targeting Ligand 4-((4-(7-((2-(4,6-Dioxo-5-azaspiro[2.5]octan-7-yl)-1,3-dioxoisoindolin-4-yl)oxy)-4-hydroxy-4-methylhept-5-yn-1-yl)piperazin-1-yl)methyl)-N-(3-methyl-4-((4-(pyridin-3-yl)pyrimidin-2-yl)amino)phenyl)benzamide To a solution of tert-butyl 7-(4-((7-chloro-4-hydroxy-4-methylhept-2-yn-1-yl)oxy)-1,3-dioxoisoindolin-2-yl)-4,6-dioxo-5-azaspiro[2.5]octane-5-carboxylate (1 equiv.) in acetone is added NaI (5 equiv.). The reaction mixture is stirred at reflux temperature for 24 h, then the solvent is removed under vacuum and crude product is dissolved in EtOAc and an aqueous solution of Na$_2$SO$_3$ (10%). Organic layer is separated, washed with water, dried (Na$_2$SO$_4$) and evaporated under vacuum. Crude iodo product is used in the next step without any further purification.

To a solution of N-(3-methyl-4-((4-(pyridin-3-yl)pyrimidin-2-yl)amino)phenyl)-4-(piperazin-1-ylmethyl)benzamide (1 equiv.) and DIEA (2.5 equiv.) in DMF is added crude iodo intermediate (1 equiv.) and the resulting solution is stirred at rt for 16 h. The solvent is evaporated and the residue is dissolved in dioxane. HCl (4N in dioxane) is added and the solution stirred at room temperature for 12 hours. The solvent is then evaporated under reduced pressure and the crude product is purified by flash column chromatography on silica gel to provide 4-((4-(7-((2-(4,6-dioxo-5-azaspiro[2.5]octan-7-yl)-1,3-dioxoisoindolin-4-yl)oxy)-4-hydroxy-4-methylhept-5-yn-1-yl)piperazin-1-yl)methyl)-N-(3-methyl-4-((4-(pyridin-3-yl)pyrimidin-2-yl)amino)phenyl)benzamide.

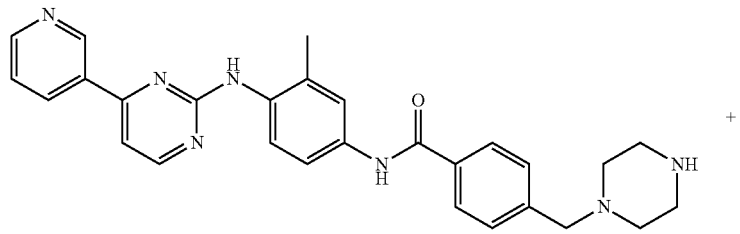

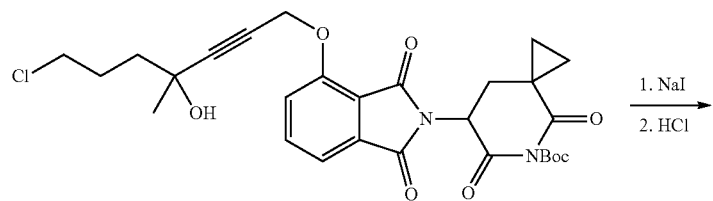

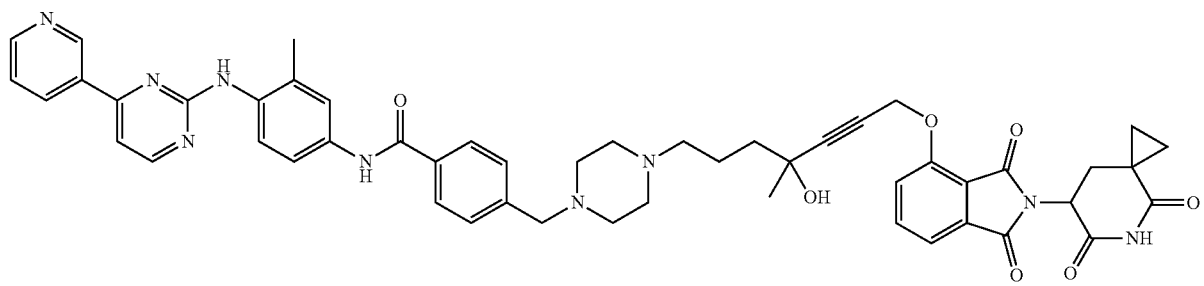

JAK2 Targeting Ligand 4-((7-(4-(4-(8-(3,5-Difluoro-4-(morpholinomethyl)phenyl)quinoxalin-2-yl)-1H-pyrazol-1-yl)piperidin-1-yl)-4-hydroxy-4-methylhept-2-yn-1-yl)oxy)-2-(4,6-dioxo-5-azaspiro[2.5]octan-7-yl)isoindoline-1,3-dione

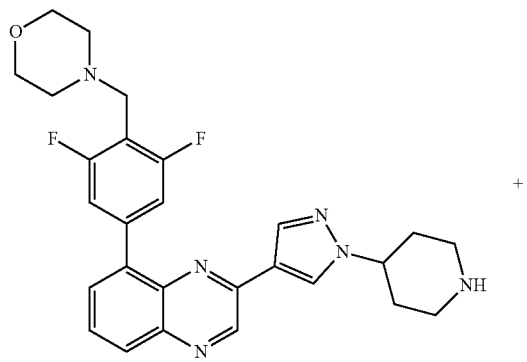

+

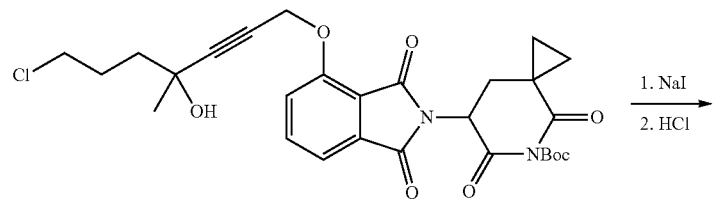

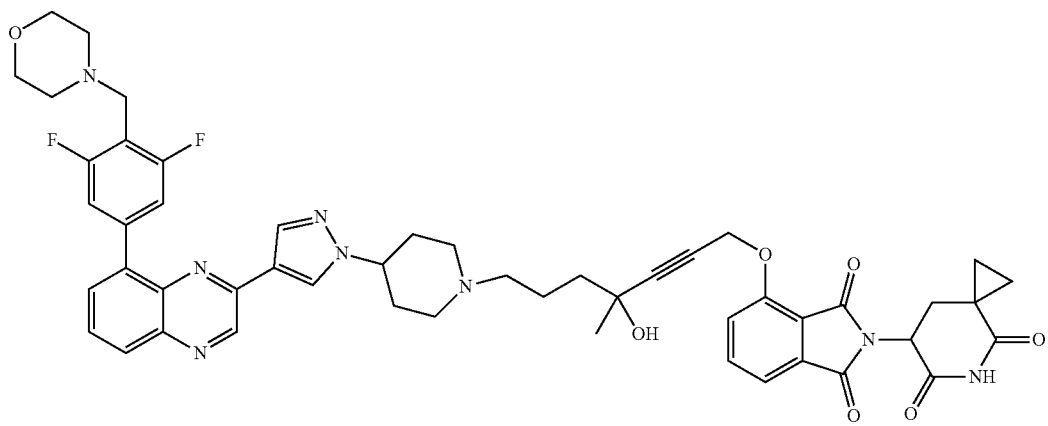

To a solution of tert-butyl 7-(4-((7-chloro-4-hydroxy-4-methylhept-2-yn-1-yl)oxy)-1,3-dioxoisoindolin-2-yl)-4,6-dioxo-5-azaspiro[2.5]octane-5-carboxylate (1 equiv.) in acetone is added NaI (5 equiv.). The reaction mixture is stirred at reflux temperature for 24 h, then the solvent is removed under vacuum and crude product is dissolved in EtOAc and an aqueous solution of Na$_2$SO$_3$ (10%). Organic layer is separated, washed with water, dried (Na$_2$SO$_4$) and evaporated under vacuum. Crude iodo product is used in the next step without any further purification.

To a solution of 4-(2,6-difluoro-4-(3-(1-(piperidin-4-yl)-1H-pyrazol-4-yl)quinoxalin-5-yl)benzyl)morpholine (1 equiv.) and DIEA (2.5 equiv.) in DMF is added crude iodo intermediate (1 equiv.) and the resulting solution is stirred at rt for 16 h. The solvent is evaporated and the residue is dissolved in dioxane. HCl (4N in dioxane) is added and the solution stirred at room temperature for 12 hours. The solvent is then evaporated under reduced pressure and the crude product is purified by flash column chromatography on silica gel to provide 4-((7-(4-(4-(8-(3,5-difluoro-4-(morpholinomethyl)phenyl)quinoxalin-2-yl)-1H-pyrazol-1-yl)piperidin-1-yl)-4-hydroxy-4-methylhept-2-yn-1-yl)oxy)-2-(4,6-dioxo-5-azaspiro[2.5]octan-7-yl)isoindoline-1,3-dione.

Additional Examples of Final Compounds
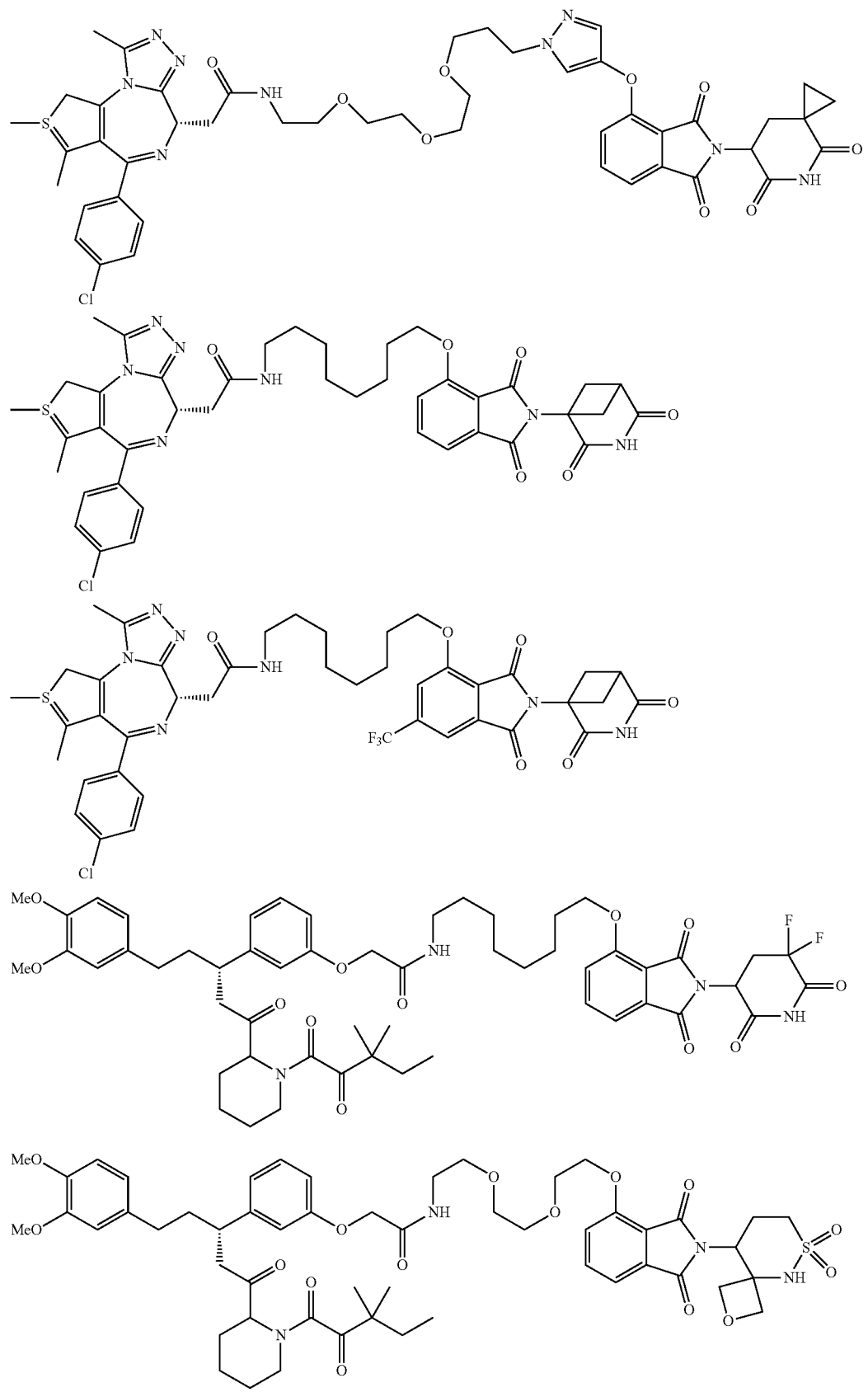

-continued
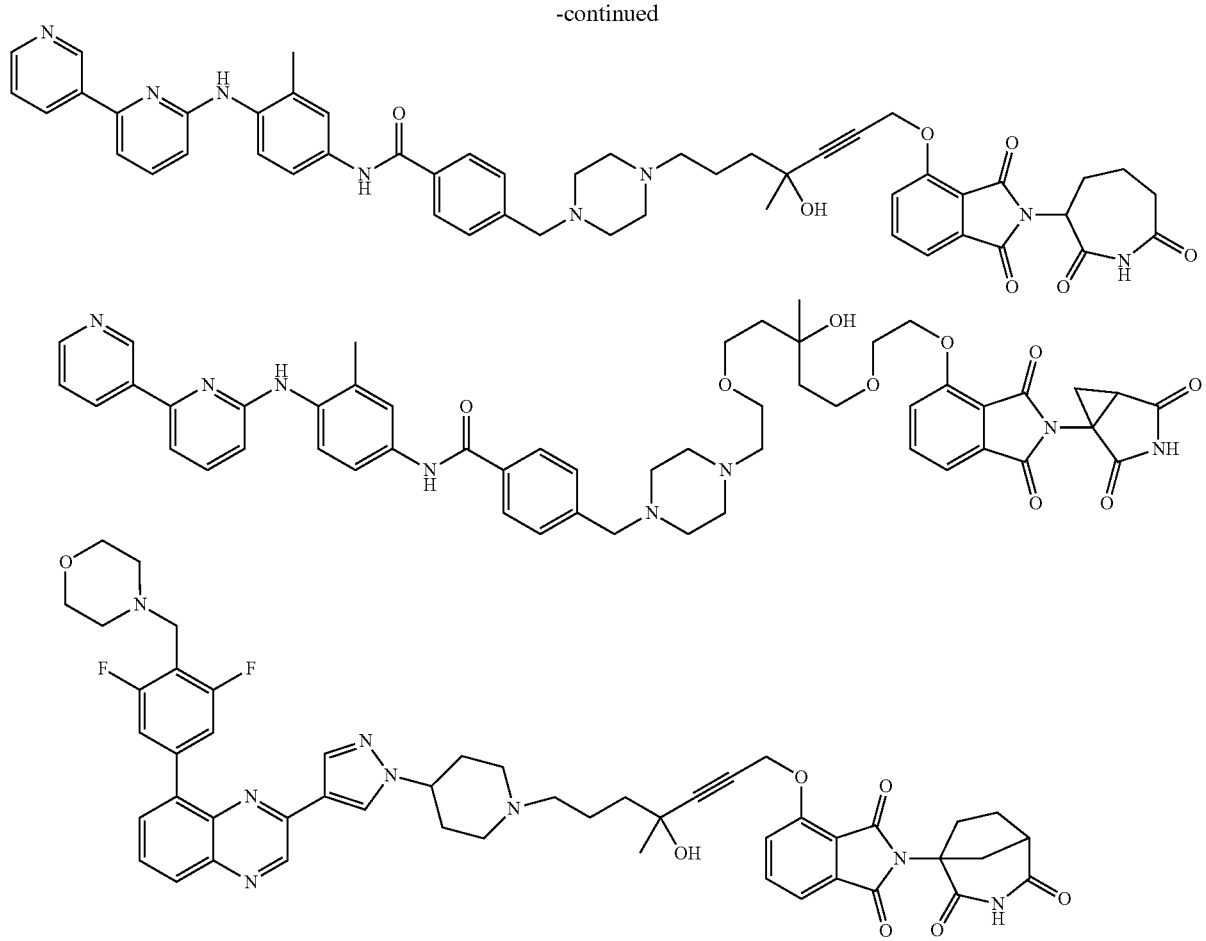
Preparation of Representative Targeting Ligands
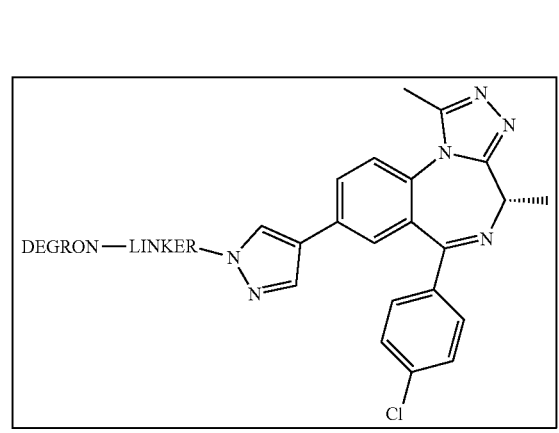
-continued
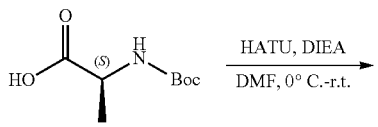
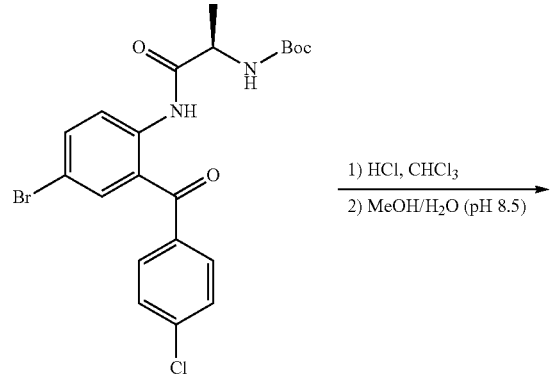

371
-continued

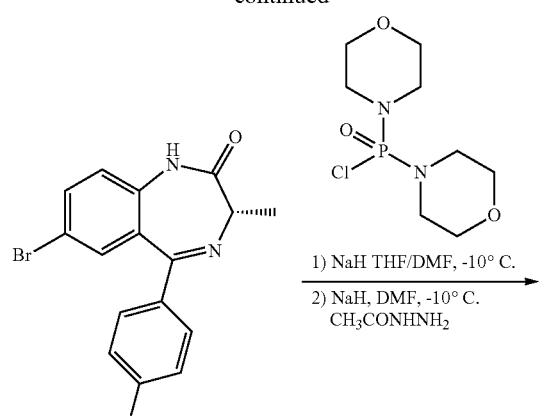

372

(S)-6-(4-Chlorophenyl)-1,4-dimethyl-8-(1H-pyrazol-4-yl)-4H-benzo[f][1,2,4]triazolo[4,3-a][1,4]diazepine

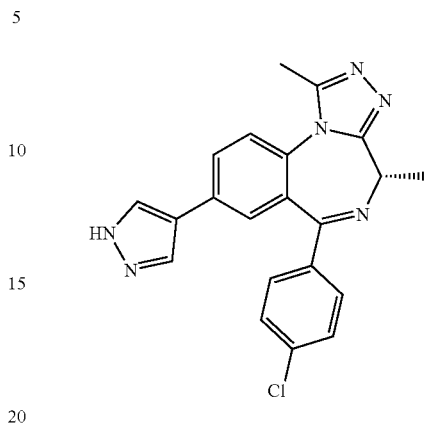

tert-Butyl (R)-(1-((4-bromo-2-(4-chlorobenzoyl)phenyl)amino)-1-oxopropan-2-yl)carbamate

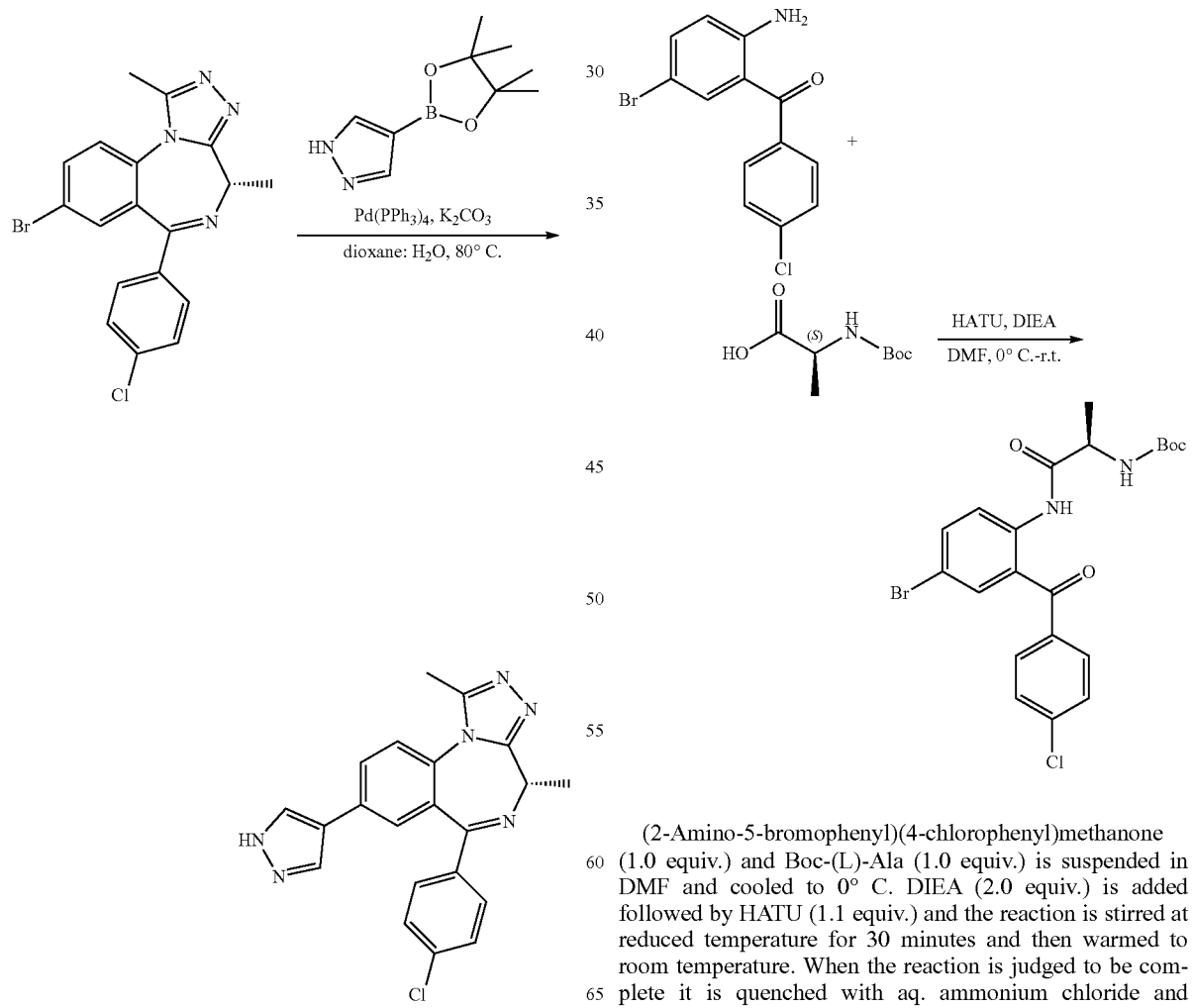

(2-Amino-5-bromophenyl)(4-chlorophenyl)methanone (1.0 equiv.) and Boc-(L)-Ala (1.0 equiv.) is suspended in DMF and cooled to 0° C. DIEA (2.0 equiv.) is added followed by HATU (1.1 equiv.) and the reaction is stirred at reduced temperature for 30 minutes and then warmed to room temperature. When the reaction is judged to be complete it is quenched with aq. ammonium chloride and extracted with ethyl acetate. The combined organic layers are dried over sodium sulfate, concentrated and purified by silica gel chromatography to provide tert-butyl (R)-(1-((4-bromo-2-(4-chlorobenzoyl)phenyl)amino)-1-oxopropan-2-yl)carbamate.

(S)-7-Bromo-5-(4-chlorophenyl)-3-methyl-1,3-dihydro-2H-benzo[e][1,4]diazepin-2-one (S)-8-Bromo-6-(4-chlorophenyl)-1,4-dimethyl-4H-benzo[f][1,2,4]triazolo[4,3-a][1,4]diazepine

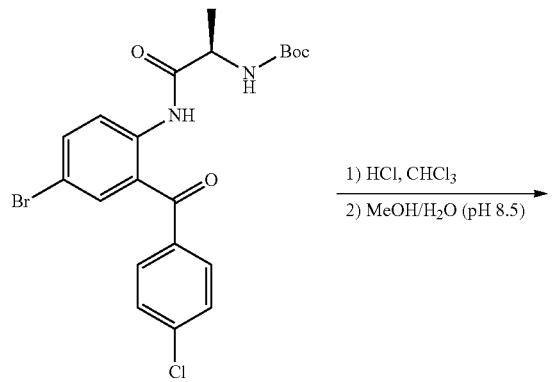

1) HCl, CHCl₃
2) MeOH/H₂O (pH 8.5)

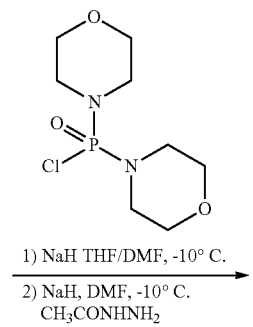

1) NaH THF/DMF, -10° C.
2) NaH, DMF, -10° C.
   CH₃CONHNH₂

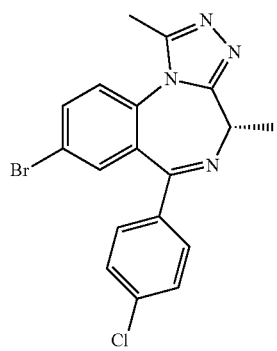

To a stirred solution of boc protected amine in CHCl₃ at r.t., is added hydrogen chloride gas slowly. After 20 minutes the addition is stopped and the reaction is stirred at r.t. until deprotection is complete. The reaction mixture is then washed with saturated bicarbonate solution (2×) and water (2×). The organic layer is concentrated under reduced pressure. The residue is dissolved in 2:1 methanol:water and the pH is adjusted to 8.5 by the addition of 1N aqueous NaOH. The reaction is then stirred at r.t. until the cyclization is complete. MeOH is then removed under reduced pressure and the solution is extracted with DCM (3×). The combined organic layer is dried over sodium sulfate, concentrated and purified by silica gel chromatography to provide (S)-7-bromo-5-(4-chlorophenyl)-3-methyl-1,3-dihydro-2H-benzo[e][1,4]diazepin-2-one (US 2010 0261711.).

A solution of diazepine (1.0 equiv.) in THF is cooled to -10° C. and Na (0.85 equiv.) is added in one portion. After an hour at reduced temperature di-4-morphilinylphosphinic chloride (1.07 equiv.) is added at -10° C. and the reaction is allowed to warm to r.t. and stir for 2 hours. To this mixture is added a solution of acetic hydrazide (1.4 equiv.) in n-butanol and stirring is continued for 30 minutes. The solvent is then removed under reduced pressure and the residue dissolved in fresh dry n-butanol before refluxing for the desired time frame. Upon the completion of the reaction the volatiles are removed by rotary evaporation and the residue is partitioned between DCM and brine. The organic layer is dried, concentrated and purified by silica gel chromatography to provide (S)-8-bromo-6-(4-chlorophenyl)-1,4-dimethyl-4H-benzo[f][1,2,4]triazolo[4,3-a][1,4]diazepine (US 2010 0261711.).

375

(S)-6-(4-Chlorophenyl)-1,4-dimethyl-8-(1H-pyrazol-4-yl)-4H-benzo[f][1,2,4]triazolo[4,3-a][1,4]diazepine

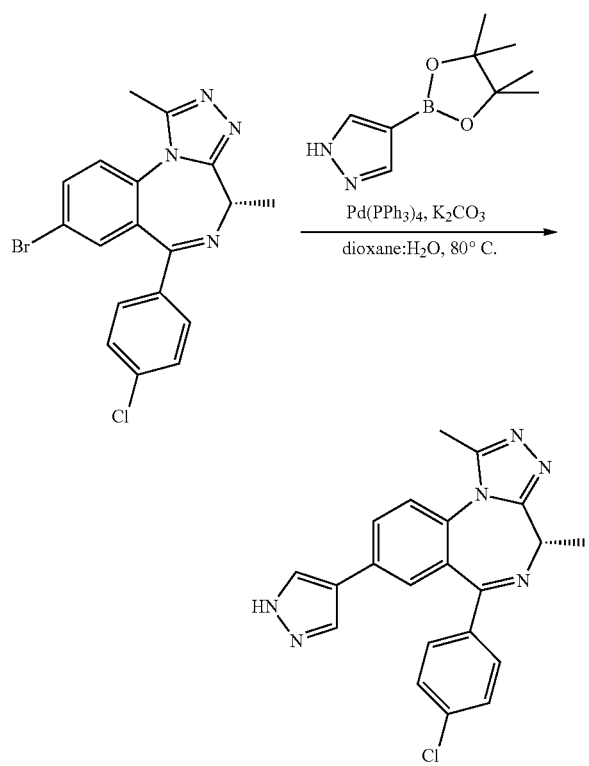

To a vial containing (S)-8-bromo-6-(4-chlorophenyl)-1,4-dimethyl-4H-benzo[f][1,2,4]triazolo[4,3-a][1,4]diazepine (1 equiv.) is added Pd(PPh3)4 (20 mol %), 4-(4,4,5,5-tetramethyl-1,3,2-dioxaborolan-2-yl)-1H-pyrazole (1.5 equiv.), and potassium carbonate (2.5 equiv.). The vial is then evacuated and purged under N2. To the vial is added dioxane:water (2:1). The contents were once again evacuated and purged under N2 and the reaction mixture was heated to 80° C. until the SM is converted. The mixture is then cooled to room temperature and filtered over a pad of Celite®. The filter pad is rinsed with EtOAc (3×) and the filtrate is concentrate. The crude material is purified by flash chromatography (WO 2015156601).

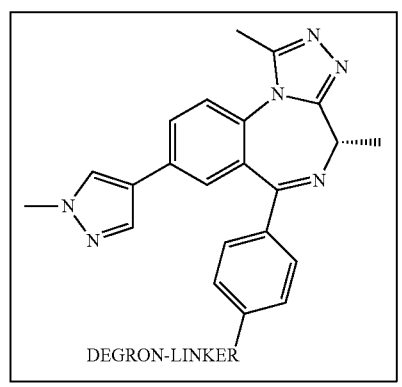

DEGRON-LINKER

376

-continued

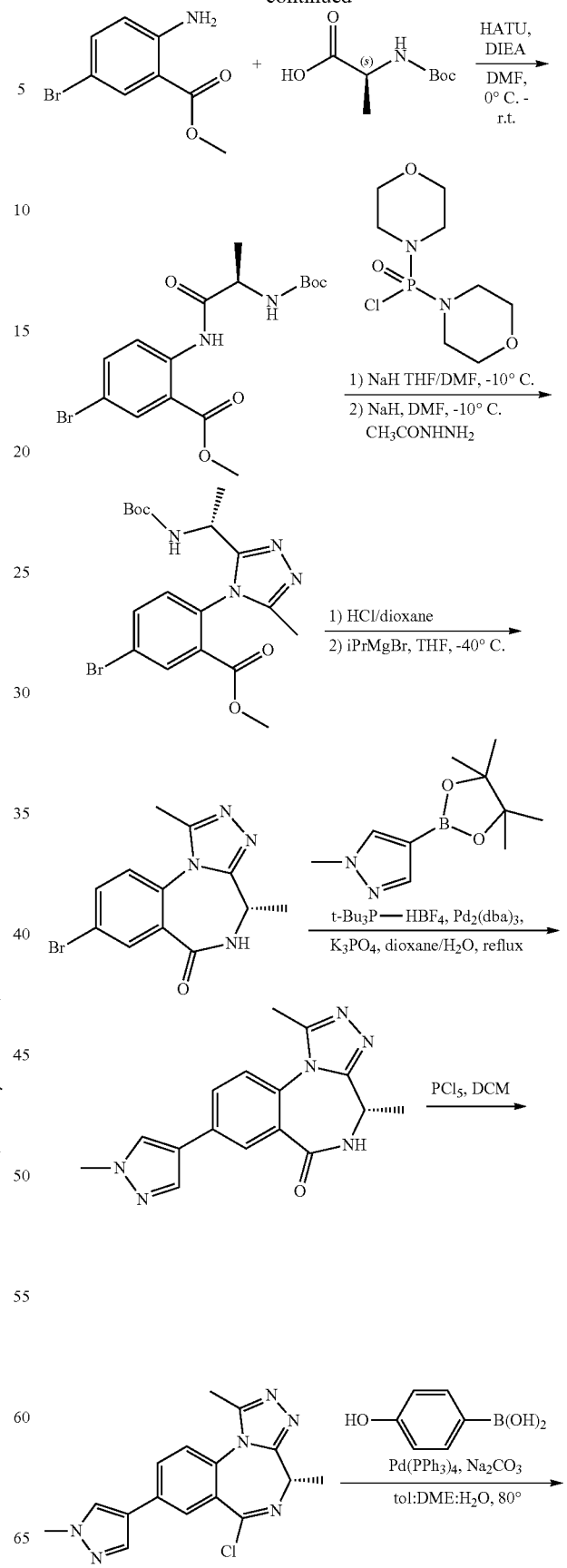

377
-continued

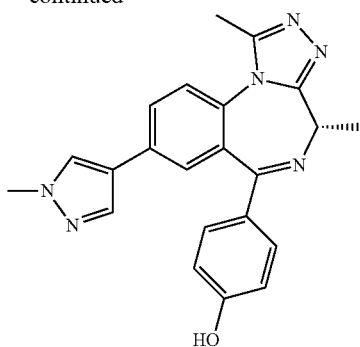

(S)-4-(1,4-Dimethyl-8-(1-methyl-1H-pyrazol-4-yl)-4H-benzo[f][1,2,4]triazolo[4,3-a][1,4]diazepin-6-yl)phenol

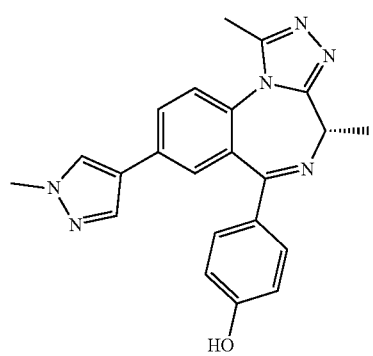

Methyl (R)-5-bromo-2-(2-((tert-butoxycarbonyl)amino)propanamido)benzoate

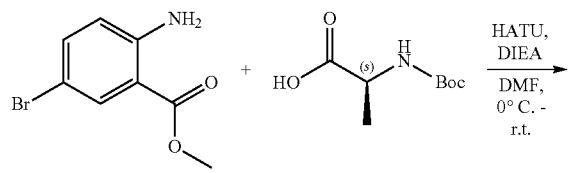

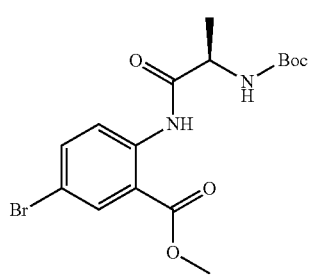

378

Methyl 2-amino-5-bromobenzoate (1.0 equiv.) and Boc-(L)-Ala (1.0 equiv.) is suspended in DMF and cooled to 0° C. DIEA (2.0 equiv.) is added followed by HATU (1.1 equiv.) and the reaction is stirred at reduced temperature for 30 minutes and then warmed to room temperature. When the reaction is judged to be complete it is quenched with aq. ammonium chloride and extracted with ethyl acetate. The combined organic layers are dried over sodium sulfate, concentrated and purified by silica gel chromatography to provide methyl (R)-5-bromo-2-(2-((tert-butoxycarbonyl)amino)propanamido)benzoate.

Methyl 5-bromo-2-(3-((R)-1-((tert-butoxycarbonyl)amino)ethyl)-5-methyl-4H-1,2,4-triazol-4-yl)benzoate

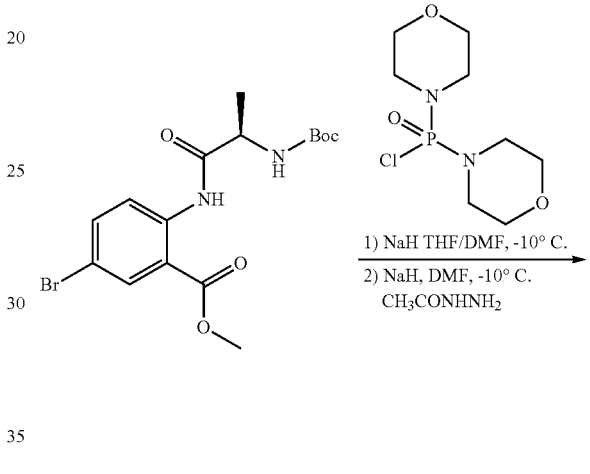

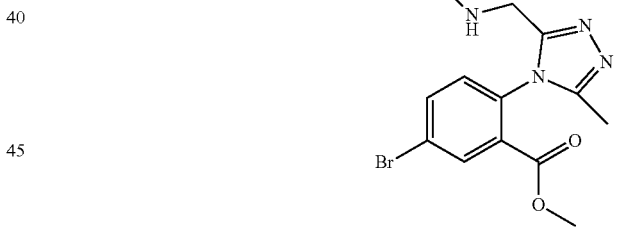

Methyl (R)-5-bromo-2-(2-((tert-butoxycarbonyl)amino)propanamido)benzoate A solution of methyl (R)-5-bromo-2-(2-((tert-butoxycarbonyl)amino)propanamido)benzoate (1.0 equiv.) in THF is cooled to −10° C. and NaH (0.85 equiv.) is added in one portion. After an hour at reduced temperature di-4-morphilinylphosphinic chloride (1.07 equiv.) is added at −10° C. and the reaction is allowed to warm to r.t. and stir for 2 hours. To this mixture is added a solution of acetic hydrazide (1.4 equiv.) in n-butanol and stirring is continued for 30 minutes. The solvent is then removed under reduced pressure and the residue dissolved in fresh dry n-butanol before refluxing for the desired time frame. Upon the completion of the reaction the volatiles are removed by rotary evaporation and the residue is partitioned between DCM and brine. The organic layer is dried, concentrated and purified by silica gel chromatography to provide methyl (R)-5-bromo-2-(2-((tert-butoxycarbonyl)amino)propanamido)benzoate (BMCL 2015, 25, 1842-48).

(S)-8-Bromo-1,4-dimethyl-4,5-dihydro-6H-benzo[f][1,2,4]triazolo[4,3-a][1,4]diazepin-6-one

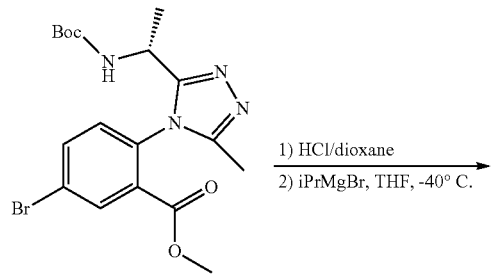

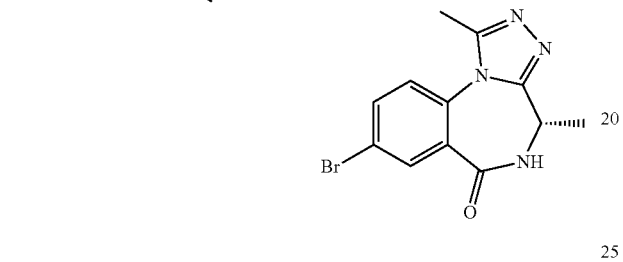

Methyl (R)-5-bromo-2-(2-((tert-butoxycarbonyl)amino)propanamido)benzoate is brought up in DCM and cooled to 0° C. 4M HCl in dioxane is added and the reaction is warmed to r.t. When deprotection is complete the reaction is concentrated and then azeotroped from toluene (2×). The crude amine salt is then dissolved in THF and cooled to −40° C. at which time iPrMgBr solution is added dropwise (2.0 equiv.) and the reaction is stirred at reduced temp until complete conversion (BMCL 2015, 25, 1842-48).

(S)-1,4-Dimethyl-8-(1-methyl-1H-pyrazol-4-yl)-4,5-dihydro-6H-benzo[f][1,2,4]triazolo[4,3-a][1,4]diazepin-6-one

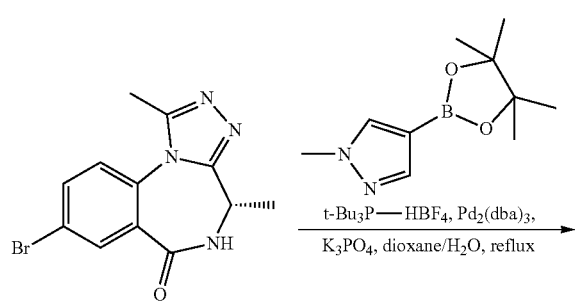

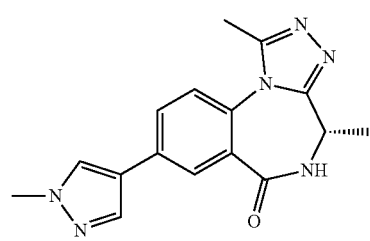

To a vial containing (S)-8-bromo-1,4-dimethyl-4,5-dihydro-6H-benzo[f][1,2,4]triazolo[4,3-a][1,4]diazepin-6-one (1 equiv.) is added Pd$_2$ (dba) 3 (10 mol %), tri-tert-butylphosphonium tetrafluoroborate (20 mol %), 1-methyl-4-(4,4,5,5-tetramethyl-1,3,2-dioxaborolan-2-yl)-1H-pyrazole (1.5 equiv.), and potassium phosphate tribasic, monohydrate (2.5 equiv.). The vial is then evacuated and purged under N2. To the vial is added 20:1 ratio by volume of dioxane:water. The contents were once again evacuated and purged under N2 (g) and the reaction mixture was heated to 100° C. until the SM is converted. The mixture is then cooled to room temperature and filtered over a pad of Celite®. The filter pad is rinsed with EtOAc (3×) and the filtrate is concentrate. The crude material is purified by flash chromatography.

(S)-6-Chloro-1,4-dimethyl-8-(1-methyl-1H-pyrazol-4-yl)-4H-benzo[f][1,2,4]triazolo[4,3-a][1,4]diazepine

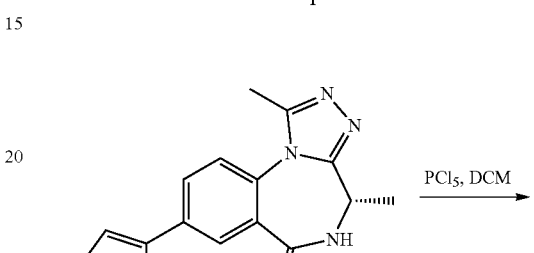

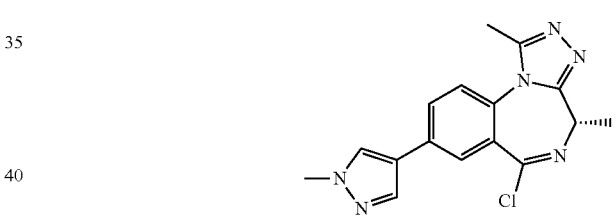

(S)-1,4-Dimethyl-8-(1-methyl-1H-pyrazol-4-yl)-4, 5-dihydro-6H-benzo[f][1,2,4]triazolo[4,3-a][1,4]diazepin-6-one (1.0 equiv.) is dissolved in DCM and PCl5 (1.7 equiv.) is added in one-portion. After conversion of SM 2M sodium carbonate is added. The biphasic mixture is subsequently extracted with EtOAc (4×). The combined organic layers were dried over sodium sulfate and concentrated to dryness. The resultant residue is purified by flash chromatography.

(S)-4-(1,4-Dimethyl-8-(1-methyl-1H-pyrazol-4-yl)-4H-benzo[f][1,2,4]triazolo[4,3-a][1,4]diazepin-6-yl)phenol

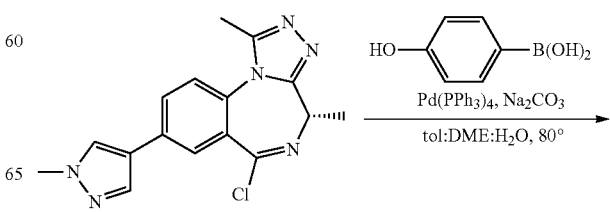

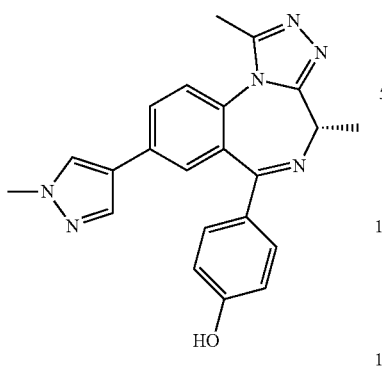

To a vial containing ((S)-6-chloro-1,4-dimethyl-8-(1-methyl-1H-pyrazol-4-yl)-4H-benzo[f][1,2,4]triazolo[4,3-a][1,4]diazepine (1 equiv.) is added Pd(PPh$_3$)$_4$ (20 mol %), 4-hydroxy-Phenyl boronic acid (1.5 equiv.), and sodium carbonate (2.5 equiv.). The vial is then evacuated and purged under N2. To the vial is added tol:DME:water (1:1:5). The contents were once again evacuated and purged under N2 and the reaction mixture was heated to 80° C. until the SM is converted. The mixture is then cooled to room temperature and filtered over a pad of Celite®. The filter pad is rinsed with EtOAc (3×) and the filtrate is concentrate. The crude material is purified by flash chromatography.

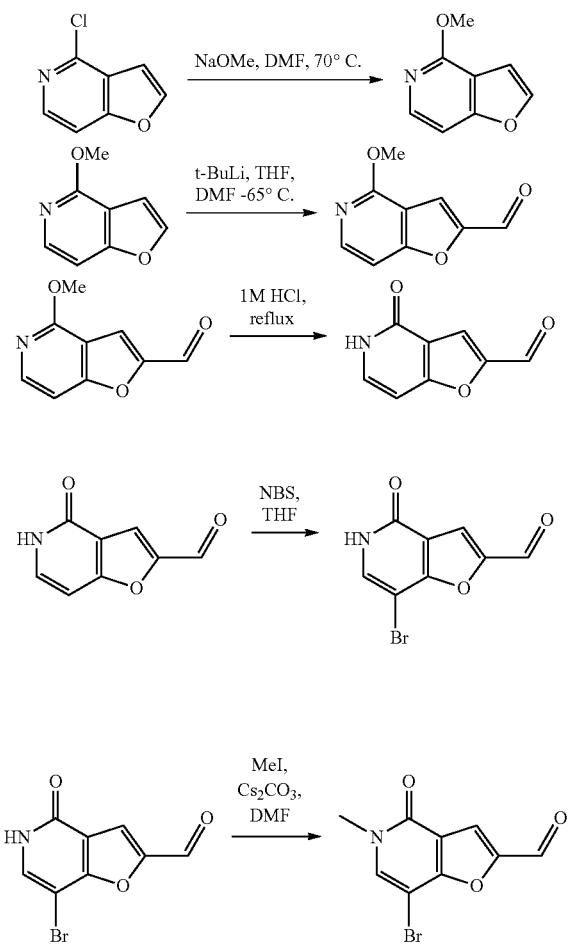

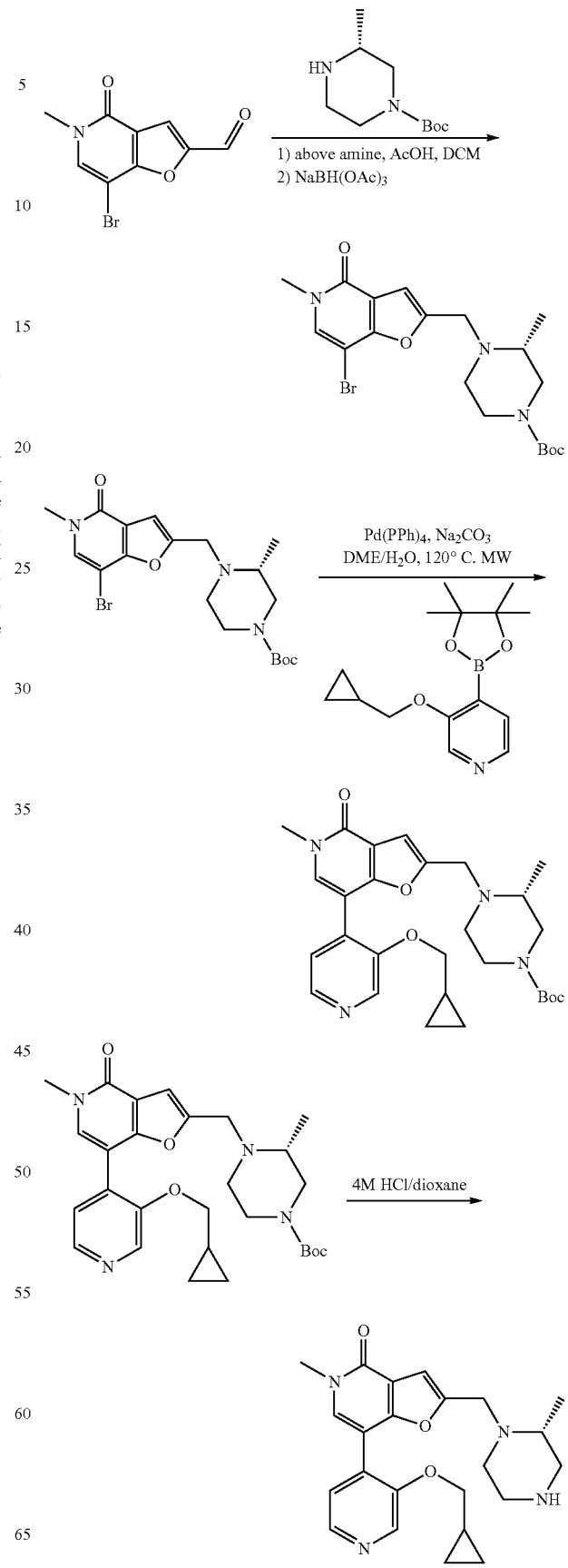

383
-continued
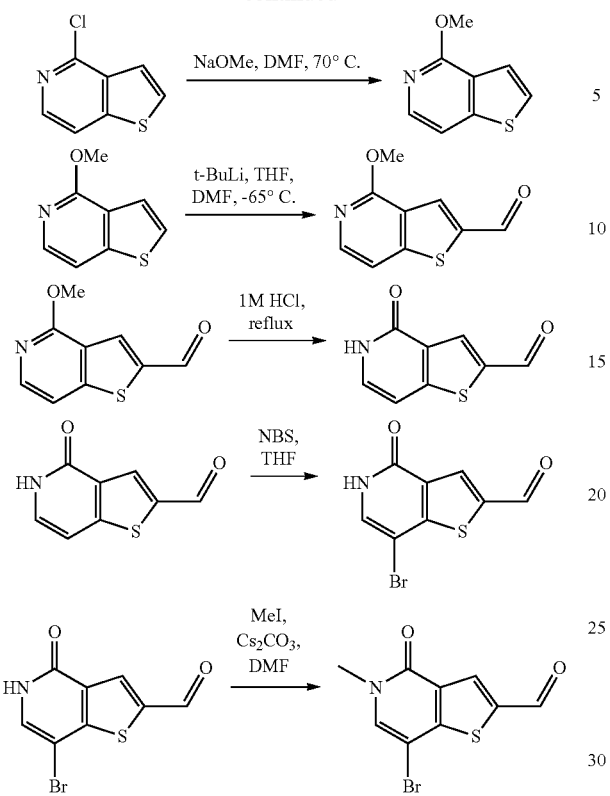
384
-continued
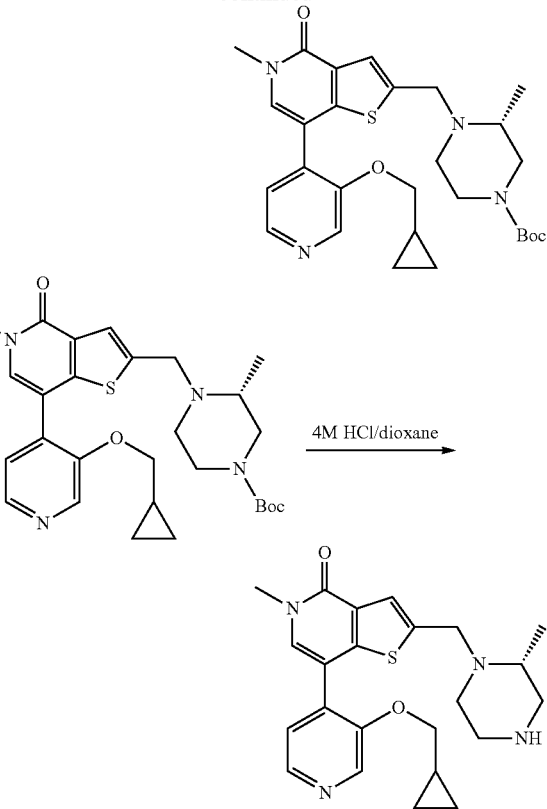
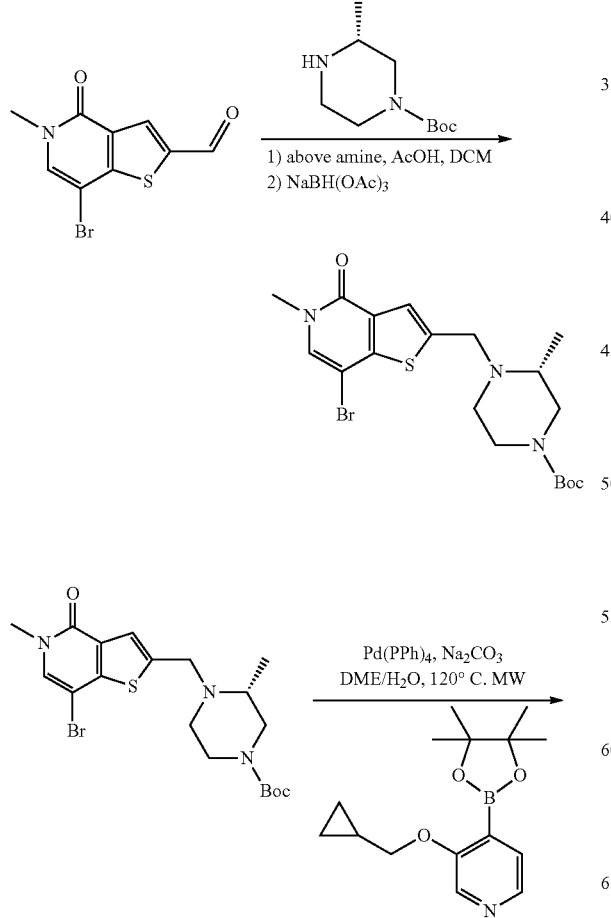
Synthesis of Selected Glutarimides
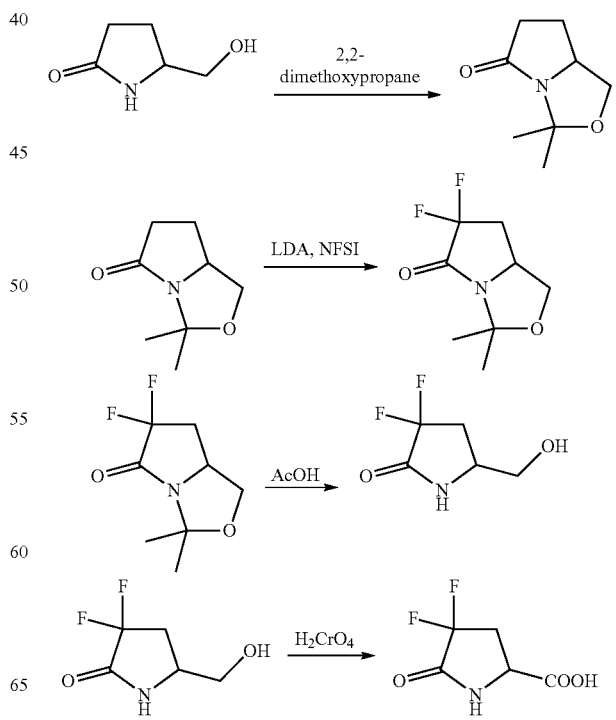

385
-continued
386
-continued
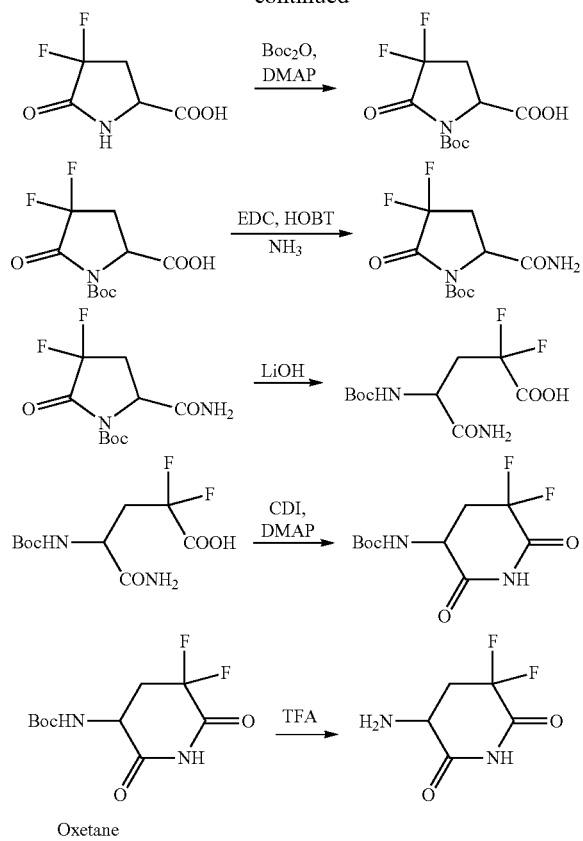
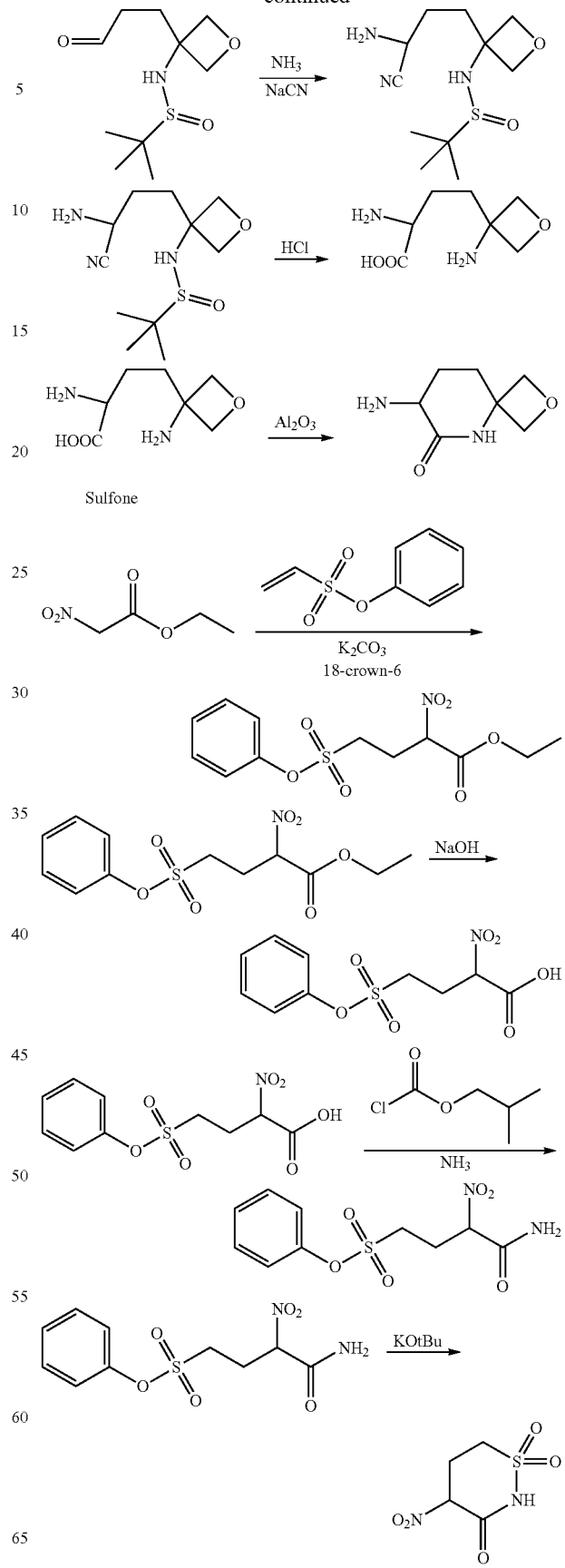
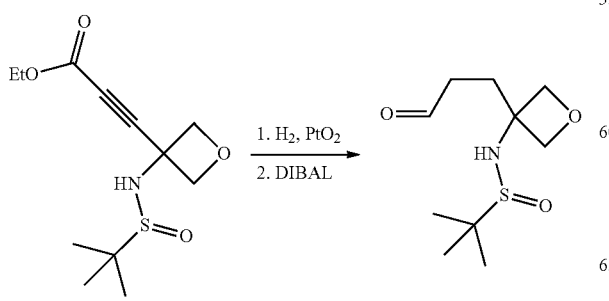
ref: OL-2010-1116

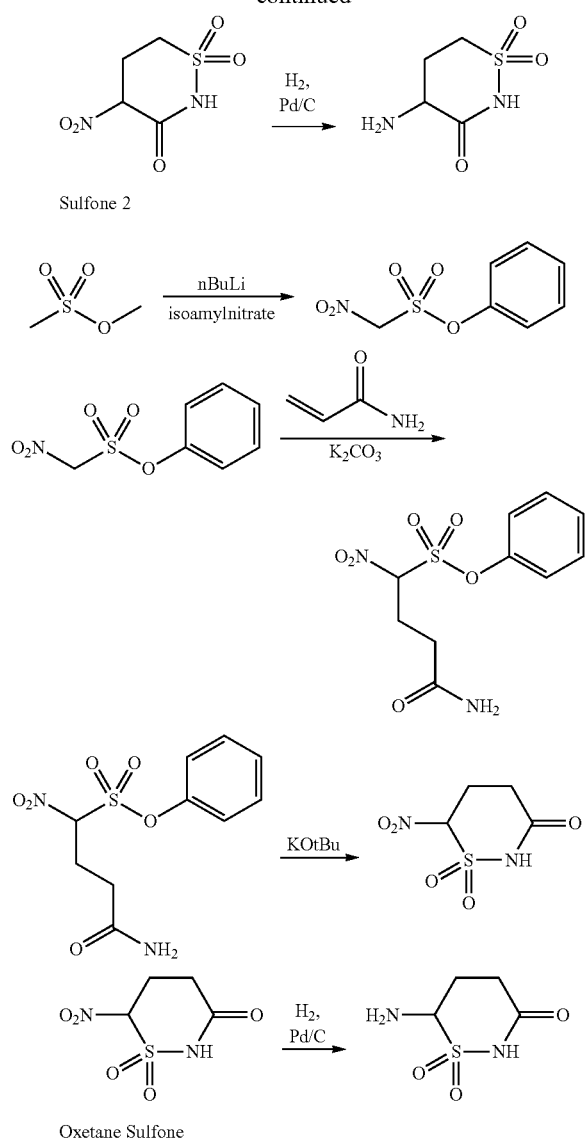
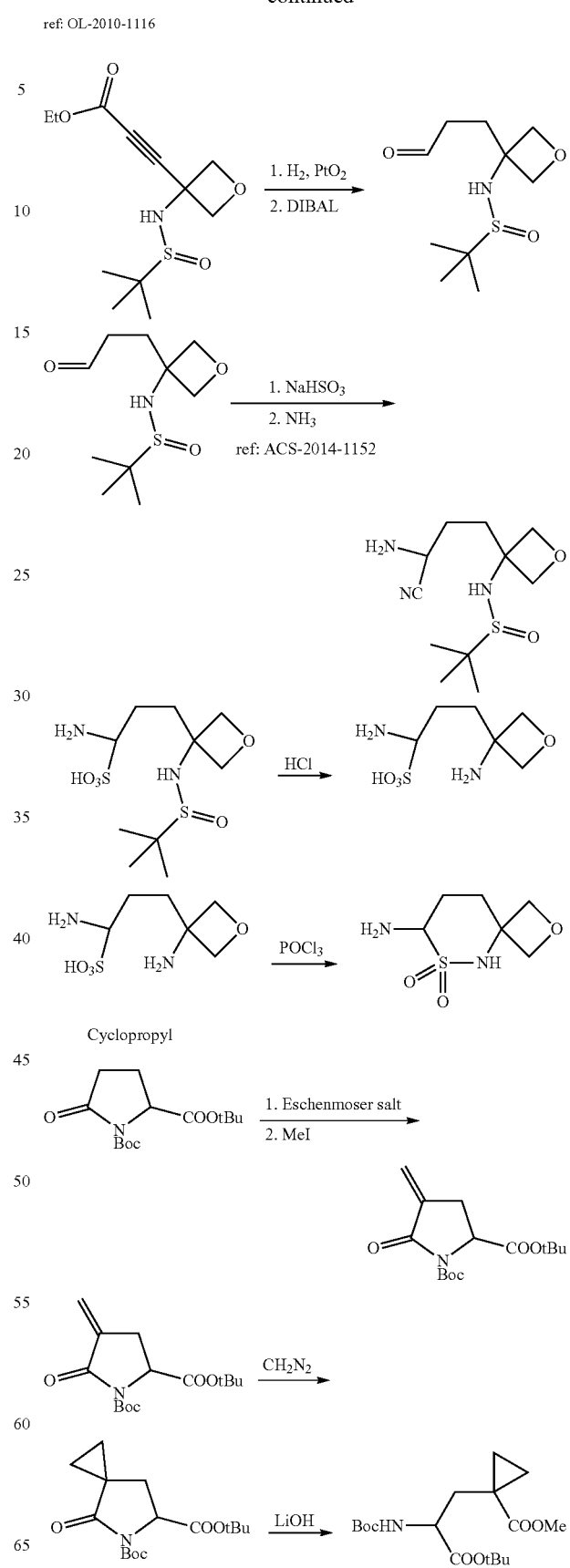

ref: J. Chem. Soc., Perkin Trans. 1, 1997, 3519

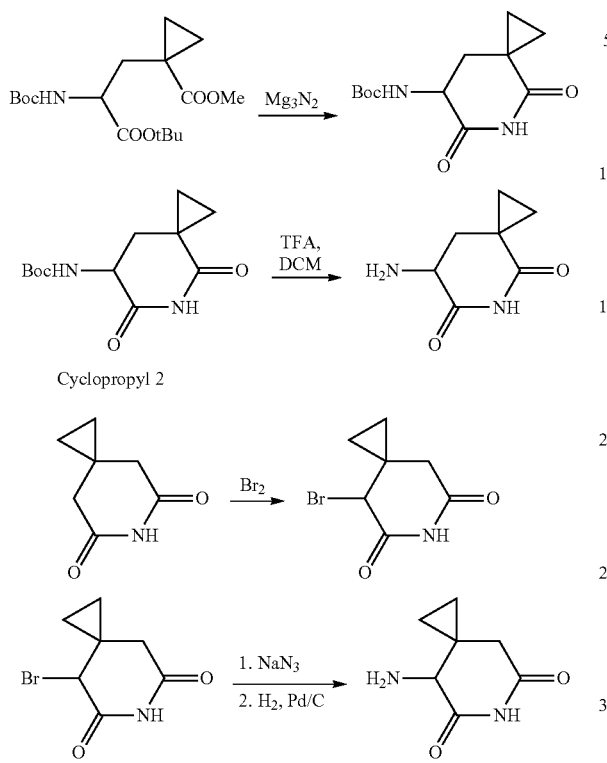

Example 1: Illustrative Preparation of 5-Member Glutarimide

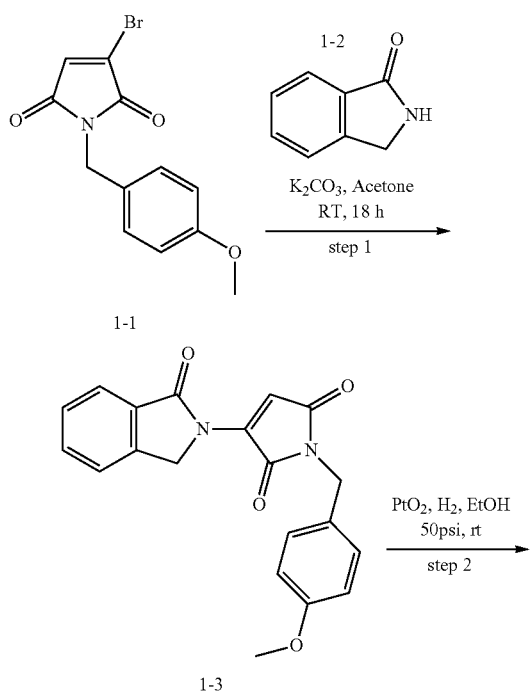

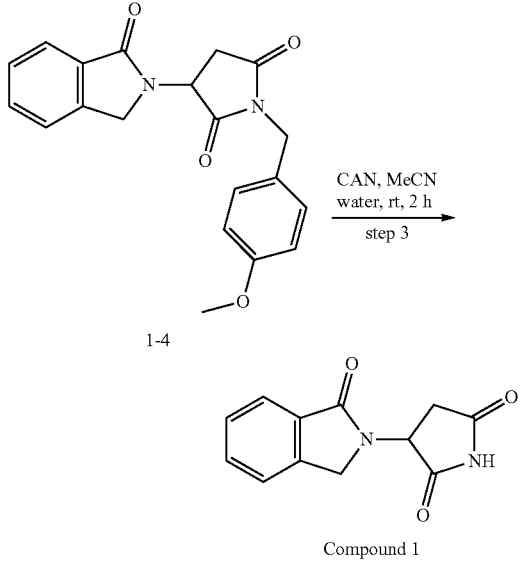

Step-1

To a stirred solution of 1-2 (448 mg, 3.37 mmol) and 1-1 (1000 mg, 3.37 mmol) and Potassium carbonate (931 mg, 6.74 mmol) in Acetone (20.0 mL). It was stirred at room temperature for 16 hours. It was diluted with water and extracted with ethyl acetate. Organic part was dried over sodium sulfate, concentrated under reduced pressure and purified by column chromatography using (silica, gradient, 0%-30% ethyl acetate in hexane to afford 3 as off white solid. Yield—20%; LC MS: ES+ 349.3.

Step-2

Compound 1-3 (100 mg, 287 µmol) was taken in Ethanol (10 mL) in a parr-shaker vessel. It was degassed with argon for 10 minutes. Platinum dioxide (6.51 mg, 28.7 µmol) was added to the reaction mixture. It was shacked in the presence of hydrogen at 50 psi for 16 h. It was filtered through celite and concentrated under reduced pressure and was purified by column chromatography using (silica, gradient, 0%-25% Ethyl acetate in hexane) to provide 1-4 as white solid. Yield—40%; LC MS: ES+ 351.1.

Step-3

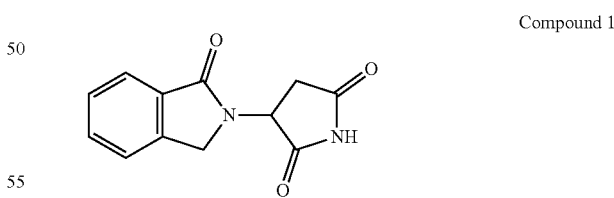

Compound 1

To a stirred solution of 1-4 (32 mg, 91.3 µmol) in Acetonitrile (0.5 mL) and Water (2 mL). Ceric ammonium nitrate (99.7 mg, 182 µmol) was added to the reaction mixture and was stirred at room temperature for 2 hours. It was diluted with water and was extracted with ethyl acetate, dried over sodium sulfate and concentrated under reduced pressure. It was purified by preparative TLC (40% ethyl acetate in hexane) to provide Compound 1 as off white solid. Yield—19%; 1H NMR (400 MHz, DMSO-d6) δ 11.51 (s, 1H), 7.71 (d, J=7.36 Hz, 1H), 7.64-7.61 (m, 2H), 7.52 (d, J=7.52 Hz, 1H), 5.23 (t, J=7.42 Hz, 1H), 4.62 (d, J=17.24 Hz, 1H), 4.37 (d, J=17.24 Hz, 1H), 2.97-2.92 (m, 1H); LC MS: ES+ 231.3.

Example 2: Illustrative Preparation of 7-Member Glutarimide

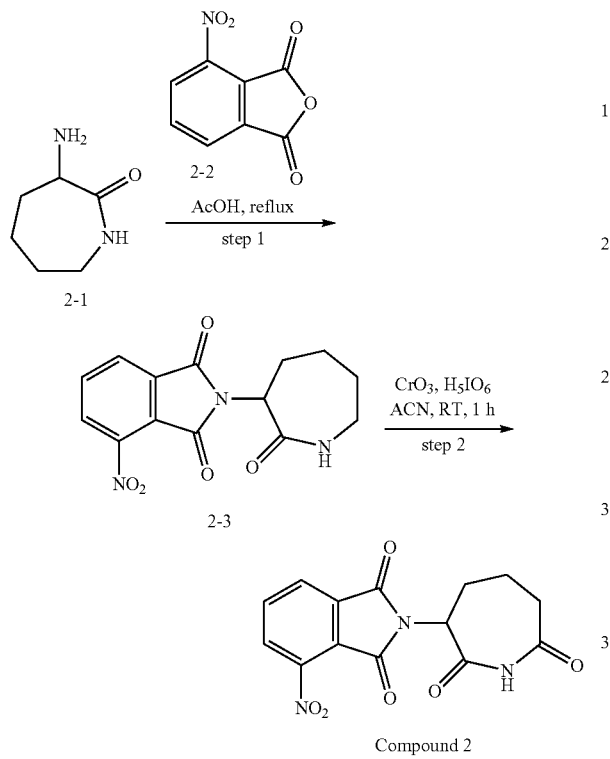

Step-1

To a mixture of 2-1 (150 mg, 780 µmol) and 2-2 (100 mg, 780 µmol) in Acetic acid (3 mL) taken was added Ammonium acetate (60.1 mg, 780 µmol) and refluxed for 2 hours. Water was then added to the reaction mixture and the compound was extracted with DCM. The organic phase was separated, dried over anhydrous sodium sulfate and evaporated in vacuo to obtain the crude which was purified by silica gel column to afford 2-3 as white solid. Yield—21%; LC MS: ES+ 304.1.

Step-2

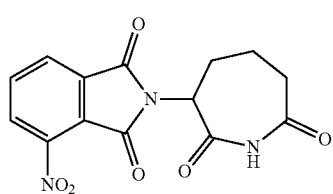 [SMILES: O=C1CCCC(N2C(=O)c3cccc([N+](=O)[O-])c3C2=O)C(=O)N1]

Compound 2

A mixture of periodic acid (224 mg, 984 µmol) and chromium trioxide (3.27 mg, 32.8 µmol) in Acetonitrile (3.0 mL) was stirred at room temperature for 30 min. Then acetic anhydride (92.5 µL, 984 µmol) was added. The reaction mixture was cooled to 0° C. and 2-3 (50 mg, 164 µmol) was added in one portion and the reaction mixture was further stirred for 30 min at room temperature. After completion of the reaction, ice-water (15-20 mL) was added and the mixture was extracted with ethyl acetate (3×50 mL). The combined organic layer was washed with saturated NaHCO$_3$ solution, saturated Na$_2$S$_2$O$_3$ solution, and finally with brine. The organic phase was dried over anhydrous sodium sulfate and the solvent was removed under reduced pressure. The crude product was filtered through silica gel column using ethyl acetate as eluent to obtain Compound 2 as white solid. Yield—40%; 1H NMR (400 MHz, DMSO-d$_6$) δ 10.86 (s, 1H), 8.34 (d, J=7.96 Hz, 1H), 8.24 (d, J=7.36 Hz, 1H), 8.11 (t, J=7.78 Hz, 1H), 5.26 (dd, J=12, 3.08 Hz, 1H), 3.18-3.09 (m, 1H), 2.66-2.52 (m, 2H), 2.18-2.12 (m, 1H), 1.99-1.82 (m, 2H); LC MS: ES+ 318.2.

Example 3: Illustrative Preparation of Spiro-Cyclopropyl Glutarimide

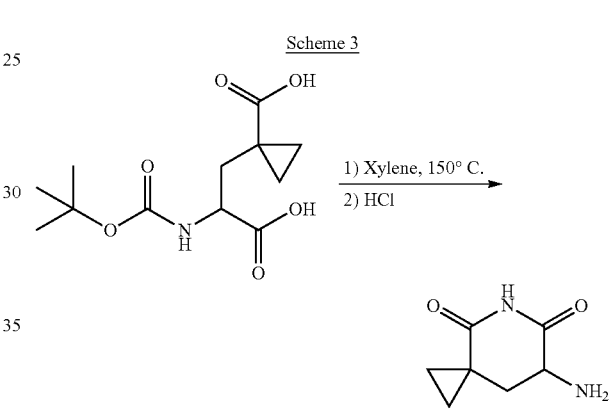

Step 1: A 25 mL 2 neck RB flask was charged with 1-(2-((tert-butoxycarbonyl)amino)-2-carboxyethyl)cyclopropanecarboxylic acid (200 mg, 731 µmol) in Xylene (5 mL). Urea (87.6 mg, 1.46 mmol) was added to the reaction mixture and was heated at 150° C. for 5 hours. It was concentrated under reduced pressure and was purified by silica gel (100-200 mesh) column chromatography by using 1% methanol in dichloromethane to provide tert-butyl (4,6-dioxo-5-azaspiro[2.5]octan-7-yl)carbamate (30.0 mg, 117 µmol, 16.2%) as off white solid.

Step 2: A 10 mL round bottom flask was charge with tert-butyl (4,6-dioxo-5-azaspiro[2.5]octan-7-yl)carbamate (20 mg, 78.6 µmol) in 4M Dioxane-HCl (1 mL) at 00 C. It was stirred at RT for 2 h. It was concentrated under reduced pressure to provide 7-amino-5-azaspiro[2.5]octane-4,6-dione hydrochloride (12.0 mg, 62.9 µmol, 80.5%) as a white solid.

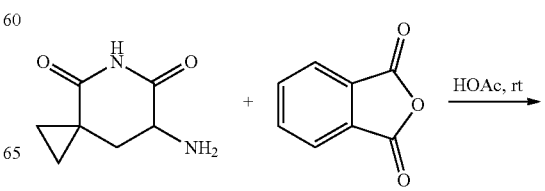

-continued

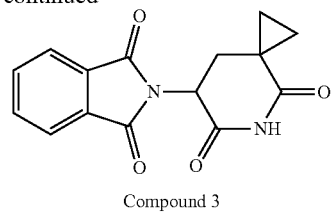

Compound 3

A 10 ml round bottom flask was charged with 7-amino-5-azaspiro[2.5]octane-4,6-dione hydrochloride (10 mg, 52.4 µmol) in Acetic acid (2 mL), Triethyl amine (7.30 µL, 52.4 µmol) was added to the reaction mixture. It was stirred at RT for 10 minutes. isobenzofuran-1,3-dione (7.76 mg, 52.4 µmol) was added to the reaction mixture. It was heated at 120° C. for 4 h. It was cooled to RT and was concentrated under reduced pressure. It was purified by preparative TLC (3% methanol-dichloromethane) to provide 2-(4,6-dioxo-5-azaspiro[2.5]octan-7-yl)isoindoline-1,3-dione (5.00 mg, 17.5 µmol, 33.7%) as off white solid. TLC system: 5% MeOH/DCM, Rf: 0.2, NMR $^1$H NMR (400 MHz, DMSO-$d_6$) δ 11.23 (s, 1H), 7.92 (m, 4H), 5.16 (dd, J=12, 5.6 Hz, 1H), 3.03 (t, J=12 Hz, 1H), 1.62 (m, 1H), 1.42 (m, 1H), 1.05 (m, 2H), 0.85 (m, 1H); LCMS ES–283.1.

TABLE 1

| Cmpd # | Structure | Kd |
|---|---|---|
| 1 | ![structure 1] | + |
| 2 | ![structure 2] | + |
| 3 | ![structure 3] | ++ |

In Table 1 above + is >100 µM and ++ is between 1 µM and 1000 µM

Example 4: CRBN-DDB1 Fluorescence Polarization (FP) Assay

Measuring compound ligand binding to CRBN-DDB1 was carried out using an established sensitive and quantitative in vitro fluorescence polarization (FP) based binding assay. (See, I. J. Enyedy et al, J. Med. Chem., 44: 313-4324 [2001]). Compounds were dispensed from serially diluted DMSO stock into black 384-well compatible fluorescence polarization plates using an Echo acoustic dispenser. Compound binding to CRBN-DDB1 was measured by displacement of either a (−)-Thalidomide-Alexa Fluor® or Pomalidomide-fluorescein conjugated probe dye. A 20 µL mixture containing 400 nM CRBN-DDB1 and 5 nM probe dye in 50 mM Hepes, pH 7.4, 200 mM NaCl, 1% DMSO and 0.1% pluronic acid-127 acid was added to wells containing compound and incubated at room temperature for 60 min. Matching control wells excluding CRBN-DDB1 were used to correct for background fluorescence. Plates were read on an Envision plate reader with appropriate FP filter sets. The corrected S (perpendicular) and P (parallel) values were used to calculate fluorescence polarization (FP) with the following equation: FP=1000*(S−G*P)/(S+G*P). The fractional amount of bound probe (FB) to CRBN-DDB1 as a function of compound concentration was fitted according to Wang; FEBS Letters 360, (1995), 111-114 to obtain fits for parameter offsets and binding constant (KA) of competitor compound.

Example 5: Cell Viability Analysis

RPMI 1640 medium and fetal bovine serum (FBS) were purchased from Gibco (Grand Island, N.Y., USA). CellTiter-Glo® 2.0 Assay was purchased from Promega (Medison, Wis., USA). MOLT4.1 (WT) cell line was purchased from ATCC (Manassas, Va., USA) and MOLT4.2 (CRBN Knock Out) cell line was generated in house. Cell culture flasks and 384-well microplates were acquired from VWR (Radnor, Pa., USA).

MOLT4.1 and MOLT4.2 cell viability was determined based on quantification of ATP using CellTiter-Glo® 2.0 luminescent Assay kit, which signals the presence of metabolically-active cells. Briefly, MOLT4.1 and MOLT4.2 cells were seeded into 384-well plates at a cell density of 750 cells per well, the plates were kept at 37° C. with 5% CO2 overnight. On the following day, test compounds were added to the cells from a top concentration of 1 µM with 10 points, half log titration in duplicates. The cells treated in the absence of the test compound were the negative control and the cells treated in the absence of CellTiter-Glo® 2.0 were the positive control. At the same day of compound treatment, CellTiter-Glo® 2.0 was added to a plate with cells treated in the absence of the test compound to establish Cytostatic control value (CTO). Cells treated with the test compound were incubated for 72 hr. CellTiter-Glo reagent was then added to the cells and Luminescence was acquired on EnVision™ Multilabel Reader (PerkinElmer, Santa Clara, Calif., USA).

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the invention as defined in the appended claims

We claim:

1. A compound of Formula:

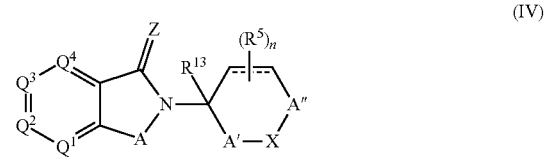

(IV)

or a pharmaceutically acceptable salt thereof;
wherein

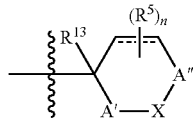

is selected from:

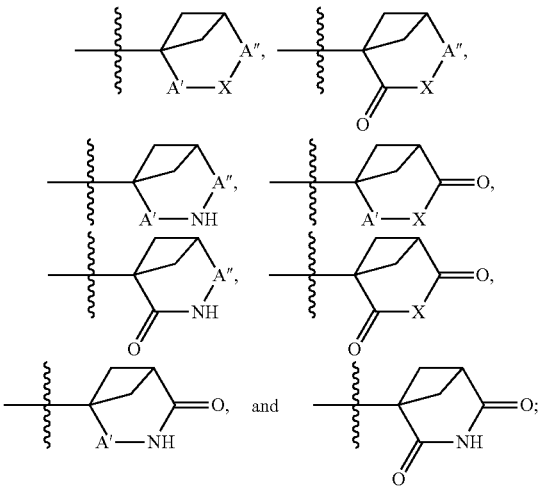

A is CR⁸R⁹, C=O, C=S, C=CH₂, SO₂, S(O), P(O)Oalkyl, P(O)NHalkyl, P(O)N(alkyl)₂, P(O)alkyl, P(O)OH, or P(O)NH₂;
A' is CR¹R², C=O, C=S, C=CH₂, SO₂, S(O), P(O)Oalkyl, P(O)NHalkyl, P(O)N(alkyl)₂, P(O)alkyl, P(O)OH, or P(O)NH₂;
A" is CR³R⁴, C=O, C=S, C=CH₂, SO₂, S(O), P(O)Oalkyl, P(O)NHalkyl, P(O)N(alkyl)₂, P(O)alkyl, P(O)OH, or P(O)NH₂;
X is independently selected from NH, NR¹¹, CH₂, CHR¹², C(R¹²)₂, O, and S;
Z is O, S, CH₂, CH(C₁-C₄alkyl), or C(C₁-C₄alkyl)₂;
n is 0, 1, 2, 3, 4, or 5;
══ is a single or double bond;
R¹, R², R³, R⁴, R⁸, R⁹, and R¹³ are independently selected from hydrogen, alkyl, hydroxyl, alkoxy, amine, —NHalkyl, and —Nalkyl₂;
or R¹ and R² form a 3-, 4-, 5-, or 6-membered spirocarbocycle, or a 4-, 5-, or 6-membered spiroheterocycle comprising 1 or 2 heteroatoms selected from N and O;
or R³ and R⁴ form a 3-, 4-, 5-, or 6-membered spirocarbocycle, or a 4-, 5-, or 6-membered spiroheterocycle comprising 1 or 2 heteroatoms selected from N and O;
or R⁸ and R⁹ form a 3-, 4-, 5-, or 6-membered spirocarbocycle, or a 4-, 5-, or 6-membered spiroheterocycle comprising 1 or 2 heteroatoms selected from N and O;
or R¹³ and R⁵ form a 3, 4, 5, or 6 carbon fused ring wherein R⁵ is on the carbon alpha to R¹³ or a 1, 2, 3, or 4 carbon bridged ring wherein R⁵ is not on the carbon alpha to R¹³;
R⁵ is selected at each instance from: alkyl, alkene, alkyne, halogen, hydroxyl, alkoxy, azide, amino, —NHalkyl, —N(alkyl)₂, —NHSO₂alkyl, —N(alkyl)SO₂alkyl, —NHSO₂aryl, —N(alkyl)SO₂aryl, —NHSO₂alkenyl, —N(alkyl)SO₂alkenyl, —NHSO₂alkynyl, —N(alkyl)SO₂alkynyl, and haloalkyl;
or two R⁵ substituents together with the carbon atom(s) to which they are bound can form a 3, 4, 5 or 6 membered ring;
Q¹, Q², Q³, and Q⁴ are independently selected from CH, CR¹², and N; and wherein no more than two of Q¹, Q², Q³, and Q⁴ are N;
R¹¹ is independently selected from alkyl, alkenyl, alkynyl, C(O)H, —C(O)OH, —C(O)alkyl, and —C(O)Oalkyl; and
R¹² is independently selected from alkyl, alkenyl, alkynyl, halogen, hydroxyl, alkoxy, azide, amino, —C(O)H, —C(O)OH, —C(O)alkyl, —C(O)Oalkyl, —NHalkyl, —N(alkyl)₂, —NHSO₂alkyl, —N(alkyl)SO₂alkyl, —NHSO₂aryl, —N(alkyl)SO₂aryl, —NHSO₂alkenyl, —N(alkyl)SO₂alkenyl, —NHSO₂alkynyl, —N(alkyl)SO₂alkynyl, cyano, nitro, nitroso, —SH, —Salkyl, and haloalkyl.

2. The compound of claim 1, wherein A is C=O, C=S, or C=CH₂.

3. The compound of claim 1, wherein A' is C=O, C=S, or C=CH₂.

4. The compound of claim 1, wherein A" is C=O, =C=S, or C=CH₂.

5. The compound of claim 1, wherein A is C=O.

6. The compound of claim 1, wherein A" is C=O.

7. The compound of claim 1, wherein X is NH, S, or O.

8. The compound of claim 1, wherein X is NH.

9. The compound of claim 1, wherein Q¹, Q², Q³, and Q⁴ are CH.

10. The compound of claim 1, wherein Q¹ is CR¹² and one of Q², Q³, and Q⁴ is N.

11. The compound of claim 10, wherein R¹² is amino.

12. The compound of claim 1 wherein

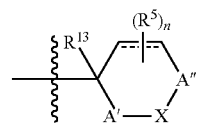

is selected from

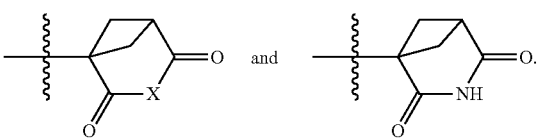

13. The compound of claim 1 selected from:

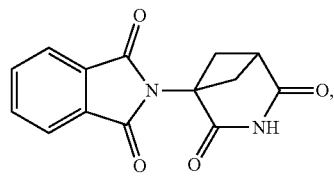

397
-continued
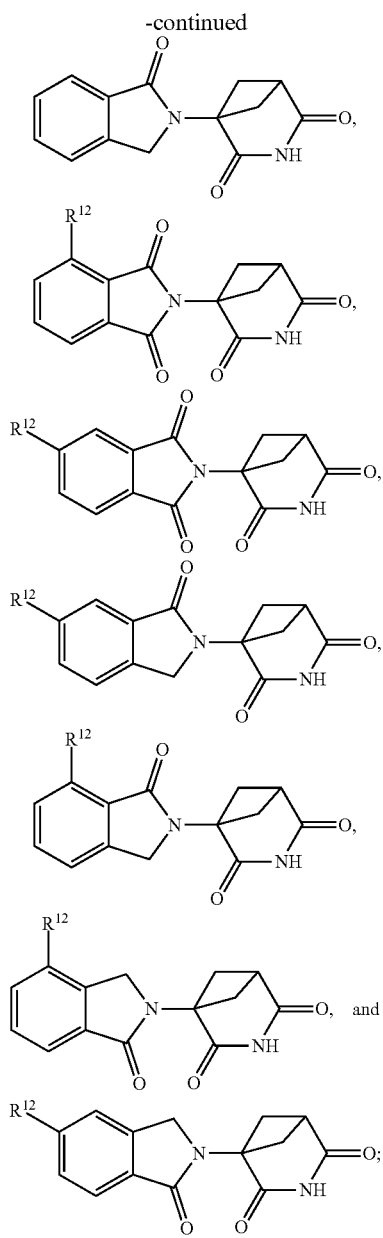
or a pharmaceutically acceptable salt thereof.
14. The compound of claim 13 selected from:
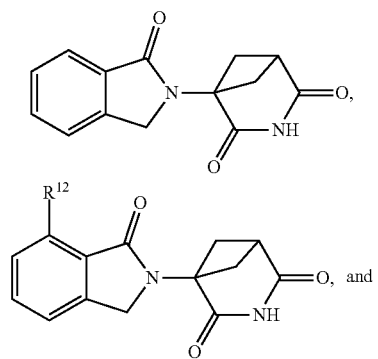
398
-continued
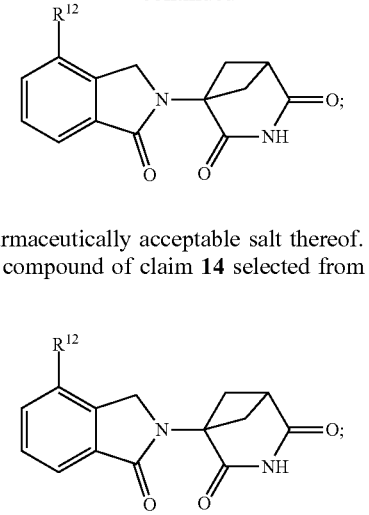
or a pharmaceutically acceptable salt thereof.
15. The compound of claim 14 selected from
[structure]
or a pharmaceutically acceptable salt thereof.
16. The compound of claim 1 selected from:
[structures with $Q^1$, $Q^2$, $Q^3$, $Q^4$, $R^{12}$]

or a pharmaceutically acceptable salt thereof.

17. The compound of claim 16 selected from
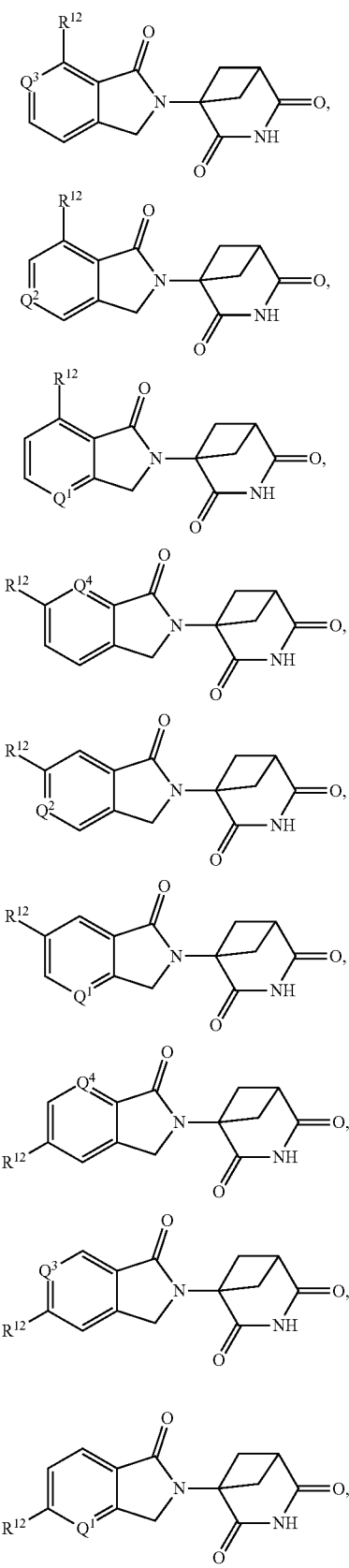
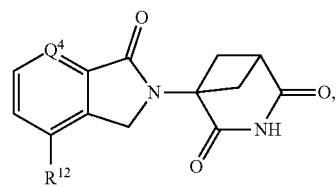
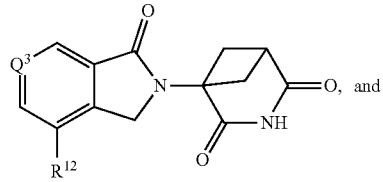
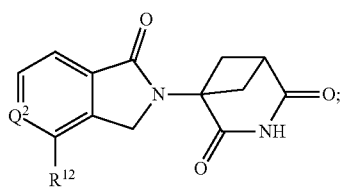
or a pharmaceutically acceptable salt thereof.
18. The compound of claim 17 selected from:
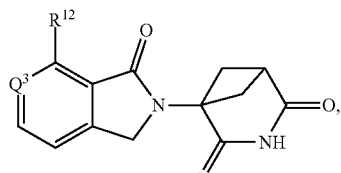
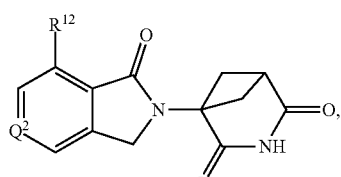
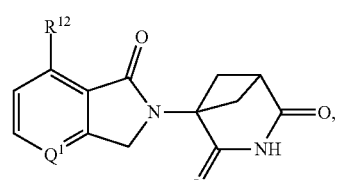
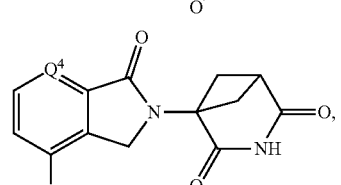
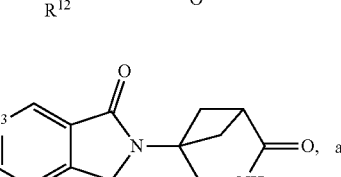
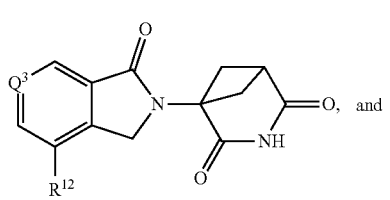

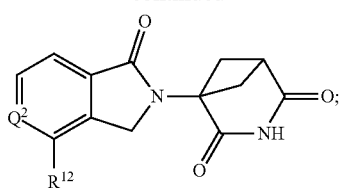
or a pharmaceutically acceptable salt thereof.
19. The compound of claim 18, wherein $R^{12}$ is amino and any one of $Q^1$, $Q^2$, $Q^3$, and $Q^4$ is N.
20. The compound of claim 1 selected from:
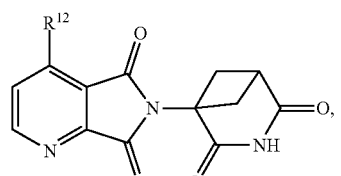
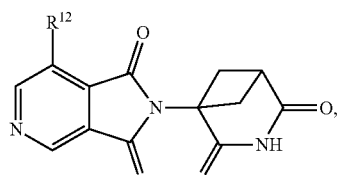
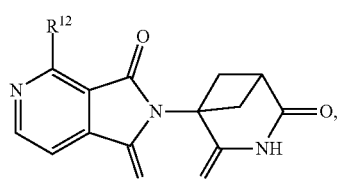
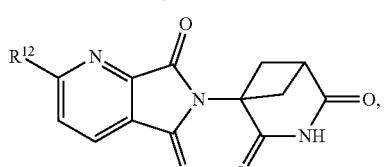
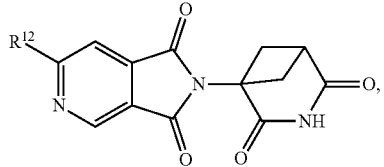
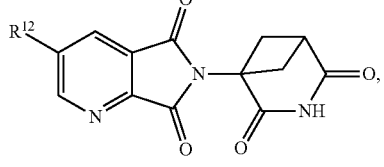
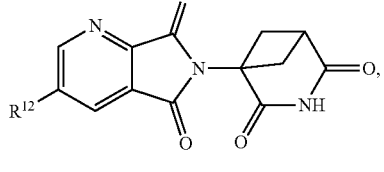
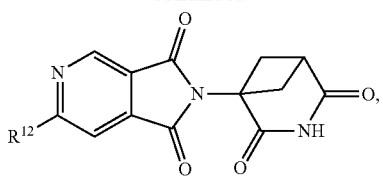
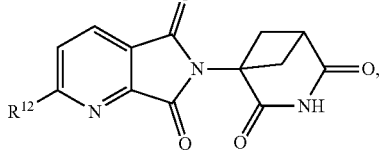
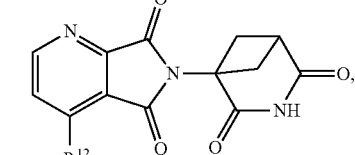
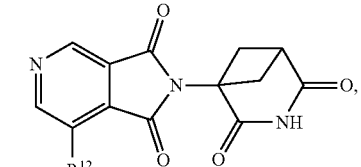
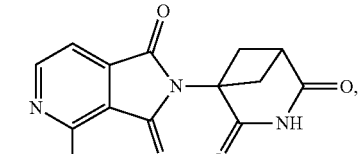
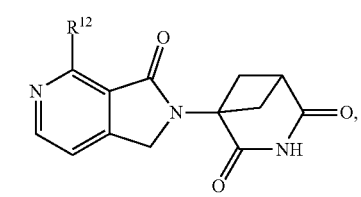
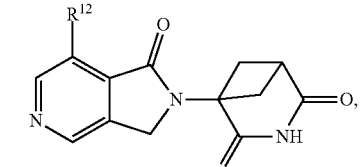
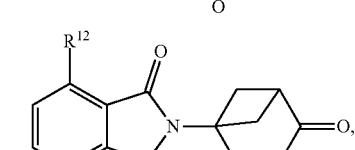
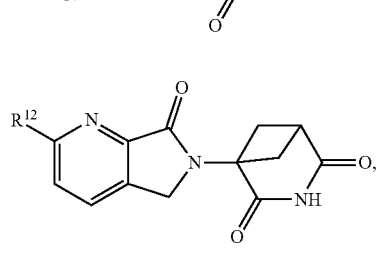

-continued
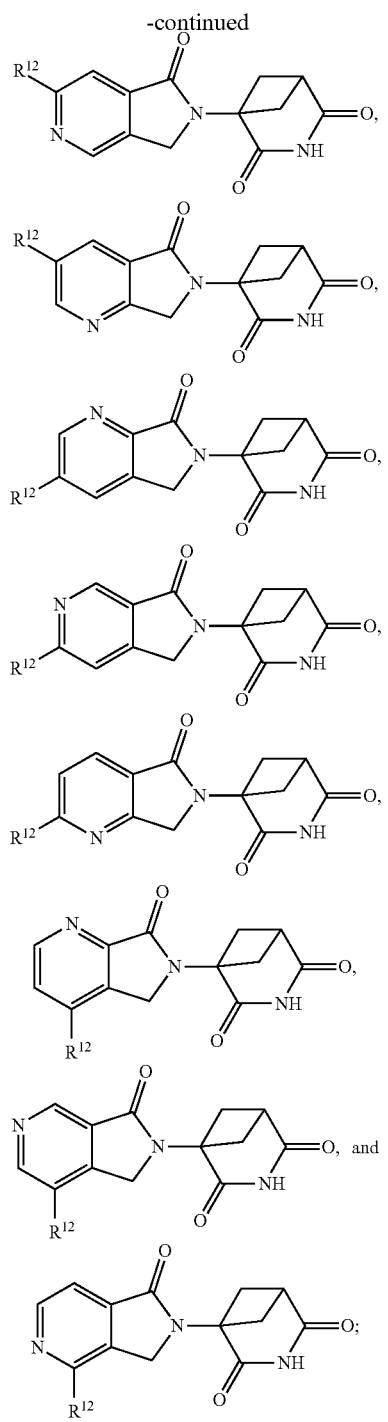
or a pharmaceutically acceptable salt thereof.
21. The compound of claim 20 selected from:
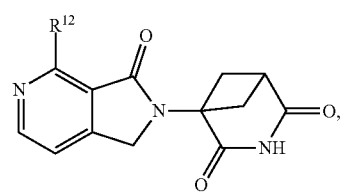
-continued
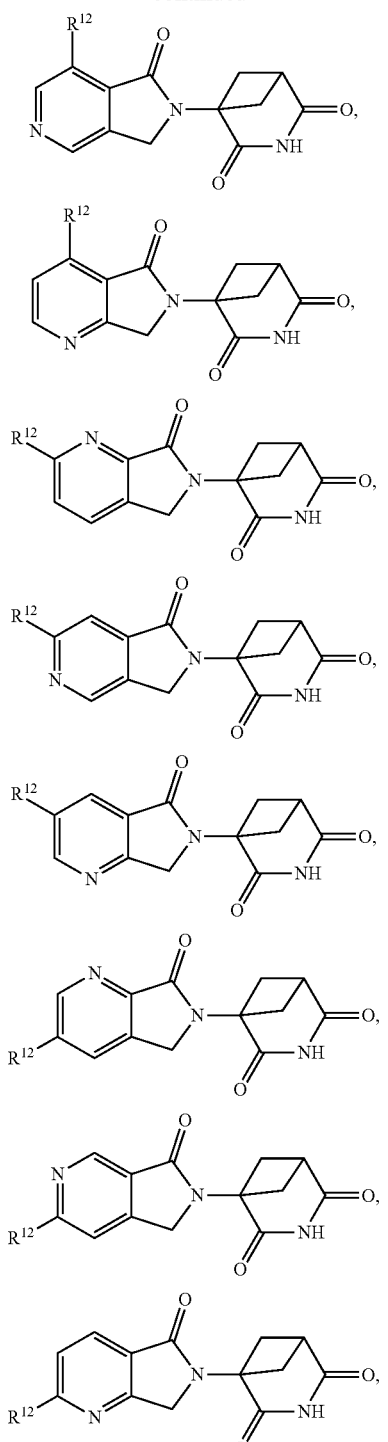
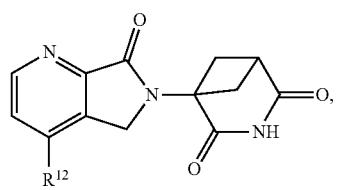

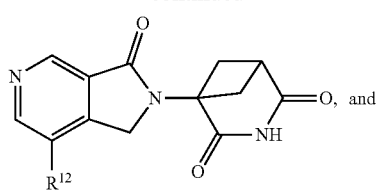
or a pharmaceutically acceptable salt thereof.
22. The compound of claim 21 selected from:
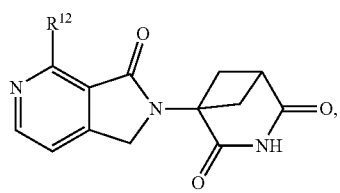
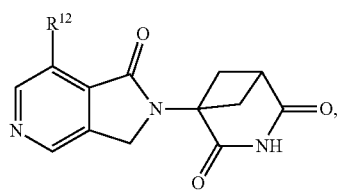
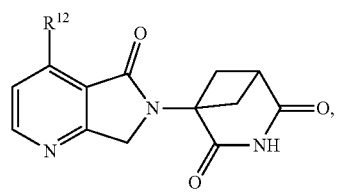
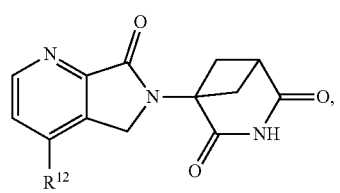
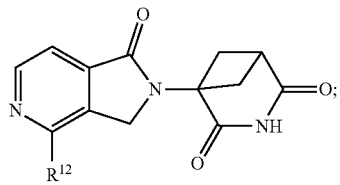
or a pharmaceutically acceptable salt thereof.
23. The compound of claim 22 selected from:
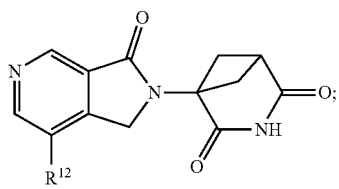
or a pharmaceutically acceptable salt thereof; wherein $R^{12}$ is amino.
24. The compound of claim 1 selected from:
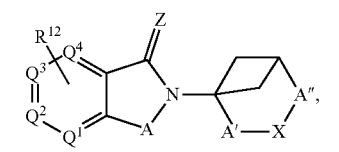
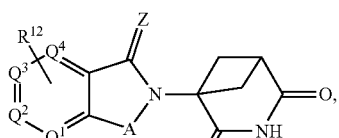
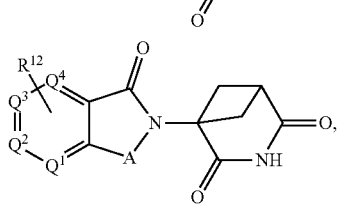
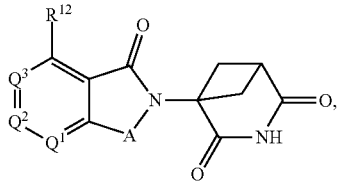
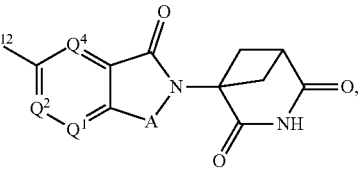
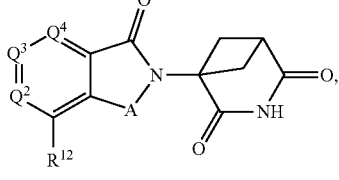
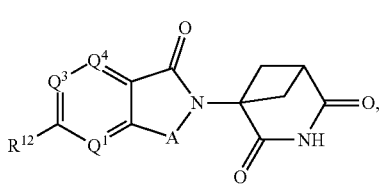

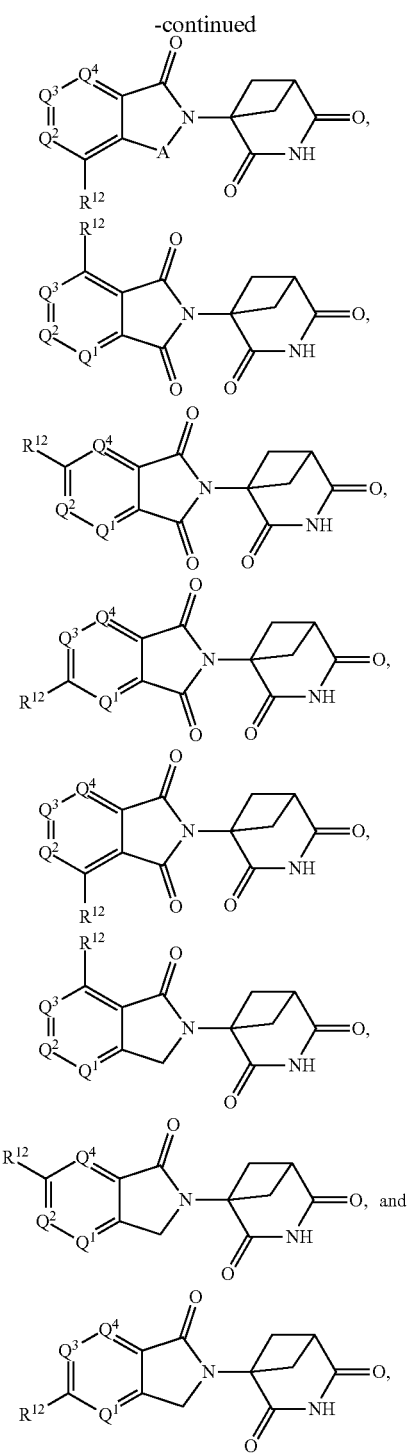
or a pharmaceutically acceptable salt thereof.
25. The compound of claim 24 selected from
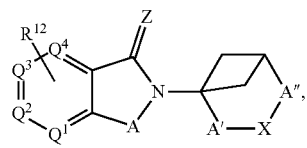
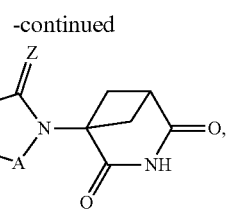
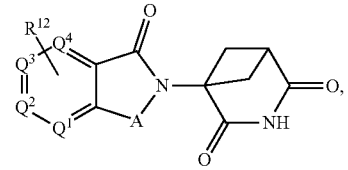
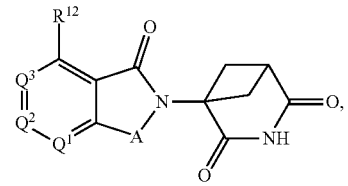
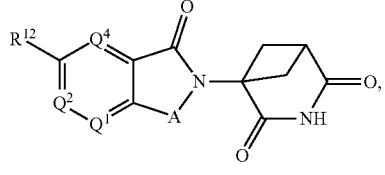
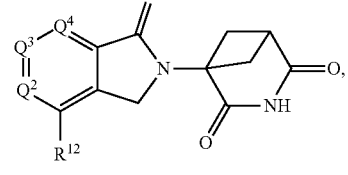
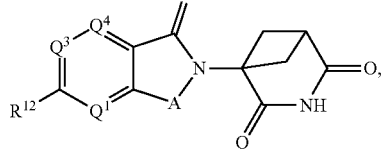
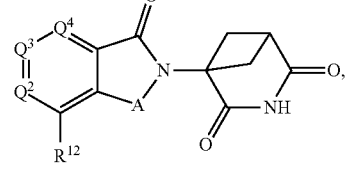
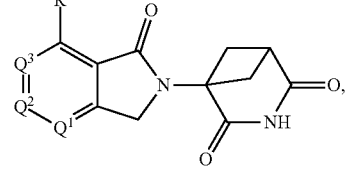
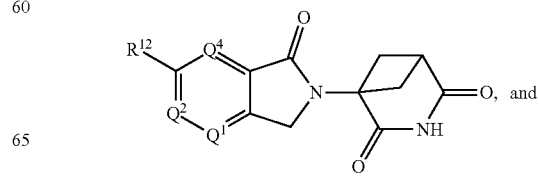

-continued
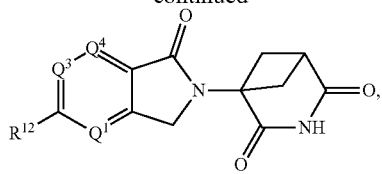
or a pharmaceutically acceptable salt thereof.
26. The compound of claim 25, selected from
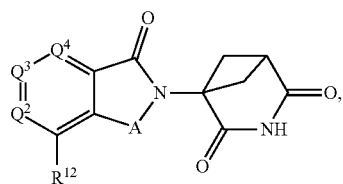
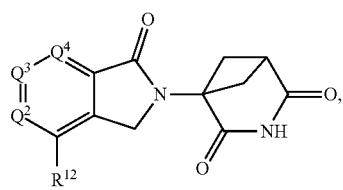
-continued
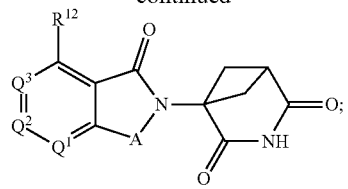
or a pharmaceutically acceptable salt thereof.
27. The compound of claim 1, wherein the compound is:
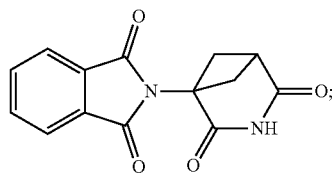 [SMILES: O=C1NC(=O)C2(N3C(=O)c4ccccc4C3=O)CC1C2]
or a pharmaceutically acceptable salt thereof.
28. The compound of claim 1, wherein the compound is:
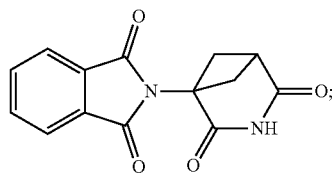 [SMILES: O=C1NC(=O)C2(N3C(=O)c4ccccc4C3=O)CC1C2]
or a pharmaceutically acceptable salt thereof.
* * * * *